United States Patent
Courtney et al.

(10) Patent No.: US 9,732,085 B2
(45) Date of Patent: Aug. 15, 2017

(54) PYRIDINONE AND PYRIMIDINONE DERIVATIVES AS FACTOR XIA

(71) Applicant: ONO PHARMACEUTICAL CO., LTD., Osaka-shi, Osaka (JP)

(72) Inventors: Steve Courtney, Oxfordshire (GB); Chris Yarnold, Oxfordshire (GB); Stuart Flanagan, Oxfordshire (GB); Gareth Brace, Oxfordshire (GB); John Barker, Oxfordshire (GB); Osamu Ichihara, Tokyo (JP); Elise Gadouleau, Oxfordshire (GB); Anthony Richardson, Oxfordshire (GB); Takashi Kondo, Osaka (JP); Akira Imagawa, Osaka (JP); Shingo Nakatani, Osaka (JP); Ryo Suzuki, Osaka (JP); Sho Kouyama, Osaka (JP)

(73) Assignee: ONO PHARMACEUTICAL CO., LTD., Osaka (JP)

( * ) Notice: Subject to any disclaimer, the term of this patent is extended or adjusted under 35 U.S.C. 154(b) by 362 days.

(21) Appl. No.: 14/366,396

(22) PCT Filed: Dec. 20, 2012

(86) PCT No.: PCT/GB2012/053217
§ 371 (c)(1),
(2) Date: Jun. 18, 2014

(87) PCT Pub. No.: WO2013/093484
PCT Pub. Date: Jun. 27, 2013

(65) Prior Publication Data
US 2015/0152112 A1   Jun. 4, 2015

(30) Foreign Application Priority Data

Dec. 21, 2011 (GB) .................................. 1122139.7
Sep. 27, 2012 (GB) .................................. 1217290.4

(51) Int. Cl.
C07D 487/04   (2006.01)
C07D 401/14   (2006.01)
C07D 403/14   (2006.01)
C07D 471/04   (2006.01)

(52) U.S. Cl.
CPC ......... *C07D 487/04* (2013.01); *C07D 401/14* (2013.01); *C07D 403/14* (2013.01); *C07D 471/04* (2013.01)

(58) Field of Classification Search
None
See application file for complete search history.

(56) References Cited

U.S. PATENT DOCUMENTS

| 2004/0058964 | A1 | 3/2004 | Devadas et al. |
| 2006/0211694 | A1 | 9/2006 | Devadas et al. |
| 2007/0088033 | A1 | 4/2007 | Devadas et al. |
| 2008/0161373 | A1 | 7/2008 | Pinto et al. |
| 2010/0016316 | A1 | 1/2010 | Pinto |
| 2010/0022506 | A1 | 1/2010 | Pinto et al. |
| 2010/0298372 | A1 | 11/2010 | Huang et al. |
| 2011/0028446 | A1 | 2/2011 | Pinto et al. |
| 2012/0088748 | A1 | 4/2012 | Ishichi et al. |
| 2012/0270853 | A1 | 10/2012 | Pinto et al. |

FOREIGN PATENT DOCUMENTS

| DE | 4407488 A1 | 9/1995 |
| EP | 0 407 342 A2 | 1/1991 |
| EP | 1 506 967 A1 | 2/2005 |
| WO | 03/068230 A1 | 8/2003 |
| WO | 2007/070826 A1 | 6/2007 |
| WO | 2008/076805 A2 | 6/2008 |
| WO | 2009/076337 A1 | 6/2009 |
| WO | 2012/046882 A1 | 4/2012 |

OTHER PUBLICATIONS

CAPLUS printout of Foreign Patent No. DE4407488, published on Sep. 14, 1995.*
Wong et al., A small-molecule factor XIa inhibitor produces antithrombotic efficacy with minimal bleeding time prolongation in rabbits. Journal of Thrombosis and Thrombolysis, 2011, 32, 129-137.*
Al-Horani et al., Factor XIa inhibitors: A review of the patent literature. Expert Opinion of Therapeutic Patents, 2016, 26, 323-345.*
Schafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
Ito et al., A medium-term rat liver bioassay for rapid in vivo detection of carcinogenic potential of chemicals. Cancer Science, 2003, 94, 3-8.*

(Continued)

*Primary Examiner* — Matthew Coughlin
*Assistant Examiner* — Po-Chih Chen
(74) *Attorney, Agent, or Firm* — Sughrue Mion, PLLC

(57) ABSTRACT

The present invention provides compounds of the general formula (I), their salts and N-oxides, and solvates and prodrugs thereof (wherein the characters are as defined in the description). The compounds of the general formula (I) are inhibitors of Factor XIa, so that they are useful in the prevention of and/or therapy for thromboembolic diseases.

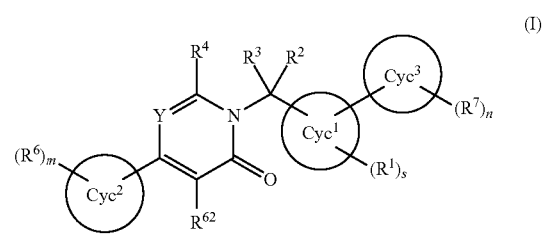

(I)

9 Claims, No Drawings

(56) References Cited

OTHER PUBLICATIONS

Office Action issued on Aug. 29, 2016, by the Australian Patent Office in counterpart Australian Application No. 2012356374.
Communication from the Indonesian Patent Office dated Mar. 17, 2017, in a counterpart Indonesian application No. P00201403648.
International Search Report (PCT/ISA/210), dated Feb. 27, 2013, issued by the International Searching Authority in counterpart International Patent Application No. PCT/GB2012/053217.

* cited by examiner

PYRIDINONE AND PYRIMIDINONE DERIVATIVES AS FACTOR XIA

TECHNICAL FIELD

The present invention relates to a series of pyridinone and pyrimidinone derivatives which are useful as inhibitors of factor XIa.

Thus, the present invention relates to a compound of formula (I):

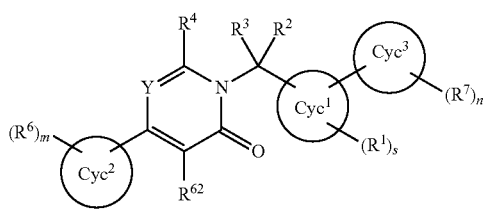

(wherein all symbols have the same meanings as described hereinafter) or a pharmaceutically acceptable salt thereof, an N-oxide thereof, a solvate thereof, or a prodrug thereof, use of such compounds in treatment and/or prevention of a thromboembolic disease and processes for the preparation of said compounds.

BACKGROUND OF THE INVENTION

Thromboembolism is an important cause of morbidity and mortality. It occurs when a blood clot breaks free and is carried by the blood stream to obstruct a blood vessel at another site. Thromboembolic disease includes venous thromboembolism, for example deep vein thrombosis or pulmonary embolism, arterial thrombosis, stroke and myocardial infarction.

Thromboembolic diseases may be treated using anticoagulants. One approach has been to target the inhibition of factor XIa (FXIa). Factor XIa is a plasma serine protease involved in the regulation of blood coagulation. Factor XIa is an activated form of factor XI, which is activated by factor XIIa, thrombin, and it is also autocatalytic. FXIa is a member of the "contact pathway" and activates factor IX by selectively cleaving Arg-Ala and Arg-Val peptide bonds. Factor IXa, in turn, activates factor X. The safety of this target is supported by the observations that FXI deficiency in humans (hemophilia C) results in a mild bleeding disorder. In addition to this, the efficacy and side effects of this target have been shown using experimental thrombosis and bleeding models in mice lacking FXI, and in baboons and rabbits treated with anti-FXI neutralizing antibodies. These results suggest that FXIa inhibitors will show a potent anti-thrombotic effect without bleeding. Therefore, factor XIa is an attractive target for anti-thrombotic therapy without any bleeding side effect.

It has been described in Patent literature 1 that compounds of formula (A):

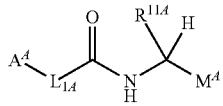

wherein $A^A$ represents a 5- to 12-membered heterocycle, etc.; $L_{1A}$ represents —CH═CH—, etc.; $R^{11A}$ represents benzyl, etc.; $M^A$ represents imidazolyl, etc; are useful as selective inhibitors of factor XIa or dual inhibitors of FXIa and plasma kallikrein.

Furthermore, it has been described in Patent literature 2 that a compound of formula (B-I):

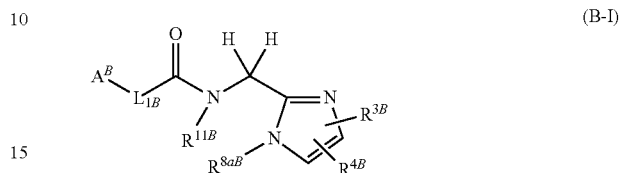

wherein $A^B$ represents a 5- to 12-membered heterocycle, etc.; $L_{1B}$ represents —CH═CH—, etc.; $R^{11B}$ represents benzyl, etc.; $R^{3B}$ represents phenyl, etc.; $R^{4B}$ represents chlorine, etc.; $R^{8aB}$ represents hydrogen, etc; or formula (B-II):

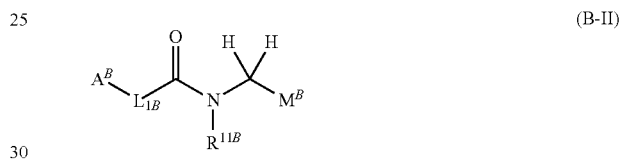

wherein $M^B$ represents pyridyl, etc.; and the other symbols have the same meanings as described above; inhibit factor XIa and/or plasma kallikrein.

Furthermore, it has been described in Patent literature 3 that compounds of formula (C):

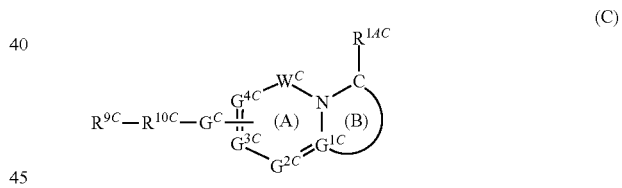

wherein $W^C$ represents CO, etc.; $G^C$ represents a direct bond, etc.; $G^{1C}$, $G^{2C}$, $G^{3C}$ and $G^{4C}$ each independently represents C or N, etc.; $R^{9C}$ represents aryl, etc.; $R^{10C}$ represents heteroaryl, etc.; $R^{14C}$ represents heteroarylalkyl, etc.; are useful as gamma secretase modulators, however, it is not reported that the compound represented by formula (C) has factor XIa inhibitory activity.

Furthermore, it has been described in Patent literature 4 that compounds of formula (D):

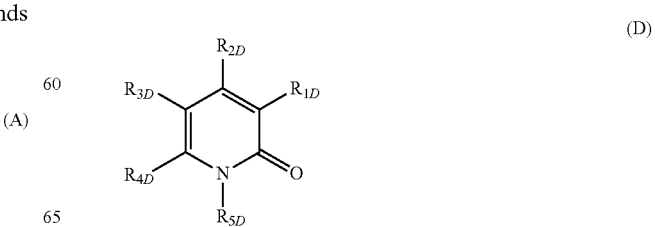

wherein $R_{1D}$ represents hydrogen, etc.; $R_{2D}$ represents aryl, etc.; $R_{3D}$ represents hydrogen, etc.; $R_{4D}$ represents hydrogen, etc.; $R_{5D}$ represents heteroarylalkyl, etc.; is useful as p38 MAP kinase modulator.

Furthermore, it has been described in Patent literature 5 that compounds of formula (E):

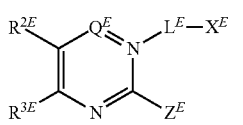

(E)

wherein $L^E$ represents a linker providing 0-6 atoms, etc.; $X^E$ represents heteroaryl, etc.; $Z^E$ represents halogen, etc.; $Q^E$ represents CO, etc.; $R^{2E}$ and $R^{3E}$ each independently represents hydrogen, aryl, etc.; are useful as dipeptidyl peptidase inhibitors.

[Patent literature 1] WO2007070826
[Patent literature 2] WO2008076805
[Patent literature 3] WO2009076337
[Patent literature 4] WO2003068230
[Patent literature 5] EP1506967A1

DISCLOSURE OF THE INVENTION

It is desirable to find new compounds which may be more effective in treating thromboembolic diseases. Advantageous compounds desirably have good inhibitory activity and selectivity for factor XIa (and preferably also for plasma kallikrein) with potent anticoagulant activity and/or good oral bioavailability.

The present inventors have made extensive studies to find a compound that can become a therapeutic agent for thromboembolic diseases. As a result, we have found that the object is achieved by a compound represented by formula (I), a salt thereof, an N-oxide thereof, a solvate thereof, or a prodrug thereof (hereinafter, which may be abbreviated to compounds of the present invention) with good factor XIa inhibitory activity, selectivity for factor XIa, potent anticoagulant activity and/or good oral bioavailability, and then we have completed the present invention.

Namely, the present invention relates to the following aspects.

(1) A compound represented by formula (I):

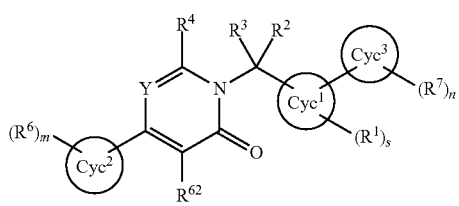

(I)

wherein $Cyc^1$ represents C3-C8 cycloalkyl, 5- to 10-membered heterocycloalkyl, C5-C10 aryl or 5- to 10-membered heteroaryl;
$Cyc^2$ represents C3-C8 cycloalkyl, 5- to 10-membered heterocycloalkyl, C5-C10 aryl or 5- or 6-membered heteroaryl;
$Cyc^3$ represents C3-C8 cycloalkyl, 5- to 10-membered heterocycloalkyl, C5-C10 aryl or 5- to 10-membered heteroaryl;

$R^1$ represents (1) C1-8 alkyl, (2) C2-8 alkenyl, (3) C2-8 alkynyl, (4) halogen, (5) nitro, (6) cyano, (7) oxo, (8) amidino, (9) —C1-8 alkylene —OR$^8$, (10) —OR$^9$, (11) —COOR$^{10}$, (12) —C1-4 alkylene —COOR$^{11}$, (13) —NHC(O)—C1-4 alkyl, (14) —C1-4 alkylene-O—C(O)—C1-8 alkyl or (15) —NHC(O)O—R$^{12}$,
wherein $R^8$, $R^9$, $R^{10}$, $R^{11}$ and $R^{12}$ each independently represents (1) hydrogen, (2) C1-8 alkyl, (3) C2-8 alkenyl, (4) C2-8 alkynyl, (5) C3-C8 cycloalkyl, (6) 5- to 10-membered heterocycloalkyl, (7) C5-C10 aryl, (8) 5- to 10-membered heteroaryl or (9) C1-4 alkyl substituted with 1 to 5 groups selected from C3-C8 cycloalkyl, 5- to 10-membered heterocycloalkyl, C5-C10 aryl and 5- to 10-membered heteroaryl;
s represents an integer of 0 to 6,
wherein s represents an integer of 2 to 6, each $R^1$ may be same or different;
$R^2$ represents (1) hydrogen, (2) C1-8 alkyl, (3) C2-8 alkenyl, (4) C2-8 alkynyl, (5) Cyc$^4$ or (6) C1-8 alkyl, C2-8 alkenyl or C2-8 alkynyl, which are substituted with 1 to 5 groups selected from halogen, nitro, trifluoromethyl, cyano, Cyc$^5$, —NR$^{13}$R$^{14}$, —OR$^{15}$, —SR$^{16}$, —NHC(O)-Cyc$^6$, —NHC(O)—C1-8 alkyl, —NHC(O)O—R$^{17}$ and Cyc$^5$ substituted with 1 to 3 groups selected from C1-8 alkyl, C2-8 alkenyl, C2-8 alkynyl, halogen, nitro, trifluoromethyl, cyano, oxo, amidino and —OR$^{18}$,
wherein $R^{13}$, $R^{14}$, $R^{15}$, $R^{16}$, $R^{17}$ and $R^{18}$ each independently represents (1) hydrogen, (2) C1-8 alkyl, (3) C2-8 alkenyl, (4) C2-8 alkynyl, (5) C3-C8 cycloalkyl, (6) 5- to 10-membered heterocycloalkyl, (7) C5-C10 aryl, (8) 5- to 10-membered heteroaryl or (9) C1-4 alkyl substituted with 1 to 5 groups selected from C3-C8 cycloalkyl, 5- to 10-membered heterocycloalkyl, C5-C10 aryl and 5- to 10-membered heteroaryl;
Cyc$^4$, Cyc$^5$ and Cyc$^6$ each independently represents C3-C8 cycloalkyl, 5- to 10-membered heterocycloalkyl, C5-C10 aryl or 5- to 10-membered heteroaryl;
$R^3$ represents (1) hydrogen, (2) C1-8 alkyl, (3) C2-8 alkenyl, (4) C2-8 alkynyl, (5) Cyc$^7$ or (6) C1-8 alkyl, C2-8 alkenyl or C2-8 alkynyl, which are substituted with 1 to 5 groups selected from halogen, nitro, trifluoromethyl, cyano, Cyc$^8$, —NR$^{19}$R$^{20}$, —OR$^{21}$, —SR$^{22}$, —NHC(O)-Cyc$^9$, —NHC(O)—C1-8 alkyl, —NHC(O)O—R$^{23}$ and Cyc$^8$ substituted with 1 to 3 groups selected from C1-8 alkyl, C2-8 alkenyl, C2-8 alkynyl, halogen, nitro, trifluoromethyl, cyano, oxo, amidino and —OR$^{24}$,
wherein $R^{19}$, $R^{20}$, $R^{21}$, $R^{22}$, $R^{23}$ and $R^{24}$ each independently represents (1) hydrogen, (2) C1-8 alkyl, (3) C2-8 alkenyl, (4) C2-8 alkynyl, (5) C3-C8 cycloalkyl, (6) 5- to 10-membered heterocycloalkyl, (7) C5-C10 aryl, (8) 5- to 10-membered heteroaryl or (9) C1-4 alkyl substituted with 1 to 5 groups selected from C3-C8 cycloalkyl, 5- to 10-membered heterocycloalkyl, C5-C10 aryl and 5- to 10-membered heteroaryl;
Cyc$^7$, Cyc$^8$ and Cyc$^9$ each independently represents C3-C8 cycloalkyl, 5- to 10-membered heterocycloalkyl, C5-C10 aryl or 5- to 10-membered heteroaryl;
Y represents N or C(R$^5$);
$R^4$ and $R^5$ each independently represents (1) hydrogen, (2) halogen, (3) C1-4 alkyl, (4) C3-C8 cycloalkyl, (5) 5- to 10-membered heterocycloalkyl, (6) C5-C10 aryl, (7) 5- to 10-membered heteroaryl or (8) C1-4 alkyl substituted with 1 to 5 groups selected from C3-C8 cycloalkyl, 5- to 10-membered heterocycloalkyl, C5-C10 aryl and 5- to 10-membered heteroaryl;

$R^2$ and $R^3$ may be taken together to form C2-8 alkylene; or $R^3$ and $R^4$ may be taken together to form C2-8 alkylene; wherein one carbon of the alkylene chain may be replaced by oxygen or sulfur;

$R^6$ represents (1) C1-8 alkyl, (2) C2-8 alkenyl, (3) C2-8 alkynyl, (4) $Cyc^{10}$, (5) halogen, (6) nitro, (7) cyano, (8) oxo, (9) amidino, (10) —$OR^{25}$, (11) —$COOR^{26}$, (12) —C1-4 alkylene —$COOR^{27}$, (13) —NHC(O)—C1-4 alkyl, (14) —NHC(O)—H, (15) —NHC(O)O—$R^{28}$, (16) trifluoromethyl, (17) —NHC(NH)NH$_2$, (18) —C(O)—C1-4 alkyl or (19) $Cyc^{10}$ substituted with 1 to 5 groups selected from C1-8 alkyl, C2-8 alkenyl, C2-8 alkynyl, halogen, nitro, trifluoromethyl, cyano, oxo, amidino, —$OR^{29}$, —$SR^{30}$, —$NR^{31}R^{32}$, —NHC(O) $NR^{33}R^{34}$, —NHC(O)—C1-4 alkylene —COOH, —NH—S(O)—C1-4 alkyl, —NH—S(O)$_2$—C1-4 alkyl, —$COOR^{35}$, —NHC(O)—$R^{36}$, —NHC(O)O—$R^{37}$, —C(O)NH—$R^{38}$ and —OC(O)NH—$R^{39}$, wherein $Cyc^{10}$ represents C3-C8 cycloalkyl, 5- to 10-membered heterocycloalkyl, C5-C10 aryl or 5- to 10-membered heteroaryl;

$R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$ and $R^{39}$ each independently represents (1) hydrogen, (2) C1-8 alkyl, (3) C2-8 alkenyl, (4) C2-8 alkynyl, (5) C3-C8 cycloalkyl, (6) 5- to 10-membered heterocycloalkyl, (7) C5-C10 aryl, (8) 5- to 10-membered heteroaryl or (9) C1-4 alkyl substituted with 1 to 5 groups selected from C3-C8 cycloalkyl, 5- to 10-membered heterocycloalkyl, C5-C10 aryl and 5- to 10-membered heteroaryl;

m represents an integer of 0 to 6, wherein m represents an integer of 2 to 6, each $R^6$ may be same or different;

$R^7$ represents (1) C1-8 alkyl, (2) C2-8 alkenyl, (3) C2-8 alkynyl, (4) halogen, (5) nitro, (6) trifluoromethyl, (7) cyano, (8) oxo, (9) amidino, (10) —$OR^{40}$, (11) —$SR^{41}$, (12) —$NR^{42}R^{43}$, (13) —NHC(O)$NR^{44}R^{45}$, (14) —NHC(O)—C1-4 alkylene —$NR^{46}R^{47}$, (15) —NHC(O)—C1-4 alkylene —COOH, (16) —NH—S(O)—C1-4 alkyl, (17) —NH—S(O)$_2$—C1-4 alkyl, (18) —$COOR^{48}$, (19) —NHC(O)—$R^{49}$, (20) —NHC(O)—C1-4 alkylene —$OR^{50}$, (21) —NHC(O)O—$R^{51}$, (22) —NHC(O)O—C1-4 alkylene —$OR^{52}$, (23) —C(O)NH—$R^{53}$, (24) —OC(O)NH—$R^{54}$, (25) —OC(O)—$R^{55}$, (26) —C(O)—$R^{56}$, (27) —CH(OH)—$R^{57}$, (28) —C1-4 alkylene —NH$_2$, (29) —C1-4 alkylene —OH, (30) —C1-4 alkylene —OC(O)—C1-4 alkyl, (31) —C1-4 alkylene —NHC(O)—C1-4 alkyl, (32) —C1-4 alkylene —NHC(O)O—C1-4 alkyl, (33) —C1-4 alkylene —NHC(O)—CF$_3$, (34) —C1-4 alkylene —NHC(O)NH—C1-4 alkyl, (35) —CH=N—$OR^{58}$, (36) —C(O)N(C1-4 alkyl)$_2$, (37) —C(O)NH—$R^{63}$, (38) —S(O)$_2$—$NR^{64}R^{65}$, (39) -T-$COOR^{66}$, (40) —B($OR^{67}$)($OR^{68}$), (41) C3-C8 cycloalkyl, 5- to 10-membered heterocycloalkyl, C5-C10 aryl or 5- or 6-membered heteroaryl, which are substituted with 1 to 5 groups selected from C1-8 alkyl, C2-8 alkenyl, C2-8 alkynyl, halogen, nitro, trifluoromethyl, —COOH, —COO—C1-4 alkyl, OH, oxo, and cyano, (42) C1-8 alkyl, C2-8 alkenyl or C2-8 alkynyl, which are substituted with 1 to 5 groups selected from halogen, trifluoromethyl, OH, oxo, —O—C1-4 alkyl, NH$_2$, and cyano, (43) —N(OH)C(O)—C1-4 alkyl, (44) —NHC(=N—$OR^{69}$)—C1-4 alkyl, (45) —NHC(S)—C1-4 alkyl, (46) —C(S)—C1-4 alkyl, (47) —S(O)$NR^{70}R^{71}$, (48) —C(O)NH(CO)$NR^{72}$, (49) —NHC(O)$R^{73}$, (50) —NHC(O)O—C1-4 alkyl substituted with 1 to 5 groups selected from —O—C1-4 alkylene-O—C1-4 alkyl, NH$_2$, and OH, (51) —NHC(O)—C1-4 alkyl substituted with 1 to 5 groups selected from —O—C1-4 alkylene-O—C1-4 alkyl, $NR^{74}R^{75}$, oxo, OH, halogen and —O—C1-4 alkylene-O—C1-4 alkyl substituted with 1 to 2 groups selected from OH, oxo and halogen, (52) —NH—C1-8 alkyl substituted with 1 to 5 groups selected from —O—C1-4 alkyl, oxo, $NR^{76}R^{77}$, C3-C8 cycloalkyl, 5- to 10-membered heterocycloalkyl, C5-C10 aryl and 5- or 6-membered heteroaryl, (53) C3-C8 cycloalkyl, (54) 5- to 10-membered heterocycloalkyl, (55) C5-C10 aryl or (56) 5- or 6-membered heteroaryl;

wherein $R^{40}$, $R^{41}$, $R^{42}$, $R^{43}$, $R^{44}$, $R^{45}$, $R^{46}$, $R^{47}$, $R^{49}$, $R^{50}$, $R^{51}$, $R^{52}$, $R^{53}$, $R^{54}$, $R^{55}$, $R^{56}$, $R^{57}$, $R^{58}$, $R^{67}$, $R^{68}$, $R^{69}$, $R^{70}$, $R^{71}$, $R^{72}$, $R^{73}$, $R^{74}$, $R^{75}$, $R^{76}$ and $R^{77}$ each independently represents (1) hydrogen, (2) trifluoromethyl, (3) C1-8 alkyl, (4) C2-8 alkenyl, (5) C2-8 alkynyl, (6) C3-C8 cycloalkyl, (7) 5- to 10-membered heterocycloalkyl, (8) C5-C10 aryl, (9) 5- to 10-membered heteroaryl or (10) C1-4 alkyl substituted with 1 to 5 groups selected from C3-C8 cycloalkyl, 5- to 10-membered heterocycloalkyl, C5-C10 aryl and 5- to 10-membered heteroaryl;

$R^{63}$ represents (1) —C1-4 alkylene-O—C1-4 alkyl, (2) —O—C1-4 alkyl, (3) cyano, (4) —C1-4 alkylene-O—C1-4 alkylene-O—C1-4 alkyl or (5) —SO$_2$—C1-4 alkyl;

$R^{64}$ and $R^{65}$ each independently represents (1) hydrogen, (2) C1-8 alkyl, (3) C2-8 alkenyl, (5) C2-8 alkynyl, (6) —C(O)—C1-4 alkyl or (7) C1-8 alkyl, C2-8 alkenyl or C2-8 alkynyl, which are substituted with 1 to 5 groups selected from OH, oxo, —O—C1-4 alkyl, —O—C1-4 alkylene-O—C1-4 alkyl, halogen, nitro and cyano;

T represents (1) C1-4 alkylene, (2) C2-4 alkenylene, (3) —O—C1-4 alkylene-, (4) —O—C2-4 alkenylene-, (5) —S—C1-4 alkylene-, (6) —S—C2-4 alkenylene-, (7) —NH—C1-4 alkylene-, (8) —NH—C2-4 alkenylene-, (9) —NH—C5-C10 aryl- or (10) —NH-5- to 10-membered heteroaryl-;

$R^{48}$ and $R^{66}$ each independently represents (1) hydrogen, (2) C1-8 alkyl, (3) C2-8 alkenyl, (4) C2-8 alkynyl, (5) C1-8 alkyl, C2-8 alkenyl or C2-8 alkynyl, which are substituted with 1 to 5 groups selected from —NH$_2$, —NH—C1-4 alkyl, —N(C1-4 alkyl)$_2$, OH, oxo, —O—C1-4 alkyl, —O—C1-4 alkylene-O—C1-4 alkyl, halogen, nitro, cyano, C3-C8 cycloalkyl, 5- to 10-membered heterocycloalkyl, C5-C10 aryl and 5- to 10-membered heteroaryl (6) C3-C10 cycloalkyl, (7) 5- to 10-membered heterocycloalkyl, (8) C5-C10 aryl, (9) 5- to 10-membered heteroaryl, (10) —C1-4 alkylene-C3-C8 cycloalkyl substituted with 1 to 5 groups selected from C1-4 alkyl, oxo, OH, trifluoromethyl and halogen, (11) —C1-4 alkylene-C5-C10 aryl substituted with 1 to 5 groups selected from C1-4 alkyl, OH, trifluoromethyl and halogen, (12) —C1-4 alkylene-5- to 10-membered heterocycloalkyl substituted with 1 to 5 groups selected from C1-4 alkyl, oxo, OH, trifluoromethyl and halogen, (13) —C1-4 alkylene-5- to 10-membered heteroaryl substituted with 1 to 5 groups selected from C1-4 alkyl, OH, trifluoromethyl and halogen or (14) —C1-4 alkylene-O—C1-8 alkyl substituted with 1 to 5 groups selected from OH, oxo, —O—C1-4 alkyl, —O—C1-4 alkylene-O—C1-4 alkyl, halogen, nitro, cyano, C3-C8 cycloalkyl, C5-C10 aryl, 5- to 10-membered heterocycloalkyl, —O-5- to 10-membered heteroaryl, —O—C3-C8 cycloalkyl, —O—C5-C10 aryl, —O-5- to 10-membered heterocycloalkyl, —O-5- to 10-membered heteroaryl, —O—C1-4 alkylene-5- to 10-membered heteroaryl, —O—C1-4 alkylene-C3-C8 cycloalkyl, —O—C1-4 alkylene-C5-C10 aryl, —O—C1-4 alkylene-5- to 10-membered heterocycloalkyl and —O—C1-4 alkylene-5- to 10-membered heteroaryl;

n represents an integer of 0 to 6, wherein n represents an integer of 2 to 6, each $R^7$ may be same or different; and $R^{62}$ represents hydrogen or halogen, a salt thereof, an N-oxide thereof, a solvate thereof, or a prodrug thereof.

(2) The compound according to (1), wherein the compound represented by formula (I) represents a compound represented by formula (I-A):

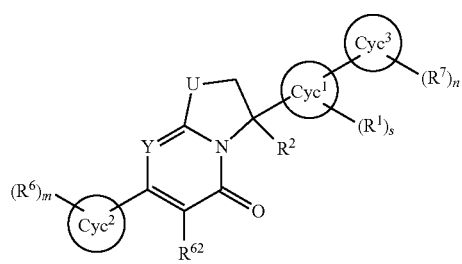

(I-A)

wherein U represents S or $CH_2$; and the other symbols have the same meanings as described above.

(3) The compound according to (1), wherein the compound represented by formula (I) represents a compound represented by formula (I-B):

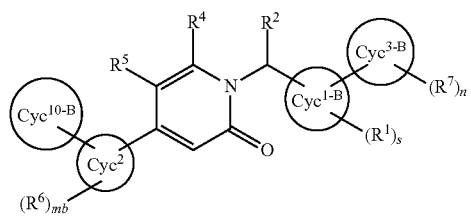

(I-B)

wherein $Cyc^{1-B}$ represents 5- to 10-membered heteroaryl;

$Cyc^{3-B}$ represents C5-C10 aryl or 5- to 10-membered heteroaryl;

$Cyc^{10-B}$ represents (1) 5- to 10-membered heteroaryl or (2) 5- to 10-membered heteroaryl substituted with 1 to 5 groups selected from halogen, cyano, nitro, trifluoromethyl, —COOH, —COO—C1-4 alkyl and —CONH$_2$;

mb represents an integer of 0 to 5; and the other symbols have the same meanings as described above.

(4) The compound according to (1), wherein the compound represented by formula (I) represents a compound represented by formula (I-C):

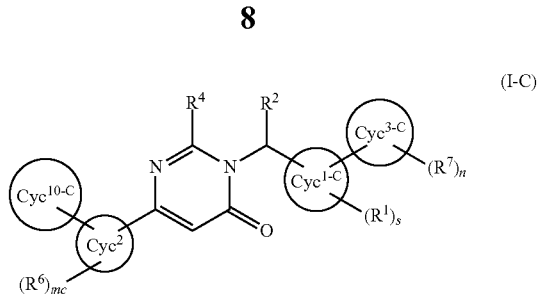

(I-C)

wherein $Cyc^{1-C}$ represents 5- to 10-membered heteroaryl;

$Cyc^{3-C}$ represents C5-C10 aryl or 5- to 10-membered heteroaryl;

$Cyc^{10-C}$ represents (1) 5- to 10-membered heteroaryl or (2) 5- to 10-membered heteroaryl substituted with 1 to 5 groups selected from halogen, cyano, nitro, trifluoromethyl, —COOH, —COO—C1-4 alkyl and —CONH$_2$;

mc represents an integer of 0 to 5; and the other symbols have the same meanings as described above.

(5) The compound according to (1) or (2), wherein $Cyc^1$ represents phenyl, imidazolyl, triazolyl, pyrrolyl, pyrazolyl, furanyl, oxazolyl, thiazolyl, isothiazolyl, furazanyl, oxadiazolyl, thiadiazolyl, thienyl, pyridazinyl, indazolyl or benzimidazolyl.

(6) The compound according to (3), wherein $Cyc^{1-B}$ represents imidazolyl, triazolyl, tetrazolyl, oxazolyl, pyridazinyl, indazolyl or benzimidazolyl.

(7) The compound according to (4), wherein $Cyc^{1-C}$ represents imidazolyl, triazolyl, tetrazolyl, oxazolyl, pyridazinyl, indazolyl or benzimidazolyl.

(8) The compound according to (1) or (2), wherein

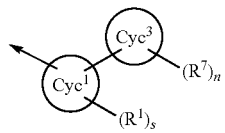

represents

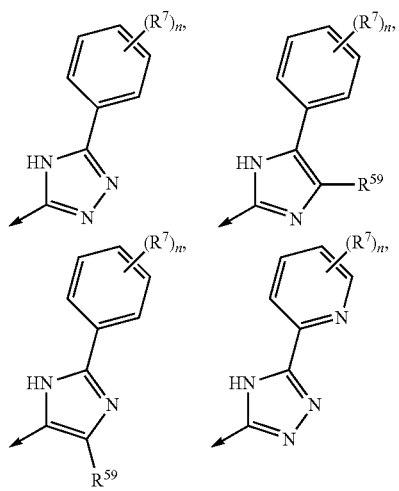

-continued

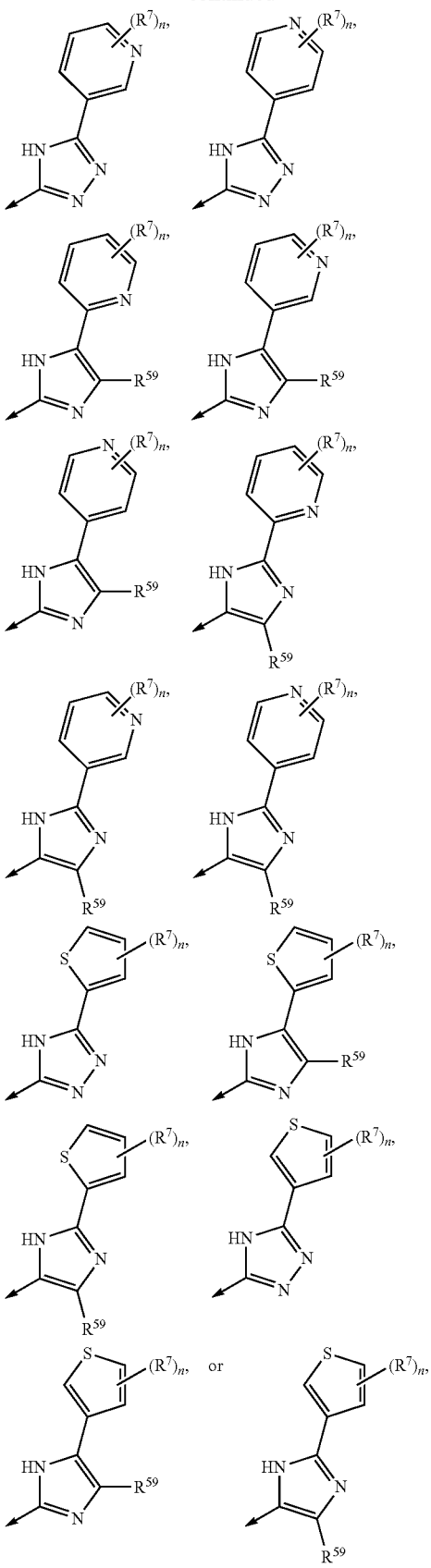

wherein R[59] represents hydrogen, C1-4 alkyl or halogen; the arrow represents a binding position; and the other symbols have the same meanings as described above.

(9) The compound according to any one of (1) to (8), wherein Cyc[2] represents pyridyl or phenyl.

(10) The compound according to any one of (1) to (9), wherein -Cyc[2]-(R[6])$_m$, Cyc[2](—R[6])$_{mb}$Cyc[10-B] or Cyc[2](—R[6])$_{mc}$Cyc[10-C] represents

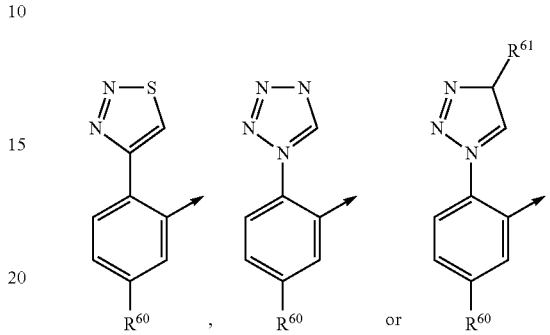

wherein R[60] represents hydrogen, methyl or halogen;
R[61] represents (1) hydrogen, (2) halogen, (3) nitro, (4) trifluoromethyl, (5) —COOH, (6) —COO—C1-4 alkyl, (7) cyano or (8) —CONH$_2$; and the arrow represents a binding position.

(11) The compound according to any one of (1) to (4), wherein Cyc[2] represents pyridyl or phenyl.

(12) The compound according to any one of (1) to (11), wherein R[7] represents (1) C1-8 alkyl, (2) halogen, (3) nitro, (4) trifluoromethyl, (5) cyano, (6) oxo, (7) —OR[40], (8) —NR[42]R[43], (9) —NHC(O)NR[44]R[45], (10) —NHC(O)—C1-4 alkylene-NR[46]R[47], (11) —NHC(O)—C1-4 alkylene-COOH, (12) —NH—S(O)$_2$—C1-4 alkyl, (13) —COOR[48], (14) —NHC(O)—R[49], (15) —NHC(O)—C1-4 alkylene-OR[50], (16) —NHC(O)O—R[51], (17) —NHC(O)O—C1-4 alkylene —OR[52], (18) —C(O)NH—R[53], (19) —OC(O)—R[55], (20) —C(O)—R[56], (21) —CH(OH)—R[57], (22) —C1-4 alkylene —NH$_2$, (23) —C1-4 alkylene-OH, (24) —C1-4 alkylene-OC(O)—C1-4 alkyl, (25) —C1-4 alkylene-NHC(O)—C1-4 alkyl, (26) —C1-4 alkylene-NHC(O)O—C1-4 alkyl, (27) —C1-4 alkylene-NHC(O)—CF$_3$, (28) —C1-4 alkylene-NHC(O)NH—C1-4 alkyl, (29) —CH=N—OR[58] or (30) -T-COOR[66].

(13) The compound according to (1) or (2), wherein is selected from the group consisting of
(1) methyl[4-(2-{(3S)-7-[5-chloro-2-(1H-tetrazol-1-yl)phenyl]-5-oxo-1,2,3,5-tetrahydro-3-indolizinyl}-1H-imidazol-4-yl)phenyl]carbamate,
(2) methyl[4-(2-{7-[5-chloro-2-(1H-tetrazol-1-yl)phenyl]-5-oxo-1,2,3,5-tetrahydro-3-indolizinyl}-1H-imidazol-4-yl)phenyl]carbamate,
(3) 4-(2-{7-[5-chloro-2-(1H-tetrazol-1-yl)phenyl]-5-oxo-1,2,3,5-tetrahydro-3-indolizinyl}-1H-imidazol-4-yl)benzamide,
(4) 6-(2-{7-[5-chloro-2-(1H-tetrazol-1-yl)phenyl]-5-oxo-1,2,3,5-tetrahydro-3-indolizinyl}-1H-imidazol-4-yl)-3,4-dihydro-2(1H)-quinolinone,
(5) methyl[4-(2-{(3S)-7-[5-chloro-2-(1H-tetrazol-1-yl)phenyl]-5-oxo-1,2,3,5-tetrahydro-3-indolizinyl}-5-methyl-1H-imidazol-4-yl)phenyl]carbamate,
(6) 6-(2-{(3S)-7-[5-chloro-2-(1H-tetrazol-1-yl)phenyl]-5-oxo-1,2,3,5-tetrahydro-3-indolizinyl}-1H-imidazol-5-yl)-3,4-dihydro-2(1H)-quinolinone,
(7) 4-(2-{(3S)-7-[5-chloro-2-(1H-tetrazol-1-yl)phenyl]-5-oxo-1,2,3,5-tetrahydro-3-indolizinyl}-1H-imidazol-5-yl)benzamide, (8) 3-[5-(3-amino-1H-indazol-6-yl)-1H-imidazol-2-yl]-7-[5-chloro-2-(1H-tetrazol-1-yl)phenyl]-2,3-dihydro-5(1H)-indolizinone, (9) (3S)-3-[5-(6-amino-3-pyridinyl)-4-chloro-1H-imidazol-2-yl]-7-[5-chloro-2-(1H-tetrazol-1-yl)phenyl]-2,3-dihydro-5(1H)-indolizinone,

(10) (3S)-3-[5-(6-amino-2-chloro-3-pyridinyl)-1H-imidazol-2-yl]-7-[5-chloro-2-(1H-tetrazol-1-yl)phenyl]-2,3-dihydro-5(1H)-indolizinone,

(11) (3S)-3 [5-(1-amino-6-iso quinolinyl)-1H-imidazol-2-yl]-7-[5-chloro-2-(1H-tetrazol-1-yl)phenyl]-2,3-dihydro-5(1H)-indolizinone,

(12) 4-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)benzamide,

(13) ethyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate,

(14) methyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)-3-methylphenyl]carbamate,

(15) methyl[4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)phenyl]carbamate,

(16) 2-methoxyethyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate,

(17) 2-methoxyethyl[4-(2-{7-[5-chloro-2-(1H-tetrazol-1-yl)phenyl]-5-oxo-1,2,3,5-tetrahydro-3-indolizinyl}-1H-imidazol-5-yl)phenyl]carbamate,

(18) methyl[6-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-3-pyridinyl]carbamate,

(19) (3S)-3-[5-(6-amino-2-fluoro-3-pyridinyl)-1H-imidazol-2-yl]-7-[5-chloro-2-(1H-tetrazol-1-yl)phenyl]-2,3-dihydro-5(1H)-indolizinone,

(20) (6S)-6-[5-(6-amino-2-chloro-3-pyridinyl)-1H-imidazol-2-yl]-2-[5-chloro-2-(1H-tetrazol-1-yl)phenyl]-7,8-dihydropyrrolo[1,2-a]pyrimidin-4(6H)-one,

(21) 2-methoxyethyl[4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)phenyl]carbamate,

(22) (3S)-3-[5-(6-amino-3-pyridinyl)-4-chloro-1H-imidazol-2-yl]-7-[5-methyl-2-(1H-tetrazol-1-yl)phenyl]-2,3-dihydro-5(1H)-indolizinone,

(23) 2-methoxyethyl[5-(2-{(3S)-7-[5-chloro-2-(1H-tetrazol-1-yl)phenyl]-5-oxo-1,2,3,5-tetrahydro-3-indolizinyl}-1H-imidazol-5-yl)-2-pyridinyl]carbamate,

(24) 2-methoxyethyl[4-(2-{(3S)-7-[5-methyl-2-(1H-tetrazol-1-yl)phenyl]-5-oxo-1,2,3,5-tetrahydro-3-indolizinyl}-1H-imidazol-5-yl)phenyl]carbamate,

(25) 2-methoxyethyl[5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-pyridinyl]carbamate,

(26) 2-methoxyethyl[6-(2-{(3S)-7-[5-chloro-2-(1H-tetrazol-1-yl)phenyl]-5-oxo-1,2,3,5-tetrahydro-3-indolizinyl}-1H-imidazol-5-yl)-3-pyridinyl]carbamate,

(27) 2-methoxyethyl[4-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate,

(28) 2-methoxyethyl[4-(4-methyl-2-{(3S)-7-[5-methyl-2-(1H-tetrazol-1-yl)phenyl]-5-oxo-1,2,3,5-tetrahydro-3-indolizinyl}-1H-imidazol-5-yl)phenyl]carbamate,

(29) 2-methoxyethyl[6-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-3-pyridinyl]carbamate,

(30) 2-ethoxyethyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate,

(31) 2-methoxyethyl[4-(2-{(6S)-2-[5-methyl-2-(1H-tetrazol-1-yl)phenyl]-4-oxo-4,6,7,8-tetrahydropyrrolo[1,2-a]pyrimidin-6-yl}-1H-imidazol-5-yl)phenyl]carbamate,

(32) 3-methoxypropyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate,

(33) methyl[4-(2-{(6S)-2-[5-methyl-2-(1H-tetrazol-1-yl)phenyl]-4-oxo-4,6,7,8-tetrahydropyrrolo[1,2-a]pyrimidin-6-yl}-1H-imidazol-5-yl)phenyl]carbamate,

(34) 3-oxetanyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate,

(35) 2-methoxyethyl[4-(2-{(3S)-7-[5-chloro-2-(1H-tetrazol-1-yl)phenyl]-5-oxo-1,2,3,5-tetrahydro-3-indolizinyl}-4-methyl-1H-imidazol-5-yl)phenyl]carbamate,

(36) methyl[4-(4-chloro-2-{(6S)-2-[5-methyl-2-(1H-tetrazol-1-yl)phenyl]-4-oxo-4,6,7,8-tetrahydropyrrolo[1,2-a]pyrimidin-6-yl}-1H-imidazol-5-yl)phenyl]carbamate,

(37) 2-methoxyethyl[4-(4-chloro-2-{(6S)-2-[5-methyl-2-(1H-tetrazol-1-yl)phenyl]-4-oxo-4,6,7,8-tetrahydropyrrolo[1,2-a]pyrimidin-6-yl}-1H-imidazol-5-yl)phenyl]carbamate,

(38) (2S)-2-methoxypropyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate,

(39) (6S)-6-[5-(6-amino-2-fluoro-3-pyridinyl)-1H-imidazol-2-yl]-2-[5-chloro-2-(1H-tetrazol-1-yl)phenyl]-7,8-dihydropyrrolo[1,2-a]pyrimidin-4(6H)-one,

(40) 2-methoxyethyl[4-(2-{(6S)-2-[5-chloro-2-(1H-tetrazol-1-yl)phenyl]-4-oxo-4,6,7,8-tetrahydropyrrolo[1,2-a]pyrimidin-6-yl}-4-methyl-1H-imidazol-5-yl)phenyl]carbamate,

(41) 2-(2-methoxyethoxyl)ethyl[5-(2-{(3S)-7-[5-chloro-2-(1H-tetrazol-1-yl)phenyl]-5-oxo-1,2,3,5-tetrahydro-3-indolizinyl}-1H-imidazol-5-yl)-2-pyridinyl]carbamate,

(42) 2-(2-methoxyethoxyl)ethyl[5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-pyridinyl]carbamate,

(43) 2-(2-methoxyethoxyl)ethyl[5-(2-{(3S)-7-[5-chloro-2-(1H-tetrazol-1-yl)phenyl]-5-oxo-1,2,3,5-tetrahydro-3-indolizinyl}-4-fluoro-1H-imidazol-5-yl)-2-pyridinyl]carbamate,

(44) 2-(2-ethoxyethoxyl)ethyl[5-(2-{(3S)-7-[5-chloro-2-(1H-tetrazol-1-yl)phenyl]-5-oxo-1,2,3,5-tetrahydro-3-indolizinyl}-1H-imidazol-5-yl)-2-pyridinyl]carbamate,

(45) 2-(2-ethoxyethoxyl)ethyl[5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-pyridinyl]carbamate,

(46) 2-(2-ethoxyethoxyl)ethyl[5-(2-{(3S)-7-[5-chloro-2-(1H-tetrazol-1-yl)phenyl]-5-oxo-1,2,3,5-tetrahydro-3-indolizinyl}-4-fluoro-1H-imidazol-5-yl)-2-pyridinyl]carbamate,

(47) 2-methoxyethyl[4-(4-chloro-2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)phenyl]carbamate,

(48) 2-methoxyethyl[6-(4-chloro-2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-3-pyridinyl]carbamate,

(49) 2-ethoxyethyl[4-(2-{(3S)-7-[5-methyl-2-(1H-tetrazol-1-yl)phenyl]-5-oxo-1,2,3,5-tetrahydro-3-indolizinyl}-1H-imidazol-5-yl)phenyl]carbamate,

(50) 2-ethoxyethyl[4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)phenyl]carbamate,

(51) 2-ethoxyethyl[4-(2-{(6S)-2-[5-methyl-2-(1H-tetrazol-1-yl)phenyl]-4-oxo-4,6,7,8-tetrahydropyrrolo[1,2-a]pyrimidin-6-yl}-1H-imidazol-5-yl)phenyl]carbamate,

(52) tetrahydro-2-furanylmethyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate,

(53) methyl[4-(5-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-2-yl)phenyl]carbamate,

(54) 3-hydroxy-3-methylbutyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate,

(55) 2-(2-ethoxyethoxyl)ethyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate,

(56) 2-(2-methoxyethoxyl)ethyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate,

(57) 2-fluoroethyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate,

(58) 2-hydroxyethyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate,

(59) 2-hydroxy-2-methylpropyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate,

(60) (3S)-3-(4-chloro-5-{6-[(1,3-oxazol-2-ylmethyl)amino]-3-pyridinyl}-1H-imidazol-2-yl)-7-[5-chloro-2-(1H-tetrazol-1-yl)phenyl]-2,3-dihydro-5 (1H)-indolizinone,

(61) 2-methoxyethyl[4-(5-{(3S)-7-[5-chloro-2-(1H-tetrazol-1-yl)phenyl]-5-oxo-1,2,3,5-tetrahydro-3-indolizinyl}-4H-1,2,4-triazol-3-yl)phenyl]carbamate,

(62) (3S)-3-[5-(6-amino-3-pyridinyl)-4-fluoro-1H-imidazol-2-yl]-7-[5-chloro-2-(1H-tetrazol-1-yl)phenyl]-2,3-dihydro-5 (1H)-indolizinone,

(63) N-[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]acetamide,

(64) methyl[4-(5-{(3S)-7-[5-chloro-2-(1H-tetrazol-1-yl)phenyl]-5-oxo-1,2,3,5-tetrahydro-3-indolizinyl}-4-fluoro-1H-imidazol-2-yl)phenyl]carbamate,

(65) 4-(2-{(3S)-7-[5-chloro-2-(1H-tetrazol-1-yl)phenyl]-5-oxo-1,2,3,5-tetrahydro-3-indolizinyl}-1H-imidazol-5-yl)-N-(2-methoxyethoxyl)benzamide,

(66) N-[4-(2-{(3S)-7-[5-chloro-2-(1H-tetrazol-1-yl)phenyl]-5-oxo-1,2,3,5-tetrahydro-3-indolizinyl}-4-fluoro-1H-imidazol-5-yl)phenyl]acetamide,

(67) 2-methoxyethyl[6-(2-{(3S)-7-[5-chloro-2-(1H-tetrazol-1-yl)phenyl]-5-oxo-1,2,3,5-tetrahydro-3-indolizinyl}-4-fluoro-1H-imidazol-5-yl)-3-pyridinyl]carbamate,

(68) N-[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]formamide,

(69) 2-methoxyethyl[6-(2-{(6S)-2-[5-chloro-2-(1H-tetrazol-1-yl)phenyl]-4-oxo-4,6,7,8-tetrahydropyrrolo[1,2-a]pyrimidin-6-yl}-4-fluoro-1H-imidazol-5-yl)-3-pyridinyl]carbamate,

(70) (1E)-N-[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]-N'-hydroxyethanimidamide,

(71) (6S)-6-[5-(6-amino-3-pyridinyl)-4-fluoro-1H-imidazol-2-yl]-2-[5-chloro-2-(1H-tetrazol-1-yl)phenyl]-7,8-dihydropyrrolo[1,2-a]pyrimidin-4(6H)-one,

(72) N-[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]-2-fluoroacetamide,

(73) (3S)-7-[5-chloro-2-(1H-tetrazol-1-yl)phenyl]-3-[5-(4-hydroxyphenyl)-1H-imidazol-2-yl]-2,3-dihydro-5(1H)-indolizinone,

(74) ethyl 5-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylate,

(75) 5-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylic acid,

(76) ethyl 5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylate,

(77) 5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylic acid,

(78) 5-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxamide,

(79) 5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxamide,

(80) 2-methoxyethyl[4-(5-{(3S)-7-[5-chloro-2-(1H-tetrazol-1-yl)phenyl]-5-oxo-1,2,3,5-tetrahydro-3-indolizinyl}-1H-imidazol-2-yl)phenyl]carbamate,

(81) 2-(2-methoxyethoxyl)ethyl[4-(5-{(3S)-7-[5-chloro-2-(1H-tetrazol-1-yl)phenyl]-5-oxo-1,2,3,5-tetrahydro-3-indolizinyl}-1H-imidazol-2-yl)phenyl]carbamate,

(82) 2-(2-methoxyethoxyl)ethyl[4-(5-{(3S)-7-[5-chloro-2-(1H-tetrazol-1-yl)phenyl]-5-oxo-1,2,3,5-tetrahydro-3-indolizinyl}-4-fluoro-1H-imidazol-2-yl)phenyl]carbamate,

(83) 2-methoxyethyl[4-(5-{(3S)-7-[5-chloro-2-(1H-tetrazol-1-yl)phenyl]-5-oxo-1,2,3,5-tetrahydro-3-indolizinyl}-4-fluoro-1H-imidazol-2-yl)phenyl]carbamate,

(84) 4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylic acid,

(85) 4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-pyridinecarboxylic acid,

(86) 5-(2-{(3S)-7-[5-chloro-2-(1H-tetrazol-1-yl)phenyl]-5-oxo-1,2,3,5-tetrahydro-3-indolizinyl}-4-fluoro-1H-imidazol-5-yl)-2-thiophenecarboxylic acid,

(87) 5-(2-{(3S)-8-chloro-7-[5-chloro-2-(1H-tetrazol-1-yl)phenyl]-5-oxo-1,2,3,5-tetrahydro-3-indolizinyl}-1H-imidazol-5-yl)-2-thiophenecarboxylic acid,

(88) 4-(2-{(3S)-8-chloro-7-[5-chloro-2-(1H-tetrazol-1-yl)phenyl]-5-oxo-1,2,3,5-tetrahydro-3-indolizinyl}-1H-imidazol-5-yl)-2-thiophenecarboxylic acid,

(89) 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-thiophenecarboxylic acid,

(90) 4-(2-{(3S)-8-chloro-7-[5-chloro-2-(1H-tetrazol-1-yl)phenyl]-5-oxo-1,2,3,5-tetrahydro-3-indolizinyl}-1H-imidazol-5-yl)-2-pyridinecarboxylic acid,

(91) 2-(2-methoxyethoxyl)ethyl[5-(5-{(3S)-7-[5-chloro-2-(1H-tetrazol-1-yl)phenyl]-5-oxo-1,2,3,5-tetrahydro-3-indolizinyl}-4-fluoro-1H-imidazol-2-yl)-2-pyridinyl]carbamate,

(92) 2-(4-morpholinyl)ethyl 5-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylate,

(93) 2-(4-morpholinyl)ethyl 5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylate,

(94) 2-methoxyethyl[5-(5-{(3S)-7-[5-chloro-2-(1H-tetrazol-1-yl)phenyl]-5-oxo-1,2,3,5-tetrahydro-3-indolizinyl}-4-fluoro-1H-imidazol-2-yl)-2-pyridinyl]carbamate,

(95) (3S)-3-[2-(6-amino-3-pyridinyl)-4-fluoro-1H-imidazol-5-yl]-7-[5-chloro-2-(1H-tetrazol-1-yl)phenyl]-2,3-dihydro-5(1H)-indolizinone,

(96) 4-(2-{(3S)-8-bromo-7-[5-chloro-2-(1H-tetrazol-1-yl)phenyl]-5-oxo-1,2,3,5-tetrahydro-3-indolizinyl}-1H-imidazol-5-yl)-2-thiophenecarboxylic acid,

(97) ethyl 4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylate,

(98) 2-(4-morpholinyl)ethyl 4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylate,

(99) 4-(2-{(3S)-7-[5-chloro-2-(1H-tetrazol-1-yl)phenyl]-5-oxo-1,2,3,5-tetrahydro-3-indolizinyl}-4-fluoro-1H-imidazol-5-yl)-2-thiophenecarboxylic acid, (100) isobutyl 4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylate, (101) 2-(dimethylamino)-2-oxoethyl 4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylate, (102) (5-methyl-2-oxo-1,3-dioxol-4-yl)methyl 4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylate, (103) [(2,2-dimethylpropanoyl)oxy]methyl 4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylate, (104) methyl 4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylate, (105) 3-methylbutyl 4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylate, (106) isopropyl 4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylate, (107) 2,3-dihydro-1H-inden-5-yl 4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylate, (108) phenyl 4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylate, (109) 2-(dimethylamino)-2-oxoethyl 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-thiophenecarboxylate, (110) methyl 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-thiophenecarboxylate, (111) 2-(diethylamino)-2-oxoethyl 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-thiophenecarboxylate, (112) 1-{[(cyclohexyloxy)carbonyl]oxy}ethyl 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-thiophenecarboxylate, (113) cyclohexyl 2-{(6S)-2-[5-chloro-2-(1H-tetrazol-1-yl)phenyl]-4-oxo-4,6,7,8-tetrahydropyrrolo[1,2-a]pyrimidin-6-yl}-5-{5-[(1-{[(cyclohexyloxy)carbonyl]oxy}ethoxy)carbonyl]-3-thienyl}-1H-imidazole-1-carboxylate, (114) 4-(2-{(3S)-7-[5-chloro-2-(1H-tetrazol-1-yl)phenyl]-5-oxo-1,2,3,5-tetrahydro-3-indolizinyl}-1H-imidazol-5-yl)-3-fluoro-2-thiophenecarboxylic acid, (115) 4-(5-{7-[5-chloro-2-(1H-tetrazol-1-yl)phenyl]-5-oxo-1,2,3,5-tetrahydro-3-indolizinyl}-4-fluoro-1H-imidazol-2-yl)-2-thiophenecarboxylic acid, (116) 4-(2-{(3S)-7-[5-chloro-2-(1H-tetrazol-1-yl)phenyl]-5-oxo-1,2,3,5-tetrahydro-3-indolizinyl}-1H-imidazol-5-yl)-3-fluoro-2-pyridinecarboxylic acid, (117) [(2,2-dimethylpropanoyl)oxy]methyl 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-thiophenecarboxylate, (118) [(2,2-dimethylpropanoyl)oxy]methyl 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1-{[(2,2-dimethylpropanoyl)oxy]methyl}-1H-imidazol-5-yl)-2-thiophenecarboxylate, (119) 2,3-dihydro-1H-inden-5-yl 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-thiophenecarboxylate, (120) ethyl 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-thiophenecarboxylate, (121) 2-oxo-2-(1-pyrrolidinyl)ethyl 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-thiophenecarboxylate, (122) 2-oxo-2-(1-piperidinyl)ethyl 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-thiophenecarboxylate, (123) 2-(4-morpholinyl)-2-oxoethyl 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-thiophenecarboxylate, (124) isobutyl 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-thiophenecarboxylate, (125) isopropyl 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-thiophenecarboxylate, (126) (5-methyl-2-oxo-1,3-dioxol-4-yl)methyl 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-thiophenecarboxylate, and (127) 2-(4-morpholinyl)ethyl 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-thiophenecarboxylate.

(14) A pharmaceutical composition which comprises the compound according to any one of (1) to (13), a salt thereof, an N-oxide thereof, a solvate thereof, or a prodrug thereof.

(15) The pharmaceutical composition according to (14), which is a factor XIa inhibitor or a factor XIa and plasma kallikrein dual inhibitor.

(16) The pharmaceutical composition according to (15), which is an agent for the treatment or prevention of a thromboembolic disease.
(17) The compound according to any one of (1) to (13), a salt thereof, an N-oxide thereof, a solvate thereof, or a prodrug thereof, for use in the treatment of the human or animal body by therapy.
(18) The compound according to any one of (1) to (13), a salt thereof, an N-oxide thereof, a solvate thereof, or a prodrug thereof, for use in treating or preventing a thromboembolic disease.
(19) The compound for use according to (18), wherein the thromboembolic disease is selected from the group consisting of arterial cardiovascular thromboembolic disorders, venous cardiovascular thromboembolic disorders, arterial cerebrovascular thromboembolic disorders, venous cerebrovascular thromboembolic disorders and thromboembolic disorders in the chambers of the heart or in the peripheral circulation.
(20) The compound for use according to (19), wherein the thromboembolic disease is selected from unstable angina, an acute coronary syndrome, atrial fibrillation, myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.
(21) A method for treating a patient suffering from or susceptible to a thromboembolic disease, which comprises administering to said patient a therapeutically effective amount of a compound according to any one of (1) to (13), a salt thereof, an N-oxide thereof, a solvate thereof, or a prodrug thereof.
(22) Use of a compound according to any one of (1) to (13), a salt thereof, an N-oxide thereof, a solvate thereof, or a prodrug thereof, in the manufacture of a medicament for use in treating or preventing a thromboembolic disease.
(23) A method for treating a patient suffering from or susceptible to a thromboembolic disease, which comprises administering to said patient a therapeutically effective amount of a compound according to (1), a salt thereof, an N-oxide thereof, a solvate thereof, or a prodrug thereof.
(24) The method according to (23), wherein the thromboembolic disease is selected from the group consisting of arterial cardiovascular thromboembolic disorders, venous cardiovascular thromboembolic disorders, arterial cerebrovascular thromboembolic disorders, venous cerebrovascular thromboembolic disorders and thromboembolic disorders in the chambers of the heart or in the peripheral circulation.
(25) The method according to (24), wherein the thromboembolic disease is selected from unstable angina, an acute coronary syndrome, atrial fibrillation, myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

Definitions:

As used herein, a C1-8 alkyl group or moiety is a linear or branched alkyl group or moiety containing from 1 to 8 carbon atoms. Typically a C1-8 alkyl group or moiety is a C1-4 alkyl group or moiety. A C1-4 alkyl group or moiety is a linear or branched alkyl group or moiety containing from 1 to 4 carbon atoms. Examples of C1-8 alkyl groups and moieties include methyl, ethyl, n-propyl, i-propyl, n-butyl, i-butyl, t-butyl, 3-methyl-butyl, pentyl, hexyl, heptyl, octyl, and isomers thereof. Examples of C1-4 alkyl groups and moieties include methyl, ethyl, n-propyl, i-propyl, n-butyl, i-butyl and t-butyl. For the avoidance of doubt, where two alkyl moieties are present in a group, the alkyl moieties may be the same or different.

In the present specification, the C2-8 alkenyl includes, for example, ethenyl, propenyl, butenyl, pentenyl, hexenyl, heptenyl, octenyl and isomers thereof.

In the present specification, the C2-8 alkynyl includes, for example, ethynyl, propynyl, butynyl, pentynyl, hexynyl, heptynyl, octynyl and iomers thereof.

In the present specification, the C1-4 alkylene includes, for example, methylene, ethylene, propylene, butylene, and the like.

In the present specification, the C1-8 alkylene includes, for example, methylene, ethylene, propylene, isopropylene, butylene, isobutylene, pentamethylene, hexamethylene, heptamethylene and octamethylene and iomers thereof.

In the present specification, the C2-4 alkenylene includes, for example, vinylene, propenylene, butenylene and isomers thereof.

In the present specification, the halogen atom includes, for example, fluorine, chlorine, bromine and iodine, and is preferably fluorine, chlorine or bromine.

In the present specification, the C3-C10 cycloalkyl includes, for example, cyclopropane, cyclobutane, cyclopentane, cyclohexane, cycloheptane, cyclooctane, cyclononane, cyclodecane, cyclobutene, cyclopentene, cyclohexene, cycloheptene, cyclooctene, cyclobutadiene, cyclopentadiene, cyclohexadiene, cycloheptadiene, cyclooctadiene, pentalene, perhydropentalene, perhydroazulene, indene, perhydroindene, indan, dihydronaphthalene, teterahydronaphthalene, perhydronaphthalene rings and the like.

$Cyc^1$ represents C3-C8 cycloalkyl, 5- to 10-membered heterocycloalkyl, C5-C10 aryl or 5- to 10-membered heteroaryl.

"C3-C8 cycloalkyl" refers to a C3-C8 cyclic hydrocarbon. Examples of C3-C8 cycloalkyl include cyclopropane, cyclobutane, cyclopentane, cyclohexane, cycloheptane, cyclooctane, cyclobutene, cyclopentene, cyclohexene, cycloheptene, cyclooctene, cyclobutadiene, cyclopentadiene, cyclohexadiene, cycloheptadiene, cyclooctadiene rings and the like.

"5- to 10-membered heterocycloalkyl" refers to a "5- to 10-membered mono- or bi-non-aromatic heterocyclic ring having 1 to 4 nitrogen atom(s), 1 or 2 oxygen atom(s) and/or 1 or 2 sulfur atom(s) as a hetero atom(s)". Examples of 5- to 10-membered heterocycloalkyl include pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrofuran, tetrahydrofuran, dihydropyran, tetrahydropyran, dihydroxepine, tetrahydroxepine, perhydroxepine, dihydrothiophene, tetrahydrothiophene, dihydrothiopyran, tetrahydrothiopyran, dihydrothiepin, tetrahydrothiepin, perhydrothiepin, dihydroxazole, tetrahydroxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydroxadiazole, tetrahydroxadiazole (oxadiazolidine), dihydroxazine, tetrahydroxazine, dihydroxadiazine, tetrahydroxadiazine, dihydroxazepine, tetrahydroxazepine, perhydroxazepine, dihydroxadiazepine, tetrahydroxadiazepine, perhydroxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dioxolane, 1,3-dioxole, dioxane, dithiolane, dithiane, dioxaindane, benzodioxane, chroman, benzodithiolane, benzodithiane, 6,7-dihydro-5H-cyclopenta[b]pyrazine, 5H-cyclopenta[b]pyrazine, 2,4-dihydro-1H-benzo[d][1,3]oxazine rings and the like.

"C5-C10 aryl" refers to a "C5-10 mono- or bi-aromatic carbocyclic ring". Examples of C5-C10 aryl include benzene, azulene, naphthalene rings and the like. Thus the C5-C10 aryl may be, for example, a phenyl ring and the like.

"5- to 10-membered heteroaryl" refers to a "5- to 10-membered mono- or bi-aromatic heterocyclic ring having 1 to 4 nitrogen atom(s), 1 or 2 oxygen atom(s) and/or 1 or 2 sulfur atom(s) as a hetero atom(s)". Examples of 5- to 10-membered heteroaryl include pyrrole, imidazole, triazole, tetrazole, pyrazole, pyridine, pyrazine, pyrimidine, pyridazine, furan, thiophene, oxazole, isoxazole, thiazole, isothiazole, furazan, oxadiazole, thiadiazole, indole, isoindole, benzofuran, isobenzofuran, benzothiophene, isobenzothiophene, indazole, quinoline, isoquinoline, purine, phthalazine, pteridine, naphthyridine, quinoxaline, quinazoline, cinnoline, benzoxazole, benzothiazole, benzimidazole, benzofurazan, benzothiadiazole, benzotriazole, isoxazolo[4,5-d]pyridazine rings and the like.

In some embodiments, $Cyc^1$ also represents $Cyc^{1-B}$ or $Cyc^{1-C}$. $Cyc^{1-B}$ and $Cyc^{1-C}$ independently represent 5- to 10-membered heteroaryl. The "5- to 10-membered heteroaryl" represented by $Cyc^{1-B}$ or $Cyc^{1-C}$ may be selected from any of the examples provided above for "5- to 10-membered heteroaryl".

$Cyc^2$ represents C3-C8 cycloalkyl, 5- to 10-membered heterocycloalkyl, C5-C10 aryl or 5- or 6-membered heteroaryl.

The "C3-C8 cycloalkyl" represented by $Cyc^2$ may be selected from any of the examples provided above for "C3-C8 cycloalkyl".

The "5- to 10-membered heterocycloalkyl" represented by $Cyc^2$ may be selected from any of the examples provided above for "5- to 10-membered heterocycloalkyl".

The "C5-C10 aryl" represented by $Cyc^2$ may be selected from any of the examples provided above for "C5-C10 aryl".

"5- to 6-membered heteroaryl" refers to a "5- to 6-membered mono-aromatic heterocyclic ring having 1 to 4 nitrogen atom(s), 1 or 2 oxygen atom(s) and/or 1 or 2 sulfur atom(s) as a hetero atom(s)". Examples of 5- to 6-membered heteroaryl include pyrrole, imidazole, triazole, tetrazole, pyrazole, pyridine, pyrazine, pyrimidine, pyridazine, furan, thiophene, oxazole, isoxazole, thiazole, isothiazole, furazan, oxadiazole, thiadiazole, rings and the like.

$Cyc^3$ represents C3-C8 cycloalkyl, 5- to 10-membered heterocycloalkyl, C5-C10 aryl or 5- to 10-membered heteroaryl.

The "C3-C8 cycloalkyl" represented by $Cyc^3$ may be selected from any of the examples provided above for "C3-C8 cycloalkyl".

The "5- to 10-membered heterocycloalkyl" represented by $Cyc^3$ may be selected from any of the examples provided above for "5- to 10-membered heterocycloalkyl".

The "C5-C10 aryl" represented by $Cyc^3$ may be selected from any of the examples provided above for "C5-C10 aryl".

The "5- to 10-membered heteroaryl" represented by $Cyc^3$ may be selected from any of the examples provided above for "5- to 10-membered heteroaryl".

In some embodiments, $Cyc^3$ also represents $Cyc^{3-B}$ or $Cyc^{3-C}$. $Cyc^{3-B}$ represents C5-C10 aryl or 5- to 10-membered heteroaryl. The "C5-C10 aryl" represented by $Cyc^{3-B}$ may be selected from any of the examples provided above for "C5-C10 aryl". The "5- to 10-membered heteroaryl" represented by $Cyc^{3-B}$ may be selected from any of the examples provided above for "5- to 10-membered heteroaryl".

$Cyc^{3-C}$ represents C5-C10 aryl or 5- to 10-membered heteroaryl. The "C5-C10 aryl" represented by $Cyc^{3-C}$ may be selected from any of the examples provided above for "C5-C10 aryl". The "5- to 10-membered heteroaryl" represented by $Cyc^{3-C}$ may be selected from any of the examples provided above for "5- to 10-membered heteroaryl".

$Cyc^4$, $Cyc^6$, $Cyc^7$ and $Cyc^9$ each independently represent C3-C8 cycloalkyl, 5- to 10-membered heterocycloalkyl, C5-C10 aryl or 5- to 10-membered heteroaryl.

The "C3-C8 cycloalkyl" represented by $Cyc^4$, $Cyc^6$, $Cyc^7$ or $Cyc^9$ may be selected from any of the examples provided above for "C3-C8 cycloalkyl".

The "5- to 10-membered heterocycloalkyl" represented by $Cyc^4$, $Cyc^6$, $Cyc^7$ or $Cyc^9$ may be selected from any of the examples provided above for "5- to 10-membered heterocycloalkyl".

The "C5-C10 aryl" represented by $Cyc^4$, $Cyc^6$, $Cyc^7$ or $Cyc^9$ may be selected from any of the examples provided above for "C5-C10 aryl".

The "5- to 10-membered heteroaryl" represented by $Cyc^4$, $Cyc^6$, $Cyc^7$ or $Cyc^9$ may be selected from any of the examples provided above for "5- to 10-membered heteroaryl".

$Cyc^5$ represents C3-C8 cycloalkyl, 5- to 10-membered heterocycloalkyl, C5-C10 aryl or 5- to 10-membered heteroaryl, any of which may be optionally substituted with 1 to 3 groups selected from C1-8 alkyl, C2-8 alkenyl, C2-8 alkynyl, halogen, nitro, trifluoromethyl, cyano, oxo, amidino and —$OR^{18}$.

$Cyc^8$ represents C3-C8 cycloalkyl, 5- to 10-membered heterocycloalkyl, C5-C10 aryl or 5- to 10-membered heteroaryl, any of which may be optionally substituted with 1 to 3 groups selected from C1-8 alkyl, C2-8 alkenyl, C2-8 alkynyl, halogen, nitro, trifluoromethyl, cyano, oxo, amidino and —$OR^{24}$.

The optionally substituted "C3-C8 cycloalkyl" represented by $Cyc^5$ or $Cyc^8$ may be selected from any of the examples provided above for "C3-C8 cycloalkyl".

The optionally substituted "5- to 10-membered heterocycloalkyl" represented by $Cyc^5$ or $Cyc^8$ may be selected from any of the examples provided above for "5- to 10-membered heterocycloalkyl".

The optionally substituted "C5-C10 aryl" represented by $Cyc^5$ or $Cyc^8$ may be selected from any of the examples provided above for "C5-C10 aryl".

The optionally substituted "5- to 10-membered heteroaryl" represented by $Cyc^5$ or $Cyc^8$ may be selected from any of the examples provided above for "5- to 10-membered heteroaryl".

$Cyc^{10}$ represents C3-C8 cycloalkyl, 5- to 10-membered heterocycloalkyl, C5-C10 aryl or 5- to 10-membered heteroaryl, any of which may be optionally substituted with 1 to 5 groups selected from C1-8 alkyl, C2-8 alkenyl, C2-8 alkynyl, halogen, nitro, trifluoromethyl, cyano, oxo, amidino, —$OR^{29}$, —$SR^{30}$, —$NR^{31}R^{32}$, —$NHC(O)NR^{33}R^{34}$, —NHC(O)—C1-4 alkylene —COOH, —NH—S(O)—C1-4 alkyl, —NH—S(O)$_2$—C1-4 alkyl, —$COOR^{35}$, —NHC(O)—$R^{36}$, —NHC(O)O—$R^{37}$, —C(O)NH—$R^{38}$ and —OC(O)NH—$R^{39}$.

The optionally substituted "C3-C8 cycloalkyl" represented by $Cyc^{10}$ may be selected from any of the examples provided above for "C3-C8 cycloalkyl".

The optionally substituted "5- to 10-membered heterocycloalkyl" represented by $Cyc^{10}$ may be selected from any of the examples provided above for "5- to 10-membered heterocycloalkyl".

The optionally substituted "C5-C10 aryl" represented by $Cyc^{10}$ may be selected from any of the examples provided above for "C5-C10 aryl".

The optionally substituted "5- to 10-membered heteroaryl" represented by $Cyc^{10}$ may be selected from any of the examples provided above for "5- to 10-membered heteroaryl".

In some embodiments, $Cyc^{10}$ also represents $Cyc^{10-B}$ or $Cyc^{10-C}$. $Cyc^{10-B}$ and $Cyc^{10-C}$ each independently represents (1) 5- to 10-membered heteroaryl or (2) 5- to 10-membered heteroaryl substituted with 1 to 5 groups selected from halogen, cyano, nitro, trifluoromethyl, —COOH, —COO—C1-4 alkyl and —$CONH_2$. The optionally substituted "5- to 10-membered heteroaryl" in options (1) or (2) of $Cyc^{10-B}$ and $Cyc^{10-C}$ may be selected from any of the examples provided above for "5- to 10-membered heteroaryl".

Preferably, $Cyc^1$ represents a C5-C10 aryl or 5- to 10-membered heteroaryl, more preferably phenyl, imidazolyl, triazolyl, tetrazolyl, pyrrolyl, pyrazolyl, furanyl, oxazolyl, thiazolyl, isothiazolyl, furazanyl, oxadiazolyl, thiadiazolyl, thienyl, pyridazinyl, indazolyl or benzimidazolyl, more preferably a 5- to 10-membered heteroaryl such as imidazolyl, triazolyl, oxazolyl, pyridazinyl, indazolyl or benzimidazolyl. In one embodiment, $Cyc^1$ preferably represents imidazolyl or triazolyl.

Preferably, $Cyc^{1-B}$ or $Cyc^{1-C}$ represents imidazolyl, triazolyl, tetrazolyl, oxazolyl, pyridazinyl, indazolyl or benzimidazolyl, more preferably imidazolyl, triazolyl, oxazolyl, pyridazinyl, indazolyl or benzimidazolyl.

Preferably, $Cyc^2$ represents a C5-C10 aryl, preferably a C5-C6 aryl, more preferably phenyl, or a 5- to 6-membered heteroaryl such as pyridyl.

Preferably, $Cyc^3$ represents (i) C5-C6 cycloalkyl, such as cyclohexane, (ii) 5- to 10-membered heterocycloalkyl such as indoline, isoindoline, dihydroquinoline, dihydroquinazoline, dihydrobenzoxazine or dihydrobenzoxazole, (iii) C5-C10 aryl, for example C5-C7 aryl, such as phenyl, or (iv) 5- to 10-membered heteroaryl, such as pyrazole, pyridine, pyrazine, thiophene, oxazole, thiazole, indazole, quinoline, isoquinoline, quinoxaline or benzimidazole. In particular, the 5- to 10-membered heterocycloalkyl such as indoline, isoindoline, dihydroquinoline, dihydroquinazoline, dihydrobenzoxazine or dihydrobenzoxazole, or 5- to 10-membered heteroaryl such as quinoline or quinoxaline may be substituted with an oxo group to form, for example, indolone, isoindolone, dihydroquinolinone, dihydroquinazolinone, benzoxazinone, benzoxazolone, quinolione or quinoxalinone. In one embodiment, $Cyc^3$ preferably represents phenyl or pyridinyl.

Preferably, $Cyc^{3-B}$ or $Cyc^{3-C}$ represents C5-C10 aryl, for example C5-C7 aryl such as phenyl, or 5- to 10-membered heteroaryl, such as pyrazole, pyridine, pyrazine, thiophene, oxazole, thiazole, indazole, quinoline, isoquinoline, quinoxaline or benzimidazole, more preferably pyrazole or pyridine.

Preferably, $Cyc^4$, $Cyc^6$, $Cyc^7$ and $Cyc^9$ each independently represent C5-C10 aryl, for example C5-C7 aryl such as phenyl.

Preferably, $Cyc^5$ and $Cyc^8$ each independently represent C5-C10 aryl, for example C5-C7 aryl such as phenyl, or a 5- to 6-membered heteroaryl such as pyridyl, any of which may be optionally substituted as set out above. Preferably, $Cyc^5$ and $Cyc^8$ are unsubstituted.

Preferably, $Cyc^{10}$ represents a 5 to 10 membered heteroaryl, preferably imidazolyl, pyrazolyl, triazolyl, tetrazolyl, oxazolyl, pyridazinyl, indazolyl, benzimidazolyl, thiazolyl or thiadiazolyl, more preferably thiadiazolyl, triazolyl or tetrazolyl, any of which may be optionally substituted as set out above.

Preferably, $Cyc^{10-B}$ or $Cyc^{10-C}$ each independently represents imidazolyl, triazolyl, tetrazolyl, oxazolyl, pyridazinyl, indazolyl, benzimidazolyl, thiazolyl or thiadiazolyl, more preferably thiadiazolyl, triazolyl or tetrazolyl, any of which may be optionally substituted with 1 to 3 groups selected from halogen, nitro, trifluoromethyl, —COOH, —COO—C1-4 alkyl, cyano and —$CONH_2$.

Preferably, $R^1$ represents C1-8 alkyl or halogen, more preferably C1-4 alkyl or halogen (preferably chlorine); and s represents an integer of 0 to 6, wherein s represents an integer of 2 to 6, each $R^1$ may be same or different.

Preferably, s represents an integer of 0, 1 or 2.

Preferably, $R^8$, $R^9$, $R^{10}$ and $R^{11}$ each independently represents hydrogen or C1-8 alkyl, more preferably C1-4 alkyl.

Preferably, $R^{12}$ represents C1-8 alkyl, more preferably C1-4 alkyl.

Preferably, $R^2$ represents (1) hydrogen, (2) C1-8 alkyl, (3) $Cyc^4$ or (4) C1-8 alkyl substituted with 1 to 3 groups selected from $Cyc^5$ and —$OR^{15}$, wherein $Cyc^4$ and $Cyc^5$ are preferably as set out above. More preferably, $R^2$ represents (1) hydrogen, (2) C1-4 alkyl, (3) $Cyc^4$ or (4) C1-4 alkyl substituted with 1 or 2 groups selected from $Cyc^5$ and —$OR^{15}$, wherein $Cyc^4$ and $Cyc^5$ are preferably as set out above and $R^{15}$ is selected from hydrogen and C1-4 alkyl.

Preferably, $R^{13}$, $R^{14}$, $R^{15}$, $R^{16}$ and $R^{18}$ each independently represents hydrogen or C1-8 alkyl, more preferably C1-4 alkyl.

Preferably, $R^{17}$ represents C1-8 alkyl, more preferably C1-4 alkyl.

When not taken together with $R^4$ to form a C2-8 alkylene, $R^3$ preferably represents (1) hydrogen, (2) C1-8 alkyl, (3) $Cyc^7$ or (4) C1-8 alkyl substituted with 1 to 3 groups selected from $Cyc^8$ and $OR^{21}$, wherein $Cyc^7$ and $Cyc^8$ are preferably as set out above. More preferably, $R^3$ represents (1) hydrogen, (2) C1-4 alkyl, (3) $Cyc^7$ or (4) C1-4 alkyl substituted with 1 or 2 groups selected from $Cyc^8$ and $OR^{21}$, wherein $Cyc^7$ and $Cyc^8$ are preferably as set out above and $R^{21}$ is selected from hydrogen and C1-4 alkyl. Most preferably, $R^3$ is hydrogen.

Preferably, $R^{19}$, $R^{20}$, $R^{21}$, $R^{22}$, and $R^{24}$ each independently represents hydrogen or C1-8 alkyl, more preferably C1-4 alkyl.

Preferably, $R^{23}$ represents C1-8 alkyl, more preferably C1-4 alkyl.

Preferably, $R^4$ and $R^5$ each independently represents hydrogen or C1-4 alkyl, more preferably hydrogen, methyl or ethyl.

In another embodiment, $R^3$ and $R^4$ are preferably taken together to form a C2-8 alkylene, preferably a C2-4 alkylene, more preferably ethylene.

Preferably, $R^6$ represents (1) $Cyc^{10}$, (2) methyl, (3) halogen (preferably chlorine), (4) amidino, or (5) $Cyc^{10}$ substituted with 1 to 3 groups selected from halogen (preferably chlorine), nitro, trifluoromethyl, cyano, —$OR^{29}$, —$COOR^{35}$, —NHC(O)—$R^{36}$ and —C(O)NH—$R^{38}$, wherein $Cyc^{10}$ is preferably as set out above. More preferably, $R^6$ represents (1) $Cyc^{10}$, (2) methyl, (3) halogen (preferably chlorine), or (4) $Cyc^{10}$ substituted with 1 to 3 groups selected from halogen (preferably chlorine), nitro, trifluoromethyl, —COOH, —COO—C1-4 alkyl, cyano or —$CONH_2$, wherein $Cyc^{10}$ is preferably as set out above; and m represents an integer of 0 to 6, wherein m represents an integer of 2 to 6, each $R^6$ may be same or different.

Preferably, $R^{25}$, $R^{26}$, $R^{27}$, $R^{29}$, $R^{30}$, $R^{31}$, $R^{32}$, $R^{33}$, $R^{34}$, $R^{35}$, $R^{36}$, $R^{38}$ and $R^{39}$ each independently represents hydrogen or C1-8 alkyl, more preferably C1-4 alkyl.

Preferably, $R^{28}$ and $R^{37}$ each independently represents C1-8 alkyl, more preferably C1-4 alkyl.

Preferably, m represents an integer of 0, 1 or 2.

Preferably, $R^7$ represents (1) C1-8 alkyl, (2) halogen, (3) nitro, (4) trifluoromethyl, (5) cyano, (6) oxo, (7) —$OR^{40}$, (8) —$NR^{42}R^{43}$, (9) —NHC(O)$NR^{44}R^{45}$, (10) —NHC(O)—C1-4 alkylene-$NR^{46}R^{47}$, (11) —NHC(O)—C1-4 alkylene-COOH, (12) —NH—S(O)$_2$—C1-4 alkyl, (13) —$COOR^{48}$, (14) —NHC(O)—$R^{49}$, (15) —NHC(O)—C1-4 alkylene-$OR^{50}$, (16) —NHC(O)O—$R^{51}$, (17) —NHC(O)O—C1-4 alkylene —$OR^{52}$, (18) —C(O)NH—$R^{53}$, (19) —OC(O)—$R^{55}$, (20) —C(O)—$R^{56}$, (21) —CH(OH)—$R^{57}$, (22) —C1-4 alkylene —$NH_2$, (23) —C1-4 alkylene-OH, (24) —C1-4 alkylene-OC(O)—C1-4 alkyl, (25) —C1-4 alkylene-NHC(O)—C1-4 alkyl, (26) —C1-4 alkylene-NHC(O)O—C1-4 alkyl, (27) —C1-4 alkylene-NHC(O)—$CF_3$, (28) —C1-4 alkylene-NHC(O)NH—C1-4 alkyl, (29) —CH=N—$OR^{58}$ or (30) -T-$COOR^{66}$. More preferably, $R^7$ represents (1) methyl, (2) ethyl, (3) fluorine, (4) chlorine, (5) bromine, (6) nitro, (7) trifluoromethyl, (8) cyano, (9) oxo, (10) —$OR^{40}$, (11) —$NR^{42}R^{43}$, (12) —NHC(O)$NR^{44}R^{45}$, (13) —NHC(O)—C1-4 alkylene —$NR^{46}R^{47}$, (14) —NHC(O)—C1-4 alkylene —COOH, (15) —NH—S(O)$_2$—C1-4 alkyl, (16) —$COOR^{48}$, (17) —NHC(O)—$R^{49}$, (18) —NHC(O)—C1-4 alkylene —$OR^{50}$, (19) —NHC(O)O—$R^{51}$, (20) —NHC(O)O—C1-4 alkylene —$OR^{52}$, (21) —C(O)NH—$R^{53}$, (22) —OC(O)—$R^{55}$, (23) —C(O)—$R^{56}$, (24) —CH(OH)—$R^{57}$, (25) —C1-4 alkylene —$NH_2$, (26) —C1-4 alkylene —OH, (27) —C1-4 alkylene —OC(O)—C1-4 alkyl, (28) —C1-4 alkylene —NHC(O)—C1-4 alkyl, (29) —C1-4 alkylene —NHC(O)O—C1-4 alkyl, (30) —C1-4 alkylene —NHC(O)—$CF_3$, (31) —C1-4 alkylene —NHC(O)NH—C1-4 alkyl, (32) —CH=N—$OR^{58}$ or (33) -T-$COOR^{66}$, wherein $R^{40}$, $R^{41}$, $R^{42}$, $R^{43}$, $R^{44}$, $R^{45}$, $R^{46}$, $R^{47}$, $R^{49}$, $R^{50}$, $R^{52}$, $R^{53}$, $R^{54}$, $R^{55}$, $R^{56}$, $R^{57}$ and $R^{58}$ are independently selected from hydrogen, C1-4 alkyl and trifluoromethyl;

$R^{51}$ represents C1-8 alkyl, more preferably C1-4 alkyl;

$R^{48}$ and $R^{66}$ each independently represents (1) hydrogen, (2) C1-8 alkyl, (3) C1-8 alkyl substituted with 1 to 5 groups selected from —N(C1-4 alkyl)$_2$, oxo, C3-C8 cycloalkyl, 5- to 10-membered heterocycloalkyl, C5-C10 aryl and 5- to 10-membered heteroaryl, (4) C3-C10 cycloalkyl, (5) 5- to 10-membered heterocycloalkyl, (6) C5-C10 aryl, (7) 5- to 10-membered heteroaryl, (8) —C1-4 alkylene-C3-C8 cycloalkyl substituted with 1 to 5 groups selected from C1-4 alkyl, oxo, OH and halogen, (9) —C1-4 alkylene-C5-C10 aryl substituted with 1 to 5 groups selected from C1-4 alkyl, OH and halogen, (10) —C1-4 alkylene-5- to 10-membered heterocycloalkyl substituted with 1 to 5 groups selected from C1-4 alkyl, oxo, OH and halogen, (11) —C1-4 alkylene-5- to 10-membered heteroaryl substituted with 1 to 5 groups selected from C1-4 alkyl, OH and halogen or (12) —C1-4 alkylene-O—C1-8 alkyl substituted with 1 to 3 groups selected from OH, oxo, —O—C1-4 alkyl, halogen, C3-C8 cycloalkyl, 5- to 10-membered heterocycloalkyl, —O—C3-C8 cycloalkyl and —O-5- to 10-membered heterocycloalkyl;

T represents C1-4 alkylene or C2-4 alkenylene; and n represents an integer of 0 to 6, wherein n represents an integer of 2 to 6, each $R^7$ may be same or different.

More preferably, $R^7$ represents (1) —$NH_2$, (2) —NHC(O)O—C1-4 alkyl, (3) —NHC(O)O—C1-4 alkylene-O—C1-4 alkyl, (4) halogen, (5) —COOH, (6) —COO—C1-8 alkyl, (7) —COO—C1-8 alkyl substituted with 1 to 5 groups selected from —N(C1-4 alkyl)$_2$, oxo and 5- to 10-membered heterocycloalkyl, (8) —COO—C5-C10 aryl, (9) —COO—C1-4 alkylene-5- to 10-membered heterocycloalkyl substituted with 1 to 5 groups selected from C1-4 alkyl, oxo, OH and halogen, (10) —COO—C1-4 alkylene-O—C1-8 alkyl substituted with 1 to 3 groups selected from OH, oxo, —O—C1-4 alkyl, halogen, C3-C8 cycloalkyl, 5- to 10-membered heterocycloalkyl, —O—C3-C8 cycloalkyl and —O-5- to 10-membered heterocycloalkyl, (11) —C1-4 alkylene-COOH, (12) —C1-4 alkylene-COO—C1-8 alkyl or (13) —C1-4 alkylene-COO—C1-8 alkyl substituted with 1 to 5 groups selected from —N(C1-4 alkyl)$_2$, oxo and 5- to 10-membered heterocycloalkyl;

n represents an integer of 0 to 3, wherein n represents an integer of 2 to 3, each $R^7$ may be same or different.

Preferably $R^{40}$, $R^{41}$, $R^{42}$, $R^{43}$, $R^{44}$, $R^{45}$, $R^{46}$, $R^{47}$, $R^{49}$, $R^{50}$, $R^{52}$, $R^{53}$, $R^{54}$, $R^{55}$, $R^{56}$, $R^{57}$ and $R^{58}$ each independently represents hydrogen, trifluoromethyl or C1-8 alkyl, more preferably hydrogen or C1-4 alkyl.

Preferably $R^{51}$ represents C1-8 alkyl, more preferably C1-4 alkyl.

Preferably, $R^{48}$ and $R^{66}$ each independently represents (1) hydrogen, (2) C1-8 alkyl, (3) C1-8 alkyl substituted with 1 to 5 groups selected from —N(C1-4 alkyl)$_2$, oxo, C3-C8 cycloalkyl, 5- to 10-membered heterocycloalkyl, C5-C10 aryl and 5- to 10-membered heteroaryl, (4) C3-C10 cycloalkyl, (5) 5- to 10-membered heterocycloalkyl, (6) C5-C10 aryl, (7) 5- to 10-membered heteroaryl, (8) —C1-4 alkylene-C3-C8 cycloalkyl substituted with 1 to 5 groups selected from C1-4 alkyl, oxo, OH and halogen, (9) —C1-4 alkylene-C5-C10 aryl substituted with 1 to 5 groups selected from C1-4 alkyl, OH and halogen, (10) —C1-4 alkylene-5- to 10-membered heterocycloalkyl substituted with 1 to 5 groups selected from C1-4 alkyl, oxo, OH and halogen, (11) —C1-4 alkylene-5- to 10-membered heteroaryl substituted with 1 to 5 groups selected from C1-4 alkyl, OH and halogen or (12) —C1-4 alkylene-O—C1-8 alkyl substituted with 1 to 3 groups selected from OH, oxo, —O—C1-4 alkyl, halogen, C3-C8 cycloalkyl, 5- to 10-membered heterocycloalkyl, —O—C3-C8 cycloalkyl and —O-5- to 10-membered heterocycloalkyl, more preferably (1) hydrogen, (2) C1-8 alkyl, (3) C1-8 alkyl substituted with 1 to 5 groups selected from —N(C1-4 alkyl)$_2$, oxo and morpholine, (4) phenyl, (5) indane, (6) C1-4 alkylene-1,3-dioxole substituted with 1 to 5 groups selected from C1-4 alkyl, oxo, OH and halogen, or (7) —C1-4 alkylene-O—C1-8 alkyl substituted with 1 to 3 groups selected from oxo and —O-cyclohexane.

Preferably, T represents C1-4 alkylene or C2-4 alkenylene.

Preferably, n represents an integer of 0, 1, 2 or 3.

Preferably, $R^{62}$ represents hydrogen or chlorine, more preferably hydrogen.

In a preferred embodiment, $Cyc^3$ represents C5-C10 aryl or 5- to 10-membered heteroaryl, more preferably phenyl or thiophene, n is 1 and $R^7$ represents (1) —NH$_2$, (2) —NHC(O)O—C1-4 alkyl, (3) —NHC(O)O—C1-4 alkylene-O—C1-4 alkyl, (4) —COOH, (5) —COO—C1-8 alkyl, (6) —COO—C1-8 alkyl substituted with 1 to 5 groups selected from —N(C1-4 alkyl)$_2$, oxo and 5- to 10-membered heterocycloalkyl, (7) —COO—C5-C10 aryl, (8) —COO—C1-4 alkylene-5- to 10-membered heterocycloalkyl substituted with 1 to 5 groups selected from C1-4 alkyl, oxo, OH and halogen, (9) —COO— indane, (10) —COO—C1-4 alkylene-1,3-dioxole substituted with 1 to 5 groups selected from C1-4 alkyl, oxo, OH and halogen, (11) —COO—C1-4 alkylene-O—C1-8 alkyl substituted with 1 to 3 groups selected from oxo and —O-cyclohexane, (12) —C1-4 alkylene-COOH, (13) —C1-4 alkylene-COO—C1-8 alkyl or (14) —C1-4 alkylene-COO—C1-8 alkyl substituted with 1 to 5 groups selected from —N(C1-4 alkyl)$_2$, oxo and 5- to 10-membered heterocycloalkyl, or n is 2 and one $R^7$ represents (1) —NH$_2$, (2) —NHC(O)O—C1-4 alkyl or (3) —NHC(O)O—C1-4 alkylene —O—C1-4 alkyl and the other $R^7$ represents halogen.

In a preferred embodiment

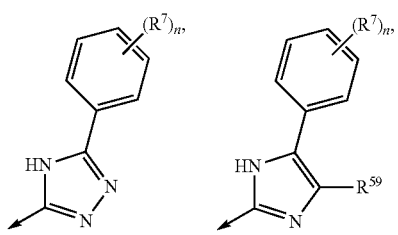

represents

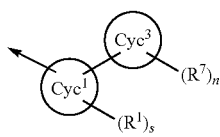

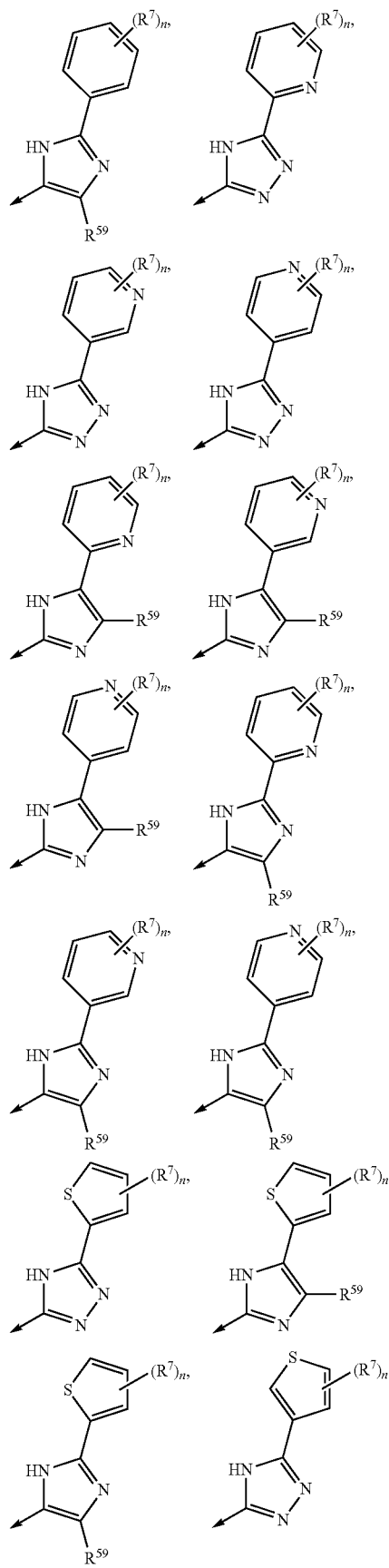

-continued

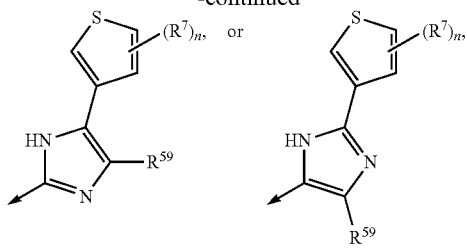

wherein $R^{59}$ represents hydrogen, C1-4 alkyl or halogen;

the arrow represents a binding position; and the other symbols have the same meanings as described above, preferably wherein n is 1 and $R^7$ represents (1) —NH$_2$, (2) —NHC(O)O—C1-4 alkyl, (3) —NHC(O)O—C1-4 alkylene —O—C1-4 alkyl, (4) —COOH, (5) —COO—C1-8 alkyl, (6) —COO—C1-8 alkyl substituted with 1 to 5 groups selected from —N(C1-4 alkyl)$_2$, oxo and 5- to 10-membered heterocycloalkyl, (7) —COO—C5-C10 aryl, (8) —COO—C1-4 alkylene-5- to 10-membered heterocycloalkyl substituted with 1 to 5 groups selected from C1-4 alkyl, oxo, OH and halogen, (9) —COO— indane, (10) —COO— C1-4 alkylene-1,3-dioxole substituted with 1 to 5 groups selected from C1-4 alkyl, oxo, OH and halogen, (11) —COO—C1-4 alkylene-O—C1-8 alkyl substituted with 1 to 3 groups selected from oxo and —O-cyclohexane, (12) —C1-4 alkylene-COOH, (13) —C1-4 alkylene-COO— C1-8 alkyl or (14) —C1-4 alkylene-COO— C1-8 alkyl substituted with 1 to 5 groups selected from —N(C1-4 alkyl)$_2$, oxo and 5- to 10-membered heterocycloalkyl, or n is 2 and one $R^7$ represents (1) —NH$_2$, (2) —NHC(O)O—C1-4 alkyl or (3) —NHC(O)O—C1-4 alkylene —O—C1-4 alkyl, (4) —COOH, (5) —COO—C1-8 alkyl, (6) —COO—C1-8 alkyl substituted with 1 to 5 groups selected from —N(C1-4 alkyl)$_2$, oxo and 5- to 10-membered heterocycloalkyl, (7) —COO— C5-C10 aryl or (8) —COO— C1-4 alkylene-5- to 10-membered heterocycloalkyl substituted with 1 to 5 groups selected from C1-4 alkyl, oxo, OH and halogen and the other $R^7$ represents halogen.

In a preferred embodiment, -Cyc$^2$-(R$^6$)$_m$ represents

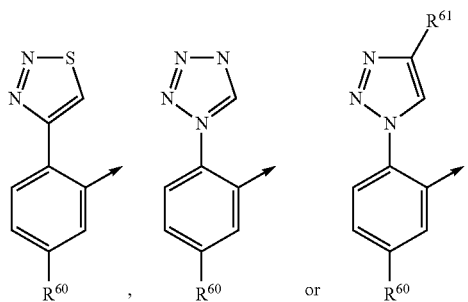

wherein $R^{60}$ represents hydrogen, methyl or halogen;

$R^{61}$ represents (1) hydrogen, (2) halogen, (3) nitro, (4) trifluoromethyl, (5) —COOH, (6) —COO—C1-4 alkyl, (7) cyano or (8) —CONH$_2$; and the arrow represents a binding position.

In one embodiment, preferred compounds of the present invention are pyridinone or pyrimidinone derivatives represented by formula (I-A):

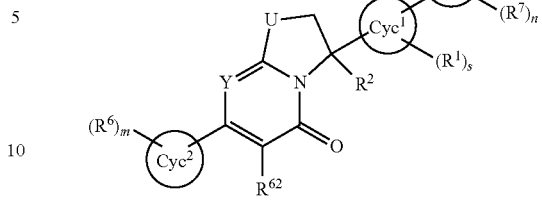

(I-A)

wherein U represents S or CH$_2$; and the other symbols have the same meanings as described above. Thus, preferred Cyc$^1$, Cyc$^2$, Cyc$^3$, R$^1$, s, R$^2$, R$^5$, R$^6$, m, R$^7$ and n in the formula (I-A) are the preferred options as described above.

Preferred compounds of formula (I-A) are those in which:

Cyc$^1$ represents a C5-C10 aryl or 5 to 10 membered heteroaryl;

Cyc$^2$ represents a C5-C10 aryl, preferably a C5-C6 aryl;

Cyc$^3$ represents cyclohexane, indoline, isoindoline, dihydroquinoline, dihydroquinazoline, dihydrobenzoxazine, dihydrobenzoxazole, phenyl, pyrazole, pyridine, pyrazine, thiophene, oxazole, thiazole, indazole, quinoline, isoquinoline, quinoxaline or benzimidazole;

$R^1$ represents C1-8 alkyl or halogen;

s represents an integer of 0 or 1;

$R^2$ represents (1) hydrogen, (2) C1-8 alkyl, (3) Cyc$^4$ or (4) C1-8 alkyl substituted with 1 to 3 groups selected from Cyc$^5$ and —OR$^{15}$;

Cyc$^4$ represents C5-C10 aryl;

Cyc$^5$ represents C5-C10 aryl, for example C5-C7 aryl, or a 5- to 6-membered heteroaryl;

$R^{15}$ is selected from hydrogen and C1-4 alkyl;

Y represents N or =CH—;

U represents S or CH$_2$;

$R^6$ represents (1) methyl, (2) Cyc$^{10}$, (3) halogen, (4) amidino, or (5) Cyc$^{10}$ substituted with 1 to 3 groups selected from halogen, trifluoromethyl, cyano, —OR$^{29}$, —COOR$^{35}$, —NHC(O)—R$^{36}$ and —C(O)NH—R$^{38}$;

$R^{29}$, $R^{35}$, $R^{36}$ and $R^{38}$ each independently represent hydrogen or C1-4 alkyl;

Cyc$^{10}$ represents imidazolyl, pyrazolyl, triazolyl, tetrazolyl, oxazolyl, pyridazinyl, indazolyl, benzimidazolyl, thiazolyl or thiadiazolyl;

m represents an integer of 0, 1 or 2, wherein m represents an integer of 2, each R$^6$ may be same or different;

$R^7$ represents (1) C1-8 alkyl, (2) halogen, (3) nitro, (4) trifluoromethyl, (5) cyano, (6) oxo, (7) —OR$^{40}$, (8) —NR$^{42}$R$^{43}$, (9) —NHC(O)NR$^{44}$R$^{45}$, (10) —NHC(O)—C1-4 alkylene —NR$^{46}$R$^{47}$, (11) —NHC(O)—C1-4 alkylene —COOH, (12) —NH—S(O)$_2$—C1-4 alkyl, (13) —COOR$^{48}$, (14) —NHC(O)—R$^{49}$, (15) —NHC(O)—C1-4 alkylene —OR$^{50}$, (16) —NHC(O)O—R$^{51}$, (17) —NHC(O)O—C1-4 alkylene —OR$^{52}$, (18) —C(O)NH—R$^{53}$, (19) —OC(O)—R$^{55}$, (20) —C(O)—R$^{56}$, (21) —CH(OH)—R$^{57}$, (22) —C1-4 alkylene —NH$_2$, (23) —C1-4 alkylene —OH, (24) —C1-4 alkylene —OC(O)—C1-4 alkyl, (25) —C1-4 alkylene —NHC(O)—C1-4 alkyl, (26) —C1-4 alkylene —NHC(O)O—C1-4 alkyl, (27) —C1-4 alkylene —NHC(O)—CF$_3$, (28) —C1-4 alkylene —NHC(O)NH—C1-4 alkyl, (29) —CH=N—OR$^{58}$ or (30) -T-COOR$^{66}$;

$R^{40}, R^{41}, R^{42}, R^{43}, R^{44}, R^{45}, R^{46}, R^{47}, R^{49}, R^{50}, R^{51}, R^{52}, R^{53}, R^{54}, R^{55}, R^{56}, R^{57}$ and $R^{58}$ each independently represent hydrogen, C1-4 alkyl or trifluoromethyl;

$R^{51}$ represents C1-8 alkyl;

T represents C1-4 alkylene or C2-4 alkenylene;

$R^{48}$ and $R^{66}$ each independently represents (1) hydrogen, (2) C1-8 alkyl, (3) C1-8 alkyl which are substituted with 1 to 5 groups selected from —N(C1-4 alkyl)$_2$, oxo, C3-C8 cycloalkyl, 5- to 10-membered heterocycloalkyl, C5-C10 aryl and 5- to 10-membered heteroaryl, (4) C3-C10 cycloalkyl, (5) 5- to 10-membered heterocycloalkyl, (6) C5-C10 aryl, (7) 5- to 10-membered heteroaryl, (8) —C1-4 alkylene —C3-C8 cycloalkyl substituted with 1 to 5 groups selected from C1-4 alkyl, oxo, OH and halogen, (9) —C1-4 alkylene —C5-C10 aryl substituted with 1 to 5 groups selected from C1-4 alkyl, OH and halogen, (10) —C1-4 alkylene-5- to 10-membered heterocycloalkyl substituted with 1 to 5 groups selected from C1-4 alkyl, oxo, OH and halogen, (11) —C1-4 alkylene-5- to 10-membered heteroaryl substituted with 1 to 5 groups selected from C1-4 alkyl, OH and halogen or (12) —C1-4 alkylene-O—C1-8 alkyl substituted with 1 to 3 groups selected from OH, oxo, —O—C1-4 alkyl, halogen, C3-C8 cycloalkyl, 5- to 10-membered heterocycloalkyl, —O—C3-C8 cycloalkyl and —O-5- to 10-membered heterocycloalkyl;

n represents an integer of 0, 1, 2 or 3, wherein n represents an integer of 2 to 3, each $R^7$ may be same or different; and $R^{62}$ represents hydrogen or chlorine.

Preferred compounds of formula (I-A) include those in which:

$Cyc^1$ represents phenyl, imidazolyl, triazolyl, tetrazolyl, pyrrolyl, pyrazolyl, furanyl, oxazolyl, thiazolyl, isothiazolyl, furazanyl, oxadiazolyl, thiadiazolyl, thienyl, pyridazinyl, indazolyl or benzimidazolyl;

$Cyc^2$ represents pyridyl or phenyl;

$Cyc^3$ represents cyclohexane, indoline, isoindoline, dihydroquinoline, dihydroquinazoline, dihydrobenzoxazine, dihydrobenzoxazole, phenyl, pyrazole, pyridine, pyrazine, thiophene, oxazole, thiazole, indazole, quinoline, isoquinoline, quinoxaline or benzimidazole;

$R^1$ represents methyl, ethyl or chlorine;

s represents an integer of 0 or 1;

$R^2$ represents hydrogen;

Y represents CH;

U represents $CH_2$;

$R^6$ represents (1) methyl, (2) $Cyc^{10}$, (3) halogen (preferably chlorine), or (4) $Cyc^{10}$ substituted with 1 to 3 groups selected from halogen (preferably chlorine), nitro, trifluoromethyl, —COOH, —COO—C1-4 alkyl, cyano or —CONH$_2$;

$Cyc^{10}$ represents pyrazolyl, thiadiazolyl, triazolyl or tetrazolyl;

m represents an integer of 0, 1 or 2, wherein m represents an integer of 2, each $R^6$ may be same or different;

$R^7$ represents (1) methyl, (2) ethyl, (3) fluorine, (4) chlorine, (5) bromine, (6) nitro, (7) trifluoromethyl, (8) cyano, (9) oxo, (10) —$OR^{40}$, (11) —$NR^{42}R^{43}$, (12) —NHC(O)$NR^{44}R^{45}$, (13) —NHC(O)—C1-4 alkylene —$NR^{46}R^{47}$, (14) —NHC(O)—C1-4 alkylene —COOH, (15) —NH—S(O)$_2$—C1-4 alkyl, (16) —$COOR^{48}$, (17) —NHC(O)—$R^{49}$, (18) —NHC(O)—C1-4 alkylene —$OR^{50}$, (19) —NHC(O)O—$R^{51}$, (20) —NHC(O)O—C1-4 alkylene —$OR^{52}$, (21) —C(O)NH—$R^{53}$, (22) —OC(O)—$R^{55}$, (23) —C(O)—$R^{56}$, (24) —CH(OH)—$R^{57}$, (25) —C1-4 alkylene —NH$_2$, (26) —C1-4 alkylene —OH, (27) —C1-4 alkylene —OC(O)—C1-4 alkyl, (28) —C1-4 alkylene —NHC(O)—C1-4 alkyl, (29) —C1-4 alkylene —NHC(O)O—C1-4 alkyl, (30) —C1-4 alkylene —NHC(O)—CF$_3$, (31) —C1-4 alkylene —NHC(O)NH—C1-4 alkyl, (32) —CH=N—$OR^{58}$, (33) —C1-4 alkylene-COOH, (34) —C1-4 alkylene-COO—C1-8 alkyl or (35) — C1-4 alkylene-COO— C1-8 alkyl substituted with 1 to 5 groups selected from —N(C1-4 alkyl)$_2$, oxo and 5- to 10-membered heterocycloalkyl;

$R^{40}, R^{41}, R^{42}, R^{43}, R^{44}, R^{45}, R^{46}, R^{47}, R^{49}, R^{50}, R^{52}, R^{53}, R^{54}, R^{55}, R^{56}, R^{57}$ and $R^{58}$ are independently selected from hydrogen, C1-4 alkyl and trifluoromethyl;

$R^{48}$ represents (1) hydrogen, (2) C1-8 alkyl, (3) C1-8 alkyl substituted with 1 to 5 groups selected from —N(C1-4 alkyl)$_2$, oxo and morpholine, (4) phenyl, (5) indane, (6) C1-4 alkylene-1,3-dioxole substituted with 1 to 5 groups selected from C1-4 alkyl, oxo, OH and halogen or (7) —C1-4 alkylene-O—C1-8 alkyl substituted with 1 to 3 groups selected from oxo and —O-cyclohexane;

$R^{51}$ represents C1-4 alkyl;

n represents an integer of 0, 1, 2 or 3, wherein n represents an integer of 2 to 3, each $R^7$ may be same or different; and $R^{62}$ represents hydrogen.

Further preferred compounds of formula (I-A) include those in which

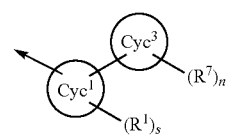

represents

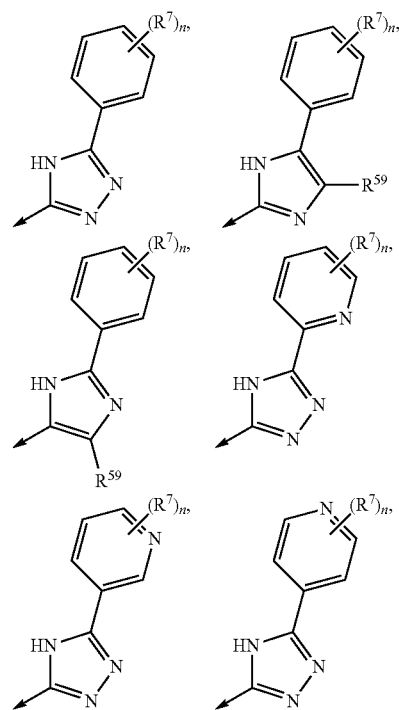

-continued

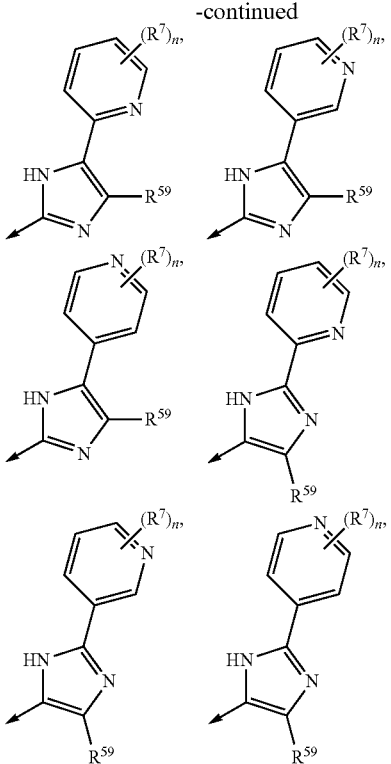

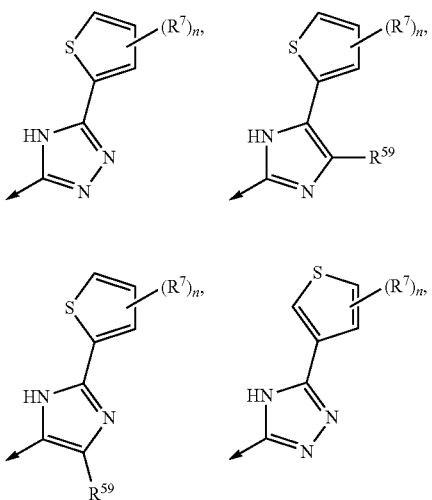

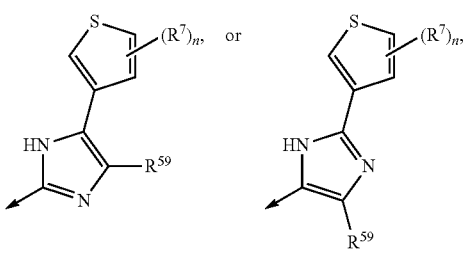

wherein R$^{59}$ represents hydrogen, C1-4 alkyl or halogen; the arrow represents a binding position; and the other symbols have the same meanings as described above, preferably wherein n is 1 and R$^7$ represents (1) —NH$_2$, (2) —NHC(O)O—C1-4 alkyl or (3) —NHC(O)O— C1-4 alkylene —O—C1-4 alkyl, (4) —COOH, (5) —COO—C1-8 alkyl, (6) —COO—C1-8 alkyl substituted with 1 to 5 groups selected from —N(C1-4 alkyl)$_2$, oxo and 5- to 10-membered heterocycloalkyl, (7) —COO— C5-C10 aryl, (8) —COO—C1-4 alkylene -5- to 10-membered heterocycloalkyl substituted with 1 to 5 groups selected from C1-4 alkyl, oxo, OH and halogen, (9) —COO— indane, (10) —COO—C1-4 alkylene 1,3-dioxole substituted with 1 to 5 groups selected from C1-4 alkyl, oxo, OH and halogen, (11) —COO—C1-4 alkylene-O—C1-8 alkyl substituted with 1 to 3 groups selected from oxo and —O-cyclohexane, (12) —C1-4 alkylene-COOH, (13) —C1-4 alkylene-COO—C1-8 alkyl or (14) —C1-4 alkylene-COO— C1-8 alkyl substituted with 1 to 5 groups selected from —N(C1-4 alkyl)$_2$, oxo and 5- to 10-membered heterocycloalkyl, or n is 2 and one R$^7$ represents (1) —NH$_2$, (2) —NHC(O)O—C1-4 alkyl or (3) —NHC(O)O—C1-4 alkylene —O—C1-4 alkyl, (4) —COOH, (5) —COO—C1-8 alkyl, (6) —COO—C1-8 alkyl substituted with 1 to 5 groups selected from —N(C1-4 alkyl)$_2$, oxo and 5- to 10-membered heterocycloalkyl, (7) —COO— C5-C10 aryl or (8) —COO— C1-4 alkylene -5- to 10-membered heterocycloalkyl substituted with 1 to 5 groups selected from C1-4 alkyl, oxo, OH and halogen and the other R$^7$ represents halogen.

Further preferred compounds of formula (I-A) include those in which -Cyc$^2$-(R$^6$)$_m$ represents

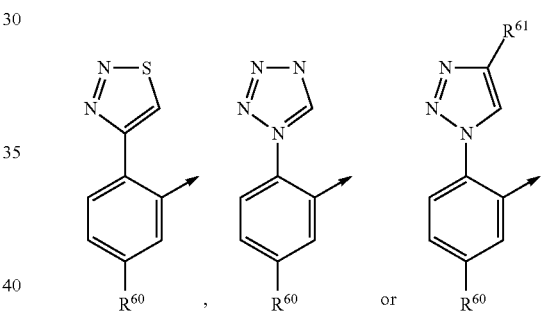

wherein R$^{60}$ represents hydrogen, methyl or halogen;

R$^{61}$ represents (1) hydrogen, (2) halogen, (3) nitro, (4) trifluoromethyl, (5) —COOH, (6) —COO—C1-4 alkyl, (7) cyano or (8) —CONH$_2$; and the arrow represents a binding position.

Further preferred compounds of formula (I-A) include a compound of (I-A-1):

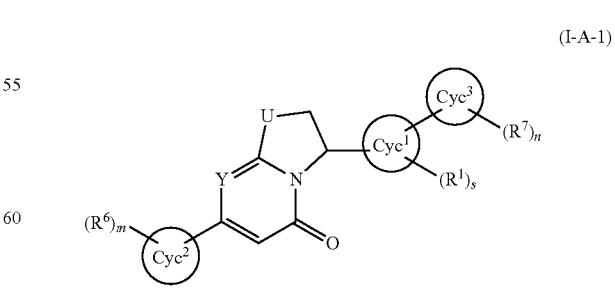

(I-A-1)

wherein all symbols have the same meanings as described above and the same preferred definitions as set out above (alone or in combination), a compound of (I-A-1-1):

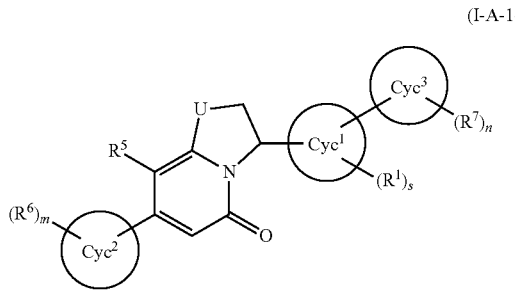

(I-A-1-1)

wherein all symbols have the same meanings as described above and the same preferred definitions as set out above (alone or in combination), a compound of (I-A-1-2):

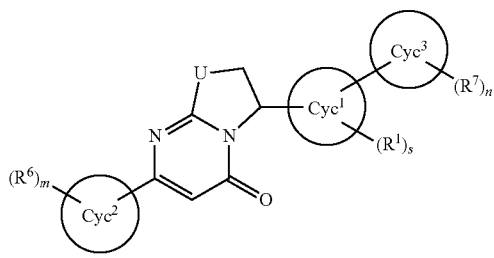

(I-A-1-2)

wherein all symbols have the same meanings as described above and the same preferred definitions as set out above (alone or in combination), a compound of (I-A-2):

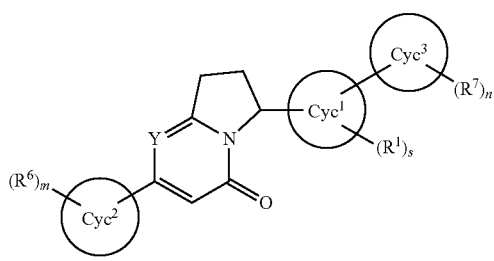

(I-A-2)

wherein all symbols have the same meanings as described above and the same preferred definitions as set out above (alone or in combination), a compound of (I-A-2-1):

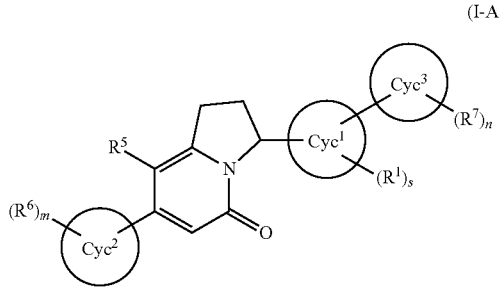

(I-A-2-1)

wherein all symbols have the same meanings as described above and the same preferred definitions as set out above (alone or in combination), a compound of (I-A-2-2):

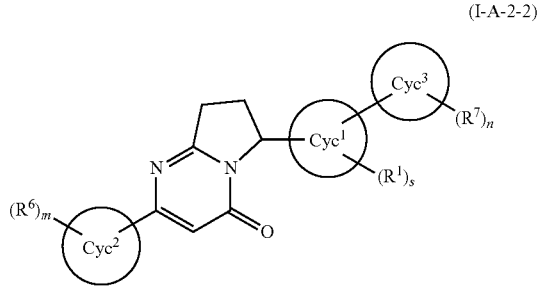

(I-A-2-2)

wherein all symbols have the same meanings as described above and the same preferred definitions as set out above (alone or in combination), a compound of (I-A-3):

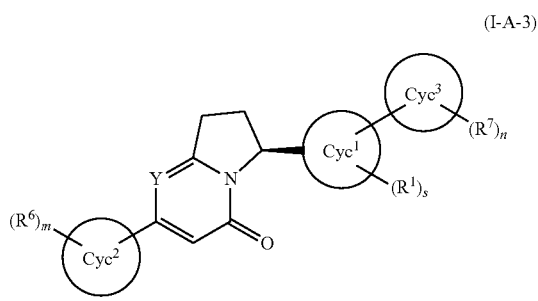

(I-A-3)

wherein all symbols have the same meanings as described above and the same preferred definitions as set out above (alone or in combination), a compound of (I-A-3-1):

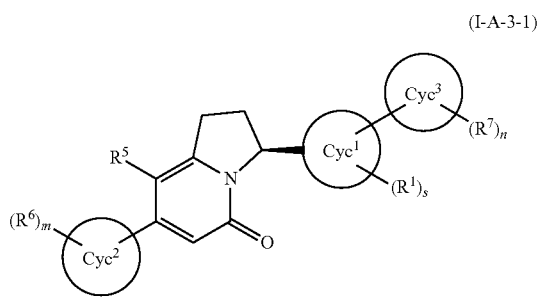

(I-A-3-1)

wherein all symbols have the same meanings as described above and the same preferred definitions as set out above (alone or in combination), a compound of (I-A-3-2):

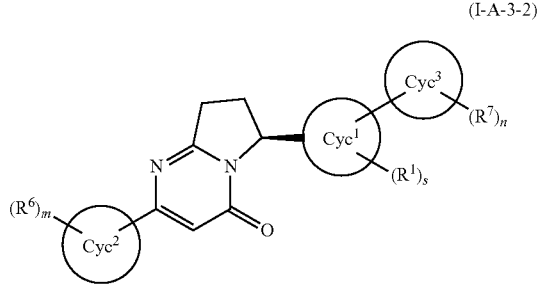

(I-A-3-2)

wherein all symbols have the same meanings as described above and the same preferred definitions as set out above (alone or in combination), a compound of (I-A-4):

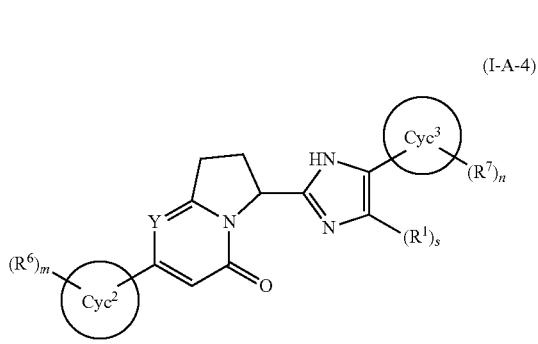

(I-A-4)

wherein s represents an integer of 0 to 1; and the other symbols have the same meanings as described above and the same preferred definitions as set out above (alone or in combination), a compound of (I-A-4-1):

(I-A-4-1)

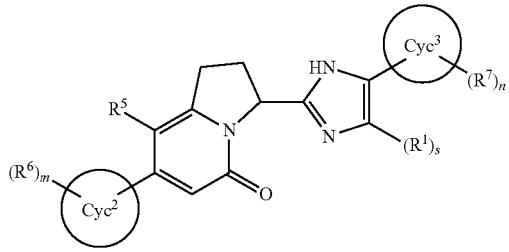

wherein s represents an integer of 0 to 1; and the other symbols have the same meanings as described above and the same preferred definitions as set out above (alone or in combination), a compound of (I-A-4-2):

(I-A-4-2)

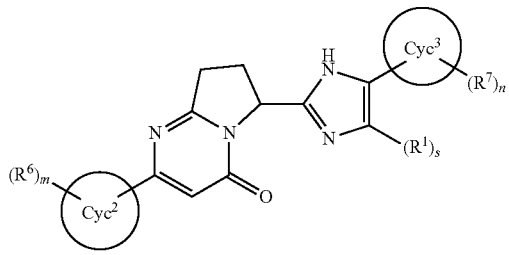

wherein s represents an integer of 0 to 1; and the other symbols have the same meanings as described above and the same preferred definitions as set out above (alone or in combination), a compound of (I-A-5):

(I-A-5)

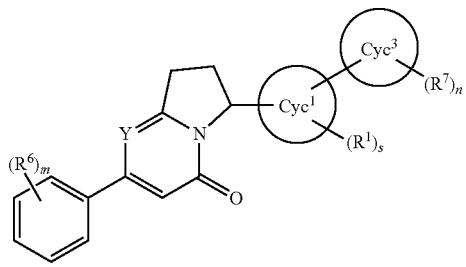

wherein m represents an integer of 0 to 5; and the other symbols have the same meanings as described above and the same preferred definitions as set out above (alone or in combination), a compound of (I-A-5-1):

(I-A-5-1)

wherein m represents an integer of 0 to 5; and the other symbols have the same meanings as described above and the same preferred definitions as set out above (alone or in combination), a compound of (I-A-5-2):

(I-A-5-2)

wherein m represents an integer of 0 to 5; and the other symbols have the same meanings as described above and the same preferred definitions as set out above (alone or in combination), a compound of (I-A-6):

(I-A-6)

wherein s represents an integer 0 to 1;
m represents an integer 0 to 5; and
the other symbols have the same meanings as described above and the same preferred definitions as set out above (alone or in combination), a compound of (I-A-6-1):

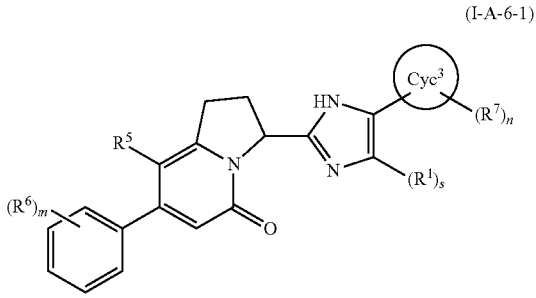

(I-A-6-1)

wherein s represents an integer 0 to 1;
m represents an integer 0 to 5; and
the other symbols have the same meanings as described above and the same preferred definitions as set out above (alone or in combination), a compound of (I-A-6-2):

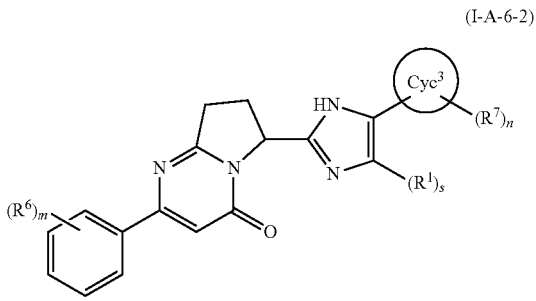

(I-A-6-2)

wherein s represents an integer 0 to 1;
m represents an integer 0 to 5; and
the other symbols have the same meanings as described above and the same preferred definitions as set out above (alone or in combination), and the like.

In another embodiment, preferred compounds of the present invention are pyridinone derivatives represented by formula (I-B):

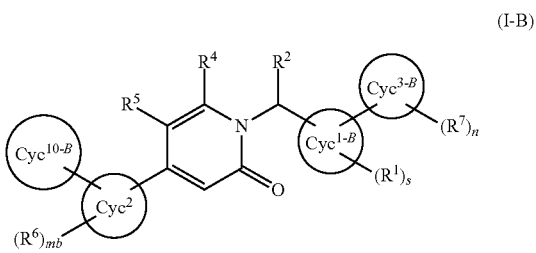

(I-B)

wherein $Cyc^{1-B}$ represents 5- to 10-membered heteroaryl;
$Cyc^{3-B}$ represents C5-C10 aryl or 5- to 10-membered heteroaryl;
$Cyc^{10-B}$ represents (1) 5- to 10-membered heteroaryl or (2) 5- to 10-membered heteroaryl substituted with 1 to 5 groups selected from halogen, cyano, nitro, trifluoromethyl, —COOH, —COO—C1-4 alkyl and —CONH$_2$;
mb represents an integer of 0 to 5; and
the other symbols have the same meanings as described above. Thus, preferred $Cyc^{1-B}$, $Cyc^2$, $Cyc^{3-B}$, $R^1$, s, $R^2$, $R^4$, $R^5$, $R^6$, $Cyc^{10-B}$, $R^7$ and n in the formula (I-B) are the preferred options as described above.

Preferred compounds of formula (I-B) are those in which:
$Cyc^{1-B}$ represents imidazolyl, triazolyl, tetrazolyl, oxazolyl, pyridazinyl, indazolyl or benzimidazolyl;
$Cyc^2$ represents a C5-C10 aryl, preferably a C5-C6 aryl;
$Cyc^{3-B}$ represents C5-C10 aryl, for example C5-C7 aryl such as phenyl, or 5- to 10-membered heteroaryl, such as pyrazole, pyridine, pyrazine, thiophene, oxazole, thiazole, indazole, quinoline, isoquinoline, quinoxaline or benzimidazole, more preferably pyrazole or pyridine;
$R^1$ represents halogen or C1-4 alkyl;
s represents an integer of 0 or 1;
$R^2$ represents (1) hydrogen, (2) C1-8 alkyl, (3) $Cyc^4$ or (4) C1-8 alkyl substituted with 1 to 3 groups selected from $Cyc^5$ and —OR$^{15}$;
$Cyc^4$ represents C5-C10 aryl;
$Cyc^5$ represents C5-C10 aryl, for example C5-C7 aryl or a 5- to 6-membered heteroaryl;
$R^{15}$ is selected from hydrogen and C1-4 alkyl;
$R^4$ represents hydrogen or C1-4 alkyl;
$R^5$ represents hydrogen;
$R^6$ represents methyl, halogen or amidino;
mb represents an integer of 0 or 1;
$Cyc^{10-B}$ represents imidazolyl, triazolyl, tetrazolyl, oxazolyl, pyridazinyl, indazolyl, benzimidazolyl, thiazolyl or thiadiazolyl, any of which optionally substituted with 1 to 3 groups selected from halogen, cyano, nitro, trifluoromethyl, —COOH, —COO—C1-4 alkyl and —CONH$_2$;
$R^7$ represents (1) C1-8 alkyl, (2) halogen, (3) nitro, (4) trifluoromethyl, (5) cyano, (6) oxo, (7) —OR$^{40}$, (8) —NR$^{42}$R$^{43}$, (9) —NHC(O)NR$^{44}$R$^{45}$, (10) —NHC(O)—C1-4 alkylene —NR$^{46}$R$^{47}$, (11) —NHC(O)—C1-4 alkylene —COOH, (12) —NH—S(O)$_2$—C1-4 alkyl, (13) —COOR$^{48}$, (14) —NHC(O)—R$^{49}$, (15) —NHC(O)—C1-4 alkylene —OR$^{50}$, (16) —NHC(O)O—R$^{51}$, (17) —NHC(O)O—C1-4 alkylene —OR$^{52}$, (18) —C(O)NH—R$^{53}$, (19) —OC(O)—R$^{55}$, (20) —C(O)—R$^{56}$, (21) —CH(OH)—R$^{57}$, (22) —C1-4 alkylene —NH$_2$, (23) —C1-4 alkylene —OH, (24) —C1-4 alkylene —OC(O)—C1-4 alkyl, (25) —C1-4 alkylene —NHC(O)—C1-4 alkyl, (26) —C1-4 alkylene —NHC(O)O—C1-4 alkyl, (27) —C1-4 alkylene —NHC(O)—CF$_3$, (28) —C1-4 alkylene —NHC(O)NH—C1-4 alkyl, (29) —CH═N—OR$^{58}$ or (30) -T-COOR$^{66}$;
$R^{40}$, $R^{41}$, $R^{42}$, $R^{43}$, $R^{44}$, $R^{45}$, $R^{46}$, $R^{47}$, $R^{49}$, $R^{50}$, $R^{52}$, $R^{53}$, $R^{54}$, $R^{55}$, $R^{56}$, $R^{57}$ and $R^{58}$ each independently represent hydrogen, C1-4 alkyl or trifluoromethyl;
T represents C1-4 alkylene or C2-4 alkenylene;
$R^{48}$ and $R^{66}$ each independently represents (1) hydrogen, (2) C1-8 alkyl, (3) C1-8 alkyl which are substituted with 1 to 5 groups selected from —N(C1-4 alkyl)$_2$, oxo, C3-C8 cycloalkyl, 5- to 10-membered heterocycloalkyl, C5-C10 aryl and 5- to 10-membered heteroaryl, (4) C3-C10 cycloalkyl, (5) 5- to 10-membered heterocycloalkyl, (6) C5-C10 aryl, (7) 5- to 10-membered heteroaryl, (8) —C1-4 alkylene —C3-C8 cycloalkyl substituted with 1 to 5 groups selected from C1-4 alkyl, oxo, OH and halogen, (9) —C1-4 alkylene —C5-C10 aryl substituted with 1 to 5 groups selected from C1-4 alkyl, OH and halogen, (10) —C1-4 alkylene -5- to 10-membered heterocycloalkyl substituted with 1 to 5 groups selected from C1-4 alkyl, oxo, OH and halogen or (11) —C1-4 alkylene-5- to 10-membered heteroaryl substituted with 1 to 5 groups selected from C1-4 alkyl, OH and halogen;

$R^{51}$ represents C1-8 alkyl; and n represents an integer of 0, 1, 2 or 3, wherein n represents an integer of 2 to 3, each $R^7$ may be same or different.

Preferred compounds of formula (I-B) include those in which:

$Cyc^{1-B}$ represents imidazolyl, triazolyl, tetrazolyl, oxazolyl, pyridazinyl, indazolyl or benzimidazolyl;

$Cyc^2$ represents pyridyl or phenyl;

$Cyc^{3-B}$ represents C5-C10 aryl, more preferably phenyl;

$R^1$ represents halogen or C1-4 alkyl;

s represents an integer of 0 or 1;

$R^2$ represents (1) hydrogen, (2) C1-4 alkyl, (3) $Cyc^4$ or (4) C1-4 alkyl substituted with 1 or 2 groups selected from $Cyc^5$ and —$OR^{15}$;

$Cyc^4$ represents phenyl;

$Cyc^5$ represents phenyl or pyridyl;

$R^{15}$ is selected from hydrogen and C1-4 alkyl;

$R^4$ represents hydrogen, methyl or ethyl;

$R^5$ represents hydrogen;

$R^6$ represents methyl or halogen (preferably chlorine);

mb represents an integer of 0 or 1;

$Cyc^{10-B}$ represents thiadiazolyl, triazolyl or tetrazolyl, any of which optionally substituted with 1 to 3 groups selected from halogen (preferably chlorine), nitro, trifluoromethyl, —COOH, —COO—C1-4 alkyl, cyano or —$CONH_2$;

$R^7$ represents (1) —$NH_2$, (2) —NHC(O)O—C1-4 alkyl, (3) —NHC(O)O—C1-4 alkylene —O—C1-4 alkyl, (4) halogen, (5) —COOH, (6) —COO—C1-8 alkyl, (7) —COO—C1-8 alkyl substituted with 1 to 5 groups selected from —N(C1-4 alkyl)$_2$, oxo and 5- to 10-membered heterocycloalkyl, (8) —COO—C5-C10 aryl, (9) —COO—C1-4 alkylene-5- to 10-membered heterocycloalkyl substituted with 1 to 5 groups selected from C1-4 alkyl, oxo, OH and halogen, (10) —C1-4 alkylene-COOH or (11) —C1-4 alkylene-COO—C1-8 alkyl or (11) —C1-4 alkylene-COO—C1-8 alkyl substituted with 1 to 5 groups selected from —N(C1-4 alkyl)$_2$, oxo and 5- to 10-membered heterocycloalkyl; and n represents an integer of 0, 1, 2 or 3, wherein n represents an integer of 2 to 3, each $R^7$ may be same or different.

Further preferred compounds of formula (I-B) include those in which -$Cyc^{1-B}$(—$R^1$)$_s$-$Cyc^{3-B}$(—$R^7$)$_n$ represents

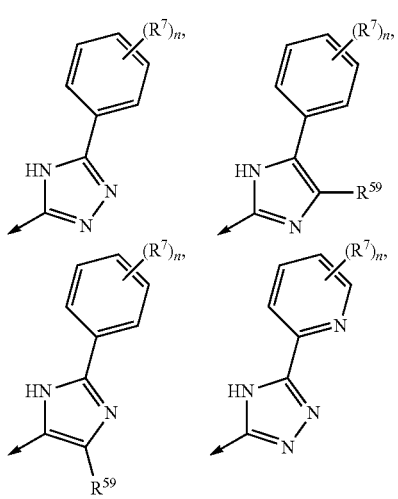

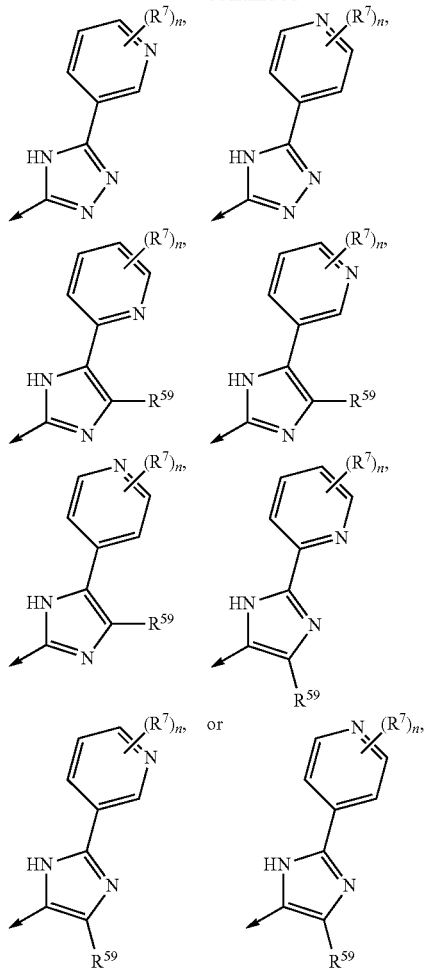

wherein $R^{59}$ represents hydrogen, C1-4 alkyl or halogen;

the arrow represents a binding position; and the other symbols have the same meanings as described above, preferably wherein n is 1 and $R^7$ represents (1) —$NH_2$, (2) —NHC(O)O—C1-4 alkyl or (3) —NHC(O)O—C1-4 alkylene —O—C1-4 alkyl, (4) —COOH, (5) —COO—C1-8 alkyl, (6) —COO—C1-8 alkyl substituted with 1 to 5 groups selected from —N(C1-4 alkyl)$_2$, oxo and 5- to 10-membered heterocycloalkyl, (7) —COO— C5-C10 aryl, (8) —COO—C1-4 alkylene -5- to 10-membered heterocycloalkyl substituted with 1 to 5 groups selected from C1-4 alkyl, oxo, OH and halogen, (9) —C1-4 alkylene-COOH, (10) —C1-4 alkylene-COO— C1-8 alkyl or (11) —C1-4 alkylene-COO— C1-8 alkyl substituted with 1 to 5 groups selected from —N(C1-4 alkyl)$_2$, oxo and 5- to 10-membered heterocycloalkyl, or n is 2 and one $R^7$ represents (1) —$NH_2$, (2) —NHC(O)O—C1-4 alkyl, (3) —NHC(O)O—C1-4 alkylene —O—C1-4 alkyl, (4) —COOH, (5) —COO—C1-8 alkyl, (6) —COO—C1-8 alkyl substituted with 1 to 5 groups selected from —N(C1-4 alkyl)$_2$, oxo and 5- to 10-membered heterocycloalkyl, (7) —COO— C5-C10 aryl or (8) —COO— C1-4 alkylene -5- to 10-membered heterocycloalkyl substituted with 1 to 5 groups selected from C1-4 alkyl, oxo, OH and halogen and the other $R^7$ represents halogen.

Further preferred compounds of formula (I-B) include those in which -$Cyc^2$(-$R^6$)$_{mb}Cyc^{10-B}$ represents

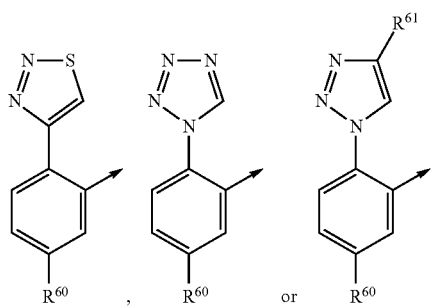

wherein R[60] represents hydrogen, methyl or halogen; R[61] represents (1) hydrogen, (2) halogen, (3) nitro, (4) trifluoromethyl, (5) —COOH, (6) —COO—C1-4 alkyl, (7) cyano or (8) —CONH$_2$; and the arrow represents a binding position.

Further preferred compounds of formula (I-B) include a compound of (I-B-1):

(I-B-1)

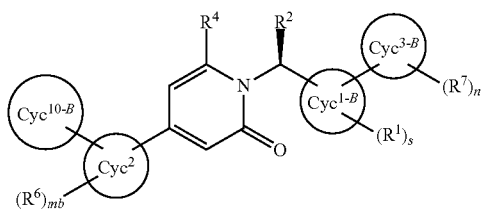

wherein all symbols have the same meanings as described above and the same preferred definitions as set out above (alone or in combination), a compound of (I-B-2):

(I-B-2)

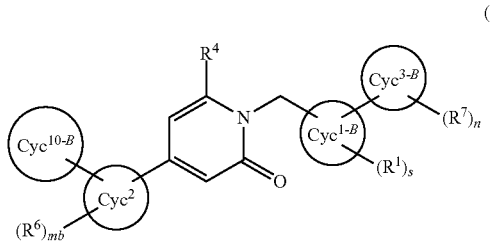

wherein all symbols have the same meanings as described above and the same preferred definitions as set out above (alone or in combination), a compound of (I-B-3):

(I-B-3)

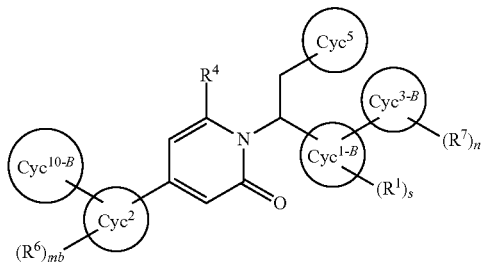

wherein all symbols have the same meanings as described above and the same preferred definitions as set out above (alone or in combination), a compound of (I-B-4):

(I-B-4)

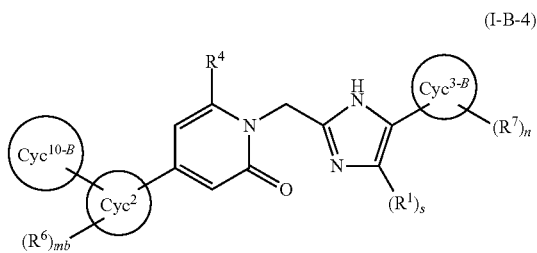

wherein s represents an integer of 0 to 1; and the other symbols have the same meanings as described above and the same preferred definitions as set out above (alone or in combination), a compound of (I-B-5):

(I-B-5)

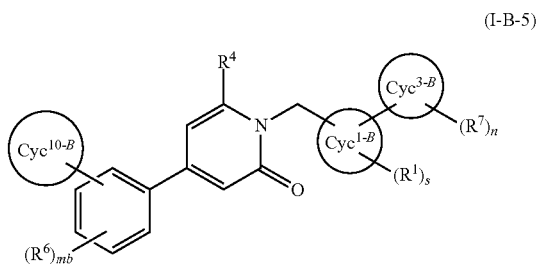

wherein mb represents an integer of 0 to 4; and the other symbols have the same meanings as described above and the same preferred definitions as set out above (alone or in combination), a compound of (I-B-6):

(I-B-6)

wherein s represents an integer 0 to 1;

mb represents an integer 0 to 4; and the other symbols have the same meanings as described above and the same preferred definitions as set out above (alone or in combination), and the like.

In another embodiment, preferred compounds of the present invention are pyrimidinone derivatives represented by formula (I-C):

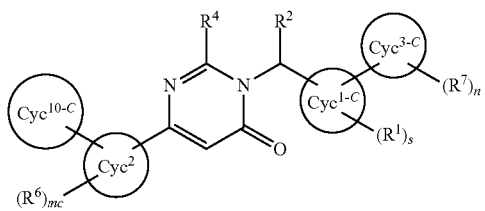

(I-C)

wherein Cyc$^{1-C}$ represents 5- to 10-membered heteroaryl;

Cyc$^{3-C}$ represents C5-C10 aryl or 5- to 10-membered heteroaryl;

Cyc$^{10-C}$ represents (1) 5- to 10-membered heteroaryl or (2) 5- to 10-membered heteroaryl substituted with 1 to 5 groups selected from halogen, cyano, nitro, trifluoromethyl, —COOH, —COO—C1-4 alkyl and —CONH$_2$;

mc represents an integer of 0 to 5; and the other symbols have the same meanings as described above. Thus, preferred Cyc$^{1-C}$, Cyc$^2$, Cyc$^{3-C}$, R$^1$, s, R$^2$, R$^4$, R$^6$, Cyc$^{10-C}$, R$^7$ and n in the formula (I-C) are the preferred options as described above.

Preferred compounds of formula (I-C) are those in which:

Cyc$^{1-C}$ represents imidazolyl, triazolyl, tetrazolyl, oxazolyl, pyridazinyl, indazolyl or benzimidazolyl;

Cyc$^2$ represents a C5-C10 aryl, preferably a C5-C6 aryl such as phenyl;

Cyc$^{3-C}$ represents C5-C10 aryl, for example C5-C7 aryl such as phenyl, or 5- to 10-membered heteroaryl, such as pyrazole, pyridine, pyrazine, thiophene, oxazole, thiazole, indazole, quinoline, isoquinoline, quinoxaline or benzimidazole, more preferably pyrazole or pyridine;

R$^1$ represents halogen or C1-4 alkyl;

s represents an integer of 0 or 1;

R$^2$ represents hydrogen, (1) C1-8 alkyl, (2) Cyc$^4$ or (3) C1-8 alkyl substituted with 1 to 3 groups selected from Cyc$^5$ and —OR$^{15}$;

Cyc$^4$ represents C5-C10 aryl;

Cyc$^5$ represents C5-C10 aryl, for example C5-C7 aryl, or a 5- to 6-membered heteroaryl;

R$^{15}$ is selected from hydrogen and C1-4 alkyl;

R$^4$ represents hydrogen or C1-4 alkyl;

R$^6$ represents methyl, halogen or amidino;

mc represents an integer of 0 or 1;

Cyc$^{10-C}$ represents imidazolyl, triazolyl, tetrazolyl, oxazolyl, pyridazinyl, indazolyl, benzimidazolyl, thiazolyl or thiadiazolyl, any of which optionally substituted with 1 to 3 groups selected from halogen, cyano, nitro, trifluoromethyl, —COOH, —COO—C1-4 alkyl and —CONH$_2$;

R$^7$ represents (1) C1-8 alkyl, (2) halogen, (3) nitro, (4) trifluoromethyl, (5) cyano, (6) oxo, (7) —OR$^{40}$, (8) —NR$^{42}$R$^{43}$, (9) —NHC(O)NR$^{44}$R$^{45}$, (10) —NHC(O)—C1-4 alkylene —NR$^{46}$R$^{47}$, (11) —NHC(O)—C1-4 alkylene —COOH, (12) —NH—S(O)$_2$—C1-4 alkyl, (13) —COOR$^{48}$, (14) —NHC(O)—R$^{49}$, (15) —NHC(O)—C1-4 alkylene —OR$^{50}$, (16) —NHC(O)O—R$^{51}$, (17) —NHC(O)O—C1-4 alkylene —OR$^{52}$, (18) —C(O)NH—R$^{53}$, (19) —OC(O)—R$^{55}$, (20) —C(O)—R$^{56}$, (21) —CH(OH)—R$^{57}$, (22) —C1-4 alkylene —NH$_2$, (23) —C1-4 alkylene —OH, (24) —C1-4 alkylene —OC(O)—C1-4 alkyl, (25) —C1-4 alkylene —NHC(O)—C1-4 alkyl, (26) —C1-4 alkylene —NHC(O)O—C1-4 alkyl, (27) —C1-4 alkylene —NHC(O)—CF$_3$, (28) —C1-4 alkylene —NHC(O)NH—C1-4 alkyl, (29) —CH=N—OR$^{58}$ or (30) -T-COOR$^{66}$;

R$^{40}$, R$^{41}$, R$^{42}$, R$^{43}$, R$^{44}$, R$^{45}$, R$^{46}$, R$^{47}$, R$^{48}$, R$^{49}$, R$^{50}$, R$^{52}$, R$^{53}$, R$^{54}$, R$^{55}$, R$^{56}$, R$^{57}$ and R$^{58}$ each independently represent hydrogen, C1-4 alkyl or trifluoromethyl;

R$^{51}$ represents C1-8 alkyl;

T represents C1-4 alkylene or C2-4 alkenylene;

R$^{48}$ and R$^{66}$ each independently represents (1) hydrogen, (2) C1-8 alkyl, (3) C1-8 alkyl which are substituted with 1 to 5 groups selected from —N(C1-4 alkyl)$_2$, oxo, C3-C8 cycloalkyl, 5- to 10-membered heterocycloalkyl, C5-C10 aryl and 5- to 10-membered heteroaryl, (4) C3-C10 cycloalkyl, (5) 5- to 10-membered heterocycloalkyl, (6) C5-C10 aryl, (7) 5- to 10-membered heteroaryl, (8) —C1-4 alkylene —C3-C8 cycloalkyl substituted with 1 to 5 groups selected from C1-4 alkyl, oxo, OH and halogen, (9) —C1-4 alkylene-C5-C10 aryl substituted with 1 to 5 groups selected from C1-4 alkyl, OH and halogen, (10) —C1-4 alkylene-5- to 10-membered heterocycloalkyl substituted with 1 to 5 groups selected from C1-4 alkyl, oxo, OH and halogen or (11) —C1-4 alkylene -5- to 10-membered heteroaryl substituted with 1 to 5 groups selected from C1-4 alkyl, OH and halogen; and n represents an integer of 0, 1, 2 or 3, wherein n represents an integer of 2 to 3, each R$^7$ may be same or different.

Preferred compounds of formula (I-C) include those in which:

Cyc$^{1-C}$ represents imidazolyl, triazolyl, tetrazolyl, oxazolyl, pyridazinyl, indazolyl or benzimidazolyl;

Cyc$^2$ represents pyridyl or phenyl;

Cyc$^{3-C}$ represents C5-C10 aryl, more preferably phenyl;

each R$^1$ independently represents halogen or C1-4 alkyl;

s represents an integer of 0 or 1;

R$^2$ represents (1) hydrogen, (2) C1-4 alkyl, (3) Cyc$^4$ or (4) C1-4 alkyl substituted with 1 or 2 groups selected from Cyc$^5$ and —OR$^{15}$;

Cyc$^4$ represents phenyl;

Cyc$^5$ represents phenyl or pyridyl;

R$^{15}$ is selected from hydrogen and C1-4 alkyl;

R$^4$ represents hydrogen, methyl or ethyl;

each R$^6$ independently represents methyl or halogen;

Cyc$^{10-C}$ represents thiadiazolyl, triazolyl or tetrazolyl, any of which optionally substituted with 1 to 3 groups selected from halogen (preferably chlorine), nitro, trifluoromethyl, —COOH, —COO—C1-4 alkyl, cyano or —CONH$_2$;

R$^7$ represents (1) —NH$_2$, (2) —NHC(O)O—C1-4 alkyl, (3) —NHC(O)O—C1-4 alkylene —O—C1-4 alkyl, (4) halogen, (5) —COOH, (6) —COO—C1-8 alkyl, (7) —COO—C1-8 alkyl substituted with 1 to 5 groups selected from —N(C1-4 alkyl)$_2$, oxo and 5- to 10-membered heterocycloalkyl, (8) —COO— C5-C10 aryl, (9) —COO— C1-4 alkylene -5- to 10-membered heterocycloalkyl substituted with 1 to 5 groups selected from C1-4 alkyl, oxo, OH and halogen, (10) —C1-4 alkylene-COOH, (11) —C1-4 alkylene-COO—C1-8 alkyl or (12) —C1-4 alkylene-COO—C1-8 alkyl substituted with 1 to 5 groups selected from —N(C1-4 alkyl)$_2$, oxo and 5- to 10-membered heterocycloalkyl; and n represents an integer of 0, 1, 2 or 3, wherein n represents an integer of 2 to 3, each R$^7$ may be same or different.

Further preferred compounds of formula (I-C) include those in which -Cyc$^{1-C}$(—R$^1$)$_s$-Cyc$^{3-C}$(-R$^7$)$_n$ represents

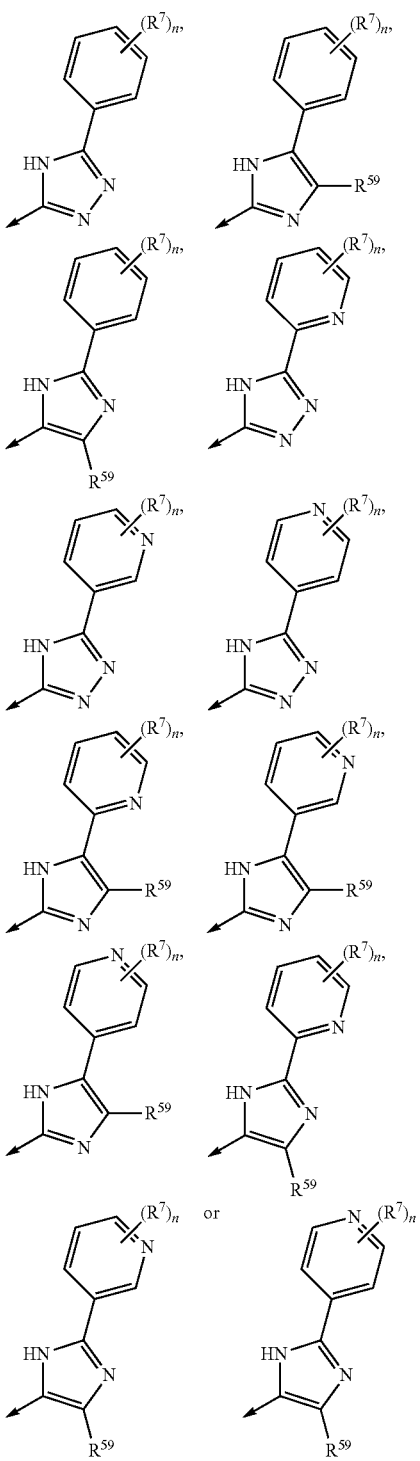

wherein R$^{59}$ represents hydrogen, C1-4 alkyl or halogen; the arrow represents a binding position; and the other symbols have the same meanings as described above, preferably wherein n is 1 and R$^7$ represents (1) —NH$_2$, (2) —NHC(O)O—C1-4 alkyl, (3) —NHC(O)O—C1-4 alkylene —O—C1-4 alkyl, (4) —COOH, (5) —COO—C1-8 alkyl, (6) —COO—C1-8 alkyl substituted with 1 to 5 groups selected from —N(C1-4 alkyl)$_2$, oxo and 5- to 10-membered heterocycloalkyl, (7) —COO— C5-C10 aryl, (8) —COO— C1-4 alkylene-5- to 10-membered het-erocycloalkyl substituted with 1 to 5 groups selected from C1-4 alkyl, oxo, OH and halogen, (9) —C1-4 alkylene-COOH, (10) —C1-4 alkylene-COO—C1-8 alkyl or (11) —C1-4 alkylene-COO— C1-8 alkyl substituted with 1 to 5 groups selected from —N(C1-4 alkyl)$_2$, oxo and 5- to 10-membered heterocycloalkyl, or n is 2 and one R$^7$ represents (1) —NH$_2$, (2) —NHC(O)O—C1-4 alkyl, (3) —NHC(O)O—C1-4 alkylene —O—C1-4 alkyl, (4) —COOH, (5) —COO—C1-8 alkyl, (6) —COO—C1-8 alkyl substituted with 1 to 5 groups selected from —N(C1-4 alkyl)$_2$, oxo and 5- to 10-membered heterocycloalkyl, (7) —COO— C5-C10 aryl or (8) —COO— C1-4 alkylene-5- to 10-membered heterocycloalkyl substituted with 1 to 5 groups selected from C1-4 alkyl, oxo, OH and halogen and the other R$^7$ represents halogen.

Further preferred compounds of formula (I-C) include those in which -Cyc$^2$(-R$^6$)$_{mc}$Cyc$^{10-C}$ represents

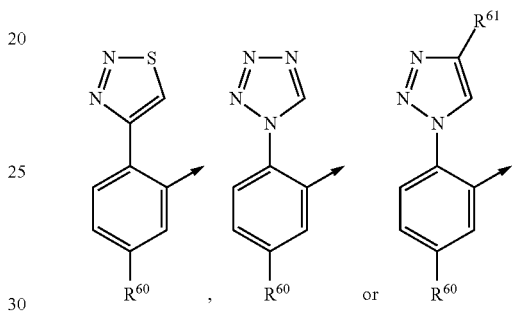

wherein R$^{60}$ represents hydrogen, methyl or halogen;

R$^{61}$ represents (1) hydrogen, (2) halogen, (3) nitro, (4) trifluoromethyl, (5) —COOH, (6) —COO—C1-4 alkyl, (7) cyano or (8) —CONH$_2$; and the arrow represents a binding position.

Further preferred compounds of formula (I-C) include a compound of (I-C-1):

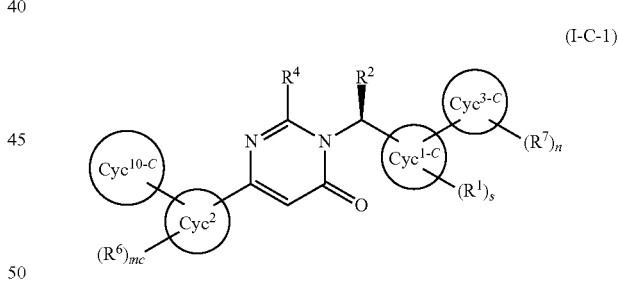

(I-C-1)

wherein all symbols have the same meanings as described above and the same preferred definitions as set out above (alone or in combination), a compound of (I-C-2):

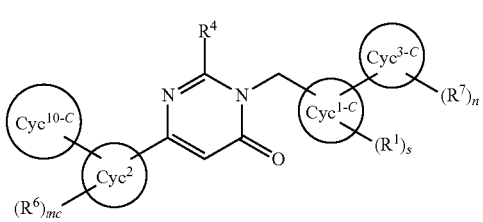

(I-C-2)

wherein all symbols have the same meanings as described above and the same preferred definitions as set out above (alone or in combination), a compound of (I-C-3):

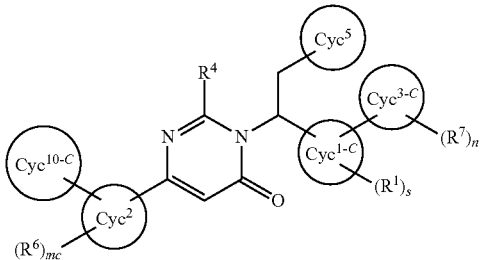
(I-C-3)

wherein all symbols have the same meanings as described above and the same preferred definitions as set out above (alone or in combination), a compound of (I-C-4):

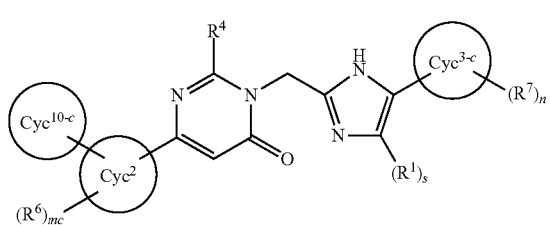
(I-C-4)

wherein s represents an integer of 0 to 1; and
the other symbols have the same meanings as described above and the same preferred definitions as set out above (alone or in combination), a compound of (I-C-5):

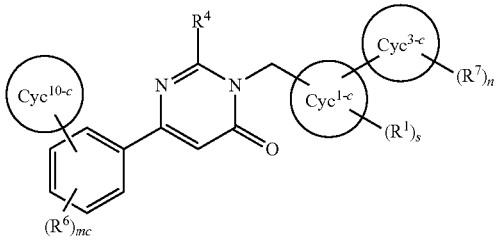
(I-C-5)

wherein mc represents an integer of 0 to 4; and
the other symbols have the same meanings as described above and the same preferred definitions as set out above (alone or in combination), a compound of (I-C-6):

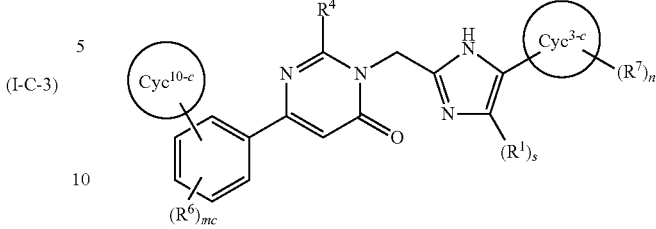
(I-C-6)

wherein s represents an integer 0 to 1;
mc represents an integer 0 to 4; and
the other symbols have the same meanings as described above and the same preferred definitions as set out above (alone or in combination), and the like.

As used herein, general references to "compounds of formula (I)" include compounds of formula (I-A), (I-B) and (I-C).

Particularly preferred compounds of formula (I) include:
4-(4-chloro-2-{(1S)-1-[4-(2,5-dichlorophenyl)-2-oxo-1 (2H)-pyridinyl]-2-phenylethyl}-1H-imidazol-5-yl)benzoic acid,
4-(2-{(1S)-1-[4-(2,5-dichlorophenyl)-2-oxo-1(2H)-pyridinyl]-2-phenylethyl}-1H-imidazol-5-yl)benzoic acid,
3-(4-chloro-2-{(1S)-1-[4-(2,5-dichlorophenyl)-2-oxo-1 (2H)-pyridinyl]-2-phenylethyl}-1H-imidazol-5-yl)benzoic acid,
3-{2-[(S)-[4-(2,5-dichlorophenyl)-2-oxo-1(2H)-pyridinyl] (phenyl)methyl]-1H-imidazol-5-yl}benzoic acid,
salts thereof, N-oxides thereof; solvates thereof, and prodrugs thereof.

Particularly preferred compounds of formula (I-A) include:
methyl[4-(2-{2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)phenyl]carbamate,
methyl[4-(2-{7-[5-chloro-2-(1H-tetrazol-1-yl)phenyl]-5-oxo-1,2,3,5-tetrahydro-3-indolizinyl}-1H-imidazol-4-yl) phenyl]carbamate,
methyl[4-(4-chloro-2-{7-[5-chloro-2-(1H-tetrazol-1-yl)phenyl]-5-oxo-1,2,3,5-tetrahydro-3-indolizinyl}-1H-imidazol-5-yl)phenyl]carbamate,
3-(4-chloro-2-{7-[5-chloro-2-(1H-tetrazol-1-yl)phenyl]-5-oxo-1,2,3,5-tetrahydro-3-indolizinyl}-1H-imidazol-5-yl) benzoic acid,
(3S)-7-[5-chloro-2-(1H-tetrazol-1-yl)phenyl]-3-(5-phenyl-1H-imidazol-2-yl)-2,3-dihydro-5(1H)-indolizinone,
methyl[4-(2-{7-[5-chloro-2-(1H-tetrazol-1-yl)phenyl]-5-oxo-1,2,3,5-tetrahydro-3-indolizinyl}-4-methyl-1H-imidazol-5-yl)phenyl]carbamate,
methyl[4-(2-{7-[5-chloro-2-(1H-tetrazol-1-yl)phenyl]-5-oxo-1,2,3,5-tetrahydro-3-indolizinyl}-4-ethyl-1H-imidazol-5-yl)phenyl]carbamate,
methyl(4-{2-[7-(5-chloro-2-formamidophenyl)-5-oxo-1,2,3,5-tetrahydro-3-indolizinyl]-4-ethyl-1H-imidazol-5-yl}phenyl)carbamate,
5-(2-{7-[5-chloro-2-(1H-tetrazol-1-yl)phenyl]-5-oxo-1,2,3,5-tetrahydro-3-indolizinyl}-1H-imidazol-4-yl)-1,3-dihydro-2H-indol-2-one,
6-(2-{7-[5-chloro-2-(1H-tetrazol-1-yl)phenyl]-5-oxo-1,2,3,5-tetrahydro-3-indolizinyl}-1H-imidazol-4-yl)-3,4-dihydro-2(1H)-quinolinone, 6-(4-chloro-2-{7-[5-chloro-2-(1H-tetrazol-1-yl)phenyl]-5-oxo-1,2,3,5-tetrahydro-3-indolizinyl}-1H-imidazol-5-yl)-3,4-dihydro-2(1H)-quinolinone, methyl[4-(2-{7-[5-chloro-2-(1H-tetrazol-1-yl)phenyl]-5-oxo-1,2,3,5-tetrahydro-3-indolizinyl}-1H-imidazol-5-yl)-2-fluorophenyl]carbamate, methyl[4-(4-chloro-2-{7-[5-chloro-2-(1H-tetrazol-1-yl)phenyl]-5-oxo-1,2,3,5-tetrahydro-3-indolizinyl}-1H-imidazol-5-yl)-2-fluorophenyl]carbamate, methyl[4-(2-{7-[5-chloro-2-(1H-tetrazol-1-yl)phenyl]-5-oxo-1,2,3,5-tetrahydro-3-indolizinyl}-1H-imidazol-5-yl)-3-fluorophenyl]carbamate, methyl[4-(4-chloro-2-{7-[5-chloro-2-(1H-tetrazol-1-yl)phenyl]-5-oxo-1,2,3,5-tetrahydro-3-indolizinyl}-1H-imidazol-5-yl)-3-fluorophenyl]carbamate, methyl[4-(2-{7-[5-chloro-2-(1H-tetrazol-1-yl)phenyl]-5-oxo-1,2,3,5-tetrahydro-3-indolizinyl}-1H-imidazol-5-yl)-3-methylphenyl]carbamate, methyl[4-(4-chloro-2-{7-[5-chloro-2-(1H-tetrazol-1-yl)phenyl]-5-oxo-1,2,3,5-tetrahydro-3-indolizinyl}-1H-imidazol-5-yl)-3-methylphenyl]carbamate, methyl[4-(2-{7-[5-chloro-2-(1H-tetrazol-1-yl)phenyl]-5-oxo-1,2,3,5-tetrahydro-3-indolizinyl}-1H-imidazol-5-yl)-3-ethylphenyl]carbamate, methyl[4-(4-chloro-2-{7-[5-chloro-2-(1H-tetrazol-1-yl)phenyl]-5-oxo-1,2,3,5-tetrahydro-3-indolizinyl}-1H-imidazol-5-yl)-3-ethylphenyl]carbamate, methyl[3-chloro-4-(2-{7-[5-chloro-2-(1H-tetrazol-1-yl)phenyl]-5-oxo-1,2,3,5-tetrahydro-3-indolizinyl}-1H-imidazol-5-yl)phenyl]carbamate, methyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)-3-methoxyphenyl]carbamate, methyl[2-bromo-4-(2-{(3S)-7-[5-chloro-2-(1H-tetrazol-1-yl)phenyl]-5-oxo-1,2,3,5-tetrahydro-3-indolizinyl}-1H-imidazol-5-yl)-5-methoxyphenyl]carbamate, methyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)-3-(trifluoromethyl)phenyl]carbamate, methyl[4-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-3-(trifluoromethyl)phenyl]carbamate, 4-(2-{7-[5-chloro-2-(1H-tetrazol-1-yl)phenyl]-5-oxo-1,2,3,5-tetrahydro-3-indolizinyl}-1H-imidazol-4-yl)benzoic acid, 4-(2-{7-[5-chloro-2-(1H-tetrazol-1-yl)phenyl]-5-oxo-1,2,3,5-tetrahydro-3-indolizinyl}-1H-imidazol-4-yl)benzamide, 4-(4-chloro-2-{7-[5-chloro-2-(1H-tetrazol-1-yl)phenyl]-5-oxo-1,2,3,5-tetrahydro-3-indolizinyl}-1H-imidazol-5-yl)benzamide, 4-(2-{7-[5-chloro-2-(1H-tetrazol-1-yl)phenyl]-5-oxo-1,2,3,5-tetrahydro-3-indolizinyl}-1H-imidazol-5-yl)-2-fluorobenzamide, 4-(2-{7-[5-chloro-2-(1H-tetrazol-1-yl)phenyl]-5-oxo-1,2,3,5-tetrahydro-3-indolizinyl}-1H-imidazol-4-yl)-N-methylbenzamide, 4-(5-chloro-2-{7-[5-chloro-2-(1H-tetrazol-1-yl)phenyl]-5-oxo-1,2,3,5-tetrahydro-3-indolizinyl}-1H-imidazol-4-yl)-N-methylbenzamide, 4-(2-{7-[5-chloro-2-(1H-tetrazol-1-yl)phenyl]-5-oxo-1,2,3,5-tetrahydro-3-indolizinyl}-1H-imidazol-4-yl)-N-ethylbenzamide, 4-(4-chloro-2-{7-[5-chloro-2-(1H-tetrazol-1-yl)phenyl]-5-oxo-1,2,3,5-tetrahydro-3-indolizinyl}-1H-imidazol-5-yl)-N-ethylbenzamide, 7-[5-chloro-2-(1H-tetrazol-1-yl)phenyl]-3-[5-(4-nitrophenyl)-1H-imidazol-2-yl]-2,3-dihydro-5(1H)-indolizinone, 3-[5-(4-aminophenyl)-1H-imidazol-2-yl]-7-[5-chloro-2-(1H-tetrazol-1-yl)phenyl]-2,3-dihydro-5(1H)-indolizinone, ethyl[4-(2-{7-[5-chloro-2-(1H-tetrazol-1-yl)phenyl]-5-oxo-1,2,3,5-tetrahydro-3-indolizinyl}-1H-imidazol-5-yl)phenyl]carbamate, isopropyl[4-(2-{7-[5-chloro-2-(1H-tetrazol-1-yl)phenyl]-5-oxo-1,2,3,5-tetrahydro-3-indolizinyl}-1H-imidazol-5-yl)phenyl]carbamate, 2-methoxyethyl[4-(2-{7-[5-chloro-2-(1H-tetrazol-1-yl)phenyl]-5-oxo-1,2,3,5-tetrahydro-3-indolizinyl}-1H-imidazol-5-yl)phenyl]carbamate, N-[4-(2-{7-[5-chloro-2-(1H-tetrazol-1-yl)phenyl]-5-oxo-1,2,3,5-tetrahydro-3-indolizinyl}-1H-imidazol-5-yl)phenyl]acetamide, N-[4-(2-{7-[5-chloro-2-(1H-tetrazol-1-yl)phenyl]-5-oxo-1,2,3,5-tetrahydro-3-indolizinyl}-1H-imidazol-5-yl)phenyl]-2-methoxyacetamide, N-[4-(2-{7-[5-chloro-2-(1H-tetrazol-1-yl)phenyl]-5-oxo-1,2,3,5-tetrahydro-3-indolizinyl}-1H-imidazol-5-yl)phenyl]-3-methoxypropanamide, N-[4-(2-{7-[5-chloro-2-(1H-tetrazol-1-yl)phenyl]-5-oxo-1,2,3,5-tetrahydro-3-indolizinyl}-1H-imidazol-5-yl)phenyl]methanesulfonamide, ethyl[4-(4-chloro-2-{7-[5-chloro-2-(1H-tetrazol-1-yl)phenyl]-5-oxo-1,2,3,5-tetrahydro-3-indolizinyl}-1H-imidazol-5-yl)phenyl]carbamate, isopropyl[4-(4-chloro-2-{7-[5-chloro-2-(1H-tetrazol-1-yl)phenyl]-5-oxo-1,2,3,5-tetrahydro-3-indolizinyl}-1H-imidazol-5-yl)phenyl]carbamate, N-[4-(4-chloro-2-{7-[5-chloro-2-(1H-tetrazol-1-yl)phenyl]-5-oxo-1,2,3,5-tetrahydro-3-indolizinyl}-1H-imidazol-5-yl)phenyl]acetamide, N-[4-(4-chloro-2-{7-[5-chloro-2-(1H-tetrazol-1-yl)phenyl]-5-oxo-1,2,3,5-tetrahydro-3-indolizinyl}-1H-imidazol-5-yl)phenyl]methanesulfonamide, 1-[4-(2-{7-[5-chloro-2-(1H-tetrazol-1-yl)phenyl]-5-oxo-1,2,3,5-tetrahydro-3-indolizinyl}-1H-imidazol-5-yl)phenyl]-3-ethylurea, 3-[4-(2-{7-[5-chloro-2-(1H-tetrazol-1-yl)phenyl]-5-oxo-1,2,3,5-tetrahydro-3-indolizinyl}-1H-imidazol-5-yl)phenyl]-1,1-dimethylurea, N-[4-(2-{7-[5-chloro-2-(1H-tetrazol-1-yl)phenyl]-5-oxo-1,2,3,5-tetrahydro-3-indolizinyl}-1H-imidazol-5-yl)phenyl]-2-(dimethylamino)acetamide, 3-{[4-(2-{7-[5-chloro-2-(1H-tetrazol-1-yl)phenyl]-5-oxo-1,2,3,5-tetrahydro-3-indolizinyl}-1H-imidazol-5-yl)phenyl]amino-3-oxopropanoic acid, 6-(2-{7-[5-chloro-2-(1H-tetrazol-1-yl)phenyl]-5-oxo-1,2,3,5-tetrahydro-3-indolizinyl}-1H-imidazol-5-yl)-4-hydroxy-2(1H)-quinolinone, 4-(2-{7-[5-chloro-2-(1H-tetrazol-1-yl)phenyl]-5-oxo-1,2,3,5-tetrahydro-3-indolizinyl}-1H-imidazol-5-yl)-2-fluorobenzonitrile, 3-[5-(3-amino-1H-indazol-6-yl)-1H-imidazol-2-yl]-7-[5-chloro-2-(1H-tetrazol-1-yl)phenyl]-2,3-dihydro-5(1H)-indolizinone, 7-(2-{7-[5-chloro-2-(1H-tetrazol-1-yl)phenyl]-5-oxo-1,2,3,5-tetrahydro-3-indolizinyl}-1H-imidazol-5-yl)-2H-1,4-benzoxazin-3(4H)-one, 7-(2-{(3S)-7-[5-chloro-2-(1H-tetrazol-1-yl)phenyl]-5-oxo-1,2,3,5-tetrahydro-3-indolizinyl}-1H-imidazol-5-yl)-4-methyl-2H-1,4-benzoxazin-3(4H)-one, 7-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-4-methyl-2H-1,4-benzoxazin-3(4H)-one, 6-(2-{7-[5-chloro-2-(1H-tetrazol-1-yl)phenyl]-5-oxo-1,2,3,5-tetrahydro-3-indolizinyl}-1H-imidazol-5-yl)-1,4-dihydro-2H-3,1-benzoxazin-2-one, 6-(4-chloro-2-{7-[5-chloro-2-(1H-tetrazol-1-yl)phenyl]-5-oxo-1,2,3,5-tetrahydro-3-indolizinyl}-1H-imidazol-5-yl)-1,4-dihydro-2H-3,1-benzoxazin-2-one, 6-(2-{7-[5-chloro-2-(1H-tetrazol-1-yl)phenyl]-5-oxo-1,2,3,5-tetrahydro-3-indolizinyl}-1H-imidazol-5-yl)-1,3-benzoxazol-2(3H)-one, 6-(4-chloro-2-{7-[5-chloro-2-(1H-tetrazol-1-yl)phenyl]-5-oxo-1,2,3,5-tetrahydro-3-indolizinyl}-1H-imidazol-5-yl)-1,3-benzoxazol-2(3H)-one, 6-(2-{7-[5-chloro-2-(1H-tetrazol-1-yl)phenyl]-5-oxo-1,2,3,5-tetrahydro-3-indolizinyl}-1H-imidazol-5-yl)-1-isoindolinone, 6-(2-{(3S)-7-[5-chloro-2-(1H-tetrazol-1-yl)phenyl]-5-oxo-1,2,3,5-tetrahydro-3-indolizinyl}-1H-imidazol-5-yl)-3-methyl-3,4-dihydro-2(1H)-quinazolinone, 6-(2-{7-[5-chloro-2-(1H-tetrazol-1-yl)phenyl]-5-oxo-1,2,3,5-tetrahydro-3-indolizinyl}-1H-imidazol-5-yl)-2(1H)-quinoxalinone, (3S)-7-[5-chloro-2-(1H-tetrazol-1-yl)phenyl]-3-[5-(1-methyl-1H-benzimidazol-5-yl)-1H-imidazol-2-yl]-2,3-dihydro-5(1H)-indolizinone, 3-[4-chloro-5-(1-methyl-1H-benzimidazol-5-yl)-1H-imidazol-2-yl]-7-[5-chloro-2-(1H-tetrazol-1-yl)phenyl]-2,3-dihydro-5(1H)-indolizinone, (3S)-7-[5-chloro-2-(1H-tetrazol-1-yl)phenyl]-3-[5-(1H-indazol-5-yl)-1H-imidazol-2-yl]-2,3-dihydro-5(1H)-indolizinone, 7-[5-chloro-2-(1H-tetrazol-1-yl)phenyl]-3-{5-[4-(hydroxymethyl)phenyl]-1H-imidazol-2-yl}-2,3-dihydro-5(1H)-indolizinone, 4-(2-{7-[5-chloro-2-(1H-tetrazol-1-yl)phenyl]-5-oxo-1,2,3,5-tetrahydro-3-indolizinyl}-1H-imidazol-5-yl)benzyl acetate, 4-(2-{(3S)-7-[5-chloro-2-(1H-tetrazol-1-yl)phenyl]-5-oxo-1,2,3,5-tetrahydro-3-indolizinyl}-1H-imidazol-5-yl)benzaldehyde oxime, 4-(2-{(3S)-7-[5-chloro-2-(1H-tetrazol-1-yl)phenyl]-5-oxo-1,2,3,5-tetrahydro-3-indolizinyl}-1H-imidazol-5-yl)benzaldehyde O-methyloxime, (3S)-3-[5-(4-acetylphenyl)-1H-imidazol-2-yl]-7-[5-chloro-2-(1H-tetrazol-1-yl)phenyl]-2,3-dihydro-5(1H)-indolizinone, (3S)-7-[5-chloro-2-(1H-tetrazol-1-yl)phenyl]-3-{5-[4-(1-hydroxyethyl)phenyl]-1H-imidazol-2-yl}-2,3-dihydro-5(1H)-indolizinone, 2-methyl-2-propanyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)benzyl]carbamate, (3S)-3-{5-[4-(aminomethyl)phenyl]-1H-imidazol-2-yl}-7-[5-chloro-2-(1H-tetrazol-1-yl)phenyl]-2,3-dihydro-5(1H)-indolizinone, methyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)benzyl]carbamate, N-[4-(2-{(3S)-7-[5-chloro-2-(1H-tetrazol-1-yl)phenyl]-5-oxo-1,2,3,5-tetrahydro-3-indolizinyl}-1H-imidazol-5-yl)benzyl]acetamide, N-[4-(2-{(3S)-7-[5-chloro-2-(1H-tetrazol-1-yl)phenyl]-5-oxo-1,2,3,5-tetrahydro-3-indolizinyl}-1H-imidazol-5-yl)benzyl]-2,2,2-trifluoroacetamide, 1-[4-(2-{(3S)-7-[5-chloro-2-(1H-tetrazol-1-yl)phenyl]-5-oxo-1,2,3,5-tetrahydro-3-indolizinyl}-1H-imidazol-5-yl)benzyl]-3-ethylurea, (3S)-7-[5-chloro-2-(1H-tetrazol-1-yl)phenyl]-3-[5-(4-pyridinyl)-1H-imidazol-2-yl]-2,3-dihydro-5(1H)-indolizinone, (3S)-7-[5-chloro-2-(1H-tetrazol-1-yl)phenyl]-3-[5-(3-pyridinyl)-1H-imidazol-2-yl]-2,3-dihydro-5(1H)-indolizinone, (3S)-7-[5-chloro-2-(1H-tetrazol-1-yl)phenyl]-3-[5-(2-pyridinyl)-1H-imidazol-2-yl]-2,3-dihydro-5(1H)-indolizinone, (3S)-7-[5-chloro-2-(1H-tetrazol-1-yl)phenyl]-3-[5-(1,3-thiazol-2-yl)-1H-imidazol-2-yl]-2,3-dihydro-5(1H)-indolizinone, (3S)-7-[5-chloro-2-(1H-tetrazol-1-yl)phenyl]-3-[5-(2-pyrazinyl)-1H-imidazol-2-yl]-2,3-dihydro-5(1H)-indolizinone, (3S)-7-[5-chloro-2-(1H-tetrazol-1-yl)phenyl]-3-[5-(2-methoxyphenyl)-1H-imidazol-2-yl]-2,3-dihydro-5(1H)-indolizinone, (3S)-7-[5-chloro-2-(1H-tetrazol-1-yl)phenyl]-3-[5-(3-methoxyphenyl)-1H-imidazol-2-yl]-2,3-dihydro-5(1H)-indolizinone, (3S)-7-[5-chloro-2-(1H-tetrazol-1-yl)phenyl]-3-[5-(4-methoxyphenyl)-1H-imidazol-2-yl]-2,3-dihydro-5(1H)-indolizinone, (3S)-7-[5-chloro-2-(1H-tetrazol-1-yl)phenyl]-3-[5-(3-fluorophenyl)-1H-imidazol-2-yl]-2,3-dihydro-5(1H)-indolizinone, (3S)-7-[5-chloro-2-(1H-tetrazol-1-yl)phenyl]-3-[5-(4-fluorophenyl)-1H-imidazol-2-yl]-2,3-dihydro-5(1H)-indolizinone, (3S)-7-[5-chloro-2-(1H-tetrazol-1-yl)phenyl]-3-[5-(2,4-dimethyl-1,3-oxazol-5-yl)-1H-imidazol-2-yl]-2,3-dihydro-5(1H)-indolizinone, (3S)-7-[5-chloro-2-(1H-tetrazol-1-yl)phenyl]-3-[5-(1-methyl-1H-pyrazol-4-yl)-1H-imidazol-2-yl]-2,3-dihydro-5(1H)-indolizinone, methyl[5-(2-{7-[5-chloro-2-(1H-tetrazol-1-yl)phenyl]-5-oxo-1,2,3,5-tetrahydro-3-indolizinyl}-1H-imidazol-5-yl)-2-thienyl]carbamate, 2-methyl-2-propanyl[trans-4-(2-{(3S)-7-[5-chloro-2-(1H-tetrazol-1-yl)phenyl]-5-oxo-1,2,3,5-tetrahydro-3-indolizinyl}-1H-imidazol-5-yl)cyclohexyl]carbamate, (3S)-3-[5-(trans-4-aminocyclohexyl)-1H-imidazol-2-yl]-7-[5-chloro-2-(1H-tetrazol-1-yl)phenyl]-2,3-dihydro-5(1H)-indolizinone, methyl[trans-4-(2-{(3S)-7-[5-chloro-2-(1H-tetrazol-1-yl)phenyl]-5-oxo-1,2,3,5-tetrahydro-3-indolizinyl}-1H-imidazol-5-yl)cyclohexyl]carbamate, (3S)-3-[5-(trans-4-aminocyclohexyl)-4-chloro-1H-imidazol-2-yl]-7-[5-chloro-2-(1H-tetrazol-1-yl)phenyl]-2,3-dihydro-5(1H)-indolizinone, (3S)-3-[5-(2-amino-4-pyridinyl)-1H-imidazol-2-yl]-7-[5-chloro-2-(1H-tetrazol-1-yl)phenyl]-2,3-dihydro-5(1H)-indolizinone, 3-[4-(6-amino-3-pyridinyl)-1H-imidazol-2-yl]-7-[5-chloro-2-(1H-tetrazol-1-yl)phenyl]-2,3-dihydro-5(1H)-indolizinone, methyl[5-(2-{(3S)-7-[5-chloro-2-(1H-tetrazol-1-yl)phenyl]-5-oxo-1,2,3,5-tetrahydro-3-indolizinyl}-1H-imidazol-5-yl)-2-pyridinyl]carbamate, methyl[5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-pyridinyl]carbamate, ethyl[5-(2-{(3S)-7-[5-chloro-2-(1H-tetrazol-1-yl)phenyl]-5-oxo-1,2,3,5-tetrahydro-3-indolizinyl}-1H-imidazol-5-yl)-2-pyridinyl]carbamate, (3S)-3-[5-(6-amino-3-pyridinyl)-4-chloro-1H-imidazol-2-yl]-7-[5-chloro-2-(1H-tetrazol-1-yl)phenyl]-2,3-dihydro-5(1H)-indolizinone, (3S)-3-[5-(6-amino-3-pyridinyl)-4-methyl-1H-imidazol-2-yl]-7-[5-chloro-2-(1H-tetrazol-1-yl)phenyl]-2,3-dihydro-5(1H)-indolizinone, methyl[5-(2-{(3S)-7-[5-chloro-2-(1H-tetrazol-1-yl)phenyl]-5-oxo-1,2,3,5-tetrahydro-3-indolizinyl}-4-methyl-1H-imidazol-5-yl)-2-pyridinyl]carbamate, (3S)-3-[5-(6-amino-2-chloro-3-pyridinyl)-1H-imidazol-2-yl]-7-[5-chloro-2-(1H-tetrazol-1-yl)phenyl]-2,3-dihydro-5(1H)-indolizinone, (3S)-3-[5-(6-amino-2-methyl-3-pyridinyl)-1H-imidazol-2-yl]-7-[5-chloro-2-(1H-tetrazol-1-yl)phenyl]-2,3-dihydro-5(1H)-indolizinone, methyl[5-(2-{(3S)-7-[5-chloro-2-(1H-tetrazol-1-yl)phenyl]-5-oxo-1,2,3,5-tetrahydro-3-indolizinyl}-1H-imidazol-5-yl)-6-methyl-2-pyridinyl]carbamate, (3S)-3-[5-(6-amino-2-fluoro-3-pyridinyl)-1H-imidazol-2-yl]-7-[5-chloro-2-(1H-tetrazol-1-yl)phenyl]-2,3-dihydro-5(1H)-indolizinone, (3S)-7-[5-chloro-2-(1H-tetrazol-1-yl)phenyl]-3-[5-(6-methyl-3-pyridinyl)-1H-imidazol-2-yl]-2,3-dihydro-5(1H)-indolizinone, (3S)-3-[4-chloro-5-(6-methyl-3-pyridinyl)-1H-imidazol-2-yl]-7-[5-chloro-2-(1H-tetrazol-1-yl)phenyl]-2,3-dihydro-5(1H)-indolizinone, 2-methyl-2-propanyl[6-(2-{7-[5-chloro-2-(1H-tetrazol-1-yl)phenyl]-5-oxo-1,2,3,5-tetrahydro-3-indolizinyl}-1H-imidazol-5-yl)-3-pyridinyl]carbamate, 3-[5-(5-amino-2-pyridinyl)-1H-imidazol-2-yl]-7-[5-chloro-2-(1H-tetrazol-1-yl)phenyl]-2,3-dihydro-5(1H)-indolizinone, 3-[5-(5-amino-2-pyridinyl)-4-chloro-1H-imidazol-2-yl]-7-[5-chloro-2-(1H-tetrazol-1-yl)phenyl]-2,3-dihydro-5(1H)-indolizinone, methyl[6-(2-(7-[5-chloro-2-(1H-tetrazol-1-yl)phenyl]-5-oxo-1,2,3,5-tetrahydro-3-indolizinyl}-1H-imidazol-5-yl)-3-pyridinyl]carbamate, methyl[6-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-3-pyridinyl]carbamate, isopropyl[6-(2-{(3S)-7-[5-chloro-2-(1H-tetrazol-1-yl)phenyl]-5-oxo-1,2,3,5-tetrahydro-3-indolizinyl}-1H-imidazol-5-yl)-3-pyridinyl]carbamate, isobutyl[6-(2-{(3S)-7-[5-chloro-2-(1H-tetrazol-1-yl)phenyl]-5-oxo-1,2,3,5-tetrahydro-3-indolizinyl}-1H-imidazol-5-yl)-3-pyridinyl]carbamate, N-[6-(2-{(3S)-7-[5-chloro-2-(1H-tetrazol-1-yl)phenyl]-5-oxo-1,2,3,5-tetrahydro-3-indolizinyl}-1H-imidazol-5-yl)-3-pyridinyl]acetamide, (3S)-3-[5-(5-amino-2-pyridinyl)-4-methyl-1H-imidazol-2-yl]-7-[5-chloro-2-(1H-tetrazol-1-yl)phenyl]-2,3-dihydro-5(1H)-indolizinone, N-[6-(2-{(3S)-7-[5-chloro-2-(1H-tetrazol-1-yl)phenyl]-5-oxo-1,2,3,5-tetrahydro-3-indolizinyl}-4-methyl-1H-imidazol-5-yl)-3-pyridinyl]acetamide, methyl[6-(2-{(3S)-7-[5-chloro-2-(1H-tetrazol-1-yl)phenyl]-5-oxo-1,2,3,5-tetrahydro-3-indolizinyl}-4-methyl-1H-imidazol-5-yl)-3-pyridinyl]carbamate, (3S)-3-[5-(2-amino-1,3-thiazol-5-yl)-1H-imidazol-2-yl]-7-[5-chloro-2-(1H-tetrazol-1-yl)phenyl]-2,3-dihydro-5(1H)-indolizinone, (3S)-3-[5-(1-amino-6-isoquinolinyl)-1H-imidazol-2-yl]-7-[5-chloro-2-(1H-tetrazol-1-yl)phenyl]-2,3-dihydro-5(1H)-indolizinone, methyl[4-(5-{7-[5-chloro-2-(1H-tetrazol-1-yl)phenyl]-5-oxo-1,2,3,5-tetrahydro-3-indolizinyl}-1H-imidazol-2-yl)phenyl]carbamate, methyl[4-(4-chloro-5-{7-[5-chloro-2-(1H-tetrazol-1-yl)phenyl]-5-oxo-1,2,3,5-tetrahydro-3-indolizinyl}-1H-imidazol-2-yl)phenyl]carbamate, 3-[5-(4-aminophenyl)-4H-1,2,4-triazol-3-yl]-7-[5-chloro-2-(1H-tetrazol-1-yl)phenyl]-2,3-dihydro-5(1H)-indolizinone, methyl[4-(5-{7-[5-chloro-2-(1H-tetrazol-1-yl)phenyl]-5-oxo-1,2,3,5-tetrahydro-3-indolizinyl}-4H-1,2,4-triazol-3-yl)phenyl]carbamate, methyl[4-(6-{7-[5-chloro-2-(1H-tetrazol-1-yl)phenyl]-5-oxo-1,2,3,5-tetrahydro-3-indolizinyl}-3-oxo-2,3-dihydro-4-pyridazinyl)phenyl]carbamate, methyl[4-(4-{7-[5-chloro-2-(1H-tetrazol-1-yl)phenyl]-5-oxo-1,2,3,5-tetrahydro-3-indolizinyl}-1H-1,2,3-triazol-1-yl)phenyl]carbamate, methyl[4-(5-{7-[5-chloro-2-(1H-tetrazol-1-yl)phenyl]-5-oxo-1,2,3,5-tetrahydro-3-indolizinyl}-1,2-oxazol-3-yl)phenyl]carbamate, methyl[4-(2-{(3S)-7-[5-chloro-2-(1H-tetrazol-1-yl)phenyl]-5-oxo-1,2,3,5-tetrahydro-3-indolizinyl}-1H-imidazol-4-yl)phenyl]carbamate, methyl[4-(2-{(3R)-7-[5-chloro-2-(1H-tetrazol-1-yl)phenyl]-5-oxo-2,3-dihydro-5H-[1,3]thiazolo[3,2-a]pyridin-3-yl}-1H-imidazol-5-yl)phenyl]carbamate, methyl[3-chloro-4-(2-{(3S)-7-[5-chloro-2-(1H-tetrazol-1-yl)phenyl]-5-oxo-1,2,3,5-tetrahydro-3-indolizinyl}-1H-imidazol-4-yl)phenyl]carbamate, 6-(2-{(3S)-7-[5-chloro-2-(1H-tetrazol-1-yl)phenyl]-5-oxo-1,2,3,5-tetrahydro-3-indolizinyl}-1H-imidazol-5-yl)-3,4-dihydro-2(1H)-quinolinone, ethyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate, 4-(2-{(3S)-7-[5-chloro-2-(1H-tetrazol-1-yl)phenyl]-5-oxo-1,2,3,5-tetrahydro-3-indolizinyl}-1H-imidazol-5-yl)benzamide, 4-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)benzamide, methyl[4-(2-{(3R)-7-[5-chloro-2-(1H-tetrazol-1-yl)phenyl]-5-oxo-1,2,3,5-tetrahydro-3-indolizinyl}-1H-imidazol-5-yl)phenyl]carbamate, methyl[4-(2-{(3S)-7-[5-chloro-2-(1H-tetrazol-1-yl)phenyl]-5-oxo-1,2,3,5-tetrahydro-3-indolizinyl}-5-methyl-1H-imidazol-4-yl)phenyl]carbamate, methyl[4-(2-{(3S)-7-[5-chloro-2-(1H-tetrazol-1-yl)phenyl]-5-oxo-1,2,3,5-tetrahydro-3-indolizinyl}-5-methyl-1,3-oxazol-4-yl)phenyl]carbamate, 2-methyl-2-propanyl 1-{4-chloro-2-[(3S)-3-(5-{4-[(methoxycarbonyl)amino]phenyl}-1H-imidazol-2-yl)-5-oxo-1,2,3,5-tetrahydro-7-indolizinyl]phenyl}-1H-1,2,3-triazole-4-carboxylate, methyl 1-{4-chloro-2-[(3S)-3-(5-{4-[(methoxycarbonyl)amino]phenyl}-1H-imidazol-2-yl)-5-oxo-1,2,3,5-tetrahydro-7-indolizinyl]phenyl}-1H-1,2,3-triazole-4-carboxylate, 1-{4-chloro-2-[(3S)-3-(5-{4-[(methoxycarbonyl)amino]phenyl}-1H-imidazol-2-yl)-5-oxo-1,2,3,5-tetrahydro-7-indolizinyl]phenyl}-1H-1,2,3-triazole-4-carboxylic acid, methyl[4-(2-{(3S)-7-[2-(4-carbamoyl-1H-1,2,3-triazol-1-yl)-5-chlorophenyl]-5-oxo-1,2,3,5-tetrahydro-3-indolizinyl}-1H-imidazol-5-yl)phenyl]carbamate, methyl[4-(2-{(3S)-7-[5-chloro-2-(4-cyano-1H-1,2,3-triazol-1-yl)phenyl]-5-oxo-1,2,3,5-tetrahydro-3-indolizinyl}-1H-imidazol-5-yl)phenyl]carbamate, methyl[4-(2-{(3S)-7-[5-chloro-2-(3-hydroxy-1H-1,2,4-triazol-1-yl)phenyl]-5-oxo-1,2,3,5-tetrahydro-3-indolizinyl}-1H-imidazol-5-yl)phenyl]carbamate, methyl[4-(2-{(3S)-7-[5-methyl-2-(1H-tetrazol-1-yl)-3-pyridinyl]-5-oxo-1,2,3,5-tetrahydro-3-indolizinyl}-1H-imidazol-5-yl)phenyl]carbamate, methyl[4-(2-{(3S)-7-[5-methyl-2-(1H-tetrazol-1-yl)phenyl]-5-oxo-1,2,3,5-tetrahydro-3-indolizinyl}-1H-imidazol-5-yl)phenyl]carbamate, methyl[4-(2-{(3S)-7-[5-chloro-2-(4-chloro-1H-1,2,3-triazol-1-yl)phenyl]-5-oxo-1,2,3,5-tetrahydro-3-indolizinyl}-1H-imidazol-5-yl)phenyl]carbamate, methyl[4-(2-{(3S)-7-[5-fluoro-2-(1H-tetrazol-1-yl)phenyl]-5-oxo-1,2,3,5-tetrahydro-3-indolizinyl}-1H-imidazol-5-yl)phenyl]carbamate, methyl[4-(2-{(3S)-5-oxo-7-[2-(1H-tetrazol-1-yl)-5-(trifluoromethyl)phenyl]-1,2,3,5-tetrahydro-3-indolizinyl}-1H-imidazol-5-yl)phenyl]carbamate, (6S)-6-[5-(6-amino-2-fluoro-3-pyridinyl)-1H-imidazol-2-yl]-2-[5-chloro-2-(1H-tetrazol-1-yl)phenyl]-7,8-dihydropyrrolo[1,2-a]pyrimidin-4(6H)-one, (6S)-6-[5-(6-amino-3-pyridinyl)-4-chloro-1H-imidazol-2-yl]-2-[5-chloro-2-(1H-tetrazol-1-yl)phenyl]-7,8-dihydropyrrolo[1,2-a]pyrimidin-4(6H)-one, (6S)-6-[5-(6-amino-2-chloro-3-pyridinyl)-1H-imidazol-2-yl]-2-[5-chloro-2-(1H-tetrazol-1-yl)phenyl]-7,8-dihydropyrrolo[1,2-a]pyrimidin-4(6H)-one, 2-methoxyethyl[6-(4-chloro-2-{(6S)-2-[5-chloro-2-(1H-tetrazol-1-yl)phenyl]-4-oxo-4,6,7,8-tetrahydropyrrolo-1H-imidazol-5-yl)-3-pyridinyl]carbamate, 3-(2-{(3S)-7-[5-chloro-2-(1H-tetrazol-1-yl)phenyl]-5-oxo-1,2,3,5-tetrahydro-3 indolizinyl}-1H-imidazol-5-yl)benzoic acid, 3-(4-chloro-2-(3S)-7-[5-chloro-2-(1H-tetrazol-1-yl)phenyl]-5-oxo-1,2,3,5-tetrahydro-3-indolizinyl}-1H-imidazol-5-yl)benzoic acid, methyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]acetate,

[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]acetic acid,

[4-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)phenyl]acetic acid,

[3-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]acetic acid,

[3-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)phenyl]acetic acid, 5-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylic acid, 5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylic acid, 5-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxamide, 5-(2-{(3S)-7-[5-chloro-2-(1H-tetrazol-1-yl)phenyl]-5-oxo-1,2,3,5-tetrahydro-3-indolizinyl}-1H-imidazol-5-yl)-N-methyl-2-thiophenecarboxamide, 5-(2-{(3S)-7-[5-chloro-2-(1H-tetrazol-1-yl)phenyl]-5-oxo-1,2,3,5-tetrahydro-3-indolizinyl}-1H-imidazol-5-yl)-N-ethyl-2-thiophenecarboxamide, 5-(2-{(3S)-7-[5-chloro-2-(1H-tetrazol-1-yl)phenyl]-5-oxo-1,2,3,5-tetrahydro-3-indolizinyl}-1H-imidazol-5-yl)-N,N-dimethyl-2-thiophenecarboxamide, 5-(2-{(3S)-7-[5-chloro-2-(1H-tetrazol-1-yl)phenyl]-5-oxo-1,2,3,5-tetrahydro-3-indolizinyl}-1H-imidazol-5-yl)-N-(2-methoxyethyl)-2-thiophenecarboxamide, 5-(2-{(3S)-7-[5-chloro-2-(1H-tetrazol-1-yl)phenyl]-5-oxo-1,2,3,5-tetrahydro-3-indolizinyl}-1H-imidazol-5-yl)-N-[2-(2-methoxyethoxyl)ethyl]-2-thiophenecarboxamide, 5-(2-{(3S)-7-[5-chloro-2-(1H-tetrazol-1-yl)phenyl]-5-oxo-1,2,3,5-tetrahydro-3-indolizinyl}-1H-imidazol-5-yl)-N-[2-(4-morpholinyl)ethyl]-2-thiophenecarboxamide, 5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxamide, 5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-N-methyl-2-thiophenecarboxamide, 5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-N-ethyl-2-thiophenecarboxamide, 5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-N,N-dimethyl-2-thiophenecarboxamide, 5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-N-(2-methoxyethyl)-2-thiophenecarboxamide, 5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-N-[2-(2-methoxyethoxy)ethyl]-2-thiophenecarboxamide, 5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-N-[2-(4-morpholinyl)ethyl]-2-thiophenecarboxamide, 5-(2-{(3S)-7-[5-chloro-2-(1H-tetrazol-1-yl)phenyl]-5-oxo-1,2,3,5-tetrahydro-3-indolizinyl}-1H-imidazol-5-yl)-N-methoxy-2-thiophenecarboxamide, 5-(2-{(3S)-7-[5-chloro-2-(1H-tetrazol-1-yl)phenyl]-5-oxo-1,2,3,5-tetrahydro-3-indolizinyl}-1H-imidazol-5-yl)-N-cyano-2-thiophenecarboxamide, 2-(4-morpholinyl)ethyl 5-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylate, 5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-N-methoxy-2-thiophenecarboxamide, 5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-N-cyano-2-thiophenecarboxamide, 2-(4-morpholinyl)ethyl 5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylate, methyl[5-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thienyl]acetate,

[5-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thienyl]acetic acid, methyl[5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-thienyl]acetate,

[5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-thienyl]acetic acid, 2-methyl-2-propanyl 4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylate, 4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylic acid, 4-(2-{(3S)-7-[5-chloro-2-(1H-tetrazol-1-yl)phenyl]-5-oxo-1,2,3,5-tetrahydro-3-indolizinyl}-4-fluoro-1H-imidazol-5-yl)-2-thiophenecarboxylic acid, 4-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylic acid, ethyl 4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylate, isopropyl 4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylate, 3-methylbutyl 4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylate, 2-(4-morpholinyl)ethyl 4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylate, (5-methyl-2-oxo-1,3-dioxol-4-yl)methyl 4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylate, phenyl 4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylate, 2,3-dihydro-1H-inden-5-yl 4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylate, isobutyl 4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylate, 2-(dimethylamino)-2-oxoethyl 4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylate, 4-(2-{(3S)-7-[5-chloro-2-(1H-tetrazol-1-yl)phenyl]-5-oxo-1,2,3,5-tetrahydro-3-indolizinyl}-1H-imidazol-5-yl)-N,N-dimethyl-2-thiophenecarboxamide, methyl 4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylate, (3S)-7-[5-chloro-2-(1H-1-tetrazol-1-yl)phenyl]-3-{5-[5-(hydroxymethyl)-3-thienyl]-1H-imidazol-2-yl}-2,3-dihydro-5(1H)-indolizinone,

[(2,2-dimethylpropanoyl)oxy]methyl 4-(2-{(3S)-7-[5-chloro-2-(1H-1-tetrazol-1-yl)phenyl]-5-oxo-1,2,3,5-tetrahydro-3-indolizinyl}-1H-imidazol-5-yl)-2-thiophenecarboxylate, 5-(2-{7-[5-methyl-2-(1H-tetrazol-1-yl)phenyl]-5-oxo-1,2,3,5-tetrahydro-3-indolizinyl}-1H-imidazol-5-yl)-2-thiophenecarboxylic acid, 5-(4-chloro-2-{7-[5-methyl-2-(1H-tetrazol-1-yl)phenyl]-5-oxo-1,2,3,5-tetrahydro-3-indolizinyl}-1H-imidazol-5-yl)-2-thiophenecarboxylic acid, 5-(2-{(3S)-7-[5-chloro-2-(1H-tetrazol-1-yl)phenyl]-5-oxo-1,2,3,5-tetrahydro-3-indolizinyl}-1H-imidazol-5-yl)-1H-indole-3-carboxylic acid, 5-(2-{(3S)-7-[5-chloro-2-(1H-tetrazol-1-yl)phenyl]-5-oxo-1,2,3,5-tetrahydro-3-indolizinyl}-1H-imidazol-5-yl)-1H-indazole-3-carboxylic acid, 4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-pyridinecarboxylic acid, 4-(2-{(3S)-8-chloro-7-[5-chloro-2-(1H-tetrazol-1-yl)phenyl]-5-oxo-1,2,3,5-tetrahydro-3-indolizinyl}-1H-imidazol-5-yl)-2-pyridinecarboxylic acid, 5-(2-{(3S)-8-chloro-7-[5-chloro-2-(1H-tetrazol-1-yl)phenyl]-5-oxo-1,2,3,5-tetrahydro-3-indolizinyl}-1H-imidazol-5-yl)-2-thiophenecarboxylic acid, 5-(4-chloro-2-{(3S)-8-chloro-7-[5-chloro-2-(1H-tetrazol-1-yl)phenyl]-5-oxo-1,2,3,5-tetrahydro-3-indolizinyl}-1H-imidazol-5-yl)-2-thiophenecarboxylic acid, 5-(4-chloro-2-{(3S)-6-chloro-7-[5-chloro-2-(1H-tetrazol-1-yl)phenyl]-5-oxo-1,2,3,5-tetrahydro-3-indolizinyl}-1H-imidazol-5-yl)-2-thiophenecarboxylic acid, 5-(2-{(3S)-6,8-dichloro-7-[5-chloro-2-(1H-tetrazol-1-yl)phenyl]-5-oxo-1,2,3,5-tetrahydro-3-indolizinyl}-1H-imidazol-5-yl)-2-thiophenecarboxylic acid, 4-(2-{(3S)-8-chloro-7-[5-chloro-2-(1H-tetrazol-1-yl)phenyl]-5-oxo-1,2,3,5-tetrahydro-3-indolizinyl}-1H-imidazol-5-yl)-2-thiophenecarboxylic acid, 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-thiophenecarboxylic acid, 4-(2-{(3S)-8-bromo-7-[5-chloro-2-(1H-tetrazol-1-yl)phenyl]-5-oxo-1,2,3,5-tetrahydro-3-indolizinyl}-1H-imidazol-5-yl)-2-thiophenecarboxylic acid, (2E)-3-[3-(2-{7-[5-chloro-2-(1H-tetrazol-1-yl)phenyl]-5-oxo-1,2,3,5-tetrahydro-3-indolizinyl}-1H-imidazol-5-yl)phenyl]acrylic acid, (2E)-3-[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]acrylic acid, 5-(2-{(3S)-7-[5-chloro-2-(1H-tetrazol-1-yl)phenyl]-5-oxo-1,2,3,5-tetrahydro-3-indolizinyl}-4-fluoro-1H-imidazol-5-yl)-2-thiophenecarboxylic acid, ethyl 5-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylate, (3S)-7-[5-chloro-2-(1H-tetrazol-1-yl)phenyl]-3-[5-(1-oxido-4-pyridinyl)-1H-imidazol-2-yl]-2,3-dihydro-5(1H)-indolizinone, (3S)-3-[5-(3-aminophenyl)-1H-imidazol-2-yl]-7-[5-chloro-2-(1H-tetrazol-1-yl)phenyl]-2,3-dihydro-5(1H)-indolizinone, 2-methoxyethyl[3-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate, methyl[3-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate, N-[3-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]acetamide, methyl 3-(2-{(3S)-7-[5-chloro-2-(1H-tetrazol-1-yl)phenyl]-5-oxo-1,2,3,5-tetrahydro-3-indolizinyl}-1H-imidazol-5-yl)benzoate, (3S)-7-[5-chloro-2-(1H-tetrazol-1-yl)phenyl]-3-{5-[3-(methylsulfonyl)phenyl]-1H-imidazol-2-yl}-2,3-dihydro-5(1H)-indolizinone, (3S)-7-[5-chloro-2-(1H-tetrazol-1-yl)phenyl]-3-{5-[3-(methoxymethyl)phenyl]-1H-imidazol-2-yl}-2,3-dihydro-5(1H)-indolizinone, (3S)-3-[5-(3-acetylphenyl)-1H-imidazol-2-yl]-7-[5-chloro-2-(1H-tetrazol-1-yl)phenyl]-2,3-dihydro-5(1H)-indolizinone, 3-(2-{(3S)-7-[5-chloro-2-(1H-tetrazol-1-yl)phenyl]-5-oxo-1,2,3,5-tetrahydro-3-indolizinyl}-1H-imidazol-5-yl)benzaldehyde O-methyloxime, 3-(2-{7-[5-chloro-2-(1H-tetrazol-1-yl)phenyl]-5-oxo-1,2,3,5-tetrahydro-3-indolizinyl}-1H-imidazol-5-yl)benzamide, 3-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)benzonitrile, (3S)-3-[4-chloro-5-(3-hydroxyphenyl)-1H-imidazol-2-yl]-7-[5-chloro-2-(1H-tetrazol-1-yl)phenyl]-2,3-dihydro-5(1H)-indolizinone, (3S)-3-[5-(2-aminophenyl)-1H-imidazol-2-yl]-7-[5-chloro-2-(1H-tetrazol-1-yl)phenyl]-2,3-dihydro-5(1H)-indolizinone, methyl[2-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate, N-[2-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]acetamide, 2-(2-{(3S)-7-[5-chloro-2-(1H-tetrazol-1-yl)phenyl]-5-oxo-1,2,3,5-tetrahydro-3-indolizinyl}-1H-imidazol-5-yl)benzoic acid,

[3-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]boronic acid,

[3-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)phenyl]boronic acid, ethyl[3-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]acetate, ethyl[3-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)phenyl]acetate, 2-[3-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]acetamide, 2-[3-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)phenyl]acetamide, 2-[3-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]-N-methylacetamide, 2-[3-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)phenyl]-N-methylacetamide, 2-[3-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]-2-methylpropanoic acid, 2-[3-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)phenyl]-2-methylpropanoic acid, 4-(2-{(3S)-7-[5-chloro-2-(1H-tetrazol-1-yl)phenyl]-5-oxo-1,2,3,5-tetrahydro-3-indolizinyl}-1H-imidazol-5-yl)-N-methoxybenzamide, 4-(2-{(3S)-7-[5-chloro-2-(1H-tetrazol-1-yl)phenyl]-5-oxo-1,2,3,5-tetrahydro-3-indolizinyl}-1H-imidazol-5-yl)-N-ethoxybenzamide, 4-(2-{(3S)-7-[5-chloro-2-(1H-tetrazol-1-yl)phenyl]-5-oxo-1,2,3,5-tetrahydro-3-indolizinyl}-1H-imidazol-5-yl)-N-(2-methoxyethyl)benzamide, 4-(2-{(3S)-7-[5-chloro-2-(1H-tetrazol-1-yl)phenyl]-5-oxo-1,2,3,5-tetrahydro-3-indolizinyl}-1H-imidazol-5-yl)-N-(3-methoxypropyl)benzamide, 4-(2-{(3S)-7-[5-chloro-2-(1H-tetrazol-1-yl)phenyl]-5-oxo-1,2,3,5-tetrahydro-3-indolizinyl}-1H-imidazol-5-yl)-N-(2-methoxyethoxyl)benzamide, 4-(2-{(3S)-7-[5-chloro-2-(1H-tetrazol-1-yl)phenyl]-5-oxo-1,2,3,5-tetrahydro-3-indolizinyl}-1H-imidazol-5-yl)-N-(2-fluoroethyl)benzamide, 4-(2-{(3S)-7-[5-chloro-2-(1H-tetrazol-1-yl)phenyl]-5-oxo-1,2,3,5-tetrahydro-3-indolizinyl}-1H-imidazol-5-yl)-N-(2,2-difluoroethyl)benzamide, 4-(2-{(3S)-7-[5-chloro-2-(1H-tetrazol-1-yl)phenyl]-5-oxo-1,2,3,5-tetrahydro-3-indolizinyl}-1H-imidazol-5-yl)-N-(3-fluoropropyl)benzamide, 4-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-N-(2-methoxyethyl)benzamide, 4-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-N-(2-methoxyethoxyl)benzamide, 4-(2-{(3S)-7-[5-chloro-2-(1H-tetrazol-1-yl)phenyl]-5-oxo-1,2,3,5-tetrahydro-3-indolizinyl}-4-methyl-1H-imidazol-5-yl)benzamide, 4-(2-{(3S)-7-[5-chloro-2-(1H-tetrazol-1-yl)phenyl]-5-oxo-1,2,3,5-tetrahydro-3-indolizinyl}-1H-imidazol-5-yl)-3-methylbenzamide, 4-(2-{7-[5-chloro-2-(1H-tetrazol-1-yl)phenyl]-5-oxo-1,2,3,5-tetrahydro-3-indolizinyl}-1H-imidazol-5-yl)-3-fluorobenzamide, 5-(2-{7-[5-chloro-2-(1H-tetrazol-1-yl)phenyl]-5-oxo-1,2,3,5-tetrahydro-3-indolizinyl}-1H-imidazol-5-yl)-2-pyridinecarboxamide, 4-(2-{7-[5-chloro-2-(1H-tetrazol-1-yl)phenyl]-5-oxo-1,2,3,5-tetrahydro-3-indolizinyl}-1H-imidazol-5-yl)benzenecarbothioamide, (3S)-7-[5-chloro-2-(1H-tetrazol-1-yl)phenyl]-3-{5-[4-(hydroxymethyl)phenyl]-1H-imidazol-2-yl}-2,3-dihydro-5(1H)-indolizinone, (3S)-3-{4-chloro-5-[4-(hydroxymethyl)phenyl]-1H-imidazol-2-yl}-7-[5-chloro-2-(1H-tetrazol-1-yl)phenyl]-2,3-dihydro-5(1H)-indolizinone, (3S)-3-{4-chloro-5-[4-(1-hydroxyethyl)phenyl]-1H-imidazol-2-yl}-7-[5-chloro-2-(1H-tetrazol-1-yl)phenyl]-2,3-dihydro-5(1H)-indolizinone, (3S)-3-{5-[2-chloro-4-(hydroxymethyl)phenyl]-1H-imidazol-2-yl}-7-[5-chloro-2-(1H-tetrazol-1-yl)phenyl]-2,3-dihydro-5(1H)-indolizinone, (3S)-7-[5-chloro-2-(1H-tetrazol-1-yl)phenyl]-3-{5-[6-(hydroxymethyl)-3-pyridinyl]-1H-imidazol-2-yl}-2,3-dihydro-5(1H)-indolizinone, (3S)-3-{4-chloro-5-[6-(hydroxymethyl)-3-pyridinyl]-1H-imidazol-2-yl}-7-[5-chloro-2-(1H-tetrazol-1-yl)phenyl]-2,3-dihydro-5(1H)-indolizinone, (3S)-3-{5-[2-chloro-6-(hydroxymethyl)-3-pyridinyl]-1H-imidazol-2-yl}-7-[5-chloro-2-(1H-tetrazol-1-yl)phenyl]-2,3-dihydro-5(1H)-indolizinone, N-[4-(2-{7-[5-chloro-2-(1H-tetrazol-1-yl)phenyl]-5-oxo-1,2,3,5-tetrahydro-3-indolizinyl}-1H-imidazol-5-yl)phenyl]-4-methoxybutanamide, N-[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]acetamide, N-[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]-2-fluoroacetamide, N-[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]-2,2-difluoroacetamide, N-[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]tetrahydro-3-furancarboxamide, N-[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]tetrahydro-2H-pyran-4-carboxamide, N-[4-(2-{(3S)-7-[5-chloro-2-(1H-tetrazol-1-yl)phenyl]-5-oxo-1,2,3,5-tetrahydro-3-indolizinyl}-4-fluoro-1H-imidazol-5-yl)phenyl]acetamide, N-[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]ethanethioamide, N-[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]formamide, N-[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]-N-hydroxyacetamide, (1E)-N-[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]-N'-hydroxyethanimidamide, (1E)-N-[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]-N'-methoxyethanimidamide, N-[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]-3-hydroxy-3-methylbutanamide, 3-{[4-(2-{(3S)-7-[5-chloro-2(1H-tetrazol-1-yl)phenyl]-5-oxo-1,2,3,5-tetrahydro-3-indolizinyl}-1H-imidazol-5-yl)phenyl]amino}-3-oxopropanoic acid, 4-{[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]amino}-4-oxobutanoic acid, 4-{[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]amino}-2,2-dimethyl-4-oxobutanoic acid, 4-{[4-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)phenyl]amino}-2,2-dimethyl-4-oxobutanoic acid, N-[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]-2-(2-methoxyethoxy)acetamide, N-[4-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)phenyl]-2-(2-methoxyethoxy)acetamide, 5-{[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]amino}-5-oxopentanoic acid, 5-{[4-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)phenyl]amino}-5-oxopentanoic acid, methyl 5-{[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]amino}-5-oxopentanoate, N-[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]-N'-methylpentanediamide, (2-{[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]amino}-2-oxoethoxy)acetic acid, (2-{[4-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)phenyl]amino}-2-oxoethoxy)acetic acid, methyl(2-{[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]amino}-2-oxoethoxy)acetate, methyl[4-(2-{(3S)-7-[5-chloro-2-(1H-tetrazol-1-yl)phenyl]-5-oxo-1,2,3,5-tetrahydro-3-indolizinyl}-4-fluoro-1H-imidazol-5-yl)phenyl]carbamate, methyl[4-(4-bromo-2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate, 2-methoxyethyl[4-(2-{(3S)-7-[5-chloro-2-(1H-tetrazol-1-yl)phenyl]-5-oxo-1,2,3,5-tetrahydro-3-indolizinyl}-4-methyl-1H-imidazol-5-yl)phenyl]carbamate, 2-methoxyethyl[4-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate, 2-fluoroethyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate, 2-ethoxyethyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate, 3-methoxypropyl[4-(2-{(3S)-7-[5-chloro-2-(1H-1-tetrazol-1-yl)phenyl]-5-oxo-1,2,3,5-tetrahydro-3-indolizinyl}-1H-imidazol-5-yl)phenyl]carbamate, 2-(2-methoxyethoxyl)ethyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate, 2-(2-ethoxyethoxyl)ethyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate, (2S)-2-methoxypropyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate, 1-methoxy-2-propanyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate, tetrahydro-3-furanyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate, tetrahydro-3-furanylmethyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate, tetrahydro-2-furanylmethyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate, 3-oxetanyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate, 2-(dimethylamino)ethyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate, 3-hydroxy-3-methylbutyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate, 2-hydroxyethyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate, 2-hydroxy-2-methylpropyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate, 2-hydroxy-2-methylpropyl[4-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate,

- 3-[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]-1,1-dimethylurea,
- 3-[4-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)phenyl]-1,1-dimethylurea,
- 3-[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]-1-methoxy-1-methylurea,
- 3-[4-(2-{(3S)-7-[5-chloro-2-(1H-tetrazol-1-yl)phenyl]-5-oxo-1,2,3,5-tetrahydro-3-indolizinyl}1H-imidazol-5-yl)phenyl]-1-(2-methoxyethyl)-1-methylurea,
- 3-[4-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)phenyl]-1-(2-methoxyethyl)-1-methylurea,
- (3S)-7-[5-chloro-2-(1H-tetrazol-1-yl)phenyl]-3-[5-(1,2,3,4-tetrahydro-6-quinolinyl)-1H-imidazol-2-yl]-2,3-dihydro-5(1H)-indolizinone,
- 6-(2-{(3S)-7-[5-chloro-2-(1H-tetrazol-1-yl)phenyl]-5-oxo-1,2,3,5-tetrahydro-3-indolizinyl}-4-methyl-1H-imidazol-5-yl)-3-methyl-3,4-dihydro-2(1H)-quinazolinone,
- 2-amino-5-(2-{(3S)-7-[5-chloro-2-(1H-tetrazol-1-yl)phenyl]-5-oxo-1,2,3,5-tetrahydro-3-indolizinyl}-1H-imidazol-5-yl)benzoic acid,
- 5-(2-{(3S)-7-[5-chloro-2-(1H-tetrazol-1-yl)phenyl]-5-oxo-1,2,3,5-tetrahydro-3-indolizinyl}-1H-imidazol-5-yl)-2-hydroxybenzoic acid,
- 5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-hydroxybenzoic acid,
- 5-(2-{(3S)-7-[5-chloro-2-(1H-tetrazol-1-yl)phenyl]-5-oxo-1,2,3,5-tetrahydro-3-indolizinyl}-1H-imidazol-5-yl)-2-methylbenzoic acid,
- 5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-methylbenzoic acid,
- (3S)-7-[5-chloro-2-(1H-tetrazol-1-yl)phenyl]-3-{5-[4-(methylsulfonyl)phenyl]-1H-imidazol-2-yl}-2,3-dihydro-5(1H)-indolizinone,
- (3S)-7-[5-chloro-2-(1H-tetrazol-1-yl)phenyl]-3-(5-{4-[(S)-methylsulfinyl]phenyl}-1H-imidazol-2-yl)-2,3-dihydro-5(1H)-indolizinone,
- (3S)-7-[5-chloro-2-(1H-tetrazol-1-yl)phenyl]-3-(5-{4-[(R)-methylsulfinyl]phenyl}-1H-imidazol-2-yl)-2,3-dihydro-5(1H)-indolizinone,
- (3S)-7-[5-chloro-2-(1H-tetrazol-1-yl)phenyl]-3-{5-[4-(S-methylsulfonimidoyl)phenyl]-1H-imidazol-2-yl}-2,3-dihydro-5(1H)-indolizinone,
- (3S)-7-[5-chloro-2-(1H-tetrazol-1-yl)phenyl]-3-{5-[4-(S-methylsulfonimidoyl)phenyl]-1H-imidazol-2-yl}-2,3-dihydro-5(1H)-indolizinone,
- (3S)-3-[5-(6-amino-2-methoxy-3-pyridinyl)-1H-imidazol-2-yl]-7-[5-chloro-2-(1H-tetrazol-1-yl)phenyl]-2,3-dihydro-5(1H)-indolizinone,
- (3S)-3-[5-(6-amino-2-fluoro-3-pyridinyl)-4-chloro-1H-imidazol-2-yl]-7-[5-chloro-2-(1H-tetrazol-1-yl)phenyl]-2,3-dihydro-5(1H)-indolizinone,
- methyl[5-(2-{(3S)-7-[5-chloro-2-(1H-tetrazol-1-yl)phenyl]-5-oxo-1,2,3,5-tetrahydro-3-indolizinyl}-1H-imidazol-5-yl)-6-fluoro-2-pyridinyl]carbamate,
- N-[6-chloro-5-(2-{(3S)-7-[5-chloro-2-(1H-1-tetrazol-1-yl)phenyl]-5-oxo-1,2,3,5-tetrahydro-3-indolizinyl}-1H-imidazol-5-yl)-2-pyridinyl]acetamide,
- 2-methoxyethyl[5-(2-{(3S)-7-[5-chloro-2-(1H-tetrazol-1-yl)phenyl]-5-oxo-1,2,3,5-tetrahydro-3-indolizinyl}-1H-imidazol-5-yl)-2-pyridinyl]carbamate,
- 2-methoxyethyl[5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-pyridinyl]carbamate,
- 2-methoxyethyl[6-(2-{(3S)-7-[5-chloro-2-(1H-tetrazol-1-yl)phenyl]-5-oxo-1,2,3,5-tetrahydro-3-indolizinyl}-1H-imidazol-5-yl)-3-pyridinyl]carbamate,
- 2-methoxyethyl[6-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-3-pyridinyl]carbamate,
- (3S)-3-[5-(6-amino-4-methyl-3-pyridinyl)-1H-imidazol-2-yl]-7-[5-chloro-2-(1H-tetrazol-1-yl)phenyl]-2,3-dihydro-5(1H)-indolizinone,
- (3S)-3-[5-(6-amino-4-methyl-3-pyridinyl)-4-chloro-1H-imidazol-2-yl]-7-[5-chloro-2-(1H-tetrazol-1-yl)phenyl]-2,3-dihydro-5(1H)-indolizinone,
- (3S)-3-[5-(6-amino-3-pyridazinyl)-1H-imidazol-2-yl]-7-[5-chloro-2-(1H-tetrazol-1-yl)phenyl]-2,3-dihydro-5(1H)-indolizinone,
- (3S)-3-[5-(6-amino-3-pyridazinyl)-4-chloro-1H-imidazol-2-yl]-7-[5-chloro-2-(1H-tetrazol-1-yl)phenyl]-2,3-dihydro-5(1H)-indolizinone,
- (3S)-3-[5-(2-amino-5-pyrimidinyl)-1H-imidazol-2-yl]-7-[5-chloro-2-(1H-tetrazol-1-yl)phenyl]-2,3-dihydro-5(1H)-indolizinone,
- (3S)-3-[5-(2-amino-5-pyrimidinyl)-4-chloro-1H-imidazol-2-yl]-7-[5-chloro-2-(1H-tetrazol-1-yl)phenyl]-2,3-dihydro-5(1H)-indolizinone,
- (3S)-7-[5-chloro-2-(1H-tetrazol-1-yl)phenyl]-3-[5-(5-hydroxy-2-pyridinyl)-1H-imidazol-2-yl]-2,3-dihydro-5(1H)-indolizinone,
- (3S)-3-[4-chloro-5-(5-hydroxy-2-pyridinyl)-1H-imidazol-2-yl]-7-[5-chloro-2-(1H-tetrazol-1-yl)phenyl]-2,3-dihydro-5(1H)-indolizinone,
- (3S)-7-[5-chloro-2-(1H-tetrazol-1-yl)phenyl]-3-[5-(6-fluoro-3-pyridinyl)-1H-imidazol-2-yl]-2,3-dihydro-5(1H)-indolizinone,
- (3S)-7-[5-chloro-2-(1H-tetrazol-1-yl)phenyl]-3-[5-(6-oxo-1,6-dihydro-3-pyridinyl)-1H-imidazol-2-yl]-2,3-dihydro-5(1H)-indolizinone,
- (3S)-3-[4-chloro-5-(6-oxo-1,6-dihydro-3-pyridinyl)-1H-imidazol-2-yl]-7-[5-chloro-2-(1H-tetrazol-1-yl)phenyl]-2,3-dihydro-5(1H)-indolizinone,
- (3S)-7-[5-chloro-2-(1H-tetrazol-1-yl)phenyl]-3-{5-[6-(methylamino)-3-pyridinyl]-1H-imidazol-2-yl}-2,3-dihydro-5(1H)-indolizinone,
- (3S)-7-[5-chloro-2-(1H-tetrazol-1-yl)phenyl]-3-{5-[2-fluoro-6-(methylamino)-3-pyridinyl]-1H-imidazol-2-yl}-2,3-dihydro-5(1H)-indolizinone,
- (3S)-3-{5-[2-chloro-6-(methylamino)-3-pyridinyl]-1H-imidazol-2-yl}-7-[5-chloro-2-(1H-tetrazol-1-yl)phenyl]-2,3-dihydro-5 (1H)-indolizinone,
- (3S)-7-[5-chloro-2-(1H-tetrazol-1-yl)phenyl]-3-{5-[6-(dimethylamino)-3-pyridinyl]-1H-imidazol-2-yl}-2,3-dihydro-5 (1H)-indolizinone,
- (3S)-7-[5-chloro-2-(1H-tetrazol-1-yl)phenyl]-3-{5-[6-(ethylamino)-3-pyridinyl]-1H-imidazol-2-yl}-2,3-dihydro-5 (1H)-indolizinone,
- (3S)-7-[5-chloro-2-(1H-tetrazol-1-yl)phenyl]-3-(5-{6-[(2-methoxyethyl)amino]-3-pyridinyl}-1H-imidazol-2-yl)-2,3-dihydro-5(1H)-indolizinone,
- (3S)-7-[5-chloro-2-(1H-tetrazol-1-yl)phenyl]-3-(5-{6-[(2-ethoxyethyl)amino]-3-pyridinyl}-1H-imidazol-2-yl)-2,3-dihydro-5(1H)-indolizinone,
- (3S)-7-[5-chloro-2-(1H-tetrazol-1-yl)phenyl]-3-(5-{6-[(3-methoxypropyl)amino]-3-pyridinyl-1H-imidazol-2-yl)-2,3-dihydro-5(1H)-indolizinone, (3S)-7-[5-chloro-2-(1H-tetrazol-1-yl)phenyl]-3-(5-{6-[(3-hydroxy-3-methylbutyl)amino]-3-pyridinyl}-1H-imidazol-2-yl)-2,3-dihydro-5(1H)-indolizinone, (3S)-7-[5-chloro-2-(1H-tetrazol-1-yl)phenyl]-3-(5-{6-[(1,3-oxazol-2-ylmethyl)amino]-3-pyridinyl}-1H-imidazol-2-yl)-2,3-dihydro-5(1H)-indolizinone, 3-{[5-(2-{(3S)-7-[5-chloro-2-(1H-tetrazol-1-yl)phenyl]-5-oxo-1,2,3,5-tetrahydro-3-indolizinyl}-1H-imidazol-5-yl)-2-pyridinyl]amino}-N,N-dimethylpropanamide, 3-{[5-(2-{(3S)-7-[5-chloro-2-(1H-tetrazol-1-yl)phenyl]-5-oxo-1,2,3,5-tetrahydro-3-indolizinyl}-1H-imidazol-5-yl)-2-pyridinyl]amino}propanamide, (3S)-7-[5-chloro-2-(1H-tetrazol-1-yl)phenyl]-3-{5-[6-(2-oxo-1-pyrrolidinyl)-3-pyridinyl]-1H-imidazol-2-yl}-2,3-dihydro-5(1H)-indolizinone, (3S)-3-{(4-chloro-5-{6-(methylamino)-3-pyridinyl}-1H-imidazol-2-yl}-7-[5-chloro-2-(1H-tetrazol-1-yl)phenyl]-2,3-dihydro-5(1H)-indolizinone, (3S)-3-{(4-chloro-5-[6-(dimethylamino)-3-pyridinyl]-1H-imidazol-2-yl}-7-[5-chloro-2-(1H-tetrazol-1-yl)phenyl]-2,3-dihydro-5(1H)-indolizinone, (3S)-3-(4-chloro-5-{6-[(2-methoxyethyl)amino]-3-pyridinyl-1H-imidazol-2-yl)-7-[5-chloro-2-(1H-tetrazol-1-yl)phenyl]-2,3-dihydro-5(1H)-indolizinone, (3S)-3-(4-chloro-5-{6-[(6-(ethylamino)-1H-imidazol-2-yl}-7-[5-chloro-2-(1H-tetrazol-1-yl)phenyl]-2,3-dihydro-5(1H)-indolizinone, (3S)-3-(4-chloro-5-{6-[(2-ethoxyethyl)amino]-3-pyridinyl}-1H-imidazol-2-yl)-7-[5-chloro-2-(1H-tetrazol-1-yl)phenyl]-2,3-dihydro-5(1H)-indolizinone, (3S)-3-(4-chloro-5-{6-[(3-methoxypropyl)amino]-3-pyridinyl}-1H-imidazol-2-yl)-7-[5-chloro-2-(1H-tetrazol-1-yl)phenyl]-2,3-dihydro-5(1H)-indolizinone, (3S)-3-(4-chloro-5-{6-[(3-hydroxy-3-methylbutyl)amino]-3-pyridinyl}-1H-imidazol-2-yl)-7-[5-chloro-2-(1H-tetrazol-1-yl)phenyl]-2,3-dihydro-5(1H)-indolizinone, (3S)-3-(4-chloro-5-{6-[(1,3-oxazol-2-ylmethyl)amino]-3-pyridinyl}-1H-imidazol-2-yl)-7-[5-chloro-2-(1H-tetrazol-1-yl)phenyl]-2,3-dihydro-5(1H)-indolizinone, 3-{[5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-pyridinyl]amino}-N,N-dimethylpropanamide, (3S)-3-{4-chloro-5-[6-(2-oxo-1-pyrrolidinyl)-3-pyridinyl]-1H-imidazol-2-yl}-7-[5-chloro-2-(1H-tetrazol-1-yl)phenyl]-2,3-dihydro-5(1H)-indolizinone, (3S)-3-[5-(2-amino-1,3-thiazol-5-yl)-4-chloro-1H-imidazol-2-yl]-7-[5-chloro-2-(1H-tetrazol-1-yl)phenyl]-2,3-dihydro-5(1H)-indolizinone, (3S)-3-[5-(2-amino-4-chloro-1,3-thiazol-5-yl)-1H-imidazol-2-yl]-7-[5-chloro-2-(1H-tetrazol-1-yl)phenyl]-2,3-dihydro-5(1H)-indolizinone, N-[4-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-pyridinyl]acetamide, methyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-pyridinyl]carbamate, (3S)-3-[5-(2-amino-3-chloro-4-pyridinyl)-1H-imidazol-2-yl]-7-[5-chloro-2-(1H-tetrazol-1-yl)phenyl]-2,3-dihydro-5(1H)-indolizinone, (3S)-3-[5-(2-amino-5-chloro-4-pyridinyl)-1H-imidazol-2-yl]-7-[5-chloro-2-(1H-tetrazol-1-yl)phenyl]-2,3-dihydro-5(1H)-indolizinone, (3S)-3-[5-(2-amino-5-chloro-4-pyridinyl)-4-chloro-1H-imidazol-2-yl]-7-[5-chloro-2-(1H-tetrazol-1-yl)phenyl]-2,3-dihydro-5(1H)-indolizinone, (3S)-3-[5-(2-amino-4-pyridinyl)-4-chloro-1H-imidazol-2-yl]-7-[5-chloro-2-(1H-tetrazol-1-yl)phenyl]-2,3-dihydro-5(1H)-indolizinone, (3S)-7-[5-chloro-2-(1H-tetrazol-1-yl)phenyl]-3-{5-(2-(methylamino)-4-pyridinyl]-1H-imidazol-2-yl}-2,3-dihydro-5(1H)-indolizinone, (3S)-3-{4-chloro-5-[2-(methylamino)-4-pyridinyl]-1H-imidazol-2-yl}-7-[5-chloro-2-(1H-tetrazol-1-yl)phenyl]-2,3-dihydro-5(1H)-indolizinone, (3S)-3-[5-(3-amino-4-pyridinyl)-1H-imidazol-2-yl]-7-[5-chloro-2-(1H-tetrazol-1-yl)phenyl]-2,3-dihydro-5(1H)-indolizinone, (3S)-7-[5-chloro-2-(1H-tetrazol-1-yl)phenyl]-3-[5-(2-methyl-4-pyridinyl)-1H-imidazol-2-yl]-2,3-dihydro-5(1H)-indolizinone, (3S)-7-[5-chloro-2-(1H-tetrazol-1-yl)phenyl]-3-[5-(2,6-dimethyl-4-pyridinyl)-1H-imidazol-2-yl]-2,3-dihydro-5(1H)-indolizinone, (3S)-3-[4-chloro-5-(2,6-dimethyl-4-pyridinyl)-1H-imidazol-2-yl]-7-[5-chloro-2-(1H-tetrazol-1-yl)phenyl]-2,3-dihydro-5(1H)-indolizinone, (3S)-3-[5-(6-amino-2-pyridinyl)-1H-imidazol-2-yl]-7-[5-chloro-2-(1H-tetrazol-1-yl)phenyl]-2,3-dihydro-5(1H)-indolizinone, (3S)-3-[5-(6-amino-2-pyridinyl)-4-chloro-1H-imidazol-2-yl]-7-[5-chloro-2-(1H-tetrazol-1-yl)phenyl]-2,3-dihydro-5(1H)-indolizinone, (3S)-3-[5-(6-amino-3-pyridinyl)-4-fluoro-1H-imidazol-2-yl]-7-[5-chloro-2-(1H-tetrazol-1-yl)phenyl]-2,3-dihydro-5(1H)-indolizinone, 2-methoxyethyl[6-(2-{(3S)-7-[5-chloro-2-(1H-tetrazol-1-yl)phenyl]-5-oxo 1,2,3,5-tetrahydro-3-indolizinyl}-4-fluoro-1H-imidazol-5-yl)-3-pyridinyl]carbamate, (3R)-3-[5-(6-amino-3-pyridinyl)-1H-imidazol-2-yl]-7-[5-chloro-2-(1H-tetrazol-1-yl)phenyl]-2,3-dihydro-5(1H)-indolizinone, (3R)-3-[5-(6-amino-3-pyridinyl)-4-chloro-1H-imidazol-2-yl]-7-[5-chloro-2-(1H-tetrazol-1-yl)phenyl]-2,3-dihydro-5(1H)-indolizinone, 2-{(3S)-7-[5-chloro-2-(1H-tetrazol-1-yl)phenyl]-5-oxo-1,2,3,5-tetrahydro-3-indolizinyl}-5-phenyl-1H-imidazole-4-carboxylic acid, 2-{(3S)-7-[5-chloro-2-(1H-tetrazol-1-yl)phenyl]-5-oxo-1,2,3,5-tetrahydro-3-indolizinyl}-5-phenyl-1H-imidazole-4-carbonitrile, 4-(5-{(3S)-7-[5-chloro-2-(1H-tetrazol-1-yl)phenyl]-5-oxo-1,2,3,5-tetrahydro-3-indolizinyl}-1H-imidazol-2-yl)benzamide, 4-(4-chloro-5-{(3S)-7-[5-chloro-2-(1H-tetrazol-1-yl)phenyl]-5-oxo-1,2,3,5-tetrahydro-3-indolizinyl}-1H-imidazol-2-yl)benzamide, (3S)-3-[2-(6-amino-3-pyridinyl)-1H-imidazol-5-yl]-7-[5-chloro-2-(1H-tetrazol-1-yl)phenyl]-2,3-dihydro-5(1H)-indolizinone, (3S)-3 [2-(6-amino-3-pyridinyl)-4-chloro-1H-imidazol-5-yl]-7-[5-chloro-2-(1H-tetrazol-1-yl)phenyl]-2,3-dihydro-5(1H)-indolizinone, methyl[5-(4-chloro-5-{(3S)-7-[5-chloro-2-(1H-tetrazol-1-yl)phenyl]-5-oxo-1,2,3,5-tetrahydro-3-indolizinyl}-1H-imidazol-2-yl)-2-pyridinyl]carbamate, methyl[6-(4-chloro-5-{(3S)-7-[5-chloro-2-(1H-tetrazol-1-yl)phenyl]-5-oxo-1,2,3,5-tetrahydro-3-indolizinyl}-1H-imidazol-2-yl)-3-pyridinyl]carbamate, methyl[4-(5-{(3S)-7-[5-chloro-2-(1H-tetrazol-1-yl)phenyl]-5-oxo-1,2,3,5-tetrahydro-3-indolizinyl}-4-fluoro-1H-imidazol-2-yl)phenyl]carbamate, (3S)-3-[2-(4-aminophenyl)-4-chloro-1H-imidazol-5-yl]-7-[5-chloro-2-(1H-tetrazol-1-yl)phenyl]-2,3-dihydro-5(1H)-indolizinone, (3S)-3-[2-(4-aminophenyl)-1H-imidazol-5-yl]-7-[5-chloro-2-(1H-tetrazol-1-yl)phenyl]-2,3-dihydro-5(1H)-indolizinone, 2-methoxyethyl[4-(5-{(3S)-7-[5-chloro-2-(1H-tetrazol-1-yl)phenyl]-5-oxo-1,2,3,5-tetrahydro-3-indolizinyl}-1H-imidazol-2-yl)phenyl]carbamate, 2-(2-methoxyethoxyl)ethyl[4-(5-{(3S)-7-[5-chloro-2-(1H-tetrazol-1-yl)phenyl]-5-oxo-1,2,3,5-tetrahydro-3-indolizinyl}-1H-imidazol-2-yl)phenyl]carbamate, (1E)-N-[4-(5-{(3S)-7-[5-chloro-2-(1H-tetrazol-1-yl)phenyl]-5-oxo-1,2,3,5-tetrahydro-3-indolizinyl}-1H-imidazol-2-yl)phenyl]-N'-hydroxyethanimidamide, N-[4-(4-chloro-5-{(3S)-7-[5-chloro-2-(1H-tetrazol-1-yl)phenyl]-5-oxo-1,2,3,5-tetrahydro-3-indolizinyl}-1H-imidazol-2-yl)phenyl]acetamide, 2-methoxyethyl[4-(4-chloro-5-{(3S)-7-[5-chloro-2-(1H-tetrazol-1-yl)phenyl]-5-oxo-1,2,3,5-tetrahydro-3-indolizinyl}-1H-imidazol-2-yl)phenyl]carbamate, 3-methoxypropyl[4-(4-chloro-5-{(3S)-7-[5-chloro-2-(1H-tetrazol-1-yl)phenyl]-5-oxo-1,2,3,5-tetrahydro-3-indolizinyl}-1H-imidazol-2-yl)phenyl]carbamate, 2-(2-methoxyethoxyl)ethyl[4-(4-chloro-5-{(3S)-7-[5-chloro-2-(1H-tetrazol-1-yl)phenyl]-5-oxo-1,2,3,5-tetrahydro-3-indolizinyl}-1H-imidazol-2-yl)phenyl]carbamate, 3-oxetanyl[4-(4-chloro-5-{(3S)-7-[5-chloro-2-(1H-tetrazol-1-yl)phenyl]-5-oxo-1,2,3,5-tetrahydro-3-indolizinyl}-1H-imidazol-2-yl)phenyl]carbamate, (1E)-N-[4-(4-chloro-5-{(3S)-7-[5-chloro-2-(1H-tetrazol-1-yl)phenyl]-5-oxo-1,2,3,5-tetrahydro-3-indolizinyl}-1H-imidazol-2-yl)phenyl]-N'-hydroxyethanimidamide, 2-methoxyethyl[4-(5-{(3S)-7-[5-chloro-2-(1H-tetrazol-1-yl)phenyl]-5-oxo-1,2,3,5-tetrahydro-3-indolizinyl}-4-fluoro-1H-imidazol-2-yl)phenyl]carbamate, 2-(2-methoxyethoxyl)ethyl[4-(5-{(3S)-7-[5-chloro-2-(1H-tetrazol-1-yl)phenyl]-5-oxo-1,2,3,5-tetrahydro-3-indolizinyl}-4-fluoro-1H-imidazol-2-yl)phenyl]carbamate, (3S)-3-[2-(6-amino-2-chloro-3-pyridinyl)-1H-imidazol-5-yl]-7-[5-chloro-2-(1H-tetrazol-1-yl)phenyl]-2,3-dihydro-5(1H)-indolizinone, (3S)-3-[2-(6-amino-2-fluoro-3-pyridinyl)-1H-imidazol-5-yl]-7-[5-chloro-2-(1H-tetrazol-1-yl)phenyl]-2,3-dihydro-5(1H)-indolizinone, (3S)-3-[2-(6-amino-2-fluoro-3-pyridinyl)-4-chloro-1H-imidazol-5-yl]-7-[5-chloro-2-(1H-tetrazol-1-yl)phenyl]-2,3-dihydro-5(1H)-indolizinone, 2-(2-methoxyethoxyl)ethyl[5-(5-{(3S)-7-[5-chloro-2-(1H-tetrazol-1-yl)phenyl]-5-oxo-1,2,3,5-tetrahydro-3-indolizinyl}-4-fluoro-1H-imidazol-2-yl)-2-pyridinyl]carbamate, 2-(2-methoxyethoxyl)ethyl[5-(4-chloro-5-{(3S)-7-[5-chloro-2-(1H-tetrazol-1-yl)phenyl]-5-oxo-1,2,3,5-tetrahydro-3-indolizinyl}-1H-imidazol-2-yl)-2-pyridinyl]carbamate, 2-methoxyethyl[5-(5-{(3S)-7-[5-chloro-2-(1H-tetrazol-1-yl)phenyl]-5-oxo-1,2,3,5-tetrahydro-3-indolizinyl}-1H-imidazol-2-yl)-2-pyridinyl]carbamate, 2-methoxyethyl[5-(5-{(3S)-7-[5-chloro-2-(1H-tetrazol-1-yl)phenyl]-5-oxo-1,2,3,5-tetrahydro-3-indolizinyl}-4-fluoro-1H-imidazol-2-yl)-2-pyridinyl]carbamate, 2-methoxyethyl[5-(4-chloro-5-{(3S)-7-[5-chloro-2-(1H-tetrazol-1-yl)phenyl]-5-oxo-1,2,3,5-tetrahydro-3-indolizinyl}-1H-imidazol-2-yl)-2-pyridinyl]carbamate, (3S)-3-[2-(6-amino-3-pyridinyl)-4-fluoro-1H-imidazol-5-yl]-7-[5-chloro-2-(1H-tetrazol-1-yl)phenyl]-2,3-dihydro-5(1H)-indolizinone, methyl[4-(5-{(3S)-7-[5-chloro-2-(1H-tetrazol-1-yl)phenyl]-5-oxo-1,2,3,5-tetrahydro-3-indolizinyl}-4H-1,2,4-triazol-3-yl)phenyl]carbamate, 2-fluoroethyl[4-(5-{(3S)-7-[5-chloro-2-(1H-tetrazol-1-yl)phenyl]-5-oxo-1,2,3,5-tetrahydro-3-indolizinyl}-4H-1,2,4-triazol-3-yl)phenyl]carbamate, 2-methoxyethyl[4-(5-{(3S)-7-[5-chloro-2-(1H-tetrazol-1-yl)phenyl]-5-oxo-1,2,3,5-tetrahydro-3-indolizinyl}-4H-1,2,4-triazol-3-yl)phenyl]carbamate, N-[4-(5-{(3S)-7-[5-chloro-2-(1H-tetrazol-1-yl)phenyl]-5-oxo-1,2,3,5-tetrahydro-3-indolizinyl}-4H-1,2,4-triazol-3-yl)phenyl]acetamide, 3-oxetanyl[4-(5-{(3S)-7-[5-chloro-2-(1H-tetrazol-1-yl)phenyl]-5-oxo-1,2,3,5-tetrahydro-3-indolizinyl}-4H-1,2,4-triazol-3-yl)phenyl]carbamate, 2-methoxyethyl[3-chloro-4-(5-{(3S)-7-[5-chloro-2-(1H-tetrazol-1-yl)phenyl]-5-oxo-1,2,3,5-tetrahydro-3-indolizinyl}-4H-1,2,4-triazol-3-yl)phenyl]carbamate, (3S)-3-[5-(6-amino-2-fluoro-3-pyridinyl)-4H-1,2,4-triazol-3-yl]-7-[5-chloro-2-(1H-tetrazol-1-yl)phenyl]-2,3-dihydro-5(1H)-indolizinone, (3S)-7-[5-chloro-2-(1H-tetrazol-1-yl)phenyl]-3-(5-phenyl-1H-pyrrol-2-yl)-2,3-dihydro-5(1H)-indolizinone, (3S)-7-[5-chloro-2-(1H-tetrazol-1-yl)phenyl]-3-[5-(4-nitrophenyl)-1H-pyrrol-2-yl]-2,3-dihydro-5(1H)-indolizinone, (3S)-3-[5-(4-aminophenyl)-1H-pyrrol-2-yl]-7-[5-chloro-2-(1H-tetrazol-1-yl)phenyl]-2,3-dihydro-5(1H)-indolizinone, methyl[4-(5-{(3S)-7-[5-chloro-2-(1H-tetrazol-1-yl)phenyl]-5-oxo-1,2,3,5-tetrahydro-3-indolizinyl}-1H-pyrrol-2-yl)phenyl]carbamate, 2-methoxyethyl[4-(5-{(3S)-7-[5-chloro-2-(1H-tetrazol-1-yl)phenyl]-5-oxo-1,2,3,5-tetrahydro-3-indolizinyl}-1H-pyrrol-2-yl)phenyl]carbamate, (3S)-3-[5-(6-amino-2-fluoro-3-pyridinyl)-1H-pyrrol-2-yl]-7-[5-chloro-2-(1H-tetrazol-1-yl)phenyl]-2,3-dihydro-5(1H)-indolizinone, (3S)-3-[1-(4-aminophenyl)-5-oxo-2,5-dihydro-1H-pyrazol-3-yl]-7-[5-chloro-2-(1H-tetrazol-1-yl)phenyl]-2,3-dihydro-5(1H)-indolizinone, methyl[4-(3-{(3S)-7-[5-chloro-2-(1H-tetrazol-1-yl)phenyl]-5-oxo-1,2,3,5-tetrahydro-3-indolizinyl}-5-oxo-2,5-dihydro-1H-pyrazol-1-yl)phenyl]carbamate, 2-methoxyethyl[4-(3-{(3S)-7-[5-chloro-2-(1H-tetrazol-1-yl)phenyl]-5-oxo-1,2,3,5-tetrahydro-3-indolizinyl}-5-oxo-2,5-dihydro-1H-pyrazol-1-yl)phenyl]carbamate, 2-(2-methoxyethoxyl)ethyl[4-(3-{(3S)-7-[5-chloro-2-(1H-tetrazol-1-yl)phenyl]-5-oxo-1,2,3,5-tetrahydro-3-indolizinyl}-5-oxo-2,5-dihydro-1H-pyrazol-1-yl)phenyl]carbamate, methyl[4-(2-{(3S)-7-[5-methoxy-2-(1H-tetrazol-1-yl)phenyl]-5-oxo-1,2,3,5-tetrahydro-3-indolizinyl}-1H-imidazol-5-yl)phenyl]carbamate, 2-methoxyethyl[4-(2-{(3S)-7-[5-methoxy-2-(1H-tetrazol-1-yl)phenyl]-5-oxo-1,2,3,5-tetrahydro-3-indolizinyl}-1H-imidazol-5-yl)phenyl]carbamate, 2-methoxyethyl[4-(4-chloro-2-{(3S)-7-[5-methoxy-2-(1H-tetrazol-1-yl)phenyl]-5-oxo-1,2,3,5-tetrahydro-3-indolizinyl}-1H-imidazol-5-yl)phenyl]carbamate, (3S)-3-[5-(6-amino-3-pyridinyl)-4-chloro-1H-imidazol-2-yl]-7-[5-methoxy-2-(1H-tetrazol-1-yl)phenyl]-2,3-dihydro-5(1H)-indolizinone, methyl[4-(2-{(3S)-7-[6-methyl-3-(1H-tetrazol-1-yl)-2-pyridinyl]-5-oxo-1,2,3,5-tetrahydro-3-indolizinyl}-1H-imidazol-5-yl)phenyl]carbamate,
(3S)-3-[5-(6-amino-3-pyridinyl)-1H-imidazol-2-yl]-7-[5-fluoro-2-(1H-tetrazol-1-yl)phenyl]-2,3-dihydro-5(1H)-indolizinone,
(3S)-3-[5-(6-amino-3-pyridinyl)-4-chloro-1H-imidazol-2-yl]-7-[5-fluoro-2-(1H-tetrazol-1-yl)phenyl]-2,3-dihydro-5(1H)-indolizinone,
(3S)-3-[5-(6-amino-3-pyridinyl)-1H-imidazol-2-yl]-7-[2,3-difluoro-6-(1H-tetrazol-1-yl)phenyl]-2,3-dihydro-5(1H)-indolizinone,
(3S)-3-[5-(6-amino-3-pyridinyl)-4-chloro-1H-imidazol-2-yl]-7-[2,3-difluoro-6-(1H-tetrazol-1-yl)phenyl]-2,3-dihydro-5(1H)-indolizinone,
(3S)-3-[5-(6-amino-3-pyridinyl)-1H-imidazol-2-yl]-7-[3,5-difluoro-2-(1H-tetrazol-1-yl)phenyl]-2,3-dihydro-5(1H)-indolizinone,
(3S)-3-[5-(6-amino-3-pyridinyl)-4-chloro-1H-imidazol-2-yl]-7-[3,5-difluoro-2-(1H-tetrazol-1-yl)phenyl]-2,3-dihydro-5(1H)-indolizinone,
(3S)-3-[5-(6-amino-3-pyridinyl)-1H-imidazol-2-yl]-7-[5-(difluoromethoxy)-2-(1H-tetrazol-1-yl)phenyl]-2,3-dihydro-5(1H)-indolizinone,
(3S)-3-[5-(6-amino-3-pyridinyl)-4-chloro-1H-imidazol-2-yl]-7-[5-(difluoromethoxy)-2-(1H-tetrazol-1-yl)phenyl]-2,3-dihydro-5(1H)-indolizinone,
(3S)-3 [5-(6-amino-2-fluoro-3-pyridinyl)-1H-imidazol-2-yl]-7-[5-(difluoromethoxy)-2-(1H-tetrazol-1-yl)phenyl]-2,3-dihydro-5(1H)-indolizinone,
3-{(3S)-3 [5-(6-amino-3-pyridinyl)-1H-imidazol-2-yl]-5-oxo-1,2,3,5-tetrahydro-7-indolizinyl}-4-(1H-tetrazol-1-yl)benzonitrile,
3-{(3S)-3-[5-(6-amino-3-pyridinyl)-4-chloro-1H-imidazol-2-yl]-5-oxo-1,2,3,5-tetrahydro-7-indolizinyl}-4-(1H-tetrazol-1-yl)benzonitrile,
3-{(3S)-3-[5-(6-amino-2-fluoro-3-pyridinyl)-1H-imidazol-2-yl]-5-oxo-1,2,3,5-tetrahydro-7-indolizinyl}-4-(1H-tetrazol-1-yl)benzonitrile,
(6S)-6-[5-(4-aminophenyl)-1H-imidazol-2-yl]-2-[5-chloro-2-(1H-tetrazol-1-yl)phenyl]-7,8-dihydropyrrolo[1,2-a]pyrimidin-4(6H)-one,
3-oxetanyl[4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)phenyl]carbamate,
2-methoxyethyl[4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)phenyl]carbamate,
2-ethoxyethyl[4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)phenyl]carbamate,
3-methoxypropyl[4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)phenyl]carbamate,
methyl[4-(2-{(6S)-2-[5-chloro-2-(1H-tetrazol-1-yl)phenyl]-4-oxo-4,6,7,8-tetrahydropyrrolo[1,2-a]pyrimidin-6-yl}-4-methyl-1H-imidazol-5-yl)phenyl]carbamate,
2-methoxyethyl[4-(2-{(6S)-2-[5-chloro-2-(1H-tetrazol-1-yl)phenyl]-4-oxo-4,6,7,8-tetrahydropyrrolo[1,2-a]pyrimidin-6-yl}-4-methyl-1H-imidazol-5-yl)phenyl]carbamate,
(6S)-6-[5-(6-amino-3-pyridinyl)-1H-imidazol-2-yl]-2-[5-chloro-2-(1H-tetrazol-1-yl)phenyl]-7,8-dihydropyrrolo[1,2-a]pyrimidin-4(6H)-one,
(6S)-2-[5-chloro-2-(1H-tetrazol-1-yl)phenyl]-6-{5-[6-(methylamino)-3-pyridinyl]-1H-imidazol-2-yl}-7,8-dihydropyrrolo[1,2-a]pyrimidin-4(6H)-one,
(6S)-2-[5-chloro-2-(1H-tetrazol-1-yl)phenyl]-6-(5-{6-[(2-methoxyethyl)amino]-3-pyridinyl}-1H-imidazol-2-yl)-7,8-dihydropyrrolo[1,2-a]pyrimidin-4(6H)-one,
methyl[6-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-3-pyridinyl]carbamate,
2-methoxyethyl[6-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-3-pyridinyl]carbamate,
methyl[4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)phenyl]carbamate,
methyl[5-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-pyridinyl]carbamate,
2-methoxyethyl[5-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-pyridinyl]carbamate,
2-methoxyethyl[6-(2-{(6S)-2-[5-chloro-2-(1H-tetrazol-1-yl)phenyl]-4-oxo-4,6,7,8-tetrahydropyrrolo[1,2-a]pyrimidin-6-yl}-4-fluoro-1H-imidazol-5-yl)-3-pyridinyl]carbamate,
2-methoxyethyl[4-(4-chloro-2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)phenyl]carbamate,
2-ethoxyethyl[4-(4-chloro-2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)phenyl]carbamate,
3-methoxypropyl[4-(4-chloro-2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)phenyl]carbamate,
(6S)-6-{4-chloro-5-[6-(methylamino)-3-pyridinyl]-1H-imidazol-2-yl}-2-[5-chloro-2-(1H-tetrazol-1-yl)phenyl]-7,8-dihydropyrrolo[1,2-a]pyrimidin-4(6H)-one,
(6S)-6-(4-chloro-5-{6-[(2-methoxyethyl)amino]-3-pyridinyl}-1H-imidazol-2-yl)-2-[5-chloro-2-(1H-tetrazol-1-yl)phenyl]-7,8-dihydropyrrolo[1,2-a]pyrimidin-4(6H)-one,
(6S)-6-[5-(6-amino-2-fluoro-3-pyridinyl)-4-chloro-1H-imidazol-2-yl]-2-[5-chloro-2-(1H-tetrazol-1-yl)phenyl]-7,8-dihydropyrrolo[1,2-a]pyrimidin-4(6H)-one,
methyl[6-(4-chloro-2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-3-pyridinyl]carbamate,
methyl[5-(4-chloro-2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-pyridinyl]carbamate,
2-methoxyethyl[5-(4-chloro-2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-pyridinyl]carbamate,
(6S)-6-[5-(6-amino-3-pyridinyl)-4-fluoro-1H-imidazol-2-yl]-2-[5-chloro-2-(1H-tetrazol-1-yl)phenyl]-7,8-dihydropyrrolo[1,2-a]pyrimidin-4(6H)-one,
methyl[4-(5-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-2-yl)phenyl]carbamate,
methyl[4-(4-chloro-5-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-2-yl)phenyl]carbamate,
(3S)-3-[5-(4-aminophenyl)-1H-imidazol-2-yl]-7-[5-methyl-2-(1H-tetrazol-1-yl)phenyl]-2,3-dihydro-5 (1H)-indolizinone,
2-methoxyethyl[4-(2-{(3S)-7-[5-methyl-2-(1H-tetrazol-1-yl)phenyl]-5-oxo-1,2,3,5-tetrahydro-3-indolizinyl}-1H-imidazol-5-yl)phenyl]carbamate, 3-oxetanyl[4-(2-{(3S)-7-[5-methyl-2-(1H-tetrazol-1-yl)phenyl]-5-oxo-1,2,3,5-tetrahydro-3-indolizinyl}-1H-imidazol-5-yl)phenyl]carbamate, methyl[4-(4-methyl-2-{(3S)-7-[5-methyl-2-(1H-tetrazol-1-yl)phenyl]-5-oxo-1,2,3,5-tetrahydro-3-indolizinyl}-1H-imidazol-5-yl)phenyl]carbamate, methyl[4-(5-methyl-2-{(3S)-7-[5-methyl-2-(1H-tetrazol-1-yl)phenyl]-5-oxo-1,2,3,5-tetrahydro-3-indolizinyl}-1,3-oxazol-4-yl)phenyl]carbamate, 2-methoxyethyl[4-(4-methyl-2-{(3S)-7-[5-methyl-2-(1H-tetrazol-1-yl)phenyl]-5-oxo-1,2,3,5-tetrahydro-3-indolizinyl}-1H-imidazol-5-yl)phenyl]carbamate, 2-ethoxyethyl[4-(2-{(3S)-7-[5-methyl-2-(1H-tetrazol-1-yl)phenyl]-5-oxo-1,2,3,5-tetrahydro-3-indolizinyl}-1H-imidazol-5-yl)phenyl]carbamate, 3-methoxypropyl[4-(2-{(3S)-7-[5-methyl-2-(1H-tetrazol-1-yl)phenyl]-5-oxo-1,2,3,5-tetrahydro-3-indolizinyl}-1H-imidazol-5-yl)phenyl]carbamate, (3S)-3-[5-(6-amino-3-pyridinyl)-1H-imidazol-2-yl]-7-[5-methyl-2-(1H-tetrazol-1-yl)phenyl]-2,3-dihydro-5(1H)-indolizinone, (3S)-3-{5-[6-(methylamino)-3-pyridinyl]-1H-imidazol-2-yl}-7-[5-methyl-2-(1H-tetrazol-1-yl)phenyl]-2,3-dihydro-5(1H)-indolizinone, (3S)-3-[5-(6-amino-2-fluoro-3-pyridinyl)-1H-imidazol-2-yl]-7-[5-methyl-2-(1H-tetrazol-1-yl)phenyl]-2,3-dihydro-5(1H)-indolizinone, (3S)-3-[5-(6-amino-2-chloro-3-pyridinyl)-1H-imidazol-2-yl]-7-[5-methyl-2-(1H-tetrazol-1-yl)phenyl]-2,3-dihydro-5(1H)-indolizinone, methyl[6-(2-{(3S)-7-[5-methyl-2-(1H-tetrazol-1-yl)phenyl]-5-oxo-1,2,3,5-tetrahydro-3-indolizinyl}-1H-imidazol-5-yl)-3-pyridinyl]carbamate, 2-methoxyethyl[6-(2-{(3S)-7-[5-methyl-2-(1H-tetrazol-1-yl)phenyl]-5-oxo-1,2,3,5-tetrahydro-3-indolizinyl}-1H-imidazol-5-yl)-3-pyridinyl]carbamate, 6-(2-{(3S)-7-[5-methyl-2-(1H-tetrazol-1-yl)phenyl]-5-oxo-1,2,3,5-tetrahydro-3-indolizinyl}-1H-imidazol-5-yl)-3,4-dihydro-2(1H)-quinolinone, methyl[5-(2-{(3S)-7-[5-methyl-2-(1H-tetrazol-1-yl)phenyl]-5-oxo-1,2,3,5-tetrahydro-3-indolizinyl}-1H-imidazol-5-yl)-2-pyridinyl]carbamate, 2-methoxyethyl[5-(2-{(3S)-7-[5-methyl-2-(1H-tetrazol-1-yl)phenyl]-5-oxo-1,2,3,5-tetrahydro-3-indolizinyl}-1H-imidazol-5-yl)-2-pyridinyl]carbamate, 2-ethoxyethyl[4-(4-chloro-2-{(3S)-7-[5-methyl-2-(1H-tetrazol-1-yl)phenyl]-5-oxo-1,2,3,5-tetrahydro-3-indolizinyl}-1H-imidazol-5-yl)phenyl]carbamate, 3-methoxypropyl[4-(4-chloro-2-{(3S)-7-[5-methyl-2-(1H-tetrazol-1-yl)phenyl]-5-oxo-1,2,3,5-tetrahydro-3-indolizinyl}-1H-imidazol-5-yl)phenyl]carbamate, 2-methoxyethyl[6-(4-chloro-2-{(3S)-7-[5-methyl-2-(1H-tetrazol-1-yl)phenyl]-5-oxo-1,2,3,5-tetrahydro-3-indolizinyl}-1H-imidazol-5-yl)-3-pyridinyl]carbamate, (3S)-3-[5-(6-amino-3-pyridinyl)-4-chloro-1H-imidazol-2-yl]-7-[5-methyl-2-(1H-tetrazol-1-yl)phenyl]-2,3-dihydro-5(1H)-indolizinone, (3S)-3-{4-chloro-5-[6-(methylamino)-3-pyridinyl]-1H-imidazol-2-yl}-7-[5-methyl-2-(1H-tetrazol-1-yl)phenyl]-2,3-dihydro-5(1H)-indolizinone, methyl[6-(4-chloro-2-{(3S)-7-[5-methyl-2-(1H-tetrazol-1-yl)phenyl]-5-oxo-1,2,3,5-tetrahydro-3-indolizinyl}-1H-imidazol-5-yl)-3-pyridinyl]carbamate, methyl[5-(4-chloro-2-{(3S)-7-[5-methyl-2-(1H-tetrazol-1-yl)phenyl]-5-oxo-1,2,3,5-tetrahydro-3-indolizinyl}-1H-imidazol-5-yl)-2-pyridinyl]carbamate, 2-methoxyethyl[5-(4-chloro-2-{(3S)-7-[5-methyl-2-(1H-tetrazol-1-yl)phenyl]-5-oxo-1,2,3,5-tetrahydro-3-indolizinyl}-1H-imidazol-5-yl)-2-pyridinyl]carbamate, methyl[4-(2-{(6S)-2-[5-methyl-2-(1H-tetrazol-1-yl)phenyl]-4-oxo-4,6,7,8-tetrahydropyrrolo[1,2-a]pyrimidin-6-yl}-1H-imidazol-5-yl)phenyl]carbamate, 2-methoxyethyl[4-(2-{(6S)-2-[5-methyl-2-(1H-tetrazol-1-yl)phenyl]-4-oxo-4,6,7,8-tetrahydropyrrolo[1,2-a]pyrimidin-6-yl}-1H-imidazol-5-yl)phenyl]carbamate, 2-ethoxyethyl[4-(2-{(6S)-2-[5-methyl-2-(1H-tetrazol-1-yl)phenyl]-4-oxo-4,6,7,8-tetrahydropyrrolo[1,2-a]pyrimidin-6-yl}-1H-imidazol-5-yl)phenyl]carbamate, 3-methoxypropyl[4-(2-{(6S)-2-[5-methyl-2-(1H-tetrazol-1-yl)phenyl]-4-oxo-4,6,7,8-tetrahydropyrrolo[1,2-a]pyrimidin-6-yl}-1H-imidazol-5-yl)phenyl]carbamate, methyl[4-(4-methyl-2-{(6S)-2-[5-methyl-2-(1H-tetrazol-1-yl)phenyl]-4-oxo-4,6,7,8-tetrahydropyrrolo[1,2-a]pyrimidin-6-yl}-1H-imidazol-5-yl)phenyl]carbamate, 2-methoxyethyl[4-(4-methyl-2-{(6S)-2-[5-methyl-2-(1H-tetrazol-1-yl)phenyl]-4-oxo-4,6,7,8-tetrahydropyrrolo[1,2-a]pyrimidin-6-yl}-1H-imidazol-5-yl)phenyl]carbamate, (6S)-6-[5-(6-amino-3-pyridinyl)-1H-imidazol-2-yl]-2-[5-methyl-2-(1H-tetrazol-1-yl)phenyl]-7,8-dihydropyrrolo[1,2-a]pyrimidin-4(6H)-one, (6S)-6-{5-[6-(methylamino)-3-pyridinyl]-1H-imidazol-2-yl}-2-[5-methyl-2-(1H-tetrazol-1-yl)phenyl]-7,8-dihydropyrrolo[1,2-a]pyrimidin-4(6H)-one, (6S)-6-[5-(6-amino-2-chloro-3-pyridinyl)-1H-imidazol-2-A-2-[5-methyl-2-(1H-tetrazol-1-yl)phenyl]-7,8-dihydropyrrolo[1,2-a]pyrimidin-4(6H)-one, methyl[6-(2-{(6S)-2-[5-methyl-2-(1H-tetrazol-1-yl)phenyl]-4-oxo-4,6,7,8-tetrahydropyrrolo[1,2-a]pyrimidin-6-yl}-1H-imidazol-5-yl)-3-pyridinyl]carbamate, 2-methoxyethyl[6-(2-{(6S)-2-[5-methyl-2-(1H-tetrazol-1-yl)phenyl]-4-oxo-4,6,7,8-tetrahydropyrrolo[1,2-a]pyrimidin-6-yl}-1H-imidazol-5-yl)-3-pyridinyl]carbamate, methyl[5-(2-{(6S)-2-[5-methyl-2-(1H-tetrazol-1-yl)phenyl]-4-oxo-4,6,7,8-tetrahydropyrrolo[1,2-a]pyrimidin-6-yl}-1H-imidazol-5-yl)-2-pyridinyl]carbamate, 2-methoxyethyl[5-(2-{(6S)-2-[5-methyl-2-(1H-tetrazol-1-yl)phenyl]-4-oxo-4,6,7,8-tetrahydropyrrolo[1,2-a]pyrimidin-6-yl}-1H-imidazol-5-yl)-2-pyridinyl]carbamate, methyl[4-(4-chloro-2-{(6S)-2-[5-methyl-2-(1H-tetrazol-1-yl)phenyl]-4-oxo-4,6,7,8-tetrahydropyrrolo[1,2-a]pyrimidin-6-yl}-1H-imidazol-5-yl)phenyl]carbamate, 2-methoxyethyl[4-(4-chloro-2-{(6S)-2-[5-methyl-2-(1H-tetrazol-1-yl)phenyl]-4-oxo-4,6,7,8-tetrahydropyrrolo[1,2-a]pyrimidin-6-yl}-1H-imidazol-5-yl)phenyl]carbamate, 2-ethoxyethyl[4-(4-chloro-2-{(6S)-2-[5-methyl-2-(1H-tetrazol-1-yl)phenyl]-4-oxo-4,6,7,8-tetrahydropyrrolo[1,2-a]pyrimidin-6-yl}-1H-imidazol-5-yl)phenyl]carbamate, 3-methoxypropyl[4-(4-chloro-2-{(6S)-2-[5-methyl-2-(1H-tetrazol-1-yl)phenyl]-4-oxo-4,6,7,8-tetrahydropyrrolo[1,2-a]pyrimidin-6-yl}-1H-imidazol-5-yl)phenyl]carbamate, (6S)-6-{4-chloro-5-[6-(methylamino)-3-pyridinyl]-1H-imidazol-2-yl}-2-[5-methyl-2-(1H-tetrazol-1-yl)phenyl]-7,8-dihydropyrrolo[1,2-a]pyrimidin-4(6H)-one, 2-methoxyethyl[6-(4-chloro-2-{(6S)-2-[5-methyl-2-(1H-tetrazol-1-yl)phenyl]-4-oxo-4,6,7,8-tetrahydropyrrolo[1,2-a]pyrimidin-6-yl}-1H-imidazol-5-yl)-3-pyridinyl]carbamate, methyl[5-(4-chloro-2-{(6S)-2-[5-methyl-2-(1H-tetrazol-1-yl)phenyl]-4-oxo-4,6,7,8-tetrahydropyrrolo[1,2-a]pyrimidin-6-yl}-1H-imidazol-5-yl)-2-pyridinyl]carbamate, 2-methoxyethyl[5-(4-chloro-2-{(6S)-2-[5-methyl-2-(1H-tetrazol-1-yl)phenyl]-4-oxo-4,6,7,8-tetrahydropyrrolo[1,2-a]pyrimidin-6-yl}-1H-imidazol-5-yl)-2-pyridinyl]carbamate, methyl[6-(4-chloro-2-{(6S)-2-[5-methyl-2-(1H-tetrazol-1-yl)phenyl]-4-oxo-4,6,7,8-tetrahydropyrrolo[1,2-a]pyrimidin-6-yl}-1H-imidazol-5-yl)-3-pyridinyl]carbamate, (6S)-6-[5-(6-amino-3-pyridinyl)-4-chloro-1H-imidazol-2-yl]-2-[5-methyl-2-(1H-tetrazol-1-yl)phenyl]-7,8-dihydropyrrolo[1,2-a]pyrimidin-4(6H)-one, 2-methoxyethyl[4-(2-{(3S)-7-[5-chloro-2-(4-chloro-1H-1,2,3-triazol-1-yl)phenyl]-5-oxo-1,2,3,5-tetrahydro-3-indolizinyl}-1H-imidazol-5-yl)phenyl]carbamate, (3S)-3-[5-(6-amino-3-pyridinyl)-1H-imidazol-2-yl]-7-[5-chloro-2-(4-chloro-1H-1,2,3-triazol-1-yl)phenyl]-2,3-dihydro-5(1H)-indolizinone, (3S)-7-[5-chloro-2-(4-chloro-1H-1,2,3-triazol-1-yl)phenyl]-3-{5-[6-(methylamino)-3-pyridinyl]-1H-imidazol-2-yl}-2,3-dihydro-5(1H)-indolizinone, (3S)-3-[5-(6-amino-2-fluoro-3-pyridinyl)-1H-imidazol-2-yl]-7-[5-chloro-2-(4-chloro-1H-1,2,3-triazol-1-yl)phenyl]-2,3-dihydro-5(1H)-indolizinone, (3S)-3-[5-(6-amino-2-chloro-3-pyridinyl)-1H-imidazol-2-yl]-7-[5-chloro-2-(4-chloro-1H-1,2,3-triazol-1-yl)phenyl]-2,3-dihydro-5(1H)-indolizinone, methyl[6-(2-{(3S)-7-[5-chloro-2-(4-chloro-1H-1,2,3-triazol-1-yl)phenyl]-5-oxo-1,2,3,5-tetrahydro-3-indolizinyl}-1H-imidazol-5-yl)-3-pyridinyl]carbamate, 2-methoxyethyl[6-(2-{(3S)-7-[5-chloro-2-(4-chloro-1H-1,2,3-triazol-1-yl)phenyl]-5-oxo-1,2,3,5-tetrahydro-3-indolizinyl}-1H-imidazol-5-yl)-3-pyridinyl]carbamate, 6-(2-{(3S)-7-[5-chloro-2-(4-chloro-1H-1,2,3-triazol-1-yl)phenyl]-5-oxo-1,2,3,5-tetrahydro-3-indolizinyl}-1H-imidazol-5-yl)-3,4-dihydro-2(1H)-quinolinone, 4-(2-{(3S)-7-[5-chloro-2-(4-chloro-1H-1,2,3-triazol-1-yl)phenyl]-5-oxo-1,2,3,5-tetrahydro-3-indolizinyl}-1H-imidazol-5-yl)benzamide, methyl[5-(2-{(3S)-7-[5-chloro-2-(4-chloro-1H-1,2,3-triazol-1-yl)phenyl]-5-oxo-1,2,3,5-tetrahydro-3-indolizinyl}-1H-imidazol-5-yl)-2-pyridinyl]carbamate, 2-methoxyethyl[5-(2-{(3S)-7-[5-chloro-2-(4-chloro-1H-1,2,3-triazol-1-yl)phenyl]-5-oxo-1,2,3,5-tetrahydro-3-indolizinyl}-1H-imidazol-5-yl)-2-pyridinyl]carbamate, (3S)-3-[5-(6-amino-3-pyridinyl)-4-chloro-1H-imidazol-2-yl]-7-[5-chloro-2-(4-chloro-1H-1,2,3-triazol-1-yl)phenyl]-2,3-dihydro-5(1H)-indolizinone, (3S)-7-[5-chloro-2-(4-chloro-1H-1,2,3-triazol-1-yl)phenyl]-3-{4-chloro-5-[6-(methylamino)-3-pyridinyl]-1H-imidazol-2-yl}-2,3-dihydro-5(1H)-indolizinone, methyl[6-(4-chloro-2-{(3S)-7-[5-chloro-2-(4-chloro-1H-1,2,3-triazol-1-yl)phenyl]-5-oxo-1,2,3,5-tetrahydro-3-indolizinyl}-1H-imidazol-5-yl)-3-pyridinyl]carbamate, 2-methoxyethyl[6-(4-chloro-2-{(3S)-7-[5-chloro-2-(4-chloro-1H-1,2,3-triazol-1-yl)phenyl]-5-oxo-1,2,3,5-tetrahydro-3-indolizinyl}-1H-imidazol-5-yl)-3-pyridinyl]carbamate, methyl[4-(2-{(6S)-2-[5-chloro-2-(4-chloro-1H-1,2,3-triazol-1-yl)phenyl]-4-oxo-4,6,7,8-tetrahydropyrrolo[1,2-a]pyrimidin-6-yl}-1H-imidazol-5-yl)phenyl]carbamate, 2-methoxyethyl[4-(2-{(6S)-2-[5-chloro-2-(4-chloro-1H-1,2,3-triazol-1-yl)phenyl]-4-oxo-4,6,7,8-tetrahydropyrrolo[1,2-a]pyrimidin-6-yl}-1H-imidazol-5-yl)phenyl]carbamate, methyl[4-(2-{(6S)-2-[5-chloro-2-(4-chloro-1H-1,2,3-triazol-1-yl)phenyl]-4-oxo-4,6,7,8-tetrahydropyrrolo[1,2-a]pyrimidin-6-yl}-4-methyl-1H-imidazol-5-yl)phenyl]carbamate, 2-methoxyethyl[4-(2-{(6S)-2-[5-chloro-2-(4-chloro-1H-1,2,3-triazol-1-yl)phenyl]-4-oxo-4,6,7,8-tetrahydropyrrolo[1,2-a]pyrimidin-6-yl}-4-methyl-1H-imidazol-5-yl)phenyl]carbamate, (6S)-6-[5-(6-amino-3-pyridinyl)-1H-imidazol-2-yl]-2-[5-chloro-2-(4-chloro-1H-1,2,3-triazol-1-yl)phenyl]-7,8-dihydropyrrolo[1,2-a]pyrimidin-4(6H)-one, (6S)-2-[5-chloro-2-(4-chloro-1H-1,2,3-triazol-1-yl)phenyl]-6-{5-[6-(methylamino)-3-pyridinyl]-1H-imidazol-2-yl}-7,8-dihydropyrrolo[1,2-a]pyrimidin-4(6H)-one, methyl[6-(2-{(6S)-2-[5-chloro-2-(4-chloro-1H-1,2,3-triazol-1-yl)phenyl]-4-oxo-4,6,7,8-tetrahydropyrrolo[1,2-a]pyrimidin-6-yl}-1H-imidazol-5-yl)-3-pyridinyl]carbamate, 2-methoxyethyl[6-(2-{(6S)-2-[5-chloro-2-(4-chloro-1H-1,2,3-triazol-1-yl)phenyl]-4-oxo-4,6,7,8-tetrahydropyrrolo[1,2-a]pyrimidin-6-yl}-1H-imidazol-5-yl)-3-pyridinyl]carbamate, 4-(2-{(6S)-2-[5-chloro-2-(4-chloro-1H-1,2,3-triazol-1-yl)phenyl]-4-oxo-4,6,7,8-tetrahydropyrrolo[1,2-a]pyrimidin-6-yl}-1H-imidazol-5-yl)benzamide, methyl[5-(2-{(6S)-2-[5-chloro-2-(4-chloro-1H-1,2,3-triazol-1-yl)phenyl]-4-oxo-4,6,7,8-tetrahydropyrrolo[1,2-a]pyrimidin-6-yl}-1H-imidazol-5-yl)-2-pyridinyl]carbamate, 2-methoxyethyl[5-(2-{(6S)-2-[5-chloro-2-(4-chloro-1H-1,2,3-triazol-1-yl)phenyl]-4-oxo-4,6,7,8-tetrahydropyrrolo[1,2-a]pyrimidin-6-yl}-1H-imidazol-5-yl)-2-pyridinyl]carbamate, methyl[4-(4-chloro-2-{(6S)-2-[5-chloro-2-(4-chloro-1H-1,2,3-triazol-1-yl)phenyl]-4-oxo-4,6,7,8-tetrahydropyrrolo[1,2-a]pyrimidin-6-yl}-1H-imidazol-5-yl)phenyl]carbamate, 2-methoxyethyl[4-(4-chloro-2-{(6S)-2-[5-chloro-2-(4-chloro-1H-1,2,3-triazol-1-yl)phenyl]-4-oxo-4,6,7,8-tetrahydropyrrolo[1,2-a]pyrimidin-6-yl}-1H-imidazol-5-yl)phenyl]carbamate, (6S)-2-[5-chloro-2-(4-chloro-1H-1,2,3-triazol-1-yl)phenyl]-6-{4-chloro-5-[6-(methylamino)-3-pyridinyl]-1H-imidazol-2-yl}-7,8-dihydropyrrolo[1,2-a]pyrimidin-4(6H)-one, methyl[6-(4-chloro-2-{(6S)-2-[5-chloro-2-(4-chloro-1H-1,2,3-triazol-1-yl)phenyl]-4-oxo-4,6,7,8-tetrahydropyrrolo[1,2-a]pyrimidin-6-yl}-1H-imidazol-5-yl)-3-pyridinyl]carbamate, 2-methoxyethyl[6-(4-chloro-2-{(6S)-2-[5-chloro-2-(4-chloro-1H-1,2,3-triazol-1-yl)phenyl]-4-oxo-4,6,7,8-tetrahydropyrrolo[1,2-a]pyrimidin-6-yl}-1H-imidazol-5-yl)-3-pyridinyl]carbamate, methyl[5-(4-chloro-2-{(6S)-2-[5-chloro-2-(4-chloro-1H-1,2,3-triazol-1-yl)phenyl]-4-oxo-4,6,7,8-tetrahydropyrrolo[1,2-a]pyrimidin-6-yl}-1H-imidazol-5-yl)-2-pyridinyl]carbamate, 2-methoxyethyl[5-(4-chloro-2-{(6S)-2-[5-chloro-2-(4-chloro-1H-1,2,3-triazol-1-yl)phenyl]-4-oxo-4,6,7,8-tetrahydropyrrolo[1,2-a]pyrimidin-6-yl}-1H-imidazol-5-yl)-2-pyridinyl]carbamate, (6S)-6-[5-(6-amino-3-pyridinyl)-4-chloro-1H-imidazol-2-yl]-2-[5-chloro-2-(4-chloro-1H-1,2,3-triazol-1-yl)phenyl]-7,8-dihydropyrrolo[1,2-a]pyrimidin-4(6H)-one, methyl[4-(2-{(3S)-7-[2-(4-chloro-1H-1,2,3-triazol-1-yl)-5-methylphenyl]-5-oxo-1,2,3,5-tetrahydro-3-indolizinyl}-1H-imidazol-5-yl)phenyl]carbamate, 2-methoxyethyl[4-(2-{(3S)-7-[2-(4-chloro-1H-1,2,3-triazol-1-yl)-5-methylphenyl]-5-oxo-1,2,3,5-tetrahydro-3-indolizinyl}-1H-imidazol-5-yl)phenyl]carbamate, methyl[4-(2-{(3S)-7-[2-(4-chloro-1H-1,2,3-triazol-1-yl)-5-methylphenyl]-5-oxo-1,2,3,5-tetrahydro-3-indolizinyl}-4-methyl-1H-imidazol-5-yl)phenyl]carbamate, 2-methoxyethyl[4-(2-{(3S)-7-[2-(4-chloro-1H-1,2,3-triazol-1-yl)-5-methylphenyl]-5-oxo-1,2,3,5-tetrahydro-3-indolizinyl}-4-methyl-1H-imidazol-5-yl)phenyl]carbamate, (3S)-3-[5-(6-amino-3-pyridinyl)-1H-imidazol-2-yl]-7-[2-(4-chloro-1H-1,2,3-triazol-1-yl)-5-methylphenyl]-2,3-dihydro-5(1H)-indolizinone, methyl[5-(2-{(3S)-7-[2-(4-chloro-1H-1,2,3-triazol-1-yl)-5-methylphenyl]-5-oxo-1,2,3,5-tetrahydro-3-indolizinyl}-1H-imidazol-5-yl)-2-pyridinyl]carbamate, 2-methoxyethyl[5-(2-{(3S)-7-[2-(4-chloro-1H-1,2,3-triazol-1-yl)-5-methylphenyl]-5-oxo-1,2,3,5-tetrahydro-3-indolizinyl}-1H-imidazol-5-yl)-2-pyridinyl]carbamate, methyl[4-(4-chloro-2-{(3S)-7-[2-(4-chloro-1H-1,2,3-triazol-1-yl)-5-methylphenyl]-5-oxo-1,2,3,5-tetrahydro-3-indolizinyl}-1H-imidazol-5-yl)phenyl]carbamate, 2-methoxyethyl[4-(4-chloro-2-{(3S)-7-[2-(4-chloro-1H-1,2,3-triazol-1-yl)-5-methylphenyl]-5-oxo-1,2,3,5-tetrahydro-3-indolizinyl}-1H-imidazol-5-yl)phenyl]carbamate, (3S)-3-[5-(6-amino-3-pyridinyl)-4-chloro-1H-imidazol-2-yl]-7-[2-(4-chloro-1H-1,2,3-triazol-1-yl)-5-methylphenyl]-2,3-dihydro-5(1H)-indolizinone, methyl[5-(4-chloro-2-{(3S)-7-[2-(4-chloro-1H-1,2,3-triazol-1-yl)-5-methylphenyl]-5-oxo-1,2,3,5-tetrahydro-3-indolizinyl}-1H-imidazol-5-yl)-2-pyridinyl]carbamate, 2-methoxyethyl[5-(4-chloro-2-{(3S)-7-[2-(4-chloro-1H-1,2,3-triazol-1-yl)-5-methylphenyl]-5-oxo-1,2,3,5-tetrahydro-3-indolizinyl}-1H-imidazol-5-yl)-2-pyridinyl]carbamate, N-carbamoyl-5-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxamide, (3S)-7-[5-chloro-2-(1H-tetrazol-1-yl)phenyl]-3-{5-[5-(methylsulfonyl)-2-thienyl]-1H-imidazol-2-yl}-2,3-dihydro-5(1H)-indolizinone, (3S)-3-{4-chloro-5-[5-(methylsulfonyl)-2-thienyl]-1H-imidazol-2-yl}-7-[5-chloro-2-(1H-tetrazol-1-yl)phenyl]-2,3-dihydro-5(1H)-indolizinone, 5-(2-{(3S)-7-[5-chloro-2-(1H-tetrazol-1-yl)phenyl]-5-oxo-1,2,3,5-tetrahydro-3-indolizinyl}-1H-imidazol-5-yl)-N-(methylsulfonyl)-2-thiophenecarboxamide, 5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-N-(methylsulfonyl)-2-thiophenecarboxamide, 5-(2-{(3S)-7-[5-chloro-2-(1H-tetrazol-1-yl)phenyl]-5-oxo-1,2,3,5-tetrahydro-3-indolizinyl}-1H-imidazol-5-yl)-2-furoic acid, 5-(2-{(3S)-7-[5-chloro-2-(1H-tetrazol-1-yl)phenyl]-5-oxo-1,2,3,5-tetrahydro-3-indolizinyl}-1H-imidazol-5-yl)-2-furamide, 5-(2-{(3S)-7-[5-chloro-2-(1H-tetrazol-1-yl)phenyl]-5-oxo-1,2,3,5-tetrahydro-3-indolizinyl}-1H-imidazol-5-yl)-N-methyl-2-furamide, 5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-furoic acid, 5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-furamide, 5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-N-methyl-2-furamide, 4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-furoic acid, 4-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-furoic acid, 2-methyl-2-propanyl 5-(2-{(3S)-7-[5-chloro-2-(1H-tetrazol-1-yl)phenyl]-5-oxo-1,2,3,5-tetrahydro-3-indolizinyl}-1H-imidazol-5-yl)-3-furoate, 5-(2-{(3S)-7-[5-chloro-2-(1H-tetrazol-1-yl)phenyl]-5-oxo-1,2,3,5-tetrahydro-3-indolizinyl}-1H-imidazol-5-yl)-3-furoic acid, 2-(2-{(3S)-7-[5-chloro-2-(1H-tetrazol-1-yl)phenyl]-5-oxo-1,2,3,5-tetrahydro-3-indolizinyl}-1H-imidazol-5-yl)-1,3-oxazole-4-carboxylic acid, 5-(2-{(3S)-7-[5-chloro-2-(1H-tetrazol-1-yl)phenyl]-5-oxo-1,2,3,5-tetrahydro-3-indolizinyl}-1H-imidazol-5-yl)-1H-pyrrole-2-carboxylic acid, 4-(2-{(3S)-7-[5-chloro-2-(1H-tetrazol-1-yl)phenyl]-5-oxo-1,2,3,5-tetrahydro-3-indolizinyl}-1H-imidazol-5-yl)-1H-pyrrole-2-carboxylic acid, 5-(2-{(3S)-7-[5-chloro-2-(1H-tetrazol-1-yl)phenyl]-5-oxo-1,2,3,5-tetrahydro-3-indolizinyl}-1H-imidazol-5-yl)-1H-pyrrole-3-carboxylic acid, (3S)-7-[5-chloro-2-(1H-tetrazol-1-yl)phenyl]-3-[5-(1-methyl-1H-pyrrol-2-yl)-1H-imidazol-2-yl]-2,3-dihydro-5(1H)-indolizinone, 5-(2-{(3S)-7-[5-chloro-2-(1H-tetrazol-1-yl)phenyl]-5-oxo-1,2,3,5-tetrahydro-3-indolizinyl}-1H-imidazol-5-yl)-1-methyl-1H-pyrrole-2-carboxylic acid, (3S)-7-[5-chloro-2-(1H-tetrazol-1-yl)phenyl]-3-[5-(3-hydroxy-1-methyl-1H-pyrazol-5-yl)-1H-imidazol-2-yl]-2,3-dihydro-5(1H)-indolizinone, ethyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thienyl]acetate,

[4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thienyl]acetic acid, ethyl[4-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-thienyl]acetate,

[4-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-thienyl]acetic acid, 4-(2-{(3S)-7-[5-chloro-2-(1H-tetrazol-1-yl)phenyl]-5-oxo-1,2,3,5-tetrahydro-3-indolizinyl}-1H-imidazol-5-yl)benzenesulfonamide, 4-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)benzenesulfonamide, 3-(2-{(3S)-7-[5-chloro-2-(1H-tetrazol-1-yl)phenyl]-5-oxo-1,2,3,5-tetrahydro-3-indolizinyl}-1H-imidazol-5-yl)benzenesulfonamide, (3S)-7-[5-chloro-2-(1H-tetrazol-1-yl)phenyl]-3-{5-[4-(5-oxo-4,5-dihydro-1,2,4-oxadiazol-3-yl)phenyl]-1H-imidazol-2-yl}-2,3-dihydro-5(1H)-indolizinone, (3S)-7-[5-chloro-2-(1H-tetrazol-1-yl)phenyl]-3-{5-[3-(5-oxo-4,5-dihydro-1,2,4-oxadiazol-3-yl)phenyl]-1H-imidazol-2-yl}-2,3-dihydro-5(1H)-indolizinone, (3S)-7-[5-chloro-2-(1H-tetrazol-1-yl)phenyl]-3-{5-[4-(trifluoroacetyl)phenyl]-1H-imidazol-2-yl}-2,3-dihydro-5(1H)-indolizinone, (3S)-7-[5-chloro-2-(1H-tetrazol-1-yl)phenyl]-3-{5-[4-(2,2,2-trifluoro-1-hydroxyethyl)phenyl]-1H-imidazol-2-yl}-2,3-dihydro-5(1H)-indolizinone,

[3-(2-{(3S)-8-chloro-7-[5-chloro-2-(1H-tetrazol-1-yl)phenyl]-5-oxo-1,2,3,5-tetrahydro-3-indolizinyl}-1H-imidazol-5-yl)phenyl]acetic acid,
2-methyl-2-propanyl {[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]thio}acetate,
{[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]thio}acetic acid,
{[3-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]thio}acetic acid,
{[3-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)phenyl]thio}acetic acid,
2-methyl-2-propanyl {[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]amino}acetate,
{[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]amino}acetic acid,
4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarbonitrile,
4-(2-{(3S)-7-[5-chloro-2-(1H-tetrazol-1-yl)phenyl]-5-oxo-1,2,3,5-tetrahydro-3-indolizinyl}-1H-imidazol-5-yl)-N-(methylsulfonyl)-2-thiophenecarboxamide,
4-(2-{(3S)-7-[5-chloro-2-(1H-tetrazol-1-yl)phenyl]-5-oxo-1,2,3,5-tetrahydro-3-indolizinyl}-1H-imidazol-5-yl)-3-fluoro-2-thiophenecarboxylic acid,
4-(2-{(3S)-7-[5-chloro-2-(1H-tetrazol-1-yl)phenyl]-5-oxo-1,2,3,5-tetrahydro-3-indolizinyl}-1H-imidazol-5-yl)-3-fluoro-2-pyridinecarboxylic acid,
4-(2-{(3S)-7-[5-chloro-2-(1H-tetrazol-1-yl)phenyl]-5-oxo-1,2,3,5-tetrahydro-3-indolizinyl}-1H-imidazol-5-yl)-3-thiophenecarboxylic acid,
4-(5-{7-[5-chloro-2-(1H-tetrazol-1-yl)phenyl]-5-oxo-1,2,3,5-tetrahydro-3-indolizinyl}-1H-pyrrol-2-yl)-2-thiophenecarboxylic acid,
ethyl 4-(5-{7-[5-chloro-2-(1H-tetrazol-1-yl)phenyl]-5-oxo-1,2,3,5-tetrahydro-3-indolizinyl}-4-fluoro-1H-imidazol-2-yl)-2-thiophenecarboxylate,
ethyl 4-(4-chloro-5-{7-[5-chloro-2-(1H-tetrazol-1-yl)phenyl]-5-oxo-1,2,3,5-tetrahydro-3-indolizinyl}-1H-imidazol-2-yl)-2-thiophenecarboxylate,
4-(5-{7-[5-chloro-2-(1H-tetrazol-1-yl)phenyl]-5-oxo-1,2,3,5-tetrahydro-3 indolizinyl}-1H-imidazol-2-yl)-2-thiophenecarboxylic acid,
4-(5-{7-[5-chloro-2-(1H-tetrazol-1-yl)phenyl]-5-oxo-1,2,3,5-tetrahydro-3-indolizinyl}-4-fluoro-1H-imidazol-2-yl)-2-thiophenecarboxylic acid,
4-(4-chloro-5-{7-[5-chloro-2-(1H-tetrazol-1-yl)phenyl]-5-oxo-1,2,3,5-tetrahydro-3-indolizinyl}-1H-imidazol-2-yl)-2-thiophenecarboxylic acid,
4-(4-chloro-5-{7-[5-chloro-2-(1H-tetrazol-1-yl)phenyl]-5-oxo-1,2,3,5-tetrahydro-3-indolizinyl}-1H-imidazol-2-yl)-2-thiophenecarboxylic acid,
(3S)-7-[5-chloro-2-(1H-tetrazol-1-yl)phenyl]-3-[5-(4-pyrimidinyl)-1H-imidazol-2-yl]-2,3-dihydro-5(1H)-indolizinone,
(3S)-7-[5-chloro-2-(1H-tetrazol-1-yl)phenyl]-3-[5-(2-fluorophenyl)-1H-imidazol-2-yl]-2,3-dihydro-5(1H)-indolizinone,
(3S)-3-[5-(4-chlorophenyl)-1H-imidazol-2-yl]-7-[5-chloro-2-(1H-tetrazol-1-yl)phenyl]-2,3-dihydro-5(1H)-indolizinone,
(3S)-3-[5-(3-chlorophenyl)-1H-imidazol-2-yl]-7-[5-chloro-2-(1H-tetrazol-1-yl)phenyl]-2,3-dihydro-5 (1H)-indolizinone,
(3S)-3-[5-(2-chlorophenyl)-1H-imidazol-2-yl]-7-[5-chloro-2-(1H-tetrazol-1-yl)phenyl]-2,3-dihydro-5 (1H)-indolizinone,
(3S)-7-[5-chloro-2-(1H-tetrazol-1-yl)phenyl]-3-{5-[4-(methylthio)phenyl]-1H-imidazol-2-yl}-2,3-dihydro-5 (1H)-indolizinone,
(3S)-7-[5-chloro-2-(1H-tetrazol-1-yl)phenyl]-3-[5-(4-methylphenyl)-1H-imidazol-2-yl]-2,3-dihydro-5(1H)-indolizinone,
4-(2-{(3S)-7-[5-chloro-2-(1H-tetrazol-1-yl)phenyl]-5-oxo-1,2,3,5-tetrahydro-3-indolizinyl}-1H-imidazol-5-yl)benzonitrile,
3-(2-{(3S)-7-[5-chloro-2-(1H-tetrazol-1-yl)phenyl]-5-oxo-1,2,3,5-tetrahydro-3-indolizinyl}-1H-imidazol-5-yl)benzonitrile,
(3S)-7-[5-chloro-2-(1H-tetrazol-1-yl)phenyl]-3-{5-[3-(trifluoromethyl)phenyl]-1H-imidazol-2-yl}-2,3-dihydro-5 (1H)-indolizinone,
(3S)-7-[5-chloro-2-(1H-tetrazol-1-yl)phenyl]-3-[5-(3-hydroxyphenyl)-1H-imidazol-2-yl]-2,3-dihydro-5(1H)-indolizinone,
(3S)-7-[5-chloro-2-(1H-tetrazol-1-yl)phenyl]-3-[5-(3-nitrophenyl)-1H-imidazol-2-yl]-2,3-dihydro-5(1H)-indolizinone,
2-methoxyethyl[4-(2-{(3S)-7-[5-chloro-2-(4-cyano-1H-1,2,3-triazol-1-yl)phenyl]-5-oxo-1,2,3,5-tetrahydro-3-indolizinyl)-1H-imidazol-5-yl)phenyl]carbamate,
2-methoxyethyl[4-(4-chloro-2-{(3S)-7-[5-chloro-2-(4-cyano-1H-1,2,3-triazol-1-yl)phenyl]-5-oxo-1,2,3,5-tetrahydro-3-indolizinyl}-1H-imidazol-5-yl)phenyl]carbamate,
1-(2-{(3S)-3-[5-(6-amino-3-pyridinyl)-4-chloro-1H-imidazol-2-yl]-5-oxo-1,2,3,5-tetrahydro-7-indolizinyl}-4-chlorophenyl)-1H-1,2,3-triazole-4-carbonitrile,
2-hydroxy-2-methylpropyl[5-(2-{(3S)-7-[5-chloro-2-(1H-tetrazol-1-yl)phenyl]-5-oxo-1,2,3,5-tetrahydro-3-indolizinyl}-1H-imidazol-5-yl)-2-pyridinyl]carbamate,
2-(2-methoxyethoxyl)ethyl[5-(2-{(3S)-7-[5-chloro-2-(1H-tetrazol-1-yl)phenyl]-5-oxo-1,2,3,5-tetrahydro-3-indolizinyl}-1H-imidazol-5-yl)-2-pyridinyl]carbamate,
2-(2-ethoxyethoxyl)ethyl[5-(2-{(3S)-7-[5-chloro-2-(1H-tetrazol-1-yl)phenyl]-5-oxo-1,2,3,5-tetrahydro-3-indolizinyl}-1H-imidazol-5-yl)-2-pyridinyl]carbamate,
3-hydroxy-3-methylbutyl[5-(4-chloro-2-{(3S)-7-[5-chloro-2-(1H-tetrazol-1-31)phenyl]-5-oxo-1,2,3,5-tetrahydro-3-indolizinyl}-1H-imidazol-5-yl)-2-pyridinyl]carbamate,
2-(2-methoxyethoxyl)ethyl[5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-pyridinyl]carbamate,
2-(2-ethoxyethoxyl)ethyl[5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-pyridinyl]carbamate,
2-(2-methoxyethoxyl)ethyl[5-(2-{(3S)-7-[5-chloro-2-(1H-tetrazol-1-yl)phenyl]-5-oxo-1,2,3,5-tetrahydro-3-indolizinyl}-4-fluoro-1H-imidazol-5-yl)-2-pyridinyl]carbamate,
2-(2-ethoxyethoxyl)ethyl[5-(2-{(3S)-7-[5-chloro-2-(1H-tetrazol-1-yl)phenyl]-5-oxo-1,2,3,5-tetrahydro-3-indolizinyl}-4-fluoro-1H-imidazol-5-yl)-2-pyridinyl]carbamate,
2-(2-methoxyethoxyl)ethyl[5-(2-{(6S)-2-[5-chloro-2-(1H-tetrazol-1-yl)phenyl]-4-oxo-4,6,7,8-tetrahydropyrrolo[1,2-a]pyrimidin-6-yl]-1H-imidazol-5-yl)-2-pyridinyl]carbamate, 2-(2-ethoxyethoxyl)ethyl[5-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-pyridinyl]carbamate,
2-(2-methoxyethoxyl)ethyl[5-(4-chloro-2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-pyridinyl]carbamate,
2-(2-ethoxyethoxyl)ethyl[5-(4-chloro-2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-pyridinyl]carbamate,
2-(2-methoxyethoxyl)ethyl[5-(2-{(6S)-2-[5-chloro-2-(1H-tetrazol-1-yl)phenyl]-4-oxo-4,6,7,8-tetrahydropyrrolo[1,2-a]pyrimidin-6-yl}-4-fluoro-1H-imidazol-5-yl)-2-pyridinyl]carbamate,
2-(2-ethoxyethoxyl)ethyl[5-(2-{(6S)-2-[5-chloro-2-(1H-tetrazol-1-yl)phenyl]-4-oxo-4,6,7,8-tetrahydropyrrolo[1,2-a]pyrimidin-6-yl}-4-fluoro-1H-imidazol-5-yl)-2-pyridinyl]carbamate,
(3S)-3-[5-(5-amino-2-pyridinyl)-4-chloro-1H-imidazol-2-yl]-7-[5-chloro-2-(1H-tetrazol-1-yl)phenyl]-2,3-dihydro-5(1H)-indolizinone,
(6S)-6-[5-(5-amino-2-pyridinyl)-4-chloro-1H-imidazol-2-yl]-2-[5-chloro-2-(1H-tetrazol-1-yl)phenyl]-7,8-dihydropyrrolo[1,2-a]pyrimidin-4(6H)-one,
methyl[4-(4-chloro-2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)phenyl]carbamate,
methyl[4-(4-chloro-2-{(3S)-7-[5-methyl-2-(1H-tetrazol-1-yl)phenyl]-5-oxo-1,2,3,5-tetrahydro-3-indolizinyl}-1H-imidazol-5-yl)phenyl]carbamate,
methyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)-3-methylphenyl]carbamate,
2-methoxyethyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate,
(3S)-7-[5-chloro-2-(1H-tetrazol-1-yl)phenyl]-3-[5-(4-hydroxyphenyl)-1H-imidazol-2-yl]-2,3-dihydro-5(1H)-indolizinone,
(3S)-3-[4-chloro-5-(4-hydroxyphenyl)-1H-imidazol-2-yl]-7-[5-chloro-2-(1H-tetrazol-1-yl)phenyl]-2,3-dihydro-5(1H)-indolizinone,
ethyl 5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylate,
3-methoxypropyl[6-(4-chloro-2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-3-pyridinyl]carbamate,
(3S)-3-[5-(6-amino-5-fluoro-3-pyridinyl)-4-chloro-1H-imidazol-2-yl]-7-[5-chloro-2-(1H-tetrazol-1-yl)phenyl]-2,3-dihydro-5(1H)-indolizinone,
3-(2-{(3S)-7-[5-chloro-2-(1H-tetrazol-1-yl)phenyl]-5-oxo-1,2,3,5-tetrahydro-3-indolizinyl}-1H-imidazol-5-yl)-2-fluorobenzoic acid,
5-(2-{(3S)-7-[5-chloro-2-(1H-tetrazol-1-yl)phenyl]-5-oxo-1,2,3,5-tetrahydro-3-indolizinyl}-1H-imidazol-5-yl)-2-fluorobenzoic acid,
3-(2-{(3S)-7-[5-chloro-2-(1H-tetrazol-1-yl)phenyl]-5-oxo-1,2,3,5-tetrahydro-3-indolizinyl}-1H-imidazol-5-yl)-2-methylbenzoic acid,
2-chloro-5-(2-{(3S)-7-[5-chloro-2-(1H-tetrazol-1-yl)phenyl]-5-oxo-1,2,3,5-tetrahydro-3-indolizinyl}-1H-imidazol-5-yl)benzoic acid,
1-[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]cyclopropanecarboxylic acid,
1-[3-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]cyclopropanecarboxylic acid,
1-[3-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)phenyl]cyclopropanecarboxylic acid,
3-(2-{(3S)-7-[5-chloro-2-(1H-tetrazol-1-yl)phenyl]-5-oxo-1,2,3,5-tetrahydro-3-indolizinyl}-1H-imidazol-5-yl)-2,6-difluorobenzoic acid,
2-chloro-3-(2-{(3S)-7-[5-chloro-2-(1H-tetrazol-1-yl)phenyl]-5-oxo-1,2,3,5-tetrahydro-3-indolizinyl}-1H-imidazol-5-yl)benzoic acid,
(2E)-3-[4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thienyl]acrylic acid,
3-[4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thienyl]propanoic acid,
5-(2-{(3S)-7-[5-chloro-2-(1H-tetrazol-1-yl)phenyl]-5-oxo-1,2,3,5-tetrahydro-3-indolizinyl}-1H-imidazol-5-yl)nicotinic acid,
2-(2-{(3S)-7-[5-chloro-2-(1H-tetrazol-1-yl)phenyl]-5-oxo-1,2,3,5-tetrahydro-3-indolizinyl}-1H-imidazol-5-yl)-1,3-thiazole-5-carboxylic acid,
6-(2-{(3S)-7-[5-chloro-2-(1H-tetrazol-1-yl)phenyl]-5-oxo-1,2,3,5-tetrahydro-3-indolizinyl}-1H-imidazol-5-yl)-2-pyridinecarboxylic acid,
4-(2-{(3S)-7-[5-chloro-2-(1H-tetrazol-1-yl)phenyl]-5-oxo-1,2,3,5-tetrahydro-3-indolizinyl}-1H-imidazol-5-yl)-1,3-thiazole-2-carboxylic acid,
4-chloro-3-(2-{(3S)-7-[5-chloro-2-(1H-tetrazol-1-yl)phenyl]-5-oxo-1,2,3,5-tetrahydro-3-indolizinyl}-1H-imidazol-5-yl)benzoic acid,
[5-(2-{(3S)-7-[5-chloro-2-(1H-tetrazol-1-yl)phenyl]-5-oxo-1,2,3,5-tetrahydro-3-indolizinyl}-1H-imidazol-5-yl)-1-benzothiophen-3-yl]acetic acid,
[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenoxy]acetic acid,
[3-(2-{(3S)-7-[5-chloro-2-(1H-tetrazol-1-yl)phenyl]-5-oxo-1,2,3,5-tetrahydro-3-indolizinyl}-1H-imidazol-5-yl)phenoxy]acetic acid,
2-(2-{(3S)-7-[5-chloro-2-(1H-tetrazol-1-yl)phenyl]-5-oxo-1,2,3,5-tetrahydro-3-indolizinyl}-1H-imidazol-5-yl)-1,3-thiazole-4-carboxylic acid,
3-(2-{(3S)-7-[5-chloro-2-(1H-tetrazol-1-yl)phenyl]-5-oxo-1,2,3,5-tetrahydro-3-indolizinyl}-1H-imidazol-5-yl)-4-fluorobenzoic acid,
[6-(2-{(3S)-7-[5-chloro-2-(1H-tetrazol-1-yl)phenyl]-5-oxo-1,2,3,5-tetrahydro-3-indolizinyl}-1H-imidazol-5-yl)-1-benzothiophen-3-yl]acetic acid,
2-(2-{(3S)-7-[5-chloro-2-(1H-tetrazol-1-yl)phenyl]-5-oxo-1,2,3,5-tetrahydro-3-indolizinyl}-1H-imidazol-5-yl)isonicotinic acid,
5-(2-{(3S)-7-[5-chloro-2-(1H-tetrazol-1-yl)phenyl]-5-oxo-1,2,3,5-tetrahydro-3-indolizinyl}-1H-imidazol-5-yl)-3-thiophenecarboxylic acid,
3-(2-{(3S)-7-[5-chloro-2-(1H-tetrazol-1-yl)phenyl]-5-oxo-1,2,3,5-tetrahydro-3-indolizinyl}-1H-imidazol-5-yl)-1H-pyrazole-5-carboxylic acid,
5-(2-{(3S)-7-[5-chloro-2-(1H-tetrazol-1-yl)phenyl]-5-oxo-1,2,3,5-tetrahydro-3-indolizinyl}-1H-imidazol-5-yl)-1H-indole-2-carboxylic acid, 5-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-1H-indole-2-carboxylic acid,

[5-(2-{(3S)-7-[5-chloro-2-(1H-tetrazol-1-yl)phenyl]-5-oxo-1,2,3,5-tetrahydro-3-indolizinyl}-1H-imidazol-5-yl)-1H-indol-3-yl]acetic acid,

[6-(2-{(3S)-7-[5-chloro-2-(1H-tetrazol-1-yl)phenyl]-5-oxo-1,2,3,5-tetrahydro-3-indolizinyl}-1H-imidazol-5-yl)-1H-indol-3-yl]acetic acid,

[5-(2-{(3S)-7-[5-chloro-2-(1H-tetrazol-1-yl)phenyl]-5-oxo-1,2,3,5-tetrahydro-3-indolizinyl}-1H-imidazol-5-yl)-1H-indazol-3-yl]acetic acid, {[3-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]amino}acetic acid,

[5-(2-{(3S)-7-[5-chloro-2-(1H-tetrazol-1-yl)phenyl]-5-oxo-1,2,3,5-tetrahydro-3-indolizinyl}-1H-imidazol-5-yl)-1H-indol-1-yl]acetic acid,

[5-(2-{(3S)-7-[5-chloro-2-(1H-tetrazol-1-yl)phenyl]-5-oxo-1,2,3,5-tetrahydro-3-indolizinyl}-1H-imidazol-5-yl)-1H-benzimidazol-1-yl]acetic acid, 5-(2-{(3S)-6-chloro-7-[5-chloro-2-(1H-tetrazol-1-yl)phenyl]-5-oxo-1,2,3,5-tetrahydro-3-indolizinyl}-1H-imidazol-5-yl)-2-thiophenecarboxylic acid, 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-pyridinecarboxylic acid, 4-(4-chloro-2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-pyridinecarboxylic acid, 4-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-pyridinecarboxylic acid, 4-(4-chloro-2-{(3S)-8-chloro-7-[5-chloro-2-(1H-tetrazol-1-yl)phenyl]-5-oxo-1,2,3,5-tetrahydro-3-indolizinyl}-1H-imidazol-5-yl)-2-pyridinecarboxylic acid, 4-(2-{(3S)-7-[5-chloro-2-(4-chloro-1H-1,2,3-triazol-1-yl)phenyl]-5-oxo-1,2,3,5-tetrahydro-3-indolizinyl}-1H-imidazol-5-yl)-2-thiophenecarboxylic acid, 4-(2-{(3S)-7-[5-chloro-2-(4-chloro-1H-1,2,3-triazol-1-yl)phenyl]-5-oxo-1,2,3,5-tetrahydro-3-indolizinyl}-1H-imidazol-5-yl)-2-pyridinecarboxylic acid, (3S)-3-[5-(6-amino-3-pyridinyl)-4-chloro-1H-imidazol-2-yl]-7-[5-chloro-2-(1,2,3-thiadiazol-4-yl)phenyl]-2,3-dihydro-5(1H)-indolizinone, methyl 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-thiophenecarboxylate, 2-oxo-2-(1-pyrrolidinyl)ethyl 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-thiophenecarboxylate, 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-N,N-dimethyl-2-thiophenecarboxamide, ethyl 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-thiophenecarboxylate, isobutyl 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-thiophenecarboxylate, 2,3-dihydro-1H-inden-5-yl 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-thiophenecarboxylate, (5-methyl-2-oxo-1,3-dioxol-4-yl)methyl 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-thiophenecarboxylate, 2-(4-morpholinyl)ethyl 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-thiophenecarboxylate, 2-(dimethylamino)-2-oxoethyl 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-thiophenecarboxylate, 2-(diethylamino)-2-oxoethyl 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-thiophenecarboxylate, 2-oxo-2-(1-piperidinyl)ethyl 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-thiophenecarboxylate, 2-(4-morpholinyl)-2-oxoethyl 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-thiophenecarboxylate, isopropyl 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-thiophenecarboxylate, 1-{[(cyclohexyloxy)carbonyl]oxy}ethyl 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-thiophenecarboxylate, cyclohexyl 2-{(6S)-2-[5-chloro-2-(1H-tetrazol-1-yl)phenyl]-4-oxo-4,6,7,8-tetrahydropyrrolo[1,2-a]pyrimidin-6-yl}-5-{5-[(1-{[(cyclohexyloxy)carbonyl]oxy}ethoxy)carbonyl]-3-thienyl}-1H-imidazole-1-carboxylate,

[(2,2-dimethylpropanoyl)oxy]methyl 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-thiophenecarboxylate,

[(2,2-dimethylpropanoyl)oxy]methyl 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1-{[(2,2-dimethylpropanoy)oxy]methyl}-1H-imidazol-5-yl)-2-thiophenecarboxylate, 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-3-fluoro-2-thiophenecarboxylic acid, 5-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-thiophenecarboxylic acid, 5-(2-{(6S)-2-[5-chloro-2-(1H-tetrazol-1-yl)phenyl]-4-oxo-4,6,7,8-tetrahydropyrrolo[1,2-a]pyrimidin-6-yl}-4-fluoro-1H-imidazol-5-yl)-2-thiophenecarboxylic acid, and methyl[6-(2-{(3S)-7-[5-chloro-2-(1H-tetrazol-1-yl)phenyl]-5-oxo-1,2,3,5-tetrahydro-3-indolizinyl}-1H-imidazol-5-yl)-3-pyridinyl]carbamate, salts thereof, N-oxides thereof, solvates thereof, and prodrugs thereof.

Particularly preferred compounds of formula (I-B) include:

4-[5-chloro-2-(1H-tetrazol-1-yl)phenyl]-1-[(5-phenyl-1H-imidazol-2-yl)methyl]-2(1H)-pyridinone, methyl{4-[2-({4-[5-chloro-2-(1H-tetrazol-1-yl)phenyl]-2-oxo-1(2H)-pyridinyl}methyl)-1H-imidazol-4-yl]phenyl}carbamate, methyl{4-[5-chloro-2-({4-[5-chloro-2-(1H-tetrazol-1-yl)
phenyl]-2-oxo-1(2H)-pyridinyl}methyl)-1H-imidazol-4-
yl]phenyl}carbamate,
methyl{4-[2-(1-{4-[5-chloro-2-(1H-tetrazol-1-yl)phenyl]-2-
oxo-1(2H)-pyridinyl}propyl)-1H-imidazol-4-yl]
phenyl}carbamate,
methyl{4-[5-chloro-2-(1-{4-[5-chloro-2-(1H-tetrazol-1-yl)
phenyl]-2-oxo-1(2H)-pyridinyl}propyl)-1H-imidazol-4-
yl]phenyl}carbamate,
methyl{4-[2-(1-{4-[5-chloro-2-(1H-tetrazol-1-yl)phenyl]-2-
oxo-1(2H)-pyridinyl}ethyl)-1H-imidazol-5-yl]
phenyl}carbamate,
methyl{4-[2-(1-{4-[5-chloro-2-(1H-tetrazol-1-yl)phenyl]-2-
oxo-1(2H)-pyridinyl}cyclopropyl)-1H-imidazol-5-yl]
phenyl}carbamate,
methyl{4-[2-(1-{4-[5-chloro-2-(1H-tetrazol-1-yl)phenyl]-2-
oxo-1(2H)-pyridinyl}-2-phenylethyl)-1H-imidazol-4-yl]
phenyl}carbamate,
methyl[4-(2-{1-[4-(2-carbamimidamido-5-chlorophenyl)-2-
oxo-1(2H)-pyridinyl]-2-phenylethyl}-1H-imidazol-4-yl)
phenyl]carbamate,
methyl{4-[5-chloro-2-(1-{4-[5-chloro-2-(1H-tetrazol-1-yl)
phenyl]-2-oxo-1(2H)-pyridinyl}-2-phenylethyl)-1H-imi-
dazol-4-yl]phenyl}carbamate,
4-[5-chloro-2-(1H-tetrazol-1-yl)phenyl]-1-{2-phenyl-1-[5-
(1H-pyrazol-1-yl)-1H-benzimidazol-2-yl]ethyl}-2(1H)-
pyridinone,
1-{1-[5-(4-aminophenyl)-1H-imidazol-2-yl]-2-phenyl-
ethyl}-4-(2,5-dichlorophenyl)-2(1H)-pyridinone,
methyl[4-(2-{1-[4-(2,5-dichlorophenyl)-2-oxo-1(2H)-
pyridinyl]-2-phenylethyl}-1H-imidazol-4-yl)phenyl]car-
bamate,
methyl[4-(5-chloro-2-{1-[4-(2,5-dichlorophenyl)-2-oxo-1
(2H)-pyridinyl]-2-phenylethyl}-1H-imidazol-4-yl)phe-
nyl]carbamate,
methyl{4-[2-({4-[5-chloro-2-(1H-tetrazol-1-yl)phenyl]-2-
oxo-1(2H)-pyridinyl}methyl)-4-methyl-1H-imidazol-5-
yl]phenyl}carbamate,
methyl{4-[2-({4-[5-chloro-2-(1H-tetrazol-1-yl)phenyl]-2-
oxo-1(2H)-pyridinyl}methyl)-4-ethyl-1H-imidazol-5-yl]
phenyl}carbamate,
6-[2-({4-[5-chloro-2-(1H-tetrazol-1-yl)phenyl]-2-oxo-1
(2H)-pyridinyl}methyl)-1H-imidazol-5-yl]-3,4-dihydro-2
(1H)-quinolinone,
6-[4-chloro-2-({4-[5-chloro-2-(1H-tetrazol-1-yl)phenyl]-2-
oxo-1(2H)-pyridinyl}methyl)-1H-imidazol-5-yl]-3,4-di-
hydro-2(1H)-quinolinone,
methyl{3-chloro-4-[2-({4-[5-chloro-2-(1H-tetrazol-1-yl)
phenyl]-2-oxo-1(2H)-pyridinyl}methyl)-1H-imidazol-5-
yl]phenyl}carbamate,
4-[2-({4-[5-chloro-2-(1H-tetrazol-1-yl)phenyl]-2-oxo-1
(2H)-pyridinyl}methyl)-1H-imidazol-5-yl]benzamide,
4-[4-chloro-2-({4-[5-chloro-2-(1H-tetrazol-1-yl)phenyl]-2-
oxo-1(2H)-pyridinyl}methyl)-1H-imidazol-5-yl]benz-
amide,
6-[2-({4-[5-chloro-2-(1H-tetrazol-1-yl)phenyl]-2-oxo-1
(2H)-pyridinyl}methyl)-1H-imidazol-5-yl]-3-methyl-3,4-
dihydro-2(1H)-quinazolinone,
6-[4-chloro-2-({4-[5-chloro-2-(1H-tetrazol-1-yl)phenyl]-2-
oxo-1(2H)-pyridinyl}methyl)-1H-imidazol-5-yl]-3-
methyl-3,4-dihydro-2(1H)-quinazolinone,
1-{[5-(6-amino-3-pyridinyl)-1H-imidazol-2-yl]methyl}-4-
[5-chloro-2-(1H-tetrazol-1-yl)phenyl]-2(1H)-pyridinone,
methyl{5-[2-({4-[5-chloro-2-(1H-tetrazol-1-yl)phenyl]-2-
oxo-1(2H)-pyridinyl}methyl)-1H-imidazol-5-yl]-2-
pyridinyl}carbamate,
1-{[5-(6-amino-2-chloro-3-pyridinyl)-1H-imidazol-2-yl]
methyl}-4-[5-chloro-2-(1H-tetrazol-1-yl)phenyl]-2(1H)-
pyridinone,
methyl{6-[2-({4-[5-chloro-2-(1H-tetrazol-1-yl)phenyl]-2-
oxo-1(2H)-pyridinyl}methyl)-1H-imidazol-5-yl]-3-
pyridinyl}carbamate,
methyl{4-[2-(1-{4-[5-chloro-2-(1H-tetrazol-1-yl)phenyl]-2-
oxo-1(2H)-pyridinyl}-3-methoxypropyl)-1H-imidazol-5-
yl]phenyl}carbamate,
methyl{4-[4-chloro-2-(1-{4-[5-chloro-2-(1H-tetrazol-1-yl)
phenyl]-2-oxo-1(2H)-pyridinyl}-3-methoxypropyl)-1H-
imidazol-5-yl]phenyl}carbamate,
methyl(4-{2-[(1S)-1-{4-[5-chloro-2-(1H-tetrazol-1-yl)phe-
nyl]-2-oxo-1(2H)-pyridinyl}-2-phenylethyl]-1H-imida-
zol-4-yl}phenyl)carbamate,
methyl{4-[2-({4-[5-chloro-2-(1H-tetrazol-1-yl)phenyl]-2-
oxo-1(2H)-pyridinyl}methyl)-4-methyl-1H-imidazol-5-
yl]phenyl}carbamate,
methyl(4-{2-[1-{4-[5-chloro-2-(1H-tetrazol-1-yl)phenyl]-2-
oxo-1(2H)-pyridinyl}-2-(3-pyridinyl)ethyl]-1H-imida-
zol-5-yl}phenyl)carbamate,
methyl(4-{4-chloro-2-[1-{4-[5-chloro-2-(1H-tetrazol-1-yl)
phenyl]-2-oxo-1(2H)-pyridinyl}-2-(3-pyridinyl)ethyl]-
1H-imidazol-5-yl}phenyl)carbamate,
methyl 1-(4-chloro-2-{1-[(1S)-1-(5-{4-[(methoxycarbonyl)
amino]phenyl}-1H-imidazol-2-yl)-2-phenylethyl]-2-oxo-
1,2-dihydro-4-pyridinyl}phenyl)-1H-1,2,3-triazole-4-car-
boxylate,
methyl[4-(2-{(1S)-1-[4-{5-chloro-2-[4-(trifluoromethyl)-
1H-1,2,3-triazol-1-yl]phenyl}-2-oxo-1(2H)-pyridinyl]-2-
phenylethyl}-1H-imidazol-4-yl)phenyl]carbamate,
methyl(4-{2-[(1S)-1-{4-[5-chloro-2-(4-chloro-1H-1,2,3-tri-
azol-1-yl)phenyl]-2-oxo-1(2H)-pyridinyl}-2-phenyl-
ethyl]-1H-imidazol-5-yl}phenyl)carbamate,
methyl(4-{2-[(1S)-1-{4-[5-chloro-2-(4-fluoro-1H-pyrazol-
1-yl)phenyl]-2-oxo-1(2H)-pyridinyl}-2-phenylethyl]-1H-
imidazol-5-yl}phenyl)carbamate,
methyl[4-(2-{(1S)-1-[4-{5-chloro-2-[4-(trifluoromethyl)-
1H-pyrazol-1-yl]phenyl}-2-oxo-1(2H)-pyridinyl]-2-phe-
nylethyl}-1H-imidazol-4-yl)phenyl]carbamate,
methyl{4-[2-(1-{4-[5-chloro-2-(1H-tetrazol-1-yl)phenyl]-6-
methyl-2-oxo-1(2H)-pyridinyl}ethyl)-1H-imidazol-5-yl]
phenyl}carbamate,
methyl{4-[2-({4-[5-chloro-2-(1H-tetrazol-1-yl)phenyl]-6-
methyl-2-oxo-1(2H)-pyridinyl}methyl)-1H-imidazol-5-
yl]phenyl}carbamate,
methyl{4-[2-({4-[5-chloro-2-(1H-tetrazol-1-yl)phenyl]-6-
ethyl-2-oxo-1(2H)-pyridinyl}methyl)-1H-imidazol-5-yl]
phenyl}carbamate,
4-[2-({4-[5-chloro-2-(1H-tetrazol-1-yl)phenyl]-6-methyl-2-
oxo-1(2H)-pyridinyl}methyl)-1H-imidazol-5-yl]-2-thio-
phenecarboxylic acid,
methyl{4-[2-({4-[5-methyl-2-(1H-tetrazol-1-yl)phenyl]-2-
oxo-1(2H)-pyridinyl}methyl)-1H-imidazol-5-yl]
phenyl}carbamate,
methyl{4-[4-chloro-2-({4-[5-methyl-2-(1H-tetrazol-1-yl)
phenyl]-2-oxo-1(2H)-pyridinyl}methyl)-1H-imidazol-5-
yl]phenyl}carbamate,
1-{[5-(4-aminophenyl)-1H-imidazol-2-yl]methyl}-4-[5-
chloro-2-(1H-tetrazol-1-yl)phenyl]-6-methyl-2(1H)-pyri-
dinone,
2-methoxyethyl{4-[2-({4-[5-chloro-2-(1H-tetrazol-1-yl)
phenyl]-6-methyl-2-oxo-1(2H)-pyridinyl}methyl)-1H-
imidazol-5-yl]phenyl}carbamate,
methyl{4-[2-({4-[5-chloro-2-(1H-tetrazol-1-yl)phenyl]-6-
methyl-2-oxo-1(2H)-pyridinyl}methyl)-4-methyl-1H-
imidazol-5-yl]phenyl}carbamate, 2-methoxyethyl{4-[2-({4-[5-chloro-2-(1H-tetrazol-1-yl)phenyl]-6-methyl-2-oxo-1(2H)-pyridinyl}methyl)-4-methyl-1H-imidazol-5-yl]phenyl}carbamate,
1-{[5-(6-amino-3-pyridinyl)-1H-imidazol-2-yl]methyl}-4-[5-chloro-2-(1H-tetrazol-1-yl)phenyl]-6-methyl-2(1H)-pyridinone,
4-[5-chloro-2-(1H-tetrazol-1-yl)phenyl]-6-methyl-1-({5-[6-(methylamino)-3-pyridinyl]-1H-imidazol-2-yl}methyl)-2(1H)-pyridinone,
1-{[5-(6-amino-2-fluoro-3-pyridinyl)-1H-imidazol-2-yl]methyl}-4-[5-chloro-2-(1H-tetrazol-1-yl)phenyl]-6-methyl-2(1H)-pyridinone,
1-{[5-(6-amino-2-chloro-3-pyridinyl)-1H-imidazol-2-yl]methyl}-4-[5-chloro-2-(1H-tetrazol-1-yl)phenyl]-6-methyl-2(1H)-pyridinone,
methyl{6-[2-({4-[5-chloro-2-(1H-tetrazol-1-yl)phenyl]-6-methyl-2-oxo-1(2H)-pyridinyl}methyl)-1H-imidazol-5-yl]-3-pyridinyl}carbamate,
2-methoxyethyl{6-[2-({4-[5-chloro-2-(1H-tetrazol-1-yl)phenyl]-6-methyl-2-oxo-1(2H)-pyridinyl}methyl)-1H-imidazol-5-yl]-3-pyridinyl}carbamate,
methyl{5-[2-({4-[5-chloro-2-(1H-tetrazol-1-yl)phenyl]-6-methyl-2-oxo-1(2H)-pyridinyl}methyl)-1H-imidazol-5-yl]-2-pyridinyl}carbamate,
2-methoxyethyl{5-[2-({4-[5-chloro-2-(1H-tetrazol-1-yl)phenyl]-6-methyl-2-oxo-1(2H)-pyridinyl}methyl)-1H-imidazol-5-yl]-2-pyridinyl}carbamate,
2-methoxyethyl{4-[4-chloro-2-({4-[5-chloro-2-(1H-tetrazol-1-yl)phenyl]-6-methyl-2-oxo-1(2H)-pyridinyl}methyl)-1H-imidazol-5-yl]phenyl}carbamate,
1-({4-chloro-5-[6-(methylamino)-3-pyridinyl]-1H-imidazol-2-yl}methyl)-4-[5-chloro-2-(1H-tetrazol-1-yl)phenyl]-6-methyl-2(1H)-pyridinone,
methyl{6-[4-chloro-2-({4-[5-chloro-2-(1H-tetrazol-1-yl)phenyl]-6-methyl-2-oxo-1(2H)-pyridinyl}methyl)-1H-imidazol-5-yl]-3-pyridinyl}carbamate,
2-methoxyethyl{6-[4-chloro-2-({4-[5-chloro-2-(1H-tetrazol-1-yl)phenyl]-6-methyl-2-oxo-1(2H)-pyridinyl}methyl)-1H-imidazol-5-yl]-3-pyridinyl}carbamate,
2-methoxyethyl{5-[4-chloro-2-({4-[5-chloro-2-(1H-tetrazol-1-yl)phenyl]-6-methyl-2-oxo-1(2H)-pyridinyl}methyl)-1H-imidazol-5-yl]-2-pyridinyl}carbamate,
1-{[5-(6-amino-3-pyridinyl)-4-chloro-1H-imidazol-2-yl]methyl}-4-[5-chloro-2-(1H-tetrazol-1-yl)phenyl]-6-methyl-2(1H)-pyridinone,
1-{[5-(6-amino-2-fluoro-3-pyridinyl)-4-chloro-1H-imidazol-2-yl]methyl}-4-[5-chloro-2-(1H-tetrazol-1-yl)phenyl]-6-methyl-2(1H)-pyridinone, and
methyl{4-[4-chloro-2-({4-[5-chloro-2-(1H-tetrazol-1-yl)phenyl]-6-methyl-2-oxo-1(2H)-pyridinyl}methyl)-1H-imidazol-5-yl]phenyl}carbamate,
salts thereof, N-oxides thereof, solvates thereof, and prodrugs thereof.

Particularly preferred compounds of formula (I-C) include:
methyl{4-[2-({4-[5-chloro-2-(1H-tetrazol-1-yl)phenyl]-2-methyl-6-oxo-1(6H)-pyrimidinyl}methyl)-1H-imidazol-5-yl]phenyl}carbamate,
2-methoxyethyl{4-[2-({4-[5-chloro-2-(1H-tetrazol-1-yl)phenyl]-2-methyl-6-oxo-1(6H)-pyrimidinyl}methyl)-1H-imidazol-5-yl]phenyl}carbamate,
2-methoxyethyl{4-[4-chloro-2-({4-[5-chloro-2-(1H-tetrazol-1-yl)phenyl]-2-methyl-6-oxo-1(6H)-pyrimidinyl}methyl)-1H-imidazol-5-yl]phenyl}carbamate,
3-{[5-(6-amino-3-pyridinyl)-1H-imidazol-2-yl]methyl}-6-[5-chloro-2-(1H-1-tetrazol-1-yl)phenyl]-2-methyl-4(3H)-pyrimidinone,
3-{[5-(6-amino-3-pyridinyl)-4-chloro-1H-imidazol-2-yl]methyl}-6-[5-chloro-2-(1H-tetrazol-1-yl)phenyl]-2-methyl-4(3H)-pyrimidinone,
methyl{4-[2-({4-[5-chloro-2-(1H-tetrazol-1-yl)phenyl]-2-isopropyl-6-oxo-1(6H)-pyrimidinyl}methyl)-1H-imidazol-5-yl]phenyl}carbamate,
methyl{4-[4-chloro-2-({4-[5-chloro-2-(1H-tetrazol-1-yl)phenyl]-2-isopropyl-6-oxo-1(6H)-pyrimidinyl}methyl)-1H-imidazol-5-yl]phenyl}carbamate,
methyl{4-[2-({4-[5-chloro-2-(1H-tetrazol-1-yl)phenyl]-2-cyclopropyl-6-oxo-1(6H)-pyrimidinyl}methyl)-1H-imidazol-5-yl]phenyl}carbamate,
methyl{4-[4-chloro-2-({4-[5-chloro-2-(1H-tetrazol-1-yl)phenyl]-2-cyclopropyl-6-oxo-1(6H)-pyrimidinyl}methyl)-1H-imidazol-5-yl]phenyl}carbamate,
methyl{4-[2-({4-[5-chloro-2-(1H-tetrazol-1-yl)phenyl]-2-cyclopropyl-6-oxo-1(6H)-pyrimidinyl}methyl)-4-fluoro-1H-imidazol-5-yl]phenyl}carbamate,
methyl{4-[2-({4-[5-chloro-2-(1H-tetrazol-1-yl)phenyl]-6-oxo-2-(tetrahydro-2H-pyran-4-yl)-1(6H)-pyrimidinyl}methyl)-1H-imidazol-5-yl]phenyl}carbamate,
methyl{4-[2-({4-[5-chloro-2-(1H-tetrazol-1-yl)phenyl]-2-(methoxymethyl)-6-oxo-1(6H)-pyrimidinyl}methyl)-1H-imidazol-5-yl]phenyl}carbamate,
methyl{4-[4-chloro-2-({4-[5-chloro-2-(1H-tetrazol-1-yl)phenyl]-2-(methoxymethyl)-6-oxo-1(6H)-pyrimidinyl}methyl)-1H-imidazol-5-yl]phenyl}carbamate, and
methyl{4-[4-chloro-2-({4-[5-chloro-2-(1H-tetrazol-1-yl)phenyl]-2-methyl-6-oxo-1(6H)-pyrimidinyl}methyl)-1H-imidazol-5-yl]phenyl}carbamate,
salts thereof, N-oxides thereof, solvates thereof, and prodrugs thereof.

Compounds of the present invention containing one or more chiral centres may be used in enantiomerically or diastereoisomerically pure form, or in the form of a mixture of isomers. For the avoidance of doubt, the compounds of the invention may be used in any tautomeric form.

Unless otherwise specifically mentioned, all isomers are included in the present invention. For example, alkyl, alkenyl, alkynyl, alkoxy and alkylthio may be straight chain or branched. Moreover, all isomers due to double bond, ring and fused ring (E-, Z-, cis- and trans-forms), isomers due to the presence of asymmetric carbon(s) etc. (R-, S-, α- and β-configuration, enantiomer and diastereomer), optically active substances having optical rotation (D-, L-, d- and l-forms), polar compounds by chromatographic separation (more polar compounds and less polar compounds), equilibrium compounds, rotational isomers, a mixture thereof in any proportion and a racemic mixture are included in the present invention.

According to the present invention, symbol 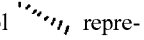 represents α-configuration, symbol  represents β-configuration and symbol 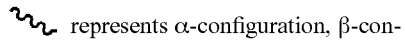 represents α-configuration, β-configuration or a mixture of them. There is no particular limitation for the ratio of α-configuration and β-configuration in the mixture.

Salts:
The salt of the compound of formula (I) includes all nontoxic salts or pharmaceutically acceptable salts. With regard to the pharmaceutically acceptable salts, those which are low-toxicity and soluble in water are preferred. Examples of appropriate salts of the compound of formula (I) are salt with alkaline metal (such as potassium, sodium and lithium), salt with alkaline earth metal (such as calcium and magnesium), ammonium salt (such as ammonium salt, tetramethylammonium salt and tetrabutylammonium salt), salt with organic amine (such as triethylamine, methylamine, dimethylamine, cyclopentylamine, benzylamine, phenethylamine, piperidine, mono ethanolamine, diethanolamine, tris(hydroxymethyl)methylamine, lysine, arginine and N-methyl-D-glucamine) and acid addition salt (such as inorganic acid salt (e.g., hydrochloride, hydrobromide, hydroiodide, sulfate, phosphate and nitrate) and organic acid salt (e.g., formate, acetate, trifluoroacetate, lactate, tartrate, oxalate, fumarate, maleate, benzoate, citrate, methanesulfonate, ethanesulfonate, benzenesulfonate, toluenesulfonate, isothionate, glucuronate and gluconate), etc.). The salt of the compound of the present invention also includes solvates and also solvates with the above-mentioned alkaline (earth) metal salt, ammonium salt, organic amine salt and acid addition salt. The solvate is preferably low-toxic and water-soluble. Examples of an appropriate solvate are solvates with water and with alcoholic solvent (such as ethanol). The compounds of the present invention are converted to low-toxicity salts or pharmaceutically acceptable salts by known methods.

Moreover, the salt includes a quaternary ammonium salt. The quaternary ammonium salt of the compound represented by formula (I) is the compound where nitrogen of the compounds represented by formula (I) is quarternalized by $R^O$ ($R^O$ is C1-8 alkyl or C1-8 alkyl substituted by phenyl.).

The salt also includes an N-oxide. The compound of the present invention can be converted into an N-oxide by known methods. The N-oxide is the compound where nitrogen of the compound represented by formula (I) is oxidized.

Prodrugs:

A prodrug of the compound of formula (I) means a compound which is converted to the compound of formula (I) by reaction with an enzyme, gastric acid or the like in the living body. For example, with regard to a prodrug of the compound of formula (I), when the compound of formula (I) has an amino group, compounds in which the amino group is, for example, acylated, alkylated or phosphorylated (e.g., compounds in which the amino group of the compound of formula (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, acetoxymethylated, tert-butylated, etc.); when the compound of formula (I) has a hydroxyl group, compounds where the hydroxyl group is, for example, acylated, alkylated, phosphorylated or borated (e.g., compounds in which the hydroxyl group of the compound of formula (I) is acetylated, palmitoylated, propanoylated, pivaloylated, succinylated, fumarylated, alanylated or dimethylaminomethylcarbonylated); and when the compound of formula (I) has a carboxyl group, compounds in which the carboxyl group is, for example, esterified or amidated (e.g., compounds in which the carboxyl group of the compound of formula (I) is made into ethyl ester, phenyl ester, phenylethyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester or methylamide). Those compounds may be produced by a known method per se. The prodrug of the compound of formula (I) may be either a hydrate or a non-hydrate. A prodrug of the compound of formula (I) may also be a compound which is converted to the compound of formula (I) under physiological conditions as described in "Iyakuhin no kaihatsu, Vol. 7 (Bunshi-sekkei), pp. 163-198 (Hirokawa-Shoten), 1990". Further, the compound of formula (I) may also be labeled by a radio isotope (such as $^2H$, $^3H$, $^{11}C$, $^{13}C$, $^{14}C$, $^{13}N$, $^{15}N$, $^{15}O$, $^{17}O$, $^{18}O$, $^{35}S$, $^{18}F$, $^{36}Cl$, $^{123}I$, $^{125}I$, etc.).

Processes for the Preparation of the Compound of the Present Invention:

The compounds of the invention can, for example, be prepared according to the following reaction schemes.

The compound of the present invention represented by the formula (I) may be prepared by known methods, for example, a method combining the following methods, the method according to these methods, the methods described in the examples and/or methods described in Comprehensive Organic Transformations: A Guide to Functional Group Preparations, 2nd Edition (Richard C. Larock, John Wiley & Sons Inc, 1999), etc., which are appropriately modified in each following method for the preparation. Salts of the starting materials may be used.

It will also be recognized that another major consideration in the planning of any synthetic route in this field is the judicious choice of the protecting group used for protection of the reactive functional groups present in the compounds described in this invention. Protection reactions may be carried out by the methods, for example, described in T. W. Greene, Protective Groups in Organic Synthesis, Wiley, New York, 1999.

The compound of formula (I) wherein $R^{62}$ represents hydrogen can be prepared from a compound represented by formula (II):

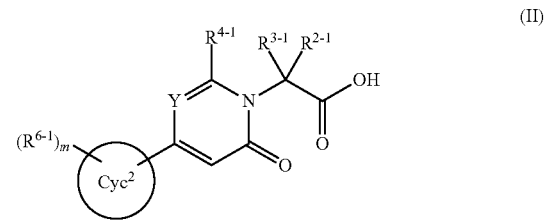

(II)

wherein $R^{2-1}$, $R^{3-1}$, $R^{4-1}$ and $R^{6-1}$ have the same meanings as $R^2$, $R^3$, $R^4$ and $R^6$ respectively, with the proviso that carboxyl, hydroxyl, amino or thiol in $R^{2-1}$, $R^{3-1}$, $R^{4-1}$ and $R^{6-1}$ may be protected, if necessary, or a compound represented by the formula (III):

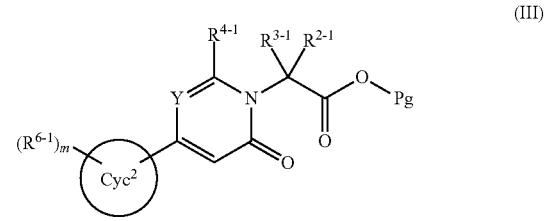

(III)

wherein Pg represents a protective group of carboxyl, such as C1-4 alkyl, and the other symbols have the same meaning described above, by $Cyc^1$ ring formation reactions described below.

1) The compound of formula (I) wherein $R^{62}$ represent hydrogen, $Cyc^1$ represents an imidazole ring which is attached to Cyc³ at the 4-position and has an R¹⁻¹, that is, a compound represented by formula (I-I):

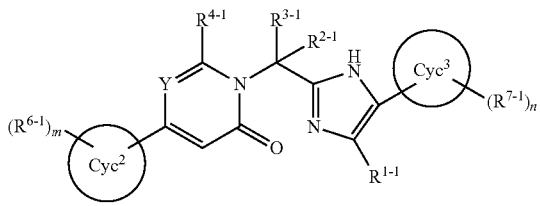

(I-I)

wherein R¹⁻¹ and R⁷⁻¹ have the same meanings as R¹ and R⁷ respectively, with the proviso that, carboxyl, hydroxyl, amino or thiol in R¹⁻¹ and R⁷⁻¹ may be protected, if necessary, and the other symbols have the same meaning described above, can be prepared as outlined in Reaction Scheme 1:

wherein X represents fluorine, chlorine, bromine or iodine, and the other symbols have the same meaning described above, can be conducted in a solvent such as dimethylformamide, tetrahydrofuran, dichloromethane, acetone or acetonitrile in the presence of a base such as sodium carbonate, potassium carbonate, cesium carbonate, sodium bicarbonate potassium bicarbonate, N,N-diisopropylethylamine or triethylamine at −20° C. to reflux temperature to form a compound represented by formula 1b wherein all symbols have the same meaning described above.

The reaction from the compound represented by formula 1b to the compound represented by formula (I-I) is an imidazole formation reaction.

The imidazole formation reaction is well known. For example, the compound represented by formula 1b and ammonium acetate or ammonium trifluoroacetate in a suitable solvent such as xylene, toluene or acetic acid, on heating and/or microwave irradiation, can form compounds of formula (I-I).

Alternatively, the compound represented by formula 1d can be prepared from the compound represented by formula Reaction Scheme 1

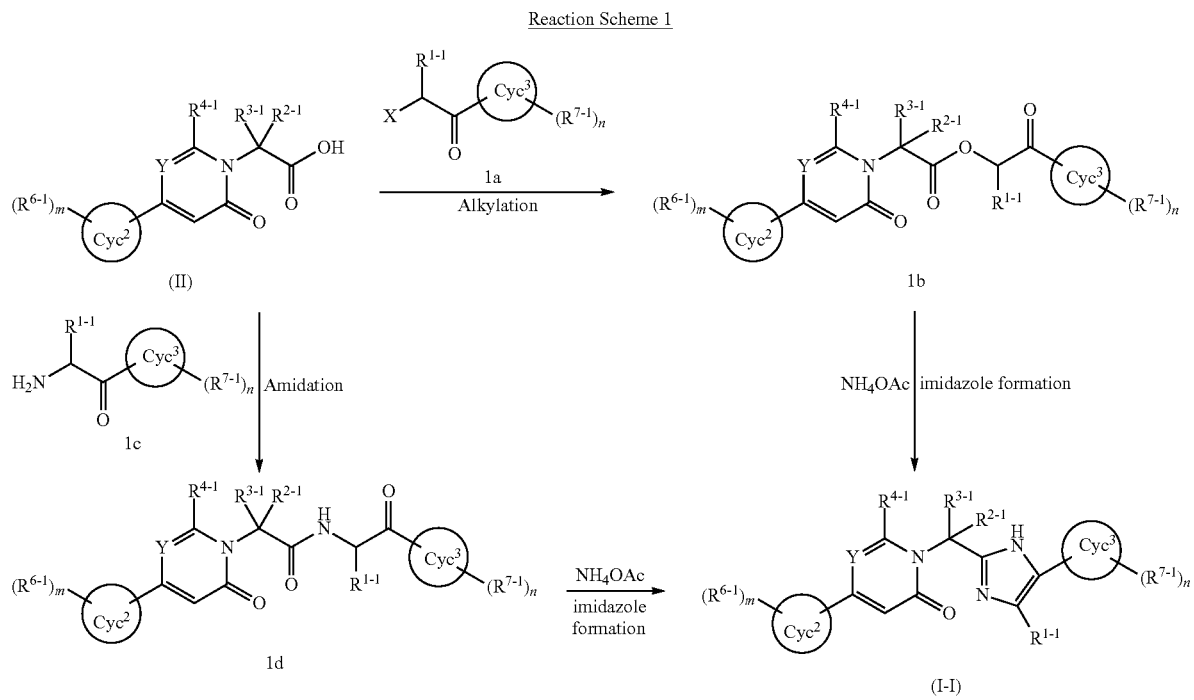

In Reaction Scheme 1, the reaction from the compound represented by formula (II) to the compound represented by formula 1b is an alkylation reaction.

The alkylation reaction is well known. For example, the compound represented by formula (II) with the compound represented by formula 1a:

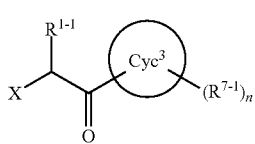

1a (II). The reaction from the compound represented by formula (II) to the compound represented by formula 1d is an amidation reaction.

The amidation reaction is well known. For example, the reaction of the compound represented by formula (II) with the compound represented by formula 1c wherein all symbols have the same meaning described above is exemplified by:

(1) A reaction procedure with use of an acid halide,
(2) A reaction procedure with use of a mixed acid anhydride, and
(3) A reaction procedure with use of a condensing agent.

Referring specifically to these reaction procedures, (1) The reaction procedure employing an acid halide is conducted in practice, for example, by reacting a carboxylic acid with an acid halogenating agent (e.g., oxalyl chloride, thionyl chloride, etc.) in an organic solvent (e.g., chloroform, dichloromethane, diethyl ether, tetrahydrofuran, dimethoxyethane, etc.) at a temperature from about −20° C. to the refluxing temperature, followed by reaction of the resultant acid halide with an amine in an organic solvent (e.g., chloroform, dichloromethane, diethyl ether, tetrahydrofuran, acetonitrile, ethyl acetate, etc.) or solvent-free in the presence of a base (e.g., pyridine, triethylamine, dimethylaniline, dimethylaminopyridine, diisopropylethylamine, etc.) at a temperature of approximately 0 to 40° C. Alternatively, the procedure can be carried out by reacting the resultant acid halide with an amine in an organic solvent (e.g., dioxane, tetrahydrofuran, dichloromethane, etc.) in the presence or absence of a phase-transfer catalyst (e.g., tetrabutylammonium chloride, triethylbenzylamrnonium chloride, tri-n-octylmethylammonium chloride, trimethyldecylammonium chloride, tetramethylammonium chloride, trimethyldecylammonium chloride, tetramethylammonium chloride, etc.) at a temperature of about 0 to 40° C., whilst using an aqueous alkali solution (e.g., an aqueous sodium bicarbonate or sodium hydroxide solution, etc.).

(2) The reaction procedure employing a mixed acid anhydride is conducted in practice, for example, by reacting a carboxylic acid with an acid halide (pivaloyl chloride, tosyl chloride, mesyl chloride, etc.) or an acid derivative (e.g., ethyl chloroformate, isobutyl chloroformate, etc.) in an organic solvent (e.g., chloroform, dichloromethane, diethyl ether, tetrahydrofuran, etc.) or solvent free in the presence of base (e.g., pyridine, triethylamine, dimethylaniline, dimethylaminopyridine, diisopropylethylamine, etc.) at a temperature of about 0 to 40° C., followed by reaction of the resultant mixed acid anhydride with an amine in an organic solvent (e.g., chloroform, dichloroethane, diethyl ether, tetrahydrofuran, etc.) at a temperature of about 0 to 40° C.

(3) The reaction procedure with use of a condensing agent is carried out, for example, by reacting a carboxylic acid with an amine in an organic solvent (e.g., chloroform, dichloromethane, dimethylformamide, diethyl ether, tetrahydrofuran, etc.) or solvent-free in the presence or absence of a base (e.g., pyridine, triethylamine, dimethylaniline, dimethylaminopyridine, etc.), with use of a condensing agent (e.g., 1,3-dicyclohexylcarbodiimide (DCC), 1-ethyl-3-[3-(dimethylamino)propyl]carbodiimide (EDC), 1,1'-carbonyldiimidazole (CDI), 2-chloro-1-methylpyridinium iodide, 1,1'-propylphosphonic acid anhydride (1-propanephosphonic acid cyclic anhydride, PPA), etc.) and with or without use of 1-hydroxybenztriazole (HOBt), at a temperature of about 0 to 40° C.

The reaction from the compound represented by formula 1d to the compound represented by formula (I-I) is an imidazole formation reaction. The imidazole formation reaction can be carried out by the same method as described above in Reaction Scheme 1.

In the course of the synthesis of the compound of the present invention represented by the formula (I-I), the deprotection reaction can be carried out at an appropriate synthetic stage, when the protective groups of carboxy, hydroxy, amino or mercapto group exists.

The deprotection reaction of the protective groups of carboxy, hydroxy, amino or mercapto group is well-known and includes, for example,
(1) a deprotection reaction by alkali hydrolysis,
(2) a deprotection under acidic conditions,
(3) a deprotection reaction by hydrogenolysis,
(4) a deprotection reaction of silyl group,
(5) a deprotection reaction using a metal,
(6) a deprotection reaction using a metal complex, etc.

To explain these methods in detail:
(1) The deprotection reaction by alkali hydrolysis is carried out, for example, in an organic solvent (methanol, tetrahydrofuran, 1,4-dioxane, etc.) using a hydroxide of alkali metals (sodium hydroxide, potassium hydroxide, lithium hydroxide, etc.), hydroxide of alkaline earth metals (barium hydroxide, calcium hydroxide, etc.), carbonate (sodium carbonate, potassium carbonate, etc.) or a solution thereof or a mixture thereof at a temperature of 0 to 40° C.

(2) The deprotection reaction under acidic conditions is carried out, for example, in an organic solvent (dichloromethane, chloroform, dioxane, ethyl acetate, anisole, etc.), in an organic acid (acetic acid, trifluoroacetic acid, methanesulfonic acid, p-toluenesulfonic acid, etc.) or an inorganic acid (hydrochloric acid, sulfuric acid, etc.) or a mixture thereof (hydrobromic acidacetic acid, etc.) in the presence or absence of 2,2,2-trifluoroethanol at a temperature of 0 to 100° C.

(3) The deprotection reaction by hydrogenolysis is, for example, carried out in a solvent (e.g. ethers such as tetrahydrofuran, 1,4-dioxane, dimethoxyethane, diethyl ether, etc.; alcohols such as methanol, ethanol, etc.; benzenes such as benzene, toluene, etc.; ketones such as acetone, methyl ethyl ketone, etc.; nitriles such as acetonitrile etc.; amides such as N,N-dimethylformamide, N,N-dimethylacetamide etc.; water, ethyl acetate, acetic acid or a mixture of two or more thereof, etc.) in the presence of a catalyst (palladium-carbon, palladium black, palladium hydroxide, platinum oxide, Raney nickel, etc.) under an atmosphere of hydrogen at normal or increased pressure, or in the presence of ammonium formate at a temperature of 0 to 200° C.

(4) The deprotection reaction of a silyl group is, for example, carried out in a water-miscible organic solvent (tetrahydrofuran, acetonitrile, etc.) using tetrabutylammonium fluoride at a temperature of 0 to 40° C.

(5) The deprotection reaction using a metal is carried out, for example, in an acidic solvent (acetic acid, a buffer of pH 4.2 to 7.2 or a mixture of the solution thereof and an organic solvent such as tetrahydrofuran etc.) in the presence of zinc powder at a temperature of 0 to 40° C. optionally under sonication.

(6) The deprotection reaction using a metal complex is carried out, for example, in an organic solvent (dichloromethane, N,N-dimethylformamide, tetrahydrofuran, ethyl acetate, acetonitrile, dioxane, ethanol, etc.), water or a mixture thereof, in the presence of a trapping reagent (tributyltin hydride, triethylsilane, dimedone, morpholine, diethylamine, pyrrolidine, 1,3-dimethylbarbituric acid, etc.), an organic acid (acetic acid, formic acid, 2-ethylhexanecarboxylic acid, etc.) and/or a salt of an organic acid (sodium 2-ethylhexanoate, potassium 2-ethylhexanoate, etc.) in the presence or absence of a phosphine reagent (triphenylphosphine etc.) using a metal complex (tetrakis(triphenylphosphine)palladium (0), palladium(II) bis(triphenylphosphine) dichloride, palladium(II) acetate, rhodium(I) tris(triphenylphosphine) chloride, etc.) at a temperature of 0 to 40° C.

In addition to the above, deprotection reactions may be carried out by the methods, for example, described in T. W. Greene, Protective Groups in Organic Synthesis, Wiley, New York, 1999.

A protective group for carboxy includes, for example, methyl, ethyl, allyl, tert-butyl, trichloroethyl, benzyl (Bn), phenacyl, p-methoxybenzyl, trityl, 2-chlorotrityl or a solid carrier containing these structures, etc.

A protective group for hydroxy includes, for example, methyl, trityl, methoxymethyl (MOM), 1-ethoxyethyl (EE), methoxyethoxymethyl (MEM), 2-tetrahydropyranyl (THP), trimethylsilyl (TMS), triethylsilyl (TES), tert-butyldimethylsilyl (TBDMS), tert-butyldiphenylsilyl (TBDPS), acetyl (Ac), pivaolyl, benzoyl, benzyl (Bn), p-methoxybenzyl, allyloxycarbonyl (Alloc) or 2,2,2-trichloroethoxycarbonyl (Troc), etc.

A protective group for amino includes, for example, benzyloxycarbonyl, tert-butoxycarbonyl, allyloxycarbonyl (Alloc), 1-methyl-1-(4-biphenyl)ethoxycarbonyl (Bpoc), trifluoroacetyl, 9-fluorenylmethoxycarbonyl (FMoc), benzyl (Bn), p-methoxybenzyl, benzyloxymethyl (BOM), 2-(trimethylsilyl)ethoxymethyl (SEM), etc.

A protective group for mercapto includes, for example, benzyl, methoxybenzyl, methoxymethyl (MOM), 2-tetrahydropyranyl (THP), diphenylmethyl, acetyl (Ac), etc.

Protective groups for carboxy, hydroxy, amino or mercapto group are not limited to those described above, but include groups which are easily and selectively deprotected. For example, those groups described in T. W. Greene, Protective Groups in Organic Synthesis, Wiley, New York, 1999.

As is easily understood by those skilled in the art, the target compound of the present invention may be prepared easily by selecting these deprotection reactions.

2) The compound of formula (I) wherein $R^{62}$ represents hydrogen, $Cyc^1$ represents an imidazole ring which is attached to $Cyc^3$ at the 4-position and possesses $R^{1-hal}$, that is, a compound represented by formula (I-II-b):

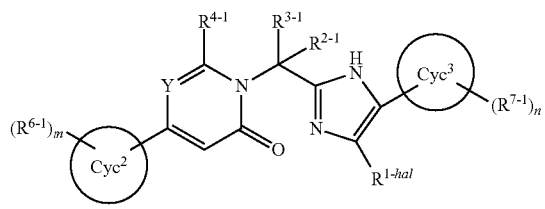

(I-II-b)

wherein $R^{1-hal}$ represents fluorine, chlorine, bromine or iodine, and the other symbols have the same meaning described above, can be prepared as outlined in Reaction Scheme 2:

Reaction Scheme 2

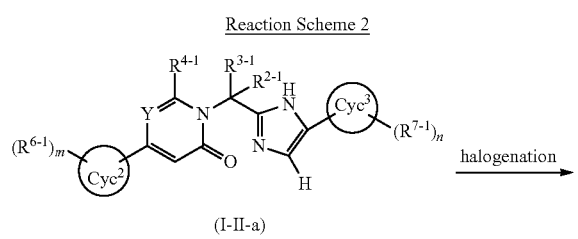

(I-II-a)

halogenation

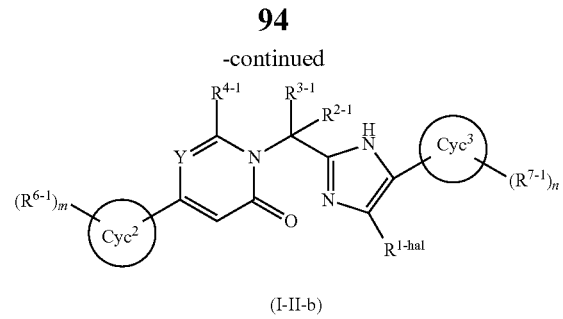

(I-II-b)

wherein all symbols have the same meaning described above.

In Reaction Scheme 2, the reaction from the compound represented by formula (I-II-a) to the compound represented by formula (I-II-b) is a halogenation reaction.

The halogenation reaction is well known. For example, the reaction of the compound represented by formula (I-II-a) with brominating or chlorinating agent, such as N-bromosuccinimide, N-chlorosuccinimide or 1,3-dichloro-5,5-dimethyl-hydantoin in a suitable solvent such as acetonitrile, chloroform or tetrahydrofuran from −20° C. to the refluxing temperature provides the compound represented by formula (I-II-b).

3) The compound of formula (I) wherein $R^{62}$ represents hydrogen, $Cyc^1$ represents imidazole ring which is attached to $Cyc^3$ at the 2-position, that is, a compound represented by formula (I-III-a):

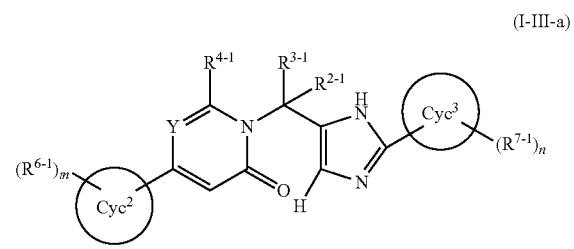

(I-III-a)

wherein all symbols have the same meaning described above, and a compound represented by formula (I-III-b):

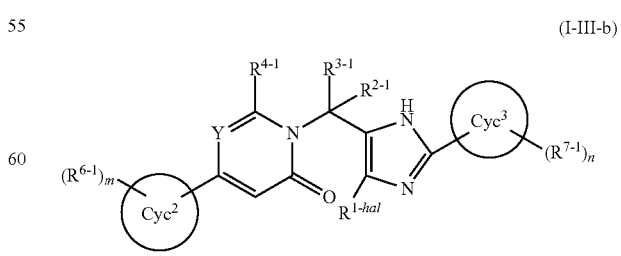

(I-III-b)

wherein all symbols have the same meaning described above, can be prepared as outlined in Reaction Scheme 3:

Reaction Scheme 3

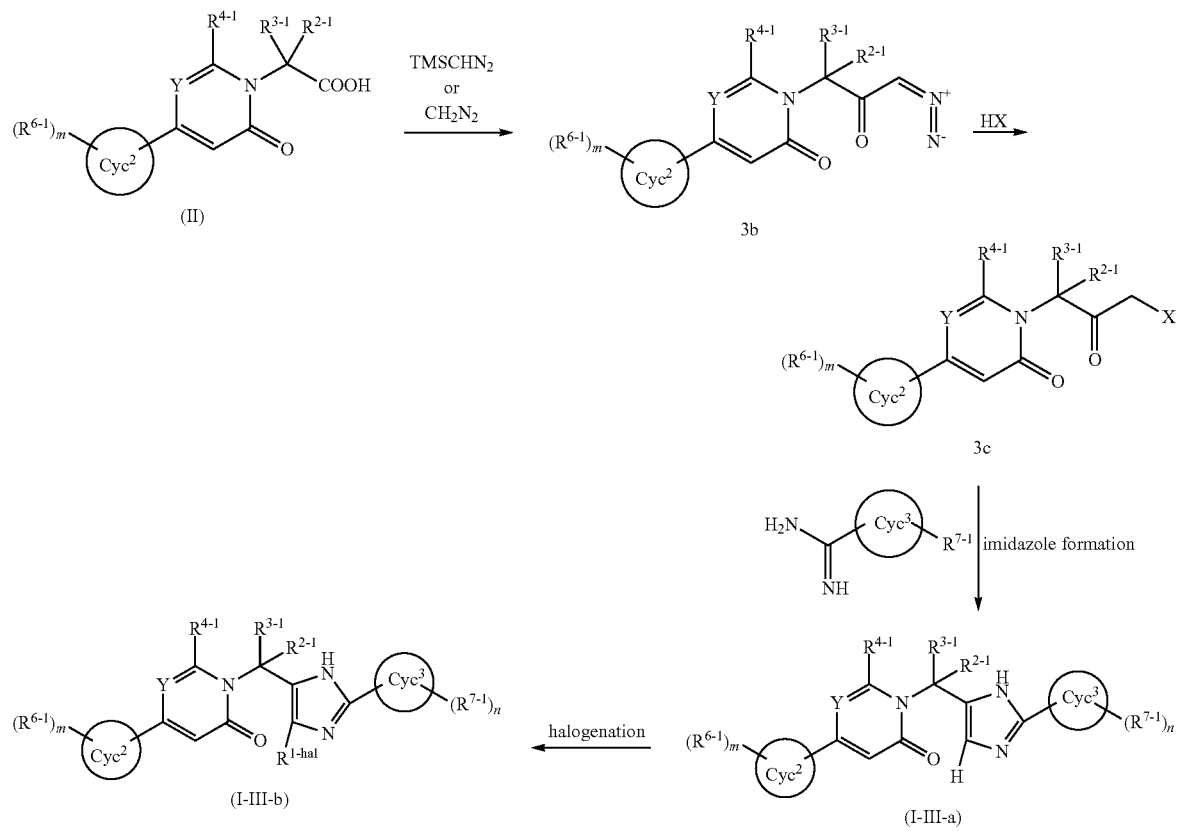

wherein all symbols have the same meaning described above.

In Reaction Scheme 3, the reaction from the compound represented by formula (II) to the compound represented by formula 3c can be prepared as described below.

The compound represented by formula 3b can be prepared by treatment of the appropriately functionalized compound represented by formula (II) with acid halogenating agent (e.g., oxalyl chloride, thionyl chloride, 1-chloro-N,N,2-trimethyl-1-propenylamine etc.) in an organic solvent (e.g., chloroform, dichloromethane, diethyl ether, tetrahydrofuran, dimethoxyethane, etc.) at a temperature from about −20° C. to the refluxing temperature, followed by reaction of the resultant acid halide with diazomethane or (trimethylsilyl) diazomethane in an organic solvent (e.g., chloroform, dichloromethane, hexane, diethyl ether, tetrahydrofuran, acetonitrile, etc.). The compound represented by formula 3c can be prepared by treatment of the compound represented by formula 3b with HX (e.g., hydrochloric acid, hydrobromic acid etc.) in an organic solvent (e.g., chloroform, dichloromethane, hexane, diethyl ether, tetrahydrofuran, acetonitrile, etc.).

The reaction from the compound represented by formula 3c to the compound represented by formula (I-III-a) is an imidazole formation reaction. The imidazole formation reaction can be carried out by the same method as described in Reaction Scheme 1 above.

The reaction from the compound represented by formula (I-III-a) to the compound represented by formula (I-III-b) is a halogenation reaction. The halogenation reaction can be carried out by the same method as described in Reaction Scheme 2.

4) The compound of formula (I) wherein $R^{62}$ represents hydrogen, $Cyc^1$ represents 1,3,4-triazole ring, that is, a compound represented by formula (I-IV):

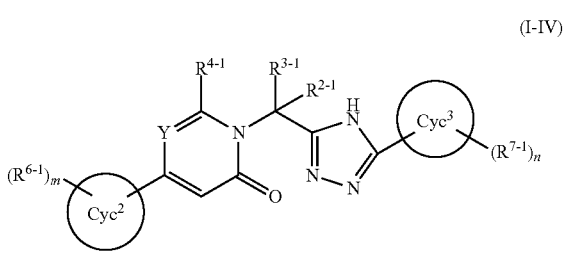

wherein all symbols have the same meaning described above, can be prepared as outlined in Reaction Scheme 4:

Reaction Scheme 4

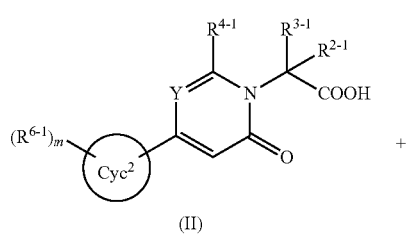

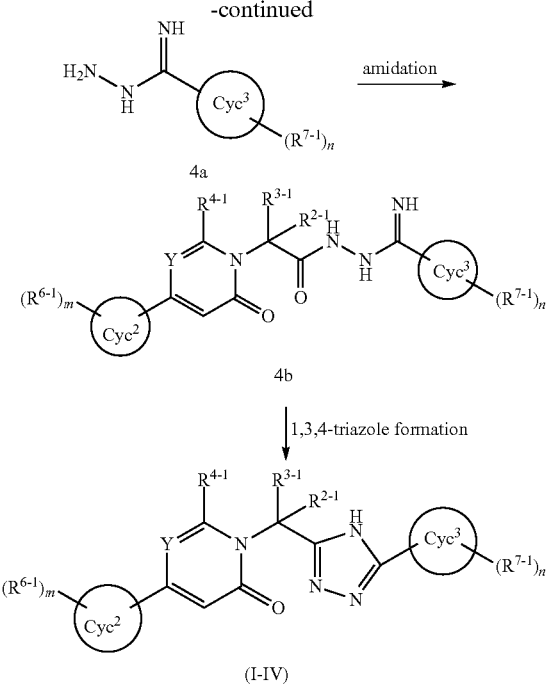

In Reaction Scheme 4, the reaction from the compound represented by formula (II) to the compound represented by formula 4b is an amidation reaction. The amidation reaction can be carried out by the same method as described in Reaction Scheme 1.

The reaction from the compound represented by formula 4b to the compound represented by formula (I-IV) is a 1,3,4-triazole formation reaction. The 1,3,4-triazole formation reaction is well known. For example, the reaction can be carried out by heating the compound represented by 4b in a suitable solvent such as acetic acid, xylene or toluene to give the compound represented by formula (I-IV).

5) The compound of formula (I) wherein $R^{62}$ represents hydrogen, $Cyc^1$ represents pyridazinone ring, that is, a compound represented by formula (I-V):

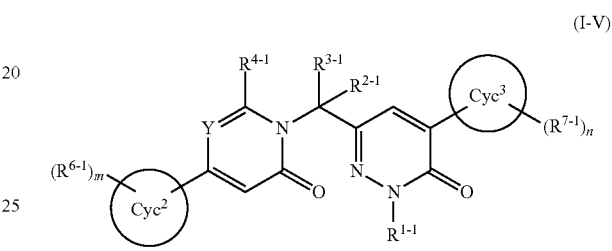

wherein all symbols have the same meaning described above.

wherein all symbols have the same meaning described above, can be prepared as outlined in Reaction Scheme 5:

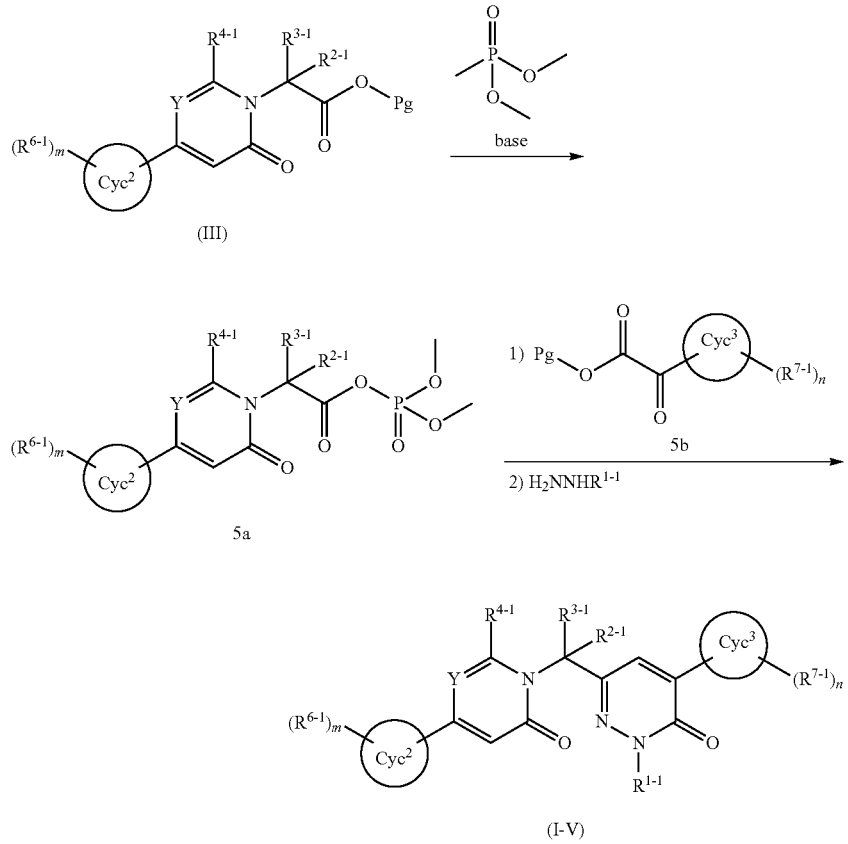

wherein all symbols have the same meaning described above.

In Reaction Scheme 5, the reaction from the compound represented by formula (III) to the compound represented by formula 5a can be prepared as described below.

The compound represented by formula 5a can be prepared by treatment of the appropriately functionalized compound represented by formula (III) with dimethylmethylphosphonate in the presence of base such as n-butyllithium in a solvent such as tetrahydrofuran.

The reaction from the compound represented by formula 5a to the compound represented by formula (I-V) is a Horner-Wadsworth-Emmons reaction.

The Horner-Wadsworth-Emmons reaction is well known. For example, the compound represented by formula 5a and the compound represented by formula 5b in the presence of base such as potassium carbonate in a solvent such as ethanol or tetrahydrofuran gives an α,β-unsaturated ketone derivative which can then be condensed with a suitably substituted hydrazine derivative represented by $H_2NNHR^{1-1}$ to give the compound represented by formula (I-V).

6) The compound of formula (I) wherein $R^{62}$ represents hydrogen, $Cyc^1$ represents a 1,2,3-triazole ring, that is, a compound represented by formula (I-VI):

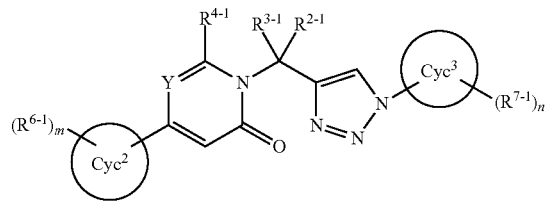

wherein all symbols have the same meaning described above, can be prepared as outlined in Reaction Scheme 6:

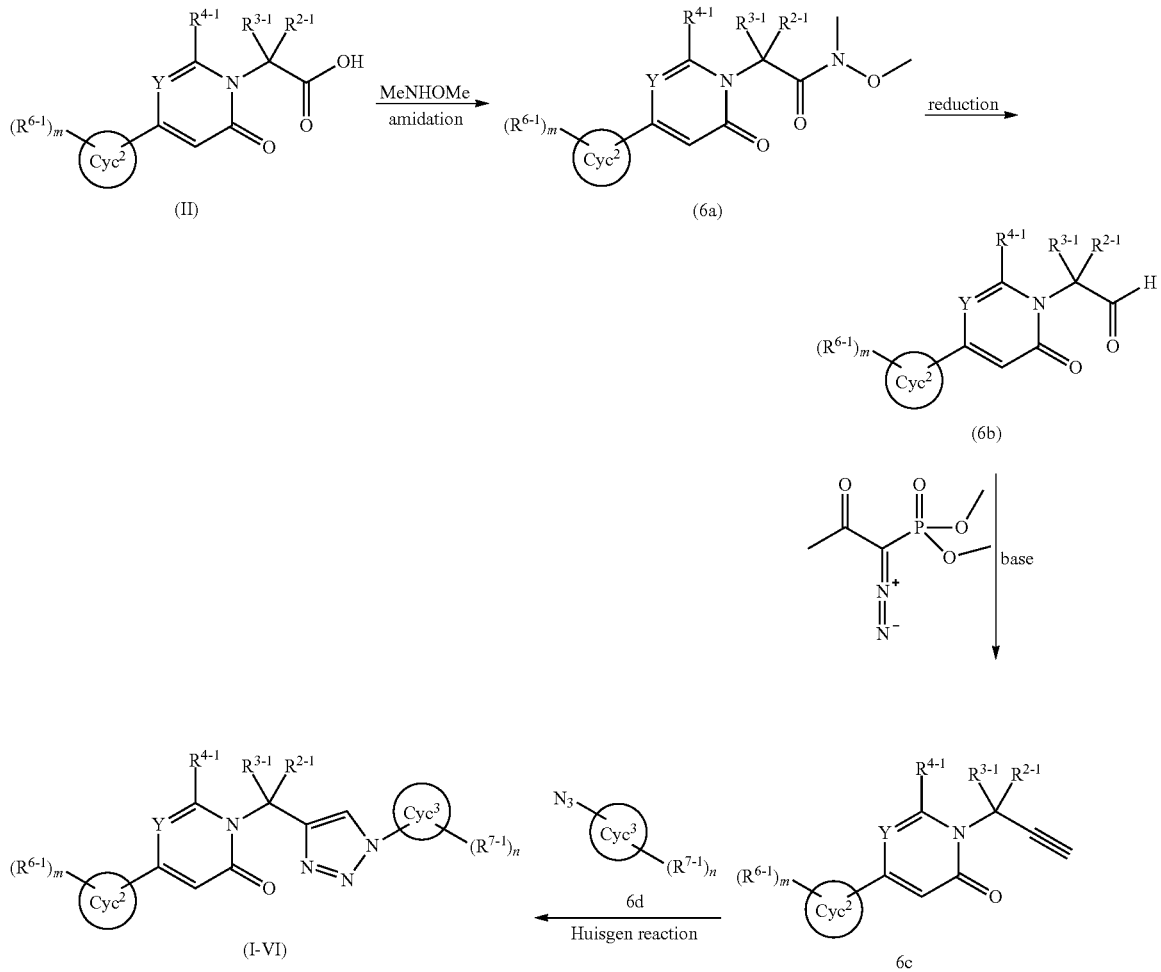

wherein all symbols have the same meaning described above.

In Reaction Scheme 6, the reaction from the compound represented by formula (II) to the compound represented by formula 6a is an amidation reaction. The amidation reaction can be carried out by the same method as described in Reaction Scheme 1 using N,O-dimethylhydroxylamine instead of the compound represented by formula 1c.

The reaction from the compound represented by formula 6a to the compound represented by formula 6b can be prepared as described below.

The compound represented by formula 6b can be prepared by treatment of the appropriately functionalized compound represented by formula 6a with lithium aluminum hydride or diisobutylaluminium hydride in tetrahydrofuran to give the compound represented by formula 6b.

The reaction from the compound represented by formula 6b to the compound represented by formula 6c can be prepared as described below.

The compound represented by formula 6c can be prepared by treatment of the appropriately functionalized compound represented by formula 6b with dimethyl(1-diazo-2-oxopropyl) phosphonate in the presence of base such as potassium carbonate in a solvent such as methanol.

The reaction from the compound represented by formula 6c to the compound represented by formula (I-VI) is a Huisgen reaction. The Huisgen reaction can be prepared as described below.

The compound represented by formula (I-VI) can be prepared by treatment of the appropriately functionalized compound represented by formula 6c and a suitably substituted compound represented by formula 6d in the presence of a copper (II) salt such as copper (II) sulfate, an ascorbate such as sodium ascorbate and a base such as sodium hydroxide which on heating and/or microwave irradiation gives the compound represented by formula (I-VI).

7) The compound of formula (I) wherein $R^{62}$ represents hydrogen, $Cyc^1$ represents 1,2-oxazole ring, that is, a compound represented by formula (I-VII):

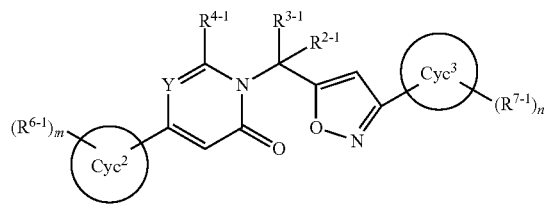

(I-VII)

wherein all symbols have the same meaning described above, can be prepared as outlined in Reaction Scheme 7:

Reaction Scheme 7

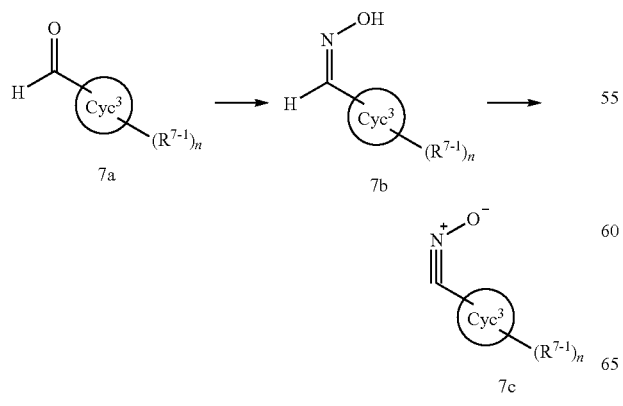

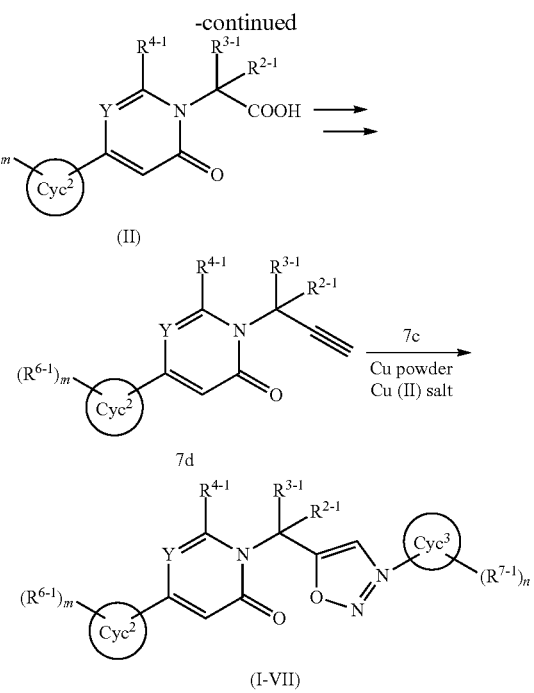

wherein all symbols have the same meaning described above.

In Reaction Scheme 7, the reaction from the compound represented by formula 7a to the compound represented by formula 7c can be prepared as described below.

The compound represented by formula 7c can be prepared by treatment of an appropriately functionalized compound represented by formula 7a with hydroxylamine hydrochloride in a solvent such as tert-butanol and water to provide the corresponding oxime compound represented by formula 7b, which can be converted to a nitrile oxide compound represented by formula 7c by treatment with an oxidant such as chloramine-T trihydrate.

The reaction from the compound represented by formula (II) to the compound represented by formula 7d can be prepared by the same method as described in Reaction Scheme 6.

The reaction from the compound represented by formula 7d to the compound represented by formula (I-VII) can be prepared as described below.

The compound represented by formula (I-VII) can be prepared by combining the compound represented by formula 7c and the compound represented by formula 7d in the presence of a copper (II) salt such as copper (II) sulfate and copper powder in a solvent such as tert-butanol and water at a temperature from approximately 20° C. to the refluxing temperature with or without microwave irradiation.

8) The compound of formula (I-A) wherein $R^{62}$ represents hydrogen, that is, a compound represented by formula (I-A-H) can be prepared from a compound represented by formula (II-A) or a compound represented by formula (III-A) by $Cyc^1$ ring formation reactions by the same methods described in Reaction Schemes 1 to 7.

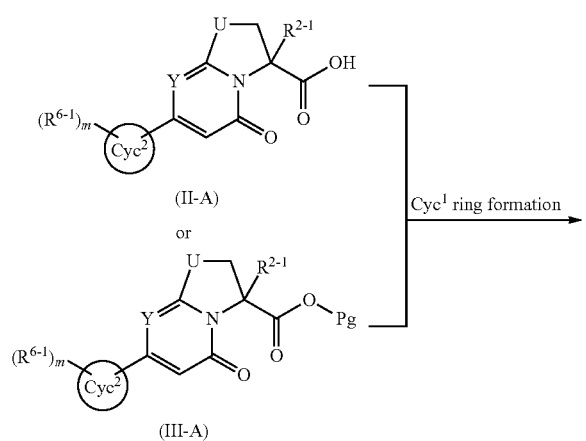
wherein all symbols have the same meaning described above.
The compound represented by formula (II-A) and formula (III-A) wherein $R^{62}$ is hydrogen, Y is C(H) and U is $CH_2$, that is, a compound represented by formula (II-A-I) and (III-A-I) respectively, can be prepared as outlined in Reaction Scheme 8:
Reaction Scheme 8
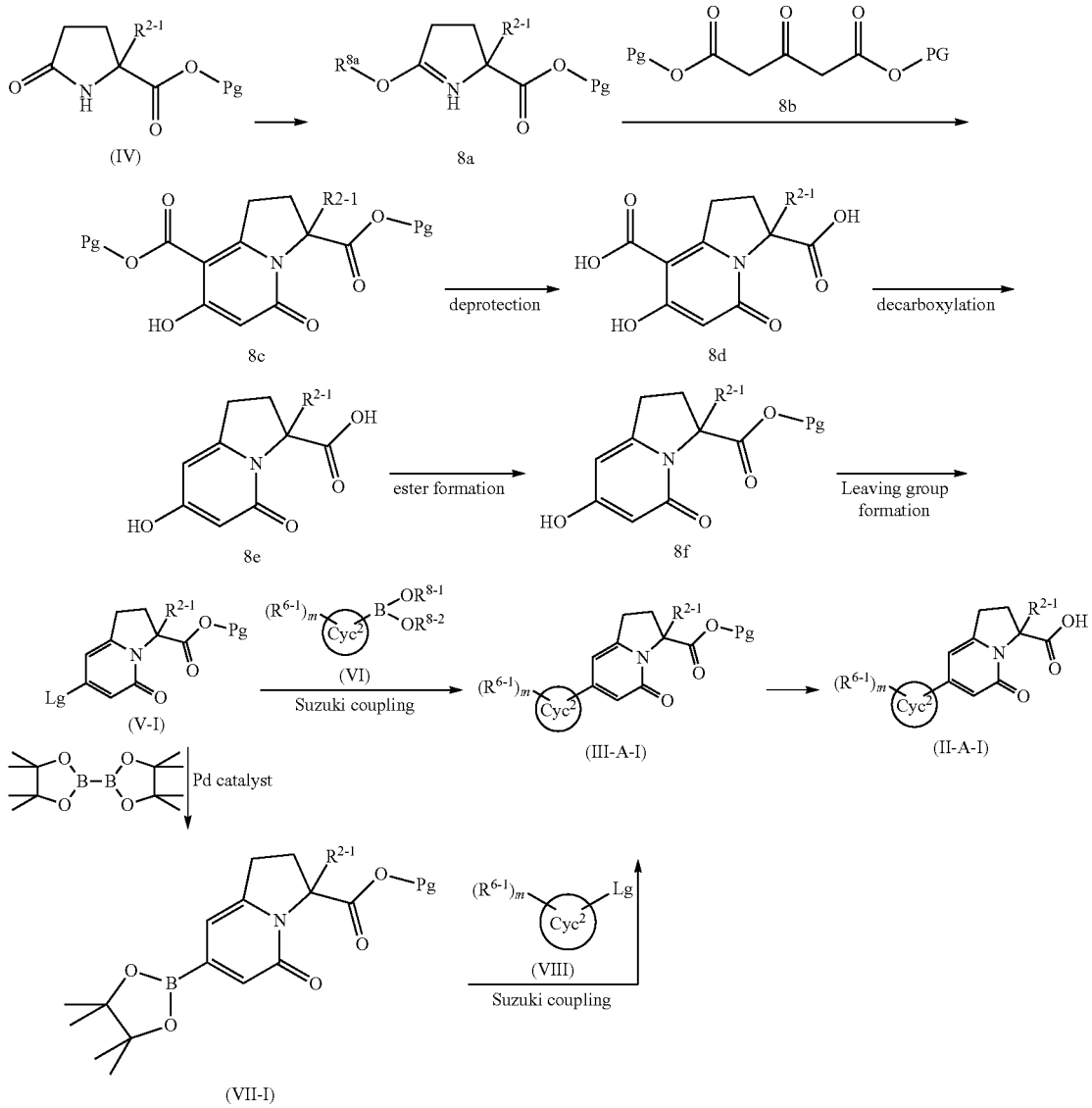

wherein Lg represents triflate, tosylate, chlorine or bromine, $R^{8a}$ represents C1-4 alkyl, $R^{B-1}$ and $R^{B-2}$ represents hydrogen, or $R^{B-1}$ and $R^{B-2}$ may be taken together to form —C(CH$_3$)$_2$C(CH$_3$)$_2$— and the other symbols have the same meaning described above.

In Reaction Scheme 8, imidate formation of an appropriately protected compound represented by formula (IV) can be conducted by using alkylating agent such as trimethyloxonium tetrafluoroborate, triethyloxonium tetrafluoroborate or dimethyl sulfate in a solvent such as dichloromethane, acetonitrile or dimethyl carbonate or without a solvent to form an imidate compound represented by formula 8a.

Imidate compounds represented by formula 8a can be condensed with a suitably protected 1,3-acetonedicarboxylic acid represented by formula 8b in an organic base such as triethylamine, N,N-diisopropylethylamine or N-methylmorpholine at a temperature from about 20° C. to the refluxing temperature to provide a diester compound represented by formula 8c.

The diester compound represented by formula 8c can be converted to the corresponding dicarboxylic acid represented by formula 8d by the same method as described above for the deprotection reaction of carboxyl.

The decarboxylation of a dicarboxylic acid represented by formula 8d can be carried out by treatment with an acid such as hydrochloric acid or 2,4,6-trichlorophenol at reflux to give the carboxylic acid represented by formula 8e.

The esterification of the compound represented by formula 8e can be conducted in a solvent such as methanol or ethanol in the presence of acid such as hydrochloric acid, sulfuric acid or p-toluenesulfonic acid at refluxing temperature to give the ester compound represented by formula 8f.

The ester compound represented by formula 8f can be converted to the compound represented by formula (V-I) by treatment with trifluoromethanesulfonic anhydride, N-phenyltrifluoromethanesulfonimide, 2-[N,N-bis(trifluoromethanesulfonyl)amino]pyridine, p-toluenesulfonyl chloride, phosphorous oxychloride, phosphorous oxybromide at a temperature from about 0° C. to refluxing temperature in a solvent such as dimethylformamide or tetrahydrofuran or solvent-free in the presence of a base such as triethylamine or diisopropylethylamine or without base.

Suzuki coupling between a compound represented by formula (V-I) and an appropriately functionalized aryl boronic acid or ester compound represented by formula (VI) in the presence of a base such as anhydrous cesium carbonate, cesium fluoride, sodium carbonate or potassium phosphate in a solvent such as 1,4-dioxane, dimethylformamide or dimethylsulfoxide using a catalyst such as tetrakis(triphenylphosphine)palladium(0), 1,1'-bis(diphenylphosphino)ferrocene palladium(II) chloride, palladium(II) acetate or bis(dibenzylideneacetone)palladium(0), with or without a phosphine ligand such as triphenylphosphine, tri-t-butylphosphine or 1,1'-bis(diphenylphosphino)ferrocene at a temperature from about 70° C. to the refluxing temperature provided the compounds represented by formula (III-A-I).

In cases where suitably substituted boronic acids or esters are not commercially available, the 4,4,5,5-tetramethyl-[1,3,2]dioxaborolane intermediate can be prepared from the corresponding aryl halide or aryl triflate by a palladium mediated coupling with a diboron species such as bis(pinacolato)diboron using the method of Ishiyama, T. et al. (*J. Org. Chem.* 1995, 60(23), 7508). Alternatively, the corresponding boronic acid can be prepared by metal-halogen exchange of the arylheteroaryl halide, quenching with a trialkoxyborate reagent and aqueous workup to provide the boronic acids (Miyaura, N.; Suzuki, A. *Chem. Review,* 1995, 95, 2457). Alternatively, a compound represented by formula (V-I) can be converted to the corresponding 4,4,5,5-tetramethyl-[1,3,2]dioxaborolane intermediate compound represented by formula (VII-I) by the same methods described above.

Suzuki coupling between a compound represented by formula (VII-I) and an appropriately functionalized aryl halide or aryl triflate compound represented by formula (VIII) provided the compounds represented by formula (III-A-I).

The compound represented by formula (III-A-I) can be converted to the compound represented by formula (II-A-I) by the deprotection reaction as described above.

9) The compound represented by formula (II-A) and formula (III-A) wherein Y is N and U is CH$_2$, that is, a compound represented by formula (II-A-II) and formula (III-A-II) respectively, can be prepared as outlined in Reaction Scheme 9:

Reaction Scheme 9

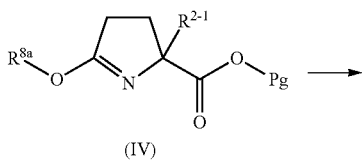

(IV)

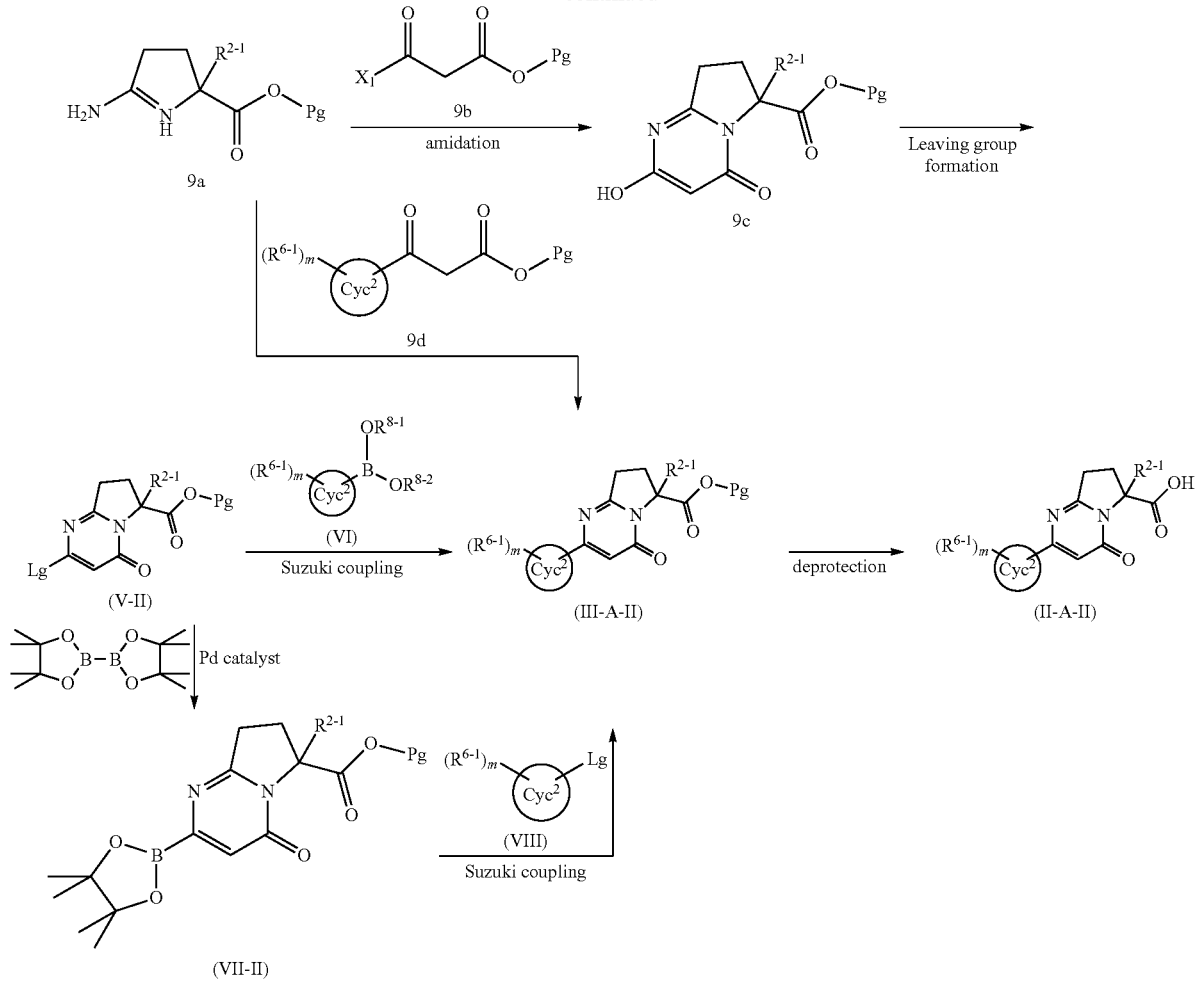

wherein $X_1$ represents hydroxyl, chlorine or —O—C1-4 alkyl and the other symbols have the same meaning described above.

In Reaction Scheme 9, treatment of an imidate compound represented by formula 8a with an ammonium salt such as ammonium chloride in a solvent such as ethanol at a temperature from about 20° C. to the refluxing temperature provides an amidine compound represented by formula 9a.

The amidine compound represented by formula 9a can be condensed with malonic acid derivatives represented by formula 9b such as mono-ethyl malonate or ethyl malonyl chloride by the same methods as described above for the amidation reaction to give the acylated amidine intermediates, which then cyclize to provide a pyrimidinone compound represented by formula 9c.

The pyrimidinone compound represented by formula 9c can be converted to the compound represented by formula (II-A-II) or formula (III-A-II) by the same method described in Reaction Scheme 8.

Alternatively, the amidine compound represented by formula 9a can be condensed with a suitably substituted beta-ketoester compound represented by formula 9d in the presence of base such as triethylamine in a solvent such as toluene at a temperature from about 20° C. to the refluxing temperature to give the compound represented by formula (III-A-II).

The compound represented by formula (III-A-II) can be converted to the compound represented by formula (II-A-II) by the deprotection reaction as described above.

10) The compound represented by formula (II-A) and formula (III-A) wherein Y is C(H) and U is S, that is, a compound represented by formula (II-A-III) and formula (III-A-III) respectively, can be prepared as outlined in Reaction Scheme 10:

Reaction Scheme 10

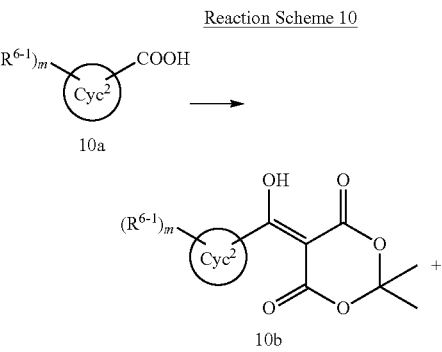

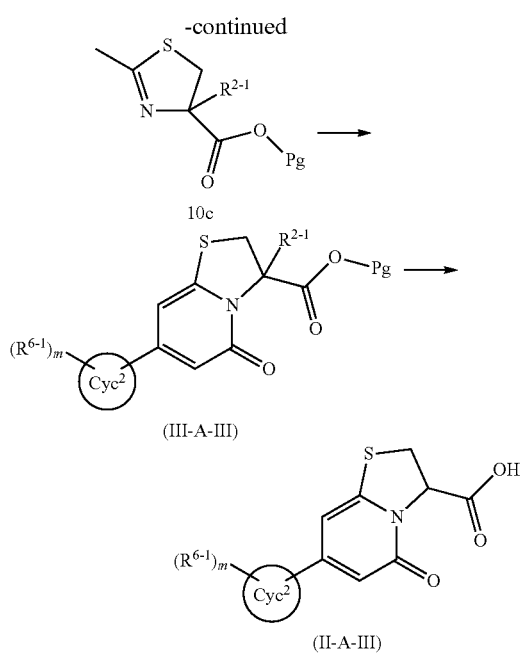

(III-A-III)

(II-A-III)

wherein all symbols have the same meaning described above.

In Reaction Scheme 10, the compound represented by formula (III-A-III) can be prepared from acylated Meldrum's acid derivatives represented by formula 10b, which are prepared from the compound represented by formula 10a using the method of Hans, E. et al. (*J. Org. Chem.* 2001, 66, 6756).

The compound represented by formula (III-A-III) can be converted to the compound represented by formula (II-A-III) by the deprotection reaction as described above.

11) The compound represented by formula (I-A) wherein $R^{62}$ is hydrogen, Y is C(H) or N, U is $CH_2$ or S and at least one of the $R^6$ is $Cyc^{10}$, that is, a compound represented by formula (I-A-IV):

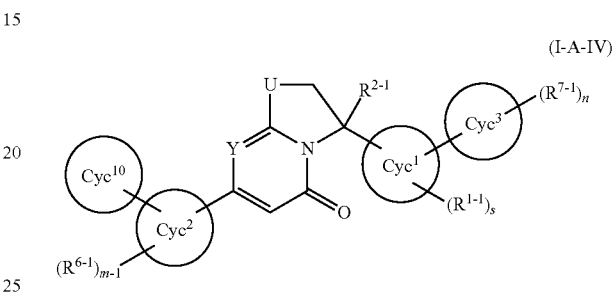

(I-A-IV)

wherein all symbols have the same meaning described above, can be prepared as outlined in Reaction Scheme 11:

Reaction Scheme 11
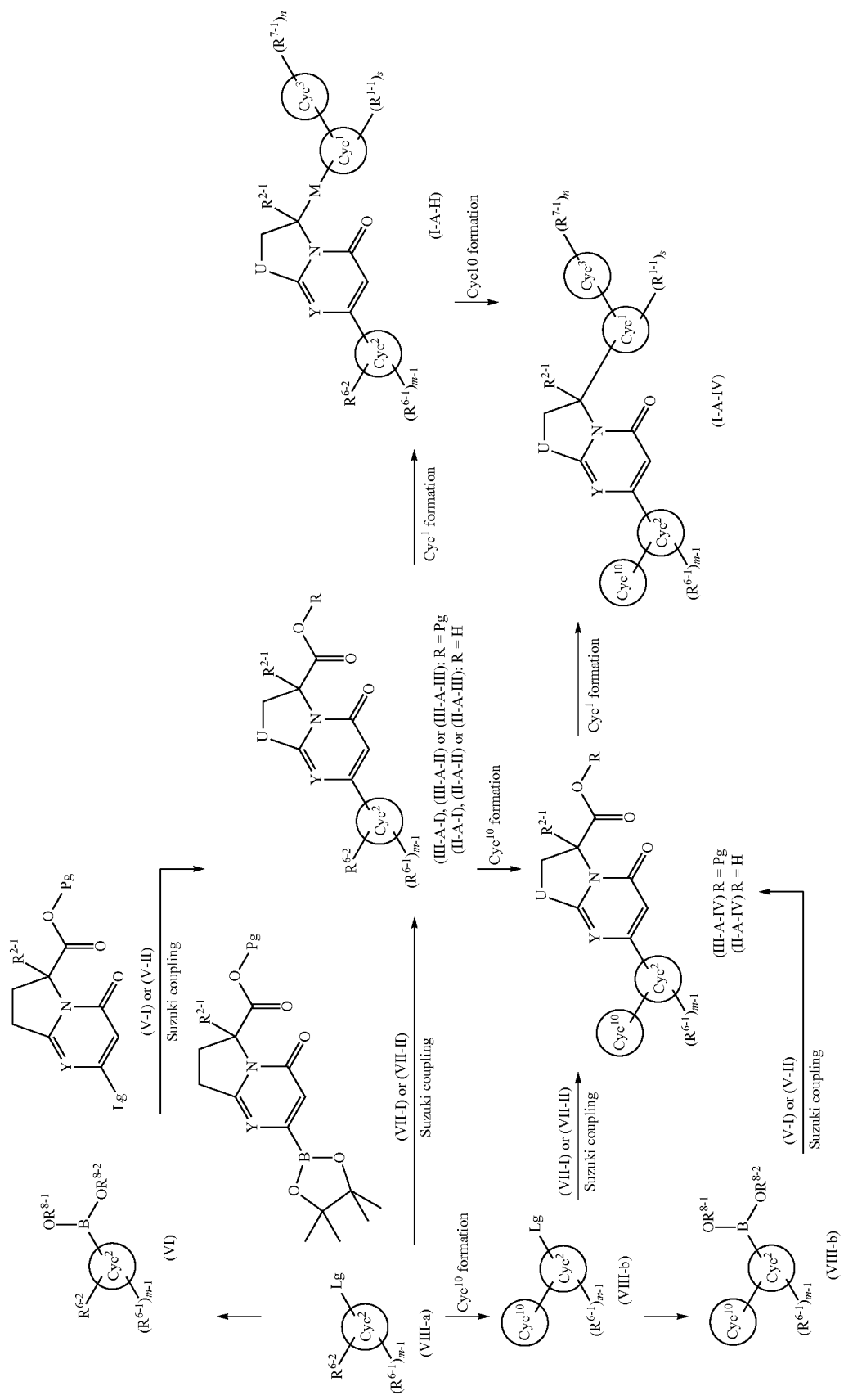

wherein $R^{6-2}$ represents amine, fluorine, chlorine, bromine or iodine and the other symbols have the same meanings as described above.

In Reaction Scheme 11, $Cyc^{10}$ can be constructed at the appropriate synthetic stage by $Cyc^{10}$ formation reaction. The $Cyc^{10}$ formation reaction can be prepared by the method described in Reaction Schemes 12 to 16 described below.

The reactions such as Suzuki coupling, $Cyc^1$ formation, etc. described in Reaction Scheme 11 can be prepared by the same methods as described above.

12) The compound represented by formula (I-A-IV) wherein $Cyc^2$ is aryl or heteroaryl and $Cyc^{10}$ is tetrazole ring which is attached to $Cyc^2$ at the 1-position, that is, a compound represented by formula (I-A-IV-I):

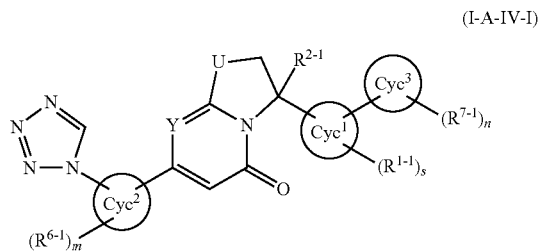

(I-A-IV-I)

wherein all symbols have the same meaning described above, can be prepared as outlined in Reaction Scheme 12:

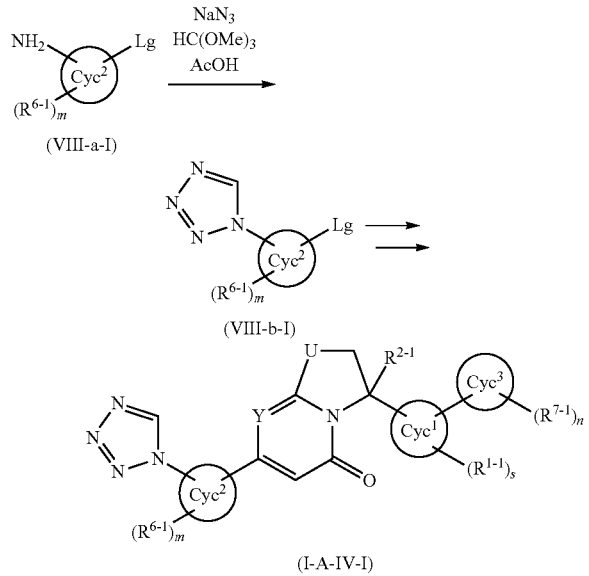

Reaction Scheme 12 wherein all symbols have the same meaning described above.

In Reaction Scheme 12, an appropriately substituted aryl or heteroaryl amine represented by formula (VIII-a-I) can be converted to tetrazole compound represented by formula (VIII-b-I) by treatment with sodium azide and trimethylorthoformate or triethylorthoformate in acetic acid at a temperature from about 0° C. to 95° C.

The compound represented by formula (VIII-b-I) can be converted to the compound represented by formula (I-A-IV-I) by the same method as described in Reaction Scheme 11.

Alternatively, the tetrazole ring formation can be conducted at the appropriate synthetic stage using an intermediate having an aryl or heteroaryl amino group as shown in Reaction Scheme 11.

13) The compound represented by formula (I-A-IV) wherein $Cyc^2$ is aryl or heteroaryl and $Cyc^{10}$ is a 1,2,3-triazole ring which is attached to $Cyc^2$ at the 1-position, that is, a compound represented by formula (I-A-IV-II):

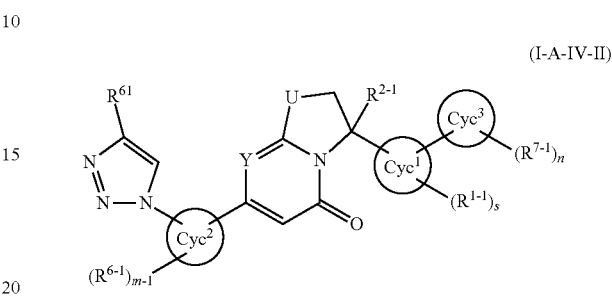

(I-A-IV-II)

wherein all symbols have the same meaning described above, can be prepared as outlined in Reaction Scheme 13:

Reaction Scheme 13

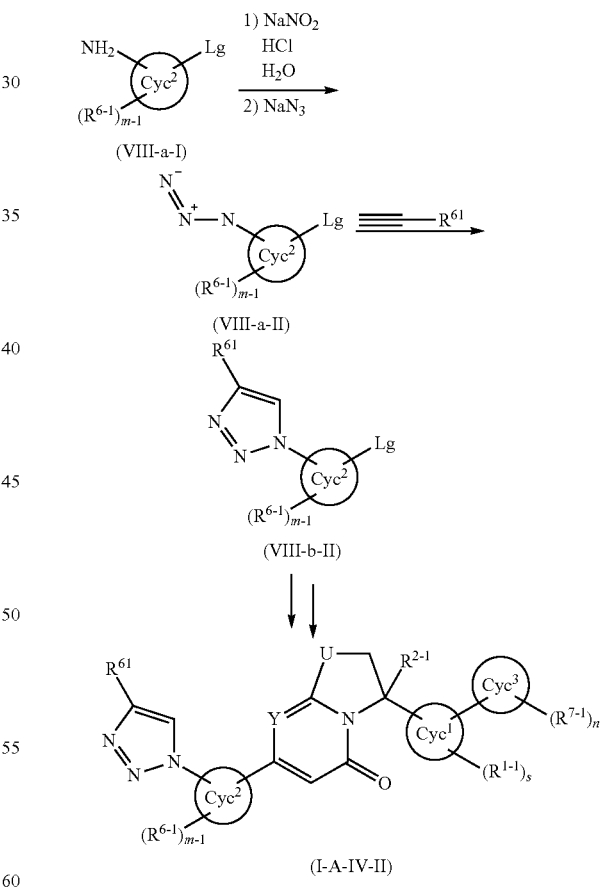

wherein all symbols have the same meaning described above.

In Reaction Scheme 13, an appropriately substituted aryl or heteroaryl amine compound represented by formula (VIII-a-I) can be treated with sodium nitrite in the presence of acid such as hydrochloric acid in water to produce the corresponding diazonium salt, which can be treated with sodium azide in water to form the corresponding azide compound represented by formula (VIII-a-II). Alternatively, an appropriately substituted aryl or heteroaryl amine compound represented by formula (VIII-a-I) can be converted to the corresponding azide compound represented by formula (VIII-a-II) treatment with trimethylsilyl azide and tert-butyl nitrite in acetonitrile at a temperature from about 0° C. to 40° C.

The azide compound represented by formula (VIII-a-II) can be treated with the appropriately substituted alkyne in a solvent such as toluene at the refluxing temperature to give 1,2,3-triazole derivatives represented by formula (VIII-b-II).

The compound represented by formula (VIII-b-II) can be converted to the compound represented by formula (I-A-IV-II) by the same method as described in Reaction Scheme 11.

Alternatively, 1,2,3-triazole ring formation can be conducted at the appropriate synthetic stage using an intermediate having an aryl or heteroaryl amino group as shown in Reaction Scheme 11.

14) The compound represented by formula (I-A-IV) wherein $Cyc^2$ is aryl or heteroaryl and $Cyc^{10}$ is 4-chloro-1,2,3-triazole attached to $Cyc^2$ at the 1-position, that is, a compound represented by formula (I-A-IV-III):

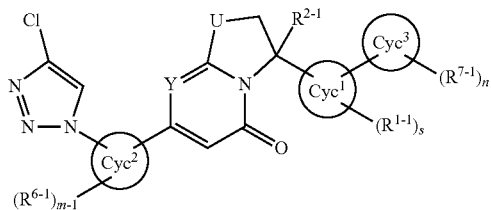

(I-A-IV-III)

wherein all symbols have the same meaning described above, can be prepared as outlined in Reaction Scheme 14:

Reaction Scheme 14

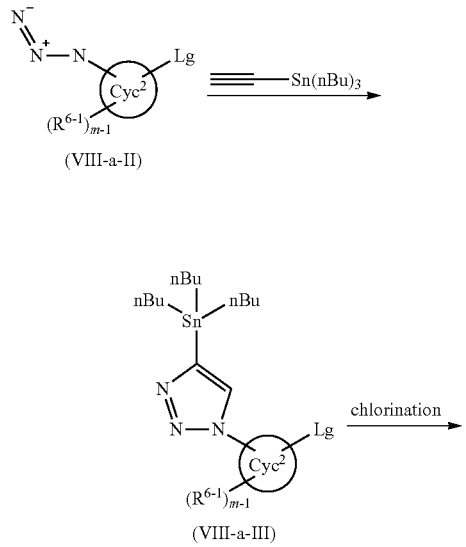

(VIII-a-II)

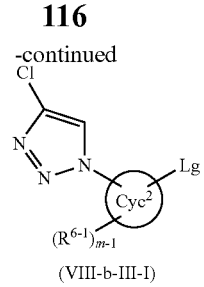

(VIII-b-III-I)

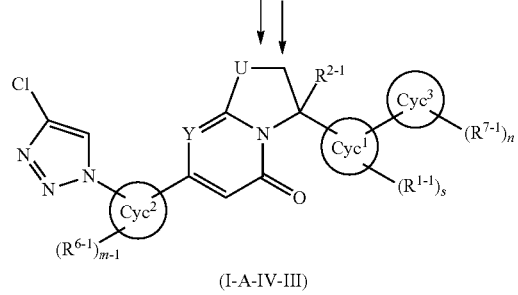

(I-A-IV-III)

wherein all symbols have the same meaning described above.

In Reaction Scheme 14, an appropriately substituted aryl or heteroaryl azide represented by formula (VIII-a-II) can be treated with ethynyl-tri-n-butyltin in a solvent such as toluene at reflux to give the 4-tributylstannyl-1,2,3-triazole represented by formula (VIII-b-III).

The compound represented by formula (VIII-b-III-I) can be prepared from the precursor compound represented by formula (VIII-b-III) by treatment with N-chlorosuccinimide or 1,3-dichloro-5,5-dimethyl-hydantoin in a solvent such as acetonitrile at a temperature from approximately 20° C. to reflux.

The compound represented by formula (VIII-b-III-I) can be converted to the compound represented by formula (I-A-IV-III) by the same method as described in Reaction Scheme 11.

Alternatively, 4-Chloro-1,2,3-triazole ring formation can be conducted at the appropriate synthetic stage using an intermediate having an aryl or heteroaryl amino group as shown in Reaction Scheme 11.

15) The compound represented by formula (I-A-IV) wherein $Cyc^2$ is aryl or heteroaryl and $Cyc^{10}$ is a 1,2-pyrazole which is attached to $Cyc^2$ at the 1-position, that is, the compound represented by formula (I-A-IV-IV):

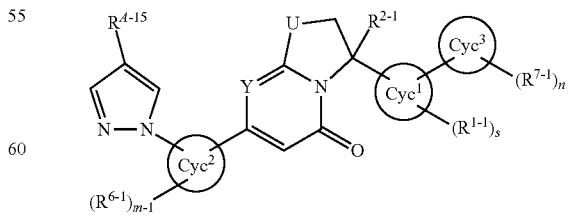

(I-A-IV-IV)

wherein $R^{4-15}$ represents hydrogen or C1-4 alkyl and the other symbols have the same meaning described above, can be prepared as outlined in Reaction Scheme 15:

Reaction Scheme 15

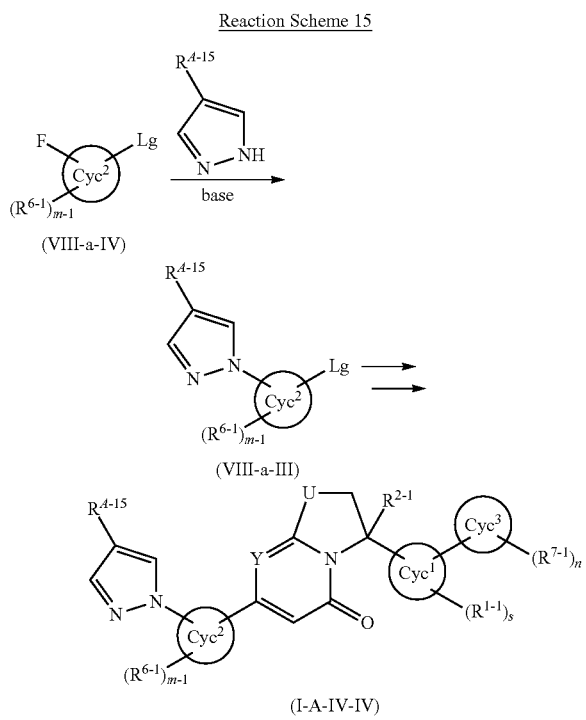

wherein all symbols have the same meaning described above.

In Reaction Scheme 15, an appropriately substituted aryl or heteroaryl fluoride represented by formula (VIII-a-IV) can be converted to the 1,2-pyrazole compound represented by formula (VIII-b-IV) by treatment with the appropriately substituted 1,2-pyrazole in the presence of a base such as cesium carbonate in a solvent such as N,N-dimethylacetamide at a temperature from approximately 20° C. to 100° C.

The compound represented by formula (VIII-b-IV) can be converted to the compound represented by formula (I-A-IV-IV) by the same method as described in Reaction Scheme 11.

16) The compound represented by formula (I-A-IV) wherein Cyc$^{10}$ represents 4-fluoro-1,2-pyrazole, that is, a compound represented by formula (I-A-IV-V):

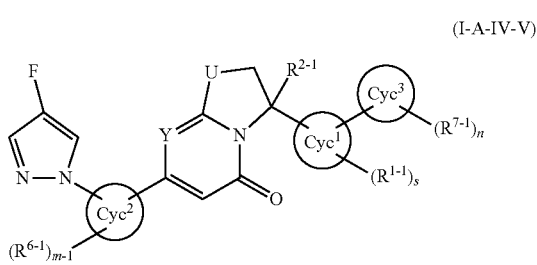

wherein all symbols have the same meaning described above, can be prepared as outlined in Reaction Scheme 16:

Reaction Scheme 16

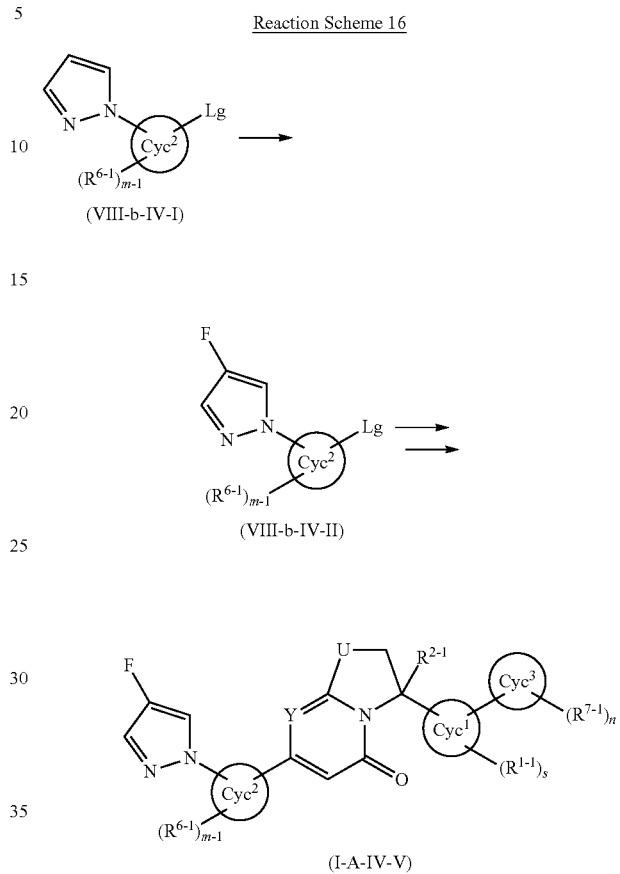

wherein all symbols have the same meaning described above.

In Reaction Scheme 16, the compound represented by formula (VIII-b-IV-I) can be converted to the 4-fluoro-1,2-pyrazole compound represented by formula (VIII-b-IV-II) by treatment with a fluorinating agent such as 1-chloromethyl-4-fluoro-1,4-diazoniabicyclo[2.2.2]octane bis(tetrafluoroborate) in a solvent such as acetonitrile at a temperature from about 20° C. to 100° C.

The compound represented by formula (VIII-b-IV-II) can be converted to the compound represented by formula (I-A-IV-V) by the same method as described in Reaction Scheme 11.

17) The compound of formula (I-B) can be prepared as outlined in Reaction Scheme 17:

Reaction Scheme 17
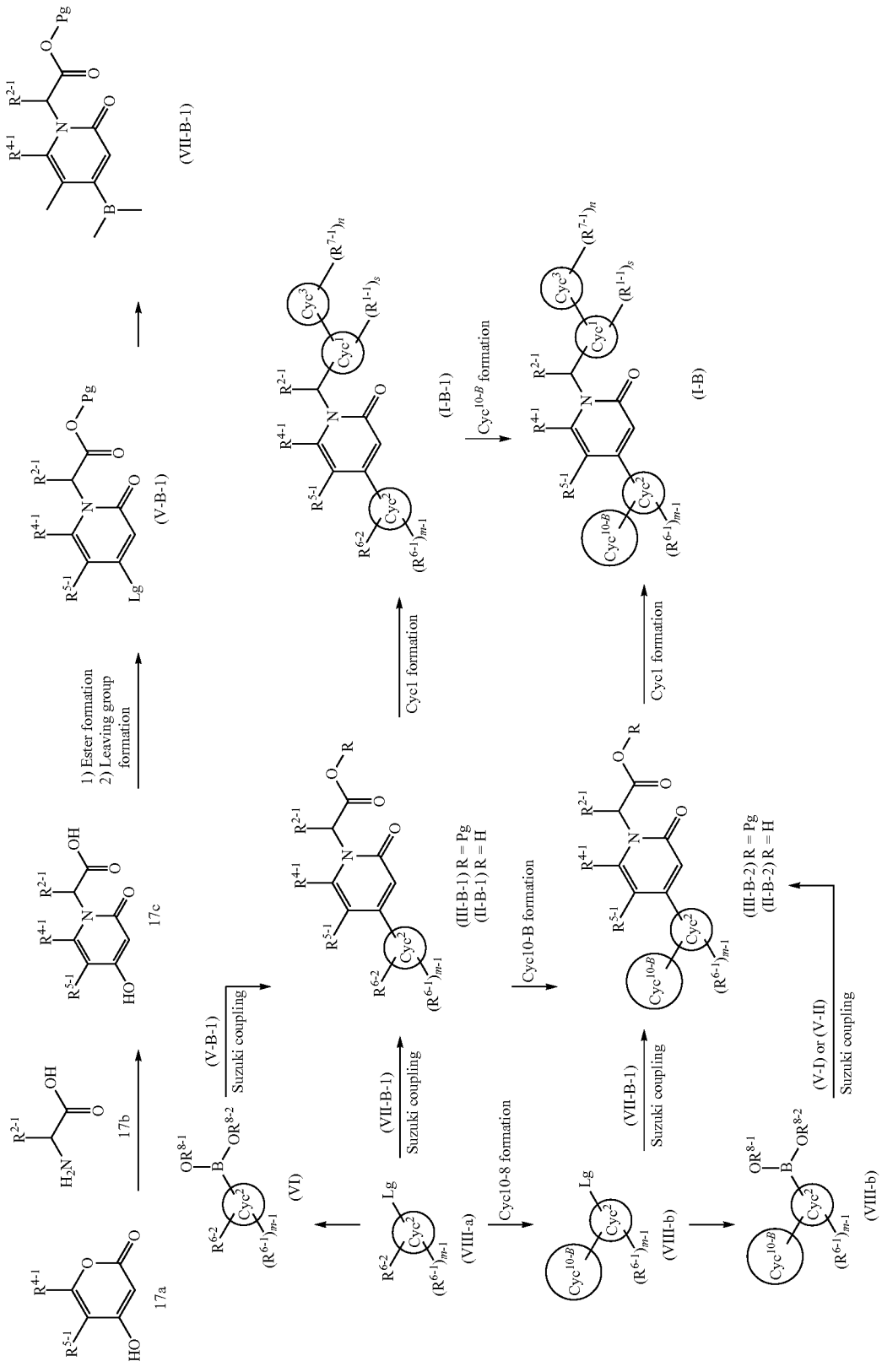

wherein all symbols have the same meaning described above.

In Reaction Scheme 17, an appropriately substituted 4-hydroxy-2-pyrone derivative 17a can be treated with a suitably substituted amino acid derivative 17b in the presence of alkali such as sodium hydroxide or potassium hydroxide in water at a temperature from about 20° C. to reflux to give the carboxylic acid compound represented by formula 17c.

The carboxylic acid represented by formula 17c can be converted to the corresponding ester compound represented by formula (V-B-I) by ester formation and leaving group formation as described previously. The ester compound represented by formula (V-B-1) can be converted to the compound represented by the formula (I-B) by the method as described above.

18) The compound of formula (I-C) can be prepared as outlined in Reaction Scheme 18:

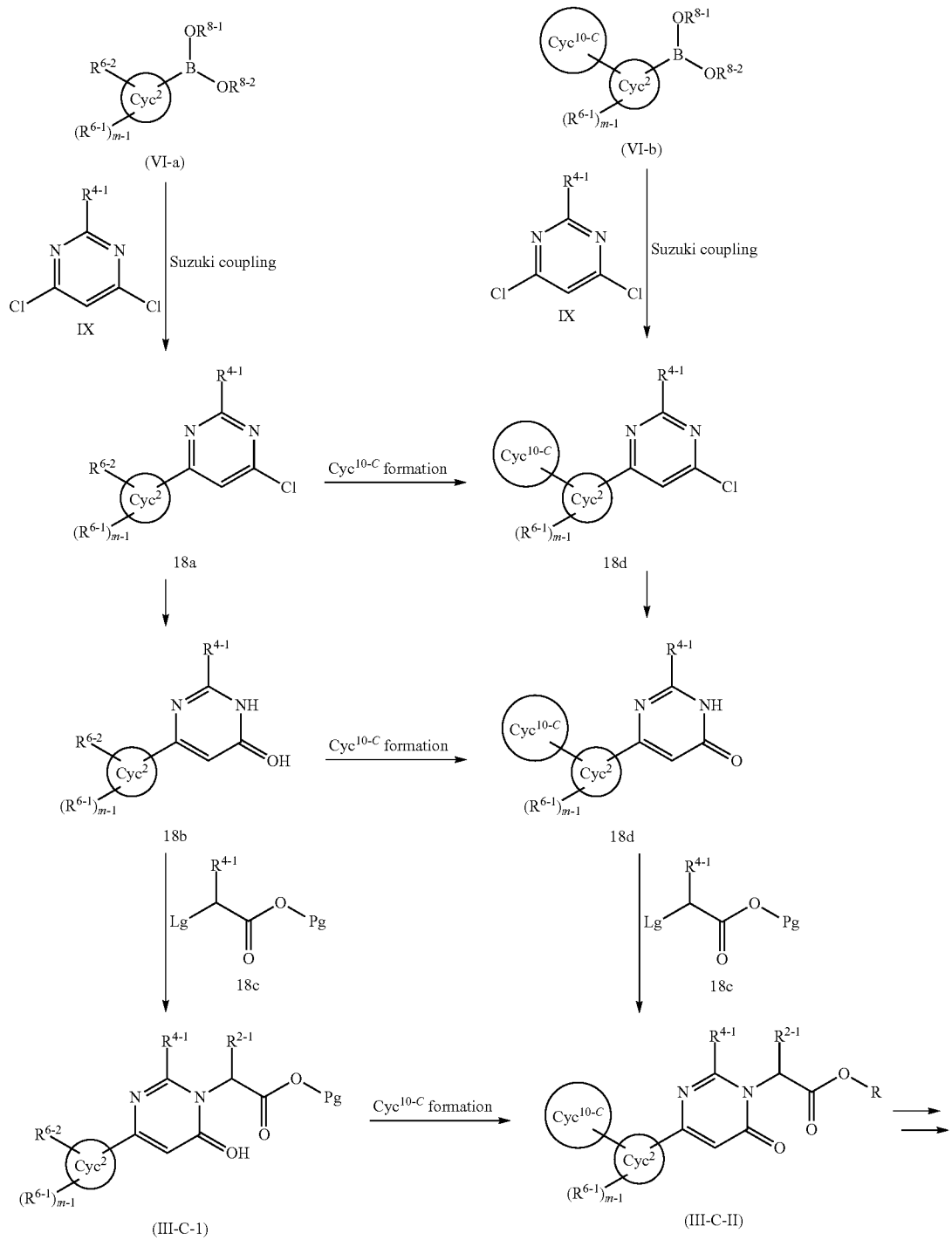

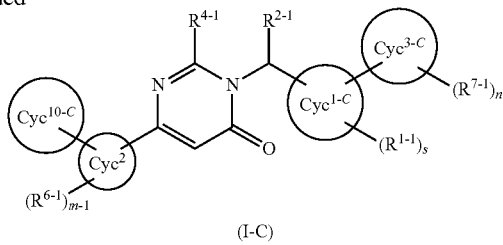

(I-C)

wherein all symbols have the same meaning described above.

In Reaction Scheme 18, appropriately substituted boronic ester derivative represented by formula (VI-a), which are commercially available or can be prepared by the method described above, can be converted to a 4-aryl-6-chloropyrimidine compound represented by formula 18a using the 2,4-dichloropyrimidine derivative represented by formula IX by a Suzuki coupling reaction as described above.

4-Aryl-6-chloropyrimidine compounds represented by formula 18a can be hydrolyzed to 4-aryl-pyrimidinone compounds represented by formula 18b by treatment with an acid such as hydrochloric acid at a temperature from approximately 20° C. to reflux.

4-Aryl-pyrimidinone compounds represented by formula 18b can be converted to the ester compounds represented by formula (III-C-I) by treatment with alkylating agents represented by the formula 18c by the same method as described above.

The ester compound represented by formula (III-C-I) can be converted to the compound represented by the formula (III-C-II) by a $Cyc^{10-C}$ formation reaction. The $Cyc^{10-C}$ formation reaction can be carried out by the same method as described previously.

The compound represented by formula (III-C-II) can be converted to the compound represented by formula (I-C) by the same method as described above for the $Cyc^1$ formation reaction.

19) The compound represented by formula (I) wherein Y represents $C(R^5)$ and at least one of the $R^5$ or $R^{62}$ represent halogen, that is, a compound represented by formula (I-II-1), (I-II-2) or (I-II-3):

(I-II-1)

(I-II-2)

(I-II-3)

wherein $R^{5-1}$ and $R^{62-1}$ represent chlorine or bromine and the other symbols have the same meanings as described above, can be prepared as outlined in Reaction Scheme 19:

Reaction Scheme 19

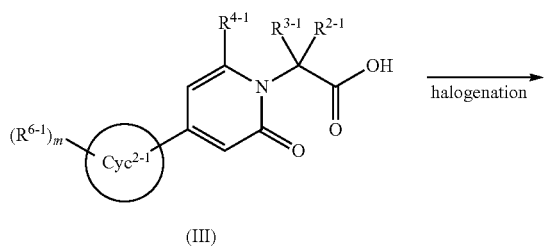

(III)

halogenation

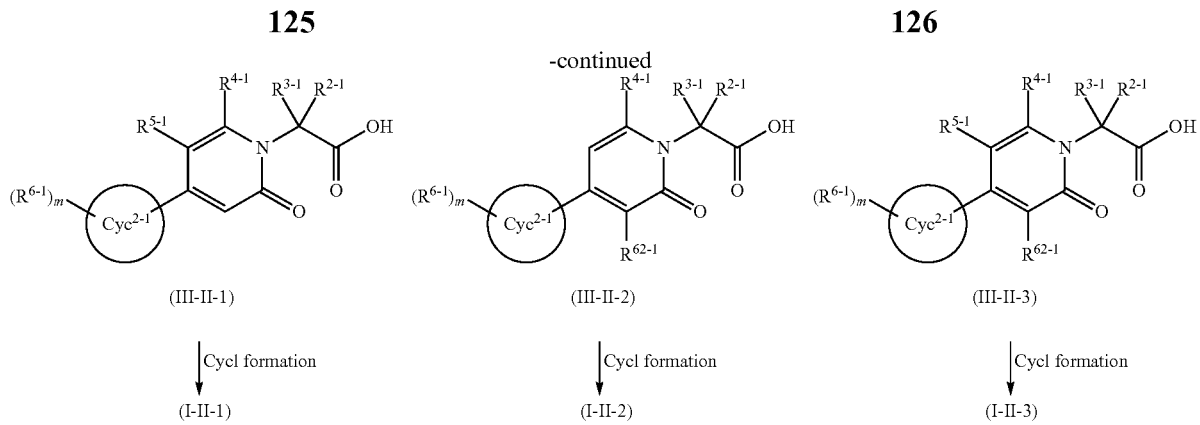

In Reaction Scheme 19, the reaction from the compound represented by formula (III) to the compound represented by formula (III-II-1), (III-II-2) and (III-II-3) is a halogenation reaction.

The halogenation reaction is well known. For example, the reaction of the compound represented by formula (III) with brominating or chlorinating agent, such as N-bromosuccinimide, N-chlorosuccinimide or 1,3-dichloro-5,5-dimethyl-hydantoin in a suitable solvent such as acetonitrile, chloroform or tetrahydrofuran from −20° C. to the refluxing temperature provides the compound represented by formula (III-II-1), (III-II-2) and (III-II-3). The carboxylic acid represented by formula (III-II-1), (III-II-2) and (III-II-3) can be converted the compound represented by formula (I-II-1), (I-II-2) and (I-II-3) respectively by the method as described above.

The compounds, of the present invention can be prepared by the reactions or modified variants of the reactions described above.

Other starting compounds or compounds used as reagents are known compounds which can be prepared easily by a combination of known methods, for example, the methods described in Comprehensive Organic Transformations: A Guide to Functional Group Preparations, 2nd Edition (Richard C. Larock, John Willey & Sons Inc, 1999) or Elmer J. Rauckman et al., J. Org. Chem., vol. 41, No. 3, 1976, p 564-565 etc.

In each reaction of the specification, the reactions with heating, as will be apparent to those skilled in the art, may be carried out using a water bath, an oil bath, a sand bath, a heating block or by microwave.

In each reaction of the specification, a solid phase reagent may be used which is supported by a polymer (for example, polystyrene, polyacrylamide, polypropylene or polyethyleneglycol etc.).

In each reaction of the specification, the products obtained may be purified by conventional techniques. For example, the purification may be carried out by distillation at atmospheric or reduced pressure, by high performance liquid chromatography with silica gel or magnesium silicate, by thin layer chromatography, by ion-exchange resin, by scavenger resin, by column chromatography, by washing, trituration or recrystallization. The purification may be carried out after each reaction stage or after several reaction stages.

In a reaction of the specification where polystyrene resin is used, the obtained products may be purified by conventional techniques. For example, the purification may be carried out by multiple washing with a solvent (for example, dimethylformamide, dichloromethane, methanol, tetrahydrofuran, toluene, acetic acid/toluene, etc.).

Toxicity:

The toxicity of the compound represented by formula (I), the salt thereof, the N-oxide thereof or the solvate thereof, or the prodrug thereof is very low and therefore it may be considered safe for pharmaceutical use.

Application to Pharmaceuticals:

The compounds of the present invention are therapeutically useful. The present invention therefore provides a compound of formula (I), as defined above, or a pharmaceutically acceptable salt thereof, an N-oxide thereof, a solvate thereof or a prodrug thereof, for use in the treatment of the human or animal body by therapy.

Also provided is a pharmaceutical composition comprising a compound of formula (I), as defined above, or a pharmaceutically acceptable salt thereof, an N-oxide thereof, a solvate thereof or a prodrug thereof, and a pharmaceutically acceptable carrier or diluent.

Said pharmaceutical composition typically contains up to 85 wt % of a compound of the invention. More typically, it contains up to 50 wt % of a compound of the invention. Preferred pharmaceutical compositions are sterile and pyrogen free. Further, the pharmaceutical compositions provided by the invention typically contain a compound of the invention which is a substantially pure optical isomer.

The compounds of the present invention may normally be administered systemically or locally, usually by oral or parenteral administration.

A therapeutically effective amount of a compound of the invention is administered to a patient. The doses to be administered are determined depending upon, for example, age, body weight, symptom, the desired therapeutic effect, the route of administration, and the duration of the treatment. In the human adult, the doses per person are generally from 1 mg to 1000 mg, by oral administration, up to several times per day, and from 1 mg to 100 mg, by parenteral administration (preferably intravenous administration), up to several times per day, or continuous administration from 1 to 24 hours per day from vein.

As mentioned above, the doses to be used depend upon various conditions. Therefore, there are cases in which doses lower than or greater than the ranges specified above may be used.

The compounds or pharmaceutical compositions of the present invention may be administered for example, in the form of a solid for oral administration, liquid forms for oral administration, injections, liniments or suppositories for parenteral administration. Preferably, the compounds or pharmaceutical compositions of the present invention are administered orally.

Solid forms for oral administration include compressed tablets, pills, capsules, dispersible powders, and granules. Capsules include hard capsules and soft capsules.

In such solid forms, one or more of the active compound(s) may be admixed with vehicles (such as lactose, mannitol, glucose, microcrystalline cellulose or starch), binders (such as hydroxypropyl cellulose, polyvinylpyrrolidone or magnesium metasilicate aluminate), disintegrants (such as cellulose calcium glycolate), lubricants (such as magnesium stearate), stabilizing agents, solution adjuvants (such as glutamic acid or aspartic acid, disaggregating agents, e.g. starch, alginic acid, alginates or sodium starch glycolate; effervescing mixtures, dyestuffs, sweeteners, wetting agents, such as lecithin, polysorbates, laurylsulphates; and, in general, non toxic and pharmacologically inactive substances used in pharmaceutical formulations, and prepared according to methods well known in normal pharmaceutical practice, for example, by means of mixing, granulating, tableting, sugar coating, or film coating processes. The solid forms may, if desired, be coated with coating agents (such as sugar, gelatin, hydroxypropyl cellulose or hydroxypropylmethyl cellulose phthalate), or be coated with two or more films. Furthermore, coating may include containment within capsules of absorbable materials such as gelatin.

Liquid forms for oral administration include pharmaceutically acceptable solutions, suspensions, emulsions, syrups and elixirs. In such forms, one or more of the active compound(s) may be dissolved, suspended or emulsified into diluent(s) commonly used in the art (such as purified water, ethanol or a mixture thereof). Besides such liquid forms may also comprise some additives, such as wetting agents, suspending agents, emulsifying agents, sweetening agents, flavoring agents, aroma, preservative or buffering agent. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for injection or infusion may contain as carrier, for example, sterile water or preferably they may be in the form of sterile, aqueous, isotonic saline solutions.

Injections for parenteral administration include sterile aqueous, suspensions, emulsions and solid forms which are dissolved or suspended into solvent(s) for injection immediately before use. In injections, one or more of the active compound(s) may be dissolved, suspended or emulsified into solvent(s). The solvents may include distilled water for injection, saline, vegetable oil, propylene glycol, polyethylene glycol, alcohol such as ethanol, or a mixture thereof Injections may comprise some additives, such as stabilizing agents, solution adjuvants (such as glutamic acid, aspartic acid or POLYSORBATE80 (registered trade mark)), suspending agents, emulsifying agents, soothing agent, buffering agents, preservative. They may be sterilized at a final step, or may be prepared according to sterile methods. They may also be manufactured in the form of sterile solid forms such as freeze-dried products, which may be dissolved in sterile water or some other sterile diluent(s) for injection immediately before use.

Other forms for parenteral administration include liquids for external use, ointments and endermic liniments, inhalations, sprays, suppositories and vaginal suppositories which comprise one or more of the active compound(s) and may be prepared by methods known per se.

Sprays may comprise additional substances other than diluents, used commonly, stabilizers such as sodium hydrogensulfite and buffers capable of imparting isotonicity, for example, isotonic buffers such as sodium chloride, sodium citrate or citric acid.

EFFECT OF THE INVENTION

The compounds of the present invention represented by formula (I) act as potent and selective inhibitors of Factor XIa, with potent anticoagulant activity and/or good oral availability. In particular, the compounds of the present invention act as a Factor XIa inhibitor or a Factor XIa and plasma kallikrein dual inhibitor. Thus the compounds of the present invention are useful in preventing and/or treating thromboembolic diseases. One advantage of the compounds of the present invention is that they can provide high inhibitory activity against FXIa and potent anticoagulant activity and/or high plasma exposure level after oral administration.

The present invention therefore provides a compound of formula (I), as defined above, or a pharmaceutically acceptable salt thereof, an N-oxide thereof, a solvate thereof or a prodrug thereof, for use in treating or preventing a thromboembolic disease. Also provided is a method for treating a patient suffering from or susceptible to a thromboembolic disease, which method comprises administering to said patient an effective amount of a compound of formula (I), as defined above, or a pharmaceutically acceptable salt thereof, an N-oxide thereof, a solvate thereof or a prodrug thereof. Further provided is the use of a compound of formula (I), as defined above, or a pharmaceutically acceptable salt thereof, an N-oxide thereof, a solvate thereof or a prodrug thereof, in the manufacture of a medicament for use in treating or preventing a thromboembolic disease.

The thromboembolic disease may be, for example, selected from the group consisting of arterial cardiovascular thromboembolic disorders, venous cardiovascular thromboembolic disorders, arterial cerebrovascular thromboembolic disorders, venous cerebrovascular thromboembolic disorders and thromboembolic disorders in the chambers of the heart or in the peripheral circulation.

More specifically, arterial cardiovascular thromboembolic disorders may be exemplified by coronary artery disease, ischemic cardiomyopathy, acute coronary syndrome, coronary arterial thrombosis, ischemic complications of unstable angina and non-Q-wave myocardial infarction, acute ST-segment elevation myocardial infarction managed medically or with subsequent percutaneous coronary intervention, angina pectoris such as stable effort angina pectoris, variant angina pectoris, unstable angina pectoris, myocardial infarction (e.g. first myocardial infarction or recurrent myocardial infarction), acute myocardial infarction, reocclusion and restenosis after coronary artery bypass surgery, reocclusion and restenosis after percutaneous transluminal cardiac angioplasty transluminal coronary artery stent placement surgery or after thrombolytic therapy for coronary artery, ischemic sudden death. Venous cardiovascular thromboembolic disorders may be exemplified by deep vein thrombosis (DVT) and/or pulmonary embolism (PE) in major general surgery, abdominal surgery, hip replacement surgery, knee replacement surgery, hip fracture surgery, multiple fracture, multiple injury, trauma, spinal cord injury, burns, critical care unit, DVT and/or PE in medical patients with severely restricted mobility during acute illness, DVT and/or PE in patients with cancer chemotherapy, DVT and/or PE in patients with stroke, symptomatic or asymptomatic DVT with or without PE, pulmonary embolism. Arterial cerebrovascular thromboembolic disorders may be exemplified by stroke, ischemic stroke, acute stroke, stroke in patients with non-valuvelar or valuvelar atrial fibrillation, cerebral arterial thrombosis, cerebral infarction, transient ischemic attack (TIA), lacuna infraction, atherosclerotic thrombotic cerebral infarction, cerebral artery embolism, cerebral thrombosis, cerebrovascular disorder, asymptomatic cerebral infarction.

Venous cerebrovascular thromboembolic disorders may be exemplified by intracranial venous thrombosis, cerebral embolism, cerevral thrombosis, sinus thrombosis, intracranial venous sinus thrombosis, cavernous sinus thrombosis. Thromboembolic disorders in the chambers of the heart or in the peripheral circulation may be exemplified by venous thrombosis, systemic venous thromboembolism, thrombophlebitis, non-valuvelar or valuvelar atrial fibrillation, disseminated intravascular coagulopathy (DIC), kidney embolism, atherosclerosis, atherothrombosis, peripheral artery occlusive disease (PAOD), peripheral arterial disease, arterial embolism, and thrombosis resulting from medical implants, devices, or procedures in which blood is exposed to an artificial surface (such as catheters, stents, artificial heart valves, or hemodialyzer) that promotes thrombosis.

Preferably, the thromboembolic disorder is selected from unstable angina, an acute coronary syndrome, atrial fibrillation, myocardial infarction (e.g. first myocardial infarction or recurrent myocardial infarction), ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface (such as catheters, stents or artificial heart valves) that promotes thrombosis.

The compounds of the present invention may also be administered in combination with one or more further therapeutic agents. Thus, in another embodiment, the present invention provides a method for treating a thromboembolic disorder, comprising: administering to a patient in need thereof a therapeutically effective amount of a first and second therapeutic agent, wherein the first therapeutic agent is a compound of formula (I), as defined above, or a pharmaceutically acceptable salt thereof, an N-oxide thereof, a solvate thereof or a prodrug thereof, and the second therapeutic agent is at least one agent selected from a second factor XIa inhibitor, an anti-coagulant agent, an anti-platelet agent, a thrombin inhibiting agent, a thrombolytic agent, and a fibrinolytic agent. Preferably, the second therapeutic agent is at least one agent selected from warfarin, unfractionated heparin, low molecular weight heparin (e.g., danaparoid, enoxaparin, bemiparin, dalteparin, nadroparin, parnaparin, reviparin, tinzaparin, ardeparin, adomiparin, semuloparin, RO-14, RO-16, GCC-4401C), synthetic pentasaccharide (e.g., fondaparinux, idraparinux, idrabiotaparinux, EP-42675, EP-217609, EP-224283), synthetic hexadecasaccharide (e.g., SSR128428), factor Xa inhibitor (e.g., rivaroxaban, edoxaban, apixaban, betrixaban, otamixaban, darexaban, letaxaban, 813893, eribaxaban, AVE-3247, R-1663, BMS-344577, TAK-239), thrombin inhibitor (argatroban, melagatran, ximelagatran, dabigatran, tanogitran, dermatan, hirudin, bivalirudin, desirudin, lepirudin, NU-172, DP-4088, RWJ-671818, BL-5030), antithrombin III (e.g., freeze-dried concentrated human antithrombin III, KW-3357), thrombomodulin (e.g., thrombomodulin alfa), non-steroidal anti-inflammatory drugs (e.g., aspirin, acetaminophen, codeine, ibuprofen, naproxen, sulindac, indomethacin, mefenamate, droxicam, indobufen, diclofenac, sulfinpyrazone, piroxicam, fentaynl, ketorolac, mefenamate, morphine, phenacetin, sufentanyl), $P2Y_{12}$ receptor antagonist (e.g., ticlopidine, clopidogrel, prasugrel, ticagrelor, elinogrel), phosphodiesterase-III inhibitor (e.g., dipyridamole, cilostazol), phosphodiesterase-V inhibitor (e.g., sildenafil) serotonin 2 antagonist (e.g., sarpogrelate), prostaglandin $E_1$ agonist (e.g., alprostadil, limaprost, ecraprost), prostaglandin $I_2$ agonist (e.g., ibudilast, iloprost, beraprost, epoprostenol), thromboxane A synthesis inhibitor (e.g., ozagrel), thromboxane A2 receptor antagonist (e.g., seratrodast, ramatroban, terutroban, ifetroban), glycoprotein IIb/IIIa blocker (e.g., tirofiban, eptifibatide, abciximab, integrelin), protease-activated receptor-1 antagonist (e.g., vorapaxar) and fibrinolytic agent (e.g., tissue plasminogen activator, anistreplase, monteplase, reteplase, tenecteplase, desmoteplase, amediplase, THR-100, urokinase, ocriplasmin, nasaruplase β, streptokinase). Preferably, the second therapeutic agent is at least one anti-platelet agent. Preferrably, the anti-platelet agent(s) are ticlopidine, clopidogrel, prasugrel ticagrelor, elinogrel, cilostazol, sarpogrelate, iroprost, dipyridamole, beraprost, limaprost, ozagrel, vorapaxar and/or aspirin, or a combination thereof. The present invention also provides a compound of formula (I), as defined above, or a pharmaceutically acceptable salt thereof, an N-oxide thereof, a solvate thereof or a prodrug thereof, in combination with a second therapeutic agent selected from those listed above, for use in treating or preventing a thromboembolic disease. The present invention also provides the use of a compound of formula (I), as defined above, or a pharmaceutically acceptable salt thereof, an N-oxide thereof, a solvate thereof or a prodrug thereof, in combination with a second therapeutic agent, in the manufacture of a medicament for use in treating or preventing a thromboembolic disease.

In another embodiment, the present invention provides a pharmaceutical composition comprising a compound of formula (I), as defined above, or a pharmaceutically acceptable salt thereof, an N-oxide thereof, a solvate thereof or a prodrug thereof and an additional therapeutic agent. Preferably, the further additional therapeutic agent(s) are selected from potassium channel openers, potassium channel blockers, calcium channel blockers, sodium hydrogen exchanger inhibitors, sodium-potassium pump inhibitors, antiarrhythmic agents, antiatherosclerotic agents, anticoagulants, antiplatelets, antithrombotic agents, prothrombolytic agents, fibrinogen antagonists, diuretics, antihypertensive agents, ATPase inhibitors, mineralocorticoid receptor antagonists, phospodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, or a combination thereof.

In another embodiment, the present invention provides a pharmaceutical composition further comprising additional therapeutic agent(s) selected from an anti-arrhythmic agent, an anti-hypertensive agent, an antidiabetic agent, an anti-coagulant agent, an anti-platelet agent, a thrombin inhibiting agent, a thrombolytic agent, a fibrinolytic agent, a calcium channel blocker, a potassium channel blocker, a cholesterol/lipid lowering agent, or a combination thereof.

In another embodiment, the present invention provides a pharmaceutical composition further comprising additional therapeutic agent(s) selected from warfarin, unfractionated heparin, low molecular weight heparin (e.g., danaparoid, enoxaparin, bemiparin, dalteparin, nadroparin, parnaparin, reviparin, tinzaparin, ardeparin, adomiparin, semuloparin, RO-14, RO-16, GCC-4401C), synthetic pentasaccharide (e.g., fondaparinux, idraparinux, idrabiotaparinux, EP-42675, EP-217609, EP-224283), synthetic hexadecasaccharide (e.g., SSR128428), factor Xa inhibitor (e.g., rivaroxaban, edoxaban, apixaban, betrixaban, otamixaban, darexaban, letaxaban, 813893, eribaxaban, AVE-3247, R-1663, BMS-344577, TAK-239), thrombin inhibitor (argatroban, melagatran, ximelagatran, dabigatran, tanogitran, dermatan, hirudin, bivalirudin, desirudin, lepirudin, NU-172, DP-4088, RWJ-671818, BL-5030), antithrombin III (e.g., freeze-dried concentrated human antithrombin III, KW-3357), thrombomodulin (e.g., thrombomodulin alfa), non-steroidal anti-inflammatory drugs (e.g., aspirin, acetaminophen, codeine, ibuprofen, naproxen, sulindac, indomethacin, mefenamate, droxicam, indobufen, diclofenac, sulfinpyrazone, piroxicam, fentaynl, ketorolac, mefenamate, morphine, phenacetin, sufentanyl), $P2Y_{12}$ receptor antagonist (e.g., ticlopidine, clopidogrel, prasugrel, ticagrelor, elinogrel), phosphodiesterase-III inhibitor (e.g., dipyridamole, cilostazol), phosphodiesterase-V inhibitor (e.g., sildenafil) serotonin 2 antagonist (e.g., sarpogrelate), prostaglandin $E_1$ agonist (e.g., alprostadil, limaprost, ecraprost), prostaglandin $I_2$ agonist (e.g., ibudilast, iloprost, beraprost, epoprostenol), thromboxane A synthesis inhibitor (e.g., ozagrel), thromboxane A2 receptor antagonist (e.g., seratrodast, ramatroban, terutroban, ifetroban), glycoprotein IIb/IIIa blocker (e.g., tirofiban, eptifibatide, abciximab, integrelin), protease-activated receptor 1 antagonist (e.g., vorapaxar) and fibrinolytic agent (e.g., tissue plasminogen activator, anistreplase, monteplase, reteplase, tenecteplase, desmoteplase, amediplase, THR-100, urokinase, ocriplasmin, nasaruplase β, streptokinase). Preferably, the second therapeutic agent is at least one anti-platelet agent. Preferably, the anti-platelet agent(s) are ticlopidine, clopidogrel, prasugrel ticagrelor, elinogrel, cilostazol, sarpogrelate, iproprost, dipyridamole, beraprost, limaprost, ozagrel, vorapaxar and/or aspirin, or a combination thereof.

In a preferred embodiment, the present invention provides a pharmaceutical composition wherein the additional therapeutic agent is an antihypertensive agent selected from angiotensin-converting enzyme inhibitors, angiotensin-1 (AT-1) receptor antagonists, beta-adrenergic receptor antagonists, endothelin A (ETA) receptor antagonists, dual ETA/AT-1 receptor antagonists, and vasopepsidase inhibitors, an antiarrythmic agent selected from IKur inhibitors, an anticoagulant selected from thrombin inhibitors, antithrombin-III activators, heparin co-factor II activators, other factor XIa inhibitors, other kallikrein inhibitors, plasminogen activator inhibitor (PAI-1) inhibitors, thrombin activatable fibrinolysis inhibitor (TAFI) inhibitors, factor VIIa inhibitors, factor IXa inhibitors, factor XIIa inhibitors and factor Xa inhibitors, or an anti-platelet agent selected from glycoprotein IIb/IIIa blockers, protease-activated receptor-1 antagonists, protease-activated receptor-4 antagonists, phosphodiesterase-III inhibitors, phosphodiesterase-V inhibitors, prostaglandin $E_1$ agonists, prostaglandin $I_2$ agonists, thromboxane A synthesis inhibitors, thromboxane $A_2$ receptor antagonists, $P2Y_1$ receptor antagonists, $P2Y_{12}$ receptor antagonists, thromboxane receptor antagonists, cyclooxygense-1 inhibitors, glycoprotein VI antagonists, glycoprotein Ib antagonists, Growth arrest-specific gene 6 product antagonists and aspirin, or a combination thereof.

In a preferred embodiment, the present invention provides a pharmaceutical composition, wherein the additional therapeutic agent(s) are an anti-platelet agent or a combination thereof

BEST MODE FOR CARRYING OUT THE INVENTION

The present invention is illustrated by the following Examples and biological Examples, but it is not limited thereto.

The run time, solvents and column conditions used in the LC/MS analysis of the following Examples is reported using a superscript a, b, c, d, e or f appended to the analytical results which corresponds to the following conditions:

a. 3 minute run time; 0.1% formic acid in water and 0.1% formic acid in acetonitrile as mobile phases, Waters Atlantis® dC18, 2.1 mm×50 mm, 3 μm column
b. 7 minute run time; 0.1% formic acid in water and 0.1% formic acid in acetonitrile as mobile phases, Waters Atlantis® dC18, 2.1 mm×100 mm, 3 μm column
c. 4.5 minute run time; 0.1% formic acid in water and 0.1% formic acid in acetonitrile as mobile phases, Waters Atlantis® dC18, 3 mm×50 mm, 3 μm column
d. 6 minute run time; 0.1% trifluoroacetic acid in water and 0.1% trifluoroacetic acid in acetonitrile as mobile phases, Waters Xterra® MS C18, 3 mm×50 mm, 5 μm column
e. 5.5 minute run time; 0.1% formic acid in water and 0.1% formic acid in acetonitrile as mobile phases, Phenomenex® Kinetex-XB® C18, 2.1 mm×100 mm, 1.7 μm column
f. 1.5 minute run time; 0.1% trifluoroacetic acid in water and 0.1% trifluoroacetic acid in acetonitrile as mobile phases, Waters ACQUITY UPLC® BEH C18, 2.1 mm×30 mm, 1.7 μm column
g. 7 minute run time; 2 mM ammonium bicarbonate in water as mobile phase A and acetonitrile as mobile phase B, Phenomenex® Gemini® C18, 2.0 mm×100 mm, 3 μm column The solvents in the parentheses described in chromatographic separation and TLC show the eluting or developing solvents, and the ratios of the solvents used are given as percentage mixtures in chromatographic separations or TLC. Where a compound is described as dried either anhydrous magnesium or sodium sulphate was used. The solvents in the parentheses in NMR show the solvents used in measurement. DMSO represents dimethylsulfoxide; $CDCl_3$ represents deuterated chloroform. The following abbreviations are used in reporting the $^1H$ NMR spectra: s (singlet), d (doublet), t (triplet), q (quartet), br. (broad), app. (apparent), obs. (obscured).

Including compounds in the following Examples, compounds used in the present specification were commonly named using a computer program capable of naming in accordance with IUPAC rules; ACD/Name® manufactured by Advanced Chemistry Development Inc., J Chem for Excel or MarvinSketch manufactured by ChemAxon Ltd., or IUPAC nomenclature. In each of the following Examples, the name of the objective compound of the Example is described subsequently to the number of the Example, and the compound is sometimes referred to as the "title compound".

EXAMPLE 1 ethyl(2S)-5-methoxy-3,4-dihydro-2H-pyrrole-2-carboxylate

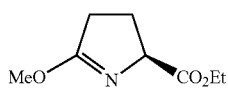

To a dichloromethane (500 mL) solution of ethyl 5-oxo-L-prolinate (51.2 g) was added trimethyloxonium tetrafluoroborate (50.5 g) and the mixture was stirred at room temperature for 3 hours. To the cooled (0° C.) reaction mixture, a saturated aqueous solution of sodium hydrogen carbonate (350 mL) and water (50 mL) was added sequentially followed by extraction with dichloromethane. The combined organic layers were dried and concentrated giving the title compound having the following physical properties (42.2 g).

TLC: Rf 0.50 (ethyl acetate).

EXAMPLE 2

3-ethyl 8-methyl(3S)-7-hydroxy-5-oxo-1,2,3,5-tetrahydroindolizine-3,8-dicarboxylate

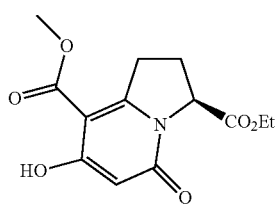 [SMILES: CCOC(=O)[C@@H]1CCc2c(C(=O)OC)c(O)cc(=O)n21]

The compound prepared in Example 1 (42.2 g) was combined with dimethyl 3-oxopentanedioate (42.9 g) and triethylamine (2.40 mL) and the mixture was stirred at 120° C. for 3 hours. On cooling, this gave the crude title compound having the following physical properties (85.6 g).

LC/MS $t_R$ 1.55 minutes; MS (ES$^+$) m/z 282 (M+H)$^a$.

EXAMPLE 3

(3S)-7-hydroxy-5-oxo-1,2,3,5-tetrahydroindolizine-3,8-dicarboxylic acid

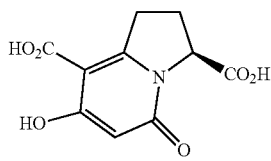 [SMILES: O=C(O)c1c(O)cc(=O)n2c1CC[C@H]2C(=O)O]

To the compound prepared in Example 2 (150.9 g), 2 M sodium hydroxide (1130 mL) was added and the mixture was stirred overnight at room temperature. To the reaction mixture, an aqueous solution of 6 M hydrochloric acid was added and the solid removed by filtration. The filter cake was washed sequentially with water and dichloromethane then dried under vacuum. The filtrate was concentrated to 850 mL and the solid removed by filtration. Washing and drying of the filter cake as detailed above gave the title compound in two batches having the following physical properties (31.7 g).

LC/MS $t_R$ 0.50 minutes; MS (ES$^+$) m/z 240 (M+H)$^a$.

EXAMPLE 4

(3S)-7-hydroxy-5-oxo-1,2,3,5-tetrahydroindolizine-3-carboxylic acid

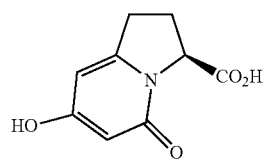 [SMILES: O=C(O)[C@@H]1CCc2cc(O)cc(=O)n21]

To the compound prepared in Example 3 (31.7 g), 6 M hydrochloric acid (1140 mL) and 12 M hydrochloric acid (200 mL) were added sequentially and the mixture stirred at 140° C. for 20 hours. The reaction mixture was concentrated and the solid azeotroped with toluene to dryness giving the title compound having the following physical properties (29.1 g).

LC/MS $t_R$ 0.63 minutes; MS (ES$^+$) m/z 196 (M+H)$^a$.

EXAMPLE 5 ethyl(3S)-7-hydroxy-5-oxo-1,2,3,5-tetrahydroindolizine-3-carboxylate

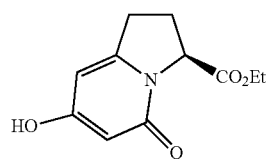 [SMILES: CCOC(=O)[C@@H]1CCc2cc(O)cc(=O)n21]

To an ethanol (115 mL) suspension of the compound prepared in Example 4 (29 g), concentrated sulfuric acid (0.96 mL) was added and the mixture was stirred at 100° C. for 4 hours. The reaction mixture was concentrated to give the title compound having the following physical properties (29.4 g).

LC/MS $t_R$ 1.21 minutes; MS (ES$^+$) m/z 224 (M+H)$^a$.

EXAMPLE 6 ethyl(3S)-5-oxo-7-{[(trifluoromethyl)sulfonyl]oxy}-1,2,3,5-tetrahydroindolizine-3-carboxylate

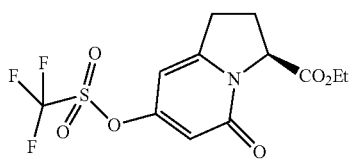 [SMILES: CCOC(=O)[C@@H]1CCc2cc(OS(=O)(=O)C(F)(F)F)cc(=O)n21]

To an N,N-dimethylformamide (190 mL) solution of the compound prepared in Example 5 (29.4 g), triethylamine (21.2 mL) and 1,1,1-trifluoro-N-phenyl-N-[(trifluoromethyl)sulfonyl]methanesulfonamide (49.4 g) were added sequentially and the mixture stirred at room temperature for 1 hour. To the reaction mixture, water (400 mL) was added followed by extraction with ethyl acetate. The combined organic layers were washed with brine, dried and concentrated. The residue was purified by column chromatography (20 to 50% ethyl acetate in heptanes) to give the title compound having the following physical properties (31.3 g).

LC/MS $t_R$ 1.89 minutes; MS (ES$^+$) m/z 356 (M+H)$^a$.

EXAMPLE 7 ethyl(3S)-7-(2-amino-5-chlorophenyl)-5-oxo-1,2,3,5-tetrahydroindolizine-3-carboxylate

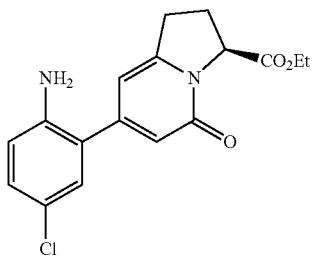 [SMILES: CCOC(=O)[C@@H]1CCc2cc(-c3cc(Cl)ccc3N)cc(=O)n21]

To a 1,4-dioxane (625 mL) solution of the compound prepared in Example 6 (31.3 g) were added 4-chloro-2-(4,4,5,5-tetramethyl-1,3,2-dioxaborolan-2-yl)aniline (22.4 g) and caesium fluoride (33.5 g) under an atmosphere of nitrogen. The mixture was degassed with nitrogen, tetrakis (triphenylphosphine)palladium(0) (2.6 g) added and the reaction mixture stirred at 105° C. for 30 minutes. To the reaction mixture, water (700 mL) was added followed by extraction with ethyl acetate. The combined organic layers were washed with brine, dried and concentrated. The residue was purified by column chromatography (25% to 100% ethyl acetate in heptanes, then 1 to 5% methanol in ethyl acetate) to give the title compound having the following physical properties (24.3 g).

LC/MS $t_R$ 1.87 minutes; MS (ES$^+$) m/z 333 (M+H)$^a$.

EXAMPLE 8

(3S)-7-(2-amino-5-chlorophenyl)-5-oxo-1,2,3,5-tetrahydroindolizine-3-carboxylic acid

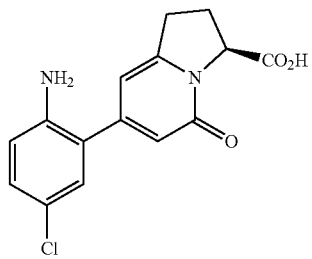 [SMILES: Nc1ccc(Cl)cc1-c1cc2n(c(=O)c1)[C@H](C(=O)O)CC2]

To a methanol (120 mL) solution of the compound prepared in Example 7 (12 g), 2 M sodium hydroxide (72 mL) was added and the mixture stirred at room temperature for 4 hours. The methanol was removed under reduced pressure and 2 M hydrochloric acid added until the solution was pH 4. The solution was extracted with ethyl acetate followed by a 1:1 mixture of 2-propanol and chloroform and the combined organic layers were dried and concentrated to give the title compound having the following physical properties (10.1 g).

LC/MS $t_R$ 1.58 minutes; MS (ES$^+$) m/z 305 (M+H)$^a$.

EXAMPLE 9

(3S)-7-[5-chloro-2-(1H-1,2,3,4-tetrazol-1-yl)phenyl]-5-oxo-1,2,3,5-tetrahydroindolizine-3-carboxylic acid

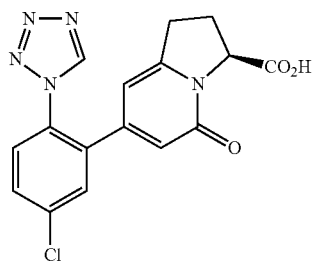 [SMILES: O=C(O)[C@@H]1CCc2cc(-c3cc(Cl)ccc3-n3cnnn3)cc(=O)n21]

To a glacial acetic acid (150 mL) solution of the compound prepared in Example 8 (9.3 g) was added trimethyl orthoformate (10 mL) followed after 30 minutes by sodium azide (5.93 g). The mixture was stirred at room temperature for 16 hours. Further trimethyl orthoformate (1.7 mL) and sodium azide (1.0 g) was added and the mixture was stirred at room temperature for a further 16 hours. To the cooled (0° C.) reaction mixture, a solution of sodium nitrite (5.32 g) in water (50 mL) was added dropwise over 30 minutes and the mixture stirred at 0° C. for a further hour followed by extraction into ethyl acetate. The combined organic layers were washed with water and brine, dried and concentrated. The residue was azeotroped with toluene to give the title compound having the following physical properties (10.9 g).

LC/MS $t_R$ 1.54 minutes; MS (ES$^+$) m/z 358 (M+H)$^a$.

EXAMPLE 10 ethyl(3S)-7-(2-{bis[(tert-butoxy)carbonyl]amino}-5-chlorophenyl)-5-oxo-1,2,3,5-tetrahydroindolizine-3-carboxylate To a tetrahydrofuran (220 mL) solution of the compound prepared in Example 7 (10 g) was sequentially added di-tert-butyl dicarbonate (14.7 g), triethylamine (8.2 mL) and 4-dimethylaminopyridine (0.73 g) and the mixture was stirred at 60° C. for 2 hours. To the reaction mixture, saturated aqueous potassium hydrogen sulfate solution (400 mL) was added followed by extraction with ethyl acetate. The combined organic layers were washed with brine, dried and concentrated to obtain the title compound having the following physical properties (16.8 g).
LC/MS $t_R$ 2.29 minutes; MS (ES$^+$) m/z 555 (M+Na), 533 (M+H), 433 (M–CO$_2$C(CH$_3$)$_3$+H)$^a$.

EXAMPLE 11

(3S)-7-(2-{[(tert-butoxy)carbonyl]amino}-5-chlorophenyl)-5-oxo-1,2,3,5-tetrahydroindolizine-3-carboxylic acid To a methanol (80 mL) solution of the crude compound prepared in Example 10 (17.6 g) was added 2 M sodium hydroxide (66 mL) and the mixture was stirred at room temperature for 48 hours. The reaction mixture was concentrated and the residue dissolved in water (200 mL) followed by extraction with dichloromethane. To the aqueous layer, 2 M hydrochloric acid (66 mL) was added followed by extraction into ethyl acetate. The combined ethyl acetate layers were washed with brine, dried and concentrated to obtain the title compound having the following physical properties (12.1 g).
LC/MS $t_R$ 1.85 minutes; MS (ES$^+$) m/z 405 (M+H)$^a$.

EXAMPLE 12

7-hydroxy-5-oxo-1,2,3,5-tetrahydroindolizine-3-carboxylic acid

To a stirred melt of 2,4,6-trichlorophenol (98.2 g) at 100° C. was added the compound prepared in Example 3 (29.7 g). The mixture was heated slowly to 180° C. whilst gas evolution occurred. The reaction mixture was maintained at 180° C. for 48 hours before cooling to room temperature and suspending the residue in dichloromethane (200 mL). The solid was collected by filtration and added to a second melt of 2,4,6-trichlorophenol (98.2 g) at 100° C. The reaction mixture was stirred at 180° C. for a further 24 hours before cooling to room temperature and suspending the residue in dichloromethane (200 mL). The solid was collected by filtration to afford the title compound having the following physical properties (24.3 g).
$^1$H NMR (500 MHz, DMSO-d$_6$) δ 10.53 (br. s, 1H), 5.82 (s, 1H), 5.43 (d, 1H), 4.78 (dd, 1H), 2.98 (dd, 2H), 2.46-2.37 (m, 1H), 2.16-2.05 (m, 1H).

EXAMPLE 13 ethyl-7-hydroxy-5-oxo-1,2,3,5-tetrahydroindolizine-3-carboxylate

The compound prepared in Example 12 (18.9 g) was treated as detailed in Example 5 to give the title compound having the following physical properties (21.5 g).
LC/MS $t_R$ 1.19 minutes; MS (ES$^+$) m/z 224 (M+H)$^a$

EXAMPLE 14 ethyl-5-oxo-7-{[(trifluoromethyl)sulfonyl]oxy}-1,2,3,5-tetrahydroindolizine-3-carboxylate The compound prepared in Example 13 (20 g) was treated as detailed in Example 6 to give the title compound having the following physical properties (31.8 g).
LC/MS $t_R$ 1.89 minutes; MS (ES$^+$) m/z 356 (M+H)$^a$.

EXAMPLE 15 ethyl-7-(2-amino-5-chlorophenyl)-5-oxo-1,2,3,5-tetrahydroindolizine-3-carboxylate The compound prepared in Example 14 (25.1 g) was treated as detailed in Example 7 to give the title compound having the following physical properties (23.8 g).
LC/MS $t_R$ 1.81 minutes; MS (ES$^+$) m/z 333 (M+H)$^a$.

EXAMPLE 16

7-(2-amino-5-chlorophenyl)-5-oxo-1,2,3,5-tetrahydroindolizine-3-carboxylic acid

The compound prepared in Example 15 (2.0 g) was treated as detailed in Example 8 to give the title compound having the following physical properties (1.83 g).
LC/MS $t_R$ 1.56 minutes; MS (ES$^+$) m/z 305 (M+H)$^a$.

EXAMPLE 17

7-[5-chloro-2-(1H-1,2,3,4-tetrazol-1-yl)phenyl]-5-oxo-1,2,3,5-tetrahydroindolizine-3-carboxylic acid The compound prepared in Example 16 (1.28 g) was treated as detailed in Example 9 to give the title compound having the following physical properties (1.17 g).
LC/MS $t_R$ 1.54 minutes; MS (ES$^+$) m/z 358 (M+H)$^a$.

EXAMPLE 18 ethyl 7-(2-{bis[(tert-butoxy)carbonyl]amino}-5-chlorophenyl)-5-oxo-1,2,3,5-tetrahydroindolizine-3-carboxylate The compound prepared in Example 15 (21.8 g) was treated as detailed in Example 10 to give the crude title compound having the following physical properties (32.9 g).
LC/MS $t_R$ 2.30 minutes; MS (ES$^+$) m/z 555 (M+Na), 533 (M+H), 433 (M–CO$_2$C(CH$_3$)$_3$+H)$^a$.

EXAMPLE 19

7-(2-{[(tert-butoxy)carbonyl]amino}-5-chlorophenyl)-5-oxo-1,2,3,5-tetrahydroindolizine-3-carboxylic acid The compound prepared in Example 18 (32.9 g) was treated as detailed in Example 11 to give the title compound having the following physical properties (20.5 g).
LC/MS $t_R$ 1.84 minutes; MS (ES$^+$) m/z 405 (M+Na)$^a$.

EXAMPLE 20 tert-butyl 2-[4-(benzyloxy)-2-oxo-1,2-dihydropyridin-1-yl]acetate

To a tetrahydrofuran (700 mL) solution of 4-benzyloxypyridone (25 g), potassium tert-butoxide (15 g), tetrabutylammonium bromide (2 g) and tert-butyl bromoacetate (18 mL) was sequentially added and the mixture was stirred at room temperature for 48 hours. To the reaction mixture, water (500 mL) was added followed by extraction with ethyl acetate. The combined organic layers were washed with brine, dried and concentrated to give the title compound having the following physical properties (35 g).

LC/MS $t_R$ 1.96 minutes; MS (ES$^+$) m/z 316 (M+H)$^a$.

EXAMPLE 21 tert-butyl 2-[4-hydroxy-2-oxo-1,2-dihydropyridin-1-yl]acetate

To an ethanol (300 mL) solution of the compound prepared in Example 20 (20 g) was added 5% palladium-carbon (4.05 g) and the mixture was stirred under an atmosphere of hydrogen for 4 hours. The reaction mixture was then filtered through Celite® and the filtrate was concentrated to give the title compound having the following physical properties (14.3 g).

LC/MS $t_R$ 1.42 minutes; MS (ES$^+$) m/z 226 (M+H)$^a$.

EXAMPLE 22 tert-butyl 2-{2-oxo-4-[(trifluromethane)sulfonyloxy]-1,2-dihydropyridin-1-yl}acetate The compound prepared in Example 21 (14.3 g) was treated as detailed in Example 6 to give the title compound having the following physical properties (16.2 g). LC/MS $t_R$ 1.97 minutes; MS (ES$^+$) m/z 301 (M-C(CH$_3$)$_3$+H)$^a$.

EXAMPLE 23 tert-butyl 2-[4-(2-amino-5-chlorophenyl)-2-oxo-1,2-dihydropyridin-1-yl]acetate

The compound prepared in Example 22 (6.4 g) was treated as detailed in Example 7 to give the title compound having the following physical properties (7.0 g).

LC/MS $t_R$ 1.95 minutes; MS (ES$^+$) m/z 335 (M+H)$^a$.

EXAMPLE 24 tert-butyl 2-{4-[5-chloro-2-(1H-1,2,3,4-tetrazol-1yl)phenyl]-2-oxo-1,2-dihydropyridin-1-yl}acetate To a glacial acetic acid (100 mL) solution of the compound prepared in Example 23 (7.0 g) was added trimethyl orthoformate (6.9 mL) followed after 30 minutes by sodium azide (4.1 g) and the mixture stirred at room temperature for 16 hours. To the reaction mixture, water (100 mL) was added followed by extraction into ethyl acetate. The combined organic layers were washed with water and saturated brine, dried and concentrated. The residue was purified by column chromatography (50 to 100% ethyl acetate in heptanes) to give the title compound having the following physical properties (6.5 g).

LC/MS $t_R$ 1.90 minutes; MS (ES$^+$) m/z 410 (M+Na)$^a$.

EXAMPLE 25

2-{4-[5-chloro-2-(1H-1,2,3,4-tetrazol-1yl)phenyl]-2-oxo-1,2-dihydropyridin-1-yl}acetic acid To a 1,4-dioxane solution (100 mL) of the compound prepared in Example 24 (6.5) was added 1 M hydrochloric acid (84 mL) and the mixture was heated at 90° C. for 3 hours. The reaction mixture was concentrated to approximately half the original volume and the resultant precipitate collected by filtration to give the title compound having the following physical properties (4.1 g).

LC/MS $t_R$ 1.48 minutes; MS (ES$^+$) m/z 332 (M+H)$^a$.

EXAMPLE 26 tert-butyl 2-[4-(benzyloxy)-2-oxo-1,2-dihydropyridin-1-yl]-3-phenylpropanoate

To a cooled (−78° C.) tetrahydrofuran (150 mL) solution of the compound prepared in Example 20 (15.3 g) was added benzyl bromide (7.76 mL) followed by a 1 M solution of lithium hexamethyldisilazide in tetrahydrofuran (52.2 mL) and the mixture was stirred at −78° C. for 90 minutes. To the cooled (−78° C.) reaction mixture, a saturated aqueous solution of ammonium chloride (150 mL) was added followed by water (150 mL) and the mixture was allowed to warm to room temperature, then extracted with ethyl acetate. The combined organic layers were washed with brine, dried and concentrated. The residue was purified by column chromatography (10 to 30% ethyl acetate in heptanes) to give the title compound having the following physical properties (11.8 g).

LC/MS $t_R$ 2.39 minutes; MS (ES$^+$) m/z 406 (M+H)$^a$.

EXAMPLE 27

2-{4-[5-chloro-2-(1H-1,2,3,4-tetrazol-1-yl)phenyl]-2-oxo-1,2-dihydropyridin-1-yl}-3-phenylpropanoic acid The same operation as in Example 21→Example 22→Example 23→Example 24→Example 25 was conducted from the compound prepared in Example 26 to give the title compound having the following physical properties.

LC/MS $t_R$ 1.84 minutes; MS (ES$^+$) m/z 422 (M+H)$^a$.

EXAMPLE 28 methyl(2S)-2-[4-(benzyloxy)-2-oxopyridin-1(2H)-yl]-3-phenylpropanoate

To a tetrahydrofuran (70 mL) solution of 4-benzyloxypyridone (10.8 g), potassium tert-butoxide (6.64 g) and tetrabutylammonium bromide (0.87 g) were added sequentially and the mixture was stirred at room temperature for 30 minutes. To the cooled (0° C.) reaction mixture, a tetrahydrofuran (70 mL) solution of methyl(2R)-3-phenyl-2-{[(trifluoromethyl)-sulfonyl]oxy}propanoate [Tetrahedron 51(38), 10513 (1995)] (16.8 g) was added over 30 minutes, then the mixture was stirred at 0° C. for 1 hour. To the reaction mixture, water (150 mL) was added followed by extraction with ethyl acetate. The combined organic layers were washed with brine, dried and concentrated. The residue was purified by column chromatography (50% to 75% ethyl acetate in heptanes) to give the title compound having the following physical properties (12.7 g).

TLC: Rf 0.60 (50% ethyl acetate in heptanes).

EXAMPLE 29 methyl(2S)-2-[4-(2,5-dichlorophenyl)-2-oxopyridin-1(2H)-yl]-3-phenylpropanoate

The same operation as in Example 21→Example 22→Example 23 was conducted from the compound prepared in Example 28 to give the title compound having the following physical properties. (Note: in the step corresponding to Example 23 in the operation, 2,5-dichlorophenylboronic acid was used).

LC/MS $t_R$ 2.33 minutes; MS (ES$^+$) m/z 402 (M+H)$^a$.

EXAMPLE 30

2-[4-(2,5-dichlorophenyl)-2-oxopyridin-1(2H)-yl]-3-phenylpropanoic acid

To a 1:1 methanol and tetrahydrofuran (18 mL) solution of the compound prepared in Example 29 (0.71 g) was added 1 M sodium hydroxide (4.4 mL) and the mixture was stirred at room temperature for 4 hours. The reaction mixture was concentrated and the residue dissolved in water (50 mL) followed by extraction with tert-butyl methyl ether. The aqueous layer was acidified to pH 1 with 1 M hydrochloric acid and extracted with ethyl acetate. The combined ethyl acetate layers were washed with brine, dried and concentrated to give the title compound having the following physical properties (0.64 g).

LC/MS $t_R$ 4.33 minutes; MS (ES$^+$) m/z 388 (M+H)$^b$.

EXAMPLE 31 tert-butyl 2-[4-(2-{bis[(tert-butoxy)carbonyl]amino}-5-chlorophenyl)-2-oxo-1,2-dihydropyridin-1-yl]acetate The compound prepared in Example 23 (4.53 g) was treated as detailed in Example 10 to give the title compound having the following physical properties (4.13 g).

LC/MS $t_R$ 2.47 minutes; MS (ES$^+$) m/z 557 (M+Na)$^a$.

EXAMPLE 32

2-[4-(2-{bis[(tert-butoxy)carbonyl]amino}-5-chlorophenyl)-2-oxo-1,2-dihydropyridin-1-yl]acetic acid The compound prepared in Example 31 (0.96 g) was treated as detailed in Example 30 to give the title compound having the following physical properties (0.76 g).

LC/MS $t_R$ 1.79 minutes; MS (ES$^+$) m/z 379 (M+H)$^a$.

EXAMPLE 33 ethyl 3-(5-chloro-2-nitrophenyl)-3-oxopropanoate

To a toluene (100 mL) solution of 5-chloro-2-nitrobenzoic acid (12 g) was added thionyl chloride (10 mL) and the mixture was stirred at reflux for 4 hours. The reaction mixture was concentrated and residual thionyl chloride removed by azeotroping with toluene. To a cooled (0 dichloromethane (550 mL) solution of the residue was sequentially added 2,2-dimethyl-1,3-dioxane-4,6-dione (7.5 g) and 4-dimethylaminopyridine (23 g) and the mixture was stirred at 0° C. for 2 hours. To the reaction mixture, 1 M hydrochloric acid (100 mL) was added and the dichloromethane layer isolated. The dichloromethane layer was washed, 1 M hydrochloric acid (100 mL×2), water (100 mL×2) and brine (100 mL), dried and concentrated. To a toluene (100 mL) solution of the residue was added ethanol (25 mL) and the mixture was stirred in a sealed system at 85° C. for 12 hours. The reaction mixture was concentrated and the residue purified by column chromatography (0 to 30% ethyl acetate in hexanes) to give the title compound having the following physical properties (2.5 g).

LC/MS $t_R$ 2.83 minutes; MS (ES$^-$) m/z 270 (M–H)$^c$.

EXAMPLE 34 ethyl 2-(5-chloro-2-nitrophenyl)-4-oxo-4,6,7,8-tetrahydropyrrolo[1,2-a]pyrimidine-6-carboxylate To an o-xylene (20 mL) solution of the compound prepared in Example 33 (2 g) was sequentially added 1,8-diazabicyclo[5.4.0]undec-7-ene (4.1 mL) and ethyl(2S)-5-aminopyrrolidine-2-carboxylate [J. Org. Chem. 52(26), 5717 (1987)] (1.2 g) and the mixture was stirred at 130° C. for 1 hour. The reaction mixture was concentrated and the residue purified by column chromatography (0 to 30% ethyl acetate in hexanes) to give the title compound having the following physical properties (0.35 g).

LC/MS $t_R$ 2.71 minutes; MS (ES$^+$) m/z 364 (M+H)$^c$.

EXAMPLE 35 ethyl 2-(2-amino-5-chlorophenyl)-4-oxo-4,6,7,8-tetrahydropyrrolo[1,2-a]pyrimidine-6-carboxylate

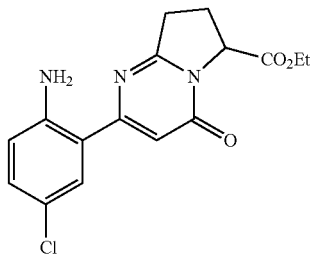 [SMILES: CCOC(=O)C1CCc2nc(-c3cc(Cl)ccc3N)cc(=O)n21]

To an ethyl acetate (15 mL) solution of the compound prepared in Example 34 (0.35 g) was sequentially added tin(II) chloride dihydrate (0.73 g) and 6 M HCl (1 mL) and the mixture was stirred at reflux for 2 hours. To the reaction mixture, a saturated aqueous solution of sodium hydrogen carbonate (25 mL) was added followed by extraction with ethyl acetate. The combined organic layers were washed with water and brine, dried and concentrated. The residue was triturated with pentane and the solid collected by filtration to give the title compound having the following physical properties (0.26 g).

LC/MS $t_R$ 2.53 minutes; MS (ES$^+$) m/z 334 (M+H)$^c$.

EXAMPLE 36 tert-butyl N-(4-chloro-2-{6-methyl-4-oxo-4H,6H,7H,8H-pyrrolo[1,2-a]pyrimidin-2-yl}phenyl)carbamate To a tert-butanol (10 mL) solution of the compound prepared in Example 35 (0.45 g) was added di-tert-butyl dicarbonate (1.17 g) and the mixture was stirred at 80° C. for 8 hours. The reaction mixture was concentrated and the residue obtained purified by column chromatography (0 to 30% ethyl acetate in hexanes) to give the title compound having the following physical properties (0.40 g).
LC/MS $t_R$ 3.35 minutes; MS (ES$^+$) m/z 434 (M+H)$^c$.

EXAMPLE 37

2-(2-{[(tert-butoxy)carbonyl]amino}-5-chlorophenyl)-4-oxo-4H,6H,7H,8H-pyrrolo[1,2-a]pyrimidine-6-carboxylic acid To a tetrahydrofuran (5 mL) solution of the compound prepared in Example 36 (0.19 g) was added 2 M sodium hydroxide (1 mL) and the mixture was stirred at room temperature for 12 hours. The reaction mixture was concentrated and the residue obtained dissolved in water (5 mL). To the aqueous solution, potassium hydrogen sulfate was added to pH of 5-6. The mixture was extracted with ethyl acetate. The combined organic layers were washed with brine, dried and concentrated to give the title compound having the following physical properties (0.13 g).
LC/MS $t_R$ 2.88 minutes; MS (ES$^+$) m/z 406 (M+H)$^c$.

EXAMPLE 38

2-{4-[(methoxycarbonyl)amino]phenyl}-2-oxoethyl 2-(2-{[(tert-butoxy)carbonyl]amino}-5-chlorophenyl)-4-oxo-4H,6H,7H,8H-pyrrolo[1,2-a]pyrimidine-6-carboxylate To an acetonitrile (15 mL) solution of the compound prepared in Example 37 (0.62 g) and methyl[4-(bromoacetyl)-phenyl]carbamate [J. Am. Chem. Soc. 119(10), 2453 (1997)] (0.46 g) was added potassium carbonate (0.53 g) and the mixture was stirred at 50° C. for 8 hours. The reaction mixture was filtered and the filtrate concentrated. The residue was purified by column chromatography (0-2% methanol in dichloromethane) to give the title compound having the following physical properties (0.60 g).
LC/MS $t_R$ 3.40 minutes; MS (ES$^+$) m/z 597 (M+H)$^c$

EXAMPLE 39 tert-butyl N-{4-chloro-2-[6-(5-{4-[(methoxycarbonyl)amino]phenyl}-1H-imidazol-2-yl)-4-oxo-4H,6H,7H,8H-pyrrolo[1,2-a]pyrimidin-2-yl]phenyl}carbamate To a toluene (10 mL) solution of the compound prepared in Example 38 (0.60 g) was added ammonium acetate (0.78 g) and the mixture was heated at reflux for 12 hours. The reaction mixture was concentrated and the residue suspended in water and extracted into ethyl acetate. The combined organic layers were washed with brine, dried and concentrated. The residue was purified by column chromatography (0-45% ethyl acetate in heptanes) to give the title compound having the following physical properties (0.41 g)
LC/MS $t_R$ 2.59 minutes; MS (ES$^+$) m/z 577 (M+H)$^c$.

EXAMPLE 40 methyl N-(4-{2-[2-(2-amino-5-chlorophenyl)-4-oxo-4H,6H,7H,8H-pyrrolo[1,2-a]pyrimidin-6-yl]-1H-imidazol-5-yl}phenyl)carbamate To a dichloromethane (5 mL) solution of the compound prepared in Example 39 (100 mg) was added trifluoroacetic acid (1 mL) and the mixture stirred at room temperature for 2 hours. To the reaction mixture, a saturated aqueous solution of sodium hydrogen carbonate (15 mL) was added followed by extraction into dichloromethane. The combined organic layers were washed with brine, dried and concentrated to give the title compound having the following physical properties (65 mg).
LC/MS $t_R$ 2.05 minutes; MS (ES$^+$) m/z 477 (M+H)$^c$.

EXAMPLE 41 methyl[4-(2-{2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)phenyl]carbamate

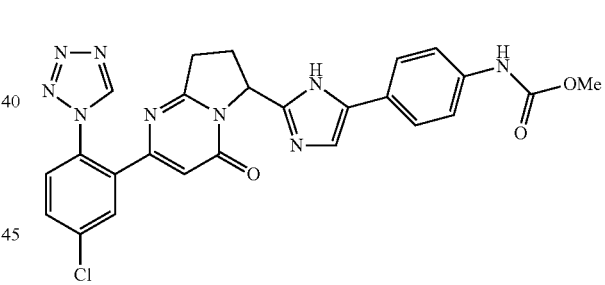

To a glacial acetic acid (1 mL) solution of the compound prepared in Example 40 (60 mg) was added triethyl orthoformate (60 µL) followed after 30 minutes by sodium azide (25 mg) and the mixture stirred in a sealed tube at 65° C. for 1 hour. The reaction mixture was then concentrated and the residue purified by column chromatography (0-5% methanol in dichloromethane) to give the title compound having the following physical properties (20 mg).
LC/MS $t_R$ 3.07 minutes; MS (ES$^+$) m/z 530 (M+H)$^b$
$^1$H NMR (500 MHz, methanol-d$_4$) δ 9.45 (s, 1 H), 7.92 (d, 1 H), 7.78 (dd, 1 H), 7.71 (d, 1 H), 7.57 (d, 2 H), 7.44 (d, 2 H), 7.25 (br. s, 1 H), 6.34 (s, 1 H), 5.72 (dd, 1 H), 3.73 (s, 3 H), 3.37-3.24 (obs. m, 1 H), 2.97-2.87 (m, 1 H), 2.73-2.62 (m, 1 H), 2.43-2.33 (m, 1 H).

EXAMPLE 42 methyl[4-(2-{7-[5-chloro-2-(1H-tetrazol-1-yl)phenyl]-5-oxo-1,2,3,5-tetrahydro-3-indolizinyl}-1H-imidazol-4-yl)phenyl]carbamate

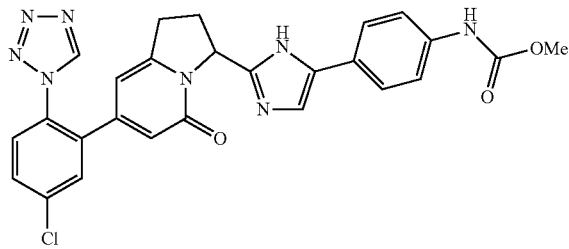 [SMILES: COC(=O)Nc1ccc(-c2cnc(C3CCc4cc(-c5cc(Cl)ccc5-n5cnnn5)cc(=O)n43)[nH]2)cc1]

The same operation as in Example 38→Example 39→Example 40→Example 41 was conducted from the compound prepared in Example 19 to give the title compound having the following physical properties.

LC/MS $t_R$ 3.04 minutes; MS (ES$^+$) m/z 529 (M+H)$^b$ $^1$H NMR (500 MHz, methanol-d$_4$) δ 9.37 (s, 1 H), 7.78-7.73 (m, 2 H), 7.70 (d, 1 H), 7.58 (d, 2 H), 7.46 (d, 2 H), 7.24 (br. s, 1 H), 6.15 (s, 1 H), 6.10 (s, 1 H), 5.83-5.72 (m, 1 H), 3.76 (s, 3 H), 3.52-3.41 (m, 1 H), 3.17-3.08 (m, 1 H), 2.71-2.59 (m, 1 H), 2.54-2.44 (m, 1 H).

EXAMPLE 43 tert-butyl N-{4-chloro-2-[3-(5-{4-[(methoxycarbonyl)amino]phenyl}-1H-imidazol-2-yl)-5-oxo-1,2,3,5-tetrahydroindolizin-7-yl]phenyl}carbamate The same operation as in Example 38→Example 39 was conducted from the compound prepared in Example 19 to give the title compound having the following physical properties.

LC/MS $t_R$ 1.75 minutes; MS (ES$^+$) m/z 576 (M+H)$^a$.

EXAMPLE 44 tert-butyl N-{4-chloro-2-[3-(4-chloro-5-{4-[(methoxycarbonyl)amino]phenyl}-1H-imidazol-2-yl)-5-oxo-1,2,3,5-tetrahydroindolizin-7-yl]phenyl}carbamate A tetrahydrofuran (20 mL) solution of the compound prepared in Example 43 (0.20 g) was cooled to 0° C. and N-chlorosuccinimide (70 mg) was added. The mixture was stirred at room temperature for 16 hours, cooled to 0° C. and further N-chlorosuccinimide (35 mg) added. The mixture was stirred for a further 24 hours, water (20 mL) was added followed by extraction into ethyl acetate. The combined organic layers were washed with brine, dried and concentrated. The residue was purified by column chromatography (40 to 50% ethyl acetate in heptanes) to give the title compound having the following physical properties (0.16 g).

TLC: Rf 0.27 (ethyl acetate).

EXAMPLE 45 methyl[4-(4-chloro-2-{7-[5-chloro-2-(1H-tetrazol-1-yl)phenyl]-5-oxo-1,2,3,5-tetrahydro-3-indolizinyl}-1H-imidazol-5-yl)phenyl]carbamate The same operation as in Example 40→Example 41 was conducted from the compound prepared in Example 44 to give the title compound having the following physical properties.

LC/MS $t_R$ 2.75 minutes; MS (ES$^+$) m/z 563 (M+H)$^c$ $^1$H NMR (300 MHz, CDCl$_3$) δ 11.23 (br. s, 1 H), 8.53 (s, 1 H), 7.68-7.28 (m, 5 H), 7.23 (d, 2 H), 6.77 (s, 1 H), 6.32 (s, 1 H), 5.80 (dd, 1 H), 5.71 (s, 1 H), 3.80 (s, 3 H), 3.52-3.35 (m, 1 H), 3.28-3.18 (m, 1 H), 3.06-2.92 (m, 1 H), 2.53-2.35 (m, 1 H).

EXAMPLE 46 methyl 3-{2-[7-(2-{[(tert-butoxy)carbonyl]amino}-5-chlorophenyl)-5-oxo-1,2,3,5-tetrahydroindolizin-3-yl]-1H-imidazol-5-yl}benzoate The same operation as in Example 38→Example 39 was conducted from the compound prepared in Example 19 to give the title compound having the following physical properties. (Note: in the step corresponding to Example 38 in the operation, methyl 3-(bromoacetyl)benzoate was used in place of methyl[4-(bromoacetyl)-phenyl]carbamate).

LC/MS $t_R$ 2.87 minutes; MS (ES") m/z 559 (M-H)$^c$.

EXAMPLE 47 methyl 3-{2-[7-(2-{[(tert-butoxy)carbonyl]amino}-5-chlorophenyl)-5-oxo-1,2,3,5-tetrahydroindolizin-3-yl]-4-chloro-1H-imidazol-5-yl}benzoate A dichloromethane (25 mL) solution of the compound prepared in Example 46 (0.25 g) was cooled to 0° C. and N-chlorosuccinimide (72 mg) was added. The mixture was stirred at room temperature for 2 hours. The reaction mixture was then filtered and the filtrate concentrated. The residue was purified by column chromatography (30 to 35% ethyl acetate in heptanes) to give the title compound having the following physical properties (0.10 g).

LC/MS $t_R$ 3.44 minutes; MS (ES$^+$) m/z 595 (M+H)$^c$.

EXAMPLE 48 methyl 3-{2-[7-(2-amino-5-chlorophenyl)-5-oxo-1,2,3,5-tetrahydroindolizin-3-yl]-4-chloro-1H-imidazol-5-yl}benzoate The compound prepared in Example 47 (0.25 g) was treated as detailed in Example 40 to give the title compound having the following physical properties (0.20 g).

LC/MS $t_R$ 3.05 minutes; MS (ES$^+$) m/z 495 (M+H)$^c$.

EXAMPLE 49

3-{2-[7-(2-amino-5-chlorophenyl)-5-oxo-1,2,3,5-tetrahydroindolizin-3-yl]-4-chloro-1H-imidazol-5-yl}benzoic acid To a solution of the compound prepared in Example 48 (0.14 g) in a 1:1 mixture of tetrahydrofuran and water (4 mL) was added lithium hydroxide monohydrate (24 mg) and the mixture stirred at room temperature for 16 hours. The reaction mixture was concentrated to approximately half its original volume and the aqueous residue acidified to pH 2-3 by portion-wise addition of potassium hydrogen sulfate followed by extraction into dichloromethane. The combined organic layers were washed with brine, dried and concentrated to give the title compound having the following physical properties (0.12 g).

LC/MS $t_R$ 2.71 minutes; MS (ES$^+$) m/z 481 (M+H)$^c$.

EXAMPLE 50

3-(4-chloro-2-{7-[5-chloro-2-(1H-tetrazol-1-yl)phenyl]-5-oxo-1,2,3,5-tetrahydro-3-indolizinyl}-1H-imidazol-5-yl)benzoic acid The compound prepared in Example 49 (75 mg) was treated as detailed in Example 41 to give the title compound having the following physical properties (60 mg).

LC/MS $t_R$ 2.65 minutes; MS (ES$^+$) m/z 534 (M+H), 506 (M-N$_2$+H)$^c$.

$^1$H NMR (300 MHz, DMSO-d$_6$) δ 13.20 (br. s, 1 H), 9.71 (s, 1 H), 8.33 (s, 1 H), 7.97 (d, 1 H), 7.88 (d, 1 H), 7.89-7.77 (m, 3 H), 7.60 (t, 1 H), 5.99 (s, 1 H), 5.95 (s, 1 H), 5.59 (dd, 1 H), 3.34-3.23 (obs. m, 1 H), 3.07-2.90 (m, 1 H), 2.56-2.40 (m, 1 H), 2.30-2.20 (m, 1 H).

EXAMPLE 51

2-oxo-2-phenylethyl(3S)-7-[5-chloro-2-(1H-tetrazol-1-yl)phenyl]-5-oxo-1,2,3,5-tetrahydro-3-indolizinecarboxylate To an N,N-dimethylformamide (3 mL) solution of the compound prepared in Example 9 (100 mg) was added potassium carbonate (151 mg) and the mixture stirred at room temperature for 30 minutes. To the reaction mixture, a solution of 2-bromo-1-phenylethan-1-one (72 mg) in N,N-dimethylformamide (3 mL) was added and the mixture stirred at room temperature for 2 hours. The reaction mixture was then diluted with ethyl acetate (30 mL), filtered and the filtrate concentrated to give the crude title compound having the following physical properties (193 mg).

LC/MS $t_R$ 1.97 minutes; MS (ES$^+$) m/z 476 (M+H)$^a$.

EXAMPLE 52

(3S)-7-[5-chloro-2-(1H-tetrazol-1-yl)phenyl]-3-(5-phenyl-1H-imidazol-2-yl)-2,3-dihydro-5(1H)-indolizinone To a toluene (5 mL) suspension of the compound prepared in Example 51 (193 mg) was sequentially added glacial acetic acid (0.50 mL) and ammonium acetate (231 mg) and the mixture stirred at reflux for 2 hours. The reaction mixture was concentrated and the residue suspended in a saturated aqueous solution of sodium hydrogen carbonate (10 mL) followed by extraction into ethyl acetate. The combined organic layers were washed with brine, dried and concentrated. The residue was purified by column chromatography (5% methanol in ethyl acetate) followed by high performance liquid chromatography (5 to 100% acetonitrile in 2 mM aqueous ammonium hydrogen carbonate) to give the title compound having the following physical properties (54.5 mg).

LC/MS $t_R$ 3.20 minutes; MS (ES$^+$) m/z 456 (M+H)$^b$

NMR analysis showed a 2:1 ratio of tautomers.

$^1$H NMR (500 MHz, CDCl$_3$) δ 11.19 and 10.77 (br. s, 1 H), 8.54 (s, 1 H), 7.78-7.73 (m, 1 H), 7.61 (dd, 1 H), 7.57-7.52 (m, 1 H), 7.52-7.43 (m, 2 H), 7.42-7.31 (m, 2 H), 7.27-7.15 (m, 2 H), 6.32 (s, 1 H), 5.92-5.79 (m, 1 H), 5.70 (s, 1 H), 3.54-3.25 (m, 2 H), 3.01 (dd, 1 H), 2.53-2.39 (m, 1 H).

EXAMPLE 53

4-[5-chloro-2-(1H-tetrazol-1-yl)phenyl]-1-[(5-phenyl-1H-imidazol-2-yl)methyl]-2(1H)-pyridinone The same operation as in Example 38→Example 39 was conducted from the compound prepared in Example 25 to give the title compound having the following physical properties.

LC/MS $t_R$ 3.16 minutes; MS (ES$^+$) m/z 430 (M+H)$^a$ $^1$H NMR (250 MHz, DMSO-d$_6$) δ 9.69 (s, 1 H), 7.80 (app. br. s, 3 H), 7.75-7.62 (m, 3 H), 7.50 (br. s, 1 H), 7.32 (t, 2 H), 7.17 (t, 1 H), 6.27 (d, 1 H), 5.86 (dd, 1 H), 5.09 (s, 2 H).

EXAMPLE 54 tert-butyl N-(4-chloro-2-{1-[(5-{4-[(methoxycarbonyl)amino]phenyl}-1H-imidazol-2-yl)methyl]-2-oxo-1,2-dihydropyridin-4-yl}phenyl)carbamate The same operation as in Example 38→Example 39 was conducted from the compound prepared in Example 32 to give the title compound having the following physical properties.

LC/MS $t_R$ 1.69 minutes; MS (ES$^+$) m/z 550 (M+H)$^a$.

EXAMPLE 55 methyl N-[4-(2-{[4-(2-amino-5-chlorophenyl)-2-oxo-1,2-dihydropyridin-1-yl]methyl}-1H-imidazol-5-yl)phenyl]carbamate To a 1,4-dioxane (0.75 mL) solution of the compound prepared in Example 54 (109 mg) was added 4 M hydrochloric acid in dioxane (0.75 mL) and the mixture was stirred at room temperature for 16 hours. To the reaction mixture, a saturated aqueous solution of sodium hydrogen carbonate was added followed by extraction into ethyl acetate. The combined organic layers were washed with brine, dried (Na$_2$SO$_4$) and concentrated to afford the title compound having the following physical properties (78 mg).

LC/MS $t_R$ 1.54 minutes; MS (ES$^+$) m/z 450 (M+H)$^a$

EXAMPLE 56 methyl{4-[2-({4-[5-chloro-2-(1H-tetrazol-1-yl)phenyl]-2-oxo-1(2H)-pyridinyl}methyl)-1H-imidazol-4-yl]phenyl}carbamate The compound prepared in Example 55 (78 mg) was treated as detailed in Example 41 to give the title compound having the following physical properties (40 mg).

LC/MS $t_R$ 3.04 minutes; MS (ES$^+$) m/z 503 (M+H)$^b$

¹H NMR (500 MHz, DMSO-d₆) δ 9.70 (s, 1 H), 9.68 (s, 1 H), 7.83-7.78 (m, 3 H), 7.70 (d, 1 H), 7.62 (d, 2 H), 7.57-7.35 (m, 4 H), 6.29 (s, 1 H), 5.89 (d, 1 H), 5.13 (s, 2 H), 3.66 (s, 3 H).

EXAMPLE 57 methyl{4-[5-chloro-2-({4-[5-chloro-2-(1H-tetrazol-1-yl)phenyl]-2-oxo-1(2H)-pyridinyl}methyl)-1H-imidazol-4-yl]phenyl}carbamate

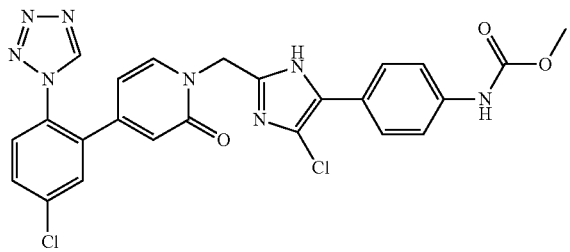 [SMILES: COC(=O)Nc1ccc(-c2[nH]c(Cn3ccc(-c4cc(Cl)ccc4-n4cnnn4)cc3=O)nc2Cl)cc1]

The compound prepared in Example 56 (72 mg) was treated as detailed in Example 47 to give the title compound having the following physical properties (16.2 mg).
LC/MS $t_R$ 3.96 minutes; MS (ES⁺) m/z 537 (M+H)$^b$
¹H NMR (500 MHz, DMSO-d₆) δ 9.76 (s, 1 H), 9.71 (s, 1 H), 7.84-7.79 (m, 3 H), 7.68 (d, 1 H), 7.63 (br. s, 1 H), 7.62 (d, 2 H), 7.52 (d, 2 H), 6.26 (d, 1 H), 5.88 (dd, 1 H), 5.04 (s, 2 H), 3.69 (s, 3 H).

EXAMPLE 58 tert-butyl 2-[4-(2-{bis[(tert-butoxy)carbonyl]amino}-5-chlorophenyl)-2-oxo-1,2-dihydropyridin-1-yl]butanoate To a cooled (−78° C.) tetrahydrofuran (25 mL) solution of the compound prepared in Example 31 (2.5 g) was added 1 M lithium hexamethyldisilazide in tetrahydrofuran (5.61 mL) and the mixture was stirred at −78° C. for 30 minutes. To the cooled (−78° C.) reaction mixture, iodoethane (0.45 mL) was added and the mixture was stirred at −78° C. for 2 hours. To the cooled (−78° C.) reaction mixture, a saturated aqueous solution of ammonium chloride was added followed by extraction into ethyl acetate. The combined organic layers were washed with brine, dried (MgSO₄) and concentrated. The residue was purified by column chromatography (10% to 20% ethyl acetate in heptanes) to give the title compound having the following physical properties (2.37 g).
LC/MS $t_R$ 2.62 minutes; MS (ES⁺) m/z 585 (M+Na)$^a$.

EXAMPLE 59 methyl{4-[2-(1-{4-[5-chloro-2-(1H-tetrazol-1-yl)phenyl]-2-oxo-1(2H)-pyridinyl}propyl)-1H-imidazol-4-yl]phenyl}carbamate The same operation as in Example 25→Example 9→Example 38→Example 39 was conducted from the compound prepared in Example 58 to give the title compound having the following physical properties.
LC/MS $t_R$ 3.54 minutes; MS (ES⁺) m/z 531 (M+H)$^b$ ¹H NMR (500 MHz, DMSO-d₆) δ 12.32 (s, 1 H), 9.68 (s, 1 H), 9.62 (s, 1 H), 7.84-7.77 (m, 3 H), 7.71 (d, 1 H), 7.68-7.39 (m, 5 H), 6.24 (s, 1 H), 5.96 (s, 1 H), 5.92 (dd, 1 H), 3.68 (s, 3 H), 2.28-1.85 (m, 2 H), 0.79 (t, 3 H).

EXAMPLE 60 methyl{4-[5-chloro-2-(1-{4-[5-chloro-2-(1H-tetrazol-1-yl)phenyl]-2-oxo-1(2H)-pyridinyl}propyl)-1H-imidazol-4-yl]phenyl}carbamate The compound prepared in Example 59 (200 mg) was treated as detailed in Example 47 to give the title compound having the following physical properties (42.5 mg).
LC/MS $t_R$ 4.22 minutes; MS (ES⁺) m/z 565 (M+H)$^b$
¹H NMR (500 MHz, DMSO-d₆) δ 12.69 (s, 1 H), 9.79 (s, 1 H), 9.69 (s, 1 H), 7.85-7.78 (m, 3 H), 7.67 (d, 1 H), 7.62 (d, 2 H), 7.54 (d, 2 H), 6.24 (d, 1 H), 6.04-5.86 (m, 2 H), 3.69 (s, 3 H), 2.23-1.83 (m, 2 H), 0.79 (t, 3 H).

EXAMPLE 61 methyl{4-[2-(1-{4-[5-chloro-2-(1H-tetrazol-1-yl)phenyl]-2-oxo-1(2H)-pyridinyl}ethyl)-1H-imidazol-5-yl]phenyl}carbamate The same operation as in Example 58→Example 25→Example 9→Example 38→Example 39 was conducted from the compound prepared in Example 31 to give the title compound having the following physical properties. (Note: in the step corresponding to Example 58 in the operation, iodomethane was used).
LC/MS $t_R$ 3.16 minutes; MS (ES⁺) m/z 517 (M+H)$^b$
¹H NMR (500 MHz, DMSO-d₆) δ 12.29 (br. s, 1 H), 9.68 (s, 1 H), 9.60 (br. s, 1 H), 7.87-7.76 (m, 3 H), 7.67 (d, 2 H), 7.60-7.38 (m, 4 H), 6.25 (s, 1 H), 6.12 (q, 1 H), 5.90 (d, 1 H), 3.66 (s, 3 H), 1.64 (d, 3 H).

EXAMPLE 62 ethyl 2-[4-(benzyloxy)-2-oxo-1,2-dihydropyridin-1-yl]prop-2-enoate

To a dichloromethane (25 mL) solution of ethyl prop-2-ynoate (0.61 mL), 4-(benzyloxy)pyridin-2(1H)-one (1.0 g) and triphenylphosphine (0.20 g) were sequentially added at 0° C. and the mixture was stirred at room temperature for 16 hours. The reaction mixture was concentrated under reduced pressure and the residue purified by column chromatography to give the title compound having the following physical properties (1.0 g).
LC/MS $t_R$ 1.87 minutes; MS (ES⁺) m/z 300 (M+H)$^a$.

EXAMPLE 63 ethyl 1-[4-(benzyloxy)-2-oxo-1,2-dihydropyridin-1-yl]cyclopropane-1-carboxylate

To a dimethylsulfoxide (8 mL) solution of trimethylsulphoxonium iodide (0.91 g), sodium hydride (0.16 g, 60% dispersion in mineral oil) was added and the mixture was stirred at room temperature for 15 minutes. A dimethylsulfoxide (6 mL) solution of the compound prepared in Example 62 (1.0 g) was added and the mixture was stirred at room temperature for 1.5 hours. To the reaction mixture, water (50 mL) was added followed by extraction with ethyl acetate. The combined organic layers were washed with brine, dried and concentrated. The residue was purified by flash chromatography to give the title compound having the following physical properties (0.39 g).

LC/MS $t_R$ 1.88 minutes; MS (ES$^+$) m/z 314 (M+H)$^a$.

EXAMPLE 64

1-[4-(benzyloxy)-2-oxo-1,2-dihydropyridin-1-yl] cyclopropane-1-carboxylic acid

The compound prepared in Example 63 (0.39 g) was treated as detailed in Example 8 to give the title compound having the following physical properties (0.27 g).

LC/MS $t_R$ 1.64 minutes; MS (ES$^-$) m/z 284 (M–H)$^a$.

EXAMPLE 65 methyl{4-[2-(1-{4-[5-chloro-2-(1H-tetrazol-1-yl) phenyl]-2-oxo-1(2H)-pyridinyl}cyclopropyl)-1H-imidazol-5-yl]phenyl}carbamate The same operation as in Example 51→Example 52→Example 21→Example 6→Example 7→Example 41 was conducted from the compound prepared in Example 64 to give the title compound having the following physical properties. (Note: in the step corresponding to Example 51 in the operation, methyl[4-(bromoacetyl)-phenyl]carbamate [J. Am. Chem. Soc. 119(10), 2453 (1997)] was used).

LC/MS $t_R$ 3.10 minutes; MS (ES$^+$) m/z 529 (M+H)$^a$ $^1$H NMR (500 MHz, DMSO-d$_6$) δ 11.72 (br. s, 1 H), 9.69 (s, 1 H), 9.59 (br. s, 1 H), 7.84-7.80 (m, 2 H), 7.79 (d, 1 H), 7.71 (d, 1 H), 7.58 (d, 2 H), 7.40 (br. d, 2 H), 7.35 (d, 1 H), 6.29 (d, 1 H), 5.79 (dd, 1 H), 3.64 (s, 3 H), 1.63 (br. s, 2 H), 1.38 (br. s, 2 H).

EXAMPLES 66(1) and 66(2)

methyl{4-[2-(1-{4-[5-chloro-2-(1H-tetrazol-1-yl) phenyl]-2-oxo-1(2H)-pyridinyl}-2-phenylethyl)-1H-imidazol-4-yl]phenyl}carbamate and methyl[4-(2-{1-[4-(2-carbamimidamido-5-chlorophenyl)-2-oxo-1 (2H)-pyridinyl]-2-phenylethyl}-1H-imidazol-4-yl) phenyl]carbamate acetate The same operation as in Example 38→Example 39 was conducted from the compound prepared in Example 27 to obtain the title products in a 5:2 ratio having the following physical properties.

EXAMPLE 66(1)

LC/MS $t_R$ 3.63 minutes; MS (ES$^+$) m/z 593 (M+H)$^b$ $^1$H NMR (500 MHz, DMSO-d$_6$) δ 12.25 (s, 1 H), 9.64 (s, 1 H), 9.61 (s, 1 H), 7.85-7.78 (m, 3 H), 7.76 (d, 1 H), 7.69 (d, 2 H), 7.48-7.38 (m, 3 H), 7.25 (t, 2 H), 7.17 (t, 1 H), 7.11 (d, 2 H), 6.33-6.21 (m, 1 H), 6.20 (s, 1 H), 5.90 (d, 1 H), 3.67 (s, 3 H), 3.56-3.46 (m, 2 H).

EXAMPLE 66(2)

LC/MS $t_R$ 3.50 minutes; MS (ES$^+$) m/z 582 (M+H)$^b$ $^1$H NMR (500 MHz, DMSO-d$_6$) δ 12.24 (s, 1 H), 9.61 (s, 1 H), 9.49 (s, 1 H), 7.99 (d, 1 H), 7.71 (d, 2 H), 7.52 (d, 2 H), 7.48-7.42 (m, 5 H), 7.37 (s, 1 H), 7.30-7.17 (m, 5 H), 7.19-7.13 (m, 1 H), 6.40 (s, 1 H), 6.35 (s, 1 H), 6.30 (d, 1 H), 3.66 (s, 3 H), 3.79-3.53 (m, 2 H), 1.88 (s, 3 H).

EXAMPLE 67 methyl{4-[5-chloro-2-(1-{4-[5-chloro-2-(1H-tetrazol-1-yl)phenyl]-2-oxo-1(2H)-pyridinyl}-2-phenyl-ethyl)-1H-imidazol-4-yl]phenyl}carbamate The compound prepared in Example 66(1) (38 mg) was treated as detailed in Example 47 to give the title compound having the following physical properties (16.8 mg).

LC/MS $t_R$ 4.51 minutes; MS (ES$^+$) m/z 627 (M+H)$^b$ $^1$H NMR (500 MHz, DMSO-d$_6$) δ 12.77 (s, 1 H), 9.78 (s, 1 H), 9.64 (s, 1 H), 7.84-7.78 (m, 3 H), 7.77 (d, 1 H), 7.60 (d, 2 H), 7.53 (d, 2 H), 7.27 (t, 2 H), 7.20 (t, 1 H), 7.09 (d, 2 H), 6.25 (t, 1 H), 6.18 (d, 1 H), 5.93 (dd, 1 H), 3.68 (s, 3 H), 3.56-3.35 (m, 2 H).

EXAMPLE 68

2-nitro-5-(1H-pyrazol-1-yl)aniline

To an N,N-dimethylformamide (4 mL) solution of 5-chloro-2-nitroaniline (200 mg) was added 1H-pyrazole (316 mg) and potassium hydroxide (98 mg) and the mixture stirred at 100° C. for 20 hours. To the reaction mixture at room temperature, water (10 mL) was added followed by extraction with ethyl acetate. The combined organic layers were washed with brine, dried and concentrated. The residue was purified by column chromatography (0 to 50% ethyl acetate in heptanes) to obtain the title compound having the following physical properties (52 mg).

LC/MS $t_R$ 1.71 minutes; MS (ES$^+$) m/z 205 (M+H)$^a$.

EXAMPLE 69

4-(1H-pyrazol-1-yl)benzene-1,2-diamine

To a 4:1 ethanol: water (2 mL) solution of the compound prepared in Example 68 (52 mg) was added a saturated aqueous solution of ammonium chloride solution (0.5 mL) and iron powder (113 mg) and the mixture stirred at room temperature for 1.5 hours. The reaction mixture was filtered through Celite® and the filtrate concentrated. The residue was triturated with dichloromethane and the precipitate formed was isolated by filtration giving the title compound with the following physical properties (49 mg).

LC/MS $t_R$ 0.70 minutes; MS (ES$^+$) m/z 175 (M+H)$^a$.

EXAMPLE 70

N-[2-amino-4-(1H-pyrazol-1-yl)phenyl]-2-{4-[5-chloro-2-(1H-1,2,3,4-tetrazol-1-yl)phenyl]-2-oxo-1, 2-dihydropyridin-1-yl}-3-phenylpropanamide To an N,N-dimethylformamide (1 mL) solution of the compound prepared in Example 69 (49 mg) and the compound prepared in Example 27 (55 mg) was added O-(7-azabenzotriazol-1-yl)-N,N,N',N'-tetramethyluronium hexafluorophosphate (59.67 mg) and diisopropylethylamine (40 μL) and the mixture stirred at room temperature for 16 hours. To the reaction mixture, water (5 mL) was added followed by extraction with ethyl acetate. The combined organic layers were washed with brine, dried and then concentrated. The residue was purified by column chromatography (0 to 50% ethyl acetate in heptanes) to obtain the title compound having the following physical properties (29 mg).

LC/MS $t_R$ 1.98 minutes; MS (ES$^+$) m/z 578 (M+H)$^a$.

EXAMPLE 71

4-[5-chloro-2-(1H-tetrazol-1-yl)phenyl]-1-{2-phenyl-1-[5-(1H-pyrazol-1-yl)-1H-benzimidazol-2-yl]ethyl}-2(1H)-pyridinone A glacial acetic acid (1 mL) solution of the compound prepared in Example 70 (29 mg) was stirred at 60° C. for 1 hour. To the cooled (0° C.) reaction mixture, 2 M sodium hydroxide (2 mL) and water (2 mL) was sequentially added followed by extraction into ethyl acetate. The combined organic layers were washed with brine, dried and concentrated. The residue was purified by high performance liquid chromatography (5 to 100% acetonitrile in 2 mM aqueous ammonium hydrogen carbonate) to give the title compound having the following physical properties (5 mg).

LC/MS $t_R$ 4.07 minutes; MS (ES$^+$) m/z 560 (M+H)$^b$ $^1$H NMR (500 MHz, DMSO-d$_6$) δ 9.20 (s, 1 H), 8.48 (d, 1 H), 7.96 (br. s, 1 H), 7.86 (d, 1 H), 7.84-7.68 (m, 5 H), 7.65 (br. s, 1 H), 7.31 (t, 2 H), 7.23 (t, 1 H), 7.12 (d, 2 H), 6.53 (t, 1 H), 6.47-6.36 (m, 1 H), 6.22 (d, 1 H), 5.90 (dd, 1 H), 3.68 (dd, 1 H), 3.46 (dd, 1 H).

EXAMPLE 72

2-[4-(2,5-dichlorophenyl)-2-oxo-1,2-dihydropyridin-1-yl]-N-[2-(4-nitrophenyl)-2-oxoethyl]-3-phenylpropanamide To a pyridine (8 mL) solution of the compound prepared in Example 30 (0.63 g) and 2-amino-1-(4-nitrophenyl)ethanone hydrochloride hydrate (0.46 g) was added N-[3-(dimethylamino)propyl]-N'-ethylcarbodiimide hydrochloride (0.40 g) and the mixture stirred at room temperature for 20 hours. To the reaction mixture, 0.5 M hydrochloric acid (50 mL) was added followed by extraction with ethyl acetate. The combined organic layers were washed with brine, dried and concentrated. The residue was purified by column chromatography (5% to 50% ethyl acetate in heptanes) to obtain the title compound having the following physical properties (0.64 g).

TLC: Rf 0.13 (50% ethyl acetate in heptanes).

EXAMPLE 73

4-(2,5-dichlorophenyl)-1-{1-[4-(4-nitrophenyl)-1H-imidazol-2-yl]-2-phenylethyl}-1,2-dihydropyridin-2-one To an o-xylene (50 mL) solution of the compound prepared in Example 72 (0.62 g) was added ammonium acetate (0.87 g) and the mixture stirred at 150° C. for 1 hour. The reaction mixture was concentrated and the residue suspended in a saturated aqueous solution of sodium hydrogen carbonate (100 mL) followed by extraction into ethyl acetate. The combined organic layers were washed with brine, dried and concentrated. The residue was purified by column chromatography (10% to 50% ethyl acetate in heptanes) to obtain the title compound having the following physical properties (0.61 g).

TLC: Rf 0.11 (50% ethyl acetate in heptanes).

EXAMPLE 74

1-{1-[5-(4-aminophenyl)-1H-imidazol-2-yl]-2-phenylethyl}dichlorophenyl)-2(1H)-pyridinone To a solution of the compound prepared in Example 73 (0.30 g) in an 8:1:1 mixture of ethanol, saturated aqueous ammonium chloride solution and water (7.5 mL) was added iron powder (0.25 g) and the mixture stirred at 50° C. for 3 hours. The reaction mixture was filtered through Celite® and the filtrate concentrated. The residue obtained was suspended in water and extracted into ethyl acetate. The combined organic layers were washed with brine, dried and concentrated. The residue was purified by column chromatography (50% ethyl acetate in heptanes) to obtain the title compound having the following physical properties (0.27 g).

LC/MS $t_R$ 3.63 minutes; MS (ES$^+$) m/z 501 (M+H)$^b$ $^1$H NMR (500 MHz, methanol-d$_4$) δ 7.89 (d, 1 H), 7.48 (d, 1 H), 7.40 (dd, 1 H), 7.37 (d, 1 H), 7.31 (app. br. s, 2 H), 7.25-7.19 (m, 4 H), 7.18 (s, 1 H), 7.18-7.13 (m, 1 H), 6.73 (d, 2 H), 6.48 (d, 0.1 H), 6.43 (d, 1 H), 6.42 (br. s, 1 H), 3.78-3.59 (m, 1 H), 3.59-3.37 (m, 1 H).

EXAMPLE 75 methyl[4-(2-{1-[4-(2,5-dichlorophenyl)-2-oxo-1(2H)-pyridinyl]-2-phenylethyl}-1H-imidazol-4-yl)phenyl]carbamate To a dichloromethane (2.5 mL) solution of the compound prepared in Example 74 (0.26 g) was sequentially added methyl chloroformate (50 µl) and N,N-diisopropylethylamine (135 µL) and the mixture stirred at room temperature for 1 hour. To the reaction mixture, water (20 mL) was added followed by extraction with dichloromethane. The combined organic layers were washed with brine, dried and concentrated. To a methanol (2.5 mL) solution of the residue, 1 M sodium hydroxide (0.51 mL) was added and the mixture was stirred at room temperature for 30 minutes. To the reaction mixture, water (30 mL) was added followed by extraction with ethyl acetate. The combined organic layers were washed with brine, dried and concentrated. The residue was purified by column chromatography (10% to 50% ethyl acetate in heptanes) to obtain the title compound having the following physical properties (0.22 g).

LC/MS $t_R$ 4.18 minutes; MS (ES$^+$) m/z 559 (M+H)$^b$ $^1$H NMR (500 MHz, methanol-d$_4$) δ 7.93 (br. s, 1 H), 7.70 (br. s, 1 H), 7.49 (d, 2 H), 7.46 (d, 2 H), 7.41 (dd, 1 H), 7.38 (d, 1 H), 7.33 (s, 1 H), 7.27-7.19 (m, 4 H), 7.19-7.12 (m, 1 H), 6.49 (d, 1 H), 6.45 (d, 1 H), 6.55-6.30 (m, 1 H), 3.74 (s, 3 H), 3.80-3.62 (m, 1 H), 3.53 (app. br. s, 1 H).

EXAMPLE 76 methyl[4-(5-chloro-2-{1-[4-(2,5-dichlorophenyl)-2-oxo-1(2H)-pyridinyl]-2-phenylethyl}-1H-imidazol-4-yl)phenyl]carbamate To an acetonitrile (3.5 mL) solution of the compound prepared in Example 75 (0.195 g) was added 1-chloropyrrolidine-2,5-dione (50 mg) and the mixture stirred at 60° C. for 5.5 hours. The reaction mixture was concentrated and the residue purified by column chromatography (5% to 50% ethyl acetate in heptanes) to obtain the title compound having the following physical properties (52 mg).

LC/MS $t_R$ 5.09 minutes; MS (ES$^+$) m/z 593 (M+H)[b]
$^1$H NMR (500 MHz, methanol-d$_4$) δ 7.94 (d, 1 H), 7.57 (d, 2 H), 7.50 (d, 2 H), 7.49 (d, 1 H), 7.41 (dd, 1 H), 7.38 (d, 1 H), 7.26-7.21 (m, 4 H), 7.21-7.15 (m, 1 H), 6.48 (s, 1 H), 6.47 (dd, 1 H), 6.42 (t, 1 H), 3.74 (s, 3 H), 3.65 (dd, 1 H), 3.45 (dd, 1 H).

EXAMPLE 77 methyl N-(4-propanoylphenyl)carbamate

To a dichloromethane (10 mL) solution of 1-(4-aminophenyl)propan-1-one (0.25 g), pyridine (0.27 mL) and methyl chloroformate (0.15 mL) were added sequentially and the mixture stirred overnight at room temperature. To the reaction mixture, water (25 mL) was added followed by extraction with dichloromethane. The combined organic layers were washed sequentially with 1 M hydrochloric acid, water and brine, dried and concentrated to obtain the title compound having the following physical properties (0.23 g).
LC/MS $t_R$ 1.68 minutes; MS (ES$^+$) m/z 208 (M+H)[a].

EXAMPLE 78 methyl N-[4-(2-bromopropanoyl)phenyl]carbamate

To a glacial acetic acid (10 mL) solution of the compound prepared in Example 77 (0.23 g) was added pyridinium tribromide (0.35 g) followed by a solution of 33 wt. % hydrogen bromide in acetic acid (0.15 mL) and the mixture stirred at room temperature overnight. The reaction mixture was concentrated and a saturated aqueous solution of sodium hydrogen carbonate (25 mL) was added to the residue followed by extraction with ethyl acetate. The combined organic layers were washed with water, brine, dried and concentrated to obtain the title compound having the following physical properties (0.29 g).
LC/MS $t_R$ 1.87 minutes; MS (ES$^+$) m/z 286 and 288 (M+H)[a].

EXAMPLE 79 formic acid—methyl[4-(2-{7-[5-chloro-2-(1H-tetrazol-1-yl)phenyl]-5-oxo-1,2,3,5-tetrahydro-3-indolizinyl}-4-methyl-1H-imidazol-5-yl)phenyl]carbamate (1:1)

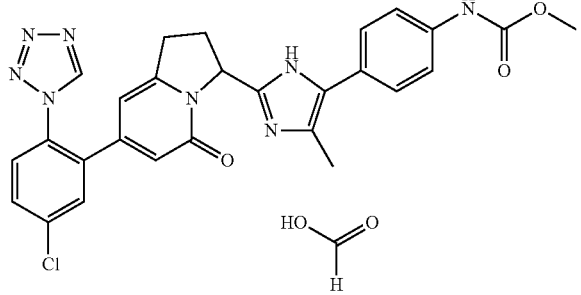

The same operation as in Example 38→Example 39→Example 40→Example 41 was conducted from the compound prepared in Example 19 to obtain the title compound having the following physical properties. (Note: in the step corresponding to Example 38 in the operation, the compound prepared in Example 78 was used in the step corresponding to Example 41 in the operation, high performance liquid chromatography [5 to 100% mobile phase B (0.1% formic acid in acetonitrile) in mobile phase A (0.1% aqueous formic acid)] was used to give the title product as the formic acid salt).
LC/MS $t_R$ 3.00 minutes; MS (ES$^+$) m/z 543 (M+H)[b]
$^1$H NMR (500 MHz, DMSO-d$_6$) δ 11.92 (s, 1 H), 9.69 (s, 1 H), 9.59 (s, 1 H), 8.51 (br. s, 1 H), 7.80-7.79 (m, 3 H), 7.52-7.39 (m, 4 H), 5.97 (s, 1 H), 5.94 (s, 1 H), 5.57-5.55 (m, 1 H), 3.66 (s, 3 H), 3.36-3.34 (obs. m, 1 H), 3.00-2.96 (m, 1 H), 2.51-2.49 (obs. m, 1 H), 2.33 (s, 3 H), 2.19 (app. br. s, 1 H).

EXAMPLE 80 methyl N-[4-(2-bromobutanoyl)phenyl]carbamate

The same operation as in Example 77→Example 78 was conducted from 1-(4-aminophenyl)butan-1-one to obtain the title compound having the following physical properties.
LC/MS $t_R$ 2.00 minutes; MS (ES$^+$) m/z 300 and 302 (M+H)[a].

EXAMPLES 81(1) AND 81(2)

formic acid—methyl[4-(2-{7-[5-chloro-2-(1H-tetrazol-1-yl)phenyl]-5-oxo-1,2,3,5-tetrahydro-3-indolizinyl}-4-ethyl-1H-imidazol-5-yl)phenyl]carbamate (1:1) and formic acid—methyl(4-{2-[7-(5-chloro-2-formamidophenyl)-5-oxo-1,2,3,5-tetrahydro-3-indolizinyl]-4-ethyl-1H-imidazol-5-yl}phenyl)carbamate (1:1)

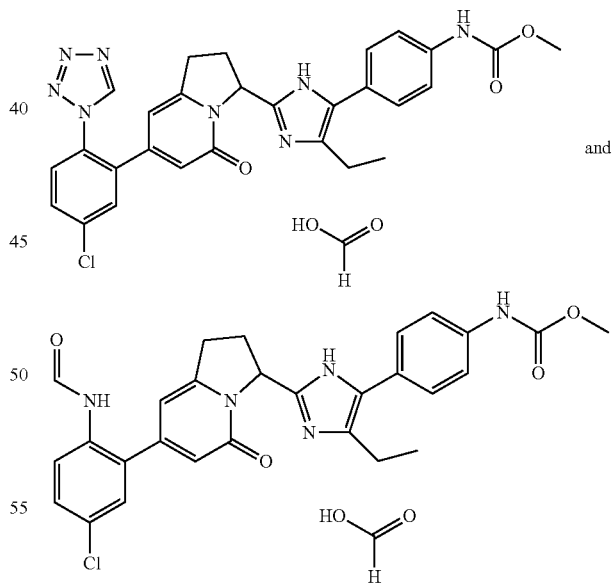

The same operation as in Example 38→Example 39→Example 40→Example 41 was conducted from the compound prepared in Example 19 to obtain the title compounds having the following physical properties. (Note: in the step corresponding to Example 38 in the operation, the compound prepared in Example 80 was used. In the step corresponding to Example 41 in the operation, high performance liquid chromatography [5 to 100% mobile phase B (0.1% formic acid in acetonitrile) in mobile phase A (0.1% aqueous formic acid)] was used to give the title products in a 4:1 ratio as their formic acid salts).

EXAMPLE 81(1)

LC/MS $t_R$ 3.10 minutes; MS (ES$^+$) m/z 557 (M+H)$^b$ $^1$H NMR (500 MHz, DMSO-d$_6$) δ 11.93 (s, 1 H), 9.69 (s, 1 H), 9.60 (s, 1 H), 8.51 (br. s, 1 H), 7.80-7.78 (m, 3 H), 7.50-7.37 (m, 4 H), 5.97 (s, 1 H), 5.94 (s, 1 H), 5.57 (d, 1 H), 3.66 (s, 3 H), 3.36-3.34 (obs. m, 2 H), 3.00-2.95 (m, 1 H), 2.73-2.71 (m, 1 H), 2.51-2.49 (obs. m, 1 H), 2.31-2.27 (m, 1 H), 1.19 (t, 3 H).

EXAMPLE 81(2)

LC/MS $t_R$ 3.04 minutes; MS (ES$^+$) m/z 532 (M+H)$^b$ $^1$H NMR (500 MHz, DMSO-d$_6$) δ 11.93 (s, 1 H), 9.73 (s, 1 H), 9.63 (s, 1 H), 8.21 (d, 1 H), 8.33 (s, 1 H), 7.99 (d, 1 H), 7.49-7.41 (m, 6 H), 6.27 (s, 1 H), 6.19 (s, 1 H), 5.65 (d, 1 H), 3.67 (s, 3 H), 3.36-3.34 (obs. m, 3 H), 3.17-3.12 (m, 1 H), 2.72-2.70 (m, 2 H), 1.18 (t, 3 H).

EXAMPLE 82 formic acid—methyl{4-[2-({4-[5-chloro-2-(1H-tetrazol-1-yl)phenyl]-2-oxo-1(2H)-pyridinyl}methyl)-4-methyl-1H-imidazol-5-yl]phenyl}carbamate (1:1)

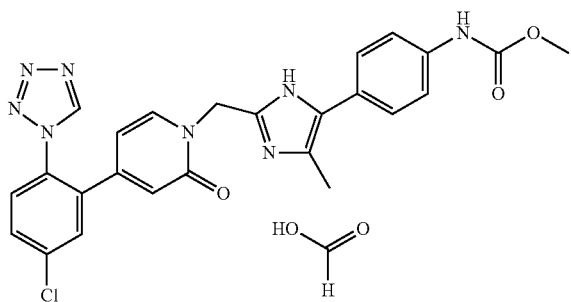

The same operation as in Example 38→Example 39 was conducted from the compound prepared in Example 25 to obtain the title compound having the following physical properties. (Note: in the step corresponding to Example 38 in the operation, the compound prepared in Example 78 was used. In the step corresponding to Example 39 in the operation, high performance liquid chromatography [5 to 100% mobile phase B (0.1% formic acid in acetonitrile) in mobile phase A (0.1% aqueous formic acid)] was used to give the title product as the formic acid salt).

LC/MS $t_R$ 3.03 minutes; MS (ES$^+$) m/z 517 (M+H)$^b$ $^1$H NMR (500 MHz, DMSO-d$_6$) δ 11.98 (br. s), 9.70 (s, 1 H), 9.63 (br. s, 1 H), 8.25 (s, 1 H), 7.86-7.73 (m, 3 H), 7.68 (d, 1 H), 7.46 (app. br. s, 4 H), 6.27 (d, 1 H), 5.88 (dd, 1 H), 5.03 (s, 2 H), 3.67 (s, 3 H), 2.30 (s, 3 H).

EXAMPLE 83 formic acid—methyl{4-[2-({4-[5-chloro-2-(1H-tetrazol-1-yl)phenyl]-2-oxo-1(2H)-pyridinyl}methyl)-4-ethyl-1H-imidazol-5-yl]phenyl}carbamate (1:1)

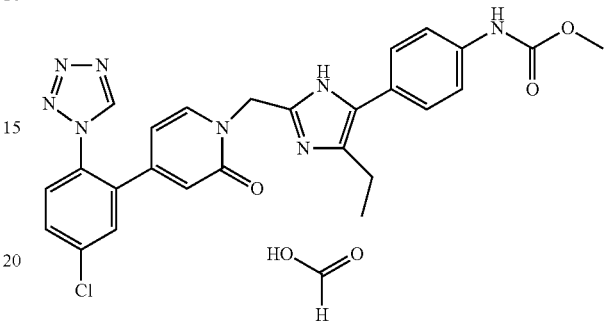

The same operation as in Example 38→Example 52 was conducted from the compound prepared in Example 25 to obtain the title compound having the following physical properties. (Note: in the step corresponding to Example 38 in the operation, the compound prepared in Example 80 was used. In the step corresponding to Example 39 in the operation, high performance liquid chromatography [5 to 100% mobile phase B (0.1% formic acid in acetonitrile) in mobile phase A (0.1% aqueous formic acid)] was used to give the title product as the formic acid salt).

LC/MS $t_R$ 3.11 minutes; MS (ES$^+$) m/z 531 (M+H)$^b$ $^1$H NMR (500 MHz, DMSO-d$_6$) δ 11.99 (br. s, 1 H), 9.70 (s, 1 H), 9.63 (br. s, 1 H), 8.26 (br. s, 1 H), 7.88-7.76 (m, 3 H), 7.68 (d, 1 H), 7.45 (app. br. d, 4 H), 6.28 (d, 1 H), 5.87 (dd, 1 H), 5.04 (s, 2 H), 3.67 (s, 3 H), 2.69 (app. br. s, 2 H), 1.17 (t, 3 H).

EXAMPLE 84

2-oxo-2-(2-oxo-2,3-dihydro-1H-indol-5-yl)ethyl 7-(2-{[(tert-butoxy)carbonyl]amino}-5-chlorophenyl)-5-oxo-1,2,3,5-tetrahydroindolizine-3-carboxylate To an acetonitrile (4 mL) solution of the compound prepared in Example 19 (0.35 g) was added 5-(bromoacetyl)-1,3-dihydro-2H-indol-2-one (0.25 g) and N,N-diisopropylethylamine (0.22 mL) and the mixture was stirred at 50° C. for 16 hours. To the reaction mixture, water was added followed by extraction with ethyl acetate. The combined organic layers were washed with brine, dried and concentrated to give the crude title compound having the following physical properties (0.67 g).

LC/MS $t_R$ 1.99 minutes; MS (ES$^+$) m/z 578 (M+H)$^a$.

EXAMPLE 85

5-(2-{7-[5-chloro-2-(1H-tetrazol-1-yl)phenyl]-5-oxo-1,2,3,5-tetrahydro-3-indolizinyl}-1H-imidazol-4-yl)-1,3-dihydro-2H-indol-2-one

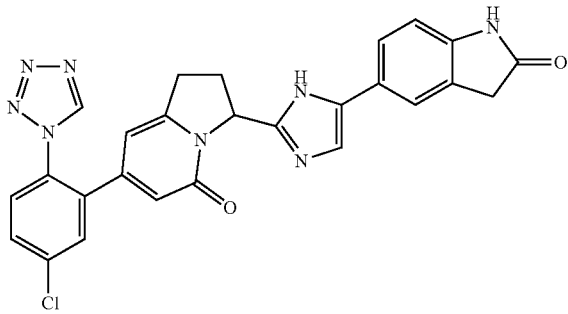 [SMILES: O=C1Cc2cc(-c3cnc(C4CCc5cc(-c6cc(Cl)ccc6-n6cnnn6)cc(=O)n54)[nH]3)ccc2N1]

The same operation as in Example 39→Example 55→Example 41 was conducted from the compound prepared in Example 84 to give the title compound having the following physical properties.

LC/MS $t_R$ 2.80 minutes; MS (ES$^+$) m/z 511 (M+H)$^b$ $^1$H NMR (500 MHz, DMSO-d$_6$) δ 12.05 (s, 1 H), 10.36 (s, 1 H), 9.70 (s, 1 H), 8.48 (br. s, 1 H), 7.95-7.63 (m, 3 H), 7.55 (s, 1 H), 7.50 (br. s, 1 H), 7.35 (s, 1 H), 6.78 (d, 1 H), 5.97 (s, 1 H), 5.95 (s, 1 H), 5.62 (dd, 1 H), 3.50 (s, 2 H), 3.45-3.30 (obs. m, 1 H), 2.99 (ddd, 1 H), 2.54-2.43 (obs. m, 1 H), 2.33 (app. br. s, 1 H).

EXAMPLE 86

6-(2-{7-[5-chloro-2-(1H-tetrazol-1-yl)phenyl]-5-oxo-1,2,3,5-tetrahydro-3-indolizinyl}-1H-imidazol-4-yl)-3,4-dihydro-2(1H)-quinolinone The same operation as in Example 84→Example 52→Example 40→Example 41 was conducted from the compound prepared in Example 19 to give the title compound having the following physical properties. (Note: in the step corresponding to Example 84 in the operation, 6-(bromoacetyl)-3,4-dihydroquinolin-2(1H)-one was used).

LC/MS $t_R$ 2.88 minutes; MS (ES$^+$) m/z 525 (M+H)$^b$ $^1$H NMR (500 MHz, DMSO-d$_6$) δ 12.09 (br. s, 1 H), 10.08 (Ix. s, 1 H), 9.69 (s, 1 H), 7.84-7.75 (m, 3 H), 7.51 (s, 1 H), 7.46 (d, 1 H), 7.38 (br. s, 1 H), 6.83 (d, 1 H), 5.98 (s, 1 H), 5.96 (s, 1 H), 5.63 (d, 1 H), 3.42-3.34 (obs. m, 1 H), 3.01 (ddd, 1 H), 2.91 (t, 2 H), 2.56-2.49 (obs. m, 1 H), 2.46 (t, 2 H), 2.35-2.26 (m, 1 H).

EXAMPLE 87

6-(4-chloro-2-{7-[5-chloro-2-(1H-tetrazol-1-yl)phenyl]-5-oxo-1,2,3,5-tetrahydro-3-indolizinyl}-1H-imidazol-5-yl)-3,4-dihydro-2(1H)-quinolinone The compound prepared in Example 86 (0.10 g) was treated as detailed in Example 44 to give the title compound having the following physical properties (0.11 g).

LC/MS $t_R$ 3.84 minutes; MS (ES$^+$) m/z 559 (M+H)$^b$ $^1$H NMR (500 MHz, DMSO-d$_6$) δ 12.78 (br. s, 1 H), 10.20 (s, 1 H), 9.71 (s, 1 H), 7.90-7.76 (m, 3 H), 7.50 (s, 1 H), 7.48 (d, 1 H), 6.93 (d, 1 H), 5.99 (s, 1 H), 5.94 (s, 1 H), 5.56 (dd, 1 H), 3.35-3.23 (obs. m, 1 H), 2.99 (dd, 1 H), 2.93 (t, 2 H), 2.62-2.42 (obs. m, 3 H), 2.23-2.14 (m, 1 H).

EXAMPLE 88

6-[2-({4-[5-chloro-2-(1H-tetrazol-1-yl)phenyl]-2-oxo-1(2H)-pyridinyl}methyl)-1H-imidazol-5-yl]-3,4-dihydro-2(1H)-quinolinone The same operation as in example Example 51→Example 52 was conducted from the compound prepared in Example 25 to give the title compound having the following physical properties. (Note: in the step corresponding to Example 51 in the operation, 6-(bromoacetyl)-3,4-dihydroquinolin-2(1H)-one was used).

LC/MS $t_R$ 2.89 minutes; MS (ES$^+$) m/z 499 (M+H)$^b$ $^1$H NMR (500 MHz, methanol-d$_4$) δ 9.38 (s, 1 H), 7.78-7.74 (m, 2 H), 7.70 (d, 1 H), 7.68 (d, 1 H), 7.54 (br. s, 1 H), 7.50 (br. d, 1 H), 7.33 (br. s, 1 H), 6.90 (d, 1 H), 6.42 (d, 1 H), 6.05 (dd, 1 H), 5.20 (s, 2 H), 3.01 (t, 2 H), 2.61 (t, 2 H).

EXAMPLE 89

6-[4-chloro-2-({4-[5-chloro-2-(1H-tetrazol-1-yl)phenyl]-2-oxo-1(2H)-pyridinyl}methyl)-1H-imidazol-5-yl]-3,4-dihydro-2(1H)-quinolinone The compound prepared in Example 88 (100 mg) was treated as detailed in Example 44 to give the title compound having the following physical properties (38 mg).

LC/MS $t_R$ 3.69 minutes; MS (ES$^+$) m/z 533 (M+H)$^b$ $^1$H NMR (500 MHz, DMSO-d$_6$) δ 12.86 (s, 1 H), 10.22 (s, 1 H), 9.72 (s, 1 H), 7.87-7.77 (m, 3 H), 7.69 (d, 1 H), 7.49 (s 1 H), 7.47 (d, 1 H), 6.92 (d, 1 H), 6.28 (s, 1 H), 5.88 (dd, 1 H), 5.05 (s, 2 H), 2.96-2.87 (m, 2 H), 2.57-2.47 (obs. m, 2 H).

EXAMPLE 90 methyl N-(4-acetyl-2-fluorophenyl)carbamate

To an N,N-dimethylformamide (9 mL) solution of methyl N-(2-fluoro-4-iodophenyl)carbamate [J. Med. Chem. 48(18), 5823 (2005)] (1.20 g) was added propane-1,3-diylbis(diphenylphosphane) (0.10 g), palladium(II) diacetate (28 mg) and 3 M aqueous potassium carbonate solution (2.28 mL). The mixture was partitioned equally across four microwavable vessels and all were degassed with nitrogen for 5 minutes. To each reaction mixture, n-butyl vinyl ether (0.66 mL) was added and the reaction mixtures were irradiated under microwave conditions (100 W) at 100° C. for 30 minutes. The reaction mixtures were combined and concentrated. The residue was suspended in tetrahydrofuran (12 mL) and 1 M hydrochloric acid (12 mL), stirred for 2 hours at room temperature and extracted with ethyl acetate. The combined organic layers were washed with brine, dried and concentrated. The residue was purified by column chromatography (2% to 100% ethyl acetate in heptanes) to afford the title compound having the following physical properties (0.49 g).

LC/MS $t_R$ 1.57 minutes; MS (ES$^+$) m/z 212 (M+H)$^a$.

EXAMPLE 91 methyl N-[4-(2-bromoacetyl)-2-fluorophenyl]carbamate

To a cooled (5° C.) glacial acetic acid (16 mL) solution of the compound prepared in Example 90 (0.49 g) was added a solution of 33 wt. % hydrogen bromide in acetic acid (0.32 mL) followed by pyridinium tribromide (0.73 g) and the mixture stirred at room temperature for 5 hours. To the reaction mixture, a saturated solution of aqueous sodium bicarbonate (100 mL) was added followed by extraction with ethyl acetate. The combined organic layers were washed with brine, dried and then concentrated. The residue was triturated with a 1:1 mixture of ethyl acetate and heptane and the precipitate isolated by filtration to give the title compound having the following physical properties (0.44 g).

LC/MS $t_R$ 1.79 minutes; MS (ES$^+$) m/z 290 and 292 (M+H)$^a$.

EXAMPLE 92 methyl[4-(2-{7-[5-chloro-2-(1H-tetrazol-1-yl)phenyl]-5-oxo-1,2,3,5-tetrahydro-3-indolizinyl}-1H-imidazol-5-yl)-2-fluorophenyl]carbamate The same operation as in Example 84→Example 39→Example 40→Example 41 was conducted from the compound prepared in Example 19 to give the title compound having the following physical properties. (Note: in the step corresponding to Example 84 in the operation, the compound prepared in Example 91 was used).

LC/MS $t_R$ 3.31 minutes; MS (ES$^+$) m/z 547 (M+H)$^b$
$^1$H NMR (500 MHz, methanol-d$_4$) δ 9.37 (s, 1 H), 7.81 (br. s, 1 H), 7.77-7.73 (m, 2 H), 7.72-7.68 (m, 1 H), 7.53-7.43 (m, 2 H), 7.42-7.34 (m, 1 H), 6.15 (s, 1 H), 6.10 (s, 1 H), 5.79 (dd, 1 H), 3.78 (s, 3 H), 3.52-3.41 (m, 1 H), 3.12 (ddd, 1 H), 2.65 (qd, 1 H), 2.52 (app. br. s, 1 H).

EXAMPLE 93 methyl[4-(4-chloro-2-{7-[5-chloro-2-(1H-tetrazol-1-yl)phenyl]-5-oxo-1,2,3,5-tetrahydro-3-indolizinyl}-1H-imidazol-5-yl)-2-fluorophenyl]carbamate The compound prepared in Example 92 (160 mg) was treated as detailed in Example 47 to give the title compound having the following physical properties (40 mg).

LC/MS $t_R$ 4.19 minutes; MS (ES$^+$) m/z 581 (M+H)$^b$
$^1$H NMR (500 MHz, DMSO-d$_6$) δ 13.03 (br. s, 1 H), 9.71 (s, 1 H), 9.48 (br. s, 1 H), 7.86-7.80 (m, 2 H), 7.80-7.72 (m, 2 H), 7.59-7.48 (m, 2 H), 5.99 (s, 1 H), 5.94 (s, 1 H), 5.57 (dd, 1 H), 3.69 (s, 3 H), 3.31-3.24 (obs. m, 1 H), 3.00 (ddd, 1 H), 2.58-2.54 (obs. m, 1 H), 2.24-2.17 (m, 1 H).

EXAMPLE 94 methyl N-[4-(2-bromoacetyl)-3-fluorophenyl]carbamate

The same operation as in Example 77→Example 90→Example 91 was conducted from 4-bromo-3-fluoroaniline to give the title compound having the following physical properties.

$^1$H NMR (500 MHz, CDCl$_3$) δ 7.86 (t, 1 H), 7.50 (dd, 1 H), 6.97 (dd, 1 H), 6.80 (br. s, 1 H), 4.42 (d, 2 H), 3.75 (s, 3 H).

EXAMPLE 95 methyl[4-(2-{7-[5-chloro-2-(1H-tetrazol-1-yl)phenyl]-5-oxo-1,2,3,5-tetrahydro-3-indolizinyl}-1H-imidazol-5-yl)-3-fluorophenyl]carbamate The same operation as in Example 84→Example 52→Example 40→Example 41 was conducted from the compared prepared in Example 19 to give the title compound having the following physical properties. (Note: in the step corresponding to Example 84 in the operation, the compound prepared in Example 94 was used).

LC/MS $t_R$ 3.36 minutes; MS (ES$^+$) m/z 547 (M+H)$^b$
$^1$H NMR (500 MHz, methanol-d$_4$) δ 9.25 (s, 1 H), 7.72 (app. br. s, 1 H), 7.65-7.61 (m, 2 H), 7.60-7.56 (m, 1 H), 7.34 (d, 1 H), 7.19 (br. s, 1 H), 7.06 (app. br. s, 1 H), 6.04 (s, 1 H), 5.98 (s, 1 H), 5.70 (dd, 1 H), 3.65 (s, 3 H), 3.39-3.30 (m, 1 H), 3.01 (ddd, 1 H), 2.53 (qd, 1 H), 2.41 (br. s, 1 H).

EXAMPLE 96 methyl[4-(4-chloro-2-{7-[5-chloro-2-(1H-tetrazol-1-yl)phenyl]-5-oxo-1,2,3,5-tetrahydro-3-indolizinyl}-1H-imidazol-5-yl)-3-fluorophenyl]carbamate The compound prepared in Example 95 (125 mg) was treated as detailed in Example 44 to give the title compound having the following physical properties (25 mg).

LC/MS $t_R$ 4.19 minutes; MS (ES$^+$) m/z 581 (M+H)$^b$
$^1$H NMR (500 MHz, DMSO-d$_6$) δ 12.81 (br. s, 1 H), 10.09 (br. s, 1 H), 9.72 (s, 1 H), 7.88-7.78 (m, 3 H), 7.60-7.41 (m, 2 H), 7.31 (d, 1 H), 5.99 (s, 1 H), 5.95 (s, 1 H), 5.59 (dd, 1 H), 3.71 (s, 3 H), 3.30-3.23 (m, 1 H), 2.98 (ddd, 1 H), 2.55-2.44 (obs. m, 1 H), 2.24-2.16 (m, 1 H).

EXAMPLE 97 methyl N-[4-(2-bromoacetyl)-3-methylphenyl]carbamate

The same operation as in Example 77→Example 90→Example 91 was conducted from 4-bromo-3-methylaniline to give the title compound having the following physical properties.

LC/MS $t_R$ 1.83 minutes; MS (ES$^+$) m/z 286 and 288 (M+H)$^a$.

EXAMPLE 98 methyl[4-(2-{7-[5-chloro-2-(1H-tetrazol-1-yl)phenyl]-5-oxo-1,2,3,5-tetrahydro-3-indolizinyl}-1H-imidazol-5-yl)-3-methylphenyl]carbamate The same operation as in Example 84→Example 52→Example 40→Example 41 was conducted from the compared prepared in Example 19 to give the title compound having the following physical properties. (Note: in the step corresponding to Example 84 in the operation, the compound prepared in Example 97 was used).

LC/MS $t_R$ 3.07 minutes; MS (ES$^+$) m/z 543 (M+H)$^b$
$^1$H NMR (500 MHz, methanol-d$_4$) δ 9.25 (s, 1 H), 7.67-7.61 (m, 2 H), 7.58 (d, 1 H), 7.22 (m, 3 H), 6.91 (br. s, 1 H), 6.02 (s, 1 H), 5.99 (s, 1 H), 5.70 (dd, 1 H), 3.64 (s, 3 H), 3.39-3.29 (m, 1 H), 3.00 (ddd, 1 H), 2.58-2.48 (m, 1 H), 2.38 (app. br. s, 1 H), 2.25 (s, 3 H).

EXAMPLE 99 methyl[4-(4-chloro-2-{7-[5-chloro-2-(1H-tetrazol-1-yl)-phenyl]-5-oxo-1,2,3,5-tetrahydro-3-indolizinyl}-1H-imidazol-5-yl)-3-methylphenyl]carbamate The compound prepared in Example 98 (90 mg) was treated as detailed in Example 44 to give the title compound having the following physical properties (48 mg). LC/MS $t_R$ 3.18 minutes; MS (ES$^+$) m/z 577 (M+H)$^b$ $^1$H NMR (500 MHz, methanol-d$_4$) δ 9.26 (s, 1 H), 7.66-7.62 (m, 2 H), 7.58 (d, 1 H), 7.30 (app. s, 1 H), 7.26 (d, 1 H), 7.12 (d, 1 H), 6.03 (s, 1 H), 5.99 (s, 1 H), 5.60 (dd, 1 H), 3.65 (s, 3 H), 3.40-3.31 (m, 1 H), 3.01 (ddd, 1 H), 2.54 (qd, 1 H), 2.37-2.30 (m, 1 H), 2.15 (s, 3 H).

EXAMPLE 100 methyl N-(3-ethylphenyl)carbamate

3-Ethylaniline (4.0 g) was treated as detailed in Example 77 to give the title compound having the following physical properties (5.9 g).

LC/MS $t_R$ 1.90 minutes; MS (ES$^+$) m/z 180 (M+H)$^a$.

EXAMPLE 101 methyl N-(4-acetyl-3-ethylphenyl)carbamate

To a dichloroethane (7 mL) solution of the compound prepared in Example 100 (0.50 g) was added acetyl chloride (0.21 mL) and aluminium trichloride (0.93 g) and the mixture stirred at room temperature overnight. To the reaction mixture, ice-water (5 mL) was cautiously added followed by extraction into dichloromethane. The combined organic layers were washed with brine, dried and concentrated. The residue was purified by column chromatography (7% to 60% ethyl acetate in heptanes) to afford the title compound having the following physical properties (0.43 g).

LC/MS $t_R$ 2.13 minutes; MS (ES$^+$) m/z 222 (M+H)$^a$.

EXAMPLE 102 methyl N-[4-(2-bromoacetyl)-3-ethylphenyl]carbamate

The compound prepared in Example 101 (0.41 g) was treated as detailed in Example 91 to give the title compound having the following physical properties (0.41 g).

LC/MS $t_R$ 1.96 minutes; MS (ES$^+$) m/z 300 and 302 (M+H)$^a$.

EXAMPLE 103 methyl[4-(2-{7-[5-chloro-2-(1H-tetrazol-1-yl)phenyl]-5-oxo-1,2,3,5-tetrahydro-3-indolizinyl}-1H-imidazol-5-yl)-3-ethylphenyl]carbamate The same operation as in Example 84→Example 52→Example 40→Example 41 was conducted from the compared prepared in Example 19 to give the title compound having the following physical properties. (Note: in the step corresponding to Example 84 in the operation, the compound prepared in Example 102 was used).

LC/MS $t_R$ 3.18 minutes; MS (ES$^+$) m/z 557 (M+H)$^b$ $^1$H NMR (500 MHz, methanol-d$_4$) δ 9.36 (s, 1 H), 7.77-7.72 (m, 2 H), 7.69 (d, 1 H), 7.45-7.26 (m, 3 H), 7.11-6.84 (m, 1 H), 6.14 (s, 1 H), 6.10 (s, 1 H), 5.82 (dd, 1 H), 3.76 (s, 3 H), 3.51-3.40 (m, 1 H), 3.12 (dd, 1 H), 2.72 (q, 2 H), 2.69-2.59 (m, 1 H), 2.51 (app. br. s, 1 H), 1.15 (app. br. s, 3 H).

EXAMPLE 104 methyl[4-(4-chloro-2-{7-[5-chloro-2-(1H-1-tetrazol-1-yl)phenyl]-5-oxo-1,2,3,5-tetrahydro-3-indolizinyl}-1H-imidazol-5-yl)-3-ethylphenyl]carbamate The compound prepared in Example 103 (40 mg) was treated as detailed in Example 44 to give the title compound having the following physical properties (26.7 mg).

LC/MS $t_R$ 4.21 minutes; MS (ES$^+$) m/z 591 (M+H)$^b$ $^1$H NMR (500 MHz, methanol-d$_4$) δ 9.38 (s, 1 H), 7.78-7.74 (m, 2 H), 7.70 (d, 1 H), 7.45 (app. s, 1 H), 7.39 (dd, 1 H), 7.19 (d, 1 H), 6.14 (s, 1 H), 6.11 (s, 1 H), 5.70 (dd, 1 H), 3.77 (s, 3 H), 3.51-3.42 (m, 1 H), 3.12 (ddd, 1 H), 2.71-2.62 (m, 1 H), 2.59 (q, 2 H), 2.47-2.40 (m, 1 H), 1.10 (t, 3 H).

EXAMPLE 105 methyl N-[4-(2-bromoacetyl)-3-chlorophenyl]carbamate

The same operation as in Example 77→Example 90→Example 91 was conducted from 4-bromo-3-chloroaniline to give the title compound having the following physical properties.

LC/MS $t_R$ 1.89 minutes; MS (ES$^+$) m/z 306 (M+H)$^a$.

EXAMPLE 106 methyl[3-chloro-4-(2-{7-[5-chloro-2-(1H-tetrazol-1-yl)phenyl]-5-oxo-1,2,3,5-tetrahydro-3-indolizinyl}-1H-imidazol-5-yl)phenyl]carbamate The same operation as in Example 84→Example 39→Example 40→Example 41 was conducted from the compound prepared in Example 19 to give the title compound having the following physical properties. (Note: in the step corresponding to Example 84 in the operation, the compound prepared in Example 105 was used).

LC/MS $t_R$ 3.38 minutes; MS (ES$^+$) m/z 563 (M+H)$^b$ $^1$H NMR (500 MHz, methanol-d$_4$) δ 9.37 (s, 1 H), 7.77-7.73 (m, 3 H), 7.73-7.66 (m, 2 H), 7.53 (app. br. s, 1 H), 7.36 (app. br. s, 1 H), 6.16 (s, 1 H), 6.10 (s, 1 H), 5.83 (dd, 1 H), 3.77 (s, 3 H), 3.53-3.42 (m, 1 H), 3.12 (ddd, 1 H), 2.70-2.60 (m, 1 H), 2.54 (app. br. s, 1 H).

EXAMPLE 107 methyl{3-chloro-4-[2-({4-[5-chloro-2-(1H-tetrazol-1-yl)phenyl]-2-oxo-1(2H)-pyridinyl}methyl)-1H-imidazol-5-yl]phenyl}carbamate The same operation as in Example 38→Example 39 was conducted from the compound prepared in Example 25 to obtain the title compound having the following physical properties. (Note: in the step corresponding to Example 38 in the operation, the compound prepared in Example 105 was used).

LC/MS $t_R$ 3.03 minutes; MS (ES$^+$) m/z 537 (M+H)$^b$ $^1$H NMR (500 MHz, DMSO-d$_6$) δ 12.28 (br. s, 1 H), 9.85 (br. s, 1 H), 9.71 (s, 1 H), 7.91 (d, 1 H), 7.86-7.77 (m, 3 H), 7.73 (d, 1 H), 7.63 (app. br. s, 1 H), 7.58 (s, 1 H), 7.41 (dd, 1 H), 6.30 (app. br. s, 1 H), 5.87 (dd, 1 H), 5.11 (s, 2 H), 3.68 (s, 3 H).

EXAMPLE 108(1) AND EXAMPLE 108(2)

methyl N-[4-(2-bromoacetyl)-3-methoxyphenyl] carbamate and methyl N-[2-bromo-4-(2-bromo-acetyl)-5-methoxyphenyl]carbamate The same operation as in Example 77→Example 90→Example 91 was conducted from 4-bromo-3-methoxyaniline to give a 3:5 mixture of the title compounds having the following physical properties.

EXAMPLE 108(1)

LC/MS $t_R$ 1.82 minutes; MS (ES$^+$) m/z 302 and 304 (M+H)$^a$.

EXAMPLE 108(2)

LC/MS $t_R$ 2.10 minutes; MS (ES$^+$) m/z 379, 381, 383 (M+H)$^a$.

EXAMPLE 109(1) AND EXAMPLE 109(2)

methyl[4-(2-{(3S)-7-[5-chloro-2-(1H-tetrazol-1-yl) phenyl]-5-oxo-1,2,3,5-tetrahydro-3-indolizinyl}-1H-imidazol-5-yl)-3-methoxyphenyl]carbamate and methyl[2-bromo-4-(2-{(3S)-7-[5-chloro-2-(1H-tetrazol-1-yl)phenyl]-5-oxo-1,2,3,5-tetrahydro-3-indolizinyl}-1H-imidazol-5-yl)-5-methoxyphenyl]carbamate The same operation as in Example 84→Example 39 was conducted from the compound prepared in Example 17 to give the title compounds in a 2:1 ratio having the following physical properties. (Note: in the step corresponding to Example 84 in the operation, the 3:5 mixture of the compounds prepared in Example 108 was used).

EXAMPLE 109(1)

LC/MS $t_R$ 3.12 minutes; MS (ES$^+$) m/z 559 (M+H)$^b$
$^1$H NMR (500 MHz, DMSO-d$_6$) δ 11.97 (s, 1 H), 9.70 (s, 1H), 9.69 (s, 1 H), 7.88-7.78 (m, 4 H), 7.31 (d, 1 H), 7.27 (s, 1 H), 7.04 (dd, 1 H), 5.99 (s, 1 H), 5.96 (s, 1 H), 5.63 (dd, 1 H), 3.83 (s, 3 H), 3.66 (s, 3 H), 3.30-3.21 (m, 1 H), 3.00 (dd, 1 H), 2.48-2.41 (m, 1 H), 2.39-2.32 (m, 1 H).

EXAMPLE 109(2)

LC/MS $t_R$ 3.59 minutes; MS (ES$^+$) m/z 637 and 639 (M+H)$^b$
$^1$H NMR (500 MHz, DMSO-d$_6$) δ 12.15 (s, 1 H), 9.70 (s, 1 H), 8.89 (s, 1 H), 8.06 (s, 1 H), 7.85-7.77 (m, 3 H), 7.45 (d, 1 H), 7.25 (s, 1 H), 5.99 (s, 1 H), 5.95 (s, 1 H), 5.64 (dd, 1 H), 3.87 (s, 3 H), 3.66 (s, 3 H), 3.45-3.38 (m, 1 H), 3.02 (dd, 1 H), 2.54-2.46 (obs. m, 1 H), 2.43-2.35 (m, 1 H).

EXAMPLE 110 methyl N-[4-(2-bromoacetyl)-3-(trifluoromethyl) phenyl]carbamate

The same operation as in Example 77→Example 90→Example 91 was conducted from 4-bromo-3-trifluoromethylaniline to give the title compound having the following physical properties.

LC/MS $t_R$ 1.38 minutes; MS (ES$^+$) m/z 340 and 342 (M+H)$^a$.

EXAMPLE 111 methyl[4-(2-{(3S)-7-[5-chloro-2-(1H-tetrazol-1-yl) phenyl]-5-oxo-1,2,3,5-tetrahydro-3-indolizinyl}-1H-imidazol-5-yl)-3-(trifluoromethyl)phenyl]carbamate The same operation as in Example 51→Example 52 was conducted from the compound prepared in Example 9 to give the title compound having the following physical properties. (Note: in the step corresponding to Example 51 in the operation, the compound prepared in Example 110 was used).

LC/MS $t_R$ 3.59 minutes; MS (ES$^+$) m/z 597 (M+H)$^b$
$^1$H NMR (500 MHz, methanol-d$_4$) δ 9.36 (s, 1 H), 7.95 (br. s, 1 H), 7.78-7.72 (m, 2 H), 7.73-7.66 (m, 2 H), 7.62-7.50 (m, 1 H), 7.13 (br. s, 1 H), 6.15 (s, 1 H), 6.10 (s, 1 H), 5.82 (dd, 1 H), 3.78 (s, 3 H), 3.53-3.40 (m, 1 H), 3.16-3.07 (m, 1 H), 2.70-2.59 (m, 1 H), 2.53 (app. br. s, 1 H).

EXAMPLE 112 methyl[4-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-3-(trifluoromethyl)phenyl] carbamate The compound prepared in Example 111 (50 mg) was treated as detailed in Example 44 to give the title compound having the following physical properties (25 mg).

LC/MS $t_R$ 4.29 minutes; MS (ES$^+$) m/z 631 (M+H)$^b$
$^1$H NMR (500 MHz, methanol-d$_4$) δ 9.38 (s, 1 H), 8.03 (s, 1 H), 7.78-7.74 (m, 3 H), 7.70 (d, 1 H), 7.43 (d, 1 H), 6.16 (s, 1 H), 6.11 (s, 1 H), 5.72 (dd, 1 H), 3.80 (s, 3 H), 3.48-3.39 (m, 1 H), 3.12 (ddd, 1 H), 2.72-2.60 (m, 1 H), 2.45-2.36 (m, 1 H).

EXAMPLE 113

4-(2-{7-[5-chloro-2-(1H-tetrazol-1-yl)phenyl]-5-oxo-1,2,3,5-tetrahydro-3-indolizinyl}-1H-imidazol-4-yl)benzoic acid ammoniate

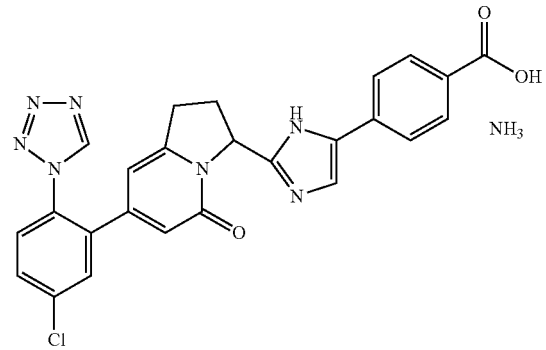

The same operation as in Example 84→Example 39→Example 37→Example 55→Example 41 was conducted from the compound prepared in Example 19 to give the title compound having the following physical properties. (Note: in the step corresponding to Example 84 in the operation, methyl 4-(2-bromoacetyl)benzoate [J. Am. Chem. Soc. 122(39), 9361 (2000)] was used. In the step corresponding to Example 41 in the operation, high performance liquid chromatography (5 to 100% acetonitrile in 2 mM aqueous ammonium hydrogen carbonate) was used to give the title product as the ammonium salt.

LC/MS $t_R$ 3.13 minutes; MS (ES$^+$) m/z 500 (M+H)$^b$ $^1$H NMR (500 MHz, DMSO-d$_6$) δ 9.70 (s, 1 H), 7.89 (d, 2 H), 7.85-7.72 (m, 5 H), 7.64 (s, 1 H), 5.98 (s, 1 H), 5.96 (s, 1 H), 5.64 (dd, 1 H), 3.45-3.30 (obs. m, 1 H), 3.00 (dd, 1 H), 2.58-2.45 (obs. in, 1 H), 2.34 (app. br. s, 1 H).

EXAMPLE 114

4-(2-{7-[5-chloro-2-(1H-tetrazol-1-yl)phenyl]-5-oxo-1,2,3,5-tetrahydro-3-indolizinyl}-1H-imidazol-4-yl)benzamide To an N,N-dimethylformamide (2 mL) solution of the compound prepared in Example 113 (88 mg) was added O-(7-azabenzotriazol-1-yl)-N,N,N',N'-tetramethyluronium hexafluorophosphate (87 mg), ammonium chloride (47 mg) and N,N-diisopropylethylamine (145 μL) and the mixture stirred at room temperature for 2 hours. To the reaction mixture, water was added followed by extraction with ethyl acetate. The combined organic layers were washed with brine, dried and concentrated. The residue obtained on concentration was purified by high performance liquid chromatography (5 to 100% acetonitrile in water) to give the title compound having the following physical properties (33.2 mg).

LC/MS $t_R$ 2.89 minutes; MS (ES$^+$) m/z 499 (M+H)$^b$ $^1$H NMR (500 MHz, DMSO-d$_6$) δ 12.22 (s, 1 H), 9.68 (s, 1 H), 7.90 (br. s, 1 H), 7.84 (d, 2 H), 7.81-7.77 (m, 3 H), 7.76 (d, 2 H), 7.63 (s, 1 H), 7.24 (br. s, 1 H), 5.96 (s, 1 H), 5.95 (s, 1 H), 5.64 (d, 1 H), 3.48-3.33 (m, 1 H), 3.00 (dd, 1 H), 2.56-2.47 (obs. m, 1 H), 2.39-2.30 (m, 1 H).

EXAMPLE 115

4-(4-chloro-2-{7-[5-chloro-2-(1H-tetrazol-1-yl)phenyl]-5-oxo-1,2,3,5-tetrahydro-3-indolizinyl}-1H-imidazol-5-yl)benzamide The compound prepared in Example 114 (88 mg) was treated as detailed in Example 44 to give the title compound having the following physical properties (9.9 mg).

LC/MS $t_R$ 3.55 minutes; MS (ES$^+$) m/z 533 (M+H)$^b$ $^1$H NMR (500 MHz, DMSO-d$_6$) δ 13.12 (s, 1 H), 9.71 (s, 1 H), 8.01 (s, 1 H), 7.97 (d, 2 H), 7.83-7.78 (m, 5 H), 7.41 (s, 1 H), 6.00 (s, 1 H), 5.95 (s, 1 H), 5.59 (dd, 1 H), 3.35-3.22 (m, 1 H), 3.00 (dd, 1 H), 2.60-2.48 (obs. m, 1 H), 2.21 (t, 1 H).

EXAMPLE 116 tert-butyl N-(4-chloro-2-{3-[4-(4-cyano-3-fluorophenyl)-1H-imidazol-2-yl]-5-oxo-1,2,3,5-tetrahydroindolizin-7-yl}phenyl)carbamate The same operation as in Example 38→Example 39 was conducted from the compound prepared in Example 19 to give the title compound having the following physical properties. (Note: in the step corresponding to Example 38 in the operation, 4-(2-bromoacetyl)-2-fluorobenzonitrile [WO2007070826, page 121] was used).

LC/MS $t_R$ 2.27 minutes; MS (ES$^+$) m/z 546 (M+H)$^a$.

EXAMPLE 117 tert-butyl N-(2-{3-[4-(4-carbamoylphenyl)-1H-imidazol-2-yl]-5-oxo-1,2,3,5-tetrahydroindolizin-7-yl}-4-chlorophenyl) carbamate To a dimethylsulfoxide (6 mL) solution of the compound prepared in Example 116 (0.106 g) was sequentially added potassium carbonate (13 mg) and 30% aqueous hydrogen peroxide solution (0.13 mL) and the mixture stirred at 50° C. for 16 hours. To the reaction mixture, a 10% aqueous solution of lithium chloride (3 mL) was added and the mixture stirred at room temperature for 15 minutes followed by extraction into ethyl acetate. The combined organic layers were sequentially washed with a saturated aqueous solution of sodium hydrogen carbonate and brine, dried and concentrated to obtain the crude title compound having the following physical properties (0.156 g).

LC/MS $t_R$ 1.83 minutes; MS (ES$^+$) m/z 564 (M+H)$^a$.

EXAMPLE 118

4-(2-{7-[5-chloro-2-(1H-tetrazol-1-yl)phenyl]-5-oxo-1,2,3,5-tetrahydro-3-indolizinyl}-1H-imidazol-5-yl)-2-fluorobenzamide The same operation as in Example 40→Example 41 was conducted from the compound prepared in Example 117 to give the title compound having the following physical properties.

LC/MS $t_R$ 3.30 minutes; MS (ES$^+$) m/z 517 (M+H)$^b$ $^1$H NMR (500 MHz, methanol-d$_4$) δ 9.37 (s, 1 H), 7.85 (t, 1 H), 7.78-7.73 (m, 2 H), 7.70 (d, 1 H), 7.66-7.52 (m, 3 H), 6.15 (s, 1 H), 6.11 (s, 1 H), 5.80 (dd, 1 H), 3.56-3.42 (m, 1 H), 3.14 (ddd, 1 H), 2.73-2.61 (m, 1 H), 2.58-2.44 (m, 1 H).

EXAMPLE 119

4-(2-bromoacetyl)benzamide

4-Acetylbenzamide [J. Org. Chem., 65(26), 9103 (2000)] (0.25 g) was treated as detailed in Example 91 to give the title compound having the following physical properties (0.37 g).

LC/MS $t_R$ 1.33 minutes; MS (ES$^+$) m/z 242 and 244 (M+H)$^a$.

EXAMPLE 120

4-[2-({4-[5-chloro-2-(1H-tetrazol-1-yl)phenyl]-2-oxo-1(2H)-pyridinyl}methyl)-1H-imidazol-5-yl]benzamide The same operation as in Example 51→Example 52 was conducted from the compound prepared in Example 25 to give the title compound having the following physical properties. (Note: in the step corresponding to Example 51 in the operation, the compound prepared in Example 119 was used).

LC/MS $t_R$ 2.88 minutes; MS (ES$^+$) m/z 473 (M+H)$^b$ $^1$H NMR (500 MHz, methanol-d$_4$) δ 9.37 (s, 1 H), 7.90 (d, 2 H), 7.80 (d, 2 H), 7.77-7.72 (m, 2 H), 7.70 (d, 1 H), 7.68 (d, 1 H), 7.55 (s, 1 H), 6.41 (d, 1 H), 6.04 (dd, 1 H), 5.22 (s, 2 H).

EXAMPLE 121

4-[4-chloro-2-({4-[5-chloro-2-(1H-tetrazol-1-yl)phenyl]-2-oxo-1(2H)-pyridinyl}methyl)-1H-imidazol-5-yl]benzamide The compound prepared in Example 120 (50 mg) was treated as detailed in Example 44 to give the title compound having the following physical properties (16 mg).
LC/MS $t_R$ 3.52 minutes; MS (ES$^+$) m/z 507 (M+H)$^b$
$^1$H NMR (500 MHz, DMSO-d$_6$) δ 13.13 (br. s, 1 H), 9.72 (s, 1 H), 7.99 (br. s, 1 H), 7.93 (d, 2 H), 7.85-7.76 (m, 5 H), 7.69 (d, 1 H), 7.38 (br. s, 1 H), 6.26 (app. s, 1 H), 5.88 (dd, 1 H), 5.05 (s, 2 H).

EXAMPLE 122

4-(2-{7-[5-chloro-2-(1H-tetrazol-1-yl)phenyl]-5-oxo-1,2,3,5-tetrahydro-3-indolizinyl}-1H-imidazol-4-yl)-N-methylbenzamide The compound prepared in Example 113 (88 mg) was treated as detailed in Example 114 using methylamine hydrochloride instead of ammonium chloride to give the title compound having the following physical properties (46.8 mg).
LC/MS $t_R$ 2.97 minutes; MS (ES$^+$) m/z 513 (M+H)$^b$
$^1$H NMR (500 MHz, DMSO-d$_6$) δ 12.23 (s, 1 H), 9.69 (s, 1 H), 8.36 (q, 1 H), 7.91-7.68 (m, 7 H), 7.63 (s, 1 H), 5.98 (s, 1 H), 5.97 (s, 1 H), 5.64 (dd, 1 H), 3.44-3.33 (m, 1 H), 3.02 (dd, 1 H), 2.78 (d, 3 H), 2.57-2.48 (obs. m, 1 H), 2.38-2.31 (m, 1 H).

EXAMPLE 123

4-(5-chloro-2-{2-[5-chloro-2-(1H-tetrazol-1-yl)phenyl]-5-oxo-1,2,3,5-tetrahydro-3-indolizinyl}-1H-imidazol-4-yl)-N-methylbenzamide The compound prepared in Example 122 (90 mg) was treated as detailed in Example 44 to give the title compound having the following physical properties (11.1 mg).
LC/MS $t_R$ 3.72 minutes; MS (ES$^+$) m/z 547 (M+H)$^b$
$^1$H NMR (500 MHz, DMSO-d$_6$) δ 13.10 (s, 1 H), 9.71 (s, 1 H), 8.48 (q, 1 H), 7.93 (d, 2 H), 7.87-7.72 (m, 5 H), 6.00 (s, 1 H), 5.95 (s, 1 H), 5.59 (dd, 1 H), 3.36-3.22 (obs. m, 1 H), 2.80 (d, 3 H), 2.59-2.50 (obs. m, 1 H), 2.39-2.12 (m, 2 H).

EXAMPLE 124

4-(2-{7-[5-chloro-2-(1H-tetrazol-1-yl)phenyl]-5-oxo-1,2,3,5-tetrahydro-3-indolizinyl}-1H-imidazol-4-yl)-N-ethylbenzamide The compound prepared in Example 113 (88 mg) was treated as detailed in Example 114 using ethylamine hydrochloride instead of ammonium chloride to give the title compound having the following physical properties (48.6 mg).
LC/MS $t_R$ 3.11 minutes; MS (ES$^+$) m/z 527 (M+H)$^b$
$^1$H NMR (500 MHz, DMSO-d$_6$) δ 12.23 (s, 1 H), 9.70 (s, 1 H), 8.40 (t, 1 H), 7.90-7.69 (m, 7 H), 7.64 (s, 1 H), 5.98 (s, 1 H); 5.97 (s, 1 H), 5.64 (dd, 1 H), 3.45-3.33 (m, 1 H), 3.32-3.23 (m, 2 H), 3.01 (dd, 1 H), 2.56-2.48 (obs. m, 1 H), 2.38-2.30 (m, 1 H), 1.13 (t, 3 H).

EXAMPLE 125

4-(4-chloro-2-{7-[5-chloro-2-(1H-tetrazol-1-yl)phenyl]-5-oxo-1,2,3,5-tetrahydro-3-indolizinyl}-1H-imidazol-5-yl)-N-ethylbenzamide The compound prepared in Example 124 (93 mg) was treated as detailed in Example 44 to give the title compound having the following physical properties (24.9 mg).
LC/MS $t_R$ 3.96 minutes; MS (ES$^+$) m/z 561 (M+H)$^b$
$^1$H NMR (500 MHz, DMSO-d$_6$) δ 13.11 (s, 1 H), 9.71 (s, 1 H), 8.51 (t, 1 H), 7.94 (d, 2 H), 7.87-7.68 (m, 5 H), 6.00 (s, 1 H), 5.95 (s, 1 H), 5.59 (dd, 1 H), 3.40-3.23 (obs. m, 3 H), 3.00 (dd, 1 H), 2.58-2.46 (obs. m, 1 H), 2.20 (t, 1 H), 1.14 (t, 3 H).

EXAMPLE 126

7-[5-chloro-2-(1H-tetrazol-1-yl)phenyl]-3-[5-(4-nitrophenyl)-1H-imidazol-2-yl]-2,3-dihydro-5(1H)-indolizinone The same operational sequence as in Example 38→Example 39→Example 40→Example 41 was conducted from the compound prepared in Example 19 to give the title compound having the following physical properties. (Note: in the step corresponding to Example 38 in the operation, 2-bromo-1-(4-nitrophenyl)-ethanone was used).
LC/MS $t_R$ 4.03 minutes; MS (ES$^+$) m/z 501 (M+H)$^b$
$^1$H NMR (500 MHz, DMSO-d$_6$) δ 12.49 (br. s, 1 H), 9.70 (s, 1 H), 8.21 (d, 2 H), 7.95 (d, 2 H), 7.89-7.77 (m, 4 H), 5.99 (s, 1 H), 5.97 (s, 1 H), 5.65 (dd, 1 H), 3.44-3.25 (obs. m, 1 H), 3.02 (dd, 1 H), 2.58-2.42 (obs. m, 1 H), 2.36-2.25 (m, 1 H).

EXAMPLE 127

3-[5-(4-aminophenyl)-1H-imidazol-2-yl]-7-[5-chloro-2-(1H-tetrazol-1-yl)phenyl]-2,3-dihydro-5(1H)-indolizinone The compound prepared in Example 126 (1.10 g) was treated as detailed in Example 74 to give the title compound having the following physical properties (0.86 g).
LC/MS $t_R$ 2.74 minutes; MS (ES$^+$) m/z 471 (M+H)$^b$
$^1$H NMR (500 MHz, methanol-d$_4$) δ 9.37 (s, 1 H), 7.78-7.73 (m, 2 H), 7.70 (d, 1 H), 7.39 (app. br. s, 2 H), 7.06 (br. s, 1 H), 6.75 (d, 2 H), 6.14 (s, 1 H), 6.10 (s, 1 H), 5.79 (dd, 1 H), 3.52-3.39 (m, 1 H), 3.11 (ddd, 1 H), 2.69-2.58 (m, 1 H), 2.47 (app. br. s, 1 H).

EXAMPLE 128 ethyl[4-(2-{7-[5-chloro-2-(1H-tetrazol-1-yl)phenyl]-5-oxo-1,2,3,5-tetrahydro-3-indolizinyl}-1H-imidazol-5-yl)phenyl]carbamate To a cooled (0° C.) dichloromethane (5 mL) solution of the compound prepared in Example 127 (130 mg), pyridine (45 μL) and ethyl chloroformate (26 μL) were added sequentially and the mixture stirred overnight at room temperature. The reaction mixture was concentrated and dissolved in methanol (5 mL), concentrated aqueous ammonia solution (0.21 mL) was added and the mixture stirred 3 hours at room temperature. The reaction mixture was concentrated, the residue suspended in water (3 mL) and extracted into ethyl acetate. The combined organic layers were washed with brine, dried and concentrated. The residue was purified by column chromatography (25% to 100% ethyl acetate in heptanes followed by 1% to 3% methanol in ethyl acetate) to afford the title compound having the following physical properties (76 mg).

LC/MS $t_R$ 3.21 minutes; MS (ES$^+$) m/z 543 (M+H)$^b$ $^1$H NMR (500 MHz, methanol-d$_4$) δ 9.37 (s, 1 H), 7.78-7.72 (m, 2 H), 7.70 (d, 1 H), 7.65-7.40 (m, 4 H), 7.36-7.10 (m, 1 H), 6.15 (s, 1 H), 6.10 (s, 1 H), 5.80 (dd, 1 H), 4.20 (q, 2 H), 3.52-3.41 (m, 1 H), 3.12 (ddd, 1 H), 2.65 (qd, 1 H), 2.50 (app. br. s, 1 H), 1.33 (t, 3 H).

EXAMPLE 129(1) TO EXAMPLE 129(6)

The compounds of the present invention having the following physical data were synthesised from the compound prepared in Example 127 and the corresponding acid chlorides, chloroformates, sulfonyl chlorides or acetic anhydride using the method as detailed in Example 128.

EXAMPLE 129(1)

isopropyl[4-(2-{7-[5-chloro-2-(1H-tetrazol-1-yl)phenyl]-5-oxo-1,2,3,5-tetrahydro-3-indolizinyl}-1H-imidazol-5-yl)phenyl]carbamate

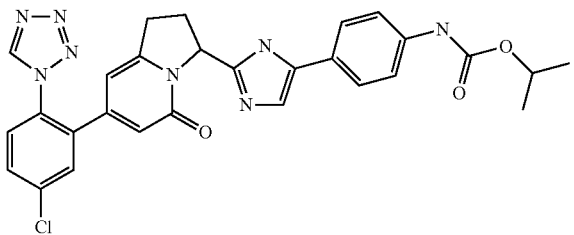 [SMILES: CC(C)OC(=O)Nc1ccc(-c2cnc(C3CCc4cc(-c5cc(Cl)ccc5-n5cnnn5)cc(=O)n43)[nH]2)cc1]

LC/MS $t_R$ 3.36 minutes; MS (ES$^+$) m/z 557 (M+H)$^b$ $^1$H NMR (500 MHz, methanol-d$_4$) δ 9.37 (s, 1 H), 7.78-7.73 (m, 2 H), 7.70 (d, 1 H), 7.65-7.38 (m, 4 H), 7.30-7.10 (m, 1 H), 6.15 (s, 1 H), 6.10 (s, 1 H), 5.80 (dd, 1 H), 5.02-4.94 (m, 1 H), 3.51-3.41 (m, 1 H), 3.12 (ddd, 1 H), 2.71-2.61 (m, 1 H), 2.52 (br. s, 1 H), 1.32 (d, 6 H).

EXAMPLE 129(2)

2-methoxyethyl[4-(2-{7-[5-chloro-2-(1H-tetrazol-1-yl)phenyl]-5-oxo-1,2,3,5-tetrahydro-3-indolizinyl}-1H-imidazol-5-yl)phenyl]carbamate LC/MS $t_R$ 3.11 minutes; MS (ES$^+$) m/z 573 (M+H), 545 (M-N$_2$+H)$^b$ $^1$H NMR (500 MHz, methanol-d$_4$) δ 9.38 (s, 1 H), 7.79-7.72 (m, 2 H), 7.72-7.67 (m, 1 H), 7.59 (app. br. s, 2 H), 7.46 (app. br. s, 2 H), 7.37-7.07 (m, 1 H), 6.14 (s, 1 H), 6.10 (s, 1 H), 5.80 (d, 1 H), 4.36-4.19 (m, 2 H), 3.72-3.61 (m, 2 H), 3.52-3.43 (m, 1 H), 3.41 (s, 3 H), 3.17-3.05 (m, 1 H), 2.71-2.59 (m, 1 H), 2.49 (app. br. s, 1 H).

EXAMPLE 129(3)

N-[4-(2-{7-[5-chloro-2-(1H-tetrazol-1-yl)phenyl]-5-oxo-1,2,3,5-tetrahydro-3-indolizinyl}-1H-imidazol-5-yl)phenyl]acetamide LC/MS $t_R$ 2.89 minutes; MS (ES$^+$) m/z 513 (M+H)$^b$ $^1$H NMR (500 MHz, methanol-d$_4$) δ 9.37 (s, 1 H), 7.77-7.73 (m, 2 H), 7.70 (d, 1 H), 7.64-7.55 (m, 4 H), 7.27 (br. s, 1 H), 6.15 (s, 1 H), 6.11 (s, 1 H), 5.80 (dd, 1 H), 3.52-3.43 (m, 1 H), 3.12 (ddd, 1 H), 2.71-2.59 (m, 1 H), 2.53-2.44 (m, 1 H), 2.14 (s, 3 H).

EXAMPLE 129(4)

N-[4-(2-{7-[5-chloro-2-(1H-tetrazol-1-yl)phenyl]-5-oxo-1,2,3,5-tetrahydro-3-indolizinyl}-1H-imidazol-5-yl)phenyl]-2-methoxyacetamide LC/MS $t_R$ 3.01 minutes; MS (ES$^+$) m/z 543 (M+H)$^b$ $^1$H NMR (500 MHz, DMSO-d$_6$) δ 12.04 (s, 1 H), 9.72 (s, 1 H), 9.68 (s, 1 H), 7.84-7.77 (m, 3 H), 7.68 (d, 2 H), 7.58 (d, 2 H), 7.43 (s, 1 H), 5.99 (s, 1 H), 5.96 (s, 1 H), 5.62 (dd, 1 H), 3.99 (s, 2 H), 3.38 (s, 3 H), 3.38-3.30 (obs. m, 1 H), 3.00 (dd, 1 H), 2.55-2.44 (obs. m, 1 H), 2.29-2.39 (m, 1 H).

EXAMPLE 129(5)

N-[4-(2-{7-[5-chloro-2-(1H-tetrazol-1-yl)phenyl]-5-oxo-1,2,3,5-tetrahydro-3-indolizinyl}-1H-imidazol-5-yl)phenyl]-3-methoxypropanamide LC/MS $t_R$ 3.03 minutes; MS (ES$^+$) m/z 579 (M+Na), 557 (M+H), 529 (M-N$_2$+H)$^b$ $^1$H NMR (500 MHz, methanol-d$_4$) δ 9.36 (s, 1 H), 7.78-7.72 (m, 2 H), 7.71-7.66 (m, 1 H), 7.59 (app. br. s, 4 H), 7.27 (br. s, 1 H), 6.14 (s, 1 H), 6.09 (s, 1 H), 5.79 (dd, 1 H), 3.74 (t, 2 H), 3.53-3.40 (m, 1 H), 3.37 (s, 3 H), 3.11 (ddd, 1 H), 2.69-2.59 (m, 3 H), 2.49 (app. br. s, 1 H).

EXAMPLE 129(6)

N-[4-(2-{7-[5-chloro-2-(1H-tetrazol-1-yl)phenyl]-5-oxo-1,2,3,5-tetrahydro-3-indolizinyl}-1H-imidazol-5-yl)phenyl]methanesulfonamide LC/MS $t_R$ 2.98 minutes; MS (ES$^+$) m/z 549 (M+H)$^b$ $^1$H NMR (500 MHz, methanol-d$_4$) δ 9.25 (s, 1 H), 7.66-7.61 (m, 2 H), 7.60-7.44 (m, 3 H), 7.22 (br. s, 1 H), 7.15 (d, 2 H), 6.03 (s, 1 H), 5.99 (s, 1 H), 5.68 (dd, 1 H), 3.40-3.29 (m, 1 H), 3.01 (ddd, 1 H), 2.86 (s, 3 H), 2.59-2.49 (m, 1 H), 2.38 (app. br. s, 1 H).

EXAMPLE 130(1) TO EXAMPLE 130(4)

The compounds of the present invention having the following physical data were synthesised from the compounds prepared in Examples 128, 129(1), 129(3) or 129(6) using the method as detailed in Example 44.

EXAMPLE 130(1)

ethyl[4-(4-chloro-2-{7-[5-chloro-2-(1H-tetrazol-1-yl)phenyl]-5-oxo-1,2,3,5-tetrahydro-3-indolizinyl}-1H-imidazol-5-yl)phenyl]carbamate

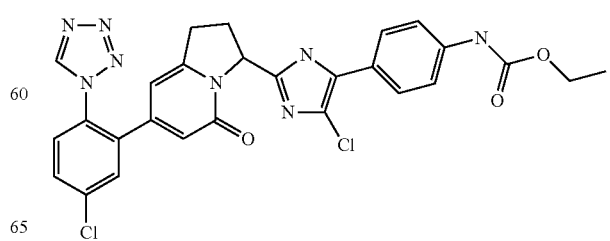

LC/MS $t_R$ 4.28 minutes; MS (ES$^+$) m/z 577 (M+H)$^b$
$^1$H NMR (500 MHz, DMSO-d$_6$) δ 12.86 (br. s, 1 H), 9.76 (s, 1 H), 9.71 (s, 1 H), 7.85-7.80 (m, 3 H), 7.60 (d, 2 H), 7.55 (d, 2 H), 5.99 (s, 1 H), 5.94 (s, 1 H), 5.57 (dd, 1 H), 4.15 (q, 2 H), 3.30-3.24 (obs. m, 1 H), 3.03-2.95 (m, 1 H), 2.58-2.54 (obs. m, 1 H), 2.23-2.17 (m, 1 H), 1.26 (t, 3 H).

EXAMPLE 130(2)

isopropyl[4-(4-chloro-2-{7-[5-chloro-2-(1H-tetrazol-1-yl)phenyl]-5-oxo-1,2,3,5-tetrahydro-3-indolizinyl}-1H-imidazol-5-yl)phenyl]carbamate LC/MS $t_R$ 4.46 minutes; MS (ES$^+$) m/z 591 (M+H)$^b$
$^1$H NMR (500 MHz, DMSO-d$_6$) δ 12.86 (br. s, 1 H), 9.71 (app. s, 2 H), 7.86-7.78 (m, 3 H), 7.64-7.52 (m, 4 H), 5.99 (s, 1 H), 5.94 (s, 1 H), 5.57 (dd, 1 H), 4.91 (quintet, 1 H), 3.30-3.25 (m, 1 H), 2.99 (ddd, 1 H), 2.58-2.54 (obs. m, 1 H), 2.20 (t, 1 H), 1.27 (d, 6 H).

EXAMPLE 130(3)

N-[4-(4-chloro-2-{7-[5-chloro-2-(1H-tetrazol-1-yl)phenyl]-5-oxo-1,2,3,5-tetrahydro-3-indolizinyl}-1H-imidazol-5-yl)phenyl]acetamide LC/MS $t_R$ 3.85 minutes; MS (ES$^+$) m/z 547 (M+H)$^b$
$^1$H NMR (500 MHz, DMSO-d$_6$) δ 12.88 (br. s, 1 H), 10.06 (s, 1 H), 9.71 (s, 1 H), 7.89-7.75 (m, 3 H), 7.72-7.58 (m, 4 H), 5.99 (s, 1 H), 5.94 (s, 1 H), 5.57 (dd, 1 H), 3.30-3.24 (m, 1 H), 2.99 (dd, 1 H), 2.59-2.55 (obs. m, 1 H), 2.25-2.16 (m, 1 H), 2.06 (s, 3 H).

EXAMPLE 130(4)

N-[4-(4-chloro-2-{7-[5-chloro-2-(1H-tetrazol-1-yl)phenyl]-5-oxo-1,2,3,5-tetrahydro-3-indolizinyl}-1H-imidazol-5-yl)phenyl]methanesulfonamide LC/MS $t_R$ 3.93 minutes; MS (ES$^+$) m/z 583 (M+H)$^b$
$^1$H NMR (500 MHz, DMSO-d$_6$) δ 12.92 (br. s, 1 H), 9.91 (br. s, 1 H), 9.71 (s, 1 H), 7.88-7.77 (m, 3 H), 7.70-7.62 (m, 2 H), 7.29 (d, 2 H), 5.99 (s, 1 H), 5.94 (s, 1 H), 5.58 (dd, 1 H), 3.30-3.25 (m, 1 H), 3.04 (s, 3 H), 3.03-2.96 (m, 1 H), 2.57-2.54 (obs. m, 1 H), 2.21 (dd, 1 H).

EXAMPLE 131

1-[4-(2-{7-[5-chloro-2-(1H-tetrazol-1-yl)phenyl]-5-oxo-1,2,3,5-tetrahydro-3-indolizinyl}-1H-imidazol-5-yl)phenyl]-3-ethylurea To a dichloromethane (7 mL) solution of the compound prepared in Example 127 (130 mg) was added ethyl isocyanate (20 μL) and the mixture stirred at room temperature for 3 hours. To the reaction mixture, further ethyl isocyanate (20 μL) was added and the mixture stirred at room temperature for 72 hours. One further treatment with ethyl isocyanate (20 μL) was required, and the mixture stirred at room temperature for 4 hours. The precipitate was collected by filtration and purified by high performance liquid chromatography (5 to 100% acetonitrile in water) to give the title compound having the following physical properties (28 mg).

LC/MS $t_R$ 2.95 minutes; MS (ES$^+$) m/z 542 (M+H)$^b$
$^1$H NMR (500 MHz, methanol-d$_4$) δ 9.37 (s, 1 H), 7.77-7.73 (m, 2 H), 7.70 (d, 1 H), 7.55 (app. br. s, 2 H), 7.39 (d, 2 H), 7.21 (br. s, 1 H), 6.14 (s, 1 H), 6.10 (s, 1 H), 5.79 (dd, 1 H), 3.52-3.41 (m, 1 H), 3.25 (q, 2 H), 3.12 (ddd, 1 H), 2.72-2.59 (m, 1 H), 2.52-2.45 (m, 1 H), 1.17 (t, 3 H).

EXAMPLE 132

3-[4-(2-{7-[5-chloro-2-(1H-tetrazol-1-yl)phenyl]-5-oxo-1,2,3,5-tetrahydro-3-indolizinyl}-1H-imidazol-5-yl)phenyl]-1,1-dimethylurea To a cooled (0° C.) dichloromethane (7 mL) solution of the compound prepared in Example 127 (130 mg) was sequentially added pyridine (45 μL) and dimethylcarbamic chloride (21 μL) and the mixture stirred at room temperature for 3 hours. To the reaction mixture, further dimethylcarbamic chloride (21 μL) was added and the mixture stirred at room temperature for 72 hours. One further treatment with dimethylcarbamic chloride (21 μL) was required, and the mixture stirred at room temperature for 4 hours. The reaction mixture was concentrated and purified by high performance liquid chromatography (5 to 100% acetonitrile in water) to give the title compound having the following physical properties (32 mg).

LC/MS $t_R$ 2.93 minutes; MS (ES$^+$) m/z 542 (M+H)$^b$
$^1$H NMR (500 MHz, methanol-d$_4$) δ 9.35 (s, 1 H), 7.75-7.70 (m, 2 H), 7.69-7.65 (m, 1 H), 7.54 (d, 2 H), 7.38 (d, 2 H), 7.20 (br. s, 1 H), 6.13 (s, 1 H), 6.08 (s, 1 H), 5.78 (d, 1 H), 3.49-3.39 (m, 1 H), 3.14-3.05 (m, 1 H), 3.02 (s, 6 H), 2.68-2.57 (m, 1 H), 2.51-2.42 (m, 1 H).

EXAMPLE 133

N-[4-(2-{7-[5-chloro-2-(1H-tetrazol-1-yl)phenyl]-5-oxo-1,2,3,5-tetrahydro-3-indolizinyl}-1H-imidazol-5-yl)phenyl]-2-(dimethylamino)acetamide To an N,N-dimethylformamide (6 mL) and pyridine (2 mL) solution of the compound prepared in Example 127 (100 mg) and N,N-dimethylglycine (26 mg) was added 1-[3-(dimethylaminopropyl)]-3-ethylcarbodiimide hydrochloride (49 mg) and the mixture stirred at room temperature for 16 hours. The reaction was concentrated and the residue suspended in water (15 mL) followed by extraction into a 3:1 mixture of ethyl acetate and propan-2-ol. The combined organic layers were washed with brine, dried and concentrated. The residue was purified by high performance liquid chromatography (5 to 100% acetonitrile in 2 mM aqueous ammonium hydrogen carbonate) to give the title compound having the following physical properties (21 mg).

LC/MS $t_R$ 2.52 minutes; MS (ES$^+$) m/z 279 [(M+2H)/2]$^b$
$^1$H NMR (500 MHz, methanol-d$_4$) δ 9.37 (s, 1 H), 7.77-7.72 (m, 2 H), 7.71-7.67 (m, 1 H), 7.63 (app. br. s, 4 H), 7.29 (br. s, 1 H), 6.14 (s, 1 H), 6.10 (s, 1 H), 5.80 (dd, 1 H), 3.53-3.38 (m, 1 H), 3.16 (s, 2 H), 3.14-3.08 (m, 1 H), 2.70-2.59 (m, 1 H), 2.55-2.43 (m, 1 H), 2.39 (s, 6 H).

EXAMPLE 134

3-{[4-(2-{7-[5-chloro-2-(1H-tetrazol-1-yl)phenyl]-5-oxo-1,2,3,5-tetrahydro-3-indolizinyl}-1H-imidazol-5-yl)phenyl]amino}-3-oxopropanoic acid methyl ester To a cooled (0° C.) dichloromethane (1 mL) solution of the compound prepared in Example 127 (54 mg) was sequentially added pyridine (11 μL) and methyl-3-chloro-3-oxopropanote (20 μL) and the mixture stirred for 3 hours at room temperature. To the reaction mixture, water (5 mL)

was added followed by extraction into dichloromethane. The combined organic layers were sequentially washed with 1 M hydrochloric acid, a saturated aqueous solution of sodium hydrogen carbonate and brine, dried and concentrated. The residue thus obtained was triturated with a 1:4 mixture of ethyl acetate in heptanes, the resultant precipitate being isolated by filtration to give the title compound having the following physical properties (56 mg).

LC/MS $t_R$ 1.21 minutes; MS (ES$^+$) m/z 571 (M+H)$^a$.

EXAMPLE 135

3-{[4-(2-{7-[5-chloro-2-(1H-tetrazol-1-yl)phenyl]-5-oxo-1,2,3,5-tetrahydro-3-indolizinyl}-1H-imidazol-5-yl)phenyl]amino}-3-oxopropanoic acid To a methanol (0.5 mL) solution of the compound prepared in Example 134 (56 mg) was added a solution of sodium carbonate (10.4 mg) in water (0.5 mL) and the mixture stirred at room temperature for 16 hours. Further sodium carbonate (10.4 mg) was then added and the mixture stirred at room temperature for 2 hours. The reaction mixture was concentrated and the residue suspended in 1 M hydrochloric acid (0.4 mL) followed by extraction into ethyl acetate. The combined organic layers were washed with brine, dried and concentrated. The residue thus obtained was triturated with a 1:4 mixture of ethyl acetate in heptanes, the resultant precipitate being isolated by filtration to give the title compound having the following physical properties (53 mg).

LC/MS $t_R$ 2.84 minutes; MS (ES$^+$) m/z 557 (M+H)$^b$
$^1$H NMR (500 MHz, DMSO-d$_6$) δ 12.59 (s, 1 H), 12.05 (s, 1 H), 9.69 (s, 1 H), 7.80 (app. s, 3 H), 7.59 (d, 2 H), 7.50 (d, 2 H), 7.40 (s, 1 H), 5.99 (s, 1 H), 5.94 (s, 1 H), 5.62 (d, 1 H), 3.44-3.30 (obs. m, 1 H), 3.05-2.92 (m, 1 H), 2.83 (s, 2 H), 2.49-2.42 (obs. m, 1 H), 2.38-2.32 (m, 1 H).

EXAMPLE 136

6-(2-{7-[5-chloro-2-(1H-tetrazol-1-yl)phenyl]-5-oxo-1,2,3,5-tetrahydro-3-indolizinyl}-1H-imidazol-5-yl)-4-hydroxy-2(1H)-quinolinone The compound prepared in Example 135 (31 mg), was suspended in Eaton's reagent (0.21 mL) and the mixture stirred at 100° C. for 2 hours. To the cooled (0° C.) reaction mixture, a saturated aqueous solution of sodium hydrogen carbonate (5 mL) was carefully added followed by extraction into ethyl acetate. The combined organic layers were washed with brine, dried and concentrated and the residue purified by high performance liquid chromatography (5 to 100% acetonitrile in water). The residue was purified further by trituration from a boiling 9:1 solution of dichloromethane and methanol. The resultant precipitate was isolated by filtration to give the title compound having the following physical properties (2.8 mg).

LC/MS $t_R$ 2.88 minutes; MS (ES$^+$) m/z 539 (M+H)$^b$
$^1$H NMR (500 MHz, DMSO-d$_6$) δ 11.30 (br. s, 1 H), 11.14 (br. s, 1 H), 9.70 (s, 1 H), 8.08 (s, 1 H), 7.87-7.76 (m, 4 H), 7.51 (br. s, 1 H), 7.24 (br. s, 1 H), 6.53 (br. s, 1 H), 5.99 (s, 1 H), 5.96 (s, 1 H), 5.74 (br. s, 1 H), 5.64 (d, 1 H), 3.36-3.27 (obs. m, 1 H), 3.02 (dd, 1 H), 2.54-2.45 (obs, m, 1 H), 2.40-2.32 (m, 1 H).

EXAMPLE 137

4-(2-{7-[5-chloro-2-(1H-tetrazol-1-yl)phenyl]-5-oxo-1,2,3,5-tetrahydro-3-indolizinyl}-1H-imidazol-5-yl)-2-fluorobenzonitrile The same operation as in Example 40→Example 41 was conducted from the compound prepared in Example 116 to give the title compound having the following physical properties.

LC/MS $t_R$ 4.12 minutes; MS (ES$^+$) m/z 499 (M+H)$^b$
$^1$H NMR (500 MHz, CDCl$_3$) δ 8.43 (s, 1 H), 7.60-7.38 (m, 6 H), 7.29 (s, 1 H), 6.21 (s, 1 H), 5.72 (d, 1 H), 5.65 (s, 1 H), 3.41-3.24 (m, 2 H), 3.02-2.91 (m, 1 H), 2.49-2.31 (m, 1 H).

EXAMPLE 138

3-[5-(3-amino-1H-indazol-6-yl)-1H-imidazol-2-yl]-7-[5-chloro-2-(1H-tetrazol-1-yl)phenyl]-2,3-dihydro-5(1H)-indolizinone To a methanol (1 mL) solution of the compound prepared in Example 137 (125 mg) was added hydrazine hydrate (105 μL) and the mixture stirred at 80° C. for 20 hours. To the reaction mixture, further hydrazine hydrate (105 μL) was added and the mixture stirred at 80° C. for 24 hours. To the reaction mixture, water (5 mL) was added followed by extraction into ethyl acetate. The combined organic layers were washed with brine, dried and concentrated. The residue was purified by high performance liquid chromatography (5 to 100% acetonitrile in 2 mM aqueous ammonium hydrogen carbonate) to give the title compound having the following physical properties (6.5 mg).

LC/MS $t_R$ 2.29 minutes; MS (ES$^+$) m/z 511 (M+H)$^b$
$^1$H NMR (500 MHz, methanol-d$_4$) δ 9.39 (s, 1 H), 7.79-7.56 (m, 5 H), 7.38 (br. s, 1 H), 7.32 (d, 1 H), 6.16 (s, 1 H), 6.12 (s, 1 H), 5.81 (dd, 1 H), 3.55-3.42 (m, 1 H), 3.14 (ddd, 1 H), 2.74-2.59 (m, 1 H), 2.52-2.49 (m, 1 H).

EXAMPLE 139

7-acetyl-3,4-dihydro-2H-1,4-benzoxazin-3-one

To an N,N-dimethylformamide (5 mL) solution of 7-bromo-2H-1,4-benzoxazin-3(4H)-one (0.50 g) was added tributyl(1-ethoxyethenyl)stannane (0.81 mL) The mixture was degassed with nitrogen for 5 minutes and tetrakis (triphenylphosphine)palladium(0) (51 mg) was added. The mixture was stirred at 120° C. in a pressure tube for 3 hours. To the reaction mixture, 1 M hydrochloric acid was added and the mixture was stirred for 2 hours then extracted into ethyl acetate. The combined organic layers were washed with brine, dried and concentrated. The residue was triturated with hot cyclohexane and the precipitate isolated by filtration to give the title compound having the following physical properties (0.35 g).

LC/MS $t_R$ 1.30 minutes; MS (ES$^+$) m/z 192 (M+H)$^a$.

EXAMPLE 140

7-(2-{7-[5-chloro-2-(1H-tetrazol-1-yl)phenyl]-5-oxo-1,2,3,5-tetrahydro-3-indolizinyl}-1H-imidazol-5-yl)-2H-1,4-benzoxazin-3(4H)-one The same operation as in Example 91→Example 84→Example 39 was conducted from the compound prepared in Example 139 to give the title compound having the following physical properties. (Note: in the step corresponding to Example 84 in the operation, the compound prepared in Example 17 was used).

LC/MS $t_R$ 2.90 minutes; MS (ES$^+$) m/z 527 (M+H)$^b$ $^1$H NMR (500 MHz, DMSO-d$_6$) δ 12.07 (s, 1 H), 10.66 (s, 1 H), 9.68 (s, 1 H), 7.85-7.75 (m, 3 H), 7.44 (br. s, 1 H), 7.29 (d, 1 H), 7.25 (s, 1 H), 6.85 (d, 1 H), 5.97 (s, 1 H), 5.94 (s, 1 H), 5.60 (dd, 1 H), 4.55 (s, 2 H), 3.45-3.34 (obs. m, 1 H), 2.99 (dd, 1 H), 2.53-2.43 (obs. m, 1 H), 2.37-2.29 (m, 1 H).

EXAMPLE 141

7-bromo-4-methyl-3,4-dihydro-2H-1,4-benzoxazin-3-one

To an N,N-dimethylformamide (15 mL) solution of 7-bromo-2H-1,4-benzoxazin-3(4H)-one (1.0 g) was sequentially added potassium carbonate (1.21 g) and iodomethane (1.0 mL) and the mixture stirred under nitrogen for 3 hours. To the reaction mixture, water (25 mL) was added followed by extraction into ethyl acetate. The combined organic layers were washed with brine, dried and concentrated to afford the title compound having the following physical properties (1.1 g).

LC/MS $t_R$ 1.93 minutes; MS (ES$^+$) m/z 242 and 244 (M+H)$^a$.

EXAMPLE 142

7-(2-{(3S)-7-[5-chloro-2-(1H-tetrazol-1-yl)phenyl]-5-oxo-1,2,3,5-tetrahydro-3-indolizinyl}-1H-imidazol-5-yl)-4-methyl-2H-1,4-benzoxazin-3(4H)-one The same operation as in Example 139→Example 91→Example 84→Example 52 was conducted from the compound prepared in Example 141 to give the title compound having the following physical properties. (Note: in the step corresponding to Example 84 in the operation, the compound prepared in Example 9 was used).

LC/MS $t_R$ 3.15 minutes; MS (ES$^+$) m/z 541 (M+H)$^b$ $^1$H NMR (500 MHz, DMSO-d$_6$) δ 12.12 (br. s, 1 H), 9.69 (s, 1 H), 7.83-7.77 (m, 3 H), 7.50 (br. s, 1 H), 7.40 (d, 1 H), 7.31 (d, 1 H), 7.11 (br. s, 1 H), 5.97 (s, 1 H), 5.93 (s, 1 H), 5.60 (dd, 1 H), 4.64 (s, 2 H), 3.27 (s, 3 H), 3.48-3.36 (obs. m, 1 H), 2.99 (dd, 1 H), 2.58-2.46 (obs. m, 1 H), 2.38-2.25 (m, 1 H).

EXAMPLE 143

7-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-4-methyl-2H-1,4-benzoxazin-3(4H)-one The compound prepared in Example 142 (100 mg) was treated as detailed in Example 44 to give the title compound having the following physical properties (28 mg).

LC/MS $t_R$ 4.09 minutes; MS (ES$^+$) m/z 575 (M+H)$^b$ $^1$H NMR (500 MHz, DMSO-d$_6$) δ 12.99 (s, 1 H), 9.71 (s, 1 H), 7.88-7.73 (m, 3 H), 7.43 (dd, 1 H), 7.34 (d, 1 H), 7.27 (d, 1 H), 5.99 (s, 1 H), 5.93 (s, 1 H), 5.56 (dd, 1 H), 4.70 (s, 2 H), 3.35-3.21 (m, 1 H), 3.30 (s, 3 H), 2.99 (dd, 1 H), 2.58-2.48 (m, 1 H), 2.20 (t, 1 H).

EXAMPLE 144

6-(2-{7-[5-chloro-2-(1H-tetrazol-1-yl)phenyl]-5-oxo-1,2,3,5-tetrahydro-3-indolizinyl}-1H-imidazol-5-yl)-1,4-dihydro-2H-3,1-benzoxazin-2-one The same operation as in Example 139→Example 91→Example 51→Example 39 was conducted from 6-bromo-1,4-dihydro-2H-3,1-benzoxazin-2-one to give the title compound having the following physical properties. (Note: in the step corresponding to Example 51 in the operation, the compound prepared in Example 17 was used).

LC/MS $t_R$ 2.91 minutes; MS (ES$^+$) m/z 527 (M+H)$^b$ $^1$H NMR (500 MHz, DMSO-d$_6$) δ 12.09 (s, 1 H), 10.12 (s, 1 H), 9.70 (s, 1 H), 7.82-7.77 (m, 3 H), 7.57 (d, 1 H), 7.54 (s, 1 H), 7.41 (d, 1 H), 6.84 (d, 1 H), 5.95 (app. s, 2 H), 5.61 (d, 1 H), 5.31 (s, 2 H), 3.38-3.26 (obs. m, 1 H), 3.00 (dd, 1 H), 2.54-2.46 (obs. m, 1 H), 2.20 (t, 1 H).

EXAMPLE 145

6-(4-chloro-2-{7-[5-chloro-2-(1H-tetrazol-1-yl)phenyl]-5-oxo-1,2,3,5-tetrahydro-3-indolizinyl}-1H-imidazol-5-yl)-1,4-dihydro-2H-3,1-benzoxazin-2-one The compound prepared in Example 144 (40 mg) was treated as detailed in Example 44 to give the title compound having the following physical properties (10.6 mg).

LC/MS $t_R$ 3.79 minutes; MS (ES$^+$) m/z 561 (M+H)$^b$ $^1$H NMR (500 MHz, DMSO-d$_6$) δ 12.75 (s, 1 H), 10.30 (s, 1 H), 9.71 (s, 1 H), 7.90-7.74 (m, 3 H), 7.57 (d, 1 H), 7.52 (app. s, 1 H), 6.97 (d, 1 H), 6.00 (s, 1 H), 5.94 (s, 1 H), 5.54 (dd, 1 H), 5.35 (s, 2 H), 3.38-3.28 (obs. m, 1 H), 2.99 (dd, 1 H), 2.59-2.48 (obs. m, 1 H), 2.21 (t, 1 H).

EXAMPLE 146

6-(2-{7-[5-chloro-2-(1H-tetrazol-1-yl)phenyl]-5-oxo-1,2,3,5-tetrahydro-3-indolizinyl}-1H-imidazol-5-yl)-1,3-benzoxazol-2(3H)-one The same operation as in Example 84→Example 52→Example 40→Example 41 was conducted from the compound prepared in Example 19 to give the title compound having the following physical properties. (Note: in the step corresponding to Example 84 in the operation, 6-(2-bromoacetyl)benzoxazol-2(3H)-one [J. Med. Chem., 34(6), 1860 (1991)] was used).

LC/MS $t_R$ 2.96 minutes; MS (ES$^+$) m/z 513 (M+H)$^b$ $^1$H NMR (500 MHz, DMSO-d$_6$) δ 12.10 (s, 1 H), 11.58 (br. s, 1 H), 9.68 (s, 1 H), 7.87-7.74 (m, 3 H), 7.57 (s, 1 H), 7.52 (d, 1 H), 7.48 (s, 1 H), 7.02 (d, 1 H), 5.98 (s, 1 H), 5.96 (s, 1 H), 5.62 (dd, 1 H), 3.45-3.36 (obs. m, 1 H), 3.11-2.88 (m, 1 H), 2.50 (obs. m, 1 H), 2.40-2.09 (m, 1 H).

EXAMPLE 147

6-(4-chloro-2-{7-[5-chloro-2-(1H-tetrazol-1-yl)phenyl]-5-oxo-1,2,3,5-tetrahydro-3-indolizinyl}-1H-imidazol-5-yl)-1,3-benzoxazol-2(3H)-one The compound prepared in Example 146 (105 mg) was treated as detailed in Example 44 to give the title compound having the following physical properties (4 mg).

LC/MS $t_R$ 3.85 minutes; MS (ES$^+$) m/z 547 (M+H)$^b$

¹H NMR (500 MHz, methanol-d₄) δ 9.36 (s, 1 H), 7.74 (s, 1 H), 7.73 (dd, 1 H), 7.68 (d, 1 H), 7.55 (d, 1 H), 7.52 (dd, 1 H), 7.16 (d, 1 H), 6.13 (s, 1 H), 6.10 (s, 1 H), 5.71 (dd, 1 H), 3.49-3.40 (m, 1 H), 3.11 (ddd, 1 H), 2.65 (ddd, 1 H), 2.40 (ddt, 1 H),

EXAMPLE 148

6-(2-{7-[5-chloro-2-(1H-tetrazol-1-yl)phenyl]-5-oxo-1,2,3,5-tetrahydro-3-indolizinyl}-1H-imidazol-5-yl)-1-isoindolinone The same operation as in Example 84→Example 52→Example 40→Example 41 was conducted from the compound prepared in Example 19 to give the title compound having the following physical properties. (Note: in the step corresponding to Example 84 in the operation, 6-(bromoacetyl)isoindolin-1-one [Bioorg. Med. Chem., 16(6), 3091 (2008)] was used).

LC/MS $t_R$ 2.98 minutes; MS (ES⁺) m/z 511 (M+H)$^b$

¹H NMR (500 MHz, methanol-d₄) δ 9.36 (s, 1 H), 7.93 (br. s, 1 H), 7.83 (br. s, 1 H), 7.75 (br. s, 1 H), 7.75-7.70 (m, 2 H), 7.68 (d, 1 H), 7.54 (br. s, 1 H), 6.14 (s, 1 H), 6.10 (s, 1 H), 5.80 (d, 1 H), 4.49 (s, 2 H), 3.56-3.39 (m, 1 H), 3.36-3.26 (obs. m, 1 H), 3.12 (ddd, 1 H), 2.71-2.58 (m, 1 H).

EXAMPLE 149

6-(2-bromoacetyl)-3-methyl-1,2,3,4-tetrahydroquinazolin-2-one

To a cooled (0° C.) suspension of aluminium trichloride (2.06 g) in 1,2-dichloroethane (5 mL) was added bromoacetyl bromide (1.1 mL) and the mixture stirred at 0° C. for 30 minutes. To the reaction mixture, a solution of 3-methyl-3,4-dihydroquinazolin-2(1H)-one (1.0 g) in 1,2-dichloroethane (5 mL) was added and the mixture stirred at 50° C. for 3 hours. The reaction mixture was concentrated and the residue suspended in iced water (20 mL). The resultant precipitate was isolated by filtration to give the title compound having the following physical properties (1.51 g).

LC/MS $t_R$ 1.53 minutes; MS (ES⁺) m/z 283 and 285 (M+H)$^a$

EXAMPLE 150

6-(2-{(3S)-7-[5-chloro-2-(1H-tetrazol-1-yl)phenyl]-5-oxo-1,2,3,5-tetrahydro-3-indolizinyl}-1H-imidazol-5-yl)-3-methyl-3,4-dihydro-2(1H)-quinazolinone The same operation as in Example 51→Example 52 was conducted from the compound prepared in Example 9 to give the title compound having the following physical properties. (Note: in the step corresponding to Example 51 in the operation, the compound prepared in Example 149 was used).

LC/MS $t_R$ 2.94 minutes; MS (ES⁺) m/z 540 (M+H)$^b$

¹H NMR (500 MHz, CDCl₃) δ 11.16 (s, 1 H), 8.25 (s, 1 H), 8.23 (s, 1 H), 8.03 (d, 1 H), 7.98-7.89 (m, 2 H), 7.47 (d, 1 H), 7.33 (dd, 1 H), 7.14 (d, 1 H), 6.47 (s, 1 H), 6.40 (br. s, 1 H), 6.22 (s, 1 H), 5.95 (d, 1 H), 3.65-3.46 (m, 2 H), 3.24 (dd, 1 H), 2.65-2.50 (m, 1 H), 2.05 (s, 2 H), 1.57 (s, 3 H).

EXAMPLE 151

6-[2-({4-[5-chloro-2-(1H-tetrazol-1-yl)phenyl]-2-oxo-1(2H)-pyridinyl}methyl)-1H-imidazol-5-yl]-3-methyl-3,4-dihydro-2(1H)-quinazolinone The same operation as in Example 38→Example 39 was conducted from the compound prepared in Example 25 to obtain the title compound having the following physical properties. (Note: in the step corresponding to Example 38 in the operation, the compound prepared in Example 149 was used).

LC/MS $t_R$ 2.90 minutes; MS (ES⁺) m/z 514 (M+H)$^b$

¹H NMR (500 MHz, DMSO-d₆) δ 12.08 (br. s, 1 H), 9.70 (s, 1 H), 9.17 (br. s, 1 H), 7.88-7.76 (m, 3 H), 7.69 (d, 1 H), 7.53-7.44 (m, 2 H), 7.39 (s, 1 H), 6.72 (d, 1 H), 6.29 (s, 1 H), 5.87 (dd, 1 H), 5.07 (s, 2 H), 4.43 (s, 2 H), 2.87 (s, 3 H).

EXAMPLE 152

6-[4-chloro-2-({4-[5-chloro-2-(1H-tetrazol-1-yl)phenyl]-2-oxo-1(2H)-pyridinyl}methyl)-1H-imidazol-5-yl]-3-methyl-3,4-dihydro-2(1H)-quinazolinone The compound prepared in Example 151 (70 mg) was treated as detailed in Example 44 to give the title compound having the following physical properties (6.0 mg).

LC/MS $t_R$ 3.68 minutes; MS (ES⁺) m/z 548 (M+H)$^b$

¹H NMR (500 MHz, DMSO-d₆) δ 12.82 (br. s, 1 H), 9.71 (s, 1 H), 9.36 (s, 1 H), 7.88-7.77 (m, 3 H), 7.69 (d, 1 H), 7.45 (d, 1 H), 7.41 (s, 1 H), 6.84 (d, 1 H), 6.28 (d, 1 H), 5.89 (dd, 1 H), 5.06 (s, 2 H), 4.46 (s, 2 H), 2.88 (s, 3 H).

EXAMPLE 153

2-bromo-1-(2-chloroquinoxalin-6-yl)ethan-1-one

To an acetonitrile (10 mL) suspension of 2-oxo-1,2-dihydroquinoxaline-6-carboxylic acid [patent WO2006040568, page 75, 82] (0.38 g) was sequentially added pyridine (8 μL), N,N-dimethylformamide (7.5 μL) and thionyl chloride (2.2 mL) and the mixture stirred at 90° C. for 1 hour. The reaction mixture was concentrated and the residue dissolved in acetonitrile (10 mL). To the cooled (0° C.) acetonitrile solution, a 2 M solution of (trimethylsilyl)diazomethane in diethyl ether (2.5 mL) was added and the mixture stirred at 0° C. for 2 hours. To the reaction mixture, a solution of 33 wt. % hydrogen bromide in acetic acid (0.86 mL) was added and the mixture stirred at 0° C. for a further 30 minutes. A saturated aqueous solution of sodium hydrogen carbonate (50 mL) was added followed by extraction into ethyl acetate. The combined organic layers were washed with brine, dried and concentrated to obtain the title compound having the following physical properties (0.35 g).

LC/MS $t_R$ 1.96 minutes; MS (ES⁺) m/z 285 and 287 (M+H)$^a$.

EXAMPLE 154

6-(2-{7-[5-chloro-2-(1H-tetrazol-1-yl)phenyl]-5-oxo-1,2,3,5-tetrahydro-3-indolizinyl}-1H-imidazol-5-yl)-2(1H)-quinoxalinone The same operation as in Example 51→Example 52→Example 40→Example 41 was conducted from the compound prepared in Example 19 to give the title compound having the following physical properties. (Note: in the step corresponding to Example 51 in the operation, the compound prepared in Example 153 was used).

LC/MS $t_R$ 2.95 minutes; MS (ES$^+$) m/z 524 (M+H)$^b$ $^1$H NMR (500 MHz, DMSO-d$_6$) δ 12.17 (br. s, 1 H), 9.69 (s, 1 H), 8.15 (s, 1 H), 8.06 (d, 1 H), 7.92 (dd, 1 H), 7.82-7.76 (m, 3 H), 7.61 (s, 1 H), 7.28 (d, 1 H), 5.98 (s, 1 H), 5.95 (s, 1 H), 5.63 (dd, 1 H), 3.45-3.37 (m, 2 H), 3.02 (dd, 1 H), 2.41-2.31 (m, 1 H).

EXAMPLE 155

(3S)-7-[5-chloro-2-(1H-tetrazol-1-yl)phenyl]-3-[5-(1-methyl-1H-benzimidazol-5-yl)-1H-imidazol-2-yl]-2,3-dihydro-5(1H)-indolizinone The same operation as in Example 51→Example 39 was conducted from the compound prepared in Example 9 to give the title compound having the following physical properties. (Note: in the step corresponding to Example 51 in the operation, 2-bromo-1-(1-methyl-1H-benzimidazol-5-yl)ethanone hydrobromide was used).

LC/MS $t_R$ 2.75 minutes; MS (ES$^+$) m/z 510 (M+H)$^b$ $^1$H NMR (500 MHz, methanol-d$_4$) δ 9.37 (s, 1 H), 8.13 (s, 1 H), 7.96 (s, 1 H), 7.76-7.74 (m, 2 H), 7.71-7.69 (m, 2 H), 7.58-7.56 (m, 1 H), 7.32 (s, 1 H), 6.15 (s, 1 H), 6.12 (s, 1 H), 5.84-5.82 (m, 1 H), 3.92 (s, 3 H), 3.53-3.46 (m, 1 H), 3.16-3.11 (m, 1 H), 2.69-2.63 (m, 1 H), 2.55-2.50 (m, 1 H).

EXAMPLE 156

3-[4-chloro-5-(1-methyl-1H-benzimidazol-5-yl)-1H-imidazol-2-yl]-7-[5-chloro-2-(1H-tetrazol-1-yl)phenyl]-2,3-dihydro-5(1H)-indolizinone The same operation as in Example 84→Example 39→Example 47→Example 40→Example 41 was conducted from the compound prepared in Example 19 to give the title compound having the following physical properties. (Note: in the step corresponding to Example 84 in the operation, 2-bromo-1-(1-methyl-1H-benzimidazol-5-yl)ethanone hydrobromide was used).

LC/MS $t_R$ 3.16 minutes; MS (ES$^+$) m/z 544 (M+H)$^b$ $^1$H NMR (500 MHz, DMSO-d$_6$) δ 12.90 (br. s, 1 H), 9.71 (s, 1 H), 8.24 (s, 1 H), 7.97 (s, 1 H), 7.84-7.78 (m, 3 H), 7.68 (d, 1 H), 7.63 (d, 1 H), 6.00 (s, 1 H), 5.94 (s, 1 H), 5.59 (dd, 1 H), 3.86 (s, 3 H), 3.32-3.25 (m, 1 H), 3.00 (dd, 1 H), 2.60-2.52 (m, 1 H), 2.29-2.16 (m, 1 H).

EXAMPLE 157

(3S)-7-[5-chloro-2-(1H-tetrazol-1-yl)phenyl]-3-[5-(1H-indazol-5-yl)-1H-imidazol-2-yl]-2,3-dihydro-5(1H)-indolizinone The same operation as in Example 51→Example 39 was conducted from the compound prepared in Example 9 to give the title compound having the following physical properties. (Note: in the step corresponding to Example 51 in the operation, 2-bromo-1-(1H-indazol-5-yl)ethan-1-one [Bioorg. Med. Chem. Lett. 21(5), 1480 (2011)] was used).

LC/MS $t_R$ 2.92 minutes; MS (ES$^+$) m/z 496 (M+H)$^b$ $^1$H NMR (500 MHz, DMSO-d$_6$) δ 12.96 (s, 1 H), 12.04 (s, 1 H), 9.69 (s, 1 H), 8.07 (d, 1 H), 8.01 (d, 1 H), 7.84-7.77 (m, 3 H), 7.73 (d, 1 H), 7.50-7.43 (m, 2 H), 5.99 (s, 1 H), 5.96 (s, 1 H), 5.64 (d, 1 H), 3.38-3.27 (obs. m, 1 H), 3.02 (dd, 1 H), 2.56-2.44 (obs. m, 1 H), 2.40-2.32 (m, 1 H).

EXAMPLE 158 ethyl 4-{2-[7-(2-{[(tert-butoxy)carbonyl]amino}-5-chlorophenyl)-5-oxo-1,2,3,5-tetrahydroindolizin-3-yl]-1H-imidazol-4-yl}benzoate The same operation as in Example 84→Example 39 was conducted from the compound prepared in Example 19 to give the title compound having the following physical properties. (Note: in the step corresponding to Example 84 in the operation, ethyl 4-acetylbenzoate [Bioorg. Med. Chem. Lett. 18, 2886 (2008)] was used).

LC/MS $t_R$ 2.16 minutes; MS (ES$^+$) m/z 575 (M+H)$^a$.

EXAMPLE 159 tert-butyl N-[4-chloro-2-(3-{4-[4-(hydroxymethyl)phenyl]-1H-imidazol-2-yl}-5-oxo-1,2,3,5-tetrahydroindolizin-7-yl)phenyl]carbamate To a cooled (0° C.) tetrahydrofuran (20 mL) solution of the compound prepared in Example 158 (0.50 g) was added a 1 M solution of lithium aluminium hydride in tetrahydrofuran (1.39 mL) and the mixture stirred at 0° C. for 1 hour. To the cooled (0° C.) reaction mixture, a saturated aqueous solution of ammonium chloride (10 mL) was added followed by extraction into ethyl acetate. The combined organic layers were washed with brine, dried and concentrated to give the title compound having the following physical properties (0.30 g).

LC/MS $t_R$ 1.71 minutes; MS (ES$^+$) m/z 533 (M+H)$^a$.

EXAMPLE 160(1) AND EXAMPLE 160(2)

7-[5-chloro-2-(1H-tetrazol-1-yl)phenyl]-3-{5-[4-(hydroxymethyl)phenyl]-1H-imidazol-2-yl}-2,3-dihydro-5(1H)-indolizinone and 4-(2-{7-[5-chloro-2-(1H-tetrazol-1-yl)phenyl]-5-oxo-1,2,3,5-tetrahydro-3-indolizinyl}-1H-imidazol-5-yl)benzyl acetate The same operation as in Example 40→Example 41 was conducted from Example 159 to give the title compounds in a 2:1 ratio having the following physical properties.

EXAMPLE 160(1)

LC/MS $t_R$ 2.89 minutes; MS (ES$^+$) m/z 486 (M+H)$^b$ $^1$H NMR (250 MHz, methanol-d$_4$) δ 9.36 (s, 1 H), 7.78-7.58 (m, 5 H), 7.42-7.25 (m, 3 H), 6.12 (s, 1 H), 6.09 (s, 1 H), 5.78 (dd, 1 H), 4.59 (s, 2 H), 3.43 (dd, 1 H), 3.13 (dd, 1 H), 2.74-2.36 (m, 2 H).

EXAMPLE 160(2)

LC/MS $t_R$ 3.31 minutes; MS (ES$^+$) m/z 528 (M+H)$^b$ $^1$H NMR (500 MHz, methanol-d$_4$) δ 9.37 (s, 1 H), 7.78-7.64 (m, 5 H), 7.38 (d, 2 H), 7.37 (br, s, 1 H), 6.15 (s, 1 H), 6.11 (s, 1 H), 5.80 (dd, 1 H), 5.12 (s, 2 H), 3.53-3.41 (m, 1 H), 3.22-3.07 (m, 1 H), 2.73-2.61 (m, 1 H), 2.55-2.40 (m, 1 H), 2.10 (s, 3 H).

EXAMPLE 161 tert-butyl N-(4-chloro-2-{3-[4-(4-formylphenyl)-1H-imidazol-2-yl]-5-oxo-1,2,3,5-tetrahydroindolizin-7-yl}phenyl)carbamate To a dichloromethane (5 mL) solution of the compound prepared in Example 159 (0.39 g) was added Dess-Martin periodinane (1,1,1-Triacetoxy-1,1-dihydro-1,2-benziodoxol-3(1H)-one) (0.33 g) and the mixture stirred at room temperature for 16 hours. To the reaction mixture, a 1:1 mixture of a saturated aqueous solution of sodium hydrogen carbonate and a saturated aqueous solution of sodium sulfite was added (10 mL) and the mixture stirred at room temperature for 15 minutes followed by extraction into dichloromethane. The combined organic layers were washed with a saturated aqueous solution of sodium hydrogen carbonate, brine, dried and concentrated to obtain the title compound having the following physical properties (0.30 g).

LC/MS $t_R$ 2.04 minutes; MS (ES$^+$) m/z 531 (M+H)$^a$.

EXAMPLE 162 tert-butyl N-{4-chloro-2-[3-(4-{4-[(hydroxyimino) methyl]phenyl}-1H-imidazol-2-yl)-5-oxo-1,2,3,5-tetrahydroindolizin-7-yl]phenyl}carbamate To an ethanol (2 mL) solution of the compound prepared in Example 161 (0.15 g) was added hydroxylamine hydrochloride (15.1 mg) and 2 M sodium hydroxide (124 μL) and the mixture stirred at room temperature for 16 hours. The reaction mixture was concentrated and the residue suspended in water (5 mL) and extracted into dichloromethane. The combined organic layers were washed with brine, dried and concentrated to obtain the title compound having the following physical properties (0.15 g).

LC/MS $t_R$ 1.84 minutes; MS (ES$^+$) m/z 546 (M+H)$^a$.

EXAMPLE 163

4-(2-{(3S)-7-[5-chloro-2-(1H-tetrazol-1-yl)phenyl]-5-oxo-1,2,3,5-tetrahydro-3-indolizinyl}-1H-imidazol-5-yl)benzaldehyde oxime The same operation as in Example 40→Example 41 was conducted from the compound prepared in Example 162 to give the title compound having the following physical properties.

LC/MS $t_R$ 3.10 minutes; MS (ES$^+$) m/z 499 (M+H)$^b$ $^1$H NMR (500 MHz, methanol-d$_4$) δ 9.38 (s, 1 H), 8.09 (s, 1 H), 7.78-7.67 (m, 5 H), 7.60 (d, 2 H), 7.40 (br. s, 1 H), 6.15 (s, 1 H), 6.11 (s, 1 H), 5.80 (dd, 1 H), 3.47 (td, 1 H), 3.13 (ddd, 1 H), 2.71-2.62 (m, 1 H), 2.49 (br. s, 1 H).

EXAMPLE 164

4-(2-{(3S)-7-[5-chloro-2-(1H-1-tetrazol-1-yl)phenyl]-5-oxo-1,2,3,5-tetrahydro-3-indolizinyl}-1H-imidazol-5-yl)benzaldehyde O-methyloxime The same operation as in Example 162→Example 40→Example 41 was conducted from the compound prepared in Example 161 to give the title compound having the following physical properties. (Note: in the step corresponding to Example 162 in the operation, methoxyamine hydrochloride was used).

LC/MS $t_R$ 3.61 minutes; MS (ES$^+$) m/z 513 (M+H)$^b$ $^1$H NMR (500 MHz, methanol-d$_4$) δ 9.38 (s, 1 H), 8.09 (s, 1 H), 7.78-7.68 (m, 5 H), 7.61 (d, 2 H), 7.42 (s, 1 H), 6.15 (s, 1 H), 6.12 (s, 1 H), 5.81 (dd, 1 H), 3.95 (s, 3 H), 3.52-3.43 (m, 1 H), 3.20-3.07 (m, 1 H), 2.71-2.62 (m, 1 H), 2.53-2.46 (m, 1 H).

EXAMPLE 165

(3S)-3-[5-(4-acetylphenyl)-1H-imidazol-2-yl]-7-[5-chloro-2-(1H-tetrazol-1-yl)phenyl]-2,3-dihydro-5 (1H)-indolizinone The same operation as in Example 84→Example 39 was conducted from the compound prepared in Example 9 to give the title compound having the following physical properties. (Note: in the step corresponding to Example 84 in the operation, 1-(4-acetylphenyl)-2-bromoethan-1-one [Chem. Pharm. Bull. 40 (5), 1170 (1992)] was used).

LC/MS $t_R$ 3.48 minutes; MS (ES$^+$) m/z 498 (M+H)$^b$ $^1$H NMR (500 MHz, methanol-d$_4$) δ 9.38 (s, 1 H), 8.01 (d, 2 H), 7.85 (app. br. s, 2 H), 7.77-7.68 (m, 3 H), 7.55 (br. s, 1 H), 6.15 (s, 1 H), 6.12 (s, 1 H), 5.81 (dd, 1 H), 3.53-3.43 (m, 1 H), 3.21-3.08 (m, 1 H), 2.72-2.65 (m, 1 H), 2.62 (s, 3 H), 2.57-2.46 (m, 1 H).

EXAMPLE 166

(3S)-7-[5-chloro-2-(1H-tetrazol-1-yl)phenyl]-3-{5-[4-(1-hydroxyethyl)phenyl]-1H-imidazol-2-yl}-2,3-dihydro-5(1H)-indolizinone To a cooled (0° C.) tetrahydrofuran (2 mL) solution of the compound prepared in Example 165 (30 mg) was added sodium borohydride (1.1 mg) and the mixture stirred at room temperature for 25 minutes. To the cooled (0° C.) reaction mixture, water (10 mL) was added followed by extraction with ethyl acetate. The combined organic layers were washed with brine, dried and concentrated. The residue was purified by column chromatography (0 to 15% methanol in dichloromethane) to obtain the title compound having the following physical properties (5.5 mg)

LC/MS $t_R$ 2.97 minutes; MS (ES$^+$) m/z 500 (M+H)$^b$ $^1$H NMR (500 MHz, methanol-d$_4$) δ 9.26 (s, 1 H), 7.68-7.60 (m, 2 H), 7.58 (d, 1 H), 7.50 (app. br. s, 2 H), 7.28 (d, 2 H), 7.17 (br. s, 1 H), 6.04 (s, 1 H), 6.00 (s, 1 H), 5.68 (dd, 1 H), 4.70 (q, 1 H), 3.41-3.30 (m, 1 H), 3.07-2.96 (m, 1 H), 2.59-2.45 (m, 1 H), 2.41-2.25 (m, 1 H), 1.34 (d, 3 H).

EXAMPLE 167

2-methyl-2-propanyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)benzyl]carbamate The same operation as in Example 51→Example 39 was conducted from the compound prepared in Example 9 to give the title compound having the following physical properties. (Note: in the step corresponding to Example 51 in the operation, tert-butyl N-{[4-(2-bromoacetyl)phenyl] methyl}carbamate [Bioorg. Med. Chem. Lett. 13(20), 3557 (2003)] was used).

LC/MS $t_R$ 3.51 minutes; MS (ES$^+$) m/z 585 (M+H)$^b$

¹H NMR (500 MHz, CDCl₃) δ 8.58 (s, 1 H), 7.62 (dd, 1 H), 7.54 (d, 1 H), 7.52 (d, 1 H), 7.28 (s, 1 H), 7.27 (app. s, 4 H), 7.22 (s, 1 H), 6.31 (s, 1 H), 5.86 (d, 1 H), 5.75 (s, 1 H), 4.88 (br. s, 1 H), 4.31 (br. d, 2 H), 3.53-3.42 (m, 1 H), 3.42-3.31 (m, 1 H), 3.03 (dd, 1 H), 2.49 (quintet, 1 H), 1.47 (s, 9 H).

EXAMPLE 168

(3S)-3-{5-[4-(aminomethyl)phenyl]-1H-imidazol-2-yl}-7-[5-chloro-2-(1H-tetrazol-1-yl)phenyl]-2,3-dihydro-5(1H)-indolizinone dihydrochloride The compound prepared in Example 167 (0.19 g) was treated in accordance with Example 55 to give the title compound having the following physical properties (0.13 g).

LC/MS $t_R$ 2.46 minutes; MS (ES⁺) m/z 485 (M+H)$^b$

¹H NMR (500 MHz, DMSO-d₆) δ 9.71 (s, 1 H), 8.39 (br. s, 3 H), 8.10 (br. s, 1 H), 7.88 (d, 2 H), 7.84 (dd, 1 H), 7.82 (d, 1 H), 7.72 (d, 1 H), 7.62 (d, 2 H), 6.10 (s, 1 H), 6.00 (s, 1 H), 5.84 (dd, 1 H), 4.14-4.02 (q, 2 H), 3.34-3.24 (m, 1 H), 3.15-3.05 (m, 1 H), 2.75-2.67 (m, 1 H), 2.41-2.30 (m, 1 H).

EXAMPLE 169 methyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)benzyl]carbamate The compound prepared in Example 168 (100 mg) was treated in accordance with Example 77 to give the title compound having the following physical properties (30 mg).

LC/MS $t_R$ 3.07 minutes; MS (ES⁺) m/z 543 (M+H)$^b$

¹H NMR (500 MHz, methanol-d₄) δ 9.37 (s, 1 H), 7.80-7.59 (m, 5 H), 7.31-7.26 (m, 3 H), 6.13 (s, 1 H), 6.09 (s, 1 H), 5.80 (dd, 1 H), 4.29 (s, 2 H), 3.68 (s, 3 H), 3.51-3.41 (m, 1 H), 3.18-3.07 (m, 1 H), 2.65-2.60 (m, 1 H), 2.52-2.41 (m, 1 H).

EXAMPLE 170

N-[4-(2-{(3S)-7-[5-chloro-2-(1H-tetrazol-1-yl)phenyl]-5-oxo-1,2,3,5-tetrahydro-3-indolizinyl}-1H-imidazol-5-yl)benzyl]acetamide To a dichloromethane (3 mL) solution of the compound prepared in Example 168 (100 mg was sequentially added pyridine (29 µL) and acetic anhydride (13.6 µL) and the mixture stirred at room temperature for 4 hours. To the cooled (0° C.) reaction mixture, 1 M hydrochloric acid (6.60 mL) was added followed by extraction into dichloromethane. The combined organic layers were washed with brine, dried and concentrated. The residue was purified by column chromatography (0 to 15% methanol in dichloromethane) to obtain the title compound having the following physical properties (27.4 mg).

LC/MS $t_R$ 2.89 minutes; MS (ES⁺) m/z 527 (M+H)$^b$

¹H NMR (500 MHz, methanol-d₄) δ 9.39 (s, 1 H), 7.77-7.68 (m, 3 H), 7.63 (d, 1 H), 7.31-7.27 (m, 3 H), 6.15 (s, 1 H), 6.14 (s, 1 H), 5.81 (dd, 1 H), 4.37 (s, 2 H), 3.54-3.37 (m, 1 H), 3.22-3.07 (m, 1 H), 2.74-2.59 (m, 1 H), 2.55-2.38 (m, 1 H), 2.02 (s, 3 H).

EXAMPLE 171

N-[4-(2-{(3S)-7-[5-chloro-2-(1H-tetrazol-1-yl)phenyl]-5-oxo-1,2,3,5-tetrahydro-3-indolizinyl}-1H-imidazol-5-yl)benzyl]-2,2,2-trifluoroacetamide To a cooled (0° C.) dichloromethane (3 mL) solution of the compound prepared in Example 168 (100 mg) was sequentially added triethylamine (57 µL) and trifluoroacetic anhydride (59 µL) and the mixture stirred at 0° C. for 3 hours. To the reaction mixture water (5 mL) was added followed by extraction with dichloromethane. The combined organic layers were washed with brine, dried and concentrated. The residue was purified by high performance liquid chromatography (5 to 100% acetonitrile in 2 mM aqueous ammonium hydrogen carbonate), then triturated with a 1:1 mixture of dichloromethane and heptanes. The precipitate was collected by filtration to give the title compound having the following physical properties (2 mg).

LC/MS $t_R$ 3.35 minutes; MS (ES⁺) m/z 581 (M+H)$^b$

¹H NMR (500 MHz, methanol-d₄) δ 9.38 (s, 1 H), 7.78-7.73 (m, 2 H), 7.69 (d, 1 H), 7.67 (app. br. s, 2 H), 7.36 (br. s, 1 H), 7.33 (d, 2 H), 6.15 (s, 1 H), 6.12 (s, 1 H), 5.80 (dd, 1 H), 4.47 (s, 2 H), 3.55-3.39 (m, 1 H), 3.14 (dd, 1 H), 2.66 (dd, 1 H), 2.52-2.36 (m, 1 H).

EXAMPLE 172

1-[4-(2-{(3S)-7-[5-chloro-2-(1H-tetrazol-1-yl)phenyl]-5-oxo-1,2,3,5-tetrahydro-3-indolizinyl}-1H-imidazol-5-yl)benzyl]-3-ethylurea To a dichloromethane (3 mL) solution of the compound prepared in Example 168 (100 mg) was added ethyl isocyanate (29 µL) and the mixture stirred at room temperature for 3 hours. To the reaction mixture water (5 mL) was added followed by extraction with dichloromethane. The combined organic layers were washed with brine, dried and concentrated. The residue was purified by high performance liquid chromatography (5 to 100% acetonitrile in 2 mM aqueous ammonium hydrogen carbonate) to give the title compound having the following physical properties (8.9 mg).

LC/MS $t_R$ 2.99 minutes; MS (ES⁺) m/z 556 (M+H)$^b$

¹H NMR (500 MHz, methanol-d₄) δ 9.27 (s, 1 H), 7.68-7.62 (m, 2 H), 7.58 (d, 1 H), 7.57-7.44 (m, 2 H), 7.28-7.11 (m, 3 H), 6.04 (s, 1 H), 6.01 (s, 1 H), 5.69 (d, 1 H), 4.22 (s, 2 H), 3.40-3.29 (m, 1 H), 3.07 (q, 2 H), 3.05-2.97 (m, 1 H), 2.61-2.42 (m, 1 H), 2.34-2.19 (m, 1 H), 1.02 (t, 3 H).

EXAMPLE 173(1) TO EXAMPLE 173(23)

The compounds of the present invention having the following physical data were prepared using the corresponding alpha-bromoketones from the compound prepared in Example 9 in the process of Example 51→Example 52.

EXAMPLE 173(1)

(3S)-7-[5-chloro-2-(1H-tetrazol-1-yl)phenyl]-3-[5-(4-pyridinyl)-1H-imidazol-2-yl]-2,3-dihydro-5(1H)-indolizinone LC/MS $t_R$ 2.81 minutes; MS (ES⁺) m/z 457 (M+H)$^b$ ¹H NMR (500 MHz, DMSO-d₆) δ 12.39 (br. s, 1 H), 9.70 (s, 1 H), 8.47 (d, 2 H), 7.94-7.73 (m, 4 H), 7.64 (d, 2 H), 5.98

(s, 1 H), 5.96 (s, 1 H), 5.63 (dd, 1 H), 3.44-3.37 (m, 1 H), 3.01 (dd, 1 H), 2.55-2.52 (m, 1 H), 2.38-2.26 (m, 1 H).

EXAMPLE 173(2)

(3S)-7-[5-chloro-2-(1H-tetrazol-1-yl)phenyl]-3-[5-(3-pyridinyl)-1H-imidazol-2-yl]-2,3-dihydro-5(1H)-indolizinone LC/MS $t_R$ 2.85 minutes; MS (ES$^+$) m/z 457 (M+H)$^b$
$^1$H NMR (500 MHz, DMSO-d$_6$) δ 11.94 (br. s, 1 H), 9.70 (s, 1 H), 8.93 (s, 1 H), 8.37 (d, 1 H), 8.03 (d, 1 H), 7.84-7.77 (m, 3 H), 7.67 (br. s, 1 H), 7.34 (s, 1 H), 5.99 (s, 1 H), 5.97 (s, 1 H), 5.62 (d, 1 H), 3.45-3.36 (obs. m, 1 H), 3.00 (dd, 1 H), 2.58-2.45 (obs. m, 1 H), 2.38-2.25 (m, 1 H).

EXAMPLE 173(3)

(3S)-7-[5-chloro-2-(1H-tetrazol-1-yl)phenyl]-3-[5-(2-pyridinyl)-1H-imidazol-2-yl]-2,3-dihydro-5(1H)-indolizinone LC/MS $t_R$ 2.91 minutes; MS (ES$^+$) m/z 457 (M+H)$^b$
NMR analysis showed a 2:1 ratio of tautomers.
Major tautomer: $^1$H NMR (500 MHz, DMSO-d$_6$) δ 12.28 (br. s, 1 H), 9.70 (s, 1 H), 8.46 (d, 1 H), 7.84-7.70 (m, 5 H), 7.59 (s, 1 H), 7.16 (td, 1 H), 5.97 (app. s, 2 H), 5.65 (d, 1 H), 3.41-3.34 (m, 1 H), 3.01 (dd, 1 H), 2.57-2.44 (obs. in, 1 H), 2.38-2.31 (m, 1 H).
Minor tautomer: $^1$H NMR (500 MHz, DMSO-d$_6$) δ 12.60 (br. s, 1 H), 9.71 (s, 1 H), 8.55 (d, 1 H), 7.84-7.70 (m, 5 H), 7.46 (s, 1 H), 7.23 (dd, 1 H), 5.97 (s, 2 H), 5.95 (s, 1 H), 5.73 (d, 1 H), 3.31-3.21 (m, 1 H), 2.98 (dd, 1 H), 2.57-2.44 (obs. m, 1 H), 2.28-2.21 (m, 1 H).

EXAMPLE 173(4)

(3S)-7-[5-chloro-2-(1H-tetrazol-1-yl)phenyl]-3-[5-(1,3-thiazol-2-yl)-1H-imidazol-2-yl]-2,3-dihydro-5(1H)-indolizinone LC/MS $t_R$ 3.62 minutes; MS (ES$^+$) m/z 463 (M+H)$^b$
$^1$H NMR (500 MHz, DMSO-d$_6$) δ 12.47 (br. s, 1 H), 9.69 (s, 1 H), 7.84-7.77 (m, 3 H), 7.69 (s, 1 H), 7.65 (s, 1 H), 5.99 (s, 1 H), 5.97 (s, 1 H), 5.62 (dd, 1 H), 3.32-3.24 (obs. m, 1 H), 3.01 (dd, 1 H), 2.59-2.52 (obs. m, 1 H), 2.37-2.25 (m, 1 H).

EXAMPLE 173(5)

(3S)-7-[5-chloro-2-(1H-tetrazol-1-yl)phenyl]-3-[5-(2-pyrazinyl)-1H-imidazol-2-yl]-2,3-dihydro-5(1H)-indolizinone In the step corresponding to Example 51 in the process, 2-bromo-1-(pyrazin-2-yl)ethan-1-one [J. Med. Chem. 41(13), 2436 (1998)] was used.
LC/MS $t_R$ 3.29 minutes; MS (ES$^+$) m/z 458 (M+H)$^b$
$^1$H NMR (500 MHz, DMSO-d$_6$) δ 12.47 (br. s, 1 H), 9.69 (s, 1 H), 8.98 (app. br. s, 1 H), 8.52 (app. br. s, 1 H), 8.42 (app. br. s, 1 H), 7.82-7.78 (m, 3 H), 7.73 (br. s, 1 H), 5.97 (s, 1 H), 5.96 (s, 1 H), 5.66 (d, 1 H), 3.45-3.34 (obs. m, 1 H), 3.01 (dd, 1 H), 2.59-2.45 (obs. m, 1 H), 2.38-2.32 (m, 1 H).

EXAMPLE 173(6)

(3S)-7-[5-chloro-2-(1H-tetrazol-1-yl)phenyl]-3-[5-(2-methoxyphenyl)-1H-imidazol-2-yl]-2,3-dihydro-5(1H)-indolizinone LC/MS $t_R$ 3.23 minutes; MS (ES$^+$) m/z 486 (M+H)$^b$
$^1$H NMR (500 MHz, CDCl$_3$) δ 11.71 (br. s, 1 H), 8.53 (s, 1 H), 7.60 (dd, 1 H), 7.59 (app. hr. s, 1 H), 7.54 (d, 1 H), 7.50 (d, 1 H), 7.30 (br. s, 1 H), 7.26-7.18 (m, 1 H), 7.05-6.90 (m, 2 H), 6.31 (s, 1 H), 5.88 (d, 1 H), 5.68 (s, 1 H), 4.02 (s, 3 H), 3.54-3.26 (m, 2 H), 3.00 (dd, 1 H), 2.45 (quintet, 1 H).

EXAMPLE 173(7)

(3S)-7-[5-chloro-2-(1H-tetrazol-1-yl)phenyl]-3-[5-(3-methoxyphenyl)-1H-imidazol-2-yl]-2,3-dihydro-5(1H)-indolizinone LC/MS $t_R$ 3.31 minutes; MS (ES$^+$) m/z 486 (M+H)$^b$
NMR analysis showed a 2:1 ratio of tautomers.
Major tautomer: $^1$H NMR (500 MHz, CDCl$_3$) δ 10.77 (br. s, 1 H), 8.54 (s, 1 H), 7.61 (d, 1 H), 7.54 (d, 1 H), 7.51 (br. s, 1 H), 7.37-6.96 (m, 4 H), 6.79 (d, 1 H), 6.32 (s, 1 H), 5.83 (d, 1 H), 5.70 (s, 1 H), 3.86 (s, 3 H), 3.53-3.25 (m, 2 H), 3.06-2.95 (m, 1 H), 2.53-2.40 (m, 1 H).
Minor tautomer: $^1$H NMR (500 MHz, CDCl$_3$) δ 11.16 (br. s, 1 H), 8.54 (s, 1 H), 7.61 (d, 1 H), 7.54 (d, 1 H), 7.51 (br. s, 1 H), 7.37-6.96 (m, 4 H), 6.82 (d, 1 H), 6.36 (s, 1 H), 5.87 (d, 1 H), 5.70 (s, 1 H), 3.84 (s, 3 H), 3.53-3.25 (m, 2 H), 3.06-2.95 (m, 1 H), 2.53-2.40 (m, 1 H).

EXAMPLE 173(8)

(3S)-7-[5-chloro-2-(1H-tetrazol-1-yl)phenyl]-3-[5-(4-methoxyphenyl)-1H-imidazol-2-yl]-2,3-dihydro-5(1H)-indolizinone LC/MS $t_R$ 3.17 minutes; MS (ES$^+$) m/z 486 (M+H)$^b$
NMR analysis showed a 3:2 ratio of tautomers.
Major tautomer: $^1$H NMR (500 MHz, CDCl$_3$) δ 10.68 (br. s, 1 H), 8.53 (s, 1 H), 7.68 (d, 2 H), 7.62 (d, 1 H), 7.54 (d, 1 H), 7.51 (s, 1 H), 7.17 (s, 1 H), 6.96-6.86 (m, 2 H), 6.32 (s, 1 H), 5.90-5.80 (m, 1 H), 5.69 (s, 1 H), 3.83 (s, 3 H), 3.54-3.27 (m, 2 H), 3.07-2.96 (m, 1 H), 2.46 (quintet, 1 H).
Minor tautomer: $^1$H NMR (500 MHz, CDCl$_3$) δ 11.02 (br. s, 1 H), 8.53 (s, 1 H), 7.62 (d, 1 H), 7.54 (d, 1 H), 7.51 (s, 1 H), 7.42 (d, 1 H), 7.11 (s, 1 H), 6.96-6.86 (m, 2 H), 6.36 (s, 1 H), 5.90-5.80 (m, 1 H), 5.69 (s, 1 H), 3.83 (s, 3 H), 3.54-3.27 (m, 2 H), 3.07-2.96 (m, 1 H), 2.46 (quintet, 1 H).

EXAMPLE 173(9)

(3S)-7-[5-chloro-2-(1H-tetrazol-1-yl)phenyl]-3-[5-(3-fluorophenyl)-1H-imidazol-2-yl]-2,3-dihydro-5(1H)-indolizinone LC/MS $t_R$ 3.59 minutes; MS (ES$^+$) m/z 474 (M+H)$^b$
$^1$H NMR (500 MHz, DMSO-d$_6$) δ 12.21 (br. s, 1 H), 9.68 (s, 1 H), 7.84-7.74 (m, 3 H), 7.60 (s, 1 H), 7.54 (d, 1 H), 7.48 (dd, 1 H), 7.35 (dd, 1 H), 6.96 (td, 1 H), 5.97 (s, 1 H), 5.96 (s, 1 H), 5.62 (dd, 1 H), 3.44-3.36 (m, 1 H), 3.00 (dd, 1 H), 2.60-2.45 (obs. m, 1 H), 2.38-2.30 (m, 1 H).

EXAMPLE 173(10)

(3S)-7-[5-chloro-2-(1H-tetrazol-1-yl)phenyl]-3-[5-(4-fluorophenyl)-1H-imidazol-2-yl]-2,3-dihydro-5(1H)-indolizinone LC/MS $t_R$ 3.38 minutes; MS (ES$^+$) m/z 474 (M+H)$^b$
$^1$H NMR (500 MHz, DMSO-d$_6$) δ 2.11 (br. s, 1 H), 9.69 (s, 1 H), 7.82-7.76 (m, 3 H), 7.72 (dd, 2 H), 7.49 (s, 1 H), 7.14 (t, 2 H), 5.97 (s, 1 H), 5.96 (s, 1 H), 5.63 (dd, 1 H), 3.47-3.35 (obs. m, 1 H), 3.01 (dd, 1 H), 2.57-2.44 (obs. m, 1 H), 2.40-2.28 (m, 1 H).

EXAMPLE 173(11)

(3S)-7-[5-chloro-2-(1H-tetrazol-1-yl)phenyl]-3-[5-(2,4-dimethyl-1,3-oxazol-5-yl)-1H-imidazol-2-yl]-2,3-dihydro-5(1H)-indolizinone LC/MS $t_R$ 3.36 minutes; MS (ES$^+$) m/z 475 (M+H)$^b$
$^1$H NMR (500 MHz, CDCl$_3$) δ 10.97 (br. s, 1 H), 8.57 (s, 1 H), 7.60 (dd, 1 H), 7.53 (s, 1 H), 7.49 (d, 1 H), 7.09 (d, 1 H), 6.29 (s, 1 H), 5.81 (d, 1 H), 5.72 (s, 1 H), 3.50-3.37 (m, 1 H), 3.34 (dd, 1 H), 3.00 (dd, 1 H), 2.51-2.44 (m, 1 H), 2.43 (s, 3 H), 2.33 (s, 3 H).

EXAMPLE 173(12)

(3S)-7-[5-chloro-2-(1H-tetrazol-1-yl)phenyl]-3-[5-(4-pyrimidinyl)-1H-imidazol-2-yl]-2,3-dihydro-5(1H)-indolizinone In the step corresponding to Example 51 in the process, 2-bromo-1-(pyrimidin-4-yl)ethan-1-one [J. Med. Chem., 51(3), 487 (2008)] was used.
LC/MS $t_R$ 3.33 minutes; MS (ES$^+$) m/z 458 (M+H)$^b$
$^1$H NMR (500 MHz, acetone-d$_6$) δ 11.59 (br. s, 1 H), 9.30 (s, 1 H), 8.98 (br. s, 1 H), 8.68 (d, 1 H), 7.88 (s, 1 H), 7.91 (s, 1 H), 7.78 (s, 2 H), 7.72 (s, 1 H), 6.12 (br. s, 1 H), 5.94 (s, 1 H), 5.83 (d, 1 H), 3.51-3.35 (m, 1 H), 3.12 (m, 1 H), 3.00 (m, 1 H), 2.62-2.53 (m, 1 H).

EXAMPLE 173(13)

(3S)-7-[5-chloro-2-(1H-tetrazol-1-yl)phenyl]-3-[5-(2-fluorophenyl)-1H-imidazol-2-yl]-2,3-dihydro-5(1H)-indolizinone LC/MS $t_R$ 3.58 minutes; MS (ES$^+$) m/z 475 (M+H)$^b$
$^1$H NMR (500 MHz, acetone-d$_6$) δ 11.35 (br. s, 1 H), 9.30 (s, 1 H), 8.17 (m, 1 H), 7.77 (s, 2 H), 7.73 (s, 1 H), 7.52 (m, 1 H), 7.25 (m, 2 H), 7.15 (m, 1 H), 6.12 (s, 1 H), 5.95 (s, 1 H), 5.85 (m, 1 H), 3.47 (m, 1 H), 3.15-3.10 (m, 1 H), 3.10-3.05 (m, 1 H), 2.6-2.5 (m, 1 H).

EXAMPLE 173(14)

(3S)-3-[5-(4-chlorophenyl)-1H-imidazol-2-yl]-7-[5-chloro-2-(1H-tetrazol-1-yl)phenyl]-2,3-dihydro-5(1H)-indolizinone LC/MS $t_R$ 3.71 minutes; MS (ES$^+$) m/z 492 (M+H)$^b$
$^1$H NMR (500 MHz, acetone-d$_6$) δ 11.25 (br. s, 1 H), 9.30 (s, 1 H), 7.85 (s, 1 H), 7.80 (d, 1 H), 7.75 (s, 2 H), 7.70 (s, 1 H), 7.55 (s, 1 H), 7.35 (d, 2 H), 6.10 (s, 1 H), 5.95 (s, 1 H), 5.78 (m, 1 H), 3.50-3.45 (m, 1 H), 3.15-3.10 (m, 1 H), 3.10-3.05 (m, 1 H), 2.6-2.5 (m, 1 H).

EXAMPLE 173(15)

(3S)-3-[5-(3-chlorophenyl)-1H-imidazol-2-yl]-7-[5-chloro-2-(1H-1-tetrazol-1-yl)phenyl]-2,3-dihydro-5(1H)-indolizinone LC/MS $t_R$ 3.81 minutes; MS (ES$^+$) m/z 492 (M+H)$^b$
$^1$H NMR (500 MHz, acetone-d$_6$) δ 11.32 (br. s, 1 H), 9.30 (s, 1 H), 7.85 (s, 1 H), 7.78-7.70 (m, 3 H), 7.73 (s, 1 H), 7.62 (s, 1 H), 7.35 (m, 1 H), 7.18 (m, 1 H), 6.10 (s, 1 H), 5.95 (s, 1 H), 5.78 (m, 1 H), 3.50-3.45 (m, 1 H), 3.15-3.10 (m, 1 H), 3.10-3.05 (m, 1 H), 2.6-2.5 (m, 1 H).

EXAMPLE 173(16)

(3S)-3-[5-(2-chlorophenyl)-1H-imidazol-2-yl]-7-[5-chloro-2-(1H-tetrazol-1-yl)phenyl]-2,3-dihydro-5(1H)-indolizinone LC/MS $t_R$ 3.64 minutes; MS (ES$^+$) m/z 492 (M+H)$^b$
$^1$H NMR (500 MHz, acetone-d$_6$) δ 11.30 (br. s, 1 H), 9.25 (s, 1 H), 8.20 (d, 1 H), 7.80 (s, 1 H), 7.75 (s, 2 H), 7.70 (s, 1 H), 7.38 (d, 1 H), 7.35 (t, 1 H), 7.18 (t, 1 H), 6.10 (s, 1 H), 5.92 (s, 1 H), 5.88 (d, 1 H), 3.50-3.45 (m, 1 H), 3.15-3.10 (m, 1 H), 3.10-3.05 (m, 1 H), 2.6-2.5 (m, 1 H).

EXAMPLE 173(17)

(3S)-7-[5-chloro-2-(1H-tetrazol-1-yl)phenyl]-3-{5-[4-(methylthio)phenyl]-1H-imidazol-2-yl}-2,3-dihydro-5(1H)-indolizinone LC/MS $t_R$ 3.33 minutes; MS (ES$^+$) m/z 502 (M+H)$^b$
$^1$H NMR (500 MHz, DMSO-d$_6$) δ 12.13 (br. s, 1 H), 9.69 (s, 1 H), 7.84-7.75 (m, 3 H), 7.63 (d, 2 H), 7.46 (br. s, 1 H), 7.23 (d, 2 H), 5.97 (s, 1 H), 5.95 (s, 1 H), 5.62 (dd, 1 H), 3.43-3.27 (obs. m, 1 H), 3.00 (dd, 1 H), 2.56-2.48 (obs. m, 1 H), 2.47 (s, 3 H), 2.38-2.22 (m, 1 H).

EXAMPLE 173(18)

(3S)-7-[5-chloro-2-(1H-tetrazol-1-yl)phenyl]-3-[5-(4-methylphenyl)-1H-imidazol-2-yl]-2,3-dihydro-5(1H)-indolizinone LC/MS $t_R$ 3.36 minutes; MS (ES$^+$) m/z 471 (M+H)$^b$
$^1$H NMR (500 MHz, CDCl$_3$) δ 11.07 (br. s, 0.45 H), 10.70 (br. s. 0.55 H), 8.53 (br. s, 1 H), 7.59-7.66 (m, 2 H), 7.53-7.56 (m, 1 H), 7.51 (m, 1 H), 7.38 (d, 1 H), 7.15-7.23 (m, 3 H), 6.37 (s, 0.45 H), 6.32 (s, 0.55 H), 5.87 (d, 0.45 H), 5.84 (d, 0.55 H), 5.69 (br. s, 1 H), 3.29-3.52 (m, 2 H), 3.01 (dd, 1 H), 2.51-2.41 (m, 1 H), 2.36 (br. s, 1.35 H), 2.35 (s, 1.65 H).

EXAMPLE 173(19)

4-(2-{(3S)-7-[5-chloro-2-(1H-tetrazol-1-yl)phenyl]-5-oxo-1,2,3,5-tetrahydro-3-indolizinyl}-1H-imidazol-5-yl)benzonitrile LC/MS $t_R$ 3.71 minutes; MS (ES$^+$) m/z 481 (M+H)$^b$
$^1$H NMR (500 MHz, acetone-d$_6$) δ 11.40 (br. s, 1 H), 9.30 (s, 1 H), 8.00 (d, 2 H), 7.75 (m, 2 H), 7.70 (m, 2 H), 6.10 (s, 1 H), 5.95 (s, 1 H), 5.80 (d, 1 H), 3.50-3.45 (m, 1 H), 3.15-3.10 (m, 1 H), 3.05-2.55 (m, 1 H), 2.6-2.5 (m, 1 H).

EXAMPLE 173(20)

3-(2-{(3S)-7-[5-chloro-2-(1H-tetrazol-1-yl)phenyl]-5-oxo-1,2,3,5-tetrahydro-3-indolizinyl}-1H-imidazol-5-yl)benzonitrile LC/MS $t_R$ 3.61 minutes; MS (ES$^+$) m/z 481 (M+H)$^b$
$^1$H NMR (500 MHz, methanol-d$_4$) δ 9.36 (s, 1 H), 8.06 (br. s, 1 H), 8.01 (d, 1 H), 7.75-7.72 (m, 2 H), 7.70-7.67 (m, 1 H), 7.59-7.49 (m, 3 H), 6.13 (s, 1 H), 6.10 (s, 1 H), 5.78 (dd, 1 H), 3.52-3.43 (m, 1 H), 3.12 (ddd, 1 H), 2.69-2.60 (m, 1 H), 2.52 (br. s, 1 H).

EXAMPLE 173(21)

(3S)-7-[5-chloro-2-(1H-tetrazol-1-yl)phenyl]-3-{5-[3-(trifluoromethyl)phenyl]-1H-imidazol-2-yl}-2,3-dihydro-5(1H)-indolizinone LC/MS $t_R$ 4.12 minutes; MS (ES$^+$) m/z 525 (M+H)$^b$
$^1$H NMR (500 MHz, CDCl$_3$) δ 10.86 (br. s, 1 H), 8.53 (s, 1 H), 8.03 (s, 1 H), 7.86-7.96 (m, 1 H), 7.44-7.74 (m, 5 H), 7.33 (d, 1 H), 6.33 (s, 1 H), 5.85 (d, 1 H), 5.72 (s, 1 H), 3.35-3.56 (m, 2 H), 2.93-3.08 (m, 1 H), 2.40-2.57 (m, 1 H).

EXAMPLE 173(22)

(3S)-7-[5-chloro-2-(1H-tetrazol-1-yl)phenyl]-3-[5-(3-hydroxyphenyl)-1H-imidazol-2-yl]-2,3-dihydro-5(1H)-indolizinone LC/MS $t_R$ 2.96 minutes; MS (ES$^+$) m/z 472 (M+H)$^b$
$^1$H NMR (500 MHz, methanol-d$_4$) δ 9.37 (s, 1 H), 7.76-7.72 (m, 2 H), 7.71-7.67 (m, 1 H), 7.24 (s, 1 H), 7.20-7.15 (m, 1 H), 7.14-7.06 (m, 2 H), 6.68 (td, 1 H), 6.14 (s, 1 H), 6.10 (s, 1 H), 5.79 (dd, 1 H), 3.50-3.40 (m, 1 H), 3.11 (ddd, 1 H), 2.69-2.59 (m, 1 H), 2.51-2.41 (m, 1 H).

EXAMPLE 173(23)

(3S)-7-[5-chloro-2-(1H-tetrazol-1-yl)phenyl]-3-[5-(3-nitrophenyl)-1H-imidazol-2-yl]-2,3-dihydro-5(1H)-indolizinone In the step corresponding to Example 51 in the process, 2-bromo-1-(3-nitrophenyl)ethan-1-one [patent W2010032010] was used.
LC/MS $t_R$ 4.03 minutes; MS (ES$^+$) m/z 501 (M+H)$^b$
$^1$H NMR (500 MHz, CDCl$_3$) δ 10.95 (br. s, 1 H), 8.60 (s, 1 H), 8.55 (s, 1 H), 8.05 (d, 2 H), 7.65 (m, 1 H), 7.60-7.50 (m, 3 H), 7.48 (s, 1 H), 6.35 (s, 1 H), 5.85 (d, 1 H), 5.72 (s, 1 H), 3.52-3.42 (m, 2 H), 3.10-3.02 (dd, 1 H), 2.55-2.45 (m, 1 H).

EXAMPLE 174

2-bromo-1-(1-methyl-1H-pyrazol-4-yl)ethan-1-one

A suspension of 1-methyl-1H-pyrazole-4-carboxylic acid (0.25 g) in thionyl chloride (4 mL) was stirred at reflux for 30 minutes. The reaction was concentrated, the residue azeotroped with toluene and dissolved in acetonitrile (5 mL). To the cooled (0° C.) solution, a 2 M solution of (trimethylsilyl)diazomethane in hexanes (1.5 mL) was added and the mixture stirred at 0° C. for 1 hour. A solution of 33 wt. % hydrogen bromide in acetic acid (1.0 mL) was added and the mixture stirred at room temperature for a further 80 minutes. To the reaction mixture, tert-butyl methyl ether (20 mL) was added and the resultant precipitate isolated by filtration to give the title product having the following physical properties (0.22 g).
LC/MS $t_R$ 1.23 minutes; MS (ES$^+$) m/z 203 and 205 (M+H)$^a$.

EXAMPLE 175

(3S)-7-[5-chloro-2-(1H-tetrazol-1-yl)phenyl]-3-[5-(1-methyl-1H-pyrazol-4-yl)-1H-imidazol-2-yl]-2,3-dihydro-5(1H)-indolizinone The same operation as in Example 51→Example 52 was conducted from the compound prepared in Example 9 to give the title compound having the following physical properties. (Note: in the step corresponding to Example 51 in the operation, the compound prepared in Example 174 was used).
LC/MS $t_R$ 2.79 minutes; MS (ES$^+$) m/z 460 (M+H)$^b$
$^1$H NMR (500 MHz, DMSO-d$_6$) δ 11.94 (br. s, 1 H), 9.74 (s, 1 H), 7.89-7.82 (m, 4 H), 7.62 (s, 1 H), 7.17 (s, 1 H), 5.98 (s, 1 H), 5.96 (s, 1 H), 5.58 (dd, 1 H), 3.87 (s, 3 H), 3.40-3.27 (obs. m, 1 H), 3.04 (dd, 1 H), 2.64-2.46 (obs. m, 1 H), 2.45-2.34 (m, 1 H).

EXAMPLE 176 methyl N-[3-bromo-5-(2-bromoacetyl)thiophen-2-yl]carbamate

To a dichloromethane (15 mL) suspension of 5-acetylthiophene-2-carboxylic acid (1.0 g) was added sequentially oxalyl chloride (0.32 mL) and N,N-dimethylformamide (15 μL) and the mixture stirred at room temperature for 2 hours. The reaction mixture was concentrated and the residue dissolved in acetone (6 mL). To the mixture a solution of sodium azide (0.50 g) in water (2 mL) was added and the reaction stirred at room temperature for 30 minutes. The resultant precipitate was isolated by filtration, dissolved in toluene (80 mL) and the mixture refluxed for 1 hour. Methanol (10 mL) was added at room temperature and the mixture stirred at room temperature for a further hour, then concentrated to approximately 30 mL. The resultant precipitate was collected by filtration to give the title compound having the following physical properties (0.56 g).
LC/MS $t_R$ 1.38 minutes; MS (ES$^+$) m/z 200 (M+H)$^a$.

EXAMPLE 177 methyl N-[3-bromo-5-(2-bromoacetyl)thiophen-2-yl]carbamate

The compound prepared in Example 176 (0.46 g) was treated as detailed in Example 91 to give the title compound having the following physical properties (0.68 g).
LC/MS $t_R$ 1.84 minutes; MS (ES$^+$) m/z 356, 358, 360 (M+H)$^a$.

EXAMPLE 178 methyl N-[5-(2-azidoacetyl)-3-bromothiophen-2-yl]carbamate

To an N,N-dimethylformamide (15 mL) solution of the compound prepared in Example 177 (0.68 g) was added sodium azide (0.25 g) and the mixture stirred at room temperature for 1 hour. To the reaction mixture, water (100 mL) was added followed by extraction with ethyl acetate. The combined organic layers were dried and concentrated to give the title compound having the following physical properties (0.51 g).

LC/MS $t_R$ 1.81 minutes; MS (ES$^+$) m/z 319 and 321 (M+H)$^a$.

EXAMPLE 179 methyl N-[5-(2-aminoacetyl)thiophen-2-yl]carbamate hydrochloride

To an ethanol (25 mL) solution of the compound prepared in Example 178 (0.51 g) was sequentially added 2 M hydrochloric acid (1.60 mL) and 5% palladium-carbon (0.10 g) and the mixture was stirred under an atmosphere of hydrogen for 16 hours. The reaction mixture was filtered through Celite® and the filtrate concentrated. The residue was dissolved in water (15 mL) and washed with ethyl acetate. The aqueous layer was concentrated to give the title compound as the hydrochloride salt having the following physical properties (0.28 g).

$^1$H NMR (500 MHz, DMSO-d$_6$) δ 11.52 (br. s, 1 H), 7.88 (d, 1 H), 6.69 (d, 1 H), 4.39 (s, 2 H), 3.77 (s, 3 H).

EXAMPLE 180 methyl N-{5-[2-({7-[5-chloro-2-(1H-1,2,3,4-tetrazol-1-yl)phenyl]-5-oxo-1,2,3,5-tetrahydroindolizin-3-yl}formamido)acetyl]thiophen-2-yl}carbamate To an N,N-dimethylformamide (1 mL) solution of the compound prepared in Example 179 (0.15 g) and the compound prepared in Example 17 (0.20 g) was sequentially added O-(7-azabenzotriazol-1-yl)-N,N,N',N'-tetramethyluronium hexafluorophosphate (0.23 g) and diisopropylethylamine (0.29 mL) and the mixture stirred at room temperature for 3 hours. To the reaction mixture, water (15 mL) was added followed by extraction into ethyl acetate. The combined organic layers were washed with brine, dried and concentrated. The residue was triturated in ethyl acetate and the precipitate collected by filtration to give the title compound having the following physical properties (0.095 g).

LC/MS $t_R$ 1.70 minutes; MS (ES$^+$) m/z 554 (M+H)$^a$.

EXAMPLE 181 methyl[5-(2-{7-[5-chloro-2-(1H-tetrazol-1-yl)phenyl]-5-oxo-1,2,3,5-tetrahydro-3-indolizinyl}-1H-imidazol-5-yl)-2-thienyl]carbamate To a toluene (3 mL) suspension of the compound prepared in Example 180 (95 mg) was sequentially added glacial acetic acid (0.30 mL) and ammonium acetate (93 mg) and the mixture stirred at reflux for 40 minutes. Further ammonium acetate (62 mg) was added and the mixture stirred at reflux for 50 minutes. To the cooled (room temperature) reaction mixture, a saturated aqueous solution of sodium hydrogen carbonate (15 mL) was added followed by extraction into ethyl acetate. The combined organic layers were washed with brine, dried and concentrated. The residue was purified by high performance liquid chromatography (5 to 100% acetonitrile in water) to give the title compound having the following physical properties (14 mg).

LC/MS $t_R$ 3.18 minutes; MS (ES$^+$) m/z 535 (M+H)$^b$ $^1$H NMR (500 MHz, methanol-d$_4$) δ 9.38 (s, 1 H), 7.78-7.73 (m, 2 H), 7.70 (d, 1 H), 7.09 (br. s, 1 H), 6.96 (d, 1 H), 6.50 (d, 1 H), 6.14 (s, 1 H), 6.10 (s, 1 H), 5.76 (dd, 1 H), 3.78 (s, 3 H), 3.50-3.41 (m, 1 H), 3.11 (ddd, 1 H), 2.67-2.59 (m, 1H), 2.48 (app. br. s, 1 H).

EXAMPLE 182(1) and 182(2)

2-({[4-(bromoacetyl)cyclohexyl]carbamoyl}oxy)-2-methylpropylidyne and 2-({[4-(chloroacetyl)cyclohexyl]carbamoyl}oxy)-2-methylpropylidyne To a dichloromethane (100 mL) solution of 4-{[(tert-butoxy)carbonyl]amino}cyclohexane-1-carboxylic acid [Eur. J. Med. Chem. 36(3), 265 (2001)] (2.80 g) was added 1-chloro-N,N,2-trimethyl-1-propenylamine (3.05 mL) and the mixture stirred at room temperature for 1 hour. To the cooled (0° C.) reaction mixture, a 2 M solution of (trimethylsilyl)diazomethane in hexanes (11.5 mL) was added and the mixture stirred at room temperature for 16 hours. The reaction was cooled (0° C.) and a solution of 48 wt. % hydrogen bromide in water (0.86 mL) was added and the mixture stirred at room temperature for 1 hour. A saturated aqueous solution of sodium hydrogen carbonate (50 mL) was added followed by extraction into ethyl acetate. The combined organic layers were washed with brine, dried and concentrated. The residue was triturated with a 1:2 mixture of ethyl acetate and heptanes and the resultant solid isolated via filtration to give the title compounds in a 1:1 ratio having the following physical properties (2.13 g).

EXAMPLE 182(1)

LC/MS $t_R$ 1.99 minutes; MS (ES$^+$) m/z 264 and 266 [M-C(CH$_3$)$_3$+H]$^a$.

EXAMPLE 182(2)

LC/MS $t_R$ 1.95 minutes; MS (ES$^+$) m/z 220 [M-C(CH$_3$)$_3$+H]$^a$.

EXAMPLE 183

2-methyl-2-propanyl[trans-4-(2-{(3S)-7-[5-chloro-2-(1H-tetrazol-1-yl)phenyl]-5-oxo-1,2,3,5-tetrahydro-3-indolizinyl}-1H-imidazol-5-yl)cyclohexyl]carbamate The same operation as in Example 178→Example 179→Example 180→Example 181 was conducted from the 1:1 mixture of compounds prepared in Example 182 to give the title compound having the following physical properties. (Note: in the step corresponding to Example 180 in the operation, the compound prepared in Example 9 was used).

LC/MS $t_R$ 3.27 minutes; MS (ES$^+$) m/z 577 (M+H)$^b$

NMR analysis showed a 2:1 ratio of tautomers.

Major tautomer: $^1$H NMR (500 MHz, methanol-d$_4$) δ 9.36 (s, 1 H), 7.78-7.70 (m, 2 H), 7.68 (d, 1 H), 6.65 (s, 1 H), 6.58 (br. s, 1 H), 6.10 (s, 1 H), 6.07 (s, 1 H), 5.71 (app. d, 1 H), 3.59 (br. s, 1 H), 3.43-3.31 (obs. m, 1 H), 3.12-3.02 (m, 1 H), 2.64-2.53 (m, 1 H), 2.49 (t, 1 H), 2.44-2.33 (m, 1 H), 2.07-1.92 (m, 4 H), 1.82-1.62 (m, 2 H), 1.44 (s, 9 H), 1.36-1.25 (m, 2 H).

Minor tautomer: $^1$H NMR (500 MHz, methanol-d$_4$) δ 9.36 (s, 1 H), 7.78-7.70 (m, 2 H), 7.68 (d, 1 H), 6.71 (s, 1 H), 6.58 (br. s, 1 H), 6.10 (s, 1 H), 6.09 (s, 1 H), 5.71 (app. d, 1 H), 3.65 (br. s, 1 H), 3.43-3.31 (obs. m, 1 H), 3.12-3.02 (m, 1 H), 2.75-2.64 (m, 1 H), 2.64-2.53 (m, 1 H), 2.44-2.33 (m, 1 H), 2.07-1.92 (m, 4 H), 1.82-1.62 (m, 2 H), 1.44 (s, 9 H), 1.36-1.25 (m, 2 H).

EXAMPLE 184

(3S)-3-[5-(trans-4-aminocyclohexyl)-1H-imidazol-2-yl]-7-[5-chloro-2-(1H-tetrazol-1-yl)phenyl]-2,3-dihydro-5(1H)-indolizinone The compound prepared in Example 183 (0.32 g) was treated as detailed in Example 40 to give the title compound having the following physical properties (0.15 g).
LC/MS $t_R$ 2.28 minutes; MS (ES$^+$) m/z 477 (M+H), 239 [(M+2H)/2]$^b$
$^1$H NMR (500 MHz, methanol-d$_4$) δ 9.35 (s, 1 H), 7.77-7.70 (m, 2 H), 7.67 (d, 1 H), 6.64 (br. s, 1 H), 6.10 (s, 1 H), 6.08 (s, 1 H), 5.70 (dd, 1 H), 3.42-3.32 (m, 1 H), 3.08 (dd, 1 H), 2.70 (tt, 1 H), 2.62-2.54 (m, 1 H), 2.54-2.45 (m, 1 H), 2.43-2.34 (m, 1 H), 2.09-1.91 (m, 4 H), 1.43 (ddt, 2 H), 1.28 (ddd, 2 H).

EXAMPLE 185 methyl[trans-4-(2-{(3S)-7-[5-chloro-2-(1H-tetrazol-1-yl)phenyl]-5-oxo-1,2,3,5-tetrahydro-3-indolizinyl}-1H-imidazol-5-yl)cyclohexyl]carbamate The compound prepared in Example 184 (78 mg) was treated as detailed in Example 128 to give the title compound having the following physical properties (19 mg). (Note: in the step corresponding to Example 128 in the operation, methyl chloroformate was used).
LC/MS $t_R$ 2.92 minutes; MS (ES$^+$) m/z 535 (M+H)$^b$
$^1$H NMR (500 MHz, methanol-d$_4$) δ 9.38 (s, 1 H), 7.79-7.72 (m, 2 H), 7.70 (d, 1 H), 6.68 (br, s, 1 H), 6.12 (s, 1 H), 6.10 (s, 1 H), 5.72 (dt, 1 H), 3.71 (br. s, 1 H), 3.63 (s, 3 H), 3.45-3.35 (m, 2 H), 3.13-3.04 (m, 1 H), 2.64-2.54 (m, 1 H), 2.41 (br. s, 1 H), 2.10-1.97 (m, 2 H), 1.80 (br. s, 2 H), 1.71 (br. s, 2 H), 1.40-1.29 (m, 2 H).

EXAMPLE 186

(3S)-3-[5-(trans-4-aminocyclohexyl)-4-chloro-1H-imidazol-2-yl]-7-[5-chloro-2-(1H-tetrazol-1-yl)phenyl]-2,3-dihydro-5(1H)-indolizinone The same operation as in Example 44→Example 40 was conducted from the compound prepared in Example 183 to give the title compound having the following physical properties.
LC/MS $t_R$ 2.94 minutes; MS (ES$^+$) m/z 511 (M+H), 255.5 [(M+2H)/2]$^b$
$^1$H NMR (500 MHz, methanol-d$_4$) δ 9.38 (s, 1 H), 7.78-7.72 (m, 2 H), 7.70 (d, 1 H), 6.11 (s, 1 H), 6.10 (s, 1 H), 5.65 (dd, 1 H), 3.48-3.35 (m, 1 H), 3.08 (ddd, 1 H), 2.75 (tt, 1 H), 2.68 (tt, 1 H), 2.64-2.54 (m, 1 H), 2.33 (ddt, 1 H), 2.01 (br. d, 2 H), 1.93-1.84 (m, 2 H), 1.68-1.56 (m, 2 H), 1.37-1.24 (m, 2 H).

EXAMPLE 187

2-{[(4-methoxyphenyl)methyl]amino}pyridine-4-carbonitrile

A mixture of 4-cyano-2-fluoropyridine (1.0 g) and 4-methoxybenzylamine (2.25 g) was stirred at 100° C. for 1 hour and purified by column chromatography (0 to 50% ethyl acetate in heptanes) to give the title compound having the following physical properties (1.69 g).
LC/MS $t_R$ 1.81 minutes; MS (ES$^+$) m/z 240 (M+H)$^a$.

EXAMPLE 188

1-(2-{[(4-methoxyphenyl)methyl]amino}pyridin-4-yl)ethan-1-one

To a diethyl ether (25 mL) solution of the compound prepared in Example 187 (0.8 g) was added a 1.4 M solution of methyl magnesium bromide in 3:1 toluene tetrahydrofuran (7.2 mL) and the mixture stirred at room temperature for 16 hours. To the reaction mixture, a saturated aqueous solution of ammonium chloride (10 mL) was added followed by 6 M hydrochloric acid (5 mL) and the mixture stirred at room temperature for 1 hour. The mixture was then basified to pH 12 by addition of 2 M sodium hydroxide and extracted into ethyl acetate. The combined organic layers were washed with brine, dried and concentrated to give the title compound having the following physical properties (0.47 g).
LC/MS $t_R$ 1.35 minutes; MS (ES$^+$) m/z 257 (M+H)$^a$.

EXAMPLE 189

1-(2-aminopyridin-4-yl)-2-bromoethan-1-one dihydrobromide

To a glacial acetic acid (7 mL) solution of the compound prepared in Example 188 (0.38 g) was sequentially added 33 wt. % hydrogen bromide in acetic acid (1.28 mL) and bromine (76 µL) and the mixture stirred at 70° C. for 2 hours. The reaction mixture was concentrated and the residue triturated with dichloromethane (10 mL). The precipitate formed was isolated by filtration to give the title compound having the following physical properties (0.38 g).
$^1$H NMR (500 MHz, methanol-d$_4$) δ 7.88-7.83 (m, 1 H), 7.24 (d, 1 H), 7.01 (dd, 1 H), 3.71 (d, 1 H), 3.64 (d, 1 H).

EXAMPLE 190

(3S)-3-[5-(2-amino-4-pyridinyl)-1H-imidazol-2-yl]-7-[5-chloro-2-(1H-tetrazol-1-yl)phenyl]-2,3-dihydro-5(1H)-indolizinone The same operation as in Example 51→Example 52 was conducted from the compound prepared in Example 9 to give the title compound having the following physical properties. (Note: in the step corresponding to Example 51 in the operation, the compound prepared in Example 189 was used).
LC/MS $t_R$ 2.85 minutes; MS (ES$^+$) m/z 472 (M+H)$^b$
$^1$H NMR (500 MHz, methanol-d$_4$) δ 9.39 (s, 1 H), 7.85 (d, 1 H), 7.78-7.74 (m, 2 H), 7.73-7.69 (m, 1 H), 7.52 (br. s, 1 H), 6.96-6.88 (m, 2 H), 6.17 (s, 1 H), 6.11 (s, 1 H), 5.80 (dd, 1 H), 3.50-3.41 (m, 1 H), 3.13 (ddd, 1 H), 2.70-2.61 (m, 1 H), 2.51-2.43 (m, 1 H).

EXAMPLE 191

2-bromo-1-(6-nitropyridin-3-yl)ethanone

To a stirred solution of 1-(6-nitropyridin-3-yl)ethan-1-one [patent WO2010089292, page 71] (0.83 g) in tetrahydrofuran (10 mL) was added N-bromosuccinimide (1.78 g) and the mixture stirred at 50° C. for 16 hours. The reaction mixture was concentrated and the residue purified by column chromatography (20 to 100% ethyl acetate in dichloromethane) giving the title compound having the following physical properties.

LC/MS $t_R$ 1.53 minutes; MS (ES$^+$) m/z 245 and 247 (M+H)$^a$.

EXAMPLE 192

3-[4-(6-amino-3-pyridinyl)-1H-imidazol-2-yl]-7-[5-chloro-2-(1H-tetrazol-1-yl)phenyl]-2,3-dihydro-5(1H)-indolizinone

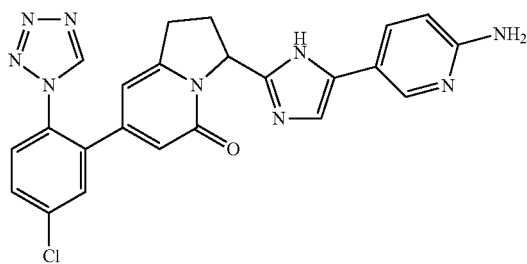 [SMILES: Nc1ccc(-c2cnc(C3CCc4cc(-c5cc(Cl)ccc5-n5cnnn5)cc(=O)n43)[nH]2)cn1]

The same operation as in Example 84→Example 39→Example 40→Example 41→Example 74 was conducted from the compound prepared in Example 19 to give the title compound having the following physical properties. (Note: in the step corresponding to Example 51 in the operation, the compound prepared in Example 191 was used).

LC/MS $t_R$ 2.66 minutes; MS (ES$^+$) m/z 472 (M+H)$^b$ $^1$H NMR (500 MHz, DMSO-d$_6$) δ 11.97 (br. s, 1 H), 9.68 (s, 1 H), 8.25 (d, 1 H), 7.83-7.75 (m, 3 H), 7.66 (dd, 1 H), 7.28 (s, 1 H), 6.43 (d, 1 H), 5.96 (s, 1 H), 5.95 (s, 1 H), 5.81 (br. s, 2 H), 5.60 (d, 1 H), 3.43-3.31 (obs. m, 1 H), 3.05-2.92 (m, 1 H), 2.52-2.43 (m, 1 H), 2.39-2.29 (m, 1 H).

EXAMPLE 193

1-(6-aminopyridin-3-yl)-2-bromoethan-1-one dihydrobromide 1-(6-aminopyridin-3-yl)ethan-1-one [patent US2007027184, page 17] (0.46 g) was treated as detailed in Example 91 to give the title compound having the following physical properties (0.70 g).

$^1$H NMR (500 MHz, methanol-d$_4$) δ 8.65 (d, 1 H), 8.01 (dd, 1 H), 6.60 (d, 1 H), 4.51 (s, 2 H).

EXAMPLE 194

(3S)-3-[4-(6-amino-3-pyridinyl)-1H-imidazol-2-yl]-7-[5-chloro-2-(1H-tetrazol-1-yl)phenyl]-2,3-dihydro-5(1H)-indolizinone The same operation as in Example 51→Example 52 was conducted from the compound prepared in Example 9 to give the title compound having the following physical properties. (Note: in the step corresponding to Example 51 in the operation, the compound prepared in Example 193 was used).

LC/MS $t_R$ 1.38 minutes; MS (ES$^+$) m/z 472 (M+H)$^a$.

EXAMPLE 195 methyl[5-(2-{(3S)-7-[5-chloro-2-(1H-tetrazol-1-yl)phenyl]-5-oxo-1,2,3,5-tetrahydro-3-indolizinyl}-1H-imidazol-5-yl)-2-pyridinyl]carbamate The compound prepared in Example 194 (80 mg) was treated as detailed in Example 128 using methyl chloroformate in place of ethyl chloroformate to give the title compound having the following physical properties (66 mg).

LC/MS $t_R$ 3.11 minutes; MS (ES$^+$) m/z 530 (M+H)$^b$ $^1$H NMR (500 MHz, methanol-d$_4$) δ 9.35 (s, 1 H), 8.56 (app. br. s, 1 H), 8.02 (app. br. s, 1 H), 7.88 (app. br. s, 1 H), 7.76-7.70 (m, 2 H), 7.69 (d, 1 H), 7.41 (br. s, 1 H), 6.13 (s, 1 H), 6.09 (s, 1 H), 5.78 (dd, 1 H), 3.77 (s, 3 H), 3.52-3.40 (m, 1 H), 3.16-3.06 (m, 1 H), 2.71-2.59 (m, 1 H), 2.52 (app. br. s, 1 H).

EXAMPLE 196 methyl[5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-pyridinyl]carbamate The compound prepared in Example 195 (46 mg) was treated as detailed in Example 44 to give the title compound having the following physical properties (20 mg).

LC/MS $t_R$ 3.92 minutes; MS (ES$^+$) m/z 564 (M+H)$^b$ $^1$H NMR (500 MHz, methanol-d$_4$) δ 9.38 (s, 1 H), 8.59 (d, 1 H), 8.07 (d, 1 H), 8.00 (d, 1 H), 7.78-7.73 (m, 2 H), 7.20 (d, 1 H), 6.15 (s, 1 H), 6.10 (s, 1 H), 5.73 (dd, 1 H), 3.52-3.41 (m, 1 H), 3.12 (ddd, 1 H), 2.72-2.61 (m, 1 H), 2.46-2.36 (m, 1 H).

EXAMPLE 197 ethyl[5-(2-{(3S)-7-[5-chloro-2-(1H-tetrazol-1-yl)phenyl]-5-oxo-1,2,3,5-tetrahydro-3-indolizinyl}-1H-imidazol-5-yl)-2-pyridinyl]carbamate The compound prepared in Example 194 (50 mg) was treated as detailed in Example 128 to give the title compound having the following physical properties (21 mg).

LC/MS $t_R$ 3.29 minutes; MS (ES$^+$) m/z 544 (M+H)$^b$ $^1$H NMR (500 MHz, methanol-d$_4$) δ 9.36 (s, 1 H), 8.56 (br. s, 1 H), 8.07-8.00 (m, 1 H), 7.91-7.84 (m, 1 H), 7.75-7.71 (m, 2 H), 7.70-7.66 (m, 1 H), 7.42 (br. s, 1 H), 6.13 (s, 1 H), 6.09 (s, 1 H), 5.78 (dd, 1 H), 4.22 (q, 2 H), 3.50-3.41 (m, 1 H), 3.15-3.06 (m, 1 H), 2.69-2.60 (m, 1 H), 2.55-2.46 (m, 1 H), 1.32 (t, 3 H).

EXAMPLE 198

(3S)-3-[5-(6-amino-3-pyridinyl)-4-chloro-1H-imidazol-2-yl]-7-[5-chloro-2-(1H-tetrazol-1-yl)phenyl]-2,3-dihydro-5(1H)-indolizinone

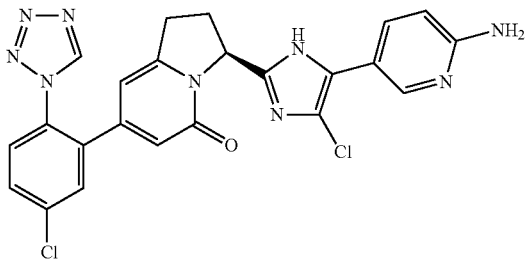 [SMILES: Nc1ccc(-c2[nH]c([C@@H]3CCc4cc(-c5cc(Cl)ccc5-n5cnnn5)cc(=O)n43)nc2Cl)cn1]

The compound prepared in Example 194 (50 mg) was treated as detailed in Example 44 to give the title compound having the following physical properties (13 mg).
LC/MS $t_R$ 2.97 minutes; MS (ES$^+$) m/z 506 (M+H)$^b$
$^1$H NMR (500 MHz, methanol-d$_4$) δ 9.36 (s, 1 H), 8.21 (s, 1 H), 7.78-7.71 (m, 3 H), 7.70-7.66 (m, 1 H), 6.65 (d, 1 H), 6.13 (s, 1 H), 6.08 (s, 1 H), 5.69 (d, 1 H), 3.49-3.39 (m, 1 H), 3.10 (dd, 1 H), 2.69-2.58 (m, 1 H), 2.42-2.34 (m, 1 H).

EXAMPLE 199

1-{[5-(6-amino-3-pyridinyl)-1H-imidazol-2-yl]methyl}-4-[5-chloro-2-(1H-tetrazol-1-yl)phenyl]-2(1H)-pyridinone The same operation as in Example 51→Example 52 was conducted from the compound prepared in Example 25 to give the title compound having the following physical properties. (Note: in the step corresponding to Example 51 in the operation, the compound prepared in Example 193 was used).
LC/MS $t_R$ 2.61 minutes MS (ES$^+$) m/z 446 (M+H)$^b$
$^1$H NMR (500 MHz, methanol-d$_4$) δ 9.37 (s, 1 H), 8.21 (br. s, 1 H), 7.81-7.72 (m, 3 H), 7.70-7.63 (m, 2 H), 7.26 (br. s, 1 H), 6.66-6.62 (m, 1 H), 6.42-6.38 (m, 1 H), 6.05-6.00 (m, 1 H), 5.17 (s, 2 H).

EXAMPLE 200 methyl{5-[2-({4-[5-chloro-2-(1H-tetrazol-1-yl)phenyl]-2-oxo-1(2H)-pyridinyl}methyl)-1H-imidazol-5-yl]-2-pyridinyl}carbamate The compound prepared in Example 199 (200 mg) was treated as detailed in Example 128 using methyl chloroformate in place of ethyl chloroformate to give the title compound having the following physical properties (9 mg).
LC/MS $t_R$ 3.06 minutes; MS (ES$^+$) m/z 504 (M+H)$^b$
$^1$H NMR (500 MHz, DMSO-d$_6$) δ 12.27 (br. s, 1 H), 10.22 (br. s, 1 H), 9.72 (s, 1 H), 8.63 (s, 1 H), 8.01 (d, 1 H), 7.92-7.75 (m, 4 H), 7.68 (d, 1 H), 7.55 (br. s, 1 H), 6.26 (s, 1 H), 5.85 (dd, 1 H), 5.09 (s, 2 H), 3.64 (s, 3 H).

EXAMPLE 201

6-amino-N-methoxy-N-methylpyridine-3-carboxamide

To an N,N-dimethylformamide (50 mL) solution of 6-aminopyridine-3-carboxylic acid (2.0 g) was added N,O-dimethylhydroxylamine hydrochloride (1.69 g), O-(7-azabenzotriazol-1-yl)-N,N,N',N'-tetramethyluronium hexafluorophosphate (6.06 g) and diisopropylethylamine (7.6 mL) and the mixture stirred at room temperature for 16 hours. To the reaction mixture, water (250 mL) was added followed by extraction into ethyl acetate. The combined organic layers were washed with brine, dried and concentrated and the residue purified by column chromatography (0 to 15% methanol in dichloromethane) to give the title compound having the following physical properties (0.61 g).
$^1$H NMR (500 MHz, DMSO-d$_6$) δ 8.31 (d, 1 H), 7.69 (dd, 1 H), 6.42 (d, 1 H), 3.57 (s, 3 H), 3.21 (s, 3 H).

EXAMPLE 202 tert-butyl N-[(tert-butoxy)carbonyl]-N-{5-[methoxy(methyl)carbamoyl]pyridin-2-yl}carbamate The compound prepared in Example 201 (0.61 g) was treated as detailed in Example 10 to give the title compound having the following physical properties (0.58 g).
LC/MS $t_R$ 1.99 minutes; MS (ES$^+$) m/z 382 (M+H)$^a$.

EXAMPLE 203 tert-butyl N-(5-propanoylpyridin-2-yl)carbamate

To a cooled (0° C.) tetrahydrofuran (10 mL) solution of the compound prepared in Example 202 (0.53 g) was added a 1 M solution of ethylmagnesium bromide in tetrahydrofuran (1.73 mL) and the mixture stirred at room temperature for 16 hours. To the cooled (0° C.) reaction mixture, a saturated aqueous solution of ammonium chloride (1.5 mL) and water (30 mL) was sequentially added followed by extraction into ethyl acetate. The combined organic layers were washed with brine, dried and concentrated to give the title compound having the following physical properties (0.43 g).
LC/MS $t_R$ 2.03 minutes; MS (ES$^+$) m/z 251 (M+H)$^a$.

EXAMPLE 204 tert-butyl N-[5-(2-bromopropanoyl)pyridin-2-yl]carbamate

To a glacial acetic acid (5 mL) solution of the compound prepared in Example 203 (0.20 g) was added a solution of 33 wt. % hydrogen bromide in acetic acid (0.28 mL) followed by bromine (41 µL) and the mixture stirred at room temperature for 1 hour. To the reaction mixture, a saturated solution of aqueous sodium bicarbonate was added (20 mL) followed by extraction into ethyl acetate. The combined organic layers were dried, filtered and concentrated and the residue purified by column chromatography (0 to 50% ethyl acetate in heptane) to give the title compound having the following physical properties (0.20 g).
LC/MS $t_R$ 2.23 minutes; MS (ES$^+$) m/z 329 and 331 (M+H)$^a$.

EXAMPLE 205 tert-butyl N-(5-{2-[(3S)-7-[5-chloro-2-(1H-1,2,3,4-tetrazol-1-yl)phenyl]-5-oxo-1,2,3,5-tetrahydroindolizin-3-yl]-4-methyl-1H-imidazol-5-yl}pyridin-2-yl)carbamate The same operation as in Example 51→Example 52 was conducted from the compound prepared in Example 9 to give the title compound having the following physical properties. (Note: in the step corresponding to Example 51 in the operation, the compound prepared in Example 204 was used).

LC/MS $t_R$ 1.66 minutes; MS (ES⁺) m/z 586 (M+H)$^a$.

EXAMPLE 206

(3S)-3-[5-(6-amino-3-pyridinyl)-4-methyl-1H-imidazol-2-yl]-7-[5-chloro-2-(1H-tetrazol-1-yl)phenyl]-2,3-dihydro-5(1H)-indolizinone To a 1,4-dioxane (0.5 mL) solution of the compound prepared in Example 205 (42 mg) was added 1 M hydrochloric acid (0.4 mL) and the mixture heated at 90° C. for 3 hours. To the reaction mixture, a saturated aqueous solution of sodium hydrogen carbonate (40 mL) was added followed by extraction into ethyl acetate. The combined organic layers were dried, filtered and concentrated to give the title compound having the following physical properties (25 mg).

LC/MS $t_R$ 2.53 minutes; MS (ES⁺) m/z 486 (M+H)$^b$

¹H NMR (500 MHz, methanol-d₄) δ 9.25 (s, 1 H), 7.91 (br. s, 1 H), 7.65-7.61 (m, 2 H), 7.60-7.55 (m, 1 H), 7.51 (d, 1 H), 6.54 (d, 1 H), 6.02 (s, 1 H), 5.98 (s, 1 H), 5.60 (dd, 1 H), 3.39-3.29 (m, 1 H), 2.98 (ddd, 1 H), 2.51 (qd, 1 H), 2.37-2.28 (m, 1 H), 2.18 (br. s, 3 H).

EXAMPLE 207 methyl[5-(2-{(3S)-7-[5-chloro-2-(1H-tetrazol-1-yl)phenyl]-5-oxo-1,2,3,5-tetrahydro-3-indolizinyl}-4-methyl-1H-imidazol-5-yl)-2-pyridinyl]carbamate The compound prepared in Example 206 (100 mg) was treated as detailed in Example 128 using methyl chloroformate in place of ethyl chloroformate to give the title compound having the following physical properties (28 mg).

LC/MS $t_R$ 3.00 minutes; MS (ES⁺) m/z 544 (M+H)$^b$

¹H NMR (500 MHz, methanol-d₄) δ 9.37 (s, 1 H), 8.41 (s, 1 H), 7.96-7.88 (m, 2 H), 7.77-7.73 (m, 2 H), 7.71-7.68 (m, 1 H), 6.14 (s, 1 H), 6.10 (s, 1 H), 5.74 (dd, 1 H), 3.79 (s, 3 H), 3.51-3.42 (m, 1 H), 3.16-3.07 (m, 1 H), 2.69-2.60 (m, 1 H), 2.51-2.42 (m, 1 H), 2.36 (s, 3 H).

EXAMPLE 208

6-chloro-5-iodopyridin-2-amine

To an N,N-dimethylformamide (30 mL) solution of 2-amino-6-chloropyridine (1.0 g) was added N-iodosuccinimide (1.75 g) and the mixture stirred at room temperature for 16 hours. To the reaction mixture, water (200 mL) was added followed by extraction into ethyl acetate. The combined organic layers were dried, filtered and concentrated. The residue was triturated with dichloromethane and the resultant precipitate collected by filtration to give the title compound having the following physical properties (0.49 g).

LC/MS $t_R$ 1.72 minutes; MS (ES⁺) m/z 254 (M+H)$^a$.

EXAMPLE 209

1-(6-amino-2-chloropyridin-3-yl)-2-bromoethan-1-one dihydrobromide

The same operation as in Example 90→Example 91 was conducted from the compound prepared in Example 208 to give the title compound having the following physical properties.

LC/MS $t_R$ 1.52 minutes; MS (ES⁺) m/z 249 and 251 (M+H)$^a$.

EXAMPLE 210

(3S)-3-[5-(6-amino-2-chloro-3-pyridinyl)-1H-imidazol-2-yl]-7-[5-chloro-2-(1H-tetrazol-1-yl)phenyl]-2,3-dihydro-5(1H)-indolizinone

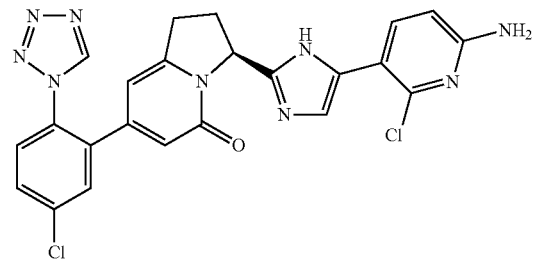 [SMILES: Nc1ccc(-c2cnc([C@@H]3CCc4cc(-c5cc(Cl)ccc5-n5cnnn5)cc(=O)n43)[nH]2)c(Cl)n1]

The same operation as in Example 51→Example 52 was conducted from the compound prepared in Example 9 to give the title compound having the following physical properties. (Note: in the step corresponding to Example 51 in the operation, the compound prepared in Example 209 was used).

LC/MS $t_R$ 2.98 minutes; MS (ES⁺) m/z 506 (M+H)$^b$

¹H NMR (500 MHz, methanol-d₄) δ 9.35 (s, 1 H), 7.81 (app. br. s, 1 H), 7.76-7.71 (m, 2 H), 7.70-7.66 (m, 1 H), 7.32 (app. br. s, 1 H), 6.56 (d, 1 H), 6.14 (s, 1 H), 6.08 (s, 1 H), 5.79 (dd, 1 H), 3.50-3.38 (m, 1 H), 3.10 (ddd, 1 H), 2.68-2.57 (m, 1 H), 2.50 (tdd, 1 H).

EXAMPLE 211

1-{[5-(6-amino-2-chloro-3-pyridinyl)-1H-imidazol-2-yl]methyl}-4-[5-chloro-2-(1H-tetrazol-1-yl)phenyl]-2(1H)-pyridinone The same operation as in Example 51→Example 52 was conducted from the compound prepared in Example 25 to give the title compound having the following physical properties. (Note: in the step corresponding to Example 51 in the operation, the compound prepared in Example 209 was used).

LC/MS $t_R$ 2.92 minutes; MS (ES⁺) m/z 481 (M+H)$^b$

¹H NMR (500 MHz, methanol-d₄) δ 9.36 (s, 1 H), 7.86 (br. s, 1 H), 7.76-7.71 (m, 2 H), 7.70-7.64 (m, 2 H), 7.39 (br. s, 1 H), 6.56 (d, 1 H), 6.40 (s, 1 H), 6.02 (dd, 1 H), 5.18 (s, 2 H).

EXAMPLE 212

1-(6-amino-2-methylpyridin-3-yl)-2-bromoethan-1-one dihydrobromide

The same operation as in Example 90→Example 189 was conducted from 5-bromo-6-methylpyridin-2-amine to give the title compound having the following physical properties.

¹H NMR (500 MHz, methanol-d₄) δ 8.39 (d, 1 H), 6.96 (d, 1 H), 4.57 (s, 2 H), 2.75 (s, 3 H).

EXAMPLE 213

(3S)-3-[5-(6-amino-2-methyl-3-pyridinyl)-1H-imidazol-2-yl]-7-[5-chloro-2-(1H-tetrazol-1-yl)phenyl]-2,3-dihydro-5(1H)-indolizinone The same operation as in Example 51→Example 52 was conducted from the compound prepared in Example 9 to give the title compound having the following physical properties. (Note: in the step corresponding to Example 51 in the operation, the compound prepared in Example 212 was used).

LC/MS $t_R$ 2.62 minutes; MS (ES$^+$) m/z 486 (M+H)$^b$ $^1$H NMR (500 MHz, methanol-d$_4$) δ 9.38 (s, 1 H), 7.77-7.73 (m, 2 H), 7.72-7.68 (m, 1 H), 7.54 (d, 1 H), 6.99 (s, 1 H), 6.48 (d, 1 H), 6.14 (s, 1 H), 6.12 (s, 1 H), 5.80 (dd, 1 H), 3.51-3.39 (m, 1 H), 3.16-3.08 (m, 1 H), 2.69-2.59 (m, 1 H), 2.52-2.46 (m, 1 H), 2.41 (s, 3 H).

EXAMPLE 214 methyl[5-(2-{(3S)-7-[5-chloro-2-(1H-tetrazol-1-yl)phenyl]-5-oxo-1,2,3,5-tetrahydro-3-indolizinyl}-1H-imidazol-5-yl)-6-methyl-2-pyridinyl]carbamate The compound prepared in Example 213 (33 mg) was treated as detailed in Example 128 using methyl chloroformate in place of ethyl chloroformate to give the title compound having the following physical properties (21 mg).

LC/MS $t_R$ 3.07 minutes; MS (ES$^+$) m/z 544 (M+H)$^b$ $^1$H NMR (500 MHz, methanol-d$_4$) δ 9.35 (s, 1 H), 7.89 (br. d, 1 H), 7.77-7.70 (m, 3 H), 7.68 (d, 1 H), 7.19 (br. s, 1 H), 6.13 (s, 1 H), 6.09 (s, 1 H), 5.80 (dd, 1 H), 3.51-3.41 (m, 1 H), 3.15-3.07 (m, 1 H), 2.68-2.60 (m, 1 H), 2.56-2.40 (obs. m, 1 H), 2.50 (s, 3 H).

EXAMPLE 215

1-(6-amino-2-fluoropyridin-3-yl)-2-bromoethan-1-one dihydrobromide

The same operation as in Example 90→Example 189 was conducted from 2-amino-6-fluoro-5-iodopyridine [J. Org. Chem. 71(8), 2922 (2006)] to give the title compound having the following physical properties.

LC/MS $t_R$ 1.50 minutes; MS (ES$^+$) m/z 233 and 235 (M+H)$^a$.

EXAMPLE 216

(3S)-3-[5-(6-amino-2-fluoro-3-pyridinyl)-1H-imidazol-2-yl]-7-[5-chloro-2-(1H-tetrazol-1-yl)phenyl]-2,3-dihydro-5(1H)-indolizinone

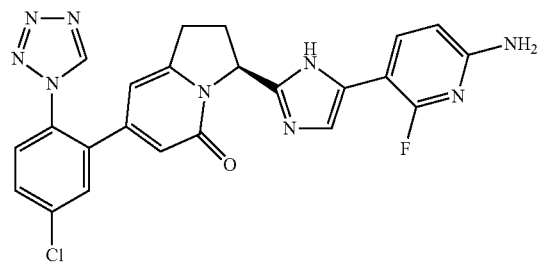 [SMILES: Nc1ccc(-c2cnc([C@@H]3CCc4cc(-c5cc(Cl)ccc5-n5cnnn5)cc(=O)n43)[nH]2)c(F)n1]

The same operation as in Example 51→Example 52 was conducted from the compound prepared in Example 9 to give the title compound having the following physical properties. (Note: in the step corresponding to Example 51 in the operation, the compound prepared in Example 215 was used).

LC/MS $t_R$ 2.94 minutes; MS (ES$^+$) m/z 490 (M+H)$^b$ $^1$H NMR (500 MHz, methanol-d$_4$) δ 9.35 (s, 1 H), 7.97 (app. br. s, 1 H), 7.75-7.70 (m, 2 H), 7.68 (d, 1 H), 7.15 (br. s, 1 H), 6.45 (dd, 1 H), 6.14 (s, 1 H), 6.07 (s, 1 H), 5.79 (d, 1 H), 3.50-3.38 (m, 1 H), 3.14-3.05 (m, 1 H), 2.67-2.56 (m, 1 H), 2.52-2.44 (m, 1 H).

EXAMPLE 217

(3S)-7-[5-chloro-2-(1H-tetrazol-1-yl)phenyl]-3-[5-(6-methyl-3-pyridinyl)-1H-imidazol-2-yl]-2,3-dihydro-5(1H)-indolizinone The same operation as in Example 204→Example 51→Example 52 was conducted from 2-methyl-5-acetylpyridine to give the title compound having the following physical properties. (Note: in the step corresponding to Example 51 in the operation, the compound prepared in Example 9 was used).

LC/MS $t_R$ 2.83 minutes; MS (ES$^+$) m/z 471 (M+H)$^b$ $^1$H NMR (500 MHz, methanol-d$_4$) δ 9.35 (s, 1 H), 8.73 (app. s, 1 H), 8.01 (d, 1 H), 7.75-7.71 (m, 2 H), 7.68 (d, 1 H), 7.46 (br. s, 1 H), 7.30 (d, 1 H), 6.13 (s, 1 H), 6.09 (s, 1 H), 5.78 (dd, 1 H), 3.51-3.41 (m, 1 H), 3.12 (ddd, 1 H), 2.70-2.59 (m, 2 H), 2.52 (s, 3 H).

EXAMPLE 218

(3S)-3-[4-chloro-5-(6-methyl-3-pyridinyl)-1H-imidazol-2-yl]-7-[5-chloro-2-(1H-tetrazol-1-vi)phenyl]-2,3-dihydro-5(1H)-indolizinone The compound prepared in Example 217 (45 mg) was treated as detailed in Example 44 to give the title compound having the following physical properties (19 mg).

LC/MS $t_R$ 3.18 minutes; MS (ES$^+$) m/z 505 (M+H)$^b$ $^1$H NMR (500 MHz, methanol-d$_4$) δ 9.36 (s, 1 H), 8.75 (d, 1 H), 8.05 (dd, 1 H), 7.76-7.72 (m, 2 H), 7.68 (d, 1 H), 7.40 (d, 1 H), 6.13 (s, 1 H), 6.10 (d, 1 H), 5.72 (dd, 1 H), 3.45 (td, 1 H), 3.12 (ddd, 1 H), 2.66 (qd, 1 H), 2.57 (s, 3 H), 2.44-2.36 (m, 1 H).

EXAMPLE 219 tert-butyl N-[6-(2-bromoacetyl)pyridin-3-yl]carbamate

The same operation as in Example 10→Example 188→Example 91 was conducted from 5-amino-2-cyanopyridine to give the title compound having the following physical properties.

LC/MS $t_R$ 2.07 minutes; MS (ES+) m/z 315 and 317 (M+H)$^a$.

EXAMPLE 220

2-methyl-2-propanyl[6-(2-{7-[5-chloro-2-(1H-tetrazol-1-yl)phenyl]-5-oxo-1,2,3,5-tetrahydro-3-indolizinyl}-1H-imidazol-5-yl)-3-pyridinyl]carbamate The same operation as in Example 84→Example 39 was conducted from the compound prepared in Example 17 to give the title compound having the following physical properties. (Note: in the step corresponding to Example 84 in the operation, the compound prepared in Example 219 was used).
LC/MS $t_R$ 3.37 minutes; MS (ES$^+$) m/z 572 (M+H)$^b$
$^1$H NMR (500 MHz, methanol-d$_4$) δ 9.36 (s, 1 H), 8.54 (d, 1 H), 7.92 (dd, 1 H), 7.79-7.64 (m, 4 H), 7.48 (s, 1 H), 6.14 (s, 1 H), 6.08 (s, 1 H), 5.80 (dd, 1 H), 3.54-3.37 (m, 1 H), 3.18-3.03 (m, 1 H), 2.72-2.43 (m, 2 H), 1.53 (s, 9 H).

EXAMPLE 221

3-[5-(5-amino-2-pyridinyl)-1H-imidazol-2-yl]-7-[5-chloro-2-(1H-tetrazol-1-yl)phenyl]-2,3-dihydro-5(1H)-indolizinone The compound prepared in Example 220 (130 mg) was treated as detailed in Example 206 to give the title compound having the following physical properties (104 mg).
LC/MS $t_R$ 2.79 minutes; MS (ES$^+$) m/z 472 (M+H)$^b$
$^1$H NMR (500 MHz, methanol-d$_4$) δ 9.35 (s, 1 H), 7.95 (br. s, 1 H), 7.75-7.71 (m, 2 H), 7.67 (d, 1 H), 7.53 (br. s, 1 H), 7.32 (br. s, 1 H), 7.10 (dd, 1 H), 6.14 (s, 1 H), 6.07 (s, 1 H), 5.79 (d, 1 H), 3.51-3.39 (m, 1 H), 3.09 (dd, 1 H), 2.65-2.56 (m, 1 H), 2.54-2.45 (m, 1 H).

EXAMPLE 222

3-[5-(5-amino-2-pyridinyl)-4-chloro-1H-imidazol-2-yl]-7-[5-chloro-2-(1H-tetrazol-1-yl)phenyl]-2,3-dihydro-5(1H)-indolizinone The same operation as in Example 44→Example 206 was conducted from the compound prepared in Example 220 to give the title compound having the following physical properties.
LC/MS $t_R$ 3.38 minutes; MS (ES$^+$) m/z 506 (M+H)$^b$
$^1$H NMR (500 MHz, methanol-d$_4$) δ 9.35 (s, 1 H), 8.04 (s, 1 H), 7.75-7.70 (m, 3 H), 7.69-7.66 (m, 1 H), 7.09 (dd, 1 H), 6.15 (s, 1 H), 6.07 (s, 1 H), 5.77 (dd, 1 H), 3.43-3.35 (m, 1 H), 3.12-3.05 (m, 1 H), 2.60 (qd, 1 H), 2.50-2.41 (m, 1 H).

EXAMPLE 223 methyl[6-(2-{7-[5-chloro-2-(1H-tetrazol-1-yl)phenyl]-5-oxo-1,2,3,5-tetrahydro-3-indolizinyl}-1H-imidazol-5-yl)-3-pyridinyl]carbamate The compound prepared in Example 221 (60 mg) was treated as detailed in Example 128 using methyl chloroformate in place of ethyl chloroformate to give the title compound having the following physical properties (30.2 mg).
LC/MS $t_R$ 3.00 minutes; MS (ES$^+$) m/z 530 (M+H)$^b$
NMR analysis showed a 2:1 ratio of tautomers.
Major tautomer: $^1$H NMR (500 MHz, DMSO-d$_6$) δ 12.18 (s, 1 H), 9.79 (br. s, 1 H), 9.69 (s, 1 H), 8.53 (d, 1 H), 7.91-7.81 (m, 1 H), 7.81-7.74 (m, 3 H), 7.69 (d, 1 H), 7.48 (d, 1 H), 5.97 (app. s, 2 H), 5.64 (dd, 1 H), 3.68 (s, 3 H), 3.40-3.30 (obs. m, 1 H), 3.07-2.90 (m, 1 H), 2.53-2.44 (obs. m, 1 H), 2.38-2.30 (m, 1 H).
Minor tautomer: $^1$H NMR (500 MHz, DMSO-d$_6$) δ 12.49 (s, 1 H), 9.89 (br. s, 1 H), 9.70 (s, 1 H), 8.63 (d, 1 H), 7.91-7.81 (m, 1 H), 7.81-7.74 (m, 3 H), 7.68 (d, 1 H), 7.33 (d, 1 H), 5.96 (s, 1 H), 5.95 (s, 1 H), 5.71 (dd, 1 H), 3.70 (s, 3 H), 3.29-3.21 (m, 1 H), 3.07-2.90 (m, 1 H), 2.53-2.44 (obs. m, 1 H), 2.29-2.21 (m, 1 H).

EXAMPLE 224

2-(5-aminopyridin-2-yl)-2-oxoethyl 2-{4-[5-chloro-2-(1,2,3,4-tetrazol-1-yl)phenyl]-2-oxopyridin-1-yl}acetate The compound prepared in Example 25 (0.55 g) was treated as detailed in Example 51 using the compound prepared in Example 219 in place of 2-bromo-1-phenylethan-1-one to give the title compound having the following physical properties (0.26 g).
LC/MS $t_R$ 1.66 minutes; MS (ES$^+$) m/z 466 (M+H)$^a$.

EXAMPLE 225

2-{5-[(methoxycarbonyl)amino]pyridin-2-yl}-2-oxoethyl 2-{4-[5-chloro-2-(1,2,3,4-tetrazol-1-yl)phenyl]-2-oxopyridin-1-yl}acetate To a dichloromethane (25 mL) solution of the compound prepared in Example 224 (0.24 g) was added diisopropylethylamine (0.10 g) and methyl chloroformate (44 µL) and the mixture stirred at room temperature for 16 hours. The reaction mixture was concentrated and the residue purified by column chromatography (0 to 80% ethyl acetate in heptanes) to give the title compound having the following physical properties (0.10 g).
LC/MS $t_R$ 3.06 minutes; MS (ES$^+$) m/z 524 (M+H)$^a$.

EXAMPLE 226 methyl{6-[2-({4-[5-chloro-2-(1H-tetrazol-1-yl)phenyl]-2-oxo-1(2H)-pyridinyl}methyl)-1H-imidazol-5-yl]-3-pyridinyl}carbamate The compound prepared in Example 225 (102 mg) was treated as detailed in Example 52 to give the title compound having the following physical properties (17 mg).
LC/MS $t_R$ 2.99 minutes; MS (ES$^+$) m/z 504 (M+H)$^b$
$^1$H NMR (500 MHz, methanol-d$_4$) δ 9.38 (s, 1 H), 8.59 (br. s, 1 H), 7.97 (br. d, 1 H), 7.77 (app. br. s, 1 H), 7.77-7.71 (m, 2 H), 7.71-7.63 (m, 2 H), 7.55 (app. br. s, 1 H), 6.42 (s, 1 H), 6.03 (d, 1 H), 5.22 (s, 2 H), 3.80 (s, 3 H).

EXAMPLE 227

2-(5-aminopyridin-2-yl)-2-oxoethyl(3S)-7-[5-chloro-2-(1H-1,2,3,4-tetrazol-1-yl)phenyl]-5-oxo-1,2,3,5-tetrahydroindolizine-3-carboxylate The compound prepared in Example 9 (0.39 g) was treated as detailed in Example 51 using the compound prepared in Example 219 in place of 2-bromo-1-phenylethan-1-one to obtain the title compound having the following physical properties (0.54 g).
LC/MS $t_R$ 1.73 minutes; MS (ES$^+$) m/z 492 (M+H)$^a$.

EXAMPLES 228(1) AND 228(2)

2-(5-{[(tert-butoxy)carbonyl]amino}pyridin-2-yl)-2-oxoethyl(3S)-7-[5-chloro-2-(1H-1,2,3,4-tetrazol-1-yl)phenyl]-5-oxo-1,2,3,5-tetrahydroindolizine-3-carboxylate and 2-(5-{bis[(tert-butoxy)carbonyl]amino}pyridin-2-yl)-2-oxoethyl(3S)-7-[5-chloro-2-(1H-1,2,3,4-tetrazol-1-yl)phenyl]-5-oxo-1,2,3,5-tetrahydroindolizine-3-carboxylate To a dichloromethane (50 mL) solution of the compound prepared in Example 227 (0.54 g) was added di-tert-butyl dicarbonate (1.19 g) and 4-dimethylaminopyridine (0.27 g) and the mixture stirred at room temperature for 16 hours. The reaction mixture was concentrated and the residue purified by column chromatography (0 to 20% methanol in dichloromethane) to obtain the title compounds in a 2:1 ratio having the following physical properties (0.65 g).

EXAMPLE 228(1)

LC/MS $t_R$ 2.09 minutes; MS (ES$^+$) m/z 592 (M+H)$^a$

EXAMPLE 228(2)

LC/MS $t_R$ 2.27 minutes; MS (ES$^+$) m/z 692 (M+H)$^a$

EXAMPLE 229

(3S)-3-[4-(5-aminopyridin-2-yl)-1H-imidazol-2-yl]-7-[5-chloro-2-(1H-1,2,3,4-tetrazol-1-yl)phenyl]-1,2,3,5-tetrahydroindolizin-5-one The same operation as in Example 52→Example 55 was conducted from the 2:1 ratio of compounds prepared in Example 228 (0.65 g) to obtain the title compound having the following physical properties (0.27 g).
LC/MS $t_R$ 1.54 minutes; MS (ES$^+$) m/z 472 (M+H)$^a$.

EXAMPLE 230 methyl[6-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-3-pyridinyl]carbamate The same operation as in Example 128→Example 44 was conducted from the compound prepared in Example 229 to obtain the title compound having the following physical properties. (Note: in the step corresponding to Example 128 in the operation, methyl chloroformate was used).
LC/MS $t_R$ 3.99 minutes; MS (ES$^+$) m/z 564 (M+H)$^b$
$^1$H NMR (500 MHz, DMSO-d$_6$) δ 12.97 (br. s, 1 H), 10.00 (br. s, 1 H), 9.70 (s, 1 H), 8.73 (s, 1 H), 7.96 (dd, 1 H), 7.90 (d, 1 H), 7.85-7.77 (m, 3 H), 5.98 (s, 1 H), 5.93 (s, 1 H), 5.67 (dd, 1 H), 3.70 (s, 3 H), 3.23 (td, 1 H), 3.02-2.92 (m, 1 H), 2.55-2.44 (obs. m, 1 H), 2.18 (t, 1 H).

EXAMPLE 231(1) to Example 231(4)

The compounds of the present invention having the following physical data were synthesised from the compound prepared in Example 229 and the corresponding chloroformates or acetic anhydride using the method as detailed in Example 128.

EXAMPLE 231(1)

isopropyl[6-(2-{(3S)-7-[5-chloro-2-(1H-tetrazol-1-yl)phenyl]-5-oxo-1,2,3,5-tetrahydro-3-indolizinyl}-1H-imidazol-5-yl)-3-pyridinyl]carbamate LC/MS $t_R$ 3.32 minutes; MS (ES$^+$) m/z 558 (M+H)$^b$
NMR analysis showed a 2:1 ratio of tautomers.
Major tautomer: $^1$H NMR (500 MHz, DMSO-d$_6$) δ 12.19 (br. s, 1 H), 9.72 (br. s, 1 H), 9.69 (s, 1 H), 8.52 (d, 1 H), 7.91-7.83 (m, 1 H), 7.82-7.77 (m, 3 H), 7.67 (d, 1 H), 7.48 (s, 1 H), 5.99-5.93 (m, 2 H), 5.63 (dd, 1 H), 4.90 (septuplet, 1 H), 3.30-3.21 (m, 1 H), 3.04-2.93 (m, 1 H), 2.56-2.42 (obs. m, 1 H), 2.38-2.29 (m, 1 H), 1.25 (d, 6 H).

Minor tautomer: $^1$H NMR (500 MHz, DMSO-d$_6$) δ 12.50 (br. s, 1 H), 9.82 (br. s, 1 H), 9.70 (s, 1 H), 8.64 (d, 1 H), 7.91-7.83 (m, 1 H), 7.82-7.77 (m, 3 H), 7.66 (d, 1 H), 7.32 (s, 1 H), 5.99-5.93 (m, 2 H), 5.70 (dd, 1 H), 4.90 (septuplet, 1 H), 3.30-3.21 (m, 1 H), 3.04-2.93 (m, 1 H), 2.56-2.42 (obs. m, 1 H), 2.28-2.20 (m, 1 H), 1.27 (d, 6 H).

EXAMPLE 231(2)

isobutyl[6-(2-{(3S)-7-[5-chloro-2-(1H-tetrazol-1-yl)phenyl]-5-oxo-1,2,3,5-tetrahydro-3-indolizinyl}-1H-imidazol-5-yl)-3-pyridinyl]carbamate LC/MS $t_R$ 3.52 minutes; MS (ES$^+$) m/z 572 (M+H)$^b$
NMR analysis showed a 1:1 ratio of tautomers.
$^1$H NMR (500 MHz, CDCl$_3$) δ 11.40 and 10.88 (br. s, 1 H), 8.55 (s, 1 H), 8.41 (br. s, 1 H), 8.13-7.92 (m, 1 H), 7.87 (d, 0.5 H), 7.61 (dd, 1 H), 7.58-7.43 (m, 3 H), 7.32 (br. s, 0.5 H), 7.14-7.02 and 6.77 (m and br. s, 1 H), 6.40 and 6.34 (br. s, 1 H), 5.86 (t, 1 H), 5.68 and 5.64 (br. s, 1 H), 3.97 (d, 2 H), 3.52-3.17 (m, 2 H), 3.00 (dd, 1 H), 2.53-2.39 (m, 1 H), 1.98 (d quintet, 1 H), 0.97 (d, 6 H).

EXAMPLE 231(3)

N-[6-(2-{(3S)-7-[5-chloro-2-(1H-tetrazol-1-yl)phenyl]-5-oxo-1,2,3,5-tetrahydro-3-indolizinyl}-1H-imidazol-5-yl)-3-pyridinyl]acetamide LC/MS $t_R$ 2.94 minutes; MS (ES$^+$) m/z 514 (M+H)$^b$
NMR analysis showed a 2:1 ratio of tautomers.
Major Tautomer: $^1$H NMR (500 MHz, DMSO-d$_6$) δ 12.21 (br. s, 1 H), 10.12 (s, 1 H), 9.69 (s, 1 H), 8.61 (d, 1 H), 8.00 (dd, 1 H), 7.82-7.77 (m, 3 H), 7.69 (d, 1 H), 7.50 (s, 1 H), 5.99-5.93 (m, 2 H), 5.63 (dd, 1 H), 3.33-3.21 (m, 1 H), 3.05-2.92 (m, 1 H), 2.56-2.42 (obs. m, 1 H), 2.38-2.29 (m, 1 H), 2.06 (s, 3 H).
Minor Tautomer: $^1$H NMR (500 MHz, DMSO-d$_6$) δ 12.52 (br. s, 1 H), 10.20 (s, 1 H), 9.70 (s, 1 H), 8.70 (d, 1 H), 8.03 (dd, 1 H), 7.82-7.77 (m, 3 H), 7.68 (d, 1 H), 7.34 (s, 1 H), 5.99-5.93 (m, 2 H), 5.70 (d, 1 H), 3.33-3.21 (m, 1 H), 3.05-2.92 (m, 1 H), 2.56-2.42 (obs. m, 1 H), 2.28-2.20 (m, 1 H), 2.07 (s, 3 H).

EXAMPLE 231(4)

methyl[6-(2-{(3S)-7-[5-chloro-2-(1H-tetrazol-1-yl)phenyl]-5-oxo-1,2,3,5-tetrahydro-3-indolizinyl}-1H-imidazol-5-yl)-3-pyridinyl]carbamate LC/MS $t_R$ 0.65 minutes; MS (ES$^+$) m/z 530 (M+H)$^f$
$^1$H NMR (300 MHz, DMSO-d$_6$) δ 12.5 (s, 0.3 H), 12.2 (s, 0.7 H), 9.88 (s, 0.3 H), 9.77 (s, 0.7 H), 9.69 (s, 0.3 H), 9.67 (s, 0.7 H), 8.61 (d, 0.3 H), 8.51 (d, 0.7 H), 7.79-7.63 (m, 5 H), 7.47 (d, 0.7 H), 7.31 (d, 0.3 H), 5.97-5.92 (m, 2 H), 5.74-5.60 (m, 1 H), 3.69 (s, 0.9 H), 3.67 (s, 2.1 H), 3.41-3.17 (m, 1 H), 3.09-2.90 (m, 1 H), 2.61-2.22 (m, 2 H).

EXAMPLES 232(1) AND 232(2)

(3S)-3-[5-(5-amino-2-pyridinyl)-4-methyl-1H-imidazol-2-yl]-7-[5-chloro-2-(1H-tetrazol-1-yl)phenyl]-2,3-dihydro-5(1H)-indolizinone and N-[6-(2-{(3S)-7-[5-chloro-2-(1H-tetrazol-1-yl)phenyl]-5-oxo-1,2,3,5-tetrahydro-3-indolizinyl}-4-methyl-1H-imidazol-5-yl)-3-pyridinyl]acetamide The same operation as in Example 188→Example 189→Example 51→Example 52 was conducted from 5-amino-2-cyanopyridine to obtain the title compounds in a 4:1 ratio having the following physical properties. (Note: in the step corresponding to Example 188 in the operation, a 3 M solution of ethyl magnesium bromide in tetrahydrofuran was used. In the step corresponding to Example 51 in the operation, the compound prepared in Example 9 was used).

EXAMPLE 232(1)

LC/MS $t_R$ 2.88 minutes; MS (ES$^+$) m/z 508 (M+Na), 486 (M+H), 243 [(M+2H)/2]$^b$ $^1$H NMR (500 MHz, methanol-d$_4$) δ 9.36 (s, 1 H), 8.00 (br. s, 1 H), 7.75-7.70 (m, 2 H), 7.70-7.66 (m, 1 H), 7.35 (app. br. s, 1 H), 7.11 (dd, 1 H), 6.13 (s, 1 H), 6.07 (s, 1 H), 5.74 (app. br. s, 1 H), 3.08 (dd, 1 H), 2.65-2.55 (m, 1 H), 2.50-2.43 (m, 2 H), 2.36 (br. s, 3 H).

EXAMPLE 232(2)

LC/MS $t_R$ 2.92 minutes; MS (ES$^+$) m/z 528 (M+H)$^b$ $^1$H NMR (500 MHz, methanol-d$_4$) δ 9.36 (s, 1 H), 8.71 (d, 1 H), 8.05 (br. s, 1 H), 7.73 (app. s, 2 H), 7.71-7.56 (m, 2 H), 6.14 (s, 1 H), 6.08 (s, 1 H), 5.75 (d, 1 H), 3.50-3.40 (m, 1 H), 3.14-3.05 (m, 1 H), 2.67-2.58 (m, 1 H), 2.52-2.43 (obs. m, 1 H), 2.46 (br. s, 3H), 2.16 (s, 3 H).

EXAMPLE 233 methyl[6-(2-{(3S)-7-[5-chloro-2-(1H-tetrazol-1-yl) phenyl]-5-oxo-1,2,3,5-tetrahydro-3-indolizinyl}-4-methyl-1H-imidazol-5-yl)-3-pyridinyl]carbamate The compound prepared in Example 232(1, 80 mg) was treated as detailed in Example 128 using methyl chloroformate in place of ethyl chloroformate to give the title compound having the following physical properties (22.9 mg).

LC/MS $t_R$ 3.04 minutes; MS (ES$^+$) m/z 544 (M+H)$^b$ $^1$H NMR (500 MHz, methanol-d$_4$) δ 9.36 (s, 1 H), 8.60 (br. s, 1 H), 7.95 (app. br. s, 1 H), 7.72 (app. s, 2 H), 7.70-7.67 (m, 1 H), 7.62 (app. br. s, 1 H), 6.14 (s, 1 H), 6.08 (s, 1 H), 5.75 (d, 1 H), 3.77 (s, 3 H), 3.51-3.39 (m, 1 H), 3.13-3.05 (m, 1 H), 2.67-2.57 (m, 1 H), 2.52-2.41 (obs. m, 1 H), 2.47 (s, 3 H).

EXAMPLE 234 tert-butyl N-[5-(2-bromoacetyl)-1,3-thiazol-2-yl]carbamate

To an cooled (0° C.) dichloromethane (4 mL) solution of 2-[(tert-butoxycarbonyl)amino]-1,3-thiazole-5-carboxylic acid (0.30 g) was added a solution of oxalyl chloride (0.13 mL) in dichloromethane (1 mL). One drop of N,N-dimethylformamide was added and the mixture stirred at room temperature for 1 hour. The reaction mixture was concentrated and the residue dissolved in acetonitrile (5 mL). To the cooled (0° C.) acetonitrile solution, a 2 M solution of (trimethylsilyl)diazomethane in hexanes (1.23 mL) was added and the mixture stirred at 0° C. for 1 hour. To the reaction mixture, a solution of 33 wt. % hydrogen bromide in acetic acid (0.20 mL) was added and the mixture stirred at 0° C. for a further 20 minutes. A saturated aqueous solution of sodium hydrogen carbonate (50 mL) was added followed by extraction with ethyl acetate. The combined organic layers were washed with brine, dried and concentrated to give the crude title compound having the following physical properties (0.37 g).

LC/MS $t_R$ 1.92 minutes; MS (ES$^+$) m/z 265 and 267 (M-C(CH$_3$)$_3$+H)$^a$.

EXAMPLE 235

(3S)-3-[5-(2-amino-1,3-thiazol-5-yl)-1H-imidazol-2-yl]-7-[5-chloro-2-(1H-tetrazol-1-yl)phenyl]-2,3-dihydro-5(1H)-indolizinone The same operation as in Example 51→Example 52→Example 40 was conducted from the compound prepared in Example 9 to give the title compound having the following physical properties. (Note: in the step corresponding to Example 51 in the operation, the compound prepared in Example 234 was used).

LC/MS $t_R$ 2.79 minutes; MS (ES$^+$) m/z 478 (M+H), 239 [(M+2H)/2]$^b$ $^1$H NMR (500 MHz, methanol-d$_4$) δ 9.35 (s, 1 H), 7.76-7.70 (m, 2 H), 7.68 (d, 1 H), 7.10 (s, 1 H), 7.09 (br. s, 1 H), 6.13 (s, 1 H), 6.07 (s, 1 H), 5.72 (dd, 1 H), 3.46-3.36 (m, 1 H), 3.09 (ddd, 1 H), 2.66-2.56 (m, 1 H), 2.46 (app. br. s, 1 H).

EXAMPLE 236

(3S)-3-[5-(1-amino-6-isoquinolinyl)-1H-imidazol-2-yl]-7-[5-chloro-2-(1H-tetrazol-1-yl)phenyl]-2,3-dihydro-5(1H)-indolizinone diacetate The same operation as in Example 90→Example 189→Example 51→Example 52 was conducted from 6-bromoisoquinolin-1-amine to give the title compound having the following physical properties. (Note: in the step corresponding to Example 51 in the operation, the compound prepared in Example 9 was used).

LC/MS $t_R$ 2.94 minutes; MS (ES$^+$) m/z 522 (M+H)$^b$ $^1$H NMR (500 MHz, methanol-d$_4$) δ 9.38 (s, 1 H), 8.24 (d, 1 H), 8.11 (br. s, 1 H), 7.99 (d, 1 H), 7.77-7.73 (m, 2 H), 7.70 (d, 1 H), 7.66 (br. s, 1 H), 7.58 (d, 1 H), 7.15 (d, 1 H), 6.16 (s, 1 H), 6.12 (s, 1 H), 5.82 (dd, 1 H), 3.53-3.43 (m, 1 H), 3.14 (ddd, 1 H), 2.67 (ddd, 1 H), 2.54-2.44 (m, 1 H), 1.98 (s, 6 H).

EXAMPLE 237 methyl N-(4-carbamimidoylphenyl)carbamate

To a cooled (0° C.) ethanol (10 mL) suspension of methyl N-(4-cyanophenyl)carbamate [J. Chem. Soc., Perkin Trans. 1, 2587 (1984)] was added acetyl chloride (4 mL) and the mixture stirred at room temperature for 16 hours. Further acetyl chloride (1 mL) was added and the mixture stirred at 50° C. for 3 hours. The reaction mixture was concentrated and the residue dissolved in ethanol (10 mL). To the solution, ammonium carbonate (2.73 g) was added and the mixture stirred at room temperature for 6 hours. The solids were removed by filtration and the filtrate concentrated. The residue was triturated with dichloromethane (10 mL) and the precipitate isolated by filtration to give the title compound having the following physical properties.

LC/MS $t_R$ 0.66 minutes; MS (ES$^+$) m/z 194 (M+H)$^a$.

EXAMPLES 238(1) AND 238(2)

tert-butyl N-{2-[3-(2-bromoacetyl)-5-oxo-2,3-dihydro-1H-indolizin-7-yl]-4-chlorophenyl}carbamate and tert-butyl N-{4-chloro-2-[3-(2-chloroacetyl)-5-oxo-2,3-dihydro-1H-indolizin-7-yl]phenyl}carbamate The compound prepared in Example 19 (0.50 g) was treated as detailed in Example 182 to give a 2:7 mixture of the title compounds having the following physical properties (22.9 mg).

EXAMPLE 238(1)

LC/MS $t_R$ 2.10 minutes; MS (ES$^+$) m/z 503 and 505 (M+Na), 481 and 483 (M+H)$^a$.

EXAMPLE 238(2)

LC/MS $t_R$ 2.07 minutes; MS (ES$^+$) m/z 459 (M+Na), 437 (M+H)$^a$.

EXAMPLE 239 tert-butyl N-{4-chloro-2-[3-(2-{4-[(methoxycarbonyl)amino]phenyl}-3H-imidazol-4-yl)-5-oxo-2,3-dihydro-1H-indolizin-7-yl]phenyl}carbamate To an acetonitrile (10 mL) suspension of the compound prepared in Example 237 (0.125 g) and the 2:7 ratio of compounds prepared in Examples 238(1) and 238(2) (0.26 g) was added potassium carbonate (0.16 g) and the mixture stirred at reflux for 4 hours. Water (50 mL) was added followed by extraction into ethyl acetate. The combined organic layers were washed with brine, dried and concentrated and the residue purified by column chromatography (0 to 5% methanol in dichloromethane) to give the title compound having the following physical properties (0.21 g).

LC/MS $t_R$ 1.78 minutes; MS (ES$^+$) m/z 576 (M+H)$^a$.

EXAMPLE 240 methyl[4-(5-{7-[5-chloro-2-(1H-tetrazol-1-yl)phenyl]-5-oxo-1,2,3,5-tetrahydro-3-indolizinyl}-1H-imidazol-2-yl)phenyl]carbamate The same operation as in Example 40→Example 41 was conducted from the compound prepared in Example 239 to give the title compound having the following physical properties.

LC/MS $t_R$ 2.99 minutes; MS (ES$^+$) m/z 529 (M+H)$^b$ $^1$H NMR (500 MHz, methanol-d$_4$) δ 9.40 (s, 1 H), 7.80-7.74 (m, 4 H), 7.71 (d, 1 H), 7.54 (d, 2 H), 6.77 (s, 1 H), 6.18 (s, 1 H), 6.09 (s, 1 H), 5.82 (d, 1 H), 3.77 (s, 3 H), 3.40-3.36 (m, 1 H), 3.06 (dd, 1 H), 2.64-2.54 (m, 1 H), 2.42 (dd, 1 H).

EXAMPLE 241 methyl[4-(4-chloro-5-{7-[5-chloro-2-(1H-tetrazol-1-yl)phenyl]-5-oxo-1,2,3,5-tetrahydro-3-indolizinyl}-1H-imidazol-2-yl)phenyl]carbamate The compound prepared in Example 240 (80 mg) was treated as detailed in Example 44 to give the title compound having the following physical properties (21 mg).

LC/MS $t_R$ 3.79 minutes; MS (ES$^+$) m/z 563 (M+H)$^b$ $^1$H NMR (500 MHz, methanol-d$_4$) δ 9.36 (s, 1 H), 7.78-7.72 (m, 4 H), 7.72-7.69 (m, 1 H), 7.55 (d, 2 H), 6.21 (s, 1 H), 6.05 (s, 1 H), 5.81 (dd, 1 H), 3.77 (s, 3 H), 3.40-3.34 (m, 1 H), 3.14 (ddd, 1 H), 2.75-2.65 (m, 1 H), 2.33 (tdd, 1 H).

EXAMPLE 242 tert-butyl N-[4-chloro-2-(3-{N'-[(4-nitrophenyl)carboximidoyl]hydrazinecarbonyl}-5-oxo-1,2,3,5-tetrahydroindolizin-7-yl)phenyl]carbamate To a cooled (0° C.) tetrahydrofuran (5 mL) solution of the compound prepared in Example 19 (0.40 g) was added ethyl chloroformate (0.11 mL) and 4-methylmorpholine (0.16 mL) and the mixture stirred at 0° C. for 25 minutes. A solution of N-amino-4-nitrobenzenecarboximidamide [Justus Liebigs Ann. Chem. 298, 51 (1897)] in tetrahydrofuran (5 mL) was added and the mixture stirred at room temperature for 16 hours. To the reaction mixture, a saturated aqueous solution of sodium hydrogen carbonate (25 mL) was added followed by extraction with ethyl acetate. The combined organic layers were washed with brine, dried and concentrated. The residue was purified by column chromatography (0 to 10% ethyl acetate in heptanes) to obtain the title compound having the following physical properties (0.23 g).

LC/MS $t_R$ 1.79 minutes; MS (ES$^+$) m/z 567 (M+H)$^a$.

EXAMPLE 243

7-(2-amino-5-chlorophenyl)-3-[5-(4-nitrophenyl)-4H-1,2,4-triazol-3-yl]-1,2,3,5-tetrahydroindolizin-5-one A glacial acetic acid (2.1 mL) solution of the compound prepared in Example 242 (0.23 g) was stirred at 110° C. for 3 hours. To the mixture, a saturated aqueous solution of sodium hydrogen carbonate (30 mL) was added followed by extraction with ethyl acetate. The combined organic layers were washed with brine, dried and concentrated. The residue was purified by column chromatography (0 to 20% methanol in ethyl acetate) to obtain the title compound having the following physical properties (0.086 g).

LC/MS $t_R$ 1.97 minutes; MS (ES$^+$) m/z 449 (M+H)$^a$.

EXAMPLE 244

3-[5-(4-aminophenyl)-4H-1,2,4-triazol-3-yl]-7-[5-chloro-2-(1H-tetrazol-1-yl)phenyl]-2,3-dihydro-5(1H)-indolizinone The same operation as in Example 41→Example 74 was conducted from the compound prepared in Example 243 (110 mg) to obtain the title compound having the following physical properties (77 mg).

LC/MS $t_R$ 3.31 minutes; MS (ES$^+$) m/z 472 (M+H)$^b$ $^1$H NMR (500 MHz, DMSO-d$_6$) δ 13.68 (br. s, 1 H), 9.68 (s, 1 H), 7.80 (app. s, 3 H), 7.58 (d, 2 H), 6.61 (d, 2 H), 5.95 (s, 1 H), 5.93 (s, 1 H), 5.62 (d, 1 H), 5.57 (br. s, 2 H), 3.27-3.08 (m, 1 H), 2.95 (dd, 1 H), 2.58-2.44 (obs. m, 1 H), 2.15-2.00 (m, 1 H).

EXAMPLE 245 methyl[4-(5-{7-[5-chloro-2-(1H-tetrazol-1-yl)phenyl]-5-oxo-1,2,3,5-tetrahydro-3-indolizinyl}-4H-1,2,4-triazol-3-yl)phenyl]carbamate The compound prepared in Example 244 (65 mg) was treated as detailed in Example 128 using methyl chloroformate in place of ethyl chloroformate to give the title compound having the following physical properties (29.6 mg).
LC/MS $t_R$ 3.67 minutes; MS (ES$^+$) m/z 530 (M+H)$^b$
$^1$H NMR (500 MHz, CDCl$_3$) δ 12.89 (br. s, 1 H), 8.71 (br. s, 1 H), 7.77 (app. br. s, 2 H), 7.65-7.53 (m, 2 H), 7.53-7.45 (m, 1 H), 7.34 (app. br. s, 2 H), 6.31 (br. s, 1 H), 5.91 (br. s, 1 H), 5.76 (app. br. s, 1 H), 3.75 (br. s, 3 H), 3.46-3.28 (m, 1 H), 3.07-2.91 (m, 1 H), 2.79-2.46 (m, 2 H).

EXAMPLE 246 methyl 7-(2-{[(tert-butoxy)carbonyl]amino}-5-chlorophenyl)-5-oxo-1,2,3,5-tetrahydroindolizine-3-carboxylate To a dichloromethane (7.5 mL) and methanol (2.5 mL) solution of the compound prepared in Example 19 (1.0 g) was added a 2 M solution of (trimethylsilyl)diazomethane in diethyl ether (2.2 mL) at 0° C. and the mixture stirred at room temperature for 16 hours. To the reaction mixture, acetic acid (0.5 mL) and a saturated aqueous solution of sodium hydrogen carbonate (30 mL) were sequentially added followed by extraction with ethyl acetate. The combined organic layers were washed with brine, dried and concentrated. The residue was purified by column chromatography (10% to 100% ethyl acetate in heptanes) to obtain the title compound having the following physical properties (0.83 g).
LC/MS $t_R$ 2.01 minutes; MS (ES$^+$) m/z 419 (M+H)$^a$.

EXAMPLE 247 tert-butyl N-(4-chloro-2-{3-[2-(dimethoxyphosphoryl)acetyl]-5-oxo-1,2,3,5-tetrahydroindolizin-7-yl}phenyl)carbamate To a cooled (−78° C.) tetrahydrofuran (20 mL) solution of dimethyl methylphosphonate (1.1 mL) was added a 2.5 M solution of n-butyllithium in hexanes (4.0 mL) and the mixture stirred at −78° C. for 30 minutes. A solution of the compound prepared in Example 246 (0.83 g) in tetrahydrofuran (10 mL) was added and the mixture stirred at −78° C. for 1 hour. To the cooled (−78° C.) reaction mixture, a saturated aqueous solution of ammonium chloride (5 mL) was added followed by water (30 mL) and the mixture was allowed to warm to room temperature then extracted with ethyl acetate. The combined organic layers were washed with brine, dried and concentrated. The residue was purified by column chromatography (20% to 100% ethyl acetate in heptanes, then 0 to 20% methanol in ethyl acetate) to obtain the title compound having the following physical properties (0.67 g).
LC/MS $t_R$ 1.92 minutes; MS (ES$^+$) m/z 511 (M+H)$^a$.

EXAMPLE 248 tert-butyl N-(4-chloro-2-{3-[5-(4-nitrophenyl)-6-oxo-1,6-dihydropyridazin-3-yl]-5-oxo-1,2,3,5-tetrahydroindolizin-7-yl}phenyl)carbamate To a cooled (0° C.) ethanol (7 mL) suspension of the compound prepared in Example 247 (0.67 g) and potassium carbonate (0.27 g) was added ethyl(4-nitrophenyl)(oxo)acetate (0.31 g) and the mixture stirred at 0° C. for 90 minutes then at room temperature for 2 hours. Hydrazine hydrate (0.6 mL) was added and the mixture stirred at room temperature for 3 hours. To the reaction mixture, 0.5 M hydrochloric acid (25 mL) was added followed by extraction with ethyl acetate. The combined organic layers were washed with brine, dried and concentrated. The residue was purified by column chromatography (0 to 100% ethyl acetate in heptanes). The product was triturated with a 1:2 mixture of dichloromethane and heptanes and the solid collected by filtration to give the title compound having the following physical properties (0.24 g)
LC/MS $t_R$ 2.08 minutes; MS (ES$^+$) m/z 576 (M+H)$^a$.

EXAMPLE 249 methyl[4-(6-{7-[5-chloro-2-(1H-tetrazol-1-yl)phenyl]-5-oxo-1,2,3,5-tetrahydro-3-indolizinyl}-3-oxo-2,3-dihydro-4-pyridazinyl)phenyl]carbamate The same operation as in Example 74→Example 128→Example 40→Example 41 was conducted from the compound prepared in Example 248 (0.24 g) to obtain the title compound having the following physical properties (0.075 g). (Note: in the step corresponding to Example 128 in the operation, methyl chloroformate was used).
LC/MS $t_R$ 3.69 minutes; MS (ES$^+$) m/z 557 (M+H)$^b$
$^1$H NMR (500 MHz, DMSO-d$_6$) δ 12.98 (br. s, 1 H), 9.89 (s, 1 H), 9.71 (s, 1 H), 7.88 (d, 2 H), 7.82-7.78 (m, 3 H), 7.61 (s, 1 H), 7.56 (d, 2 H), 5.96 (s, 1 H), 5.94 (s, 1 H), 5.55 (dd, 1 H), 3.68 (s, 3 H), 3.16-3.05 (m, 1 H), 2.97 (ddd, 1 H), 2.59-2.46 (obs. m, 1 H), 2.25-2.15 (m, 1 H).

EXAMPLE 250 tert-butyl N-(4-chloro-2-{3-[methoxy(methyl)carbamoyl]-5-oxo-1,2,3,5-tetrahydroindolizin-7-yl}phenyl)carbamate To an N,N-dimethylformamide (12.5 mL) solution of the compound prepared in Example 19 (1.0 g) was added N,O-dimethylhydroxylamine hydrochloride (0.36 g), O-(7-azabenzotriazol-1-yl)-N,N,N',N'-tetramethyluronium hexafluorophosphate (1.0 g) and diisopropylethylamine (1.2 mL) and the mixture stirred at room temperature for 16 hours. The reaction mixture was concentrated and the residue suspended in a saturated aqueous solution of sodium hydrogen carbonate (30 mL) followed by extraction into ethyl acetate. The combined organic layers were washed with brine, dried and concentrated. The residue was purified by column chromatography (0% to 20% methanol in ethyl acetate) to obtain the title compound having the following physical properties (0.73 g).
LC/MS $t_R$ 1.99 minutes; MS (ES$^+$) m/z 448 (M+H)$^a$.

EXAMPLE 251 tert-butyl N-[4-chloro-2-(3-formyl-5-oxo-1,2,3,5-tetrahydroindolizin-7-yl)phenyl]carbamate To a cooled (−45° C.) tetrahydrofuran (6.5 mL) solution of the compound prepared in Example 250 (0.60 g) was added a 1 M solution of lithium aluminium hydride in tetrahydrofuran (1.6 mL) over 10 minutes. The reaction mixture was stirred at −45° C. for 30 minutes, 0° C. for 90 minutes then cooled to −45° C. and a solution of potassium hydrogen sulfate (0.36 g) in water (1.0 mL) added. The mixture was warmed to room temperature and extracted into ethyl acetate. The combined organic layers were washed sequentially with 1 M hydrochloric acid (25 mL), a saturated aqueous solution of sodium hydrogen carbonate (30 mL) and brine (25 mL), dried and concentrated to give the title compound having the following physical properties (0.45 g).

LC/MS $t_R$ 1.84 minutes; MS (ES$^+$) m/z 389 (M+H)$^a$.

EXAMPLE 252 tert-butyl N-[4-chloro-2-(3-ethynyl-5-oxo-1,2,3,5-tetrahydroindolizin-7-yl)phenyl]carbamate To a methanol (15 mL) suspension of the compound prepared in Example 251 (0.45 g) and potassium carbonate (0.32 g) was added dimethyl(1-diazo-2-oxopropyl)phosphonate (0.2 mL) and the mixture stirred at room temperature for 4 hours. To the reaction mixture, a saturated aqueous solution of sodium hydrogen carbonate (25 mL) was added followed by extraction into ethyl acetate. The combined organic layers were washed with brine, dried and concentrated. The residue was purified by column chromatography (0 to 100% ethyl acetate in heptanes) to obtain the title compound having the following physical properties (0.29 g).

LC/MS $t_R$ 2.02 minutes; MS (ES$^+$) m/z 385 (M+H)$^a$.

EXAMPLE 253 tert-butyl N-(2-{3-[1-(4-aminophenyl)-1H-1,2,3-triazol-4-yl]-5-oxo-1,2,3,5-tetrahydroindolizin-7-yl}-4-chlorophenyl)carbamate To an acetonitrile (1.2 mL) solution of the compound prepared in Example 252 (0.14 g) was added 4-azidoaniline hydrochloride (59 mg), copper(II) sulfate pentahydrate (8 mg), a solution of sodium ascorbate (31 mg) in water (0.60 mL) and 1 M sodium hydroxide (0.35 mL). The reaction mixture was irradiated under microwave conditions (120 W) at 80° C. for 1 hour and a saturated aqueous solution of sodium hydrogen carbonate (30 mL) was added followed by extraction with ethyl acetate. The combined organic layers were washed with brine, dried and concentrated. The residue was purified by column chromatography ((0 to 100% ethyl acetate in heptanes) to obtain the title compound having the following physical properties (0.16 g).

LC/MS $t_R$ 2.01 minutes; MS (ES$^+$) m/z 519 (M+H)$^a$.

EXAMPLE 254 methyl[4-(4-{7-[5-chloro-2-(1H-tetrazol-1-yl)phenyl]-5-oxo-1,2,3,5-tetrahydro-3-indolizinyl}-1H-1,2,3-triazol-1-yl)phenyl]carbamate The same operation as in Example 128→Example 40→Example 41 was conducted from the compound prepared in Example 253 (0.16 g) to obtain the title compound having the following physical properties (0.11 g). (Note: in the step corresponding to Example 128 in the operation, methyl chloroformate was used).

LC/MS $t_R$ 3.88 minutes; MS (ES$^+$) m/z 530 (M+H)$^b$ $^1$H NMR (500 MHz, DMSO-d$_6$) δ 9.94 (s, 1 H), 9.69 (s, 1 H), 8.55 (s, 1 H), 7.83-7.74 (m, 5 H), 7.64 (d, 2 H), 5.96 (s, 1 H), 5.95 (s, 1 H), 5.79 (d, 1H), 3.69 (s, 3 H), 3.39-3.33 (m, 1 H), 3.04 (dd, 1 H), 2.61-2.52 (m, 1 H), 2.32 (dd, 1 H).

EXAMPLE 255 tert-butyl N-(4-chloro-2-{3-[3-(4-nitrophenyl)-1,2-oxazol-5-yl]-5-oxo-1,2,3,5-tetrahydroindolizin-7-yl}phenyl)carbamate To a tert-butanol (1.0 mL) and water (1.0 mL) suspension of 4-nitrobenzaldehyde (63 mg) was added hydroxylamine hydrochloride (29 mg) and the mixture stirred at room temperature for 1 hour. Chloramine-T trihydrate (117 mg) was added and the mixture stirred at room temperature for 5 minutes to afford the intermediate nitrile oxide.

To the suspension, copper powder (2.4 mg), copper(II) sulfate pentahydrate (9.4 mg) and a solution of the compound prepared in Example 252 (145 mg) in tort-butanol (1.0 mL) was sequentially added and the mixture stirred at room temperature for 16 hours. The nitrile oxide was re-prepared as detailed above, added to the reaction and the mixture stirred at room temperature for 16 hours then at 80° C. for 20 hours. To the reaction mixture, a 10% aqueous solution of ammonia (20 mL) was added followed by extraction into ethyl acetate. The combined organic layers were washed with brine, dried and concentrated. The residue obtained on concentration was purified by column chromatography (12% to 80% ethyl acetate in heptanes) to obtain the title compound having the following physical properties (49.5 mg).

LC/MS $t_R$ 2.33 minutes; MS (ES$^+$) m/z 549 (M+H)$^a$.

EXAMPLE 256 methyl[4-(5-{7-[5-chloro-2-(1H-tetrazol-1-yl)phenyl]-5-oxo-1,2,3,5-tetrahydro-3-indolizinyl}-1,2-oxazol-3-yl)phenyl]carbamate The same operation as in Example 40→Example 41→Example 74→Example 128 was conducted from the compound prepared in Example 255 (49.5 mg) to obtain the title compound having the following physical properties (8.4 mg). (Note: in the step corresponding to Example 128 in the operation, methyl chloroformate was used).

LC/MS $t_R$ 4.12 minutes; MS (ES$^+$) m/z 530 (M+H)$^b$ $^1$H NMR (500 MHz, DMSO-d$_6$) δ 9.91 (s, 1 H), 9.71 (s, 1 H), 7.83-7.79 (m, 3 H), 7.77 (d, 2 H), 7.58 (d, 2 H), 6.75 (s, 1 H), 6.02 (s, 1 H), 6.00 (s, 1 H), 5.86 (dd, 1 H), 3.69 (s, 3 H), 3.18 (td, 1 H), 3.09-2.99 (m, 1 H), 2.61-2.53 (m, 1 H), 2.27-2.19 (m, 1 H).

EXAMPLE 257

2-methyl-2-propanyl(2S)-2-[2-oxo-4-{[(trifluoromethyl)sulfonyl]oxy}-1(2H)-pyridinyl]-3-phenylpropanoate The same operation as in Example 20→Example 21→Example 22 was conducted from 2-methyl-2-propanyl (2R)-3-phenyl-2-{[(trifluoromethyl)sulfonyl]oxy}propanoate (WO200657961) to give the title compound having the following physical properties.

TLC: Rf 0.33 (20% ethyl acetate in hexane).

EXAMPLE 258

(2S)-2-[4-(2,5-dichlorophenyl)-2-oxo-1(2H)-pyridinyl]-3-phenylpropanoic acid

The same operation as in Example 23→Example 25 was conducted from the compound prepared in Example 257 to give the title compound having the following physical properties. (Note: in the step corresponding to Example 23 in the operation, 2,5-dichlorophenylboronic acid was used).

TLC: Rf 0.18 (10% methanol in dichloromethane).

EXAMPLE 259

4-(4-chloro-2-{(1S)-1-[4-(2,5-dichlorophenyl)-2-oxo-1(2H)-pyridinyl]-2-phenylethyl}-1H-imidazol-5-yl)benzoic acid The same operation as in Example 72→Example 73→Example 76→Example 49 was conducted from the compound prepared in Example 258 to give the title compound having the following physical properties. (Note: in the step corresponding to Example 72 in the operation, methyl 4-(bromoacetyl)benzoate was used).

TLC: Rf 0.41 (10% methanol in dichloromethane)

$^1$H NMR (300 MHz, DMSO-d$_6$) δ 13.21 (br. s, 1 H), 8.10-7.92 (m, 3 H), 7.85 (s, 2 H), 7.66-7.44 (m, 3 H), 7.34-7.11 (m, 5 H), 6.51-6.31 (m, 3 H), 3.60 (dd, 1 H), 3.39 (dd, 1 H).

EXAMPLE 260

4-(2-{(1S)-1-[4-(2,5-dichlorophenyl)-2-oxo-1(2H)-pyridinyl]-2-phenylethyl}-1H-imidazol-5-yl)benzoic acid The same operation as in Example 72→Example 73→Example 49 was conducted from the compound prepared in Example 258 to give the title compound having the following physical properties. (Note: in the step corresponding to Example 72 in the operation, methyl 4-(bromoacetyl)benzoate was used).

TLC: Rf 0.47 (10% methanol in dichloromethane)

$^1$H NMR (300 MHz, DMSO-d$_6$) δ 12.98 (br. s, 1 H), 8.08-7.91 (m, 5 H), 7.86 (d, 1 H), 7.68-7.40 (m, 3 H), 7.36-7.03 (m, 5 H), 6.45 (s, 1 H), 6.38-6.32 (m, 1 H), 6.32-6.23 (m, 1 H), 3.86-3.72 (m, 1 H), 3.65-3.48 (m, 1 H).

EXAMPLE 261

3-(4-chloro-2-{(1S)-1-[4-(2,5-dichlorophenyl)-2-oxo-1(2H)-pyridinyl]-2-phenylethyl}-1H-imidazol-5-yl)benzoic acid The same operation as in Example 72→Example 73→Example 76→Example 49 was conducted from the compound prepared in Example 258 to give the title compound having the following physical properties. (Note: in the step corresponding to Example 72 in the operation, methyl 3-(bromoacetyl)benzoate was used).

TLC: Rf 0.45 (10% methanol in dichloromethane)

$^1$H NMR (300 MHz, DMSO-d$_6$) δ 13.29 (br. s, 1 H), 12.98 (br. s, 1 H), 8.31 (s, 1 H), 8.03-7.94 (m, 2 H), 7.89 (d, 1 H), 7.66-7.45 (m, 4 H), 7.31-7.11 (m, 5 H), 6.50-6.32 (m, 3 H), 3.60 (dd, 1 H), 3.47-3.36 (m, 1 H).

EXAMPLE 262

3-{2-[(S)-[4-(2,5-dichlorophenyl)-2-oxo-1(2H)-pyridinyl](phenyl)methyl]-1H-imidazol-5-yl}benzoic acid The same operation as in Example 20→Example 21→Example 22→Example 23→Example 30→Example 72→Example 73→Example 49 was conducted from methyl (2R)-chloro(phenyl)acetate [Justus Liebigs Annalen der Chemie, 501, 208, (1933)] to give the title compound having the following physical properties. (Note: in the step corresponding to Example 23 in the operation, 2,5-dichlorophenylboronic acid was used. In the step corresponding to Example 72 in the operation, methyl 3-(bromoacetyl)benzoate was used).

TLC: Rf 0.57 (10% methanol in dichloromethane)

$^1$H NMR (300 MHz, DMSO-d$_6$) δ 13.21 (br. s, 1 H), 12.71 (br. s, 1 H), 8.32 (br. s, 1 H), 7.97 (d, 2 H), 7.77 (d, 2 H), 7.65-7.23 (m, 10 H), 6.54 (d, 1 H), 6.42 (d, 1 H).

EXAMPLE 263 methyl{4-[2-(1-{4-[5-chloro-2-(1H-tetrazol-1-yl)phenyl]-2-oxo-1(2H)-pyridinyl}-3-methoxypropyl)-1H-imidazol-5-yl]phenyl}carbamate The same operation as in Example 26→Example 21→Example 22→Example 23→Example 24→Example 25→Example 38→Example 39 was conducted from the compound prepared in Example 20 to give the title compound having the following physical properties. (Note: in the step corresponding to Example 26 in the operation, 2-chloroethyl methyl ether was used).

TLC: Rf 0.26 (ethyl acetate)

$^1$H NMR (300 MHz, CDCl$_3$) δ 11.17 (br. s, 1 H), 8.67-8.51 (m, 1 H), 7.82-7.33 (m, 8 H), 7.20 (br. s, 1 H), 6.53-5.99 (m, 2 H), 5.84-5.64 (m, 1 H), 3.89-3.68 (m, 3 H), 3.50-3.30 (m, 2 H), 3.28-3.08 (m, 3 H), 2.71-2.33 (m, 2 H).

EXAMPLE 264 methyl{4-[4-chloro-2-(1-{4-[5-chloro-2-(1H-tetrazol-1-yl)phenyl]-2-oxo-1(2H)-pyridinyl]-3-methoxypropyl)-1H-imidazol-5-yl}phenyl}carbamate The compound prepared in Example 263 (40 mg) was treated as detailed in Example 47 to give the title compound having the following physical properties (18 mg).

TLC: Rf 0.57 (5% methanol in ethyl acetate)

$^1$H NMR (300 MHz, CDCl$_3$) δ 11.78 (br. s, 1 H), 8.59 (s, 1 H), 7.79-7.39 (m, 8 H), 6.77 (s, 1 H), 6.40 (s, 1 H), 6.19 (br. s, 1 H), 5.79 (d, 1 H), 3.79 (s, 3 H), 3.53-3.32 (m, 2 H), 3.32-3.06 (m, 3 H), 2.59 (d, 1 H), 2.45 (br. s, 1 H).

EXAMPLE 265 methyl(4-{2-[(1S)-1-{4-[5-chloro-2-(1H-tetrazol-1-yl)phenyl]-2-oxo-1(2H)-pyridinyl}-2-phenylethyl]-1H-imidazol-4-yl}phenyl)carbamate The same operation as in Example 23→Example 24→Example 25→Example 38→Example 39 was conducted from the compound prepared in Example 257 to give the title compound having the following physical properties.

TLC: Rf 0.57 (80% ethyl acetate in hexane)

$^1$H NMR (300 MHz, DMSO-d$_6$) δ 12.30 (s, 1 H), 9.76-9.49 (m, 2 H), 7.91-7.61 (m, 5 H), 7.61-7.35 (m, 4 H), 7.34-6.99 (m, 5 H), 6.40-6.10 (m, 2 H), 5.89 (dd, 1 H), 3.66 (s, 3 H), 3.58-3.43 (m, 1 H), 3.27 (br. s, 1 H).

EXAMPLE 266 methyl[4-(2-{(3S)-7-[5-chloro-2-(1H-tetrazol-1-yl)phenyl]-5-oxo-1,2,3,5-tetrahydro-3-indolizinyl}-1H-imidazol-4-yl)phenyl]carbamate

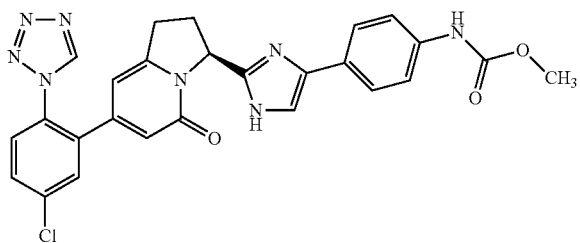 [SMILES: COC(=O)Nc1ccc(-c2c[nH]c([C@@H]3CCc4cc(-c5cc(Cl)ccc5-n5cnnn5)cc(=O)n43)n2)cc1]

The same operation as in Example 38→Example 39→Example 40→Example 41 was conducted from the compound prepared in Example 11 to give the title compound having the following physical properties.

TLC: Rf 0.29 (ethyl acetate)

$^1$H NMR (300 MHz, DMSO-$d_6$) δ 12.03 (s, 1 H), 9.75-9.63 (m, 1 H), 9.58 (s, 1 H), 7.87-7.72 (m, 3 H), 7.66-7.31 (m, 5 H), 6.01-5.88 (m, 2 H), 5.68-5.53 (m, 1 H), 3.72-3.59 (m, 3 H), 3.48-3.34 (m, 1 H), 2.99 (dd, 1 H), 2.46-2.10 (m, 2 H).

EXAMPLE 267

5-[(5-chloro-2-nitrophenyl)(hydroxy)methylene]-2,2-dimethyl-1,3-dioxane-4,6-dione A mixture of 5-chloro-2-nitrobenzoic acid (11.0 g) and thionyl chloride (11.8 mL) was stirred at 90° C. for 2 hours then concentrated. The resulting residue was dissolved in dichloromethane (50 mL) and added to a stirred solution of 2,2-dimethyl-1,3-dioxane-4,6-dione (7.86 g) and 4-(dimethylamino)pyridine (13.3 g) in dichloromethane (200 mL) at −12° C. After being stirred for 2 hours, the reaction mixture was washed with 1 M hydrochloric acid (100 mL×3) and water, dried and concentrated. The residue thus obtained was triturated with acetonitrile followed by acetone to afford the title compound having the following physical properties (6.0 g).

TLC: Rf 0.43 (ethyl acetate).

EXAMPLE 268 methyl(3R)-7-(5-chloro-2-nitrophenyl)-5-oxo-2,3-dihydro-5H-[1,3]thiazolo[3,2-a]pyridine-3-carboxylate To a dichloromethane (80 mL) solution of the compound prepared in Example 267 (7.67 g) was added (4S)-methyl 2-methyl-4,5-dihydro-1,3-thiazole-4-carboxylate [Journal of Organic Chemistry, 66(20), 6756, (2001)] (1.57 g) and the stirred mixture treated with gaseous hydrogen chloride at 0° C. for 15 minutes. The reaction mixture was then heated for 24 hours at 64° C. for before allowing to cool to room temperature. To the reaction mixture, water was added followed by extraction with dichloromethane. The combined organic layers were washed sequentially with a saturated aqueous solution of sodium hydrogen carbonate and brine, dried and concentrated. The residue was purified by column chromatography (30-55% ethyl acetate in hexanes) to give the title compound having the following physical properties (310 mg).

TLC: Rf 0.35 (50% ethyl acetate in hexane).

EXAMPLE 269 methyl(3R)-7-[2-(bis{[(2-methyl-2-propanyl)oxy]carbonyl}amino)-5-chlorophenyl]-5-oxo-2,3-dihydro-5H-[1,3]thiazolo[3,2-a]pyridine-3-carboxylate To a mixture of ammonium chloride (250 mg) and zinc powder (341 mg) in water (2.5 mL) was added a solution of the compound prepared in Example 268 (234 mg) in ethyl acetate (12.5 mL) and the mixture stirred for 3 hours at room temperature. The reaction mixture was filtered through Celite® and the filtrate was washed with brine, dried and concentrated. The residue thus obtained was dissolved in tetrahydrofuran (5 mL) and to this solution triethylamine (0.16 mL), 4-(dimethylamino)pyridine (13 mg) and di-tert-butyl dicarbonate (247 mg) were sequentially added. The reaction mixture was warmed to 60° C. for 1 hour before allowing to cool to room temperature. To the reaction mixture, a saturated aqueous solution of potassium bisulfate was added followed by extraction with ethyl acetate. The combined organic layers were washed with brine, dried and concentrated. The residue was purified by column chromatography (70% ethyl acetate in hexanes) to give the title compound having the following physical properties (189 mg).

TLC: Rf 0.63 (80% ethyl acetate in hexane).

EXAMPLE 270 methyl[4-(2-{(3R)-7-[5-chloro-2-(1H-tetrazol-1-yl)phenyl]-5-oxo-2,3-dihydro-5H-[1,3]thiazolo[3,2-a]pyridin-3-yl}-1H-imidazol-5-yl)phenyl]carbamate The same operation as in Example 11→Example 38→Example 39→Example 40→Example 41 was conducted from the compound prepared in Example 269 to give the title compound having the following physical properties.

TLC: Rf 0.49 (5% methanol in ethyl acetate, NH Silica)

$^1$H NMR (300 MHz, CDCl$_3$) δ 10.58 (br. s, 1 H), 8.58 (s, 1 H), 7.72 (d, 2 H), 7.67-7.28 (m, 4 H), 7.26-7.06 (m, 2 H), 6.80-6.45 (m, 1 H), 6.23 (d, 1 H), 6.17-5.97 (m, 1 H), 5.80 (s, 1 H), 4.71 (d, 1 H), 4.00-3.65 (m, 4 H).

EXAMPLE 271(1) TO EXAMPLE 271(4)

The compounds of the present invention having the following physical data were prepared using the corresponding alpha-bromoketones from the compound prepared in Example 11 in the process of Example 38→Example 39→Example 40→Example 41

EXAMPLE 271(1)

methyl[3-chloro-4-(2-{(3S)-7-[5-chloro-2-(1H-tetrazol-1-yl)phenyl]-5-oxo-1,2,3,5-tetrahydro-3-indolizinyl}-1H-imidazol-4-yl)phenyl]carbamate TLC 0.55 (5% methanol in ethyl acetate, NH Silica)

$^1$H NMR (300 MHz, DMSO-$d_6$) δ 12.20 (s, 1 H), 9.82 (s, 1 H), 9.74-9.58 (m, 1 H), 7.93-7.84 (m, 1 H), 7.84-7.72 (m, 3 H), 7.62 (d, 1 H), 7.58-7.36 (m, 2 H), 5.96 (s, 2 H), 5.73-5.55 (m, 1 H), 3.73-3.61 (m, 3 H), 3.46-3.33 (m, 1 H), 3.10-2.87 (m, 1 H), 2.47-2.19 (m, 2 H).

EXAMPLE 271(2)

6-(2-{(3S)-7-[5-chloro-2-(1H-tetrazol-1-yl)phenyl]-5-oxo-1,2,3,5-tetrahydro-3-indolizinyl}-1H-imidazol-5-yl)-3,4-dihydro-2 (1H)-quinolinone TLC: Rf 0.28 (10% methanol in ethyl acetate, NH Silica)
$^1$H NMR (300 MHz, DMSO-$d_6$) δ 12.01 (s, 1 H), 10.03 (s, 1 H), 9.79-9.50 (m, 1 H), 7.85-7.70 (m, 3 H), 7.60-7.28 (m, 3 H), 6.98-6.61 (m, 1 H), 6.13-5.84 (m, 2 H), 5.60 (d, 1 H), 3.54-3.19 (m, 3 H), 3.10-2.77 (m, 3 H), 2.45-2.07 (m, 2 H).

EXAMPLE 271(3)

ethyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate TLC: Rf 0.52 (10% methanol in ethyl acetate)
$^1$H NMR (300 MHz, DMSO-$d_6$) δ 12.02 (s, 1 H), 9.79-9.60 (m, 1 H), 9.54 (s, 1 H), 7.95-7.68 (m, 3 H), 7.68-7.34 (m, 5 H), 6.09-5.80 (m, 2 H), 5.73-5.48 (m, 1 H), 4.19-4.06 (m, 2 H), 3.46-3.35 (m, 1 H), 2.99 (dd, 1 H), 2.61-2.53 (m, 1 H), 2.40-2.24 (m, 1 H), 1.24 (t, 3 H).

EXAMPLE 271 (4)

4-(2-{(3S)-7-[5-chloro-2-(1H-tetrazol-1-yl)phenyl]-5-oxo-1,2,3,5-tetrahydro-3-indolizinyl}-1H-imidazol-5-yl)benzamide TLC: Rf 0.55 (10% methanol in dichloromethane)
$^1$H NMR (300 MHz, DMSO-$d_6$) δ 12.22 (s, 1 H), 9.72-9.66 (m, 1 H), 7.99-7.60 (m, 9 H), 7.25 (br. s, 1 H), 6.07-5.82 (m, 2 H), 5.67-5.53 (m, 1 H), 3.52-3.35 (m, 1 H), 3.01 (dd, 1 H), 2.46-2.24 (m, 2 H).

EXAMPLE 272

4-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)benzamide The compound prepared in Example 271(4) (250 mg) was treated as detailed in Example 44 to give the title compound having the following physical properties (152 mg).
TLC: Rf 0.64 (6% methanol in ethyl acetate)
$^1$H NMR (300 MHz, DMSO-$d_6$) δ 13.11 (s, 1 H), 9.70 (s, 1 H), 8.12-7.74 (m, 8 H), 7.40 (br. s, 1 H), 6.06-5.82 (m, 2 H), 5.58 (dd, 1 H), 3.28-3.15 (m, 1 H), 3.00 (dd, 1 H), 2.65-2.54 (m, 1 H), 2.33-2.11 (m, 1 H).

EXAMPLE 273 methyl[4-(2-{(3R)-7-[5-chloro-2-(1H-tetrazol-1-yl)phenyl]-5-oxo-1,2,3,5-tetrahydro-3-indolizinyl}-1H-imidazol-5-yl)phenyl]carbamate The compound prepared in example 42 was separated by preparative chiral HPLC (CHIRALPAK IB 50 mm×250 mm, hexane/tetrahydrofuran/diethylamine=20/80/0.1) to give the title compound having the following physical properties.

TLC: Rf 0.50 (ethyl acetate)
$^1$H NMR (300 MHz, DMSO-$d_6$) δ 12.03 (s, 1 H), 9.81-9.63 (m, 1 H), 9.58 (s, 1 H), 7.87-7.73 (m, 3 H), 7.68-7.29 (m, 5 H), 6.04-5.89 (m, 2 H), 5.68-5.54 (m, 1 H), 3.71-3.59 (m, 3 H), 3.47-3.35 (m, 1 H), 2.99 (dd, 1 H), 2.43-2.14 (m, 2 H).

EXAMPLE 274(1) AND EXAMPLE 274(2)

2-methyl-2-propanyl{4-chloro-2-[(3S)-3-(5-{4-[(methoxycarbonyl)amino]phenyl}-4-methyl-1H-imidazol-2-yl)-5-oxo-1,2,3,5-tetrahydro-7-indolizinyl]phenyl}carbamate and 2-methyl-2-propanyl{4-chloro-2-[(3S)-3-(4-{4-[(methoxycarbonyl)amino]phenyl}-5-methyl-1,3-oxazol-2-yl)-5-oxo-1,2,3,5-tetrahydro-7-indolizinyl]phenyl}carbamate The same operation as in Example 38→Example 39 was conducted from the compound prepared in Example 11 to obtain the title products in a 1:1 ratio having the following physical properties. (Note: in the step corresponding to Example 38 in the operation, the compound prepared in Example 78 was used)

EXAMPLE 274(1)

LC/MS $t_R$ 4.13 minutes; MS (ES$^+$) m/z 589 (M+H)$^d$.

EXAMPLE 274(2)

LC/MS $t_R$ 4.59 minutes; MS (ES$^+$) m/z 590 (M+H)$^d$.

EXAMPLE 275 methyl[4-(2-{(3S)-7-[5-chloro-2-(1H-tetrazol-1-yl)phenyl]-5-oxo-1,2,3,5-tetrahydro-3-indolizinyl}-5-methyl-1H-imidazol-4-yl)phenyl]carbamate The same operation as in Example 40→Example 41 was conducted from the compound prepared in Example 274(1) to give the title compound having the following physical properties.
TLC: Rf 0.54 (5% methanol in ethyl acetate, NH Silica)
$^1$H NMR (300 MHz, DMSO-$d_6$) δ 11.87 (s, 1 H), 9.81-9.62 (m, 1 H), 9.58 (s, 1 H), 7.92-7.68 (m, 3 H), 7.54-7.36 (m, 4 H), 6.06-5.84 (m, 2 H), 5.63-5.40 (m, 1 H), 3.72-3.60 (m, 3 H), 3.47-3.35 (m, 1 H), 3.10-2.86 (m, 1 H), 2.47-2.39 (m, 2 H), 2.32 (s, 3 H).

EXAMPLE 276 methyl[4-(2-{(3S)-7-[5-chloro-2-(1H-tetrazol-1-yl)phenyl]-5-oxo-1,2,3,5-tetrahydro-3-indolizinyl}-5-methyl-1,3-oxazol-4-yl)phenyl]carbamate The same operation as in Example 40→Example 41 was conducted from the compound prepared in Example 274(2) to give the title compound having the following physical properties.
TLC: Rf 0.45 (5% methanol in ethyl acetate, NH Silica)
$^1$H NMR (300 MHz, DMSO-$d_6$) δ 9.86-9.51 (m, 2 H), 7.81 (app. s, 3 H), 7.52 (app. s, 4 H), 6.00-5.97 (m, 2 H), 5.66

(dd, 1 H), 3.67 (s, 3 H), 3.25-3.09 (m, 1 H), 3.08-2.94 (m, 1 H), 2.48 (s, 3 H), 2.31-2.10 (m, 2 H).

EXAMPLE 277 methyl{4-[2-({4-[5-chloro-2-(1H-tetrazol-1-yl)phenyl]-2-oxo-1(2H)-pyridinyl}methyl)-4-methyl-1H-imidazol-5-yl]phenyl}carbamate The same operation as in Example 38→Example 39→Example 40→Example 41 was conducted from the compound prepared in Example 32 to obtain the title compound having the following physical properties. (Note: in the step corresponding to Example 38 in the operation, the compound prepared in Example 78 was used)
TLC: Rf 0.32 (5% methanol in ethyl acetate, NH Silica)
$^1$H NMR (300 MHz, CDCl$_3$) δ 10.01 (br. s, 1 H), 8.53 (s, 1 H), 7.68-7.59 (m, 1 H), 7.59-7.32 (m, 7 H), 6.63 (br. s, 1 H), 6.54 (d, 1 H), 5.73 (d, 1 H), 5.08 (s, 2 H), 3.80 (s, 3 H), 2.40 (br. s, 3 H).

EXAMPLE 278 methyl(4-{2-[1-{4-[5-chloro-2-(1H-tetrazol-1-yl)phenyl]-2-oxo-1(2H)-pyridinyl}-2-(3-pyridinyl)ethyl]-1H-imidazol-5-yl}phenyl)carbamate The same operation as in Example 26→Example 21→Example 22→Example 23→Example 24→Example 25→Example 38→Example 39 was conducted from the compound prepared in Example 20 to give the title compound having the following physical properties. (Note: in the step corresponding to Example 26 in the operation, 3-(chloromethyl)pyridine hydrochloride was used).
TLC: Rf 0.30 (5% methanol in ethyl acetate, NH Silica)
$^1$H NMR (300 MHz, DMSO-d$_6$) δ 12.32 (s, 1 H), 9.80-9.59 (m, 2 H), 8.47-8.29 (m, 2 H), 7.87-7.61 (m, 6 H), 7.61-7.35 (m, 4 H), 7.34-7.19 (m, 1 H), 6.44-6.07 (m, 2 H), 5.92 (d, 1 H), 3.66 (s, 3 H), 3.62-3.40 (m, 1 H), 3.33-3.16 (m, 1 H).

EXAMPLE 279 methyl(4-{4-chloro-2-[1-{4-[5-chloro-2-(1H-tetrazol-1-yl)phenyl]-2-oxo-1(2H)-pyridinyl}-2-(3-pyridinyl)ethyl]-1H-imidazol-5-yl}phenyl)carbamate The compound prepared in Example 278 (126 mg) was treated as detailed in Example 47 to give the title compound having the following physical properties (60 mg).
TLC: Rf 0.21 (5% methanol in ethyl acetate)
$^1$H NMR (300 MHz, DMSO-d$_6$) δ 12.94 (s, 1 H), 9.80 (s, 1 H), 9.64 (s, 1 H), 8.56-8.24 (m, 2 H), 7.95-7.68 (m, 4 H), 7.56 (q, 4 H), 7.45-7.12 (m, 2 H), 6.34-6.20 (m, 1 H), 6.16 (d, 1 H), 5.95 (dd, 1 H), 3.74-3.62 (m, 3 H), 3.54 (dd, 1 H), 3.28 (br. s, 1 H).

EXAMPLE 280

1-azido-2-bromo-4-chlorobenzene

To a solution of concentrated hydrochloric acid (100 mL) in water (300 mL) was added 2-bromo-4-chloroaniline (10.0 g).). To this stirred suspension, a solution of sodium nitrite (3.68 g) in water (150 mL) was added dropwise at −5° C. After being stirred at −5° C. for 1 hour, a solution of sodium azide (3.46 g) in water (15 mL) was added dropwise and the resulting suspension stirred at −5° C. for a further hour. The reaction mixture was then extracted with ethyl acetate and the organic layer washed with brine, dried and concentrated to obtain the title compound having the following physical properties (10.7 g).
$^1$H NMR (300 MHz, CDCl$_3$) δ 7.56 (d, 1 H), 7.32 (dd, 1 H), 7.09 (d, 1 H).

EXAMPLE 281

2-methyl-2-propanyl 1-(2-bromo-4-chlorophenyl)-1H-1,2,3-triazole-4-carboxylate

To a toluene (50 mL) solution of the compound prepared in Example 280 (2.4 g), tert-butyl propiolate (3 mL) was added and the mixture stirred at reflux for 6 hours. The reaction mixture was concentrated and the residue purified by column chromatography (7 to 20% ethyl acetate in hexane) to give the title compound having the following physical properties (2.3 g).
LC/MS $t_R$ 4.51 minutes; MS (ES$^+$) m/z 358 and 360 (M+H)$^d$.

EXAMPLE 282 ethyl(3S)-5-oxo-7-(4,4,5,5-tetramethyl-1,3,2-dioxaborolan-2-yl)-1,2,3,5-tetrahydro-3-indolizinecarboxylate To a 1,4-dioxane (7 mL) solution of the compound prepared in Example 6 (500 mg) was sequentially added bis(pinacolate)diboron (393 mg) and potassium acetate (415 mg). The mixture was degassed with argon then 1,1'-bis (diphenylphosphino)ferrocene palladium (II) dichloride dichloromethane complex (115 mg) was added and the reaction mixture stirred at 100° C. for 3 hours. To the reaction mixture, ethyl acetate was added followed by filtration with Celite. The filtrate was washed with water and brine, dried and concentrated to obtain the title compound having the following physical properties (412 mg).
$^1$H NMR (300 MHz, CDCl$_3$) δ 6.86 (br s, 1 H), 6.40 (br s, 1 H), 5.11 (dd, 1 H), 4.39-4.17 (m, 2 H), 3.25-3.10 (m, 1 H), 3.09-2.96 (m, 1 H), 2.55-2.39 (m, 1 H), 2.32-2.20 (m, 1 H), 1.39-1.21 (m, 15 H).

EXAMPLE 283 ethyl(3S)-7-[5-chloro-2-(4-{[(2-methyl-2-propanyl)oxy]carbonyl}-1H-1,2,3-triazol-1-yl)phenyl]-5-oxo-1,2,3,5-tetrahydro-3-indolizinecarboxylate To a 1,4-dioxane (30 mL) solution of the compound prepared in Example 281 (1.01 g) was added the compound prepared in Example 282 (1.10 g) and a solution of sodium carbonate (1.20 g) in water (6.0 mL). To the reaction mixture, tetrakis(triphenylphosphine)palladium(0) (487 mg) was added then the mixture degassed with argon and stirred for 16 h at 100° C. The reaction mixture was concentrated and the residue thus obtained suspended in ethyl acetate and washed with water and brine. The organic layer was dried and concentrated and the residue purified by column chromatography (15% methanol in ethyl acetate) to give the title compound having the following physical properties (613 mg).
LC/MS $t_R$ 4.30 minutes; MS (ES$^+$) m/z 485 (M+H)$^d$.

EXAMPLE 284

2-methyl-2-propanyl 1-{4-chloro-2-[(3S)-3-(5-{4-[(methoxycarbonyl)amino]phenyl}-1H-imidazol-2-yl)-5-oxo-1,2,3,5-tetrahydro-7-indolizinyl]phenyl}-1H-1,2,3-triazole-4-carboxylate The same operation as in Example 8→Example 38→Example 39 was conducted from the compound prepared in Example 283 to give the title compound having the following physical properties.
TLC: Rf 0.72 (6% methanol in ethyl acetate)
$^1$H NMR (300 MHz, DMSO-d$_6$) δ 12.02 (s, 1 H), 9.57 (s, 1 H), 8.99 (s, 1 H), 7.80-7.70 (m, 3 H), 7.62-7.37 (m, 5 H), 6.07 (s, 1 H), 5.93-5.89 (m, 1 H), 5.60 (d, 1 H), 3.70-3.63 (m, 3 H), 3.52-3.36 (m, 1 H), 3.03 (dd, 1 H), 2.47-2.33 (m, 2 H), 1.59-1.47 (m, 9 H).

EXAMPLE 285 methyl 1-{4-chloro-2-[(3S)-3-(5-{4-[(methoxycarbonyl)amino]phenyl}-1H-imidazol-2-yl)-5-oxo-1,2,3,5-tetrahydro-7-indolizinyl]phenyl}-1H-1,2,3-triazole-4-carboxylate To a methanol (1 mL) solution of the compound prepared in Example 284 (91 mg) was added a 20% solution of sodium methoxide in methanol (50 μL) and the mixture stirred for 2 hours at 40° C. To the cooled (0° C.) reaction mixture, a saturated aqueous solution of sodium bisulfate was added followed by extraction with ethyl acetate. The combined organic layers were washed with brine, dried and concentrated and the residue purified by column chromatography (20% ethyl acetate in methanol) to give the title compound having the following physical properties (52 mg).
TLC: Rf 0.55 (6% methanol in ethyl acetate)
$^1$H NMR (300 MHz, DMSO-d$_6$) δ 12.02 (s, 1 H), 9.57 (s, 1 H), 9.11 (s, 1 H), 7.79-7.70 (m, 3 H), 7.61-7.36 (m, 5 H), 6.01 (s, 1 H), 5.92 (s, 1 H), 5.59 (d, 1 H), 3.87-3.80 (m, 3 H), 3.65 (s, 3 H), 3.51-3.35 (m, 1 H), 3.06-2.95 (m, 1 H), 2.47-2.25 (m, 2 H).

EXAMPLE 286

1-{4-chloro-2-[(3S)-3-(5-{4-[(methoxycarbonyl)amino]phenyl}-1H-imidazol-2-yl)-5-oxo-1,2,3,5-tetrahydro-7-indolizinyl]phenyl}-1H-1,2,3-triazole-4-carboxylic acid To a dichloromethane (1.5 mL) solution of the compound prepared in Example 284 (51 mg) was added trifluoroacetic acid (0.5 mL). After stirring for 5 hours at 45° C., the reaction mixture was concentrated and the resulting residue triturated with ethyl acetate to give the title compound having the following physical properties (27 mg).
TLC: Rf 0.41 (ethyl acetate/methanol/acetic acid, 10/5/2)
$^1$H NMR (300 MHz, DMSO-d$_6$) δ 9.84 (s, 1 H), 9.03 (s, 1 H), 7.94-7.60 (m, 7 H), 7.60-7.45 (m, 2 H), 6.12 (s, 1 H), 5.98 (d, 1 H), 5.75 (dd, 1 H), 3.68 (s, 3 H), 3.30 (dt, 1 H), 3.20-2.94 (m, 1 H), 2.76-2.56 (m, 1 H), 2.40-2.16 (m, 1 H).

EXAMPLE 287

1-(2-bromo-4-chlorophenyl)-1H-1,2,3-triazole-4-carboxylic acid

To a dichloromethane (10 mL) solution of the compound prepared in Example 281 (2.3 g), was added trifluoroacetic acid (10 mL). After being stirred at room temperature for 1 hour, the reaction mixture was concentrated and the resulting residue triturated with dichloromethane to give the title compound having the following physical properties (1.5 g).
LC/MS t$_R$ 4.07 minutes; MS (ES$^+$) m/z 302, 304 (M+H)$^d$.

EXAMPLE 288

1-(2-bromo-4-chlorophenyl)-1H-1,2,3-triazole-4-carboxamide

To an N,N-dimethylformamide (3 mL) solution of the compound prepared in Example 287 (500 mg) was sequentially added triethylamine (0.69 mL) and O-(7-azabenzotriazol-1-yl)-N,N,N',N'-tetramethyluronium hexafluorophosphate (753 mg). After being stirred at room temperature for 15 minutes, a 28% aqueous solution of ammonia (0.7 mL) was added and the mixture stirred at room temperature for a further 15 minutes. To the reaction mixture, water was added and the resulting precipitate collected by filtration. The precipitate was washed with water and dried to give the title compound having the following physical properties (463 mg).
LC/MS t$_R$ 4.02 minutes; MS (ES$^+$) m/z 301, 303 (M+H)$^d$.

EXAMPLE 289 methyl[4-(2-{(3S)-7-[2-(4-carbamoyl-1H-1,2,3-triazol-1-yl)-5-chlorophenyl]-5-oxo-1,2,3,5-tetrahydro-3-indolizinyl}-1H-imidazol-5-yl)phenyl]carbamate The same operation as in Example 283→Example 8→Example 38→Example 39 was conducted from the compound prepared in Example 288 to give the title compound having the following physical properties.
TLC: Rf 0.34 (10% methanol in ethyl acetate, NH Silica)
$^1$H NMR (300 MHz, DMSO-d$_6$) δ 12.10-11.89 (m, 1 H), 9.57 (s, 1 H), 8.94-8.69 (m, 1 H), 7.97 (s, 1 H), 7.83-7.64 (m, 3 H), 7.64-7.26 (m, 6 H), 6.08-5.99 (m, 1 H), 5.93 (s, 1 H), 5.61 (d, 1 H), 3.73-3.59 (m, 3 H), 3.50-3.40 (m, 1 H), 3.09-2.93 (m, 1 H), 2.43-2.27 (m, 2 H).

EXAMPLE 290 methyl[4-(2-{(3S)-7-[5-chloro-2-(4-cyano-1H-1,2,3-triazol-1-yl)phenyl]-5-oxo-1,2,3,5-tetrahydro-3-indolizinyl}-1H-imidazol-5-yl)phenyl]carbamate To a dichloromethane (50 mL) solution of the compound prepared in Example 289 (70 mg) was added triethylamine (0.17 mL) and trifluoroacetic anhydride (0.17 mL) and the reaction stirred at room temperature for 1 hour. The reaction mixture was concentrated and the resulting residue purified by column chromatography (5% ethyl acetate in methanol, NH silica) to give the title compound having the following physical properties (55 mg).
TLC: Rf 0.53 (10% methanol in ethyl acetate, NH Silica)
$^1$H NMR (300 MHz, DMSO-d$_6$) δ 12.04 (s, 1 H), 9.57 (s, 1 H), 9.37 (d, 1 H), 7.84-7.76 (m, 3 H), 7.62-7.51 (m, 2 H), 7.49-7.37 (m, 3 H), 5.97 (s, 1 H), 5.94 (s, 1 H), 5.65-5.57 (m, 1 H), 3.68-3.63 (m, 3 H), 3.47-3.36 (m, 1 H), 3.01 (dd, 1 H), 2.41-2.08 (m, 2 H).

EXAMPLE 291 methyl 1-(2-bromo-4-chlorophenyl)-1H-1,2,3-triazole-4-carboxylate

To a methanol (5 mL) solution of the compound prepared in Example 287 was added concentrated sulfuric acid (0.2 mL) and the mixture heated at reflux for 6 hours before allowing to cool to room temperature. The reaction mixture was concentrated, diluted with water (5 mL) and neutralized with a saturated aqueous solution of sodium hydrogen carbonate followed by extraction with ethyl acetate. The combined organic layers were washed with brine, dried and concentrated to give the title compound having the following physical properties (132 mg).

TLC: Rf 0.50 (50% ethyl acetate in hexane).

EXAMPLE 292

2-methyl-2-propanyl(2S)-2-[2-oxo-4-(4,4,5,5-tetramethyl-1,3,2-dioxaborolan-2-yl)-1(2M-pyridinyl]-3-phenylpropanoate The compound prepared in Example 257 (1.88 g) was treated as detailed in Example 282 to give the title compound having the following physical properties (1.35 g).

$^1$H NMR (300 MHz, CDCl$_3$) δ 7.30-7.05 (m, 6 H), 6.93 (br s, 1 H), 6.27 (dd, 1 H), 5.47 (dd, 1 H), 3.43 (dd, 1 H), 3.25 (dd, 1 H), 1.40 (s, 9 H), 1.30 (s, 12 H).

EXAMPLE 293 methyl 1-(4-chloro-2-{1-[(1S)-1-(5-{4-[(methoxycarbonyl)amino]phenyl}-1H-imidazol-2-yl)-2-phenylethyl]-2-oxo-1,2-dihydro-4-pyridinyl}phenyl)-1H-1,2,3-triazole-4-carboxylate The same operation as in Example 283→Example 25→Example 38→Example 39 was conducted from the compound prepared in Example 292 to give the title compound having the following physical properties. (Note: in the step corresponding to Example 283 in the operation, the compound prepared in Example 291 was used)

$^1$H NMR (300 MHz, DMSO-d$_6$) δ 12.29 (s, 1 H), 9.61 (s, 1 H), 9.20-8.90 (m, 1 H), 7.92-7.60 (m, 6 H), 7.57-7.35 (m, 3 H), 7.30-7.06 (m, 5 H), 6.39-6.08 (m, 2 H), 6.03-5.84 (m, 1 H), 3.85 (s, 3 H), 3.73-3.61 (m, 3 H), 3.59-3.40 (m, 1 H), 3.31-3.09 (m, 1 H).

EXAMPLE 294

1-(2-bromo-4-chlorophenyl)-4-(trifluoromethyl)-1H-1,2,3-triazole

The compound prepared in Example 280 (2.0 g) was treated as detailed in Example 281 using 3,3,3-trifluoropropyne in place of tert-butyl propiolate to give the title compound having the following physical properties (100 mg)

$^1$H NMR (300 MHz, CDCl$_3$) δ 8.25 (m, 1 H), 7.81 (m, 1 H), 7.50-7.55 (m, 2 H).

EXAMPLE 295 methyl[4-(2-{(1S)-1-[4-{5-chloro-2-[4-(trifluoromethyl)-1H-1,2,3-triazol-1-yl]phenyl}-2-oxo-1(2H)-pyridinyl]-2-phenylethyl}-1H-imidazol-4-yl)phenyl]carbamate The same operation as in Example 283→Example 25→Example 38→Example 39 was conducted from the compound prepared in Example 292 to give the title compound having the following physical properties. (Note: in the step corresponding to Example 283 in the operation, the compound prepared in Example 294 was used)

TLC: Rf 0.53 (66% ethyl acetate in hexane)

$^1$H NMR (300 MHz, DMSO-d$_6$) δ 12.00 (br. s, 1 H), 9.19 (s, 1 H), 8.99 (s, 1 H), 7.87-7.60 (m, 5 H), 7.58-7.38 (m, 3 H), 7.38-7.31 (m, 1 H), 7.30-6.98 (m, 5 H), 6.43-6.12 (m, 2 H), 5.88 (dd, 1 H), 3.69 (s, 3 H), 3.57 (dd, 1 H), 3.27 (dd, 1 H).

EXAMPLE 296

1-(2-bromo-4-chlorophenyl)-4-(tributylstannyl)-1H-1,2,3-triazole

The compound prepared in Example 280 (1.86 g) was treated as detailed in Example 281 using ethynyltri-n-butyltin in place of tert-butyl propiolate to give the title compound having the following physical properties (5.03 g)

$^1$H NMR (300 MHz, CDCl$_3$) δ 7.83 (m, 1 H), 7.75 (dd, 1 H), 7.50 (dd, 1 H), 7.45 (dd, 1 H), 1.64-1.50 (m, 6 H), 1.42-1.24 (m, 6 H), 1.22-1.12 (m, 6 H), 0.89 (t, 9 H).

EXAMPLE 297

1-(2-bromo-4-chlorophenyl)-4-chloro-1H-1,2,3-triazole

To an acetonitrile (72 mL) solution of the compound prepared in Example 296 (2.42 g) was added N-chlorosuccinimide (885 mg) and the mixture stirred for 15 hours at 60° C. before cooling to room temperature. The reaction mixture was concentrated and the resulting residue purified by column chromatography (20% ethyl acetate in hexane) to give the title compound having the following physical properties (1.0 g). $^1$H NMR (300 MHz, CDCl$_3$) δ 7.91 (s, 1 H), 7.79 (t, 1 H), 7.48-7.51 (m, 2 H).

EXAMPLE 298 methyl(4-{2-[(1S)-1-{4-[5-chloro-2-(4-chloro-1H-1,2,3-triazol-1-yl)phenyl]-2-oxo-1(2H)-pyridinyl}-2-phenylethyl]-1H-imidazol-5-yl}phenyl)carbamate The same operation as in Example 283→Example 25→Example 38→Example 39 was conducted from the compound prepared in Example 292 to give the title compound having the following physical properties. (Note: in the step corresponding to Example 283 in the operation, the compound prepared in Example 297 was used)

TLC: Rf 0.62 (66% ethyl acetate in hexane)

$^1$H NMR (300 MHz, DMSO-d$_6$) δ 12.30 (br. s, 1 H), 9.61 (s, 1 H), 8.65 (s, 1 H), 7.96-7.63 (m, 5 H), 7.63-7.35 (m, 4 H), 7.35-7.05 (m, 5 H), 6.47-6.09 (m, 2 H), 5.89 (d, 1 H), 3.77-3.62 (m, 3 H), 3.52 (dd, 1 H), 3.26 (d, 1 H).

EXAMPLE 299

1-(2-bromo-4-chlorophenyl)-1H-pyrazole

To a N,N-dimethylacetamide (20 mL) solution of 2-bromo-4-chloro-1-fluorobenzene (2.0 g) was added cesium carbonate (5.39 g) and pyrazole (780 mg) and the reaction mixture stirred for 3 hours at 100° C. before allowing to cool to room temperature. The reaction mixture was diluted with ethyl acetate, washed with water and brine, dried and concentrated to give the title compound having the following physical properties (1.52 g).

¹H NMR (300 MHz, CDCl₃) δ 7.81 (d, 1 H), 7.73 (d, 1 H), 7.71 (d, 1 H), 7.46 (d, 1 H), 7.40 (dd, 1 H), 6.47 (t, 1 H).

EXAMPLE 300

1-(2-bromo-4-chlorophenyl)-4-fluoro-1H-pyrazole

To an acetonitrile (4.5 mL) solution of the compound prepared in Example 299 (300 mg) was added 1-chloromethyl-4-fluoro-1,4-diazoniabicyclo[2.2.2]octane bis(tetrafluoroborate) (619 mg) and the reaction mixture stirred for 18 hours at 70° C. before allowing to cool to room temperature. The reaction mixture was diluted with ethyl acetate, washed with a saturated aqueous solution of sodium hydrogen carbonate and brine, dried and concentrated. The residue thus obtained was purified by column chromatography (20% ethyl acetate in hexane) to obtained the title compound having the following physical properties (131 mg).
¹H NMR (300 MHz, CDCl₃) δ 7.75-7.69 (m, 2 H), 7.60 (dd, 1 H), 7.44 (dd, 1 H), 7.40 (dd, 1 H).

EXAMPLE 301 methyl(4-{2-[(1S)-1-{4-[5-chloro-2-(4-fluoro-1H-pyrazol-1-yl)phenyl]-2-oxo-1(2H)-pyridinyl}-2-phenylethyl]-1H-imidazol-5-yl}phenyl)carbamate The same operation as in Example 283→Example 25→Example 38→Example 39 was conducted from the compound prepared in Example 292 to give the title compound having the following physical properties. (Note: in the step corresponding to Example 283 in the operation, the compound prepared in Example 300 was used)
TLC: Rf 0.40 (50% ethyl acetate in hexane)
¹H NMR (300 MHz, DMSO-d₆) δ 12.30 (s, 1 H), 9.61 (s, 1 H), 8.05-7.92 (m, 1 H), 7.81 (d, 1 H), 7.76-7.38 (m, 9 H), 7.38-7.03 (m, 5 H), 6.47-6.10 (m, 2 H), 5.99-5.64 (m, 1 H), 3.69-3.61 (m, 3 H), 3.61-3.43 (m, 1 H), 3.30-3.16 (m, 1 H).

EXAMPLE 302

1-(2-bromo-4-chlorophenyl)-4-(trifluoromethyl)-1H-pyrazole 2-bromo-4-chloro-1-fluorobenzene (40 mg) was treated with 4-(trifluoromethyl)-1H-pyrazole as detailed in Example 299 to give the title compound having the following physical properties (18 mg).
¹H NMR (300 MHz, CDCl₃) δ 8.07 (t, 1 H), 7.93 (s, 1 H), 7.74 (dd, 1 H), 7.47 (dd, 1 H), 7.44 (dd, 1 H).

EXAMPLE 303 methyl[4-(2-{(1S)-1-[4-{5-chloro-2-[4-(trifluoromethyl)-1H-pyrazol-1-yl]phenyl}-2-oxo-1(2H)-pyridinyl]-2-phenylethyl}-1H-imidazol-4-yl)phenyl]carbamate The same operation as in Example 283→Example 25→Example 38→Example 39 was conducted from the compound prepared in Example 292 to give the title compound having the following physical properties. (Note: in the step corresponding to Example 283 in the operation, the compound prepared in Example 302 was used)
TLC: Rf 0.72 (66% ethyl acetate in hexane)
¹H NMR (300 MHz, DMSO-d₆) δ 12.29 (s, 1 H), 9.61 (s, 1 H), 8.70-8.42 (m, 1 H), 8.14-7.95 (m, 1 H), 7.90-7.59 (m, 6 H), 7.59-7.37 (m, 3 H), 7.33-6.98 (m, 5 H), 6.43-6.06 (m, 2 H), 5.96-5.68 (m, 1 H), 3.66 (s, 3 H), 3.56-3.42 (m, 1 H), 3.29-3.06 (m, 1 H).

EXAMPLE 304

1-(2-bromo-4-chlorophenyl)-1H-1,2,4-triazol-3-ol

2-Bromo-4-chloro-phenylhydrazine [Journal of the American Chemical Society, 79, 934, (1957)] (800 mg) and urea (317 mg) were suspended in xylene (12 mL) and the suspension treated with concentrated sulfuric acid (266 mg) with vigorous stirring. The reaction mixture was heated for 6 hours at 135° C. then allowed to cool to 90° C., whereupon formic acid (420 mg) and concentrated sulfuric acid (46 mg) was added sequentially. The mixture was heated for 15 hours at 90° C. at which juncture additional formic acid (1.26 g) and concentrated sulfuric acid (549 mg) were added. The mixture was stirred for a further 3 hours at 90° C. then allowed to cool to room temperature. The resulting precipitate was collected by filtration, washed with water and dried in vacuo to give the title compound having the following physical properties (520 mg).
¹H NMR (300 MHz, DMSO-d₆) δ 10.4 (br. s, 1 H), 8.48 (s, 1 H), 8.01 (d, 1 H), 7.66-7.58 (m, 2 H).

EXAMPLE 305

1-(2-bromo-4-chlorophenyl)-3-[(4-methoxybenzyl)oxy]-1H-1,2,4-triazole

To a N,N-dimethylformamide (5 mL) solution of the compound prepared in Example 304 was sequentially added potassium carbonate (452 mg) and 4-methoxybenzylchloride (256 mg) and the mixture stirred for 3 days at room temperature. To the reaction mixture, water was added followed by extraction with ethyl acetate. The combined organic layers were washed with brine, dried and concentrated and the residue purified by column chromatography (30% ethyl acetate in hexane) to obtain the title compound having the following physical properties (120 mg).
TLC: Rf 0.87 (66% ethyl acetate in hexane).

EXAMPLE 306 methyl[4-(2-{(3S)-7-[5-chloro-2-(3-hydroxy-1H-1,2,4-triazol-1-yl)phenyl]-5-oxo-1,2,3,5-tetrahydro-3-indolizinyl}-1H-imidazol-5-yl)phenyl]carbamate The same operation as in Example 283→Example 8→Example 38→Example 39→Example 40 was conducted from the compound prepared in Example 305 to give the title compound having the following physical properties.
TLC: Rf 0.43 (10% methanol in dichloromethane)
¹H NMR (300 MHz, methanol-d₄) δ 8.12 (s, 1 H), 7.73-7.50 (m, 5 H), 7.43 (d, 2 H), 7.23 (s, 1 H), 6.26 (s, 1 H), 6.17 (s, 1 H), 5.80 (dd, 1 H), 3.82-3.69 (m, 3 H), 3.59-3.39 (m, 1 H), 3.24-3.03 (m, 1 H), 2.73-2.58 (m, 1 H), 2.56-2.45 (m, 1 H).

EXAMPLE 307 ethyl(3S)-7-(2-amino-5-methyl-3-pyridinyl)-5-oxo-1,2,3,5-tetrahydro-3-indolizinecarboxylate To a 1,4-dioxane (20 mL) solution of 2-amino-3-bromo-5-methylpyridine (1.0 g) was added bis(pinacolate)diboron (1.63 g) and potassium acetate (788 mg) and the mixture degassed with argon. 1,1'-Bis(diphenylphosphino)ferrocene palladium (II) dichloride dichloromethane complex (218 mg) was then added and the reaction mixture stirred for 3 hours at 110° C. before allowing to cool to room temperature. The reaction mixture was diluted with ethyl acetate, filtered and the filtrate washed with brine, dried and concentrated. The resulting residue was treated with the compound prepared in Example 282 as detailed in Example 283 to give the title compound having the following physical properties (290 mg).

LC/MS $t_R$ 3.32 minutes; MS (ES$^+$) m/z 314 (M+H)$^d$.

EXAMPLE 308 methyl[4-(2-{(3S)-7-[5-methyl-2-(1H-tetrazol-1-yl)-3-pyridinyl]-5-oxo-1,2,3,5-tetrahydro-3-indolizinyl}-1H-imidazol-5-yl)phenyl]carbamate The same operation as in Example 8→Example 38→Example 39→Example 41 was conducted from the compound prepared in Example 307 to give the title compound having the following physical properties.

TLC: Rf 0.38 (5% methanol in ethyl acetate, NH Silica)

$^1$H NMR (300 MHz, DMSO-d$_6$) δ 12.11-11.96 (m, 1 H), 9.95-9.80 (m, 1 H), 9.58 (s, 1 H), 8.58 (d, 1 H), 8.07 (d, 1 H), 7.63-7.51 (m, 2 H), 7.49-7.37 (m, 3 H), 6.18-5.93 (m, 2 H), 5.63 (d, 1 H), 3.76-3.56 (m, 3 H), 3.49-3.30 (m, 1 H), 3.20-2.90 (m, 1 H), 2.65-2.54 (m, 1 H), 2.47 (br. s, 3 H), 2.40-2.27 (m, 1 H).

EXAMPLE 309 methyl[4-(2-{(3S)-7-[5-methyl-2-(1H-tetrazol-1-yl)phenyl]-5-oxo-1,2,3,5-tetrahydro-3-indolizinyl}-1H-imidazol-5-yl)phenyl]carbamate The same operation as in Example 7→Example 8→Example 38→Example 39→Example 41 was conducted from the compound prepared in Example 6 to give the title compound having the following physical properties. (Note: in the step corresponding to Example 7 in the operation, 2-amino-5-methylphenylboronic acid pinacol ester was used)

$^1$H NMR (300 MHz, DMSO-d$_6$) δ 12.03 (s, 1 H), 9.65 (s, 1 H), 9.58 (s, 1 H), 7.62-7.54 (m, 3 H), 7.50 (d, 3 H), 7.45-7.37 (m, 3 H), 5.93 (s, 1 H), 5.86 (s, 1 H), 5.60 (d, 1 H), 3.65 (s, 3 H), 3.45-3.35 (m, 1 H), 3.07-2.89 (m, 1 H), 2.46 (s, 3 H), 2.40-2.23 (m, 2 H).

EXAMPLE 310 methyl[4-(2-{(3S)-7-[5-chloro-2-(4-chloro-1H-1,2,3-triazol-1-yl)phenyl]-5-oxo-1,2,3,5-tetrahydro-3-indolizinyl}-1H-imidazol-5-yl)phenyl]carbamate The same operation as in Example 283→Example 8→Example 38→Example 39 was conducted from the compound prepared in Example 282 to give the title compound having the following physical properties. (Note: in the step corresponding to Example 283 in the operation, the compound prepared in Example 297 was used)

$^1$H NMR (300 MHz, DMSO-d$_6$) δ 12.03 (s, 1 H), 9.57 (s, 1 H), 8.79-8.58 (m, 1 H), 7.83-7.65 (m, 3 H), 7.65-7.30 (m, 5 H), 6.04-5.81 (m, 2 H), 5.61 (dd, 1 H), 3.74-3.59 (m, 3 H), 3.49-3.36 (m, 1 H), 3.01 (dd, 1 H), 2.55 (br. s, 1 H), 2.43-2.13 (m, 1 H).

EXAMPLE 311

1-(2-bromo-4-fluorophenyl)-1H-tetrazole

To a glacial acetic acid (10 mL) solution of 2-bromo-4-fluoroaniline (570 mg) was added trimethyl orthoformate (1 mL) followed after 30 minutes by sodium azide (5.93 g) and the mixture stirred for 7 hours at 90° C. The reaction mixture was concentrated and the resulting residue suspended in ethyl acetate. The suspension thus formed was washed sequentially with water, a saturated aqueous solution of sodium hydrogen carbonate and brine, dried and concentrated. The residue thus obtained was purified by column chromatography (60% ethyl acetate in hexane) to obtained the title compound having the following physical properties (700 mg).

TLC Rf 0.26 (25% ethyl acetate in hexane).

EXAMPLE 312 methyl[4-(2-{(3S)-7-[5-fluoro-2-(1H-tetrazol-1-yl)phenyl]-5-oxo-1,2,3,5-tetrahydro-3-indolizinyl}-1H-imidazol-5-yl)phenyl]carbamate The same operation as in Example 283→Example 8→Example 38→Example 39 was conducted from the compound prepared in Example 282 to give the title compound having the following physical properties. (Note: in the step corresponding to Example 283 in the operation, the compound prepared in Example 311 was used)

TLC Rf 0.33 (5% methanol in ethyl acetate, NH Silica)

$^1$H NMR (300 MHz, DMSO-d$_6$) δ 12.04 (s, 1 H), 9.68 (s, 1 H), 9.58 (s, 1 H), 7.87-7.78 (m, 1 H), 7.63-7.51 (m, 4 H), 7.49-7.37 (m, 3 H), 5.94 (app. s, 2 H), 5.60 (d, 1 H), 3.68-3.63 (m, 3 H), 3.30-3.21 (m, 1 H), 3.05-2.92 (m, 1 H), 2.46-2.23 (m, 2 H).

EXAMPLE 313

1-[2-iodo-4-(trifluoromethyl)phenyl]-1H-tetrazole 2-iodo-4-trifluoromethylaniline (861 mg) was treated as detailed in Example 311 to give the title compound having the following physical properties (873 mg).

TLC Rf 0.24 (25% ethyl acetate in hexane).

EXAMPLE 314 methyl[4-(2-{(3S)-5-oxo-7-[2-(1H-tetrazol-1-yl)-5-(trifluoromethyl)phenyl]-1,2,3,5-tetrahydro-3-indolizinyl}-1H-imidazol-5-yl)phenyl]carbamate The same operation as in Example 283→Example 8→Example 38→Example 39 was conducted from the compound prepared in Example 282 to give the title compound having the following physical properties. (Note: in the step corresponding to Example 283 in the operation, the compound prepared in Example 313 was used)

TLC Rf 0.55 (5% methanol in ethyl acetate)

$^1$H NMR (300 MHz, DMSO-d$_6$) δ 2.03 (s, 1 H), 9.75-9.73 (m, 1 H), 9.58 (s, 1 H), 8.15-8.10 (m, 1 H), 8.04-8.01 (m, 2

H), 7.66-7.35 (m, 5 H), 6.04-5.96 (m, 2 H), 5.62 (d, 1 H), 3.67-3.64 (m, 3 H), 3.46-3.35 (m, 1 H), 3.12-2.90 (m, 1 H), 2.46-2.28 (m, 2 H).

EXAMPLE 315

2-(4-hydroxy-6-methyl-2-oxo-1(2H)-pyridinyl)propanoic acid

A suspension of 4-hydroxy-6-methyl-2-pyrone (2.52 g) and DL-alanine (1.78 g) in 1 M sodium hydroxide (20 mL) was heated at reflux for 15 hours. To the reaction mixture, an aqueous solution of 1 M hydrochloric acid (22 mL) was added and the resulting precipitate collected by filtration. The filter cake was washed with 1 M hydrochloric acid and dried in vacuo to obtain the title compound having the following physical properties (2.3 g).
LC/MS $t_R$ 2.90 minutes; MS (ES$^+$) m/z 198 (M+H)$^d$.

EXAMPLE 316 ethyl 2-(4-hydroxy-6-methyl-2-oxo-1(2H)-pyridinyl)propanoate

An ethanol (15 mL) suspension of the compound prepared in Example 315 (2.3 g) was treated with concentrated sulphuric acid (43 µL) and the mixture stirred for 15 hours at 90° C. The forthcoming precipitate was collected by filtration, washed with ethanol and dried to obtain the title compound having the following physical properties (0.78 g).
LC/MS $t_R$ 3.47 minutes; MS (ES$^+$) m/z 226 (M+H)$^d$.

EXAMPLE 317 methyl{4-[2-(1-{4-[5-chloro-2-(1H-tetrazol-1-yl)phenyl]-6-methyl-2-oxo-1(2H)-pyridinyl}ethyl)-1H-imidazol-5-yl]phenyl}carbamate

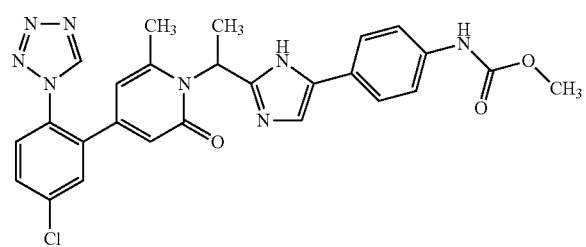 [SMILES: COC(=O)Nc1ccc(-c2cnc(C(C)n3c(C)cc(-c4cc(Cl)ccc4-n4cnnn4)cc3=O)[nH]2)cc1]

The same operation as in Example 6→Example 7→Example 9→Example 11→Example 38→Example 39 was conducted from the compound prepared in Example 316 to give the title compound having the following physical properties.
TLC Rf 0.58 (5% methanol in ethyl acetate)
$^1$H NMR (300 MHz, CDCl$_3$) δ 11.01 (br. s, 1 H), 8.69-8.37 (m, 1 H), 7.76-7.45 (m, 5 H), 7.39 (d, 2 H), 7.18 (s, 1 H), 6.69 (br. s, 1 H), 6.36 (s, 1 H), 5.73 (br. s, 1 H), 5.62-5.46 (m, 1 H), 3.85-3.70 (m, 3 H), 2.50 (br. s, 3 H), 1.99 (d, 3 H).

EXAMPLE 318 methyl{4-[2-({4-[5-chloro-2-(1H-tetrazol-1-yl)phenyl]-6-methyl-2-oxo-1(2H)-pyridinyl}methyl)-1H-imidazol-5-yl]phenyl}carbamate The same operation as in Example 315→Example 316→Example 6→Example 7→Example 9→Example 11→Example 38→Example 39 was conducted to give the title compound having the following physical properties. (Note: in the step corresponding to Example 315 in the operation, glycine was used in place of DL-alanine.)
TLC Rf 0.42 (5% methanol in ethyl acetate, NH Silica)
$^1$H NMR (300 MHz, DMSO-d$_6$) δ 11.97 (s, 1 H), 9.75-9.64 (m, 1 H), 9.58 (s, 1 H), 7.86-7.73 (m, 3 H), 7.63-7.50 (m, 2 H), 7.49-7.36 (m, 3 H), 6.12-5.95 (m, 1 H), 5.91 (d, 1 H), 5.25-5.08 (m, 2 H), 3.70-3.60 (m, 3 H), 2.55-2.53 (m, 3 H).

EXAMPLE 319 methyl{4-[2-({4-[5-chloro-2-(1H-tetrazol-1-yl)phenyl]-6-ethyl-2-oxo-1(2H)-pyridinyl}methyl)-1H-imidazol-5-yl]phenyl}carbamate The same operation as in Example 315→Example 316→Example 6→Example 7→Example 9→Example 11→Example 38→Example 39 was conducted from 6-ethyl-4-hydroxy-2-pyrone to give the title compound having the following physical properties. (Note: in the step corresponding to Example 315 in the operation, glycine was used in place of DL-alanine.)
TLC Rf 0.50 (ethyl acetate)
$^1$H NMR (300 MHz, DMSO-d$_6$) δ 11.93 (s, 1 H), 9.77-9.63 (m, 1 H), 9.58 (s, 1 H), 7.85-7.80 (m, 3 H), 7.65-7.36 (m, 5 H), 6.33-6.04 (m, 1 H), 5.72-5.49 (m, 1 H), 5.17 (s, 2 H), 3.74-3.61 (m, 3 H), 3.00-2.75 (m, 2 H), 1.10-0.91 (m, 3 H).

EXAMPLE 320

4-chloro-2-(6-chloro-2-methyl-4-pyrimidinyl)aniline

To a 1,4-dioxane (150 mL) solution of 4,6-dichloro-2-methylpyrimidine (2.0 g) stirring under an atmosphere of argon was added 4-chloro-2-(4,4,5,5-tetramethyl-1,3,2-dioxaborolan-2-yl)aniline (3.11 g) and 2 M aqueous sodium carbonate solution (18.5 mL). The mixture was degassed with argon then tetrakis(triphenylphosphine) palladium(0) (0.71 g) added and the mixture stirred for 2 hours at 100° C. To the reaction mixture, ethyl acetate was added and the organic layer washed with a saturated aqueous solution of sodium hydrogen carbonate and brine, dried and concentrated. The residue thus obtained was triturated with dichloromethane to give the title compound having the following physical properties (1.6 g).
$^1$H NMR (300 MHz, CDCl$_3$) δ 7.54 (d, 1 H), 7.48 (s, 1 H), 7.18 (dd, 1 H), 6.69 (d, 1 H), 6.13 (br, s, 2 H), 2.75 (s, 3 H).

EXAMPLE 321

6-(2-amino-5-chlorophenyl)-2-methyl-4(3H)-pyrimidinone

A suspension of the compound prepared in Example 320 (1.2 g) in 5 M hydrochloric acid (30 mL) was refluxed for 2 hours. The reaction mixture was concentrated and the residue azeotroped with ethanol and toluene to obtain the title compound having the following physical properties (1.7 g).
$^1$H NMR (300 MHz, DMSO-d$_6$) δ 7.38 (d, 1 H), 7.17 (dd, 1 H), 6.80 (d, 1 H), 6.46 (s, 1 H), 2.37 (s, 3 H), 4.50-3.50 (obs. m, 3 H).

EXAMPLE 322

2-methyl-2-propanyl[4-(2-amino-5-chlorophenyl)-2-methyl-6-oxo-1(6H)-pyrimidinyl]acetate To an N,N-dimethylformamide (30 mL) solution of the compound prepared in Example 321 (0.69 g) was added tert-butyl bromoacetate (0.45 mL) and potassium carbonate (1.06 g) and the mixture stirred at room temperature for 3 hours. The reaction mixture was then diluted with ethyl acetate, washed with water and brine, dried and concentrated. The residue thus obtained was purified by column chromatography (15 to 50% ethyl acetate in hexane) to give the title compound having the following physical properties (370 mg).

$^1$H NMR (300 MHz, CDCl$_3$) δ 7.37 (d, 1 H), 7.12 (dd, 1 H), 6.62 (d, 1 H), 6.60 (s, 1 H), 5.38 (br. s, 2 H), 4.74 (s, 2 H), 2.51 (s, 3 H), 1.50 (s, 9 H).

EXAMPLE 323 methyl{4-[2-({4-[5-chloro-2-(1H-tetrazol-1-yl)phenyl]-2-methyl-6-oxo-1(6H)-pyrimidinyl}methyl)-1H-imidazol-5-yl]phenyl}carbamate

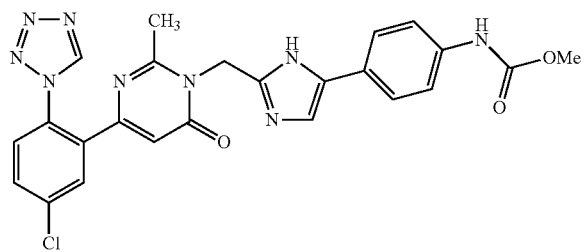 [SMILES: COC(=O)Nc1ccc(-c2cnc(Cn3c(C)nc(-c4cc(Cl)ccc4-n4cnnn4)cc3=O)[nH]2)cc1]

The same operation as in Example 24→Example 25→Example 38→Example 39 was conducted from the compound prepared in Example 322 to give the title compound having the following physical properties.

TLC Rf 0.58 (5% methanol in ethyl acetate)

$^1$H NMR (300 MHz, DMSO-d$_6$) δ 12.10 (br. s, 1 H), 9.73 (s, 1 H), 9.57 (s, 1 H), 7.98 (s, 1 H), 7.92-7.70 (m, 2 H), 7.60 (d, 2 H), 7.55-7.26 (m, 3 H), 6.53 (s, 1 H), 5.18 (s, 2 H), 3.65 (s, 3 H), 2.55-2.44 (obs. m, 3 H).

EXAMPLE 324

2-methoxyethyl[4-(bromoacetyl)phenyl]carbamate

The same operation as in Example 77→Example 78 was conducted from 4-aminoacetophenone to give the title compound having the following physical properties. (Note: in the step corresponding to Example 77 in the operation, 2-methoxyethyl chloroformate was used)

TLC Rf 0.40 (50% ethyl acetate in hexane).

EXAMPLE 325

2-methoxyethyl{4-[2-({4-[5-chloro-2-(1H-tetrazol-1-yl)phenyl]-2-methyl-6-oxo-1(6H)-pyrimidinyl}methyl)-1H-imidazol-5-yl]phenyl}carbamate The same operation as in Example 24→Example 25→Example 38→Example 39 was conducted from the compound prepared in Example 322 to give the title compound having the following physical properties. (Note: in the step corresponding to Example 38 in the operation, the compound prepared in Example 324 was used)

TLC Rf 0.52 (5% methanol in ethyl acetate)

$^1$H NMR (300 MHz, DMSO-d$_6$) δ 12.10 (s, 1 H), 9.75-9.63 (m, 2 H), 8.04-7.92 (m, 1 H), 7.92-7.69 (m, 2 H), 7.62-7.34 (m, 5 H), 6.70-6.33 (m, 1 H), 5.18 (s, 2 H), 4.23-4.13 (m, 2 H), 3.71-3.46 (m, 2 H), 3.28-3.26 (m, 3 H), 2.55-2.44 (obs. m, 3 H).

EXAMPLE 326

2-methoxyethyl{4-[4-chloro-2-({4-[5-chloro-2-(1H-tetrazol-1-yl)phenyl]-2-methyl-6-oxo-1(6H)-pyrimidinyl}methyl)-1H-imidazol-5-yl]phenyl}carbamate The compound prepared in Example 325 (39 mg) was treated as detailed in Example 44 to give the title compound having the following physical properties (11 mg).

TLC Rf 0.83 (5% methanol in ethyl acetate)

$^1$H NMR (300 MHz, DMSO-d$_6$) δ 12.84 (s, 1 H), 9.88 (s, 1 H), 9.74 (s, 1 H), 8.01 (d, 1 H), 7.91-7.71 (m, 2 H), 7.69-7.34 (m, 4 H), 6.51 (s, 1 H), 5.17 (s, 2 H), 4.28-4.13 (m, 2 H), 3.67-3.49 (m, 2 H), 3.29 (s, 3 H), 2.39 (s, 3 H).

EXAMPLE 327

3-{[5-(6-amino-3-pyridinyl)-1H-imidazol-2-yl]methyl}-6-[5-chloro-2-(1H-tetrazol-1-yl)phenyl]-2-methyl-4(3H)-pyrimidinone The same operation as in Example 24→Example 25→Example 38→Example 39 was conducted from the compound prepared in Example 322 to give the title compound having the following physical properties. (Note: in the step corresponding to Example 38 in the operation, the compound prepared in Example 193 was used)

TLC Rf 0.20 (5% methanol in ethyl acetate)

$^1$H NMR (300 MHz, DMSO-d$_6$) δ 12.07 (s, 1 H), 9.73 (s, 1 H), 8.29-8.17 (m, 1 H), 7.98 (s, 1 H), 7.92-7.73 (m, 2 H), 7.65 (d, 2 H), 7.31 (s, 1 H), 6.52 (s, 1 H), 6.42 (d, 1 H), 5.78 (d, 1 H), 5.17 (s, 2 H), 2.55-2.44 (obs. m, 3 H).

EXAMPLE 328

3-{[5-(6-amino-3-pyridinyl)-4-chloro-1H-imidazol-2-yl]methyl}-6-[5-chloro-2-(1H-tetrazol-1-yl)phenyl]-2-methyl-4(3H)-pyrimidinone The compound prepared in Example 327 (30 mg) was treated as detailed in Example 44 to give the title compound having the following physical properties (7 mg).

TLC Rf 0.62 (5% methanol in ethyl acetate)

$^1$H NMR (300 MHz, methanol-d$_4$) δ 9.44 (s, 1 H), 8.18 (d, 1 H), 8.03-7.85 (m, 1 H), 7.84-7.56 (m, 3 H), 6.64 (dd, 1 H), 6.50 (s, 1 H), 5.25 (s, 2 H), 2.46 (s, 3 H).

EXAMPLE 329

(6S)-6-[5-(6-amino-2-fluoro-3-pyridinyl)-1H-imidazol-2-yl]-2-[5-chloro-2-(1H-tetrazol-1-yl)phenyl]-7,8-dihydropyrrolo[1,2-a]pyrimidin-4(6H)-one

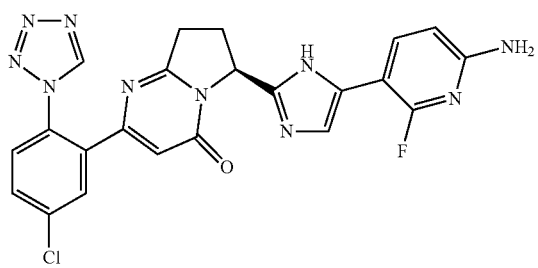

The same operation as in Example 8→Example 9→Example 51→Example 52 was conducted from the compound prepared in Example 35 to give the title compound having the following physical properties. (Note: in the step corresponding to Example 51 in the operation, the compound prepared in Example 215 was used).

LC/MS $t_R$ 2.86 minutes; MS (ES$^+$) m/z 491 (M+H)$^b$ $^1$H NMR (300 MHz, DMSO-d$_6$) δ 12.22 (br. s, 1 H), 9.73 (s, 1 H), 7.99 (dd, 1 H), 7.96 (d, 1 H), 7.85 (dd, 1 H), 7.82 (d, 1 H), 7.11 (d, 1 H), 6.36 (dd, 1 H), 6.35 (s, 1 H), 6.26 (br. s, 2 H), 5.62 (dd, 1 H), 3.18 (ddd, 1 H), 2.76 (ddd, 1 H), 2.59-2.52 (obs. m, 1 H), 2.24-2.16 (m, 1 H).

EXAMPLE 330

(6S)-6-[5-(6-amino-3-pyridinyl)-4-chloro-1H-imidazol-2-yl]-2-[5-chloro-2-(1H-tetrazol-1-yl)phenyl]-7,8-dihydropyrrolo[1,2-a]pyrimidin-4(6H)-one

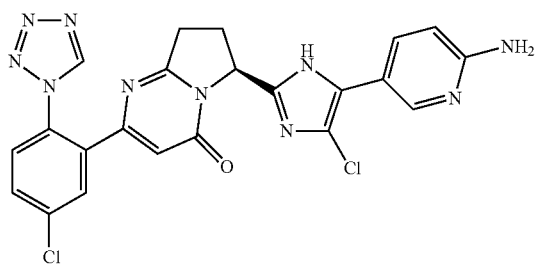 [SMILES: Nc1ccc(-c2[nH]c([C@@H]3CCc4nc(-c5cc(Cl)ccc5-n5cnnn5)cc(=O)n43)nc2Cl)cn1]

The same operation as in Example 8→Example 9→Example 51→Example 52→Example 44 was conducted from the compound prepared in Example 35 to give the title compound having the following physical properties. (Note: in the step corresponding to Example 51 in the operation, the compound prepared in Example 193 was used).

LC/MS $t_R$ 2.78 minutes; MS (ES$^+$) m/z 507 (M+H)$^b$ $^1$H NMR (300 MHz, methanol-d$_4$) δ 9.45 (s, 1 H), 8.20 (d, 1 H), 7.92 (d, 1 H), 7.80-7.73 (m, 2 H), 7.70 (d, 1 H), 6.65 (d, 1 H), 6.36 (s, 1 H), 5.65 (dd, 1 H), 3.30-3.22 (m, 1 H), 2.91 (ddd, 1 H), 2.67 (dq, 1 H), 2.34 (ddt, 1 H).

EXAMPLE 331

(6S)-6-[5-(6-amino-2-chloro-3-pyridinyl)-1H-imidazol-2-yl]-2-[5-chloro-2-(1H-tetrazol-1-yl)phenyl]-7,8-dihydropyrrolo[1,2-a]pyrimidin-4(6H)-one

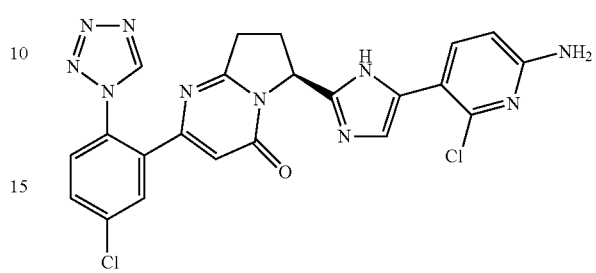

The same operation as in Example 8→Example 9→Example 51→Example 52 was conducted from the compound prepared in Example 35 to give the title compound having the following physical properties. (Note: in the step corresponding to Example 51 in the operation, the compound prepared in Example 209 was used).

TLC Rf 0.40 (10% methanol in ethyl acetate)

$^1$H NMR (300 MHz, DMSO-d$_6$) δ 12.23 (s, 1 H), 9.71 (s, 1 H), 8.02-7.91 (m, 2 H), 7.88-7.72 (m, 2 H), 7.42 (d, 1 H), 6.55-6.24 (m, 4 H), 5.62 (dd, 1 H), 3.25-3.07 (m, 1 H), 2.83-2.66 (m, 1 H), 2.59-2.52 (obs. m, 1 H), 2.31-2.13 (m, 1 H).

EXAMPLE 332

2-methoxyethyl[6-(4-chloro-2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-3-pyridinyl]carbamate

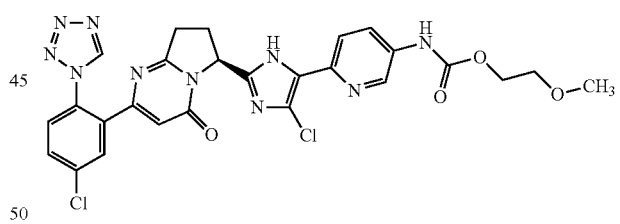

The same operation as Example 8→Example 9→Example 51→Example 52→Example 55→Example 128→Example 44 was conducted from the compound prepared in Example 35 to obtain the title compound having the following physical properties. (Note: in the step corresponding to Example 51 in the operation, the compound prepared in Example 219 was used. In the step corresponding to Example 128 in the operation, 2-methoxyethyl chloroformate was used).

LC/MS $t_R$ 3.87 minutes; MS (ES$^+$) m/z 609 (M+H)$^b$ $^1$H NMR (500 MHz, DMSO-d$_6$) δ 13.09 (br. s, 1 H), 10.12 (br. s, 1 H), 9.73 (s, 1 H), 8.76 (d, 1 H), 8.00 (d, 1 H), 7.96 (dd, 1 H), 7.91 (d, 1 H), 7.86 (dd, 1 H), 7.82 (d, 1 H), 6.33 (s, 1 H), 5.65 (dd, 1 H), 4.25 (dd, 2 H), 3.61-3.57 (m, 2 H), 3.30 (s, 3 H), 3.08 (td, 1 H), 2.77 (ddd, 1 H), 2.60-2.53 (m, 1 H), 2.18-2.08 (m, 1 H).

EXAMPLE 333 ethyl(6S)-2-[(4-methylbenzenesulfonyl)oxy]-4-oxo-4H,6H,7H,8H-pyrrolo[1,2-a]pyrimidine-6-carboxylate

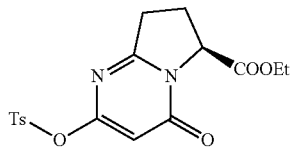 [SMILES: CCOC(=O)[C@@H]1CCc2nc(OS(=O)(=O)c3ccc(C)cc3)cc(=O)n21]

To a stirred suspension of ethyl(2S)-5-aminopyrrolidine-2-carboxylate [J. Org. Chem. 52(26), 5717 (1987)] (300 mg), malonic acid monoethyl ester potassium salt (531 mg) and EDC.HCl (598 mg) in N,N-dimethylformamide (3 mL) was added diisopropylethylamine (0.326 mL). The suspension was stirred at 60° C. for 16 hours. The mixture was cooled to 5° C. then treated with diisopropylethylamine (0.326 mL) and p-toluenesulfonyl chloride (357 mg). The mixture was stirred at room temperature for 2 hours. Water was poured into the reaction mixture. The aqueous mixture was extracted with ethyl acetate. The combined organic solution was washed with brine and concentrated under reduced pressure. The residue was purified by column chromatography (70% ethyl acetate in heptanes) to give the title compound having the following physical properties (362 mg)

LC/MS $t_R$ 1.93 minutes; MS (ES$^+$) m/z 401 (M+Na), 379 (M+H)$^a$.

EXAMPLE 334 ethyl(6S)-2-(2-amino-5-chlorophenyl)-4-oxo-4H,6H,7H,8H-pyrrolo[1,2-a]pyrimidine-6-carboxylate

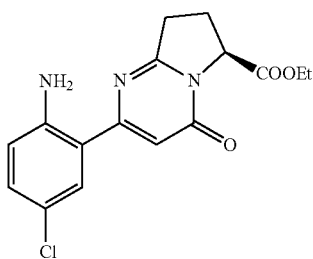 [SMILES: CCOC(=O)[C@@H]1CCc2nc(-c3cc(Cl)ccc3N)cc(=O)n21]

To a mixture of the compound prepared in Example 333 (30 g), 4-chloro-2-(4,4,5,5-tetramethyl-1,3,2-dioxaborolan-2-yl)aniline (24.1 g) and triphenylphosphine (2.08 g) in toluene (360 mL), were added sodium carbonate (25.2 g) in water (120 ml) and palladium(II) bis(triphenylphosphine)dichloride (2.78 g). The mixture was stirred at 100° C. for 6 hours under an atmosphere of argon. The insoluble materials were removed by filtration. The resulting residue was washed with ethyl acetate (150 mL) and water (150 mL). The organic layer was separated and the aqueous layer was extracted with ethyl acetate (150 mL). The combined organic layers were washed with brine (90 mL), dried and concentrated. The resulting residue was purified by column chromatography (70% ethyl acetate in heptanes) to give the title compound having the following physical properties (19.3 g).

LC/MS $t_R$ 1.81 minutes; MS (ES$^+$) m/z 334 (M+H)$^a$.

EXAMPLE 335

(6S)-2-(2-amino-5-chlorophenyl)-4-oxo-4H,6H,7H,8H-pyrrolo[1,2-a]pyrimidine-6-carboxylic acid

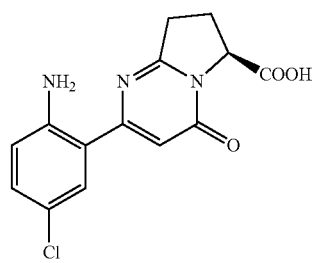 [SMILES: Nc1ccc(Cl)cc1-c1cc(=O)n2c(n1)CC[C@H]2C(=O)O]

A suspension of the compound prepared in Example 334 (17.5 g) in 2 M hydrochloric acid (160 mL) and 1,4-dioxane (40 mL) was stirred at 90° C. for 8 hours. The reaction mixture was cooled to room temperature. The resulting precipitate was collected by filtration, washed with 1,4-dioxane and dried to give the title compound (10.4 g) as the hydrochloride salt. The filtrate was cooled on an ice bath and treated with 5 M sodium hydroxide to pH 3-4. The aqueous mixture was saturated with ammonium sulfate and extracted with ethyl acetate methanol (8515). The combined organic layers were dried and concentrated to give the title compound (7.2 g) as the free base.

LC/MS $t_R$ 1.52 minutes; MS (ES$^+$) m/z 306 (M+H)$^a$.

EXAMPLE 336

(6S)-2-[5-chloro-2-(1H-1,2,3,4-tetrazol-1-yl)phenyl]-4-oxo-4H,6H,7H,8H-pyrrolo[1,2-a]pyrimidine-6-carboxylic acid

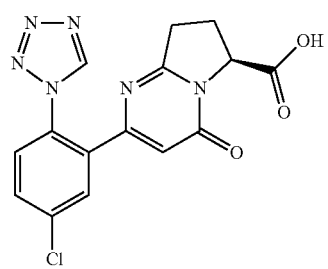 [SMILES: O=C(O)[C@@H]1CCc2nc(-c3cc(Cl)ccc3-n3cnnn3)cc(=O)n21]

The compound prepared in Example 335 (4.34 g) was treated as detailed in Example 9 to give the title compound having the following physical properties (3.24 g).

LC/MS $t_R$ 1.40 minutes; MS (ES$^+$) m/z 739 (2M+Na), 381 (M+Na), 359 (M+H), 331 (M-N$_2$+H)$^a$.

EXAMPLE 337

3-(2-{(3S)-7-[5-chloro-2-(1H-tetrazol-1-yl)phenyl]-5-oxo-1,2,3,5-tetrahydro-3-indolizinyl}-1H-imidazol-5-yl)benzoic acid

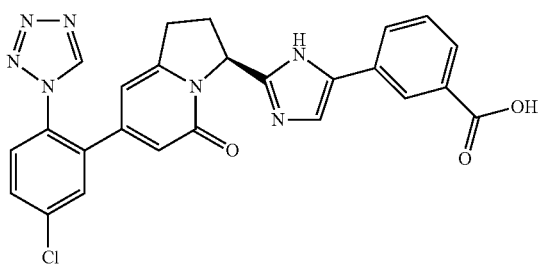 [SMILES: O=C(O)c1cccc(-c2cnc([C@@H]3CCc4cc(-c5cc(Cl)ccc5-n5cnnn5)cc(=O)n43)[nH]2)c1]

The same operation as in Example 51→Example 52→Example 37→Example 55→Example 24 was conducted from the compound prepared in Example 11 to give the title compound having the following physical properties. (Note: in the step corresponding to Example 51 in the operation, methyl 3-(2-bromoacetyl)benzoate [J. Med. Chem., 13(4), 674 (1970)] was used).

LC/MS $t_R$ 3.08 minutes; MS (ES$^+$) m/z 500 (M+H)$^b$ $^1$H NMR (500 MHz, methanol-d$_4$) δ 9.38 (s, 1 H), 8.32 (app. s, 1 H), 7.93-7.84 (m, 2 H), 7.78-7.72 (m, 2 H), 7.70 (d, 1 H), 7.47 (t, 1 H), 7.41 (s, 1 H), 6.15 (s, 1 H), 6.11 (s, 1 H), 5.81 (dd, 1 H), 3.48 (td, 1 H), 3.13 (ddd, 1 H), 2.72-2.62 (m, 1 H), 2.55-2.44 (m, 1 H).

EXAMPLE 338

3-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)benzoic acid

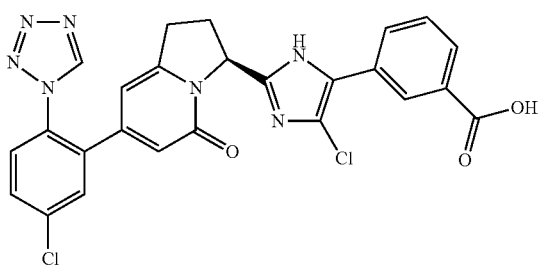 [SMILES: O=C(O)c1cccc(-c2[nH]c([C@@H]3CCc4cc(-c5cc(Cl)ccc5-n5cnnn5)cc(=O)n43)nc2Cl)c1]

To a cooled (0° C.) tetrahydrofuran (5 mL) solution of the compound prepared in Example 337 (90 mg) was added a solution of 1,3-dichloro-5,5-dimethyl imidazolidine-2,4-dione (25 mg) in tetrahydrofuran (0.5 mL) and the reaction mixture stirred at 0° C. for 0.5 hours. To the reaction mixture, a 20% aqueous solution of sodium thiosulfate (1 mL) was added and the mixture stirred for 5 minutes before diluting with water and extracting into ethyl acetate. The combined organic layers were washed with brine, dried and concentrated. The residue obtained was purified by high performance liquid chromatography [5 to 100% mobile phase B (0.1% formic acid in acetonitrile) in mobile phase A (0.1% aqueous formic acid)] to give the title compound having the following physical properties (18 mg).

LC/MS $t_R$ 3.88 minutes; MS (ES$^+$) m/z 534 (M+H)$^b$ $^1$H NMR (500 MHz, methanol-d$_4$) δ 9.38 (s, 1 H), 8.40 (app. s, 1 H), 8.04-7.92 (m, 2 H), 7.79-7.68 (m, 3 H), 7.58 (t, 1 H), 6.18 (s, 1 H), 6.08 (s, 1 H), 5.75 (dd, 1 H), 3.53-3.41 (m, 1 H), 3.13 (ddd, 1 H), 2.72-2.61 (m, 1 H), 2.46-2.34 (m, 1 H).

EXAMPLE 339 methyl 2-(4-acetylphenyl)acetate

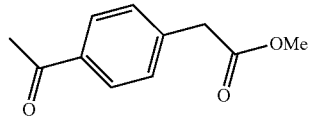

Methyl(4-bromophenyl)acetate (0.50 g) was treated as detailed in Example 139 to give the title compound having the following physical properties (0.26 g).

LC/MS $t_R$ 1.60 minutes; MS (ES$^+$) m/z 234 (M+H+MeCN), 193 (M+H)$^a$.

EXAMPLE 340 methyl 2-[4-(2-bromoacetyl)phenyl]acetate

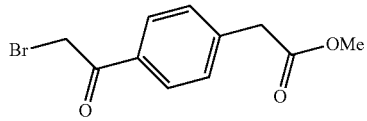 [SMILES: COC(=O)Cc1ccc(C(=O)CBr)cc1]

To a dichloromethane (4 mL) solution of the compound prepared in Example 339 (0.21 g) was added bromine (53 µL) and the mixture stirred at room temperature for 3 hours. The reaction mixture was concentrated to give the crude title product having the following physical properties (0.28 g).

LC/MS $t_R$ 1.82 minutes; MS (ES$^+$) m/z 271 and 273 (M+H)$^a$.

EXAMPLE 341 methyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]acetate The same operation as in Example 51→Example 52 was conducted from the compound prepared in Example 340 to give the title compound having the following physical properties.

LC/MS $t_R$ 1.54 minutes; MS (ES$^+$) m/z 528 (M+H)$^a$.

EXAMPLE 342

[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]acetic acid

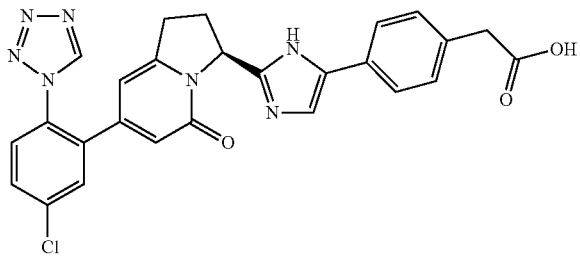 [SMILES: O=C(O)Cc1ccc(-c2cnc([C@@H]3CCc4cc(-c5cc(Cl)ccc5-n5cnnn5)cc(=O)n43)[nH]2)cc1]

To a 1,4-dioxane (2 mL) solution of the compound prepared in Example 341 (90 mg) was added 1 M hydrochloric acid (0.85 mL) and the mixture warmed at 90° C. for 3 hours. The solvents were removed in vacuo and the residue purified by high performance liquid chromatography [5 to 100% mobile phase B (0.1% formic acid in acetonitrile) in mobile phase A (0.1% aqueous formic acid)] to give the title compound having the following physical properties (21 mg).

LC/MS $t_R$ 2.96 minutes; MS (ES$^+$) m/z 514 (M+H)$^b$ $^1$H NMR (500 MHz, DMSO-d$_6$) δ 12.39 (br. s, 1 H), 9.70 (s, 1 H), 8.05 (br. s, 1 H), 7.86-7.80 (m, 2 H), 7.77-7.69 (m, 3 H), 7.41 (d, 2 H), 6.07 (s, 1 H), 6.02 (s, 1 H), 5.81 (dd, 1 H), 3.64 (s, 2 H), 3.27-3.24 (m, 1 H), 3.14-3.05 (m, 1 H), 2.75-2.65 (m, 1 H), 2.38-2.30 (m, 1 H).

EXAMPLE 343

[4-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)phenyl]acetic acid

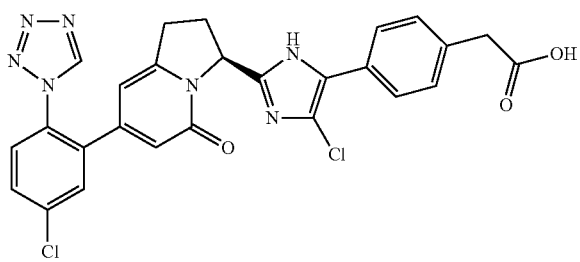 [SMILES: O=C(O)Cc1ccc(-c2[nH]c([C@@H]3CCc4cc(-c5cc(Cl)ccc5-n5cnnn5)cc(=O)n43)nc2Cl)cc1]

The same operation as in Example 338→Example 342 was conducted from the compound prepared in Example 341 to give the title compound having the following physical properties.

LC/MS $t_R$ 3.83 minutes; MS (ES$^+$) m/z 548 (M+H)$^b$ $^1$H NMR (500 MHz, DMSO-d$_6$) δ 12.99 (br. s, 1 H), 9.71 (s, 1 H), 7.88-7.78 (m, 3 H), 7.63 (d, 2 H), 7.35 (d, 2 H), 5.99 (s, 1 H), 5.94 (s, 1 H), 5.58 (dd, 1 H), 3.59 (s, 2 H), 3.40-3.20 (obs. m, 1 H), 2.99 (dd, 1 H), 2.60-2.50 (obs. m, 1 H), 2.25-2.15 (m, 1 H).

EXAMPLE 344 methyl 2-(3-{2-[(3S)-7-[5-chloro-2-(1H-1,2,3,4-tetrazol-1-yl)phenyl]-5-oxo-1,2,3,5-tetrahydroindolizin-3-yl]-1H-imidazol-5-yl}phenyl)acetate The same operation as in Example 139→Example 340→Example 51→Example 52 was conducted from methyl(3-bromophenyl)acetate to give the title compound having the following physical properties.

LC/MS $t_R$ 1.57 minutes; MS (ES$^+$) m/z 528 (M+H)$^a$.

EXAMPLE 345

[3-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]acetic acid

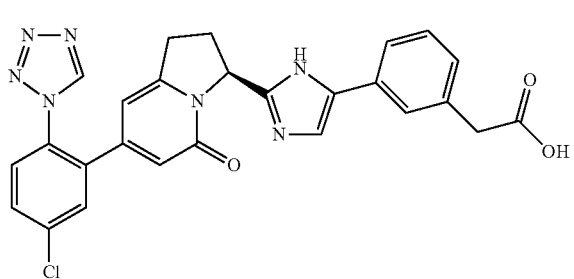 [SMILES: O=C(O)Cc1cccc(-c2cnc([C@@H]3CCc4cc(-c5cc(Cl)ccc5-n5cnnn5)cc(=O)n43)[nH]2)c1]

The compound prepared in Example 344 (270 mg) was treated using the method as detailed in Example 342 to give the title compound having the following physical properties (260 mg).

LC/MS $t_R$ 3.00 minutes; MS (ES$^+$) m/z 514 (M+H)$^b$ $^1$H NMR (500 MHz, DMSO-d$_6$) δ 12.34 (br. s, 1 H), 12.15 (br. s, 1 H), 9.70 (s, 1 H), 7.87-7.74 (m, 3 H), 7.62-7.54 (m, 2 H), 7.51 (br. s, 1 H), 7.30 (m, 1 H), 7.10 (m, 1 H), 5.99 (s, 1 H), 5.96 (s, 1 H), 5.65 (d, 1 H), 3.40-3.30 (obs. m, 1 H), 3.59 (s, 2 H), 3.02 (dd, 1 H), 2.55-2.45 (obs. m, 1 H), 2.35 (m, 1 H).

EXAMPLE 346

[3-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)phenyl]acetic acid

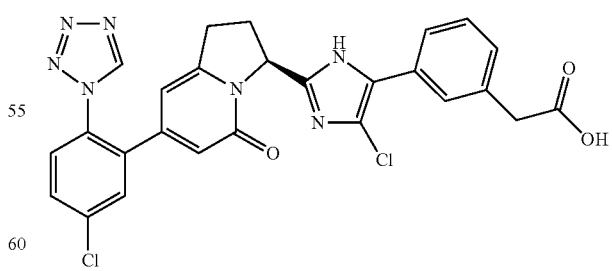

The same operation as in Example 338→Example 342 was conducted from the compound prepared in Example 344 to give the title compound having the following physical properties.

LC/MS $t_R$ 3.84 minutes; MS (ES$^+$) m/z 548 (M+H)$^b$

¹H NMR (500 MHz, DMSO-d₆) δ 13.02 (br. s, 1 H), 12.42 (br. s, 1 H), 9.71 (s, 1 H), 7.89-7.75 (m, 3 H), 7.65-7.56 (m, 2 H), 7.42 (t, 1 H), 7.23 (d, 1 H), 5.99 (s, 1 H), 5.94 (s, 1 H), 5.58 (dd, 1 H), 3.62 (s, 2 H), 3.30-3.23 (m, 1 H), 2.99 (dd, 1 H), 2.58-2.53 (m, 1 H), 2.20 (app. t, 1 H).

EXAMPLE 347

5-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylic acid

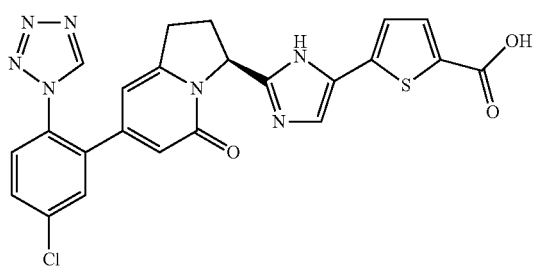 [SMILES: O=C(O)c1ccc(-c2cnc([C@@H]3CCc4cc(-c5cc(Cl)ccc5-n5cnnn5)cc(=O)n43)[nH]2)s1]

The same operation as in Example 234→Example 51→Example 52→Example 8→Example 55→Example 24 was conducted from 5-(methoxycarbonyl)thiophene-2-carboxylic acid to give the title compound having the following physical properties. (Note: in the step corresponding to Example 51 in the operation, the compound prepared in Example 11 was used).

LC/MS t$_R$ 3.38 minutes; MS (ES⁺) m/z 506 (M+H)$^b$

¹H NMR (500 MHz, methanol-d₄) δ 9.36 (s, 1 H), 7.73 (m, 2 H), 7.70-7.65 (m, 2 H), 7.41 (s, 1 H), 7.27 (d, 1 H), 6.13 (s, 1 H), 6.09 (s, 1 H), 5.76 (dd, 1 H), 3.50-3.40 (m, 1 H), 3.11 (ddd, 1 H), 2.64 (qd, 1 H), 2.49 (tdd, 1 H).

EXAMPLE 348

5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylic acid

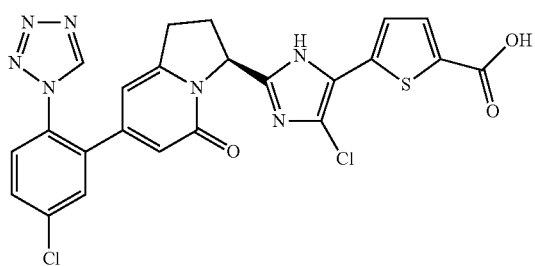 [SMILES: O=C(O)c1ccc(-c2[nH]c([C@@H]3CCc4cc(-c5cc(Cl)ccc5-n5cnnn5)cc(=O)n43)nc2Cl)s1]

The compound prepared in Example 347 (95 mg) was treated using the method as detailed in Example 338 to give the title compound having the following physical properties (17 mg).

LC/MS t$_R$ 3.81 minutes; MS (ES⁺) m/z 540 (M+H)$^b$

¹H NMR (500 MHz, methanol-d₄) δ 9.37 (s, 1 H), 7.78-7.65 (m, 4 H), 7.38 (d, 1 H), 6.14 (s, 1 H), 6.09 (s, 1 H), 5.70 (dd, 1 H), 3.50-3.39 (m, 1 H), 3.11 (ddd, 1 H), 2.66 (qd, 1 H), 2.43-2.33 (m, 1 H).

EXAMPLE 349(1) TO EXAMPLE 349(4)

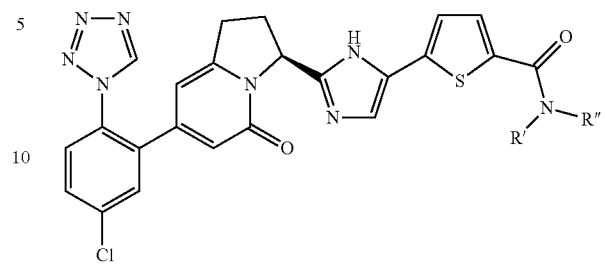

The compounds of the present invention having the following physical data were synthesised from the compound prepared in Example 347 using the corresponding amine hydrochloride salts, employing the method as detailed in Example 114.

EXAMPLE 349(1)

5-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxamide LC/MS t$_R$ 3.11 minutes; MS (ES⁺) m/z 505 (M+H)$^b$ ¹H NMR (500 MHz, methanol-d₄) δ 9.38 (s, 1 H), 7.77-7.67 (m, 3 H), 7.62 (d, 1 H), 7.39 (s, 1 H), 7.26 (d, 1 H), 6.14 (s, 1 H), 6.11 (s, 1 H), 5.77 (dd, 1 H), 3.46 (td, 1 H), 3.12 (ddd, 1 H), 2.72-2.58 (m, 1 H), 2.54-2.44 (m, 1 H).

EXAMPLE 349(2)

5-(2-{(3S)-7-[5-chloro-2-(1H-tetrazol-1-yl)phenyl]-5-oxo-1,2,3,5-tetrahydro-3-indolizinyl}-1H-imidazol-5-yl)-N-methyl-2-thiophenecarboxamide LC/MS t$_R$ 3.22 minutes; MS (ES⁺) m/z 519 (M+H)$^b$ ¹H NMR (500 MHz, methanol-d₄) δ 9.36 (s, 1 H), 7.78-7.64 (m, 3 H), 7.53 (d, 1 H), 7.37 (s, 1 H), 7.23 (d, 1 H), 6.13 (s, 1 H), 6.09 (s, 1 H), 5.75 (dd, 1 H), 3.44 (td, 1 H), 3.11 (ddd, 1 H), 2.89 (s, 3 H), 2.68-2.57 (m, 1 H), 2.53-2.41 (m, 1 H).

EXAMPLE 349(3)

5-(2-{(3S)-7-[5-chloro-2-(1H-tetrazol-1-yl)phenyl]-5-oxo-1,2,3,5-tetrahydro-3-indolizinyl}-1H-imidazol-5-yl)-N-ethyl-2-thiophenecarboxamide LC/MS t$_R$ 3.40 minutes; MS (ES⁺) m/z 533 (M+H)$^b$ ¹H NMR (500 MHz, methanol-d₄) δ 9.36 (s, 1 H), 7.78-7.63 (m, 3 H), 7.57 (d, 1 H), 7.41 (s, 1 H), 7.25 (d, 1 H), 6.12 (s, 1 H), 6.09 (s, 1 H), 5.76 (dd, 1 H), 3.49-3.33 (m, 3 H), 3.12 (ddd, 1 H), 2.72-2.59 (m, 1 H), 2.46 (tt, 1 H), 1.21 (t, 3 H).

EXAMPLE 349(4)

5-(2-{(3S)-7-[5-chloro-2-(1H-tetrazol-1-yl)phenyl]-5-oxo-1,2,3,5-tetrahydro-3-indolizinyl}-1H-imidazol-5-yl)-N,N-dimethyl-2-thiophenecarboxamide LC/MS $t_R$ 3.36 minutes; MS (ES$^+$) m/z 533 (M+H)$^b$
$^1$H NMR (500 MHz, methanol-$d_4$) δ 9.36 (s, 1 H), 7.76-7.64 (m, 3 H), 7.42 (app. s, 2 H), 7.26 (d, 1 H), 6.12 (s, 1 H), 6.09 (s, 1 H), 5.76 (dd, 1 H), 3.41 (dd, 1 H), 3.21 (br. s, 6 H), 3.11 (ddd, 1 H), 2.74-2.60 (m, 1 H), 2.52-2.40 (m, 1 H).

EXAMPLE 350(1) to Example 350(3)

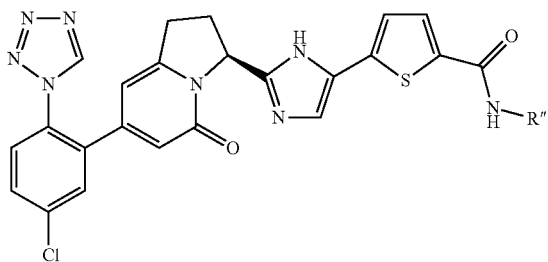

The compounds of the present invention having the following physical data were synthesised from the compound prepared in Example 347 using the corresponding amines, employing the method as detailed in Example 70.

EXAMPLE 350(1)

5-(2-{(3S)-7-[5-chloro-2-(1H-tetrazol-1-yl)phenyl]-5-oxo-1,2,3,5-tetrahydro-3-indolizinyl}-1H-imidazol-5-yl)-N-(2-methoxyethyl)-2-thiophenecarboxamide LC/MS $t_R$ 3.29 minutes; MS (ES$^+$) m/z 563 (M+H)$^b$
$^1$H NMR (500 MHz, methanol-$d_4$) δ 9.36 (s, 1 H), 7.75-7.71 (m, 2 H), 7.70-7.66 (m, 1 H), 7.58 (d, 1 H), 7.37 (br. s, 1 H), 7.23 (d, 1 H), 6.12 (s, 1 H), 6.08 (s, 1 H), 5.75 (dd, 1 H), 3.56-3.50 (m, 4 H), 3.49-3.40 (m, 1 H), 3.37 (s, 3 H), 3.10 (ddd, 1 H), 2.63 (qd, 1 H), 2.48 (app. br. s, 1 H).

EXAMPLE 350(2)

5-(2-{(3S)-7-[5-chloro-2-(1H-tetrazol-1-yl)phenyl]-5-oxo-1,2,3,5-tetrahydro-3-indolizinyl}-1H-imidazol-5-yl)-N-[2-(2-methoxyethoxyl)ethyl]-2-thiophenecarboxamide LC/MS $t_R$ 3.34 minutes; MS (ES$^+$) m/z 607 (M+H)$^b$
$^1$H NMR (500 MHz, methanol-$d_4$) δ 9.37 (s, 1 H), 7.76-7.72 (m, 2 H), 7.71-7.67 (m, 1 H), 7.60 (d, 1 H), 7.37 (br. s, 1 H), 7.25 (d, 1 H), 6.14 (s, 1 H), 6.10 (s, 1 H), 5.76 (dd, 1 H), 3.66-3.62 (m, 4 H), 3.58-3.52 (m, 4 H), 3.49-3.40 (m, 1 H), 3.37 (s, 3 H), 3.11 (ddd, 1 H), 2.64 (qd, 1 H), 2.53-2.44 (m, 1 H).

EXAMPLE 350(3)

5-(2-{(3S)-7-[5-chloro-2-(1H-tetrazol-1-yl)phenyl]-5-oxo-1,2,3,5-tetrahydro-3-indolizinyl}-1H-imidazol-5-yl)-N-[2-(4-morpholinyl)ethyl]-2-thiophenecarboxamide LC/MS $t_R$ 2.70 minutes; MS (ES$^+$) m/z 618 (M+H), 309.5 [(M+2H)/2]$^b$
$^1$H NMR (500 MHz, methanol-$d_4$) δ 9.36 (s, 1 H), 7.75-7.71 (m, 2 H), 7.70-7.65 (m, 1 H), 7.56 (d, 1 H), 7.39 (br. s, 1 H), 7.24 (d, 1 H), 6.12 (s, 1 H), 6.08 (s, 1 H), 5.75 (dd, 1 H), 3.70 (app. t, 4 H), 3.51 (t, 2 H), 3.48-3.39 (m, 1 H), 3.10 (ddd, 1 H), 2.69-2.43 (m, 8 H).

EXAMPLE 351(1) to Example 351(4)

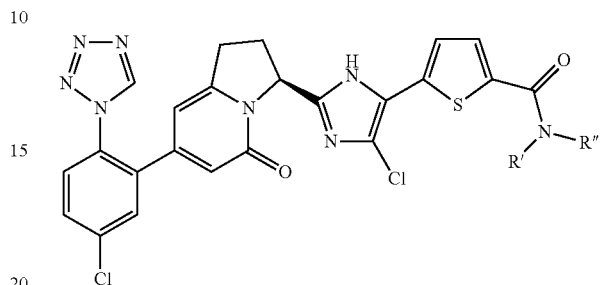

The compounds of the present invention having the following physical data were synthesised from the compound prepared in Example 348 using the corresponding amine hydrochloride salts, employing the method as detailed in Example 114.

EXAMPLE 351(1)

5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-thiopheneearboxamide LC/MS $t_R$ 3.57 minutes; MS (ES$^+$) m/z 539 and 541 (M+H)$^b$
$^1$H NMR (500 MHz, DMSO-$d_6$) δ 13.31 (br. s, 1 H), 9.71 (s, 1 H), 8.00 (s, 1 H), 7.89-7.76 (m, 3 H), 7.72 (d, 1 H), 7.54-7.19 (m, 2 H), 5.98 (s, 1 H), 5.93 (s, 1 H), 5.54 (d, 1 H), 3.33-3.21 (obs. m, 1 H), 2.98 (dd, 1 H), 2.60-2.52 (obs. m, 1 H), 2.25-2.12 (m, 1 H).

EXAMPLE 351(2)

5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-N-methyl-2-thiophenecarboxamide LC/MS $t_R$ 3.71 minutes; MS (ES$^+$) m/z 553 and 555 (M+H)$^b$
$^1$H NMR (500 MHz, DMSO-$d_6$) δ 13.29 (br. s, 1H), 9.71 (s, 1 H), 8.50 (app. s, 1 H), 7.88-7.76 (m, 3 H), 7.68 (d, 1 H), 7.39 (d, 1 H), 5.99 (s, 1 H), 5.93 (s, 1 H), 5.54 (d, 1H), 3.31-3.20 (obs. m, 1 H), 2.99 (dd, 1 H), 2.76 (d, 3 H), 2.59-2.52 (obs. m, 1 H), 2.27-2.14 (m, 1 H).

EXAMPLE 351(3)

5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-N-ethyl-2-thiophenecarboxamide LC/MS $t_R$ 3.87 minutes; MS (ES$^+$) m/z 567 and 569 (M+H)$^b$
$^1$H NMR (500 MHz, DMSO-$d_6$) δ 13.28 (br. s, 1 H), 9.71 (s, 1 H), 8.52 (app. s, 1 H), 7.90-7.75 (m, 3 H), 7.70 (d, 1 H), 7.39 (d, 1 H), 5.99 (s, 1 H), 5.93 (s, 1 H), 5.54 (dd, 1 H), 3.31-3.19 (m, 3 H), 2.98 (dd, 1 H), 2.60-2.50 (obs. m, 1 H), 2.23-2.13 (m, 1 H), 1.12 (t, 3 H).

EXAMPLE 351(4)

5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-N,N-dimethyl-2-thiophenecarboxamide LC/MS $t_R$ 3.87 minutes; MS (ES$^+$) m/z 567 and 569 (M+H)$^b$ $^1$H NMR (500 MHz, DMSO-d$_6$) δ 13.32 (br. s, 1 H), 9.71 (s, 1 H), 7.93-7.70 (m, 3 H), 7.53 (d, 1 H), 7.40 (d, 1 H), 5.99 (s, 1 H), 5.94 (s, 1 H), 5.55 (dd, 1 H), 3.35-3.22 (obs. m, 1 H), 3.12 (br. s, 6 H), 2.99 (dd, 1 H), 2.59-2.50 (obs. m, 1 H), 2.25-2.12 (m, 1 H).

EXAMPLE 352(1) to Example 352(3)

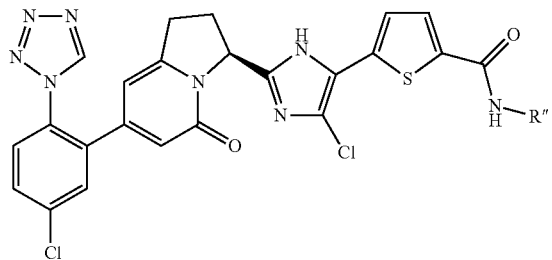

The compounds of the present invention having the following physical data were synthesised from the compounds prepared in Examples 350(1), 350(2) and 350(3) using the method as detailed in Example 338.

EXAMPLE 352(1)

5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-N-(2-methoxyethyl)-2-thiophenecarboxamide LC/MS $t_R$ 3.80 minutes; MS (ES$^+$) m/z 597 and 599 (M+H)$^b$ $^1$H NMR (500 MHz, CDCl$_3$) δ 11.97 (br. s, 1 H), 8.70 (br. s, 1 H), 7.63 (dd, 1 H), 7.58 (d, 1 H), 7.55 (d, 1 H), 7.35 (d, 1 H), 6.99 (br. s, 1 H), 6.57 (app. br. s, 1 H), 6.32 (s, 1 H), 5.84 (s, 1 H), 5.81 (d, 1 H), 3.67-3.47 (m, 5 H), 3.40 (s, 3 H), 3.04 (dd, 1 H), 2.95-2.86 (m, 1 H), 2.59-2.46 (m, 1 H).

EXAMPLE 352(2)

5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-N-(2-methoxyethoxy)ethyl)-2-thiophenecarboxamide LC/MS $t_R$ 3.76 minutes; MS (ES$^+$) m/z 641 and 643 (M+H)$^b$ $^1$H NMR (500 MHz, methanol-d$_4$) δ 9.37 (s, 1 H), 7.77-7.72 (m, 2 H), 7.71-7.65 (m, 2 H), 7.37 (d, 1 H), 6.14 (s, 1 H), 6.10 (s, 1 H), 5.71 (dd, 1 H), 3.67-3.62 (m, 4 H), 3.59-3.54 (m, 4 H), 3.49-3.40 (m, 1 H), 3.38 (s, 3 H), 3.12 (ddd, 1 H), 2.72-2.60 (m, 1 H), 2.42-2.32 (m, 1 H).

EXAMPLE 352(3)

5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-N-[2-(4-morpholinyl)ethyl]-2-thiophenecarboxamide LC/MS $t_R$ 2.96 minutes; MS (ES$^+$) m/z 652 and 654 (M+H), 326.5 and 327.5 [(M+2H)/2]$^b$ $^1$H NMR (500 MHz, methanol-d$_4$) δ 9.37 (s, 1 H), 7.77-7.71 (m, 2 H), 7.70-7.66 (m, 1 H), 7.64 (d, 1 H), 7.36 (d, 1 H), 6.13 (s, 1 H), 6.10 (s, 1 H), 5.70 (dd, 1 H), 3.76-3.66 (m, 4 H), 3.53 (t, 2 H), 3.43 (td, 1 H), 3.11 (ddd, 1 H), 2.65 (qd, 1 H), 2.59 (t, 2 H), 2.55 (app. br. s, 4 H), 2.41-2.34 (m, 1 H).

EXAMPLE 353

5-(2-{(3S)-7-[5-chloro-2-(1H-tetrazol-1-yl)phenyl]-5-oxo-1,2,3,5-tetrahydro-3-indolizinyl}-1H-imidazol-5-yl)-N-methoxy-2-thiophenecarboxamide

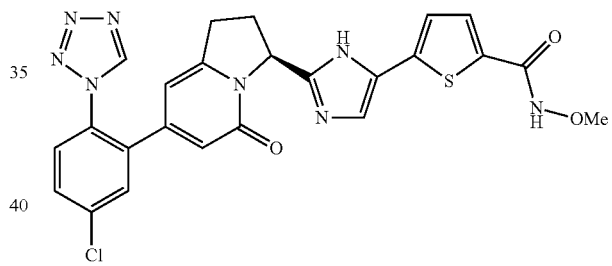

To an N,N-dimethylformamide (6 mL) solution of the compound prepared in Example 347 (150 mg) was added 1-[3-(dimethylaminopropyl)]-3-ethylcarbodiimide hydrochloride (170 mg), 4-dimethylaminopyridine (18 mg) and methoxamide hydrochloride (136 mg). Triethylamine (270 μL) was added and the mixture stirred at room temperature for 16 hours. A saturated aqueous solution of sodium hydrogen carbonate was added followed by extraction with ethyl acetate. The combined organic layers were washed with saturated saline, dried and concentrated. The residue was purified by column chromatography (0 to 15% methanol in dichloromethane, NH silica) to give the title compound having the following physical properties (21.6 mg).

LC/MS $t_R$ 3.23 minutes; MS (ES$^+$) m/z 535 (M+H)$^b$ $^1$H NMR (500 MHz, methanol-d$_4$) δ 9.36 (s, 1 H), 7.76-7.70 (m, 2 H), 7.69-7.65 (m, 1 H), 7.51 (br. s, 1 H), 7.38 (br. s, 1 H), 7.24 (d, 1 H), 6.12 (s, 1 H), 6.08 (s, 1 H), 5.75 (dd, 1 H), 3.79 (s, 3 H), 3.49-3.39 (m, 1 H), 3.10 (ddd, 1 H), 2.63 (qd, 1 H), 2.53-2.42 (m, 1 H).

EXAMPLE 354

5-(2-{(3S)-7-[5-chloro-2-(1H-tetrazol-1-yl)phenyl]-5-oxo-1,2,3,5-tetrahydro-3-indolizinyl}-1H-imidazol-5-yl)-N-cyano-2-thiophenecarboxamide

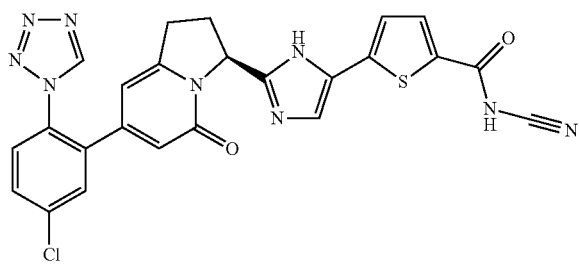 [SMILES: N#CNC(=O)c1ccc(-c2cnc([C@@H]3CCc4cc(-c5cc(Cl)ccc5-n5cnnn5)cc(=O)n43)[nH]2)s1]

To an N,N-dimethylformamide (4 mL) solution of the compound prepared in Example 347 (100 mg) was added (benzotriazol-1-yloxy)tris(dimethylamino)phosphonium hexafluorophosphate (105 mg), cyanamide (12.5 mg) and diisopropylethylamine (98 μL) and the mixture stirred at room temperature for 16 hours. Water was added followed by extraction with a 2:1 mixture of dichloromethane and propan-2-ol. The combined organic layers were washed with saturated saline, dried and concentrated. The residue was purified by column chromatography (0 to 40% methanol in dichloromethane) followed by high performance liquid chromatography (5 to 100% acetonitrile in 2 mM aqueous ammonium hydrogen carbonate) to give the title compound having the following physical properties (32 mg).

LC/MS $t_R$ 3.24 minutes; MS (ES$^+$) m/z 530 (M+H)$^b$ $^1$H NMR (500 MHz, 2:1 methanol-d$_4$ and D$_2$O) δ 9.38 (s, 1 H), 7.76-7.71 (m, 2 H), 7.70-7.65 (m, 1 H), 7.53 (d, 1 H), 7.32 (br. s, 1 H), 7.19 (d, 1 H), 6.14 (s, 1 H), 6.09 (s, 1 H), 5.77 (d, 1 H), 3.47-3.38 (m, 1 H), 3.11 (ddd, 1 H), 2.71-2.59 (m, 1 H), 2.50-2.39 (m, 1 H).

EXAMPLE 355

2-(4-morpholinyl)ethyl 5-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylate

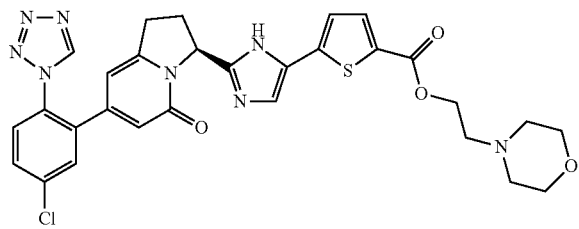 [SMILES: O=C(OCCN1CCOCC1)c1ccc(-c2cnc([C@@H]3CCc4cc(-c5cc(Cl)ccc5-n5cnnn5)cc(=O)n43)[nH]2)s1]

To a cooled (0° C.) dichloromethane (15 mL) suspension of the compound prepared in Example 347 (150 mg) was added oxalyl chloride (75.3 μL) followed by one drop of N,N-dimethylformamide and the mixture stirred at room temperature for 3 hours. The reaction mixture was concentrated and the residue re-dissolved in dichloromethane (15 mL). To this cooled (0° C.) solution, N-(2-hydroxyethyl)morpholine (108 μL) and triethylamine (124 μL) were added and the mixture stirred at room temperature for 1 hour. Water was added followed by extraction with dichloromethane. The combined organic layers were washed with saturated saline, dried and concentrated. The residue was purified by column chromatography (0 to 5% methanol in ethyl acetate) to give the title compound having the following physical properties (60 mg).

LC/MS $t_R$ 1.72 minutes; MS (ES$^+$) m/z 619 (M+H), 310 [(M+2H)/2]$^e$ $^1$H NMR (500 MHz, methanol-d$_4$) δ 9.36 (s, 1 H), 7.78-7.71 (m, 3 H), 7.70-7.65 (m, 1 H), 7.45 (br. s, 1 H), 7.28 (d, 1 H), 6.13 (s, 1 H), 6.09 (s, 1 H), 5.75 (dd, 1 H), 4.43 (t, 2 H), 3.72-3.68 (m, 4 H), 3.50-3.40 (m, 1 H), 3.11 (ddd, 1 H), 2.77 (t, 2 H), 2.69-2.61 (m, 1 H), 2.62-2.56 (m, 4 H), 2.50 (app. br. s, 1 H).

EXAMPLE 356(1) TO EXAMPLE 356(3)

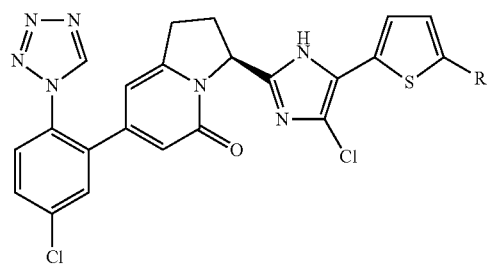

The compounds of the present invention having the following physical data were synthesised from the compounds prepared in Examples 353, 354, and 355 using the method as detailed in Example 338.

EXAMPLE 356(1)

5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-N-methoxy-2-thiophenecarboxamide LC/MS $t_R$ 2.68 minutes; MS (ES$^+$) m/z 569 and 571 (M+H)$^e$ $^1$H NMR (500 MHz, methanol-d$_4$) δ 9.37 (s, 1 H), 7.78-7.73 (m, 2 H), 7.70-7.64 (m, 1 H), 7.59 (app. br. s, 1 H), 7.37 (d, 1 H), 6.13 (s, 1 H), 6.10 (s, 1 H), 5.70 (dd, 1 H), 3.81 (s, 3 H), 3.44 (td, 1 H), 3.16-3.06 (m, 1 H), 2.72-2.59 (m, 1 H), 2.41-2.32 (m, 1 H).

EXAMPLE 356(2)

5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-N-cyano-2-thiophenecarboxamide LC/MS $t_R$ 3.05 minutes; MS (ES$^+$) m/z 564 and 566 (M+H)$^e$ $^1$H NMR (500 MHz, methanol-d$_4$) δ 9.37 (s, 1 H), 7.76-7.71 (m, 2 H), 7.68 (d, 1 H), 7.59 (d, 1 H), 7.32 (d, 1 H), 6.13 (s, 1 H), 6.08 (s, 1 H), 5.69 (dd, 1 H), 3.42 (td, 1 H), 3.10 (ddd, 1 H), 2.71-2.60 (m, 1 H), 2.41-2.33 (m, 1 H).

EXAMPLE 356(3)

2-(4-morpholinyl)ethyl 5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylate

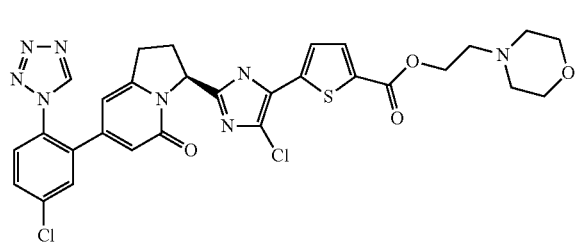 [SMILES: O=C(OCCN1CCOCC1)c1ccc(-c2[nH]c([C@@H]3CCc4cc(-c5cc(Cl)ccc5-n5cnnn5)cc(=O)n43)nc2Cl)s1]

LC/MS $t_R$ 3.11 minutes; MS (ES$^+$) m/z 653 and 655 (M+H), 327 and 328 [(M+2H)/2]$^b$ $^1$H NMR (500 MHz, methanol-d$_4$) δ 9.36 (s, 1 H), 7.80 (d, 1 H), 7.75-7.72 (m, 2 H), 7.70-7.66 (m, 1 H), 7.39 (d, 1 H), 6.13 (s, 1 H), 6.10 (s, 1 H), 5.70 (dd, 1 H), 4.47 (t, 2 H), 3.73-3.69 (m, 4 H), 3.49-3.39 (m, 1 H), 3.12 (ddd, 1 H), 2.82 (t, 2 H), 2.69-2.61 (m, 5 H), 2.42-2.33 (m, 1 H).

EXAMPLE 357 methyl[5-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thienyl]acetate

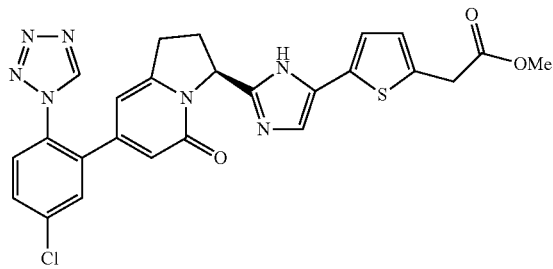 [SMILES: COC(=O)Cc1ccc(-c2cnc([C@@H]3CCc4cc(-c5cc(Cl)ccc5-n5cnnn5)cc(=O)n43)[nH]2)s1]

The same operation as in Example 51→Example 52 was conducted from methyl 2-[5-(2-chloroacetyl)thiophen-2-yl]acetate to give the title compound having the following physical properties.

LC/MS $t_R$ 3.46 minutes; MS (ES$^+$) m/z 534 (M+H)$^b$ $^1$H NMR (500 MHz, methanol-d$_4$) δ 9.36 (s, 1 H), 7.76-7.71 (m, 2 H), 7.70-7.65 (m, 1 H), 7.19 (s, 1 H), 7.08 (d, 1 H), 6.85 (d, 1 H), 6.13 (s, 1 H), 6.09 (s, 1 H), 5.76 (dd, 1 H), 3.86 (s, 2 H), 3.72 (s, 3 H), 3.43 (td, 1 H), 3.10 (ddd, 1 H), 2.64 (qd, 1 H), 2.46 (tdd, 1 H).

EXAMPLE 358

[5-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thienyl]acetic acid hydrochloride

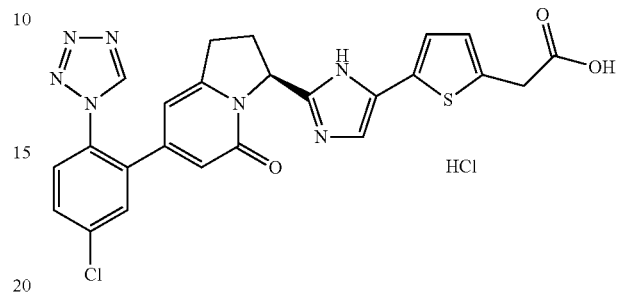

The compound prepared in Example 357 (18.2 mg) was treated as detailed in Example 342 to give, on trituration with a 9:1 mixture of dichloromethane and acetonitrile, the title compound as the hydrochloride salt having the following physical properties (14.5 mg).

LC/MS $t_R$ 3.08 minutes; MS (ES$^+$) m/z 520 (M+H)$^b$ $^1$H NMR (500 MHz, DMSO-d$_6$) δ 12.68 (br. s, 1 H), 9.70 (s, 1 H), 7.94-7.55 (m, 4 H), 7.29 (br. s, 1 H), 6.96 (app. s, 1 H), 6.04 (s, 1 H), 6.01 (s, 1 H), 5.72 (dd, 1 H), 3.87 (s, 2 H), 3.31-3.24 (obs. m, 1 H), 3.11-3.01 (m, 1 H), 2.70-2.58 (m, 1 H), 2.37-2.26 (m, 1 H).

EXAMPLE 359 methyl[5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-thienyl]acetate

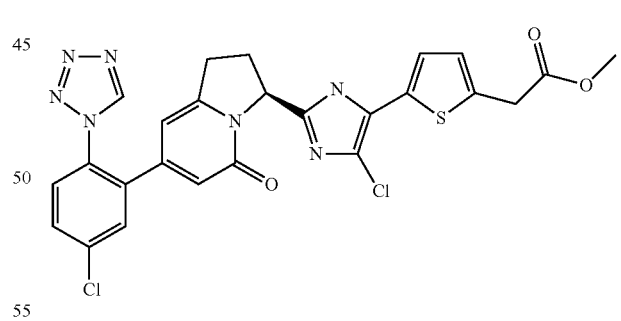

The compound prepared in Example 357 (69 mg) was treated as detailed in Example 338 to give the title compound having the following physical properties (35 mg).

LC/MS $t_R$ 4.18 minutes; MS (ES$^+$) m/z 568 and 570 (M+H)$^b$ $^1$H NMR (500 MHz, CDCl$_3$) δ 11.37 (br. s, 1 H), 8.59 (s, 1 H), 7.64 (dd, 1 H), 7.59-7.53 (m, 2 H), 7.09 (d, 1 H), 6.90 (d, 1 H), 6.36 (s, 1 H), 5.81 (d, 1 H), 5.76 (s, 1 H), 3.85 (s, 2 H), 3.76 (s, 3 H), 3.50-3.38 (m, 1 H), 3.17 (dd, 1 H), 3.02 (dd, 1 H), 2.54-2.41 (m, 1 H).

EXAMPLE 360

[5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-thienyl]acetic acid hydrochloride

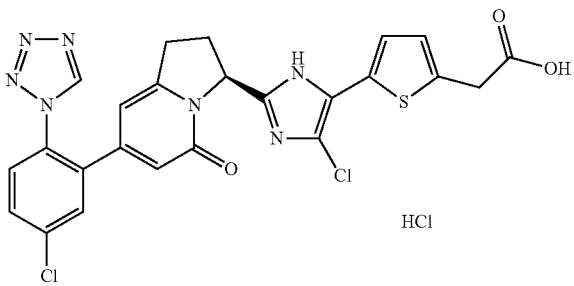 [SMILES: O=C(O)Cc1ccc(-c2[nH]c([C@@H]3CCc4cc(-c5cc(Cl)ccc5-n5cnnn5)cc(=O)n43)nc2Cl)s1 ; Cl]

The compound prepared in Example 359 (20 mg) was treated as detailed in Example 342 to give, on trituration with a 9:1 mixture of dichloromethane and acetonitrile, the title compound as the hydrochloride salt having the following physical properties (11.5 mg).

LC/MS $t_R$ 3.08 minutes; MS (ES$^+$) m/z 554 and 556 (M+H)$^b$ $^1$H NMR (500 MHz, DMSO-d$_6$) δ 13.11 (br. s, 1 H), 12.61 (s, 1 H), 9.71 (s, 1 H), 7.86-7.76 (m, 3 H), 7.25 (d, 1 H), 6.96 (d, 1 H), 5.98 (s, 1 H), 5.94 (s, 1 H), 5.54 (dd, 1 H), 3.85 (s, 2 H), 3.33-3.22 (m, 1 H), 2.98 (dd, 1 H), 2.58-2.49 (obs. m, 1 H), 2.24-2.11 (m, 1H).

EXAMPLE 361 tert-butyl 4-(2-bromoacetyl)thiophene-2-carboxylate

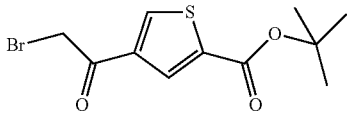

To a tetrahydrofuran (100 mL) solution of tert-butyl 4-acetylthiophene-2-carboxylate [patent EP1357123, 2003] (7.91 g) was added a solution of phenyltrimethylammonium tribromide (12.5 g) in tetrahydrofuran (20 mL) and the mixture stirred at room temperature for 3 hours. To the reaction mixture, water (100 mL) was added followed by extraction with ethyl acetate. The combined organic layers were washed with brine, dried and concentrated. The residue was purified by column chromatography (0-20% ethyl acetate in heptanes) to give the title product having the following physical properties (7.73 g).

$^1$H NMR (500 MHz, CDCl$_3$) δ 8.29 (d, 1 H), 8.11 (d, 1 H), 4.31 (s, 2 H), 1.60 (s, 9H).

EXAMPLE 362

2-methyl-2-propanyl 4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylate The same operation as in Example 51→Example 52 was conducted from the compound prepared in Example 361 to give the title compound having the following physical properties.

LC/MS $t_R$ 1.92 minutes; MS (ES$^+$) m/z 562 (M+H)$^a$ $^1$H NMR (500 MHz, methanol-d$_4$) δ 9.36 (s, 1 H), 7.95 (s, 1 H), 7.77 (s, 1 H), 7.75-7.71 (m, 2 H), 7.71-7.67 (m, 1 H), 7.34 (br. s, 1 H), 6.13 (s, 1 H), 6.09 (s, 1 H), 5.76 (dd, 1H), 3.49-3.39 (m, 1 H), 3.11 (ddd, 1 H), 2.64 (qd, 1 H), 2.47 (app. br. s, 1 H), 1.59 (s, 9 H).

EXAMPLE 363

4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylic acid hydrochloride

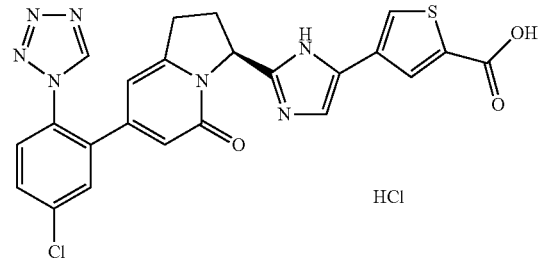 [SMILES: O=C(O)c1cc(-c2cnc([C@@H]3CCc4cc(-c5cc(Cl)ccc5-n5cnnn5)cc(=O)n43)[nH]2)cs1 ; Cl]

To a 1,4-dioxane (60 mL) solution of the compound prepared in Example 362 (3.0 g) was added 1 M hydrochloric acid (26.7 mL) and the mixture heated at 90° C. for 5 hours. On cooling the solvent was reduced in volume in vacuo to give a precipitate which was isolated by filtration and washed with water. Drying of the filter cake in vacuo gave the title compound having the following physical properties (2.28 g). LC/MS $t_R$ 1.47 minutes; MS (ES$^+$) m/z 506 (M+H)$^a$ $^1$H NMR (500 MHz, DMSO-d$_6$) δ 14.63 (br. s, 1 H), 13.42 (br. s, 1 H), 9.70 (s, 1 H), 8.25 (br. s, 1 H), 8.17 (s, 1 H), 8.01 (br. s, 1 H), 7.88-7.77 (m, 2 H), 7.72 (d, 1 H), 6.05 (s, 1 H), 6.02 (s, 1 H), 5.77 (dd, 1 H), 3.32-3.28 (m, 1 H), 3.15-3.04 (m, 1 H), 2.76-2.60 (m, 1 H), 2.39-2.30 (m, 1 H).

EXAMPLE 364 tert-butyl 4-{2-[(3S)-7-[5-chloro-2-(1H-1,2,3,4-tetrazol-1-yl)phenyl]-5-oxo-1,2,3,5-tetrahydroindolizin-3-yl]-4-fluoro-1H-imidazol-5-yl}thiophene-2-carboxylate To an N,N-dimethylformamide (2 mL) solution of the compound prepared in Example 362 (100 mg) was added sodium carbonate (24.5 mg) and Accufluor® (126 mg) and the suspension stirred at room temperature for 1 hour. Water (10 mL) was added followed by extraction with ethyl acetate. The combined organic layers were washed with brine, dried and concentrated. The residue was purified by column chromatography (25-100% ethyl acetate in heptanes) to give the title product having the following physical properties (29 mg).

LC/MS $t_R$ 2.31 minutes; MS (ES$^+$) m/z 602 (M+Na), 524 [M-C(CH$_3$)$_3$+H]$^a$ $^1$H NMR (500 MHz, methanol-d$_4$) δ 9.35 (s, 1 H), 7.86 (s, 1 H), 7.75-7.71 (m, 2 H), 7.70-7.66 (m, 1 H), 7.64 (d, 1 H), 6.12 (s, 1 H), 6.09 (s, 1 H), 5.66 (dd, 1 H), 3.48-3.38 (m, 1 H), 3.10 (ddd, 1 H), 2.68-2.58 (m, 1 H), 2.40-2.33 (m, 1 H), 1.59 (s, 9 H).

EXAMPLE 365

4-(2-{(3S)-7-[5-chloro-2-(1H-tetrazol-1-yl)phenyl]-5-oxo-1,2,3,5-tetrahydro-3-indolizinyl}-4-fluoro-1H-imidazol-5-yl)-2-thiophenecarboxylic acid hydrochloride

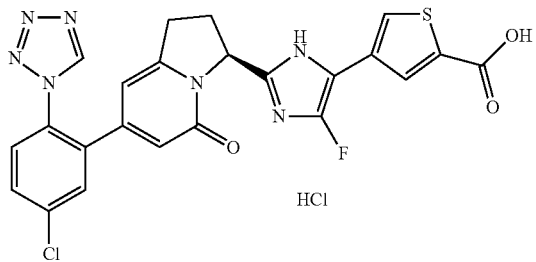 [SMILES: O=C(O)c1cc(-c2[nH]c([C@@H]3CCc4cc(-c5cc(Cl)ccc5-n5cnnn5)cc(=O)n43)nc2F)cs1 ; Cl]

The compound prepared in Example 364 (26 mg) was treated as detailed in Example 363 to give, on concentration of the reaction mixture, the title compound as the hydrochloride salt having the following physical properties (25 mg).

LC/MS $t_R$ 3.79 minutes; MS (ES$^+$) m/z 524 (M+H)$^b$ $^1$H NMR (500 MHz, DMSO-d$_6$) δ 13.12 (very br. s, 1 H), 12.97 (br. s, 1 H), 9.70 (s, 1 H), 7.93 (s, 1 H), 7.84 (d, 1 H), 7.81-7.77 (m, 3 H), 5.97 (s, 1 H), 5.94 (s, 1 H), 5.51 (d, 1 H), 3.33-3.23 (m, 1 H), 2.98 (dd, 1 H), 2.58-2.54 (m, 1 H), 2.22-2.13 (m, 1 H).

EXAMPLE 366

4-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylic acid hydrochloride

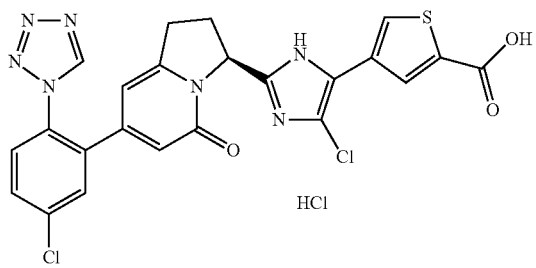

The same operation as in Example 338→Example 363 was conducted from the compound prepared in Example 362 to give the title compound having the following physical properties.

LC/MS $t_R$ 3.84 minutes; MS (ES$^+$) m/z 540 and 542 (M+H)$^b$ $^1$H NMR (500 MHz, DMSO-d$_6$) δ 13.24 (br. s, 1 H), 9.71 (s, 1 H), 8.14 (d, 1 H), 8.08 (d, 1 H), 7.83-7.79 (m, 3 H), 5.99 (s, 1 H), 5.94 (s, 1 H), 5.54 (dd, 1 H), 3.32-3.24 (m, 1 H), 2.99 (dd, 1 H), 2.59-2.53 (m, 1 H), 2.19 (t, 1 H).

EXAMPLE 367 ethyl 4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylate

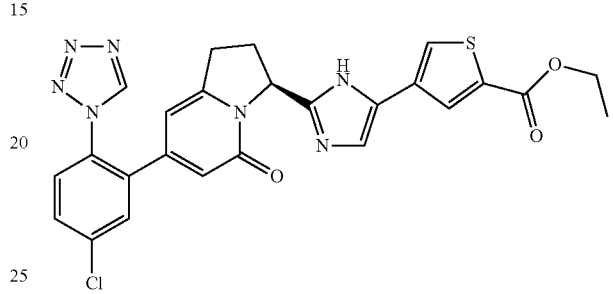

To an N,N-dimethylformamide (2 mL) suspension of the compound prepared in Example 363 (80 mg) was added ethanol (92 µL), (1H-benzotriazol-1-yloxy) [tris(dimethylamino)]phosphonium hexafluorophosphate (77 mg) and N,N-diisopropylethylamine (68 µL) and the mixture stirred at room temperature for 16 hours. Water (10 mL) was added followed by extraction into ethyl acetate. The combined organic layers were washed with brine, dried and concentrated. The residue was purified by column chromatography (50-100% ethyl acetate in heptanes, then 0-5% methanol in ethyl acetate) to give the title product having the following physical properties (59 mg).

LC/MS $t_R$ 3.64 minutes; MS (ES+) m/z 534 (M+H)$^b$ $^1$H NMR (500 MHz, methanol-d$_4$) δ 9.36 (s, 1 H), 8.04 (d, 1 H), 7.82 (d, 1 H), 7.77-7.72 (m, 2 H), 7.71-7.66 (m, 1 H), 7.33 (br. s, 1 H), 6.13 (s, 1 H), 6.09 (s, 1 H), 5.76 (dd, 1 H), 4.34 (q, 2 H), 3.44 (td, 1 H), 3.11 (ddd, 1 H), 2.64 (qd, 1 H), 2.46 (app. br. s, 1 H), 1.37 (t, 3 H).

EXAMPLE 368(1) to Example 368(7)

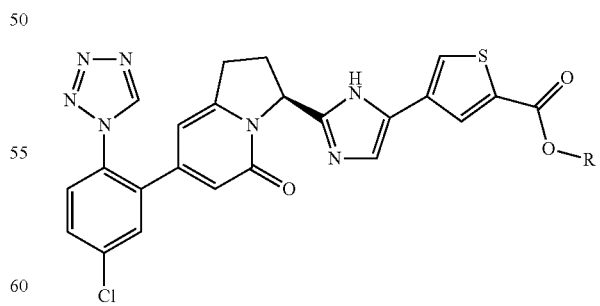

The compounds of the present invention having the following physical data were synthesised from the compound prepared in Example 363 using the corresponding commercially available alcohols, employing the method as detailed in Example 367.

EXAMPLE 368(1)

isopropyl 4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylate Note: in this instance, the reaction was heated at 50° C. for an additional 24 hours to achieve sufficient conversion to the ester.

LC/MS $t_R$ 3.84 minutes; MS (ES$^+$) m/z 548 (M+H)$^b$ $^1$H NMR (500 MHz, methanol-d$_4$) δ 9.36 (s, 1 H), 8.02 (d, 1 H), 7.81 (d, 1 H), 7.76-7.72 (m, 2 H), 7.70-7.67 (m, 1 H), 7.32 (s, 1 H), 6.13 (s, 1 H), 6.09 (s, 1 H), 5.77 (dd, 1 H), 5.19 (td, 1 H), 3.50-3.39 (m, 1 H), 3.11 (ddd, 1 H), 2.64 (qd, 1 H), 2.52-2.39 (m, 1 H), 1.37 (d, 6 H).

EXAMPLE 368(2)

3-methylbutyl 4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylate LC/MS $t_R$ 4.32 minutes; MS (ES$^+$) m/z 576 (M+H)$^b$ $^1$H NMR (500 MHz, methanol-d$_4$) δ 9.36 (s, 1 H), 8.03 (d, 1 H), 7.83 (d, 1 H), 7.77-7.72 (m, 2 H), 7.72-7.65 (m, 1 H), 7.33 (br. s, 1 H), 6.14 (s, 1 H), 6.09 (s, 1 H), 5.77 (dd, 1 H), 4.35 (t, 2 H), 3.52-3.38 (m, 1 H), 3.11 (ddd, 1 H), 2.65 (qd, 1 H), 2.47 (app. br. s, 1 H), 1.85-1.72 (m, 1 H), 1.66 (app. q, 2 H), 0.99 (d, 6 H).

EXAMPLE 368(3)

2-(4-morpholinyl)ethyl 4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylate

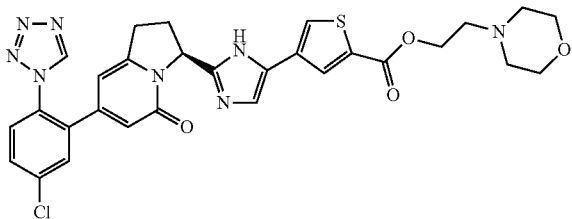 [SMILES: O=C(OCCN1CCOCC1)c1cc(-c2cnc([C@@H]3CCc4cc(-c5cc(Cl)ccc5-n5cnnn5)cc(=O)n43)[nH]2)cs1]

LC/MS $t_R$ 2.73 minutes; MS (ES$^+$) m/z 619 (M+H), 310 [(M+2H)/2]$^b$ $^1$H NMR (500 MHz, methanol-d$_4$) δ 9.36 (s, 1 H), 8.07 (d, 1 H), 7.84 (s, 1 H), 7.76-7.71 (m, 2 H), 7.70-7.66 (m, 1 H), 7.35 (br. s, 1 H), 6.13 (s, 1 H), 6.09 (s, 1 H), 5.76 (dd, 1 H), 4.45 (t, 2 H), 3.72-3.67 (m, 4 H), 3.49-3.39 (m, 1 H), 3.11 (ddd, 1 H), 2.78 (t, 2 H), 2.68-2.54 (m, 5 H), 2.46 (app. br. s, 1 H).

EXAMPLE 368(4)

(5-methyl-2-oxo-1,3-dioxol-4-yl)methyl 4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiopheneearboxylate

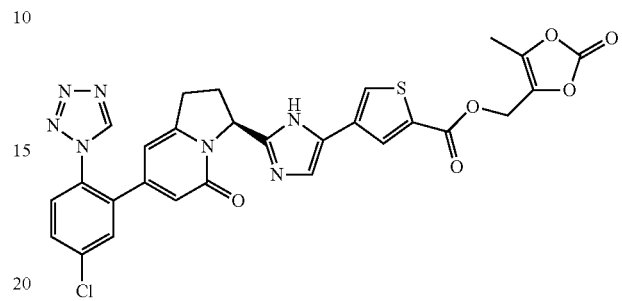

LC/MS $t_R$ 3.68 minutes; MS (ES$^+$) m/z 618 (M+H)$^b$ $^1$H NMR (500 MHz, methanol-d$_4$) δ 9.37 (s, 1 H), 8.10 (d, 1 H), 7.88 (d, 1 H), 7.79-7.65 (m, 3 H), 7.34 (br. s, 1 H), 6.13 (s, 1 H), 6.10 (s, 1 H), 5.77 (dd, 1 H), 5.15 (s, 2 H), 3.54-3.37 (m, 1 H), 3.10 (dd, 1 H), 2.72-2.55 (m, 1 H), 2.54-2.31 (m, 1 H), 2.24 (s, 3 H).

EXAMPLE 368(5)

phenyl 4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylate LC/MS $t_R$ 4.10 minutes; MS (ES$^+$) m/z 582 (M+H)$^b$ $^1$H NMR (500 MHz, methanol-d$_4$) δ 9.36 (s, 1 H), 8.24 (d, 1 H), 7.96 (s, 1 H), 7.76-7.71 (m, 2 H), 7.71-7.65 (m, 1 H), 7.49-7.42 (m, 2 H), 7.39 (br. s, 1 H), 7.32-7.27 (m, 1 H), 7.24 (d, 2 H), 6.14 (s, 1 H), 6.10 (s, 1 H), 5.78 (dd, 1 H), 3.46 (td, 1 H), 3.12 (ddd, 1 H), 2.65 (qd, 1 H), 2.48 (app. br. s, 1 H).

EXAMPLE 368(6)

2,3-dihydro-1H-inden-5-yl 4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylate LC/MS $t_R$ 4.55 minutes; MS (ES$^+$) m/z 622 (M+H)$^b$ $^1$H NMR (500 MHz, DMSO-d$_6$) δ 12.17 (br. s, 1 H), 9.69 (s, 1 H), 8.23 (s, 1 H), 7.98 (s, 1 H), 7.84-7.75 (m, 3 H), 7.58 (br. s, 1 H), 7.28 (d, 1 H), 7.13 (s, 1 H), 7.01 (d, 1 H), 5.98 (s, 1 H), 5.96 (s, 1 H), 5.62 (d, 1 H), 3.45-3.34 (obs. m, 1 H), 3.00 (dd, 1 H), 2.88 (q, 4 H), 2.55-2.44 (obs. m, 1 H), 2.38-2.28 (m, 1 H), 2.06 (quintet, 2 H).

EXAMPLE 368(7)

isobutyl 4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylate

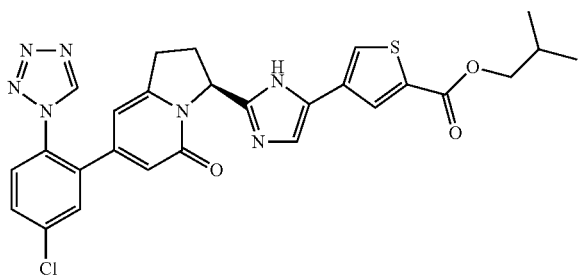 [SMILES: CC(C)COC(=O)c1cc(-c2cnc([C@@H]3CCc4cc(-c5cc(Cl)ccc5-n5cnnn5)cc(=O)n43)[nH]2)cs1]

LC/MS $t_R$ 4.06 minutes; MS (ES$^+$) m/z 562 (M+H)$^b$ $^1$H NMR (500 MHz, methanol-d$_4$) δ 9.36 (s, 1 H), 8.04 (d, 1 H), 7.83 (s, 1 H), 7.77-7.72 (m, 2 H), 7.71-7.65 (m, 1 H), 7.36 (br. s, 1 H), 6.13 (s, 1 H), 6.09 (s, 1 H), 5.76 (dd, 1 H), 4.09 (d, 2 H), 3.49-3.38 (m, 1 H), 3.11 (ddd, 1 H), 2.64 (qd, 1 H), 2.47 (app. br. s, 1 H), 2.06 (td, 1 H), 1.02 (d, 6 H).

EXAMPLE 369(1) and 369(2)

2-(dimethylamino)-2-oxoethyl 4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylate and 4-(2-{(3S)-7-[5-chloro-2-(1H-tetrazol-1-yl)phenyl]-5-oxo-1,2,3,5-tetrahydro-3-indolizinyl}-1H-imidazol-5-yl)-N,N-dimethyl-2-thiophenecarboxamide

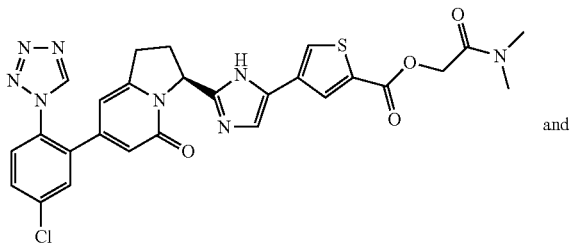

and

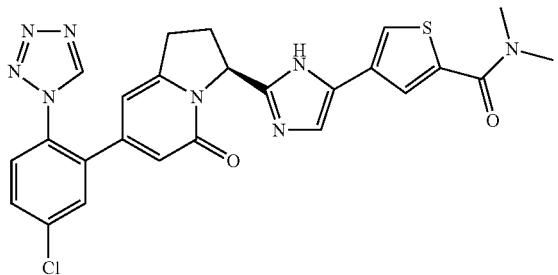

The compound prepared in Example 363 (100 mg) was treated as detailed in Example 367 to give the two title compounds having the following physical properties.

EXAMPLE 369(1)

20 mg

LC/MS $t_R$ 3.15 minutes; MS (ES$^+$) m/z 591 (M+H)$^b$ $^1$H NMR (500 MHz, methanol-d$_4$) δ 9.36 (s, 1 H), 8.13 (d, 1 H), 7.87 (d, 1 H), 7.78-7.71 (m, 2 H), 7.71-7.63 (m, 1 H), 7.32 (s, 1 H), 6.13 (s, 1 H), 6.09 (s, 1 H), 5.77 (dd, 1 H), 5.03 (s, 2 H), 3.52-3.40 (m, 1 H), 3.10 (ddd, 1 H), 3.08 (s, 3 H), 2.97 (s, 3 H), 2.71-2.56 (m, 1 H), 2.51-2.40 (m, 1 H).

EXAMPLE 369(2)

12 mg

LC/MS $t_R$ 2.99 minutes; MS (ES$^+$) m/z 533 (M+H)$^b$ $^1$H NMR (500 MHz, methanol-d$_4$) δ 9.37 (s, 1 H), 7.76-7.72 (m, 4 H), 7.70 (d, 1 H), 7.31 (s, 1 H), 6.13 (s, 1 H), 6.10 (s, 1 H), 5.77 (dd, 1 H), 3.45 (td, 1 H), 3.25 (very br. s, 6H), 3.13 (dd, 1 H), 2.71-2.59 (m, 1 H), 2.51-2.39 (m, 1 H).

EXAMPLE 370 methyl 4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylate

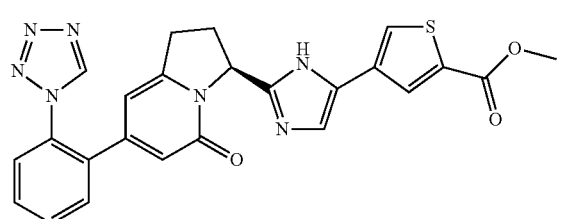

To a solution of the compound prepared in Example 363 (100 mg) in a 4:1 mixture of dichloromethane and methanol (2.5 mL) was added a 2 M solution of (trimethylsilyl)diazomethane in diethyl ether (296 µL) and the mixture stirred at room temperature for 16 hours. The reaction mixture was concentrated and the residue purified by column chromatography (50-100% ethyl acetate in heptanes, then 0-10% methanol in ethyl acetate) to give the title product having the following physical properties (72 mg).

LC/MS $t_R$ 3.46 minutes; MS (ES$^+$) m/z 520 (M+H)$^b$ $^1$H NMR (500 MHz, methanol-d$_4$) δ 9.36 (s, 1 H), 8.05 (d, 1 H), 7.83 (d, 1 H), 7.77-7.71 (m, 2 H), 7.72-7.65 (m, 1 H), 7.32 (br. s, 1 H), 6.14 (s, 1 H), 6.09 (s, 1 H), 5.77 (dd, 1 H), 3.89 (s, 3 H), 3.52-3.39 (m, 1 H), 3.11 (ddd, 1 H), 2.64 (qd, 1 H), 2.47 (app. br. s, 1 H).

EXAMPLE 371

(3S)-7-[5-chloro-2-(1H-tetrazol-1-yl)phenyl]-3-{5-[5-(hydroxymethyl)-3-thienyl]-1H-imidazol-2-yl}-2,3-dihydro-5(1H)-indolizinone

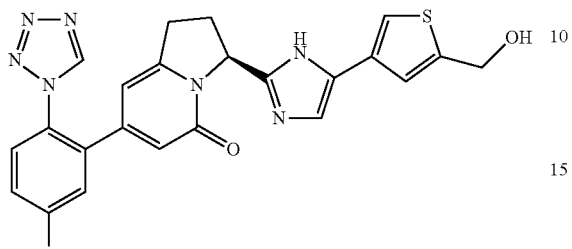

To a cooled (0° C.) tetrahydrofuran (6 mL) solution of the compound prepared in Example 370 (66 mg) was added a 1.2 M solution of diisobutylaluminium hydride in toluene (0.13 mL). The mixture was allowed to warm to room temperature and stirred 1.5 hours. The reaction mixture was cooled to 0° C., a 1.2 M solution of diisobutylaluminium hydride in toluene (0.13 mL) added then the mixture warmed to room temperature and stirred 16 hours. To the reaction mixture, a 10% aqueous solution of potassium sodium tartrate was added (10 mL) followed by extraction into ethyl acetate. The combined organic layers were washed with brine, dried and concentrated. The residue was purified by column chromatography (0-10% methanol in dichloromethane) to give the title product having the following physical properties (36 mg).

LC/MS $t_R$ 2.89 minutes; MS (ES+) m/z 492 (M+H)[b]

$^1$H NMR (500 MHz, methanol-$d_4$) δ 9.35 (s, 1 H), 7.78-7.71 (m, 2 H), 7.70-7.64 (m, 1 H), 7.44 (s, 1 H), 7.24 (s, 1 H), 7.17 (br. s, 1 H), 6.12 (s, 1 H), 6.09 (s, 1 H), 5.76 (dd, 1 H), 4.73 (s, 2 H), 3.49-3.37 (m, 1 H), 3.10 (ddd, 1 H), 2.63 (qd, 1 H), 2.44 (app. br. s, 1 H).

EXAMPLE 372

4-{2-[(3S)-7-[5-chloro-2-(1H-1,2,3,4-tetrazol-1-yl)phenyl]-5-oxo-1,2,3,5-tetrahydroindolizin-3-yl]-1-[(prop-2-en-1-yloxy)carbonyl]-1H-imidazol-5-yl}thiophene-2-carboxylic acid To an acetonitrile (8 mL) suspension of the compound prepared in Example 363 (400 mg) was added N,N-diisopropylethylamine (0.34 mL). The solution was cooled to 0° C. and a solution of allyl chloroformate (84 µL) in acetonitrile (0.5 mL) added. The mixture was warmed to room temperature and stirred 16 hours before diluting with ethyl acetate (20 mL) and water (10 mL). The layers were separated and 1 M hydrochloric acid was added to the aqueous layer until pH 2 was attained. The aqueous layer was washed with dichloromethane, then a 9:1 mixture of dichloromethane and propan-2-ol. The combined dichloromethane layers were dried and concentrated and the residue triturated with ethyl acetate. Isolation of the solids by filtration gave the title product having the following physical properties (335 mg).

LC/MS $t_R$ 1.97 minutes; MS (ES+) m/z 590 (M+H)[a].

EXAMPLE 373

[(2,2-dimethylpropanoyl)oxy]methyl 4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylate

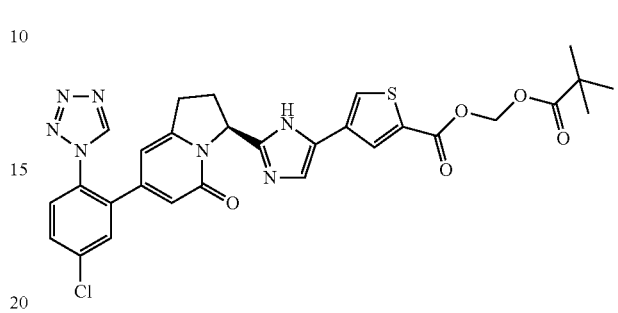

To an N,N-dimethylformamide (4 mL) solution of the compound prepared in Example 372 (330 mg) was added potassium carbonate (116 mg) and the suspension stirred at room temperature for 10 minutes. A solution of chloromethyl pivalate (89 µL) in N,N-dimethylformamide (1 mL) was added and the mixture stirred at room temperature for 16 hours. Water (10 mL) was added followed by extraction into ethyl acetate. The combined organic layers were washed with brine, dried and concentrated. The residue was purified by column chromatography (20-100% ethyl acetate in heptanes, then 0-10% methanol in ethyl acetate) to give the title product having the following physical properties (131 mg).

LC/MS $t_R$ 4.17 minutes; MS (ES+) m/z 620 (M+H)[b]

$^1$H NMR (500 MHz, methanol-$d_4$) δ 9.36 (s, 1 H), 8.11 (d, 1 H), 7.90 (d, 1 H), 7.79-7.64 (m, 3 H), 7.36 (br. s, 1 H), 6.12 (s, 1 H), 6.09 (s, 1 H), 5.95 (s, 2 H), 5.76 (dd, 1 H), 3.54-3.35 (m, 1 H), 3.19-3.01 (m, 1 H), 2.78-2.53 (m, 1 H), 2.45 (app. br. s, 1 H), 1.21 (s, 9 H).

EXAMPLE 374

2-methyl-2-propanyl 5-(bromoacetyl)-2-thiophenecarboxylate

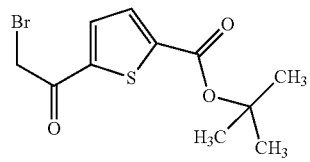 [SMILES: CC(C)(C)OC(=O)c1ccc(C(=O)CBr)s1]

tert-butyl 5-acetylthiophene-2-carboxylate (4.5 g) was treated as detailed in Example 361 to give the title compound having the following physical properties (3.9 g).

TLC Rf 0.25 (10% ethyl acetate in hexane)

EXAMPLE 375

7-[5-methyl-2-(1H-tetrazol-1-yl)phenyl]-5-oxo-1,2,3,5-tetrahydro-3-indolizinecarboxylic acid

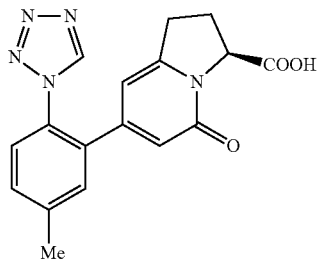 [SMILES: Cc1ccc(-n2cnnn2)c(-c2cc3n(c(=O)c2)[C@H](C(=O)O)CC3)c1]

The same operation as in Example 7→Example 8→Example 9 was conducted from the compound prepared in Example 6 to give the title compound having the following physical properties. (Note: in the step corresponding to Example 7 in the operation, 2-amino-5-methylphenylboronic acid pinacol ester and 1,1'-bis(diphenylphosphino)ferrocene palladium (II) dichloride dichloromethane complex were used).
TLC Rf 0.18 (25% methanol in dichloromethane).

EXAMPLE 376

5-(2-{7-[5-methyl-2-(1H-tetrazol-1-yl)phenyl]-5-oxo-1,2,3,5-tetrahydro-3-indolizinyl}-1H-imidazol-5-yl)-2-thiophenecarboxylic acid hydrochloride The same operation as in Example 51→Example 52→Example 363 was conducted from the compound prepared in Example 375 to give the title compound having the following physical properties. (Note: in the step corresponding to Example 51 in the operation, the compound prepared in Example 374 was used).
LC/MS $t_R$ 0.67 minutes; MS (ESI) m/z 484 (M-H)$^-$
$^1$H NMR (300 MHz, DMSO-d$_6$) δ 9.65 (s, 1 H), 7.88 (m, 1 H), 7.69 (m, 1 H), 7.60 (d, 1 H), 7.55-7.42 (m, 3 H), 5.98 (s, 1 H), 5.89 (s, 1 H), 5.71 (m, 1 H), 3.30 (m, 1 H), 3.05 (m, 1 H), 2.50-2.02 (m, 2 H), 2.46 (s, 3 H).

EXAMPLE 377

5-(4-chloro-2-{7-[5-methyl-2-(1H-tetrazol-1-yl)phenyl]-5-oxo-1,2,3,5-tetrahydro-3-indolizinyl}-1H-imidazol-5-yl)-2-thiophenecarboxylic acid hydrochloride

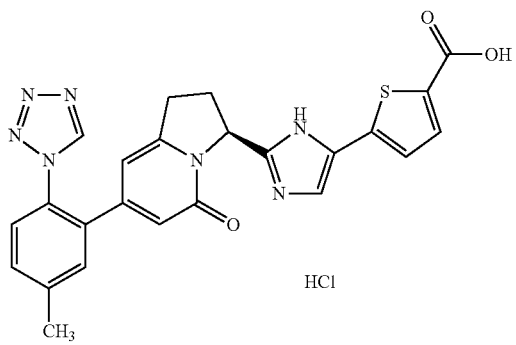 [SMILES: Cc1ccc(-n2cnnn2)c(-c2cc3n(c(=O)c2)[C@H](c2ncc(-c4ccc(C(=O)O)s4)[nH]2)CC3)c1 ; Cl]

The same operation as in Example 51→Example 52→Example 338→Example 363 was conducted from the compound prepared in Example 375 to give the title compound having the following physical properties. (Note: in the step corresponding to Example 51 in the operation, the compound prepared in Example 374 was used).
LC/MS $t_R$ 0.79 minutes; MS (ESI$^-$) m/z 518 (M-H)$^-$
$^1$H NMR (300 MHz, DMSO-d$_6$) δ 9.66 (s, 1 H), 7.72 (d, 1 H), 7.58 (d, 1 H), 7.56-7.42 (m, 3 H), 5.94 (s, 1 H), 5.85 (s, 1 H), 5.55 (d, 1 H), 3.25 (m, 1 H), 3.00 (m, 1 H), 2.60-2.10 (m, 2 H), 2.46 (s, 3 H).

EXAMPLE 378

2-methyl-2-propanyl 5-bromo-1H-indole-3-carboxylate

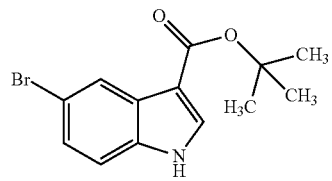 [SMILES: CC(C)(C)OC(=O)c1c[nH]c2ccc(Br)cc12]

A suspension of 5-bromo-1H-indole-3-carboxylic acid (500 mg) in N,N-dimethylformamide di-tert-butyl acetal (2.5 mL) was stirred at 100° C. for 17 hours. The reaction mixture was cooled to room temperature. Water was added followed by extraction with ethyl acetate. The combined organic layers were washed with brine, dried and concentrated. The residue was purified by column chromatography (5-40% ethyl acetate in hexane) to give the title product having the following physical properties (173 mg).
LC/MS $t_R$ 1.07 minutes; MS (ESI$^+$) m/z 297 (M+H)$^+$.

EXAMPLE 379 bis(2-methyl-2-propanyl) 5-bromo-1H-indole-1,3-dicarboxylate

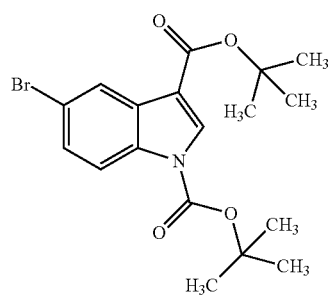 [SMILES: CC(C)(C)OC(=O)c1cn(C(=O)OC(C)(C)C)c2ccc(Br)cc12]

To a dichloromethane (2 mL) solution of compound prepared in Example 378 were added di-tert-butyl dicarbonate (153 mg), triethylamine (0.12 mL) and 4-dimethylaminopyridine (7.1 mg) and the mixture was stirred at room temperature for 30 minutes. The reaction mixture was concentrated and the residue was purified by column chromatography (5-20% ethyl acetate in hexane) to give the title product having the following physical properties (204 mg).
TLC Rf 0.70 (25% ethyl acetate in hexane).

EXAMPLE 380

5-(2-{(3S)-7-[5-chloro-2-(1H-tetrazol-1-yl)phenyl]-5-oxo-1,2,3,5-tetrahydro-3-indolizinyl}-1H-imidazol-5-yl)-1H-indole-3-carboxylic acid hydrochloride

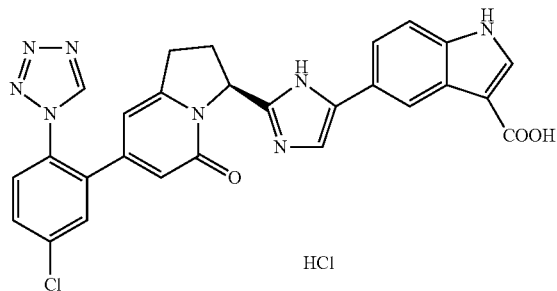 [SMILES: O=C(O)c1c[nH]c2ccc(-c3cnc([C@@H]4CCc5cc(-c6cc(Cl)ccc6-n6cnnn6)cc(=O)n54)[nH]3)cc12 ; Cl]

The same operation as in Example 139→Example 361→Example 51→Example 52→Example 363 was conducted from the compound prepared in Example 379 to give the title compound having the following physical properties.

LC/MS $t_R$ 0.61 minutes; MS (ES+) m/z 539 (M+H)+

$^1$H NMR (300 MHz, DMSO-d$_6$) δ 12.05 (s, 1 H), 9.69 (s, 1 H), 8.39 (s, 1 H), 8.09 (d, 1 H), 7.98 (d, 1 H), 7.86-7.82 (m, 2 H), 7.71 (s, 1 H), 7.61-7.58 (m, 2 H), 6.09-6.03 (m, 2 H), 5.87-5.76 (m, 1 H), 3.50-3.10 (m, 2 H), 2.65-2.30 (m, 2 H).

EXAMPLE 381

2-methyl-2-propanyl 5-bromo-1-(2-methyl-2-propanyl)-1H-indazole-3-carboxylate

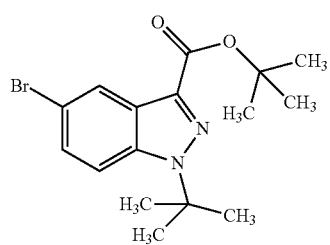 [SMILES: CC(C)(C)OC(=O)c1nn(C(C)(C)C)c2ccc(Br)cc12]

5-bromo-1H-indazole-3-carboxylic acid (395 mg) was treated as detailed in Example 378 to give the title compound having the following physical properties (484 mg).

TLC Rf 0.91 (33% Ethyl acetate in hexane).

EXAMPLE 382

5-(2-{(3S)-7-[5-chloro-2-(1H-tetrazol-1-yl)phenyl]-5-oxo-1,2,3,5-tetrahydro-3-indolizinyl}-1H-imidazol-5-yl)-1H-indazole-3-carboxylic acid

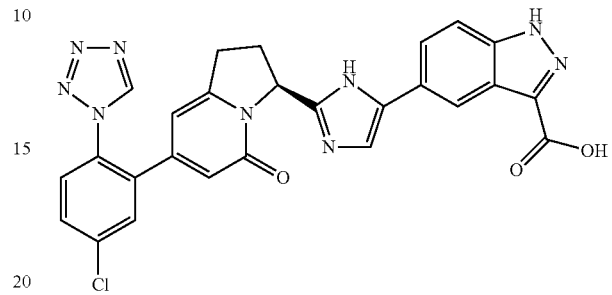

The same operation as in Example 139→Example 361→Example 51→Example 52→Example 363 was conducted from the compound prepared in Example 381 to give the title compound having the following physical properties.

LC/MS $t_R$ 0.59 minutes; MS (EKE) m/z 540 (M+H)+

$^1$H NMR (300 MHz, DMSO-d$_6$) δ 9.68 (s, 1 H), 8.18 (s, 1 H), 7.82-7.62 (m, 4 H), 7.59-7.40 (m, 2 H), 5.98 (s, 1 H), 5.92 (s, 1 H), 5.62 (m, 1 H), 3.52-2.90 (m, 2 H), 2.60-2.30 (m, 2 H).

EXAMPLE 383(1), (2) and (3)

8-chloro-7-[5-chloro-2-(1H-tetrazol-1-yl)phenyl]-5-oxo-1,2,3,5-tetrahydro-3-indolizinecarboxylic acid, 6-chloro-7-[5-chloro-2-(1H-tetrazol-1-yl)phenyl]-5-oxo-1,2,3,5-tetrahydro-3-indolizinecarboxylic acid and 6,8-dichloro-7-[5-chloro-2-(1H-tetrazol-1-yl)phenyl]-5-oxo-1,2,3,5-tetrahydro-3-indolizinecarboxylic acid

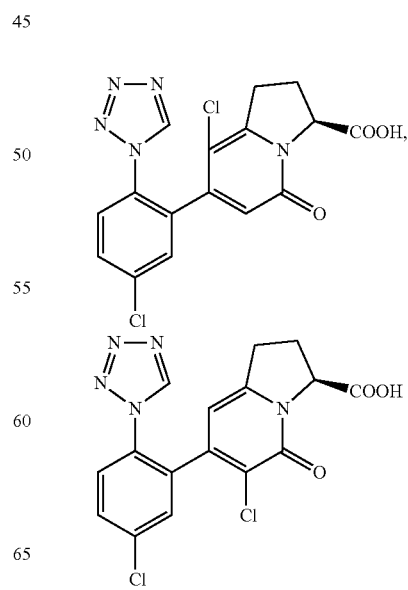

and

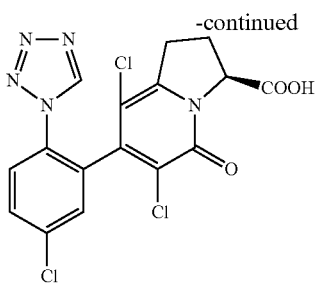

To a tetrahydrofuran (5 mL) solution of the compound prepared in Example 9 (500 mg) was added 1,3-dichloro-5,5-dimethyl imidazolidine-2,4-dione (206 mg) and the reaction mixture stirred at 40° C. for 0.5 hours. The reaction mixture was concentrated. The residue obtained was purified by high performance liquid chromatography [5 to 95% mobile phase B (0.1% trifluoroacetic acid in acetonitrile) in mobile phase A (0.1% aqueous trifluoroacetic acid)] to give the title compounds having the following physical properties.

EXAMPLE 383(1)

143 mg

LC/MS $t_R$ 0.71 minutes; MS (ES$^+$) m/z 392 and 394 (M+14)$^f$.

EXAMPLE 383(2)

121 mg

LC/MS $t_R$ 0.69 minutes; MS (ES$^+$) m/z 392 and 394 (M+H)$^f$.

EXAMPLE 383(3)

75 mg

LC/MS $t_R$ 0.73 minutes; MS (ES$^+$) m/z 426, 428 and 430 (M+H)$^f$.

Example 384

2-methyl-2-propanyl 4-(bromoacetyl)-2-pyridinecarboxylate

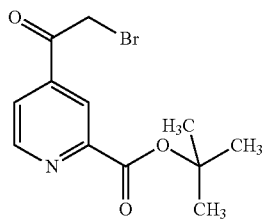 [SMILES: CC(C)(C)OC(=O)c1cc(C(=O)CBr)ccn1]

The same operation as in Example 378→Example 139→Example 361 was conducted from 4-bromo-2-pyridinecarboxylic acid to give the title compound having the following physical properties.

$^1$H NMR (300 MHz, CDCl$_3$) δ 8.99 (d, 1 H), 8.50-8.46 (m, 1 H), 7.91 (dd, 1 H), 4.47 (s, 2 H), 1.68 (s, 9 H).

EXAMPLE 385

4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-pyridinecarboxylic acid trifluoroacetate

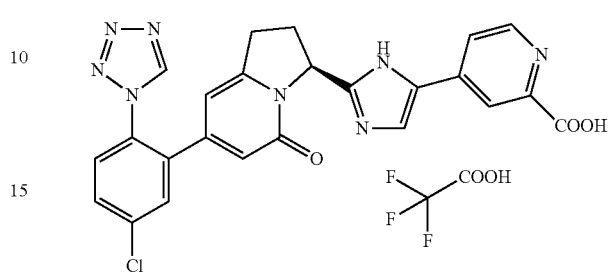

The same operation as in Example 51→Example 52→Example 363 was conducted from the compound prepared in Example 384 to give the title compound having the following physical properties. (Note: high performance liquid chromatography [5 to 100% mobile phase B (0.1% trifluoroacetic acid in acetonitrile) in mobile phase A (0.1% aqueous trifluoroacetic acid)] was used to give the title product as the trifluoroacetic acid salt).

LC/MS $t_R$ 0.58 minutes; MS (ES$^+$) m/z 501 (M+H)$^f$ $^1$H NMR (300 MHz, DMSO-d$_6$) δ 9.68 (s, 1 H), 8.70 (d, 1 H), 8.48 (s, 1 H), 8.36 (s, 1 H), 8.12 (d, 1 H), 7.90-7.79 (m, 2 H), 7.74 (s, 1 H), 6.01 (s, 1 H), 5.97 (s, 1 H), 5.75-5.67 (m, 1 H), 3.40-3.23 (m, 1 H), 3.14-2.97 (m, 1 H), 2.70-2.25 (m, 2 H).

EXAMPLE 386

4-(2-{(3S)-8-chloro-7-[5-chloro-2-(1H-tetrazol-1-yl)phenyl]-5-oxo-1,2,3,5-tetrahydro-3-indolizinyl}-1H-imidazol-5-yl)-2-pyridinecarboxylic acid hydrochloride

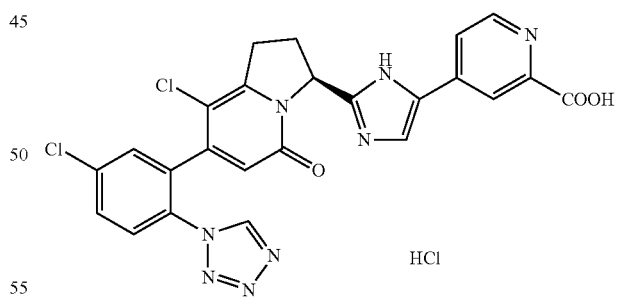

The same operation as in Example 51→Example 52→Example 363 was conducted from the compound prepared in Example 384 to give the title compound having the following physical properties. (Note: in the step corresponding to Example 51 in the operation, the compound prepared in Example 383(1) was used).

LC/MS $t_R$ 0.64 minutes; MS (ES$^+$) m/z 535 and 537 (M+H)$^f$ $^1$H NMR (300 MHz, DMSO-d$_6$) δ 9.79-9.70 (m, 1 H), 8.34 (d, 1 H), 8.59-8.47 (m, 1 H), 8.43 (s, 1 H), 8.27-8.17 (m, 1 H), 7.95-7.84 (m, 2 H), 7.74-7.67 (m, 1 H), 6.40-6.31 (m, 1 H), 5.94-5.77 (m, 1 H), 3.46-3.25 (m, 1 H), 3.24-3.10 (m, 1 H), 2.77-2.32 (m, 2 H).

EXAMPLE 387

5-(2-{(3S)-8-chloro-7-[5-chloro-2-(1H-tetrazol-1-yl)phenyl]-5-oxo-1,2,3,5-tetrahydro-3-indolizinyl}-1H-imidazol-5-yl)-2-thiophenecarboxylic acid hydrochloride

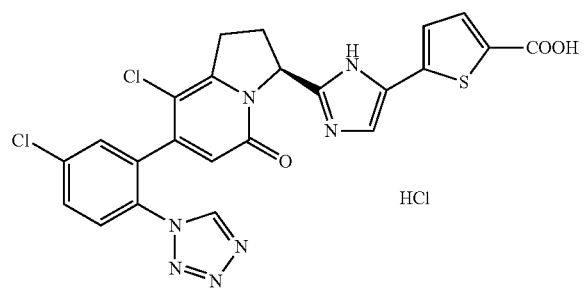 [SMILES: O=C(O)c1ccc(-c2cnc([C@@H]3CCc4c(Cl)c(-c5cc(Cl)ccc5-n5cnnn5)cc(=O)n43)[nH]2)s1 ; Cl]

The same operation as in Example 51→Example 52→Example 363 was conducted from the compound prepared in Example 374 to give the title compound having the following physical properties. (Note: in the step corresponding to Example 51 in the operation, the compound prepared in Example 383(1) was used).

LC/MS $t_R$ 0.75 minutes; MS (ES+) m/z 540 and 542 (M+H)+

$^1$H NMR (300 MHz, DMSO-$d_6$) δ 9.77-9.65 (m, 1 H), 7.89-7.84 (m, 2 H), 7.75-7.60 (m, 3 H), 7.45-7.20 (m, 1 H), 6.36-6.30 (m, 1 H), 5.80-5.69 (m, 1 H), 3.50-3.25 (m, 1 H), 3.22-3.05 (m, 1 H), 2.75-2.20 (m, 2 H).

EXAMPLE 388

5-(4-chloro-2-{(3S)-8-chloro-7-[5-chloro-2-(1H-tetrazol-1-yl)phenyl]-5-oxo-1,2,3,5-tetrahydro-3-indolizinyl}-1H-imidazol-5-yl)-2-thiophenecarboxylic acid trifluoroacetate The same operation as in Example 51→Example 52→Example 338→Example 363 was conducted from the compound prepared in Example 374 to give the title compound having the following physical properties. (Note: in the step corresponding to Example 51 in the operation, the compound prepared in Example 383(1) was used, high performance liquid chromatography [5 to 100% mobile phase B (0.1% trifluoroacetic acid in acetonitrile) in mobile phase A (0.1% aqueous trifluoroacetic acid)] was used to give the title product as the trifluoroacetic acid salt).

LC/MS $t_R$ 0.86 minutes; MS (ES+) m/z 574, 576 and 578 (M+H)+

$^1$H NMR (300 MHz, DMSO-$d_6$) δ 9.75-9.69 (m, 1 H), 7.91-7.79 (m, 2 H), 7.77-7.66 (m, 2 H), 7.46 (d, 1 H), 6.34-6.28 (m, 1 H), 5.72-5.59 (m, 1 H), 3.40-3.22 (m, 1 H), 3.20-3.04 (m, 1 H), 2.75-2.15 (m, 2 H).

EXAMPLE 389

5-(4-chloro-2-{(3S)-6-chloro-7-[5-chloro-2-(1H-tetrazol-1-yl)phenyl]-5-oxo-1,2,3,5-tetrahydro-3-indolizinyl}-1H-imidazol-5-yl)-2-thiophenecarboxylic acid trifluoroacetate The same operation as in Example 51→Example 52→Example 338→Example 363 was conducted from the compound prepared in Example 374 to give the title compound having the following physical properties. (Note: in the step corresponding to Example 51 in the operation, the compound prepared in Example 383(2) was used, high performance liquid chromatography [5 to 100% mobile phase B (0.1% trifluoroacetic acid in acetonitrile) in mobile phase A (0.1% aqueous trifluoroacetic acid)] was used to give the title product as the trifluoroacetic acid salt).

LC/MS $t_R$ 0.84 minutes; MS (ES+) m/z 574, 576 and 578 (M+H)+

$^1$H NMR (300 MHz, DMSO-$d_6$) δ 9.70 (s, 1 H), 7.91-7.81 (m, 2 H), 7.77-7.65 (m, 2 H), 7.47 (d, 1 H), 6.35 (s, 1 H), 5.71-5.57 (m, 1 H), 3.45-3.25 (m, 1 H), 3.20-3.03 (m, 1 H), 2.70-2.15 (m, 2 H).

EXAMPLE 390

5-(2-{(3S)-6,8-dichloro-7-[5-chloro-2-(1H-tetrazol-1-yl)phenyl]-5-oxo-1,2,3,5-tetrahydro-3-indolizinyl}-1H-imidazol-5-yl)-2-thiophenecarboxylic acid trifluoroacetate The same operation as in Example 51→Example 52→Example 363 was conducted from the compound prepared in Example 374 to give the title compound having the following physical properties. (Note: in the step corresponding to Example 51 in the operation, the compound prepared in Example 383(3) was used, high performance liquid chromatography [5 to 100% mobile phase B (0.1% trifluoroacetic acid in acetonitrile) in mobile phase A (0.1% aqueous trifluoroacetic acid)] was used to give the title product as the trifluoroacetic acid salt).

LC/MS $t_R$ 0.78 minutes; MS (ES+) m/z 574, 576 and 578 (M+H)+

$^1$H NMR (300 MHz, DMSO-$d_6$) δ 9.84 (s, 1 H), 7.99-7.88 (m, 2 H), 7.81 (d, 1 H), 7.69-7.61 (m, 2 H), 7.30 (d, 1 H), 5.88-5.82 (m, 1 H), 3.53-3.35 (m, 1 H), 3.30-3.16 (m, 1 H), 2.75-2.30 (m, 2 H).

EXAMPLE 391

4-(2-{(3S)-8-chloro-7-[5-chloro-2-(1H-tetrazol-1-yl)phenyl]-5-oxo-1,2,3,5-tetrahydro-3-indolizinyl}-1H-imidazol-5-yl)-2-thiophenecarboxylic acid trifluoroacetate

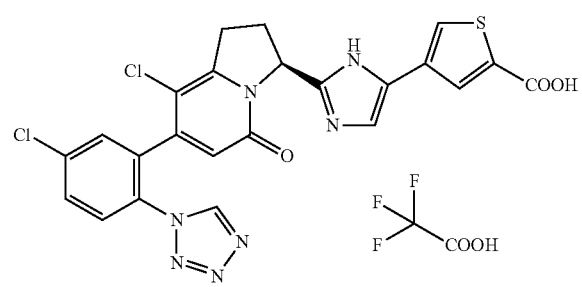 [SMILES: O=C(O)c1cc(-c2cnc([C@@H]3CCc4c(Cl)c(-c5cc(Cl)ccc5-n5cnnn5)cc(=O)n43)[nH]2)cs1 ; O=C(O)C(F)(F)F]

The same operation as in Example 51→Example 52→Example 363 was conducted from the compound prepared in Example 361 to give the title compound having the following physical properties. (Note: in the step corresponding to Example 51 in the operation, the compound prepared in Example 381(1) was used, high performance liquid chromatography [5 to 100% mobile phase B (0.1% trifluoroacetic acid in acetonitrile) in mobile phase A (0.1% aqueous trifluoroacetic acid)] was used to give the title product as the trifluoroacetic acid salt).

LC/MS $t_R$ 0.68 minutes; MS (ES$^+$) m/z 540 and 542 (M+H)$^f$ $^1$H NMR (300 MHz, DMSO-d$_6$) δ 9.77-9.67 (m, 1 H), 8.22-8.11 (m, 2 H), 8.00-7.85 (m, 3 H), 7.98-7.86 (m, 1 H), 6.37 (s, 1 H), 5.94-5.77 (m, 1 H), 3.45-3.10 (m, 2 H), 2.80-2.30 (m, 2 H).

EXAMPLE 392

4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-thiophenecarboxylic acid hydrochloride

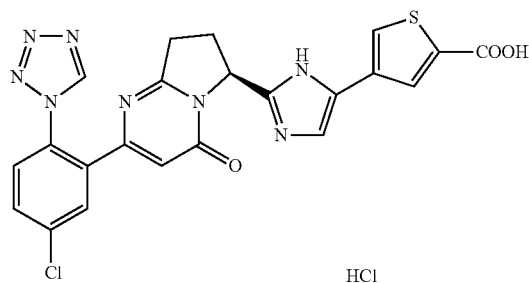 [SMILES: O=C(O)c1cc(-c2cnc([C@@H]3CCc4nc(-c5cc(Cl)ccc5-n5cnnn5)cc(=O)n43)[nH]2)cs1 ; Cl]

The same operation as in Example 51→Example 52→Example 363 was conducted from the compound prepared in Example 361 to give the title compound having the following physical properties. (Note: in the step corresponding to Example 51 in the operation, the compound prepared in Example 336 was used).

LC/MS $t_R$ 0.60 minutes; MS (ES$^+$) m/z 507 (M+H)$^f$ $^1$H NMR (300 MHz, DMSO-d$_6$) δ 9.71 (s, 1 H), 8.20 (s, 1 H), 8.13 (s, 1 H), 7.99 (s, 1 H), 7.93 (d, 1 H), 7.90-7.80 (m, 2 H), 6.40 (s, 1 H), 5.83-5.74 (m, 1 H), 3.21-3.04 (m, 1 H), 2.96-2.81 (m, 1 H), 2.75-2.20 (m, 2 H).

EXAMPLE 393(1) and 393(2)

8-bromo-7-[5-chloro-2-(1H-tetrazol-1-yl)phenyl]-5-oxo-1,2,3,5-tetrahydro-3-indolizinecarboxylic acid and 6-bromo-7-[5-chloro-2-(1H-tetrazol-1-yl)phenyl]-5-oxo-1,2,3,5-tetrahydro-3-indolizinecarboxylic acid

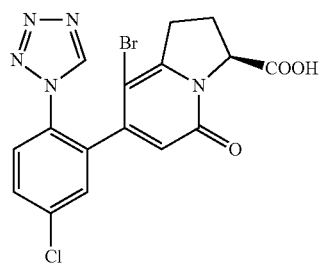

and

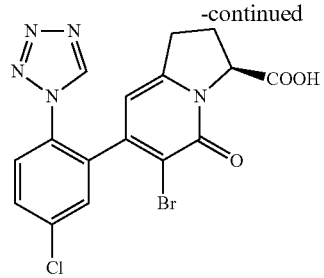

To a cooled (0° C.) tetrahydrofuran (5 mL) solution of the compound prepared in Example 9 (300 mg) was added N-bromosuccinimide (117 mg) and the reaction mixture stirred at 0° C. for 0.5 hours. To the reaction mixture, sodium thiosulfate was added and the mixture stirred for 0.5 hours before concentration. The residue obtained was purified by high performance liquid chromatography [5 to 100% mobile phase B (0.1% trifluoroacetic acid in acetonitrile) in mobile phase A (0.1% aqueous trifluoroacetic acid)] to give the title compounds having the following physical properties.

EXAMPLE 393(1)

145 mg

LC/MS $t_R$ 0.93 minutes; MS (ES$^+$) m/z 436 and 438 (M+H)$^f$.

EXAMPLE 393(2)

100 mg

LC/MS $t_R$ 0.88 minutes; MS (ES$^+$) m/z 436 and 438 (M+H)$^f$.

EXAMPLE 394

4-(2-{(3S)-8-bromo-7-[5-chloro-2-(1H-tetrazol-1-yl)phenyl]-5-oxo-1,2,3,5-tetrahydro-3-indolizinyl}-1H-imidazol-5-yl)-2-thiophenecarboxylic acid hydrochloride

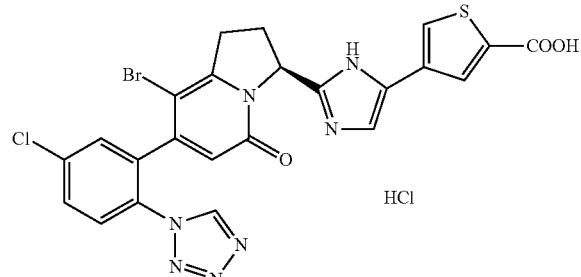

The same operation as in Example 51→Example 52→Example 363 was conducted from the compound prepared in Example 361 to give the title compound having the following physical properties. (Note: in the step corresponding to Example 51 in the operation, the compound prepared in Example 393(1) was used)

LC/MS $t_R$ 0.69 minutes; MS (ES$^+$) m/z 584 and 586 (M+H)$^f$

¹H NMR (300 MHz, DMSO-d₆) δ 9.73-9.64 (m, 1 H), 8.25-8.08 (m, 2 H), 7.96-7.82 (m, 3 H), 7.65-7.56 (m, 1 H), 6.37-6.33 (m, 1 H), 5.96-5.81 (m, 1 H), 3.46-3.25 (m, 1 H), 3.23-3.08 (m, 1 H), 2.65-2.30 (m, 2 H).

EXAMPLE 395

3-[5-(3-bromophenyl)-1H-imidazol-2-yl]-7-[5-chloro-2-(1H-tetrazol-1-yl)phenyl]-2,3-dihydro-5(1H)-indolizinone

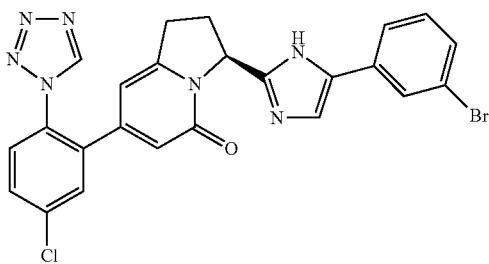 [SMILES: O=c1cc(-c2cc(Cl)ccc2-n2cnnn2)cc2n1[C@H](c1ncc(-c3cccc(Br)c3)[nH]1)CC2]

The same operation as in Example 51→Example 52 was conducted from 2-bromo-1-(3-bromophenyl)ethanone to give the title compound having the following physical properties.
LC/MS t_R 0.85 minutes; MS (ES⁺) m/z 534 and 536 (M+H)⁺.

EXAMPLE 396

2-methyl-2-propanyl(2E)-3-[3-(2-{7-[5-chloro-2-(1H-tetrazol-1-yl)phenyl]-5-oxo-1,2,3,5-tetrahydro-3-indolizinyl}-1H-imidazol-5-yl)phenyl]acrylate To a 1,4-dioxane (1 mL) solution of the compound prepared in Example 395 (30 mg) was sequentially added N,N-dicyclohexylmethylamine (18 µL) and tert-butyl acrylate (11 mg). The mixture was degassed with argon then bis(tri-tert-butylphosphine) palladium (1.4 mg) added and the reaction mixture irradiated under microwave conditions (100 W) at 110° C. for 10 minutes before concentration. The residue obtained was purified by high performance liquid chromatography [5 to 100% mobile phase B (0.1% trifluoroacetic acid in acetonitrile) in mobile phase A (0.1% aqueous trifluoroacetic acid)] to give the title compound having the following physical properties (15 mg).
LC/MS t_R 0.92 minutes; MS (ES⁺) m/z 582 (M+H)⁺.

EXAMPLE 397

(2E)-3-[3-(2-{7-[5-chloro-2-(1H-tetrazol-1-yl)phenyl]-5-oxo-1,2,3,5-tetrahydro-3-indolizinyl}-1H-imidazol-5-yl)phenyl]acrylic acid hydrochloride

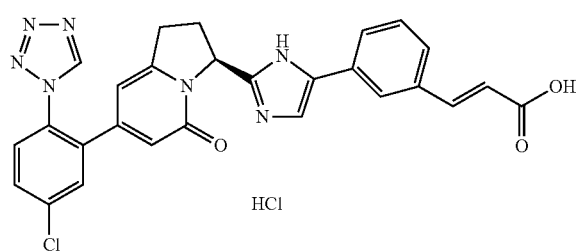 [SMILES: O=C(O)/C=C/c1cccc(-c2cnc([C@@H]3CCc4cc(-c5cc(Cl)ccc5-n5cnnn5)cc(=O)n43)[nH]2)c1 ; Cl]

The compound prepared in Example 396 (22 mg) was treated as detailed in Example 363 to give the title compound having the following physical properties (20 mg).
LC/MS t_R 0.66 minutes; MS (ES⁺) m/z 526 (M+H)⁺
¹H NMR (300 MHz, DMSO-d₆) δ 9.69 (s, 1 H), 8.22-8.16 (m, 1 H), 7.90-7.79 (m, 3 H), 7.80-7.50 (m, 5 H), 6.67 (d, 1 H), 6.05 (s, 1 H), 6.02 (s, 1 H), 5.86-5.77 (m, 1 H), 3.40-3.20 (m, 1 H), 3.19-3.02 (m, 1 H), 2.80-2.20 (m, 2 H).

EXAMPLE 398

(2E)-3-[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]acrylic acid trifluoroacetate

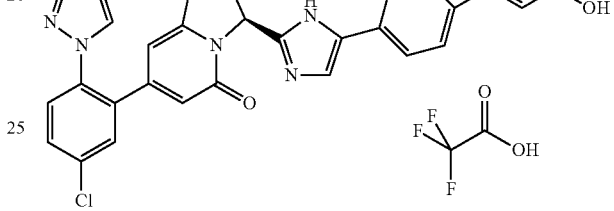

The same operation as in Example 51→Example 52→Example 396→Example 363 was conducted from 2-bromo-1-(4-bromophenyl)ethanone to give the title compound having the following physical properties. (Note: high performance liquid chromatography [5 to 100% mobile phase B (0.1% trifluoroacetic acid in acetonitrile) in mobile phase A (0.1% aqueous trifluoroacetic acid)] was used to give the title product as the trifluoroacetic acid salt).
LC/MS t_R 0.67 minutes; MS (ES⁺) m/z 526 (M+H)⁺
¹H NMR (300 MHz, DMSO-d₆) δ 9.68 (s, 1 H), 8.15-7.70 (m, 8 H), 7.58 (d, 1 H), 6.57 (d, 1 H), 6.03 (s, 1 H), 6.00 (s, 1 H), 5.80-5.75 (m, 1 H), 3.50-3.20 (m, 1 H), 3.15-3.00 (m, 1 H), 2.70-2.20 (m, 2 H).

EXAMPLE 399

5-(2-{(3S)-7-[5-chloro-2-(1H-tetrazol-1-yl)phenyl]-5-oxo-1,2,3,5-tetrahydro-3-indolizinyl}-4-fluoro-1H-imidazol-5-yl)-2-thiophenecarboxylic acid trifluoroacetate

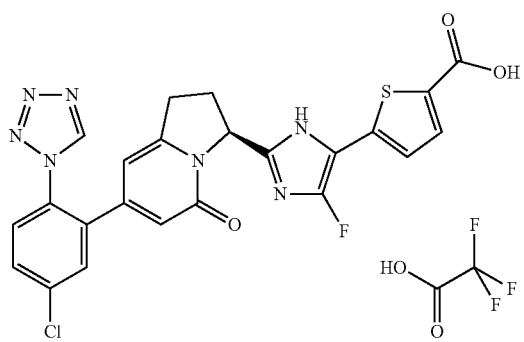 [SMILES: O=C(O)c1ccc(-c2[nH]c([C@@H]3CCc4cc(-c5cc(Cl)ccc5-n5cnnn5)cc(=O)n43)nc2F)s1 ; O=C(O)C(F)(F)F]

The same operation as in Example 51→Example 52→Example 364→Example 363 was conducted from the compound prepared in Example 374 to give the title compound having the following physical properties. (Note: high performance liquid chromatography [5 to 100% mobile phase B (0.1% trifluoroacetic acid in acetonitrile) in mobile phase A (0.1% aqueous trifluoroacetic acid)] was used to give the title product as the trifluoroacetic acid salt).

LC/MS $A_z$ 0.80 minutes; MS (EST") m/z 522 (M-H)$^f$ $^1$H NMR (300 MHz, methanol-$d_4$) δ 9.34 (s, 1 H), 7.80-7.62 (m, 4 H), 7.19 (d, 1 H), 6.11 (s, 1 H), 6.07 (s, 1 H), 5.65 (m, 1 H), 3.40 (m, 1 H), 3.08 (m, 1 H), 2.62 (m, 1 H), 2.37 (m, 1 H).

EXAMPLE 400

4-[2-({4-[5-chloro-2-(1H-tetrazol-1-yl)phenyl]-6-methyl-2-oxo-1(2H)-pyridinyl}methyl)-1H-imidazol-5-yl]-2-thiophenecarboxylic acid hydrochloride

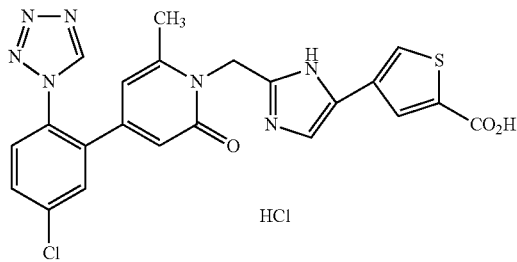 [SMILES: Cc1cc(-c2cc(Cl)ccc2-n2cnnn2)cc(=O)n1Cc1ncc(-c2csc(C(=O)O)c2)[nH]1 ; Cl]

The same operation as in Example 6→Example 7→Example 8→Example 9 Example 51→Example 52→Example 363 was conducted from methyl 2-(4-hydroxy-6-methyl-2-oxo-1,2-dihydropyridin-1-yl)acetate [J. Het. Chem., 27(5), 1401 (1990)] to give the title compound having the following physical properties. (Note: in the step corresponding to Example 51 in the operation, the compound prepared in Example 361 was used).

TLC Rf 0.65 (10% methanol, 1% acetic acid in dichloromethane)

$^1$H NMR (300 MHz, DMSO-$d_6$) δ 9.68 (s, 1 H), 8.17 (s, 1 H), 8.12 (d, 1 H), 7.90 (br. s, 1 H), 7.81 (app. s, 2 H), 7.72 (s, 1 H), 6.10 (d, 1 H), 6.01 (d, 1 H), 5.31 (s, 2 H), 2.40 (s, 3 H).

EXAMPLE 401 ethyl 5-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylate

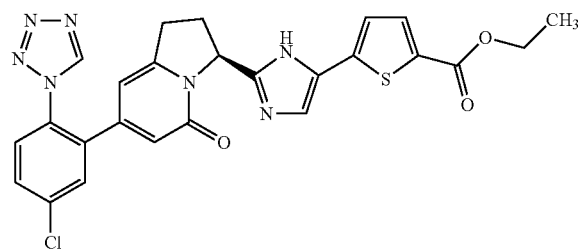 [SMILES: CCOC(=O)c1ccc(-c2cnc([C@@H]3CCc4cc(-c5cc(Cl)ccc5-n5cnnn5)cc(=O)n43)[nH]2)s1]

The same operation as in Example 361→Example 51→Example 52 was conducted from 5-acetyl-thiophene-2-carboxylic acid ethyl ester to give the title compound having the following physical properties.

TLC Rf 0.28 (ethyl acetate)

$^1$H NMR (300 MHz, CDCl$_3$) δ 10.88 (s, 1 H), 8.53 (s, 1 H), 7.69 (d, 1 H), 7.61 (dd, 1 H), 7.53 (d, 1 H), 7.49 (d, 1 H), 7.25 (m, 1 H), 7.19 (d, 1 H), 6.30 (d, 1 H), 5.80 (d, 1 H), 5.72 (s, 1 H), 4.33 (q, 2 H), 3.50-3.30 (m, 2 H), 3.10-2.95 (m, 1 H), 2.55-2.40 (m, 1 H), 1.37 (t, 3 H).

EXAMPLE 402

(3S)-7-[5-chloro-2-(1H-tetrazol-1-yl)phenyl]-3-[5-(1-oxido-4-pyridinyl)-1H-imidazol-2-yl]-2,3-dihydro-5(1H)-indolizinone The same operational sequence as in Example 78→Example 51→Example 52 was conducted from 4-acetylpyridine-N-oxide [patent WO9509853] to give the title compound having the following physical properties.

LC/MS $t_R$ 3.19 minutes; MS (ES$^+$) m/z 472 (M+H)$^b$ $^1$H NMR (500 MHz, DMSO-$d_6$) δ 12.44 (br. s, 0.7 H), 9.69 (s, 1 H), 8.29 (s, 0.3 H), 8.12 (d, 2 H), 7.75-7.89 (m, 3 H), 7.73 (br. s, 1 H), 7.66 (d, 2 H), 5.96 (d, 2 H), 5.62 (d, 1 H), 3.29-3.39 (m, 1 H), 3.00 (dd, 1 H), 2.54 (br.s, 1 H), 2.29 (t, 1 H).

EXAMPLE 403

(3S)-3-[5-(3-aminophenyl)-1H-imidazol-2-yl]-7-[5-chloro-2-(1H-tetrazol-1-yl)phenyl]-2,3-dihydro-5(1H)-indolizinone The compound prepared in Example 173(21) (350 mg) was treated as detailed in Example 74 to give the title compound having the following physical properties (288 mg).

LC/MS $t_R$ 2.98 minutes; MS (ES$^+$) m/z 471 (M+H)$^b$ $^1$H NMR (500 MHz, methanol-$d_4$) δ 9.35 (s, 1 H), 7.70-7.75 (m, 2 H), 7.64-7.69 (m, 1 H), 6.82-7.35 (m, 4 H), 6.62 (d, 1 H), 6.13 (s, 1 H), 6.07 (s, 1 H), 5.78 (dd, 1 H), 4.35-4.75 (m, 1 H), 3.36-3.49 (m, 1 H), 3.02-3.14 (m, 1 H), 2.61 (qd, 1 H), 2.44 (m, 1 H).

EXAMPLE 404(1) to Example 404(3)

The compounds of the present invention having the following physical data were synthesised from the compound prepared in Example 403 and the corresponding acid chlorides or chloroformates using the method as detailed in Example 128.

EXAMPLE 404(1)

2-methoxyethyl[3-(2-{(3S)-7-[5-chloro-2-(1H-tetrazol-1-yl)phenyl]-5-oxo-1,2,3,5-tetrahydro-3-indolizinyl)-1H-imidazol-5-yl)phenyl]carbamate LC/MS $t_R$ 3.25 minutes; MS (ES$^+$) m/z 573 (M+H)$^b$ $^1$H NMR (500 MHz, DMSO-$d_6$) δ 12.10 (br. s, 1 H), 9.51-9.86 (m, 2 H), 7.68-7.93 (m, 4 H), 7.03-7.45 (m, 4 H), 5.82-6.11 (2×s, 2 H), 5.51-5.75 (m, 1 H), 4.12-4.25 (m, 2 H), 3.56 (m, 2 H), 3.31 (s, 2 H), 3.28 (s, 3 H), 3.01 (dd, 1 H), 2.30-2.42 (m, 1 H).

EXAMPLE 404(2)

methyl[3-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate LC/MS $t_R$ 3.22 minutes; MS (ES$^+$) m/z 529 (M+H)$^b$ $^1$H NMR (500 MHz, methanol-$d_4$) δ 9.36 (s, 1 H), 8.91 (d, 0.66 H), 8.62-8.49 (m, 0.34 H), 8.09 (t, 0.66 H), 7.79-7.60 (m, 4.33 H), 7.45-7.10 (br. m, 4 H), 6.13 (s, 1 H), 6.09 (s, 1 H), 5.79 (d, 1 H), 3.74 (s, 3 H), 3.51-3.38 (m, 1 H), 3.11 (ddd, 1 H), 2.70-2.57 (m, 1 H), 2.56-2.31 (m, 1 H).

EXAMPLE 404(3)

N-[3-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]acetamide LC/MS $t_R$ 3.04 minutes; MS (ES$^+$) m/z 513 (M+H)$^b$ $^1$H NMR (500 MHz, methanol-$d_4$) δ 9.37 (s, 1H), 8.36 (s, 1 H), 7.79 (s, 1 H), 7.76-7.71 (m, 2 H), 7.71-7.66 (m, 1 H), 7.49 (d, 1 H), 7.38 (d, 1 H), 7.33-7.26 (m, 2 H), 6.14 (s, 1 H), 6.09 (s, 1 H), 5.79 (dd, 1 H), 3.48-3.40 (m, 1 H), 3.11 (dd, 1 H), 2.68-2.59 (m, 1 H), 2.50-2.41 (m, 1 H), 2.14 (s, 3 H).

EXAMPLE 405(1) TO EXAMPLE 405(2)

The compounds of the present invention having the following physical data were prepared using the corresponding carboxylic acids from the compound prepared in Example 9 in the process of Example 234→Example 51→Example 52.

EXAMPLE 405(1)

methyl 3-(2-{(3S)-7-[5-chloro-2-(1H-tetrazol-1-yl)phenyl]-5-oxo-1,2,3,5-tetrahydro-3-indolizinyl}-1H-imidazol-5-yl)benzoate LC/MS $t_R$ 3.58 minutes; MS (ES$^+$) m/z 514 (M+H)$^b$ $^1$H NMR (500 MHz, methanol-$d_4$) δ 9.36 (s, 1 H), 8.32 (s, 1 H), 7.87 (d, 1 H), 7.90 (d, 1 H), 7.70-7.75 (m, 2 H), 7.65-7.70 (m, 1 H), 7.47 (t, 1 H), 7.42 (s, 1 H), 6.09 (s, 1 H), 6.13 (s, 1 H), 5.79 (dd, 1 H), 3.92 (s, 3 H), 3.41-3.52 (m, 1 H), 3.11 (ddd, 1 H), 2.60-2.69 (m, 1 H), 2.45-2.54 (m, 1 H).

EXAMPLE 405(2)

(3S)-7-[5-chloro-2-(1H-tetrazol-1-yl)phenyl]-3-{5-[3-(methylsulfonyl)phenyl]-1H-imidazol-2-yl}-2,3-dihydro-5(1H)-indolizinone LC/MS $t_R$ 3.41 minutes; MS (ES$^+$) m/z 534 (M+H)$^b$ $^1$H NMR (500 MHz, methanol-$d_4$) δ 9.35 (s, 1 H), 8.25 (br. s, 1 H), 8.01 (d, 1 H), 7.78 (d, 1 H), 7.69-7.75 (m, 2 H), 7.64-7.69 (m, 1 H), 7.60 (t, 1 H), 7.53 (br. s, 1 H), 6.12 (s, 1 H), 6.09 (s, 1 H), 5.79 (dd, 1 H), 3.47 (td, 1 H), 3.14-3.16 (s, 3 H), 3.08-3.19 (m, 1 H), 2.59-2.70 (m, 1 H), 2.51 (br. s, 1 H).

EXAMPLE 406

3-(methoxymethyl)benzoic acid

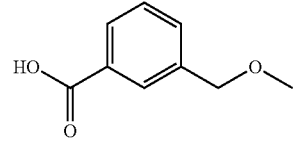

A mixture of 3-bromomethyl benzoic acid methyl ester (0.573 g) and potassium carbonate (691 mg) in methanol (8 mL) and tetrahydrofuran (8 mL) was heated and stirred under nitrogen at 55° C. for 2 h. The reaction mixture was filtered and the filtrate containing 3-methoxymethylbenzoic acid methyl ester used directly in the next stage. 1 M sodium hydroxide (3.75 ml) was added and the reaction was stirred at 70° C. for 30 minutes. The solvent was evaporated and the residue dissolved water and acidified (pH~2) by the addition of 1 N HCl. The aqueous layer was extracted with ethyl acetate and the organic layer washed with water, saturated brine and dried to afford the required product as a white solid (395 mg) having the following physical properties.

$^1$H NMR (500 MHz, CDCl$_3$) δ 8.10 (s, 1 H), 8.06 (d, 1 H), 7.62 (d, 1 H), 7.49 (t, 1 H), 4.54 (s, 2H), 3.44 (s, 3H).

EXAMPLE 407

(3S)-7-[5-chloro-2-(1H-tetrazol-1-yl)phenyl]-3-{5-[3-(methoxymethyl)phenyl]-1H-imidazol-2-yl}-2,3-dihydro-5(1H)-indolizinone The same operational sequence as in Example 234→Example 51→Example 52 was conducted from the compound prepared in Example 406 to give the title compound having the following physical properties.

LC/MS $t_R$ 3.28 minutes; MS (ES$^+$) m/z 500 (M+H)$^b$ $^1$H NMR (500 MHz, methanol-$d_4$) δ 9.36 (s, 1 H), 7.70-7.76 (m, 2 H), 7.66-7.70 (m, 1 H), 7.64 (s, 1 H), 7.58 (d, 1 H), 7.29-7.38 (m, 2 H), 7.21 (d, 1 H), 6.09 (s, 1 H), 6.12 (s, 1 H), 5.79 (dd, 1 H), 4.48 (s, 2 H), 3.41-3.49 (m, 1 H), 3.39 (s, 3 H), 3.10 (ddd, 1 H), 2.64 (qd, 1 H), 2.42-2.51 (m, 1 H).

EXAMPLE 408

(3S)-3-[5-(3-acetylphenyl)-1H-imidazol-2-yl]-7-[5-chloro-2-(1H-tetrazol-1-yl)phenyl]-2,3-dihydro-5(1H)-indolizinone The same operational sequence as in Example 340→Example 51→Example 52 was conducted from 1,3-diacetylbenzene to give the title compound having the following physical properties.

LC/MS $t_R$ 3.40 minutes; MS (ES$^+$) m/z 498 (M+H)$^b$ $^1$H NMR (500 MHz, methanol-$d_4$) δ 9.37 (s, 1 H), 8.31 (br. s, 1 H), 7.92 (br. s, 1 H), 7.86 (m, 2 H), 7.76-7.71 (m, 2 H), 7.71-7.62 (m, 2 H), 7.61-7.34 (m, 3H), 6.14 (s, 1 H), 6.11 (s, 1 H), 5.81 (dd, 1 H), 3.54-3.41 (m, 1 H), 3.13 (ddd, 1 H), 2.73-2.60 (m, 4 H), 2.52 (br. s, 1 H).

EXAMPLE 409

(3S)-{2-[(3S)-7-[5-chloro-2-(1H-1,2,3,4-tetrazol-1-yl)phenyl]-5-oxo-1,2,3,5-tetrahydroindolizin-3-yl]-1H-imidazol-5-yl}benzaldehyde The same operational sequence as in Example 51→Example 52 was conducted from 3-(2-bromoacetyl)benzaldehyde [J. Med. Chem., 50(18), 4405 (2007)] to give the title compound having the following physical properties.
LC/MS $t_R$ 1.64 minutes; MS (ES$^+$) m/z 484 (M+H)$^a$.

EXAMPLE 410

3-(2-{(3S)-7-[5-chloro-2-(1H-tetrazol-1-yl)phenyl]-5-oxo-1,2,3,5-tetrahydro-3-indolizinyl}-1H-imidazol-5-yl)benzaldehyde O-methyloxime The compound prepared in Example 409 (100 mg) was vigorously stirred with hydroxylamine hydrochloride (35 mg) and sodium acetate (34 mg) in ethanol (2.5 mL) overnight. The reaction was stirred for a further 6 days, ethanol evaporated under a stream of nitrogen and further hydroxylamine hydrochloride (70 mg) and sodium acetate (68 mg) added in 2 mL of a 4:1 mixture of acetic acid and water. The reaction was heated at for a further 16 hours at 100° C. The solvent was evaporated and purified by high performance liquid chromatography (5 to 100% acetonitrile in 2 mM aqueous ammonium hydrogen carbonate) to give the title compound having the following physical properties (6.5 mg).
LC/MS $t_R$ 3.60 minutes; MS (ES$^+$) m/z 513 (M+H)$^b$
$^1$H NMR (500 MHz, DMSO-d$_6$) δ 9.69 (s, 1 H), 8.26 (s, 1 H), 7.91 (s, 1 H), 7.80 (m, 3 H), 7.72 (d, 1 H), 7.50 (br. s, 1 H), 7.44-7.40 (m, 1 H), 7.39-7.35 (m, 1 H), 5.97 (s, 1 H), 5.95 (s, 1 H), 5.63 (d, 1 H), 4.08 (br. s, 1 H), 3.90 (s, 3 H), 3.00 (dd, 1 H), 2.49-2.45 (m, 1 H), 2.35-2.26 (m, 1 H).

EXAMPLE 411

3-(2-{7-[5-chloro-2-(1H-tetrazol-1-yl)phenyl]-5-oxo-1,2,3,5-tetrahydro-3-indolizinyl}-1H-imidazol-5-yl)benzamide The same operational sequence as in Example 51→Example 52→Example 117→Example 55→Example 24 was conducted from 3-(bromoacetyl)benzonitrile to give the title compound having the following physical properties.
LC/MS $t_R$ 2.97 minutes; MS (ES$^+$) m/z 499 (M+H)$^b$
$^1$H NMR (500 MHz, methanol-d$_4$) δ 9.38 (s, 1 H), 8.20 (s, 1 H), 7.85 (d, 1 H), 7.76 (m, 3 H), 7.70 (d, 1 H), 7.49 (t, 1 H), 7.46 (s, 1 H), 6.14 (s, 1 H), 6.10 (s, 1 H), 5.80 (dd, 1 H), 3.51-3.41 (m, 1 H), 3.11 (ddd, 1 H), 2.65 (ddd, 1 H), 2.0 (m, 1 H).

EXAMPLE 412

3-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)benzonitrile The compound prepared in Example 173(20) (91 mg) was treated using the method as detailed in Example 338 to give the title compound having the following physical properties (32 mg).
LC/MS $t_R$ 4.12 minutes; MS (ES$^+$) m/z 515 (M+H)$^b$ $^1$H NMR (500 MHz, methanol-d$_4$) δ 9.37 (s, 1 H), 8.06-7.99 (m, 2 H), 7.76-7.72 (m, 2 H), 7.70 (s, 2 H), 7.67-7.61 (m, 1 H), 6.14 (s, 1 H), 6.11 (s, 1 H), 5.73 (dd, 1 H), 3.50-3.41 (m, 1 H), 3.12 (ddd, 1 H), 2.71-2.61 (m, 1 H), 2.44-2.36 (m, 1 H).

EXAMPLE 413

(3S)-3-[4-chloro-5-(3-hydroxyphenyl)-1H-imidazol-2-yl]-7-[5-chloro-2-(1H-tetrazol-1-yl)phenyl]-2,3-dihydro-5(1H)-indolizinone The compound prepared in Example 173(22) (84 mg) was treated using the method as detailed in Example 338 to give the title compound having the following physical properties (57 mg).
LC/MS $t_R$ 3.81 minutes; MS (ES$^+$) m/z 506 (M+H)$^b$
$^1$H NMR (500 MHz, methanol-d$_4$) δ 9.37 (s, 1 H), 7.76-7.72 (m, 2 H), 7.71-7.65 (m, 1 H), 7.28-7.23 (m, 1 H), 7.18 (t, 1 H), 7.14 (d, 1 H), 6.76 (dd, 1 H), 6.13 (s, 1 H), 6.09 (s, 1 H), 5.72 (dd, 1 H), 3.49-3.39 (m, 1 H), 3.10 (ddd, 1 H), 2.64 (qd, 1 H), 2.43-2.34 (m, 1 H).

EXAMPLE 414

(3S)-3-[5-(2-aminophenyl)-1H-imidazol-2-yl]-7-[5-chloro-2-(1H-tetrazol-1-yl)phenyl]-2,3-dihydro-5(1H)-indolizinone The same operation as in Example 51→Example 52→Example 74 was conducted from 2-bromo-1-(2-nitrophenyl)ethanone to give the title compound having the following physical properties.
LC/MS $t_R$ 3.01 minutes; MS (ES$^+$) m/z 471 (M+H)$^b$
$^1$H NMR (500 MHz, methanol-d$_4$) δ 9.35 (s, 1 H), 7.75-7.71 (m, 2 H), 7.70-7.66 (m, 1 H), 7.39-7.20 (m, 2 H), 7.04-6.93 (m, 1 H), 6.78 (d, 1 H), 6.68 (br. s, 1 H), 6.16 (s, 1 H), 6.05 (s, 1 H), 5.82 (dd, 1 H), 3.49-3.38 (m, 1 H), 3.10 (dd, 1 H), 2.69-2.47 (m, 2 H).

EXAMPLE 415 methyl[2-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate The compound prepared in Example 414 (50 mg) was treated with methyl chloroformate following the method of Example 128 to give the title compound having the following physical properties (30 mg).
LC/MS $t_R$ 4.09 minutes; MS (ES$^+$) m/z 529 (M+H)$^b$
$^1$H NMR (500 MHz, DMSO-d$_6$) δ 12.65 (br. s, 1 H), 11.88 (br. s, 1 H), 9.68 (s, 1 H), 8.11 (d, 1 H), 7.81 (m, 2 H), 7.75 (s, 1 H), 7.68-7.63 (m, 2 H), 7.18 (t, 1 H), 6.99 (t, 1 H), 6.00 (s, 1 H), 5.99 (s, 1 H), 5.70 (d, 1 H), 3.63 (s, 3 H), 3.53-3.45 (m, 1 H), 3.07 (dd, 1 H), 2.62-2.54 (m, 1 H), 2.39-2.26 (m, 1 H).

EXAMPLE 416

N-[2-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]acetamide The compound prepared in Example 414 (20 mg) was treated with acetyl chloride following the method of Example 128 to give the title compound having the following physical properties (12.7 mg).

LC/MS $t_R$ 3.45 minutes; MS (ES$^+$) m/z 513 (M+H)$^b$ $^1$H NMR (500 MHz, DMSO-d$_6$) δ 12.66 (br. s, 1 H), 11.96 (s, 1 H), 9.71 (s, 1 H), 8.38 (d, 1 H), 7.86-7.78 (m, 2 H), 7.74 (d, 1 H), 7.70-7.64 (m, 2 H), 7.16 (t, 1 H), 7.02 (t, 1 H), 6.00 (s, 1 H), 5.99 (s, 1 H), 5.71 (d, 1 H), 3.33-3.29 (m, 1 H), 3.06 (dd, 1 H), 2.62-2.55 (m, 1 H), 2.30 (dd, 1 H), 1.93 (s, 3 H).

EXAMPLE 417 prop-2-en-1-yl 2-acetylbenzoate

To an N,N-dimethylformamide (60 mL) suspension of 2-acetylbenzoic acid (5 g) was added potassium carbonate (5 g) and the mixture stirred at room temperature for 30 minutes. To the reaction mixture, allyl bromide (2.8 mL) was added and the mixture stirred at room temperature for 18 hours. The reaction mixture was concentrated and the residue suspended in water (50 mL) followed by extraction into ethyl acetate. The combined organic layers were washed with water, saturated saline, dried and concentrated to give the title compound having the following physical properties (6.04 g).

LC/MS $t_R$ 1.82 minutes; MS (ES$^+$) m/z 205 (M+H)$^a$.

EXAMPLE 418 prop-2-en-1-yl 2-{1-[(trimethylsilyl)oxy]ethenyl}benzoate

To a cooled (0° C.) dichloromethane (50 mL) solution of the compound prepared in Example 417 (2 g), triethylamine (3.06 mL) and bromo(trimethyl)silane (2.33 mL) were added sequentially and the mixture stirred at room temperature for 60 hours. To the reaction mixture, water (30 mL) was added followed by extraction into dichloromethane. The combined organic layers were washed with saturated saline, dried and concentrated to give the title compound having the following physical properties (2.53 g).

$^1$H NMR (250 MHz, CDCl$_3$) δ 7.64-7.57 (m, 1 H), 7.50-7.45 (m, 1 H), 7.41 (dt, 1 H), 7.34 (dt, 1 H), 6.03 (tdd, 1 H), 5.41 (qd, 1 H), 5.27 (qd, 1 H), 4.78 (td, 2 H), 4.63 (d, 1 H), 4.49 (d, 1 H), 0.18 (s, 9 H).

EXAMPLE 419 prop-2-en-1-yl 2-(2-bromoacetyl)benzoate

To a tetrahydrofuran (50 mL) solution of the compound prepared in Example 418 (2.53 g) was added N-bromosuccinimide (1.63 g) and the reaction stirred at room temperature for 1 hour. To the reaction mixture, water (25 mL) and saturated aqueous solution of sodium carbonate (25 mL) was added followed by extraction into ethyl acetate. The combined organic layers were washed with water, saturated saline, dried and concentrated to give the title compound having the following physical properties (2.33 g).

$^1$H NMR (500 MHz, CDCl$_3$) δ 8.05 (dd, 1 H), 7.65 (dt, 1 H), 7.56 (dt, 1 H), 7.42 (dd, 1 H), 6.02 (tdd, 1 H), 5.43 (qd, 1 H), 5.33 (dd, 1 H), 4.83 (td, 2 H), 4.34 (s, 2 H).

EXAMPLE 420

2-(2-{(3S)-7-[5-chloro-2-(1H-tetrazol-1-yl)phenyl]-5-oxo-1,2,3,5-tetrahydro-3-indolizinyl}-1H-imidazol-5-yl)benzoic acid The same operation as in Example 51→Example 52 was conducted from the compound prepared in Example 419 to give the title compound having the following physical properties. Hydrolysis of the allyl ester occurred under the conditions employed in the step corresponding to Example 52 in the operation.

LC/MS $t_R$ 3.32 minutes; MS (ES$^+$) m/z 500 (M+H)$^b$ $^1$H NMR (500 MHz, CDCl$_3$) δ 10.72 (br. s, 1 H), 9.98 (br. s, 1 H), 8.71 (s, 1 H), 8.28 (d, 1 H), 7.80-7.64 (m, 3 H), 7.63-7.56 (m, 1 H), 7.56-7.49 (m, 2 H), 7.43 (t, 1 H), 6.36 (s, 1 H), 5.78 (s, 1 H), 5.50 (d, 1 H), 3.34-3.19 (m, 1 H), 2.93 (dd, 1 H), 2.86-2.69 (m, 1 H), 2.36 (td, 1 H).

EXAMPLE 421

2-bromo-1-[3-(tetramethyl-1,3,2-dioxaborolan-2-yl)phenyl]ethan-1-one

To a dichloromethane (3 mL) and glacial acetic acid (0.06 mL) solution of 1-[3-(4,4,5,5-tetramethyl-1,3,2-dioxaborolan-2-yl)phenyl]ethanone (300 mg) was added bromine (62.64 μL) and the mixture stirred at room temperature for 2 hours. The reaction mixture was concentrated and a saturated aqueous solution of sodium hydrogen carbonate (25 mL) was added to the residue followed by extraction with dichloromethane. The combined organic layers were washed with water, saturated saline, dried and concentrated to obtain the title compound having the following physical properties (0.37 g).

LC/MS $t_R$ 2.34 minutes; MS (ES$^+$) m/z 325 (M+H)$^a$.

EXAMPLE 422

(3S)-7-[5-chloro-2-(1H-1,2,3,4-tetrazol-1-yl)phenyl]-3-{5-[3-(tetramethyl-1,3,2-dioxaborolan-2-yl)phenyl]-1H-imidazol-2-yl}-1,2,3,5-tetrahydroindolizin-5-one The same operation as in Example 51→Example 52 was conducted from Example 421 to give the title compound having the following physical properties. LC/MS $t_R$ 1.83 minutes; MS (ES$^+$) m/z 582 (M+H)$^a$.

EXAMPLE 423

[3-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]boronic acid To a 1,4-dioxane (1 mL) solution of the compound prepared in Example 422 (40 mg) was added 1 M hydrochloric acid in water (0.34 mL) and the mixture was stirred overnight at 90° C. To the reaction mixture, a saturated aqueous solution of sodium hydrogen carbonate was added followed by extraction into dichloromethane. The combined organic layers were washed with saturated saline, dried (Na$_2$SO$_4$) and then concentrated. The residue was purified by high performance liquid chromatography [5 to 100% mobile phase B (0.1% formic acid in acetonitrile) in mobile phase A (0.1% aqueous formic acid)] was used to give the title compound having the following physical properties (10 mg).

LC/MS $t_R$ 2.90 minutes; MS (ES$^+$) m/z 499 (M+H)$^b$ $^1$H NMR (500 MHz, DMSO-d$_6$) δ 12.08 (s, 1 H), 9.70 (s, 1 H), 8.27 (s, 1 H), 8.16-8.07 (m, 2 H), 7.82-7.77 (m, 3 H), 7.72 (d, 1 H), 7.58 (d, 1 H), 7.43 (d, 1 H), 7.28 (t, 1 H), 5.99 (s, 1 H), 5.94 (s, 1 H), 5.68-5.58 (m, 1 H), 3.48-3.42 (m, 1 H), 3.01 (dd, 1 H), 2.54-2.53 (m, 1 H), 2.42-2.33 (m, 1 H).

EXAMPLE 424

[3-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)phenyl]boronic acid The same operation as in Example 338→Example 423 was conducted from the compound prepared in Example 422 to give the title compound having the following physical properties.

LC/MS $t_R$ 3.69 minutes; MS (ES$^+$) m/z 534 (M+H)$^b$
$^1$H NMR (500 MHz, DMSO-d$_6$) δ 13.00 (s, 1 H), 9.72 (s, 1 H), 8.30 (br. s, 2 H), 8.07 (s, 1 H), 7.85-7.78 (m, 3 H), 7.73 (t, 2 H), 7.44 (t, 1 H), 5.99 (s, 1 H), 5.94 (s, 1 H), 5.59 (dd, 1 H), 3.28-3.25 (m, 1 H), 3.03-2.94 (m, 1 H), 2.59-2.54 (m, 1 H), 2.23-2.14 (m, 1 H).

EXAMPLE 425 ethyl[3-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]acetate To an ethanol (1 mL) solution of the compound prepared in Example 345 (39 mg) was added 2 M hydrochloric acid in ether (18.97 µL) and the mixture was stirred at 90° C. for 2 hours. The reaction mixture was concentrated and water was added to the residue and then neutralized with a saturated aqueous solution of sodium hydrogen carbonate followed by extraction with dichloromethane. The combined organic layers were washed with water, saturated saline, dried and then concentrated. The residue was purified by column chromatography (eluent: 50% to 100% ethyl acetate in heptanes and then 1% methanol in ethyl acetate) to afford the title compound having the following physical properties (30 mg).

LC/MS $t_R$ 3.47 minutes; MS (ES$^+$) m/z 542 (M+H)$^b$
$^1$H NMR (500 MHz, methanol-d$_4$) δ 9.36 (s, 1 H), 7.76-7.71 (m, 2 H), 7.71-7.66 (m, 1 H), 7.64-7.46 (m, 2 H), 7.42-7.26 (m, 2 H), 7.15 (br. s, 1 H), 6.13 (s, 1 H), 6.09 (s, 1 H), 5.79 (d, 1 H), 4.14 (q, 2 H), 3.67 (s, 2 H), 3.51-3.38 (m, 1 H), 3.11 (ddd, 1 H), 2.70-2.58 (m, 1 H), 2.57-2.44 (m, 1 H), 1.24 (t, 3 H).

EXAMPLE 426 ethyl[3-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)phenyl]acetate The compound prepared in Example 346 (50 mg) was treated using the method as detailed in Example 425 to give the title compound having the following physical properties (28 mg).

LC/MS $t_R$ 4.07 minutes; MS (ES$^+$) m/z 576 (M+H)$^b$
$^1$H NMR (500 MHz, methanol-d$_4$) δ 9.37 (s, 1 H), 7.77-7.72 (m, 2 H), 7.71-7.67 (m, 1 H), 7.65-7.60 (m, 2 H), 7.42 (t, 1 H), 7.27 (d, 1 H), 6.14 (s, 1 H), 6.10 (s, 1 H), 5.73 (dd, 1 H), 4.16 (q, 2 H), 3.70 (s, 2 H), 3.50-3.40 (m, 1 H), 3.11 (ddd, 1 H), 2.65 (qd, 1 H), 2.45-2.35 (m, 1 H), 1.26 (t, 3 H).

EXAMPLE 427

2-[3-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]acetamide The compound prepared in Example 345 (45 mg) was treated using the method as detailed in Example 114 to give the title compound having the following physical properties (18 mg).

LC/MS $t_R$ 2.86 minutes; MS (ES$^+$) m/z 513 (M+H)$^b$
$^1$H NMR (500 MHz, DMSO-d$_6$) δ 12.10 (br. s, 1 H), 9.71 (s, 1 H), 7.85-7.75 (m, 3 H), 7.59 (s, 1 H), 7.54-7.46 (m, 3 H), 7.23 (t, 1 H), 7.06 (d, 1 H), 6.88 (br. s, 1 H), 5.98 (s, 1 H), 5.95 (s, 1 H), 5.62 (dd, 1 H), 3.42-3.39 (m, 3 H), 3.01 (dd, 1 H), 2.55-2.45 (m, obs. 1 H), 2.40-2.33 (m, 1 H).

EXAMPLE 428

2-[3-(4-chloro-2-{(3S)-7-[5-chloro-2-(1H-tetrazol-1-yl)phenyl]-5-oxa-1,2,3,5-tetrahydro-3-indolizinyl}-1H-imidazol-5-yl)phenyl]acetamide The compound prepared in Example 346 (50 mg) was treated using the method as detailed in Example 114 to give the title compound having the following physical properties (21 mg).

LC/MS $t_R$ 3.65 minutes; MS (ES$^+$) m/z 547 (M+H)$^b$
$^1$H NMR (500 MHz, DMSO-d$_6$) δ 13.01 (br. s, 1 H), 9.71 (s, 1 H), 7.87-7.77 (m, 3 H), 7.63-7.48 (m, 3 H), 7.40 (t, 1 H), 7.22 (d, 1 H), 6.93 (br. s, 1 H), 5.99 (s, 1 H), 5.94 (s, 1 H), 5.58 (dd, 1 H), 3.42 (s, 2 H), 3.30-3.23 (m, 1 H), 3.07-2.87 (m, 1 H), 2.59-2.54 (m, 1 H), 2.19 (t, 1 H).

EXAMPLE 429

2-[3-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]-N-methylacetamide The compound prepared in Example 345 (45 mg) was treated using the method as detailed in Example 114 using methylamine hydrochloride to give the title compound having the following physical properties (17 mg).

LC/MS $t_R$ 2.95 minutes; MS (ES$^+$) m/z 527 (M+H)$^b$
$^1$H NMR (500 MHz, DMSO-d$_6$) δ 12.11 (br. s, 1 H), 9.70 (s, 1 H), 7.94 (m, 1 H), 7.85-7.75 (m, 3 H), 7.58 (s, 1 H), 7.54 (m, 2 H), 7.48-7.45 (m, 1 H), 7.23 (t, 1 H), 5.98 (s, 1 H), 5.95 (s, 1 H), 5.62 (dd, 1 H), 3.44-3.40 (m, 1 H), 3.39 (s, 2 H), 3.01 (dd, 1 H), 2.57 (s, 3 H), 2.55-2.45 (m, obs. 1 H), 2.38-2.35 (m, 1 H).

EXAMPLE 430

2-[3-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)phenyl]-N-methylacetamide The compound prepared in Example 346 (50 mg) was treated using the method as detailed in Example 114 using methylamine hydrochloride to give the title compound having the following physical properties (20 mg).

LC/MS $t_R$ 3.77 minutes; MS (ES$^+$) m/z 561 (M+H)$^b$
$^1$H NMR (500 MHz, DMSO-d$_6$) δ 13.01 (br. s, 1 H), 9.71 (s, 1 H), 8.00 (d, 1 H), 7.87-7.75 (m, 3 H), 7.63-7.51 (m, 2 H), 7.39 (t, 1 H), 7.21 (d, 1 H), 5.99 (s, 1 H), 5.94 (s, 1 H), 5.58 (dd, 1 H), 3.44 (s, 2 H), 3.31-3.19 (m, 1 H), 3.04-2.90 (m, 1 H), 2.58 (s, 3 H), 2.55-2.45 (m, obs. 1 H), 2.19 (t, 1 H).

EXAMPLE 431

2-[3-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]-2-methylpropanoic acid—formic acid (1:1)

The same operation as in Example 139→Example 340→Example 51→Example 52→Example 342 was conducted from methyl 2-(3-bromophenyl)-2-methylpropanoate to give the title compound having the following physical properties.

LC/MS $t_R$ 3.23 minutes; MS (ES$^+$) m/z 542 (M+H)$^b$
$^1$H NMR (500 MHz, DMSO-d$_6$) δ 12.71 (br. s, 1 H), 12.11 (br. s, 1 H), 9.69 (s, 1 H), 8.17 (s, 1 H), 7.84-7.76 (m, 3 H), 7.70-7.61 (m, 1 H), 7.58-7.41 (m, 2 H), 7.35-7.24 (m, 1 H), 7.19-7.09 (m, 1 H), 5.97 (s, 1 H), 5.95 (s, 1 H), 5.62 (dd, 1 H), 3.50-3.20 (obs. m, 1 H), 3.00 (dd, 1 H), 2.53-2.47 (obs. m, 1 H), 2.40-2.30 (m, 1 H), 1.49 (s, 6 H).

EXAMPLE 432

2-[3-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)phenyl]-2-methylpropanoic acid The same operation as in Example 139→Example 340→Example 51→Example 52→Example 338→Example 342 was conducted from methyl 2-(3-bromophenyl)-2-methylpropanoate to give the title compound having the following physical properties.

LC/MS $t_R$ 3.82 minutes; MS (ES$^+$) m/z 576 (M+H)$^b$
$^1$H NMR (500 MHz, DMSO-d$_6$) δ 13.07 (br. s, 1 H), 9.72 (s, 1 H), 7.87-7.77 (m, 3 H), 7.69 (s, 1 H), 7.59 (d, 1 H), 7.43 (t, 1 H), 7.30 (d, 1 H), 5.99 (s, 1 H), 5.94 (s, 1 H), 5.58 (dd, 1 H), 3.28-3.21 (m, 1 H), 3.06-2.91 (m, 1 H), 2.60-2.55 (m, 1 H), 2.26-2.16 (m, 1 H), 1.52 (s, 6 H).

EXAMPLE 433

4-{2-[(3S)-7-[5-chloro-2-(1H-1,2,3,4-tetrazol-1-yl)phenyl]-5-oxo-1,2,3,5-tetrahydro indolizin-3-yl]-1H-imidazol-4-yl}benzoic acid The same operation as in Example 51→Example 52→Example 37→Example 55→Example 24 was conducted from ethyl 4-(2-bromoacetyl)benzoate [Chem. Pharm. Bull., 54(9), 1318 (2006)] to give the title compound having the following physical properties. (Note: in the step corresponding to Example 51 in the operation, the compound prepared in Example 11 was used).

LC/MS $t_R$ 3.14 minutes; MS (ES$^+$) m/z 500 (M+H)$^b$
$^1$H NMR (500 MHz, DMSO-d$_6$) δ 12.30 (s, 1 H), 9.70 (s, 1 H), 7.96-7.74 (m, 7 H), 7.69 (s, 1 H), 5.98 (s, 1 H), 5.96 (s, 1 H), 5.66 (m, 1 H), 3.35 (obs. m, 1 H), 3.01 (dd, 1 H), 2.50 (obs. m, 1 H), 2.40-2.20 (m, 1 H).

EXAMPLE 434(1) TO EXAMPLE 434(8)

The compounds of the present invention having the following physical data were synthesised from the compound prepared in Example 433 and the corresponding amines or amine HCl salts using the method as detailed in Example 114.

EXAMPLE 434(1)

formic acid—4-(2-{(3S)-7-[5-chloro-2-(1H-tetrazol-1-yl)phenyl]-5-oxo-1,2,3,5-tetrahydro-3-indolizinyl}-1H-imidazol-5-yl)-N-methoxybenzamide (1:1)

LC/MS $t_R$ 3.01 minutes; MS (ES$^+$) m/z 529 (M+H)$^b$
$^1$H NMR (500 MHz, methanol-d$_4$) δ 9.38 (s, 1 H), 8.19 (br. s, 1 H), 7.83-7.67 (m, 7 H), 7.49 (s, 1 H), 6.14 (s, 1 H), 6.12 (s, 1 H), 5.81 (dd, 1 H), 3.83 (s, 3 H), 3.53-3.43 (m, 1 H), 3.22-3.09 (m, 1 H), 2.74-2.61 (m, 1 H), 2.55-2.43 (m, 1 H).

EXAMPLE 434(2)

formic acid—4-(2-{(3S)-7-[5-chloro-2-(1H-tetrazol-1-yl)phenyl]-5-oxo-1,2,3,5-tetrahydro-3-indolizinyl}-1H-imidazol-5-yl)-N-ethoxybenzamide (1:1)

LC/MS $t_R$ 3.11 minutes; MS (ES$^+$) m/z 543 (M+H)$^b$
$^1$H NMR (500 MHz, methanol-d$_4$) δ 9.38 (s, 1 H), 7.84-7.67 (m, 7 H), 7.48 (s, 1 H), 6.14 (s, 1 H), 6.10 (s, 1 H), 5.80 (dd, 1 H), 4.04 (q, 2 H), 3.54-3.40 (m, 1 H), 3.13 (ddd, 1 H), 2.71-2.58 (m, 1 H), 2.54-2.44 (m, 1 H), 1.33 (t, 3 H).

EXAMPLE 434(3)

4-(2-{(3S)-7-[5-chloro-2-(1H-tetrazol-1-yl)phenyl]-5-oxo-1,2,3,5-tetrahydro-3-indolizinyl}-1H-imidazol-5-yl)-N-(2-methoxyethyl)benzamide LC/MS $t_R$ 3.09 minutes; MS (ES$^+$) m/z 557 (M+H)$^b$
$^1$H NMR (500 MHz, methanol-d$_4$) δ 9.38 (s, 1 H), 7.86-7.68 (m, 7 H), 7.54-7.35 (m, 1 H), 6.18 (s, 1 H), 6.12 (s, 1 H) 5.80 (d, 1 H), 3.59 (s, 4 H), 3.52-3.44 (m, 1 H), 3.40 (s, 3 H), 3.17-3.09 (m, 1 H), 2.71-2.61 (m, 1 H), 2.56-2.48 (m, 1 H).

EXAMPLE 434(4)

formic acid—4-(2-{(3S)-7-[5-chloro-2-(1H-tetrazol-1-yl)phenyl]-5-oxo-1,2,3,5-tetrahydro-3-indolizinyl}-1H-imidazol-5-yl)-N-(3-methoxypropyl)benzamide (1:1)

LC/MS $t_R$ 3.17 minutes; MS (ES$^+$) m/z 571 (M+H)$^b$
$^1$H NMR (500 MHz, methanol-d$_4$) δ 9.38 (s, 1 H), 7.87-7.68 (m, 7 H), 7.47 (s, 1 H), 6.13 (2×s, 2 H), 5.81 (dd, 1 H), 3.50 (td, 5 H), 3.38 (s, 3 H), 3.20-3.10 (m, 1 H), 2.73-2.60 (m, 1 H), 2.54-2.45 (m, 1 H), 1.90 (m, 2 H).

EXAMPLE 434(5)

formic acid—4-(2-{(3S)-7-[5-chloro-2-(1H-tetrazol-1-yl)phenyl]-5-oxo-1,2,3,5-tetrahydro-3-indolizinyl}-1H-imidazol-5-yl)-N-(2-methoxyethoxyl)benzamide (1:1)

LC/MS $t_R$ 3.05 minutes; MS (ES$^+$) m/z 573 (M+H)$^b$
$^1$H NMR (500 MHz, methanol-d$_4$) δ 9.38 (s, 1 H), 7.83-7.67 (m, 7 H), 7.49 (s, 1 H), 6.14 (s, 1 H), 6.10 (s, 1 H), 5.81 (dd, 1 H), 4.13 (dd, 2 H), 3.75-3.68 (m, 2 H), 3.52-3.42 (m, 1 H), 3.41 (s, 3 H), 3.18-3.07 (m, 1 H), 2.68 (s, 1 H), 2.56-2.44 (m, 1 H).

EXAMPLE 434(6)

formic acid—4-(2-{(3S)-7-[5-chloro-2-(1H-tetrazol-1-yl)phenyl]-5-oxo-1,2,3,5-tetrahydro-3-indolizinyl}-1H-imidazol-5-yl)-N-(2-fluoroethyl)benzamide (1:1)

LC/MS $t_R$ 3.13 minutes; MS (ES$^+$) m/z 545 (M+H)$^b$
$^1$H NMR (500 MHz, methanol-d$_4$) δ 9.38 (s, 1 H), 7.91-7.66 (m, 7 H), 7.48 (s, 1 H), 6.16 (s, 1 H), 6.11 (s, 1 H), 5.81 (dd, 1 H), 4.63 (t, 1 H), 4.53 (t, 1 H), 3.76-3.62 (m, 2 H), 3.53-3.41 (m, 1 H), 3.13 (m, 1 H), 2.74-2.60 (m, 1 H), 2.54-2.42 (m, 1 H).

EXAMPLE 434(7)

4-(2-{(3S)-7-[5 chloro-2-(1H-tetrazol-1-yl)phenyl]-5-oxo-1,2,3,5-tetrahydro-3-indolizinyl}-1H-imidazol-5-yl)-N-(2,2-difluoroethyl)benzamide LC/MS $t_R$ 3.28 minutes; MS (ES$^+$) m/z 563 (M+H)$^b$ $^1$H NMR (500 MHz, methanol-d$_4$) δ 9.38 (s, 1 H), 7.93-7.80 (m, 4 H), 7.79-7.66 (m, 4 H), 7.53 (br. s, 1 H), 6.20-6.09 (2×s, 2 H), 6.06-5.89 (m, 1 H), 5.81 (m, 1 H), 3.75 (m, 2 H), 3.47 (br. s, 1 H), 3.13 (m, 1 H), 2.71-2.58 (m, 1 H), 2.56-2.47 (m, 1 H).

EXAMPLE 434(8)

4-(2-{(3S)-7-[5-chloro-2-(1H-tetrazol-1-yl)phenyl]-5-oxo-1,2,3,5-tetrahydro-3-indolizinyl}-1H-imidazol-5-yl)-N-(3-fluoropropyl)benzamide LC/MS $t_R$ 3.22 minutes; MS (ES$^+$) m/z 559 (M+H)$^b$ $^1$H NMR (500 MHz, methanol-d$_4$) δ 9.42 (s, 1 H), 7.87-7.66 (m, 7 H), 7.47 (s, 1 H), 6.14 (s, 1 H), 6.11 (s, 1 H), 5.81 (m, 1 H), 4.60 (t, 1 H), 4.50 (t, 1 H), 3.56-3.43 (m, 3 H), 3.18-3.09 (m, 1 H), 2.73-2.59 (m, 1 H), 2.54-2.43 (m, 1 H), 2.09-1.92 (m, 2 H).

EXAMPLE 435

4-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-N-(2-methoxyethyl)benzamide The compound prepared in Example 434(3) (20 mg) was treated using the method as detailed in Example 338 to give the title compound having the following physical properties (2 mg).

LC/MS $t_R$ 3.84 minutes; MS (ES$^+$) m/z 591 (M+H)$^b$ $^1$H NMR (500 MHz, methanol-d$_4$) δ 9.39 (s, 1 H), 7.93 (d, 2 H), 7.84 (d, 2 H), 7.78-7.68 (m, 3 H), 6.15 (s, 1 H), 6.13 (s, 1 H), 5.81-5.69 (m, 1 H), 3.60 (s, 4 H), 3.46 (m, 1 H), 3.41 (s, 3 H), 3.19-3.09 (m, 1 H), 2.71-2.63 (m, 1 H), 2.46-2.38 (m, 1 H).

EXAMPLE 436 formic acid—4-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-N-(2-methoxyethoxyl)benzamide (1:1)

The compound prepared in Example 434(5) (50 mg) was treated using the method as detailed in Example 338 to give the title compound having the following physical properties (7 mg).

LC/MS $t_R$ 3.77 minutes; MS (ES$^+$) m/z 607 (M+H)$^b$ $^1$H NMR (500 MHz, methanol-d$_4$) δ 9.39 (s, 1 H), 7.88-7.81 (m, 4 H), 7.78-7.68 (m, 3 H), 6.15 (s, 1 H), 6.13 (s, 1 H) 5.75 (dd, 1 H), 4.18-4.12 (m, 2 H), 3.72 (m, 2 H), 3.43 (m, s, 4 H), 3.18-3.09 (m, 1 H), 2.68 (m, 1 H), 2.46-2.38 (m, 1 H).

EXAMPLE 437

4-(2-{(3S)-7-[5-chloro-2-(1H-tetrazol-1-yl)phenyl]-5-oxo-1,2,3,5-tetrahydro-3-indolizinyl}-4-methyl-1H-imidazol-5-yl)benzamide The same operation as in Example 114→Example 78→Example 51→Example 52 was conducted from 4-propanoylbenzoic acid to give the title compound having the following physical properties.

LC/MS $t_R$ 2.84 minutes; MS (ES$^+$) m/z 513 (M+H)$^b$ $^1$H NMR (500 MHz, methanol-d$_4$) δ 9.41 (s, 1 H), 7.97-7.89 (m, 2 H), 7.74 (m, 6 H), 6.16-6.08 (m, 2 H), 5.78-5.72 (m, 1 H), 3.52-3.42 (m, 1 H), 3.17-3.08 (m, 1 H), 2.71-2.61 (m, 1 H), 2.52-2.36 (m, 4 H).

EXAMPLE 438

4-(2-{(3S)-7-[5-chloro-2-(1H-tetrazol-1-yl)phenyl]-5-oxo-1,2,3,5-tetrahydro-3-indolizinyl}-1H-imidazol-5-yl)-3-methylbenzamide The same operation as in Example 139→Example 78→Example 51→Example 52 was conducted from 4-bromo-3-methylbenzamide to give the title compound having the following physical properties.

LC/MS $t_R$ 2.93 minutes; MS (ES$^+$) m/z 514 (M+H)$^b$ $^1$H NMR (500 MHz, DMSO-d$_6$) δ 12.29 (s, 1 H), 9.70 (s, 1 H), 7.90 (s, 1 H), 7.82 (m, 4 H), 7.72 (s 1 H), 7.70 (d, 1 H), 7.39 (s, 1 H), 7.25 (s, 1 H), 5.98 (s, 2 H), 3.41-3.3 (obs, 2 H), 3.04-2.95 (m, 1 H), 2.45 (s, 3 H), 2.35 (m, 1 H).

EXAMPLE 439

4-(2-{7-[5-chloro-2-(1H-tetrazol-1-yl)phenyl]-5-oxo-1,2,3,5-tetrahydro 3-indolizinyl}-1H-imidazol-5-yl)-3-fluorobenzamide The same operation as in Example 234→Example 84→Example 52→Example 117→Example 55→Example 24 was conducted from 4-cyano-2-fluorobenzoic acid to give the title compound having the following physical properties.

LC/MS $t_R$ 3.23 minutes; MS (ES$^+$) m/z 517 (M+H)$^b$ $^1$H NMR (500 MHz, methanol-d$_4$) δ 9.37 (s, 1 H), 8.10 (br. s, 1 H), 7.80-7.64 (m, 5 H), 7.56-7.46 (m, 1 H), 6.17 (s, 1 H), 6.10 (s, 1 H), 5.89-5.76 (m, 1 H), 3.56-3.43 (m, 1 H), 3.19-3.07 (m, 1 H), 2.71-2.61 (m, 1 H), 2.58-2.47 (m, 1 H).

EXAMPLE 440

5-(2-bromoacetyl)pyridine-2-carbonitrile 6-cyanopyridine-3-carboxylic acid (750 mg) was treated using the method as detailed in Example 234 to give the title compound having the following physical properties (655 mg).

¹H NMR (500 MHz, CDCl₃) δ 9.14-9.03 (m, 1 H), 8.24 (dd, 1 H), 7.69 (dd, 1 H), 4.25 (s, 2 H).

EXAMPLE 441

2-(6-cyanopyridin-3-yl)-2-oxoethyl 7-(2-{[(tert-butoxy)carbonyl]amino}-5-chlorophenyl)-5-oxo-1,2,3,5-tetrahydroindolizine-3-carboxylate The compound prepared in Example 19 (400 mg) was dissolved in acetonitrile (4 mL). N,N-diisopropylethylamine (64.1 μl) was added and the reaction stirred at room temperature for 10 minutes. Tetrabutyl ammonium iodide (164 mg) and 6-cyanopyridine-3-carboxylic acid (67.9 mg) was added and the reaction stirred at 50° C. for 1 h. The reaction mixture was diluted with water and extracted into ethyl acetate. The organic layer was washed with brine, dried and concentrated in vacuo to give the title compound having the following physical properties (196 mg).
LC/MS $t_R$ 2.14 minutes; MS (ES⁺) m/z 493 (M+H)$^a$.

EXAMPLE 442

5-(2-{7-[5-chloro-2-(1H-tetrazol-1-yl)phenyl]-5-oxo-1,2,3,5-tetrahydro-3-indolizinyl}-1H-imidazol-5-yl)-2-pyridinecarboxamide The same operation as in Example 52→Example 117→Example 55→Example 24 was conducted from the compound prepared in Example 441 to give the title compound having the following physical properties.
LC/MS $t_R$ 3.16 minutes; MS (ES⁺) m/z 500 (M+H)$^b$
¹H NMR (500 MHz, DMSO-d₆) δ 12.40 (s, 1 H), 9.69 (s, 1 H), 8.95 (d, 1 H), 8.26-8.15 (m, 1 H), 8.01 (m, 2 H), 7.87-7.74 (m, 4 H), 7.61-7.50 (m, 1 H), 5.98 (s, 1 H), 5.97 (s, 1 H), 5.65 (dd, 1 H), 3.35 (obs. m, 1 H), 3.17 (d, 1 H), 3.08-2.98 (m, 1 H), 2.40-2.30 (m, 1 H).

EXAMPLE 443

4-(2-{7-[5-chloro-2-(1H-tetrazol-1-yl)phenyl]-5-oxo-1,2,3,5-tetrahydro-3-indolizinyl}-1H-imidazol-5-yl)benzenecarbothioamide To a tetrahydrofuran (5 mL) solution of Example 114 (125 mg) was added Lawesson's reagent (71 mg) and the reaction heated at 70° C. overnight. Further Lawesson's reagent (70 mg) was added and the reaction heated at 70° C. for 3 h. On concentration, the residue was suspended in a saturated aqueous solution of sodium hydrogen carbonate (5 mL) and extracted into ethyl acetate. The combined organic layers were washed with brine, dried and concentrated. The residue was purified by column chromatography (0%-20% methanol in dichloromethane) followed by preparative TLC (10% methanol in dichloromethane) to give the title product (4.4 mg) having the following physical properties.
LC/MS $t_R$ 3.22 minutes; MS (ES⁺) m/z 515 (M+H)$^b$
¹H NMR (500 MHz, methanol-d₄) δ 9.28 (s, 1 H), 7.87 (d, 2 H), 7.64-7.56 (m, 5 H), 7.49 (s, 1 H), 6.02 (s, 1 H), 6.00 (s, 1 H), 5.71 (m, 1 H), 3.39-3.31 (m, 1 H), 3.09-3.02 (m, 1 H), 2.62-2.55 (m, 1 H), 2.41-2.33 (m, 1 H).

EXAMPLE 444

(3S)-7-[5-chloro-2-(1H-tetrazol-1-yl)phenyl]-3-{5-[4-(hydroxymethyl)phenyl]-1H-imidazol-2-yl}-2,3-dihydro-5(1H)-indolizinone The same operation as in Example 51→Example 52→Example 371 was conducted from ethyl 4-(2-bromo-acetyl)benzoate [Chem. Pharm. Bull., 54(9), 1318 (2006)] to give the title compound having the following physical properties.
LC/MS $t_R$ 2.84 minutes; MS (ES⁻) m/z 486 (M+H)$^b$
¹H NMR (500 MHz, methanol-d₄) δ 9.38 (s, 1 H), 7.80-7.56 (m, 5 H), 7.37 (br. s, 3 H), 6.15 (s, 1 H), 6.13 (s, 1 H), 5.86-5.75 (m, 1 H), 4.62 (s, 2 H), 3.54-3.40 (m, 1 H), 3.13 (ddd, 1 H), 2.72-2.60 (m, 1 H), 2.48-2.31 (m, 1 H).

EXAMPLE 445

(3S)-3-{4-chloro-5-[4-(hydroxymethyl)phenyl]-1H-imidazol-2-yl}-7-[5-chloro-2-(1H-tetrazol-1-yl)phenyl]-2,3-dihydro-5(1H)-indolizinone The compound prepared in Example 444 (70 mg) was treated using the method as detailed in Example 338 to give the title compound having the following physical properties (47.7 mg).
LC/MS $t_R$ 3.81 minutes; MS (ES⁺) m/z 520 (M+H)$^b$
¹H NMR (500 MHz, methanol-d₄) δ 9.38 (s, 1 H), 7.79-7.67 (m, 5 H), 7.46 (d, 2 H), 6.13 (d, 2 H), 5.74 (dd, 1 H), 4.66 (s, 2 H), 3.52-3.41 (m, 1 H), 3.12 (ddd, 1 H), 2.66 (m, 1 H), 2.46-2.36 (m, 1 H).

EXAMPLE 446

(3S)-3-{4-chloro-5-[4-(1-hydroxyethyl)phenyl]-1H-imidazol-2-yl}-7-[5-chloro-2-(1H-tetrazol-1-yl)phenyl]-2,3-dihydro-5(1H)-indolizinone The compound prepared in Example 166 (73 mg) was treated using the method as detailed in Example 338 to give the title compound having the following physical properties (24.5 mg).
LC/MS $t_R$ 3.93 minutes; MS (ES⁺) m/z 534 (M+H)$^b$
¹H NMR (500 MHz, methanol-d₄) δ 9.39 (s, 1 H), 7.78-7.74 (m, 2 H), 7.72-7.68 (m, 3 H), 7.48 (d, 2 H), 6.13 (d, 2 H), 5.74 (dd, 1 H), 4.89-4.85 (m, 1 H), 3.52-3.42 (m, 1 H), 3.12 (ddd, 1 H), 2.71-2.62 (m, 1 H), 2.41 (dd, 1 H), 1.48 (d, 3 H).

EXAMPLE 447

(3S)-3-{5-[2-chloro-4-(hydroxymethyl)phenyl]-1H-imidazol-2-yl}-7-[5-chloro-2-(1H-tetrazol-1-yl)phenyl]-2,3-dihydro-5(1H)-indolizinone The same operation as in Example 234→Example 51→Example 52→Example 371 was conducted from 2-chloro-4-(methoxycarbonyl)benzoic acid [Bioorg. Med. Chem. Lett., 20(22), 6748 (2010)] to give the title compound having the following physical properties.
LC/MS $t_R$ 3.11 minutes; MS (ES⁺) m/z 521 (M+H)$^b$
¹H NMR (500 MHz, methanol-d₄) δ 9.37 (s, 1 H), 7.85 (br. s, 1 H), 7.78-7.69 (m, 3 H), 7.62-7.50 (m, 2 H), 7.33 (d, 1 H), 6.18 (s, 1 H), 6.12 (s, 1 H), 5.83 (m, 1 H), 4.62 (s, 2 H), 3.54-3.42 (m, 1 H), 3.18-3.08 (m, 1 H), 2.71-2.61 (m, 1 H), 2.54 (br. s, 1 H).

EXAMPLE 448 methyl 5-(1-ethoxyethenyl)pyridine-2-carboxylate

To an N,N-dimethylformamide (10 mL) solution of methyl 5-bromopyridine-2-carboxylate (1.0 g) was added tributyl(1-ethoxyethenyl)stannane (1.72 mL). The mixture was degassed with nitrogen for 5 minutes, tetrakis(triphenylphosphine)palladium(0) (107 mg) added and the mixture heated at 120° C. for 3 hours. On cooling to room temperature, water (30 mL) was added followed by extraction into ethyl acetate. The combined organic layers were washed with brine, dried and concentrated. The residue was purified by column chromatography (0-70% ethyl acetate in heptanes) to give the title product having the following physical properties (618 mg).

LC/MS $t_R$ 1.80 minutes; MS (ES$^+$) m/z 208 (M+H)$^a$ $^1$H NMR (500 MHz, DMSO-d$_6$) δ 8.96 (d, 1 H), 8.16 (dd, 1 H), 8.06 (d, 1 H), 5.08 (d, 1 H), 4.56 (d, 1 H), 3.95 (q, 2 H), 3.89 (s, 3 H), 1.37 (t, 3 H).

EXAMPLE 449 methyl 5-(2-bromoacetyl)pyridine-2-carboxylate

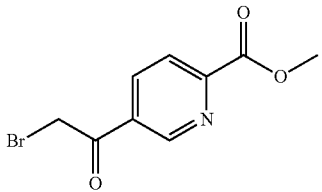

To a tetrahydrofuran (28.7 ml) solution of the compound prepared in Example 448 (594 mg) was added water (1.9 ml) followed by N-bromosuccinimide (510 mg) and the mixture stirred at room temperature for 20 minutes. On concentration, the residue was purified by column chromatography (10-70% ethyl acetate in heptanes) to give the title product having the following physical properties (568 mg).

LC/MS $t_R$ 1.48 minutes; MS (ES$^+$) m/z 258 (M+H)$^a$ $^1$H NMR (500 MHz, DMSO-d$_6$) δ 9.24 (d, 1 H), 8.52 (dd, 1 H), 8.21 (d, 1 H), 5.07 (s, 2 H), 3.97-3.88 (m, 3 H).

EXAMPLE 450

(3S)-7-[5-chloro-2-(1H-tetrazol-1-yl)phenyl]-3-{5-[6-(hydroxymethyl)-3-pyridinyl]-1H-imidazol-2-yl}-2,3-dihydro-5(1H)-indolizinone The same operation as in Example 51→Example 52→Example 371 was conducted from the compound prepared in Example 449 to give the title compound having the following physical properties.

LC/MS $t_R$ 2.78 minutes; MS (ES$^+$) m/z 487 (M+H)$^b$ $^1$H NMR (500 MHz, methanol-d$_4$) δ 9.26 (m, 1 H), 8.77-8.64 (m, 1 H), 8.09-7.98 (m, 1 H), 7.68 (m, 2 H), 7.55 (d, 1 H), 7.49-7.39 (m, 2 H), 6.08 (s, 1 H) 5.95 (s, 1 H), 5.69 (dd, 1 H), 4.62-4.57 (m, 2 H), 3.41-3.30 (m, 1 H), 3.09-2.97 (m, 1 H), 2.61-2.43 (m, 1 H), 2.41-2.30 (m, 1 H).

EXAMPLE 451

(3S)-3-{4-chloro-5-[6-(hydroxymethyl)-3-pyridinyl]-1H-imidazol-2-yl}-7-[5-chloro-2-(1H-tetrazol-1-yl)phenyl]-2,3-dihydro-5(1H)-indolizinone The compound prepared in Example 450 (15 mg) was treated using the method as detailed in Example 338 to give the title compound having the following physical properties (7.4 mg).

LC/MS $t_R$ 3.24 minutes; MS (ES$^+$) m/z 521 (M+H)$^b$ $^1$H NMR (500 MHz, methanol-d$_4$) δ 9.40 (s, 1 H), 8.88 (m, 1 H), 8.19 (m, 1 H), 7.76 (m, 2 H), 7.71-7.62 (m, 2 H), 6.15 (s, 1 H), 6.11 (s, 1 H), 5.72 (m, 1 H), 4.75 (s, 2 H), 3.52-3.40 (m, 1 H), 3.21-3.10 (m, 1 H), 2.75-2.61 (m, 1 H), 2.47-2.36 (m, 1 H).

EXAMPLE 452 methyl 5-bromo-6-chloropyridine-2-carboxylate

To a stirred solution of 5-bromo-2-(methoxycarbonyl)pyridine-N-oxide [Bioorg. Med. Chem. Lett., 18(4), 1407 (2008)] (2.1 g) in toluene (40 ml) was added phosphorus oxychloride (0.76 mL) and the mixture stirred at 80° C. for 16 h. To the reaction mixture, water (50 mL) was added followed by extraction into ethyl acetate. The combined organic layers were sequentially washed with a saturated aqueous solution of sodium hydrogen carbonate, water and brine then dried and concentrated. The residue was purified by column chromatography (50% ethyl acetate in heptanes) to give the title compound having the following physical properties (0.65 g).

LC/MS $t_R$ 1.81 minutes; MS (ES$^4$) m/z 250 (M+H)$^a$ $^1$H NMR (500 MHz, methanol-d$_4$) δ 8.34 (d, 1 H), 7.98 (d, 1 H), 4.02-3.93 (m, 3 H).

EXAMPLE 453

(3S)-3-{5-[2-chloro-6-(hydroxymethyl)-3-pyridinyl]-1H-imidazol-2-yl}-7-[5-chloro-2-(1H-tetrazol-1-yl)phenyl]-2,3-dihydro-5(1H)-indolizinone The same operation as in Example 448→Example 449→Example 51→Example 52→Example 371 was conducted from the compound prepared in Example 452 to give the title compound having the following physical properties.

LC/MS $t_R$ 3.24 minutes; MS (ES$^+$) m/z 521 (M+H)$^b$ $^1$H NMR (500 MHz, methanol-d$_4$) δ 9.26 (s, 1 H), 8.31-8.22 (m, 1 H), 7.63-7.55 (m, 4 H), 7.46 (d, 1 H), 6.09 (s, 1 H), 5.91 (s, 1 H), 5.71 (m, 1 H), 4.55 (s, 2 H), 3.43-3.31 (m, 1 H), 3.09-2.96 (m, 1 H), 2.62-2.48 (m, 1 H), 2.47-2.36 (m, 1 H).

EXAMPLE 454

N-[4-(2-{7-[5-chloro-2-(1H-tetrazol-1-yl)phenyl]-5-oxo-1,2,3,5-tetrahydro-3-indolizinyl}-1H-imidazol-5-yl)phenyl]-4-methoxybutanamide The compound prepared in Example 127 (105 mg) was treated with 4-methoxybutanoic acid (33 µL) following the method of Example 133 to give the title compound having the following physical properties (37.3 mg).

LC/MS $t_R$ 3.24 minutes; MS (ES$^+$) m/z 571 (M+H)$^b$ $^1$H NMR (500 MHz, methanol-d$_4$) δ 9.35 (s, 1 H), 7.75-7.69 (m, 2 H), 7.69-7.65 (m, 1 H), 7.62-7.53 (m, 4 H), 7.25 (s, 1 H), 6.12 (s, 1 H), 6.08 (s, 1 H), 5.77 (dd, 1 H), 3.46 (t, 2 H), 3.48-3.39 (m, 1 H), 3.34 (s, 3 H), 3.09 (ddd, 1 H), 2.68-2.58 (m, 1 H), 2.44 (t, 2 H), 2.50-2.41 (m, 1 H), 1.94 (quintet, 1 H).

EXAMPLE 455

(3S)-7-[5-chloro-2-(1H-1,2,3,4-tetrazol-1-yl)phenyl]-3-[5-(4-nitrophenyl)-1H-imidazol-2-yl]-1,2,3,5-tetrahydroindolizin-5-one The same operation as in Example 51→Example 52 was conducted from 2-bromo-1-(4-nitrophenyl)ethanone to give the title compound having the following physical properties.
LC/MS $t_R$ 1.90 minute; MS (ES$^+$) m/z 520 (M+H)$^a$.

EXAMPLE 456

(3S)-3-[5-(4-aminophenyl)-1H-imidazol-2-yl]-7-[5-chloro-2-(1H-1,2,3,4-tetrazol-1-yl)phenyl]-1,2,3,5-tetrahydroindolizin-5-one The compound prepared in Example 455 (4.26 g) was treated as detailed in Example 74 to give the title compound having the following physical properties (1.76 g). LC/MS $t_R$ 1.36 minutes; MS (ES$^+$) m/z 471 (M+H)$^a$.

EXAMPLE 457(1) to Example 457(5)

The compounds of the present invention having the following physical data were synthesised from the compound prepared in Example 456 and the corresponding acid chlorides or anhydrides using the method as detailed in Example 128.

EXAMPLE 457(1)

N-[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]acetamide LC/MS $t_R$ 2.90 minutes; MS (ES$^+$) m/z 513 (M+H)$^b$
$^1$H NMR (500 MHz, methanol-d$_4$) δ 9.36 (s, 1 H), 7.75-7.71 (m, 2 H), 7.70-7.66 (m, 1 H), 7.66-7.49 (m, 4 H), 7.36-7.14 (m, 1 H), 6.13 (s, 1 H), 6.09 (s, 1 H), 5.78 (dd, 1 H), 3.49-3.39 (m, 1 H), 3.10 (ddd, 1 H), 2.68-2.59 (m, 1 H), 2.47 (br. s, 1 H), 2.13 (s, 3 H).

Example 457(2)

N-[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]-2-fluoroacetamide LC/MS $t_R$ 2.99 minutes; MS (ES$^+$) m/z 531 (M+H)$^b$
$^1$H NMR (500 MHz, DMSO-d$_6$) δ 12.09 (s, 1 H), 10.06 (s, 1 H), 9.69 (s, 1 H), 7.83-7.76 (m, 3 H), 7.70-7.56 (m, 4 H), 7.44 (d, 1 H), 5.97 (s, 1 H), 5.95 (s, 1 H), 5.62 (dd, 1 H), 4.96 (d, 2 H), 3.47-3.36 (m, 2 H), 3.04-2.94 (m, 1 H), 2.38-2.30 (m, 1 H).

EXAMPLE 457(3)

N-[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]-2,2-difluoroacetamide LC/MS $t_R$ 3.15 minutes; MS (ES$^+$) m/z 549 (M+H)$^b$
$^1$H NMR (500 MHz, methanol-d$_4$) δ 9.36 (s, 1 H), 7.75-7.60 (m, 7 H), 7.33 (br. s, 1 H), 6.13 (s, 1 H), 6.09 (s, 1 H), 6.16 (t, 1 H), 5.78 (dd, 1 H), 3.49-3.40 (m, 1 H), 3.10 (ddd, 1 H), 2.68-2.59 (m, 1 H), 2.48 (br. s, 1 H).

EXAMPLE 457(4)

N-[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]tetrahydro-3-furancarboxamide LC/MS $t_R$ 2.98 minutes; MS (ES$^+$) m/z 569 (M+H)$^b$
$^1$H NMR (500 MHz, methanol-d$_4$) δ 9.36 (s, 1 H), 7.72 (m, 2 H), 7.70-7.66 (m, 1 H), 7.58 (br. s, 4 H), 7.29 (br. s, 1 H), 6.12 (s, 1 H), 6.09 (s, 1 H), 5.78 (dd, 1 H), 4.06-4.00 (m, 1 H), 3.96-3.87 (m, 2 H), 3.86-3.80 (m, 1 H), 3.49-3.39 (m, 1 H), 3.23-3.16 (m, 1 H), 3.10 (ddd, 1 H), 2.68-2.58 (m, 1 H), 2.46 (br. s, 1 H), 2.20 (m, 2 H).

EXAMPLE 457(5)

N-[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]tetrahydro-2H-pyran-4-carboxamide LC/MS $t_R$ 3.03 minutes; MS (ES$^+$) m/z 583 (M+H)$^b$
$^1$H NMR (500 MHz, methanol-d$_4$) δ 9.35 (s, 1 H), 7.76-7.70 (m, 2 H), 7.70-7.65 (m, 1 H), 7.65-7.48 (m, 4 H), 7.35-7.10 (m, 1 H), 6.12 (br. s, 1 H), 6.08 (br. s, 1 H), 5.78 (d, 1 H), 4.05-3.97 (m, 2 H), 3.53-3.39 (m, 3 H), 3.14-3.05 (m, 1 H), 2.69-2.58 (m, 2 H), 2.55-2.37 (m, 1 H), 1.91-1.80 (m, 2 H), 1.80-1.73 (m, 2 H).

EXAMPLE 458 formic acid—N-[4-(2-{(3S)-7-[5-chloro-2-(1H-tetrazol-1-yl)phenyl]-5-oxo-1,2,3,5-tetrahydro-3-indolizinyl}-4-fluoro-1H-imidazol-5-yl)phenyl]acetamide (1:1)

The compound prepared in Example 457(1) (70 mg) was treated as detailed in Example 364 to give the title compound having the following physical properties (14 mg).
LC/MS $t_R$ 3.79 minutes; MS (ES$^+$) m/z 531 (M+H), 553 (M+Na)$^b$
$^1$H NMR (500 MHz, methanol-d$_4$) δ 9.36 (s, 1 H), 7.76-7.71 (m, 2 H), 7.70-7.66 (m, 1 H), 7.61 (d, 2 H), 7.50 (d, 2 H), 6.12 (s, 1 H), 6.09 (s, 1 H), 5.69 (dd, 1 H), 3.47-3.39 (m, 1 H), 3.10 (ddd, 1 H), 2.67-2.58 (m, 1 H), 2.40-2.34 (m, 1 H), 2.13 (s, 3 H).

EXAMPLE 459 formic acid—N-[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]ethanethioamide (1:1)

To a tetrahydrofuran solution (2 mL) of the compound prepared in Example 457(1) (70 mg) was added Lawesson's reagent (55 mg) and the mixture heated at 50° C. for 2 hours, then warmed to 70° C. and stirred 3 hours. Further Lawesson's reagent (55 mg) was added and the mixture cooled to 50° C. and stirred 16 hours. An additional portion of Lawesson's reagent (55 mg) was added, the mixture stirred 50° C. for 6 hours, then further Lawesson's reagent (55 mg) added and the mixture stirred at 50° C. for 16 hours. On cooling to room temperature, the mixture was diluted with a saturated aqueous solution of sodium hydrogen carbonate (20 mL) and extracted into ethyl acetate. The combined organic layers were dried and concentrated and the residue purified by column chromatography (0-6% methanol in dichloromethane) followed by high performance liquid chromatography [5 to 100% mobile phase B (0.1% formic acid in acetonitrile) in mobile phase A (0.1% aqueous formic acid)] to give the title compound having the following physical properties (17 mg).

LC/MS $t_R$ 3.17 minutes; MS (ES$^+$) m/z 529 (M+H)$^b$ $^1$H NMR (500 MHz, DMSO-d$_6$) δ 12.16 (br. s, 1 H), 11.64-11.51 (m, 1 H), 9.70 (s, 1 H), 7.84-7.76 (m, 5 H), 7.74-7.66 (m, 2 H), 7.51 (br. s, 1 H), 5.97 (s, 1 H), 5.95 (s, 1 H), 5.62 (d, 1 H), 3.56-3.24 (m, 1 H), 3.04-2.96 (m, 1 H), 2.59 (s, 3 H), 2.53-2.50 (m, 1 H), 2.35-2.28 (m, 1 H).

EXAMPLE 460

N-[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]formamide A mixture of acetic anhydride (28 μL) and formic acid (14 μL) was stirred at 60° C. for 2 hours. On cooling to room temperature, this solution was added to a stirred tetrahydrofuran solution (2 mL) of the compound prepared in Example 456 (80 mg) and this mixture stirred at room temperature for 1 hour 30 minutes. To the reaction mixture, water (20 mL) was added followed by extraction into ethyl acetate. The combined organic layers were dried and concentrated and the residue purified by column chromatography (0-8% methanol in dichloromethane) to give the title compound having the following physical properties (53 mg).

LC/MS $t_R$ 2.87 minutes; MS (ES$^+$) m/z 499 (M+H)$^b$ $^1$H NMR (500 MHz, methanol-d$_4$) δ 9.36 (s, 1 H), 8.26 (s, 1 H), 7.79-7.52 (m, 7 H), 7.36-7.16 (m, 1 H), 6.13 (s, 1 H), 6.09 (s, 1 H), 5.78 (dd, 1 H), 3.50-3.39 (m, 1 H), 3.11 (ddd, 1 H), 2.70-2.58 (m, 1 H), 2.55-2.39 (m, 1 H).

EXAMPLE 461

N-[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]-N-hydroxyacetamide To an N,N-dimethylformamide solution (30 mL) of the compound prepared in Example 455 (150 mg) was added water (1 mL), ammonium chloride (64 mg) and zinc dust (78 mg) and the mixture stirred at room temperature for 1 hour and 30 minutes. To the reaction mixture, water (15 mL) was added followed by extraction into dichloromethane. The combined organic layers were dried and concentrated. To a dichloromethane (10 mL) solution of this crude residue was added N,N-diisopropylethylamine (53 μL) and acetyl chloride (21 μL) and the mixture stirred at room temperature for 45 minutes. An additional aliquot of acetyl chloride (21 μL) was added and the mixture stirred at room temperature for a further 2 hours before diluting with water (30 mL) and extraction into ethyl acetate. The combined organic layers were dried and concentrated and the residue purified by column chromatography (0-10% methanol in dichloromethane) to give the title compound having the following physical properties (33 mg).

LC/MS $t_R$ 2.93 minutes; MS (ES$^+$) m/z 529 (M+H)$^b$ $^1$H NMR (500 MHz, methanol-d$_4$) δ 9.35 (s, 1 H), 7.78-7.52 (m, 7 H), 7.31 (br. s, 1 H), 6.11 (s, 1 H), 6.08 (s, 1 H), 5.78 (dd, 1 H), 3.49-3.39 (m, 1 H), 3.09 (ddd, 1 H), 2.68-2.57 (m, 1 H), 2.50-2.42 (m, 1 H), 2.29 (br. s, 3 H).

EXAMPLE 462

(1E)-N-[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]-1\r-hydroxyethanimidamide To an ethanol suspension (1 mL) of the compound prepared in Example 456 (80 mg) was added ethyl N-hydroxyethenecarboximidate (35 mg) and the mixture stirred at 80° C. for 3 days. On concentration the residue was purified by column chromatography (0-6% methanol in dichloromethane) to give the title compound having the following physical properties (13 mg).

LC/MS $t_R$ 2.72 minutes; MS (ES$^+$) m/z 528 (M+H), 264.5 (M/2+H)$^b$ $^1$H NMR (500 MHz, methanol-d$_4$) δ 9.36 (s, 1 H), 7.73 (m, 2 H), 7.70-7.66 (m, 1 H), 7.66-7.56 (m, 2 H), 7.27 (br. s, 1 H), 7.13 (d, 2 H), 6.13 (s, 1 H), 6.09 (s, 1 H), 5.78 (dd, 1 H), 3.50-3.40 (m, 1 H), 3.11 (ddd, 1 H), 2.69-2.59 (m, 1 H), 2.47 (br. s, 1 H), 1.93 (s, 3 H).

EXAMPLE 463 formic acid—(1E)-N-[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]-N'-methoxyethanimidamide (2:1)

The compound prepared in Example 456 (80 mg) was treated as detailed in Example 462 using ethyl N-methoxyethenecarboximidate [Tetrahedron, 40(19), 3769 (1984)] in place of N-hydroxyacetimidate to give the title compound having the following physical properties (2.4 mg).

LC/MS $t_R$ 2.99 minutes; MS (ES$^+$) m/z 542 (M+H), 271.5 (M/2+H)$^b$ $^1$H NMR (500 MHz, methanol-d$_4$) δ 9.37 (s, 1 H), 7.76-7.72 (m, 2 H), 7.71-7.67 (m, 1 H), 7.62 (d, 2 H), 7.28 (s, 1 H), 7.12 (d, 2 H), 6.13 (s, 1 H), 6.10 (s, 1 H), 5.78 (dd, 1 H), 3.78 (s, 3 H), 3.49-3.40 (m, 1 H), 3.15-3.07 (m, 1 H), 2.67-2.59 (m, 1 H), 2.51-2.43 (m, 1 H), 1.89 (s, 2 H).

EXAMPLE 464

N-[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]-3-hydroxy-3-methylbutanamide The compound prepared in Example 456 (80 mg) was treated with 3-hydroxy-3-methyl butyric acid (22 mg) following the method of Example 133 to give the title compound having the following physical properties (26 mg).

LC/MS $t_R$ 2.99 minutes; MS (ES$^+$) m/z 571 (M+H)$^b$ $^1$H NMR (500 MHz, methanol-d$_4$) δ 9.36 (s, 1 H), 7.75-7.71 (m, 2 H), 7.70-7.66 (m, 1 H), 7.66-7.52 (m, 4 H), 7.36-7.16 (m, 1 H), 6.13 (s, 1 H), 6.09 (s, 1 H), 5.78 (dd, 1 H), 3.50-3.40 (m, 1 H), 3.11 (ddd, 1 H), 2.69-2.59 (m, 1 H), 2.52 (s, 2 H), 2.53-2.40 (m, 1 H), 1.33 (s, 6 H).

EXAMPLE 465

3-{[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]amino}-3-oxopropanoic acid The same operation as in Example 134→Example 135 was conducted from the compound prepared in Example 456 to give the title compound having the following physical properties.

LC/MS $t_R$ 2.84 minutes; MS (ES+) m/z 557 (M+H)[b]

$^1$H NMR (500 MHz, DMSO-$d_6$) δ 12.08 (br. s, 1 H), 10.53 (br. s, 1 H), 9.69 (s, 1 H), 7.93-7.74 (m, 3 H), 7.68-7.49 (m, 4 H), 7.41 (br. s, 1 H), 5.97 (s, 1 H), 5.95 (s, 1 H), 5.61 (dd, 1 H), 3.51-3.27 (m, 1 H), 3.24 (s, 2 H), 3.06-2.94 (m, 1 H), 2.52-2.44 (m, 1 H), 2.37-2.27 (m, 1 H).

EXAMPLE 466

4-{[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]amino}-4-oxobutanoic acid To a stirred dichloromethane solution (2 mL) of the compound prepared in Example 456 (60 mg) was added triethylamine (274) and succinic anhydride (19 mg) and the mixture stirred at room temperature for 16 hours. To the reaction mixture, water (10 mL) and dichloromethane (10 mL) were added and the resultant precipitate isolated by filtration to give the title compound having the following physical properties (24 mg).

LC/MS $t_R$ 2.84 minutes; MS (ES+) m/z 570 (M+H)[b]

$^1$H NMR (500 MHz, DMSO-$d_6$) δ 12.06 (br. s, 1 H), 9.94 (s, 1 H), 9.69 (s, 1 H), 7.82-7.77 (m, 3 H), 7.63-7.52 (m, 4 H), 7.41 (d, 1 H), 5.97 (s, 1 H), 5.95 (s, 1 H), 5.61 (d, 1 H), 3.43-3.37 (m, 1 H), 3.03-2.96 (m, 1 H), 2.57-2.50 (m, 5 H), 2.38-2.30 (m, 1 H).

EXAMPLE 467

4-{[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]amino}-2,2-dimethyl-4-oxobutanoic acid The compound prepared in Example 456 (50 mg) was treated with 2,2-dimethylsuccinic anhydride (18 μL) following the method of Example 466 to give the title compound having the following physical properties (13 mg).

LC/MS $t_R$ 3.05 minutes; MS (ES+) m/z 599 (M+H)[b]

$^1$H NMR (500 MHz, methanol-$d_4$) δ 9.39 (s, 1 H), 7.75 (dd, 1 H), 7.72 (d, 1 H), 7.69 (d, 1 H), 7.68-7.60 (m, 5 H), 6.16 (s, 1 H), 6.14 (s, 1 H), 5.86 (dd, 1 H), 3.43-3.36 (m, 1 H), 3.35 (s, 2 H), 3.26-3.15 (m, 1 H), 2.87-2.77 (m, 1 H), 2.69 (s, 2 H), 2.49-2.39 (m, 1 H), 1.31 (s, 6 H).

EXAMPLE 468

4-{[4-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)phenyl]amino}-2,2-dimethyl-4-oxobutanoic acid The compound prepared in Example 467 (17 mg) was treated as detailed in Example 44 to give the title compound having the following physical properties (6.3 mg).

LC/MS $t_R$ 3.87 minutes; MS (ES+) m/z 633 (M+H)[b]

NMR analysis showed a 2:1 ratio of tautomers.

Major tautomer: $^1$H-NMR (500 MHz, DMSO-$d_6$) δ 12.90 (s, 1 H), 12.05 (br. s, 1 H), 10.02 (s, 1 H), 9.71 (s, 1 H), 7.84-7.77 (m, 3 H), 7.66 (d, 2 H), 7.61 (d, 2 H), 5.99 (s, 1 H), 5.93 (s, 1 H), 5.56 (dd, 1 H), 3.30-3.23 (m, 1 H), 3.04-2.95 (m, 1 H), 2.59 (s, 2 H), 2.55-2.46 (obs. m, 1 H), 2.23-2.16 (m, 1 H), 1.21 (s, 6 H).

Minor tautomer: $^1$H-NMR (500 MHz, DMSO-$d_6$) δ 12.90 (s, 1 H), 12.05 (br. s, 1 H), 9.88 (br. s, 1 H), 9.69 (s, 1 H), 7.84-7.77 (m, 3 H), 7.61-7.30 (m, 4 H), 5.99 (s, 1 H), 5.96 (s, 1 H), 5.67-5.59 (m, 1 H), 3.30-3.23 (m, 1 H), 3.04-2.95 (m, 1 H), 2.57 (s, 2 H), 2.55-2.46 (obs. m, 1 H), 2.35-2.25 (m, 1 H), 1.20 (s, 6 H).

EXAMPLE 469

N-[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]-2-(2-methoxyethoxy)acetamide The compound prepared in Example 456 (80 mg) was treated with (2-methoxyethoxy)acetic acid (21 μL) following the method of Example 133 to give the title compound having the following physical properties (18.4 mg).

LC/MS $t_R$ 3.07 minutes; MS (ES+) m/z 587 (M+H)[b]

$^1$H NMR (500 MHz, DMSO-$d_6$) δ 12.09 (br. s, 1 H), 9.69 (s, 1 H), 9.60 (s, 1 H), 7.84-7.76 (m, 3 H), 7.64 (d, 2 H), 7.59 (d, 2 H), 7.43 (s, 1 H), 5.97 (s, 1 H), 5.95 (s, 1 H), 5.61 (d, 1 H), 4.06 (s, 2 H), 3.70-3.64 (m, 2 H), 3.56-3.50 (m, 2 H), 3.46-3.28 (obs. m, 1 H), 3.30 (s, 3 H), 3.00 (dd, 1 H), 2.58-2.44 (obs. m, 1 H), 2.38-2.28 (m, 1 H).

EXAMPLE 470

(3S)-3-[5-(4-aminophenyl)-4-chloro-1H-imidazol-2-yl]-7-[5-chloro-2-(1H-1,2,3,4-tetrazol-1-yl)phenyl]-1,2,3,5-tetrahydroindolizin-5-one The same operation as in Example 51→Example 52→Example 338→Example 74 was conducted from 2-bromo-1-(4-nitrophenyl)ethanone to give the title compound having the following physical properties.

LC/MS $t_R$ 2.07 minutes; MS (ES+) m/z 535 (M+H)[a].

EXAMPLE 471

N-[4-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)phenyl]-2-(2-methoxyethoxy)acetamide The compound prepared in Example 470 (50 mg) was treated with (2-methoxyethoxy)acetic acid (8.4 μL) following the method of Example 133 to give the title compound having the following physical properties (13.8 mg).

LC/MS $t_R$ 3.95 minutes; MS (ES+) m/z 621 (M+H)[b]

$^1$H NMR (500 MHz, DMSO-$d_6$) δ 12.93 (br. s, 1 H), 9.78 (s, 1 H), 9.71 (s, 1 H), 7.85-7.78 (m, 3 H), 7.73 (d, 2 H), 7.65 (d, 2 H), 5.99 (s, 1 H), 5.93 (s, 1 H), 5.57 (dd, 1 H), 4.09 (s, 2 H), 3.68 (dd, 2 H), 3.54 (dd, 2 H), 3.30 (s, 3 H), 3.29-3.22 (m, 1 H), 2.99 (dd, 1 H), 2.58-2.43 (obs. m, 1 H), 2.19 (t, 1 H).

EXAMPLE 472

5-{[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]amino}-5-oxopentanoic acid—formic acid (1:1)

The compound prepared in Example 456 (170 mg) was treated with glutaric anhydride (62 mg) following the method of Example 466 to give the title compound after purification by high performance liquid chromatography [5 to 100% mobile phase B (0.1% formic acid in acetonitrile) in mobile phase A (0.1% aqueous formic acid)] as the formic acid salt having the following physical properties (19 mg).
LC/MS $t_R$ 2.90 minutes; MS (ES$^+$) m/z 585 (M+H)$^b$
$^1$H NMR (500 MHz, DMSO-d$_6$) δ 12.07 (br. s, 1 H), 9.89 (br. s, 1 H), 9.69 (s, 1 H), 8.19 (s, 1 H), 7.84-7.77 (m, 3 H), 7.59 (d, 2 H), 7.56 (d, 2 H), 7.38 (br. s, 1 H), 5.97 (s, 1 H), 5.94 (s, 1 H), 5.61 (dd, 1 H), 3.42-3.32 (obs. m, 1 H), 2.99 (dd, 1 H), 2.55-2.44 (obs. m, 1 H), 2.34 (t, 2 H), 2.38-2.24 (obs. m, 1 H), 2.27 (t, 2 H), 1.80 (quintet, 2 H).

EXAMPLE 473

5-{[4-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)phenyl]amino}-5-oxopentanoic acid The compound prepared in Example 470 (100 mg) was treated with glutaric anhydride (23 mg) following the method of Example 466 to give the title compound having the following physical properties (30.8 mg).
LC/MS $t_R$ 3.70 minutes; MS (ES$^+$) m/z 619 (M+H)$^b$
$^1$H NMR (500 MHz, DMSO-d$_6$) δ 12.91 (br. s, 1 H), 10.10 (s, 1 H), 9.71 (s, 1 H), 7.84-7.77 (m, 3 H), 7.68 (d, 2 H), 7.62 (d, 2 H), 5.98 (s, 1 H), 5.93 (s, 1 H), 5.56 (dd, 1 H), 3.29-3.23 (m, 1 H), 2.98 (ddd, 1 H), 2.54 (s, 3 H), 2.53-2.47 (obs. m, 1 H), 2.36 (t, 2 H), 2.26 (t, 2 H), 2.22-2.16 (m, 1 H), 1.80 (quintet, 1 H).

EXAMPLE 474 methyl 5-{[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]amino}-5-oxopentanoate A methanol (5 mL) solution of the compound prepared in Example 472 (125 mg) was stirred at room temperature for 2 days. The reaction mixture was concentrated and the residue purified by column chromatography (0% to 20% methanol in dichloromethane) to afford the title compound having the following physical properties (9 mg).
LC/MS $t_R$ 3.15 minutes; MS (ES$^+$) m/z 599 (M+H)$^b$
$^1$H NMR (500 MHz, methanol-d$_4$) δ 9.35 (s, 1 H), 7.75-7.70 (m, 2 H), 7.69-7.65 (m, 1 H), 7.59 (d, 2 H), 7.56 (d, 2 H), 7.25 (br. s, 1 H), 6.12 (s, 1 H), 6.08 (s, 1 H), 5.78 (dd, 1 H), 3.66 (s, 3 H), 3.49-3.39 (m, 1 H), 3.10 (ddd, 1 H), 2.63 (qd, 1 H), 2.43 (t, 4 H), 2.50-2.38 (obs. m, 1 H), 1.99 (quintet, 2 H).

EXAMPLE 475

N-[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]-N'-methylpentanediamide The compound prepared in Example 472 (98 mg) was treated with methylamine hydrochloride (19 mg) following the method of Example 114 to give the title compound having the following physical properties (2.0 mg).
LC/MS $t_R$ 2.89 minutes; MS (ES$^+$) m/z 598 (M+H), 300 (M+2H)/2$^b$
$^1$H NMR (500 MHz, DMSO-d$_6$) δ 12.06 (s, 1 H), 9.85 (s, 1 H), 9.69 (s, 1 H), 7.83-7.78 (m, 3 H), 7.77-7.71 (m, 1 H), 7.63-7.58 (m, 2 H), 7.57-7.52 (m, 2 H), 7.40 (d, 1 H), 5.97 (s, 1 H), 5.95 (s, 1 H), 5.61 (dd, 1 H), 3.44-3.35 (m, 1 H), 3.00 (dd, 1 H), 2.56 (d, 3 H), 2.54-2.45 (obs. m, 1 H), 2.28 (t, 2 H), 2.35-2.25 (m, 1 H), 2.10 (t, 2 H), 1.84-1.75 (m, 2 H).

EXAMPLE 476

(2-{[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]amino}-2-oxoethoxy)acetic acid The compound prepared in Example 456 (170 mg) was treated with diglycolic anhydride (63 mg) following the method of Example 466 to give the title compound having the following physical properties (87 mg).
LC/MS $t_R$ 2.89 minutes; MS (ES$^+$) m/z 587 (M+H)$^b$
$^1$H NMR (500 MHz, DMSO-d$_6$) δ 12.54 (br. s, 1 H), 12.08 (br. s, 1 H), 10.03 (br. s, 1 H), 9.69 (s, 1 H), 7.84-7.74 (m, 3 H), 7.62 (br. s, 4 H), 7.43 (br. s, 1 H), 5.97 (s, 1 H), 5.95 (s, 1 H), 5.62 (d, 1 H), 4.19 (s, 2 H), 4.16 (s, 2 H), 3.52-3.17 (obs. m, 1 H), 2.99 (dd, 1 H), 2.57-2.46 (obs. m, 1 H), 2.38-2.21 (m, 1 H).

EXAMPLE 477

(2-{[4-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)phenyl]amino}-2-oxoethoxy)acetic acid The compound prepared in Example 470 (100 mg) was treated with diglycolic anhydride (23 mg) following the method of Example 466 to give the title compound having the following physical properties (25.2 mg).
LC/MS $t_R$ 3.68 minutes; MS (ES$^+$) m/z 621 (M+H)$^b$
$^1$H NMR (500 MHz, DMSO-d$_6$) δ 12.93 (s, 1 H), 10.88 (br. s, 1 H), 9.71 (s, 1 H), 7.84-7.78 (m, 3 H), 7.77 (d, 2 H), 7.64 (d, 2 H), 5.98 (s, 1 H), 5.94 (s, 1 H), 5.57 (dd, 1 H), 4.16 (s, 2 H), 4.12 (s, 2 H), 3.32-3.23 (obs. m, 1 H), 2.98 (ddd, 1 H), 2.56-2.45 (obs. m, 1 H), 2.24-2.16 (m, 1 H).

EXAMPLE 478 methyl(2-{[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]amino}-2-oxoethoxy)acetate The compound prepared in Example 476 (100 mg) was treated as detailed in Example 474 to give the title compound having the following physical properties (17 mg).
LC/MS $t_R$ 3.10 minutes; MS (ES$^+$) m/z 601 (M+H)$^b$
$^1$H NMR (500 MHz, methanol-d$_4$) δ 9.36 (s, 1 H), 7.76-7.71 (m, 2 H), 7.70-7.54 (m, 5 H), 7.34 (br. s, 1 H), 6.13 (s, 1 H), 6.09 (s, 1 H), 5.78 (dd, 1 H), 4.34 (s, 2 H), 4.22 (s, 2 H), 3.79 (s, 3 H), 3.51-3.38 (m, 1 H), 3.10 (ddd, 1 H), 2.63 (qd, 1 H), 2.57-2.31 (m, 1 H).

EXAMPLE 479 methyl[4-(2-{(3S)-7-[5-chloro-2-(1H-tetrazol-1-yl)phenyl]-5-oxo-1,2,3,5-tetrahydro-3-indolizinyl}-4-fluoro-1H-imidazol-5-yl)phenyl]carbamate The compound prepared in Example 266 (200 mg) was treated as detailed in Example 364 to give the title compound having the following physical properties (23 mg).
LC/MS $t_R$ 4.02 minutes; MS (ES$^+$) m/z 547 (M+H)$^b$
$^1$H NMR (500 MHz, DMSO-d$_6$) δ 12.75 (s, 1 H), 9.75 (s, 1 H), 9.71 (s, 1 H), 7.88-7.76 (m, 3 H), 7.56-7.44 (m, 4 H), 5.98 (s, 1 H), 5.94 (s, 1 H), 5.54 (d, 1 H), 3.68 (s, 3 H), 3.32-3.23 (m, 1 H), 3.05-2.93 (m, 1 H), 2.59-2.52 (m, 1 H), 2.23-2.12 (m, 1 H).

EXAMPLE 480 methyl[4-(4-bromo-2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate To a cooled (0° C.) dichloromethane (3 mL) solution of the compound prepared in Example 266 (200 mg) was added N-bromosuccinimide (67.3 mg) and the mixture stirred at 0° C. for 75 minutes. The reaction mixture was then diluted with dichloromethane and washed with water. The aqueous layer was extracted twice more with dichloromethane and the combined organic layers washed with saturated saline, dried and concentrated. The residue was purified by column chromatography (0 to 10% methanol in dichloromethane) to give the title compound having the following physical properties (54.2 mg).
LC/MS $t_R$ 4.08 minutes; MS (ES$^+$) m/z 607 (M+H)$^b$
$^1$H NMR (500 MHz, methanol-d$_4$) δ 9.35 (s, 1 H), 7.74-7.69 (m, 2 H), 7.69-7.65 (m, 1 H), 7.63-7.58 (m, 2 H), 7.54-7.47 (m, 2 H), 6.12 (s, 1 H), 6.07 (s, 1 H), 5.72 (dd, 1 H), 3.75 (s, 3 H), 3.49-3.36 (m, 1 H), 3.16-3.00 (m, 1 H), 2.70-2.54 (m, 1 H), 2.47-2.29 (m, 1 H).

EXAMPLE 481

2-methoxyethyl N-[4-(2-bromopropanoyl)phenyl]carbamate

The same operation as in Example 77→Example 78 was conducted from 1(4-aminophenyl)propan-1-one to give the title compound having the following physical properties (Note: in the step corresponding to Example 77 in the operation, 2-methoxy ethyl chloroformate was used).
LC/MS $t_R$ 1.91 minutes; MS (ES$^+$) m/z 330 and 332 (M+H)$^a$.

EXAMPLE 482

2-methoxyethyl[4-(2-{(3S)-7-[5-chloro-2-(1H-tetrazol-1-yl)phenyl]-5-oxo-1,2,3,5-tetrahydro-3-indolizinyl}-4-methyl-1H-imidazol-5-yl)phenyl]carbamate The same operation as in Example 51→Example 52 was conducted from the compound prepared in Example 481 to give the title compound having the following physical properties.
LC/MS $t_R$ 3.01 minutes; MS (ES$^+$) m/z 587 (M+H)$^b$
$^1$H NMR (500 MHz, methanol-d$_4$) δ 9.38 (s, 1 H), 7.77-7.73 (m, 2 H), 7.72-7.67 (m, 1 H), 7.49 (br. s, 2 H), 7.47-7.39 (m, 2 H), 6.12 (2×s, 2 H), 5.74 (dd, 1 H), 4.34-4.24 (m, 2 H), 3.69-3.63 (m, 2 H), 3.46 (td, 1 H), 3.42-3.40 (m, 3 H), 3.11 (ddd, 1 H), 2.69-2.59 (m, 1 H), 2.45 (br. s, 1 H), 2.33 (br. s, 3 H).

EXAMPLE 483

2-methoxyethyl[4-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate The same operation as in Example 128→Example 44 was conducted from the compound prepared in Example 456 to give the title compound having the following physical properties. (Note: in the step corresponding to Example 128 in the operation, 2-methoxyethyl chloroformate was used).
LC/MS $t_R$ 4.07 minutes; MS (ES$^+$) m/z 607 (M+H)$^b$
$^1$H NMR (500 MHz, methanol-d$_4$) δ 9.35 (s, 1 H), 7.77-7.63 (m, 3 H), 7.60 (d, 2 H), 7.50 (d, 2 H), 6.11 (s, 1 H), 6.07 (s, 1 H), 5.71 (dd, 1 H), 4.33-4.21 (m, 2 H), 3.70-3.60 (m, 2 H), 3.53-3.35 (obs. m, 1H), 3.39 (s, 3 H), 3.17-2.99 (m, 1 H), 2.72-2.53 (m, 1 H), 2.46-2.29 (m, 1 H).

EXAMPLE 484 formic acid—2-fluoroethyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate (1:1)

To a 1,4-dioxane (1 mL) solution of the compound prepared in Example 456 (100 mg) was added N,N-diisopropylethylamine (106 µl) followed by a solution of 2-fluoroethyl chloroformate (50 µL) in 1,4-dioxane (1 mL) and the mixture stirred at room temperature for 16 hours. The reaction mixture was concentrated, the residue re-dissolved in methanol (2 mL) and concentrated ammonia solution (59 µL) added. The mixture was stirred for 1 hour at room temperature then concentrated. The residue was suspended in water (25 mL) and extracted into ethyl acetate. The combined organic layers were washed with saturated saline, dried and concentrated. The residue was purified by column chromatography (0-10% methanol in dichloromethane) followed by high performance liquid chromatography [5 to 100% mobile phase B (0.1% formic acid in acetonitrile) in mobile phase A (0.1% aqueous formic acid)] to give the title compound as the formic acid salt having the following physical properties (61.1 mg).
LC/MS $t_R$ 3.13 minutes; MS (ES$^+$) m/z 561 (M+H)$^b$
$^1$H NMR (500 MHz, methanol-d$_4$) δ 9.36 (s, 1 H), 8.17 (s, 0.5 formate salt), 7.74-7.72 (m, 2 H), 7.69-7.67 (m, 1 H), 7.57 (d, 2 H), 7.45 (d, 2 H), 7.25 (s, 1 H), 6.13 (s, 1 H), 6.09 (s, 1 H), 5.78 (dd, 1 H), 4.71-4.66 (m, 1 H), 4.61-4.56 (m, 1 H), 4.42-4.38 (m, 1 H), 4.36-4.32 (m, 1 H), 3.48-3.41 (m, 1 H), 3.11 (ddd, 1 H), 2.68-2.60 (m, 1 H), 2.49-2.43 (m, 1 H).

EXAMPLE 485

2-ethoxyethyl chloroformate

To a cooled (0° C.) tetrahydrofuran (50 mL) solution of triphosgene (4.11 g) was added N,N-diisopropylethylamine (0.11 mL) and the mixture stirred for 5 minutes. A solution of 2-ethoxyethanol (2.68 mL) in tetrahydrofuran (15 mL) was added slowly and the mixture stirred at room temperature for 18 hours. The reaction mixture was concentrated and the residue dissolved in ethyl acetate (100 mL) and washed sequentially with 0.2 M hydrochloric acid and saturated saline, dried and concentrated to afford the title compound having the following physical properties (2.77 g).

$^1$H NMR (250 MHz, CDCl$_3$) δ 4.49-4.41 (m, 2 H), 3.74-3.67 (m, 2 H), 3.56 (q, 2 H), 1.23 (t, 3 H).

EXAMPLE 486

2-ethoxyethyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate The compound prepared in Example 456 (100 mg) was treated with 2-ethoxyethyl chloroformate (100 mg) as detailed in Example 484 to give the title compound having the following physical properties (48.8 mg).

LC/MS $t_R$ 3.26 minutes; MS (ES$^+$) m/z 587 (M+H)$^b$ $^1$H NMR (500 MHz, methanol-d$_4$) δ 9.34 (s, 1 H), 7.75-7.69 (m, 2 H), 7.68-7.63 (m, 1 H), 7.55 (app. br. s, 2 H), 7.42 (d, 2 H), 7.22 (br. s, 1 H), 6.11 (s, 1 H), 6.06 (s, 1 H), 5.77 (dd, 1 H), 4.30-4.18 (m, 2 H), 3.72-3.64 (m, 2 H), 3.56 (q, 2 H), 3.43 (td, 1 H), 3.08 (ddd, 1 H), 2.61 (qd, 1 H), 2.45 (app. br. s, 1 H), 1.20 (t, 3 H).

EXAMPLE 487

3-methoxypropyl chloroformate

2-Methoxypropan-1-ol (2.49 g) was treated as detailed in Example 485 to give the title compound having the following physical properties (3.97 g).

$^1$H NMR (500 MHz, CDCl$_3$) δ 4.43 (t, 2 H), 3.48 (t, 2 H), 3.35 (s, 3 H), 2.00 (quintet, 2 H).

EXAMPLE 488

3-methoxypropyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate The compound prepared in Example 456 (100 mg) was treated with 3-methoxypropyl chloroformate (81 mg) as detailed in Example 484 to give the title compound having the following physical properties (95 mg).

LC/MS $t_R$ 3.19 minutes; MS (ES$^+$) m/z 587 (M+H)$^b$ $^1$H NMR (250 MHz, methanol-d$_4$) δ 9.35 (s, 1 H), 7.75-7.70 (m, 2 H), 7.69-7.65 (m, 1 H), 7.56 (app. br. s, 2 H), 7.44 (app. br. s, 2 H), 7.25 (br. s, 1 H), 6.12 (s, 1 H), 6.08 (s, 1 H), 5.77 (dd, 1 H), 4.20 (t, 2 H), 3.52 (t, 2 H), 3.49-3.38 (m, 1 H), 3.34 (s, 3 H), 3.10 (ddd, 1 H), 2.63 (qd, 1 H), 2.47 (app. br. s, 1 H), 1.94 (quintet, 2 H).

EXAMPLE 489

2-(2-methoxyethoxy)-ethyl chloroformate 2-(2-Methoxyethoxy)-ethan-1-ol (1 g) was treated as detailed in Example 485 to give the title compound having the following physical properties (1.20 g).

$^1$H NMR (250 MHz, CDCl$_3$) δ 4.52-4.41 (m, 2 H), 3.83-3.73 (m, 2 H), 3.70-3.62 (m, 2 H), 3.61-3.52 (m, 2 H), 3.39 (s, 3 H).

EXAMPLE 490 formic acid—2-(2-methoxyethoxy)ethyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate (1:1)

The compound prepared in Example 456 (100 mg) was treated with 2-(2-methoxyethoxy)-ethyl chloroformate (96.9 mg) as detailed in Example 484 to give the title compound having the following physical properties (95 mg).

LC/MS $t_R$ 3.09 minutes; MS (ES$^+$) m/z 617 (M+H)$^b$ $^1$H NMR (500 MHz, methanol-d$_4$) δ 9.36 (s, 1 H), 7.76-7.71 (m, 2 H), 7.70-7.66 (m, 1 H), 7.57 (d, 2 H), 7.44 (d, 2 H), 7.23 (s, 1 H), 6.13 (s, 1 H), 6.09 (s, 1 H), 5.78 (dd, 1 H), 4.30-4.24 (m, 2 H), 3.76-3.71 (m, 2 H), 3.68-3.64 (m, 2 H), 3.58-3.53 (m, 2 H), 3.49-3.39 (m, 1 H), 3.36 (s, 3 H), 3.10 (ddd, 1 H), 2.64 (qd, 1 H), 2.50-2.42 (m, 1 H).

EXAMPLE 491

2-(2-ethoxyethoxy)-ethyl chloroformate 2-(2-Ethoxyethoxy)-ethan-1-ol (1 g) was treated as detailed in Example 485 to give the title compound having the following physical properties (1.26 g).

$^1$H NMR (250 MHz, CDCl$_3$) δ 4.48-4.39 (m, 2 H), 3.79-3.71 (m, 2 H), 3.67-3.60 (m, 2 H), 3.60-3.54 (m, 2 H), 3.51 (q, 2 H), 1.19 (t, 3 H).

EXAMPLE 492 formic acid—2-(2-ethoxyethoxy)ethyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate (1:1)

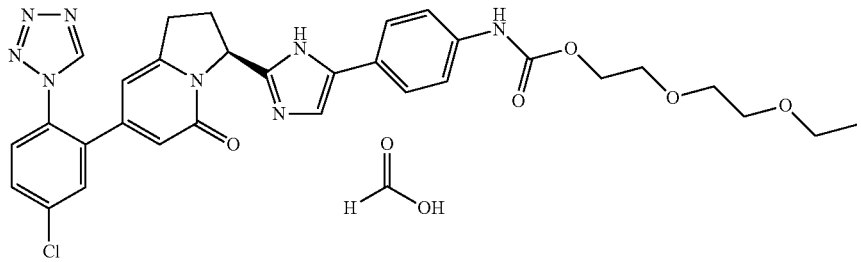

The compound prepared in Example 456 (100 mg) was treated with the chloroformate prepared in 2-(2ethoxyethoxy)chloroformate (104 mg) as detailed in Example 484 to give the title compound having the following physical properties (95 mg).

LC/MS $t_R$ 3.22 minutes; MS (ES$^+$) m/z 631 (M+H)$^b$
$^1$H NMR (500 MHz, methanol-d$_4$) δ 9.36 (s, 1 H), 7.76-7.71 (m, 2 H), 7.70-7.65 (m, 1 H), 7.57 (d, 2 H), 7.45 (d, 2 H), 7.23 (s, 1 H), 6.13 (s, 1 H), 6.09 (s, 1 H), 5.78 (dd, 1 H), 4.30-4.26 (m, 2 H), 3.77-3.72 (m, 2 H), 3.68-3.64 (m, 2 H), 3.61-3.58 (m, 2 H), 3.53 (q, 2 H), 3.49-3.39 (m, 1 H), 3.10 (ddd, 1 H), 2.64 (qd, 1 H), 2.50-2.41 (m, 1 H), 1.18 (t, 3 H).

EXAMPLE 493(1) to Example 493(5)

The compounds of the present invention having the following physical data were prepared from the compound prepared in Example 456 using the corresponding alcohols in the process of Example 485→Example 484.

EXAMPLE 493(1)

(2S)-2-methoxypropyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate LC/MS $t_R$ 3.16 minutes; MS (ES$^+$) m/z 587 (M+H)$^b$
$^1$H NMR (500 MHz, methanol-d$_4$) δ 9.34 (s, 1 H), 7.74-7.69 (m, 2 H), 7.68-7.64 (m, 1 H), 7.63-7.35 (m, 4 H), 7.34-7.00 (m, 1 H), 6.11 (s, 1 H), 6.07 (s, 1 H), 5.77 (dd, 1 H), 4.15 (dd, 1 H), 4.07 (dd, 1 H), 3.68-3.59 (m, 1 H), 3.40 (s, 3 H), 3.50-3.36 (m, 1 H), 3.09 (ddd, 1 H), 2.62 (qd, 1 H), 2.46 (app. br. s, 1 H), 1.20 (d, 3 H).

EXAMPLE 493(2)

1-methoxy-2-propanyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate LC/MS $t_R$ 3.20 minutes; MS (ES$^+$) m/z 587 (M+H)$^b$
$^1$H NMR (500 MHz, methanol-d$_4$) δ 9.36 (s, 1 H), 7.75-7.71 (m, 2 H), 7.70-7.65 (m, 1 H), 7.56 (d, 2 H), 7.44 (d, 2 H), 7.22 (br. s, 1 H), 6.13 (s, 1 H), 6.09 (s, 1 H), 5.78 (dd, 1 H), 5.05-4.98 (m, 1 H), 3.51 (dd, 1 H), 3.49-3.39 (m, 2 H), 3.38 (s, 3 H), 3.10 (ddd, 1 H), 2.63 (qd, 1 H), 2.47 (app. br, s, 1 H), 1.27 (d, 3 H).

EXAMPLE 493(3)

tetrahydro-3-furanyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate LC/MS $t_R$ 3.05 minutes; MS (ES$^+$) m/z 585 (M+H)$^b$
$^1$H NMR (500 MHz, methanol-d$_4$) δ 9.36 (s, 1 H), 7.76-7.71 (m, 2 H), 7.70-7.65 (m, 1 H), 7.56 (app. br. s, 2 H), 7.44 (app. br. s, 2 H), 7.23 (br. s, 1 H), 6.13 (s, 1 H), 6.09 (s, 1 H), 5.78 (dd, 1 H), 5.31 (dd, 1 H), 3.97-3.83 (m, 4 H), 3.44 (td, 1 H), 3.10 (ddd, 1 H), 2.63 (qd, 1 H), 2.46 (app. hr. s, 1 H), 2.23 (dtd, 1 H), 2.14-2.04 (m, 1 H).

EXAMPLE 493(4)

formic acid—tetrahydro-3-furanylmethyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate (1:1)

LC/MS $t_R$ 3.14 minutes; MS (ES$^+$) m/z 599 (M+H)$^b$
$^1$H NMR (500 MHz, methanol-d$_4$) δ 9.36 (s, 1 H), 7.76-7.72 (m, 2 H), 7.70-7.65 (m, 1 H), 7.57 (d, 2 H), 7.45 (d, 2 H), 7.25 (s, 1 H), 6.13 (s, 1 H), 6.09 (s, 1 H), 5.78 (dd, 1 H), 4.16 (dd, 1 H), 4.05 (dd, 1 H), 3.92-3.83 (m, 2 H), 3.76 (q, 1 H), 3.64 (dd, 1 H), 3.49-3.39 (m, 1 H), 3.11 (ddd, 1 H), 2.70-2.59 (m, 2 H), 2.50-2.41 (m, 1 H), 2.14-2.05 (m, 1 H), 1.72 (dt, 1 H).

EXAMPLE 493(5)

tetrahydro-2-furanylmethyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate LC/MS $t_R$ 3.16 minutes; MS (ES$^+$) m/z 599 (M+H)$^b$
$^1$H NMR (250 MHz, methanol-d$_4$) δ 9.36 (s, 1 H), 7.76-7.70 (m, 2 H), 7.70-7.64 (m, 1 H), 7.56 (app. br. s, 2 H), 7.46 (app. hr. s, 2 H), 7.27 (br. s, 1 H), 6.12 (s, 1 H), 6.08 (s, 1 H), 5.78 (dd, 1 H), 4.23-4.02 (m, 3 H), 3.95-3.73 (m, 2 H), 3.44 (td, 1 H), 3.10 (ddd, 1 H), 2.73-2.55 (m, 1 H), 2.46 (app. br. s, 1 H), 2.13-1.84 (m, 3 H), 1.80-1.63 (m, 1 H).

EXAMPLE 494

3-oxetanyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate To an acetonitrile (26 mL) suspension of N,N'-disuccinimidyl carbonate (2.05 g) was added oxetan-3-ol (0.44 mL) and the mixture stirred at room temperature for 5 minutes. To the reaction mixture, N,N-diisopropylethylamine (3.3 mL) was added and the mixture stirred at room temperature for 20 hours to form a 0.25 M solution of the mixed carbonate product.

To a 2.5 M solution in acetonitrile (4 mL) of the above prepared mixed carbonate, the compound prepared in Example 456 (100 mg) and N,N-diisopropylethylamine (105 µL) were added sequentially and the mixture stirred at room temperature for 18 hours. On concentration, the residue was dissolved in methanol (2 mL) whereupon concentrated aqueous ammonia (60 µL) was added and the mixture stirred at room temperature for 2 hours. The reaction mixture was concentrated, the residue suspended in saturated sodium carbonate solution (30 mL) and extracted into ethyl acetate. The combined organic layers were washed with saturated saline, dried and concentrated. The residue was purified by high performance liquid chromatography (5 to 100% acetonitrile in water) to afford the title compound having the following physical properties (72 mg). LC/MS $t_R$ 2.98 minutes; MS (ES$^+$) m/z 571 (M+H)[b]

$^1$H NMR (500 MHz, methanol-d$_4$) δ 9.34 (s, 1 H), 7.74-7.69 (m, 2 H), 7.68-7.64 (m, 1 H), 7.56 (app. br. s, 2 H), 7.43 (d, 2 H), 7.23 (br. s, 1 H), 6.12 (s, 1 H), 6.07 (s, 1 H), 5.77 (dd, 1 H), 5.51-5.42 (m, 1 H), 4.92 (t, 2 H), 4.68 (dd, 2 H), 3.49-3.36 (m, 1 H), 3.09 (ddd, 1 H), 2.62 (qd, 1 H), 2.45 (app. br. s, 1 H).

EXAMPLE 495(1) to Example 495(3)

The compounds of the present invention having the following physical data were synthesised from the compound prepared in Example 456 and the corresponding alcohols using the method as detailed in Example 494.

EXAMPLE 495(1)

2-(dimethylamino)ethyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate LC/MS $t_R$ 2.50 minutes; MS (ES") m/z 586 (M+H), 293 (M+2H)/2[b]

$^1$H NMR (500 MHz, methanol-d$_4$) δ 9.35 (s, 1 H), 7.76-7.69 (m, 2 H), 7.69-7.64 (m, 1 H), 7.56 (app. br. s, 2 H), 7.45 (app. br. s, 2 H), 7.23 (br. s, 1 H), 6.12 (s, 1 H), 6.07 (s, 1 H), 5.77 (dd, 1 H), 4.26 (t, 2 H), 3.50-3.37 (m, 1 H), 3.09 (ddd, 1 H), 2.67 (t, 2 H), 2.65-2.56 (m, 1 H), 2.55-2.38 (m, 1 H), 2.33 (s, 6 H).

EXAMPLE 495(2)

2-(oxan-2-yloxy)ethyl N-(4-{2-[(3S)-7-[5-chloro-2-(1H-1,2,3,4-tetrazol-1-yl)phenyl]-5-oxo-1,2,3,5-tetrahydroindolizin-3-yl]-1H-imidazol-5-yl}phenyl)carbamate LC/MS $t_R$ 1.70 minutes; MS (ES$^+$) m/z 643 (M+H), 559 (M-C$_5$H$_7$O+2H)/2[a].

EXAMPLE 495(3)

3-hydroxy-3-methylbutyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate LC/MS $t_R$ 3.08 minutes; MS (ES$^+$) m/z 601 (M+H)[b]

$^1$H NMR (500 MHz, methanol-d$_4$) δ 9.35 (s, 1 H), 7.75-7.70 (m, 2 H), 7.69-7.65 (m, 1 H), 7.65-7.36 (m, 4 H), 7.35-7.00 (m, 1 H), 6.12 (s, 1 H), 6.08 (s, 1 H), 5.77 (d, 1 H), 4.28 (t, 2 H), 3.51-3.35 (m, 1 H), 3.10 (ddd, 1 H), 2.66-2.57 (m, 1 H), 2.57-2.28 (m, 1 H), 1.88 (t, 2 H), 1.26 (s, 6 H).

EXAMPLE 496

2-hydroxyethyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate To a 1,4-dioxane (4 mL) solution of the compound prepared in Example 495(2) (137 mg) was added 1 M hydrochloric acid (2.1 mL) and the mixture stirred at room temperature for 4 hours. To the reaction mixture, a saturated aqueous solution of sodium hydrogen carbonate (25 mL) was added followed by extraction into ethyl acetate. The combined organic layers were washed with saturated saline, dried and concentrated. The residue was purified by high performance liquid chromatography (5 to 100% acetonitrile in water) to afford the title compound having the following physical properties (24 mg).

LC/MS $t_R$ 2.84 minutes; MS (ES$^+$) m/z 559 (M+H)[b]

$^1$H NMR (500 MHz, DMSO-d$_6$) δ 12.04 (br. s, 1 H), 9.68 (s, 1 H), 9.63 (br. s, 1 H), 7.83-7.75 (m, 3 H), 7.59 (d, 2 H), 7.42 (d, 2 H), 7.39 (s, 1 H), 5.97 (s, 1 H), 5.95 (s, 1 H), 5.61 (d, 1 H), 4.81 (t, 1 H), 4.09 (t, 2 H), 3.61 (q, 2 H), 3.44-3.37 (m, 1 H), 2.99 (dd, 1 H), 2.56-2.43 (obs. m, 1 H), 2.38-2.29 (m, 1 H).

EXAMPLE 497

2-hydroxy-2-methylpropyl N-(4-acetylphenyl)carbamate

To a dichloromethane (62 mL) solution of 4-acetylphenyl isocyanate (1 g) and 4-dimethylaminopyridine (76 mg) was added 2-methylpropane-1,2-diol [patent US2010249087] (0.58 g) and the mixture stirred at room temperature for 3 hours. The reaction mixture was concentrated and the residue purified by column chromatography (0 to 100% EtOAc in heptanes) to give the title compound having the following physical properties (0.92 g).

LC/MS $t_R$ 1.49 minutes; MS (ES$^+$) m/z 252 (M+H)[a].

EXAMPLE 498

2-hydroxy-2-methylpropyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate The same operation as in Example 204→Example 51→Example 52 was conducted from the compound prepared in Example 497 to give the title compound having the following physical properties.

LC/MS $t_R$ 3.01 minutes; MS (ES$^+$) m/z 587 (M+H)$^b$ $^1$H NMR (500 MHz, methanol-d$_4$) δ 9.35 (s, 1 H), 7.76-7.69 (m, 2 H), 7.69-7.65 (m, 1 H), 7.64-7.36 (m, 4 H), 7.36-7.01 (m, 1 H), 6.12 (s, 1 H), 6.08 (s, 1 H), 5.78 (dd, 1 H), 3.99 (s, 2 H), 3.51-3.35 (m, 1 H), 3.09 (ddd, 1 H), 2.68-2.56 (m, 1 H), 2.56-2.28 (m, 1 H), 1.26 (s, 6 H).

EXAMPLE 499

2-hydroxy-2-methylpropyl[4-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate The compound prepared in Example 498 (104 mg) was treated as detailed in Example 338 to give the title compound having the following physical properties (59.7 mg).

LC/MS $t_R$ 3.94 minutes; MS (ES$^+$) m/z 621 (M+H)$^b$ $^1$H NMR (500 MHz, methanol-d$_4$) δ 9.36 (s, 1 H), 7.75-7.70 (m, 2 H), 7.69-7.65 (m, 1 H), 7.61 (d, 2 H), 7.53 (d, 2 H), 6.12 (s, 1 H), 6.08 (s, 1 H), 5.71 (dd, 1 H), 4.00 (s, 2 H), 3.44 (td, 1 H), 3.09 (ddd, 1 H), 2.63 (qd, 1 H), 2.43-2.32 (m, 1 H), 1.27 (s, 6 H).

EXAMPLE 500

3-[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]-1,1-dimethylurea The compound prepared in Example 456 (400 mg) was treated as detailed in Example 132 to give the title compound having the following physical properties (128 mg).

LC/MS $t_R$ 2.90 minutes; MS (ES$^+$) m/z 542 (M+H)$^b$ $^1$H NMR (250 MHz, methanol-d$_4$) δ 9.36 (s, 1H), 7.77-7.65 (m, 3 H), 7.56 (d, 2 H), 7.39 (d, 2 H), 7.22 (s, 1 H), 6.12 (s, 1 H), 6.09 (d, 1 H), 5.78 (dd, 1 H), 3.53-3.36 (m, 1 H), 3.18-3.07 (m, 1 H), 3.02 (s, 6 H), 2.70-2.54 (m, 1 H), 2.53-2.36 (m, 1 H).

EXAMPLE 501

3-[4-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)phenyl]-1,1-dimethylurea The compound prepared in Example 500 (48 mg) was treated as detailed in Example 338 to give the title compound having the following physical properties (28.6 mg).

LC/MS $t_R$ 3.85 minutes; MS (ES$^+$) m/z 576 and 578 (M+H)$^b$ $^1$H NMR (500 MHz, methanol-d$_4$) δ 9.36 (s, 1 H), 7.73 (app. s, 1 H), 7.72 (dd, 1 H), 7.68 (d, 1 H), 7.59 (d, 2 H), 7.48 (d, 2 H), 6.12 (s, 1 H), 6.08 (s, 1 H), 5.70 (dd, 1 H), 3.43 (td, 1 H), 3.09 (ddd, 1 H), 3.03 (s, 6 H), 2.68-2.58 (m, 1 H), 2.43-2.33 (m, 1 H).

EXAMPLE 502 formic acid—3-[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]-1-methoxy-1-methylurea (1:1)

The compound prepared in Example 456 (100 mg) was treated as detailed in Example 484 using N-methoxy-N-methylcarbamoyl chloride [Chem. Pharm. Bull., 55(2), 328 (2007)] in place of 2-fluoroethyl chloroformate to give the title compound having the following physical properties (13.9 mg).

LC/MS $t_R$ 3.11 minutes; MS (ES$^+$) m/z 558 (M+H)$^b$ $^1$H NMR (500 MHz, methanol-d$_4$) δ 9.36 (s, 1 H), 7.75-7.71 (m, 2 H), 7.70-7.65 (m, 1 H), 7.59 (d, 2 H), 7.51 (d, 2 H), 7.25 (s, 1 H), 6.13 (s, 1 H), 6.09 (s, 1 H), 5.78 (dd, 1 H), 3.76 (s, 3 H), 3.44 (td, 1 H), 3.15 (s, 3 H), 3.10 (ddd, 1 H), 2.69-2.58 (m, 1 H), 2.51-2.41 (m, 1 H).

EXAMPLE 503

3-[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]-1-(2-methoxyethyl)-1-methylurea The compound prepared in Example 456 (50 mg) was treated as detailed in Example 484 using N-(2-methoxyethyl)-N-methylcarbamoyl chloride [Chem. Pharm. Bull., 55(2), 328 (2007)] in place of 2-fluoroethyl chloroformate to give the title compound having the following physical properties (10.4 mg).

LC/MS $t_R$ 3.05 minutes; MS (ES$^+$) m/z 586 (M+H)$^b$ $^1$H NMR (500 MHz, methanol-d$_4$) δ 9.36 (s, 1 H), 7.76-7.71 (m, 2 H), 7.70-7.65 (m, 1 H), 7.56 (d, 2 H), 7.35 (d, 2 H), 7.22 (s, 1 H), 6.13 (s, 1 H), 6.09 (s, 1 H), 5.78 (dd, 1 H), 3.63-3.59 (m, 2 H), 3.58-3.54 (m, 2 H), 3.49-3.39 (m, 1 H), 3.43 (s, 3 H), 3.10 (ddd, 1 H), 3.05 (s, 3 H), 2.69-2.58 (m, 1 H), 2.50-2.42 (m, 1 H).

EXAMPLE 504

3-[4-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)phenyl]-1-(2-methoxyethyl)-1-methylurea The compound prepared in Example 503 (43.5 mg) was treated as detailed in Example 338 to give the title compound having the following physical properties (17.4 mg).

LC/MS $t_R$ 4.01 minutes; MS (ES$^+$) m/z 620 (M+H)$^b$ $^1$H NMR (500 MHz, methanol-d$_4$) δ 9.37 (s, 1 H), 7.77-7.71 (m, 2 H), 7.68 (dd, 1 H), 7.61 (d, 2 H), 7.43 (d, 2 H), 6.13 (s, 1 H), 6.09 (s, 1 H), 5.71 (dd, 1 H), 3.64-3.60 (m, 2 H), 3.59-3.55 (m, 2 H), 3.50-3.38 (m, 1 H), 3.43 (s, 3 H), 3.14-3.07 (m, 1 H), 3.06 (s, 3 H), 2.69-2.59 (m, 1 H), 2.43-2.34 (m, 1 H).

EXAMPLE 505

1-(1,2,3,4-tetrahydroquinolin-1-yl)ethan-1-one

To a dichloromethane (25 mL) solution of 1,2,3,4-tetrahydroquinoline (1.89 mL) was added N,N-diisopropylethylamine (3.12 mL). To the cooled (0° C.) reaction mixture, acetyl chloride (1.18 mL) was added and the mixture stirred at room temperature for 2 hours. To the reaction mixture, dichloromethane was added and the organic layer washed with water. The aqueous layer was extracted with dichloromethane and the combined organic layers washed with saturated saline, dried and concentrated to give the title compound having the following physical properties (2.97 g).

LC/MS $t_R$ 1.66 minutes; MS (ES$^+$) m/z 176 (M+H)$^a$.

EXAMPLE 506

1-(1-acetyl-1,2,3,4-tetrahydroquinolin-6-yl)-2-bromoethan-1-one

To a cooled (0° C.) 1,2-dichloroethane (15 mL) solution of aluminum trichloride (5.65 g) was added bromoacetyl bromide (2.96 mL) and the mixture was stirred at 0° C. for 30 minutes. The compound prepared in Example 505 (2.97 g) was added and the mixture stirred at room temperature for 2 hours. On concentration, the residue was suspended in water followed by extraction into ethyl acetate. The combined organic layers were washed with saturated saline, dried and concentrated to obtain the title compound having the following physical properties (6.17 g).

LC/MS $t_R$ 1.75 minutes; MS (ES$^+$) m/z 296 (M+H)$^a$.

EXAMPLE 507

2-chloro-1-(1,2,3,4-tetrahydroquinolin-6-yl)ethan-1-one hydrochloride

The compound prepared in Example 506 (6.17 g) was suspended in concentrated hydrochloric acid (100 mL) and the mixture stirred at 80° C. for 2 hours. On concentration, the residue was triturated with a 1:1 mixture of ethyl acetate and dichloromethane, the resultant precipitate being collected by filtration to give the title compound having the following physical properties (1.08 g).

LC/MS $t_R$ 1.78 minutes; MS (ES$^+$) m/z 210 (M+H)$^a$.

EXAMPLE 508

(3S)-7-[5-chloro-2-(1H-tetrazol-1-yl)phenyl]-3-[5-(1,2,3,4-tetrahydro-6-quinolinyl)-1H-imidazol-2-yl]-2,3-dihydro-5(1H)-indolizinone The same operation as in Example 51→Example 52 was conducted from the compound prepared in Example 507 to give the title compound having the following physical properties.

LC/MS $t_R$ 3.05 minutes; MS (ES$^+$) m/z 511 (M+H)$^b$ $^1$H NMR (500 MHz, DMSO-d$_6$) δ 11.76 (s, 1 H), 9.69 (s, 1 H), 7.95-7.58 (m, 3 H), 7.23-7.06 (m, 3 H), 6.38 (d, 1 H), 6.00-5.90 (m, 2 H), 5.64-5.51 (m, 2 H), 3.52-3.48 (m, 1 H), 3.22-3.11 (m, 2 H), 3.04-2.91 (m, 1 H), 2.71-2.66 (m, 2 H), 2.51-2.48 (m, 1 H), 2.38-2.31 (m, 1 H), 1.87-1.74 (m, 2 H).

EXAMPLE 509

6-(2-{(3S)-7-[5-chloro-2-(1H-tetrazol-1-yl)phenyl]-5-oxo-1,2,3,5-tetrahydro-3-indolizinyl}-4-methyl-1H-imidazol-5-yl)-3-methyl-3,4-dihydro-2(1H)-quinazolinone The same operation as in Example 506→Example 51→Example 52 was conducted from 3-methyl-3,4-dihydroquinazolin-2(1H)-one to give the title compound having the following physical properties. (Note: in the step corresponding to Example 506 in the operation, 2-bromopropanoyl bromide was used).

LC/MS $t_R$ 2.93 minutes; MS (ES$^+$) m/z 554 (M+H)$^b$ $^1$H NMR (500 MHz, DMSO-d$_6$) δ 11.86 (s, 1 H), 9.69 (s, 1 H), 9.15 (s, 1 H), 7.92-7.67 (m, 3 H), 7.36-7.12 (m, 2 H), 6.76 (d, 1 H), 5.96 (s, 1 H), 5.94 (s, 1 H), 5.63-5.46 (m, 1 H), 4.44 (s, 2 H), 3.43-3.36 (m, 1 H), 3.02-2.92 (m, 1 H), 2.87 (s, 3 H), 2.48-2.42 (m, 1 H), 2.30 (s, 3 H), 2.24-2.16 (m, 1 H).

EXAMPLE 510

2-amino-5-(2-{(3S)-7-[5-chloro-2-(1H-tetrazol-1-yl)phenyl]-5-oxo-1,2,3,5-tetrahydro-3-indolizinyl}-1H-imidazol-5-yl)benzoic acid The same operation as in Example 448→Example 449→Example 51→Example 52 was conducted from 6-bromo-2H-3,1-benzoxazine-2,4(1H)-dione to give the title compound having the following physical properties. (Note: in the step corresponding to Example 52 in the operation, the deprotection of the amino acid is also accomplished).

LC/MS $t_R$ 2.80 minutes; MS (ES$^+$) m/z 514 (M+H)$^a$ $^1$H NMR (500 MHz, methanol-d$_4$) δ 9.38 (s, 1 H), 7.85 (s, 1 H), 7.78-7.66 (m, 3 H), 7.50 (d, 1 H), 7.18 (s, 1 H), 6.79 (d, 1 H), 6.12 (d, 2 H), 5.79 (dd, 1 H), 3.52-3.41 (m, 1 H), 3.12 (ddd, 1 H), 2.69-2.59 (m, 1 H), 2.50-2.44 (m, 1 H).

EXAMPLE 511

6-acetyl-2,2-dimethyl-2,4-dihydro-1,3-benzodioxin-4-one

To a solution of 5-acetyl-2-hydroxybenzoic acid (500 mg) in trifluoroacetic acid (4 ml) and acetone (1.2 ml) was added trifluoroacetic anhydride (1.17 ml) and the mixture heated at 90° C. for 16 h. The reaction mixture was concentrated, the residue dissolved in ethyl acetate and washed sequentially with a saturated solution of sodium hydrogen carbonate and saturated saline, dried and concentrated. The residue was purified by column chromatography (0-60% ethyl acetate in heptanes) to afford the title compound having the following physical properties (432 mg).

$^1$H NMR (500 MHz, methanol-d$_4$) δ 8.55 (d, 1 H), 8.27 (dd, 1 H), 7.17 (d, 1 H), 2.63 (s, 3 H), 1.77 (s, 6 H).

EXAMPLE 512

6-(2-bromoacetyl)-2,2-dimethyl-2,4-dihydro-1,3-benzodioxin-4-one

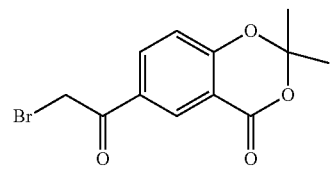 [SMILES: CC1(C)OC(=O)c2cc(C(=O)CBr)ccc2O1]

To a dichloromethane (6 mL) solution of the compound prepared in Example 511 (362 mg) was added acetic acid (0.2 ml) followed by bromine (93 μl) and the mixture stirred at room temperature for 2 hrs. The reaction mixture was concentrated to give the crude title compound having the following physical properties (534 mg).

$^1$H NMR (500 MHz, methanol-d$_4$) δ 8.52-8.45 (m, 1 H), 8.21 (dd, 1 H), 7.11 (d, 1 H), 4.58 (s, 2 H), 1.73-1.64 (s, 6 H).

EXAMPLE 513

(3S)-7-[5-chloro-2-(1H-1,2,3,4-tetrazol-1-yl)phenyl]-3-[5-(2,2-dimethyl-4-oxo-2,4-dihydro-1,3-benzodioxin-6-yl)-1H-imidazol-2-yl]-1,2,3,5-tetrahydroindolizin-5-one The same operation as in Example 51→Example 52 was conducted from the compound prepared in Example 512 to give the title compound having the following physical properties.

LC/MS t$_R$ 1.73 minutes; MS (ES$^+$) m/z 556 (M+H)$^a$.

EXAMPLE 514

5-(2-{(3S)-7-[5-chloro-2-(1H-tetrazol-1-yl)phenyl]-5-oxo-1,2,3,5-tetrahydro-3-indolizinyl}-1H-imidazol-5-yl)-2-hydroxybenzoic acid To a 1,4-dioxane (2 mL) solution of the compound prepared in Example 513 (100 mg) was added a 4 M solution of hydrogen chloride in 1,4-dioxane (2 mL) followed by water (1 mL) and the mixture heated at 60° C. for 3 hours. On cooling to room temperature, the reaction mixture was diluted with ethyl acetate (30 mL) and washed with a saturated aqueous solution of sodium hydrogen carbonate. The combined aqueous layers were treated with concentrated hydrochloric acid until pH 2-3 was attained, extracted once into ethyl acetate then washed twice more with a 1:3 mixture of propan-2-ol and chloroform. The combined organic phases were dried and concentrated and the residue triturated with dichloromethane. The resultant precipitate was collected by filtration to give the title compound having the following physical properties (29.6 mg).

LC/MS t$_R$ 3.06 minutes; MS (ES$^+$) m/z 516 (M+H)$^b$ $^1$H NMR (500 MHz, methanol-d$_4$) δ 9.43 (s, 1 H), 8.29 (d, 1 H), 7.89-7.82 (m, 2 H), 7.81-7.68 (m, 3 H), 7.12 (d, 1 H), 6.21 (s, 1 H), 6.19 (s, 1 H), 5.91 (dd, 1 H), 3.43-3.36 (m, 1 H), 3.31-3.22 (m, 1 H), 2.94-2.81 (m, 1 H), 2.51-2.39 (m, 1 H).

EXAMPLE 515

5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-hydroxybenzoic acid The same operation as in Example 338→Example 514 was conducted from the compound prepared in Example 513 to give the title compound having the following physical properties.

LC/MS t$_R$ 3.92 minutes; MS (ES$^+$) m/z 550 (M+H)$^b$ $^1$H NMR (500 MHz, methanol-d$_4$) δ 9.38 (s, 1 H), 8.25-8.17 (m, 1 H), 7.81-7.64 (m, 4 H), 7.01-6.95 (d, 1 H), 6.13 (s, 1 H), 6.10 (s, 1 H), 5.73 (dd, 1 H), 3.50-3.41 (m, 1 H), 3.11 (ddd, 1 H), 2.66-2.60 (m, 1 H), 2.43-2.33 (m, 1 H).

EXAMPLE 516

5-(2-{(3S)-7-[5-chloro-2-(1H-tetrazol-1-yl)phenyl]-5-oxo-1,2,3,5-tetrahydro-3-indolizinyl}-1H-imidazol-5-yl)-2-methylbenzoic acid The same operation as in Example 139→Example 78→Example 51 (with example 11)→Example 52→Example 8→Example 55→Example 24 was conducted from methyl 5-bromo-2-methylbenzoate to give the title compound having the following physical properties. (Note: in the step corresponding to Example 51 in the operation, the compound prepared in Example 11 was used).

LC/MS t$_R$ 3.15 minutes; MS (ES$^+$) m/z 514 (M+H)$^b$ $^1$H NMR (500 MHz, methanol-d$_4$) δ 9.38 (s, 1 H), 8.20 (m, 1 H), 7.79-7.65 (m, 4 H), 7.35 (s, 1 H), 7.30 (d, 1 H), 6.14 (s, 1 H), 6.14 (s, 1 H), 5.81 (dd, 1 H), 3.55-3.41 (m, 1 H), 3.19-3.08 (m, 1 H), 2.74-2.62 (m, 1 H), 2.58 (s, 3 H), 2.53-2.45 (m, 1 H).

EXAMPLE 517

5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-methylbenzoic acid The compound prepared in Example 516 (90 mg) was treated as detailed in Example 338 to give the title compound having the following physical properties (26 mg).

LC/MS t$_R$ 4.00 minutes; MS (ES$^+$) m/z 548 (M+H)$^b$ $^1$H NMR (500 MHz, methanol-d$_4$) δ 9.39 (s, 1 H), 8.26 (s, 1 H), 7.82-7.67 (m, 4 H), 7.39 (d, 1 H), 6.18 (s, 1 H), 6.08 (s, 1 H), 5.74 (dd, 1 H), 3.51-3.40 (m, 1 H), 3.17-3.07 (m, 1 H), 2.67 (m, 1 H), 2.62 (s, 3 H), 2.40 (d, 1 H).

EXAMPLE 518

(3S)-7-[5-chloro-2-(1H-tetrazol-1-yl)phenyl]-3-{5-[4-(methylsulfonyl)phenyl]-1H-imidazol-2-yl}-2,3-dihydro-5(1H)-indolizinone To a dichloromethane (1 mL) solution of the compound prepared in Example 173(17) (50 mg) was added a solution of meta-chloroperbenzoic acid (45 mg, 77% in water) in dichloromethane (1 mL) and the mixture stirred at room temperature for 45 minutes. To the reaction mixture, water (10 mL) was added followed by extraction into dichloromethane. The combined organic layers were washed with saturated sodium hydrogen carbonate, saturated saline, dried and concentrated. The residue was purified by column chromatography (0-100% ethyl acetate in heptanes, then 0-10% methanol in ethyl acetate) to give the title compound having the following physical properties (53 mg).

LC/MS t$_R$ 3.33 minutes; MS (ES$^+$) m/z 534 (M+H)$^b$ $^1$H NMR (500 MHz, DMSO-d$_6$) δ 12.37 (br. s, 1 H), 9.69 (s, 1 H), 7.94 (d, 2 H), 7.86 (d, 2 H), 7.82-7.74 (m, 4 H), 5.98 (s, 1 H), 5.96 (s, 1 H), 5.64 (dd, 1 H), 3.43-3.27 (obs. m, 1 H), 3.19 (s, 3 H), 3.01 (dd 1 H), 2.55-2.45 (obs. m, 1 H), 2.38-2.29 (m, 1 H).

EXAMPLE 519

(3S)-7-[5-chloro-2-(1H-tetrazol-1-yl)phenyl]-3-(5-{4-[(S)-methylsulfinyl]phenyl}-1H-imidazol-2-yl)-2,3-dihydro-5(1H)-indolizinone To a dichloromethane (8 mL) solution of titanium(IV) isopropoxide (0.3 mL) and diethyl(2S,3S)-2,3-dihydroxybutanedioate (0.34 mL) was added water (18 μL) and the mixture stirred at room temperature for 20 minutes. A dichloromethane (2 mL) solution of the compound prepared in Example 173(17) (0.50 g) was added and the reaction mixture cooled to –20° C. A 2.84 M solution of tert-butyl hydroperoxide in toluene (0.39 mL) [Org. Synth. Coll., 7, 461, 1990] was added and the reaction stood at –18° C. for 20 hours. To the chilled (–20° C.) reaction mixture, water (0.18 mL) was added and the mixture allowed to warm to room temperature over 1.5 hours. Alumina was added and the solids removed by filtration through Celite®, washing the filter cake with dichloromethane. The filtrate was then washed with a saturated aqueous solution of sodium sulphite (30 mL) then saturated saline, dried and concentrated. The residue was purified by column chromatography (50-100% ethyl acetate in heptanes, then 0-20% methanol in ethyl acetate) to give the title compound having the following physical properties (321 mg).

LC/MS $t_R$ 1.81 minutes; MS (ES$^+$) m/z 518 (M+H)$^e$ $^1$H NMR (500 MHz, DMSO-d$_6$) δ 12.32 (br. s, 1 H), 9.69 (s, 1 H), 7.88 (d, 2 H), 7.83-7.75 (m, 3 H), 7.74-7.55 (m, 3 H), 5.98 (s, 1 H), 5.96 (s, 1 H), 5.64 (dd, 1 H), 3.42-3.36 (obs. m, 1 H), 3.01 (ddd 1 H), 2.73 (s, 3 H), 2.57-2.51 (obs. m, 1 H), 2.38-2.28 (m, 1 H).

EXAMPLE 520

(3S)-7-[5-chloro-2-(1H-tetrazol-1-yl)phenyl]-3-(5-{4-[(R)-methylsulfinyl]phenyl}-1H-imidazol-2-yl)-2,3-dihydro-5(1H)-indolizinone The compound prepared in Example 173(17) (0.50 g) was treated as detailed in Example 519 using diethyl(2R,3R)-2,3-dihydroxybutanedioate in place of diethyl(2S,3S)-2,3-dihydroxybutanedioate to give the title compound having the following physical properties (350 mg).

LC/MS $t_R$ 1.81 minutes; MS (ES$^+$) m/z 518 (M+H)$^e$ $^1$H NMR (500 MHz, DMSO-d$_6$) δ 12.32 (br. s, 1 H), 9.69 (s, 1 H), 7.88 (d, 2 H), 7.84-7.76 (m, 3 H), 7.74-7.57 (m, 3 H), 5.98 (s, 1 H), 5.96 (s, 1 H), 5.65 (dd, 1 H), 3.42-3.37 (obs. m, 1 H), 3.01 (dd, 1 H), 2.73 (s, 3 H), 2.57-2.51 (obs. m, 1 H), 2.38-2.27 (m, 1 H).

EXAMPLE 521

(3S)-7-[5-chloro-2-(1H-tetrazol-1-yl)phenyl]-3-{5-[4-(S-methylsulfonimidoyl)phenyl]-1H-imidazol-2-yl}-2,3-dihydro-5(1H)-indolizinone To a dichloromethane (5 mL) solution of the compound prepared in Example 519 (261 mg), rhodium(II)acetate dimer (5.7 mg), magnesium oxide (81 mg), 2,2,2-trifluoroacetamide (114 mg) and (diacetoxyiodo)benzene (243 mg) were added sequentially and the mixture stirred at room temperature for 16 hours. To the reaction mixture, dichloromethane (30 mL) was added and the solids removed by filtration through Celite®, washing the filter cake with dichloromethane. The filtrate was concentrated and the residue dissolved in methanol (5 mL) whereupon potassium carbonate (348 mg) was added and the mixture stirred at room temperature for 2 hours. To the reaction mixture, dichloromethane (30 mL) was added and the solids removed by filtration through Celite®, washing the filter cake with dichloromethane. The filtrate was concentrated and the residue purified by column chromatography (0% to 10% methanol in dichloromethane) followed by high performance liquid chromatography (5 to 100% acetonitrile in 2 mM aqueous ammonium hydrogen carbonate) to give the title compound having the following physical properties (29.2 mg).

LC/MS $t_R$ 3.49 minutes; MS (ES$^+$) m/z 533 (M+H)$^g$ $^1$H NMR (500 MHz, methanol-d$_4$) δ 9.37 (s, 1 H), 8.03 (d, 2 H), 7.98 (d, 2 H), 7.76-7.72 (m, 2 H), 7.71-7.67 (m, 1 H), 7.64 (br. s, 1 H), 6.14 (s, 1 H), 6.11 (s, 1 H), 5.80 (dd, 1 H), 3.46 (td, 1 H), 3.33 (s, 3 H), 3.14 (ddd, 1 H), 2.72-2.61 (m, 1 H), 2.49 (tt, 1 H).

EXAMPLE 522

(3S)-7-[5-chloro-2-(1H-tetrazol-1-yl)phenyl]-3-{5-[4-(S-methylsulfonimidoyl phenyl]-1H-imidazol-2-yl}-2,3-dihydro-5(1H)-indolizinone The compound prepared in Example 520 (296 mg) was treated as detailed in Example 521 to give the title compound having the following physical properties (3.4 mg).

LC/MS $t_R$ 3.47 minutes; MS (ES$^+$) m/z 533 (M+H)$^g$ $^1$H NMR (500 MHz, DMSO-d$_6$) δ 9.36 (s, 1 H), 8.06-7.84 (m, 4 H), 7.76-7.71 (m, 2 H), 7.71-7.66 (m, 1 H), 7.59 (br. s, 1 H), 6.14 (s, 1 H), 6.10 (s, 1 H), 5.79 (dd, 1 H), 3.47 (td, 1 H), 3.16 (s, 3 H), 3.12 (ddd, 1 H), 2.70-2.60 (m, 1 H), 2.51 (app. br. s, 1 H).

EXAMPLE 523

1-(6-amino-2-fluoropyridin-3-yl)ethan-1-one 2-amino-6-fluoro-5-iodopyridine [J. Org. Chem. 71(8), 2922 (2006)] (1.5 g) was treated as detailed in Example 90 to give the title compound having the following physical properties (0.46 g).

LC/MS $t_R$ 1.19 minutes; MS (ES$^+$) m/z 155 (M+H)$^a$.

EXAMPLE 524

1-(6-amino-2-methoxypyridin-3-yl)ethan-1-one

A methanol (3 mL) suspension of the compound prepared in Example 523 (150 mg) and potassium tert-butoxide (546 mg) was heated at 60° C. for 3 hours. On cooling to room temperature, the reaction mixture was diluted with water (20 mL) and extracted into ethyl acetate. The combined organic layers were dried and concentrated to give the title compound having the following properties (138 mg).

LC/MS $t_R$ 1.35 minutes; MS (ES$^+$) m/z 167 (M+H)$^a$.

EXAMPLE 525

(3S)-3-[5-(6-amino-2-methoxy-3-pyridinyl)-1H-imidazol-2-yl]-7-[5-chloro-2-(1H-tetrazol-1-yl)phenyl]-2,3-dihydro-5(1H)-indolizinone The same operation as in Example 204→Example 51→Example 52 was conducted from the compound prepared in Example 524 to give the title compound having the following physical properties.

LC/MS $t_R$ 2.99 minutes; MS (ES$^+$) m/z 502 (M+H)$^b$
$^1$H NMR (500 MHz, methanol-d$_4$) δ 9.36 (s, 1 H), 7.79-7.60 (m, 4 H), 7.12 (br. s, 1 H), 6.21-6.15 (m, 2 H), 6.12-6.07 (m, 1 H), 5.86 (br. s, 1 H), 3.99 (br. s, 3 H), 3.48-3.37 (m, 1 H), 3.16-3.08 (m, 1 H), 2.66-2.55 (m, 2 H).

EXAMPLE 526

(3S)-3-[5-(6-amino-2-fluoro-3-pyridinyl)-4-chloro-1H-imidazol-2-yl]-7-[5-chloro-2-(1H-tetrazol-1-yl)phenyl]-2,3-dihydro-5(1H)-indolizinone The compound prepared in Example 216 (94 mg) was treated as detailed in Example 44 to give the title compound having the following physical properties (38 mg). LC/MS $t_R$ 3.75 minutes; MS (ES$^+$) m/z 524 (M+H)$^b$
$^1$H NMR (500 MHz, methanol-d$_4$) δ 9.35 (s, 1 H), 7.78-7.71 (m, 3 H), 7.70-7.66 (m, 1 H), 6.46 (dd, 1 H), 6.14 (s, 1 H), 6.07 (s, 1 H), 5.72 (dd, 1 H), 3.46-3.37 (m, 1 H), 3.13-3.05 (m, 1 H), 2.67-2.57 (m, 1 H), 2.45-2.38 (m, 1 H).

EXAMPLE 527 methyl[5-(2-{(3S)-7-[5-chloro-2-(1H-tetrazol-1-yl)phenyl]-5-oxo-1,2,3,5-tetrahydro-3-indolizinyl}-1H-imidazol-5-yl)-6-fluoro-2-pyridinyl]carbamate The compound prepared in Example 216 (60 mg) was treated with methyl chloroformate following the method of Example 128 to give the title compound having the following physical properties (24 mg).
LC/MS $t_{it}$ 3.54 minutes; MS (ES$^+$) m/z 548 (M+H)$^b$
$^1$H NMR (500 MHz, methanol-d$_4$) δ 9.35 (s, 1 H), 8.30 (br. s, 1 H), 7.82 (d, 1 H), 7.76-7.70 (m, 2 H), 7.70-7.65 (m, 1 H), 7.32 (br. s, 1 H), 6.14 (s, 1 H), 6.08 (s, 1 H), 5.80 (dd, 1 H), 3.77 (s, 3 H), 3.51-3.40 (m, 1 H), 3.11 (dd, 1 H), 2.68-2.58 (m, 1 H), 2.55-2.47 (m, 1 H).

EXAMPLE 528

N-[6-chloro-5-(2-{(3S)-7-[5-chloro-2-(1H-tetrazol-1-yl)phenyl]-5-oxo-1,2,3,5-tetrahydro-3-indolizinyl}-1H-imidazol-5-yl)-2-pyridinyl]acetamide To a dichloromethane (5 mL) solution of the compound prepared in Example 210 (150 mg) was added triethylamine (83 μL) followed by acetyl chloride (42 μL) and the mixture stirred at room temperature for 2 hours. To the reaction mixture, further triethylamine (83 μL) and acetyl chloride (42 μL) was added and the mixture stirred at room temperature for 16 hours. At this juncture, an additional aliquot of acetyl chloride (42 μL) was added and the mixture stirred at room temperature for 16 hours. A final aliquot of acetyl chloride (42 μL) was then added and the mixture stirred at room temperature for 72 hours.
To the reaction mixture, water (10 mL) was added followed by extraction with dichloromethane. The combined organic layers were dried and concentrated and the residue dissolved in methanol (10 mL). To this methanolic solution, concentrated ammonia solution (0.10 mL) was added and the mixture stirred at room temperature for 1 hour. On concentration, the residue was purified by high performance liquid chromatography (5 to 100% acetonitrile in 2 mM aqueous ammonium hydrogen carbonate) to give the title compound having the following physical properties (28 mg).
LC/MS $t_R$ 3.41 minutes; MS (ES$^+$) m/z 548 (M+H)$^b$ $^1$H NMR (500 MHz, methanol-d$_4$) δ 9.35 (s, 1 H), 8.26 (br. s, 1 H), 8.11 (d, 1 H), 7.76-7.71 (m, 2 H), 7.70-7.66 (m, 1 H), 7.61 (br. s, 1 H), 6.14 (s, 1 H), 6.08 (s, 1 H), 5.81 (d, 1 H), 3.51-3.42 (m, 1 H), 3.11 (dd, 1 H), 2.68-2.59 (m, 1 H), 2.57-2.49 (m, 1 H), 2.16 (s, 3 H).

EXAMPLE 529

2-methoxyethyl[5-(2-{(3S)-7-[5-chloro-2-(1H-tetrazol-1-yl)phenyl]-5-oxo-1,2,3,5-tetrahydro-3-indolizinyl}-1H-imidazol-5-yl)-2-pyridinyl]carbamate The same operation as in Example 51→Example 52→Example 128 was conducted from the compound prepared in Example 193 to give the title compound having the following physical properties. (Note: in the step corresponding to Example 128 in the operation, 2-methoxyethyl chloroformate was used).
LC/MS $t_R$ 3.19 minutes; MS (ES$^+$) m/z 574 (M+H), 288 (M/2+H)$^b$
$^1$H NMR (500 MHz, methanol-d$_4$) δ 9.36 (s, 1 H), 8.56 (br. s, 1 H), 8.01 (br. s, 1 H), 7.88 (d, 1 H), 7.75-7.71 (m, 2 H), 7.70-7.66 (m, 1 H), 7.40 (br. s, 1 H), 6.13 (s, 1 H), 6.09 (s, 1 H), 5.78 (dd, 1 H), 4.33-4.28 (m, 2 H), 3.68-3.64 (m, 2 H), 3.50-3.41 (m, 1 H), 3.39 (s, 3 H), 3.11 (ddd, 1 H), 2.69-2.59 (m, 1 H), 2.49 (br. s, 1 H).

EXAMPLE 530

2-methoxyethyl[5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-pyridinyl]carbamate The compound prepared in Example 529 (71 mg) was treated as detailed in Example 44 to give the title compound having the following physical properties (27 mg).
LC/MS $t_R$ 3.93 minutes; MS (ES$^+$) m/z 608 (M+H)$^b$
$^1$H NMR (500 MHz, methanol-d$_4$) δ 9.36 (s, 1 H), 8.57 (s, 1 H), 8.03 (dd, 1 H), 7.98 (d, 1 H), 7.75-7.71 (m, 2 H), 7.70-7.66 (m, 1 H), 6.13 (s, 1 H), 6.09 (s, 1 H), 5.71 (dd, 1 H), 4.34-4.30 (m, 2 H), 3.69-3.64 (m, 2 H), 3.49-3.41 (m, 1 H), 3.39 (s, 3 H), 3.11 (ddd, 1 H), 2.70-2.60 (m, 1 H), 2.43-2.35 (m, 1 H).

EXAMPLE 531

2-methoxyethyl[6-(2-{(3S)-7-[5-chloro-2-(1H-tetrazol-1-yl)phenyl]-5-oxo-1,2,3,5-tetrahydro-3-indolizinyl}-1H-imidazol-5-yl)-3-pyridinyl]carbamate The compound prepared in Example 229 (160 mg) was treated with 2-methoxyethyl chloroformate following the method of Example 484 to give the title compound having the following physical properties (133 mg).
LC/MS $t_R$ 3.15 minutes; MS (ES$^+$) m/z 574 (M+H)$^b$
$^1$H NMR (250 MHz, methanol-d$_4$) δ 9.36 (s, 1 H), 8.56 (d, 1 H), 7.94 (dd, 1 H), 7.85-7.62 (m, 4 H), 7.49 (br. s, 1 H), 6.14 (s, 1 H), 6.08 (s, 1 H), 5.80 (dd, 1 H), 4.35-4.24 (m, 2 H), 3.72-3.60 (m, 2 H), 3.56-3.42 (m, 1 H), 3.39 (s, 3 H), 3.19-2.99 (m, 1 H), 2.75-2.38 (m, 2 H).

EXAMPLE 532

2-methoxyethyl[6-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-3-pyridinyl]carbamate The compound prepared in Example 531 (89 mg) was treated as detailed in Example 44 to give the title compound having the following physical properties (94 mg).

LC/MS $t_R$ 4.00 minutes; MS (ES$^+$) m/z 608 (M+H)$^b$
$^1$H NMR (250 MHz, DMSO-d$_6$) δ 12.95 (br. s, 1 H), 10.10 (br. s, 1 H), 9.70 (s, 1 H), 8.74 (d, 1 H), 7.96 (dd, 1 H), 7.89 (d, 1 H), 7.84-7.77 (m, 3 H), 5.98 (s, 1 H), 5.93 (s, 1 H), 5.67 (dd, 1 H), 4.27-4.21 (m, 2 H), 3.60-3.56 (m, 2 H), 3.34 (s, 3 H), 3.27-3.18 (m, 1 H), 2.97 (ddd, 1 H), 2.54-2.43 (obs. m, 1 H), 2.24-2.12 (m, 1 H).

EXAMPLE 533 tert-butyl N-(5-acetyl-4-methylpyridin-2-yl)carbamate tert-Butyl-(5-bromo-4-methylpyridin-2-yl)-N-[(tert-butoxy)carbonyl]carbamate [Bioorg. Med. Chem., 12(5), 1151 (2004)] (3.23 g) was treated as detailed in Example 90 to give the title compound having the following physical properties (0.22 g).

LC/MS $t_R$ 1.93 minutes; MS (ES$^+$) m/z 251 (M+H), 195 (M-t-Bu+H)$^a$.

EXAMPLE 534 tert-butyl N-[5-(2-bromoacetyl)-4-methylpyridin-2-yl]carbamate hydrobromide

To a tetrahydrofuran solution (5 mL) of the compound prepared in Example 533 (236 mg) was added a 33% weight solution of hydrogen bromide in acetic acid (0.23 mL) followed by bromine (23 µL) and the mixture stirred at room temperature for 1 hour. Concentration of the reaction mixture gave the crude title compound having the following physical properties (0.28 g).

LC/MS $t_R$ 2.14 minutes; MS (ES$^+$) m/z 329 and 331 (M+H), 273 and 275 (M-t-Bu+H)$^a$.

EXAMPLE 535 tert-butyl N-(5-{2-[(3S)-7-[5-chloro-2-(1H-1,2,3,4-tetrazol-1-yl)phenyl]-5 oxo-1,2,3,5-tetrahydroindolizin-3-yl]-1H-imidazol-5-yl}-4-methylpyridin-2-yl)carbamate The same operation as in Example 51→Example 52 was conducted from the compound prepared in Example 534 to give the title compound having the following physical properties.

LC/MS $t_R$ 1.71 minutes; MS (ES$^+$) m/z 586 (M+H), 265.5 (M/2+H)$^a$.

EXAMPLE 536

(3S)-3-[5-(6-amino-4-methyl-3-pyridinyl)-1H-imidazol-2-yl]-7-[5-chloro-2-(1H-tetrazol-1-yl)phenyl]-2,3-dihydro-5(1H)-indolizinone The compound prepared in Example 535 (35 mg) was treated as detailed in Example 55 to give the title compound having the following physical properties (15 mg). LC/MS $t_R$ 2.73 minutes; MS (ES$^+$) m/z 286 (M+H), 244 (M-t-Bu+H)$^b$
$^1$H NMR (500 MHz, methanol-d$_4$) δ 9.35 (s, 1 H), 7.91 (s, 1 H), 7.76-7.71 (m, 2 H), 7.70-7.66 (m, 1 H), 7.00 (br. s, 1 H), 6.49 (s, 1 H), 6.12 (s, 1 H), 6.09 (s, 1 H), 5.78 (dd, 1 H), 3.49-3.38 (m, 1 H), 3.10 (ddd, 1 H), 2.68-2.57 (m, 1 H), 2.54-2.43 (m, 1 H), 2.26 (s, 3 H).

EXAMPLE 537

(3S)-3-[5-(6-amino-4-methyl-3-pyridinyl)-4-chloro-1H-imidazol-2-yl]-7-[5-chloro-2-(1H-tetrazol-1-yl)phenyl]-2,3-dihydro-5(1H)-indolizinone The same operation as in Example 44→Example 55 was conducted from the compound prepared in Example 535 to give the title compound having the following physical properties.

LC/MS $t_R$ 2.97 minutes; MS (ES$^+$) m/z 520 (M+H)$^b$
$^1$H NMR (500 MHz, methanol-d$_4$) δ 9.36 (s, 1 H), 7.78 (s, 1 H), 7.75-7.72 (m, 2 H), 7.70-7.66 (m, 1 H), 6.52 (s, 1 H), 6.12 (s, 1 H), 6.09 (s, 1 H), 5.68 (dd, 1 H), 3.49-3.40 (m, 1 H), 3.10 (ddd, 1 H), 2.69-2.59 (m, 1 H), 2.47-2.38 (m, 1 H), 2.16 (s, 3 H).

EXAMPLE 538

1-(6-aminopyridazin-3-yl)ethan-1-one

A solution of 1-(6-chloropyridazin-3-yl)ethan-1-one [Bioorg. Med. Chem., 13(11), 3705 (2005)] (1.30 g) in concentrated aqueous ammonia (1.5 mL) was heated for 50 minutes at 120° C. by microwave irradiation. The reaction mixture was then extracted into ethyl acetate. The combined organic layers were dried and concentrated and the residue purified by column chromatography (0-10% methanol in dichloromethane) to give the title compound having the following physical properties (0.42 g).

$^1$H NMR (500 MHz, methanol-d$_4$) δ 7.85 (d, 1H), 6.93 (d, 1H), 2.67 (s, 3H).

EXAMPLE 539

(3S)-3-[5-(6-amino-3-pyridazinyl)-1H-imidazol-2-yl]-7-[5-chloro-2-(1H-tetrazol-1-yl)phenyl]-2,3-dihydro-5(1H)-indolizinone The same operation as in Example 204→Example 51→Example 52 was conducted from the compound prepared in Example 538 to give the title compound having the following physical properties.

LC/MS $t_R$ 2.79 minutes; MS (ES$^+$) m/z 473 (M+H)$^b$
$^1$H NMR (500 MHz, methanol-d$_4$) δ 9.36 (s, 1 H), 7.83-7.71 (m, 3 H), 7.70-7.66 (m, 1 H), 7.56 (br. s, 1 H), 6.97 (d, 1 H), 6.15 (s, 1 H), 6.08 (s, 1 H), 5.81 (d, 1 H), 3.50-3.37 (m, 1 H), 3.10 (ddd, 1 H), 2.69-2.58 (m, 1 H), 2.55-2.42 (m, 1 H).

EXAMPLE 540

(3S)-3-[5-(6-amino-3-pyridazinyl)-4-chloro-1H-imidazol-2-yl]-7-[5-chloro-2-(1H-tetrazol-1-yl)phenyl]-2,3-dihydro-5(1H)-indolizinone The same operation as in Example 228→Example 534→Example 51→Example 52→Example 44→Example 55 was conducted from the compound prepared in Example 538 to give the title compound having the following physical properties.

LC/MS $t_R$ 3.06 minutes; MS (ES$^+$) m/z 507 (M+H)$^b$ $^1$H NMR (500 MHz, methanol-d$_4$) δ 9.36 (s, 1 H), 7.98 (d, 1 H), 7.75-7.72 (m, 2 H), 7.70-7.67 (m, 1 H), 6.99 (d, 1 H), 6.15 (s, 1 H), 6.08 (s, 1 H), 5.77 (dd, 1 H), 3.45-3.36 (m, 1 H), 3.10 (ddd, 1 H), 2.69-2.60 (m, 1 H), 2.44-2.37 (m, 1 H).

EXAMPLE 541

(3S)-3-[5-(2-{bis[(4-methoxyphenyl)methyl]amino}pyrimidin-5-yl)-1H-imidazol-2-yl]-7-[5-chloro-2-(1H-1,2,3,4-tetrazol-1-yl)phenyl]-1,2,3,5-tetrahydroindolizin-5-one The same operation as in Example 51→Example 52 was conducted from 1-(2-{bis[(4-methoxyphenyl)methyl]amino}pyrimidin-5-yl)-2-bromoethan-1-one [patent WO2011/141713] to give the title compound having the following physical properties. LC/MS $t_R$ 2.04 minutes; MS (ES$^+$) m/z 713 (M+H)$^a$.

EXAMPLE 542

(3S)-3-[5-(2-amino-5-pyrimidinyl)-1H-imidazol-2-yl]-7-[5-chloro-2-(1H-tetrazol-1-yl)phenyl]-2,3-dihydro-5(1H)-indolizinone To a cooled (0° C.) 1,2-dichloroethane (2 mL) solution of the compound prepared in Example 541 (0.13 g) was added trifluoroacetic acid (1 mL) followed by concentrated sulfuric acid (2 drops) and the mixture stirred for 25 minutes at 0° C. then warmed to room temperature and stirred a further 72 hours. On concentration, the residue was dissolved in water (2 mL) and treated with a saturated aqueous solution of sodium hydrogen carbonate until pH 8 was attained followed by extraction into ethyl acetate. The combined organic layers were washed with saturated saline, dried and concentrated. The residue was purified by column chromatography (0-10% methanol in dichloromethane then 100% methanol) to afford the title compound having the following physical properties (38 mg).

LC/MS $t_R$ 2.78 minutes; MS (ES$^+$) m/z 473 (M+H)$^b$ $^1$H NMR (500 MHz, methanol-d$_4$) δ 9.36 (s, 1 H), 8.56 (s, 2 H), 7.75-7.71 (m, 2 H), 7.70-7.66 (m, 1 H), 7.31 (br. s, 1 H), 6.12 (s, 1 H), 6.09 (s, 1 H), 5.77 (dd, 1 H), 3.49-3.40 (m, 1 H), 3.11 (ddd, 1 H), 2.68-2.58 (m, 1 H), 2.51-2.42 (m, 1 H).

EXAMPLE 543

(3S)-3-[5-(2-amino-5-pyrimidinyl)-4-chloro-1H-imidazol-2-A]-7-[5-chloro-2-(1H-tetrazol-1-yl)phenyl]-2,3-dihydro-5(1H)-indolizinone The same operation as in Example 338→Example 542 was conducted from the compound prepared in Example 541 to give the title compound having the following physical properties.

LC/MS $t_R$ 3.42 minutes; MS (ES$^+$) m/z 507 (M+H)$^b$ $^1$H NMR (500 MHz, DMSO-d$_5$) δ 12.92 (s, 1 H), 9.71 (s, 1 H), 8.49 (s, 2 H), 7.85-7.78 (m, 3 H), 6.94 (s, 2 H), 5.99 (s, 1 H), 5.93 (s, 1 H), 5.54 (dd, 1 H), 3.31-3.24 (m, 1 H), 2.98 (ddd, 1 H), 2.53-2.51 (m, 1 H), 2.23-2.15 (m, 1 H).

EXAMPLE 544

1-(5-hydroxypyridin-2-yl)ethan-1-one

To a cooled (0° C.) tetrahydrofuran (15 mL) solution of 5-hydroxypyridine-2-carbonitrile (0.92 g) was added a 1.4 M solution of methyl magnesium bromide in a 3:1 mixture of toluene and tetrahydrofuran (16.5 mL) and the mixture warmed to room temperature and stirred 16 hours. At this juncture, a 1.4 M solution of methyl magnesium bromide in a 3:1 mixture of toluene and tetrahydrofuran (8.25 mL) was added and the reaction mixture stirred a further 2 hours at room temperature. To the cooled (0° C.) reaction mixture, a saturated aqueous solution of ammonium chloride (5 mL) was added followed by concentrated sulfuric acid (1.85 mL). To this mixture, a 4 M solution of sodium hydroxide was added until pH 5 was attained, whereupon the mixture was extracted into ethyl acetate. The combined organic layers were dried and concentrated to give the title compound having the following physical properties (1 g). LC/MS $t_R$ 0.96 minutes; MS (ES$^+$) m/z 138 (M+H)$^a$.

EXAMPLE 545 formic acid—(3S)-7-[5-chloro-2-(1H-tetrazol-1-yl)phenyl]-3-[5-(5-hydroxy-2-pyridinyl)-1H-imidazol-2-yl]-2,3-dihydro-5(1H)-indolizinone (2:1)

The same operation as in Example 204→Example 51→Example 52 was conducted from the compound prepared in Example 544 to give the title compound after purification by high performance liquid chromatography [5 to 100% mobile phase B (0.1% formic acid in acetonitrile) in mobile phase A (0.1% aqueous formic acid)] as the formic acid salt having the following physical properties.

LC/MS $t_R$ 2.88 minutes; MS (ES$^+$) m/z 473 (M+H)$^b$ $^1$H NMR (500 MHz, methanol-d$_4$) δ 9.36 (s, 1 H), 8.42 (s, 2 H), 8.05 (d, 1 H), 7.75-7.72 (m, 2 H), 7.70-7.64 (m, 2 H), 7.40 (s, 1 H), 7.24 (dd, 1 H), 6.14 (s, 1 H), 6.09 (s, 1 H), 5.81 (dd, 1 H), 3.49-3.40 (m, 1 H), 3.11 (ddd, 1 H), 2.68-2.58 (m, 1 H), 2.54-2.47 (m, 1 H).

EXAMPLE 546

(3S)-3-[4-chloro-5-(5-hydroxy-2-pyridinyl)-1H-imidazol-2-yl]-7-[5-chloro-2-(1H-tetrazol-1-yl)phenyl]-2,3-dihydro-5(1H)-indolizinone The compound prepared in Example 545 (19 mg) was treated as detailed in Example 338 to give the title compound having the following physical properties (6.8 mg).

LC/MS $t_R$ 4.12 minutes; MS (ES$^+$) m/z 507 (M+H)$^b$ $^1$H NMR (500 MHz, methanol-d$_1$) δ 9.36 (s, 1 H), 8.16 (d, 1 H), 7.87 (d, 1 H), 7.77-7.70 (m, 2 H), 7.70-7.65 (m, 1 H), 7.27 (dd, 1 H), 6.15 (s, 1 H), 6.08 (s, 1 H), 5.77 (dd, 1 H), 3.46-3.34 (m, 1 H), 3.09 (ddd, 1 H), 2.62 (qd, 1 H), 2.50-2.39 (m, 1 H).

EXAMPLE 547

(3S)-7-[5-chloro-2-(1H-tetrazol-1-yl)phenyl]-3-[5-(6-fluoro-3-pyridinyl)-1H-imidazol-2-yl]-2,3-dihydro-5(1H)-indolizinone The same operation as in Example 204→Example 51→Example 52 was conducted from 1-(6-fluoropyridin-3- yl)ethan-1-one [patent WO2006082392] to give the title compound having the following physical properties.

LC/MS $t_R$ 3.39 minutes; MS (ES$^+$) m/z 475 (M+H)$^b$ $^1$H NMR (500 MHz, DMSO-d$_6$) δ 12.29 (br. s, 1 H), 9.69 (s, 1 H), 8.54 (d, 1 H), 8.25-8.19 (m, 1 H), 7.82-7.76 (m, 3 H), 7.64 (d, 1 H), 7.14 (dd, 1 H), 5.97 (br. s, 1 H), 5.96 (s, 1 H), 5.63 (dd, 1 H), 3.42-3.35 (m, 1 H), 3.00 (dd, 1 H), 2.55-2.51 (m, 1 H), 2.37-2.30 (m, 1 H).

EXAMPLE 548

(3S)-7-[5-chloro-2-(1H-tetrazol-1-yl)phenyl]-3-[5-(6-oxo-1,6-dihydro-3-pyridinyl)-1H-imidazol-2-yl]-2,3-dihydro-5(1H)-indolizinone To a 1,2-dimethoxyethane (3 mL) suspension of the compound prepared in Example 547 (80 mg) was added 3 M hydrochloric acid and the mixture stirred at 80° C. for 2 hours 30 minutes. To the reaction mixture, a saturated aqueous solution of sodium hydrogen carbonate (12 mL) was added followed by extraction into ethyl acetate. The combined organic layers were dried and concentrated and the residue triturated in dichloromethane (3 mL), the resultant precipitate being collected by filtration to give the title compound having the following physical properties (61 mg).

LC/MS $t_R$ 2.73 minutes; MS (ES$^+$) m/z 473 (M+H)$^b$ $^1$H NMR (500 MHz, methanol-d$_4$) δ 9.37 (s, 1 H), 7.92 (dd, 1 H), 7.78-7.71 (m, 3 H), 7.71-7.67 (m, 1 H), 7.29 (s, 1 H), 6.59 (d, 1 H), 6.13 (s, 1 H), 6.09 (s, 1 H), 5.76 (dd, 1 H), 3.47-3.38 (m, 1 H), 3.11 (ddd, 1 H), 2.68-2.59 (m, 1 H), 2.48-2.41 (m, 1 H).

EXAMPLE 549

(3S)-3-[4-chloro-5-(6-oxo-1,6-dihydro-3-pyridinyl)-1H-imidazol-2-yl]-7-[5-chloro-2-(1H-tetrazol-1-yl)phenyl]-2,3-dihydro-5(1H)-indolizinone The compound prepared in Example 548 (49 mg) was treated as detailed in Example 338 to give the title compound having the following physical properties (15 mg).

LC/MS $t_R$ 3.35 minutes; MS (ES$^+$) m/z 507 (M+H)$^b$ $^1$H NMR (500 MHz, methanol-d$_4$) δ 9.36 (s, 1 H), 7.89 (d, 1 H), 7.79-7.71 (m, 3 H), 7.71-7.66 (m, 1 H), 6.64 (d, 1 H), 6.12 (s, 1 H), 6.10 (s, 1 H), 5.68 (dd, 1 H), 3.48-3.40 (m, 1 H), 3.11 (ddd, 1 H), 2.70-2.58 (m, 1 H), 2.42-2.34 (m, 1 H).

EXAMPLE 550

1-[6-(methylamino)pyridin-3-yl]ethan-1-one

A suspension of 1-(6-chloropyridin-3-yl)ethanone (0.30 g) in a 40% weight solution of methylamine in water (4.5 mL) was heated at 145° C. for 50 minutes by microwave irradiation. On cooling to room temperature, the reaction mixture was extracted into ethyl acetate. The combined organic layers were dried and concentrated and the residue purified by column chromatography (0-70% ethyl acetate in heptanes) to give the title compound having the following physical properties (0.19 g).

$^1$H NMR (500 MHz, CDCl$_3$) δ 8.73 (d, 1 H), 8.03 (dd, 1 H), 6.40 (d, 1 H), 3.01 (d, 3 H), 2.51 (s, 3 H).

EXAMPLE 551

2-bromo-1-[6-(methylamino)pyridin-3-yl]ethan-1-one dihydrobromide

The compound prepared in Example 550 (0.17 g) was treated as detailed in Example 204 to give the title compound having the following physical properties (0.20

LC/MS $t_R$ 0.89 minute; MS (ES$^+$) m/z 229 and 231 (M+H)$^a$.

EXAMPLE 552

(3S)-7-[5-chloro-2-(1H-tetrazol-1-yl)phenyl]-3-{5-[6-(methylamino)-3-pyridinyl]-1H-imidazol-2-yl}-2,3-dihydro-5(1H)-indolizinone The same operation as in Example 51→Example 52 was conducted from the compound prepared in Example 551 to give the title compound having the following physical properties.

LC/MS $t_R$ 2.73 minutes; MS (ES$^+$) m/z 486 (M+H), 244 (M/2+H)$^b$ $^1$H NMR (500 MHz, methanol-d$_4$) δ 9.35 (s, 1 H), 8.24 (d, 1 H), 7.72 (s, 3 H), 7.69 (s, 1 H), 7.17 (br. s, 1 H), 6.56 (d, 1 H), 6.12 (s, 1 H), 6.08 (s, 1 H), 5.77 (dd, 1 H), 3.49-3.39 (m, 1 H), 3.10 (ddd, 1 H), 2.88 (s, 3 H), 2.68-2.58 (m, 1 H), 2.50-2.42 (m, 1 H).

EXAMPLE 553 tert-butyl N-(5-acetyl-6-fluoropyridin-2-yl)carbamate

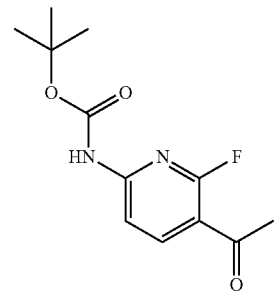 [SMILES: CC(=O)c1ccc(NC(=O)OC(C)(C)C)nc1F]

The same operation as in Example 90→Example 228 was conducted from 2-amino-6-fluoro-5-iodopyridine [J. Org. Chem. 71(8), 2922 (2006)] to give the title compound having the following physical properties.

LC/MS $t_R$ 2.01 minute; MS (ES$^+$) m/z 199 (M-t-Bu+H)$^a$.

EXAMPLE 554 tert-butyl N-(5-acetyl-6-fluoropyridin-2-yl)-N-methylcarbamate

To an N,N-dimethylformamide (2 mL) suspension of sodium hydride (46 mg, 60% dispersion in mineral oil) was added a solution of the compound prepared in Example 553 (314 mg) in N,N-dimethylformamide (5 mL) and the mixture stirred at room temperature for 10 minutes. At this juncture, iodomethane (72 μL) was added and the mixture stirred at room temperature for 16 hours. To the reaction mixture, water (10 mL) was added followed by extraction into ethyl acetate. The organic layer was washed sequentially with water and saturated saline, dried and concentrated. The residue was purified by column chromatography (0-40% ethyl acetate in heptanes) to give the title compound having the following physical properties (146 mg).

LC/MS $t_R$ 2.24 minute; MS (ES$^+$) m/z 213 (M+H)$^a$.

EXAMPLE 555

(3S)-7-[5-chloro-2-(1H-tetrazol-1-yl)phenyl]-3-{5-[2-fluoro-6-(methylamino)-3-pyridinyl]-1H-imidazol-2-yl}-2,3-dihydro-5(1H)-indolizinone The same operation as in Example 204→Example 51→Example 52 was conducted from the compound prepared in Example 554 to give the title compound having the following physical properties.

LC/MS $t_R$ 3.13 minutes; MS (ES$^+$) m/z 504 (M+H)$^b$
$^1$H NMR (500 MHz, CDCl$_3$) δ 10.72 (br. s, 1 H), 8.53 (s, 1 H), 8.26 (dd, 1 H), 7.64-7.60 (m, 1 H), 7.56-7.53 (m, 1 H), 7.51 (d, 1 H), 6.35 (s, 1 H), 6.30 (dd, 1 H), 5.83 (d, 1 H), 5.65 (s, 1 H), 4.62-4.53 (m, 1 H), 3.50-3.23 (m, 2 H), 2.99 (dd, 1 H), 2.94 (s, 3 H), 2.52-2.40 (m, 1 H).

EXAMPLE 556

(3S)-3-{5-[2-chloro-6-(methylamino)-3-pyridinyl]-1H-imidazol-2-yl}-7-[5-chloro-2-(1H-tetrazol-1-yl)phenyl]-2,3-dihydro-5(1H)-indolizinone The same operation as in Example 550→Example 90→Example 204→Example 51→Example 52 was conducted from 2,6-dichloro-3-iodopyridine to give the title compound having the following physical properties.

LC/MS $t_R$ 3.20 minutes; MS (ES$^+$) m/z 520 (M+H)$^b$
$^1$H NMR (500 MHz, methanol-d$_4$) δ 9.35 (s, 1 H), 7.82-7.71 (m, 3 H), 7.71-7.66 (m, 1 H), 7.30 (br. s, 1 H), 6.48 (d, 1 H), 6.14 (s, 1 H), 6.08 (s, 1 H), 5.79 (dd, 1 H), 3.48-3.39 (m, 1 H), 3.10 (ddd, 1 H), 2.87 (s, 3 H), 2.67-2.57 (m, 1 H), 2.53-2.46 (m, 1 H).

EXAMPLE 557

(3S)-7-[5-chloro-2-(1H-tetrazol-1-yl)phenyl]-3-{5-[6-(dimethylamino)-3-pyridinyl]-1H-imidazol-2-yl}-2,3-dihydro-5(1H)-indolizinone The same operation as in Example 550→Example 204→Example 51→Example 52 was conducted from 1-(6-chloropyridin-3-yl)ethan-1-one to give the title compound having the following physical properties. (Note: in the step corresponding to Example 550 in the operation, a 40% weight solution of dimethylamine in water was used).

LC/MS $t_R$ 2.89 minutes; MS (ES$^+$) m/z 500 (M+H)$^b$
$^1$H NMR (500 MHz, methanol-d$_4$) δ 9.36 (s, 1 H), 8.34 (br. s, 1 H), 7.80 (br. s, 1 H), 7.76-7.71 (m, 2 H), 7.70-7.66 (m, 1 H), 7.22 (br. s, 1 H), 6.70 (d, 1 H), 6.13 (s, 1 H), 6.09 (s, 1 H), 5.77 (dd, 1 H), 3.49-3.39 (m, 1 H), 3.14-3.10 (m, 1 H), 3.09 (s, 6 H), 2.68-2.59 (m, 1 H), 2.55-2.41 (m, 1 H).

EXAMPLE 558

(3S)-7-[5-chloro-2-(1H-tetrazol-1-yl)phenyl]-3-{5-[6-(ethylamino)-3-pyridinyl]-1H-imidazol-2-yl}-2,3-dihydro-5(1H)-indolizinone The same operation as in Example 550→Example 204→Example 51→Example 52 was conducted from 1-(6-chloropyridin-3-yl)ethan-1-one to give the title compound having the following physical properties. (Note: in the step corresponding to Example 550 in the operation, a 70% weight solution of ethylamine in water was used). LC/MS $t_R$ 2.78 minutes; MS (ES$^+$) m/z 500 (M+H)$^b$ $^1$H NMR (500 MHz, methanol-d$_4$) δ 9.38 (s, 1 H), 8.24 (d, 1 H), 7.77-7.68 (m, 4 H), 7.18 (br. s, 1 H), 6.57 (d, 1 H), 6.14 (s, 1 H), 6.11 (s, 1 H), 5.78 (dd, 1 H), 3.35-3.31 (m, 2 H), 3.50-3.41 (m, 1 H), 3.12 (ddd, 1 H), 2.65 (ddd, 1 H), 2.51-2.44 (m, 1 H), 1.25 (t, 3 H).

EXAMPLE 559

1-{6-[(2-methoxyethyl)amino]pyridin-3-yl}ethan-1-one

To a propan-2-ol (7 mL) solution of 1-(6-chloropyridin-3-yl)ethanone (0.70 g) was added 2-methoxyethylamine (1.57 mL) and the mixture was heated at 180° C. for 50 minutes by microwave irradiation. On cooling to room temperature, the reaction mixture was diluted with water (40 mL) and extracted into ethyl acetate. The combined organic layers were dried and concentrated and the residue purified by column chromatography (0-80% ethyl acetate in heptanes) to give the title compound having the following physical properties (0.55 g).

LC/MS $t_R$ 0.80 minute; MS (ES$^+$) m/z 195 (M+H)$^a$.

EXAMPLE 560

2-bromo-1-{6-[(2-methoxyethyl)amino]pyridin-3-yl}ethan-1-one dihydrobromide

The compound prepared in Example 559 (0.30 g) was treated as detailed in Example 204 to give the title compound having the following physical properties (0.67 g).

LC/MS $t_R$ 1.25 minute; MS (ES$^+$) m/z 273 and 275 (M+H)$^a$

EXAMPLE 561

(3S)-7-[5-chloro-2-(1H-tetrazol-1-yl)phenyl]-3-(5-{6-[(2-methoxyethyl)amino]-3-pyridinyl}-1H-imidazol-2-yl)-2,3-dihydro-5(1H)-indolizinone The same operation as in Example 51→Example 52 was conducted from the compound prepared in Example 560 to give the title compound having the following physical properties.

LC/MS $t_R$ 3.06 minutes; MS (ES$^+$) m/z 530 (M+H), 265.5 (M/2+H)$^b$
$^1$H NMR (500 MHz, methanol-d$_4$) δ 9.36 (s, 1 H), 8.23 (d, 1 H), 7.75-7.70 (m, 3 H), 7.69 (s, 1 H), 7.17 (s, 1 H), 6.61 (d, 1 H), 6.12 (s, 1 H), 6.09 (s, 1 H), 5.77 (dd, 1 H), 3.60-3.55 (m, 2 H), 3.51-3.46 (m, 2 H), 3.46-3.39 (m, 1 H), 3.38 (s, 3 H), 3.10 (ddd, 1 H), 2.69-2.58 (m, 1 H), 2.50-2.42 (m, 1 H).

EXAMPLE 562

(3S)-7-[5-chloro-2-(1H-tetrazol-1-yl)phenyl]-3-(5-{6-[(2-ethoxyethyl)amino]-3-pyridinyl}-1H-imidazol-2-yl)-2,3-dihydro-5(1H)-indolizinone The same operation as in Example 559→Example 204→Example 51→Example 52 was conducted from 1-(6-chloropyridin-3-yl)ethan-1-one to give the title compound having the following physical properties. (Note: in the step corresponding to Example 559 in the operation, 2-ethoxyethylamine was used).

LC/MS $t_R$ 2.90 minutes; MS (ES$^+$) m/z 544 (M+H), 272.5 (M/2+H)$^b$ $^1$H NMR (500 MHz, methanol-d$_4$) δ 9.36 (s, 1 H), 8.23 (d, 1 H), 7.75-7.71 (m, 3 H), 7.69-7.65 (m, 1 H), 7.18 (s, 1 H), 6.62 (d, 1 H), 6.12 (s, 1 H), 6.09 (s, 1 H), 5.77 (dd, 1 H), 3.62 (t, 1 H), 3.55 (q, 2 H), 3.48 (t, 2 H), 3.46-3.39 (m, 1 H), 3.10 (ddd, 1 H), 2.68-2.58 (m, 1 H), 2.49-2.42 (m, 1 H), 1.20 (t, 3 H).

EXAMPLE 563

(3S)-7-[5-chloro-2-(1H-tetrazol-1-yl)phenyl]-3-(5-{6-[(3-methoxypropyl)amino]-3-pyridinyl}-1H-imidazol-2-yl)-2,3-dihydro-5(1H)-indolizinone The same operation as in Example 559→Example 204→Example 51→Example 52 was conducted from 1-(6-chloropyridin-3-yl)ethan-1-one to give the title compound having the following physical properties. (Note: in the step corresponding to Example 559 in the operation, 3-methoxypropylamine was used).

LC/MS $t_R$ 2.85 minutes; MS (ES$^+$) m/z 544 (M+H)$^b$ $^1$H NMR (500 MHz, methanol-d$_4$) δ 9.36 (s, 1 H), 8.22 (br. s, 1 H), 7.76-7.66 (m, 4 H), 7.16 (br. s, 1 H), 6.56 (d, 1 H), 6.12 (s, 1 H), 6.09 (s, 1 H), 5.77 (dd, 1 H), 3.51 (t, 2 H), 3.42-3.46 (m, 1 H), 3.37 (t, 2 H), 3.35 (s, 3 H), 3.10 (ddd, 1 H), 2.68-2.58 (m, 1 H), 2.52-2.41 (m, 1 H), 1.87 (quintet, 2 H).

EXAMPLE 564

(3S)-7-[5-chloro-2-(1H-tetrazol-1-yl)phenyl]-3-(5-{6-[(3-hydroxy-3-methylbutyl)amino]-3-pyridinyl}-1H-imidazol-2-yl)-2,3-dihydro-5(1H)-indolizinone The same operation as in Example 559→Example 204→Example 51→Example 52 was conducted from 1-(6-chloropyridin-3-yl)ethan-1-one to give the title compound having the following physical properties. (Note: in the step corresponding to Example 559 in the operation, 4-amino-2-methylbutan-2-ol was used).

LC/MS $t_R$ 2.85 minutes; MS (ES$^+$) m/z 558 (M+H), 279.5 (M/2+H)$^b$ $^1$H NMR (500 MHz, methanol-d$_4$) δ 9.36 (s, 1 H), 8.23 (d, 1 H), 7.76-7.70 (m, 3 H), 7.70-7.66 (m, 1 H), 7.17 (s, 1 H), 6.57 (d, 1 H), 6.12 (s, 1 H), 6.09 (s, 1 H), 5.77 (dd, 1 H), 3.49-3.42 (m, 1 H), 3.41-3.37 (m, 2 H), 3.10 (ddd, 1 H), 2.68-2.58 (m, 1 H), 2.50-2.42 (m, 1 H), 1.83-1.77 (m, 2 H), 1.26 (s, 6 H).

EXAMPLE 565

1-{6-[(1,3-oxazol-2-ylmethyl)amino]pyridin-3-yl}ethan-1-one

To a propan-2-ol (10 mL) solution of 1-(6-fluoropyridin-3-yl)ethanone [patent WO2006082392] (0.50 g) was added 1-(1,3-oxazol-2-yl)methylamine hydrochloride (0.73 g) and N,N-diisopropylethylamine (1.25 mL) and the mixture was heated at 110° C. for 30 minutes by microwave irradiation. On cooling to room temperature, the reaction mixture was diluted with water (20 mL) and extracted into ethyl acetate. The combined organic layers were dried and concentrated and the residue purified by column chromatography (0-100% ethyl acetate in heptanes) to give the title compound having the following physical properties (0.22 g).

LC/MS $t_R$ 1.04 minute; MS (ES$^+$) m/z 218 (M+H)$^a$.

EXAMPLE 566

(3S)-7-[5-chloro-2-(1H-tetrazol-1-yl)phenyl]-3-(5-{6-[(1,3-oxazol-2-ylmethyl)amino]-3-pyridinyl}-1H-imidazol-2-yl)-2,3-dihydro-5(1H)-indolizinone The same operation as in Example 204→Example 51→Example 52 was conducted from the compound prepared in Example 565 to give the title compound having the following physical properties.

LC/MS $t_R$ 2.83 minutes; MS (ES$^+$) m/z 553 (M+H), 277 (M/2+H)$^b$ $^1$H NMR (500 MHz, methanol-d$_4$) δ 9.35 (s, 1 H), 8.26 (d, 1 H), 7.84 (s, 1 H), 7.76-7.71 (m, 3 H), 7.69-7.66 (m, 1 H), 7.17 (br. s, 1 H), 7.09 (s, 1 H), 6.65 (d, 1 H), 6.12 (s, 1 H), 6.08 (s, 1 H), 5.76 (dd, 1 H), 4.67 (s, 2 H), 3.48-3.39 (m, 1 H), 3.09 (ddd, 1 H), 2.67-2.58 (m, 1 H), 2.49-2.42 (m, 1 H).

EXAMPLE 567(1) AND 567(2)

3-{[5-(2-{(3S)-7-[5-chloro-2-(1H-tetrazol-1-yl)phenyl]-5-oxo-1,2,3,5-tetrahydro-3-indolizinyl}-1H-imidazol-5-yl)-2-pyridinyl]amino}-N,N-dimethylpropanamide and 3-{[5-(2-{(3S)-7-[5-chloro-2-(1H-tetrazol-1-yl)phenyl]-5-oxo-1,2,3,5-tetrahydro-3-indolizinyl}-1H-imidazol-5-yl)-2-pyridinyl]amino}propanamide The same operation as in Example 565→Example 55→Example 250→Example 204→Example 51→Example 52 was conducted from 1-(6-fluoropyridin-3-yl)ethan-1-one [patent WO2006082392] to give the title compounds in a 1:1 ratio having the following physical properties (Note: in the step corresponding to Example 565 in the operation, β-alanine hydrochloride tert-butyl ester was used. In the step corresponding to Example 250 in the operation, dimethylamine hydrochloride was used).

EXAMPLE 567(1)

LC/MS $t_R$ 2.82 minutes; MS (ES$^+$) m/z 571 (M+H), 286 (M/2+H)$^b$ $^1$H NMR (500 MHz, methanol-d$_4$) δ 9.36 (s, 1 H), 8.25 (s, 1 H), 7.73 (d, 4 H), 7.17 (br. s, 1 H), 6.57 (d, 1 H), 6.12 (s, 1 H), 6.09 (s, 1 H), 5.77 (dd, 1 H), 3.60 (t, 2 H), 3.48-3.40 (m, 1 H), 3.10 (ddd, 1 H), 3.04 (s, 3 H), 2.94 (s, 3 H), 2.69 (t, 2 H), 2.66-2.60 (m, 1 H), 2.50-2.42 (m, 1 H).

EXAMPLE 567(2)

LC/MS $t_R$ 2.67 minutes; MS (ES$^+$) m/z 543 (M+H), 272 (M/2+H)$^b$ $^1$H NMR (500 MHz, methanol-d$_4$) δ 9.36 (s, 1 H), 8.25 (d, 1 H), 7.77-7.65 (m, 4 H), 7.17 (br. s, 1 H), 6.58 (d, 1 H), 6.12 (s, 1 H), 6.09 (s, 1 H), 5.77 (dd, 1 H), 3.59 (t, 2 H), 3.50-3.39 (m, 1 H), 3.10 (ddd, 1 H), 2.66-2.58 (m, 1 H), 2.52 (t, 2 H), 2.49-2.41 (m, 1 H).

EXAMPLE 568 trifluoroacetic acid—4-[(5-acetylpyridin-2-yl)amino]butanoic acid (1:1)

The same operation as in Example 565→Example 40 was conducted from 1-(6-fluoropyridin-3-yl)ethan-1-one [patent WO2006082392] to give the title compound having the following physical properties. (Note: in the step corresponding to Example 565 in the operation, tert-butyl 4-aminobutanoate was used).

LC/MS $t_R$ 0.63 minutes; MS (ES$^+$) m/z 223 (M+H)$^a$.

EXAMPLE 569

1-(5-acetylpyridin-2-yl)pyrrolidin-2-one

The compound prepared in Example 568 (360 mg) was treated as detailed in Example 250 to give the title compound having the following physical properties (65 mg).

LC/MS $t_R$ 1.40 minute; MS (ES$^+$) m/z 205 (M+H)$^a$.

EXAMPLE 570

(3S)-7-[5-chloro-2-(1H-tetrazol-1-yl)phenyl]-3-{5-[6-(2-oxo-1-pyrrolidinyl)-3-pyridinyl]-1H-imidazol-2-yl}-2,3-dihydro-5 (1H)-indolizinone The same operation as in Example 204→Example 51→Example 52 was conducted from the compound prepared in Example 569 to give the title compound having the following physical properties.

LC/MS $t_R$ 3.21 minutes; MS (ES$^+$) m/z 540 (M+H), 562 (M+Na), 270.5 (M/2+H)$^b$ $^1$H NMR (500 MHz, CDCl$_3$) δ 8.65 (s, 1 H), 8.61 (s, 1 H), 8.36 (d, 1 H), 7.93 (d, 1 H), 7.62 (dd, 1 H), 7.55 (m, 2 H), 7.29-7.24 (m, 1 H), 6.27 (s, 1 H), 5.89 (d, 1 H), 5.83 (s, 1 H), 4.10 (t, 2 H), 3.53-3.44 (m, 1 H), 3.25-3.17 (m, 1 H), 3.06 (dd, 1 H), 2.67 (t, 2 H), 2.60-2.51 (m, 1 H), 2.15 (quintet, 2 H).

EXAMPLE 571(1) to Example 571(3)

The compounds of the present invention having the following physical data were synthesised from the compounds prepared in Examples 552, 557 and 561 using the method as detailed in Example 44.

EXAMPLE 571(1)

(3S)-3-{4-chloro-5-[6-(methylamino)-3-pyridinyl]-1H-imidazol-2-yl}-7-[5-chloro-2-(1H-tetrazol-1-yl)phenyl]-2,3-dihydro-5(1H)-indolizinone LC/MS $t_R$ 3.03 minutes; MS (ES$^+$) m/z 520 (M+H)$^b$ $^1$H NMR (500 MHz, methanol-d$_4$) δ 9.35 (s, 1 H), 8.27 (d, 1 H), 7.76-7.71 (m, 3 H), 7.70-7.66 (m, 1 H), 6.58 (d, 1 H), 6.12 (s, 1 H), 6.08 (s, 1 H), 5.69 (dd, 2 H), 3.49-3.38 (m, 1 H), 3.09 (ddd, 1 H), 2.89 (s, 3 H), 2.68-2.58 (m, 1 H), 2.42-2.34 (m, 1 H).

EXAMPLE 571(2)

(3S)-3{4-chloro-5-[6-(dimethylamino)-3-pyridinyl]-1H-imidazol-2-yl}-7-[5-chloro-2-(1H-tetrazol-1-yl)phenyl]-2,3-dihydro-5(1H)-indolizinone LC/MS $t_R$ 3.21 minutes; MS (ES$^+$) m/z 534 (M+H)$^b$ $^1$H NMR (500 MHz, methanol-d$_4$) δ 9.38 (s, 1 H), 8.39 (d, 1 H), 7.83 (dd, 1 H), 7.78-7.73 (m, 2 H), 7.72-7.68 (m, 1 H), 6.76 (d, 1 H), 6.14 (s, 1 H), 6.11 (s, 1 H), 5.72 (dd, 1 H), 3.51-3.42 (m, 1 H), 3.16-3.08 (m, 7 H), 2.65 (qd, 1 H), 2.44-2.36 (m, 1 H).

EXAMPLE 571(3)

(3S)-3-(4-chloro-5-{6-[(2-methoxyethyl)amino]-3-pyridinyl}-1H-imidazol-2-yl)-7-[5-chloro-2-(1H-tetrazol-1-yl)phenyl]-2,3-dihydro-5(1H)-indolizinone LC/MS $t_R$ 3.21 minutes; MS (ES$^+$) m/z 564 (M+H)$^b$ $^1$H NMR (500 MHz, methanol-d$_4$) δ 9.36 (s, 1 H), 8.26 (d, 1 H), 7.75-7.70 (m, 3 H), 7.70-7.66 (m, 1 H), 6.63 (d, 1 H), 6.13 (s, 1 H), 6.09 (s, 1 H), 5.69 (dd, 1 H), 3.58 (t, 2 H), 3.51 (t, 2 H), 3.48-3.40 (m, 1 H), 3.38 (s, 3 H), 3.10 (ddd, 1 H), 2.68-2.59 (m, 1 H), 2.42-2.34 (m, 1 H).

EXAMPLE 572(1) to Example 572(7)

The compounds of the present invention having the following physical data were synthesised from the compounds prepared in Examples 558, 562, 563, 564, 566, 567(1) and 570 using the method as detailed in Example 338.

EXAMPLE 572(1)

(3S)-3-{4-chloro-5-[6-(ethylamino)-3-pyridinyl]-1H-imidazol-2-yl}-7-[5-chloro-2-(1H-tetrazol-1-yl)phenyl]-2,3-dihydro-5(1H)-indolizinone LC/MS $t_R$ 3.04 minutes; MS (ES$^+$) m/z 534 (M+H)$^b$ $^1$H NMR (500 MHz, methanol-d$_4$) δ 9.36 (s, 1 H), 8.24 (d, 1 H), 7.79-7.64 (m, 4 H), 6.57 (d, 1 H), 6.12 (s, 1 H), 6.09 (s, 1 H), 5.70 (dd, 1 H), 3.48-3.39 (m, 1 H), 3.35-3.31 (m, 2 H), 3.09 (ddd, 1 H), 2.57-2.68 (m, 1 H), 2.41-2.33 (m, 1 H), 1.24 (t, 3 H).

EXAMPLE 572(2)

(3S)-3-(4-chloro-5-{6-[(2-ethoxyethyl)amino]-3-pyridinyl}-1H-imidazol-2-yl)-7-[5-chloro-2-(1H-tetrazol-1-yl)phenyl]-2,3-dihydro-5 (1H)-indolizinone LC/MS $t_R$ 3.16 minutes; MS (ES$^+$) m/z 578 (M+H)$^b$ $^1$H NMR (500 MHz, methanol-d$_4$) δ 9.36 (s, 1 H), 8.26 (d, 1 H), 7.75-7.71 (m, 3 H), 7.70-7.67 (m, 1 H), 6.64 (d, 1 H), 6.13 (s, 1 H), 6.09 (s, 1 H), 5.69 (dd, 1 H), 3.63 (t, 2 H), 3.55 (q, 2 H), 3.51 (t, 2 H), 3.48-3.39 (m, 1 H), 3.10 (ddd, 1 H), 2.68-2.58 (m, 1 H), 2.42-2.34 (m, 1 H), 1.20 (t, 3 H).

EXAMPLE 572(3)

(3S)-3-(4-chloro-5-{6-[(3-methoxypropyl)amino]-3-pyridinyl}-1H-imidazol-2-yl)-7-[5-chloro-2-(1H-tetrazol-1-yl)phenyl]-2,3-dihydro-5(1H)-indolizinone LC/MS $t_R$ 2.20 minutes; MS (ES$^+$) m/z 578 (M+H)$^b$ $^1$H NMR (500 MHz, methanol-d$_4$) δ 9.36 (s, 1 H), 8.24 (d, 1 H), 7.74-7.70 (m, 2 H), 7.70-7.66 (m, 2 H), 6.57 (d, 1 H), 6.12 (s, 1 H), 6.08 (s, 1 H), 5.70 (dd, 1 H), 3.50 (t, 2 H), 3.48-3.40 (m, 1 H), 3.38 (t, 2 H), 3.34 (s, 3 H), 3.09 (ddd, 1 H), 2.67-2.58 (m, 1 H), 2.40-2.33 (m, 1 H), 1.87 (quintet, 2 H).

EXAMPLE 572(4)

(3S)-3-(4-chloro-5-{6-[(3-hydroxy-3-methylbutyl)amino]-3-pyridinyl}-1H-imidazol-2-yl)-7-[5-chloro-2-(1H-tetrazol-1-yl)phenyl]-2,3-dihydro-5(1H)-indolizinone LC/MS $t_R$ 3.05 minutes; MS (ES$^+$) m/z 592 (M+H)$^b$
$^1$H NMR (500 MHz, methanol-d$_4$) δ 9.36 (s, 1 H), 8.26 (d, 1 H), 7.75-7.71 (m, 3 H), 7.70-7.67 (m, 1 H), 6.59 (d, 1 H), 6.13 (s, 1 H), 6.09 (s, 1 H), 5.69 (dd, 1 H), 3.48-3.39 (m, 3 H), 3.10 (ddd, 1 H), 2.68-2.58 (m, 1 H), 2.42-2.34 (m, 1 H), 1.83-1.78 (m, 2 H), 1.27 (s, 6 H).

EXAMPLE 572(5)

(3S)-3-(4-chloro-5-{6-[(1,3-oxazol-2-ylmethyl)amino]-3-pyridinyl}-1H-imidazol-2-yl)-7-[5-chloro-2-(1H-tetrazol-1-yl)phenyl]-2,3-dihydro-5(1H)-indolizinone LC/MS $t_R$ 3.33 minutes; MS (ES$^+$) m/z 587 (M+H)$^b$
$^1$H NMR (500 MHz, methanol-d$_4$) δ 9.40-9.34 (m, 1 H), 8.27 (br. s, 1 H), 7.85 (s, 1 H), 7.78-7.71 (m, 3 H), 7.70-7.66 (m, 1 H), 7.10 (s, 1 H), 6.72-6.67 (m, 1 H), 6.12 (s, 1 H), 6.08 (s, 1 H), 5.69 (dd, 1 H), 4.70 (s, 2 H), 3.47-3.39 (m, 1 H), 3.13-3.05 (m, 1 H), 2.68-2.58 (m, 1 H), 2.41-2.34 (m, 1 H).

EXAMPLE 572(6)

3-{[5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-pyridinyl]amino}-N,N-dimethylpropanamide LC/MS $t_R$ 3.06 minutes; MS (ES$^+$) m/z 605 (M+H)$^b$
$^1$H NMR (500 MHz, methanol-d$_4$) δ 9.37 (s, 1 H), 8.28 (br. s, 1 H), 7.76-7.66 (m, 4 H), 6.62-6.57 (m, 1 H), 6.12 (s, 1 H), 6.09 (s, 1 H), 5.70 (dd, 1 H), 3.65-3.60 (m, 2 H), 3.48-3.39 (m, 1 H), 3.13-3.06 (m, 1 H), 3.05 (s, 3 H), 2.94 (s, 3 H), 2.70 (t, 2 H), 2.67-2.58 (m, 1 H), 2.42-2.34 (m, 1 H).

EXAMPLE 572(7)

formic acid—(3S)-3-{4-chloro-5-[6-(2-oxo-1-pyrrolidinyl)-3-pyridinyl]-1H-imidazol-2-yl}-7-[5-chloro-2-(1H-tetrazol-1-yl)phenyl]-2,3-dihydro-5(1H)-indolizinone (1:1)

LC/MS $t_R$ 3.99 minutes; MS (ES$^+$) m/z 574 (M+H)$^b$
$^1$H NMR (500 MHz, methanol-d$_4$) δ 9.37 (s, 1 H), 8.70 (d, 1 H), 8.41 (d, 1 H), 8.08 (dd, 1 H), 7.74 (s, 2 H), 7.70-7.67 (m, 1 H), 6.13 (s, 1 H), 6.10 (s, 1 H), 5.72 (dd, 1 H), 4.14 (t, 2 H), 3.50-3.40 (m, 1 H), 3.12 (ddd, 1 H), 2.68 (t, 2 H), 2.66-2.61 (m, 1 H), 2.43-2.36 (m, 1 H), 2.17 (quintet, 2 H).

EXAMPLE 573

(3S)-3-[5-(2-amino-1,3-thiazol-5-yl)-4-chloro-1H-imidazol-2-yl]-7-[5-chloro-2-(1H-tetrazol-1-yl)phenyl]-2,3-dihydro-5(1H)-indolizinone The compound prepared in Example 235 (67 mg) was treated as detailed in Example 44 to give the title compound having the following physical properties (1.8 mg).

LC/MS $t_R$ 3.18 minutes; MS (ES$^+$) m/z 512 (M+H)$^b$
$^1$H NMR (500 MHz, methanol-d$_4$) δ 9.37 (s, 1 H), 7.77-7.71 (m, 2 H), 7.71-7.66 (m, 1 H), 7.22 (s, 1 H), 6.13 (s, 1 H), 6.08 (s, 1 H), 5.65 (dd, 1 H), 3.41 (td, 1 H), 3.09 (ddd, 1 H), 2.70-2.56 (m, 1 H), 2.39-2.30 (m, 1 H).

EXAMPLE 574

(3S)-3-[5-(2-amino-4-chloro-1,3-thiazol-5-yl)-1H-imidazol-2-yl]-7-[5-chloro-2-(1H-tetrazol-1-yl)phenyl]-2,3-dihydro-5(1H)-indolizinone The same operation as in Example 201→Example 203→Example 204→Example 51→Example 52 was conducted from 2-{[(tert-butoxy)carbonyl]amino}-4-chloro-1,3-thiazole-5-carboxylic acid [Bioorg. Med. Chem., 12(23), 6171 (2004)] to give the title compound having the following physical properties. (Note: in the step corresponding to Example 203 in the operation, methyl magnesium bromide was used. In the step corresponding to Example 204 in the operation, removal of the tert-butoxycarbonyl group was also accomplished).

LC/MS $t_R$ 3.38 minutes; MS (ES$^+$) m/z 512 (M+H)$^b$
$^1$H NMR (500 MHz, methanol-d$_4$) δ 9.35 (s, 1 H), 7.77-7.71 (m, 2 H), 7.70-7.65 (m, 1 H), 7.37 (br. s, 1 H), 6.14 (s, 1 H), 6.06 (s, 1 H), 5.74 (d, 1 H), 3.47-3.36 (m, 1 H), 3.14-3.02 (m, 1 H), 2.68-2.54 (m, 1 H), 2.52-2.41 (m, 1 H).

EXAMPLE 575

N-[4-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-pyridinyl]acetamide The compound prepared in Example 190(2) (50 mg) was treated as detailed in Example 44 to give the title compound having the following physical properties (14 mg). LC/MS $t_R$ 3.49 minutes; MS (ES$^+$) m/z 548 (M+H)$^b$
$^1$H NMR (500 MHz, methanol-d$_4$) δ 9.37 (s, 1 H), 8.52 (app. br. s, 1 H), 8.32 (d, 1 H), 7.78-7.72 (m, 2 H), 7.70-7.66 (m, 1 H), 7.43 (d, 1 H), 6.14 (s, 1 H), 6.10 (s, 1 H), 5.74 (dd, 1 H), 3.51-3.38 (m, 1 H), 3.19-3.07 (m, 1 H), 2.74-2.62 (m, 1 H), 2.44-2.35 (m, 1 H), 2.20 (s, 3 H).

EXAMPLE 576 methyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-pyridinyl]carbamate The compound prepared in Example 190(1) (67 mg) was treated with methyl chloroformate following the method of Example 128 to give the title compound having the following physical properties (40 mg).

LC/MS $t_R$ 3.13 minutes; MS (ES$^+$) m/z 530 (M+H)$^b$
$^1$H-NMR (500 MHz, DMSO-d$_6$) δ 9.97 (br. s, 1 H), 9.69 (s, 1 H), 8.14-8.02 (m, 2 H), 7.83-7.70 (m, 3 H), 7.58 (br. s, 1 H), 7.29 (d, 1 H), 5.98 (s, 1 H), 5.92 (s, 1 H), 5.61 (d, 1 H), 3.67 (s, 3 H), 3.35 (obs. m, 1 H), 2.98 (dd, 1 H), 2.50 (obs. m, 1 H), 2.33-2.22 (m, 1 H).

EXAMPLES 577(1), 577(2) AND 577(3)

(3S)-3-[5-(2-amino-3-chloro-4-pyridinyl)-1H-imidazol-2-yl]-7-[5-chloro-2-(1H-tetrazol-1-yl)phenyl]-2,3-dihydro-5(1H)-indolizinone, (3S)-3-[5-(2-amino-5-chloro-4-pyridinyl)-1H-imidazol-2-yl]-7-[5-chloro-2-(1H-tetrazol-1-yl)phenyl]-2,3-dihydro-5(1H)-indolizinone and (3S)-3-[5-(2-amino-5-chloro-4-pyridinyl)-4-chloro-1H-imidazol-2-yl]-7-[5-chloro-2-(1H-tetrazol-1-yl)phenyl]-2,3-dihydro-5(1H)-indolizinone The compound prepared in Example 190(1) (97 mg) was treated as detailed in Example 44 to give the title products having the following physical properties.

EXAMPLE 577(1)

9.7 mg

LC/MS $t_R$ 2.97 minutes; MS (ES$^+$) m/z 506 (M+H)$^b$
$^1$H NMR (500 MHz, DMSO-d$_6$) δ 9.68 (s, 1 H), 7.82-7.74 (m, 4 H), 7.70 (s, 1 H), 7.16 (d, 1 H), 6.00 (s, 2 H), 5.94 (s, 1 H), 5.92 (s, 1 H), 5.63 (dd, 1 H), 3.65-3.07 (obs. m, 1 H), 2.92-2.92 (m, 1 H), 2.94 (dd, 1 H), 2.48-2.39 (m, 1 H), 2.29-2.20 (m, 1 H).

EXAMPLE 577(2)

12.6 mg

LC/MS $t_R$ 3.01 minutes; MS (ES$^+$) m/z 506 (M+H)$^b$
$^1$H NMR (500 MHz, DMSO-d$_6$) δ 9.70 (s, 1 H), 7.88 (s, 1 H), 7.82-7.79 (m, 2 H), 7.79-7.76 (m, 1 H), 7.74 (s, 1 H), 7.05 (s, 1 H), 6.04 (s, 2 H), 5.98 (s, 1 H), 5.96 (s, 1 H), 5.65 (dd, 1 H), 3.52-3.18 (obs. m, 1 H), 3.05-2.95 (m, 1 H), 2.58-2.43 (obs. m, 1 H), 2.35-2.27 (m, 1 H).

EXAMPLE 577(3)

8.6 mg

LC/MS $t_R$ 3.40 minutes; MS (ES$^+$) m/z 540 (M+H)$^b$
$^1$H NMR (500 MHz, DMSO-d$_6$) δ 9.67 (s, 1 H), 7.97 (s, 1 H), 7.84-7.73 (m, 3 H), 7.23 (br. s, 1 H), 6.44 (br. s, 2 H), 5.96 (s, 2 H), 5.67 (dd, 1 H), 3.49-3.19 (obs. m, 1 H), 2.97 (dd, 1 H), 2.57-2.43 (obs. m, 1 H), 2.39-2.25 (m, 1 H).

EXAMPLE 578(1) AND 578(2)

tert-butyl N-(4-{2-[(3S)-7-[5-chloro-2-(1H-1,2,3,4-tetrazol-1-yl)phenyl]-5-oxo-1,2,3,5-tetrahydroindolizin-3-yl]-1H-imidazol-5-yl}pyridin-2-yl)carbamate and tert-butyl N-[(tert-butoxy)carbonyl]-N-(4-{2-[(3S)-7-[5-chloro-2-(1H-1,2,3,4-tetrazol-1-yl)phenyl]-5-oxo-1,2,3,5-tetrahydroindolizin-3-yl]-1H-imidazol-5-yl}pyridin-2-yl)carbamate To a tert-butanol (1.3 mL) solution of the compound prepared in Example 190(1) (123 mg) was added di-tert-butyl dicarbonate (250 mg). The mixture was stirred at room temperature for 36 hours then at 50° C. for a further 3 hours. To the ambient reaction mixture, concentrated ammonia solution (0.15 mL) was added and the mixture stirred at room temperature for 6 hours then at 50° C. for a further hour. The reaction mixture was concentrated and the residue purified by column chromatography (0-15% methanol in ethyl acetate) to give the title products in a 4:1 ratio.

EXAMPLE 578(1)

LC/MS $t_R$ 1.69 minutes; MS (ES$^+$) m/z 572 (M+H)$^a$.

EXAMPLE 578(2)

LC/MS $t_R$ 2.10 minutes; MS (ES$^+$) m/z 672 (M+H)$^a$.

EXAMPLE 579

(3S)-3-[5-(2-amino-4-pyridinyl)-4-chloro-1H-imidazol-2-yl]-7-[5-chloro-2-(1H-tetrazol-1-yl)phenyl]-2,3-dihydro-5(1H)-indolizinone The same operation as in Example 44→Example 206 was conducted from the 4:1 ratio of compounds prepared in Example 578 to give the title compound having the following physical properties.
LC/MS $t_R$ 3.04 minutes; MS (ES$^+$) m/z 506 (M+H)$^b$
$^1$H NMR (500 MHz, DMSO-d$_6$) δ 13.09 (br. s, 1 H), 9.71 (s, 1 H), 7.96 (d, 1 H), 7.85-7.76 (m, 3 H), 6.85-6.75 (m, 2 H), 6.06 (br. s, 2 H), 5.99 (s, 1 H), 5.94 (s, 1 H), 5.57 (dd, 1 H), 3.29-3.21 (m, 1 H), 3.04-2.93 (m, 1 H), 2.58-2.52 (obs m, 1 H), 2.23-2.13 (m, 1 H).

EXAMPLE 580 tert-butyl N-(4-acetylpyridin-2-yl)-N-methylcarbamate

The same operation as in Example 550→Example 228 was conducted from 1-(2-chloropyridin-4-yl)ethanone to give the title compound having the following physical properties.
LC/MS $t_R$ 2.05 minutes; MS (ES$^+$) m/z 251 (M+H)$^a$.

EXAMPLE 581

2-bromo-1-[2-(methylamino)pyridin-4-yl]ethan-1-one

To a tetrahydrofuran (6 mL) solution of the compound prepared in Example 580 (161 mg) was added a 33% weight solution of hydrogen bromide in acetic acid (222 μL) followed by bromine (33 μL) and the mixture was stirred at room temperature for 1 hour. The reaction mixture was concentrated and the residue triturated with a 1:3 mixture of dichloromethane and tert-butyl methyl ether (20 mL), the resultant precipitate being isolated by filtration to give the title compound having the following physical properties.
LC/MS $t_R$ 0.71 minutes; MS (ES$^+$) m/z 229 (M+H)$^a$.

EXAMPLE 582

(3S)-7-[5-chloro-2-(1H-tetrazol-1-yl)phenyl]-3-{5-[2-(methylamino)-4-pyridinyl]-1H-imidazol-2-yl}-2,3-dihydro-5(1H)-indolizinone The same operation as in Example 51→Example 52 was conducted from the compound prepared in Example 581 to give the title compound having the following physical properties.
LC/MS $t_R$ 2.93 minutes; MS (ES$^+$) m/z 486 (M+H)$^b$
$^1$H NMR (500 MHz, methanol-d$_4$) δ 9.36 (s, 1 H), 7.87 (d, 1 H), 7.72 (m, 2 H), 7.68 (dd, 1 H), 7.49 (br. s, 1 H), 6.84

(app. d, 2 H), 6.14 (s, 1 H), 6.08 (s, 1 H), 5.78 (dd, 1 H), 3.43 (td, 1 H), 3.11 (ddd, 1 H), 2.89 (s, 3 H), 2.64 (qd, 1 H), 2.51-2.38 (m, 1 H).

EXAMPLE 583 prop-2-en-1-yl N-(4-{4-chloro-2-[(3S)-7-[5-chloro-2-(1H-1,2,3,4-tetrazol-1-yl)phenyl]-5-oxo-1,2,3,5-tetrahydroindolizin-3-yl]-1H-imidazol-5-yl}pyridin-2-yl)-N-methylcarbamate The same operation as in Example 484→Example 44 was conducted from the compound prepared in Example 582 to give the title compound having the following physical properties. (Note: in the step corresponding to Example 484 in the operation, allyl chloroformate was used).
LC/MS $t_R$ 2.04 minutes; MS (ES$^+$) m/z 604 (M+H)$^a$.

EXAMPLE 584

(3S)-3-{4-chloro-5-[2-(methylamino)-4-pyridinyl]-1H-imidazol-2-yl}-7-[5-chloro-2-(1H-tetrazol-1-yl)phenyl]-2,3-dihydro-5(1H)-indolizinone To a nitrogen degassed tetrahydrofuran (1.5 mL) solution of the compound prepared in Example 583 (93 mg) and N,N'-dimethylbarbituric acid (29 mg) was added tetrakis(triphenylphosphine)palladium(0) (9 mg) and the mixture stirred at room temperature for 2.5 hours. To the reaction mixture, saturated sodium hydrogen carbonate solution (30 mL) was added followed by extraction into ethyl acetate. The combined organic layers were washed with saturated saline, dried and concentrated. The residue was purified by high performance liquid chromatography (5 to 100% acetonitrile in water) to give the title compound having the following physical properties (36 mg).
LC/MS $t_R$ 3.10 minutes; MS (ES$^+$) m/z 520 (M+H)$^b$
$^1$H NMR (500 MHz, methanol-d$_4$) δ 9.37 (s, 1 H), 7.96 (dd, 1 H), 7.79-7.63 (m, 3 H), 6.91-6.82 (m, 2 H), 6.12 (s, 1 H), 6.11 (s, 1 H), 5.72 (dd, 1 H), 3.53-3.35 (m, 1 H), 3.19-3.02 (m, 1 H), 2.89 (s, 3 H), 2.65 (qd, 1 H), 2.45-2.29 (m, 1 H).

EXAMPLE 585

(3S)-3-[5-(3-amino-4-pyridinyl)-1H-imidazol-2-yl]-7-[5-chloro-2-(1H-tetrazol-1-yl)phenyl]-2,3-dihydro-5(1H)-indolizinone The same operation as in Example 51→Example 52→Example 74 was conducted from 2-bromo-1-(3-nitropyridin-4-yl)ethan-1-one [J. Med. Chem., 53(2), 787 (2010)] to give the title compound having the following physical properties.
LC/MS $t_R$ 2.95 minutes; MS (ES$^+$) m/z 472 (M+H)$^b$
$^1$H NMR (500 MHz, methanol-d$_4$) δ 9.35 (s, 1 H), 8.00 (s, 1 H), 7.78-7.64 (m, 4 H), 7.59 (s, 1 H), 7.39 (d, 1 H), 6.18 (s, 1 H), 6.05 (s, 1 H), 5.83 (dd, 1 H), 3.48-3.37 (m, 1 H), 3.11 (dd, 1 H), 2.65-2.56 (m, 1 H), 2.56-2.47 (m, 1 H).

EXAMPLE 586

(3S)-7-[5-chloro-2-(1H-tetrazol-1-yl)phenyl]-3-[5-(2-methyl-4-pyridinyl)-1H-imidazol-2-yl]-2,3-dihydro-5(1H)-indolizinone acetate The same operation as in Example 51→Example 52 was conducted from 2-bromo-1-(2-methylpyridin-4-yl)ethan-1-one [J. Med. Chem., 53(2), 787 (2010)] to give the title compound having the following physical properties.
LC/MS $t_R$ 2.91 minutes; MS (ES$^+$) m/z 471 (M+H)$^b$
$^1$H NMR (500 MHz, methanol-d$_4$) δ 9.36 (s, 1 H), 8.33 (d, 1 H), 7.77-7.62 (m, 5 H), 7.56 (br. s, 1 H), 6.14 (s, 1 H), 6.10 (s, 1 H), 5.79 (dd, 1 H), 3.51-3.39 (m, 1H), 3.12 (ddd, 1 H), 2.70-2.59 (m, 1 H), 2.55 (s, 3 H), 2.52-2.43 (m, 1 H).

EXAMPLE 587

(3S)-7-[5-chloro-2-(1H-tetrazol-1-yl)phenyl]-3-[5-(2,6-dimethyl-4-pyridinyl)-1H-imidazol-2-yl]-2,3-dihydro-5(1H)-indolizinone The same operation as in Example 139→Example 204→Example 51→Example 52 was conducted from 4-bromo-2,6-dimethylpyridine to give the title compound having the following physical properties.
LC/MS $t_R$ 2.99 minutes; MS (ES$^+$) m/z 485 (M+H)$^b$
$^1$H NMR (500 MHz, methanol-d$_4$) δ 9.36 (s, 1 H), 7.76-7.71 (m, 2 H), 7.70-7.67 (m, 1 H), 7.61 (br. s, 1 H), 7.40 (br. s, 2 H), 6.13 (s, 1 H), 6.10 (s, 1 H), 5.78 (dd, 1 H), 3.51-3.40 (m, 1 H), 3.12 (ddd, 1 H), 2.65 (qd, 1 H), 2.52-2.43 (obs. m, 1 H), 2.50 (s, 6 H).

EXAMPLE 588

(3S)-3-[4-chloro-5-(2,6-dimethyl-4-pyridinyl)-1H-imidazol-2-yl]-7-[5-chloro-2-(1H-tetrazol-1-yl)phenyl]-2,3-dihydro-5(1H)-indolizinone The compound prepared in Example 587 (69 mg) was treated as detailed in Example 44 to give the title compound having the following physical properties (3 mg).
LC/MS $t_R$ 3.13 minutes; MS (ES$^+$) m/z 519 (M+H)$^b$
$^1$H NMR (500 MHz, methanol-d$_4$) δ 9.37 (s, 1 H), 7.76-7.72 (m, 2 H), 7.71-7.67 (m, 1 H), 7.46 (s, 2 H), 6.13 (s, 1 H), 6.11 (s, 1 H), 5.72 (dd, 1 H), 3.47-3.39 (m, 1 H), 3.12 (ddd, 1 H), 2.71-2.61 (m, 1 H), 2.54 (s, 6 H), 2.42-2.34 (m, 1 H).

EXAMPLE 589

1-(6-aminopyridin-2-yl)ethan-1-one dihydrobromide

The same operation as in Example 187→Example 188→Example 189 was conducted from 6-fluoropyridine-2-carbonitrile to give the title compound having the following physical properties.
$^1$H NMR (250 MHz, DMSO-d$_6$) δ 7.96 (t, 1 H), 7.59 (d, 1 H), 7.15 (d, 1 H), 4.95 (s, 2 H), 4.12 (br. s, 3 H).

EXAMPLE 590 prop-2-en-1-yl N-(6-{2-[(3S)-7-[5-chloro-2-(1H-1,2,3,4-tetrazol-1-yl)phenyl]-5-oxo-1,2,3,5-tetrahydroindolizin-3-yl]-1H-imidazol-5-yl}pyridin-2-yl)carbamate The same operation as in Example 51→Example 484→Example 52 was conducted from the compound prepared in Example 589 to give the title compound having the following physical properties. (Note: in the step corresponding to Example 484 in the operation, allyl chloroformate was used. Additionally, in the same step in the operation, the stage employing methanol and concentrated ammonia solution was omitted and the crude product extracted into ethyl acetate from water).
LC/MS $t_R$ 1.73 minutes; MS (ES$^+$) m/z 556 (M+H)$^a$.

EXAMPLE 591

(3S)-3-[5-(6-amino-2-pyridinyl)-1H-imidazol-2-yl]-7-[5-chloro-2-(1H-tetrazol-1-yl)phenyl]-2,3-dihydro-5(1H)-indolizinone The compound prepared in Example 590 (75 mg) was treated as detailed in Example 584 to give the title compound having the following physical properties (11.5 mg).
LC/MS $t_R$ 2.83 minutes; MS (ES$^+$) m/z 472 (M+H)$^b$
$^1$H NMR (500 MHz, methanol-d$_4$) δ 9.36 (s, 1 H), 7.76-7.70 (m, 2 H), 7.70-7.65 (m, 1 H), 7.51-7.36 (m, 2 H), 7.01 (br. s, 1 H), 6.44 (d, 1 H), 6.14 (s, 1 H), 6.08 (s, 1 H), 5.81 (dd, 1 H), 3.49-3.37 (m, 1 H), 3.10 (ddd, 1 H), 2.68-2.57 (m, 1 H), 2.55-2.46 (m, 1 H).

EXAMPLE 592

(3S)-3-[5-(6-amino-2-pyridinyl)-4-chloro-1H-imidazol-2-yl]-7-[5-chloro-2-(1H-tetrazol-1-yl)phenyl]-2,3-dihydro-5(1H)-indolizinone The same operation as in Example 338→Example 584 was conducted from the compound prepared in Example 590 to give the title compound having the following physical properties.
LC/MS $t_R$ 3.19 minutes; MS (ES$^+$) m/z 506 (M+H)$^b$
$^1$H NMR (500 MHz, methanol-d$_4$) δ 9.36 (s, 1 H), 7.75-7.70 (m, 2 H), 7.70-7.65 (m, 1 H), 7.47 (t, 1 H), 7.25 (d, 1 H), 6.46 (d, 1 H), 6.16 (s, 1 H), 6.08 (s, 1 H), 5.80 (dd, 1 H), 3.39 (td, 1 H), 3.09 (ddd, 1 H), 2.67-2.56 (m, 1 H), 2.53-2.44 (m, 1 H).

EXAMPLE 593 formic acid-(3S)-3-[5-(6-amino-3-pyridinyl)-4-fluoro-1H-imidazol-2-yl]-7-[5-chloro-2-(1H-tetrazol-1-yl)phenyl]-2,3-dihydro-5(1H)-indolizinone (1:1)

The same operation as in Example 484→Example 364→Example 584 was conducted from the compound prepared in Example 194 to give the title compound after purification by high performance liquid chromatography [5 to 100% mobile phase B (0.1% formic acid in acetonitrile) in mobile phase A (0.1% aqueous formic acid)] as the formic acid salt having the following physical properties. (Note: in the step corresponding to Example 484 in the operation, allyl chloroformate was used).
LC/MS $t_R$ 2.93 minutes; MS (ES$^+$) m/z 490 (M+H)$^b$
$^1$H NMR (500 MHz, methanol-d$_4$) δ 9.38 (s, 1 H), 8.19 (br. s, 1 H), 8.09 (br. s, 1 H), 7.78-7.67 (m, 4 H), 6.73 (d, 1 H), 6.13 (s, 1 H), 6.11 (s, 1 H), 5.68 (dd, 1 H), 3.45 (td, 1 H), 3.12 (ddd, 1 H), 2.70-2.59 (m, 1 H), 2.43-2.34 (m, 1 H).

EXAMPLE 594

2-methoxyethyl[6-(2-{(3S)-7-[5-chloro-2-(1H-tetrazol-1-yl)phenyl]-5-oxo-1,2,3,5-tetrahydro-3-indolizinyl}-4-fluoro-1H-imidazol-5-yl)-3-pyridinyl]carbamate The compound prepared in Example 531 (200 mg) was treated as detailed in Example 364 to give the title product having the following physical properties (10.5 mg).

LC/MS $t_R$ 3.95 minutes; MS (ES$^+$) m/z 592 (M+H)$^b$
$^1$H NMR (500 MHz, methanol-d$_4$) δ 9.35 (s, 1 H), 8.58 (s, 1 H), 7.93 (d, 1 H), 7.75-7.70 (m, 2 H), 7.67 (d, 1 H), 7.49 (d, 1 H), 6.15 (s, 1 H), 6.07 (s, 1 H), 5.75 (d, 1 H), 4.31-4.27 (m, 2 H), 3.68-3.63 (m, 2 H), 3.45-3.35 (m, 1 H), 3.39 (s, 3 H), 3.09 (ddd, 1 H), 2.61 (qd, 1 H), 2.45-2.38 (m, 1 H).

EXAMPLE 595 ethyl(3R)-7-[5-chloro-2-(1H-1,2,3,4-tetrazol-1-yl)phenyl]-5-oxo-1,2,3,5-tetrahydroindolizine-3-carboxylate The same operation as in Example 1→Example 2→Example 3→Example 4→Example 5→Example 6→Example 7→Example 9 was conducted from ethyl 5-oxo-D-prolinate to give the title compound having the following physical properties. LC/MS $t_R$ 3.70 minutes; MS (ES$^+$) m/z 793 (2M+Na), 771 (2M+H), 408 (M+Na), 386 (M+H), 358 (M-N$_2$+H)$^b$.

EXAMPLE 596

(3R)-7-[5-chloro-2-(1H-1,2,3,4-tetrazol-1-yl)phenyl]-5-oxo-1,2,3,5-tetrahydroindolizine-3-carboxylic acid To a 1,4-dioxane (3.8 mL) solution of the compound prepared in Example 595 (1.28 g) was added 2 M hydrochloric acid (6.4 mL) and the reaction stirred at 70° C. for 2 hours. A second aliquot of 2 M hydrochloric acid (6.4 mL) was added and the mixture stirred at the same temperature a further 2 hours. A third aliquot of 2 M hydrochloric acid (6.4 mL) was added and the reaction stirred at 70° C. for a further 2 hours before cooling to room temperature. To the reaction mixture, ammonium sulfate (13.1 g) was added and the resultant suspension extracted into ethyl acetate. The combined organic layers were washed with saturated saline, dried and concentrated. The residue was triturated with a 1:1 mixture of ethyl acetate and heptane to give the title compound having the following physical properties (1.15 g).
LC/MS $t_R$ 3.19 minutes; MS (ES$^+$) m/z 737 (2M+Na), 715 (2M+H), 380 (M+Na), 358 (M+H), 330 (M-N$_2$+H)$^b$.

EXAMPLE 597

(3R)-3-[5-(6-amino-3-pyridinyl)-1H-imidazol-2-yl]-7-[5-chloro-2-(1H-tetrazol-1-yl)phenyl]-2,3-dihydro-5(1H)-indolizinone The same operation as in Example 51→Example 52 was conducted from the compound prepared in Example 596 to give the title compound having the following physical properties. (Note: in the step corresponding to Example 51 in the process, the compound prepared in Example 193 was used)
LC/MS $t_R$ 2.68 minutes; MS (ES$^+$) m/z 472 (M+H)$^b$
$^1$H NMR (500 MHz, methanol-d$_4$) δ 9.36 (s, 1 H), 8.20 (app. br. s, 1 H), 7.79-7.70 (m, 3 H), 7.67 (d, 1 H), 7.18 (br. s, 1 H), 6.60 (d, 1 H), 6.12 (s, 1 H), 6.08 (s, 1 H), 5.78 (dd, 1 H), 3.44 (td, 1 H), 3.10 (ddd, 1 H), 2.63 (qd, 1 H), 2.46 (app. br. s, 1 H).

EXAMPLE 598 formic acid-(3R)-3-[5-(6-amino-3-pyridinyl)-4-chloro-1H-imidazol-2-yl]-7-[5-chloro-2-(1H-tetrazol-1-yl)phenyl]-2,3-dihydro-5(1H)-indolizinone (1:1)

The compound prepared in Example 597 (250 mg) was treated as detailed in Example 44 to give the title compound after purification by high performance liquid chromatography [5 to 100% mobile phase B (0.1% formic acid in acetonitrile) in mobile phase A (0.1% aqueous formic acid)] as the formic acid salt having the following physical properties (86 mg).

LC/MS $t_R$ 2.94 minutes; MS (ES$^+$) m/z 506 and 508 (M+H)$^b$ $^1$H NMR (500 MHz, methanol-d$_4$) δ 9.38 (s, 1 H), 8.21 (d, 1 H), 8.17 (br. s, 1 H), 7.85 (d, 1 H), 7.79-7.73 (m, 2 H), 7.72-7.69 (m, 1 H), 6.74 (d, 1 H), 6.14 (s, 1 H), 6.12 (s, 1 H), 5.71 (dd, 1 H), 3.46 (td, 1 H), 3.12 (ddd, 1 H), 2.65 (qd, 1 H), 2.44-2.36 (m, 1 H).

EXAMPLE 599 prop-2-en-1-yl 2-[(diphenylmethylidene)amino]acetate

To a dichloromethane (16 mL) solution of glycine allyl ester [J. Org. Chem., 66(15), 5241 (2001)] (5.05 g) was added benzophenone imine (5.6 mL) and the reaction stirred at room temperature for 22 hours. To the reaction mixture, dichloromethane (25 mL) was added and the suspension filtered through Celite®. The filtrate was concentrated to half the original volume and tert-butyl methyl ether added. The suspension was filtered once more through Celite® and the filtrate concentrated to give the title compound having the following physical properties (8.56 g).

$^1$H NMR (500 MHz, CDCl$_3$) δ 7.71-7.64 (m, 2 H), 7.53-7.45 (m, 3 H), 7.44-7.39 (m, 1 H), 7.35 (app. t, 2 H), 7.19 (dd, 2 H), 6.00-5.87 (m, 1 H), 5.37-5.29 (m, 1 H), 5.25 (dd, 1 H), 4.66 (d, 2 H), 4.25 (s, 2 H).

EXAMPLE 600 prop-2-en-1-yl 2-amino-3-oxo-3-phenylpropanoate hydrochloride

To a cooled (−78° C.) tetrahydrofuran (7.2 mL) solution of the compound prepared in Example 599 (1.0 g) was added a solution of 1 M lithium bis(trimethylsilyl)amide in tetrahydrofuran (3.6 mL) and the mixture stirred at −78° C. for 30 minutes. The resultant solution was added to a cooled (−78° C.) tetrahydrofuran (3.6 mL) solution of benzoyl chloride (0.42 mL) and the mixture stirred at −78° C. for 2 hours. To the cooled (−78° C.) reaction mixture, a 1 M aqueous solution of hydrochloric acid (7.2 mL) was added and the reaction stirred at room temperature for 1 hour. The reaction mixture was concentrated and the residue triturated with tert-butyl methyl ether. The resultant precipitate was collected by filtration to give the title compound having the following physical properties (1.13 g).

LC/MS $t_R$ 1.13 minutes; MS (ES$^+$) m/z 220 (M+H)$^a$.

EXAMPLE 601 prop-2-en-1-yl 2-{[(3S)-7-[5-chloro-2-(1H-1,2,3,4-tetrazol-1-yl)phenyl]-5-oxo-1,2,3,5-tetrahydroindolizin-3-yl]formamido}-3-oxo-3-phenylpropanoate To a cooled (−20° C.) tetrahydrofuran (6 mL) solution of the compound prepared in Example 9 (1.1 g) and N-methylmorpholine (0.85 mL) was added isobutyl chloroformate (0.41 mL) and the mixture stirred at −20° C. for 40 minutes then at room temperature for 5 minutes. To the reaction mixture, an N,N-dimethylformamide (7 mL) suspension of the compound prepared in Example 600 (1.01 g) and N-methylmorpholine (0.85 mL) was added and the mixture stirred at room temperature for 1 hour. To the reaction mixture, water (20 mL) and a saturated aqueous solution of sodium hydrogen carbonate (20 mL) were added followed by extraction into ethyl acetate. The combined organic layers were washed sequentially with 1 M hydrochloric acid and saturated saline, dried and concentrated. The residue was purified by column chromatography (20%-100% ethyl acetate in heptanes) to give the title compound having the following physical properties (1.17 g).

LC/MS $t_R$ 1.99 minutes; MS (ES$^+$) m/z 559 (M+H)$^a$.

EXAMPLE 602 prop-2-en-1-yl 2-[(3S)-7-[5-chloro-2-(1H-1,2,3,4-tetrazol-1-yl)phenyl]-5-oxo-1,2,3,5-tetrahydroindolizin-3-yl]-5-phenyl-1H-imidazole-4-carboxylate To an acetic acid (8.1 mL) suspension of the compound prepared in Example 601 (0.9 g) was added ammonium acetate (1.84 g) and the mixture stirred at reflux for 2 hours. To the ambient reaction mixture, saturated sodium hydrogen carbonate was added followed by extraction into ethyl acetate. The combined organic layers were washed with saturated saline, dried and concentrated. The residue was purified by column chromatography (20%-100% ethyl acetate in heptanes) to give the title compound having the following physical properties (358 mg).

LC/MS $t_R$ 2.03 minutes; MS (ES$^+$) m/z 540 (M+H)$^a$.

EXAMPLE 603

2-{(3S)-7-[5-chloro-2-(1H-tetrazol-1-yl)phenyl]-5-oxo-1,2,3,5-tetrahydro-3-indolizinyl}-5-phenyl-1H-imidazole-4-carboxylic acid The compound prepared in Example 602 (100 mg) was treated as detailed in Example 584 to give the title compound having the following physical properties (38 mg).

LC/MS $t_R$ 3.62 minutes; MS (ES$^+$) m/z 500 (M+H)$^b$ $^1$H NMR (500 MHz, methanol-d$_4$) δ 9.36 (s, 1 H), 7.77-7.70 (m, 4 H), 7.70-7.65 (m, 1 H), 7.42-7.32 (m, 3 H), 6.13 (s, 1 H), 6.08 (s, 1 H), 5.76 (dd, 1 H), 3.47 (td, 1 H), 3.11 (ddd, 1 H), 2.65 (qd, 1 H), 2.52-2.42 (m, 1 H).

EXAMPLE 604

2-[(3S)-7-[5-chloro-2-(1H-1,2,3,4-tetrazol-1-yl)phenyl]-5-oxo-1,2,3,5-tetrahydroindolizin-3-yl]-5-phenyl-1H-imidazole-4-carbonitrile To an N,N-dimethylformamide (2 mL) solution of the compound prepared in Example 603 (50 mg) was added 1.1'-carbonyldiimidazole (14 mg) and the mixture stirred at 100° C. for 16 hours. Further 1.1'-carbonyldiimidazole (14 mg) was added and the mixture stirred a further 24 hours at 100° C. The mixture was then allowed to cool to room temperature whereupon concentrated ammonia solution (67 µL) was added. The mixture was transferred to a sealed tube and heated at 50° C. for 16 hours. To the ambient reaction mixture, a saturated aqueous solution of sodium hydrogen carbonate was added followed by extraction into ethyl acetate. The combined organic layers were washed with water and saturated saline, dried and concentrated. The residue was purified by column chromatography (25%-100% ethyl acetate in heptanes) to afford the title compound having the following physical properties (6 mg).

LC/MS $t_R$ 1.67 minutes; MS (ES$^+$) m/z 499 (M+H)$^a$.

EXAMPLE 605

2-{(3S)-7-[5-chloro-2-(1H-tetrazol-1-yl)phenyl]-5-oxo-1,2,3,5-tetrahydro-3-indolizinyl}-5-phenyl-1H-imidazole-4-carbonitrile To a dichloromethane (0.5 mL) solution of the compound prepared in Example 604 (6 mg) was added (methoxycarbonylsulfamoyl)triethylammonium hydroxide, inner salt (8.6 mg) and the mixture stirred at room temperature for 2 hours. To the reaction mixture, a saturated aqueous solution of sodium hydrogen carbonate was added followed by extraction into dichloromethane. The combined organic layers were washed with saturated saline, dried and concentrated. The residue was purified by column chromatography (80%-100% ethyl acetate in heptanes) to afford the title compound having the following physical properties (3.5 mg).

LC/MS $t_R$ 4.06 minutes; MS (ES$^+$) m/z 481 (M+H)$^b$ $^1$H NMR (500 MHz, methanol-d$_4$) δ 9.38 (s, 1 H), 7.80 (d, 2 H), 7.78-7.72 (m, 2 H), 7.71-7.68 (m, 1 H), 7.54-7.49 (m, 2 H), 7.47-7.42 (m, 1 H), 6.15 (s, 1 H), 6.10 (s, 1 H 5.77 (dd, 1 H), 3.48-3.38 (m, 1 H), 3.12 (ddd, 1 H), 2.72-2.61 (m, 1 H), 2.45-2.35 (m, 1 H).

EXAMPLE 606(1) AND 606(2)

3-(2-chloroacetyl)-7-[5-chloro-2-(1H-1,2,3,4-tetrazol-1-yl)phenyl]-1,2,3,5-tetrahydroindolizin-5-one and 3-(2-bromoacetyl)-7-[5-chloro-2-(1H-1,2,3,4-tetrazol-1-yl)phenyl]-1,2,3,5-tetrahydroindolizin-5-one The compound prepared in Example 9 (0.50 g) was treated as detailed in Example 234 to give a 2:1 ratio of the title compounds having the following physical properties (0.65 g).

EXAMPLE 606(1)

LC/MS $t_R$ 1.73 minutes; MS (ES$^+$) m/z 412 and 414 (M+Na); 390 and 392 (M+H)$^a$.

EXAMPLE 606(2)

LC/MS $t_R$ 1.76 minutes; MS (ES$^+$) m/z 456 and 458 (M+Na); 434 and 436 (M+H)$^a$.

EXAMPLE 607

4-(5-{(3S)-7-[5-chloro-2-(1H-tetrazol-1-yl)phenyl]-5-oxo-1,2,3,5-tetrahydro-3-indolizinyl}-1H-imidazol-2-yl)benzamide The 2:1 mixture of compounds prepared in Example 606 (32 mg) were treated with 4-amidinobenzamide hydrochloride following the method of Example 239 to give the title compound having the following physical properties (3.9 mg).

LC/MS $t_R$ 2.98 minutes; MS (ES$^+$) m/z 499 (M+H)$^b$ $^1$H NMR (500 MHz, DMSO-d$_6$) δ 12.61 (s, 1 H), 9.71 (s, 1 H), 8.01 (s, 1 H), 7.97-7.91 (m, 4 H), 7.84-7.77 (m, 3 H), 7.40 (s, 1 H), 6.99 (s, 1 H), 5.92 (s, 2 H), 5.62-5.60 (m, 1 H), 3.02-2.90 (m, 1 H), 2.54-2.51 (m, 1 H), 2.47-2.35 (m, 1 H), 2.33-2.21 (m, 1 H).

EXAMPLE 608

4-(4-chloro-5-{(3S)-7-[5-chloro-2-(1H-tetrazol-1-yl)phenyl]-5-oxo-1,2,3,5-tetrahydro-3-indolizinyl}-1H-imidazol-2-yl)benzamide The compound prepared in Example 607 (60 mg) was treated using the method as detailed in Example 44 to give the title compound having the following physical properties (6.0 mg).

LC/MS $t_R$ 3.64 minutes; MS (ES$^+$) m/z 533 (M+H)$^b$ $^1$H NMR (500 MHz, DMSO-d$_6$) δ 13.04 (s, 1 H), 9.66 (s, 1 H), 8.03 (s, 1 H), 7.96 (d, 2 H), 7.92 (d, 2 H), 7.82 (s, 2 H), 7.76 (s, 1 H), 7.42 (s, 1 H), 6.00 (s, 1 H), 5.94 (s, 1 H), 5.66-5.63 (m, 1 H), 3.24-3.10 (m, 1 H), 3.09-2.98 (m, 1 H), 2.64-2.55 (m, 1 H), 2.20-2.09 (m, 1 H).

EXAMPLE 609 tert-butyl N-[5-(N-hydroxycarbamimidoyl)pyridin-2-yl]carbamate

To an ethanol (5 mL) solution of tert-butyl 5-cyano-2-pyridinylcarbamate (0.30 g) was added hydroxylamine hydrochloride (0.95 g) followed by N,N-diisopropylethylamine (244 µL) and the mixture stirred at 80° C. for 1.5 hours. The reaction mixture was concentrated and azeotroped with chloroform to give the title compound having the following physical properties (0.345 g).

LC/MS $t_R$ 1.21 minutes; MS (ES$^+$) m/z 253 (M+H)$^a$.

EXAMPLE 610

(6-{[(tert-butoxy)carbonyl]amino}pyridin-3-yl)methanimidamido acetate

To an acetic acid (10 mL) solution of the compound prepared in Example 609 (0.345 g) was added acetic anhydride (3.85 mL) and the mixture stirred at room temperature for 30 minutes. The reaction mixture was concentrated, the residue dissolved in ethyl acetate and washed sequentially with a saturated aqueous solution of sodium hydrogen carbonate and saturated saline, dried and concentrated to obtain the title compound having the following physical properties (0.244 g).

LC/MS $t_R$ 1.60 minutes; MS (ES$^+$) m/z 295 (M+H)$^a$.

EXAMPLE 611 acetic acid-tert-butyl N-(5-carbamimidoylpyridin-2-yl)carbamate (1:1)

To an ethanol (3 mL) solution of the compound prepared in Example 610 (0.244 g) was added palladium on carbon (50 mg) and the mixture stirred at room temperature under at atmosphere of hydrogen for 1 hour. The reaction mixture was filtered through Celite® and the filtrate concentrated to give the title compound having the following physical properties (0.174 g).

LC/MS $t_R$ 1.15 minutes; MS (ES$^+$) m/z 237 (M+H)$^a$.

EXAMPLE 612 tert-butyl N-(5-{5-[7-[5-chloro-2-(1H-1,2,3,4-tetrazol-1-yl)phenyl]-5-oxo-1,2,3,5-tetrahydroindolizin-3-yl]-1H-imidazol-2-yl}pyridin-2-yl)carbamate To a tetrahydrofuran (2 mL) and water (0.6 mL) solution of the 2:1 mixture of compounds prepared in Example 606 (109 mg) was added sodium hydrogen carbonate (85 mg) and the mixture warmed to 70° C. for 30 minutes. The compound prepared in Example 611 (109 mg) was added and the mixture stirred at 70° C. for 3 hours. The reaction mixture was diluted with ethyl acetate and washed sequentially with water and saturated saline, dried and concentrated. The residue was purified by column chromatography (0-100% methanol in dichloromethane) to give the title compound having the following physical properties (18.5 mg).

LC/MS $t_R$ 1.68 minutes; MS (ES$^+$) m/z 572 (M+H)$^a$.

EXAMPLE 613

(3S)-3-[2-(6-amino-3-pyridinyl)-1H-imidazol-5-yl]-7-[5-chloro-2-(1H-tetrazol-1-yl)phenyl]-2,3-dihydro-5(1H)-indolizinone hydrochloride The compound prepared in Example 612 (18.5 mg) was treated using the method as detailed in Example 55 to give the title compound having the following physical properties (6.8 mg).

LC/MS $t_R$ 2.79 minutes; MS (ES$^+$) m/z 472 (M+H)$^b$ $^1$H NMR (500 MHz, DMSO-d$_6$) δ 9.73 (s, 1 H), 8.79 (s, 1 H), 8.46 (d, 2 H), 7.83 (s, 2 H), 7.77 (s, 1 H), 7.37 (s, 1 H), 7.09 (d, 1 H), 6.00 (s, 2 H), 5.79-5.60 (m, 1 H), 3.31-3.20 (m, 1 H), 3.06-2.94 (m, 1 H), 2.61-2.55 (m, 1 H), 2.33-2.24 (m, 1 H).

EXAMPLE 614

(3S)-3-[2-(6-amino-3-pyridinyl)-4-chloro-1H-imidazol-5-yl]-7-[5-chloro-2-(1H-tetrazol-1-yl)phenyl]-2,3-dihydro-5(1H)-indolizinone hydrochloride The same operation as in Example 44→Example 55 was conducted from the compound prepared in Example 612 to give the title compound having the following physical properties.

LC/MS $t_R$ 3.03 minutes; MS (ES$^+$) m/z 506 (M+H)$^b$ $^1$H NMR (500 MHz, DMSO-d$_6$) δ 11.08 (s, 1 H), 9.67 (s, 1 H), 8.51-8.10 (m, 4 H), 7.84-7.79 (m, 2 H), 7.74 (d, 1 H), 7.08 (d, 1 H), 5.97 (s, 1 H), 5.94 (s, 1 H), 5.63 (dd, 1 H), 3.21-2.97 (m, 2 H), 2.62-2.06 (m, 2 H).

EXAMPLE 615 methyl[5-(4-chloro-5-{(3S)-7-[5-chloro-2-(1H-tetrazol-1-yl)phenyl]-5-oxo-1,2,3,5-tetrahydro-3-indolizinyl}-1H-imidazol-2-yl)-2-pyridinyl]carbamate The compound prepared in Example 614 (25 mg) was treated with methyl chloroformate following the method of Example 128 to give the title compound having the following physical properties (3.8 mg).

LC/MS $t_R$ 3.70 minutes; MS (ES$^+$) m/z 564 (M+H)$^b$ $^1$H NMR (500 MHz, methanol-d$_4$) δ 9.35 (s, 1 H), 8.69 (d, 1 H), 8.13 (dd, 1 H), 7.99 (d, 1 H), 7.76-7.71 (m, 2 H), 7.71-7.66 (m, 1 H), 6.20 (s, 1 H), 6.04 (s, 1 H), 5.82-5.77 (m, 1 H), 3.79 (s, 3 H), 3.42-3.38 (m, 1 H), 3.15-3.10 (m, 1 H), 2.75-2.62 (m, 1 H), 2.31-2.28 (m, 1 H).

EXAMPLE 616 methyl[6-(4-chloro-5-{(3S)-7-[5-chloro-2-(1H-tetrazol-1-yl)phenyl]-5-oxo-1,2,3,5-tetrahydro-3-indolizinyl}-1H-imidazol-2-yl)-3-pyridinyl]carbamate The same operation as in Example 77→Example 609→Example 610→Example 611→Example 612→Example 44 was conducted from 5-aminopyridine-2-carbonitrile to give the title compound having the following physical properties.

LC/MS $t_R$ 3.82 minutes; MS (ES$^+$) m/z 564 (M+H)$^b$ $^1$H NMR (500 MHz, DMSO-d$_6$) δ 13.08 (s, 1 H), 10.05 (s, 1 H), 9.64 (s, 1 H), 8.73 (s, 1 H), 7.95 (d, 1 H), 7.88 (d, 1 H), 7.81 (s, 2 H), 7.75 (s, 1 H), 5.99 (s, 1 H), 5.91 (s, 1 H), 5.73-5.66 (m, 1 H), 3.72 (s, 3 H), 3.18-2.94 (m, 2 H), 2.56-2.07 (m, 2 H).

EXAMPLE 617 tert-butyl N-{4-chloro-2-[3-(2-chloroacetyl)-5-oxo-2,3-dihydro-1H-indolizin-7-yl]phenyl}carbamate

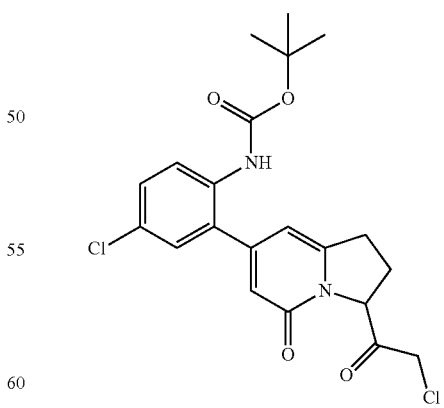

To a dichloromethane (100 mL) solution of the compound prepared in Example 19 (2.5 g) was added 1-chloro-N,N,2-trimethylprop-1-en-1-amine (1.80 ml) and the mixture stirred at room temperature for 1 hour. A 2 M solution of (trimethylsilyl)diazomethane in diethyl ether (6.2 mL) was added and the mixture stirred at room temperature for 45 minutes. Concentrated hydrochloric acid (0.53 mL) was then added and the mixture stirred vigourously at room temperature for 30 minutes. To the reaction mixture, a saturated aqueous solution of sodium hydrogen carbonate (50 mL) was added followed by extraction into dichloromethane. The combined organic layers were washed with saturated saline, dried and concentrated. The residue was purified by column chromatography (20%-100% ethyl acetate in heptanes) to give the title compound having the following physical properties (1.79 g).

LC/MS $t_R$ 2.09 minutes; MS (ES$^+$) m/z 459 (M+Na), 437 (M+H)$^a$.

EXAMPLE 618 methyl[4-(5-{(3S)-7-[5-chloro-2-(1H-tetrazol-1-yl)phenyl]-5-oxo-1,2,3,5-tetrahydro-3-indolizinyl}-4-fluoro-1H-imidazol-2-yl)phenyl]carbamate The same operation as in Example 239→Example 40→Example 24→Example 364 was conducted from the compound prepared in Example 617 to give the title compound having the following physical properties.

LC/MS $t_R$ 3.89 minutes; MS (ES$^+$) m/z 547 (M+H)$^b$
$^1$H NMR (500 MHz, CDCl$_3$) δ 9.33 (s, 1 H), 7.80-7.63 (m, 5 H), 7.52 (d, 2 H), 6.17 (s, 1 H), 6.04 (s, 1 H), 5.79 (dd, 1 H), 3.75 (s, 3 H), 3.39-3.32 (obs. m, 1 H), 3.18-3.07 (m, 1 H), 2.65 (qd, 1 H), 2.48-2.37 (m, 1 H).

EXAMPLE 619 prop-2-en-1-yl N-(4-carbamimidoylphenyl)carbamate

The same operation as in Example 225→Example 237 was conducted from 4-aminobenzonitrile to give the title compound having the following physical properties. (Note: in the step corresponding to Example 225 in the operation, allyl chloroformate was used in place of methyl chloroformate).

LC/MS $t_R$ 1.05 minutes; MS (ES$^+$) m/z 220 (M+H)$^a$.

EXAMPLE 620 tert-butyl N-(4-chloro-2-{5-oxo-3-[2-(4-{[(prop-2-en-1-yloxy)carbonyl]amino}phenyl)-1H-imidazol-5-yl]-1,2,3,5-tetrahydroindolizin-7-yl}phenyl)carbamate To a dimethylsulfoxide (3.5 mL) solution of the compounds prepared in Example 617 (200 mg) and Example 619 (83 mg) was added potassium carbonate (135 mg). The mixture was stirred at room temperature for 2.5 hours then at 90° C. for 1 hour. To the reaction mixture, water (30 mL) was added followed by extraction into ethyl acetate. The combined organic layers were washed with water and saturated saline, dried and concentrated. The residue was purified by column chromatography (0% to 10% methanol in dichloromethane) to give the title compound having the following physical properties (84.9 mg).

LC/MS $t_R$ 1.75 minutes; MS (ES$^+$) m/z 602 (M+H)$^a$.

EXAMPLE 621

(3S)-3-[2-(4-aminophenyl)-4-chloro-1H-imidazol-5-yl]-7-[5-chloro-2-(1H-tetrazol-1-yl)phenyl]-2,3-dihydro-5(1H)-indolizinone The same operation as in Example 40→Example 24→Example 44→Example 584 was conducted from the compound prepared in Example 620 to give the title compound having the following physical properties.

LC/MS $t_R$ 3.29 minutes; MS (ES$^+$) m/z 505 (M+H)$^b$
$^1$H NMR (500 MHz, DMSO-d$_6$) δ 12.34 (br. s, 1 H), 9.65 (s, 1 H), 7.84-7.78 (m, 3 H), 7.77-7.73 (m, 1 H), 7.51 (d, 2 H), 6.60 (d, 2 H), 5.98 (s, 1 H), 5.91 (s, 1 H), 5.60 (d, 1 H), 5.66-5.40 (m, 1 H), 3.20-3.09 (m, 1 H), 3.04-2.94 (m, 1 H), 2.60-2.49 (m, 1 H), 2.14-2.05 (m, 1 H).

EXAMPLE 622

(3S)-7-(2-{bis[(tert-butoxy)carbonyl]amino}-5-chlorophenyl)-5-oxo-1,2,3,5-tetrahydroindolizine-3-carboxylic acid To a methanol solution (130 mL) of the compound prepared in Example 10 (17.54 g) was added 2 M sodium hydroxide (54.6 mL) and the mixture stirred at room temperature for 1 hour 30 minutes. The methanol was removed in vacuo and the residual aqueous solution diluted with water (200 mL) and washed with dichloromethane. The aqueous layer was then treated with 2 M hydrochloric acid (30 mL) and extracted into ethyl acetate. The combined organic layers were dried and concentrated to give the title compound having the following physical properties (14.75 g).

LC/MS $t_R$ 2.05 minutes; MS (ES$^+$) m/z 405 (M-Boc+H), 527 (M+Na)$^a$.

EXAMPLE 623 tert-butyl N-[(tert-butoxy)carbonyl]-N-{4-chloro-2-[3-(2-chloroacetyl)-5-oxo-1,2,3,5-tetrahydroindolizin-7-yl]phenyl}carbamate

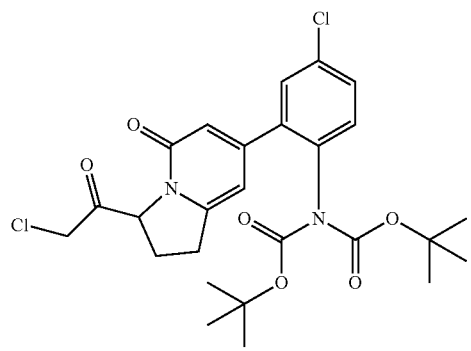 [SMILES: CC(C)(C)OC(=O)N(C(=O)OC(C)(C)C)c1ccc(Cl)cc1-c1cc2n(c(=O)c1)C(C(=O)CCl)CC2]

To a dichloromethane (160 mL) solution of the compound prepared in Example 617 (6.0 g) was added 1-chloro-N,N,2-trimethylprop-1-en-1-amine (3.46 mL) and the mixture stirred at room temperature for 1 hour. A 2 M solution of (trimethylsilyl)diazomethane in diethyl ether (11.9 mL) was added and the reaction mixture stirred at room temperature for 45 minutes. Concentrated hydrochloric acid (1.0 mL)

was then added dropwise and the reaction stirred vigorously at room temperature for 30 minutes. To the reaction mixture, a saturated aqueous solution of sodium hydrogen carbonate (250 mL) was added followed by extraction into dichloromethane. The combined organic layers were dried and concentrated to afford the title compound having the following physical properties (8.87 g).

LC/MS $t_R$ 2.28 minutes; MS (ES$^+$) m/z 437 (M-Boc+H), 559 (M+Na)$^a$.

EXAMPLE 624

(3S)-3-[2-(4-aminophenyl)-1H-imidazol-5-yl]-7-[5-chloro-2-(1H-tetrazol-1-yl)phenyl]-2,3-dihydro-5(1H)-indolizinone The same operation as in Example 620→Example 40→Example 24→Example 584 was conducted from the compound prepared in Example 623 to give the title compound having the following physical properties.

LC/MS $t_R$ 2.88 minutes; MS (ES$^+$) m/z 471 (M+H)$^b$
$^1$H NMR (500 MHz, DMSO-d$_6$) δ 11.93 (br. s, 1 H), 9.69 (s, 1 H), 7.82-7.77 (m, 3 H), 7.53 (d, 2 H), 6.73 (br. s, 1 H), 6.57 (d, 2 H), 5.93-5.88 (m, 2 H), 5.56 (d, 1 H), 5.31 (br. s, 2 H), 3.38-3.27 (m, 1 H), 2.95-2.87 (m, 1 H), 2.43-2.34 (m, 1 H), 2.27-2.20 (m, 1 H).

EXAMPLE 625

2-methoxyethyl[4-(5-{(3S)-7-[5-chloro-2-(1H-tetrazol-1-yl)phenyl]-5-oxo-1,2,3,5-tetrahydro-3-indolizinyl}-1H-imidazol-2-yl)phenyl]carbamate To a dichloromethane (1 mL) solution of the compound prepared in Example 624 (30 mg) was added N,N-diisopropylethylamine (23 µL) followed by 2-methoxyethyl chloroformate (7.5 µL) and the reaction mixture stirred at room temperature for 16 hours. Further N,N-diisopropylethylamine (13 µL) and 2-methoxyethyl chloroformate (7.5 µL) was added and the mixture stirred at room temperature for 2 hours. To the reaction mixture, water (10 mL) was added followed by extraction into dichloromethane. The combined organic layers were dried and concentrated, the residue dissolved in methanol (1 mL) and treated with concentrated ammonia solution (0.20 mL). After stirring 1 hour at room temperature the mixture was concentrated and the residue purified by column chromatography (0 to 6% methanol in dichloromethane) to give the title compound having the following physical properties (22 mg).

LC/MS $t_R$ 3.04 minutes; MS (ES$^+$) m/z 573 (M+H)$^b$
$^1$H NMR. (500 MHz, methanol-d$_4$) δ 9.39 (s, 1 H), 7.78-7.72 (m, 4 H), 7.71-7.67 (m, 1 H), 7.53 (d, 2 H), 6.74 (s, 1 H), 6.15 (s, 1 H), 6.07 (s, 1 H), 5.80 (d, 1 H), 4.31-4.25 (m, 2 H), 3.68-3.63 (m, 2 H), 3.39 (s, 3 H), 3.36-3.31 (m, 1 H), 3.08-3.00 (m, 1 H), 2.62-2.51 (m, 1 H), 2.44-2.36 (m, 1 H).

EXAMPLE 626

2-(2-methoxyethoxyl)ethyl[4-(5-{(3S)-7-[5-chloro-2-(1H-tetrazol-1-yl)phenyl]-5-oxo-1,2,3,5-tetrahydro-3-indolizinyl}-1H-imidazol-2-yl)phenyl]carbamate The compound prepared in Example 624 (30 mg) was treated as detailed in Example 625 using the chloroformate prepared in Example 489 to give the title compound having the following physical properties (15 mg).

LC/MS $t_R$ 3.09 minutes; MS (ES$^+$) m/z 617 (M+H)$^b$
$^1$H NMR (500 MHz, methanol-d$_4$) δ 9.39 (s, 1 H), 7.77-7.72 (m, 4 H), 7.71-7.67 (m, 1 H), 7.53 (d, 2 H), 6.74 (s, 1 H), 6.15 (s, 1 H), 6.07 (s, 1 H), 5.80 (d, 1 H), 4.31-4.27 (m, 2 H), 3.76-3.72 (m, 2 H), 3.68-3.64 (m, 2 H), 3.57-3.54 (m, 2 H), 3.36 (s, 3 H), 3.34-3.29 (m, 1 H), 3.08-3.00 (m, 1 H), 2.61-2.51 (m, 1 H), 2.43-2.36 (m, 1 H).

EXAMPLE 627

(1E)-N-[4-(5-{(3S)-7-[5-chloro-2-(1H-tetrazol-1-yl)phenyl]-5-oxo-1,2,3,5-tetrahydro-3-indolizinyl}-1H-imidazol-2-yl)phenyl]-N'-hydroxyethanimidamide The compound prepared in Example 624 (35 mg) was treated as detailed in Example 462 to give the title compound having the following physical properties (1.4 mg).

LC/MS $t_R$ 2.67 minutes; MS (ES$^+$) m/z 528 (M+H), 264.5 (M/2+H)$^b$
$^1$H NMR (500 MHz, DMSO-d$_6$) δ 12.34 (br. s, 0.3 H), 12.20 (br. s, 0.4 H), 12.07 (br. s, 0.3 H), 9.71-9.68 (m, 1.3 H), 9.62 (s, 0.3 H), 9.27 (s, 0.4 H), 8.21 (s, 0.4 H), 8.01 (s, 0.3 H), 7.79 (d, 3.3 H), 7.74 (d, 0.6 H), 7.69 (d, 0.8 H), 7.54 (d, 0.8 H), 7.52-7.47 (m, 0.6 H), 7.14 (d, 0.6 H), 6.86 (d, 0.3 H), 6.81-6.75 (m, 1.3 H), 5.93-5.86 (m, 2 H), 5.60-5.52 (m, 1 H), 3.42-3.29 (m, 1 H), 2.97-2.86 (m, 1 H), 2.44-2.37 (m, 1 H), 2.30-2.21 (m, 1 H), 1.98 (s, 1.2 H), 1.92 (s, 1.8 H).

EXAMPLE 628

N-[4-(4-chloro-5-{(3S)-7-[5-chloro-2-(1H-tetrazol-1-yl)phenyl]-5-oxo-1,2,3,5-tetrahydro-3-indolizinyl}-1H-imidazol-2-yl)phenyl]acetamide The compound prepared in Example 621 (25 mg) was treated with acetyl chloride following the method of Example 484 to give the title compound having the following physical properties (18.8 mg).

LC/MS $t_R$ 3.63 minutes; MS (ES$^+$) m/z 547 (M+H)$^b$
$^1$H NMR (500 MHz, methanol-d$_4$) δ 9.34 (s, 1 H), 7.77-7.70 (m, 4 H), 7.68 (d, 1 H), 7.65 (d, 2 H), 6.19 (s, 1 H), 6.03 (s, 1 H), 5.79 (dd, 1 H), 3.38-3.32 (obs. m, 1 H), 3.12 (ddd, 1 H), 2.74-2.62 (m, 1 H), 2.36-2.26 (m, 1 H), 2.14 (s, 3 H).

EXAMPLE 629

2-methoxyethyl[4-(4-chloro-5-{(3S)-7-[5-chloro-2-(1H-tetrazol-1-yl)phenyl]-5-oxo-1,2,3,5-tetrahydro-3-indolizinyl}-1H-imidazol-2-yl)phenyl]carbamate The compound prepared in Example 621 (25 mg) was treated with 2-methoxyethyl chloroformate following the method of Example 484 to give the title compound having the following physical properties (17.1 mg).

LC/MS $t_R$ 3.91 minutes; MS (ES$^+$) m/z 607 (M+H)$^b$
$^1$H NMR (500 MHz, methanol-d$_4$) δ 9.34 (s, 1 H), 7.76-7.70 (m, 4 H), 7.68 (d, 1 H), 7.53 (d, 2 H), 6.20 (br. s, 1 H), 6.03 (s, 1 H), 5.79 (dd, 1 H), 4.31-4.25 (m, 2 H), 3.68-3.62 (m, 2 H), 3.39 (s, 3 H), 3.43-3.33 (obs. m, 1 H), 3.18-3.06 (m, 1 H), 2.74-2.61 (m, 1 H), 2.37-2.25 (m, 1 H).

EXAMPLE 630

3-methoxypropyl[4-(4-chloro-5-{(3S)-7-[5-chloro-2-(1H-tetrazol-1-yl)phenyl]-5-oxo-1,2,3,5-tetrahydro-3-indolizinyl}-1H-imidazol-2-yl)phenyl]carbamate The compound prepared in Example 621 (30 mg) was treated with the chloroformate prepared in Example 487 following the method of Example 625 to give the title compound having the following physical properties (12 mg).
LC/MS $t_R$ 3.87 minutes; MS (ES$^+$) m/z 621 (M+H)$^b$
$^1$H NMR (500 MHz, DMSO-d$_6$) δ 12.69 (br. s, 1 H), 9.83 (br. s, 1 H), 9.65 (s, 1 H), 7.81 (s, 2 H), 7.77-7.72 (m, 3 H), 7.53 (d, 2 H), 5.99 (br. s, 1 H), 5.91 (s, 1 H), 5.62 (d, 1 H), 4.14 (t, 2 H), 3.43 (t, 2 H), 3.25 (s, 3 H), 3.19-3.10 (m, 1 H), 3.05-2.96 (m, 1 H), 2.61-2.55 (m, 1 H), 2.16-2.08 (m, 1 H), 1.86 (quintet, 2 H).

EXAMPLE 631

2-(2-methoxyethoxy)ethyl[4-(4-chloro-5-{(3S)-7-[5-chloro-2-(1H-tetrazol-1-yl)phenyl]-5-oxo-1,2,3,5-tetrahydro-3-indolizinyl}-1H-imidazol-2-yl)phenyl]carbamate The compound prepared in Example 621 (30 mg) was treated with the chloroformate prepared in Example 489 following the method of Example 625 to give the title compound having the following physical properties (15 mg).
LC/MS $t_R$ 3.76 minutes; MS (ES$^+$) m/z 651 (M+H)$^b$
$^1$H NMR (500 MHz, DMSO-d$_6$) δ 12.69 (br. s, 1 H), 9.95 (br. s, 1 H), 9.65 (s, 1 H), 7.85-7.72 (m, 5 H), 7.54 (d, 2 H), 5.99 (s, 1 H), 5.91 (s, 1 H), 5.63 (dd, 1 H), 4.23-4.19 (m, 2 H), 3.67-3.63 (m, 2 H), 3.58-3.54 (m, 2 H), 3.47-3.43 (m, 2 H), 3.24 (s, 3 H), 3.20-3.10 (m, 1 H), 3.05-2.96 (m, 1 H), 2.62-2.54 (m, 1 H), 2.17-2.08 (m, 1 H).

EXAMPLE 632

3-oxetanyl[4-(4-chloro-5-{(3S)-7-[5-chloro-2-(1H-tetrazol-1-yl)phenyl]-5-oxo-1,2,3,5-tetrahydro-3-indolizinyl}-1H-imidazol-2-yl)phenyl]carbamate The compound prepared in Example 621 (30 mg) was treated as detailed in Example 494 to give the title compound having the following physical properties (15 mg).
LC/MS $t_R$ 3.67 minutes; MS (ES$^+$) m/z 605 (M+H)$^b$
$^1$H NMR (500 MHz, DMSO-d$_6$) δ 12.72 (s, 1 H), 10.11 (br. s, 1 H), 9.64 (s, 1 H), 7.83-7.80 (m, 2 H), 7.79-7.72 (m, 3 H), 7.53 (d, 2 H), 5.99 (s, 1 H), 5.91 (s, 1 H), 5.63 (dd, 1 H), 5.43 (quintet, 1 H), 4.83 (t, 2 H), 4.56 (dd, 2 H), 3.19-3.10 (m, 1 H), 3.01 (ddd, 1 H), 2.60-2.55 (m, 1 H), 2.16-2.08 (m, 1 H).

EXAMPLE 633

(1E)-N-[4-(4-chloro-5-{(3S)-7-[5-chloro-2-(1H-tetrazol-1-yl)phenyl]-5-oxo-1,2,3,5-tetrahydro-3-indolizinyl}-1H-imidazol-2-yl)phenyl]-N'-hydroxyethanimidamide The compound prepared in Example 621 (46 mg) was treated as detailed in Example 462 to give the title compound having the following physical properties (2.5 mg).

LC/MS $t_R$ 3.09 minutes; MS (ES$^+$) m/z 562 (M+H), 281.5 (M/2+H)$^b$
$^1$H NMR (500 MHz, methanol-d$_4$) δ 9.35 (s, 1 H), 7.79-7.62 (m, 6 H), 7.19 (d, 2 H), 6.20 (s, 1 H), 6.04 (s, 1 H), 5.80 (ddd, 1 H), 3.36-3.30 (m, 1 H), 3.18-3.08 (m, 1 H), 2.73-2.65 (m, 1 H), 2.36-2.27 (m, 1 H), 2.00 (s, 3 H).

EXAMPLE 634

3-[2-(4-aminophenyl)-4-fluoro-1H-imidazol-5-yl]-7-[5-chloro-2-(1H-1,2,3,4-tetrazol-1-yl)phenyl]-1,2,3,5-tetrahydroindolizin-5-one The same operation as in Example 620→Example 40→Example 24→Example 364→Example 584 was conducted from the compound prepared in Example 623 to give the title compound having the following physical properties.
LC/MS $t_R$ 1.65 minutes; MS (ES$^+$) m/z 489 (M+H)$^a$.

EXAMPLE 635

2-methoxyethyl[4-(5-{(3S)-7-[5-chloro-2-(1H-tetrazol-1-yl)phenyl]-5-oxo-1,2,3,5-tetrahydro-3-indolizinyl}-4-fluoro-1H-imidazol-2-yl)phenyl]carbamate The compound prepared in Example 634 (28 mg) was treated with as detailed in Example 625 to give the title compound having the following physical properties (11 mg).
LC/MS $t_R$ 3.86 minutes; MS (ES$^+$) m/z 591 (M+H)$^b$
$^1$H NMR (500 MHz, methanol-d$_4$) δ 9.33 (s, 1 H), 7.76-7.66 (m, 5 H), 7.53 (d, 2 H), 6.18 (s, 1 H), 6.04 (s, 1 H), 5.79 (dd, 1 H), 4.30-4.26 (m, 2 H), 3.67-3.63 (m, 2 H), 3.39 (s, 3 H), 3.34-3.30 (m, 1 H), 3.16-3.09 (m, 1 H), 2.70-2.60 (m, 1 H), 2.46-2.39 (m, 1 H).

EXAMPLE 636

2-(2-methoxyethoxy)ethyl[4-(5-{(3S)-7-[5-chloro-2-(1H-tetrazol-1-yl)phenyl]-5-oxo-1,2,3,5-tetrahydro-3-indolizinyl}-4-fluoro-1H-imidazol-2-yl)phenyl]carbamate The compound prepared in Example 634 (28 mg) was treated with the chloroformate prepared in Example 489 following the method of Example 625 to give the title compound having the following physical properties (12 mg).
LC/MS $t_R$ 3.86 minutes; MS (ES$^+$) m/z 635 (M+H)$^b$
$^1$H NMR (500 MHz, methanol-d$_4$) δ 9.35 (s, 1 H), 7.78-7.67 (m, 5 H), 7.54 (d, 2 H), 6.19 (s, 1 H), 6.06 (s, 1 H), 5.81 (dd, 1 H), 4.33-4.28 (m, 2 H), 3.78-3.74 (m, 2 H), 3.70-3.66 (m, 2 H), 3.59-3.55 (m, 2 H), 3.38 (s, 3 H), 3.35-3.32 (m, 1 H), 3.18-3.10 (m, 1 H), 2.71-2.61 (m, 1 H), 2.48-2.40 (m, 1 H).

EXAMPLE 637 prop-2-en-1-yl N-(6-chloro-5-cyanopyridin-2-yl)carbamate

To an acetonitrile (40 mL) solution of 6-amino-2-chloropyridine-3-carbonitrile [Bioorg. Med. Chem. Lett., 20(5), 1697 (2010)] (1.56 g) was added allyl chloroformate (2.71 mL) followed by N,N-diisopropylethylamine (5.0 mL) and 4-dimethylaminopyridine (0.12 g) and the mixture stirred at room temperature for 72 hours. Further aliquots of allyl chloroformate (1.1 mL) and N,N-diisopropylethylamine (1.67 mL) were then added and the reaction mixture stirred at room temperature for 29 hours. The mixture was concentrated and the residue purified by column chromatography (0-50% ethyl acetate in heptanes) to give the title compound having the following physical properties (1.31 g).

LC/MS $t_R$ 1.90 minute; MS (ES$^+$) m/z 238 (M+H)$^a$.

EXAMPLE 638 prop-2-en-1-yl N-(5-carbamimidoyl-6-chloropyridin-2-yl)carbamate

The same operation as in Example 609→Example 610→Example 611 was conducted from the compound prepared in Example 619 to give the title compound having the following physical properties.

LC/MS $t_R$ 0.92 minute; MS (ES$^+$) m/z 255 (M+H)$^a$.

EXAMPLE 639

(3S)-3-[2-(6-amino-2-chloro-3-pyridinyl)-1H-imidazol-5-yl]-7-[5-chloro-2-(1H-tetrazol-1-yl)phenyl]-2,3-dihydro-5(1H)-indolizinone The same operation as in Example 620→Example 40→Example 24→Example 584 was conducted from the compound prepared in Example 623 to give the title compound having the following physical properties. (Note: in the step corresponding to Example 620 in the operation, the compound prepared in Example 638 was used).

LC/MS $t_R$ 2.90 minutes; MS (ES$^+$) m/z 506 (M+H)$^a$ $^1$H NMR (500 MHz, DMSO-d$_6$) δ 11.86 (s, 1 H), 9.69 (s, 1 H), 7.82-7.77 (m, 3 H), 7.75 (d, 1 H), 6.87 (d, 1 H), 6.65 (s, 1 H), 6.47 (d, 1 H), 5.91 (s, 1 H), 5.89 (s, 1 H), 5.58 (d, 1 H), 3.31-3.26 (m, 1 H), 2.95-2.88 (m, 1 H), 2.42-2.37 (m, 1 H), 2.30-2.23 (m, 1 H).

EXAMPLE 640

6-amino-2-fluoropyridine-3-carbonitrile

To an N,N-dimethylformamide (60 mL) suspension of 6-fluoro-5-iodopyridin-2-amine [J. Org. Chem., 71(7), 2922 (2006)] (8.0 g) was added zinc cyanide (4.15 g) and the mixture degassed with nitrogen for 10 minutes. Tetrakis(triphenyl-phosphine)palladium(0) (1.94 g) was then added and the reaction heated at 90° C. for 2 hours 30 minutes. To the ambient reaction mixture, water (300 mL) was added followed by extraction into ethyl acetate. The combined organic layers were dried and concentrated and the residue purified by column chromatography (0 to 50% ethyl acetate in heptanes) to give the title compound having the following physical properties (3.42 g).

LC/MS $t_R$ 1.18 minute; MS (ES$^+$) m/z 138 (M+H)$^a$.

EXAMPLE 641 prop-2-en-1-yl N-(5-carbamimidoyl-6-fluoropyridin-2-yl)carbamate

The same operation as in Example 637→Example 609→Example 610→Example 611 was conducted from the compound prepared in Example 640 to give the title compound having the following physical properties.

LC/MS $t_R$ 0.93 minute; MS (ES$^+$) m/z 239 (M+H)$^a$.

EXAMPLE 642

(3S)-3-[2-(6-amino-2-fluoro-3-pyridinyl)-1H-imidazol-5-yl]-7-[5-chloro-2-(1H-tetrazol-1-yl)phenyl]-2,3-dihydro-5(1H)-indolizinone The same operation as in Example 620→Example 40→Example 24→Example 584 was conducted from the compound prepared in Example 623 to give the title compound having the following physical properties. (Note: in the step corresponding to Example 620 in the operation, the compound prepared in Example 641 was used).

LC/MS $t_R$ 2.87 minutes; MS (ES$^+$) m/z 490 (M+H)$^b$ $^1$H NMR (500 MHz, DMSO-d$_6$) δ 11.73 (s, 1 H), 9.70 (s, 1 H), 7.96 (dd, 1 H), 7.83-7.77 (m, 3 H), 6.81 (d, 1 H), 6.65 (s, 1 H), 6.41 (dd, 1 H), 5.92 (s, 1 H), 5.89 (s, 1 H), 5.58 (d, 1 H), 3.32-3.27 (m, 1 H), 2.95-2.88 (m, 1 H), 2.43-2.34 (m, 1 H), 2.29-2.21 (m, 1 H).

EXAMPLE 643

(3S)-3-[2-(6-amino-2-fluoro-3-pyridinyl)-4-chloro-1H-imidazol-5-yl]-7-[5-chloro-2-(1H-tetrazol-1-yl)phenyl]-2,3-dihydro-5 (1H)-indolizinone The same operation as in Example 620→Example 40→Example 24→Example 44→Example 584 was conducted from the compound prepared in Example 623 to give the title compound having the following physical properties. (Note: in the step corresponding to Example 620 in the operation, the compound prepared in Example 641 was used).

LC/MS $t_R$ 3.58 minutes; MS (ES$^+$) m/z 524 (M+H)$^b$ $^1$H NMR (500 MHz, DMSO-d$_6$) δ 12.18 (br. s, 1 H), 9.65 (s, 1 H), 7.95-7.88 (m, 1 H), 7.83-7.80 (m, 2 H), 7.75 (s, 1 H), 6.76 (s, 2 H), 6.40 (dd, 1 H), 6.00 (s, 1 H), 5.91 (s, 1 H), 5.72 (d, 1 H), 3.15-3.04 (m, 1 H), 3.03-2.95 (m, 1 H), 2.56-2.47 (m, 1 H), 2.17-2.09 (m, 1 H).

EXAMPLE 644

2-(2-methoxyethoxy)ethyl N-(5-cyanopyridin-2-yl)carbamate

To an acetonitrile (150 mL) solution of 6-aminopyridine-3-carbonitrile (3.70 g) was added the chloroformate prepared in Example 489 (7.94 g) followed by N,N-diisopropylethylamine (7.72 mL) and the mixture stirred at room temperature for 16 hours. The precipitate formed in the reaction mixture was isolated by filtration to give the title compound (2.12 g). To the filtrate, water (300 mL) was added followed by extraction into ethyl acetate. The combined organic layers were washed with saturated saline, dried and concentrated. The residue was suspended in acetonitrile (25 mL), concentrated ammonia solution (5 mL) added and the mixture stirred at room temperature for 16 hours. The resultant precipitate was isolated by filtration to give a second batch of the title compound (2.52 g) having the following physical properties.

LC/MS $t_R$ 1.42 minutes; MS (ES$^+$) m/z 288 (M+Na), 266 (M+H)$^a$.

EXAMPLE 645

2-(2-methoxyethoxyl)ethyl N-(5-carbamimidoylpyridin-2-yl)carbamate

The same operation as in Example 609→Example 610→Example 611 was conducted from the compound prepared in Example 644 to give the title compound having the following physical properties.
LC/MS $t_R$ 0.84 minutes; MS (ES$^+$) m/z 283 (M+H)$^a$.

EXAMPLE 646

2-(2-methoxyethoxy)ethyl[5-(5-{(3S)-7-[5-chloro-2-(1H-tetrazol-1-yl)phenyl]-5-oxo-1,2,3,5-tetrahydro-3-indolizinyl}-4-fluoro-1H-imidazol-2-yl)-2-pyridinyl]carbamate The same operation as in Example 620→Example 40→Example 24→Example 364 was conducted from the compound prepared in Example 623 to give the title compound having the following physical properties. (Note: in the step corresponding to Example 620, the compound prepared in Example 645 was used). LC/MS $t_R$ 3.74 minutes; MS (ES$^+$) m/z 636 (M+H)$^b$
$^1$H NMR (500 MHz, DMSO-d$_6$) δ 12.75 (br. s, 1 H), 10.41 (s, 1 H), 9.66 (s, 1 H), 8.76-8.66 (m, 1 H), 8.15 (dd, 1 H), 7.89 (d, 1 H), 7.83-7.78 (m, 2 H), 7.78-7.75 (m, 1 H), 5.97 (s, 1 H), 5.93 (s, 1 H), 5.63 (dd, 1 H), 4.26-4.20 (m, 2 H), 3.67-3.62 (m, 2 H), 3.58-3.54 (m, 2 H), 3.47-3.43 (m, 2 H), 3.24 (s, 3 H), 3.24-3.16 (m, 1 H), 3.00 (ddd, 1 H), 2.62-2.53 (m, 1 H), 2.23-2.16 (m, 1 H).

EXAMPLE 647

2-(2-methoxyethoxyl)ethyl-[5-(4-chloro-5-{(3S)-7-[5-chloro-2-(1H-tetrazol-1-yl)phenyl]-5-oxo-1,2,3,5-tetrahydro-3-indolizinyl}-1H-imidazol-2-yl)-2-pyridinyl]carbamate The same operation as in Example 620→Example 40→Example 24→Example 44 was conducted from the compound prepared in Example 623 to give the title compound having the following physical properties. (Note: in the step corresponding to Example 620, the compound prepared in Example 645 was used). LC/MS $t_R$ 3.67 minutes; MS (ES$^+$) m/z 652 and 654 (M+H), 326.5 and 327.5 [(M+2H)/2]$^b$
$^1$H NMR (500 MHz, DMSO-d$_6$) δ 13.00 (br. s, 1 H), 10.43 (s, 1 H), 9.65 (s, 1 H), 8.72 (d, 1 H), 8.16 (dd, 1 H), 7.90 (d, 1 H), 7.85-7.78 (m, 2 H), 7.75 (app. s, 1 H), 5.98 (s, 1 H), 5.92 (s, 1 H), 5.63 (dd, 1 H), 4.25-4.21 (m, 2 H), 3.67-3.63 (m, 2 H), 3.58-3.54 (m, 2 H), 3.46-3.43 (m, 2 H), 3.24 (s, 3 H), 3.22-3.12 (m, 1 H), 3.05-2.97 (m, 1 H), 2.61-2.53 (m, 1 H), 2.17-2.08 (m, 1 H).

EXAMPLE 648

2-methoxyethyl N-(5-carbamimidoylpyridin-2-yl)carbamate

The same operation as in Example 644→Example 609→Example 610→Example 611 was conducted from 6-aminopyridine-3-carbonitrile to give the title compound having the following physical properties. (Note: in the step corresponding to Example 644, 2-methoxyethyl chloroformate was used).
LC/MS $t_R$ 0.66 minutes; MS (ES$^+$) m/z 239 (M+H)$^a$.

EXAMPLE 649 tert-butyl N-[(tert-butoxy)carbonyl]-N-(4-chloro-2-{3-[2-(6-{[(2-methoxyethoxy)carbonyl]amino}pyridin-3-yl)-1H-imidazol-5-yl]-5-oxo-1,2,3,5-tetrahydroindolizin-7-yl}phenyl)carbamate The compound prepared in Example 623 (3.55 g) was treated with the compound prepared in Example 648 following the method of Example 620 to give the title compound having the following physical properties (1.09 g).
LC/MS $t_R$ 1.91 minutes; MS (ES$^+$) m/z 721 (M+H), 621 {M-[CO$_2$C(CH$_3$)$_3$]+H}$^a$.

EXAMPLE 650

2-methoxyethyl[5-(5-{(3S)-7-[5-chloro-2-(1H-tetrazol-1-yl)phenyl]-5-oxo-1,2,3,5-tetrahydro-3-indolizinyl}-1H-imidazol-2-yl)-2-pyridinyl]carbamate The same operation as in Example 40→Example 24 was conducted from the compound prepared in Example 649 to give the title compound having the following physical properties.
LC/MS $t_R$ 2.96 minutes; MS (ES$^+$) m/z 574 (M+H), 287.5 [(M+2H)/2]$^b$
$^1$H NMR (500 MHz, DMSO-d$_6$) δ 12.50 (s, 1 H), 10.36 (s, 1 H), 9.69 (s, 1 H), 8.74 (d, 1 H), 8.18 (dd, 1 H), 7.88 (d, 1 H), 7.82-7.77 (m, 3 H), 6.93 (d, 1 H), 5.92 (s, 1 H), 5.90 (s, 1 H), 5.60 (d, 1 H), 4.26-4.21 (m, 2 H), 3.59-3.55 (m, 2 H), 3.28 (s, 3 H), 3.31-3.26 (obs. m, 1 H), 2.93 (dd, 1 H), 2.45-2.39 (m, 1 H), 2.29-2.22 (m, 1 H).

EXAMPLE 651

2-methoxyethyl[5-(5-{(3S)-7-[5-chloro-2-(1H-tetrazol-1-yl)phenyl]-5-oxo-1,2,3,5-tetrahydro-3-indolizinyl}-4-fluoro-1H-imidazol-2-yl)-2-pyridinyl]carbamate The compound prepared in Example 650 (380 mg) was treated as detailed in Example 364 to give the title compound having the following physical properties (21.3 mg).
LC/MS $t_R$ 3.75 minutes; MS (ES$^+$) m/z 592 (M+H)$^b$
$^1$H NMR (500 MHz, DMSO-d$_6$) δ 12.75 (br. s, 1 H), 10.40 (s, 1 H), 9.67 (s, 1 H), 8.71 (d, 1 H), 8.15 (dd, 1 H), 7.89 (d, 1 H), 7.83-7.77 (m, 2 H), 7.77-7.74 (m, 1 H), 5.97 (s, 1 H), 5.93 (s, 1 H), 5.63 (dd, 1 H), 4.24 (dd, 2 H), 3.57 (dd, 2 H), 3.28 (s, 3 H), 3.21 (td, 1 H), 3.00 (ddd, 1 H), 2.62-2.53 (m, 1 H), 2.24-2.16 (m, 1 H).

EXAMPLE 652

2-methoxyethyl[5-(4-chloro-5-{(3S)-7-[5-chloro-2-(1H-tetrazol-1-yl)phenyl]-5-oxo-1,2,3,5-tetrahydro-3-indolizinyl}-1H-imidazol-2-yl)-2-pyridinyl]carbamate The compound prepared in Example 650 (100 mg) was treated as detailed in Example 44 to give the title compound having the following physical properties (40.4 mg).
LC/MS $t_R$ 3.68 minutes; MS (ES$^+$) m/z 608 and 610 (M+H), 304.5 and 305.5 [(M+2H)/2]$^b$
$^1$H NMR (500 MHz, DMSO-d$_6$) δ 13.02 (br. s, 1 H), 10.42 (s, 1 H), 9.65 (s, 1 H), 8.72 (d, 1 H), 8.16 (dd, 1 H), 7.90 (d, 1 H), 7.84-7.78 (m, 2 H), 7.75 (app. s, 1 H), 5.98 (s, 1 H), 5.92 (s, 1 H), 5.63 (dd, 1 H), 4.27-4.21 (m, 2 H), 3.60-3.55 (m, 2 H), 3.28 (s, 3 H), 3.22-3.13 (m, 1 H), 3.01 (ddd, 1 H), 2.63-2.54 (m, 1 H), 2.17-2.09 (m, 1 H).

EXAMPLE 653 tert-butyl N-(2-{3-[2-(6-aminopyridin-3-yl)-1H-imidazol-5-yl]-5-oxo-1,2,3,5-tetrahydroindolizin-7-yl}-4-chlorophenyl)carbamate To a methanol (5.5 mL) solution of the compound prepared in Example 649 (185 mg) was added 6 M sodium hydroxide (5.5 mL) and the mixture stirred at room temperature for 24 hours. The methanol was removed in vacuo and the aqueous residue treated with 1 M hydrochloric acid (11 mL) and water (20 mL) followed by extraction into ethyl acetate. The combined organic layers were washed with saturated saline, dried and concentrated. The residue obtained on concentration was purified by column chromatography (0 to 10% methanol in dichloromethane) to obtain the title compound having the following physical properties (107 mg).
LC/MS $t_R$ 1.51 minutes; MS (ES$^+$) m/z 519 (M+H), 463 {M-[C(CH$_3$)$_3$]+H}$^a$.

EXAMPLE 654

(3S)-3-[2-(6-amino-3-pyridinyl)-4-fluoro-1H-imidazol-5-yl]-7-[5-chloro-2-(1H-tetrazol-1-yl)phenyl]-2,3-dihydro-5(1H)-indolizinone The same operation as in Example 637→Example 40→Example 24→Example 364→Example 584 was conducted from the compound prepared in Example 653 to give the title compound having the following physical properties.
LC/MS $t_R$ 3.01 minutes; MS (ES$^+$) m/z 490 (M+H)$^b$
$^1$H NMR (500 MHz, DMSO-d$_6$) δ 12.17 (s, 1 H), 9.66 (s, 1 H), 8.38 (d, 1 H), 7.83-7.78 (m, 2 H), 7.78-7.73 (m, 2 H), 6.47 (d, 1 H), 6.26 (br. s, 2 H), 5.96 (s, 1 H), 5.91 (s, 1 H), 5.59 (dd, 1 H), 3.20 (td, 1 H), 2.98 (ddd, 1 H), 2.59-2.52 (m, 1 H), 2.21-2.14 (m, 1 H).

EXAMPLE 655

(3S)-3-[5-(4-aminophenyl)-4H-1,2,4-triazol-3-yl]-7-[5-chloro-2-(1H-1,2,3,4-tetrazol-1-yl)phenyl]-1,2,3,5-tetrahydroindolizin-5-one The same operation as in Example 242→Example 243→Example 74 was conducted from the compound prepared in Example 9 to give the title compound having the following physical properties.
LC/MS $t_R$ 1.54 minutes; MS (ES$^+$) m/z 472 (M+H)$^a$.

EXAMPLE 656(1) to 656(4)

The compounds of the present invention having the following physical data were synthesised from the compound prepared in Example 655 and the corresponding acid chlorides and chloroformates using the method as detailed in Example 484.

EXAMPLE 656(1)

methyl[4-(5-{(3S)-7-[5-chloro-2-(1H-tetrazol-1-yl)phenyl]-5-oxo-1,2,3,5-tetrahydro-3-indolizinyl}-4H-1,2,4-triazol-3-yl)phenyl]carbamate LC/MS $t_R$ 3.61 minutes; MS (ES$^+$) m/z 530 (M+H)$^b$
$^1$H NMR (500 MHz, methanol-d$_4$) δ 9.36 (s, 1 H), 7.85 (d, 2 H), 7.77-7.72 (m, 2 H), 7.69 (d, 1 H), 7.58 (d, 2 H), 6.17 (s, 1 H), 6.09 (s, 1 H), 5.85 (dd, 1 H), 3.76 (s, 3 H), 3.40-3.33 (obs. m, 1 H), 3.10 (ddd, 1 H), 2.73-2.62 (m, 1 H), 2.37-2.27 (m, 1 H).

EXAMPLE 656(2)

formic acid-2-fluoroethyl[4-(5-{(3S)-7-[5-chloro-2-(1H-tetrazol-1-yl)phenyl]-5-oxo-1,2,3,5-tetrahydro-3-indolizinyl}-4H-1,2,4-triazol-3-yl)phenyl]carbamate (1:1)

LC/MS $t_R$ 3.72 minutes; MS (ES$^+$) m/z 562 (M+H)$^b$
$^1$H NMR (500 MHz, methanol-d$_4$) δ 9.36 (s, 1 H), 7.86 (d, 2 H), 7.78-7.72 (m, 2 H), 7.70 (d, 1 H), 7.60 (d, 2 H), 6.17 (s, 1 H), 6.09 (s, 1 H), 5.85 (dd, 1 H), 4.71-4.66 (m, 1 H), 4.62-4.56 (m, 1 H), 4.44-4.39 (m, 1 H), 4.38-4.33 (m, 1 H), 3.41-3.23 (m, 1 H), 3.10 (dd, 1 H), 2.73-2.62 (m, 1 H), 2.32 (app. br. s, 1 H).

EXAMPLE 656(3)

formic acid-2-methoxyethyl[4-(5-{(3S)-7-[5-chloro-2-(1H-tetrazol-1-yl)phenyl]-5-oxo-1,2,3,5-tetrahydro-3-indolizinyl}-4H-1,2,4-triazol-3-yl)phenyl]carbamate (1:1)

LC/MS $t_R$ 3.64 minutes; MS (ES$^+$) m/z 574 (M+H)$^b$
$^1$H NMR (500 MHz, DMSO-d$_6$) δ 14.12 (br. s, 1 H), 9.99 (br. s, 1 H), 9.69 (s, 1 H), 7.84 (d, 2 H), 7.82-7.75 (m, 3 H), 7.58 (d, 2 H), 5.97 (s, 1 H), 5.94 (s, 1 H), 5.67 (dd, 1 H), 4.25-4.18 (m, 2 H), 3.60-3.53 (m, 2 H), 3.28 (s, 3 H), 3.27-3.18 (m, 1 H), 2.98 (dd, 1 H), 2.59-2.52 (obs. m, 1 H), 2.16-2.05 (m, 1 H).

EXAMPLE 656(4)

N-[4-(5-{(3S)-7-[5-chloro-2-(1H-tetrazol-1-yl)phenyl]-5-oxo-1,2,3,5-tetrahydro-3-indolizinyl}-4H-1,2,4-triazol-3-yl)phenyl]acetamide LC/MS $t_R$ 3.51 minutes; MS (ES$^+$) m/z 514 (M+H)$^b$
$^1$H NMR (500 MHz, methanol-d$_4$) δ 9.36 (s, 1 H), 7.88 (d, 2 H), 7.76-7.72 (m, 2 H), 7.72-7.67 (m, 3 H), 6.16 (s, 1 H), 6.09 (s, 1 H), 5.85 (dd, 1 H), 3.40-3.32 (obs. m, 1H), 3.10 (ddd, 1 H), 2.73-2.62 (m, 1 H), 2.37-2.28 (m, 1 H), 2.15 (s, 3 H).

EXAMPLE 657 formic acid-3-oxetanyl[4-(5-{(3S)-7-[5-chloro-2-(1H-tetrazol-1-yl)phenyl]-5-oxo-1,2,3,5-tetrahydro-3-indolizinyl}-4H-1,2,4-triazol-3-yl)phenyl]carbamate (1:1)

The compound prepared in Example 655 (75 mg) was treated as detailed in Example 494 to give the title compound having the following physical properties (12.9 mg).
LC/MS $t_R$ 3.65 minutes; MS (ES$^+$) m/z 572 (M+H)$^b$
$^1$H NMR (500 MHz, methanol-d$_4$) δ 9.36 (s, 1 H), 7.86 (d, 2 H), 7.76-7.72 (m, 2 H), 7.71-7.67 (m, 1 H), 7.58 (d, 2 H), 6.16 (s, 1 H), 6.09 (s, 1 H), 5.85 (dd, 1 H), 5.53-5.46 (m, 1 H), 4.93 (t, 2 H), 4.69 (dd, 2 H), 3.39-3.32 (obs. m, 1 H), 3.10 (ddd, 1 H), 2.72-2.62 (m, 1 H), 2.37-2.28 (m, 1 H).

EXAMPLE 658

(3S)-7-[5-chloro-2-(1H-1,2,3,4-tetrazol-1-yl)phenyl]-5-oxo-1,2,3,5-tetrahydroindolizine-3-carbonitrile The same operation as in Example 114→Example 605 was conducted from the compound prepared in Example 9 to give the title compound having the following physical properties.

LC/MS $t_R$ 1.60 minutes; MS (ES$^+$) m/z 339 (M+H) 361 (M+Na)$^a$.

EXAMPLE 659

(3S)-N-amino-7-[5-chloro-2-(1H-1,2,3,4-tetrazol-1-yl)phenyl]-5-oxo-1,2,3,5-tetrahydroindolizine-3-carboximidamide To a methanol (2 mL) suspension of the compound prepared in Example 658 (90 mg) was added hydrazine hydrate (120 μL) and the mixture stirred at 60° C. for 1.5 hours. The reaction mixture was concentrated to give the crude title compound having the following physical properties (95 mg).

LC/MS $t_R$ 1.16 minutes; MS (ES$^+$) m/z 371 (M+H)$^a$.

EXAMPLE 660

2-methoxyethyl[3-chloro-4-(5-{(3S)-7-[5-chloro-2-(1H-tetrazol-1-yl)phenyl]-5-oxo-1,2,3,5-tetrahydro-3-indolizinyl}-4H-1,2,4-triazol-3-yl)phenyl]carbamate The same operation as in Example 242→Example 243→Example 74→Example 484 was conducted from the compound prepared in Example 659 to give the title compound having the following physical properties. (Note: in the step corresponding to Example 242 in the operation, 2-chloro-4-nitrobenzoic acid was used. In the step corresponding to Example 484 in the operation, 2-methoxyethyl chloroformate was used).

LC/MS $t_R$ 3.76 minutes; MS (ES$^+$) m/z 608 (M+H)$^b$ $^1$H NMR (500 MHz, DMSO-d$_6$) δ 14.02 (br. s, 1 H), 10.20 (br. s, 1 H), 9.69 (s, 1 H), 7.82-7.78 (m, 3 H), 7.76-7.68 (m, 2 H), 7.51 (d, 1 H), 5.97 (s, 1 H), 5.95 (s, 1 H), 5.71 (d, 1 H), 4.26-4.21 (m, 2 H), 3.58 (dd, 2 H), 3.28 (s, 3 H), 3.21-3.13 (m, 1 H), 3.03-2.94 (m, 1 H), 2.59-2.54 (m, 1 H), 2.19-2.09 (m, 1 H).

EXAMPLE 661 tert-butyl N-[(tert-butoxy)carbonyl]-N-(6-fluoro-5-iodopyridin-2-yl)carbamate

The compound prepared in Example 640 (5.0 g) was treated as detailed in Example 228 to give the title compound having the following physical properties (5.26 g).

LC/MS $t_R$ 2.47 minutes; MS (ES$^+$) m/z 461 (M+Na) 283 [M-boc-tBu]$^{+a}$.

EXAMPLE 662(1) and 662(2)

6-{bis[(tert-butoxy)carbonyl]amino}-2-fluoropyridine-3-carboxylic acid and 6-{[(tert-butoxy)carbonyl]amino}-2-fluoropyridine-3-carboxylic acid To a cooled (0° C.) tetrahydrofuran (40 mL) solution of the compound prepared in Example 661 (2.0 g) was added a 2 M solution of isopropylmagnesium chloride in tetrahydrofuran (2.28 mL) and the mixture stirred at 0° C. for 30 minutes. The cooled (0° C.) reaction mixture was treated with an excess of solid carbon dioxide and slowly allowed to warm to room temperature. To the reaction mixture, a saturated aqueous solution of ammonium chloride was added followed by a saturated aqueous solution of sodium hydrogen carbonate and this mixture was washed with ethyl acetate. The aqueous layer was treated with 2 M hydrochloric acid until pH 1 had been attained then extracted into dichloromethane. The combined organic layers were washed with saturated saline, dried and concentrated to give the title compounds in a 9:1 ratio having the following physical properties (0.73 g).

EXAMPLE 662(1)

LC/MS $t_R$ 2.05 minutes; MS (ES$^+$) m/z 356 (M+Na) 201 [M-boc-tBu]$^{+a}$.

EXAMPLE 662(2)

LC/MS $t_R$ 1.74 minutes; MS (ES$^+$) m/z 279 (M+Na) 201 [M-tBu]$^{+a}$.

EXAMPLE 663(1) and 663(2)

tert-butyl N-[(tert-butoxy)carbonyl]-N-(5-{N'-[(3S)-7-[5-chloro-2-(1H-1,2,3,4-tetrazol-1-yl)phenyl]-5-oxo-1,2,3,5-tetrahydroindolizine-3-carboximidoyl]hydrazinecarbonyl}-6-fluoropyridin-2-yl)carbamate and tert-butyl N-(5-{N'-[(3S)-7-[5-chloro-2-(1H-1,2,3,4-tetrazol-1-yl)phenyl]-5-oxo-1,2,3,5-tetrahydroindolizine-3-carboximidoyl]hydrazinecarbonyl}-6-fluoropyridin-2-yl)carbamate To a cooled (0° C.) dichloromethane (2 mL) suspension of the 9:1 mixture of compounds prepared in Example 662 (52 mg) was added oxalyl chloride (13.5 μL) followed by 1 drop of N,N-dimethylformamide and the mixture stirred at 0° C. for 1 hour. The reaction mixture was concentrated, the residue dissolved in tetrahydrofuran (2 mL) and added to a cooled (0° C.) tetrahydrofuran (2 mL) solution of the compound prepared in Example 659 (70 mg). The mixture was stirred 18 hours at room temperature then concentrated and the residue suspended in a saturated aqueous solution of sodium hydrogen carbonate, followed by extraction into ethyl acetate. The combined organic layers were washed with water and saturated saline, dried and concentrated to obtain the title compounds in a 3:2 ratio having the following physical properties (120 mg).

EXAMPLE 663(1)

LC/MS $t_R$ 1.85 minutes; MS (ES$^+$) m/z 709 (M+H) 609 [M-boc]$^{+a}$.

EXAMPLE 663(2)

LC/MS $t_R$ 1.59 minutes; MS (ES$^+$) m/z 609 (M+H)$^a$.

EXAMPLE 664

(3S)-3-[5-(6-amino-2-fluoro-3-pyridinyl)-4H-1,2,4-triazol-3-yl]-7-[5-chloro-2-(1H-tetrazol-1-yl)phenyl]-2,3-dihydro-5 (1H)-indolizinone The 3:2 mixture of compounds prepared in Example 663 (160 mg) was treated as detailed in Example 243 to give the title compound having the following physical properties (25 mg).

LC/MS $t_R$ 3.35 minutes; MS (ES$^+$) m/z 491 (M+H)$^b$ $^1$H NMR (500 MHz, methanol-d$_4$) δ 9.35 (s, 1 H), 8.07 (t, 1 H), 7.77-7.72 (m, 2 H), 7.71-7.68 (m, 1 H), 6.50 (dd, 1 H), 6.16 (s, 1 H), 6.08 (s, 1 H), 5.84 (d, 1 H), 3.37-3.34 (m, 1 H), 3.08 (dd, 1 H), 2.73-2.59 (m, 1 H), 2.36-2.22 (m, 1 H).

EXAMPLE 665 ethyl 2-benzoyl-4-[7-(2-{[(tert-butoxy)carbonyl]amino}-5-chlorophenyl)-5-oxo-1,2,3,5-tetrahydro indolizin-3-yl]-4-oxobutanoate To a cooled (0° C.) tetrahydrofuran (5 mL) suspension of sodium hydride (11 mg, 60% dispersion in mineral oil) and sodium iodide (34 mg), ethyl benzoylacetate (48 μL) was added and the mixture was stirred at 0° C. for 30 minutes. A tetrahydrofuran (1.2 mL) solution of the compound prepared in Example 617 (100 mg) was added and the mixture was stirred at room temperature for 16 hours. To the reaction mixture, 0.5 M hydrochloric acid in water (30 mL) was added followed by extraction into ethyl acetate. The combined organic layers were washed with saturated saline, dried and concentrated. The residue was purified by column chromatography (20 to 100% ethyl acetate in heptanes) to give the title compound having the following physical properties (112 mg). LC/MS $t_R$ 2.33 minutes; MS (ES$^+$) m/z 593 (M+H)$^a$.

EXAMPLE 666

1-[7-(2-amino-5-chlorophenyl)-5-oxo-1,2,3,5-tetrahydroindolizin-3-yl]-4-phenylbutane-1,4-dione To a 1,4-dioxane (3 mL) solution of the compound prepared in Example 665 was added 6 M hydrochloric acid in water (3 mL) and the mixture stirred at 100° C. for 3 hours. The mixture was then diluted with water, basified to pH 8 by addition of sodium hydrogen carbonate and extracted into ethyl acetate. The combined organic layers were washed with saturated saline, dried and concentrated. The residue was purified by column chromatography (20% to 100% ethyl acetate in heptanes, then 0 to 15% methanol in ethyl acetate) to give the title compound having the following physical properties (29.4 mg).

LC/MS $t_R$ 2.00 minutes; MS (ES$^+$) m/z 421 (M+H)$^a$.

EXAMPLE 667

7-(2-amino-5-chlorophenyl)-3-(5-phenyl-1H-pyrrol-2-yl)-1,2,3,5-tetrahydroindolizin-5-one To an acetic acid (1 mL) solution of the compound prepared in Example 666 (39 mg) was added ammonium acetate (100 mg) and the mixture was stirred at 90° C. for 1 hour. To the reaction mixture, a saturated aqueous solution of sodium hydrogen carbonate (30 mL) was added followed by extraction into ethyl acetate. The combined organic layers were washed with saturated saline, dried and concentrated to give the title compound having the following physical properties (50 mg).

LC/MS $t_R$ 2.26 minutes; MS (ES$^+$) m/z 402 (M+H)$^a$.

EXAMPLE 668

(3S)-7-[5-chloro-2-(1H-tetrazol-1-yl)phenyl]-3-(5-phenyl-1H-pyrrol-2-yl)-2,3-dihydro-5(1H)-indolizinone The compound prepared in Example 667 (37 mg) was treated as detailed in Example 24 to give the title compound having the following physical properties (20 mg).

LC/MS $t_R$ 4.51 minutes; MS (ES$^+$) m/z 455 (M+H)$^b$ $^1$H NMR (500 MHz, CDCl$_3$) δ 10.47 (br. s, 1 H), 8.52 (s, 1 H), 7.61 (dd, 1 H), 7.54 (d, 1H), 7.52-7.48 (m, 3 H), 7.35 (t, 2 H), 7.23-7.17 (m, 1 H), 6.41 (s, 1 H), 6.40 (t, 1 H), 6.18 (t, 1 H), 5.96 (d, 1 H), 5.58 (s, 1 H), 3.28 (ddd, 1 H), 2.98 (dd, 1 H), 2.69 (dd, 1 H), 2.49 (tt, 1 H).

EXAMPLE 669

(3S)-7-[5-chloro-2-(1H-tetrazol-1-yl)phenyl]-3-[5-(4-nitrophenyl)-1H-pyrrol-2-yl]-2,3-dihydro-5(1H)-indolizinone The same operation as in Example 665→Example 666→Example 667→Example 24 was conducted from the compound prepared in Example 623 to give the title compound having the following physical properties. (Note: in the step corresponding to Example 665 in the operation, ethyl 4-nitrobenzoylacetate was used). LC/MS $t_R$ 4.51 minutes; MS (ES$^+$) m/z 500 (M+H)$^b$ $^1$H NMR (500 MHz, DMSO-d$_6$) δ 11.69 (br. s, 1 H), 9.71 (s, 1 H), 8.22 (d, 2 H), 7.86-7.77 (m, 5 H), 6.74 (t, 1 H), 6.01 (s, 1 H), 5.95 (s, 1 H), 5.76-5.69 (m, 2 H), 3.17-3.06 (m, 1 H), 2.96 (dd, 1 H), 2.57-2.51 (obs. m, 1 H), 2.18 (dd, 1 H).

EXAMPLE 670

(3S)-3-[5-(4-aminophenyl)-1H-pyrrol-2-yl]-7-[5-chloro-2-(1H-tetrazol-1-yl)phenyl]-2,3-dihydro-5(1H)-indolizinone The compound prepared in Example 669 (608 mg) was treated as detailed in Example 74 to give the title compound having the following physical properties (161 mg).

LC/MS $t_R$ 3.40 minutes; MS (ES$^+$) m/z 470 (M+H)$^b$ $^1$H NMR (500 MHz, DMSO-d$_6$) δ 11.03 (br. s, 1 H), 9.70 (s, 1 H), 8.05 (br. s, 2 H), 7.83-7.77 (m, 3 H), 7.45 (d, 2 H), 6.95 (d, 2 H), 6.25 (t, 1 H), 6.01 (s, 1 H), 5.93 (s, 1 H), 5.71 (d, 1 H), 5.66 (t, 1 H), 3.17-3.07 (m, 1 H), 2.95 (dd, 1 H), 2.47-2.42 (obs. m, 1H), 2.22 (dd, 1 H).

EXAMPLE 671 methyl[4-(5-{(3S)-7-[5-chloro-2-(1H-tetrazol-1-yl)phenyl]-5-oxo-1,2,3,5-tetrahydro-3-indolizinyl}-1H-pyrrol-2-yl)phenyl]carbamate The compound prepared in Example 670 (65 mg) was treated with methyl chloroformate following the method of Example 484 to give the title compound having the following physical properties (45.2 mg).

LC/MS $t_R$ 4.19 minutes; MS (ES$^+$) m/z 528 (M+H)$^b$ $^1$H NMR (500 MHz, CDCl$_3$) δ 10.40 (br. s, 1 H), 8.53 (s, 1 H), 7.60 (dd, 1 H), 7.54 (d, 1H), 7.50 (d, 1 H), 7.44 (d, 2 H), 7.38 (d, 2 H), 6.77 (br. s, 1 H), 6.41 (s, 1 H), 6.33 (t, 1

H), 6.15 (t, 1 H), 5.95 (d, 1 H), 5.59 (s, 1 H), 3.28 (ddd, 1 H), 2.97 (dd, 1 H), 2.68 (dd, 1H), 2.48 (tt, 1 H).

EXAMPLE 672

2-methoxyethyl[4-(5-{(3S)-7-[5-chloro-2-(1H-tetrazol-1-yl)phenyl]-5-oxo-1,2,3,5-tetrahydro-3-indolizinyl}-1H-pyrrol-2-yl)phenyl]carbamate The compound prepared in Example 670 (65 mg) was treated with 2-methoxyethyl chloroformate following the method of Example 484 to give the title compound having the following physical properties (32.2 mg).
LC/MS $t_R$ 4.20 minutes; MS (ES$^+$) m/z 572 (M+H)$^b$
$^1$H NMR (500 MHz, CDCl$_3$) δ 10.40 (br. s, 1 H), 8.53 (s, 1 H), 7.61 (dd, 1 H), 7.54 (d, 1H), 7.50 (d, 1 H), 7.44 (d, 2 H), 7.37 (d, 2 H), 6.80 (br. s, 1 H), 6.42 (s, 1 H), 6.33 (t, 1H), 6.16 (app. br. s, 1 H), 5.95 (d, 1 H), 5.58 (s, 1 H), 4.37-4.31 (m, 2 H), 3.69-3.62 (m, 2 H), 3.42 (s, 3 H), 3.33-3.22 (m, 1 H), 2.97 (dd, 1 H), 2.68 (dd, 1 H), 2.48 (tt, 1 H).

EXAMPLE 673 methyl 6-amino-2-fluoropyridine-3-carboxylate

To a methanol (20 mL) solution of 2-amino-6-fluoro-5-iodopyridine (1.0 g), triethylamine (0.76 mL), palladium(II) dichloride (12 mg) and 1,1'-binaphthalene-2,2'-diylbis(diphenylphosphane) (45 mg) were added and the mixture heated at 100° C. under an atmosphere of carbon monoxide (3.8 bar) for 20 hours. The reaction mixture was concentrated and the residue purified by column chromatography (10% to 80% ethyl acetate in heptanes) to obtain the title compound having the following physical properties (615 mg).
LC/MS $t_R$ 1.24 minutes; MS (ES$^+$) m/z 171 (M+H)$^a$.

EXAMPLE 674 methyl 6-{bis[(prop-2-en-1-yloxy)carbonyl]amino}-2-fluoropyridine-3-carboxylate

To an acetonitrile (3.2 mL) solution of the compound prepared in Example 673 (276 mg), 4-dimethylaminopyridine (20 mg), N,N-diisopropylethylamine (2.0 mL) and allyl chloroformate (2.6 mL) were added and the mixture stirred at room temperature for 5 days. To the reaction mixture, a saturated aqueous solution of sodium hydrogen carbonate (40 mL) was added followed by extraction into ethyl acetate. The combined organic layers were washed with saturated saline, dried and concentrated. The residue was purified by column chromatography (0% to 60% ethyl acetate in heptanes) to obtain the title compound having the following physical properties (134 mg).
LC/MS $t_R$ 1.98 minutes; MS (ES$^+$) m/z 339 (M+H)$^a$.

EXAMPLE 675(1) and 675(2)

2-fluoro-6-{[(prop-2-en-1-yloxy)carbonyl]amino}pyridine-3-carboxylic acid and 2-fluoro-6-[(methoxycarbonyl)amino]pyridine-3-carboxylic acid To a methanol (3.5 mL) and tetrahydrofuran (3.5 mL) solution of the compound prepared in Example 674 was added 1 M sodium hydroxide (3.4 mL) and the mixture stirred at room temperature for 16 hours. The reaction mixture was concentrated and the residue diluted with water (20 mL) and washed with ethyl acetate. The aqueous layer was acidified with 1 M hydrochloric acid to attain pH 3-4 then extracted into ethyl acetate. The combined organic layers were washed with saturated saline, dried and concentrated to obtain the title products in a 2:1 ratio.

EXAMPLE 675(1)

LC/MS $t_R$ 1.53 minutes; MS (ES$^+$) m/z 241 (M+H)$^a$.

EXAMPLE 675(2)

LC/MS $t_R$ 1.23 minutes; MS (ES$^+$) m/z 215 (M+H)$^a$.

EXAMPLE 676 ethyl 3-(2-fluoro-6-{[(prop-2-en-1-yloxy)carbonyl]amino}pyridin-3-yl)-3-oxopropanoate To a cooled (0° C.) dichloromethane (12 mL) solution of the 2:1 mixture of compounds prepared in Example 675 (287 mg) was added oxalyl chloride (145 μL) and N,N-dimethylformamide (5 μL) and the mixture stirred at room temperature for 2 hours. The reaction mixture was then concentrated and the residue dissolved in acetonitrile (5 mL).
Separately, to an acetonitrile (5 mL) suspension of ethyl potassium malonate (488 mg) was added sequentially triethylamine (620 μL) and magnesium chloride (310 mg) and the mixture stirred at room temperature for 4 hours. To this reaction mixture, the above prepared acid chloride solution and triethylamine (167 μL) were added sequentially and the mixture stirred at room temperature for 2 days. To the reaction mixture, 0.5 M hydrochloric acid (30 mL) was added and the mixture stirred at room temperature for 10 minutes. The mixture was then extracted into ethyl acetate and the combined organic layers washed with saturated saline, dried and concentrated. The residue was purified by column chromatography (0% to 50% ethyl acetate in heptanes) to obtain the title compound having the following physical properties (208 mg).
LC/MS $t_R$ 1.90 minutes; MS (ES$^+$) m/z 311 (M+H)$^a$.

EXAMPLE 677 ethyl 4-{7-[5-chloro-2-(1H-1,2,3,4-tetrazol-1-yl)phenyl]-5-oxo-1,2,3,5-tetrahydroindolizin-3-yl}-2-(2-fluoro-6-{[(prop-2-en-1-yloxy)carbonyl]amino}pyridine-3-carbonyl)-4-oxobutanoate The same operation as in Example 665→Example 40→Example 24 was conducted from the compound prepared in Example 623 to give the title compound having the following physical properties. (Note: in the step corresponding to Example 665 in the operation, the compound prepared in Example 676 was used).
LC/MS $t_R$ 2.09 minutes; MS (ES$^+$) m/z 664 (M+H)$^a$.

EXAMPLE 678 prop-2-en-1-yl N-[5-(4-{7-[5-chloro-2-(1H-1,2,3,4-tetrazol-1-yl)phenyl]-5-oxo-1,2,3,5-tetrahydroindolizin-3-yl}-4-oxobutanoyl)-6-fluoropyridin-2-yl]carbamate To a 1,4-dioxane (2 mL) solution of the compound prepared in Example 677 (164 mg) was added 2 M hydrochloric acid (1 mL) and the mixture stirred at 100° C. for 5.5 hours. To the reaction mixture, a saturated aqueous solution of sodium hydrogen carbonate (30 mL) was added followed by extraction into ethyl acetate. The combined organic layers were washed with saturated saline, dried and concentrated. The residue was purified by column chromatography (50 to 100% ethyl acetate in heptanes, then 0 to 10% methanol in ethyl acetate) to give the title compound having the following physical properties (37.2 mg).

LC/MS $t_R$ 2.00 minutes; MS (ES$^+$) m/z 592 (M+H)$^a$.

EXAMPLE 679

(3S)-3-[5-(6-amino-2-fluoro-3-pyridinyl)-1H-pyrrol-2-yl]-7-[5-chloro-2-(1H-tetrazol-1-yl)phenyl]-2,3-dihydro-5(1H)-indolizinone

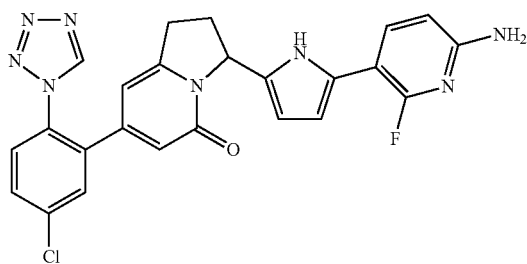 [SMILES: Nc1ccc(-c2ccc(C3CCc4cc(-c5cc(Cl)ccc5-n5cnnn5)cc(=O)n43)[nH]2)c(F)n1]

The same operation as in Example 667→Example 584 was conducted from the compound prepared in Example 678 to give the title compound having the following physical properties.

LC/MS $t_R$ 3.97 minutes; MS (ES$^+$) m/z 489 (M+H)$^b$ $^1$H NMR (500 MHz, DMSO-d$_6$) δ 10.78 (br. s, 1 H), 9.70 (s, 1 H), 7.82-7.78 (m, 3 H), 7.74 (dd, 1 H), 6.40-6.31 (m, 3 H), 6.17 (app. br. s, 1 H), 6.05 (s, 1 H), 5.93 (s, 1 H), 5.81 (t, 1 H), 5.74 (d, 1 H), 3.17-3.06 (m, 1 H), 2.96 (dd, 1 H), 2.46-2.40 (m, 1 H), 2.30 (dd, 1 H).

EXAMPLE 680(1) and 680(2)

ethyl 3-[7-(2-{bis[(tert-butoxy)carbonyl]amino}-5-chlorophenyl)-5-oxo-1,2,3,5-tetrahydroindolizin-3-yl]-3-oxopropanoate and ethyl 3-[7-(2-{[(tert-butoxy)carbonyl]amino}-5-chlorophenyl)-5-oxo-1,2,3,5-tetrahydroindolizin-3-yl]-3-oxopropanoate The compound prepared in Example 622 (3.0 g) was treated as detailed in Example 676 to give the title products in a 6:5 ratio having the following physical properties.

EXAMPLE 680(1)

LC/MS $t_R$ 2.26 minutes; MS (ES$^+$) m/z 597 (M+Na)$^a$.

EXAMPLE 680(2)

LC/MS $t_R$ 2.05 minutes; MS (ES$^+$) m/z 475 (M+H)$^a$.

Example 681(1) and 681(2)

tert-butyl N-[(tert-butoxy)carbonyl]-N-{4-chloro-2-[5-oxo-3-(5-oxo-2,5-dihydro-1H-pyrazol-3-yl)-1,2,3,5-tetrahydroindolizin-7-yl]phenyl}carbamate and tert-butyl N-{4-chloro-2-[5-oxo-3-(5-oxo-2,5-dihydro-1H-pyrazol-3-yl)-1,2,3,5-tetrahydroindolizin-7-yl]phenyl}carbamate To an ethanol (12 mL) solution of the 6:5 mixture of compounds prepared in Example 680 (2.15 g) was added a 35% weight solution of hydrazine hydrate in water (0.65 mL) and the mixture stirred at 50° C. for 3 hours. The reaction mixture was concentrated and the residue purified by column chromatography (0% to 10% methanol in dichloromethane) to give the title products in a 1:2 ratio.

EXAMPLE 681(1)

LC/MS $t_R$ 1.97 minutes; MS (ES$^+$) m/z 543 (M+H), 443 (M-CO$_2$C(CH$_3$)$_3$+2H)$^a$.

EXAMPLE 681(2)

LC/MS $t_R$ 1.76 minutes; MS (ES$^+$) m/z 443 (M+H)$^a$.

EXAMPLE 682(1) and 682(2)

tert-butyl N-[(tert-butoxy)carbonyl]-N-{4-chloro-2-[(3S)-3-[1-(4-nitrophenyl)-5-oxo-2,5-dihydro-1H-pyrazol-3-yl]-5-oxo-1,2,3,5-tetrahydroindolizin-7-yl]phenyl}carbamate and tert-butyl N-{4-chloro-2-[(3S)-3-(1-(4-nitrophenyl)-5-oxo-2,5-dihydro-1H-pyrazol-3-yl]-5-oxo-1,2,3,5-tetrahydroindolizin-7-yl]phenyl}carbamate To a dimethylsulfoxide (12 mL) solution of the 1:2 mixture of compounds prepared in Example 681 (1.03 g) was added 1-fluoro-4-nitrobenzene (0.32 g) and potassium carbonate (0.48 g) and the mixture stirred at 50° C. for 3 hours. To the reaction mixture, water (40 mL) was added followed by extraction into ethyl acetate. The combined organic layers were washed with saturated saline, dried and concentrated. The residue was purified by flash chromatography (30% to 100% ethyl acetate in heptanes) to give the title products in a 1:2 ratio.

EXAMPLE 682(1)

LC/MS $t_R$ 2.39 minutes; MS (ES$^+$) m/z 686 (M+Na)$^a$.

EXAMPLE 682(2)

LC/MS $t_R$ 2.20 minutes; MS (ES$^+$) m/z 564 (M+H)$^a$.

EXAMPLE 683

(3S)-3-[1-(4-aminophenyl)-5-oxo-2,5-dihydro-1H-pyrazol-3-yl]-7-[5-chloro-2-(1H-tetrazol-1-yl)phenyl]-2,3-dihydro-5(1H)-indolizinone The same operation as in Example 40→Example 24→Example 74 was conducted from the 1:2 mixture of compounds prepared in Example 682 to give the title compound having the following physical properties.

LC/MS $t_R$ 2.90 minutes; MS (ES$^+$) m/z 487 (M+H)$^b$ $^1$H NMR (500 MHz, DMSO-d$_6$) δ 12.17 (br. s, 1 H), 9.68 (s, 1 H), 7.86-7.70 (m, 3 H), 6.82 (d, 2 H), 6.62 (d, 2 H), 5.97 (br. s, 1 H), 5.91 (br. s, 1 H), 5.75 (br. s, 2 H), 5.60 (d, 1 H), 5.43 (br. s, 1 H), 3.21-3.06 (m, 1 H), 2.94 (dd, 1 H), 2.59-2.42 (obs. m, 1 H), 2.21-2.09 (m, 1 H).

EXAMPLE 684 methyl[4-(3-{(3S)-7-[5-chloro-2-(1H-tetrazol-1-yl)phenyl]-5-oxo-1,2,3,5-tetrahydro-3-indolizinyl}-5-oxo-2,5-dihydro-1H-pyrazol-1-yl)phenyl]carbamate The compound prepared in Example 683 (110 mg) was treated with methyl chloroformate following the method of Example 484 to give the title compound having the following physical properties (19 mg).

LC/MS $t_R$ 3.71 minutes; MS (ES$^+$) m/z 545 (M+H)[b]

$^1$H NMR (500 MHz, methanol-d$_4$) δ 9.34 (s, 1 H), 7.76-7.71 (m, 2 H), 7.70-7.65 (m, 1H), 7.40 (d, 2 H), 7.03-6.98 (m, 2 H), 6.17 (s, 1 H), 6.03 (s, 1H), 5.76 (d, 1H), 5.59 (s, 1 H), 3.72 (s, 3 H), 3.29-3.20 (m, 1 H), 3.06 (dd, 1 H), 2.65-2.54 (m, 1 H), 2.33 (dd, 1H).

EXAMPLE 685

2-methoxyethyl[4-(3-{(3S)-7-[5-chloro-2-(1H-tetrazol-1-yl)phenyl]-5-oxo-1,2,3,5-tetrahydro-3-indolizinyl}-5-oxo-2,5-dihydro-1H-pyrazol-1-yl)phenyl] carbamate The compound prepared in Example 683 (110 mg) was treated with 2-methoxyethyl chloroformate following the method of Example 484 to give the title compound having the following physical properties (39 mg).

LC/MS $t_R$ 3.79 minutes; MS (ES$^+$) m/z 589 (M+H)[b]

$^1$H NMR (500 MHz, methanol-d$_4$) δ 9.34 (s, 1 H), 7.76-7.71 (m, 2 H), 7.70-7.65 (m, 1H), 7.40 (d, 2 H), 7.03-6.97 (m, 2 H), 6.16 (s, 1 H), 6.03 (s, 1 H), 5.76 (d, 1 H), 5.60 (s, 1 H), 4.28-4.22 (m, 2 H), 3.67-3.60 (m, 2 H), 3.38 (s, 3 H), 3.29-3.20 (m, 1 H), 3.05 (dd, 1 H), 2.65-2.54 (m, 1 H), 2.32 (dd, 1 H).

EXAMPLE 686

2-(2-methoxyethoxyl)ethyl[4-(3-{(3S)-7-[5-chloro-2-(1H-tetrazol-1-yl)phenyl]-5-oxo-1,2,3,5-tetrahydro-3-indolizinyl}-5-oxo-2,5-dihydro-1H-pyrazol-1-yl)phenyl]carbamate The compound prepared in Example 683 (100 mg) was treated with the chloroformate as prepared in Example 489 following the method of Example 484 to give the title compound having the following physical properties (51.6 mg).

LC/MS $t_R$ 3.78 minutes; MS (ES$^+$) m/z 633 (M+H)[b]

$^1$H NMR (500 MHz, methanol-d$_4$) δ 9.34 (s, 1 H), 7.76-7.70 (m, 2 H), 7.69-7.64 (m, 1H), 7.39 (d, 2 H), 7.03-6.97 (m, 2 H), 6.16 (s, 1 H), 6.02 (s, 1 H), 5.76 (d, 1 H), 5.59 (s, 1 H), 4.27-4.22 (m, 2 H), 3.74-3.68 (m, 2 H), 3.66-3.61 (m, 2 H), 3.57-3.51 (m, 2H), 3.35 (s, 3 H), 3.29-3.18 (m, 1 H), 3.05 (dd, 1 H), 2.65-2.53 (m, 1 H), 2.32 (dd, 1H).

EXAMPLE 687 tert-butyl 2-[2-oxo-4-(tetramethyl-1,3,2-dioxaborolan-2-yl)-1,2-dihydropyridin-1-yl]acetate The compound prepared in Example 22 (0.50 g) was treated as detailed in Example 282 to give the crude title compound having the following physical properties (0.50 g). (Note: the reaction time was limited to 40 minutes).

LC/MS $t_R$ 1.35 minutes; MS (ES$^+$) m/z 254 (M-C$_6$H$_{10}$+H), 198 (M-C$_6$H$_{10}$—C(CH$_3$)$_3$+H)[a].

EXAMPLE 688 tert-butyl 2-[4-(2-amino-5-methylphenyl)-2-oxo-1,2-dihydropyridin-1-yl]acetate

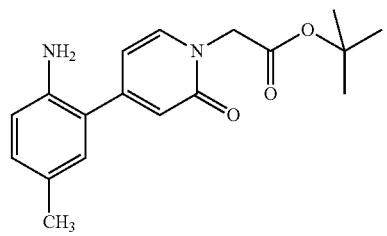 [SMILES: Cc1ccc(N)c(-c2ccn(CC(=O)OC(C)(C)C)c(=O)c2)c1]

To a 1,4-dioxane (4.5 mL) solution of the compound prepared in Example 687 (150 mg) was added 2-bromo-4-methylaniline (83 mg) and caesium fluoride (154 mg) under an atmosphere of nitrogen. The mixture was degassed with nitrogen, tetrakis(triphenylphosphine)palladium(0) (23.5 mg) added and the mixture stirred at 90° C. for 1.5 hours. On cooling to room temperature, ethyl acetate (18 mL) was added, the resultant suspension filtered through Celite® and the filtrate concentrated. The residue was purified by column chromatography (0% to 10% methanol in ethyl acetate) to give the title compound having the following physical properties (100 mg).

LC/MS $t_R$ 1.78 minutes; MS (ES$^+$) m/z 315 (M+H), 259 (M-C(CH$_3$)$_3$+H)[a].

EXAMPLE 689 methyl{4-[2-({4-[5-methyl-2-(1H-tetrazol-1-yl)phenyl]-2-oxo-1(2H)-pyridinyl}methyl)-1H-imidazol-5-yl]phenyl}carbamate The same operation as in Example 24→Example 25→Example 51→Example 52 was conducted from the compound prepared in Example 688 to give the title compound having the following physical properties. (Note: in the step corresponding to Example 51 in the operation, methyl[4-(bromoacetyl)-phenyl]carbamate [J. Am. Chem. Soc. 119(10), 2453 (1997)] was used).

LC/MS $t_R$ 3.03 minutes; MS (ES$^+$) m/z 483 (M+H)[b]

$^1$H NMR (500 MHz, DMSO-d$_6$) δ 12.11 (br. s, 1 H), 9.67 (s, 1 H), 9.61 (br. s, 1 H), 7.68 (d, 1 H), 7.63-7.60 (m, 3 H), 7.52 (d, 1 H), 7.51 (s, 1 H), 7.44 (d, 1 H), 7.41 (d, 2 H), 6.20 (d, 1 H), 5.83 (dd, 1 H), 5.07 (s, 2 H), 3.65 (s, 3 H), 2.45 (s, 3 H).

EXAMPLE 690 methyl{4-[4-chloro-2-({4-[5-methyl-2-(1H-tetrazol-1-yl)phenyl]-2-oxo-1(2H)-pyridinyl}methyl)-1H-imidazol-5-yl]phenyl}carbamate The compound prepared in Example 689 (35 mg) was treated as detailed in Example 44 to give the title compound having the following physical properties (9 mg). LC/MS $t_R$ 3.86 minutes; MS (ES$^+$) m/z 517 (M+H)[b]

$^1$H NMR (500 MHz, DMSO-d$_6$) δ 12.87 (br. s, 1 H), 9.80 (br. s, 1 H), 9.69 (s, 1 H), 7.67 (d, 1 H), 7.64-7.57 (m, 3 H), 7.57-7.47 (m, 4 H), 6.19 (d, 1 H), 5.85 (dd, 1 H), 5.06 (s, 2 H), 3.68 (s, 3 H), 2.46 (s, 3 H).

EXAMPLE 691 methyl(3S)-5-oxo-7-(tetramethyl-1,3,2-dioxaborolan-2-yl)-1,2,3,5-tetrahydroindolizine-3-carboxylate

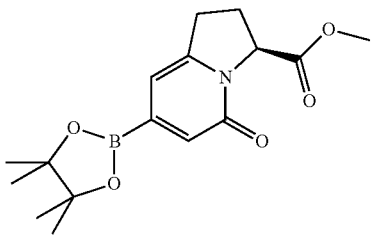

The same operation as in Example 5→Example 6→Example 282 was conducted from the compound prepared in Example 4 to give the title compound having the following physical properties. (Note: in the step corresponding to Example 5 in the operation, methanol was used in place of ethanol).

LC/MS $t_R$ 1.05 minutes; MS (ES$^+$) m/z 238 (M-C$_4$H$_{10}$+H)$^a$.

EXAMPLE 692

(3S)-7-[5-methoxy-2-(1H-1,2,3,4-tetrazol-1-yl)phenyl]-5-oxo-1,2,3,5-tetrahydroindolizine-3-carboxylic acid The same operation as in Example 688→Example 8→Example 9 was conducted from the compound prepared in Example 691 to give the title compound having the following physical properties. (Note: in the step corresponding to Example 688 in the operation, 2-bromo-4-methoxyaniline was used).

LC/MS $t_R$ 1.44 minutes; MS (ES$^+$) m/z 354 (M+H)$^a$.

EXAMPLE 693 methyl[4-(2-{(3S)-7-[5-methoxy-2-(1H-tetrazol-1-yl)phenyl]-5-oxo-1,2,3,5-tetrahydro-3-indolizinyl}-1H-imidazol-5-yl)phenyl]carbamate The same operation as in Example 51→Example 52 was conducted from the compound prepared in Example 692 to give the title compound having the following physical properties. (Note: in the step corresponding to Example 51 in the operation, methyl[4-(bromoacetyl)-phenyl]carbamate [J. Am. Chem. Soc. 119(10), 2453 (1997)] was used).

LC/MS $t_R$ 3.03 minutes; MS (ES$^+$) m/z 525 (M+H)$^b$
$^1$H NMR (500 MHz, DMSO-d$_6$) δ 12.04 (br. s, 1 H), 9.63 (s, 1 H), 9.59 (br. s, 1 H), 7.63 (d, 1 H), 7.59 (d, 2 H), 7.44-7.35 (m, 3 H), 7.22 (dd, 1 H), 7.16 (d, 1 H), 5.94 (s, 1 H), 5.92 (s, 1 H), 5.60 (d, 1 H), 3.89 (s, 3 H), 3.65 (s, 3 H), 3.43-3.36 (m, 1 H), 2.99 (dd, 1H), 2.57-2.42 (obs. m, 1 H), 2.39-2.29 (m, 1 H).

EXAMPLE 694

2-methoxyethyl[4-(2-{(3S)-7-[5-methoxy-2-(1H-tetrazol-1-yl)phenyl]-5-oxo-1,2,3,5-tetrahydro-3-indolizinyl}-1H-imidazol-5-yl)phenyl]carbamate The same operation as in Example 51→Example 52 was conducted from the compound prepared in Example 692 to give the title compound having the following physical properties. (Note: in the step corresponding to Example 51 in the operation, the compound prepared in Example 324 was used).

LC/MS $t_R$ 2.94 minutes; MS (ES$^+$) m/z 569 (M+H)$^b$
$^1$H NMR (500 MHz, methanol-d$_4$) δ 9.27 (s, 1 H), 7.54 (d, 1 H), 7.54 (app. br. s, 2 H), 7.43 (app. br. s, 2 H), 7.20 (dd, 1 H), 7.14 (d, 1 H), 7.26 (br. s, 1 H), 6.10 (s, 1 H), 6.07 (s, 1 H), 5.76 (dd, 1 H), 4.29-4.22 (m, 2 H), 3.91 (s, 3 H), 3.67-3.61 (m, 2 H), 3.48-3.39 (m, 1 H), 3.38 (s, 3 H), 3.07 (ddd, 1 H), 2.60 (qd, 1 H), 2.46 (app. br. s, 1 H).

EXAMPLE 695

2-methoxyethyl[4-(4-chloro-2-{(3S)-7-[5-methoxy-2-(1H-tetrazol-1-yl)phenyl]-5-oxo-1,2,3,5-tetrahydro-3-indolizinyl}-1H-imidazol-5-yl)phenyl]carbamate The compound prepared in Example 694 (83 mg) was treated as detailed in Example 338 to give the title compound having the following physical properties (59.5 mg).

LC/MS $t_R$ 3.90 minutes; MS (ES$^+$) m/z 603 (M+H)$^b$
$^1$H NMR (500 MHz, methanol-d$_4$) δ 9.29 (s, 1 H), 7.64-7.58 (m, 2 H), 7.55 (d, 1 H), 7.52 (d, 2 H), 7.22 (dd, 1 H), 7.17 (d, 1 H), 6.11 (s, 1 H), 6.09 (s, 1 H), 5.70 (dd, 1 H), 4.30-4.25 (m, 2 H), 3.93 (s, 3 H), 3.68-3.62 (m, 2 H), 3.48-3.41 (m, 1 H), 3.39 (s, 3H), 3.09 (ddd, 1 H), 2.62 (qd, 1 H), 2.42-2.34 (m, 1 H).

EXAMPLE 696

(3S)-3-[5-(6-amino-3-pyridinyl)-4-chloro-1H-imidazol-2-yl]-7-[5-methoxy-2-(1H-tetrazol-1-yl)phenyl]-2,3-dihydro-5(1H)-indolizinone The same operation as in Example 51→Example 52→Example 484→Example 338→Example 584 was conducted from the compound prepared in Example 692 to give the title compound having the following physical properties. (Note: in the step corresponding to Example 51 in the operation, the compound prepared in Example 193 was used. In the step corresponding to Example 484 in the operation, allyl chloroformate was used).

LC/MS $t_R$ 2.82 minutes; MS (ES$^+$) m/z 502 (M+H)$^b$
$^1$H NMR (500 MHz, methanol-d$_4$) δ 9.29 (s, 1 H), 8.21 (s, 1 H), 7.75 (dd, 1 H), 7.56 (d, 1 H), 7.22 (dd, 1 H), 7.17 (d, 1 H), 6.65 (d, 1 H), 6.11 (s, 1 H), 6.09 (s, 1 H), 5.68 (dd, 1H), 3.93 (s, 3 H), 3.50-3.36 (m, 1 H), 3.09 (ddd, 1 H), 2.62 (qd, 1 H), 2.43-2.30 (m, 1H).

EXAMPLE 697 methyl[4-(2-{(3S)-7-[6-methyl-3-(1H-tetrazol-1-yl)-2-pyridinyl]-5-oxo-1,2,3,5-tetrahydro-3-indolizinyl}-1H-imidazol-5-yl)phenyl]carbamate The same operation as in Example 688→Example 8→Example 24→Example 51→Example 52 was conducted from the compound prepared in Example 691 to give the title compound having the following physical properties. (Note: in the step corresponding to Example 688 in the operation, 2-bromo-6-methylpyridin-3-amine was used. In the step corresponding to Example 51 in the operation, methyl[4-(bromoacetyl)-phenyl]carbamate [J. Am. Chem. Soc. 119 (10), 2453 (1997)] was used).

LC/MS $t_R$ 2.90 minutes; MS (ES$^+$) m/z 510 (M+H), 482 (M-N$_2$+H)$^b$ $^1$H NMR (500 MHz, DMSO-d$_6$) δ 12.05 (br. s, 1 H), 9.74 (s, 1 H), 9.58 (br. s, 1 H), 8.12 (d, 1 H), 7.63 (d, 1 H), 7.59 (d, 2 H), 7.40 (d, 2 H), 7.38 (s, 1 H), 6.19 (s, 1 H), 5.78 (s, 1H), 5.61 (d, 1 H), 3.71-3.62 (obs. m, 1 H), 3.65 (s, 3 H), 3.46-3.36 (obs. m, 1 H), 3.07 (dd, 1 H), 2.65 (s, 3 H), 2.34-2.27 (m, 1 H).

EXAMPLE 698

(3S)-3-[5-(6-amino-3-pyridinyl)-1H-imidazol-2-yl]-7-[5-fluoro-2-(1H-tetrazol-1-yl)phenyl]-2,3-dihydro-5(1H)-indolizinone The same operation as in Example 7→Example 9→Example 596→Example 51→Example 52 was conducted from the compound prepared in Example 6 to give the title compound having the following physical properties. (Note: in the step corresponding to Example 7 in the operation, 4-fluoro-2-(tetramethyl-1,3,2-dioxaborolan-2-yl) aniline [patent EP 1719773 (2006)] was used. In the step corresponding to Example 51 in the operation, the compound prepared in Example 193 was used).

LC/MS $t_R$ 2.50 minutes; MS (ES$^+$) m/z 456 (M+H)$^b$ $^1$H NMR (500 MHz, methanol-d$_4$) δ 9.35 (s, 1 H), 8.19 (d, 1 H), 7.77 (dd, 1 H), 7.74-7.69 (m, 1 H), 7.51-7.44 (m, 2 H), 7.20 (s, 1 H), 6.63 (d, 1 H), 6.12 (s, 1 H), 6.09 (s, 1H), 5.76 (dd, 1 H), 3.50-3.39 (m, 1 H), 3.10 (ddd, 1 H), 2.62 (qd, 1 H), 2.50-2.41 (m, 1 H).

EXAMPLE 699

(3S)-3-[5-(6-amino-3-pyridinyl)-4-chloro-1H-imidazol-2-yl]-7-[5-fluoro-2-(1H-tetrazol-1-yl)phenyl]-2,3-dihydro-5(1H)-indolizinone The compound prepared in Example 698 (103 mg) was treated as detailed in Example 338 to give the title compound having the following physical properties (51 mg).

LC/MS $t_R$ 2.78 minutes; MS (ES$^+$) m/z 490 (M+H)$^b$ $^1$H NMR (500 MHz, methanol-d$_4$) δ 9.37 (s, 1 H), 8.21 (app. s, 1 H), 7.83-7.64 (m, 2H), 7.58-7.39 (m, 2 H), 6.65 (d, 1 H), 6.13 (s, 1 H), 6.10 (s, 1 H), 5.71 (dd, 1 H), 3.52-3.38 (m, 1 H), 3.11 (td, 1 H), 2.74-2.54 (m, 1 H), 2.45-2.30 (m, 1 H).

EXAMPLE 700

(3S)-3-[5-(6-amino-3-pyridinyl)-1H-imidazol-2-yl]-7-[2,3-difluoro-6-(1H-tetrazol-1-yl)phenyl]-2,3-dihydro-5(1H)-indolizinone The same operation as in Example 688→Example 9→Example 596→Example 51→Example 52 was conducted from the compound prepared in Example 282 to give the title compound having the following physical properties. (Note: in the step corresponding to Example 688 in the operation, 2-bromo-3,4-difluoroaniline was used. In the step corresponding to Example 51 in the operation, the compound prepared in Example 193 was used)

LC/MS $t_R$ 2.57 minutes; MS (ES$^+$) m/z 474 (M+H)$^b$ $^1$H NMR (500 MHz, methanol-d$_4$) δ 9.35 (s, 1 H), 8.20 (app, br. s, 1 H), 7.75 (d, 1 H), 7.65 (q, 1 H), 7.60-7.54 (m, 1 H), 7.19 (br. s, 1 H), 6.61 (d, 1 H), 6.21 (s, 1 H), 6.18 (s, 1 H), 5.77 (dd, 1 H), 3.49 (td, 1 H), 3.14 (ddd, 1 H), 2.64 (qd, 1 H), 2.52-2.42 (m, 1 H).

EXAMPLE 701

(3S)-3-[5-(6-amino-3-pyridinyl)-4-chloro-1H-imidazol-2-yl]-7-[2,3-difluoro-6-(1H-tetrazol-1-yl)phenyl]-2,3-dihydro-5(1H)-indolizinone The compound prepared in Example 700 (75 mg) was treated as detailed in Example 338 to give the title compound having the following physical properties (28.9 mg).

LC/MS $t_R$ 2.85 minutes; MS (ES$^+$) m/z 508 (M+H)$^b$ $^1$H NMR (500 MHz, methanol-d$_4$) δ 9.37 (s, 1 H), 8.22 (d, 1 H), 7.77 (dd, 1 H), 7.67 (q, 1 H), 7.61-7.55 (m, 1 H), 6.66 (d, 1 H), 6.23 (s, 1 H), 6.20 (s, 1 H), 5.71 (dd, 1 H), 3.51 (td, 1 H), 3.15 (ddd, 1 H), 2.66 (qd, 1 H), 2.41 (tdd, 1 H).

EXAMPLE 702 formic acid-(3S)-3-[5-(6-amino-3-pyridinyl)-1H-imidazol-2-yl]-7-[3,5-difluoro-2-(1H-tetrazol-1-yl)phenyl]-2,3-dihydro-5(1H)-indolizinone (2:1)

The same operation as in Example 688→Example 9→Example 596→Example 51→Example 52 was conducted from the compound prepared in Example 282 to give the title compound after purification by high performance liquid chromatography [5 to 100% mobile phase B (0.1% formic acid in acetonitrile) in mobile phase A (0.1% aqueous formic acid)] as the formic acid salt having the following physical properties. (Note: in the step corresponding to Example 688 in the operation, 2-bromo-4,6-difluoroaniline was used. In the step corresponding to Example 51 in the operation, the compound prepared in Example 193 was used).

LC/MS $t_R$ 2.60 minutes; MS (ES$^+$) m/z 474 (M+H)$^b$ $^1$H NMR (500 MHz, methanol-d$_4$) δ 9.47 (s, 1 H), 8.29 (br. s, 2 H), 8.15 (d, 1 H), 7.96 (dd, 1 H), 7.56-7.47 (m, 1 H), 7.41-7.35 (m, 1 H), 7.31 (s, 1 H), 6.80 (d, 1 H), 6.14 (s, 1 H), 6.13 (s, 1 H), 5.75 (dd, 1 H), 3.51-3.38 (m, 1 H), 3.11 (ddd, 1 H), 2.70-2.52 (m, 1 H), 2.48-2.38 (m, 1 H).

EXAMPLE 703 formic acid-(3S)-3-[5-(6-amino-3-pyridinyl)-4-chloro-1H-imidazol-2-yl]-7-[3,5-difluoro-2-(1H-tetrazol-1-yl)phenyl]-2,3-dihydro-5(1H)-indolizinone (1:1)

The compound prepared in Example 702 (40 mg) was treated as detailed in Example 338 to give the title compound after purification by high performance liquid chromatography [5 to 100% mobile phase B (0.1% formic acid in acetonitrile) in mobile phase A (0.1% aqueous formic acid)] as the formic acid salt having the following physical properties (8.7 mg).

LC/MS $t_R$ 2.87 minutes; MS (ES$^+$) m/z 508 (M+H)$^b$ $^1$H NMR (500 MHz, methanol-d$_4$) δ 9.47 (s, 1 H), 8.30 (br. s, 1 H), 8.20 (d, 1 H), 7.78 (dd, 1 H), 7.57-7.48 (m, 1 H), 7.39 (dd, 1 H), 6.68 (d, 1 H), 6.14 (s, 1 H), 6.13 (s, 1 H), 5.67 (dd, 1 H), 3.44 (td, 1 H), 3.10 (ddd, 1 H), 2.69-2.55 (m, 1 H), 2.37 (tdd, 1 H).

EXAMPLE 704

(3S)-7-[5-(difluoromethoxy)-2-(1H-1,2,3,4-tetrazol-1-yl)phenyl]-5-oxo-1,2,3,5-tetrahydroindolizine-3-carboxylic acid The same operation as in Example 688→Example 9→Example 596 was conducted from the compound prepared in Example 282 to give the title compound having the following physical properties. (Note: in the step corresponding to Example 688 in the operation, 2-bromo-4-(difluoromethoxy)aniline [patent WO2009/44632] was used).

LC/MS $t_R$ 1.51 minutes; MS (ES$^+$) m/z 390 (M+H), 362 (M-N$_2$+H)$^a$.

EXAMPLE 705

(3S)-3-[5-(6-amino-3-pyridinyl)-1H-imidazol-2-yl]-7-[5-(difluoromethoxy)-2-(1H-tetrazol-1-yl)phenyl]-2,3-dihydro-5(1H)-indolizinone The same operation as in Example 51→Example 52 was conducted from the compound prepared in Example 704 to give the title compound having the following physical properties. (Note: in the step corresponding to Example 51 in the operation, the compound prepared in Example 193 was used)

LC/MS $t_R$ 2.71 minutes; MS (ES$^+$) m/z 504 (M+H), 252.5 [(M+2H)/2]$^b$ $^1$H NMR (500 MHz, methanol-d$_4$) δ 9.35 (s, 1 H), 8.19 (d, 1 H), 7.75 (dd, 1 H), 7.72 (d, 1 H), 7.47 (dd, 1 H), 7.43 (d, 1 H), 7.19 (s, 1 H), 7.08 (t, 1 H), 6.62 (d, 1 H), 6.12 (s, 1H), 6.10 (s, 1 H), 5.76 (dd, 1 H), 3.44 (td, 1 H), 3.10 (ddd, 1 H), 2.63 (qd, 1 H), 2.49-2.41 (m, 1 H).

EXAMPLE 706

(3S)-3-[5-(6-amino-3-pyridinyl)-4-chloro-1H-imidazol-2-yl]-7-[5-(difluoromethoxy)-2-(1H-tetrazol-1-yl)phenyl]-2,3-dihydro-5 (1H)-indolizinone The compound prepared in Example 705 (90 mg) was treated as detailed in Example 338 to give the title compound having the following physical properties (50 mg).

LC/MS $t_R$ 2.95 minutes; MS (ES$^+$) m/z 538 (M+H)$^b$ $^1$H NMR (500 MHz, methanol-d$_4$) δ 9.38 (s, 1 H), 8.22 (d, 1 H), 7.77 (dd, 1 H), 7.74 (d, 1 H), 7.51-7.48 (m, 1 H), 7.46 (d, 1 H), 7.11 (t, 1 H), 6.67 (d, 1 H), 6.15 (s, 1 H), 6.12 (s, 1 H), 5.71 (dd, 1 H), 3.44 (td, 1 H), 3.12 (ddd, 1 H), 2.65 (qd, 1 H), 2.44-2.34 (m, 1H).

EXAMPLE 707

(3S)-3-[5-(6-amino-2-fluoro-3-pyridinyl)-1H-imidazol-2-yl]-7-[5-(difluoromethoxy)-2-(1H-tetrazol-1-yl)phenyl]-2,3-dihydro-5(1H)-indolizinone The same operation as in Example 51→Example 52 was conducted from the compound prepared in Example 704 to give the title compound having the following physical properties. (Note: in the step corresponding to Example 51 in the operation, the compound prepared in Example 215 was used).

LC/MS $t_R$ 2.94 minutes; MS (ES$^+$) m/z 522 (M+H)$^b$ $^1$H NMR (500 MHz, methanol-d$_4$) δ 9.37 (s, 1 H), 7.98 (app. br. s, 1 H), 7.74 (d, 1 H), 7.49 (dd, 1 H), 7.45 (d, 1 H), 7.16 (br. s, 1 H), 7.09 (t, 1 H), 6.47 (dd, 1 H), 6.16 (s, 1 H), 6.10 (s, 1 H), 5.80 (dd, 1 H), 3.45 (td, 1 H), 3.11 (ddd, 1 H), 2.64 (qd, 1 H), 2.52-2.45 (m, 1 H).

EXAMPLE 708

(3S)-7-[5-cyano-2-(1H-1,2,3,4-tetrazol-1-yl)phenyl]-5-oxo-1,2,3,5-tetrahydroindolizine-3-carboxylic acid The same operation as in Example 688→Example 9→Example 596 was conducted from the compound prepared in Example 282 to give the title compound having the following physical properties. (Note: in the step corresponding to Example 688 in the operation, 2-bromo-4-cyanoaniline was used).

LC/MS $t_R$ 1.51 minutes; MS (ES$^+$) m/z 719 (2M+Na), 697 (2M+H)$^a$.

EXAMPLE 709

3-{(3S)-3-[5-(6-amino-3-pyridinyl)-1H-imidazol-2-yl]-5-oxo-1,2,3,5-tetrahydro-7-indolizinyl}-4-(1H-tetrazol-1-yl)benzonitrile The same operation as in Example 51→Example 52 was conducted from the compound prepared in Example 708 to give the title compound having the following physical properties. (Note: in the step corresponding to Example 51 in the operation, the compound prepared in Example 193 was used).

LC/MS $t_R$ 2.42 minutes; MS (ES$^+$) m/z 463 (M+H), 435 (M-N$_2$+H)$^b$ $^1$H NMR (500 MHz, methanol-d$_4$) δ 9.41 (s, 1 H), 8.20 (app. s, 1 H), 8.13-8.05 (m, 2H), 7.90 (d, 1 H), 7.75 (dd, 1 H), 7.20 (br. s, 1 H), 6.62 (d, 1 H), 6.17 (s, 1 H), 6.10 (s, 1H), 5.78 (dd, 1 H), 3.45 (td, 1 H), 3.11 (ddd, 1 H), 2.64 (qd, 1 H), 2.52-2.40 (m, 1 H).

EXAMPLE 710

3-{(3S)-3-[5-(6-amino-3-pyridinyl)-4-chloro-1H-imidazol-2-yl]-5-oxo-1,2,3,5-tetrahydro-7-indolizinyl}-4-C1H-tetrazol-1-yl)benzonitrile The compound prepared in Example 709 (70 mg) was treated as detailed in Example 338 to give the title compound having the following physical properties (22.9 mg).

LC/MS $t_R$ 2.73 minutes; MS (ES$^+$) m/z 497 (M+H), 469 (M-N$_2$+H)$^b$ $^1$H NMR (500 MHz, methanol-d$_4$) δ 9.44 (s, 1 H), 8.23 (d, 1 H), 8.15-8.07 (m, 2 H), 7.93 (d, 1 H), 7.79 (dd, 1 H), 6.68 (d, 1 H), 6.19 (s, 1 H), 6.12 (s, 1 H), 5.72 (dd, 1 H), 3.47 (td, 1 H), 3.13 (ddd, 1 H), 2.67 (qd, 1 H), 2.45-2.37 (m, 1 H).

EXAMPLE 711

3-{(3S)-3-[5-(6-amino-2-fluoro-3-pyridinyl)-1H-imidazol-2-yl]-5-oxo-1,2,3,5-tetrahydro-7-indolizinyl}-4-(1H-tetrazol-1-yl)benzonitrile The same operation as in Example 51→Example 52 was conducted from the compound prepared in Example 708 to give the title compound having the following physical properties. (Note: in the step corresponding to Example 51 in the operation, the compound prepared in Example 215 was used).

LC/MS $t_R$ 2.66 minutes; MS (ES$^+$) m/z 481 (M+H)$^b$ $^1$H NMR (500 MHz, methanol-d$_4$) δ 9.42 (s, 1 H), 8.12-8.08 (m, 2 H), 7.98 (br. s, 1 H), 7.92 (d, 1 H), 7.17 (d, 1 H), 6.47 (dd, 1 H), 6.20 (s, 1 H), 6.11 (s, 1 H), 5.82 (dd, 1 H), 3.46 (td, 1 H), 3.12 (ddd, 1 H), 2.65 (qd, 1 H), 2.54-2.47 (m, 1 H).

EXAMPLE 712 methyl N-[6-(2-bromoacetyl)pyridin-3-yl]carbamate

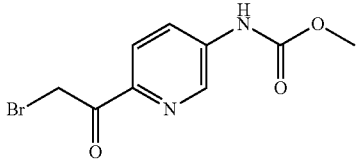

The same operation as in Example 10→Example 188→Example 55→Example 128→Example 204 was conducted from 5-amino-2-cyanopyridine to give the title compound having the following physical properties. (Note: in the step corresponding to Example 128 in the operation, methyl chloroformate was used).

LC/MS $t_R$ 1.68 minutes; MS (ES+) m/z 273 and 275 (M+H)$^a$.

EXAMPLE 713

2-methoxyethyl N-[6-(2-bromoacetyl)pyridin-3-yl]carbamate

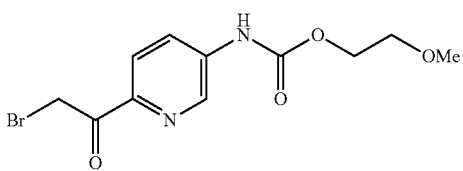 [SMILES: COCCOC(=O)Nc1ccc(C(=O)CBr)nc1]

The same operation as in Example 128→Example 188→Example 204 was conducted from 5-amino-2-cyanopyridine to give the title compound having the following physical properties. (Note: in the step corresponding to Example 128 in the operation, 2-methoxyethyl chloroformate was used)

LC/MS $t_R$ 1.69 minutes; MS (ES+) m/z 317 and 319 (M+H)$^a$.

EXAMPLE 714

2-ethoxyethyl N-[4-(2-bromoacetyl)phenyl]carbamate

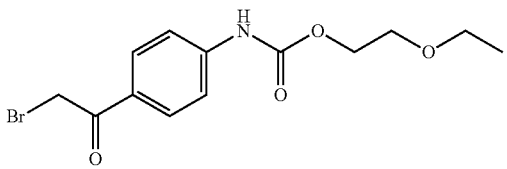 [SMILES: CCOCCOC(=O)Nc1ccc(C(=O)CBr)cc1]

The same operation as in Example 128→Example 78 was conducted from 4-aminoacetophenone to give the title compound having the following physical properties. (Note: in the step corresponding to Example 128 in the operation, the chloroformate prepared in Example 485 was used)

LC/MS $t_R$ 1.85 minutes; MS (ES+) m/z 330 and 332 (M+H)$^a$.

EXAMPLE 715

3-methoxypropyl N-[4-(2-bromoacetyl)phenyl]carbamate

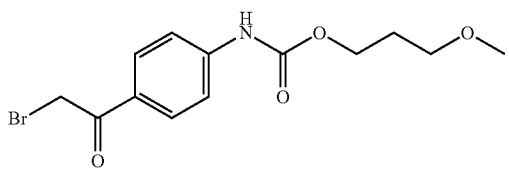 [SMILES: COCCCOC(=O)Nc1ccc(C(=O)CBr)cc1]

The same operation as in Example 128→Example 78 was conducted from 4-aminoacetophenone to give the title compound having the following physical properties. (Note: in the step corresponding to Example 128 in the operation, the chloroformate prepared in Example 487 was used)

LC/MS $t_R$ 1.83 minutes; MS (ES+) m/z 330 and 332 (M+H)$^a$.

EXAMPLE 716

(6S)-6-[5-(4-aminophenyl)-1H-imidazol-2-yl]-2-[5-chloro-2-(1H-tetrazol-1-yl)phenyl]-7,8-dihydropyrrolo[1,2-a]pyrimidin-4(6H)-one The same operation as in Example 51→Example 52→Example 74 was conducted from the compound prepared in Example 336 to give the title compound having the following physical properties. (Note: in the step corresponding to Example 51 in the operation, 2-bromo-1-(4-nitrophenyl)ethan-1-one was used). LC/MS $t_R$ 2.64 minutes; MS (ES+) m/z 472 (M+H)$^b$ $^1$H NMR (500 MHz, methanol-d$_4$) δ 9.45 (s, 1 H), 7.92 (d, 1 H) 7.80-7.66 (m, 2 H), 7.44-7.36 (m, 2 H), 7.10 (s, 1 H), 6.78-6.71 (m, 2 H), 6.35 (s, 1 H), 5.73 (dd, 1 H), 3.29-3.25 (m, 1 H), 2.92-2.88 (m, 1 H), 2.67-2.63 (m, 1 H), 2.38-2.35 (m, 1 H).

EXAMPLE 717

3-oxetanyl[4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)phenyl]carbamate The compound prepared in Example 716 (100 mg) was treated as detailed in Example 494 to give the title compound having the following physical properties (13.4 mg).

LC/MS $t_R$ 2.96 minutes; MS (ES+) m/z 572 (M+H)$^b$ $^1$H NMR (500 MHz, DMSO-d$_6$) δ 12.13 (s, 1 H), 9.74 (s, 1 H) 7.97 (d, 1 H) 7.89-7.79 (m, 2 H) 7.61 (br. s, 1 H) 7.43 (d, 2 H) 6.34 (s, 1 H) 5.61 (dd, 1 H) 5.41 (t, 1 H) 4.82-4.78 (m, 2 H) 4.59-4.51 (m, 2 H) 3.20-3.18 (m, 1 H) 2.81-2.72 (m, 1 H) 2.59-2.54 (m, 1 H) 2.26-2.18 (m, 1 H).

EXAMPLE 718(1) to Example 718(13)

The compounds of the present invention having the following physical data were prepared using the corresponding alpha-bromoketones from the compound prepared in Example 336 in the process of Example 51→Example 52.

EXAMPLE 718(1)

2-methoxyethyl[4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)phenyl]carbamate In the step corresponding to Example 51 in the process, the compound prepared in Example 324 was used.

LC/MS $t_R$ 3.06 minutes; MS (ES$^+$) m/z 574 (M+H)$^b$ $^1$H NMR (500 MHz, methanol-d$_4$) δ 9.46 (s, 1 H), 7.92 (d, 1 H), 7.81-7.67 (m, 2 H), 7.59 (d, 2 H), 7.46 (d, 2 H), 7.27 (s, 1 H), 6.36 (s, 1 H), 5.74 (dd, 1 H), 4.32-4.24 (m, 2H), 3.66 (dd, 2 H), 3.41 (s, 3 H), 3.30-3.24 (m, 1 H), 3.01-2.87 (m, 1 H), 2.77-2.59 (m, 1 H), 2.45-2.34 (m, 1 H).

EXAMPLE 718(2)

2-ethoxyethyl[4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)phenyl]carbamate In the step corresponding to Example 51 in the process, the compound prepared in Example 714 was used.

LC/MS $t_R$ 2.93 minutes; MS (ES$^+$) m/z 588 (M+H)$^b$ $^1$H-NMR (500 MHz, DMSO-d$_6$) δ 12.15 (s, 1 H), 9.68 (s, 2 H), 7.99 (s, 1 H), 7.88-7.80 (m, 2 H), 7.64-7.40 (m, 5 H), 6.36 (s, 1 H), 5.64-5.59 (m, 1 H), 4.22-4.16 (m, 2 H), 3.63-3.57 (m, 2 H), 3.51-3.43 (m, 2 H), 3.26-3.12 (m, 1 H), 2.80-2.72 (m, 1 H), 2.60-2.54 (m, 1 H), 2.26-2.12 (m, 1 H) 1.10 (t, 3 H).

EXAMPLE 718(3)

3-methoxypropyl[4-(2-{(6S)-2-[5-chloro-2-(1H-tetrazol-1-yl)phenyl]4-oxo-4,6,7,8-tetrahydropyrrolo[1,2-a]pyrimidin-6-yl}-1H-imidazol-5-yl)phenyl]carbamate In the step corresponding to Example 51 in the process, the compound prepared in Example 715 was used.

LC/MS $t_R$ 3.22 minutes; MS (ES$^+$) m/z 589 (M+H)$^b$ $^1$H NMR (500 MHz, methanol-d$_4$) δ 9.44 (s, 1 H), 7.90 (d, 1 H), 7.76 (dd, 1 H), 7.69 (d, 1 H), 7.59-7.54 (bd, 2 H), 7.46-7.41 (bd, 2 H), 7.28-7.22 (bs, 1 H), 6.34 (s, 1 H), 5.72 (dd, 10.0 Hz, 1 H), 4.20 (t, 2 H), 3.51 (t, 2 H), 3.34 (s, 3 H), 3.29-3.25 (m, 1 H), 2.94-2.98 (m, 1 H), 2.70-2.62 (m, 1 H), 2.41-2.34 (m, 1 H), 1.93 (quintet, 2 H).

EXAMPLE 718(4)

methyl[4-(2-{(6S)-2-[5-chloro-2-(1H-tetrazol-1-yl)phenyl]-4-oxo-4,6,7,8-tetrahydropyrrolo[1,2-a]pyrimidin-6-yl}-4-methyl-1H-imidazol-5-yl)phenyl]carbamate In the step corresponding to Example 51 in the process, the compound prepared in Example 78 was used.

LC/MS $t_R$ 3.00 minutes; MS (ES$^+$) m/z 544 (M+H)$^b$ $^1$H-NMR (500 MHz, DMSO-d$_6$) δ 11.99 (s, 1 H), 9.77 (s, 1 H), 9.57 (s, 1 H), 8.02-7.94 (m, 1 H), 7.89-7.77 (m, 2 H), 7.57-7.35 (m, 4 H), 6.36 (s, 1 H), 5.59-5.50 (m, 1 H), 3.72 (s, 3 H), 3.20 (s, 1 H), 2.76-2.71 (m, 1 H), 2.55-2.50 (m, 1 H), 2.35-2.15 (m, 4H).

EXAMPLE 718(5)

2-methoxyethyl[4-(2-{(6S)-2-[5-chloro-2-(1H-tetrazol-1-yl)phenyl]-4-oxo-4,6,7,8-tetrahydropyrrolo[1,2-a]pyrimidin-6-yl}-4-methyl-1H-imidazol-5-yl)phenyl]carbamate In the step corresponding to Example 51 in the process, the compound prepared in Example 481 was used.

LC/MS $t_R$ 3.01 minutes; MS (ES$^+$) m/z 588 (M+H)$^b$ $^1$H-NMR (500 MHz, DMSO-d$_6$) δ 11.98 (s, 1 H), 9.85 (s, 2 H), 8.02 (d, 1 H), 7.89-7.78 (m, 2 H), 7.56-7.36 (m, 4 H), 6.36 (s, 1 H), 5.61-5.48 (m, 1 H), 4.25 (t, 2 H), 3.50 (t, 2 H), 3.25 (s, 3 H), 3.25-3.13 (m, 1 H), 2.81-2.78 (m, 1 H), 2.69-2.65 (m, 1H), 2.35-2.16 (m, 4 H).

EXAMPLE 718(6)

(6S)-6-[5-(6-amino-3-pyridinyl)-1H-imidazol-2-yl]-2-[5-chloro-2-(1H-tetrazol-1-yl)phenyl]-7,8-dihydropyrrolo[1,2-a]pyrimidin-4(6H)-one In the step corresponding to Example 51 in the process, the compound prepared in Example 193 was used.

LC/MS $t_R$ 2.52 minutes; MS (ES$^+$) m/z 473 (M+H)$^b$ $^1$H NMR (500 MHz, methanol-d$_4$) δ 9.47 (s, 1 H), 8.22 (s, 1 H), 7.93 (d, 1 H), 7.82-7.69 (m, 3 H), 7.24 (br. s., 1 H), 6.65 (d, 1 H), 6.36 (s, 1 H), 5.74 (dd, 1 H), 3.31-3.26 (m, 1 H), 2.94 (ddd, 1 H), 2.75-2.62 (m, 1 H), 2.44-2.34 (m, 1 H).

EXAMPLE 718(7)

(6S)-2-[5-chloro-2-(1H-tetrazol-1-yl)phenyl]-6-{5-[6-(methylamino)-3-pyridinyl]-1H-imidazol-2-yl}-7,8-dihydropyrrolo[1,2-a]pyrimidin-4(6H)-one In the step corresponding to Example 51 in the process, the compound prepared in Example 551 was used.

LC/MS $t_R$ 2.59 minutes; MS (ES$^+$) m/z 487 (M+H)$^b$ $^1$H NMR (500 MHz, DMSO-d$_6$) δ 12.08 (s, 1 H), 9.67 (s, 1 H), 8.36 (s, 1 H), 7.99 (s, 1H), 7.89-7.79 (m, 2 H), 7.71-7.57 (m, 1 H), 7.34 (s, 1 H), 6.63-6.29 (m, 3 H), 5.64-5.53 (m, 1 H), 3.21 (dd, 1 H), 2.83-2.73 (m, 4 H), 2.62-2.55 (m, 1 H), 2.32-2.13 (m, 1 H).

EXAMPLE 718(8)

(6S)-2-[5-chloro-2-(1H-tetrazol-1-yl)phenyl]-6-(5-{6-[(2-methoxyethyl)amino]-3-pyridinyl}-1H-imidazol-2-yl)-7,8-dihydropyrrolo[1,2-a]pyrimidin-4(6H)-one In the step corresponding to Example 51 in the process, the compound prepared in Example 560 was used.

LC/MS $t_R$ 2.68 minutes; MS (ES$^+$) m/z 531 (M+H)$^b$ $^1$H NMR (500 MHz, methanol-d$_4$) δ 9.34 (s, 1 H), 8.09 (d, 1 H), 7.81-7.73 (m, 2H), 7.69-7.64 (m, 1 H), 7.62-7.55 (m, 1 H), 7.18 (s, 1 H), 6.64 (d, 1 H), 6.24 (s, 1 H), 5.62 (dd, 1 H), 3.54-3.45 (m, 2 H), 3.43-3.36 (m, 2 H), 3.29 (s, 3 H), 3.20-3.12 (m, 1H), 2.82 (ddd, 1 H), 2.56 (dd, 1 H), 2.32-2.21 (m, 1 H).

EXAMPLE 718(9)

(6S)-6-[5-(6-amino-2-fluoro-3-pyridinyl)-1H-imidazol-2-yl]-2-[5-chloro-2-(1H-tetrazol-1-yl)phenyl]-7,8-dihydropyrrolo[1,2-a]pyrimidin-4(6H)-one (enantiopure)

In the step corresponding to Example 51 in the process, the compound prepared in Example 215 was used.

LC/MS $t_R$ 2.86 minutes; MS (ES$^+$) m/z 491 (M+H)$^b$ $^1$H-NMR (500 MHz, DMSO-d$_6$) δ 12.22 (s, 1 H), 9.74 (s, 1 H), 8.02-7.95 (m, 2 H), 7.86 (dd, 1 H), 7.83 (d, 1 H), 7.12 (d, 1 H), 6.42-6.34 (m, 2 H), 6.27 (s, 2 H), 5.62 (dd, 1 H), 3.19 (td, 1 H), 2.81-2.71 (m, 1 H), 2.60-2.55 (m, 1 H), 2.26-2.16 (m, 1 H).

EXAMPLE 718(10)

(6S)-6-[5-(6-amino-2-chloro-3-pyridinyl)-1H-imidazol-2-yl]-2-[5-chloro-2-(1H-tetrazol-1-yl)phenyl]-7,8-dihydropyrrolo[1,2-a]pyrimidin-4(6H)-one In the step corresponding to Example 51 in the process, the compound prepared in Example 209 was used.

TLC Rf 0.40 (10% methanol in ethyl acetate)

$^1$H NMR (300 MHz, DMSO-d$_6$) δ 12.23 (s, 1 H), 9.71 (s, 1 H), 8.02-7.91 (m, 2 H), 7.88-7.72 (m, 2 H), 7.42 (d, 1 H), 6.55-6.24 (m, 4 H), 5.62 (dd, 1 H), 3.25-3.07 (m, 1 H), 2.83-2.66 (m, 1 H), 2.59-2.52 (obs. m, 1 H), 2.31-2.13 (m, 1 H).

EXAMPLE 718(11)

methyl[6-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-3-pyridinyl]carbamate In the step corresponding to Example 51 in the process, the compound prepared in Example 712 was used.

LC/MS $t_R$ 2.94 minutes; MS (ES$^+$) m/z 531 (M+H)$^b$ $^1$H NMR (500 MHz, methanol-d$_4$) δ 9.50 (s, 1 H), 8.55 (s, 1 H), 8.00-7.88 (m, 3 H), 7.83-7.49 (m, 3 H), 6.40 (s, 1 H), 5.81-5.70 (m, 1 H), 3.78 (s, 3 H), 3.41-3.34 (m, 1H), 2.99-2.83 (m, 1 H), 2.74-2.66 (m, 1 H), 2.51-2.40 (m, 1 H).

EXAMPLE 718(12)

2-methoxyethyl[6-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-3-pyridinyl]carbamate In the step corresponding to Example 51 in the process, the compound prepared in Example 713 was used.

LC/MS $t_R$ 2.97 minutes; MS (ES$^+$) m/z 575 (M+H)$^b$ $^1$H-NMR (500 MHz, DMSO-d$_6$) δ 12.26 (s, 1 H), 9.87 (s, 1 H), 9.78 (s, 1 H), 8.39 (s, 1H), 8.00-7.64 (m, 4 H), 7.55-7.30 (m, 1 H), 6.39-6.27 (m, 1 H), 5.74-5.46 (m, 1 H), 4.31-4.10 (m, 2 H), 3.65-3.53 (m, 2 H), 3.29 (s, 3 H), 3.23-3.04 (m, 1 H), 2.83-2.68 (m, 1 H), 2.62-2.56 (m, 1 H), 2.28-2.10 (m, 1 H).

EXAMPLE 718(13)

methyl[4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)phenyl]carbamate

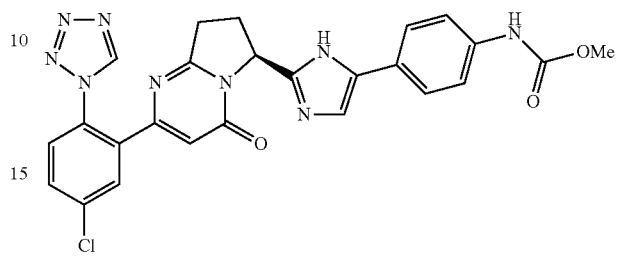

LC/MS $t_R$ 0.68 minutes; MS (ES$^+$) m/z 530 (M+H)$^f$ $^1$H NMR (300 MHz, DMSO-d$_6$) δ 12.5 (s, 0.3 H), 12.2 (s, 0.7 H), 9.75-9.65 (s, 1.3 H), 9.57 (s, 0.7 H), 7.98-7.92 (m, 1 H), 7.91-7.77 (m, 2 H), 7.65-7.35 (m, 4.7 H), 7.12 (s, 0.3 H), 6.33 (s, 0.7 H), 6.30 (s, 0.3 H), 5.65-5.54 (m, 1 H), 3.66 (s, 0.9 H), 3.64 (s, 2.1H), 3.39-3.10 (m, 1 H), 2.80-2.68 (m, 1 H), 2.58-2.13 (m, 2 H).

EXAMPLE 719(1) to 719(2)

The compounds of the present invention having the following physical data were synthesised from the compound prepared in Example 718(6) and the corresponding chloroformates using the method as detailed in Example 128.

EXAMPLE 719(1)

methyl[5-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-pyridinyl]carbamate LC/MS $t_R$ 1.48 minutes; MS (ES$^+$) m/z 531 (M+H)$^a$ $^1$H NMR (300 MHz, DMSO-d$_6$) δ 12.3 (s, 1 H), 10.1 (s, 1 H), 9.71 (s, 1 H), 8.59 (d, 1H), 8.06-7.75 (m, 5 H), 7.56 (d, 1 H), 6.34 (s, 1 H), 5.65-5.57 (m, 1 H), 3.65 (s, 3 H), 3.26-3.17 (m, 1 H), 2.82-2.71 (m, 1 H), 2.71-2.38 (m, 1 H), 2.32-2.17 (m, 1 H).

EXAMPLE 719(2)

2-methoxyethyl[5-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-pyridinyl]carbamate LC/MS $t_R$ 3.10 minutes; MS (ES$^+$) m/z 575 (M+H)$^b$ $^1$H NMR (500 MHz, DMSO-d$_6$) δ 12.35 (s, 1 H), 10.16 (s, 1 H), 9.79 (s, 1 H), 8.70 (s, 1H), 8.13-8.01 (m, 2 H), 7.95-7.81 (m, 3 H), 7.64 (s, 1 H), 6.45-6.35 (m, 1 H), 5.69 (d, 1 H), 4.33-4.23 (m, 2 H), 3.67-3.58 (m, 2 H), 3.34 (s, 3 H), 3.32-3.19 (m, 1 H), 2.90-2.79 (m, 1 H), 2.67-2.62 (m, 1 H), 2.33-2.22 (m, 1 H).

EXAMPLE 720

2-methoxyethyl[6(2-{(6S)-2-[5-chloro-2-(1H-tetrazol-1-yl)phenyl]-4-oxo-4,6,7,8-tetrahydropyrrolo[1,2-a]pyrimidin-6-yl}-4-fluoro-1H-imidazol-5-yl)-3-pyridinyl]carbamate The compound prepared in Example 718(12) (267 mg) was treated as detailed in Example 364 to give the title product having the following physical properties (11.4 mg).
LC/MS $t_R$ 3.79 minutes; MS (ES$^+$) m/z 593 (M+H)$^b$
$^1$H NMR (500 MHz, methanol-d$_4$) δ 9.44 (s, 1 H), 8.62 (br. s, 1 H), 7.97-7.87 (m, 2 H), 7.77 (dd, 1 H), 7.70 (d, 1 H), 7.52 (d, 1 H), 6.37 (s, 1 H), 5.69 (dd, 1 H), 4.33-4.27 (m, 2 H), 3.69-3.62 (m, 2 H), 3.39 (s, 3 H), 3.25 (td, 1 H), 2.90 (ddd, 1 H), 2.65 (qd, 1 H), 2.39-2.30 (m, 1 H).

EXAMPLE 721(1) to Example 721(10)

The compounds of the present invention having the following physical data were synthesised from the compounds prepared in Examples 718(1), 718(2), 718(3), 718(7), 718(8), 718(9), 718(11), 718(12), 719(1), 719(2) using the method as detailed in Example 338.

EXAMPLE 721(1)

2-methoxyethyl[4-(4-chloro-2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)phenyl]carbamate LC/MS $t_R$ 3.94 minutes; MS (ES$^+$) m/z 608 (M+H)$^b$
$^1$H NMR (500 MHz, DMSO-d$_6$) δ 12.92 (s, 1 H), 9.91 (s, 1 H), 9.76 (s, 1 H), 8.00 (d, 1H), 7.86 (dd, 1 H), 7.83 (d, 1 H), 7.60 (d, 2 H), 7.56 (d, 2 H), 6.34 (s, 1 H), 5.57 (dd, 1H), 4.24-4.20 (m, 2 H), 3.60-3.55 (m, 2 H), 3.29 (s, 3 H), 3.17-3.07 (m, 1 H), 2.82-2.72 (m, 1 H), 2.62-2.55 (m, 1 H), 2.22-2.12 (m, 1 H).

EXAMPLE 721(2)

2-ethoxyethyl[4-(4-chloro-2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)phenyl]carbamate LC/MS $t_R$ 4.12 minutes; MS (ES$^+$) m/z 623 (M+H)$^b$
$^1$H NMR (500 MHz, DMSO-d$_6$) δ 12.92 (s, 1 H), 9.92 (br. s, 1 H), 9.74 (s, 1 H), 8.00 (d, 1 H), 7.88-7.81 (m, 2 H), 7.63-7.54 (m, 4 H), 6.34 (s, 1 H), 5.57 (dd, 1 H), 4.23-4.19 (m, 2 H), 3.63-3.59 (m, 2 H), 3.48 (q, 2 H), 3.17-3.08 (m, 1 H), 2.77 (d, 1 H), 2.61-2.56 (m, 1 H), 2.17 (d, 1 H), 1.13 (t, 3 H).

EXAMPLE 721(3)

3-methoxypropyl[4-(4-chloro-2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)phenyl]carbamate LC/MS $t_R$ 4.05 minutes; MS (ES$^+$) m/z 622 (M+H)$^b$
$^1$H NMR (500 MHz, methanol-d$_4$) δ 9.45 (s, 1 H), 7.91 (d, 1 H), 7.76 (dd, 1 H), 7.70 (d, 1 H), 7.61 (d, 2 H), 7.52 (d, 2 H), 6.35 (s, 1 H), 5.66 (dd, 1 H), 4.21 (t, 2 H), 3.52 (t, 2H), 3.34 (s, 3 H), 3.29-3.25 (m, 1 H), 2.94-2.87 (m, 1 H), 2.70-2.62 (m, 1 H), 2.36-2.30 (m, 1 H), 1.94 (quintet, 2 H).

EXAMPLE 721(4)

(6S)-6-{4-chloro-5-[6-(methylamino)-3-pyridinyl]-1H-imidazol-2-yl}-2-[5-chloro-2-(1H-tetrazol-1-yl)phenyl]-7,8-dihydropyrrolo[1,2-a]pyrimidin-4(6H)-one LC/MS $t_R$ 2.82 minutes; MS (ES$^+$) m/z 521 (M+H)$^b$
$^1$H NMR (500 MHz, DMSO-d$_6$) δ 12.81 (s, 1 H), 9.76 (s, 1 H), 8.29 (d, 1 H), 8.00 (d, 1H), 7.86 (dd, Hz, 1 H), 7.83 (d, 1 H), 7.65 (dd, 1 H), 6.76 (d, 1 H), 6.54 (d, 1 H), 6.34 (s, 1 H), 5.55 (dd, 1 H), 3.17-3.08 (m, 1 H), 2.80 (s, 3 H), 2.78-2.72 (m, 1 H), 2.61-2.54 (m, 1 H), 2.22-2.12 (m, 1 H).

EXAMPLE 721(5)

(6S)-6-(4-chloro-5-{6-[(2-methoxyethyl)amino]-3-pyridinyl}-1H-imidazol-2-yl)-2-[5-chloro-2-(1H-tetrazol-1-yl)phenyl]-7,8-dihydropyrrolo[1,2-a]pyrimidin-4(6H)-one LC/MS $t_R$ 2.94 minutes; MS (ES$^+$) m/z 565 (M+H)$^b$
$^1$H NMR (500 MHz, methanol-d$_4$) δ 9.46 (s, 1 H), 8.27 (d, 1 H), 7.92 (d, 1 H), 7.80-7.68 (m, 3 H), 6.65 (d, 1 H), 6.37 (s, 1 H), 5.67 (dd, 1 H), 3.65-3.57 (m, 2 H), 3.55-3.50 (m, 2 H), 3.40 (s, 3 H), 3.30-3.25 (m, 1 H), 2.97-2.86 (m, 1 H), 2.68 (dd, 1 H), 2.39-2.30 (m, 1 H).

EXAMPLE 721(6)

(6S)-6-[5-(6-amino-2-fluoro-3-pyridinyl)-4-chloro-1H-imidazol-2-yl]-2-[5-chloro-2-(1H-tetrazol-1-yl)phenyl]-7,8-dihydropyrrolo[1,2-a]pyrimidin-4(6H)-one LC/MS $t_R$ 3.63 minutes; MS (ES$^+$) m/z 525 (M+H)$^b$
$^1$H NMR (500 MHz, DMSO-d$_6$) δ 12.71 (s, 1 H), 9.75 (s, 1 H), 8.00 (d, 1 H), 7.86 (dd, 1H), 7.82 (d, 1 H), 7.61 (dd, 1 H), 6.66 (s, 2 H), 6.41 (dd, 1 H), 6.34 (s, 1 H), 5.57 (dd, 1H), 3.16-3.06 (m, 1 H), 2.80-2.70 (m, 1 H), 2.60-2.54 (m, 1 H), 2.20-2.10 (m, 1H).

EXAMPLE 721(7)

methyl[6-(4-chloro-2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-3-pyridinyl]carbamate LC/MS $t_R$ 3.83 minutes; MS (ES$^+$) m/z 565 (M+H)$^b$
$^1$H NMR (500 MHz, DMSO-d$_6$) δ 13.15 (s, 1 H), 10.06 (s, 1 H), 9.80 (s, 1 H), 8.80 (s, 1H), 8.06 (d, 1 H), 8.03 (dd, 1 H), 7.97 (d, 1 H), 7.92 (dd, 1 H), 7.88 (d, 1 H), 6.38 (s, 1H), 5.71 (dd, 1 H), 3.77 (s, 3 H), 3.20-3.08 (m, 1 H), 2.89-2.77 (m, 1 H), 2.66-2.58 (m, 1 H), 2.24-2.14 (m, 1 H).

EXAMPLE 721(8)

2-methoxyethyl[6-(4-chloro-2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-3-pyridinyl]carbamate LC/MS $t_R$ 3.87 minutes; MS (ES$^+$) m/z 609 (M+H)$^b$
$^1$H NMR (500 MHz, DMSO-d$_6$) δ 13.09 (s, 1 H), 10.12 (s, 1 H), 9.74 (s, 1 H), 8.76 (d, 1H), 8.00 (d, 1 H), 7.97 (d, 1 H), 7.91 (d, 1 H), 7.86 (dd, 1 H), 7.82 (s, 1 H), 6.33 (s, 1 H), 5.65 (dd, 1 H), 4.29-4.21 (m, 2 H), 3.64-3.53 (m, 2 H), 3.30 (s, 3 H), 3.13-3.01 (m, 1H), 2.83-2.70 (m, 1 H), 2.60-2.53 (m, 1 H), 2.18-2.07 (m, 1 H).

EXAMPLE 721(9)

methyl[5-(4-chloro-2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-pyridinyl]carbamate LC/MS $t_R$ 3.77 minutes; MS (ES$^+$) m/z 565 (M+H)$^b$
$^1$H NMR (500 MHz, DMSO-d$_6$) δ 13.20 (s, 1 H), 10.41 (s, 1 H), 9.81 (s, 1 H), 8.62 (s, 1H), 8.09-7.90 (m, 3 H), 7.88-7.80 (m, 2 H), 6.36 (s, 1 H), 5.61-5.53 (m, 1 H), 3.73-3.64 (s, 3 H), 3.21-3.08 (m, 1 H), 2.83-2.69 (m, 1 H), 2.61-2.56 (m, 1 H), 2.21-2.14 (m, 1 H).

EXAMPLE 721(10)

2-methoxyethyl[5-(4-chloro-2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-pyridinyl]carbamate LC/MS $t_R$ 3.77 minutes; MS (ES$^+$) m/z 609 (M+H)$^b$
$^1$H NMR (500 MHz, methanol-d$_4$) δ 9.46 (s, 1 H), 8.60 (d, 1 H), 8.08 (dd, 1 H), 8.00 (d, 1 H), 7.95 (d, 1 H), 7.79 (dd, 1 H), 7.72 (d, 1 H), 6.39 (s, 1 H), 5.70 (dd, 1 H), 4.34 (t, 2H), 3.69 (t, 2 H), 3.42 (s, 3 H), 3.30-3.27 (m, 1 H), 2.98-2.90 (m, 1 H), 2.75-2.65 (m, 1 H), 2.41-2.33 (m, 1 H).

EXAMPLE 722

(6S)-6-[5-(6-amino-3-pyridinyl)-4-fluoro-1H-imidazol-2-yl]-2-[5-chloro-2-(1H-tetrazol-1-yl)phenyl]-7,8-dihydropyrrolo[1,2-a]pyrimidin-4(6H)-one The same operation as in Example 484→Example 364→Example 584 was conducted from the compound prepared in Example 718(6) to give the title compound having the following physical properties. (Note: in the step corresponding to Example 484 in the operation, allyl chloroformate was used).
LC/MS $t_R$ 2.80 minutes; MS (ES$^+$) m/z 491 (M+H)$^b$
$^1$H NMR (500 MHz, methanol-d$_4$) δ 9.43 (s, 1 H), 8.09 (s, 1 H), 7.89 (d, 1 H), 7.75 (dd, 1 H), 7.68 (d, 1 H), 7.62 (dd, 1 H), 6.63 (d, 1 H), 6.34 (s, 1 H), 5.62 (dd, 1 H), 3.29-3.21 (m, 1 H), 2.89 (ddd, 1 H), 2.65 (qd, 1 H), 2.37-2.28 (m, 1 H).

EXAMPLE 723

((6S)-6-[5-(6-amino-3-pyridinyl)-4-chloro-1H-imidazol-2-yl]-2-[5-chloro-2-(1H-tetrazol-1-yl)phenyl]-7,8-dihydropyrrolo[1,2-a]pyrimidin-4(6H)-one (enantiopure)

The same operation as in Example 128→Example 338→Example 584 was conducted from the compound prepared in Example 718(6) to give the title compound having the following physical properties. (Note: in the step corresponding to Example 128 in the operation, allyl chloroformate was used).
LC/MS $t_R$ 2.78 minutes; MS (ES$^+$) m/z 507 (M+H)$^b$
$^1$H NMR (500 MHz, methanol-d$_4$) δ 9.46 (s, 1 H), 8.24-8.20 (m, 1 H), 7.93 (d, 1 H), 7.81-7.76 (m, 2 H), 7.74-7.69 (m, 1 H), 6.67 (d, 1 H), 6.38 (s, 1 H), 5.69-5.63 (m, 1H), 3.31-3.25 (m, 1 H), 2.97-2.87 (m, 1 H), 2.73-2.63 (m, 1 H), 2.40-2.30 (m, 1 H).

EXAMPLE 724 methyl[4-(5-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-2-yl)phenyl]carbamate The same operation as in Example 234→Example 239 was conducted from the compound prepared in Example 336 to give the title compound having the following physical properties.
LC/MS $t_R$ 2.93 minutes; MS (ES') m/z 530 (M+H)$^b$
$^1$H NMR (500 MHz, CDCl$_3$) δ 8.82 (s, 1 H), 7.73-7.65 (m, 3 H), 7.62 (dd, 1 H), 7.50 (d, 1 H), 7.38 (d, 2 H), 7.00 (br. s, 1 H), 6.94 (s, 1 H), 6.34 (s, 1 H), 5.75 (dd, 1 H), 3.79 (s, 3 H), 3.48-3.36 (m, 1 H), 2.88 (ddd, 1 H), 2.60-2.47 (m, 2 H).

EXAMPLE 725 methyl[4-(4-chloro-5-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-2-yl)phenyl]carbamate The compound prepared in Example 724 (55 mg) was treated as detailed in Example 338 to give the title compound having the following physical properties (5.6 mg).
LC/MS $t_R$ 3.70 minutes; MS (ES$^+$) m/z 564 (M+H)$^b$
$^1$H NMR (500 MHz, methanol-d$_4$) δ 9.43 (s, 1 H), 7.90 (d, 1 H), 7.77 (dd, 1 H), 7.73 (d, 2 H), 7.71 (d, 1 H), 7.54 (d, 2 H), 6.42 (s, 1 H), 5.76 (dd, 1 H), 3.75 (s, 3 H), 3.26-3.14 (m, 1 H), 2.96 (ddd, 1 H), 2.76-2.64 (m, 1 H), 2.28 (tdd, 1 H).

EXAMPLE 726

6-(5-chloro-2-nitrophenyl)-2-(propan-2-yl)-3,4-dihydropyrimidin-4-one

To an N,N-dimethylformamide (3 mL) solution of the compound prepared in Example 33 (0.60 g) was added potassium carbonate (0.46 g) and 2-methylpropanimidamide hydrochloride (0.30 g) and the mixture stirred at 100° C. for 5 hours. The reaction mixture was then concentrated and the residue purified by column chromatography (10 to 100% ethyl acetate in heptanes) to give the title compound having the following physical properties (0.31 g).
$^1$H NMR (500 MHz, CDCl$_3$) δ 12.29 (br. s, 1 H), 7.86 (d, 1 H), 7.61-7.52 (m, 2 H), 6.56 (s, 1 H), 2.93 (td, 1 H), 1.32 (d, 6 H).

EXAMPLE 727 methyl{4-[2-({4-[5-chloro-2-(1H-tetrazol-1-yl)phenyl]-2-isopropyl-6-oxo-1(6H)-pyrimidinyl}methyl)-1H-imidazol-5-yl]phenyl}carbamate The same operation as in Example 322→Example 74→Example 9→Example 25→Example 51→Example 52 was conducted from the compound prepared in Example 726 to give the title compound having the following physical properties. (Note: in the step corresponding to Example 51 in the operation, methyl[4-(bromoacetyl)-phenyl]carbamate [J. Am. Chem. Soc. 119(10), 2453 (1997)] was used).

LC/MS $t_R$ 3.40 minutes; MS (ES$^+$) m/z 546 (M+H)$^b$ $^1$H NMR (500 MHz, DMSO-d$_6$) δ 12.16 (br. s, 1 H), 9.77 (s, 1 H), 9.60 (br. s, 1 H), 7.97 (d, 1 H), 7.89-7.84 (m, 1 H), 7.83-7.78 (m, 1 H), 7.59 (d, 2 H), 7.44 (s, 1 H), 7.40 (d, 2 H), 6.71 (s, 1 H), 5.25 (s, 2 H), 3.65 (s, 3 H), 3.32-3.30 (obs. m, 1 H), 0.87 (d, 6 H).

EXAMPLE 728 methyl{4-[4-chloro-2-({4-[5-chloro-2-(1H-tetrazol-1-yl)phenyl]-2-isopropyl-6-oxo-1(6H)-pyrimidinyl}methyl)-1H-imidazol-5-yl]phenyl}carbamate The compound prepared in Example 727 (55 mg) was treated as detailed in Example 338 to give the title compound having the following physical properties (17 mg).

LC/MS $t_R$ 4.32 minutes; MS (ES$^+$) m/z 580 (M+H)$^b$ $^1$H NMR (500 MHz, DMSO-d$_6$) δ 12.87 (br. s, 1 H), 9.80 (br. s, 1 H), 9.79 (s, 1 H), 8.00 (d, 1 H), 7.88-7.84 (m, 1 H), 7.84-7.79 (m, 1 H), 7.62-7.57 (m, 2 H), 7.57-7.49 (m, 2 H), 6.71 (s, 1 H), 5.23 (s, 2 H), 3.68 (s, 3 H), 3.16 (td, 1 H), 0.84 (d, 6 H).

EXAMPLE 729 methyl{4-[2-({4-[5-chloro-2-(1H-tetrazol-1-yl)phenyl]-2-cyclopropyl-6-oxo-1(6H)-pyrimidinyl}methyl)-1H-imidazol-5-yl]phenyl}carbamate The same operation as in Example 726→Example 20→Example 74→Example 9→Example 25→Example 51→Example 52 was conducted from cyclopropanecarboximidamide hydrochloride to give the title compound having the following physical properties. (Note: in the step corresponding to Example 51 in the operation, methyl[4-(bromoacetyl)-phenyl]carbamate [J. Am. Chem. Soc. 119(10), 2453 (1997)] was used).

LC/MS $t_R$ 3.30 minutes; MS (ES$^+$) m/z 544 (M+H)$^b$ $^1$H NMR (500 MHz, methanol-d$_4$) δ 9.41 (s, 1 H), 7.87 (d, 1 H), 7.78-7.72 (m, 1 H), 7.67 (d, 1 H), 7.60 (m, 2 H), 7.44 (m, 2 H), 7.37-7.25 (br. s, 1 H), 6.61 (s, 1 H), 5.52 (s, 2 H), 3.74 (s, 3 H), 2.22-2.10 (m, 1 H), 0.89 (m, 2 H), 0.63-0.56 (m, 2 H).

EXAMPLE 730 methyl{4-[4-chloro-2-({4-[5-chloro-2-(1H-tetrazol-1-yl)phenyl]-2-cyclopropyl-6-oxo-1(6H)-pyrimidinyl}methyl)-1H-imidazol-5-yl]phenyl}carbamate The compound prepared in Example 729 (70 mg) was treated as detailed in Example 338 to give the title compound having the following physical properties (40 mg).

LC/MS $t_R$ 4.21 minutes; MS (ES$^+$) m/z 578 (M+H)$^b$ $^1$H NMR (500 MHz, DMSO-d$_6$) δ 12.87 (br. s, 1 H), 9.81 (br. s, 1 H), 9.74 (s, 1 H), 7.97 (d, 1 H), 7.88-7.77 (m, 2 H), 7.64-7.50 (m, 4 H), 6.64 (s, 1 H), 5.36 (s, 2 H), 3.68 (s, 3H), 2.20-2.09 (m, 1 H), 0.81 (m, 2 H), 0.44 (m, 2 H).

EXAMPLE 731 methyl{4-[2-({4-[5-chloro-2-(1H-tetrazol-1-yl)phenyl]-2-cyclopropyl-6-oxo-1(6H)-pyrimidinyl}methyl)-4-fluoro-1H-imidazol-5-yl]phenyl}carbamate The compound prepared in Example 729 (70 mg) was treated as detailed in Example 364 to give the title compound having the following physical properties (20 mg).

LC/MS $t_R$ 4.18 minutes; MS (ES$^+$) m/z 562 (M+H)$^b$ $^1$H NMR (500 MHz, DMSO-d$_6$) δ 12.71 (br. s, 1 H), 9.74 (m, 2 H), 7.95 (s, 1 H), 7.87-7.75 (m, 2 H), 7.57-7.40 (m, 4 H), 6.63 (s, 1 H), 5.34 (s, 2 H), 3.67 (s, 3 H), 2.23-2.04 (m, 1 H), 0.88-0.72 (m, 2 H), 0.44 (m, 2 H).

EXAMPLE 732 methyl{4-[2-({4-[5-chloro-2-(1H-tetrazol-1-yl)phenyl]-6-oxo-2-(tetrahydro-2H-pyran-4-yl)-1(6H)-pyrimidinyl}methyl)-1H-imidazol-5-yl]phenyl}carbamate The same operation as in Example 726→Example 20→Example 74→Example 9→Example 25→Example 51 Example 52 was conducted from tetrahydro-2H-pyran-4-carboximidamide hydrochloride to give the title compound having the following physical properties. (Note: in the step corresponding to Example 51 in the operation, methyl[4-(bromoacetyl)-phenyl]carbamate [J. Am. Chem. Soc. 119 (10), 2453 (1997)] was used).

LC/MS $t_R$ 3.27 minutes; MS (ES$^+$) m/z 588 (M+H)$^b$ $^1$H NMR (500 MHz, DMSO-d$_6$) δ 12.20 (br. s, 1 H), 9.79 (s, 1 H), 9.60 (br, s, 1 H), 7.96 (d, 1 H), 7.85 (d, 1 H), 7.82 (s, 1 H), 7.58 (d, 2 H), 7.44 (s, 1 H), 7.39 (d, 2 H), 6.68 (s, 1 H), 5.31 (s, 2 H), 3.77 (m, 2 H), 3.65 (s, 3 H), 3.41 (m, 1 H), 3.29 (t, 2 H), 1.44 (m, 2H), 1.28-1.18 (m, 2 H).

EXAMPLE 733 methyl{4-[2-({4-[5-chloro-2-(1H-tetrazol-1-yl)phenyl]-2-(methoxymethyl)-6-oxo-1(6H)-pyrimidinyl}methyl)-1H-imidazol-5-yl]phenyl}carbamate The same operation as in Example 726→Example 20→Example 74→Example 9→Example 25→Example 51→Example 52 was conducted from methoxyacetamidine hydrochloride to give the title compound having the following physical properties. (Note: in the step corresponding to Example 51 in the operation, methyl[4-(bromoacetyl)-phenyl]carbamate [J. Am. Chem. Soc. 119(10), 2453 (1997)] was used).

LC/MS $t_R$ 3.13 minutes; MS (ES$^+$) m/z 548 (M+H)$^b$ $^1$H NMR (500 MHz, DMSO-d$_6$) δ 12.13 (br. s, 1 H), 9.78 (s, 1 H), 9.60 (br. s, 1 H), 7.99 (d, 1 H), 7.89-7.85 (m, 1 H), 7.84-7.80 (m, 1 H), 7.59 (d, 2 H), 7.44-7.36 (m, 3 H), 6.70 (s, 1 H), 5.24 (s, 2 H), 4.49 (s, 2 H), 3.65 (s, 3 H), 3.15 (s, 3 H).

EXAMPLE 734 methyl{4-[4-chloro-2-({4-[5-chloro-2-(1H-tetrazol-1-yl)phenyl]-2-(methoxymethyl)-6-oxo-1(6H)-pyrimidinyl}methyl)-1H-imidazol-5-yl]phenyl}carbamate The compound prepared in Example 733 (85 mg) was treated as detailed in Example 338 to give the title compound having the following physical properties (26 mg).

LC/MS tR 4.04 minutes; MS (ES+) m/z 582 (M+H)$^b$ $^1$H NMR (500 MHz, DMSO-d$_6$) δ 12.84 (br. s, 1 H), 9.86-9.73 (m, 2 H), 8.03 (s, 1 H), 7.92-7.78 (m, 2 H), 7.63-7.47 (m, 4 H), 6.71 (s, 1 H), 5.21 (s, 2 H), 4.35 (s, 2 H), 3.67 (s, 3 H), 3.12 (s, 3 H).

EXAMPLE 735

(3S)-3-[5-(4-aminophenyl)-1H-imidazol-2-yl]-7-[5-methyl-2-(1H-tetrazol-1-yl)phenyl]-2,3-dihydro-5(1H)-indolizinone The same operation as in Example 51→Example 52→Example 74 was conducted from the compound prepared in Example 375 to give the title compound having the following physical properties. (Note: in the step corresponding to Example 51 in the operation, 2-bromo-1-(4-nitrophenyl)ethanone was used).

LC/MS $t_R$ 2.72 minutes; MS (ES$^+$) m/z 451 (M+H)$^b$ $^1$H NMR (500 MHz, methanol-d$_4$) δ 9.32 (s, 1 H), 7.53 (m, 2 H), 7.49 (s, 1 H), 7.37 (m, 2 H), 7.04 (br. s, 1 H), 6.74 (d, 2 H), 6.11 (s, 1 H), 6.07 (s, 1 H), 5.77 (dd, 1 H), 3.48-3.38 (m, 1 H), 3.13-3.04 (m, 1 H), 2.65-2.56 (m, 1 H), 2.52 (s, 3 H), 2.51-2.41 (m, 1H).

EXAMPLE 736

2-methoxyethyl[4-(2-{(3S)-7-[5-methyl-2-(1H-tetrazol-1-yl)phenyl]-5-oxo-1,2,3,5-tetrahydro-3-indolizinyl}-1H-imidazol-5-yl)phenyl]carbamate The compound prepared in Example 735 (40 mg) was treated with 2-methoxyethyl chloroformate following the method of Example 128 to give the title compound having the following physical properties (36 mg).

LC/MS $t_R$ 3.12 minutes; MS (ES$^+$) m/z 553 (M+H)$^b$ $^1$H NMR (500 MHz, methanol-d$_4$) δ 9.30 (s, 1 H), 7.55 (d, 2 H), 7.52-7.45 (m, 3 H), 7.43 (d, 2 H), 7.21 (s, 1 H), 6.09 (s, 1 H), 6.05 (s, 1 H), 5.77 (dd, 1 H), 4.28-4.22 (m, 2H), 3.67-3.61 (m, 2 H), 3.47-3.40 (m, 1 H), 3.38 (s, 3 H), 3.12-3.02 (m, 1 H), 2.66-2.55 (m, 1 H), 2.50 (s, 3 H), 2.48-2.40 (m, 1 H).

EXAMPLE 737

3-oxetanyl[4-(2-{(3S)-7-[5-methyl-2-(1H-tetrazol-1-yl)phenyl]-5-oxo-1,2,3,5-tetrahydro-3-indolizinyl}-1H-imidazol-5-yl)phenyl]carbamate The compound prepared in Example 735 (100 mg) was treated as detailed in Example 494 to give the title compound having the following physical properties (15 mg).

LC/MS $t_R$ 2.93 minutes; MS (ES$^+$) m/z 551 (M+H)$^b$ $^1$H NMR (500 MHz, methanol-d$_4$) δ 9.31 (s, 1 H), 7.65-7.54 (m, 2 H), 7.54-7.46 (m, 3H), 7.46-7.36 (m, 2 H), 7.36-7.20 (m, 1 H), 6.10 (s, 1 H), 6.06 (s, 1 H), 5.77 (d, 1 H), 5.47 (quintet, 1 H), 4.92 (t, 2 H), 4.68 (dd, 2 H), 3.50-3.37 (m, 1 H), 3.08 (ddd, 1 H), 2.62 (qd, 1 H), 2.51 (s, 3 H), 2.49-2.39 (m, 1 H).

EXAMPLE 738(1) TO EXAMPLE 738(12)

The compounds of the present invention having the following physical data were prepared using the corresponding alpha-bromoketones from the compound prepared in Example 375 in the process of Example 51→Example 52.

EXAMPLE 738(1) AND 738(2)

methyl[4-(4-methyl-2-{(3S)-7-[5-methyl-2-(1H-tetrazol-1-yl)phenyl]-5-oxo-1,2,3,5-tetrahydro-3-indolizinyl}-1H-imidazol-5-yl)phenyl]carbamate and methyl[4-(5-methyl-2-{(3S)-7-[5-methyl-2-(1H-tetrazol-1-yl)phenyl]-5-oxo-1,2,3,5-tetrahydro-3-indolizinyl}-1,3-oxazol-4-yl)phenyl]carbamate The title compounds were obtained in a (1.9:1) ratio and separated by column chromatography. (Note: in the step corresponding to Example 51 in the process, the compound prepared in Example 78 was used).

EXAMPLE 738(1)

LC/MS $t_R$ 2.94 minutes; MS (ES$^+$) m/z 523 (M+H)$^b$ $^1$H NMR (500 MHz, DMSO-d$_6$) δ 11.88 (s, 1 H), 9.65 (s, 1 H), 9.59 (br. s, 1 H), 7.59 (d, 1 H), 7.50 (m, 2 H), 7.45 (m, 3 H), 7.38 (d, 1 H), 5.93 (s, 1 H), 5.85 (s, 1 H), 5.59-5.49 (m, 1 H), 3.65 (s, 3 H), 3.40-3.38 (m, 1 H), 3.36-3.33 (obs. m, 1 H), 3.02-2.90 (m, 1H), 2.45 (s, 3 H), 2.35-2.26 (s, 3 H), 2.23-2.16 (m, 1 H).

Example 738(2)

LC/MS A$_R$ 4.02 minutes; MS (ES$^+$) m/z 524 (M+H)$^b$ $^1$H NMR (500 MHz, methanol-d$_4$) δ 9.31 (s, 1 H), 7.54-7.46 (m, 7 H), 6.13 (s, 1 H), 6.05 (s, 1 H), 5.76 (dd, 1 H), 3.73 (s, 3 H), 3.34 (s, 3 H), 3.32-3.27 (obs. m, 1 H), 3.17-3.01 (m, 1 H), 2.70-2.58 (m, 1 H), 2.51 (s, 3 H), 2.48 (s, 3 H), 2.43-2.24 (m, 1 H).

EXAMPLE 738(3)

2-methoxyethyl[4-(4-methyl-2-{(3S)-7-[5-methyl-2-(1H-tetrazol-1-yl)phenyl]-5-oxo-1,2,3,5-tetrahydro-3-indolizinyl}-1H-imidazol-5-yl)phenyl]carbamate In the step corresponding to Example 51 in the process, the compound prepared in Example 481 was used.

LC/MS $t_R$ 3.11 minutes; MS (ES$^+$) m/z 567 (M+H)$^b$ $^1$H NMR (500 MHz, methanol-d$_4$) δ 9.31 (s, 1 H), 7.54-7.49 (m, 3 H), 7.49-7.45 (m, 2H), 7.45-7.37 (m, 2 H), 6.10 (s, 1 H), 6.06 (s, 1 H), 5.71 (d, 1 H), 4.28-4.25 (m, 2 H), 3.66-3.62 (m, 2 H), 3.48-3.41 (m, 1 H), 3.39 (s, 3 H), 3.07 (ddd, 1 H), 2.61 (qd, 1 H), 2.51 (s, 3 H), 2.47-2.37 (m, 1 H), 2.31 (app. br. s, 3 H).

EXAMPLE 738(4)

2-ethoxyethyl[4-(2-{(3S)-7-[5-methyl-2-(1H-tetrazol-1-yl)phenyl]-5-oxo-1,2,3,5-tetrahydro-3-indolizinyl}-1H-imidazol-5-yl)phenyl]carbamate In the step corresponding to Example 51 in the process, the compound prepared in Example 714 was used.

LC/MS $t_R$ 3.13 minutes; MS (ES$^+$) m/z 567 (M+H)$^b$
$^1$H NMR (500 MHz, methanol-d$_4$) δ 9.32 (s, 1 H), 7.57 (d, 2 H), 7.54-7.47 (m, 3 H), 7.45 (d, 2 H), 7.23 (s, 1 H), 6.11 (s, 1 H), 6.07 (s, 1 H), 5.78 (dd, 1 H), 4.28-4.25 (m, 2H), 3.71-3.67 (m, 2 H), 3.60-3.54 (m, 2 H), 3.48-3.39 (m, 1 H), 3.13-3.04 (m, 1 H), 2.63 (qd, 1 H), 2.52 (s, 3 H), 2.50-2.43 (m, 1 H), 1.20 (t, 3 H).

EXAMPLE 738(5)

3-methoxypropyl[4-(2-{(3S)-7-[5-methyl-2-(1H-tetrazol-1-yl)phenyl]-5-oxo-1,2,3,5-tetrahydro-3-indolizinyl}-1H-imidazol-5-yl)phenyl]carbamate In the step corresponding to Example 51 in the process, the compound prepared in Example 715 was used.
LC/MS $t_R$ 3.11 minutes; MS (ES$^+$) m/z 567 (M+H)$^b$
$^1$H NMR (500 MHz, methanol-d$_4$) δ 9.32 (s, 1 H), 7.64-7.56 (m, 1 H), 7.55-7.47 (m, 4H), 7.46-7.38 (m, 2 H), 7.29 (br. s, 1 H), 6.11 (s, 1 H), 6.07 (s, 1 H), 5.78 (d, 1 H), 4.21 (t, 2 H), 3.53 (t, 2 H), 3.48-3.39 (m, 1 H), 3.35 (s, 3 H), 3.09 (ddd, 1 H), 2.68-2.57 (m, 1 H), 2.52 (s, 3 H), 2.50-2.39 (m, 1 H), 1.94 (quintet, 2 H).

EXAMPLE 738(6)

(3S)-3-[5-(6-amino-3-pyridinyl)-1H-imidazol-2-yl]-7-[5-methyl-2-(1H-tetrazol-1-yl)phenyl]-2,3-dihydro-5(1H)-indolizinone In the step corresponding to Example 51 in the process, the compound prepared in Example 193 was used.
LC/MS $t_R$ 2.67 minutes; MS (ES$^+$) m/z 452 (M+H) 227 (M+H)/2$^b$
$^1$H NMR (500 MHz, methanol-d$_4$) δ 9.32 (s, 1 H), 8.29-8.08 (m, 1 H), 7.81-7.67 (m, 1H), 7.57-7.50 (m, 2 H), 7.49 (s, 1 H), 7.36-6.99 (m, 1 H), 6.61 (d, 1 H), 6.11 (s, 1 H), 6.07 (s, 1 H), 5.76 (dd, 1 H), 3.51-3.38 (m, 1 H), 3.15-3.01 (dd, 1 H), 2.70-2.56 (m, 1 H), 2.52 (s, 3 H), 2.50-2.32 (m, 1 H).

EXAMPLE 738(7)

(3S)-3-{5-[6-(methylamino)-3-pyridinyl]-1H-imidazol-2-yl}-7-[5-methyl-2-(1H-tetrazol-1-yl)phenyl]-2,3-dihydro-5(1H)-indolizinone In the step corresponding to Example 51 in the process, the compound prepared in Example 551 was used.
LC/MS $t_R$ 2.76 minutes; MS (ES$^+$) m/z 466 (M+H) 234 (M+H)/2$^b$
$^1$H NMR (500 MHz, methanol-d$_4$) δ 9.32 (s, 1 H), 8.33-8.17 (m, 1 H), 7.79-7.64 (m, 1H), 7.57-7.51 (m, 2 H), 7.49 (s, 1 H), 7.21 (br. s, 1 H), 6.54 (d, 1 H), 6.10 (s, 1 H), 6.07 (s, 1 H), 5.76 (dd, 1 H), 3.53-3.38 (m, 1 H), 3.09 (ddd, 1 H), 2.90 (s, 3 H), 2.69-2.58 (m, 1 H), 2.52 (s, 3 H), 2.49-2.37 (m, 1 H).

EXAMPLE 738(8)

(3S)-3-[5-(6-amino-2-fluoro-3-pyridinyl)-1H-imidazol-2-yl]-7-[5-methyl-2-(1H-tetrazol-1-yl)phenyl]-2,3-dihydro-5(1H)-indolizinone In the step corresponding to Example 51 in the process, the compound prepared in Example 215 was used.
LC/MS $t_R$ 3.06 minutes; MS (ES$^+$) m/z 470 (M+H)$^b$
$^1$H NMR (500 MHz, methanol-d$_4$) δ 9.31 (s, 1 H), 8.16-7.76 (m, 1 H), 7.55-7.49 (m, 2H), 7.47 (s, 1 H), 7.14 (br. s, 1 H), 6.45 (d, 1 H), 6.12 (s, 1 H), 6.05 (s, 1 H), 5.78 (d, 1H), 3.48-3.37 (m, 1 H), 3.08 (dd, 1 H), 2.68-2.55 (m, 1 H), 2.53-2.43 (m, 4 H).

EXAMPLE 738(9)

(3S)-3-[5-(6-amino-2-chloro-3-pyridinyl)-1H-imidazol-2-yl]-7-[5-methyl-2-(1H-tetrazol-1-yl)phenyl]-2,3-dihydro-5(1H)-indolizinone In the step corresponding to Example 51 in the process, the compound prepared in Example 209 was used.
LC/MS $t_R$ 3.11 minutes; MS (ES$^+$) m/z 486 (M+H)$^b$
$^1$H NMR (500 MHz, methanol-d$_4$) δ 9.31 (s, 1 H), 7.99-7.65 (m, 1 H), 7.55-7.50 (m, 2H), 7.48 (s, 1 H), 7.37 (br. s, 1 H), 6.56 (d, 1 H), 6.12 (s, 1 H), 5.79 (dd, 1 H), 3.49-3.38 (m, 1 H), 3.09 (dd, 1 H), 2.65-2.57 (m, 1 H), 2.55-2.44 (m, 4 H).

EXAMPLE 738(10)

methyl[6-(2-{(3S)-7-[5-methyl-2-(1H-tetrazol-1-yl)phenyl]-5-oxo-1,2,3,5-tetrahydro-3-indolizinyl}-1H-imidazol-5-yl)-3-pyridinyl]carbamate In the step corresponding to Example 51 in the process, the compound prepared in Example 712 was used.
LC/MS $t_R$ 3.07 minutes; MS (ES$^+$) m/z 510 (M+H)$^b$
$^1$H NMR (500 MHz, methanol-d$_4$) δ 9.32 (s, 1 H), 8.64-8.46 (m, 1 H), 7.95 (d, 1 H), 7.81 (br. s, 1 H), 7.58-7.30 (m, 4 H), 6.13 (s, 1 H), 6.06 (s, 1 H), 5.80 (d, 1 H), 3.77 (s, 3 H), 3.50-3.40 (m, 1 H), 3.10 (ddd, Hz, 1 H), 2.68-2.56 (m, 1 H), 2.52 (m, 4 H).

EXAMPLE 738(11)

formic acid-2-methoxyethyl[6-(2-{(3S)-7-[5-methyl-2-(1H-tetrazol-1-yl)phenyl]-5-oxo-1,2,3,5-tetrahydro-3-indolizinyl}-1H-imidazol-5-yl)-3-pyridinyl]carbamate (1:1)

In the step corresponding to Example 51 in the process, the compound prepared in Example 713 was used. In the step corresponding to Example 52 in the process, high performance liquid chromatography [5 to 100% mobile phase B (0.1% formic acid in acetonitrile) in mobile phase A (0.1% aqueous formic acid)] was used to give the title product as the formic acid salt.
LC/MS $t_R$ 2.98 minutes; MS (ES$^+$) m/z 554 (M+H)$^b$
$^1$H NMR (500 MHz, methanol-d$_4$) δ 9.32 (s, 1 H), 8.58 (s, 1 H), 8.17 (s, 1 H), 7.96 (d, 1H), 7.76 (d, 1 H), 7.56-7.46 (m, 4 H), 6.13 (s, 1 H), 6.07 (s, 1 H), 5.81 (dd, 1 H), 4.33-4.25 (m, 2 H), 3.69-3.62 (m, 2 H), 3.52-3.41 (m, 1 H), 3.40 (s, 3 H), 3.10 (ddd, 1 H), 2.69-2.57 (m, 1 H), 2.55-2.45 (m, 4 H).

EXAMPLE 738(12)

6-(2-{(3S)-7-[5-methyl-2-(1H-tetrazol-1-yl)phenyl]-5-oxo-1,2,3,5-tetrahydro-3-indolizinyl}-1H-imidazol-5-yl)-3,4-dihydro-2(1H)-quinolinone In the step corresponding to Example 51 in the process, 6-(bromoacetyl)-3,4-dihydroquinolin-2(1H)-one was used.
LC/MS $t_R$ 2.97 minutes; MS (ES$^+$) m/z 505 (M+H)$^b$ $^1$H NMR (500 MHz, methanol-$d_4$) δ 9.32 (s, 1 H), 7.55-7.43 (m, 5 H), 7.24 (br. s, 1 H), 6.86 (d, 1 H), 6.11 (s, 1 H), 6.07 (s, 1 H), 5.77 (dd, 1 H), 3.44 (td, 1 H), 3.09 (ddd, 1 H), 2.98 (t, 2 H), 2.68-2.60 (m, 1 H), 2.60-2.55 (m, 2 H), 2.52 (s, 3 H), 2.50-2.42 (m, 1H).

EXAMPLE 739 methyl[5-(2-{(3S)-7-[5-methyl-2-(1H-tetrazol-1-yl)phenyl]-5-oxo-1,2,3,5-tetrahydro-3-indolizinyl}-1H-imidazol-5-yl)-2-pyridinyl]carbamate The compound prepared in Example 738(6) (200 mg) was treated with methyl chloroformate following the method of Example 484 to give the title compound having the following physical properties (213 mg).

LC/MS $t_R$ 3.12 minutes; MS (ES$^+$) m/z 510 (M+H) 256 (M+H)/2$^b$ $^1$H NMR (500 MHz, methanol-$d_4$) δ 9.32 (s, 1 H), 8.62-8.48 (m, 1 H), 8.10-7.97 (m, 1H), 7.88 (d, 1 H), 7.55-7.47 (m, 3 H), 7.40 (br. s, 1 H), 6.11 (s, 1 H), 6.07 (s, 1 H), 5.78 (dd, 1 H), 3.77 (s, 3 H), 3.51-3.39 (m, 1 H), 3.10 (ddd, 1 H), 2.70-2.58 (m, 1 H), 2.52 (s, 4 H).

EXAMPLE 740

2-methoxyethyl[5-(2-{(3S)-7-[5-methyl-2-(1H-tetrazol-1-yl)phenyl]-5-oxo-1,2,3,5-tetrahydro-3-indolizinyl}-1H-imidazol-5-yl)-2-pyridinyl]carbamate The compound prepared in Example 738(6) (124 mg) was treated with 2-methoxyethyl chloroformate following the method of Example 484 to give the title compound having the following physical properties (81 mg).

LC/MS $t_R$ 3.13 minutes; MS (ES$^+$) m/z 554 (M+H) 278 (M+H)/2$^b$ $^1$H NMR (500 MHz, methanol-$d_4$) δ 9.32 (s, 1 H), 8.62-8.49 (m, 1 H), 8.03 (d, 1 H), 7.89 (d, 1 H), 7.55-7.47 (m, 3 H), 7.40 (br. s, 1 H), 6.11 (s, 1 H), 6.08 (s, 1 H), 5.78 (dd, 1 H), 4.31 (dd, 2 H), 3.69-3.64 (m, 2 H), 3.51-3.43 (m, 1 H), 3.40 (s, 3 H), 3.11 (ddd, 1 H), 2.64 (qd, 1 H), 2.52 (s, 4 H).

EXAMPLE 741(1) to Example 741(3)

The compounds of the present invention having the following physical data were synthesised from the compounds prepared in Examples 738(4), 738(5) and 738(11) using the method as detailed in Example 338.

EXAMPLE 741(1)

2-ethoxyethyl[4-(4-chloro-2-{(3S)-7-[5-methyl-2-(1H-tetrazol-1-yl)phenyl]-5-oxo-1,2,3,5-tetrahydro-3-indolizinyl}-1H-imidazol-5-yl)phenyl]carbamate LC/MS $t_R$ 4.14 minutes; MS (ES$^+$) m/z 601 (M+H)$^b$ $^1$H NMR (500 MHz, methanol-$d_4$) δ 9.32 (s, 1 H), 7.62 (d, 2 H), 7.56-7.51 (m, 4 H), 7.50 (s, 1 H), 6.11 (s, 1 H), 6.07 (s, 1 H), 5.71 (dd, 1H), 4.30-4.25 (m, 2 H), 3.72-3.67 (m, 2 H), 3.57 (q, 2 H), 3.48-3.38 (m, 1 H), 3.09 (ddd, 1 H), 2.69-2.57 (m, 1 H), 2.52 (s, 3 H), 2.44-2.35 (m, 1 H), 1.21 (t, 3 H).

EXAMPLE 741(2)

3-methoxypropyl[4-(4-chloro-2-{(3S)-7-[5-methyl-2-(1H-tetrazol-1-yl)phenyl]-5-oxo-1,2,3,5-tetrahydro-3-indolizinyl}-1H-imidazol-5-yl)phenyl]carbamate LC/MS $t_R$ 4.10 minutes; MS (ES$^+$) m/z 601 (M+H)$^b$ $^1$H NMR (500 MHz, methanol-$d_4$) δ 9.33 (s, 1 H), 7.62 (d, 2 H), 7.56-7.51 (m, 4 H), 7.50 (s, 1 H), 6.11 (s, 1 H), 6.07 (s, 1 H), 5.71 (dd, 1 H), 4.25-4.20 (m, 2 H), 3.53 (t, 2H), 3.44 (td, 1 H), 3.36 (s, 3 H), 3.09 (ddd, 1 H), 2.64 (qd, 1 H), 2.52 (s, 3 H), 2.44-2.35 (m, 1 H), 1.95 (quintet, 2 H).

EXAMPLE 741(3)

2-methoxyethyl[6-(4-chloro-2-{(3S)-7-[5-methyl-2-(1H-tetrazol-1-yl)phenyl]-5-oxo-1,2,3,5-tetrahydro-3-indolizinyl}-1H-imidazol-5-yl)-3-pyridinyl]carbamate LC/MS $t_R$ 3.96 minutes; MS (ES$^+$) m/z 588 (M+H)$^b$ $^1$H NMR (500 MHz, methanol-$d_4$) δ 9.32 (s, 1 H), 8.68-8.61 (m, 1 H), 8.01-7.89 (m, 2H), 7.56-7.45 (m, 3 H), 6.13 (s, 1 H), 6.06 (s, 1 H), 5.78 (dd, 1 H), 4.33-4.26 (m, 2 H), 3.71-3.62 (m, 2 H), 3.44-3.35 (m, 4 H), 3.14-3.04 (m, 1H), 2.66-2.55 (m, 1 H), 2.51 (s, 3 H), 2.48-2.41 (m, 1 H).

EXAMPLE 742(1) TO EXAMPLE 742(5)

The compounds of the present invention having the following physical data were synthesised from the compounds prepared in Examples 738(6), 738(7), 738(10), 739 and 740 using the method as detailed in Example 44.

EXAMPLE 742(1)

(3S)-3-[5-(6-amino-3-pyridinyl)-4-chloro-1H-imidazol-2-yl]-7-[5-methyl-2-(1H-tetrazol-1-yl)phenyl]-2,3-dihydro-5(1H)-indolizinone LC/MS $t_R$ 2.96 minutes; MS (ES$^+$) m/z 486 (M+H)$^b$ $^1$H NMR (500 MHz, methanol-$d_4$) δ 9.32 (s, 1 H), 8.21 (d, 1 H), 7.76 (dd, 1 H), 7.55-7.51 (m, 2 H), 7.51-7.48 (m, 1 H), 6.65 (d, 1 H), 6.10 (s, 1 H), 6.07 (s, 1 H), 5.69 (dd, 1 H), 3.48-3.39 (m, 1 H), 3.09 (ddd, 1 H), 2.69-2.57 (m, 1 H), 2.52 (s, 3 H), 2.42-2.33 (m, 1 H).

EXAMPLE 742(2)

formic acid-(3S)-3-{4-chloro-5-[6-(methylamino)-3-pyridinyl]-1H-imidazol-2-yl}-7-[5-methyl-2-(1H-tetrazol-1-yl)phenyl]-2,3-dihydro-5 (1H)-indolizinone (1:1)

Purification by high performance liquid chromatography [5 to 100% mobile phase B (0.1% formic acid in acetonitrile) in mobile phase A (0.1% aqueous formic acid)] gave the title compound as the formic acid salt.

LC/MS $t_R$ 3.00 minutes; MS (ES$^+$) m/z 500 (M+H) 250 (M+H)/2$^b$ $^1$H NMR (500 MHz, methanol-$d_4$) δ 9.32 (s, 1 H), 8.26 (d, 1 H), 8.15 (s, 1 H), 7.78 (dd, 1 H), 7.55-7.51 (m, 2 H), 7.50 (s, 1 H), 6.64 (d, 1 H), 6.10 (s, 1 H), 6.07 (s, 1 H), 5.69 (dd, 1 H), 3.48-3.38 (m, 1 H), 3.09 (ddd, 1 H), 2.91 (s, 3 H), 2.63 (qd, 1 H), 2.52 (s, 3H), 2.42-2.33 (m, 1 H).

EXAMPLE 742(3)

formic acid-methyl[6-(4-chloro-2-{(3S)-7-[5-methyl-2-(1H-tetrazol-1-yl)phenyl]-5-oxo-1,2,3,5-tetrahydro-3-indolizinyl}-1H-imidazol-5-yl)-3-pyridinyl]carbamate (1:1)

LC/MS $t_R$ 3.95 minutes; MS (ES$^+$) m/z 544 (M+H) 250 (M+H)/2$^b$
$^1$H NMR (500 MHz, DMSO-d$_6$) δ 12.96 (br. s, 1 H), 10.00 (br. s, 1 H), 9.67 (s, 1 H), 8.73 (s, 1 H), 8.02-7.93 (m, 1 H), 7.92-7.86 (m, 1 H), 7.60 (d, 1 H), 7.55-7.47 (m, 2H), 5.95 (s, 1 H), 5.86 (s, 1 H), 5.66 (dd, 1 H), 3.70 (s, 3 H), 3.21-3.16 (m, 1 H), 3.02-2.92 (m, 1 H), 2.55-2.48 (obs. m, 1 H), 2.46 (s, 3 H), 2.26-2.10 (m, 1 H).

EXAMPLE 742(4)

methyl[5-(4-chloro-2-{(3S)-7-[5-methyl-2-(1H-tetrazol-1-yl)phenyl]-5-oxo-1,2,3,5-tetrahydro-3-indolizinyl}-1H-imidazol-5-yl)-2-pyridinyl]carbamate LC/MS $t_R$ 3.88 minutes; MS (ES$^+$) m/z 544 (M+H)$^b$
$^1$H NMR (500 MHz, methanol-d$_4$) δ 9.33 (s, 1 H), 8.58 (d, 1 H), 8.07-8.02 (m, 1 H), 8.02-7.96 (m, 1 H), 7.54-7.52 (m, 2 H), 7.50 (s, 1 H), 6.11 (s, 1 H), 6.08 (s, 1 H), 5.71 (dd, 1 H), 3.79 (s, 3 H), 3.45 (td, 1 H), 3.10 (ddd, 1 H), 2.65 (qd, 1 H), 2.53 (s, 3 H), 2.44-2.35 (m, 1 H).

EXAMPLE 742(5)

2-methoxyethyl[5-(4-chloro-2-{(3S)-7-[5-methyl-2-(1H-tetrazol-1-yl)phenyl]-5-oxo-1,2,3,5-tetrahydro-3-indolizinyl}-1H-imidazol-5-yl)-2-pyridinyl]carbamate LC/MS $t_R$ 3.87 minutes; MS (ES$^+$) m/z 588 (M+H)$^b$
$^1$H NMR (500 MHz, DMSO-d$_6$) δ 13.09 (br. s, 1 H), 10.37 (s, 1 H), 9.68 (s, 1 H), 8.57 (d, 1 H), 8.04 (dd, 1 H), 7.91 (d, 1 H), 7.60 (d, 1 H), 7.55-7.49 (m, 2 H), 5.96 (s, 1 H), 5.86 (s, 1 H), 5.57 (dd, 1 H), 4.24 (dd, 2 H), 3.58 (dd, 2 H), 3.29 (s, 3 H), 3.27-3.22 (m, 1 H), 3.00 (dd, 1 H), 2.55-2.53 (m, 1 H), 2.47 (s, 3 H), 2.24-2.14 (m, 1 H).

EXAMPLE 743 ethyl(6S)-2-hydroxy-4-oxo-4H,6H,7H,8H-pyrrolo[1,2-a]pyrimidine-6-carboxylate

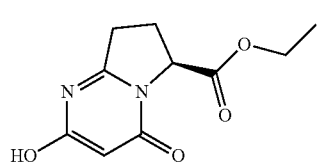 [SMILES: CCOC(=O)[C@@H]1CCc2nc(O)cc(=O)n21]

To a 1,4-dioxane (570 mL) suspension of ethyl(2S)-5-aminopyrrolidine-2-carboxylate hydrochloride [J. Org. Chem. 52(26), 5717 (1987)] (28.3 g) was sequentially added triethylamine (51.2 mL) and ethyl malonyl chloride (20.8 mL) and the mixture stirred at 80° C. for 1 hour. The reaction mixture was cooled to room temperature, diluted with ethyl acetate (500 mL), filtered and the filtrate concentrated to give the crude title compound having the following physical properties (42.6 g).
LC/MS $t_R$ 0.80 minutes; MS (ES$^+$) m/z 225 (M+H)$^a$.

EXAMPLE 744 ethyl(6S)-2-chloro-4-oxo-4H,6H,7H,8H-pyrrolo[1,2-a]pyrimidine-6-carboxylate

The compound prepared in Example 743 (30.2 g) was suspended in phosphorous(V) oxychloride (125 mL) and the mixture stirred at 100° C. for 1 hour. The reaction mixture was cooled to room temperature, concentrated, the residue suspended in a 1 M aqueous solution of sodium hydrogen carbonate (100 mL) and extracted into ethyl acetate. The combined organic layers were washed with saturated saline, dried and concentrated. The residue was purified by column chromatography (0 to 70% ethyl acetate in heptanes) to give the title compound having the following physical properties (5.31 g).
LC/MS $t_R$ 1.43 minutes; MS (ES$^+$) m/z 265 (M+Na), 243 (M+H)$^a$.

EXAMPLE 745 ethyl(6S)-2-(2-amino-5-methylphenyl)-4-oxo-4H,6H,7H,8H-pyrrolo[1,2-a]pyrimidine-6-carboxylate To a 1,4-dioxane (290 mL) solution of the compound prepared in Example 744 (7.32 g) was added 4-methyl-2-(4,4,5,5-tetramethyl-1,3,2-dioxa-borolan-2-yl)aniline hydrochloride (9.50 g) and a 2 M aqueous solution of sodium carbonate (45.2 mL) under an atmosphere of nitrogen. The mixture was degassed with nitrogen, 1,1'-bis(diphenylphosphino)ferrocene palladium (II) dichloride dichloromethane complex (1.31 g) added and the mixture stirred at 100° C. for 4 hours before cooling to room temperature. The reaction mixture was diluted with ethyl acetate (300 mL) and the organic layer isolated, dried and concentrated. The residue was purified by column chromatography (10% to 100% ethyl acetate in heptanes) to give the title compound having the following physical properties (6.50 g).
LC/MS $t_R$ 1.52 minutes; MS (ES$^+$) m/z 314 (M+H)$^a$.

EXAMPLE 746

(6S)-2-[5-methyl-2-(1H-1,2,3,4-tetrazol-1-yl)phenyl]-4-oxo-4H,6H,7H,8H-pyrrolo[1,2-a]pyrimidine-6-carboxylic acid

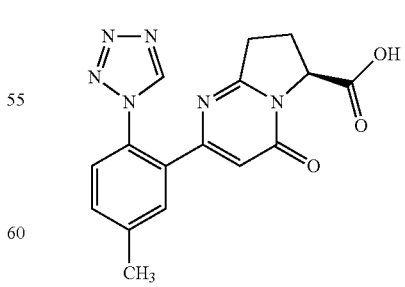

The same operation as in Example 8→Example 9 was conducted from the compound prepared in Example 745 to give the title compound having the following physical properties.

LC/MS t_R 1.37 minutes; MS (ES+) m/z 699 (2M+Na), 677 (2M+H), 361 (M+Na), 339 (M+H), 311 (M-N_2+H)

EXAMPLE 747(1) TO EXAMPLE 747(11)

The compounds of the present invention having the following physical data were prepared using the corresponding alpha-bromoketones from the compound prepared in Example 746 in the process of Example 51→Example 52.

EXAMPLE 747(1)

methyl[4-(2-{(6S)-2-[5-methyl-2-(1H-tetrazol-1-yl)phenyl]-4-oxo-4,6,7,8-tetrahydropyrrolo[1,2-a]pyrimidin-6-yl}-1H-imidazol-5-yl)phenyl]carbamate In the step corresponding to Example 51 in the process, methyl[4-(bromoacetyl)-phenyl]carbamate [J. Am. Chem. Soc. 119(10), 2453 (1997)] was used.
LC/MS t_R 2.99 minutes; MS (ES+) m/z 510 (M+H)$^b$
$^1$H NMR (500 MHz, methanol-d_4) δ 9.40 (s, 1 H), 7.67 (s, 1 H), 7.63-7.51 (m, 4 H), 7.44 (br. s, 2 H), 7.29 (br. s, 1 H), 6.33 (s, 1 H), 5.72 (dd, 1 H), 3.74 (s, 3 H), 3.33 (br. s, 1 H), 3.30-3.23 (m, 1 H), 2.96-2.84 (m, 1 H), 2.66 (qd, 1 H), 2.52 (s, 3 H), 2.39 (d, 1H).

EXAMPLE 747(2)

2-methoxyethyl[4-(2-{(6S)-2-[5-methyl-2-(1H-tetrazol-1-yl)phenyl]-4-oxo-4,6,7,8-tetrahydropyrrolo[1,2-a]pyrimidin-6-yl}-1H-imidazol-5-yl)phenyl]carbamate In the step corresponding to Example 51 in the process, the compound prepared in Example 324 was used.
LC/MS t_R 3.04 minutes; MS (ES+) m/z 554 (M+H)$^b$
$^1$H NMR (500 MHz, methanol-d_4) δ 9.41 (s, 1 H), 7.68 (s, 1 H), 7.58 (app. br. s, 2 H), 7.56 (app. s, 2 H), 7.46 (app. br. s, 2 H), 7.28 (br. s, 1 H), 6.35 (s, 1 H), 5.74 (dd, 1 H), 4.28 (dd, 2 H), 3.66 (dd, 2 H), 3.41 (s, 3 H), 3.35-3.25 (m, 1 H), 2.91 (ddd, 1 H), 2.68 (qd, 1 H), 2.54 (s, 3 H), 2.40 (app. br. s, 1 H).

EXAMPLE 747(3)

2-ethoxyethyl[4-(2-{(6S)-2-[5-methyl-2-(1H-tetrazol-1-yl)phenyl]-4-oxo-4,6,7,8-tetrahydropyrrolo[1,2-a]pyrimidin-6-yl}-1H-imidazol-5-yl)phenyl]carbamate In the step corresponding to Example 51 in the process, the compound prepared in Example 714 was used.
LC/MS t_R 3.11 minutes; MS (ES+) m/z 568 (M+H)$^b$
$^1$H NMR (500 MHz, methanol-d_4) δ 9.40 (s, 1 H), 7.70-7.13 (m, 8 H), 6.33 (s, 1 H), 5.72 (dd, 1 H), 4.33-4.19 (m, 2 H), 3.73-3.65 (m, 2 H), 3.57 (q, 2 H), 3.33 (m, 1 H), 2.90 (m, 1 H), 2.71-2.61 (m, 1 H), 2.53 (s, 3 H), 2.40 (br. s, 1 H), 1.20 (t, 3 H).

EXAMPLE 747(4)

3-methoxypropyl[4-(2-{(6S)-2-[5-methyl-2-(1H-tetrazol-1-yl)phenyl]-4-oxo-4,6,7,8-tetrahydropyrrolo[1,2-a]pyrimidin-6-yl}-1H-imidazol-5-yl)phenyl]carbamate In the step corresponding to Example 51 in the process, the compound prepared in Example 715 was used.

LC/MS t_R 1.54 minutes; MS (ES+) m/z 568 (M+H)$^a$
$^1$H NMR (500 MHz, methanol-d_4) δ 9.39 (s, 1 H), 7.84-6.91 (m, 9 H), 6.33 (s, 1 H), 5.72 (dd, 1 H), 4.62 (br. s, 1 H), 4.20 (t, 2 H), 3.52 (t, 2 H), 3.34 (s, 3 H), 3.29-3.20 (m, 1 H), 2.90 (ddd, 1 H), 2.65 (m, 1 H), 2.52 (s, 3 H), 2.39 (br. s, 1 H), 1.93 (quintet, 2 H).

EXAMPLE 747(5)

formic acid-methyl[4-(4-methyl-2-{(6S)-2-[5-methyl-2-(1H-tetrazol-1-yl)phenyl]-4-oxo-4,6,7,8-tetrahydropyrrolo[1,2-a]pyrimidin-6-yl}-1H-imidazol-5-10 yl)phenyl]carbamate (1:1)

In the step corresponding to Example 51 in the process, the compound prepared in Example 78 was used. In the step corresponding to Example 52 in the process, high performance liquid chromatography [5 to 100% mobile phase B (0.1% formic acid in acetonitrile) in mobile phase A (0.1% aqueous formic acid)] was used to give the title product as the formic acid salt
LC/MS t_R 2.93 minutes; MS (ES+) m/z 524 (M+H)$^b$
$^1$H NMR (500 MHz, DMSO-d_6) δ 12.03 (br. s, 1 H), 9.69 (br. s, 1 H), 9.64 (br. s, 1 H), 8.21 (br. s, 1 H), 7.83-7.24 (m, 7 H), 6.18 (br. s, 1 H), 5.55 (d, 1 H), 3.66 (s, 3 H), 3.68-3.56 (obs. m, 1 H), 3.28-3.10 (m, 1 H), 2.84-2.68 (m, 1 H), 2.47 (s, 3 H), 2.29 (br. s, 3 H), 2.19 (br. s, 1 H).

EXAMPLE 747(6)

2-methoxyethyl[4-(4-methyl-2-{(6S)-2-[5-methyl-2-(1H-tetrazol-1-yl)phenyl]-4-oxo-4,6,7,8-tetrahydropyrrolo[1,2-a]pyrimidin-6-yl}-1H-imidazol-5-yl)phenyl]carbamate In the step corresponding to Example 51 in the process, the compound prepared in Example 481 was used.
LC/MS t_R 3.03 minutes; MS (ES+) m/z 568 (M+H)$^b$
NMR analysis showed a 3:2 ratio of tautomers.
Major tautomer: $^1$H NMR (500 MHz, DMSO-d_6) δ 12.00 (s, 1 H), 9.70 (br. s, 1 H), 9.69 (s, 1 H), 7.70 (br. s, 1 H), 7.61 (s, 1 H), 7.59-7.35 (m, 5 H), 6.19 (s, 1 H), 5.55 (dd, 1H), 4.21-4.17 (m, 2 H), 3.58-3.54 (m, 2 H), 3.28 (s, 3 H), 3.26-3.13 (m, 1 H), 2.81-2.70 (m, 1 H), 2.58-2.48 (m, 1 H), 2.47 (s, 3 H), 2.33 (s, 3 H), 2.26-2.17 (m, 1 H).
Minor tautomer: $^1$H NMR (500 MHz, DMSO-d_6) δ 12.20 (s, 1 H), 9.82 (br. s, 1 H), 9.71 (s, 1 H), 7.72 (br. s, 1 H), 7.63 (s, 1 H), 7.59-7.35 (m, 5 H), 6.18 (s, 1 H), 5.56 (dd, 1H), 4.24-4.20 (m, 2 H), 3.60-3.56 (m, 2 H), 3.29 (s, 3 H), 3.26-3.13 (m, 1 H), 2.81-2.70 (m, 1 H), 2.58-2.48 (m, 1 H), 2.48 (s, 3 H), 2.19 (s, 3 H), 2.19-2.11 (m, 1 H).

EXAMPLE 747(7)

(6S)-6-[5-(6-amino-3-pyridinyl)-1H-imidazol-2-yl]-2-[5-methyl-2-(1H-tetrazol-1-yl)phenyl]-7,8-dihydropyrrolo[1,2-a]pyrimidin-4(6H)-one In the step corresponding to Example 51 in the process, the compound prepared in Example 193 was used.
LC/MS t_R 2.54 minutes; MS (ES+) m/z 453 (M+H)$^b$
$^1$H NMR (500 MHz, methanol-d_4) δ 9.40 (s, 1 H), 8.25-8.15 (br. s, 1 H), 7.80-7.70 (br. s, 1 H), 7.65 (s, 1 H), 7.55 (s, 2 H), 7.30-7.20 (br. s, 1 H), 6.58 (d, 1 H), 6.32 (s, 1H), 5.70 (m, 1 H), 3.35 (m, 1 H), 2.92-2.85 (m, 1 H), 2.70-2.60 (m, 1 H), 2.52 (s, 3H), 2.43-2.30 (br. s, 1 H).

EXAMPLE 747(8)

formic acid-(6S)-6-{5-[6-(methylamino)-3-pyridinyl]-1H-imidazol-2-yl}-2-[5-methyl-2-(1H-tetrazol-1-yl)phenyl]-7,8-dihydropyrrolo[1,2-a]pyrimidin-4(6H)-one (1:1)

In the step corresponding to Example 51 in the process, the compound prepared in Example 551 was used.

LC/MS $t_R$ 2.51 minutes; MS (ES$^+$) m/z 467 (M+H)$^b$ $^1$H NMR (500 MHz, methanol-d$_4$) δ 9.40 (s, 1 H), 8.25 (s, 1 H), 8.20 (s, 1 H), 7.87 (d, 1H), 7.67 (s, 1 H), 7.56 (m, 2 H), 7.28 (s, 1 H), 6.70 (d, 1 H), 6.34 (s, 1 H), 5.72 (dd, 1 H), 3.30-3.23 (m, 1 H), 3.01-2.85 (m, 1 H), 2.93 (s, 3 H), 2.67 (dt, 1 H), 2.53 (s, 3 H), 2.38 (td, 1 H).

EXAMPLE 747(9)

(6S)-6-[5-(6-amino-2-chloro-3-pyridinyl)-1H-imidazol-2-yl]-2-[5-methyl-2-(1H-tetrazol-1-yl)phenyl]-7,8-dihydropyrrolo[1,2-a]pyrimidin-4(6H)-one In the step corresponding to Example 51 in the process, the compound prepared in Example 209 was used.

LC/MS $t_R$ 2.20 minutes; MS (ES$^+$) m/z 487 (M+H)$^b$ $^1$H NMR (500 MHz, methanol-d$_4$) δ 9.41 (s, 1 H), 7.91 (br. s, 1 H), 7.68 (s, 1 H), 7.57 (app. s, 2 H), 7.39 (br. s, 1 H), 6.57 (d, 1 H), 6.36 (s, 1 H), 5.76 (ddd, 1 H), 3.36-3.26 (obs. m, 1 H), 2.91 (ddd, 1 H), 2.67 (qd, 1 H), 2.54 (s, 3 H), 2.48-2.36 (m, 1 H).

EXAMPLE 747(10)

methyl[6-(2-{(6S)-2-[5-methyl-2-(1H-tetrazol-1-yl)phenyl]-4-oxo-4,6,7,8-tetrahydropyrrolo[1,2-a]pyrimidin-6-yl}-1H-imidazol-5-yl)-3-pyridinyl]carbamate In the step corresponding to Example 51 in the process, the compound prepared in Example 712 was used.

LC/MS $t_R$ 2.94 minutes; MS (ES$^+$) m/z 511 (M+H)$^b$ $^1$H NMR (500 MHz, methanol-d$_4$) δ 9.40 (s, 1 H), 8.56 (br. s, 1 H), 7.94 (d, 1 H), 7.76 (br. s, 1 H), 7.66 (s, 1 H), 7.55 (app. s, 2 H), 7.51 (br. s, 1 H), 6.34 (s, 1 H), 5.75 (dd, 1H), 3.76 (s, 3 H), 3.36-3.25 (obs. m, 1 H), 2.90 (ddd, 1 H), 2.66 (qd, 1 H), 2.52 (s, 3 H), 2.47-2.37 (m, 1 H).

EXAMPLE 747(11)

2-methoxyethyl[6-(2-{(6S)-2-[5-methyl-2-(1H-tetrazol-1-yl)phenyl]-4-oxo-4,6,7,8-tetrahydropyrrolo[1,2-a]pyrimidin-6-yl}-1H-imidazol-5-yl)-3-pyridinyl]carbamate In the step corresponding to Example 51 in the process, the compound prepared in Example 713 was used.

LC/MS $t_R$ 2.88 minutes; MS (ES$^+$) m/z 555 (M+H)$^b$ $^1$H NMR (500 MHz, methanol-d$_4$) δ 9.40 (s, 1 H), 8.57 (br. s, 1 H), 7.94 (d, 1 H), 7.87-7.31 (m, 5 H), 6.35 (s, 1 H), 5.75 (d, 1 H), 4.60 (br. s, 1 H), 4.34-4.23 (m, 2 H), 3.71-3.61 (m, 2 H), 3.43-3.37 (m, 3 H), 3.28-3.36 (m, 1 H), 2.91 (ddd, 1 H), 2.72-2.61 (m, 1H), 2.53 (s, 3 H), 2.35-2.47 (m, 1 H).

EXAMPLE 748 methyl[5-(2-{(6S)-2-[5-methyl-2-(1H-tetrazol-1-yl)phenyl]-4-oxo-4,6,7,8-tetrahydropyrrolo[1,2-a]pyrimidin-6-yl}-1H-imidazol-5-yl)-2-pyridinyl]carbamate The compound prepared in Example 747(7) (212 mg) was treated with methyl chloroformate following the method of Example 128 to give the title compound having the following physical properties (181 mg).

LC/MS $t_R$ 2.87 minutes; MS (ES$^+$) m/z 511 (M+H)$^b$ $^1$H NMR (500 MHz, methanol-d$_4$) δ 9.40 (s, 1 H), 8.55 (s, 1 H), 8.02 (d, 1 H), 7.89 (d, 1H), 7.67 (s, 1 H), 7.56 (s, 2 H), 7.40 (br. s, 1 H), 6.34 (s, 1 H), 5.73 (dd, 1 H), 3.77 (s, 3H), 3.25-3.38 (m, 1 H), 2.91 (ddd, 1 H), 2.67 (qd, 1 H), 2.53 (s, 3 H), 2.35-2.46 (m, 1H).

EXAMPLE 749

2-methoxyethyl[5-(2-{(6S)-2-[5-methyl-2-(1H-tetrazol-1-yl)phenyl]-4-oxo-4,6,7,8-tetrahydropyrrolo[1,2-a]pyrimidin-6-yl}-1H-imidazol-5-yl)-2-pyridinyl]carbamate The compound prepared in Example 747(7) (212 mg) was treated with 2-methoxyethyl chloroformate following the method of Example 128 to give the title compound having the following physical properties (235 mg).

LC/MS $t_R$ 2.98 minutes; MS (ES$^+$) m/z 555 (M+H)$^b$ $^1$H NMR (500 MHz, methanol-d$_4$) δ 9.40 (s, 1 H), 8.56 (br. s, 1 H), 8.03 (d, 1 H), 7.88 (d, 1 H), 7.67 (s, 1 H), 7.56 (s, 2 H), 7.41 (br. s, 1 H), 6.34 (s, 1 H), 5.73 (dd, 1 H), 4.62 (br. s, 1 H), 4.25-4.35 (m, 2 H), 3.61-3.70 (m, 2 H), 3.39 (s, 3 H), 3.32-3.35 (m, 1 H), 2.91 (ddd, 1 H), 2.67 (qd, 1 H), 2.53 (s, 3 H), 2.35-2.46 (m, 1 H).

EXAMPLE 750(1) to Example 750(8)

The compounds of the present invention having the following physical data were synthesised from the compounds prepared in Examples 747(1), 747(2), 747(3), 747(4), 747(8), 747(11), 748 and 749 using the method as detailed in Example 338.

EXAMPLE 750(1)

methyl[4-(4-chloro-2-{(6S)-2-[5-methyl-2-(1H-tetrazol-1-yl)phenyl]-4-oxo-4,6,7,8-tetrahydropyrrolo[1,2-a]pyrimidin-6-yl}-1H-imidazol-5-yl)phenyl]carbamate LC/MS $t_R$ 3.82 minutes; MS (ES$^+$) m/z 544 (M+H)$^b$ $^1$H NMR (500 MHz, DMSO-d$_6$) δ 12.90 (br. s, 1 H), 9.80 (s, 1 H), 9.71 (s, 1 H), 7.72 (s, 1 H), 7.60 (m, 3 H), 7.52 (m, 3 H), 5.75 (m, 1 H), 3.75 (s, 3 H), 3.20-3.05 (m, 1 H), 2.8-2.7 (m, 1 H), 2.62-2.50 (obs. m, 2 H), 2.45 (s, 3 H).

EXAMPLE 750(2)

2-methoxyethyl[4-(4-chloro-2-{(6S)-2-[5-methyl-2-(1H-tetrazol-1-yl)phenyl]-4-oxo-4,6,7,8-tetrahydropyrrolo[1,2-a]pyrimidin-6-yl}-1H-imidazol-5-yl)phenyl]carbamate LC/MS $t_R$ 3.82 minutes; MS (ES$^+$) m/z 588 (M+H)$^b$ $^1$H NMR (500 MHz, DMSO-d$_6$) δ 12.91 (br. s, 1 H), 9.91 (br. s, 1 H), 9.71 (s, 1 H), 7.73 (s, 1 H), 7.66-7.58 (m, 3 H), 7.58-7.52 (m, 3 H), 6.21 (s, 1 H), 5.57 (dd, 1 H), 4.22 (dd, 2 H), 3.58 (dd, 2 H), 3.29 (s, 3 H), 3.18-3.06 (m, 1 H), 2.77 (ddd, 1 H), 2.63-2.53 (m, 1 H), 2.48 (s, 3 H), 2.21-2.12 (m, 1 H).

EXAMPLE 750(3)

2-ethoxyethyl[4-(4-chloro-2-{(6S)-2-[5-methyl-2-(1H-tetrazol-1-yl)phenyl]-4-oxo-4,6,7,8-tetrahydropyrrolo[1,2-a]pyrimidin-6-yl}-1H-imidazol-5-yl)phenyl]carbamate LC/MS $t_R$ 4.00 minutes; MS (ES$^+$) m/z 602 (M+H)$^b$
$^1$H NMR (500 MHz, methanol-d$_4$) δ 9.40 (s, 1 H), 7.68 (s, 1 H), 7.64 (s, 1 H), 7.62 (s, 1 H), 7.57-7.48 (m, 3 H), 6.35 (s, 1 H), 5.66 (dd, 1 H), 4.36-4.17 (m, 2 H), 3.78-3.63 (m, 2 H), 3.57 (q, 2 H), 3.29-3.22 (m, 1 H), 2.90 (ddd, 1 H), 2.75-2.60 (m, 2 H), 2.53 (s, 3 H), 2.40-2.24 (m, 1 H), 1.21 (t, 3 H).

EXAMPLE 750(4)

3-methoxypropyl[4-(4-chloro-2-{(6S)-2-[5-methyl-2-(1H-tetrazol-1-yl)phenyl]-4-oxo-4,6,7,8-tetrahydropyrrolo[1,2-a]pyrimidin-6-yl}-1H-imidazol-5-yl)phenyl]carbamate LC/MS $t_R$ 3.95 minutes; MS (ES$^+$) m/z 602 (M+H)$^b$
$^1$H NMR (500 MHz, methanol-d$_4$) δ 9.40 (s, 1 H), 7.68 (s, 1 H), 7.62 (d, 2 H), 7.59-7.43 (m, 4 H), 6.35 (s, 1 H), 5.66 (dd, 1 H), 4.28-4.16 (m, 2H), 3.53 (t, 2 H), 3.35 (s, 3H), 3.30-3.22 (m, 1 H), 2.90 (ddd, 1 H), 2.67 (qd, 1 H), 2.53 (s, 3 H), 2.41-2.28 (m, 1H), 1.95 (quintet, 2 H).

EXAMPLE 750(5)

formic acid-(6S)-6-{4-chloro-5-[6-(methylamino)-3-pyridinyl]-1H-imidazol-2-yl}-2-[5-methyl-2-(1H-tetrazol-1-yl)phenyl]-7,8-dihydropyrrolo[1,2-a]pyrimidin-4(6H)-one (1:1)

LC/MS $t_R$ 2.75 minutes; MS (ES$^+$) m/z 501 (M+H)$^b$
$^1$H NMR (500 MHz, DMSO-d$_6$) δ 12.81 (br. s, 1 H), 9.70 (s, 1 H), 8.29 (d, 1 H), 8.16 (s, 2 H), 7.72 (s, 1 H), 7.64 (dd, 1 H), 7.62 (d, 1 H), 7.58-7.52 (m, 1 H), 6.72-6.78 (m, 1H), 6.53 (d, 1 H), 6.20 (s, 1 H), 5.55 (dd, 1 H), 3.12 (td, 1 H), 2.83-2.71 (m, 4 H), 2.62-2.52 (m, 1 H), 2.48 (s, 3 H), 2.16 (tdd, 1 H).

EXAMPLE 750(6)

2-methoxyethyl[6-(4-chloro-2-{(6S)-2-[5-methyl-2-(1H-tetrazol-1-yl)phenyl]-4-oxo-4,6,7,8-tetrahydropyrrolo[1,2-a]pyrimidin-6-yl}-1H-imidazol-5-yl)-3-pyridinyl]carbamate LC/MS $t_R$ 3.76 minutes; MS (ES$^+$) m/z 589 (M+H)$^b$
$^1$H NMR (500 MHz, DMSO-d$_6$) δ 13.08 (br. s, 1 H), 10.11 (br. s, 1 H), 9.69 (s, 1 H), 8.75 (s, 1 H), 8.00-7.93 (m, 1 H), 7.93-7.87 (m, 1 H), 7.73 (s, 1 H), 7.62 (d, 1 H), 7.55 (d, 1 H), 6.19 (s, 1 H), 5.64 (dd, 1 H), 4.27-4.19 (m, 2 H), 3.66-3.51 (m, 2 H), 3.29 (s, 3 H), 3.07 (td, 1 H), 2.77 (ddd, 1 H), 2.61-2.52 (m, 1 H), 2.48 (s, 3 H), 2.16-2.07 (m, 1 H).

EXAMPLE 750(7)

methyl[5-(4-chloro-2-{(6S)-2-[5-methyl-2-(1H-tetrazol-1-yl)phenyl]-4-oxo-4,6,7,8-tetrahydropyrrolo[1,2-a]pyrimidin-6-yl}-1H-imidazol-5-yl)-2-pyridinyl]carbamate LC/MS $t_R$ 3.63 minutes; MS (ES$^+$) m/z 545 (M+H)$^b$
$^1$H NMR (500 MHz, methanol-d$_4$) δ 9.42 (s, 1 H), 8.60 (d, 1 H), 8.04-8.10 (m, 1 H), 7.98-8.03 (m, 1 H), 7.70 (s, 1 H), 7.55-7.60 (m, 2 H), 6.37 (s, 1 H), 5.69 (dd, 1 H), 3.80 (s, 3 H), 3.35 (d, 1 H), 2.92 (ddd, 1 H), 2.69 (qd, 1 H), 2.55 (s, 3 H), 2.32-2.41 (m, 1 H).

EXAMPLE 750(8)

2-methoxyethyl[5-(4-chloro-2-{(6S)-2-[5-methyl-2-(1H-tetrazol-1-yl)phenyl]-4-oxo-4,6,7,8-tetrahydropyrrolo[1,2-a]pyrimidin-6-yl}-1H-imidazol-5-yl)-2-pyridinyl]carbamate LC/MS $t_R$ 3.66 minutes; MS (ES$^+$) m/z 589 (M+H)$^b$
$^1$H NMR (500 MHz, methanol-d$_4$) δ 9.40 (s, 1 H), 8.58 (d, 1 H), 8.02-8.11 (m, 1 H), 7.92-8.03 (m, 1 H), 7.68 (s, 1 H), 7.50-7.62 (m, 2 H), 6.35 (s, 1 H), 5.67 (dd, 1 H), 4.23-4.41 (m, 2 H), 3.60-3.75 (m, 2 H), 3.40 (s, 3 H), 3.36 (br. s, 1 H) 2.90 (ddd, 1H), 2.68 (qd, 1 H), 2.53 (s, 3 H), 2.35 (qd, 1 H).

EXAMPLE 751 methyl[6-(4-chloro-2-{(6S)-2-[5-methyl-2-(1H-tetrazol-1-yl)phenyl]-4-oxo-4,6,7,8-tetrahydropyrrolo[1,2-a]pyrimidin-6-yl}-1H-imidazol-5-yl)-3-pyridinyl]carbamate The compound prepared in Example 747(10) (106 mg) was treated as detailed in Example 44 to give the title compound having the following physical properties (20 mg).
LC/MS $t_R$ 3.78 minutes; MS (ES$^+$) m/z 545 (M+H)$^b$
$^1$H NMR (500 MHz, DMSO-d$_6$) δ 13.08 (br. s, 1 H), 10.00 (br. s, 1 H), 9.69 (s, 1 H), 8.73 (s, 1 H), 7.96 (dd, 1 H), 7.90 (d, 1 H), 7.73 (s, 1 H), 7.61 (d, 1 H), 7.55 (dd, 1 H), 6.19 (s, 1 H), 5.64 (dd, 1 H), 3.70 (s, 3 H), 3.07 (td, 1 H), 2.76 (ddd, 1 H), 2.60-2.52 (obs. m, 1 H), 2.48 (3 H, s), 2.16-2.07 (m, 1 H).

EXAMPLE 752

(6S)-6-[5-(6-amino-3-pyridinyl)-4-chloro-1H-imidazol-2-yl]-2-[5-methyl-2-(1H-tetrazol-1-yl)phenyl]-7,8-dihydropyrrolo[1,2-a]pyrimidin-4(6H)-one The same operation as in Example 228→Example 338→Example 55 was conducted from the compound prepared in Example 747(7) to give the title compound having the following physical properties.
LC/MS $t_R$ 2.70 minutes; MS (ES$^+$) m/z 487 (M+H)$^b$
$^1$H NMR (500 MHz, methanol-d$_4$) δ 9.40 (s, 1 H), 8.21 (d, 1 H), 7.76 (dd, 1 H), 7.67 (s, 1 H), 7.59-7.51 (m, 2 H), 6.65 (d, 1 H), 6.34 (s, 1 H), 5.64 (dd, 1 H), 3.30-3.22 (m, 1H), 2.89 (ddd, 1 H), 2.71-2.60 (m, 3 H), 2.53 (s, 3 H), 2.33 (tdd, 1 H).

EXAMPLE 753 ethyl(3S)-7-(2-azido-5-chlorophenyl)-5-oxo-1,2,3,5-tetrahydroindolizine-3-carboxylate To a cooled (0° C.) acetonitrile (100 mL) solution of the compound prepared in Example 7 (8.95 g) was sequentially added azidotrimethylsilane (4.24 mL) and tert-butyl nitrite (4.84 mL) and the mixture stirred at 0° C. for 1 hour. The reaction mixture was concentrated and the residue purified by column chromatography (10% to 75% ethyl acetate in heptanes) to give the title compound having the following physical properties (7.0 g).

LC/MS $t_R$ 2.10 minutes; MS (ES$^+$) m/z 359 (M+H)$^a$.

EXAMPLE 754 ethyl(3S)-7-{5-chloro-2-[4-(tributylstannyl)-1H-1,2,3-triazol-1-yl]phenyl}-5-oxo-1,2,3,5-tetrahydroindolizine-3-carboxylate To a toluene (50 mL) solution of the compound prepared in Example 753 (5.0 g) was added tributyl(ethynyl)stannane (6.1 mL) and the mixture stirred at reflux for 3 hours. The reaction mixture was concentrated and the residue purified by column chromatography (5% to 75% ethyl acetate in heptanes) to give the title compound having the following physical properties (6.42 g).

LC/MS $t_R$ 2.95 minutes; MS (ES$^+$) m/z 671, 673 and 675 (M+H)$^a$.

EXAMPLE 755 ethyl(3S)-7-[5-chloro-2-(4-chloro-1H-1,2,3-triazol-1-yl)phenyl]-5-oxo-1,2,3,5-tetrahydroindolizine-3-carboxylate To a cooled (0° C.) THF (540 mL) solution of copper(II) chloride (1.51 g) was added a solution of the compound prepared in Example 754 (3.4 g) in THF (36 mL) dropwise over 15 minutes. The mixture was stirred at 0° C. a further 15 minutes then concentrated. The residue was dissolved in acetonitrile, washed with hexane and the acetonitrile layer concentrated. The residue was suspended in water and extracted into ethyl acetate. The combined organic layers were washed with saturated saline, dried and concentrated. The residue was purified by column chromatography (50 to 100% ethyl acetate in heptanes) to give the title compound having the following physical properties (1.12 g).

LC/MS $t_R$ 1.92 minutes; MS (ES$^+$) m/z 441 and 443 (M+Na), 419 and 421 (M+H)$^a$.

EXAMPLE 756

(3S)-7-[5-chloro-2-(4-chloro-1H-1,2,3-triazol-1-yl)phenyl]-5-oxo-1,2,3,5-tetrahydroindolizine-3-carboxylic acid

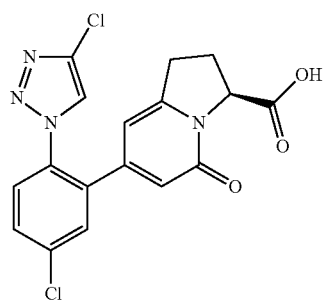 [SMILES: O=C(O)[C@@H]1CCc2cc(-c3cc(Cl)ccc3-n3cc(Cl)nn3)cc(=O)n21]

The compound prepared in Example 755 (0.90 g) was treated as detailed in Example 8 to give the title compound having the following physical properties (0.81 g).

LC/MS $t_R$ 1.67 minutes; MS (ES$^+$) m/z 391 and 393 (M+H)$^a$.

EXAMPLE 757(1) to Example 757(9)

The compounds of the present invention having the following physical data were prepared using the corresponding alpha-bromoketones from the compound prepared in Example 756 in the process of Example 51→Example 52.

EXAMPLE 757(1)

2-methoxyethyl[4-(2-{(3S)-7-[5-chloro-2-(4-chloro-1H-1,2,3-triazol-1-yl)phenyl]-5-oxo-1,2,3,5-tetrahydro-3-indolizinyl}-1H-imidazol-5-yl)phenyl]carbamate In the step corresponding to Example 51 in the process, the compound prepared in Example 324 was used.

LC/MS $t_R$ 3.38 minutes; MS (ES$^+$) m/z 606 and 608 (M+H)$^b$ $^1$H NMR (500 MHz, methanol-d$_4$) δ 8.30 (s, 1 H), 7.73-7.69 (m, 2 H), 7.65 (d, 1 H), 7.59 (app. br. s, 2 H), 7.45 (app. br. s, 2 H), 7.35-7.12 (m, 1 H), 6.16 (s, 1 H), 6.15 (s, 1 H), 5.81 (d, 1 H), 4.31-4.26 (m, 2 H), 3.69-3.63 (m, 2 H), 3.52-3.45 (m, 1 H), 3.41 (s, 3 H), 3.14 (ddd, 1 H), 2.66 (qd, 1 H), 2.51 (app. br. s, 1 H).

EXAMPLE 757(2)

(3S)-3-[5-(6-amino-3-pyridinyl)-1H-imidazol-2-yl]-7-[5-chloro-2-(4-chloro-1H-1,2,3-triazol-1-yl)phenyl]-2,3-dihydro-5(1H)-indolizinone In the step corresponding to Example 51 in the process, the compound prepared in Example 193 was used.

LC/MS $t_R$ 2.92 minutes; MS (ES$^+$) m/z 505 and 507 (M+H), 253 and 254 [(M+2H)/2]$^b$ $^1$H NMR (500 MHz, methanol-d$_4$) δ 8.30 (s, 1 H), 8.22 (d, 1 H), 7.78 (dd, 1 H), 7.74-7.68 (m, 2 H), 7.65 (d, 1 H), 7.22 (br. s, 1 H), 6.64 (d, 1 H), 6.16 (s, 1 H), 6.14 (s, 1 H), 5.80 (dd, 1 H), 3.48 (td, 1 H), 3.14 (ddd, 1 H), 2.66 (qd, 1 H), 2.53-2.45 (m, 1 H).

EXAMPLE 757(3)

(3S)-7-[5-chloro-2-(4-chloro-1H-1,2,3-triazol-1-yl)phenyl]-3-{5-[6-(methylamino)-3-pyridinyl]-1H-imidazol-2-yl}-2,3-dihydro-5 (1H)-indolizinone In the step corresponding to Example 51 in the process, the compound prepared in Example 551 was used.

LC/MS $t_R$ 2.98 minutes; MS (ES$^+$) m/z 519 and 521 (M+H), 260 and 261 [(M+2H)/2]$^b$ $^1$H NMR (500 MHz, methanol-d$_4$) δ 8.28 (s, 1 H), 8.25 (br. s, 1 H), 7.73 (br. s, 1 H), 7.72-7.67 (m, 2 H), 7.63 (d, 1 H), 7.17 (br. s, 1 H), 6.54 (d, 1 H), 6.14 (s, 1 H), 6.12 (s, 1

H), 5.78 (dd, 1 H), 3.47 (td, 1 H), 3.13 (ddd, 1 H), 2.88 (s, 3 H), 2.64 (qd, 1 H), 2.49 (app. br. s, 1 H).

EXAMPLE 757(4)

(3S)-3-[5-(6-amino-2-fluoro-3-pyridinyl)-1H-imidazol-2-yl]-7-[5-chloro-2-(4-chloro-1H-1,2,3-triazol-1-yl)phenyl]-2,3-dihydro-5(1H)-indolizinone In the step corresponding to Example 51 in the process, the compound prepared in Example 215 was used.

LC/MS $t_R$ 3.22 minutes; MS (ES$^+$) m/z 523 and 525 (M+H)$^b$ $^1$H NMR (500 MHz, methanol-d$_4$) δ 8.28 (s, 1 H), 8.04 (app. br. s, 1 H), 7.72-7.67 (m, 2 H), 7.64 (d, 1 H), 7.18 (br. s, 1 H), 6.44 (d, 1 H), 6.14 (s, 1 H), 6.13 (s, 1 H), 5.84-5.76 (m, 1 H), 3.52-3.40 (m, 1 H), 3.12 (ddd, 1 H), 2.63 (qd, 1 H), 2.55-2.46 (m, 1 H).

EXAMPLE 757(5)

(3S)-3-[5-(6-amino-2-chloro-3-pyridinyl)-1H-imidazol-2-yl]-7-[5-chloro-2-(4-chloro-1H-1,2,3-triazol-1-yl)phenyl]-2,3-dihydro-5(1H)-indolizinone In the step corresponding to Example 51 in the process, the compound prepared in Example 209 was used.

LC/MS $t_R$ 3.23 minutes; MS (ES$^+$) m/z 539, 541 and 543 (M+H), 270, 271 and 272 [(M+2H)/2]$^b$ $^1$H NMR (500 MHz, methanol-d$_4$) δ 8.27 (s, 1 H), 7.88 (app. hr. s, 1 H), 7.72-7.65 (m, 2 H), 7.62 (d, 1 H), 7.38 (br. s, 1 H), 6.53 (d, 1 H), 6.13 (s, 1 H), 6.11 (s, 1 H), 5.80 (d, 1H), 3.54-3.39 (m, 1 H), 3.11 (dd, 1 H), 2.68-2.56 (m, 1 H), 2.55-2.47 (m, 1 H).

EXAMPLE 757(6)

methyl[6-(2-{(3S)-7-[5-chloro-2-(4-chloro-1H-1,2,3-triazol-1-yl)phenyl]-5-oxo-1,2,3,5-tetrahydro-3-indolizinyl}-1H-imidazol-5-yl)-3-pyridinyl]carbamate In the step corresponding to Example 51 in the process, the compound prepared in Example 712 was used.

LC/MS $t_R$ 3.31 minutes; MS (ES$^+$) m/z 585 and 587 (M+Na), 563 and 565 (M+H), 282 and 283 [(M+2H)/2]$^b$ $^1$H NMR (500 MHz, methanol-d$_4$) δ 8.56 (app. br. s, 1 H), 8.28 (s, 1 H), 7.94 (d, 1 H), 7.81 (app. br. s, 1 H), 7.72-7.67 (m, 2 H), 7.66-7.61 (m, 1 H), 7.54 (br. s, 1 H), 6.14 (app. s, 2 H), 5.82 (app. br. s, 1 H), 3.77 (s, 3 H), 3.49 (app. br. s, 1 H), 3.13 (ddd, 1 H), 2.64 (qd, 1 H), 2.54 (app. br. s, 1 H).

EXAMPLE 757(7)

formic acid—2-methoxyethyl[6-(2-{(3S)-7-[5-chloro-2-(4-chloro-1H-1,2,3-triazol-1-yl)phenyl]-5-oxo-1,2,3,5-tetrahydro-3-indolizinyl}-1H-imidazol-5-yl)-3-pyridinyl]carbamate (1:1)

In the step corresponding to Example 51 in the process, the compound prepared in Example 713 was used. In the step corresponding to Example 52 in the process, high performance liquid chromatography [5 to 100% mobile phase B (0.1% formic acid in acetonitrile) in mobile phase A (0.1% aqueous formic acid)] was used to give the title product as the formic acid salt.

LC/MS $t_R$ 3.27 minutes; MS (ES$^+$) m/z 607 and 609 (M+H), 304 and 305 [(M+2H)/2]$^b$ NMR analysis showed a 2:1 ratio of tautomers.

Major tautomer: $^1$H-NMR (500 MHz, DMSO-d$_6$) δ 12.21 (br. s, 1 H), 9.90 (br. s, 1 H), 8.70 (s, 1 H), 8.52 (br. s, 1 H), 8.23 (br. s, 0.5 H), 7.90-7.82 (m, 1 H), 7.79-7.71 (m, 3 H), 7.68 (d, 1 H), 7.48 (br. s, 1 H), 5.98 (s, 1 H), 5.96 (br. s, 1 H), 5.64 (d, 1 H), 4.24-4.19 (m, 2 H), 3.59-3.54 (m, 2 H), 3.42-3.34 (obs. m, 1 H), 3.28 (s, 3 H), 3.06-2.95 (m, 1 H), 2.55-2.50 (obs. m, 1 H), 2.37-2.29 (m, 1 H).

Minor tautomer: $^1$H-NMR (500 MHz, DMSO-d$_6$) δ 12.50 (br. s, 1 H), 10.00 (br. s, 1 H), 8.70 (s, 1 H), 8.63 (br. s, 1 H), 8.23 (br. s, 0.5 H), 7.90-7.82 (m, 1 H), 7.79-7.71 (m, 3 H), 7.68 (d, 1 H), 7.33 (br. s, 1 H), 5.98 (s, 1 H), 5.95 (br. s, 1 H), 5.71 (app. br. s, 1H), 4.24-4.19 (m, 2 H), 3.59-3.54 (m, 2 H), 3.42-3.34 (obs. m, 1 H), 3.28 (s, 3 H), 3.06-2.95 (m, 1 H), 2.55-2.50 (obs. m, 1 H), 2.31-2.21 (app. br. s, 1 H).

EXAMPLE 757(8)

6-(2-{(3S)-7-[5-chloro-2-(4-chloro-1H-1,2,3-triazol-1-yl)phenyl]-5-oxo-1,2,3,5-tetrahydro-3-indolizinyl}-1H-imidazol-5-yl)-3,4-dihydro-2(1H)-quinolinone In the step corresponding to Example 51 in the process, 6-(bromoacetyl)-3,4-dihydroquinolin-2(1H)-one was used.

LC/MS $t_R$ 3.16 minutes; MS (ES$^+$) m/z 558 and 560 (M+H)$^b$ $^1$H NMR (500 MHz, methanol-d$_4$) δ 8.29 (s, 1 H), 7.72-7.67 (m, 2 H), 7.66-7.60 (m, 1H), 7.50 (br. s, 1 H), 7.46 (d, 1 H), 7.24 (br. s, 1 H), 6.86 (d, 1 H), 6.15 (s, 1 H), 6.13 (s, 1 H), 5.79 (dd, 1 H), 3.47 (td, 1 H), 3.13 (ddd, 1 H), 2.98 (t, 2 H), 2.65 (qd, 1 H), 2.58 (t, 2 H), 2.54-2.43 (m, 1 H).

EXAMPLE 757(9)

formic acid-4-(2-{(3S)-7-[5-chloro-2-(4-chloro-1H-1,2,3-triazol-1-yl)phenyl]-5-oxo-1,2,3,5-tetrahydro-3-indolizinyl}-1H-imidazol-5-yl)benzamide (1:1)

In the step corresponding to Example 51 in the process, the compound prepared in Example 119 was used. In the step corresponding to Example 52 in the process, high performance liquid chromatography [5 to 100% mobile phase B (0.1% formic acid in acetonitrile) in mobile phase A (0.1% aqueous formic acid)] was used to give the title product as the formic acid salt.

LC/MS $t_R$ 3.12 minutes; MS (ES$^+$) m/z 532 and 534 (M+H)$^b$ $^1$H NMR (500 MHz, DMSO-d$_6$) δ 12.26 (br. s, 1 H), 8.69 (s, 1 H), 8.22 (br. s, 1 H), 7.93 (br. s, 1 H), 7.84 (d, 2 H), 7.79-7.67 (m, 5 H), 7.62 (br. s, 1 H), 7.28 (br. s, 1 H), 5.98 (s, 1 H), 5.96 (s, 1 H), 5.64 (d, 1 H), 3.42-3.34 (obs. m, 1 H), 3.02 (dd, 1 H), 2.58-2.50 (obs. m, 1 H), 2.32 (app. br. s, 1 H).

EXAMPLE 758 methyl[5-(2-{(3S)-7-[5-chloro-2-(4-chloro-1H-1,2,3-triazol-1-yl)phenyl]-5-oxo-1,2,3,5-tetrahydro-3-indolizinyl}-1H-imidazol-5-yl)-2-pyridinyl]carbamate The compound prepared in Example 757(2) (50 mg) was treated with methyl chloroformate following the method of Example 484 to give the title compound having the following physical properties (27 mg).

LC/MS $t_R$ 3.42 minutes; MS (ES$^+$) m/z 563 and 565 (M+H), 282 and 283 [(M+2H)/2]$^b$ ¹H NMR (500 MHz, methanol-d₄) δ 8.56 (app. br. s, 1 H), 8.28 (s, 1 H), 8.07-7.97 (m, 1 H), 7.93-7.83 (m, 1 H), 7.73-7.67 (m, 2 H), 7.66-7.62 (m, 1 H), 7.41 (br. s, 1 H), 6.14 (s, 1 H), 6.13 (s, 1 H), 5.80 (dd, 1 H), 3.77 (s, 3 H), 3.48 (td, 1 H), 3.14 (ddd, 1 H), 2.65 (qd, 1 H), 2.51 (app. br. s, 1 H).

EXAMPLE 759

2-methoxyethyl[5-(2-{(3S)-7-[5-chloro-2-(4-chloro-1H-1,2,3-triazol-1-yl)phenyl]-5-oxo-1,2,3,5-tetrahydro-3-indolizinyl}-1H-imidazol-5-yl)-2-pyridinyl]carbamate The compound prepared in Example 757(2) (50 mg) was treated with 2-methoxyethyl chloroformate following the method of Example 128 to give the title compound having the following physical properties (30.7 mg).

LC/MS $t_R$ 3.47 minutes; MS (ES⁺) m/z 607 and 609 (M+H), 304 and 305 [(M+2H)/2]$^b$ ¹H NMR (500 MHz, methanol-d₄) δ 8.57 (app. br. s, 1 H), 8.28 (s, 1 H), 8.09-7.98 (m, 1 H), 7.92-7.82 (m, 1 H), 7.72-7.67 (m, 2 H), 7.66-7.61 (m, 1 H), 7.42 (br. s, 1 H), 6.13 (app. s, 2 H), 5.80 (dd, 1 H), 4.34-4.27 (m, 2 H), 3.69-3.63 (m, 2 H), 3.49 (td, 1H), 3.39 (s, 3 H), 3.14 (ddd, 1 H), 2.65 (qd, 1 H), 2.52 (app. br. s, 1 H).

EXAMPLE 760(1) TO EXAMPLE 760(3)

The compounds of the present invention having the following physical data were synthesised from the compounds prepared in Examples 757(2), 757(3) and 757(6) using the method as detailed in Example 44.

EXAMPLE 760(1)

(3S)-3-[5-(6-amino-3-pyridinyl)-4-chloro-1H-imidazol-2-yl]-7-[5-chloro-2-(4-chloro-1H-1,2,3-triazol-1-yl)phenyl]-2,3-dihydro-5(1H)-indolizinone LC/MS $t_R$ 3.18 minutes; MS (ES⁺) m/z 539, 541 and 543 (M+H), 270, 271 and 272 [(M+2H)/2]$^b$ ¹H NMR (500 MHz, methanol-d₄) δ 8.28 (s, 1 H), 8.21 (d, 1 H), 7.76 (dd, 1 H), 7.72-7.67 (m, 2 H), 7.63 (d, 1 H), 6.65 (d, 1 H), 6.15 (s, 1 H), 6.12 (s, 1 H), 5.71 (dd, 1 H), 3.47 (td, 1 H), 3.12 (ddd, 1 H), 2.65 (qd, 1 H), 2.44-2.36 (m, 1 H).

EXAMPLE 760(2)

(3S)-7-[5-chloro-2-(4-chloro-1H-1,2,3-triazol-1-yl)phenyl]-3-{4-chloro-5-[6-(methylamino)-3-pyridinyl]-1H-imidazol-2-yl}-2,3-dihydro-5(1H)-indolizinone LC/MS $t_R$ 3.18 minutes; MS (ES⁺) m/z 553, 555 and 557 (M+H), 277, 278 and 279 [(M+2H)/2]$^b$ ¹H NMR (500 MHz, methanol-d₄) δ 8.28 (s, 1 H), 8.27 (d, 1 H), 7.74 (dd, 1 H), 7.72-7.67 (m, 2 H), 7.63 (d, 1 H), 6.59 (d, 1 H), 6.15 (s, 1 H), 6.12 (s, 1 H), 5.71 (dd, 1 H), 3.47 (td, 1 H), 3.12 (ddd, 1 H), 2.90 (s, 3 H), 2.65 (qd, 1 H), 2.44-2.36 (m, 1 H).

EXAMPLE 760(3)

methyl[6-(4-chloro-2-{(3S)-7-[5-chloro-2-(4-chloro-1H-1,2,3-triazol-1-yl)phenyl]-5-oxo-1,2,3,5-tetrahydro-3-indolizinyl}-1H-imidazol-5-yl)-3-pyridinyl]carbamate LC/MS $t_R$ 4.27 minutes; MS (ES⁺) m/z 597, 599 and 601 (M+H), 299, 300 and 301 [(M+2H)/2]$^b$ ¹H NMR (500 MHz, methanol-d₄) δ 8.64 (d, 1 H), 8.28 (s, 1 H), 8.01-7.92 (m, 2 H), 7.72-7.67 (m, 2 H), 7.63 (d, 1 H), 6.15 (app. s, 2 H), 5.81 (dd, 1 H), 3.77 (s, 3 H), 3.44 (td, 1 H), 3.12 (ddd, 1 H), 2.63 (qd, 1 H), 2.50-2.42 (m, 1 H).

EXAMPLE 761 formic acid-2-methoxyethyl[6-(4-chloro-2-{(3S)-7-[5-chloro-2-(4-chloro-1H-1,2,3-triazol-1-yl)phenyl]-5-oxo-1,2,3,5-tetrahydro-3-indolizinyl}-1H-imidazol-5-yl)-3-pyridinyl]carbamate (1:1)

The compound prepared in Example 757(7) (54 mg) was treated as detailed in Example 338 to give the title compound after purification by high performance liquid chromatography [5 to 100% mobile phase B (0.1% formic acid in acetonitrile) in mobile phase A (0.1% aqueous formic acid)] as the formic acid salt having the following physical properties (4 mg).

LC/MS $t_R$ 4.33 minutes; MS (ES⁺) m/z 641, 643 and 645 (M+H), 321, 322 and 323 [(M+2H)/2]$^b$ ¹H NMR (500 MHz, DMSO-d₆) δ 12.98 (br. s, 1 H), 10.12 (br. s, 1 H), 8.75 (app. br. s, 1 H), 8.72 (s, 1 H), 8.51 (s, 0.5 H), 7.97 (d, 1 H), 7.90 (d, 1 H), 7.81-7.76 (m, 2 H), 7.74 (d, 1 H), 6.01 (s, 1 H), 5.94 (s, 1 H), 5.69 (dd, 1 H), 4.27-4.22 (m, 2 H), 3.62-3.56 (m, 2 H), 3.30 (s, 3 H), 3.25 (td, 1 H), 3.00 (dd, 1 H), 2.54-2.45 (obs. m, 1 H), 2.25-2.16 (m, 1 H).

EXAMPLE 762

(6S)-2-[5-chloro-2-(4-chloro-1H-1,2,3-triazol-1-yl)phenyl]-4-oxo-4H,6H,7H,8H-pyrrolo(1,2-a)pyrimidine-6-carboxylic acid

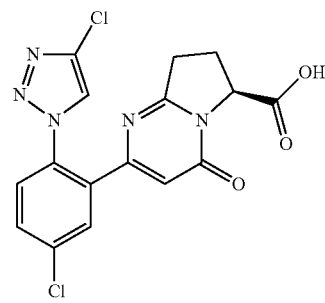 [SMILES: O=C(O)[C@@H]1CCc2nc(-c3cc(Cl)ccc3-n3cc(Cl)nn3)cc(=O)n21]

The same operation as in Example 753→Example 754→Example 755→Example 8 was conducted from the compound prepared in Example 334 to give the title compound having the following physical properties.

LC/MS $t_R$ 1.59 minutes; MS (ES⁺) m/z 392 and 394 (M+H)$^a$.

EXAMPLE 763(1) TO EXAMPLE 763(9)

The compounds of the present invention having the following physical data were prepared using the corresponding alpha-bromoketones from the compound prepared in Example 762 in the process of Example 51→Example 52.

EXAMPLE 763(1)

methyl[4-(2-{(6S)-2-[5-chloro-2-(4-chloro-1H-1,2,3-triazol-1-yl)phenyl]-4-oxo-4,6,7,8-tetrahydropyrrolo[1,2-a]pyrimidin-6-yl}-1H-imidazol-5-yl)phenyl]carbamate In the step corresponding to Example 51 in the process, methyl[4-(bromoacetyl)-phenyl]carbamate [J. Am. Chem. Soc. 119(10), 2453 (1997)] was used.

LC/MS $t_R$ 3.24 minutes; MS (ES$^+$) m/z 563 (M+H)$^b$ $^1$H NMR (500 MHz, methanol-d$_4$) δ 8.36 (s, 1 H), 7.88 (d, 1 H), 7.72 (dd, 1 H), 7.64 (d, 1 H), 7.61-7.51 (m, 2 H), 7.50-7.37 (m, 2 H), 7.26 (br. s, 1 H), 6.16 (s, 1 H), 5.74 (dd, 1 H), 3.73 (s, 3 H), 3.39 (td, 1 H), 3.01 (ddd, 1 H), 2.69 (qd, 1 H), 2.51-2.35 (m, 1 H).

EXAMPLE 763(2)

2-methoxyethyl[4-(2-{(6S)-2-[5-chloro-2-(4-chloro-1H-1,2,3-triazol-1-yl)phenyl]-4-oxo-4,6,7,8-tetrahydropyrrolo[1,2-a]pyrimidin-6-yl}-1H-imidazol-5-yl)phenyl]carbamate In the step corresponding to Example 51 in the process, the compound prepared in Example 324 was used.

LC/MS $t_R$ 3.29 minutes; MS (ES$^+$) m/z 607 (M+H)$^b$ $^1$H NMR (500 MHz, methanol-d$_4$) δ 8.38 (s, 1 H), 7.89 (d, 1 H), 7.73 (dd, 1 H), 7.65 (d, 1 H), 7.63-7.53 (m, 2 H), 7.49-7.39 (m, 2 H), 7.29 (br. s, 1 H), 6.17 (s, 1 H), 5.75 (dd, 1 H), 4.30-4.21 (m, 2 H), 3.70-3.61 (m, 2 H), 3.48-3.35 (m, 4 H), 3.02 (ddd, 1 H), 2.71 (qd, 1 H), 2.51-2.33 (m, 1 H).

EXAMPLE 763(3)

methyl[4-(2-{(6S)-2-[5-chloro-2-(4-chloro-1H-1,2,3-triazol-1-yl)phenyl]-4-oxo-4,6,7,8-tetrahydropyrrolo[1,2-a]pyrimidin-6-yl}-4-methyl-1H-imidazol-5-yl)phenyl]carbamate In the step corresponding to Example 51 in the process, the compound prepared in Example 78 was used.

LC/MS $t_R$ 3.19 minutes; MS (ES$^+$) m/z 577 (M+H)$^b$ $^1$H NMR (500 MHz, methanol-d$_4$) δ 8.38 (s, 1 H), 7.89 (d, 1 H), 7.73 (dd, 1 H), 7.65 (d, 1 H), 7.55-7.39 (m, 4 H), 6.16 (s, 1 H), 5.69 (dd, 1 H), 3.78-3.71 (s, 3 H), 3.47-3.35 (m, 1 H), 3.01 (ddd, 1 H), 2.69 (qd, 1 H), 2.46-2.20 (m, 4 H).

EXAMPLE 763(4)

2-methoxyethyl[4-(2-{(6S)-2-[5-chloro-2-(4-chloro-1H-1,2,3-triazol-1-yl)phenyl]-4-oxo-4,6,7,8-tetrahydropyrrolo[1,2-a]pyrimidin-6-yl}-4-methyl-1H-imidazol-5-yl)phenyl]carbamate In the step corresponding to Example 51 in the process, the compound prepared in Example 481 was used.

LC/MS $t_R$ 3.20 minutes; MS (ES$^+$) m/z 621 (M+H)$^b$ $^1$H NMR (500 MHz, methanol-d$_4$) δ 8.39 (s, 1 H), 7.90 (d, 1 H), 7.74 (dd, 1 H), 7.66 (d, 1 H), 7.58-7.36 (m, 4 H), 6.17 (s, 1 H), 5.71 (dd, 1 H), 4.35-4.23 (m, 2 H), 3.72-3.61 (m, 2 H), 3.49-3.36 (m, 4 H), 3.02 (ddd, 1 H), 2.80-2.60 (m, 1 H), 2.52-2.23 (m, 4H).

EXAMPLE 763(5)

(6S)-6-[5-(6-amino-3-pyridinyl)-1H-imidazol-2-yl]-2-[5-chloro-2-(4-chloro-1H-1,2,3-triazol-1-yl)phenyl]-7,8-dihydropyrrolo[1,2-a]pyrimidin-4(6H)-one In the step corresponding to Example 51 in the process, the compound prepared in Example 193 was used.

LC/MS $t_R$ 2.86 minutes; MS (ES$^+$) m/z 506 (M+H)$^b$ $^1$H NMR (500 MHz, methanol-d$_4$) δ 8.27 (s, 1 H), 8.10 (s, 1 H), 7.79 (d, 1 H), 7.70-7.60 (m, 2 H), 7.55 (d, 1 H), 7.12 (br. s, 1 H), 6.52 (d, 1 H), 6.06 (s, 1 H), 5.63 (dd, 1 H), 3.29 (td, 1 H), 2.92 (ddd, 1 H), 2.65-2.53 (m, 1 H), 2.36-2.26 (m, 1 H).

EXAMPLE 763(6)

formic acid—(6S)-2-[5-chloro-2-(4-chloro-1H-1,2,3-triazol-1-yl)phenyl]-6-{5-[6-(methylamino)-3-pyridinyl]-1H-imidazol-2-yl}-7,8-dihydropyrrolo[1,2-a]pyrimidin-4(6H)-one (1:1)

In the step corresponding to Example 51 in the process, the compound prepared in Example 551 was used. In the step corresponding to Example 52 in the process, high performance liquid chromatography [5 to 100% mobile phase B (0.1% formic acid in acetonitrile) in mobile phase A (0.1% aqueous formic acid)] was used to give the title product as the formic acid salt.

LC/MS $t_R$ 2.81 minutes; MS (ES$^+$) m/z 520 (M+H)$^b$ $^1$H NMR (500 MHz, methanol-d$_4$) δ 8.38 (s, 1 H), 8.22 (s, 1 H), 8.20 (s, 1 H), 7.94-7.87 (m, 2 H), 7.73 (dd, 1 H), 7.65 (d, 1 H), 7.31 (s, 1 H), 6.73 (d, 1 H), 6.17 (s, 1 H), 5.74 (dd, 1 H), 3.46-3.35 (m, 1 H), 3.03 (ddd, 1 H), 2.94 (s, 3 H), 2.77-2.64 (m, 1 H), 2.48-2.33 (m, 1 H).

EXAMPLE 763(7)

formic acid-methyl[6-(2-{(6S)-2-[5-chloro-2-(4-chloro-1H-1,2,3-triazol-1-yl)phenyl]-4-oxo-4,6,7,8-tetrahydropyrrolo[1,2-a]pyrimidin-6-yl}-1H-imidazol-5-yl)-3-pyridinyl]carbamate (1:1)

In the step corresponding to Example 51 in the process, the compound prepared in Example 712 was used. In the step corresponding to Example 52 in the process, high performance liquid chromatography [5 to 100% mobile phase B (0.1% formic acid in acetonitrile) in mobile phase A (0.1% aqueous formic acid)] was used to give the title product as the formic acid salt.

LC/MS $t_R$ 3.16 minutes; MS (ES$^+$) m/z 564 (M+H)$^b$ $^1$H NMR (500 MHz, methanol-d$_4$) δ 8.58-8.53 (m, 1 H), 8.36 (s, 1 H), 8.18 (s, 1 H), 7.96-7.90 (m, 1 H), 7.88 (d, 1 H), 7.78-7.68 (m, 2 H), 7.66-7.61 (m, 1 H), 7.51 (s, 1H), 6.18 (s, 1 H), 5.77 (dd, 1 H), 3.76 (s, 3 H), 3.41 (td, 1 H), 3.01 (ddd, 1 H), 2.70 (qd, 1 H), 2.45 (tdd, 1 H).

EXAMPLE 763(8)

2-methoxyethyl[6-(2-{(6S)-2-[5-chloro-2-(4-chloro-1H-1,2,3-triazol-1-yl)phenyl]-4-oxo-4,6,7,8-tetrahydropyrrolo[1,2-a]pyrimidin-6-yl}-1H-imidazol-5-yl)-3-pyridinyl]carbamate In the step corresponding to Example 51 in the process, the compound prepared in Example 713 was used.

LC/MS $t_R$ 3.16 minutes; MS (ES$^+$) m/z 608 (M+H)$^b$
$^1$H NMR (500 MHz, methanol-d$_4$) δ 8.58 (app. br. s, 1 H), 8.39 (s, 1 H), 7.96 (d, 1 H), 7.90 (d, 1 H), 7.82-7.72 (m, 2 H), 7.67 (d, 1 H), 7.53 (br. s, 1 H), 6.20 (s, 1 H), 5.79 (dd, 1 H), 4.33-4.29 (m, 2 H), 3.69-3.65 (m, 2 H), 3.48-3.38 (m, 4 H), 3.04 (ddd, 1H), 2.77-2.67 (m, 1 H), 2.51-2.42 (m, 1 H).

EXAMPLE 763(9)

formic acid-4-(2-{(6S)-2-[5-chloro-2-(4-chloro-1H-1,2,3-triazol-1-yl)phenyl]-4-oxo-4,6,7,8-tetrahydro-pyrrolo[1,2-a]pyrimidin-6-yl}-1H-imidazol-5-yl) benzamide (1:1)

In the step corresponding to Example 51 in the process, the compound prepared in Example 119 was used. In the step corresponding to Example 52 in the process, high performance liquid chromatography [5 to 100% mobile phase B (0.1% formic acid in acetonitrile) in mobile phase A (0.1% aqueous formic acid)] was used to give the title product as the formic acid salt.
LC/MS $t_R$ 3.09 minutes; MS (ES$^+$) m/z 533 and 535 (M+H)$^b$
$^1$H NMR (500 MHz, methanol-d$_4$) δ 8.37 (s, 1 H), 8.35 (br. s, 1 H), 7.92-7.83 (m, 3 H), 7.77 (d, 2 H), 7.72 (dd, 1 H), 7.64 (d, 1 H), 7.49 (s, 1 H), 6.17 (s, 1 H), 5.76 (dd, 1 H), 3.41 (td, 1 H), 3.03 (ddd, 1 H), 2.71 (qd, 1 H), 2.49-2.39 (m, 1 H).

EXAMPLE 764 methyl[5-(2-{(6S)-2-[5-chloro-2-(4-chloro-1H-1,2,3-triazol-1-yl)phenyl]-4-oxo-4,6,7,8-tetrahydropyrrolo[1,2-a]pyrimidin-6-yl}-1H-imidazol-5-yl)-2-pyridinyl]carbamate The compound prepared in Example 763(5) (175 mg) was treated with methyl chloroformate following the method of Example 128 to give the title compound having the following physical properties (162 mg).
LC/MS $t_R$ 3.33 minutes; MS (ES$^+$) m/z 565 (M+H)$^b$
$^1$H NMR (500 MHz, methanol-d$_4$) δ 8.58 (br. s, 1 H), 8.39 (s, 1 H), 8.04 (d, 1 H), 7.93-7.88 (m, 2 H), 7.75 (dd, 1 H), 7.69-7.64 (m, 1 H), 7.44 (br. s, 1 H), 6.19 (s, 1 H), 5.77 (dd, 1 H), 3.79 (s, 3 H), 3.48-3.38 (m, 1 H), 3.05 (ddd, 1 H), 2.79-2.68 (m, 1 H), 2.51-2.41 (m, 1 H).

EXAMPLE 765

2-methoxyethyl[5-(2-{(6S)-2-[5-chloro-2-(4-chloro-1H-1,2,3-triazol-1-yl)phenyl]-4-oxo-4,6,7,8-tetrahy-dropyrrolo[1,2-a]pyrimidin-6-yl}-1H-imidazol-5-yl)-2-pyridinyl]carbamate The compound prepared in Example 763(5) (175 mg) was treated with 2-methoxyethyl chloroformate following the method of Example 128 to give the title compound having the following physical properties (116 mg).
LC/MS $t_R$ 3.38 minutes; MS (ES$^+$) m/z 608 (M+H)$^b$
$^1$H NMR (500 MHz, methanol-d$_4$) δ 8.58 (br. s, 1 H), 8.39 (s, 1 H), 8.04 (d, 1 H), 7.94-7.88 (m, 2 H), 7.75 (dd, 1 H), 7.69-7.65 (m, 1 H), 7.44 (br. s, 1 H), 6.19 (s, 1 H), 5.77 (dd, 1 H), 4.34-4.31 (m, 2 H), 3.69-3.67 (m, 2 H), 3.48-3.38 (m, 4 H), 3.05 (ddd, 1H), 2.73 (qd, 1 H), 2.46 (m, 1 H).

EXAMPLE 766(1) TO EXAMPLE 766(7)

The compounds of the present invention having the following physical data were synthesised from the compounds prepared in Examples 763(1), 763(2), 763(6), 763(7), 763(8), 764 and 765 using the method as detailed in Example 338.

EXAMPLE 766(1)

methyl[4-(4-chloro-2-{(6S)-2-[5-chloro-2-(4-chloro-1H-1,2,3-triazol-1-yl)phenyl]-4-oxo-4,6,7,8-tetrahy-dropyrrolo[1,2-a]pyrimidin-6-yl}-1H-imidazol-5-yl) phenyl]carbamate LC/MS $t_R$ 4.22 minutes; MS (ES$^+$) m/z 597 (M+H)$^b$
$^1$H NMR (500 MHz, DMSO-d$_6$) δ 12.91 (s, 1 H), 9.81 (s, 1 H), 8.77 (s, 1 H), 7.96 (d, 1H), 7.85-7.80 (m, 1 H), 7.77-7.74 (m, 1 H), 7.62-7.58 (m, 2 H), 7.57-7.52 (m, 2 H), 6.15 (s, 1 H), 5.58 (dd, 1 H), 3.68 (s, 3 H), 3.24-3.15 (m, 1 H), 2.86 (ddd, 1 H), 2.66-2.57 (m, 1 H), 2.23-2.15 (m, 1 H).

EXAMPLE 766(2)

2-methoxyethyl[4-(4-chloro-2-{(6S)-2-[5-chloro-2-(4-chloro-1H-1,2,3-triazol-1-yl)phenyl]-4-oxo-4,6,7,8-tetrahydropyrrolo[1,2-a]pyrimidin-6-yl}-1H-imi-dazol-5-yl)phenyl]carbamate LC/MS $t_R$ 4.22 minutes; MS (ES+) m/z 641 (M+H)$^b$
$^1$H NMR (500 MHz, methanol-d$_4$) δ 8.39 (s, 1 H), 7.91 (d, 1 H), 7.75 (dd, 1 H), 7.69-7.63 (m, 3 H), 7.55 (d, 2 H), 6.20 (s, 1 H), 5.70 (dd, 1 H), 4.32-4.28 (m, 2 H), 3.69-3.66 (m, 2 H), 3.45-3.37 (m, 4 H), 3.03 (ddd, 1 H), 2.72 (qd, 1 H), 2.39 (tdd, 1 H).

EXAMPLE 766(3)

(6S)-2-[5-chloro-2-(4-chloro-1H-1,2,3-triazol-1-yl) phenyl]-6-{4-chloro-5-[6-(methylamino)-3-pyridi-nyl]-1H-imidazol-2-yl}-7,8-dihydropyrrolo[1,2-a] pyrimidin-4(6H)-one LC/MS $t_R$ 3.05 minutes; MS (ES$^+$) m/z 554 (M+H)$^b$
$^1$H NMR (500 MHz, methanol-d$_4$) δ 8.36 (s, 1 H), 8.26 (d, 1 H), 7.89 (d, 1 H), 7.77-7.69 (m, 2 H), 7.65 (d, 1 H), 6.59 (d, 1 H), 6.17 (s, 1 H), 5.66 (dd, 1 H), 3.37 (qd, 1 H), 3.00 (ddd, 1 H), 2.89 (s, 3 H), 2.69 (qd, 1 H), 2.37 (tdd, 1 H).

EXAMPLE 766(4)

formic acid-methyl[6-(4-chloro-2-{(6S)-2-[5-chloro-2-(4-chloro-1H-1,2,3-triazol-1-yl)phenyl]-4-oxo-4,6,7,8-tetrahydropyrrolo[1,2-a]pyrimidin-6-yl}-1H-imidazol-5-yl)-3-pyridinyl]carbamate (1:1)

Purification by high performance liquid chromatography [5 to 100% mobile phase B (0.1% formic acid in acetonitrile) in mobile phase A (0.1% aqueous formic acid)] gave the title product as the formic acid salt.
LC/MS $t_R$ 4.19 minutes; MS (ES$^+$) m/z 598 (M+H)$^b$
$^1$H NMR (500 MHz, methanol-d$_4$) δ 8.69 (s, 1 H), 8.39 (s, 1 H), 8.37 (s, 1 H), 8.02-7.94 (m, 2 H), 7.90 (d, 1 H), 7.77-7.71 (m, 1 H), 7.66 (d, 1 H), 6.19 (s, 1 H), 5.75 (dd, 1

H), 3.78 (s, 3 H), 3.41-3.34 (m, 1 H), 3.01 (ddd, 1 H), 2.75-2.65 (m, 1 H), 2.44-2.34 (m, 1 H).

EXAMPLE 766(5)

2-methoxyethyl[6-(4-chloro-2-{(6S)-2-[5-chloro-2-(4-chloro-1H-1,2,3-triazol-1-yl)phenyl]-4-oxo-4,6,7,8-tetrahydropyrrolo[1,2-a]pyrimidin-6-yl}-1H-imidazol-5-yl)-3-pyridinyl]carbamate LC/MS $t_R$ 4.17 minutes; MS (ES$^+$) m/z 642 (M+H)$^b$ $^1$H NMR (500 MHz, DMSO-d$_6$) δ 13.11 (br. s, 1 H), 10.12 (br. s, 1 H), 8.77 (s, 1 H), 8.76 (d, 1 H), 7.99-7.96 (m, 2 H), 7.93-7.90 (m, 1 H), 7.85-7.81 (m, 1 H), 7.78-7.74 (m, 1 H), 6.13 (s, 1 H), 5.67 (dd, 1 H), 4.26-4.23 (m, 2 H), 3.60-3.58 (m, 2 H), 3.30 (s, 3 H), 3.21-3.13 (m, 1 H), 2.90-2.82 (m, 1 H), 2.61-2.55 (m, 1 H), 2.19-2.12 (m, 1 H).

EXAMPLE 766(6)

methyl[5-(4-chloro-2-{(6S)-2-[5-chloro-2-(4-chloro-1H-1,2,3-triazol-1-yl)phenyl]-4-oxo-4,6,7,8-tetrahydropyrrolo[1,2-a]pyrimidin-6-yl}-1H-imidazol-5-yl)-2-pyridinyl]carbamate LC/MS $t_R$ 4.05 minutes; MS (ES$^+$) m/z 598 (M+H)$^b$ $^1$H NMR (500 MHz, DMSO-d$_6$) δ 13.11 (br. s, 1 H), 10.38 (s, 1H), 8.77 (s, 1 H), 8.57 (s, 1 H), 8.08-8.01 (m, 1 H), 7.98-7.89 (m, 2 H), 7.86-7.79 (m, 1 H), 7.78-7.71 (m, 1 H), 6.15 (s, 1 H), 5.59 (dd, 1 H), 3.69 (s, 3 H), 3.21 (td, 1 H), 2.87 (ddd, 1 H), 2.68-2.58 (m, 1 H), 2.30-2.12 (m, 1 H).

EXAMPLE 766(7)

2-methoxyethyl[5-(4-chloro-2-{(6S)-2-[5-chloro-2-(4-chloro-1H-1,2,3-triazol-1-yl)phenyl]-4-oxo-4,6,7,8-tetrahydropyrrolo[1,2-a]pyrimidin-6-yl}-1H-imidazol-5-yl)-2-pyridinyl]carbamate LC/MS $t_R$ 4.07 minutes; MS (ES$^+$) m/z 642 (M+H)$^b$ $^1$H NMR (500 MHz, DMSO-d$_6$) δ 13.12 (br. s, 1 H), 10.39 (s, 1 H), 8.80-8.76 (s, 1 H), 8.60-8.54 (m, 1 H), 8.07-8.01 (m, 1 H), 7.98-7.89 (m, 2 H), 7.86-7.80 (m, 1 H), 7.78-7.72 (m, 1 H), 6.18-6.12 (s, 1 H), 5.59 (dd, 1 H), 4.30-4.17 (m, 2 H), 3.62-3.53 (m, 2 H), 3.30-3.27 (s, 3 H), 3.25-3.14 (m, 1 H), 2.87 (ddd, 1 H), 2.61 (qd, 1 H), 2.27-2.13 (m, 1 H).

EXAMPLE 767

(6S)-6-[5-(6-amino-3-pyridinyl)-4-chloro-1H-imidazol-2-yl]-2-[5-chloro-2-(4-chloro-1H-1,2,3-triazol-1-yl)phenyl]-7,8-dihydropyrrolo[1,2-a]pyrimidin-4(6H)-one The compound prepared in Example 763(5) (160 mg) was treated as detailed in Example 44 to give the title compound having the following physical properties (60 mg).

LC/MS $t_R$ 3.11 minutes; MS (ES$^+$) m/z 541 (M+H)$^b$ $^1$H NMR (500 MHz, methanol-d$_4$) δ 8.39 (s, 1 H), 8.23 (d, 1 H), 7.91 (d, 1 H), 7.82-7.73 (m, 2 H), 7.67 (d, 1 H), 6.67 (dd, 1 H), 6.20 (s, 1 H), 5.69 (dd, 1 H), 3.45-3.36 (m, 1 H), 3.03 (ddd, 1 H), 2.75-2.67 (m, 1 H), 2.44-2.35 (m, 1 H).

EXAMPLE 768

(3S)-7-[2-(4-chloro-1H-1,2,3-triazol-1-yl)-5-methylphenyl]-5-oxo-1,2,3,5-tetrahydroindolizine-3-carboxylic acid

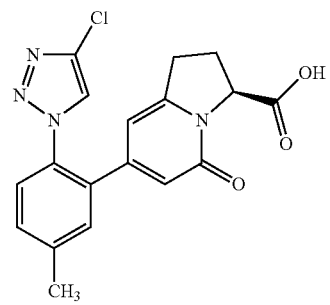 [SMILES: Cc1ccc(-n2cc(Cl)nn2)c(-c2cc3n(c(=O)c2)[C@H](C(=O)O)CC3)c1]

The same operation as in Example 7→Example 753→Example 754→Example 755→Example 8 was conducted from the compound prepared in Example 6 to give the title compound having the following physical properties. (Note: in the step corresponding to Example 7 in the operation, 2-amino-5-methylphenylboronic acid pinacol ester and 1,1'-bis(diphenylphosphino)ferrocene palladium (II) dichloride dichloromethane complex were used).

LC/MS $t_R$ 1.63 minutes; MS (ES$^+$) m/z 371 and 373 (M+H)$^a$.

EXAMPLE 769(1) TO EXAMPLE 769(5)

The compounds of the present invention having the following physical data were prepared using the corresponding alpha-bromoketones from the compound prepared in Example 768 in the process of Example 51→Example 52.

EXAMPLE 769(1)

methyl[4-(2-{(3S)-7-[2-(4-chloro-1H-1,2,3-triazol-1-yl)-5-methylphenyl]-5-oxo-1,2,3,5-tetrahydro-3-indolizinyl}-1H-imidazol-5-yl)phenyl]carbamate In the step corresponding to Example 51 in the process, methyl[4-(bromoacetyl)-phenyl]carbamate [J. Am. Chem. Soc. 119(10), 2453 (1997)] was used.

LC/MS tR 3.19 minutes; MS (ES+) m/z 542 (M+H)$^b$ $^1$H NMR (500 MHz, methanol-d$_4$) δ 8.23 (s, 1 H), 7.57 (d, 2 H), 7.49-7.47 (m, 2 H), 7.47-7.42 (m, 3 H), 7.23 (s, 1 H), 6.13-6.10 (m, 2 H), 5.79 (dd, 1 H), 3.74 (s, 3 H), 3.51-3.42 (m, 1 H), 3.11 (ddd, 1 H), 2.69-2.59 (m, 1 H), 2.52-2.47 (m, 4 H).

EXAMPLE 769(2)

2-methoxyethyl[4-(2-{(3S)-7-[2-(4-chloro-1H-1,2,3-triazol-1-yl)-5-methylphenyl]-5-oxo-1,2,3,5-tetrahydro-3-indolizinyl}-1H-imidazol-5-yl)phenyl]carbamate In the step corresponding to Example 51 in the process, the compound prepared in Example 324 was used.

LC/MS tR 3.24 minutes; MS (ES+) m/z 586 (M+H)$^b$
$^1$H NMR (500 MHz, methanol-d$_4$) δ 8.23 (s, 1 H), 7.57 (br. s, 2 H), 7.49-7.38 (m, 5 H), 7.33-7.13 (m, 1 H), 6.11 (s, 2 H), 5.79 (dd, 1 H), 4.29-4.24 (m, 2 H), 3.67-3.62 (m, 2H), 3.51-3.41 (m, 1 H), 3.39 (s, 3 H), 3.11 (ddd, 1 H), 2.68-2.58 (m, 1 H), 2.55-2.42 (m, 4 H).

EXAMPLE 769(3)

methyl[4-(2-{(3S)-7-[2-(4-chloro-1H-1,2,3-triazol-1-yl)-5-methylphenyl]-5-oxo-1,2,3,5-tetrahydro-3-indolizinyl}-4-methyl-1H-imidazol-5-yl)phenyl]carbamate In the step corresponding to Example 51 in the process, the compound prepared in Example 78 was used.
LC/MS tR 3.18 minutes; MS (ES+) m/z 556 (M+H)$^b$
$^1$H NMR (500 MHz, methanol-d$_4$) δ 8.24 (s, 1 H), 7.51-7.44 (m, 5 H), 7.44-7.40 (m, 2H), 6.12 (s, 1 H), 6.11 (s, 1 H), 5.74 (dd, 1 H), 3.74 (s, 3 H), 3.51-3.42 (m, 1 H), 3.10 (ddd, 1 H), 2.67-2.58 (m, 1 H), 2.50 (s, 3 H), 2.49-2.42 (m, 1 H), 2.31 (s, 3 H).

EXAMPLE 769(4)

2-methoxyethyl[4-(2-{(3S)-7-[2-(4-chloro-1H-1,2,3-triazol-1-yl)-5-methylphenyl]-5-oxo-1,2,3,5-tetrahydro-3-indolizinyl}-4-methyl-1H-imidazol-5-yl)phenyl]carbamate In the step corresponding to Example 51 in the process, the compound prepared in Example 481 was used.
LC/MS tR 3.19 minutes; MS (ES+) m/z 600 (M+H)$^b$
$^1$H NMR (500 MHz, methanol-d$_4$) δ 8.23 (s, 1 H), 7.52-7.38 (m, 7 H), 6.14-6.08 (m, 2H), 5.77-5.71 (m, 1 H), 4.29-4.25 (m, 2 H), 3.67-3.62 (m, 2 H), 3.52-3.42 (m, 1 H), 3.39 (s, 3 H), 3.10 (ddd, 1 H), 2.65-2.57 (m, 1 H), 2.50 (s, 3 H), 2.49-2.41 (m, 1 H), 2.31 (br. s, 3 H).

EXAMPLE 769(5)

(3S)-3-[5-(6-amino-3-pyridinyl)-1H-imidazol-2-yl]-7-[2-(4-chloro-1H-1,2,3-triazol-1-yl)-5-methylphenyl]-2,3-dihydro-5(1H)-indolizinone In the step corresponding to Example 51 in the process, the compound prepared in Example 193 was used.
LC/MS tR 2.87 minutes; MS (ES+) m/z 485 (M+H)$^b$
$^1$H NMR (500 MHz, methanol-d$_4$) δ 8.23 (s, 1 H), 8.21 (br. s, 1 H), 7.75 (d, 1 H), 7.50-7.48 (m, 2 H), 7.46 (s, 1 H), 7.20 (br. s, 1 H), 6.61 (d, 1 H), 6.12 (s, 1 H), 6.11 (s, 1 H), 5.78 (dd, 1 H), 3.52-3.41 (m, 1 H), 3.18-3.08 (m, 1 H), 2.69-2.59 (m, 1 H), 2.50 (s, 3H), 2.55-2.45 (m, 1 H).

EXAMPLE 770 methyl[5-(2-{(3S)-7-[2-(4-chloro-1H-1,2,3-triazol-1-yl)-5-methylphenyl]-5-oxo-1,2,3,5-tetrahydro-3-indolizinyl}-1H-imidazol-5-yl)-2-pyridinyl]carbamate The compound prepared in Example 769(5) (140 mg) was treated with methyl chloroformate following the method of Example 128 to give the title compound having the following physical properties (84 mg).
LC/MS tR 3.32 minutes; MS (ES+) m/z 543 (M+H), 272 (M/2+H)$^b$
$^1$H NMR (500 MHz, methanol-d$_4$) δ 8.55 (br. s, 1 H), 8.22 (s, 1 H), 8.01 (d, 1 H), 7.87 (d, 1 H), 7.46-7.49 (m, 2 H), 7.45 (br. s, 1 H), 7.39 (br. s, 1 H), 6.11 (s, 2 H), 5.79 (dd, 1 H), 3.77 (s, 3 H), 3.41-3.53 (m, 1 H), 3.12 (ddd, 1 H), 2.64 (qd, 1 H), 2.46-2.55 (m, 4 H).

EXAMPLE 771

2-methoxyethyl[5-(2-{(3S)-7-[2-(4-chloro-1H-1,2,3-triazol-1-yl)-5-methylphenyl]-5-oxo-1,2,3,5-tetrahydro-3-indolizinyl}-1H-imidazol-5-yl)-2-pyridinyl]carbamate The compound prepared in Example 769(5) (140 mg) was treated with 2-methoxyethyl chloroformate following the method of Example 128 to give the title compound having the following physical properties (98 mg).
LC/MS tR 3.32 minutes; MS (ES+) m/z 587 (M+H), 294 (M/2+H)$^b$
$^1$H NMR (500 MHz, methanol-d$_4$) δ 8.57 (br. s, 1 H), 8.24 (s, 1 H), 8.03 (br. s, 1 H), 7.88 (d, 1 H), 7.51-7.48 (m, 2 H), 7.46 (s, 1 H), 7.42 (br. s, 1 H), 6.15-6.10 (m, 2 H), 5.80 (dd, 1 H), 4.34-4.29 (m, 2 H), 3.69-3.65 (m, 2 H), 3.53-3.44 (m, 1 H), 3.40 (s, 3H), 3.13 (ddd, 1 H), 2.70-2.60 (m, 1 H), 2.51 (s, 3 H), 2.57-2.47 (m, 1 H).

EXAMPLE 772(1) TO EXAMPLE 772(2)

The compounds of the present invention having the following physical data were synthesised from the compounds prepared in Examples 769(1) and 769(2) using the method as detailed in Example 338.

EXAMPLE 772(1)

methyl[4-(4-chloro-2-{(3S)-7-[2-(4-chloro-1H-1,2,3-triazol-1-yl)-5-methylphenyl]-5-oxo-1,2,3,5-tetrahydro-3-indolizinyl}-1H-imidazol-5-yl)phenyl]carbamate LC/MS tR 4.29 minutes; MS (ES+) m/z 576 (M+H)$^b$
$^1$H NMR (500 MHz, DMSO-d$_6$) δ 12.85 (br. s, 1 H), 9.80 (s, 1 H), 8.68 (s, 1 H), 7.63-7.59 (m, 2 H), 7.57-7.52 (m, 3 H), 7.52-7.46 (m, 2 H), 5.98 (s, 1 H), 5.86 (s, 1 H), 5.57 (dd, 1 H), 3.68 (s, 3 H), 3.31-3.25 (m, 1 H), 3.04-2.96 (m, 1 H), 2.57-2.53 (m, 1 H), 2.45 (s, 3 H), 2.23-2.16 (m, 1 H).

EXAMPLE 772(2)

2-methoxyethyl[4-(4-chloro-2-{(3S)-7-[2-(4-chloro-1H-1,2,3-triazol-1-yl)-5-methylphenyl]-5-oxo-1,2,3,5-tetrahydro-3-indolizinyl}-1H-imidazol-5-yl)phenyl]carbamate LC/MS tR 4.31 minutes; MS (ES+) m/z 620 (M+H)$^b$
$^1$H NMR (500 MHz, methanol-d$_4$) δ 8.23 (s, 1 H), 7.63 (d, 2 H), 7.53 (d, 2 H), 7.50-7.48 (m, 2 H), 7.47 (s, 1 H), 6.13 (s, 1 H), 6.11 (s, 1 H), 5.73 (dd, 1 H), 4.30-4.27 (m, 2 H), 3.67-3.64 (m, 2 H), 3.51-3.42 (m, 1 H), 3.40 (s, 3 H), 3.12 (ddd, 1 H), 2.69-2.60 (m, 1 H), 2.51 (s, 3 H), 2.44-2.37 (m, 1 H).

EXAMPLE 773(1) TO EXAMPLE 773(3)

The compounds of the present invention having the following physical data were synthesised from the compounds prepared in Examples 769(5), 770 and 771 using the method as detailed in Example 44

EXAMPLE 773(1)

(3S)-3-[5-(6-amino-3-pyridinyl)-4-chloro-1H-imidazol-2-yl]-7-[2-(4-chloro-1H-1,2,3-triazol-1-yl)-5-methylphenyl]-2,3-dihydro-5 (1H)-indolizinone LC/MS tR 3.05 minutes; MS (ES+) m/z 519 (M+H)[b]
$^1$H NMR (500 MHz, methanol-d$_4$) δ 8.23 (s, 1 H), 8.22 (d, 1 H), 7.77 (dd, 1 H), 7.50-7.48 (m, 2 H), 7.47 (s, 1 H), 6.65 (d, 1 H), 6.13 (s, 1 H), 6.10 (s, 1 H), 5.70 (dd, 1 H), 3.51-3.42 (m, 1 H), 3.11 (ddd, 1 H), 2.69-2.59 (m, 1 H), 2.51 (s, 3 H), 2.43-2.36 (m, 1 H).

EXAMPLE 773(2)

methyl[5-(4-chloro-2-{(3S)-7-[2-(4-chloro-1H-1,2,3-triazol-1-yl)-5-methylphenyl]-5-oxo-1,2,3,5-tetrahydro-3-indolizinyl}-1H-imidazol-5-yl)-2-pyridinyl]carbamate LC/MS tR 4.14 minutes; MS (ES+) m/z 577 (M+H)[b]
$^1$H NMR (500 MHz, methanol-d$_4$) δ 8.58 (d, 1 H), 8.23 (s, 1 H), 8.05-8.02 (m, 1 H), 8.00-7.96 (m, 1 H), 7.49-7.47 (m, 2 H), 7.46 (s, 1 H), 6.13 (s, 1 H), 6.11 (s, 1 H), 5.73 (dd, 1 H), 3.78 (s, 3 H), 3.52-3.43 (m, 1 H), 3.12 (ddd, 1 H), 2.70-2.61 (m, 1 H), 2.50 (s, 3 H), 2.44-2.37 (m, 1 H).

EXAMPLE 773(3)

2-methoxyethyl[5-(4-chloro-2-{(3S)-7-[2-(4-chloro-1H-1,2,3-triazol-1-yl)-5-methylphenyl]-5-oxo-1,2,3,5-tetrahydro-3-indolizinyl}-1H-imidazol-5-yl)-2-pyridinyl]carbamate LC/MS tR 4.15 minutes; MS (ES+) m/z 621 (M+H), 311 (M/2+H)[b]
$^1$H NMR (500 MHz, methanol-d$_4$) δ 8.58 (d, 1 H), 8.23 (s, 1 H), 8.07-8.03 (m, 1 H), 8.00-7.97 (m, 1 H), 7.50-7.48 (m, 2 H), 7.47 (s, 1 H), 6.14 (s, 1 H), 6.11 (s, 1 H), 5.72 (dd, 1 H), 4.34-4.30 (m, 2 H), 3.69-3.65 (m, 2 H), 3.52-3.43 (m, 1 H), 3.40 (s, 3H), 3.12 (ddd, 1 H), 2.70-2.61 (m, 1 H), 2.51 (s, 3 H), 2.45-2.37 (m, 1 H).

EXAMPLE 774

2-{4-[5-chloro-2-(1H-1,2,3,4-tetrazol-1-yl)phenyl]-6-methyl-2-oxo-1,2-dihydropyridin-1-yl}acetic acid

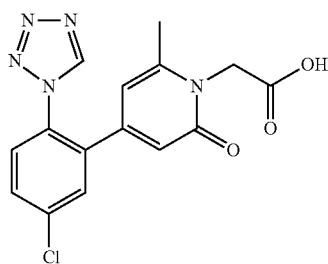 [SMILES: Cc1cc(-c2cc(Cl)ccc2-n2cnnn2)cc(=O)n1CC(=O)O]

The same operation as in Example 6→Example 7→Example 8→Example 9 was conducted from methyl 2-(4-hydroxy-6-methyl-2-oxo-1,2-dihydropyridin-1-yl)acetate [J. Het. Chem., 27(5), 1401 (1990)] to give the title compound having the following physical properties.
LC/MS t$_R$ 1.53 minutes; MS (ES$^+$) m/z 713 (2M+Na), 691 (2M+H), 368 (M+Na), 346 (M+H), 318 (M-N$_2$+H)$^a$.

EXAMPLE 775

1-{[5-(4-aminophenyl)-1H-imidazol-2-yl]methyl}-4-[5-chloro-2-(1H-tetrazol-1-yl)phenyl]-6-methyl-2 (1H)-pyridinone The same operation as in Example 51→Example 52→Example 74 was conducted the compound prepared in Example 774 to give the title compound having the following physical properties. (Note: in the step corresponding to Example 51 in the process, 2-bromo-1-(4-nitrophenyl)ethan-1-one was used).
LC/MS t$_R$ 2.87 minutes; MS (ES$^+$) m/z 459 (M+H)[b]
$^1$H NMR (500 MHz, methanol-d$_4$) δ 9.35 (s, 1 H), 7.75 (m, 2 H), 7.70 (d, 1 H), 7.45-7.35 (br. s, 2 H), 7.20-7.00 (br. s, 1 H), 6.72 (d, 2 H), 6.25 (s, 1 H), 5.95 (s, 1 H), 5.32 (s, 2 H), 2.67 (s, 2 H), 2.47 (s, 3 H).

EXAMPLE 776

2-methoxyethyl{4-[2-({4-[5-chloro-2-(1H-tetrazol-1-yl)phenyl]-6-methyl-2-oxo-1(2H)-pyridinyl}methyl)-1H-imidazol-5-yl]phenyl}carbamate The compound prepared in Example 775 (232 mg) was treated with 2-methoxyethyl chloroformate following the method of Example 128 to give the title compound having the following physical properties (70 mg).
LC/MS t$_R$ 3.22 minutes; MS (ES$^+$) m/z 561 (M+H)[b]
$^1$H NMR (500 MHz, methanol-d$_4$) δ 9.35 (s, 1 H), 7.75-7.65 (m, 3 H), 7.50-7.40 (br. d, 2 H), 7.30-7.20 (br. d, 2H), 7.17-7.05 (br. s, 1 H), 6.27 (s, 1 H), 5.95 (s, 1 H), 5.35 (s, 2 H), 4.25 (m, 2 H), 3.65 (m, 2 H), 3.4 (s, 3 H), 2.45 (s, 3 H).

EXAMPLE 777(1) TO EXAMPLE 777(8)

The compounds of the present invention having the following physical data were prepared using the corresponding alpha-bromoketones from the compound prepared in Example 774 in the process of Example 51→Example 52

EXAMPLE 777(1)

methyl{4-[2-({4-[5-chloro-2-(1H-tetrazol-1-yl)phenyl]-6-methyl-2-oxo-1(2H)-pyridinyl}methyl)-4-methyl-1H-imidazol-5-yl]phenyl}carbamate In the step corresponding to Example 51 in the process, the compound prepared in Example 78 was used.
LC/MS t$_R$ 3.06 minutes; MS (ES$^+$) m/z 531 (M+H)[b]
$^1$H NMR (500 MHz, DMSO-d$_6$) δ 11.80 (s, 1 H), 9.70 (m, 1 H), 9.60 (br. s, 1 H), 7.82 (m, 3 H), 7.50-7.35 (m, 4 H), 6.05 (s, 1 H), 5.95 (s, 1 H), 5.10 (s, 2 H), 3.15 (s, 3 H), 2.55 (s, 3 H), 2.30 (s, 3 H).

EXAMPLE 777(2)

2-methoxyethyl{4-[2-({4-[5-chloro-2-(1H-tetrazol-1-yl)phenyl]-6-methyl-2-oxo-1(2H)-pyridinyl}methyl)-4-methyl-1H-imidazol-5-yl]phenyl}carbamate In the step corresponding to Example 51 in the process, the compound prepared in Example 481 was used.
LC/MS $t_R$ 3.09 minutes; MS (ES$^+$) m/z 575 (M+H)$^b$
$^1$H NMR (500 MHz, DMSO-d$_6$) δ 11.76 (s, 1 H), 9.72 (m, 2 H), 7.80 (m, 3 H), 7.60-7.40 (m, 4 H), 6.27 (s, 1 H), 5.95 (s, 1 H), 5.10 (s, 2 H), 4.24 (m, 2 H), 3.60 (m, 2 H), 3.30 (s, 3 H), 2.5 (s, 3 H), 2.30 (s, 3 H).

EXAMPLE 777(3)

1-{[5-(6-amino-3-pyridinyl)-1H-imidazol-2-yl]methyl}-4-[5-chloro-2-(1H-tetrazol-1-yl)phenyl]-6-methyl-2(1H)-pyridinone In the step corresponding to Example 51 in the process, the compound prepared in Example 193 was used.
LC/MS $t_R$ 2.68 minutes; MS (ES$^+$) m/z 460 (M+H)$^b$
$^1$H NMR (250 MHz, DMSO-d$_6$) δ 11.89 (s, 1 H), 9.68 (s, 1 H), 8.24 (s, 1 H), 8.07-7.72 (m, 3 H), 7.65 (d, 1 H), 7.26 (s, 1 H), 6.41 (d, 1 H), 6.02 (s, 2 H), 5.96-5.70 (m, 2 H), 5.13 (s, 2 H), 3.32 (d, 3 H).

EXAMPLE 777(4)

4-[5-chloro-2-(1H-tetrazol-1-yl)phenyl]-6-methyl-1-({5-[6-(methylamino)-3-pyridinyl]-1H-imidazol-2-yl}methyl)-2(1H)-pyridinone In the step corresponding to Example 51 in the process, the compound prepared in Example 551 was used.
LC/MS $t_R$ 2.73 minutes; MS (ES$^+$) m/z 474 (M+H)$^b$
$^1$H NMR (500 MHz, methanol-d$_4$) δ 9.36 (s, 1 H), 8.32-8.22 (br. s., 1 H), 7.80-7.73 (m, 3 H), 7.70 (d, 1 H), 7.3-7.2 (br. s, 1 H), 6.55 (d, 1 H), 6.29 (s, 1 H), 6.00 (s, 1 H), 5.34 (s, 2 H), 2.89 (s, 3 H), 2.50 (s, 3 H).

EXAMPLE 777(5)

1-{[5-(6-amino-2-fluoro-3-pyridinyl)-1H-imidazol-2-yl]methyl}-4-[5-chloro-2-(1H-tetrazol-1-yl)phenyl]-6-methyl-2(1H)-pyridinone In the step corresponding to Example 51 in the process, the compound prepared in Example 215 was used.
LC/MS $t_R$ 3.04 minutes; MS (ES$^+$) m/z 478 (M+H), 500 (M+Na)$^b$
$^1$H NMR (500 MHz, DMSO-d$_6$) δ 11.95 (s, 1 H), 9.70 (s, 1 H), 7.95 (dd, 1 H), 7.80 (m, 3 H), 7.05 (s, 1 H), 6.35 (d, 1 H), 6.27 (s, 2 H), 6.05 (s, 1 H), 5.70 (s, 1 H), 5.16 (s, 2 H), 3.30 (s, 3 H).

EXAMPLE 777(6)

1-{[5-(6-amino-2-chloro-3-pyridinyl)-1H-imidazol-2-yl]methyl}-4-[5-chloro-2-(1H-tetrazol-1-yl)phenyl]-6-methyl-2(1H)-pyridinone In the step corresponding to Example 51 in the process, the compound prepared in Example 209 was used.
LC/MS $t_R$ 3.04 minutes; MS (ES$^+$) m/z 494 (M+H), 516 (M+Na)$^b$
$^1$H NMR (500 MHz, DMSO-d$_6$) δ 12.05 (s, 1 H), 9.70 (s, 1 H), 7.95 (d, 1 H), 7.80 (m, 3 H), 7.40 (s, 1 H), 6.50 (d, 1 H), 6.33 (s, 2 H), 6.08 (s, 1 H), 5.90 (s, 1 H), 5.17 (s, 2 H), 3.30 (s, 3 H).

EXAMPLE 777(7)

methyl{6-[2-({4-[5-chloro-2-(1H-tetrazol-1-yl)phenyl]-6-methyl-2-oxo-1(2H)-pyridinyl}methyl)-1H-imidazol-5-yl]-3-pyridinyl}carbamate In the step corresponding to Example 51 in the process, the compound prepared in Example 712 was used.
LC/MS $t_R$ 1.52 minutes; MS (ES$^+$) m/z 518 (M+H)$^a$
$^1$H NMR (250 MHz, methanol-d$_4$) δ 9.36 (s, 1 H), 8.56 (s, 1 H), 7.95 (d, 1 H), 7.73 (m, 4 H), 7.50 (s, 1 H), 6.26 (s, 1 H), 5.97 (s, 1 H), 5.49 (s, 1 H), 5.34 (s, 2 H), 3.76 (s, 3 H), 2.49 (s, 3 H).

EXAMPLE 777(8)

2-methoxyethyl{6-[2-({4-[5-chloro-2-(1H-tetrazol-1-yl)phenyl]-6-methyl-2-oxo-1(2H)-pyridinyl}methyl)-1H-imidazol-5-yl]-3-pyridinyl}carbamate In the step corresponding to Example 51 in the process, the compound prepared in Example 713 was used.
LC/MS $t_R$ 3.04 minutes; MS (ES$^+$) m/z 562 (M+H)$^b$
$^1$H NMR (250 MHz, methanol-d$_4$) δ 9.36 (s, 1 H), 8.56 (s, 1 H), 8.03-7.86 (m, 1 H), 7.87-7.60 (m, 4 H), 7.51 (s, 1 H), 6.27 (s, 1 H), 5.98 (s, 1 H), 5.35 (s, 2 H), 4.37-4.16 (m, 2 H), 3.82-3.62 (m, 2 H), 3.39 (s, 3 H), 2.49 (s, 3 H).

EXAMPLE 778 methyl{5-[2-({4-[5-chloro-2-(1H-tetrazol-1-yl)phenyl]-6-methyl-2-oxo-1(2H)-pyridinyl}methyl)-1H-imidazol-5-yl]-2-pyridinyl}carbamate The compound prepared in Example 777(3) (30 mg) was treated with methyl chloroformate following the method of Example 128 to give the title compound having the following physical properties (7 mg).
LC/MS $t_R$ 3.22 minutes; MS (ES$^+$) m/z 518 (M+H)$^b$
$^1$H NMR (250 MHz, DMSO-d$_6$) δ 12.10 (s, 1 H), 10.13 (s, 1 H), 9.68 (s, 1 H), 8.58 (s, 1 H), 8.01 (d, 1 H), 7.78 (d, 4 H), 7.52 (s, 1 H), 6.04 (s, 1 H), 5.91 (s, 1 H), 5.16 (s, 2 H), 3.65 (s, 3 H), 2.50 (obs. s, 3 H).

EXAMPLE 779

2-methoxyethyl{5-[2-({4-[5-chloro-2-(1H-tetrazol-1-yl)phenyl]-6-methyl-2-oxo-1(2H)-pyridinyl}methyl)-1H-imidazol-5-yl]-2-pyridinyl}carbamate The same operation as in Example 51→Example 128→Example 52 was conducted the compound prepared in Example 774 to give the title compound having the following physical properties. (Note: in the step corresponding to Example 51 in the process, the compound prepared in Example 193 was used. In the step corresponding to Example 128 in the process, 2-methoxyethyl chloroformate was used).

LC/MS $t_R$ 3.19 minutes; MS (ES$^+$) m/z 562 (M+H)$^b$
$^1$H NMR (250 MHz, DMSO-d$_6$) δ 10.15 (br. s., 2 H), 9.70 (s, 1 H), 8.60 (s, 1 H), 8.02 (d, 1 H), 7.79 (m, 4 H), 7.52 (br. s, 1 H), 6.08 (s, 1 H), 5.92 (s, 1 H), 5.20 (s, 2 H), 4.22 (m, 2 H), 3.58 (m, 2 H), 3.30 (s, 3 H), 2.50 (obs. s, 3 H).

EXAMPLE 780(1) TO EXAMPLE 780(5)

The compounds of the present invention having the following physical data were synthesised from the compounds prepared in Examples 776, 777(4), 777(7), 777(8) and 779 using the method as detailed in Example 338.

EXAMPLE 780(1)

2-methoxyethyl{4-[4-chloro-2-({4-[5-chloro-2-(1H-tetrazol-1-yl)phenyl]-6-methyl-2-oxo-1(2H)-pyridinyl}methyl)-1H-imidazol-5-yl]phenyl}carbamate LC/MS $t_R$ 4.08 minutes; MS (ES$^+$) m/z 595 (M+H)$^b$
$^1$H NMR (250 MHz, DMSO-d$_6$) δ 12.80 (br. s, 1 H), 9.86 (s, 1 H), 9.70 (s, 1 H), 7.80 (m, 3 H), 7.55 (dd, 4 H), 6.00 (s, 1 H), 5.90 (s, 1 H), 5.12 (s, 2 H), 4.20 (m, 2 H), 3.55 (m, 2 H), 3.30 (s, 3 H), 2.40 (s, 3 H).

EXAMPLE 780(2)

1-({4-chloro-5-[6-(methylamino)-3-pyridinyl]-1H-imidazol-2-yl}methyl)-4-[5-chloro-2-(1H-tetrazol-1-yl)phenyl]-6-methyl-2(1H)-pyridinone LC/MS $t_R$ 3.00 minutes; MS (ES$^+$) m/z 508 (M+H)$^b$
$^1$H NMR (500 MHz, DMSO-d$_6$) δ 9.71 (s, 1 H), 8.29 (s, 1 H), 7.80 (m, 3 H), 7.63 (m, 1 H), 6.71 (m, 1 H), 6.52 (d, 1 H), 6.03 (s, 1 H), 5.94 (s, 1 H), 5.15 (s, 2 H), 2.80 (s, 3 H), 2.45 (s, 3 H).

EXAMPLE 780(3)

methyl{6-[4-chloro-2-({4-[5-chloro-2-(1H-tetrazol-1-yl)phenyl]-6-methyl-2-oxo-1(2H)-pyridinyl}methyl)-1H-imidazol-5-yl]-3-pyridinyl}carbamate LC/MS $t_R$ 4.01 minutes; MS (ES$^+$) m/z 552 (M+H)$^b$
$^1$H NMR (250 MHz, DMSO-d$_6$) δ 12.92 (s, 1 H), 9.98 (s, 1 H), 9.70 (s, 1 H), 8.71 (s, 1 H), 7.98-7.91 (m, 1 H), 7.87 (d, 1 H), 7.81 (m, 3 H), 6.00 (s, 1 H), 5.93 (s, 1 H), 5.17 (s, 2 H), 3.69 (s, 3 H), 2.38 (s, 3 H).

EXAMPLE 780(4)

2-methoxyethyl{6-[4-chloro-2-({4-[5-chloro-2-(1H-tetrazol-1-yl)phenyl]-6-methyl-2-oxo-1(2H)-pyridinyl}methyl)-1H-imidazol-5-yl]-3-pyridinyl}carbamate LC/MS $t_R$ 4.03 minutes; MS (ES$^+$) m/z 596 (M+H)$^b$
$^1$H NMR (500 MHz, DMSO-d$_6$) δ 12.92 (s, 1 H), 10.09 (s, 1 H), 9.70 (s, 1 H), 8.73 (d, 1 H), 7.99-7.91 (m, 1 H), 7.87 (d, 1 H), 7.81 (m, 3 H), 6.00 (s, 1 H), 5.93 (s, 1 H), 5.17 (s, 2 H), 4.30-4.16 (m, 2 H), 3.65-3.52 (m, 2 H), 3.28 (s, 3 H), 2.38 (s, 3 H).

EXAMPLE 780(5)

2-methoxyethyl{5-[4-chloro-2-({4-[5-chloro-2-(1H-tetrazol-1-yl)phenyl]-6-methyl-2-oxo-1(2H)-pyridinyl}methyl)-1H-imidazol-5-yl]-2-pyridinyl}carbamate LC/MS $t_R$ 3.94 minutes; MS (ES$^+$) m/z 596 (M+H)$^b$
$^1$H NMR (500 MHz, DMSO-d$_6$) δ 9.72 (s, 1 H), 8.58 (s, 1 H), 8.03 (m, 1 H), 7.90 (m, 1 H), 7.82 (m, 4 H), 6.04 (s, 1 H), 5.95 (s, 1 H), 5.18 (s, 2 H), 4.25 (m, 2 H), 3.59 (m, 2 H), 3.30 (s, 3 H), 2.48 (s, 3 H).

EXAMPLE 781(1) TO EXAMPLE 781(2)

The compounds of the present invention having the following physical data were synthesised from the compounds prepared in Examples 777(3) and 777(5) using the method as detailed in Example 44.

EXAMPLE 781(1)

1-{[5-(6-amino-3-pyridinyl)-4-chloro-1H-imidazol-2-yl]methyl}-4-[5-chloro-2-(1H-tetrazol-1-yl)phenyl]-6-methyl-2(1H)-pyridinone LC/MS $t_R$ 3.05 minutes; MS (ES$^+$) m/z 494 (M+H)$^b$
$^1$H NMR (250 MHz, DMSO-d$_6$) δ 12.71 (s, 1 H), 9.70 (s, 1 H), 8.19 (d, 1 H), 7.97-7.70 (m, 3 H), 7.62 (d, 1 H), 6.49 (d, 1 H), 6.17 (s, 2 H), 6.01 (d, 1 H), 5.93 (s, 1 H), 5.11 (s, 2 H), 2.45 (m, 3 H).

EXAMPLE 781(2)

1-{[5-(6-amino-2-fluoro-3-pyridinyl)-4-chloro-1H-imidazol-2-yl]methyl}-4-[5-chloro-2-(1H-tetrazol-1-yl)phenyl]-6-methyl-2(1H)-pyridinone LC/MS $t_R$ 3.84 minutes; MS (ES$^+$) m/z 512 (M+H)$^b$
$^1$H NMR (250 MHz, methanol-d$_4$) δ 9.37 (s, 1 H), 7.79-7.64 (m, 4 H), 6.45 (m, 1 H), 6.23 (s, 1 H), 5.97 (s, 1 H), 5.28 (s, 2 H), 2.69 (s, 2 H), 2.45 (s, 3 H).

EXAMPLE 782

N-carbamoyl-5-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxamide To an N,N-dimethylformamide (1 mL) solution of the compound prepared in Example 347 (25 mg) was added (benzotriazol-1-yloxy)tris(dimethylamino)phosphonium hexafluorophosphate (26.2 mg), cyanamide (3.1 mg) and diisopropylethylamine (24.5 μL) and the mixture stirred at room temperature for 16 hours. To the reaction mixture, concentrated hydrochloric acid (1 mL) was added and the mixture stirred at room temperature for 24 hours then warmed to 50° C. and stirred a further 16 hours. The reaction mixture was cooled to room temperature, diluted with water (6 mL) and sufficient solid sodium hydrogen carbonate added to basify the supernatant to pH 9. The resultant suspension was extracted into a 1:1 mixture of ethyl acetate and propan-2-ol, the combined organic layers washed with saturated saline, dried and concentrated. The residue obtained on concentration was triturated with dichloromethane, the resultant precipitate being isolated by filtration to obtain the title compound having the following physical properties (5.3 mg).

LC/MS $t_R$ 3.29 minutes; MS (ES$^+$) m/z 548 (M+H)$^b$ $^1$H NMR (500 MHz, DMSO-d$_6$) δ 12.40 (br. s, 1 H), 10.50 (br. s, 1 H), 9.69 (s, 1 H), 8.09 (d, 1 H), 7.91 (br. s, 1 H), 7.84-7.75 (m, 3 H), 7.60 (s, 1 H), 7.33 (br. s, 1 H), 7.28 (d, 1 H), 5.99 (s, 1 H), 5.94 (s, 1 H), 5.60 (d, 1 H), 3.36-3.26 (obs. m, 1 H), 3.00 (dd, 1 H), 2.57-2.49 (obs. m, 1 H), 2.39-2.27 (m, 1 H).

EXAMPLE 783

(3S)-7-[5-chloro-2-(1H-tetrazol-1-yl)phenyl]-3-{5-[5-(methylsulfonyl)-2-thienyl]-1H-imidazol-2-yl}-2,3-dihydro-5(1H)-indolizinone The same operation as in Example 234→Example 51→Example 52 was conducted from 5-methanesulfonyl-thiophene-2-carboxylic acid to give the title compound having the following physical properties.

LC/MS $t_R$ 3.61 minutes; MS (ES$^+$) m/z 540 (M+H)$^b$ $^1$H NMR (500 MHz, CDCl$_3$) δ 11.21 (br. s, 1 H), 8.62 (s, 1 H), 7.62 (dd, 1 H), 7.59 (d, 1 H), 7.55 (d, 1 H), 7.52 (d, 1 H), 7.27 (obs. s, 1 H), 7.20 (d, 1 H), 6.28 (s, 1 H), 5.83 (d, 1 H), 5.81 (br. s, 1 H), 3.51-3.40 (m, 1 H), 3.31-3.22 (m, 1 H), 3.18 (s, 3 H), 3.05 (dd, 1 H), 2.59-2.45 (m, 1 H).

EXAMPLE 784

(3S)-3-{4-chloro-5-[5-(methylsulfonyl)-2-thienyl]-1H-imidazol-2-yl}-7-[5-chloro-2-(1H-tetrazol-1-yl)phenyl]-2,3-dihydro-5(1H)-indolizinone The compound prepared in Example 783 (100 mg) was treated as detailed in Example 338 to give the title compound having the following physical properties (60 mg).

LC/MS $t_R$ 3.91 minutes; MS (ES$^+$) m/z 596 and 598 (M+Na), 574 and 576 (M+H)$^b$ $^1$H NMR (500 MHz, CDCl$_3$) δ 12.35 (br. s, 1 H), 8.71 (s, 1 H), 7.68-7.60 (m, 2 H), 7.57 (d, 1 H), 7.56-7.52 (m, 1 H), 7.05 (app. br. s, 1 H), 6.32 (s, 1 H), 5.95 (s, 1 H), 5.84 (d, 1 H), 3.64-3.52 (m, 1 H), 3.22 (s, 3 H), 3.10 (dd, 1 H), 2.85 (app. br. s, 1 H), 2.65-2.52 (m, 1 H).

EXAMPLE 785

5-(2-{(3S)-7-[5-chloro-2-(1H-tetrazol-1-yl)phenyl]-5-oxo-1,2,3,5-tetrahydro-3-indolizinyl}-1H-imidazol-5-yl)-N-(methylsulfonyl)-2-thiophenecarboxamide The compound prepared in Example 347 (62 mg) was treated as detailed in Example 355 using methanesulfonamide in place of N-(2-hydroxyethyl)morpholine to give, on purification by high performance liquid chromatography [5 to 100% mobile phase B (0.1% formic acid in acetonitrile) in mobile phase A (0.1% aqueous formic acid)], the title compound having the following physical properties (11 mg).

LC/MS $t_R$ 3.47 minutes; MS (ES$^+$) m/z 583 (M+H)$^b$ $^1$H NMR (500 MHz, methanol-d$_4$) δ 9.36 (s, 1 H), 7.78-7.72 (m, 3 H), 7.71-7.67 (m, 1 H), 7.45 (s, 1 H), 7.29 (d, 1 H), 6.13 (s, 1 H), 6.10 (s, 1 H), 5.76 (dd, 1 H), 3.50-3.40 (m, 1 H), 3.33 (s, 3 H), 3.12 (ddd, 1 H), 2.69-2.60 (m, 1 H), 2.53-2.45 (m, 1 H).

EXAMPLE 786

5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-N-(methylsulfonyl)-2-thiophenecarboxamide The compound prepared in Example 785 (26 mg) was treated as detailed in Example 338 to give, on purification by high performance liquid chromatography [5 to 100% mobile phase B (0.1% formic acid in acetonitrile) in mobile phase A (0.1% aqueous formic acid)], the title compound having the following physical properties (4.5 mg).

LC/MS $t_R$ 3.91 minutes; MS (ES$^+$) m/z 617 and 619 (M+H)$^b$ $^1$H NMR (500 MHz, DMSO-d$_6$) δ 9.37 (s, 1 H), 7.82 (d, 1 H), 7.78-7.72 (m, 2 H), 7.71-7.66 (m, 1 H), 7.40 (d, 1 H), 6.14 (s, 1 H), 6.10 (s, 1 H), 5.70 (dd, 1 H), 3.49-3.39 (m, 1 H), 3.33 (s, 3 H), 3.12 (ddd, 1 H), 2.71-2.61 (m, 1 H), 2.42-2.34 (m, 1 H).

EXAMPLE 787

5-(2-{(3S)-7-[5-chloro-2-(1H-tetrazol-1-yl)phenyl]-5-oxo-1,2,3,5-tetrahydro-3-indolizinyl}-1H-imidazol-5-yl)-2-furoic acid The same operation as in Example 51→Example 52→Example 8→Example 55→Example 24 was conducted from the compound prepared in Example 662 to give the title compound having the following physical properties. (Note: in the step corresponding to Example 51 in the process, methyl 5-(2-bromoacetyl)furan-2-carboxylate [patent US2007265265] was used).

LC/MS $t_R$ 3.20 minutes; MS (ES$^+$) m/z 490 (M+H)$^b$ $^1$H NMR (500 MHz, DMSO-d$_6$) δ 13.02 (br. s, 1 H), 12.44 (br. s, 1 H), 9.69 (s, 1 H), 7.84-7.76 (m, 3 H), 7.50 (d, 1 H), 7.21 (d, 1 H), 6.63 (d, 1 H), 5.98 (s, 1 H), 5.94 (s, 1 H), 5.62 (dd, 1 H), 3.31-3.28 (m, 1 H), 3.00 (dd, 1 H), 2.56-2.52 (m, 1 H), 2.33-2.24 (m, 1 H).

EXAMPLE 788

5-(2-{(3S)-7-[5-chloro-2-(1H-tetrazol-1-yl)phenyl]-5-oxo-1,2,3,5-tetrahydro-3-indolizinyl}-1H-imidazol-5-yl)-2-furamide The compound prepared in Example 787 (40 mg) was treated as detailed in Example 114 to give the title compound having the following physical properties (16 mg).

LC/MS $t_R$ 3.07 minutes; MS (ES$^+$) m/z 489 (M+H)$^b$ $^1$H NMR (500 MHz, methanol-d$_4$) δ 9.37 (s, 1 H), 7.76-7.72 (m, 2 H), 7.71-7.66 (m, 1 H), 7.53 (br. s, 1 H), 7.16 (d, 1 H), 6.70 (d, 1 H), 6.14 (s, 1 H), 6.10 (s, 1 H), 5.78 (dd, 1 H), 3.48-3.39 (m, 1 H), 3.12 (ddd, 1 H), 2.66 (qd, 1 H), 2.51-2.40 (m, 1 H).

EXAMPLE 789

5-(2-{(3S)-7-[5-chloro-2-(1H-tetrazol-1-yl)phenyl]-5-oxo-1,2,3,5-tetrahydro-3-indolizinyl}-1H-imidazol-5-yl)-N-methyl-2-furamide The compound prepared in Example 787 (40 mg) was treated as detailed in Example 114 using methylamine hydrochloride in place of ammonium chloride to give the title compound having the following physical properties (19 mg).

LC/MS $t_R$ 3.18 minutes; MS (ES$^+$) m/z 502 (M+H)$^b$ $^1$H NMR (500 MHz, methanol-d$_4$) δ 9.38 (s, 1 H), 7.77-7.72 (m, 2 H), 7.71-7.67 (m, 1 H), 7.52 (br. s, 1 H), 7.10 (d, 1 H), 6.68 (d, 1 H), 6.14 (s, 1 H), 6.10 (s, 1 H), 5.78 (dd, 1 H), 3.48-3.39 (m, 1 H), 3.13 (ddd, 1 H), 2.92 (s, 3 H), 2.66 (qd, 1 H), 2.52-2.40 (m, 1 H).

EXAMPLE 790

5-(4-chloro-2-{(3S)-7-[5-chloro-2-(1H-1-tetrazol-1-yl)phenyl]-5-oxo-1,2,3,5-tetrahydro-3-indolizinyl}-1H-imidazol-5-yl)-2-furoic acid The compound prepared in Example 787 (50 mg) was treated using the method as detailed in Example 338 to give the title compound having the following physical properties (30 mg).

LC/MS $t_R$ 3.81 minutes; MS (ES$^+$) m/z 524 (M+H)$^b$ $^1$H NMR (500 MHz, DMSO-d$_6$) δ 13.53 (br. s, 1 H), 9.71 (s, 1 H), 7.82 (d, 1 H), 7.81-7.80 (m, 2 H), 7.25 (d, 1 H), 6.82 (d, 1 H), 5.98 (s, 1 H), 5.94 (s, 1 H), 5.60 (dd, 1 H), 3.27-3.23 (m, 1 H), 2.99 (ddd, 1 H), 2.56-2.52 (m, 1 H), 2.17 (dd, 1 H).

EXAMPLE 791

5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-furamide The compound prepared in Example 790 (60 mg) was treated as detailed in Example 114 to give the title compound having the following physical properties (9 mg).

LC/MS $t_R$ 3.64 minutes; MS (ES$^+$) m/z 523 (M+H)$^b$ $^1$H NMR (500 MHz, methanol-d$_4$) δ 9.37 (s, 1 H), 7.76-7.72 (m, 2 H), 7.71-7.67 (m, 1 H), 7.23 (d, 1 H), 6.84 (d, 1 H), 6.14 (s, 1 H), 6.10 (s, 1 H), 5.72 (dd, 1 H), 3.45 (td, 1 H), 3.12 (ddd, 1 H), 2.70-2.61 (m, 1 H), 2.42 (tdd, 1 H).

EXAMPLE 792 formic acid-5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-N-methyl-2-furamide (1:1)

The compound prepared in Example 790 (60 mg) was treated using the method as detailed in Example 114 using methylamine hydrochloride in place of ammonium chloride, to give the title compound after purification by high performance liquid chromatography [5 to 100% mobile phase B (0.1% formic acid in acetonitrile) in mobile phase A (0.1% aqueous formic acid)] as the formic acid salt having the following physical properties (12 mg).

LC/MS $t_R$ 3.76 minutes; MS (ES$^+$) m/z 537 (M+H)$^b$ $^1$H NMR (500 MHz, methanol-d$_4$) δ 9.37 (s, 1 H), 8.13 (br. s, 1 H), 7.77-7.72 (m, 2 H), 7.72-7.66 (m, 1 H), 7.17 (d, 1 H), 6.83 (d, 1 H), 6.14 (s, 1 H), 6.11 (s, 1 H), 5.72 (dd, 1 H), 3.45 (td, 1 H), 3.20-3.07 (m, 1 H), 2.94 (s, 3 H), 2.73-2.59 (m, 1 H), 2.43 (tdd, 1 H).

EXAMPLE 793 tert-butyl 4-{2-[(3S)-7-[5-chloro-2-(1H-1,2,3,4-tetrazol-1-yl)phenyl]-5-oxo-1,2,3,5-tetrahydroindolizin-3-yl]-1H-imidazol-5-yl}furan-2-carboxylate The same operation as in Example 139→Example 361→Example 51→Example 52 was conducted from tert-butyl 4-bromofuran-2-carboxylate [patent EP1489077, 2004] to give the title compound having the following physical properties.

LC/MS $t_R$ 1.81 minutes; MS (ES$^+$) m/z 546 (M+H), 490 (M-C(CH$_3$)$_3$+H)$^a$.

EXAMPLE 794

4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-furoic acid hydrochloride The compound prepared in Example 793 (100 mg) was treated as detailed in Example 363 to give the title compound as the hydrochloride salt having the following physical properties (17.7 mg).

LC/MS $t_R$ 2.85 minutes; MS (ES$^+$) m/z 490 (M+H)$^b$ $^1$H NMR (500 MHz, DMSO-d$_6$) δ 13.46 (br. s, 1 H), 9.71 (s, 1 H), 8.40 (br. s, 1 H), 7.89 (br. s, 1 H), 7.86-7.80 (m, 2 H), 7.72 (d, 1 H), 7.68 (s, 1 H), 6.05 (s, 1 H), 6.01 (s, 1 H), 5.77 (dd, 1 H), 3.34-3.28 (m, 1 H), 3.12-3.04 (m, 1 H), 2.72-2.62 (m, 1 H), 2.38-2.29 (m, 1 H).

EXAMPLE 795

4-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-furoic acid—formic acid (1:1)

The same operation as in Example 338→Example 363 was conducted from the compound prepared in Example 793 to give the title compound after purification by high performance liquid chromatography [5 to 100% mobile phase B (0.1% formic acid in acetonitrile) in mobile phase A (0.1% aqueous formic acid)] as the formic acid salt having the following physical properties.

LC/MS $t_R$ 3.70 minutes; MS (ES$^+$) m/z 524 (M+H)$^b$ $^1$H NMR (500 MHz, DMSO-d$_6$) δ 13.09 (br. s, 1 H), 9.71 (s, 1 H), 8.19 (s, 1 H), 8.18 (s, 0.5 H), 7.83-7.77 (m, 3 H), 7.48 (s, 1 H), 5.98 (s, 1 H), 5.93 (s, 1 H), 5.54 (dd, 1 H), 3.34-3.23 (m, 1 H), 2.98 (dd, 1 H), 2.58-2.48 (m, 1 H), 2.23-2.14 (m, 1 H).

EXAMPLE 796

2-methyl-2-propanyl 5-(2-{(3S)-7-[5-chloro-2-(1H-tetrazol-1-yl)phenyl]-5-oxo-1,2,3,5-tetrahydro-3-indolizinyl}-1H-imidazol-5-yl)-3-furoate The same operation as in Example 378→Example 139→Example 361→Example 51→Example 52 was conducted from 5-bromofuran-3-carboxylic acid to give the title compound having the following physical properties.

LC/MS $t_R$ 4.22 minutes; MS (ES$^+$) m/z 546 (M+H), 490 (M-C(CH$_3$)$_3$+H), 462 (M+N$_2$—C(CH$_3$)$_3$+H)$^b$ $^1$H NMR (250 MHz, methanol-d$_4$) δ 9.36 (s, 1 H), 7.98 (s, 1 H), 7.76-7.68 (m, 3 H), 7.30 (s, 1 H), 6.80 (s, 1 H), 6.12

(s, 1 H), 6.09 (s, 1 H), 5.76 (dd, 1 H), 3.51-3.38 (m, 1 H), 3.17-3.04 (m, 1 H), 2.70-2.57 (m, 1 H), 2.50-2.40 (m, 1 H), 1.55 (s, 9 H).

EXAMPLE 797

5-(2-{(3S)-7-[5-chloro-2-(1H-tetrazol-1-yl)phenyl]-5-oxo-1,2,3,5-tetrahydro-3-indolizinyl}-1H-imidazol-5-yl)-3-furoic acid-formic acid (1:1)

The compound prepared in Example 796 (135 mg) was treated as detailed in Example 363 to give the title compound after purification by high performance liquid chromatography [5 to 100% mobile phase B (0.1% formic acid in acetonitrile) in mobile phase A (0.1% aqueous formic acid)] as the formic acid salt having the following physical properties (62.6 mg).

LC/MS $t_R$ 3.22 minutes; MS (ES$^+$) m/z 490 (M+H)$^b$ $^1$H NMR (500 MHz, DMSO-d$_6$) δ 12.32 (br. s, 1 H), 9.69 (s, 1 H), 8.18 (app. s, 2 H), 7.83-7.78 (m, 3 H), 7.36 (br. s, 1 H), 6.67 (br. s, 1 H), 5.98 (s, 1 H), 5.95 (s, 1 H), 5.61 (dd, 1 H), 3.39-3.30 (m, 1 H), 3.00 (dd, 1 H), 2.54-2.44 (obs. m, 1 H), 2.32-2.25 (m, 1 H).

EXAMPLE 798

2-(2-{(3S)-7-[5-chloro-2-(1H-tetrazol-1-yl)phenyl]-5-oxo-1,2,3,5-tetrahydro-3-indolizinyl}-1H-imidazol-5-yl)-1,3-oxazole-4-carboxylic acid The same operation as in Example 361→Example 51→Example 52→Example 8→Example 55→Example 24 was conducted from ethyl 2-acetyl-1,3-oxazole-4-carboxylate [patent WO2010/43116] to give the title compound after purification by high performance liquid chromatography [5 to 100% mobile phase B (0.1% formic acid in acetonitrile) in mobile phase A (0.1% aqueous formic acid)] as the formic acid salt having the following physical properties. (Note: in the step corresponding to Example 51 in the operation, the compound prepared in Example 11 was used).

LC/MS $t_R$ 3.16 minutes; MS (ES$^+$) m/z 491 (M+H)$^b$ $^1$H NMR (500 MHz, DMSO-d$_6$) δ 12.73 (br. s, 1 H), 9.71 (s, 1 H), 8.56 (br. s, 1 H), 8.20 (s, 0.5 H), 7.84-7.72 (m, 4 H), 6.00 (s, 1 H), 5.92 (s, 1 H), 5.64 (d, 1 H), 3.40-3.29 (obs. m, 1 H), 3.01 (dd, 1 H), 2.58-2.47 (obs. m, 1 H), 2.32-2.22 (m, 1 H).

EXAMPLE 799

5-(2-{(3S)-7-[5-chloro-2-(1H-tetrazol-1-yl)phenyl]-5-oxo-1,2,3,5-tetrahydro-3-indolizinyl}-1H-imidazol-5-yl)-1H-pyrrole-2-carboxylic acid The same operation as in Example 51→Example 52→Example 8→Example 55→Example 24 was conducted from methyl 5-(2-bromoacetyl)-1H-pyrrole-2-carboxylate [Chem. Pharm. Bull., 46(4), 559 (1998)] to give the title compound after purification by high performance liquid chromatography [5 to 100% mobile phase B (0.1% formic acid in acetonitrile) in mobile phase A (0.1% aqueous formic acid)] as the formic acid salt having the following physical properties. (Note: in the step corresponding to Example 51 in the operation, the compound prepared in Example 622 was used).

LC/MS $t_R$ 3.02 minutes; MS (ES$^+$) m/z 489 (M+H)$^b$ $^1$H NMR (250 MHz, DMSO-d$_6$) δ 12.04 (br. s, 1 H), 11.57 (br. s, 1 H), 9.69 (s, 1 H), 8.19 (s, 0.5 H), 7.85-7.75 (m, 3 H), 7.50 (br. s, 1 H), 6.71 (dd, 1 H), 6.33 (br. s, 1 H), 5.96 (s, 1 H), 5.94 (s, 1 H), 5.60 (dd, 1 H), 3.47-3.28 (obs. m, 1 H), 3.05-2.91 (m, 1H), 2.56-2.39 (obs. m, 1 H), 2.38-2.20 (m, 1 H).

EXAMPLE 800

4-(2-{(3S)-7-[5-chloro-2-(1H-tetrazol-1-yl)phenyl]-5-oxo-1,2,3,5-tetrahydro-3-indolizinyl}-1H-imidazol-5-yl)-1H-pyrrole-2-carboxylic acid The same operation as in Example 51→Example 52→Example 8→Example 55→Example 24 was conducted from ethyl 4-(2-chloroacetyl)-1H-pyrrole-2-carboxylate [Chem. Pharm. Bull., 44(1), 48 (1996)] to give the title compound after purification by high performance liquid chromatography [5 to 100% mobile phase B (0.1% formic acid in acetonitrile) in mobile phase A (0.1% aqueous formic acid)] having the following physical properties. (Note: in the step corresponding to Example 51 in the operation, the compound prepared in Example 11 was used).

LC/MS $t_R$ 2.74 minutes; MS (ES$^+$) m/z 489 (M+H)$^b$ $^1$H NMR (500 MHz, DMSO-d$_6$) δ 12.53-11.33 (m, 2 H), 9.69 (s, 1 H), 7.83-7.74 (m, 3 H), 7.28-6.77 (m, 3 H), 5.95 (s, 1 H), 5.93 (s, 1 H), 5.57 (d, 1 H), 3.42-3.31 (m, 1 H), 2.97 (dd, 1 H), 2.51-2.42 (m, 1 H), 2.26 (app. br. s, 1 H).

EXAMPLE 801

5-(2-{(3S)-7-[5-chloro-2-(1H-tetrazol-1-yl)phenyl]-5-oxo-1,2,3,5-tetrahydro-3-indolizinyl}-1H-imidazol-5-yl)-1H-pyrrole-3-carboxylic acid-formic acid (1:1)

The same operation as in Example 378→Example 139→Example 361→Example 51→Example 52→Example 363 was conducted from 5-bromo-1H-pyrrole-3-carboxylic acid to give the title compound after purification by high performance liquid chromatography [5 to 100% mobile phase B (0.1% formic acid in acetonitrile) in mobile phase A (0.1% aqueous formic acid)] as the formic acid salt having the following physical properties.

LC/MS $t_R$ 2.85 minutes; MS (ES$^+$) m/z 489 (M+H)$^b$ $^1$H NMR (500 MHz, DMSO-d$_6$) δ 12.02 (br. s, 1 H), 11.40 (br. s, 1 H), 9.70 (s, 1 H), 8.24 (s, 0.5 H), 7.83-7.80 (m, 3 H), 7.31-7.18 (m, 2 H), 6.50 (br. s, 1 H), 5.97 (s, 1 H), 5.95 (s, 1 H), 5.60 (dd, 1 H), 3.40-3.30 (obs. m, 1 H), 2.98 (dd, 1 H), 2.52-2.43 (obs. m, 1 H), 2.33 (app. br, s, 1 H).

EXAMPLE 802 tert-butyl 5-{2-[(3S)-7-[5-chloro-2-(1H-1,2,3,4-tetrazol-1-yl)phenyl]-5-oxo-1,2,3,5-tetrahydroindolizin-3-yl]-1H-imidazol-5-yl}-1-methyl-1H-pyrrole-2-carboxylate The same operation as in Example 378→Example 139→Example 361→Example 51→Example 52 was conducted from 5-bromo-1-methyl-1H-pyrrole-2-carboxylic acid to give the title compound having the following physical properties. LC/MS $t_R$ 4.08 minutes; MS (ES$^+$) m/z 559 (M+H), 503 (M-C(CH$_3$)$_3$+H)$^b$

EXAMPLE 803

(3S)-7-[5-chloro-2-(1H-tetrazol-1-yl)phenyl]-3-[5-(1-methyl-1H-pyrrol-2-yl)-1H-imidazol-2-yl]-2,3-dihydro-5(1H)-indolizinone The compound prepared in Example 802 (135 mg) was treated as detailed in Example 363 to give the title compound after purification by high performance liquid chromatography [5 to 100% mobile phase B (0.1% formic acid in acetonitrile) in mobile phase A (0.1% aqueous formic acid)] having the following physical properties (42.9 mg).

LC/MS $t_R$ 3.02 minutes; MS (ES$^+$) m/z 459 (M+H)$^b$ $^1$H NMR (500 MHz, methanol-d$_4$) δ 9.36 (s, 1 H), 7.76-7.71 (m, 2 H), 7.68 (d, 1 H), 7.12 (s, 1 H), 6.73 (t, 1 H), 6.28 (dd, 1 H), 6.13 (s, 1 H), 6.10 (d, 1 H), 6.07 (dd, 1 H), 5.79 (dd, 1 H), 3.67 (s, 3 H), 3.43-3.36 (m, 1 H), 3.13 (ddd, 1 H), 2.72-2.63 (m, 1 H), 2.45 (tdd, 1 H).

EXAMPLE 804

5-(2-{(3S)-7-[5-chloro-2-(1H-tetrazol-1-yl)phenyl]-5-oxo-1,2,3,5-tetrahydro-3-indolizinyl}-1H-imidazol-5-yl)-1-methyl-1H-pyrrole-2-carboxylic acid To a cooled (0° C.) dichloromethane (12.6 mL) solution of the compound prepared in Example 802 (35 mg) was added a 1 M solution of titanium(IV) chloride in dichloromethane (0.63 mL), the mixture warmed to room temperature and stirred 1 hour. The reaction mixture was cooled to 0° C., 1 M hydrochloric acid (12.6 mL) added and the mixture stirred vigorously for 5 minutes before filtering through a pad of Celite®. The filter cake was sequentially washed with water (30 mL), propan-2-ol (50 mL) and dichloromethane (50 mL). The organic layer of the biphasic filtrate was isolated and the pH of the aqueous phase adjusted to 2-3 by addition of solid sodium hydrogen carbonate. The aqueous was extracted with a 1:1 mixture of propan-2-ol and dichloromethane, the organic layers combined, washed with saturated saline, dried and concentrated. The residue was purified by high performance liquid chromatography [5 to 100% mobile phase B (0.1% formic acid in acetonitrile) in mobile phase A (0.1% aqueous formic acid)] to give the title compound having the following physical properties (14.9 mg).

LC/MS $t_R$ 3.11 minutes; MS (ES$^+$) m/z 503 (M+H)$^b$ $^1$H NMR (500 MHz, DMSO-d$_6$) δ 12.30 (br. s, 1 H), 9.67 (s, 1 H), 7.86-7.73 (m, 3 H), 7.32 (br. s, 1 H), 6.79 (d, 1 H), 6.21 (app. br. s, 1 H), 5.95 (app. s, 2 H), 5.63 (d, 1 H), 3.98 (br. s, 3 H), 3.51-3.17 (obs. m, 1 H), 2.99 (dd, 1 H), 2.55-2.44 (obs. m, 1 H), 2.35-2.26 (m, 1 H).

EXAMPLE 805

(3S)-7-[5-chloro-2-(1H-tetrazol-1-yl)phenyl]-3-[5-(3-hydroxy-1-methyl-1H-pyrazol-5-yl)-1H-imidazol-2-yl]-2,3-dihydro-5(1H)-indolizinone The same operation as in Example 234→Example 51→Example 52 was conducted from 3-hydroxy-1-methyl-1H-pyrazole-5-carboxylic acid [Chem. Ber., 109, 268 (1976)] to give the title compound after purification by high performance liquid chromatography [5 to 100% mobile phase B (0.1% formic acid in acetonitrile) in mobile phase A (0.1% aqueous formic acid)] having the following physical properties.

LC/MS $t_R$ 3.02 minutes; MS (ES$^+$) m/z 476 (M+H)$^b$ $^1$H NMR (500 MHz, methanol-d$_4$) δ 9.34 (s, 1 H), 7.76-7.70 (m, 2 H), 7.68 (d, 1 H), 7.26 (br. s, 1 H), 6.13 (s, 1 H), 6.08 (s, 1 H), 5.78 (dd, 1 H), 5.69 (s, 1 H), 3.75 (s, 3 H), 3.43 (td, 1 H), 3.11 (ddd, 1 H), 2.68-2.57 (m, 1 H), 2.52-2.42 (m, 1 H).

EXAMPLE 806 ethyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thienyl]acetate The same operation as in Example 139→Example 361→Example 51→Example 52 was conducted from ethyl 2-(4-bromothiophen-2-yl)acetate [U.S. Pat. No. 6,184,245, 2001] to give the title compound having the following physical properties.

LC/MS $t_R$ 3.33 minutes; MS (ES$^+$) m/z 548 (M+H)$^b$ $^1$H NMR (500 MHz, CDCl$_3$) δ 11.05 (br. s, 1 H), 8.62 (s, 1 H), 7.63 (dd, 1 H), 7.56 (d, 1H), 7.54 (d, 1 H), 7.35 (br. s, 1 H), 7.14 (s, 1 H), 7.08 (s, 1 H), 6.31 (s, 1 H), 5.86 (d, 1 H), 5.78 (s, 1 H), 4.21 (q, 2 H), 3.83 (s, 2 H), 3.55-3.45 (m, 1 H), 3.35-3.26 (m, 1 H), 3.04 (dd, 1 H), 2.56-2.45 (m, 1 H), 1.30 (t, 3 H).

EXAMPLE 807

[4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thienyl]acetic acid—formic acid (1:1)

The compound prepared in Example 806 (75 mg) was treated as detailed in Example 342 to give the title compound after purification by high performance liquid chromatography [5 to 100% mobile phase B (0.1% formic acid in acetonitrile) in mobile phase A (0.1% aqueous formic acid)] as the formic acid salt having the following physical properties (52.7 mg).

LC/MS $t_R$ 2.90 minutes; MS (ES$^+$) m/z 520 (M+H)$^b$ $^1$H NMR (500 MHz, DMSO-d$_6$) δ 12.61 (br. s, 1 H), 12.01 (br. s, 1 H), 9.70 (s, 1 H), 8.15 (s, 1 H), 7.84-7.76 (m, 3 H), 7.34 (br. s, 1 H), 7.30 (br. s, 1 H), 7.20 (br. s, 1 H), 5.97 (s, 1 H), 5.95 (s, 1 H), 5.60 (d, 1 H), 3.80 (s, 2 H), 3.40-3.20 (obs. m, 1 H), 2.99 (dd, 1 H), 2.59-2.48 (obs. m, 1 H), 2.33 (app. br. s, 1 H).

EXAMPLE 808 ethyl[4-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-thienyl]acetate The compound prepared in Example 806 (153 mg) was treated as detailed in Example 338 to give the title compound having the following physical properties (92 mg).

LC/MS $t_R$ 4.44 minutes; MS (ES$^+$) m/z 604 and 606 (M+Na), 582 and 584 (M+H)$^b$ $^1$H NMR (500 MHz, CDCl$_3$) δ 11.23 (br. s, 1 H), 8.49 (s, 1 H), 7.55 (dd, 1 H), 7.48-7.44 (m, 2 H), 7.35 (s, 1 H), 7.11 (s, 1 H), 6.26 (s, 1 H), 5.73 (d, 1 H), 5.67 (s, 1 H), 4.13 (q, 2 H), 3.75 (s, 2 H), 3.40-3.31 (m, 1 H), 3.10 (dd, 1 H), 2.93 (dd, 1 H), 2.44-2.33 (m, 1 H), 1.23 (t, 3 H).

EXAMPLE 809

[4-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-thienyl]acetic acid hydrochloride The compound prepared in Example 808 (50 mg) was treated as detailed in Example 342 to give, on concentration of the reaction mixture, the title compound as the hydrochloride salt having the following physical properties (48.5 mg).
LC/MS $t_R$ 3.86 minutes; MS (ES$^+$) m/z 554 and 556 (M+H)$^b$
$^1$H NMR (500 MHz, DMSO-d$_6$) δ 13.00 (br. s, 1 H), 9.71 (s, 1 H), 7.91-7.74 (m, 3 H), 7.64 (s, 1 H), 7.39 (s, 1 H), 5.98 (s, 1 H), 5.94 (s, 1 H), 5.55 (dd, 1 H), 3.87 (s, 2 H), 3.34-3.21 (m, 1 H), 2.98 (dd, 1 H), 2.58-2.47 (obs. m, 1 H), 2.18 (app. t, 1 H).

EXAMPLE 810

4-(2-{(3S)-7-[5-chloro-2-(1H-tetrazol-1-yl)phenyl]-5-oxo-1,2,3,5-tetrahydro-3-indolizinyl}-1H-imidazol-5-yl)benzenesulfonamide The same operation as in Example 51→Example 52 was conducted from 4-(2-bromoacetyl)benzene-1-sulfonamide [patent WO2009009122] to give the title compound having the following physical properties.
LC/MS $t_R$ 3.05 minutes; MS (ES$^+$) m/z 535 (M+H)$^b$
$^1$H NMR (500 MHz, DMSO-d$_6$) δ 12.32 (br. s, 1 H), 9.70 (s, 1 H), 7.88 (d, 2 H), 7.84-7.78 (m, 3 H), 7.77 (d, 2 H), 7.70 (d, 1 H), 7.30 (br. s, 2 H), 5.99 (s, 1 H), 5.97 (s, 1 H), 5.64 (dd, 1 H), 3.42-3.32 (m, 1 H), 3.02 (dd, 1 H), 2.58-2.49 (m, 1 H), 2.38-2.31 (m, 1 H).

EXAMPLE 811

4-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)benzenesulfonamide The compound prepared in Example 810 (70 mg) was treated as detailed in Example 338 to give the title compound having the following physical properties (31 mg).
LC/MS $t_R$ 3.69 minutes; MS (ES$^+$) m/z 569 and 571 (M+H)$^b$
$^1$H NMR (500 MHz, methanol-d$_4$) δ 9.37 (s, 1 H), 7.96 (d, 2 H), 7.86 (d, 2 H), 7.75-7.71 (m, 2 H), 7.70-7.66 (m, 1 H), 6.13 (s, 1 H), 6.11 (s, 1 H), 5.73 (dd, 1 H), 3.50-3.40 (m, 1 H), 3.12 (ddd, 1 H), 2.66 (qd, 1 H), 2.43-2.36 (m, 1 H).

EXAMPLE 812

3-(2-{(3S)-7-[5-chloro-2-(1H-tetrazol-1-yl)phenyl]-5-oxo-1,2,3,5-tetrahydro-3-indolizinyl}-1H-imidazol-5-yl)benzenesulfonamide The same operation as in Example 51→Example 52 was conducted from 3-(2-bromoacetyl)benzene-1-sulfonamide [Chem. Pharm. Bull., 30(11), 4092 (1982)] to give the title compound having the following physical properties.
LC/MS $t_R$ 3.09 minutes; MS (ES$^+$) m/z 535 (M+H)$^b$
$^1$H NMR (250 MHz, DMSO-d$_6$) δ 12.27 (br. s, 1 H), 9.69 (s, 1 H), 8.14 (s, 1 H), 7.88 (d, 1 H), 7.82-7.73 (m, 3 H), 7.65-7.43 (m, 3 H), 7.35 (s, 2 H), 5.98 (s, 1 H), 5.94 (s, 1 H), 5.62 (dd, 1 H), 3.49-3.38 (m, 1 H), 3.09-2.92 (m, 1 H), 2.62-2.52 (m, 1 H), 2.43-2.28 (m, 1 H).

EXAMPLE 813

(3S)-7-[5-chloro-2-(1H-tetrazol-1-yl)phenyl]-3-{5-[4-(5-oxo-4,5-dihydro-1,2,4-oxadiazol-3-yl)phenyl]-1H-imidazol-2-yl}-2,3-dihydro-5(1H)-indolizinone The same operation as in Example 139→Example 361→Example 51→Example 52 was conducted from 3-(4-bromophenyl)-4,5-dihydro-1,2,4-oxadiazol-5-one to give the title compound having the following physical properties.
LC/MS $t_R$ 3.29 minutes; MS (ES$^+$) m/z 540 (M+H)$^b$
$^1$H NMR (500 MHz, DMSO-d$_6$) δ 12.91 (br. s, 1 H), 12.32 (br. s, 1 H), 9.69 (s, 1 H), 7.89 (d, 2 H), 7.84-7.75 (m, 5 H), 7.71 (s, 1 H), 5.98 (s, 1 H), 5.96 (s, 1 H), 5.63 (dd, 1H), 3.44-3.33 (obs. m, 1 H), 3.01 (dd, 1 H), 2.59-2.48 (obs. m, 1 H), 2.38-2.30 (m, 1 H).

EXAMPLE 814

(3S)-7-[5-chloro-2-(1H-tetrazol-1-yl)phenyl]-3-{5-[3-(5-oxo-4,5-dihydro-1,2,4-oxadiazol-3-yl)phenyl]-1H-imidazol-2-yl}-2,3-dihydro-5(1H)-indolizinone The same operation as in Example 139→Example 361→Example 51→Example 52 was conducted from 3-(3-bromophenyl)-4,5-dihydro-1,2,4-oxadiazol-5-one to give the title compound having the following physical properties.
LC/MS $t_R$ 3.34 minutes; MS (ES$^+$) m/z 540 (M+H)$^b$
$^1$H NMR (250 MHz, DMSO-d$_6$) δ 12.94 (br. s, 1 H), 12.25 (br. s, 1 H), 9.70 (s, 1 H), 8.14 (s, 1 H), 7.93 (d, 1 H), 7.85-7.74 (m, 3 H), 7.66-7.46 (m, 3 H), 5.99 (s, 1 H), 5.95 (s, 1 H), 5.64 (dd, 1 H), 3.53-3.28 (obs. m, 1 H), 3.02 (dd, 1 H), 2.59-2.28 (obs. m, 2 H).

EXAMPLE 815

2-(4-bromophenyl)-2-(trifluoromethyl)-1,3-dioxolane

A vigorously stirred solution of 1-(4-bromophenyl)-2,2,2-trifluoroethanone (2.0 g) and 2-chloroethanol (0.79 mL) in N,N-dimethylformamide (4 mL) and tetrahydrofuran (2 mL) was cooled to −60° C. and a solution of potassium tert-butoxide (1.33 g) in N,N-dimethylformamide (3 mL) added dropwise over 20 minutes. The reaction mixture was stirred at −60° C. for 90 minutes whereupon a saturated aqueous solution of ammonium chloride (10 mL) was added. On warming to room temperature, water (5 mL) was added followed by saturated saline (5 mL) and the mixture extracted into ethyl acetate. The combined organic layers were washed twice with water and once with saturated saline, dried and concentrated. The residue was purified by column chromatography (0-40% ethyl acetate in heptanes) to give the title compound having the following physical properties.
$^1$H NMR (500 MHz, CDCl$_3$) δ 7.54 (d, 2 H), 7.49 (d, 2 H), 4.33-4.24 (m, 2 H), 4.13-4.04 (m, 2 H).

EXAMPLE 816

(3S)-7-(2-amino-5-chlorophenyl)-3-(5-{4-[2-(trifluoromethyl)-1,3-dioxolan-2-yl]phenyl}-1H-imidazol-2-yl)-1,2,3,5-tetrahydroindolizin-5-one The same operation as in Example 139→Example 361→Example 51→Example 52→Example 40 was conducted from the compound prepared in Example 815 to give the title compound having the following physical properties. (Note: in the step corresponding to Example 51 in the operation, the compound prepared in Example 11 was used).

LC/MS $t_R$ 1.89 minutes; MS (ES$^+$) m/z 543 (M+H)$^a$

EXAMPLE 817

(3S)-7-(2-amino-5-chlorophenyl)-3-{5-[4-(trifluoro-acetyl)phenyl]-1H-imidazol-2-yl}-1,2,3,5-tetrahy-droindolizin-5-one To a cooled (0° C.) dichloromethane (6.8 mL) solution of the compound prepared in Example 816 (131 mg) was added a 1 M solution of boron tribromide in dichloromethane (1.33 mL) and the mixture stirred at 0° C. for 1 hour then warmed to room temperature and stirred 16 hours. To the cooled (0° C.) reaction mixture, a saturated aqueous solution of sodium hydrogen carbonate was added followed by extraction with dichloromethane. The combined dichloromethane layers were washed with saturated saline, dried and concentrated. The residue was purified by column chromatography (0-15% methanol in ethyl acetate) to give the title compound having the following physical properties (50 mg).

LC/MS $t_R$ 1.57 minutes; MS (ES$^+$) m/z 517 (M+H$_2$O+H)$^a$

EXAMPLE 818

(3S)-7-[5-chloro-2-(1H-tetrazol-1-yl)phenyl]-3-{5-[4-(trifluoroacetyl)phenyl]-1H-imidazol-2-yl}-2,3-dihydro-5(1H)-indolizinone The compound prepared in Example 817 (67.9 mg) was treated as detailed in Example 24 to give the title compound having the following physical properties (60.1 mg).

LC/MS $t_R$ 4.31 minutes; MS (ES$^+$) m/z 570 (M+H$_2$O+H), 552 (M+H)$^g$ $^1$H NMR (500 MHz, methanol-d$_4$) δ 9.35 (s, 1 H), 7.74-7.66 (m, 5 H), 7.59 (d, 2 H), 7.38 (s, 1 H), 6.13 (s, 1 H), 6.09 (s, 1 H), 5.79 (dd, 1 H), 3.45 (td, 1 H), 3.11 (ddd, 1 H), 2.64 (qd, 1 H), 2.53-2.44 (m, 1 H).

EXAMPLE 819

(3S)-7-[5-chloro-2-(1H-tetrazol-1-yl)phenyl]-3-{5-[4-(2,2,2-trifluoro-1-hydroxyethyl)phenyl]-1H-imidazol-2-yl}-2,3-dihydro-5(1H)-indolizinone To a methanol (3.2 mL) solution of the compound prepared in Example 818 (32 mg) was added sodium borohydride (5.1 mg) and the mixture stirred one hour at room temperature. On concentration, the residue was suspended in a saturated aqueous solution of ammonium chloride (5 mL) and extracted into ethyl acetate. The combined organic layers were washed with saturated saline, dried and concentrated. The residue was purified by column chromatography (0-10% methanol in dichloromethane) to give the title compound having the following physical properties (25.3 mg).

LC/MS $t_R$ 3.30 minutes; MS (ES$^+$) m/z 554 (M+H)$^b$ $^1$H NMR (500 MHz, methanol-d$_4$) δ 9.35 (s, 1 H), 7.79-7.57 (m, 5 H), 7.47 (app. br. s, 2 H), 7.43-7.20 (m, 1 H), 6.12 (s, 1 H), 6.08 (s, 1 H), 5.79 (d, 1 H), 5.07-4.96 (m, 1 H), 3.51-3.38 (m, 1 H), 3.10 (ddd, 1 H), 2.64 (qd, 1 H), 2.56-2.34 (m, 1 H).

EXAMPLE 823

[3-(2-{(3S)-8-chloro-7-[5-chloro-2-(1H-tetrazol-1-yl)phenyl]-5-oxo-1,2,3,5-tetrahydro-3-indolizinyl}-1H-imidazol-5-yl)phenyl]acetic acid The compound prepared in Example 345 (150 mg) was treated using the method as detailed in Example 338 to give the title compound after purification by high performance liquid chromatography [5 to 100% mobile phase B (0.1% formic acid in acetonitrile) in mobile phase A (0.1% aqueous formic acid)] as the formic acid salt having the following physical properties (10 mg).

LC/MS $t_R$ 3.22 minutes; MS (ES$^+$) m/z 548 and 550 (M+H)$^b$

NMR analysis showed a 2:1 ratio of atropisomers

Major atropisomer: $^1$H NMR (500 MHz, DMSO-d$_6$) δ 12.20 (br. s, 1 H), 9.76 (s, 1 H), 8.21 (app. s, 1 H), 7.91-7.82 (m, 2 H), 7.79 (s, 1 H), 7.66-7.39 (m, 3 H), 7.35-7.20 (m, 1 H), 7.13-7.03 (m, 1 H), 6.29 (s, 1 H), 5.74 (dd, 1 H), 3.55 (s, 2 H), 3.36-3.25 (m, 1 H), 3.18-3.05 (m, 1 H), 2.66-2.54 (m, 1 H), 2.35 (app. br. s, 1 H).

Minor atropisomer: $^1$H NMR (500 MHz, DMSO-d$_6$) δ 12.67 (very br. s, 1 H), 9.70 (s, 1H), 8.22 (app. s, 1 H), 7.91-7.82 (m, 2 H), 7.72 (s, 1 H), 7.66-7.39 (m, 3 H), 7.35-7.20 (m, 1 H), 7.13-7.03 (m, 1 H), 6.34 (s, 1 H), 5.72 (dd, 1 H), 3.65 (s, 2 H), 3.36-3.25 (m, 1 H), 3.18-3.05 (m, 1 H), 2.66-2.54 (m, 1 H), 2.35 (app. br. s, 1 H).

EXAMPLE 824

2-methyl-2-propanyl{[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]thio}acetate The same operation as in Example 139→Example 361→Example 51→Example 52 was conducted from tert-butyl 2-[(4-bromophenyl)sulfanyl]acetate [patent US2004010019] to give the title compound having the following physical properties. LC/MS $t_R$ 3.89 minutes; MS (ES$^+$) m/z 602 (M+H)$^b$ $^1$H NMR (250 MHz, DMSO-d$_6$) δ 12.15 (br. s, 1 H), 9.69 (s, 1 H), 7.78-7.74 (m, 3 H), 7.66 (d, 2 H), 7.53 (s, 1 H), 7.31 (d, 2 H), 5.97 (s, 1 H), 5.96 (s, 1 H), 5.61 (d, 1 H), 3.71 (s, 2 H), 3.49-3.31 (obs. m, 1 H), 3.08-2.89 (m, 1 H), 2.60-2.41 (obs. m, 1 H), 2.42-2.25 (m, 1 H), 1.33 (s, 9 H).

EXAMPLE 825

{[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]thio}acetic acid The compound prepared in Example 824 (235 mg) was treated as detailed in Example 363 to give the title compound after purification by high performance liquid chromatography [5 to 100% mobile phase B (0.1% formic acid in acetonitrile) in mobile phase A (0.1% aqueous formic acid)] having the following physical properties (104 mg).

LC/MS $t_R$ 3.13 minutes; MS (ES$^+$) m/z 546 (M+H)$^b$ $^1$H NMR (500 MHz, DMSO-d$_6$) δ 12.12 (br. s, 1 H), 9.68 (s, 1 H), 7.83-7.76 (m, 3 H), 7.64 (d, 2 H), 7.50 (s, 1 H), 7.29 (d, 2 H), 5.96 (s, 1 H), 5.95 (s, 1 H), 5.62 (dd, 1 H), 3.74 (s, 2 H), 3.44-3.30 (obs. m, 1 H), 2.99 (dd, 1 H), 2.53-2.44 (obs. m, 1 H), 2.38-2.30 (m, 1 H).

EXAMPLE 826 tert-butyl 2-[(3-{2-[(3S)-7-[5-chloro-2-(1H-1,2,3,4-tetrazol-1-yl)phenyl]-5-oxo-1,2,3,5-tetrahydroindolizin-3-yl]-1H-imidazol-5-yl}phenyl)sulfanyl]acetate The same operation as in Example 139→Example 361→Example 51→Example 52 was conducted from tert-butyl 2-[(3-bromophenyl)sulfanyl]acetate [J. Med. Chem., 47(1), 18 (2004)] to give the title compound having the following physical properties. LC/MS $t_R$ 1.92 minutes; MS (ES$^+$) m/z 602 (M+H)$^a$.

EXAMPLE 827

{[3-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]thio}acetic acid The compound prepared in Example 826 (80 mg) was treated as detailed in Example 363 to give the title compound after purification by high performance liquid chromatography [5 to 100% mobile phase B (0.1% formic acid in acetonitrile) in mobile phase A (0.1% aqueous formic acid)] having the following physical properties (40 mg).

LC/MS $t_R$ 3.14 minutes; MS (ES$^+$) m/z 546 (M+H)$^b$
$^1$H NMR (500 MHz, DMSO-d$_6$) δ 12.16 (br. s, 1 H), 9.69 (s, 1 H), 7.85-7.76 (m, 3 H), 7.64 (app. s, 1 H), 7.58-7.44 (m, 2 H), 7.33-7.23 (m, 1 H), 7.18-7.10 (m, 1 H), 5.97 (s, 1 H), 5.94 (s, 1 H), 5.62 (dd, 1 H), 3.79 (s, 2 H), 3.43-3.30 (obs. m, 1 H), 3.00 (dd, 1 H), 2.57-2.49 (obs. m, 1 H), 2.41-2.29 (m, 1 H).

EXAMPLE 828

{[3-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)phenyl]thio}acetic acid The same operation as in Example 338→Example 363 was conducted from the compound prepared in Example 826 to give the title compound after purification by high performance liquid chromatography [5 to 100% mobile phase B (0.1% formic acid in acetonitrile) in mobile phase A (0.1% aqueous formic acid)] having the following physical properties.

LC/MS $t_R$ 4.02 minutes; MS (ES$^+$) m/z 580 and 582 (M+H)$^b$
$^1$H NMR (500 MHz, DMSO-d$_6$) δ 13.08 (br. s, 1 H), 9.71 (s, 1 H), 7.85-7.77 (m, 3 H), 7.64 (app. s, 1 H), 7.53 (d, 1 H), 7.41 (t, 1 H), 7.28 (d, 1 H), 5.98 (s, 1 H), 5.94 (s, 1 H), 5.57 (dd, 1 H), 3.83 (s, 2 H), 3.35-3.23 (obs. m, 1 H), 2.99 (dd, 1 H), 2.59-2.48 (obs. m, 1 H), 2.24-2.17 (m, 1 H).

EXAMPLE 829

2-methyl-2-propanyl{[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]amino}acetate The same operation as in Example 90→Example 361→Example 51→Example 52 was conducted from tert-butyl 2-[(4-bromophenyl)amino]acetate [patent WO2004/13279] to give the title compound having the following physical properties.

LC/MS $t_R$ 3.40 minutes; MS (ES$^+$) m/z 585 (M+H)$^b$ $^1$H NMR (500 MHz, CDCl$_3$) δ 10.96 (br. s, 1 H), 8.57 (s, 1 H), 7.61 (dd, 1 H), 7.54 (d, 1H), 7.51 (d, 1 H), 7.42 (app. br. s, 2 H), 7.07 (s, 1 H), 6.60 (d, 2 H), 6.32 (s, 1 H), 5.85 (d, 1 H), 5.71 (s, 1 H), 4.36 (br. s, 1 H), 3.82 (s, 2 H), 3.53-3.40 (m, 1 H), 3.39-3.28 (m, 1 H), 3.01 (dd, 1 H), 2.52-2.40 (m, 1 H), 1.50 (s, 9 H).

EXAMPLE 830

{[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]amino}acetic acid hydrochloride To a 1,4-dioxane (1.5 mL) solution of the compound prepared in Example 829 (25.6 mg) was added concentrated hydrochloric acid (40 μL) and the mixture stirred at room temperature for 7 hours. On concentration, the residue was triturated with dichloromethane and the resultant precipitate collected by filtration to give the title compound having the following physical properties (20 mg).

LC/MS $t_R$ 1.66 minutes; MS (ES$^+$) m/z 529 (M+H)
$^1$H NMR (500 MHz, DMSO-d$_6$) δ 14.68 (br. s, 1 H), 14.51 (br. s, 1 H), 9.70 (s, 1 H), 7.84-7.79 (m, 3 H), 7.71 (d, 1 H), 7.53 (d, 2 H), 6.68 (d, 2 H), 6.06 (d, 1 H), 6.01 (s, 1H), 5.80 (dd, 1 H), 3.87 (s, 2 H), 3.32-3.23 (m, 1 H), 3.14-3.05 (m, 1 H), 2.74-2.65 (m, 1 H), 2.38-2.29 (m, 1 H).

EXAMPLE 831

4-{2-[(3S)-7-[5-chloro-2-(1H-1,2,3,4-tetrazol-1-yl)phenyl]-5-oxo-1,2,3,5-tetrahydroindolizin-3-yl]-1H-imidazol-5-yl}thiophene-2-carboxamide

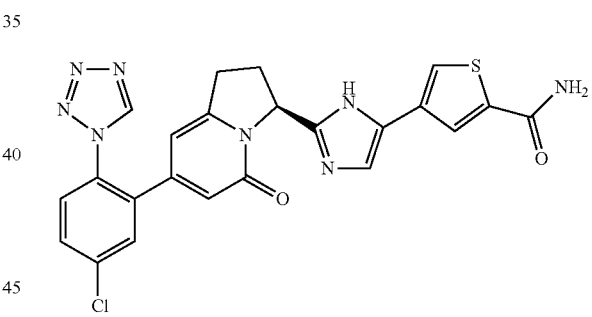

The compound prepared in Example 363 (20 mg) was treated as detailed in Example 114 to give the title compound having the following physical properties (16 mg).

LC/MS $t_R$ 1.36 minutes; MS (ES$^+$) m/z 505 (M+H)$^a$.

EXAMPLE 832

4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarbonitrile To a pyridine (0.5 mL) solution of the compound prepared in Example 831 (16 mg) was added methanesulfonyl chloride (2.45 μL). The mixture was stirred at room temperature for 20 hours, then warmed to 50° C. and stirred 7 hours. The reaction was cooled to room temperature, further methanesulfonyl chloride (4.90 μL) added and the mixture stirred at room temperature for 16 hours. On concentration, the residue was dissolved in methanol (0.5 mL), treated with concentrated aqueous ammonia solution (12.3 μL) and stirred at room temperature for 5 days. On concentration, the residue was suspended in saturated aqueous solution of sodium hydrogen carbonate and extracted into a 9:1 mixture of dichloromethane and methanol. The combined organic phases were dried and concentrated and the residue purified by high performance liquid chromatography [5 to 100% mobile phase B (0.1% formic acid in acetonitrile) in mobile phase A (0.1% aqueous formic acid)] to give the title compound having the following physical properties (8 mg).

LC/MS $t_R$ 3.60 minutes; MS (ES$^+$) m/z 487 (M+H)$^b$ $^1$H NMR (500 MHz, DMSO-d$_6$) δ 12.24 (br. s, 1 H), 9.68 (s, 1 H), 8.20 (s, 1 H), 7.97 (s, 1 H), 7.85-7.73 (m, 3 H), 7.48 (s, 1 H), 5.96 (s, 1 H), 5.95 (s, 1 H), 5.61 (d, 1 H), 3.38-3.28 (obs. m, 1 H), 2.99 (dd, 1 H), 2.53-2.44 (obs. m, 1 H), 2.35-2.25 (m, 1 H).

EXAMPLE 833

4-(2-{(3S)-7-[5-chloro-2-(1H-tetrazol-1-yl)phenyl]-5-oxo-1,2,3,5-tetrahydro-3-indolizinyl}-1H-imidazol-5-yl)-N-(methylsulfonyl)-2-thiophenecarboxamide To a cooled (0° C.) tetrahydrofuran (2.5 mL) suspension of the compound prepared in Example 363 (170 mg) was sequentially added triethylamine (159 μL) followed by isobutyl chloroformate (95.9 μL) and the mixture stirred at room temperature for 2 hours. On cooling to 0° C., a solution of methanesulfonamide (164 mg) and triethylamine (93.7 μL) in tetrahydrofuran (2.5 mL) was added. 4-Dimethylaminopyridine (40.8 mg) was then added and stirring continued at room temperature for 16 hours. To the reaction mixture, concentrated aqueous ammonia solution (125 μL) was added and the mixture stirred at room temperature a further hour then concentrated. The residue was suspended in 1 M hydrochloric acid (5 mL) and extracted into a 9:1 mixture of dichloromethane and methanol. The aqueous layer was extracted thrice more with a 9:1 mixture of chloroform and propan-2-ol, the combined organic layers dried and concentrated. The residue was purified by high performance liquid chromatography [5 to 100% mobile phase B (0.1% formic acid in acetonitrile) in mobile phase A (0.1% aqueous formic acid)] then further purified by trituration from dichloromethane, the resultant precipitate being isolated by filtration to obtain the title compound (11.5 mg). The filtrate was concentrated and residual 2-methyl-propan-1-ol removed by azeotroping with deuterated chloroform to give a second batch of the title compound having the following physical properties (13 mg).

LC/MS $t_R$ 3.15 minutes; MS (ES$^+$) m/z 583 (M+H)$^b$ $^1$H NMR (500 MHz, DMSO-d$_6$) δ 13.03-11.93 (m, 2 H), 9.69 (s, 1 H), 8.22 (s, 1 H), 7.87 (s, 1 H), 7.82-7.74 (m, 3 H), 7.31 (br. s, 1 H), 5.97 (s, 1 H), 5.95 (s, 1 H), 5.62 (dd, 1 H), 3.44-3.28 (obs. m, 1 H), 3.27 ((s, 3 H), 3.01 (dd, 1 H), 2.56-2.48 (obs. m, 1 H), 2.34 (app. br. s, 1 H).

EXAMPLE 834

4-(2-{(3S)-7-[5-chloro-2-(1H-tetrazol-1-yl)phenyl]-5-oxo-1,2,3,5-tetrahydro-3-indolizinyl}-1H-imidazol-5-yl)-3-fluoro-2-thiophenecarboxylic acid The same operation as in Example 139→Example 361→Example 51→Example 52→Example 8→Example 55→Example 24 was conducted from methyl 4-bromo-3-fluorothiophene-2-carboxylate [Tetrahedron Lett., 42(50), 8797 (2001)] to give, after trituration from dichloromethane, the title compound having the following physical properties. (Note: in the step corresponding to Example 51 in the operation, the compound prepared in Example 11 was used).

LC/MS $t_R$ 3.34 minutes; MS (ES$^+$) m/z 524 (M+H)$^b$ $^1$H NMR (500 MHz, DMSO-d$_6$) δ 13.30 (br. s, 1 H), 12.26 (br. s, 1 H), 9.68 (s, 1 H), 7.85-7.78 (m, 3 H), 7.77 (s, 1 H), 7.29 (s, 1 H), 5.96 (app. s, 2 H), 5.63 (dd, 1 H), 3.38-3.27 (obs. m, 1 H), 2.99 (dd, 1 H), 2.53-2.47 (obs. m, 1 H), 2.35-2.28 (m, 1 H).

EXAMPLE 835 tert-butyl 4-{2-[(3S)-7-[5-chloro-2-(1H-1,2,3,4-tetrazol-1-yl)phenyl]-5-oxo-1,2,3,5-tetrahydroindolizin-3-yl]-1H-imidazol-5-yl}-3-fluoropyridine-2-carboxylate The same operation as in Example 378→Example 139→Example 361→Example 51→Example 52 was conducted from 4-chloro-3-fluoropyridine-2-carboxylic acid [Eur. J. Org. Chem., 10, 2116 (2005)] to give the title compound having the following physical properties.

LC/MS $t_R$ 2.00 minutes; MS (ES$^+$) m/z 575 (M+H), 519 (M-C(CH$_3$)$_3$+H)+; 447 (M-CO$_2$C(CH$_3$)$_3$—N$_2$+H)$^a$.

EXAMPLE 836

4-(2-{(3S)-7-[5-chloro-2-(1H-tetrazol-1-yl)phenyl]-5-oxo-1,2,3,5-tetrahydro-3-indolizinyl}-1H-imidazol-5-yl)-3-fluoro-2-pyridinecarboxylic acid To a 1,4-dioxane (4.2 mL) solution of the compound prepared in Example 835 (102 mg) was added 6 M hydrochloric acid (4.2 mL) and the mixture heated at 60° C. for 1 hour. On concentration the residue was purified by high performance liquid chromatography [5 to 100% mobile phase B (0.1% formic acid in acetonitrile) in mobile phase A (0.1% aqueous formic acid)] to give the title compound having the following physical properties (33.1 mg).

LC/MS $t_R$ 3.16 minutes; MS (ES$^+$) m/z 519 (M+H), 447 (M-CO$_2$—N$_2$+H)$^b$ $^1$H NMR (500 MHz, DMSO-d$_6$) δ 13.52 (br. s, 1 H), 12.63 (br. s, 1 H), 9.69 (s, 1 H), 8.41 (d, 1 H), 8.04 (t, 1 H), 7.86-7.75 (m, 3 H), 7.69 (d, 1 H), 5.98 (app. s, 2 H), 5.77-5.58 (m, 1 H), 3.37-3.25 (obs. m, 1 H), 3.02 (dd, 1 H), 2.59-2.45 (m, 1 H), 2.39-2.28 (m, 1 H).

EXAMPLE 837

4-(2-{(3S)-7-[5-chloro-2-(1H-tetrazol-1-yl)phenyl]-5-oxo-1,2,3,5-tetrahydro-3-indolizinyl}-1H-imidazol-5-yl)-3-thiophenecarboxylic acid hydrochloride The same operation as in Example 378→Example 139→Example 361→Example 51→Example 52→Example 363 was conducted from 4-bromothiophene-3-carboxylic acid to give the title compound as the hydrochloride salt having the following physical properties.

LC/MS $t_R$ 3.37 minutes; MS (ES$^+$) m/z 506 (M+H)$^b$ $^1$H NMR (500 MHz, DMSO-d$_6$) δ 14.34 (br. s, 1 H), 9.69 (s, 1 H), 8.46 (d, 1 H), 7.96 (d, 1 H), 7.84 (dd, 1 H), 7.82 (d, 1 H), 7.79 (s, 1 H), 7.71 (d, 1 H), 6.06-6.04 (m, 1 H), 6.03-6.01 (m, 1 H), 5.82 (dd, 1 H), 3.26 (td, 1 H), 3.14-3.05 (m, 1 H), 2.76-2.66 (m, 1 H), 2.33-2.21 (m, 1 H).

EXAMPLE 838(1) and 838(2)

2-tert-butyl 4-methyl thiophene-2,4-dicarboxylate and 4-(methoxycarbonyl)thiophene-2-carboxylic acid tert-Butyl 4-bromothiophene-2-carboxylate [J. Med. Chem., 55(12), 5982, supporting information (2012)] (1.0 g) was treated as detailed in Example 673 to give the title compounds having the following physical properties.

EXAMPLE 838(1)

309 mg $^1$H NMR (500 MHz, CDCl$_3$) δ 8.22 (d, 1 H), 8.07 (d, 1 H), 3.89 ((s, 3 H), 1.59 (s, 9 H).

EXAMPLE 838(2)

363 mg $^1$H NMR (500 MHz, CDCl$_3$) δ 8.35 (d, 1 H), 8.27 (d, 1 H), 3.91 (s, 3 H).

EXAMPLE 839

5-[(tert-butoxy)carbonyl]thiophene-3-carboxylic acid

To a stirred solution of the compound prepared in Example 838(1) (305 mg) in tetrahydrofuran (12.8 mL) and water (12.8 mL) was added lithium hydroxide monohydrate (63.1 mg) and the mixture stirred at room temperature for 5 hours. To the reaction mixture, water (20 mL) and tert-butyl methyl ether (30 mL) were added and the phases separated. The organic layer was washed with a saturated aqueous solution of sodium hydrogen carbonate (30 mL), the aqueous layers then combined and treated with 2 M hydrochloric acid until pH 1-2 was attained. This aqueous suspension was extracted with ethyl acetate, the combined organic layers washed with saturated saline, dried and concentrated to give the title compound having the following physical properties (269 mg).

$^1$H NMR (500 MHz, DMSO-d$_6$) δ 13.04 (br. s, 1 H), 8.51 (d, 1 H), 7.87 (d, 1 H), 1.53 (s, 9H).

EXAMPLE 840

4-(5-{7-[5-chloro-2-(1H-tetrazol-1-yl)phenyl]-5-oxo-1,2,3,5-tetrahydro-3-indolizinyl}-1H-pyrrol-2-yl)-2-thiophenecarboxylic acid The same operation as in Example 676→Example 665→Example 666→Example 667→Example 24 was conducted from the compound prepared in Example 839 to give the title compound having the following physical properties. (Note: in the step corresponding to Example 665 in the operation, the compound prepared in Example 617 was used).

LC/MS t$_R$ 3.94 minutes; MS (ES$^+$) m/z 505 (M+H)$^b$ $^1$H NMR (500 MHz, DMSO-d$_6$) δ 13.08 (br. s, 1 H), 11.22 (br. s, 1 H), 9.70 (s, 1 H), 7.97 (d, 1 H), 7.84-7.73 (m, 4 H), 6.32 (t, 1 H), 6.00 (s, 1 H), 5.92 (s, 1 H), 5.67 (d, 1 H), 5.62 (t, 1 H), 3.13 (td, 1 H), 2.94 (dd, 1 H), 2.55-2.41 (obs. m, 1 H), 2.18 (dd, 1 H).

EXAMPLE 841 ethyl 4-cyanothiophene-2-carboxylate

To an N,N-dimethylformamide (75 mL) solution of ethyl 4-bromothiophene-2-carboxylate [patent US2012/022123] (4.98 g) was added copper(I) cyanide (2.09 g) and the mixture heated at 150° C. for 9.5 hours. The reaction mixture was cooled to room temperature, diluted with ethyl acetate (350 mL) and washed with water (200 mL) and 2 M aqueous ammonia solution (200 mL). The organic layer was dried, concentrated and the residue purified by column chromatography (0-20% ethyl acetate in heptanes) to give the title compound having the following physical properties (2.39 g).

$^1$H NMR (500 MHz, CDCl$_3$) δ 8.07 (d, 1 H), 7.93 (d, 1 H), 4.39 (q, 2 H), 1.39 (t, 3 H).

EXAMPLE 842 ethyl 4-carbamimidoylthiophene-2-carboxylate

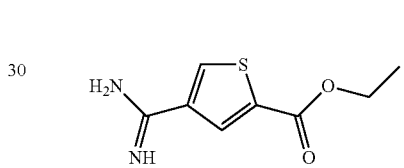

The compound prepared in Example 841 (1.79 g) was treated as detailed in Example 237 to give, after trituration from a mixture of water (15 mL) and a saturated aqueous solution of sodium hydrogen carbonate (15 mL), the title compound having the following physical properties (1.08 g).

$^1$H NMR (500 MHz, DMSO-d$_6$) δ 8.37 (d, 1 H), 8.18 (d, 1 H), 7.36 (br. s, 3 H), 4.31 (q, 2 H), 1.31 (t, 3 H).

EXAMPLE 843 ethyl 4-{5-[7-(2-{bis[(tert-butoxy)carbonyl]amino}-5-chlorophenyl)-5-oxo-1,2,3,5-tetrahydroindolizin-3-yl]-1H-imidazol-2-yl}thiophene-2-carboxylate

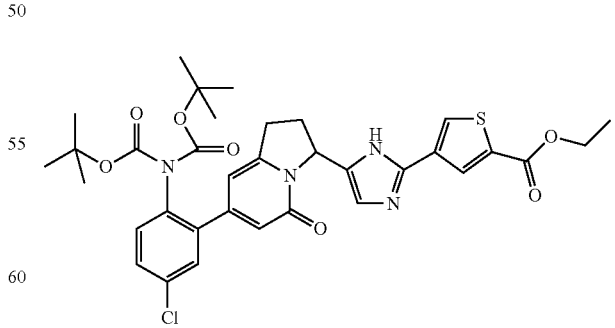

The compound prepared in Example 842 (0.57 g) was treated with the compound prepared in Example 623 (1.60 g) as detailed in Example 620 to give the title compound having the following physical properties (1.44 g).

LC/MS $t_R$ 2.08 minutes; MS (ES$^+$) m/z 704 (M+Na), 681 (M+H)$^a$.

EXAMPLE 844 ethyl 4-(5-{7-[5-chloro-2-(1H-tetrazol-1-yl)phenyl]-5-oxo-1,2,3,5-tetrahydro-3-indolizinyl}-1H-imidazol-2-yl)-2-thiophenecarboxylate The same operation as in Example 40→Example 24 was conducted from the compound prepared in Example 843 to give the title compound having the following physical properties.

LC/MS $t_R$ 3.46 minutes; MS (ES$^+$) m/z 534 (M+H)$^b$ $^1$H NMR (500 MHz, DMSO-d$_6$) δ 12.48 (br. s, 1 H), 9.68 (s, 1 H), 8.18 (d, 1 H), 8.15 (d, 1 H), 7.85-7.74 (m, 3 H), 6.89 (s, 1 H), 5.91 (app. s, 2 H), 5.58 (d, 1 H), 4.32 (q, 2 H), 3.36-3.25 (m, 1 H), 2.93 (dd, 1 H), 2.47-2.38 (m, 1 H), 2.26 (dd, 1 H), 1.32 (t, 3 H).

EXAMPLE 845 ethyl 4-(5-{7-[5-chloro-2-(1H-tetrazol-1-yl)phenyl]-5-oxo-1,2,3,5-tetrahydro-3-indolizinyl}-4-fluoro-1H-imidazol-2-yl)-2-thiophenecarboxylate The compound prepared in Example 844 (296 mg) was treated as detailed in Example 364 to give the title compound having the following physical properties (20.4 mg).

LC/MS $t_R$ 4.25 minutes; MS (ES$^+$) m/z 552 (M+H)$^b$ $^1$H NMR (500 MHz, CDCl$_3$) δ 11.26 (br. s, 1 H), 8.62 (s, 1 H), 8.07 (s, 1 H), 7.93 (s, 1 H), 7.62 (dd, 1 H), 7.58-7.51 (m, 2 H), 6.36 (s, 1 H), 5.85 (d, 1 H), 5.79 (s, 1 H), 4.36 (q, 2 H), 3.42-3.27 (m, 1 H), 3.06 (dd, 1 H), 2.84 (dd, 1 H), 2.61-2.46 (m, 1 H), 1.39 (t, 3 H).

EXAMPLE 846 ethyl 4-(4-chloro-5-{7-[5-chloro-2-(1H-tetrazol-1-yl)phenyl]-5-oxo-1,2,3,5-tetrahydro-3-indolizinyl}-1H-imidazol-2-yl)-2-thiophenecarboxylate The compound prepared in Example 844 (90 mg) was treated as detailed in Example 44 to give the title compound having the following physical properties (54.9 mg).

LC/MS $t_R$ 4.10 minutes; MS (ES$^+$) m/z 568 and 570 (M+H)$^b$ $^1$H NMR (500 MHz, DMSO-d$_6$) δ 12.90 (br. s, 1 H), 9.64 (s, 1 H), 8.21 (d, 1 H), 8.17 (d, 1 H), 7.84-7.78 (m, 2 H), 7.76-7.72 (m, 1 H), 5.98 (s, 1 H), 5.92 (s, 1 H), 5.60 (dd, 1 H), 4.32 (q, 2 H), 3.18 (td, 1 H), 3.02 (ddd, 1 H), 2.63-2.53 (m, 1 H), 2.16-2.08 (m, 1 H), 1.32 (t, 3 H).

EXAMPLE 847

4-(5-{7-[5-chloro-2-(1H-tetrazol-1-yl)phenyl]-5-oxo-1,2,3,5-tetrahydro-3-indolizinyl}-1H-imidazol-2-yl)-2-thiophenecarboxylic acid The same operation as in Example 8→Example 40→Example 24 was conducted from the compound prepared in Example 843 to give the title compound having the following physical properties.

LC/MS $t_R$ 2.96 minutes; MS (ES$^+$) m/z 506 (M+H), 478 (M-N$_2$+H)$^b$ $^1$H NMR (500 MHz, DMSO-d$_6$) δ 13.25 (br. s, 1 H), 12.46 (br. s, 1 H), 9.69 (s, 1 H), 8.18-8.06 (m, 2 H), 7.84-7.76 (m, 3 H), 6.88 (br. s, 1 H), 5.92 (app. s, 2 H), 5.60 (d, 1 H), 3.40-3.26 (obs. m, 1 H), 2.94 (dd, 1 H), 2.48-2.38 (m, 1 H), 2.26 (dd, 1 H).

EXAMPLE 848

4-(5-{7-[5-chloro-2-(1H-tetrazol-1-yl)phenyl]-5-oxo-1,2,3,5-tetrahydro-3-indolizinyl}-4-fluoro-1H-imidazol-2-yl)-2-thiophenecarboxylic acid The same operation as in Example 364→Example 8→Example 40→Example 24 was conducted from the compound prepared in Example 843 to give the title compound having the following physical properties.

LC/MS $t_R$ 3.66 minutes; MS (ES$^+$) m/z 524 (M+H)$^b$ $^1$H NMR (500 MHz, DMSO-d$_6$) δ 13.32 (br. s, 1 H), 12.57 (s, 1 H), 9.66 (s, 1 H), 8.12-8.03 (m, 2 H), 7.85-7.77 (m, 2 H), 7.76 (d, 1 H), 5.97 (s, 1 H), 5.91 (s, 1 H), 5.60 (dd, 1 H), 3.25-3.15 (m, 1 H), 3.05-2.95 (m, 1 H), 2.62-2.53 (m, 1 H), 2.24-2.13 (m, 1 H).

EXAMPLE 849

4-(4-chloro-5-{7-[5-chloro-2-(1H-tetrazol-1-yl)phenyl]-5-oxo-1,2,3,5-tetrahydro-3-indolizinyl}-1H-imidazol-2-yl)-2-thiophenecarboxylic acid The compound prepared in Example 847 (70 mg) was treated as detailed in Example 338. The reaction mixture was concentrated directly and purified by high performance liquid chromatography [5 to 100% mobile phase B (0.1% formic acid in acetonitrile) in mobile phase A (0.1% aqueous formic acid)] to give the title compound having the following physical properties (18.1 mg).

LC/MS $t_R$ 2.57 minutes; MS (ES$^+$) m/z 540 and 542 (M+H)$^e$ $^1$H NMR (500 MHz, DMSO-d$_6$) δ 13.30 (br. s, 1 H), 12.85 (br. s, 1 H), 9.64 (s, 1 H), 8.13 (s, 1 H), 8.09 (s, 1 H), 7.83-7.78 (m, 2 H), 7.74 (app. s, 1 H), 5.99 (s, 1 H), 5.91 (s, 1 H), 5.61 (dd, 1 H), 3.21-3.12 (m, 1 H), 3.06-2.97 (m, 1 H), 2.62-2.53 (m, 1 H), 2.16-2.07 (m, 1 H).

EXAMPLE 850

2-methoxyethyl[4-(2-{(3S)-7-[5-chloro-2-(4-cyano-1H-1,2,3-triazol-1-yl)phenyl]-5-oxo-1,2,3,5-tetrahydro-3-indolizinyl}-1H-imidazol-5-yl)phenyl]carbamate The same operation as in Example 283→Example 8→Example 38→Example 39→Example 290 was conducted from the compound prepared in Example 288 to give the title compound having the following physical properties. (Note: in the step corresponding to Example 38 in the operation, the compound prepared in Example 324 was used)

LC/MS $t_R$ 0.72 minutes; MS (ES$^+$) m/z 597 (M+H)$^f$ $^1$H NMR (300 MHz, DMSO-d$_6$) δ 12.6-11.8 (m, 1 H), 9.85-9.55 (m, 1 H), 9.35 (s, 1 H), 7.85-7.73 (m, 3 H), 7.64-7.02 (m, 5 H), 5.95 (s, 1 H), 5.94 (s, 1 H), 5.60 (d, 1 H), 4.18 (dd, 2 H), 3.56 (dd, 2 H), 3.46-3.30 (m, 1 H), 3.27 ((s, 3 H), 2.99 (dd, 1 H), 2.60-2.45 (m, 1 H), 2.40-2.25 (m, 1 H).

EXAMPLE 851

2-methoxyethyl[4-(4-chloro-2-{(3S)-7-[5-chloro-2-(4-cyano-1H-1,2,3-triazol-1-yl)phenyl]-5-oxo-1,2,3,5-tetrahydro-3-indolizinyl}-1H-imidazol-5-yl)phenyl]carbamate The same operation as in Example 44 was conducted from the compound prepared in Example 850 to give the title compound having the following physical properties.
TLC: Rf 0.51 ($CH_2Cl_2$/AcOEt/MeOH, 8/4/1)
$^1$H NMR (300 MHz, DMSO-$d_6$) δ 12.8 (s, 1 H), 9.89 (s, 1 H), 9.36 (s, 1 H), 7.85-7.77 (m, 3 H), 7.63-7.48 (m, 4 H), 5.96 (s, 1 H), 5.94 (s, 1 H), 5.56 (dd, 1 H), 4.20 (dd, 2 H), 3.56 (dd, 2 H), 3.28 ((s, 3 H), 3.25-3.17 (m, 1 H), 3.06-2.90 (m, 1 H), 2.60-2.45 (m, 1 H), 2.28-2.14 (m, 1 H).

EXAMPLE 852

1-(2-{(3S)-3-[5-(6-amino-3-pyridinyl)-4-chloro-1H-imidazol-2-yl]-5-oxo-1,2,3,5-tetrahydro-7-indolizinyl}-4-chlorophenyl)-1H-1,2,3-triazole-4-carbonitrile The same operation as in Example 283→Example 8→Example 38→Example 39→Example 10→Example 290→Example 338→Example 287 was conducted from the compound prepared in Example 288 to give the title compound having the following physical properties. (Note: in the step corresponding to Example 38 in the operation, the compound prepared in Example 193 was used)
LC/MS $t_R$ 0.70 minutes; MS (ES$^+$) m/z 530 (M+H)$^+$
$^1$H NMR (300 MHz, DMSO-$d_6$) δ 12.7 (s, 1 H), 9.36 (s, 1 H), 8.19 (d, 1 H), 7.83-7.72 (m, 3 H), 7.63 (dd, 1 H), 6.50 (d, 1 H), 6.17 (s, 2 H), 5.95 (s, 1 H), 5.93 (s, 1 H), 5.53 (dd, 1 H), 3.30-3.06 (m, 1 H), 3.05-2.92 (m, 1 H), 2.60-2.45 (m, 1 H), 2.24-2.12 (m, 1 H).

EXAMPLE 853(1) TO EXAMPLE 853(2)

The same operation as in Example 485 was conducted from corresponding alcohols to give the title compounds having the following physical properties.

EXAMPLE 853(1)

3-hydroxy-3-methylbutyl carbonochloridate

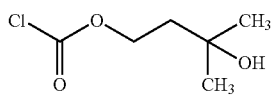

$^1$H NMR (300 MHz, CDCl$_3$) δ 4.51 (t, 2 H), 1.94 (t, 2 H), 1.29 (s, 6 H).

EXAMPLE 853(2)

2-hydroxy-2-methylpropyl carbonochloridate

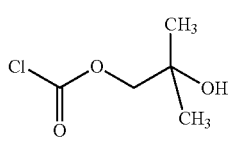

$^1$H NMR (300 MHz, CDCl$_3$) δ 4.18 (s, 2 H), 1.30 (s, 6 H).

EXAMPLE 854(1) TO EXAMPLE 854(3)

The compounds of the present invention having the following physical data were prepared using the compound prepared in Example 194 and the corresponding chloroformates using the method as detailed in Example 128.

EXAMPLE 854(1)

2-hydroxy-2-methylpropyl[5-(2-{(3S)-7-[5-chloro-2-(1H-tetrazol-1-yl)phenyl]-5-oxo-1,2,3,5-tetrahydro-3-indolizinyl}-1H-imidazol-5-yl)-2-pyridinyl]carbamate LC/MS $t_R$ 0.66 minutes; MS (ES$^+$) m/z 588 (M+H)$^+$
$^1$H NMR (300 MHz, DMSO-$d_6$) δ 12.7-12.1 (m, 1 H), 10.1-9.98 (m, 1 H), 9.70-9.60 (m, 1 H), 8.62-8.52 (m, 1 H), 8.05-7.95 (m, 1 H), 7.86-7.72 (m, 4 H), 7.52-7.20 (m, 1 H), 5.97-5.88 (m, 2 H), 5.60 (d, 1 H), 4.54 (m, 1 H), 3.90-3.83 (m, 2 H), 3.38 (m, 1 H), 2.98 (m, 1 H), 2.60-2.20 (m, 2 H), 1.13 (s, 6 H).

EXAMPLE 854(2)

2-(2-methoxyethoxyl)ethyl[5-(2-{(3S)-7-[5-chloro-2-(1H-tetrazol-1-yl)phenyl]-5-oxo-1,2,3,5-tetrahydro-3-indolizinyl}-1H-imidazol-5-yl)-2-pyridinyl]carbamate

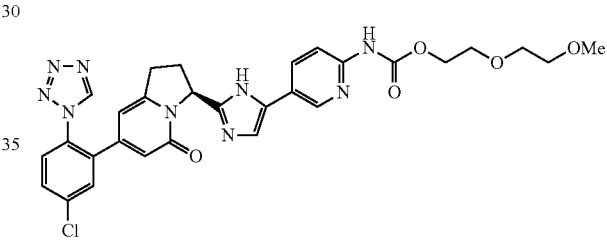

LC/MS $t_R$ 0.69 minutes; MS (ES$^+$) m/z 618 (M+H)$^+$
$^1$H NMR (300 MHz, DMSO-$d_6$) δ 12.7 (s, 0.2 H), 12.2 (s, 0.8 H), 10.3 (s, 0.2 H), 10.1 (s, 0.8 H), 9.69 (s, 0.2 H), 9.67 (s, 0.8 H), 8.60-8.51 (m, 1 H), 8.03-7.95 (m, 1 H), 7.85-7.75 (m, 4 H), 7.52 (d, 0.8 H), 7.21 (d, 0.2 H), 5.97-5.90 (m, 2 H), 5.64-5.58 (m, 1 H), 4.23-4.16 (m, 2 H), 3.66-3.59 (m, 2 H), 3.58-3.52 (m, 2 H), 3.50-3.32 (m, 5 H), 3.05-2.92 (m, 1 H), 2.62-2.18 (m, 2 H), 1.07 (t, 3 H).

EXAMPLE 854(3)

2-(2-ethoxyethoxyl)ethyl[5-(2-{(3S)-7-[5-chloro-2-(1H-tetrazol-1-yl)phenyl]-5-oxo-1,2,3,5-tetrahydro-3-indolizinyl}-1H-imidazol-5-yl)-2-pyridinyl]carbamate

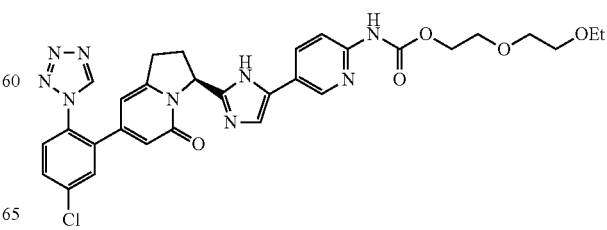

LC/MS $t_R$ 0.72 minutes; MS (ES$^+$) m/z 632 (M+H)$^f$ $^1$H NMR (300 MHz, DMSO-d$_6$) δ 12.7 (s, 0.2 H), 12.2 (s, 0.8 H), 10.3 (s, 0.2 H), 10.1 (s, 0.8 H), 9.69 (s, 0.2 H), 9.67 (s, 0.8 H), 8.59-8.51 (m, 1 H), 8.03-7.95 (m, 1 H), 7.82-7.75 (m, 4 H), 7.53 (d, 0.8 H), 7.22 (d, 0.2 H), 5.97-5.92 (m, 2 H), 5.64-5.58 (m, 1 H), 4.24-4.16 (m, 2 H), 3.66-3.56 (m, 2 H), 3.56-3.51 (m, 2 H), 3.46-3.28 (m, 3 H), 3.24 ((s, 3 H), 3.05-2.92 (m, 1 H), 2.60-2.18 (m, 2 H).

EXAMPLE 855(1) TO EXAMPLE 855(3)

The compounds of the present invention having the following physical data were prepared using the compound prepared in Example 198 and the corresponding chloroformates using the method as detailed in Example 128.

EXAMPLE 855(1)

3-hydroxy-3-methylbutyl[5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-pyridinyl]carbamate LC/MS $t_R$ 0.82 minutes; MS (ES$^+$) m/z 636 (M+H)$^f$ $^1$H NMR (300 MHz, DMSO-d$_6$) δ 13.0 (brs, 1 H), 10.2 (s, 1 H), 9.69 (s, 1 H), 8.55 (d, 1H), 8.04 (dd, 1 H), 7.92 (d, 1 H), 7.86-7.75 (m, 3 H), 5.97 (s, 1 H), 5.92 (s, 1 H), 5.55 (dd, 1 H), 4.35 (s, 1 H), 4.20 (t, 2 H), 3.28 (m, 1 H), 2.98 (m, 1 H), 2.52 (m, 1 H), 2.20 (m, 1 H), 1.74 (t, 2 H), 1.13 (s, 6 H).

EXAMPLE 855(2)

2-(2-methoxyethoxyl)ethyl[5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-pyridinyl]carbamate

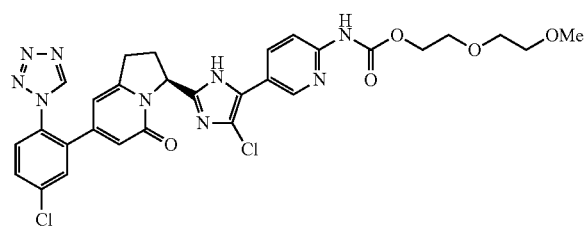 [SMILES: COCCOCCOC(=O)Nc1ccc(-c2[nH]c([C@@H]3CCc4cc(-c5cc(Cl)ccc5-n5cnnn5)cc(=O)n43)nc2Cl)cn1]

LC/MS $t_R$ 0.82 minutes; MS (ES$^+$) m/z 652 (M+H)$^f$ $^1$H NMR (300 MHz, DMSO-d$_6$) δ 13.1 (s, 1 H), 10.4 (s, 1 H), 9.70 (s, 1 H), 8.56 (d, 1H), 8.02 (dd, 1 H), 7.91 (d, 1 H), 7.84-7.77 (m, 3 H), 5.98 (s, 1 H), 5.93 (s, 1 H), 5.59-5.52 (m, 1 H), 4.26-4.19 (m, 2 H), 3.67-3.61 (m, 2 H), 3.59-3.52 (m, 2 H), 3.47-3.40 (m, 2 H), 3.37-3.24 (m, 1 H), 3.23 ((s, 3 H), 3.04-2.92 (m, 1 H), 2.60-2.28 (m, 1 H), 2.27-2.13 (m, 1 H).

EXAMPLE 855(3)

2-(2-ethoxyethoxyl)ethyl[5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-pyridinyl]carbamate LC/MS $t_R$ 0.86 minutes; MS (ES$^+$) m/z 666 (M+H)$^f$ $^1$H NMR (300 MHz, DMSO-d$_6$) δ 13.1 (s, 1 H), 10.4 (s, 1 H), 9.70 (s, 1 H), 8.56 (d, 1 H), 8.02 (dd, 1 H), 7.91 (d, 1 H), 7.84-7.77 (m, 3 H), 5.98 (s, 1 H), 5.93 (s, 1 H), 5.59-5.52 (m, 1 H), 4.26-4.19 (m, 2 H), 3.68-3.61 (m, 2 H), 3.59-3.52 (m, 2 H), 3.51-3.20 (m, 5 H), 3.04-2.92 (m, 1 H), 2.60-2.28 (m, 1 H), 2.27-2.13 (m, 1 H), 1.08 (t, 3 H).

EXAMPLE 856(1) TO EXAMPLE 856(2)

The compounds of the present invention having the following physical data were prepared using the compound prepared in Example 593 and the corresponding chloroformates using the method as detailed in Example 128.

EXAMPLE 856(1)

2-(2-methoxyethoxyl)ethyl[5-(2-{(3S)-7-[5-chloro-2-(1H-tetrazol-1-yl)phenyl]-5-oxo-1,2,3,5-tetrahydro-3-indolizinyl}-4-fluoro-1H-imidazol-5-yl)-2-pyridinyl]carbamate

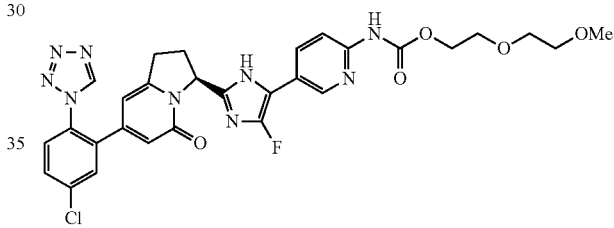

LC/MS $t_R$ 0.82 minutes; MS (ES$^+$) m/z 636 (M+H)$^f$ $^1$H NMR (300 MHz, DMSO-d$_6$) δ 12.9 (s, 1 H), 10.3 (s, 1 H), 9.69 (s, 1 H), 8.46 (s, 1H), 7.92-7.77 (m, 5 H), 5.96 (s, 1 H), 5.93 (s, 1 H), 5.53 (d, 1 H), 4.25-4.18 (m, 2 H), 3.67-3.60 (m, 2 H), 3.59-3.52 (m, 2 H), 3.47-3.40 (m, 2 H), 3.37-3.24 (m, 1 H), 3.23 ((s, 3 H), 3.03-2.92 (m, 1 H), 2.60-2.28 (m, 1 H), 2.27-2.13 (m, 1 H).

EXAMPLE 856(2)

2-(2-ethoxyethoxyl)ethyl[5-(2-{(3S)-7-[5-chloro-2-(1H-tetrazol-1-yl)phenyl]-5-oxo-1,2,3,5-tetrahydro-3-indolizinyl}-4-fluoro-1H-imidazol-5-yl)-2-pyridinyl]carbamate LC/MS $t_R$ 0.85 minutes; MS (ES$^+$) m/z 650 (M+H)$^f$ $^1$H NMR (300 MHz, DMSO-d$_6$) δ 12.9 (s, 1 H), 10.3 (s, 1 H), 9.69 (s, 1 H), 8.45 (s, 1 H), 7.91-7.77 (m, 5 H), 5.96 (s, 1 H), 5.93 (s, 1 H), 5.52 (d, 1 H), 4.25-4.18 (m, 2 H), 3.67-3.60 (m, 2 H), 3.58-3.52 (m, 2 H), 3.50-3.19 (m, 5 H), 3.03-2.92 (m, 1 H), 2.60-2.28 (m, 1 H), 2.27-2.13 (m, 1 H), 1.08 (t, 3 H).

EXAMPLE 857(1) TO EXAMPLE 857(2)

The compounds of the present invention having the following physical data were prepared using the compound prepared in Example 718(6) and the corresponding chloroformates using the method as detailed in Example 128.

EXAMPLE 857(1)

2-(2-methoxyethoxyl)ethyl[5-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-pyridinyl]carbamate

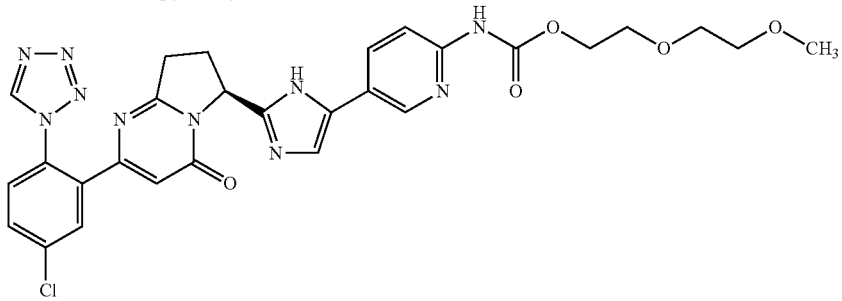 [SMILES: COCCOCCOC(=O)Nc1ccc(-c2cnc([C@@H]3CCc4nc(-c5cc(Cl)ccc5-n5cnnn5)cc(=O)n43)[nH]2)cn1]

LC/MS $t_R$ 0.67 minutes; MS (ES$^+$) m/z 619 (M+H)$^f$
$^1$H NMR (300 MHz, methanol-d$_4$) δ 9.43 (s, 1 H), 8.63-8.50 (m, 1 H), 8.10-7.97 (m, 1H), 7.97-7.83 (m, 2 H), 7.77 (dd, 1 H), 7.70 (d, 1 H), 7.49-7.39 (m, 1 H), 6.34 (s, 1 H), 5.78-5.69 (m, 1 H), 4.31 (t, 2 H), 3.77 (t, 2 H), 3.69-3.63 (m, 2 H), 3.58-3.52 (m, 2 H), 3.36 ((s, 3 H), 3.28-3.21 (m, 1 H), 3.01-2.85 (m, 1 H), 2.76-2.60 (m, 1 H), 2.50-2.32 (m, 1 H).

EXAMPLE 857(2)

2-(2-ethoxyethoxyl)ethyl[5-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-pyridinyl]carbamate LC/MS $t_R$ 0.70 minutes; MS (ES$^+$) m/z 633 (M+H)$^f$
$^1$H NMR (300 MHz, methanol-d$_4$) δ 9.43 (s, 1 H), 8.60-8.49 (m, 1 H), 8.08-7.98 (m, 1 H), 7.93-7.83 (m, 2 H), 7.77 (dd, 1 H), 7.69 (d, 1 H), 7.49-7.39 (m, 1 H), 6.35 (s, 1 H), 5.78-5.70 (m, 1 H), 4.32 (t, 2 H), 3.76 (t, 2 H), 3.69-3.63 (m, 2 H), 3.62-3.57 (m, 2 H), 3.53 (q, 2 H), 3.28-3.22 (m, 1 H), 3.01-2.86 (m, 1 H), 2.77-2.59 (m, 1 H), 2.51-2.32 (m, 1 H), 1.17 (t, 3 H).

EXAMPLE 858(1) TO EXAMPLE 858(2)

The compounds of the present invention having the following physical data were prepared using the compound prepared in Example 330 and the corresponding chloroformates using the method as detailed in Example 128.

EXAMPLE 858(1)

2-(2-methoxyethoxy)ethyl[5-(4-chloro-2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-pyridinyl]carbamate

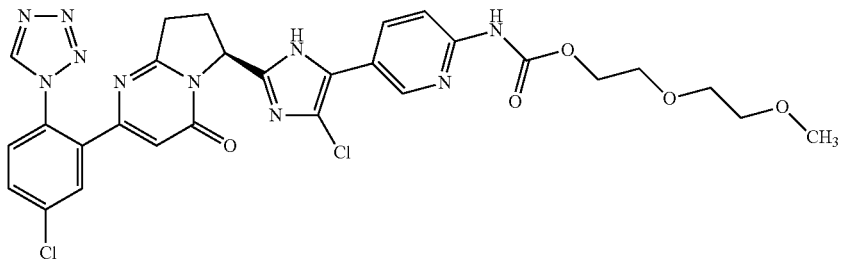 [SMILES: COCCOCCOC(=O)Nc1ccc(-c2[nH]c([C@@H]3CCc4nc(-c5cc(Cl)ccc5-n5cnnn5)cc(=O)n43)nc2Cl)cn1]

LC/MS $t_R$ 0.80 minutes; MS (ES$^+$) m/z 653 (M+H)$^f$
$^1$H NMR (300 MHz, methanol-d$_4$) δ 9.44 (s, 1 H), 8.58 (d, 1 H), 8.05 (dd, 1 H), 7.99 (d, 1 H), 7.92 (d, 1 H), 7.77 (d, 1 H), 7.70 (d, 1 H), 6.37 (s, 1 H), 5.71-5.64 (m, 1 H), 4.33 (t, 2 H), 3.76 (t, 2 H), 3.72-3.62 (m, 2 H), 3.59-3.52 (m, 2 H), 3.36 ((s, 3 H), 3.26-3.20 (m, 1 H), 2.99-2.85 (m, 1 H), 2.76-2.60 (m, 1 H), 2.43-2.29 (m, 1 H).

EXAMPLE 858(2)

2-(2-ethoxyethoxyl)ethyl[5-(4-chloro-2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-pyridinyl]carbamate LC/MS $t_R$ 0.83 minutes; MS (ES$^+$) m/z 667 (M+H)$^f$
$^1$H NMR (300 MHz, methanol-d$_4$) δ 9.44 (s, 1 H), 8.62-8.55 (m, 1 H), 8.09-7.96 (m, 2 H), 7.92 (d, 1 H), 7.78 (dd, 1 H), 7.70 (d, 1 H), 6.36 (s, 1 H), 5.71-5.63 (m, 1 H), 4.33 (t, 2 H), 3.77 (t, 2 H), 3.69-3.63 (m, 2 H), 3.62-3.57 (m, 2 H), 3.53 (q, 2 H), 3.28-3.20 (m, 1 H), 3.00-2.85 (m, 1 H), 2.77-2.61 (m, 1 H), 2.43-2.29 (m, 1 H), 1.17 (t, 3 H).

EXAMPLE 859(1) TO EXAMPLE 859(2)

The compounds of the present invention having the following physical data were prepared using the compound prepared in Example 722 and the corresponding chloroformates using the method as detailed in Example 128.

EXAMPLE 859(1)

2-(2-methoxyethoxyl)ethyl[5-(2-{(6S)-2-[5-chloro-2-(1H-tetrazol-1-yl)phenyl]-4-oxo-4,6,7,8-tetrahydropyrrolo[1,2-a]pyrimidin-6-yl}-4-fluoro-1H-imidazol-5-yl)-2-pyridinyl]carbamate

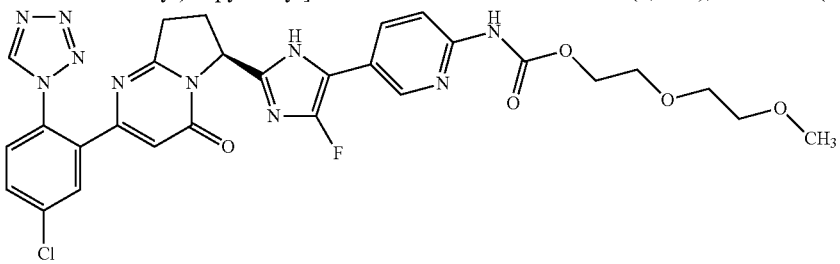

LC/MS $t_R$ 0.79 minutes; MS (ES$^+$) m/z 637 (M+H)$^f$
$^1$H NMR (300 MHz, methanol-d$_4$) δ 9.43 (s, 1 H), 8.46 (d, 1 H), 7.99-7.87 (m, 3 H), 7.77 (dd, 1 H), 7.70 (d, 1 H), 6.36 (s, 1 H), 5.67-5.61 (m, 1 H), 4.32 (t, 2 H), 3.78 (t, 2H), 3.69-3.61 (m, 2 H), 3.59-3.52 (m, 2 H), 3.37-3.34 (m, 3 H), 3.26-3.20 (m, 1H), 2.99-2.85 (m, 1 H), 2.76-2.62 (m, 1 H), 2.41-2.29 (m, 1 H).

EXAMPLE 859(2)

2-(2-ethoxyethoxyl)ethyl[5-(2-{(6S)-2-[5-chloro-2-(1H-tetrazol-1-yl)phenyl]-4-oxo-4,6,7,8-tetrahydropyrrolo[1,2-a]pyrimidin-6-yl}-4-fluoro-1H-imidazol-5-yl)-2-pyridinyl]carbamate LC/MS $t_R$ 0.83 minutes; MS (ES$^+$) m/z 651 (M+H)$^f$
$^1$H NMR (300 MHz, methanol-d$_4$) δ 9.43 (s, 1 H), 8.45 (d, 1 H), 7.99-7.88 (m, 3 H), 7.77 (dd, 1 H), 7.70 (d, 1 H), 6.35 (s, 1 H), 5.67-5.61 (m, 1 H), 4.33 (t, 2 H), 3.76 (t, 2 H), 3.69-3.63 (m, 2 H), 3.62-3.57 (m, 2 H), 3.53 (q, 2 H), 3.28-3.20 (m, 1 H), 3.00-2.85 (m, 1 H), 2.75-2.58 (m, 1 H), 2.42-2.27 (m, 1 H), 1.17 (t, 3 H).

EXAMPLE 860

(3S)-3-[5-(5-amino-2-pyridinyl)-4-chloro-1H-imidazol-2-yl]-7-[5-chloro-2-(1H-tetrazol-1-yl)phenyl]-2,3-dihydro-5(1H)-indolizinone The same operation as in Example 52→Example 44→Example 55 was conducted from the compound prepared in Example 228 to give the title compound having the following physical properties.
LC/MS $t_R$ 0.71 minutes; MS (ES$^+$) m/z 506 (M+H)$^f$
$^1$H NMR (300 MHz, DMSO-d$_6$) δ 12.6 (brs, 1 H), 9.68 (s, 1 H), 8.02-7.70 (m, 4 H), 7.65 (d, 1 H), 7.00 (d, 1 H), 5.96 (s, 1 H), 5.92 (s, 1 H), 5.63 (d, 1 H), 5.54 (brs, 2 H), 3.22 (m, 1 H), 2.98 (m, 1 H), 2.45 (m, 1 H), 2.20 (m, 1 H).

EXAMPLE 861

(6S)-6-[5-(5-amino-2-pyridinyl)-4-chloro-1H-imidazol-2-yl]-2-[5-chloro-2-(1H-tetrazol-1-yl)phenyl]-7,8-dihydropyrrolo f 1,2-al pyrimidin-4(6H)-one The same operation as in Example 51→Example 52→Example 44→Example 55 was conducted from the compound prepared in Example 336 to give the title compound having the following physical properties. (Note: in the step corresponding to Example 51 in the operation, the compound prepared in Example 219 was used)
LC/MS $t_R$ 0.68 minutes; MS (ES$^+$) m/z 507 (M+H)$^f$
$^1$H NMR (300 MHz, CDCl$_3$) δ 8.77 (s, 1 H), 8.07 (d, 1 H), 7.84 (d, 1 H), 7.67-7.60 (m, 2 H), 7.46 (d, 1 H), 7.01 (dd, 1 H), 6.41 (s, 1 H), 5.74 (dd, 1 H), 3.79 (s, 2 H), 3.46-3.15 (m, 2 H), 2.95-2.80 (m, 1 H), 2.55-2.39 (m, 1 H).

EXAMPLE 862 methyl[4-(4-chloro-2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)phenyl]carbamate The same operation as in Example 44 was conducted from the compound prepared in Example 718(13) to give the title compound having the following physical properties.
LC/MS $t_R$ 0.84 minutes; MS (ES$^+$) m/z 564 (M+H)$^f$
$^1$H NMR (300 MHz, DMSO-d$_6$) δ 12.9 (s, 1 H), 9.79 (s, 1 H), 9.74 (s, 1 H), 7.98 (d, 1 H), 7.88-7.78 (m, 2 H), 7.62-7.50 (m, 4 H), 6.32 (s, 1 H), 5.59-5.52 (m, 1 H), 3.67 ((s, 3 H), 3.20-3.02 (m, 1 H), 2.81-2.71 (m, 1 H), 2.62-2.39 (m, 1 H), 2.18-2.09 (m, 1 H).

EXAMPLE 863 methyl[4-(4-chloro-2-{(3S)-7-[5-methyl-2-(1H-tetrazol-1-yl)phenyl]-5-oxo-1,2,3,5-tetrahydro-3-indolizinyl}-1H-imidazol-5-yl)phenyl]carbamate The same operation as in Example 44 was conducted from the compound prepared in Example 309 to give the title compound having the following physical properties.

LC/MS $t_R$ 2.18 minutes; MS (ES$^+$) m/z 543 (M+H)$^d$
$^1$H NMR (300 MHz, methanol-d$_4$) δ 9.31 (s, 1 H), 7.66-7.46 (m, 7 H), 6.10 (s, 1 H), 6.06 (s, 1 H), 5.69 (dd, 1 H), 3.74 ((s, 3 H), 3.42 (m, 1 H), 3.08 (m, 1 H), 2.62 (m, 1 H), 2.51 ((s, 3 H), 2.38 (m, 1 H).

EXAMPLE 864(1) TO EXAMPLE 864(3)

The compounds of the present invention having the following physical data were prepared from the compound prepared in Example 9 using the corresponding alpha-bromoketones in the process of Example 51→Example 52.

EXAMPLE 864(1)

Methyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)-3-methylphenyl]carbamate LC/MS $t_R$ 3.73 minutes; MS (ES$^+$) m/z 543 (M+H)$^d$
$^1$H NMR (300 MHz, DMSO-d$_6$) δ 12.26-12.10 (m, 1 H), 9.74-9.57 (m, 2 H), 7.84-7.80 (m, 3 H), 7.62 (d, 1 H), 7.39-7.30 (m, 2 H), 7.19 (d, 1 H), 5.99 (s, 2 H), 5.69-5.66 (m, 1 H), 3.73-3.69 (m, 3 H), 3.48-3.30 (m, 1 H), 3.08-3.00 (m, 1 H), 2.56-2.53 (m, 2 H), 2.38-2.30 (m, 3 H).

EXAMPLE 864(2)

2-methoxyethyl[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]carbamate LC/MS $t_R$ 0.66 minutes; MS (ES$^+$) m/z 573 (M+H)$^f$
$^1$H NMR (300 MHz, DMSO-d$_6$) δ 12.02 (brs, 1 H), 9.69 (s, 1 H), 9.68 (s, 1 H), 7.85-7.74 (m, 3 H), 7.59 (d, 2 H), 7.41 (d, 2 H), 7.39 (d, 1 H), 6.02-5.90 (m, 2 H), 5.61 (d, 1 H), 4.28-4.12 (m, 2 H), 3.62-3.50 (m, 2 H), 3.45-3.21 (m, 1 H), 3.32 ((s, 3 H), 3.06-2.93 (m, 1 H), 2.57-2.25 (m, 2 H).

EXAMPLE 864(3)

(3S)-7-[5-chloro-2-(1H-tetrazol-1-yl)phenyl]-3-[5-(4-hydroxyphenyl)-1H-imidazol-2-yl]-2,3-dihydro-5(1H)-indolizinone LC/MS $t_R$ 0.64 minutes; MS (ES$^+$) m/z 472 (M+H)$^f$
$^1$H NMR (300 MHz, DMSO-d$_6$) δ 12.3 (s, 0.3 H), 11.9 (s, 0.7 H), 9.69 (s, 0.3 H), 9.67 (s, 0.7 H), 9.47 (s, 0.3 H), 9.24 (s, 0.7 H), 7.80-7.75 (m, 3 H), 7.51-7.37 (m, 2 H), 7.26 (d, 0.7 H), 6.98 (d, 0.3 H), 6.79-6.67 (m, 2 H), 5.97-5.90 (m, 2 H), 5.62-5.55 (m, 1 H), 3.43-3.21 (m, 1 H), 3.02-2.91 (m, 1 H), 2.63-2.13 (m, 2 H).

EXAMPLE 865(1) to Example 865(2)

The compounds of the present invention having the following physical data were prepared from the compound prepared in Example 9 using the corresponding alpha-bromoketones in the process of Example 51→Example 52→Example 44.

EXAMPLE 865(1)

(3S)-3-[4-chloro-5-(4-hydroxyphenyl)-1H-imidazol-2-yl]-7-[5-chloro-2-(1H-tetrazol-1-yl)phenyl]-2,3-dihydro-5(1H)-indolizinone LC/MS $t_R$ 0.82 minutes; MS (ES$^+$) m/z 506 (M+H)$^f$
$^1$H NMR (300 MHz, DMSO-d$_6$) δ 12.7 (s, 1 H), 9.70 (s, 1 H), 9.66 (s, 1 H), 7.85-7.77 (m, 3 H), 7.48 (d, 2 H), 6.84 (d, 2 H), 5.97 (s, 1 H), 5.92 (s, 1 H), 5.54 (dd, 1 H), 3.40-3.20 (m, 1 H), 3.02-2.89 (m, 1 H), 2.62-2.30 (m, 1 H), 2.24-2.14 (m, 1 H).

EXAMPLE 865(2)

ethyl 5-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-thiophenecarboxylate

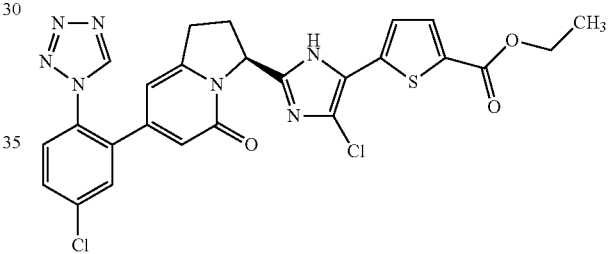

TLC Rf 0.52 (ethyl acetate)
$^1$H NMR (300 MHz, CDCl$_3$) δ 9.34 (s, 1 H), 7.75-7.65 (m, 4 H), 7.37 (d, 1 H), 6.12 (d, 1 H), 6.08 (d, 1 H), 5.68 (dd, 1 H), 4.34 (q, 2 H), 3.50-3.30 (m, 1 H), 3.08-3.10 (m, 1 H), 2.70-2.58 (m, 1 H), 2.43-2.30 (m, 1 H), 1.37 (t, 3 H).

EXAMPLE 867

3-methoxypropyl[6-(4-chloro-2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-3-pyridinyl]carbamate

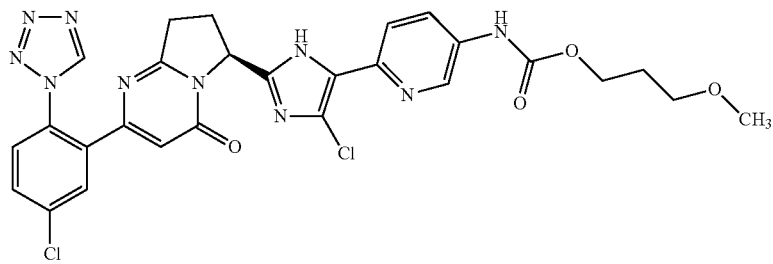 [SMILES: COCCCOC(=O)Nc1ccc(-c2[nH]c([C@@H]3CCc4nc(-c5cc(Cl)ccc5-n5cnnn5)cc(=O)n43)nc2Cl)nc1]

The same operation as in Example 128→Example 188→Example 204→Example 51→Example 52→Example 338 was conducted from 5-amino-2-cyanopyridine to give the title compound having the following physical properties. (Note: in the step corresponding to Example 128 in the operation, 3-methoxypropyl chloroformate was used. In the step corresponding to Example 51 in the operation, the compound prepared in Example 336 was used)

LC/MS $t_R$ 0.85 minutes; MS (ES$^+$) m/z 623 (M+H)$^f$ $^1$H NMR (300 MHz, CDCl$_3$) δ 11.45-11.25 (m, 1 H), 8.82 (s, 1 H), 8.20 (d, 1 H), 8.13-8.03 (m, 1 H), 7.90 (d, 1 H), 7.70-7.60 (m, 2 H), 7.48 (d, 1 H), 7.20-7.12 (m, 1 H), 6.48 (s, 1 H), 5.85-5.79 (m, 1 H), 4.30 (t, 2 H), 3.57-3.40 (m, 3 H), 3.36 ((s, 3 H), 3.16-3.03 (m, 1 H), 2.96-2.82 (m, 1 H), 2.60-2.42 (m, 1 H), 2.03-1.92 (m, 2 H).

EXAMPLE 868 bis(2-methyl-2-propanyl)[5-(bromoacetyl)-3-fluoro-2-pyridinyl]imidodicarbonate

The same operation as in Example 90→Example 228→Example 361 was conducted from (5-iodo-3-fluoro-pyridin-2-yl)-amine to give the title compound having the following physical properties.

$^1$H NMR (300 MHz, CDCl$_3$) δ 8.87 (dd, 1 H), 8.03 (dd, 1 H), 4.42 (s, 2 H), 1.44 (s, 18H).

EXAMPLE 869

(3S)-3-[5-(6-amino-5-fluoro-3-pyridinyl)-4-chloro-1H-imidazol-2-yl]-7-[5-chloro-2-(1H-tetrazol-1-yl)phenyl]-2,3-dihydro-5(1H)-indolizinone The same operation as in Example 51→Example 52→Example 338→Example 55 was conducted from the compound prepared in Example 9 to give the title compound having the following physical properties. (Note: in the step corresponding to Example 51 in the operation, the compound prepared in Example 868 was used)

LC/MS $t_R$ 0.75 minutes; MS (ES$^+$) m/z 524 (M+H)$^f$ $^1$H NMR (300 MHz, DMSO-d$_6$) δ 12.9 (s, 1 H), 9.70 (s, 1 H), 8.09 (s, 1 H), 7.86-7.74 (m, 3 H), 7.60 (dd, 1 H), 6.49 (s, 2 H), 5.97 (s, 1 H), 5.92 (s, 1 H), 5.52 (dd, 1 H), 3.30-3.17 (m, 1 H), 3.03-2.92 (m, 1 H), 2.60-2.45 (m, 1 H), 2.24-2.12 (m, 1 H).

EXAMPLE 870

3-(2-{(3S)-7-[5-chloro-2-(1H-tetrazol-1-yl)phenyl]-5-oxo-1,2,3,5-tetrahydro-3-indolizinyl}-1H-imidazol-5-yl)-2-fluorobenzoic acid hydrochloride The same operation as in Example 378→Example 90→Example 361→Example 51→Example 52→Example 363 was conducted from 3-bromo-2-fluorobenzoic acid to give the title compound having the following physical properties. LC/MS $t_R$ 0.68 minutes; MS (ES$^+$) m/z 518 (M+H)$^f$ $^1$H NMR (300 MHz, DMSO-d$_6$) δ 9.68 (s, 1 H), 8.12-8.04 (m, 1 H), 7.88-7.71 (m, 5 H), 7.43-7.36 (m, 1 H), 6.02 (s, 1 H), 6.00 (s, 1 H), 5.80-5.72 (m, 1 H), 3.45-3.21 (m, 1 H), 3.17-2.98 (m, 1 H), 2.72-2.25 (m, 2 H).

EXAMPLE 871

5-(2-{(3S)-7-[5-chloro-2-(1H-tetrazol-1-yl)phenyl]-5-oxo-1,2,3,5-tetrahydro-3-indolizinyl}-1H-imidazol-5-yl)-2-fluorobenzoic acid The same operation as in Example 378→Example 90→Example 361→Example 51→Example 52→Example 363 was conducted from 5-bromo-2-fluorobenzoic acid to give the title compound having the following physical properties. LC/MS $t_R$ 0.65 minutes; MS (ES$^+$) m/z 518 (M+H)$^f$ $^1$H NMR (300 MHz, DMSO-d$_6$) δ 9.69 (s, 1 H), 8.29-8.21 (m, 1 H), 8.07-7.93 (m, 2 H), 7.85-7.81 (m, 2 H), 7.76-7.72 (m, 1 H), 7.50-7.40 (m, 1 H), 6.03 (s, 1 H), 6.00 (s, 1 H), 5.78-5.70 (m, 1 H), 3.37-3.20 (m, 1 H), 3.15-3.00 (m, 1 H), 2.71-2.59 (m, 1 H), 2.42-2.28 (m, 1 H).

EXAMPLE 872

3-(2-{(3S)-7-[5-chloro-2-(1H-tetrazol-1-yl)phenyl]-5-oxo-1,2,3,5-tetrahydro-3-indolizinyl}-1H-imidazol-5-yl)-2-methylbenzoic acid hydrochloride The same operation as in Example 378→Example 90→Example 361→Example 51→Example 52→Example 363 was conducted from 3-bromo-2-methylbenzoic acid to give the title compound having the following physical properties. LC/MS $t_R$ 0.60 minutes; MS (ES$^+$) m/z 514 (M+H)$^f$ $^1$H NMR (300 MHz, DMSO-d$_6$) δ 9.67 (s, 1 H), 7.86-7.76 (m, 4 H), 7.70 (d, 1 H), 7.56 (dd, 1 H), 7.42 (dd, 1 H), 6.04 (s, 1 H), 6.03 (s, 1 H), 5.84-5.75 (m, 1 H), 3.42-3.00 (m, 2 H), 3.79-2.23 (m, 5 H).

EXAMPLE 873

2-chloro-5-(2-{(3S)-7-[5-chloro-2-(1H-tetrazol-1-yl)phenyl]-5-oxo-1,2,3,5-tetrahydro-3-indolizinyl}-1H-imidazol-5-yl)benzoic acid hydrochloride The same operation as in Example 378→Example 90→Example 361→Example 51→Example 52→Example 363 was conducted from 2-chloro-5-iodobenzoic acid to give the title compound having the following physical properties.

LC/MS $t_R$ 0.69 minutes; MS (ES$^+$) m/z 534 (M+H)$^f$ $^1$H NMR (300 MHz, DMSO-d$_6$) δ 9.68 (s, 1 H), 8.18 (d, 1 H), 8.13 (s, 1 H), 7.92 (dd, 1 H), 7.83-7.79 (m, 2 H), 7.73-7.65 (m, 2 H), 6.04 (s, 1 H), 6.01 (s, 1 H), 5.80-5.72 (m, 1 H), 3.39-3.21 (m, 1 H), 3.18-3.00 (m, 1 H), 2.74-2.23 (m, 2 H).

EXAMPLE 874

1-[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]cyclopropanecarboxylic acid The same operation as in Example 378→Example 90→Example 361→Example 51→Example 52→Example 363 was conducted from 1-(4-bromophenyl)cyclopropanecarboxylic acid to give the title compound having the following physical properties.

LC/MS t$_R$ 0.68 minutes; MS (ES$^+$) m/z 540 (M+H)$^f$
$^1$H NMR (300 MHz, methanol-d$_4$) δ 9.39 (s, 1 H), 7.83 (s, 1 H), 7.77 (dd, 1 H), 7.74-7.71 (m, 1 H), 7.79-7.63 (m, 3 H), 7.52 (d, 2 H), 6.18 (s, 1 H), 6.15 (s, 1 H), 5.94-5.85 (m, 1 H), 2.97-2.79 (m, 2 H), 2.52-2.36 (m, 2 H), 1.66-1.61 (m, 2 H), 1.27-1.21 (m, 2 H).

EXAMPLE 875

1-[3-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]cyclopropanecarboxylic acid The same operation as in Example 378→Example 90→Example 361→Example 51→Example 52→Example 363 was conducted from 1-(3-bromophenyl)cyclopropanecarboxylic acid to give the title compound having the following physical properties.
LC/MS t$_R$ 0.69 minutes; MS (ES$^+$) m/z 540 (M+H)$^f$
$^1$H NMR (300 MHz, methanol-d$_4$) δ 9.39 (s, 1 H), 7.87 (s, 1 H), 7.80-7.67 (m, 4 H), 7.63-7.57 (m, 1 H), 7.51-7.44 (m, 2 H), 6.18 (s, 1 H), 6.15 (s, 1 H), 5.93-5.86 (m, 1 H), 2.95-2.80 (m, 2 H), 2.55-2.38 (m, 2 H), 1.68-1.62 (m, 2 H), 1.31-1.24 (m, 2H).

EXAMPLE 876

1-[3-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)phenyl]cyclopropanecarboxylic acid The same operation as in Example 378→Example 90→Example 361→Example 51→Example 52→Example 338→Example 363 was conducted from 1-(3-bromophenyl)cyclopropanecarboxylic acid to give the title compound having the following physical properties.
LC/MS t$_R$ 0.87 minutes; MS (ES$^+$) m/z 574 (M+H)$^f$
$^1$H NMR (300 MHz, CDCl$_3$) δ 8.69-8.56 (m, 1 H), 7.67-7.44 (m, 5 H), 7.39-7.19 (m, 2 H), 6.30-6.10 (m, 1 H), 5.93-5.73 (m, 2 H), 3.67-3.45 (m, 1 H), 3.12-2.85 (m, 1 H), 2.65-2.40 (m, 2 H), 1.80-1.60 (m, 2 H), 1.40-1.20 (m, 2 H).

EXAMPLE 877

3-(2-{(3S)-7-[5-chloro-2-(1H-tetrazol-1-yl)phenyl]-5-oxo-1,2,3,5-tetrahydro-3-indolizinyl}-1H-imidazol-5-yl)-2,6-difluorobenzoic acid hydrochloride The same operation as in Example 378→Example 90→Example 361→Example 51→Example 52→Example 363 was conducted from 3-bromo-2,6-difluorobenzoic acid to give the title compound having the following physical properties.
LC/MS t$_R$ 0.65 minutes; MS (ES$^+$) m/z 536 (M+H)$^f$
$^1$H NMR (300 MHz, DMSO-d$_6$) δ 9.67 (s, 1 H), 8.06-7.94 (m, 1 H), 7.82-7.71 (m, 3H), 7.65-7.56 (m, 1 H), 7.34-7.24 (m, 1 H), 5.99 (s, 1 H), 5.98 (s, 1 H), 5.74-5.67 (m, 1 H), 3.39-3.22 (m, 1 H), 3.08-2.96 (m, 1 H), 2.75-2.25 (m, 2 H).

EXAMPLE 878

2-chloro-3-(2-{(3S)-7-[5-chloro-2-(1H-tetrazol-1-yl)phenyl]-5-oxo-1,2,3,5-tetrahydro-3-indolizinyl}-1H-imidazol-5-yl)benzoic acid trifluoroacetate The same operation as in Example 378→Example 90→Example 361→Example 51→Example 52→Example 363 was conducted from 3-bromo-2-chlorobenzoic acid to give the title compound having the following physical properties. (Note: high performance liquid chromatography [5 to 100% mobile phase B (0.1% trifluoroacetic acid in acetonitrile) in mobile phase A (0.1% aqueous trifluoroacetic acid)] was used to give the title product as the trifluoroacetic acid salt)
LC/MS t$_R$ 0.64 minutes; MS (ES$^+$) m/z 534 (M+H)$^f$
$^1$H NMR (300 MHz, DMSO-d$_6$) δ 9.68 (s, 1 H), 8.03-7.93 (m, 1 H), 7.85-7.74 (m, 4 H), 7.61-7.54 (m, 1 H), 7.47 (t, 1 H), 6.02-5.97 (m, 2 H), 5.75-5.67 (m, 1 H), 3.43-3.23 (m, 2 H), 3.11-2.97 (m, 2 H).

EXAMPLE 879

(2E)-3-[4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thienyl]acrylic acid hydrochloride The same operation as in Example 378→Example 139→Example 361→Example 51→Example 52→Example 363 was conducted from (2E)-3-(4-bromo-2-thienyl)acrylic acid to give the title compound having the following physical properties.
LC/MS t$_R$ 0.63 minutes; MS (ES$^+$) m/z 532 (M+H)$^f$
$^1$H NMR (300 MHz, DMSO-d$_6$) δ 9.70 (s, 1 H), 8.23 (s, 1H), 7.97 (s, 1H), 7.95 (d, 1H), 7.82 (s, 2H), 7.78-7.66 (m, 3H), 6.27 (d, 1H), 6.05 (s, 1H), 5.99 (s, 1 H), 5.83-5.79 (m, 1H), 3.39-3.24 (m, 1H), 3.18-3.04 (m, 1H), 2.79-2.63 (m, 1 H), 2.46-2.26 (m, 1 H).

EXAMPLE 880

3-[4-(2-{(3S)-7-[5-chloro-2-(1H-tetrazol-1-yl)phenyl]-5-oxo-1,2,3,5-tetrahydro-3-indolizinyl}-1H-imidazol-5-yl)-2-thienyl]propanoic acid hydrochloride The same operation as in Example 378→Example 139→Example 21→Example 361→Example 51→Example 52→Example 363 was conducted from (2E)-3-(4-bromo-2-thienyl)acrylic acid to give the title compound having the following physical properties.
LC/MS t$_R$ 0.58 minutes; MS (ES$^+$) m/z 535 (M+H)$^f$
$^1$H NMR (300 MHz, DMSO-d$_6$) δ 9.68 (s, 1 H), 7.84-7.76 (m, 3H), 7.69 (s, 1H), 7.28 (s, 1H), 6.04 (s, 1H), 6.00 (s, 1 H), 5.79-5.75 (m, 1H), 3.35-3.20 (m, 1H), 3.18-3.04 (m, 1H), 3.04 (t, 1H), 2.76-2.63 (m, 1 H), 2.61 (t, 1H), 2.40-2.19 (m, 1 H).

EXAMPLE 881

5-(2-{(3S)-7-[5-chloro-2-(1H-tetrazol-1-yl)phenyl]-5-oxo-1,2,3,5-tetrahydro-3-indolizinyl}-1H-imidazol-5-yl)nicotinic acid dihydrochloride The same operation as in Example 378→Example 139→Example 361→Example 51→Example 52→Example 363 was conducted from 5-bromonicotinic acid to give the title compound having the following physical properties.
LC/MS t$_R$ 0.59 minutes; MS (ES$^+$) m/z 501 (M+H)$^f$
$^1$H NMR (300 MHz, DMSO-d$_6$) δ 9.68 (s, 1 H), 9.21 (d, 1 H), 9.01 (d, 1 H), 8.65 (t, 1 H), 8.21-8.15 (m, 1 H), 7.84-7.80 (m, 2 H), 7.73 (s, 1 H), 6.03 (s, 1 H), 6.00 (s, 1 H), 5.81-5.73 (m, 1 H), 3.41-3.25 (m, 1 H), 3.18-3.01 (m, 2 H), 2.71-2.61 (m, 1 H).

EXAMPLE 882

2-(2-{(3S)-7-[5-chloro-2-(1H-tetrazol-1-yl)phenyl]-5-oxo-1,2,3,5-tetrahydro-3-indolizinyl}-1H-imidazol-5-yl)-1,3-thiazole-5-carboxylic acid trifluoroacetate The same operation as in Example 378→Example 139→Example 361→Example 51→Example 52→Example 363 was conducted from 2-bromo-1,3-thiazole-5-carboxylic acid to give the title compound having the following physical properties. (Note: high performance liquid chromatography [5 to 100% mobile phase B (0.1% trifluoroacetic acid in acetonitrile) in mobile phase A (0.1% aqueous trifluoroacetic acid)] was used to give the title product as the trifluoroacetic acid salt)

LC/MS $t_R$ 0.67 minutes; MS (ES$^+$) m/z 507 (M+H)$^f$ $^1$H NMR (300 MHz, DMSO-d$_6$) δ 9.34 (s, 1 H), 8.27 (s, 1H), 7.81 (s, 1H), 7.74-7.65 (m, 3 H), 6.14 (s, 1 H), 6.10 (s, 1H), 5.82-5.77 (m, 1 H), 3.51-3.40 (m, 1 H), 3.20-3.08 (m, 1H), 2.76-2.61 (m, 1 H), 2.60-2.46 (m, 1 H).

EXAMPLE 883

6-(2-{(3S)-7-[5-chloro-2-(1H-tetrazol-1-yl)phenyl]-5-oxo-1,2,3,5-tetrahydro-3-indolizinyl}-1H-imidazol-5-yl)-2-pyridinecarboxylic acid trifluoroacetate

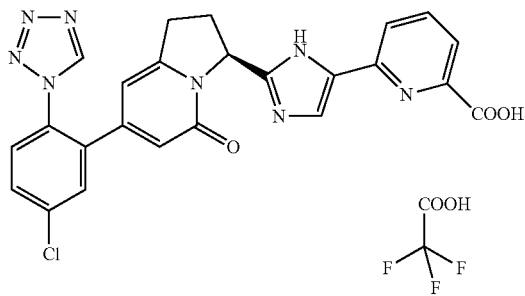 [SMILES: O=C(O)c1cccc(-c2cnc([C@@H]3CCc4cc(-c5cc(Cl)ccc5-n5cnnn5)cc(=O)n43)[nH]2)n1 ; O=C(O)C(F)(F)F]

The same operation as in Example 378→Example 139→Example 361→Example 51→Example 52→Example 363 was conducted from 6-bromo-2-pyridinecarboxylic acid to give the title compound having the following physical properties. (Note: high performance liquid chromatography [5 to 100% mobile phase B (0.1% trifluoroacetic acid in acetonitrile) in mobile phase A (0.1% aqueous trifluoroacetic acid)] was used to give the title product as the trifluoroacetic acid salt)

LC/MS $t_R$ 0.62 minutes; MS (ES$^+$) m/z 501 (M+H)$^f$ $^1$H NMR (300 MHz, DMSO-d$_6$) δ 9.68 (s, 1 H), 8.13-8.01 (m, 3 H), 8.00-7.90 (m, 1 H), 7.86-7.72 (m, 3 H), 6.05-5.98 (m, 2 H), 5.84-5.72 (m, 1 H), 3.40-3.20 (m, 2H), 3.15-2.98 (m, 2 H).

EXAMPLE 884

4-(2-{(3S)-7-[5-chloro-2-(1H-tetrazol-1-yl)phenyl]-5-oxo-1,2,3,5-tetrahydro-3-indolizinyl}-1H-imidazol-5-yl)-1,3-thiazole-2-carboxylic acid hydrochloride The same operation as in Example 378→Example 139→Example 361→Example 51→Example 52→Example 363 was conducted from 4-bromo-1,3-thiazole-2-carboxylic acid to give the title compound having the following physical properties. LC/MS $t_R$ 0.58 minutes; MS (ES$^+$) m/z 507 (M+H)$^f$ $^1$H NMR (300 MHz, DMSO-d$_6$) δ 9.69 (s, 1 H), 8.46 (s, 1 H), 8.10 (s, 1 H), 7.87-7.78 (m, 2 H), 7.71 (s, 1 H), 6.03 (s, 1 H), 6.01 (s, 1 H), 5.86-5.75 (m, 1 H), 3.35-3.05 (m, 4 H).

EXAMPLE 885

4-chloro-3-(2-{(3S)-7-[5-chloro-2-(1H-tetrazol-1-yl)phenyl]-5-oxo-1,2,3,5-tetrahydro-3-indolizinyl}-1H-imidazol-5-yl)benzoic acid trifluoroacetate The same operation as in Example 378→Example 139→Example 361→Example 51→Example 52→Example 363 was conducted from 3-bromo-4-chlorobenzoic acid to give the title compound having the following physical properties. (Note: high performance liquid chromatography [5 to 100% mobile phase B (0.1% trifluoroacetic acid in acetonitrile) in mobile phase A (0.1% aqueous trifluoroacetic acid)] was used to give the title product as the trifluoroacetic acid salt)

LC/MS $t_R$ 0.70 minutes; MS (ES") m/z 534 (M+H)$^r$ $^1$H NMR (300 MHz, DMSO-d$_6$) δ 9.37 (s, 1 H), 8.31 (s, 1H), 8.07-8.04 (m, 1 H), 7.88 (s, 1H), 7.76-7.66 (m, 4H), 6.16 (s, 1 H), 6.14 (s, 1H), 5.94-5.89 (m, 1 H), 3.42-3.10 (m, 2 H), 3.90-2.79 (m, 1H), 2.53-2.41 (m, 1 H).

EXAMPLE 886

[5-(2-{(3S)-7-[5-chloro-2-(1H-tetrazol-1-yl)phenyl]-5-oxo-1,2,3,5-tetrahydro-3-indolizinyl}-1H-imidazol-5-yl)-1-benzothiophen-3-yl]acetic acid trifluoroacetate The same operation as in Example 139→Example 361→Example 51→Example 52→Example 363 was conducted from 2-methyl-2-propanyl(5-chloro-1-benzothiophen-3-yl)acetate to give the title compound having the following physical properties. (Note: high performance liquid chromatography [5 to 100% mobile phase B (0.1% trifluoroacetic acid in acetonitrile) in mobile phase A (0.1% aqueous trifluoroacetic acid)] was used to give the title product as the trifluoroacetic acid salt)

LC/MS $t_R$ 0.67 minutes; MS (ES$^+$) m/z 570 (M+H)$^f$ $^1$H NMR (300 MHz, DMSO-d$_6$) δ 9.68 (s, 1 H), 8.19 (s, 1H), 8.14-8.09 (m, 2H), 7.82 (s, 2H), 7.79-7.70 (m, 3H), 6.06 (s, 1 H), 6.03 (s, 1H), 5.84-5.79 (m, 1 H), 3.91 (s, 2H), 3.36-3.22 (m, 1H), 3.18-3.05 (m, 1H), 2.78-2.63 (m, 1 H), 2.43-2.29 (m, 1H).

EXAMPLE 887

[4-(2-{(3S)-7-[5-chloro-2-(1H-tetrazol-1-yl)phenyl]-5-oxo-1,2,3,5-tetrahydro-3-indolizinyl}-1H-imidazol-5-yl)phenoxy]acetic acid trifluoroacetate The same operation as in Example 139→Example 361→Example 51→Example 52→Example 363 was conducted from 2-methyl-2-propanyl(3-iodophenoxy)acetate [patent EP1386913] to give the title compound having the following physical properties. (Note: high performance liquid chromatography [5 to 100% mobile phase B (0.1% trifluoroacetic acid in acetonitrile) in mobile phase A (0.1% aqueous trifluoroacetic acid)] was used to give the title product as the trifluoroacetic acid salt)

LC/MS $t_R$ 0.59 minutes; MS (ES$^+$) m/z 530 (M+H)$^f$ $^1$H NMR (300 MHz, DMSO-d$_6$) δ 9.38 (s, 1 H), 7.76-7.70 (m, 4 H), 7.63 (d, 2H), 7.07 (d, 2H), 6.16 (s, 1 H), 6.14 (s, 1H), 5.90-5.85 (m, 1 H), 3.35-3.17 (m, 2 H), 2.94-2.79 (m, 1 H), 2.49-2.35 (m, 1 H).

EXAMPLE 888

[3-(2-{(3S)-7-[5-chloro-2-(1H-tetrazol-1-yl)phenyl]-5-oxo-1,2,3,5-tetrahydro-3-indolizinyl}-1H-imidazol-5-yl)phenoxy]acetic acid trifluoroacetate The same operation as in Example 139→Example 361→Example 51→Example 52→Example 363 was conducted from 2-methyl-2-propanyl(4-iodophenoxy)acetate [patent EP1386913] to give the title compound having the following physical properties. (Note: high performance liquid chromatography [5 to 100% mobile phase B (0.1% trifluoroacetic acid in acetonitrile) in mobile phase A (0.1% aqueous trifluoroacetic acid)] was used to give the title product as the trifluoroacetic acid salt)

LC/MS $t_R$ 0.62 minutes; MS (ES$^+$) m/z 530 (M+H)$^f$ $^1$H NMR (300 MHz, DMSO-d$_6$) δ 9.38 (s, 1 H), 7.85 (s, 1H), 7.76-7.67 (m, 3 H), 7.42 (t, 1H), 7.30 (d, 1H), 7.29 (d, H), 7.04 (dd, 1 H), 6.16 (s, 1 H), 6.15 (s, 1H), 5.92-5.86 (m, 1 H), 3.41-3.17 (m, 2 H), 2.94-2.79 (m, 1 H), 2.49-2.39 (m, 1 H).

EXAMPLE 889

2-(2-{(3S)-7-[5-chloro-2-(1H-tetrazol-1-yl)phenyl]-5-oxo-1,2,3,5-tetrahydro-3-indolizinyl}-1H-imidazol-5-yl)-1,3-thiazole-4-carboxylic acid trifluoroacetate The same operation as in Example 139→Example 361→Example 51→Example 52→Example 363 was conducted from 2-methyl-2-propanyl 2-bromo-1,3-thiazole-4-carboxylate [patent WO200854701] to give the title compound having the following physical properties. (Note: high performance liquid chromatography [5 to 100% mobile phase B (0.1% trifluoroacetic acid in acetonitrile) in mobile phase A (0.1% aqueous trifluoroacetic acid)] was used to give the title product as the trifluoroacetic acid salt)

LC/MS $t_R$ 0.69 minutes; MS (ES$^+$) m/z 507 (M+H)$^f$ $^1$H NMR (300 MHz, DMSO-d$_6$) δ 9.35 (s, 1 H), 8.31 (s, 1H), 7.90 (s, 1H), 7.75-7.65 (m, 3 H), 6.15 (s, 1 H), 6.09 (s, 1H), 5.83-5.79 (m, 1 H), 3.48-3.37 (m, 1 H), 3.20-3.08 (m, 1H), 2.78-2.62 (m, 1 H), 2.57-2.43 (m, 1 H).

EXAMPLE 890

3-(2-{(3S)-7-[5-chloro-2-(1H-tetrazol-1-yl)phenyl]-5-oxo-1,2,3,5-tetrahydro-3-indolizinyl}-1H-imidazol-5-yl)-4-fluorobenzoic acid trifluoroacetate The same operation as in Example 139→Example 361→Example 51→Example 52→Example 363 was conducted from 2-methyl-2-propanyl 3-bromo-4-fluorobenzoate [patent WO201037210] to give the title compound having the following physical properties. (Note: high performance liquid chromatography [5 to 100% mobile phase B (0.1% trifluoroacetic acid in acetonitrile) in mobile phase A (0.1% aqueous trifluoroacetic acid)] was used to give the title product as the trifluoroacetic acid salt)

LC/MS $t_R$ 0.69 minutes; MS (ES$^+$) m/z 518 (M+H)$^f$ $^1$H NMR (300 MHz, DMSO-d$_6$) δ 9.66 (s, 1 H), 8.51-8.47 (m, 1H), 7.90-7.82 (m, 1H), 7.78 (s, 1H), 7.75 (s, 1 H), 7.63-7.59 (m, 1H), 7.43-7.37 (m, 1H), 6.01 (s, 1 H), 5.96 (s, 1H), 5.71-5.68 (m, 1 H), 3.40-3.27 (m, 1H), 3.13-3.02 (m, 1 H), 2.71-2.24 (m, 2 H).

EXAMPLE 891 methyl(6-{[(trifluoromethyl)sulfonyl]oxy}-1-benzothiophen-3-yl)acetate

To a solution of methyl(6-hydroxy-1-benzothiophen-3-yl) acetate (883 mg) and triethylamine (1.1 mL) in CH$_2$Cl$_2$ (5 mL) was added trifluoromethanesulfonic anhydride (1.23 g) at 0° C. After being stirred for 25 min at 0° C., the reaction mixture was poured into a saturated aqueous solution of ammonium chloride. The mixture was extracted with dichloromethane. The organic layers were dried over Na$_2$SO$_4$ and concentrated. The residue was purified by column chromatography (10-20% ethyl acetate in hexane) to give the title compound having the following physical properties (1.16 g).

TLC: Rf 0.76 (30% ethyl acetate in hexane).

EXAMPLE 892

[6-(2-{(3S)-7-[5-chloro-2-(1H-tetrazol-1-yl)phenyl]-5-oxo-1,2,3,5-tetrahydro-3-indolizinyl}-1H-imidazol-5-yl)-1-benzothiophen-3-yl]acetic acid trifluoroacetate The same operation as in Example 139→Example 361→Example 51→Example 52→Example 342 was conducted from the compound prepared in Example 891 to give the title compound having the following physical properties. (Note: high performance liquid chromatography [5 to 100% mobile phase B (0.1% trifluoroacetic acid in acetonitrile) in mobile phase A (0.1% aqueous trifluoroacetic acid)] was used to give the title product as the trifluoroacetic acid salt)

LC/MS $t_R$ 0.64 minutes; MS (ES$^+$) m/z 570 (M+H)$^f$ $^1$H NMR (300 MHz, DMSO-d$_6$) δ 9.68 (s, 1 H), 8.36 (s, 1H), 8.07 (s, 1H), 7.89 (d, 1H), 7.84-7.71 (m, 3H), 7.70 (d, 1H), 7.67 (s, 1H), 6.05 (s, 1 H), 6.02 (s, 1H), 5.83-5.78 (m, 1 H), 3.88 (s, 2H), 3.37-3.22 (m, 1H), 3.18-3.06 (m, 1H), 2.78-2.63 (m, 1 H), 2.43-2.24 (m, 1 H).

EXAMPLE 893

2-(2-{(3S)-7-[5-chloro-2-(1H-tetrazol-1-yl)phenyl]-5-oxo-1,2,3,5-tetrahydro-3-indolizinyl}-1H-imidazol-5-yl)isonicotinic acid trifluoroacetate The same operation as in Example 139→Example 361→Example 51→Example 52→Example 342 was conducted from methyl 2-bromoisonicotinate to give the title compound having the following physical properties. (Note: high performance liquid chromatography [5 to 100% mobile phase B (0.1% trifluoroacetic acid in acetonitrile) in mobile phase A (0.1% aqueous trifluoroacetic acid)] was used to give the title product as the trifluoroacetic acid salt)

LC/MS $t_R$ 0.60 minutes; MS (ES$^+$) m/z 501 (M+H)$^f$ $^1$H NMR (300 MHz, DMSO-d$_6$) δ 9.68 (s, 1 H), 8.75 (d, 1 H), 8.28 (s, 1 H), 8.17-8.05 (m, 1 H), 7.91-7.69 (m, 4 H), 6.01 (s, 1 H), 5.98 (s, 1 H), 5.79-5.70 (m, 1 H), 3.40-3.23 (m, 1 H), 3.14-2.98 (m, 2 H), 2.65-2.30 (m, 1 H).

EXAMPLE 894

5-(2-{(3S)-7-[5-chloro-2-(1H-tetrazol-1-yl)phenyl]-5-oxo-1,2,3,5-tetrahydro-3-indolizinyl}-1H-imidazol-5-yl)-3-thiophenecarboxylic acid trifluoroacetate

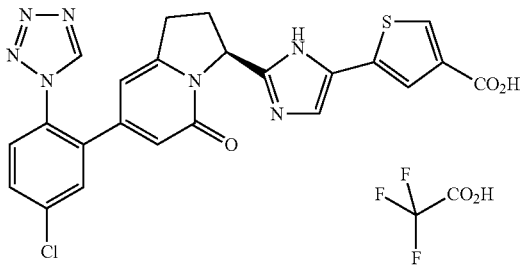 [SMILES: O=C(O)c1csc(-c2cnc([C@@H]3CCc4cc(-c5cc(Cl)ccc5-n5cnnn5)cc(=O)n43)[nH]2)c1 ; O=C(O)C(F)(F)F]

The same operation as in Example 90→Example 361→Example 51→Example 52→Example 342 was conducted from methyl 5-iodo-3-thiophenecarboxylate to give the title compound having the following physical properties. (Note: high performance liquid chromatography [5 to 100% mobile phase B (0.1% trifluoroacetic acid in acetonitrile) in mobile phase A (0.1% aqueous trifluoroacetic acid)] was used to give the title product as the trifluoroacetic acid salt)

LC/MS $t_R$ 0.73 minutes; MS (ES$^+$) m/z 506 (M+H)$^f$ $^1$H NMR (300 MHz, DMSO-$d_6$) δ 9.68 (s, 1 H), 8.25 (s, 1 H), 7.92 (s, 1 H), 7.83-7.75 (m, 3 H), 7.71 (s, 1 H), 6.03 (s, 1 H), 5.99 (s, 1 H), 5.73 (dd, 1 H), 3.40-3.20 (m, 1 H), 3.14-2.98 (m, 1 H), 2.65-2.25 (m, 2 H).

EXAMPLE 895

2-methyl-2-propanyl 3-acetyl-1H-pyrazole-5-carboxylate

To a stirred solution of indium (III) chloride (22 mg) in water (3 mL) was added 3-butyn-2-one (340 mg) and tert-butyl diazoacetate (710 mg) at room temperature. After being stirred at room temperature for 1 hour, the resulting precipitate was collected by filtration, washed with water and dried in vacuo to give the title compound having the following physical properties (1.05 g).

TLC: Rf 0.74 (50% ethyl acetate in hexane).

EXAMPLE 896

3-(2-{(3S)-7-[5-chloro-2-(1H-tetrazol-1-yl)phenyl]-5-oxo-1,2,3,5-tetrahydro-3-indolizinyl}-1H-imidazol-5-yl)-1H-pyrazole-5-carboxylic acid The same operation as in Example 361→Example 51→Example 52→Example 363 was conducted from the compound prepared in Example 895 to give the title compound having the following physical properties.

LC/MS $t_R$ 0.59 minutes; MS (ES$^+$) m/z 490 (M+H)$^f$ $^1$H NMR (300 MHz, methanol-$d_4$) δ 9.34 (s, 1 H), 7.78-7.62 (m, 3 H), 7.30 (s, 1 H), 6.87 (s, 1 H), 6.13 (s, 1 H), 6.07 (s, 1 H), 5.78 (dd, 1 H), 3.40-3.02 (m, 2 H), 2.72-2.40 (m, 2 H).

EXAMPLE 897

5-(2-{(3S)-7-[5-chloro-2-(1H-tetrazol-1-yl)phenyl]-5-oxo-1,2,3,5-tetrahydro-3-indolizinyl}-1H-imidazol-5-yl)-1H-indole-2-carboxylic acid trifluoroacetate The same operation as in Example 378→Example 139→Example 379→Example 361→Example 51→Example 52→Example 363 was conducted from 5-bromo-1H-indole-2-carboxylic acid to give the title compound having the following physical properties. (Note: high performance liquid chromatography [5 to 100% mobile phase B (0.1% trifluoroacetic acid in acetonitrile) in mobile phase A (0.1% aqueous trifluoroacetic acid)] was used to give the title product as the trifluoroacetic acid salt)

LC/MS $t_R$ 0.59 minutes; MS (ES$^+$) m/z 539 (M+H)$^f$ $^1$H NMR (300 MHz, DMSO-$d_6$) δ 11.56 (s, 1H), 9.39 (s, 1 H), 7.96 (d, 1H), 7.99 (s, 1H), 7.76-7.66 (m, 4H), 7.57 (s, 2H), 7.21 (s, 1H), 6.17 (s, 1 H), 6.15 (s, 1H), 5.94-5.88 (m, 1 H), 3.43-3.18 (m, 2 H), 2.94-2.80 (m, 1 H), 2.52-2.39 (m, 1 H).

EXAMPLE 898

5-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-1H-indole-2-carboxylic acid hydrochloride The same operation as in Example 378→Example 139→Example 379→Example 361→Example 51→Example 52→Example 363 was conducted from 5-bromo-1H-indole-2-carboxylic acid to give the title compound having the following physical properties. (Note: in the step corresponding to Example 51 in the operation, the compound prepared in Example 336 was used)

LC/MS $t_R$ 0.58 minutes; MS (ES$^+$) m/z 540 (M+H)$^f$ $^1$H NMR (300 MHz, DMSO-$d_6$) δ 12.05 (s, 1 H), 9.73 (s, 1 H), 8.09 (s, 1 H), 8.04 (s, 1H), 7.94 (d, 1 H), 7.91-7.79 (m, 2 H), 7.69-7.62 (m, 1 H), 7.58-7.51 (m, 1 H), 7.17 (s, 1 H), 6.41 (s, 1 H), 5.87 (dd, 1 H), 3.21-3.04 (m, 1 H), 3.01-2.83 (m, 1 H), 2.81-2.61 (m, 1 H) 2.42-2.28 (m, 1 H).

EXAMPLE 899

[5-(2-{(3S)-7-[5-chloro-2-(1H-tetrazol-1-yl)phenyl]-5-oxo-1,2,3,5-tetrahydro-3-indolizinyl}-1H-imidazol-5-yl)-1H-indol-3-yl]acetic acid hydrochloride The same operation as in Example 378→Example 379→Example 139→Example 361→Example 51→Example 52→Example 363 was conducted from (5-bromo-1H-indol-3-yl)acetic acid to give the title compound having the following physical properties.

LC/MS $t_R$ 0.60 minutes; MS (ES$^+$) m/z 553 (M+H)$^f$ $^1$H NMR (300 MHz, DMSO-$d_6$) δ 11.23 (s, 1H), 9.69 (s, 1 H), 7.96 (d, 1H), 7.95 (s, 1H), 7.82 (s, 2H), 7.71 (s, 1H), 7.48 (s, 2H), 7.34 (s, 1H), 6.06 (s, 1 H), 6.03 (s, 1H), 5.84-5.79 (m, 1 H), 3.70 (s, 2H), 3.39-3.22 (m, 1 H), 3.18-3.05 (m, 1H), 2.80-2.64 (m, 1H), 2.43-2.28 (m, 1 H).

EXAMPLE 900

[6-(2-{(3S)-7-[5-chloro-2-(1H-tetrazol-1-yl)phenyl]-5-oxo-1,2,3,5-tetrahydro-3-indolizinyl}-1H-imidazol-5-yl)-1H-indol-3-yl]acetic acid hydrochloride The same operation as in Example 378→Example 379→Example 139→Example 361→Example 51→Example 52→Example 363 was conducted from (6-bromo-1H-indol-3-yl)acetic acid to give the title compound having the following physical properties.

LC/MS $t_R$ 0.62 minutes; MS (ES$^+$) m/z 553 (M+H)$^f$ $^1$H NMR (300 MHz, DMSO-d$_6$) δ 11.3 (s, 1 H), 9.69 (s, 1 H), 8.03 (s, 1 H), 7.86-7.75 (m, 3 H), 7.71 (d, 1 H), 7.62 (d, 1 H), 7.40 (d, 1 H), 7.36 (d, 1 H), 6.06 (s, 1 H), 6.04 (s, 1 H), 5.82 (dd, 1 H), 3.67 (s, 2 H), 3.28 (m, 1 H), 3.14 (m, 1 H), 2.72 (m, 1 H), 2.38 (m, 1 H).

EXAMPLE 901

[5-(2-{(3S)-7-[5-chloro-2-(1H-tetrazol-1-yl)phenyl]-5-oxo-1,2,3,5-tetrahydro-3-indolizinyl}-1H-imidazol-5-yl)-1H-indazol-3-yl]acetic acid dihydrochloride The same operation as in Example 379→Example 378→Example 139→Example 361→Example 51→Example 52→Example 363 was conducted from (5-bromo-1H-indazol-3-yl)acetic acid to give the title compound having the following physical properties.

LC/MS $t_R$ 0.56 minutes; MS (ES$^+$) m/z 554 (M+H)$^f$ $^1$H NMR (300 MHz, DMSO-d$_6$) δ 14.66 (br s, 1 H), 13.2 (br s, 1 H), 9.70 (s, 1 H), 8.18-8.16 (m, 1 H), 8.05 (s, 1 H), 7.86-7.78 (m, 2 H), 7.75 (dd, 1 H), 7.71 (dd, 1 H), 7.64 (dd, 1 H), 6.06 (s, 1 H), 6.03 (s, 1 H), 5.82 (dd, 1 H), 3.95 (s, 2 H), 3.39-3.22 (m, 1 H), 3.20-3.03 (m, 1 H), 2.80-2.62 (m, 1 H), 2.44-2.31 (m, 1 H).

EXAMPLE 902 tert-butyl 2-(3-acetylanilino)acetate

To a solution of 1-(3-aminophenyl)ethanone (600 mg) in acetone (20 mL) were added potassium carbonate (1.23 g) and tert-butyl 2-bromoacetate (1.73 g). The mixture was refluxed overnight then cooled to room temperature. The insoluble material was removed by filtration. The filtrate was concentrated. The residue was purified by column chromatography (10-20% ethyl acetate in hexane) to give the title compound having the following physical properties (1.10 g).

TLC: Rf 0.62 (20% ethyl acetate in hexane).

EXAMPLE 903

{[3-(2-{(3S)-7-[5-chloro-2-(1H-tetrazol-1-yl)phenyl]-5-oxo-1,2,3,5-tetrahydro-3-indolizinyl}-1H-imidazol-5-yl)phenyl]amino}acetic acid dihydro chloride

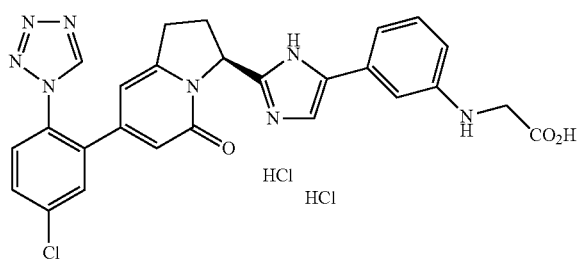 [SMILES: O=C(O)CNc1cccc(-c2cnc([C@@H]3CCc4cc(-c5cc(Cl)ccc5-n5cnnn5)cc(=O)n43)[nH]2)c1 ; Cl ; Cl]

The same operation as in Example 379→Example 361→Example 51→Example 52→Example 363 was conducted from the compound prepared in Example 902 to give the title compound having the following physical properties.

LC/MS $t_R$ 0.57 minutes; MS (ES$^+$) m/z 529 (M+H)$^f$ $^1$H NMR (300 MHz, DMSO-d$_6$) δ 9.68 (s, 1 H), 7.98 (s, 1 H), 7.81 (s, 2 H), 7.69 (d, 1 H), 7.63-7.45 (m, 1 H), 7.18 (d, 1 H), 7.06-6.88 (m, 2 H), 6.67 (d, 1 H), 6.04 (s, 1 H), 6.00 (s, 1 H), 5.88-5.72 (m, 1 H), 3.88 (s, 2 H), 3.34-3.18 (m, 1 H), 3.16-2.98 (m, 1 H), 2.77-2.60 (m, 1 H) 2.43-2.28 (m, 1 H).

EXAMPLE 904

2-(1H-indol-5-yl)-2-oxoethyl(3S)-7-[5-chloro-2-(1H-tetrazol-1-yl)phenyl]-5-oxo-1,2,3,5-tetrahydro-3-indolizinecarboxylate The same operation as in Example 361→Example 51→Example 363 was conducted from 2-methyl-2-propanyl 5-acetyl-1H-indole-1-carboxylate [patent WO200526175] to give the title compound having the following physical properties. TLC: Rf 0.47 (20% ethyl acetate in hexane).

EXAMPLE 905

2-(1-{2-[(2-methyl-2-propanyl)oxy]-2-oxoethyl}-1H-indol-5-yl)-2-oxoethyl(3S)-7-[5-chloro-2-(1H-tetrazol-1-yl)phenyl]-5-oxo-1,2,3,5-tetrahydro-3-indolizinecarboxylate To a solution of the compound prepared in Example 904 (140 mg) in N,N-dimethylformamide (3 mL) were added potassium carbonate (792 mg) and tert-butyl 2-bromoacetate (395 mg) at room temperature. After being stirred for 1 hour at room temperature, the reaction mixture was poured into a saturated aqueous solution of ammonium chloride. The mixture was extracted with ethyl acetate. The combined organic layers were dried over Na$_2$SO$_4$ and concentrated. The residue was purified by column chromatography (0-10% methanol in ethyl acetate) to give the title compound having the following physical properties (99 mg).

TLC: Rf 0.53 (ethyl acetate).

EXAMPLE 906

[5-(2-{(3S)-7-[5-chloro-2-(1H-tetrazol-1-yl)phenyl]-5-oxo-1,2,3,5-tetrahydro-3-indolizinyl}-1H-imidazol-5-yl)-1H-indol-1-yl]acetic acid The same operation as in Example 52→Example 363 was conducted from the compound prepared in Example 905 to give the title compound having the following physical properties.

LC/MS $t_R$ 0.63 minutes; MS (ES$^+$) m/z 553 (M+H)$^f$ $^1$H NMR (300 MHz, DMSO-d$_6$) δ 9.69 (s, 1 H), 7.88-7.02 (m, 8 H), 6.35 (brs, 1 H), 5.97 (brs, 1 H), 5.94 (s, 1 H), 5.63 (d, 1 H), 4.57 (s, 2 H), 3.53-2.85 (m, 2 H), 2.62-2.38 (m, 2 H).

EXAMPLE 907

2-methyl-2-propanyl(5-bromo-1H-benzimidazol-1-yl)acetate

To a stirred suspension of sodium hydride (487 mg) in N,N-dimethylformamide (10 mL) was added a solution of 5-bromo-1H-benzimidazole (2 g) in N,N-dimethylformamide (5 mL) at room temperature. To the resulting mixture was added tert-butyl 2-bromoacetate (2.38 g) at room temperature. After being stirred for 20 minutes, the reaction mixture was poured into a saturated aqueous solution of ammonium chloride. The mixture was extracted with ethyl acetate. The combined organic layers were dried over $Na_2SO_4$ and concentrated. The residue was purified by column chromatography (0-50% ethyl acetate in hexane) to give the title compound having the following physical properties (3.16 g).

TLC: Rf 0.59 (ethyl acetate).

EXAMPLE 908

[5-(2-{(3S)-7-[5-chloro-2-(1H-tetrazol-1-yl)phenyl]-5-oxo-1,2,3,5-tetrahydro-3-indolizinyl}-1H-imidazol-5-yl)-1H-benzimidazol-1-yl]acetic acid dihydrochloride The same operation as in Example 139→Example 361→Example 51→Example 52→Example 363 was conducted from the compound prepared in Example 907 to give the title compound having the following physical properties.

LC/MS $t_R$ 0.55 minutes; MS (ES$^+$) m/z 554 (M+H)$^f$ $^1$H NMR (300 MHz, DMSO-$d_6$) δ 9.70 (s, 1 H), 9.22 (brs, 1 H), 8.31 (s, 1 H), 8.17 (s, 1 H), 8.06-7.92 (m, 2 H), 7.85-7.78 (m, 2 H), 7.71 (s, 1 H), 6.07 (s, 1 H), 6.01 (s, 1 H), 5.86 (dd, 1 H), 5.38 (s, 2 H), 3.32 (m, 1 H), 3.12 (m, 1 H), 2.72 (m, 1 H), 2.42 (m, 1 H).

EXAMPLE 909

5-(2-{(3S)-6-chloro-7-[5-chloro-2-(1H-tetrazol-1-yl)phenyl]-5-oxo-1,2,3,5-tetrahydro-3-indolizinyl}-1H-imidazol-5-yl)-2-thiophenecarboxylic acid hydrochloride

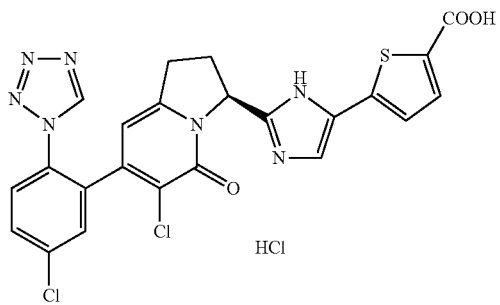 [SMILES: O=C(O)c1ccc(-c2cnc([C@@H]3CCc4cc(-c5cc(Cl)ccc5-n5cnnn5)c(Cl)c(=O)n43)[nH]2)s1 ; Cl]

The same operation as in Example 51→Example 52→Example 363 was conducted from the compound prepared in Example 383(2) to give the title compound having the following physical properties. (Note: in the step corresponding to Example 51 in the operation, the compound prepared in Example 374 was used).

LC/MS $t_R$ 0.64 minutes; MS (ES$^+$) m/z 540 (M+H)$^f$ $^1$H NMR (300 MHz, DMSO-$d_6$) δ 9.73-9.63 (m, 1 H), 7.91-7.85 (m, 2 H), 7.78-7.61 (m, 3 H), 7.41-7.31 (m, 1 H), 6.43-6.35 (m, 1 H), 5.79-5.68 (m, 1 H), 3.80-3.05 (m, 4 H).

EXAMPLE 910

4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-pyridinecarboxylic acid hydrochloride The same operation as in Example 51→Example 52→Example 363 was conducted from the compound prepared in Example 336 to give the title compound having the following physical properties. (Note: in the step corresponding to Example 51 in the operation, the compound prepared in Example 384 was used)

LC/MS $t_R$ 0.55 minutes; MS (ES$^+$) m/z 502 (M+H)$^f$ $^1$H NMR (300 MHz, DMSO-$d_6$) δ 9.73 (s, 1 H), 8.78-8.71 (m, 1 H), 8.53 (s, 1 H), 8.47 (s, 1 H), 8.21 (d, 1 H), 7.95 (s, 1 H), 7.91-7.80 (m, 2 H), 6.36 (s, 1 H), 5.82-5.71 (m, 1 H), 3.24-3.05 (m, 2 H), 2.95-2.78 (m, 2 H).

EXAMPLE 911

4-(4-chloro-2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-pyridinecarboxylic acid hydrochloride

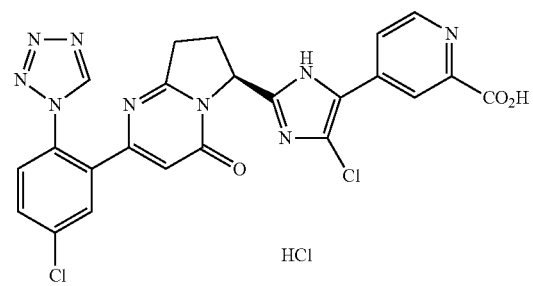 [SMILES: O=C(O)c1cc(-c2[nH]c([C@@H]3CCc4nc(-c5cc(Cl)ccc5-n5cnnn5)cc(=O)n43)nc2Cl)ccn1 ; Cl]

The same operation as in Example 51→Example 52→Example 338→Example 363 was conducted from the compound prepared in Example 336 to give the title compound having the following physical properties. (Note: in the step corresponding to Example 51 in the operation, the compound prepared in Example 384 was used)

LC/MS $t_R$ 0.59 minutes; MS (ES$^+$) m/z 536 (M+H)$^f$ $^1$H NMR (300 MHz, DMSO-$d_6$) δ 9.74 (s, 1 H), 8.78 (d, 1 H), 8.53 (d, 1 H), 8.13 (dd, 1 H), 7.98 (d, 1 H), 7.84 (dd, 1 H), 7.81 (d, 1 H), 6.34 (s, 1 H), 5.63 (dd, 1 H), 3.13-3.03 (m, 1 H), 2.85-2.73 (m, 1 H), 2.65-2.52 (m, 1 H), 2.26-2.15 (m, 1 H).

EXAMPLE 912

4-(4-chloro-2-{(3S)-7-[5-chloro-2-(1H-tetrazol-1-yl)phenyl]-5-oxo-1,2,3,5-tetrahydro-3-indolizinyl}-1H-imidazol-5-yl)-2-pyridinecarboxylic acid trifluoroacetate

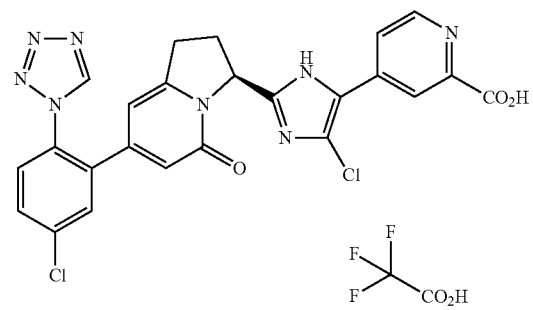 [SMILES: O=C(O)c1cc(-c2[nH]c([C@@H]3CCc4cc(-c5cc(Cl)ccc5-n5cnnn5)cc(=O)n43)nc2Cl)ccn1 ; O=C(O)C(F)(F)F]

The same operation as in Example 51→Example 52→Example 338→Example 363 was conducted from the compound prepared in Example 384 to give the title compound having the following physical properties. (Note: high performance liquid chromatography [5 to 100% mobile phase B (0.1% trifluoroacetic acid in acetonitrile) in mobile phase A (0.1% aqueous trifluoroacetic acid)] was used to give the title product as the trifluoroacetic acid salt)

LC/MS $t_R$ 0.63 minutes; MS (ES$^+$) m/z 535 (M+H)$^f$ $^1$H NMR (300 MHz, DMSO-d$_6$) δ 9.70 (s, 1 H), 8.75 (d, 1 H), 8.46 (d, 1 H), 7.98 (dd, 1 H), 7.83-7.76 (m, 3 H), 5.99 (s, 1 H), 5.94 (s, 1 H), 5.59 (dd, 1 H), 3.38-3.20 (m, 1 H), 3.07-2.91 (m, 1 H), 2.50-2.30 (m, 1 H), 2.28-2.16 (m, 1 H).

EXAMPLE 913

4-(4-chloro-2-{(3S)-8-chloro-7-[5-chloro-2-(1H-tetrazol-1-yl)phenyl]-5-oxo-1,2,3,5-tetrahydro-3-indolizinyl}-1H-imidazol-5-yl)-2-pyridinecarboxylic acid trifluoroacetate The same operation as in Example 51→Example 52→Example 338→Example 363 was conducted from the compound prepared in Example 383(1) to give the title compound having the following physical properties. (Note: in the step corresponding to Example 51 in the operation, the compound prepared in Example 384 was used. High performance liquid chromatography [5 to 100% mobile phase B (0.1% trifluoroacetic acid in acetonitrile) in mobile phase A (0.1% aqueous trifluoroacetic acid)] was used to give the title product as the trifluoroacetic acid salt)

LC/MS $t_R$ 0.69 minutes; MS (ES$^+$) m/z 569 (M+H)$^f$ $^1$H NMR (300 MHz, DMSO-d$_6$) δ 9.74-9.72 (m, 1 H), 8.77-8.75 (m, 1 H), 8.45-8.43 (m, 1 H), 8.00-7.95 (m, 1 H), 7.89-7.68 (m, 3 H), 6.32-6.25 (m, 1 H), 5.74-5.68 (m, 1 H), 3.40-3.21 (m, 1 H), 3.19-3.03 (m, 1 H), 2.77-2.60 (m, 1 H), 2.42-2.39 (m, 1 H).

EXAMPLE 914

4-(2-{(3S)-7-[5-chloro-2-(4-chloro-1H-1,2,3-triazol-1-yl)phenyl]-5-oxo-1,2,3,5-tetrahydro-3-indolizinyl}-1H-imidazol-5-yl)-2-thiophenecarboxylic acid hydrochloride

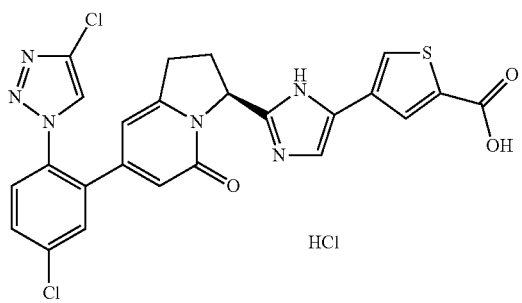 [SMILES: O=C(O)c1cc(-c2cnc([C@@H]3CCc4cc(-c5cc(Cl)ccc5-n5cc(Cl)nn5)cc(=O)n43)[nH]2)cs1 ; Cl]

The same operation as in Example 51→Example 52→Example 363 was conducted from the compound prepared in Example 756 to give the title compound having the following physical properties. (Note: in the step corresponding to Example 51 in the operation, the compound prepared in Example 361 was used)

LC/MS $t_R$ 0.68 minutes; MS (ES$^+$) m/z 539 (M+H)$^f$ $^1$H NMR (300 MHz, DMSO-d$_6$) δ 8.70 (s, 1 H), 8.29 (s, 1 H), 8.17 (s, 1 H), 8.05 (s, 1 H), 7.78 (dd, 1 H), 7.73 (d, 1 H), 7.68 (d, 1 H), 6.10 (s, 1 H), 5.82 (s, 1 H), 5.79 (dd, 1 H), 3.30 (m, 1 H), 3.14 (m, 1 H), 2.72 (m, 1 H), 2.36 (m, 1 H).

EXAMPLE 915

4-(2-{(3S)-7-[5-chloro-2-(4-chloro-1H-1,2,3-triazol-1-yl)phenyl]-5-oxo-1,2,3,5-tetrahydro-3-indolizinyl}-1H-imidazol-5-yl)-2-pyridinecarboxylic acid hydrochloride The same operation as in Example 51→Example 52→Example 363 was conducted from the compound prepared in Example 756 to give the title compound having the following physical properties. (Note: in the step corresponding to Example 51 in the operation, the compound prepared in Example 384 was used)

LC/MS $t_R$ 0.65 minutes; MS (ES$^+$) m/z 534 (M+H)$^f$ $^1$H NMR (300 MHz, DMSO-d$_6$) δ 8.73 (d, 1 H), 8.70 (s, 1 H), 8.52 (d, 1 H), 8.44 (s, 1 H), 8.18 (dd, 1 H), 7.78 (dd, 1 H), 7.77-7.68 (m, 2 H), 6.04 (s, 1 H), 5.96 (s, 1 H), 5.73 (dd, 1 H), 3.38 (m, 1 H), 3.08 (m, 1 H), 2.68-2.25 (m, 2 H).

EXAMPLE 916

5-chloro-2-(1,2,3-thiadiazol-4-yl)phenol

The same operation as in the literature [Tetrahedron 56 (24), 3933 (2000)] was conducted from 1-(4-chloro-2-hydroxyphenyl)ethanone to give the title compound having the following physical properties. (Note: in the step corresponding to Example 51 in the operation, the compound prepared in Example 384 was used)

TLC: Rf 0.74 (50% ethyl acetate in hexane).

EXAMPLE 917

(3S)-3-[5-(6-amino-3-pyridinyl)-4-chloro-1H-imidazol-2-yl]-7-[5-chloro-2-(1,2,3-thiadiazol-4-yl)phenyl]-2,3-dihydro-5(1H)-indolizinone The same operation as in Example 6→Example 283→Example 8→Example 51→Example 52→Example 10→Example 338→Example 363 was conducted from the compound prepared in Example 916 to give the title compound having the following physical properties. (Note: in the step corresponding to Example 51 in the operation, the compound prepared in Example 193 was used)

LC/MS $t_R$ 0.71 minutes; MS (ES$^+$) m/z 522 (M+H)$^f$ $^1$H NMR (300 MHz, DMSO-d$_6$) δ 12.72 (brs, 1 H), 9.04 (d, 1 H), 8.20 (d, 1 H), 7.86 (d, 1 H), 7.73-7.57 (m, 3 H), 6.51 (d, 1 H), 6.18 (brs, 2 H), 5.98 (d, 1 H), 5.56 (d, 1 H), 3.45-3.14 (m, 1 H), 3.04-2.88 (m, 1 H), 2.60-2.34 (m, 1 H), 2.29-2.12 (m, 1 H).

EXAMPLE 918 methyl 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-thiophenecarboxylate

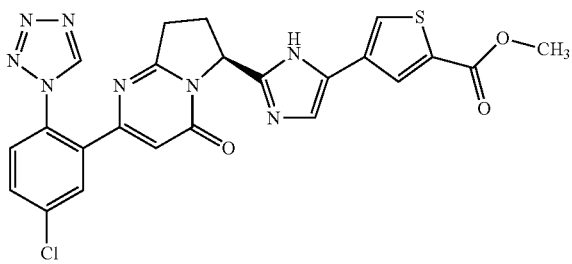 [SMILES: COC(=O)c1cc(-c2cnc([C@@H]3CCc4nc(-c5cc(Cl)ccc5-n5cnnn5)cc(=O)n43)[nH]2)cs1]

The same operation as in Example 370 was conducted from the compound prepared in Example 392 to give the title compound having the following physical properties.

LC/MS $t_R$ 0.71 minutes; MS (ES$^+$) m/z 521 (M+H)$^f$ $^1$H NMR (300 MHz, Methanol-d$_4$) δ 9.44 (s, 1 H), 8.04 (d, 1 H), 7.91 (d, 1 H), 7.82 (d, 1 H) 7.79-7.73 (m, 1 H) 7.72-7.66 (m, 1 H) 7.40-7.34 (m, 1 H), 6.34 (s, 1 H), 5.71 (dd, 1 H), 3.87 ((s, 3 H), 3.27-3.20 (m, 1 H), 3.02-2.84 (m, 1 H), 2.77-2.55 (m, 1 H), 2.49-2.29 (m, 1 H).

EXAMPLE 919(1) and Example 919(2)

2-oxo-2-(1-pyrrolidinyl)ethyl 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-thiophenecarboxylate trifluoroacetate and 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-N,N-dimethyl-2-thiophenecarboxamide

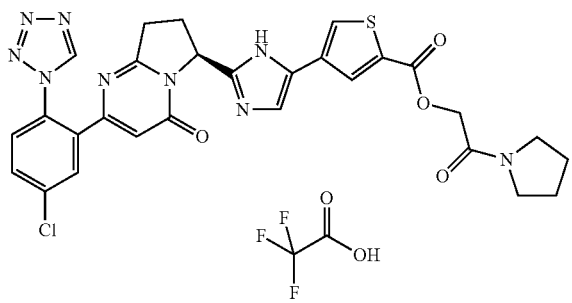

and

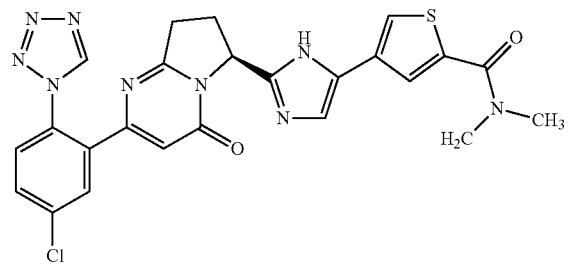

To a solution of the compound prepared in Example 392 (100 mg), 2-hydroxy-1-pyrrolidin-1-yl-ethanone (48 mg), and N,N-diisopropylethylamine (0.080 mL) in N,N-dimethylformamide (2 mL) was added O-(7-azabenzotriazol-1-yl)-N,N,N',N'-tetramethyluronium hexafluorophosphate (84 mg) at room temperature. After being stirred at 40° C. for 15 hours, the reaction mixture was poured into saturated aqueous solution of sodium hydrogen carbonate and extracted with ethyl acetate. The combined organic layer was dried and concentrated. The residue was purified by high performance liquid chromatography [5 to 100% mobile phase B (0.1% trifluoroacetic acid in acetonitrile) in mobile phase A (0.1% aqueous trifluoroacetic acid)] to give the title compounds having the following physical properties.

EXAMPLE 919(1)

48 mg

LC/MS $t_R$ 0.71 minutes; MS (ES$^+$) m/z 618 (M+H)$^f$ $^1$H NMR (300 MHz, DMSO-d$_6$) δ 9.72 (s, 1 H), 8.16 (s, 1 H), 8.07 (s, 1 H), 7.95 (d, 1 H), 7.92-7.79 (m, 2 H), 7.76 (brs, 1H), 6.37 (s, 1 H), 5.68 (dd, 1 H), 4.91 (s, 2 H), 3.50-3.02 (m, 5 H), 2.82 (m, 1 H), 2.60 (m, 1 H), 2.24 (m, 1 H), 1.96-1.92 (m, 2 H), 1.82-1.70 (m, 2 H).

EXAMPLE 919(2)

20 mg

LC/MS $t_R$ 0.61 minutes; MS (ES$^+$) m/z 534 (M+H)$^f$ $^1$H NMR (300 MHz, CDCl$_3$) δ 10.7-10.4 (m, 1 H), 8.78 (m, 1 H), 7.72-7.35 (m, 5 H), 7.18-7.08 (m 1 H), 6.42-6.37 (m, 1 H), 5.75 (m, 1 H), 3.48-3.00 (m, 8 H), 2.92 (m, 1 H), 2.48 (m, 1 H).

EXAMPLE 920(1) TO EXAMPLE 920(9)

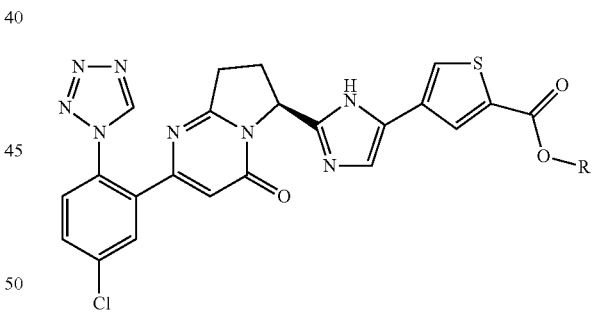

The compounds of the present invention having the following physical data were synthesised from the compound prepared in Example 392 using the corresponding alcohols, employing the method as detailed in Example 367.

EXAMPLE 920(1)

Ethyl 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-thiophenecarboxylate LC/MS $t_R$ 0.77 minutes; MS (ES$^+$) m/z 535 (M+H)$^f$ $^1$H NMR (300 MHz, CDCl$_3$) δ 8.78 (s, 1 H), 8.00 (s, 1 H), 7.72-7.62 (m, 3 H), 7.47 (d, 1 H), 7.18 (s, 1 H), 6.39 (s, 1

H), 5.76 (d, 1 H), 4.35 (q, 2H), 3.41-3.35 (m, 2 H), 2.96-2.87 (m, 1 H), 2.53-2.47 (m, 1 H), 1.39 (t, 3 H).

EXAMPLE 920(2)

Isobutyl 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-thiophenecarboxylate LC/MS $t_R$ 0.88 minutes; MS (ES$^+$) m/z 563 (M+H)$^f$
$^1$H NMR (300 MHz, CDCl$_3$) δ 8.78 (s, 1 H), 7.98 (s, 1 H), 7.68-7.61 (m, 3 H), 7.47 (d, 1 H), 7.18 (s, 1 H), 6.39 (s, 1 H), 5.76 (d, 1 H), 4.09 (d, 2 H), 3.43-3.35 (m, 2 H), 2.96-2.91 (m, 1 H), 2.54-2.47 (m, 1 H), 2.12-2.07 (m, 1 H), 1.01 (d, 6 H).

EXAMPLE 920(3)

2,3-dihydro-1H-inden-5-yl 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-thiophenecarboxylate

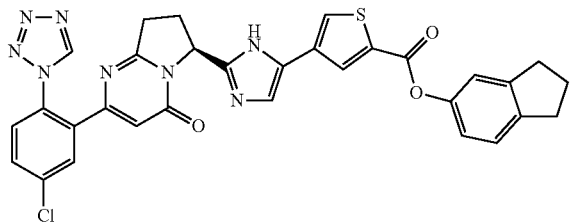 [SMILES: O=C(Oc1ccc2c(c1)CCC2)c1cc(-c2cnc([C@@H]3CCc4nc(-c5cc(Cl)ccc5-n5cnnn5)cc(=O)n43)[nH]2)cs1]

LC/MS $t_R$ 0.99 minutes; MS (ES$^+$) m/z 623 (M+H)$^f$
$^1$H NMR (300 MHz, CDCl$_3$) δ 10.39 (s, 1H), 8.79 (s, 1 H), 8.16 (s, 1H), 7.79 (s, 1H), 7.68 (d, 1H), 7.67-7.62 (m, 1H), 7.47 (d, 1H), 7.21 (s, 1H), 7.06 (s, 1H), 6.97-6.94 (m, 1 H), 6.39 (s, 1H), 5.76 (d, 1H), 3.47-3.35 (m, 2H), 2.92 (q, 4H), 2.58-2.43 (m, 1H), 2.18-2.06 (m, 3H).

EXAMPLE 920(4)

(5-methyl-2-oxo-1,3-dioxol-4-yl)methyl 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-thiophenecarboxylate

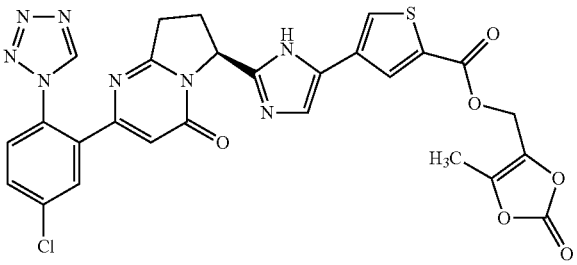 [SMILES: Cc1oc(=O)oc1COC(=O)c1cc(-c2cnc([C@@H]3CCc4nc(-c5cc(Cl)ccc5-n5cnnn5)cc(=O)n43)[nH]2)cs1]

LC/MS $t_R$ 0.76 minutes; MS (ES$^+$) m/z 619 (M+H)$^f$
$^1$H NMR (300 MHz, CDCl$_3$) δ 10.7-10.3 (m, 1 H), 8.79 (m, 1 H), 8.05-7.90 (m, 1 H), 7.81-7.43 (m, 4 H), 7.22-7.14 (m, 1 H), 6.42-6.37 (m, 1 H), 5.80-5.70 (m, 1 H), 5.06 (s, 2 H), 3.46-3.25 (m, 2 H), 2.93 (m, 1 H), 2.50 (m, 1 H), 2.25 (m, 3 H).

EXAMPLE 920(5)

2-(4-morpholinyl)ethyl 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-thiophenecarboxylate LC/MS $t_R$ 0.56 minutes; MS (ES$^+$) m/z 620 (M+H)$^f$
$^1$H NMR (300 MHz, CDCl$_3$) δ 10.7-10.4 (m, 1 H), 8.78 (m, 1 H), 8.01-7.88 (m, 1 H), 7.75-7.59 (m, 3 H), 7.47 (m, 1 H), 7.21-7.12 (m 1 H), 6.42-6.37 (m, 1 H), 5.80-5.70 (m, 1 H), 4.46-4.40 (m, 2 H), 3.72 (t, 4 H), 3.48-3.18 (m, 2 H), 2.92 (m, 1 H), 2.76 (t, 2 H), 2.57 (t, 4 H), 2.51 (m, 1 H).

EXAMPLE 920(6)

2-(dimethylamino)-2-oxoethyl 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-thiophenecarboxylate

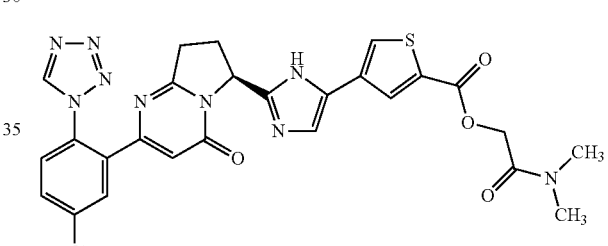

LC/MS $t_R$ 0.66 minutes; MS (ES$^+$) m/z 592 (M+H)$^f$
$^1$H NMR (300 MHz, CDCl$_3$) δ 10.4 (brs, 1 H), 8.79 (m, 1 H), 8.04 (brs, 1 H), 7.75 (brs, 1 H), 7.67 (d, 1 H), 7.62 (dd, 1 H), 7.47 (d, 1 H), 7.14 (s, 1H), 6.38 (s, 1 H), 5.75 (d, 1 H), 4.94 (s, 2 H), 3.39 (m, 1 H), 3.21 (m, 1 H), 3.04 ((s, 3 H), 3.00 ((s, 3 H), 2.93 (m, 1 H), 2.51 (m, 1 H).

EXAMPLE 920(7)

2-(diethylamino)-2-oxoethyl 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-thiophenecarboxylate TLC Rf 0.42 (10% methanol in ethyl acetate)
$^1$H NMR (300 MHz, CDCl$_3$) δ 10.36 (br. s, 1 H), 8.78 (s, 1 H), 8.16-7.93 (m, 1 H), 7.83-7.55 (m, 3 H), 7.47 (d, 1 H), 7.21-7.09 (m, 1 H), 6.50-6.29 (m, 1 H), 5.74 (d, 1 H), 4.93 (s, 2 H), 3.65-3.22 (m, 6 H), 3.22-3.65 (m, 6 H), 3.01-2.83 (m, 1 H), 2.64-2.37 (m, 1 H), 1.26 (t, 3 H), 1.15 (t, 3 H).

EXAMPLE 920(8)

2-oxo-2-(1-piperidinyl)ethyl 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-thiophenecarboxylate trifluoroacetate

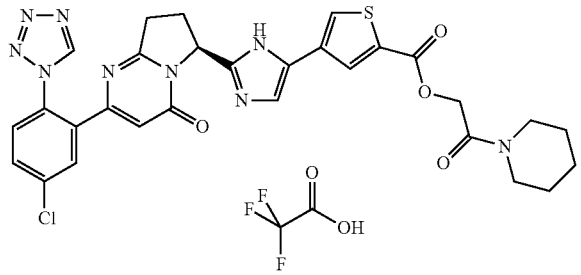 [SMILES: O=C(OCC(=O)N1CCCCC1)c1cc(-c2cnc([C@@H]3CCc4nc(-c5cc(Cl)ccc5-n5cnnn5)cc(=O)n43)[nH]2)cs1 ; O=C(O)C(F)(F)F]

LC/MS $t_R$ 0.76 minutes; MS (ES$^+$) m/z 632 (M+H)$^f$
$^1$H NMR (300 MHz, DMSO-d$_6$) δ 9.72 (s, 1 H), 8.20 (s, 1 H), 8.15 (s, 1 H), 7.98-7.80 (m, 4 H), 6.41 (s, 1 H), 5.73 (dd, 1 H), 5.03 (s, 2 H), 3.46-3.25 (m, 4 H), 3.12 (m, 1 H), 2.83 (m, 1 H), 2.65 (m, 1 H), 2.28 (m, 1 H), 1.65-1.12 (m, 6 H).

EXAMPLE 920(9)

2-(4-morpholinyl)-2-oxoethyl 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-thiophenecarboxylate LC/MS $t_R$ 0.65 minutes; MS (ES$^+$) m/z 634 (M+H)$^f$
$^1$H NMR (300 MHz, DMSO-d$_6$) δ 9.72 (s, 1H), 8.11 (s, 1H), 7.98 (s, 1H), 7.95 (d, 1H), 7.86-7.78 (m, 2H), 7.60 (s, 1H), 6.35 (s, 1H), 5.65-5.61 (m, 1H), 5.03 (s, 2H), 3.62-3.54 (m, 2H), 3.44-3.40 (m, 2H), 3.21-3.10 (m, 1H), 2.82-2.71 (m, 1H), 2.62-2.50 (m, 1H), 2.26-2.19 (m, 1H).

EXAMPLE 921

Isopropyl 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-thiophenecarboxylate The same operation as in Example 367 was conducted from the compound prepared in Example 392 and 2-propanol to give the title compound having the following physical properties.
LC/MS $t_R$ 0.82 minutes; MS (ES$^+$) m/z 549 (M+H)$^f$
$^1$H NMR (300 MHz, CDCl$_3$) δ 8.78 (s, 1 H), 7.96 (s, 1 H), 7.68-7.61 (m, 3 H), 7.47 (d, 1 H), 7.17 (s, 1 H), 6.39 (s, 1 H), 5.27-5.18 (m, 1 H), 3.42-3.35 (m, 2 H), 2.96-2.87 (m, 1 H), 2.54-2.47 (m, 1 H), 1.37 (d, 6 H).

EXAMPLE 922(1) and Example 922(2)

1-{[(cyclohexyloxy)carbonyl]oxy}ethyl 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-thiophenecarboxylate and cyclohexyl 2-{(6S)-2-[5-chloro-2-(1H-tetrazol-1-yl)phenyl]-4-oxo-4,6,7,8-tetrahydropyrrolo[1,2-a]pyrimidin-6-yl}-5-{5-[1-(1-{[(cyclohexyloxy)carbonyl]oxy}ethoxy)carbonyl]-3-thienyl}-1H-imidazole-1-carboxylate

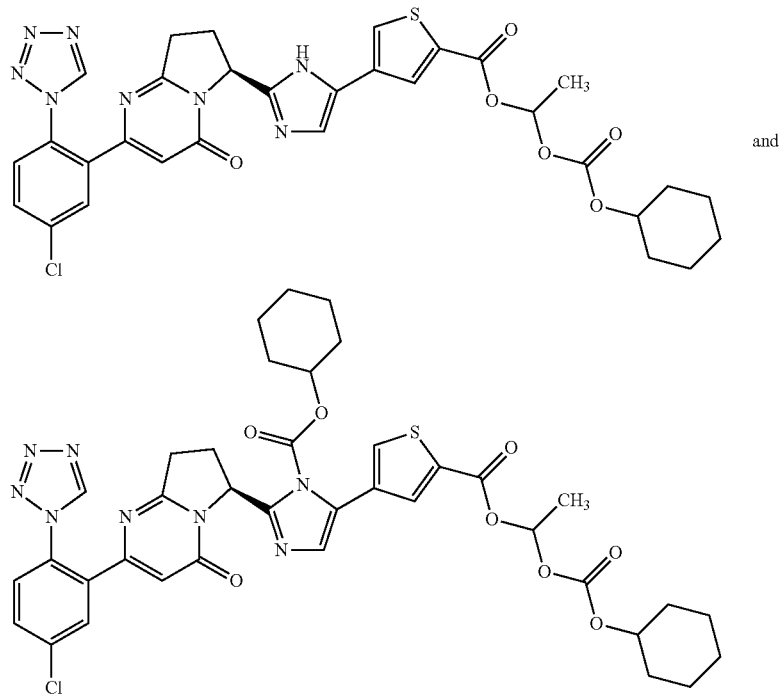

The same operation as in Example 373 was conducted from the compound prepared in Example 392 and 1-chloroethyl cyclohexyl carbonate to give the title compounds having the following physical properties.

EXAMPLE 922(1)

LC/MS $t_R$ 0.99 minutes; MS (ES$^+$) m/z 677 (M+H)$^f$
$^1$H NMR (300 MHz, CDCl$_3$) δ 10.41 (s, 1H), 8.79 (s, 1H), 8.02 (s, 1H), 7.75 (s, 1H), 7.67 (d, 1H), 7.65-7.61 (m, 1H), 7.47 (d, 1H), 7.17 (s, 1H), 6.98 (q, 1H), 6.38 (s, 1H), 5.75 (d, 1H), 4.69-4.60 (m, 1H), 3.43-3.33 (m, 2H), 2.96-2.85 (m, 1H), 2.60-2.43 (m, 1H), 1.98-1.90 (m, 2H), 1.81-1.71 (m, 2H), 1.64 (d, 3H), 1.60-1.21 (m, 6H).

EXAMPLE 922(2)

LC/MS $t_R$ 1.24 minutes; MS (ES$^+$) m/z 803 (M+H)$^f$
$^1$H NMR (300 MHz, CDCl$_3$) δ 8.78 (s, 1 H), 7.96 (d, 1H), 7.88 (d, 1H), 7.74 (d, 1H), 7.66-7.62 (m, 1H), 7.55 (s, 1H), 7.52 (d, 1H), 7.52 (s, 1H), 6.97 (q, 1H), 6.42 (s, 1H), 6.35-6.32 (m, 1H), 5.08-4.98 (m, 1H), 4.69-4.60 (m, 1H), 3.20-3.08 (m, 1H), 2.80-2.77 (m, 1H), 2.69-2.55 (m, 1H), 2.31-2.21 (m, 1H), 2.08-1.21 (m, 20H), 1.63 (d, 3H).

EXAMPLE 923(1) AND EXAMPLE 923(2)

[(2,2-dimethylpropanoyl)oxy]methyl 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-thiophenecarboxylate and [(2,2-dimethylpropanoyl)oxy]methyl 4-(2-{(6S)-2-[5-chloro-2-(1H-tetrazol-1-yl)phenyl]-4-oxo-4,6,7,8-tetrahydropyrrolo[1,2-a]pyrimidin-6-yl}-1-{[(2,2-dimethylpropanoyl)oxy]methyl}-1H-imidazol-5-yl)-2-thiophenecarboxylate

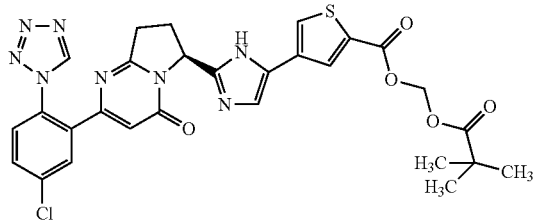

and

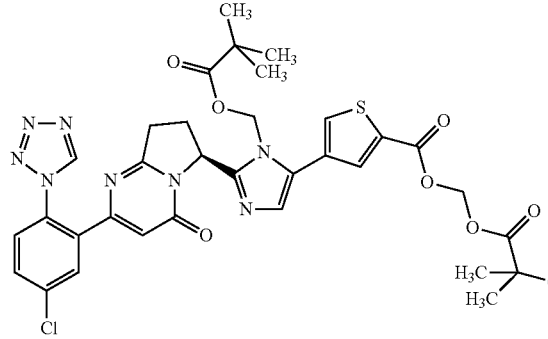

The same operation as in Example 373 was conducted from the compound prepared in Example 392 and chloromethyl 2,2-dimethylpropanoate to give the title compounds having the following physical properties.

EXAMPLE 923(1)

LC/MS $t_R$ 0.90 minutes; MS (ES$^+$) m/z 621 (M+H)$^f$
$^1$H NMR (300 MHz, CDCl$_3$) δ 10.43 (s, 1H), 8.79 (s, 1 H), 8.05 (s, 1H), 7.68 (s, 1H), 7.66 (d, 1H), 7.64-7.62 (m, 1H), 7.47 (d, 1H), 7.17 (s, 1H), 6.38 (s, 1 H), 5.96 (s, 2H), 5.75 (d, 1 H), 3.48-3.32 (m, 2H), 2.97-2.85 (m, 1H), 2.60-2.43 (m, 1 H), 1.23 (s, 9H).

EXAMPLE 923(2)

LC/MS $t_R$ 1.13 minutes; MS (ES$^+$) m/z 735 (M+H)$^f$
$^1$H NMR (300 MHz, CDCl$_3$) δ 8.78 (s, 1 H), 8.01 (d, 1H), 7.79 (d, 1H), 7.68 (d, 1H), 7.64-7.60 (m, 1H), 7.49 (d, 1H), 7.21 (s, 1H), 6.45 (d, 1H), 6.27 (s, 1 H), 5.94 (s, 2H), 5.91 (d, 1H), 5.87-5.83 (m, 1 H), 3.77-3.62 (m, 1H), 2.98-2.85 (m, 1 H), 2.65-2.49 (m, 2 H), 1.21 (s, 9H), 1.18 (s, 9H).

EXAMPLE 924

4-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-3-fluoro-2-thiophenecarboxylic acid

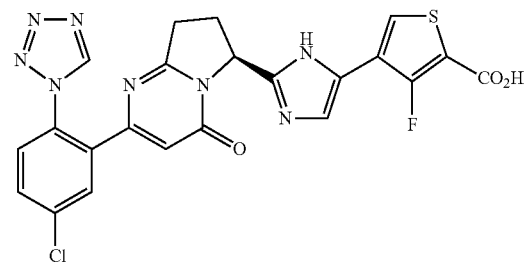 [SMILES: O=C(O)c1scc(-c2cnc([C@@H]3CCc4nc(-c5cc(Cl)ccc5-n5cnnn5)cc(=O)n43)[nH]2)c1F]

LC/MS $t_R$ 0.63 minutes; MS (ES$^+$) m/z 525 (M+H)$^f$
$^1$H NMR (300 MHz, DMSO-d$_6$) δ 9.71 (s, 1 H), 7.94 (d, 1 H), 7.89 (d, 1 H), 7.87-7.78 (m, 2 H), 7.35 (d, 1 H), 6.34 (s, 1 H), 5.63 (dd, 1 H), 3.21-3.04 (m, 1 H), 2.84-2.68 (m, 1 H), 2.63-2.51 (m, 1 H) 2.28-2.11 (m, 1 H).

EXAMPLE 925

5-(2-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-5-yl)-2-thiophenecarboxylic acid hydrochloride

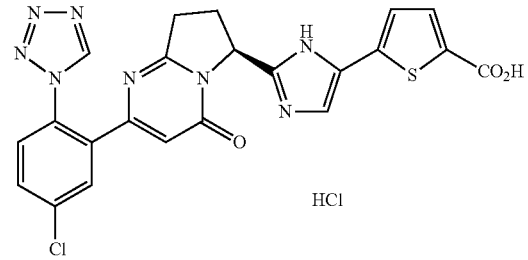 [SMILES: O=C(O)c1ccc(-c2cnc([C@@H]3CCc4nc(-c5cc(Cl)ccc5-n5cnnn5)cc(=O)n43)[nH]2)s1 ; Cl]

LC/MS $t_R$ 0.65 minutes; MS (ES$^+$) m/z 507 (M+H)$^f$
$^1$H NMR (300 MHz, DMSO-d$_6$) δ 9.72 (s, 1 H), 7.97-7.90 (m, 2H), 7.88-7.80 (m, 3H), 7.70 (d, 1H), 7.54 (d, 1H), 6.36 (s, 1 H), 5.80-5.74 (m, 1 H), 3.20-3.06 (m, 1H), 2.92-2.80 (m, 1H), 2.70-2.56 (m, 1 H), 2.36-2.23 (m, 1 H).

EXAMPLE 926

5-(2-{(6S)-2-[5-chloro-2-(1H-tetrazol-1-yl)phenyl]-4-oxo-4,6,7,8-tetrahydropyrrolo[1,2-a]pyrimidin-6-yl}-4-fluoro-1H-imidazol-5-yl)-2-thiophenecarboxylic acid hydrochloride

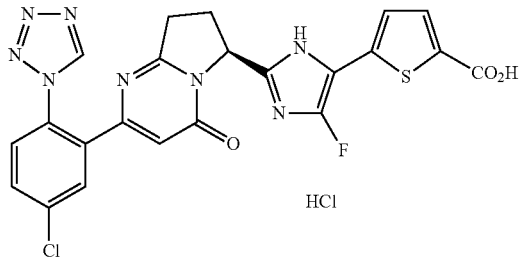 [SMILES: O=C(O)c1ccc(-c2[nH]c([C@@H]3CCc4nc(-c5cc(Cl)ccc5-n5cnnn5)cc(=O)n43)nc2F)s1 ; Cl]

LC/MS $t_R$ 0.75 minutes; MS (ES$^+$) m/z 525 (M+H)$^f$
$^1$H NMR (300 MHz, DMSO-d$_6$) δ 13.28 (s, 1H), 9.74 (s, 1 H), 7.97 (d, 1H), 7.87-7.79 (m, 2H), 7.69 (d, 1H), 7.26 (d, 1H), 6.35 (s, 1 H), 5.57-5.50 (m, 1 H), 3.17-3.01 (m, 1H), 2.83-2.70 (m, 1H), 2.63-2.47 (m, 1 H), 2.21-2.10 (m, 1 H).

EXAMPLE 927 methyl{4-[4-chloro-2-({4-[5-chloro-2-(1H-tetrazol-1-yl)phenyl]-6-methyl-2-oxo-1(2H)-pyridinyl}methyl)-1H-imidazol-5-yl]phenyl}carbamate The same operation as in Example 44 was conducted from the compound prepared in Example 318 to give the title compounds having the following physical properties.
TLC Rf 0.80 (10% methanol in ethyl acetate)
$^1$H NMR (300 MHz, DMSO-d$_6$) δ 12.81 (s, 1 H), 9.86-9.59 (m, 2 H), 7.90-7.70 (m, 3 H), 7.68-7.44 (m, 4 H), 6.02 (s, 1 H), 5.94 (s, 1 H), 5.15 (s, 2 H), 3.67 (s, 3 H), 2.43 (s, 3 H).

EXAMPLE 928 methyl{4-[4-chloro-2-({4-[5-chloro-2-(1H-tetrazol-1-yl)phenyl]-2-methyl-6-oxo-1(6H)-pyrimidinyl}methyl)-1H-imidazol-5-yl]phenyl}carbamate The same operation as in Example 44 was conducted from the compound prepared in Example 323 to give the title compounds having the following physical properties.
TLC Rf 0.63 (1% methanol in ethyl acetate)
$^1$H NMR (300 MHz, DMSO-d$_6$) δ 12.84 (s, 1 H), 9.78 (s, 2 H), 8.01 (d, 1 H), 7.90-7.75 (m, 2 H), 7.67-7.41 (m, 4 H), 6.51 (s, 1 H), 5.17 (s, 2 H), 3.68 ((s, 3 H), 2.39 (s, 3 H).

Pharmacological Activities

The compounds of the present invention possess Factor XIa inhibitory activity and oral bioavailability, for example, such an effect of the compounds of the present invention was confirmed by the following tests.

All the procedures were conducted by conventionally used techniques on the basis of basic biological methods. Furthermore, the measuring method of the present invention was modified to improve the accuracy and/or sensitivity of measurement for evaluating the compound of the present invention. The detailed experimental method was as follows.

Experimental Method
(1) In Vitro Assay
Inhibitory activities of compounds of the present invention against factor XIa, Xa, XIIa, IXa, VIIa, plasma kallikrein or thrombin were evaluated using appropriate purified proteases and synthetic substrates. The rate of hydrolysis of the chromogenic substrate by the relevant protease was continuously measured at 405 nm.
Inhibitory activity against each enzyme was calculated as % inhibition using the equation described below.

% Inhibition=[[(rate without compound)−(rate with compound)](rate without compound)]×100%.

Each half maximal inhibitory concentration (IC$_{50}$) value was determined by plotting the concentration of compound of the invention against the % inhibition.
(1-1) Factor XIa Enzyme Activity
Human Factor XIa (Haematologic Technologies Inc.) activity was measured at an enzyme concentration of 0.1 U/mL in 150 mM NaCl, 5 mM KCl, 1 mg/mL PEG6000, 50 mM HEPES-NaOH (pH7.4) with 300 μM S-2366 (pyroGlu-Pro-Arg-pNA, Chromogenix).
(1-2) Plasma Kallikrein Enzyme Activity
Human plasma kallikrein (Enzyme Research Laboratories Ltd) activity was measured at an enzyme concentration of 0.605 mU/mL in 200 mM NaCl, 5 mg/mL PEG6000, 100 mM Phosphate-NaOH (pH7.4) with 150 μM S-2302 (H-D-Pro-Phe-Arg-pNA, Chromogenix).
(1-3) Factor Xa and Thrombin Enzyme Activity
Human Factor Xa (American Diagnostica Inc.) and human thrombin (Sigma) activities were measured at the enzyme concentrations of 0.18 U/mL and 0.12 U/mL, respectively in the same buffer containing 150 mM NaCl, 2 mg/mL PEG6000, 50 mM Tris-HCl (pH7.4), except that the reactions were started with 300 μM S-2222 (phenyl-Ile-Glu-Gly-Arg-pNA, Chromogenix) and 300 μM S-2366, respectively.
(1-4) Factor XIIa Enzyme Activity
Human Factor α-XIIa (Enzyme Research Laboratories Ltd) activity was measured at an enzyme concentration of 0.17 U/mL in 150 mM NaCl, 50 mM Tris-HCl (pH7.4) with 300 μM S-2302 (H-D-Pro-Phe-Arg-pNA, Chromogenix).
(1-5) Factor IXa Enzyme Activity
Human Factor IXa (American Diagnostica Inc.) activity was measured at an enzyme concentration of 13 U/mL in 100 mM NaCl, 5 mM CaCl$_2$, 30% ethylene glycol, 50 mM Tris-HCl (pH7.4) with 3 mM Pefachrome IXa 3960 (Leu-Ph'Gly-Arg-pNA, Pentapharm).
(1-6) Factor VIIa Enzyme Activity
Human Factor VIIa activity was measured using recombinant human Factor VIIa (American Diagnostica Inc.) in the presence of recombinant human tissue factor which was produced according to the method described in the literature (Protein expression and purification, 3, 453-460 (1992) in a buffer containing 150 mM NaCl, 5 mM CaCl$_2$, 0.5 mg/mL PEG6000, 50 mM HEPES-NaCl (pH7.4) with 3 mM S-2288 (Ile-Pro-Arg-pNA, Chromogenix).
(1-7) APTT, PT Measurement
Activated partial thromboplastin time (APTT) and prothrombin time (PT) were measured using automatic coagulation analyzer (CA-1500, Sysmex Corporation). For the APTT or PT measurement, standard human plasma (Siemens Healthcare Diagnostics GmbH) were mixed with each compound dilutions followed by the automatic addition of APTT reagent (Siemens Healthcare Diagnostics GmbH) and 0.02 M calcium chloride or PT reagent (Siemens Healthcare Diagnostics GmbH) to start clot formation. The anticoagulant activities (APTT2 or PT2) of the compounds of the invention were expressed as the concentrations necessary to double the clotting time in vehicle (1% DMSO) group. APTT2 or PT2 was determined by plotting the concentration of compound of the invention against the fold increase of clotting time.

(2) Rat Oral Administration Test

Each compound of the present invention in a solution of 20% wellsolve (celeste) was given to fasted male Crj:CD (SD)IGS rats as a single 3 mg/kg, p.o. dose by gavage. Blood samples were drawn from jugular vein into syringes containing 3.2% sodium citrate (the volume ratio of blood to anticoagulant=9:1) after oral administration at 0.5, 1, 2, 4 and 6 hours. Plasma was harvested by centrifugation and stored at −20° C. until measurement of plasma concentration.

To measure plasma concentrations of the compounds of the present invention, plasma samples were deproteinized with acetonitrile, followed by evaporation of the acetonitrile to dryness. The residual was then re-dissolved with DMSO and its FXIa inhibitory activity was measured by enzyme assay described above. Plasma concentrations of each compound of the present invention were quantitated by generating a standard curve of known compound concentration in rat plasma.

The compounds of the present invention were tested in the Factor XIa assay and the rat oral administration test described above, and found to have a good Factor XIa inhibitory activity and good oral bioavailability. Table 1 described below lists Factor XIa $IC_{50}$ values measured for the following examples.

TABLE 1

| Example No | In vitro FXIa inhibitory activity $IC_{50}$ (μM) |
|---|---|
| 41 | 0.0065 |
| 45 | 0.015 |
| 57 | 0.0024 |
| 60 | 0.0072 |

TABLE 1-continued

| Example No | In vitro FXIa inhibitory activity $IC_{50}$ (μM) |
|---|---|
| 61 | 0.014 |
| 86 | 0.0039 |
| 129(2) | 0.0046 |
| 181 | 0.047 |
| 198 | 0.0015 |
| 210 | 0.0028 |
| 216 | 0.0038 |
| 230 | 0.011 |
| 241 | 0.0048 |
| 245 | 0.017 |
| 264 | 0.0061 |
| 270 | 0.011 |
| 278 | 0.0057 |
| 290 | 0.0025 |
| 309 | 0.0083 |
| 310 | 0.0049 |
| 347 | 0.0042 |
| 363 | 0.0014 |
| 387 | 0.0016 |
| 391 | 0.0011 |
| 392 | 0.0021 |
| 399 | 0.0011 |
| 400 | 0.013 |
| 834 | 0.0016 |
| 848 | 0.0017 |

Compatitive Experiments

CompEx1, Ex2, Ex3 and Ex4 as comparative compounds are prepared according to the reported preparation in WO2007070826 (Ex.64 and Ex.254), WO2008076805 (Ex.1) and WO2009076337 (Ex.1). The comparative compounds were also tested in the Factor XIa assay and the rat oral administration test described above. Table 2 described below lists Factor XIa $IC_{50}$ values and plasma concentrations measured for the comparative compounds and the typical compound of the present invention.

TABLE 2

| Example No | Structure | In vitro FXIa inhibitory activity $IC_{50}$ (μM) | rat plasma concentration after po administration Cmax (μM) at 3 mpk |
|---|---|---|---|
| 45 | (structure) | 0.015 | 1.25 |

TABLE 2-continued
| Example No | Structure | In vitro FXIa inhibitory activity IC$_{50}$ (μM) | rat plasma concentration after po administration Cmax (μM) at 3 mpk |
|---|---|---|---|
| 41 | 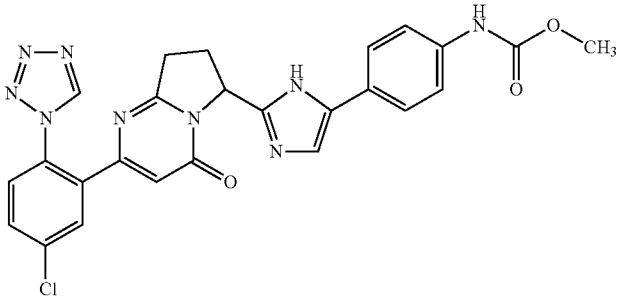 [SMILES: COC(=O)Nc1ccc(-c2cnc(C3CCc4nc(-c5cc(Cl)ccc5-n5cnnn5)cc(=O)n43)[nH]2)cc1] | 0.0065 | 2.28 |
| 57 | 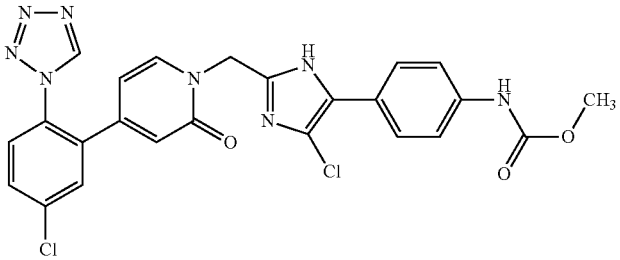 [SMILES: COC(=O)Nc1ccc(-c2[nH]c(Cn3ccc(-c4cc(Cl)ccc4-n4cnnn4)cc3=O)nc2Cl)cc1] | 0.0024 | 0.51 |
| Comp Ex 1 | 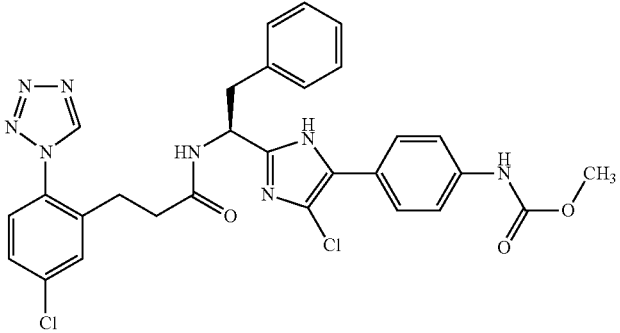 [SMILES: COC(=O)Nc1ccc(-c2[nH]c([C@H](Cc3ccccc3)NC(=O)CCc3cc(Cl)ccc3-n3cnnn3)nc2Cl)cc1] | 0.0036 | 0.015 |
| Comp Ex 2 | 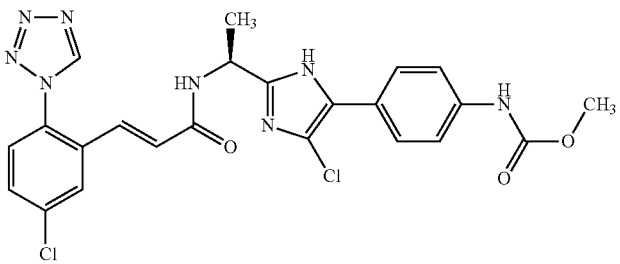 [SMILES: COC(=O)Nc1ccc(-c2[nH]c([C@H](C)NC(=O)/C=C/c3cc(Cl)ccc3-n3cnnn3)nc2Cl)cc1] | 0.040 | 0.025 |
| Comp Ex 3 | 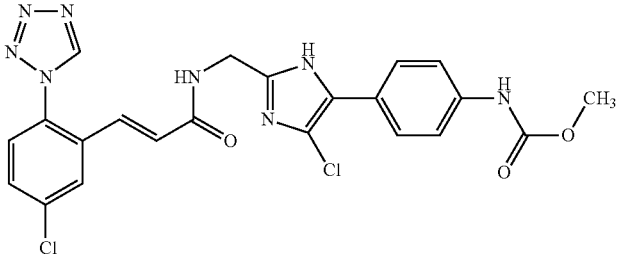 [SMILES: COC(=O)Nc1ccc(-c2[nH]c(CNC(=O)/C=C/c3cc(Cl)ccc3-n3cnnn3)nc2Cl)cc1] | 0.130 | 0.088 |

TABLE 2-continued

| Example No | Structure | In vitro FXIa inhibitory activity IC$_{50}$ (μM) | rat plasma concentration after po administration Cmax (μM) at 3 mpk |
|---|---|---|---|
| Comp. Ex 4 | 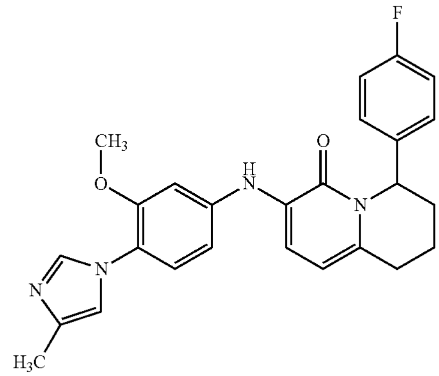 [SMILES: COc1cc(Nc2ccc3n(c2=O)C(c2ccc(F)cc2)CCC3)ccc1-n1cnc(C)c1] | >10 | Not tested |

As a result, the compounds of the present invention showed good oral bioavailability compared with the comparative compounds described above.

Therefore, the results indicated that the compounds of the present invention possess Factor XIa inhibitory activity, with good oral bioavailability.

Additionally, the good oral bioavailability of compounds of the present invention can be determined using the following experimental methods.

(3-1) Pharmacokinetic (PK) Study in Rat

Each compound of the present invention in a solution of 20% wellsolve (celeste) was given to fasted male Crj:CD (SD) rats as a single 3 mg/kg, p.o. dose by gavage. Blood samples were drawn from jugular vein into syringes containing 3.2% sodium citrate (the volume ratio of blood to anticoagulant=9:1) or heparinized syringes at 0.5, 1, 3, 7 hours after oral administration. Plasma was obtained by centrifugation and stored at −20° C. until measurement of plasma concentration.

To measure plasma concentrations of the compounds of the present invention, plasma samples were deproteinized with acetonitrile, followed by evaporation of the acetonitrile to dryness. Then the sample was reconstituted in the mobile phase and analyzed by LC/MS/MS. An analytical column (Shim-pack XR-ODS II, 2.0 mm×75 mm, 2.2 μm) and mobile phase (0.1% formic acid in water and 0.1% formic acid in acetonitrile, flow rate of 0.5 mL/min) were used. The system was used in multiple reaction monitoring (MRM) mode with positive ion detection.

(3-2) Pharmacokinetic (PK) Study of the Compound which has an Ester Group(s) in Rat Each compound of the present invention in a solution of 20% wellsolve (celeste) was given to fasted male Crj:CD (SD) rats as a single 3 mg/kg, p.o. dose by gavage. Blood samples were drawn from jugular vein into syringes treated with heparin-diisopropyl fluorophosphate mixture (500:1) at 0.5, 1, 3, 7 hours after oral administration. Plasma was obtained by centrifugation and stored at −20° C. until measurement of plasma concentration.

To measure plasma concentrations of the compounds of the present invention, plasma samples were deproteinized with acetonitrile, followed by evaporation of the acetonitrile to dryness. Then the sample was reconstituted in the mobile phase and analyzed by LC/MS/MS. An analytical column (Shim-pack XR-ODS II, 2.0 mm×75 mm, 2.2 μm) and mobile phase (0.1% formic acid in water and 0.1% formic acid in acetonitrile, flow rate of 0.5 mL/min) were used. The system was used in multiple reaction monitoring (MRM) mode with positive ion detection.

TABLE 3

| Example No. of administered compound | rat plasma concentration of ester compound after po administration Cmax (μM) at 3mpk | rat plasma concentration of corresponding carboxylic acid after po administration Cmax (μM) at 3mpk |
|---|---|---|
| 401 | 0.96 | 5.6 |

Additionally, enzymatic hydrolysis of an ester group in the compound of the present invention can be determined using the following experimental methods.

(4-1) Analysis of Enzymatic Hydrolysis of an Ester Group(s) in the Compounds of the Present Invention Using Hepatocytes Prepared from Various Species (Rat, Dog, Monkey., Human)

A typical assay procedure was conducted by using cryopreserved hepatocytes prepared from various species. A mixture of hepatocytes, buffer (pH 7.4), and each test compound were incubated. The final test compound concentration was typically 100 ng/mL, with a usual cell density of 1,000,000 cells/ml for all species. The incubation was at 37° C., with time-points taken over 120 minutes. Reaction termination was achieved by addition of an aliquot of the hepatocyte test compound mixture to acetonitrile/ethanol (73) to effect protein precipitation, followed by centrifugation. Then the sample was diluted with distilled water and analyzed by LC/MS/MS. An analytical column (Shim-pack XR-ODS II, 2.0 mm×75 mm, 2.2 μm) and mobile phase (0.1% formic acid in water and 0.1% formic acid in acetonitrile, flow rate of 0.5 mL/min) were used. The system was used in multiple reaction monitoring (MRM) mode with positive ion detection.

(4-2) Analysis of Enzymatic Hydrolysis of the Compound which has an Ester Group(s) Using Blood from Various Species (Rat, Dog, Monkey, Human)

Each compound of the present invention in a solution of acetonitrile were incubated in blood from various species. The incubation was typically performed at a concentration of 100 ng/mL of test compound at 37° C., with time points taken over 60 minutes. The reaction was terminated by addition of an aliquot of blood test compound mixture to acetonitrile/ethanol (73) to effect protein precipitation, followed by centrifugation. Then the sample was diluted with distilled water and analyzed by LC/MS/MS. An analytical column (Shim-pack XR-ODS II, 2.0 mm×75 mm, 2.2 μm) and mobile phase (0.1% formic acid in water and 0.1% formic acid in acetonitrile, flow rate of 0.5 mL/min) were used. The system was used in multiple reaction monitoring (MRM) mode with positive ion detection.

FORMULATION EXAMPLE 1

The following components were admixed in conventional method and punched out to obtain 10,000 tablets each containing 10 mg of active ingredient.

| | |
|---|---|
| methyl [4-(2-{(3S)-7-[5-chloro-2-(1H-tetrazol-1-yl)phenyl]-5-oxo-1,2,3,5-tetrahydro-3-indolizinyl}-5-methyl-1H-imidazol-4-yl)phenyl]carbamate | 100 g |
| Carboxymethylcellulose calcium (disintegrating agent) | 20 g |
| Magnesium stearate (lubricating agent) | 10 g |
| Microcrystalline cellulose | 870 g |

FORMULATION EXAMPLE 2

The following components were admixed in conventional method. The solution was sterilized in conventional manner, filtered through dust removal equipment, placed 5 mL portions into ampoules and sterilized by autoclave to obtain 10,000 ampoules each containing 20 mg of the active ingredient.

| | |
|---|---|
| methyl [4-(2-{(3S)-7-[5-chloro-2-(1H-tetrazol-1-yl)phenyl]-5-oxo-1,2,3,5-tetrahydro-3-indolizinyl}-5-methyl-1H-imidazol-4-yl)phenyl]carbamate | 200 g |
| mannitol | 20 g |
| distilled water | 50 L |

INDUSTRIAL APPLICABILITY

The compounds of the present invention represented by formula (I) act as potent and selective inhibitors of Factor XIa, with potent anticoagulant activity and/or good oral availability. In particular, the compounds of the present invention act as a Factor XIa inhibitor or a Factor XIa and plasma kallikrein dual inhibitor. Thus the compounds of the present invention are useful in preventing and/or treating thromboembolic diseases, for example arterial cardiovascular thromboembolic disorders, venous cardiovascular thromboembolic disorders, arterial cerebrovascular thromboembolic disorders, venous cerebrovascular thromboembolic disorders and thromboembolic disorders in the chambers of the heart or in the peripheral circulation. The compound of the present invention is therefore useful as a medicament.

The invention claimed is:
1. A compound represented by formula (I):

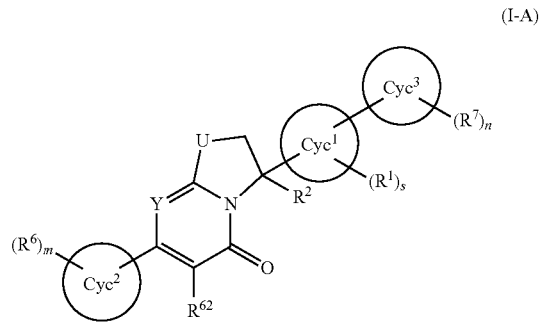

(I-A)

wherein U represents S or $CH_2$;
$R^2$ represents (1) hydrogen, (2) C1-8 alkyl, (3) C2-8 alkenyl, (4) C2-8 alkynyl, (5) $Cyc^4$ or (6) C1-8 alkyl, C2-8 alkenyl or C2-8 alkynyl, which are substituted with 1 to 5 groups selected from halogen, nitro, trifluoromethyl, cyano, $Cyc^5$, $-NR^{13}R^{14}$, $-OR^{15}$, $-SR^{16}$, $-NHC(O)-Cyc^6$, $-NHC(O)-C1-8$ alkyl, $-NHC(O)O-R^{17}$ and $Cyc^5$ substituted with 1 to 3 groups selected from C1-8 alkyl, C2-8 alkenyl, C2-8 alkynyl, halogen, nitro, trifluoromethyl, cyano, oxo, amidino and $-OR^{18}$,
wherein $R^{13}$, $R^{14}$, $R^{15}$, $R^{16}$, $R^{17}$ and $R^{18}$ each independently represents (1) hydrogen, (2) C1-8 alkyl, (3) C2-8 alkenyl, (4) C2-8 alkynyl, (5) C3-C8 cycloalkyl, (6) 5- to 10-membered heterocycloalkyl, (7) C5-C10 aryl, (8) 5- to 10-membered heteroaryl or (9) C1-4 alkyl substituted with 1 to 5 groups selected from C3-C8 cycloalkyl, 5- to 10-membered heterocycloalkyl, C5-C10 aryl and 5- to 10-membered heteroaryl;
$Cyc^4$, $Cyc^5$ and $Cyc^6$ each independently represents C3-C8 cycloalkyl, 5- to 10-membered heterocycloalkyl, C5-C10 aryl or 5- to 10-membered heteroaryl;
Y represents N or $C(R^5)$;
$R^5$ represents (1) hydrogen, (2) halogen, (3) C1-4 alkyl, (4) C3-C8 cycloalkyl, (5) 5- to 10-membered heterocycloalkyl, (6) C5-C10 aryl, (7) 5- to 10-membered heteroaryl or (8) C1-4 alkyl substituted with 1 to 5 groups selected from C3-C8 cycloalkyl, 5- to 10-membered heterocycloalkyl, C5-C10 aryl and 5- to 10-membered heteroaryl;
wherein

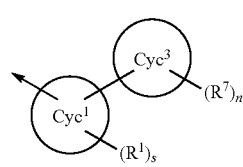

represents

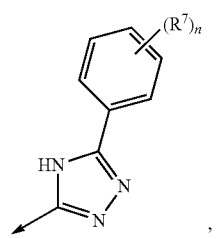

,

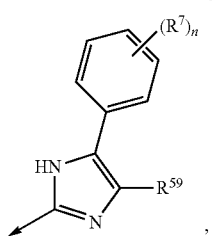,
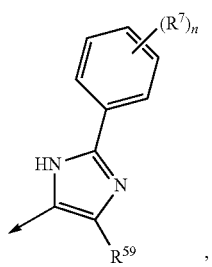,
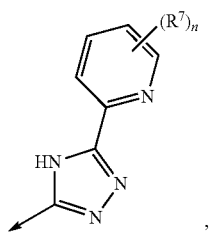,
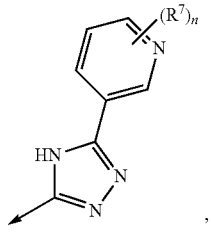,
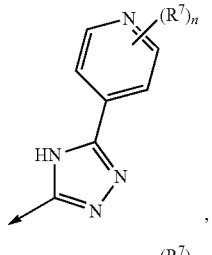,
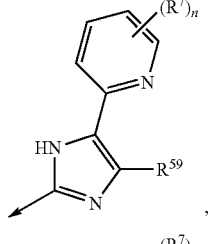,
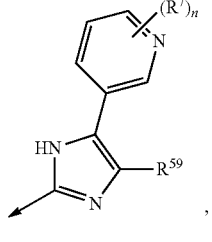,
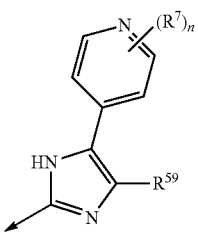,
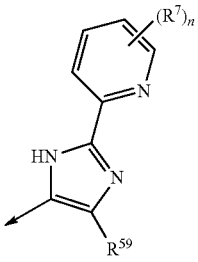,
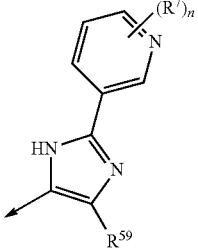,
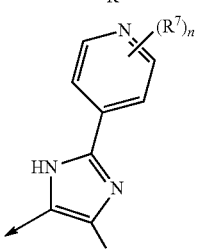,
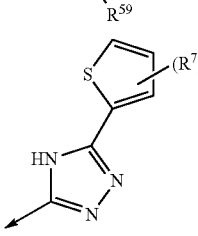,
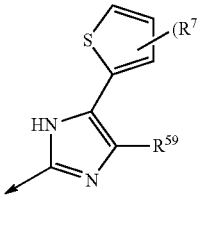,
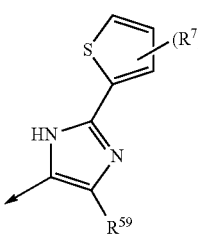,

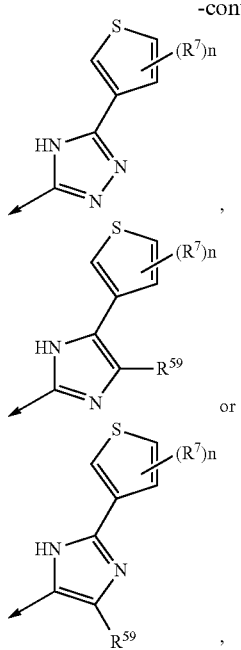

wherein R⁵⁹ represents hydrogen, C1-4 alkyl or halogen;
the arrow represents a binding positon;
-Cyc²—(R⁶)$_m$ represents

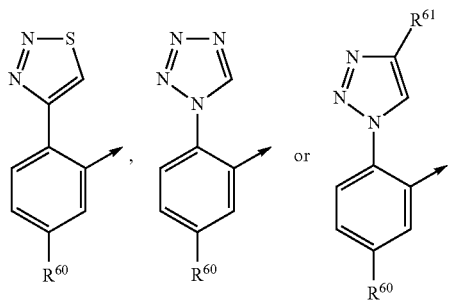

wherein R⁶⁰ represents hydrogen, methyl or halogen;
R⁶¹ represents (1) hydrogen, (2) halogen, (3) nitro, (4) trifluoromethyl, (5) —COOH, (6) —COO—C1-4 alkyl, (7) cyano or (8) —CONH₂; and the arrow represents a binding position;
R⁷ represents (1) C1-8 alkyl, (2) halogen, (3) nitro, (4) trifluoromethyl, (5) cyano, (6) oxo, (7) —OR⁴⁰, (8) —NR⁴²R⁴³, (9) —NHC(O)NR⁴⁴R⁴⁵, (10) —NHC(O)—C1-4 alkylene-NR⁴⁶R⁴⁷, (11) —NHC(O)—C1-4 alkylene-COOH, (12) —NH—S(O)₂—C1-4 alkyl, (13) —COOR⁴⁸, (14) —NHC(O)—R⁴⁹, (15) —NHC(O)—C1-4 alkylene-OR⁵⁰, (16) —NHC(O)O—R⁵¹, (17) —NHC(O)O—C1-4 alkylene —OR⁵², (18) —C(O)NH—R⁵³, (19) —OC(O)—R⁵⁵, (20) —C(O)—R⁵⁶, (21) —CH(OH)—R⁵⁷ (22) —C1-4 alkylene —NH₂, (23) —C1-4 alkylene-OH, (24) —C1-4 alkylene-OC(O)—C1-4 alkyl, (25) —C1-4 alkylene-NHC(O)—C1-4 alkyl, (26) —C1-4 alkylene-NHC(O)—C1-4 alkyl, (27) —C1-4 alkylene-NHC(O)—CF₃, (28) —C1-4 alkylene-NHC(O)NH—C1-4 alkyl, (29) —CH=N—OR⁵⁸ or (30) -T-COOR⁶⁶;
wherein R⁴⁰, R⁴², R⁴³, R⁴⁴, R⁴⁵, R⁴⁶, R⁴⁷, R⁴⁹, R⁵⁰, R⁵¹, R⁵², R⁵³, R⁵⁵, R⁵⁶, R⁵⁷ and R⁵⁸ each independently represents (1) hydrogen, (2) trifluoromethyl, (3) C1-8 alkyl, (4) C2-8 alkenyl, (5) C2-8 alkynyl, (6) C3-C8 cycloalkyl, (7) 5- to 10-membered heterocycloalkyl, (8) C5-C10 aryl, (9) 5- to 10-membered heteroaryl or (10) C1-4 alkyl substituted with 1 to 5 groups selected from C3-C8 cycloalkyl, 5- to 10-membered heterocycloalkyl, C5-C10 aryl and 5- to 10-membered heteroaryl;
T represents (1) C1-4 alkylene, (2) C2-4 alkenylene, (3) —O—C1-4 alkylene-, (4) —O—C2-4 alkenylene-, (5) —S—C1-4 alkylene-, (6) —S—C2-4 alkenylene-, (7) —NH—C1-4 alkylene-, (8) —NH—C2-4 alkenylene-, (9) —NH—C5-C10 aryl- or (10) —NH-5- to 10-membered heteroaryl-;
R⁴⁸ and R⁶⁶ each independently represents (1) hydrogen, (2) C1-8 alkyl, (3) C2-8 alkenyl, (4) C2-8 alkynyl, (5) C1-8 alkyl, C2-8 alkenyl or C2-8 alkynyl, which are substituted with 1 to 5 groups selected from —NH₂, —NH—C1-4 alkyl, —N(C1-4 alkyl)₂, OH, oxo, —O—C1-4 alkyl, —O—C1-4 alkylene-O—C1-4 alkyl, halogen, nitro, cyano, C3-C8 cycloalkyl, 5- to 10-membered heterocycloalkyl, C5-C10 aryl and 5- to 10-membered heteroaryl (6) C3-C10 cycloalkyl, (7) 5- to 10-membered heterocycloalkyl, (8) C5-C10 aryl, (9) 5- to 10-membered heteroaryl, (10) —C1-4 alkylene-C3-C8 cycloalkyl substituted with 1 to 5 groups selected from C1-4 alkyl, oxo, OH, trifluoromethyl and halogen, (11) —C1-4 alkylene-C5-C10 aryl substituted with 1 to 5 groups selected from C1-4 alkyl, OH, trifluoromethyl and halogen, (12) —C1-4 alkylene-5- to 10-membered heterocycloalkyl substituted with 1 to 5 groups selected from C1-4 alkyl, oxo, OH, trifluoromethyl and halogen, (13) —C1-4 alkylene-5- to 10-membered heteroaryl substituted with 1 to 5 groups selected from C1-4 alkyl, OH, trifluoromethyl and halogen or (14) —C1-4 alkylene-O—C1-8 alkyl substituted with 1 to 5 groups selected from OH, oxo, —O—C1-4 alkyl, —O—C1-4 alkylene-O—C1-4 alkyl, halogen, nitro, cyano, C3-C8 cycloalkyl, C5-C10 aryl, 5- to 10-membered heterocycloalkyl, —O-5- to 10-membered heteroaryl, —O—C3-C8 cycloalkyl, —O—C5-C10 aryl, —O-5- to 10-membered heterocycloalkyl, —O-5- to 10-membered heteroaryl, —O—C1-4 alkylene-5- to 10-membered heterocycloalkyl, —O—C1-4 alkylene-C3-C8 cycloalkyl, —O—C1-4 alkylene-C5-C10 aryl, —O—C1-4 alkylene-5- to 10-membered heterocycloalkyl and —O—C1-4 alkylene-5- to 10-membered heteroaryl;
n represents an integer of 0 to 5,
wherein n represents an integer of 2 to 5, each R⁷ may be same or different; and
R⁶² represents hydrogen or halogen,
a salt thereof, an N-oxide thereof, a solvate thereof, or a prodrug thereof.

2. The compound according to claim 1, wherein n is 2 and one R⁷ represents (1) —NH₂, (2) —NHC(O)O—C1-4 alkyl (3) —NHC(O)O—C1-4 alkylene —O—C1-4 alkyl, (4) —COOH, (5) —COO—C1-8 alkyl, (6) —COO—C1-8 alkyl substituted with 1 to 5 groups selected from —N(C1-4 alkyl)₂, oxo and 5- to 10-membered heterocycloalkyl, (7) —COO— C5-C10 aryl or (8) —COO— C1-4 alkylene -5- to 10-membered heterocycloalkyl substituted with 1 to 5 groups selected from C1-4 alkyl, oxo, OH and halogen and the other R⁷ represents halogen.

3. A pharmaceutical composition which comprises the compound according to claim 1 or 2 a salt thereof, an N-oxide thereof, a solvate thereof, or a prodrug thereof.

4. The pharmaceutical composition according to claim 3, which is a factor XIa inhibitor or a factor XIa and plasma kallikrein dual inhibitor.

5. The pharmaceutical composition according to claim 4 which is an agent for the treatment or prevention of a thromboembolic disease mediated by factor XIa.

6. The compound according to claim 1 or 2 a salt thereof, an N-oxide thereof, a solvate thereof, or a prodrug thereof, for use in treating or preventing a thromboembolic disease mediated by factor XIa.

7. The compound for use according to claim 6, wherein the thromboembolic disease is selected from the group consisting of arterial cardiovascular thromboembolic disorders, venous cardiovascular thromboembolic disorders, arterial cerebrovascular thromboembolic disorders, venous cerebrovascular thromboembolic disorders and thromboembolic disorders in the chambers of the heart or in the peripheral circulation.

8. The compound for use according to claim 7 wherein the thromboembolic disease is selected from unstable angina, an acute coronary syndrome, atrial fibrillation, myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

9. A method for treating a patient suffering from or susceptible to a thromboembolic disease, which comprises administering to said patient a therapeutically effective amount of a compound according to claim 1, a salt thereof, an N-oxide thereof, a solvate thereof, or a prodrug thereof.

* * * * *

UNITED STATES PATENT AND TRADEMARK OFFICE
CERTIFICATE OF CORRECTION

PATENT NO. : 9,732,085 B2  
APPLICATION NO. : 14/366396  
DATED : August 15, 2017  
INVENTOR(S) : Steve Courtney et al.

Page 1 of 2

It is certified that error appears in the above-identified patent and that said Letters Patent is hereby corrected as shown below:

Claim 1, Column 487, Line 3:  
"$(R^7)n$" has been replaced with --$(R^7)_n$--

Claim 1, Column 487, Line 10:  
"$(R^7)n$" has been replaced with --$(R^7)_n$--

Claim 1, Column 487, Line 18:  
"$(R^7)n$" has been replaced with --$(R^7)_n$--

Claim 1, Column 487, Line 28:  
"positon" has been replaced with --position--

Claim 1, Column 487, Lines 52-53:  
"-NHC (O)-C 1-4" has been replaced with -- -NHC(O)-C1-4--

Claim 1, Column 487, Line 62:  
"alkylene-NHC(O)-C1-4" has been replaced with --alkylene-NHC(O)O-C1-4--

Claim 3, Column 488, Line 66:  
After "1 or 2", insert --,--

Claim 5, Column 489, Line 4:  
After "claim 4", insert --,--

Claim 5, Column 489, Line 6:  
"X1a" has been replaced with --XIa--

Claim 6, Column 489, Line 7:  
After "1 or 2", insert --,--

Signed and Sealed this  
Fourteenth Day of August, 2018

Andrei Iancu  
*Director of the United States Patent and Trademark Office*

CERTIFICATE OF CORRECTION (continued)
U.S. Pat. No. 9,732,085 B2

Claim 6, Column 489, Line 10:
"X1a" has been replaced with --XIa--

Claim 8, Column 490, Line 1:
After "claim 7", insert --,--